US008916565B2

(12) United States Patent
Hadida Ruah et al.

(10) Patent No.: US 8,916,565 B2
(45) Date of Patent: Dec. 23, 2014

(54) PYRROLOPYRAZINE-SPIROCYCLIC PIPERIDINE AMIDES AS MODULATORS OF ION CHANNELS

(75) Inventors: Sara Sabina Hadida Ruah, La Jolla, CA (US); Edward Adam Kallel, Escondido, CA (US); Mark Thomas Miller, San Diego, CA (US); Vijayalaksmi Arumugam, San Marcos, CA (US); Jason McCartney, Cardiff by the Sea, CA (US); Corey Anderson, San Diego, CA (US); Peter Diederik Jan Grootenhuis, San Diego, CA (US); Licong Jiang, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 13/364,586

(22) Filed: Feb. 2, 2012

(65) Prior Publication Data

US 2012/0196869 A1 Aug. 2, 2012

Related U.S. Application Data

(60) Provisional application No. 61/438,685, filed on Feb. 2, 2011, provisional application No. 61/440,987, filed on Feb. 9, 2011, provisional application No. 61/495,538, filed on Jun. 10, 2011.

(51) Int. Cl.
*A61K 31/4985* (2006.01)
*C07D 471/20* (2006.01)
*C07D 519/00* (2006.01)

(52) U.S. Cl.
CPC ............ *C07D 471/20* (2013.01); *C07D 519/00* (2013.01)
USPC .......................................... 514/250; 544/346

(58) Field of Classification Search
CPC .......................... A61K 31/4985; C07D 471/20
USPC .......................................... 514/250; 544/346
See application file for complete search history.

(56) References Cited

U.S. PATENT DOCUMENTS

| | | | |
|---|---|---|---|
| 3,939,159 | A | 2/1976 | Dornauer et al. |
| 4,353,901 | A | 10/1982 | Clark |
| 5,206,240 | A | 4/1993 | Baldwin et al. |
| 2002/0013325 | A1 | 1/2002 | Fisher et al. |
| 2002/0082264 | A1 | 6/2002 | Nikolic et al. |
| 2002/0151712 | A1 | 10/2002 | Lin et al. |
| 2004/0014744 | A1 | 1/2004 | Haviv et al. |
| 2004/0266802 | A1 | 12/2004 | Calvet et al. |
| 2005/0209262 | A1 | 9/2005 | Tomori et al. |
| 2006/0052597 | A1 | 3/2006 | Best et al. |
| 2007/0066584 | A1 | 3/2007 | Yao et al. |
| 2007/0078120 | A1 | 4/2007 | Ban et al. |
| 2007/0117824 | A1 | 5/2007 | Berk et al. |
| 2008/0255154 | A1 | 10/2008 | Yao et al. |
| 2009/0169567 | A1 | 7/2009 | Kokubo et al. |
| 2009/0192182 | A1 | 7/2009 | Kusumi et al. |
| 2009/0325992 | A1 | 12/2009 | Hanada et al. |
| 2010/0113418 | A1 | 5/2010 | Fukatsu et al. |
| 2011/0306607 | A1 | 12/2011 | Hadida-Ruah et al. |
| 2012/0245136 | A1 | 9/2012 | Hadida-Ruah et al. |
| 2012/0264749 | A1 | 10/2012 | Hadida-Ruah et al. |

FOREIGN PATENT DOCUMENTS

| | | |
|---|---|---|
| CA | 2489255 | 12/2003 |
| EP | 0 002 937 | 7/1979 |
| EP | 0 370 732 | 5/1990 |
| EP | 0 431 943 | 6/1991 |
| EP | 2 123 652 | 11/2009 |
| GB | 1 590 155 | 5/1981 |
| JP | 4 297458 | 10/1992 |
| WO | WO 92/15304 | 9/1992 |
| WO | WO 95/15327 | 6/1995 |
| WO | WO 95/30642 | 11/1995 |
| WO | WO 97/02248 | 1/1997 |
| WO | WO 97/11940 | 4/1997 |
| WO | WO 97/16729 | 5/1997 |
| WO | WO 02/20509 | 3/2002 |
| WO | WO 03/095427 | 11/2003 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Artico, M., et al. "One-Pot Synthesis of Novel Spiro-Annelated Pyrrole-Containing Heterocyclic Systems from Suitable Synthons", J. Heterocyclic Chem., 1992, p. 241-245, vol. 29.
Fletcher, Stephen, et al., "4-(Phenylsulfonyl)piperidines: Novel, Selective, and Bioavailable 5-HT$_{2A}$ Receptor Antagonists", J. Med. Chem, 2002, p. 492-503, vol. 45.
Shen, Hong C., et al. "Discovery of spirocyclic secondary amine-derived ureas as highly potent, selective and bioavailable soluble epoxide hydrolase inhibitors", Bioorganic & Medicinal Chemistry Letters, 2009, p. 3398-3404, vol. 19.
International Search Report completed Mar. 16, 2012, in International Application No. PCT/US2012/023593, filed Feb. 2, 2012.
Office Action dated May 13, 2014, in U.S. Appl. No. 13/398,184, filed Feb. 16, 2012.
Office Action dated Dec. 19, 2013, in U.S. Appl. No. 13/418,737, filed.

*Primary Examiner* — Douglas M Willis
(74) *Attorney, Agent, or Firm* — Brinks Gilson & Lione

(57) ABSTRACT

The invention relates to pyrrolopyrazine-spirocyclic piperidine amide compounds of formula (I) useful as inhibitors of ion channels:

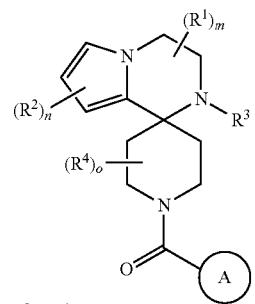

wherein $R^1$, $R^2$, $R^3$, $R^4$, A, m, n, and o are as defined in the description. The invention also provides pharmaceutically acceptable compositions comprising the compounds of the invention and methods of using the compositions in the treatment of various disorders.

35 Claims, No Drawings

(56) References Cited

FOREIGN PATENT DOCUMENTS

| | | |
|---|---|---|
| WO | WO 03/104240 | 12/2003 |
| WO | WO 2004/037800 | 5/2004 |
| WO | WO 2004/037828 | 5/2004 |
| WO | WO 2004/054974 | 7/2004 |
| WO | WO 2004/076418 | 9/2004 |
| WO | WO 2004/092179 | 10/2004 |
| WO | WO 2005/003128 | 1/2005 |
| WO | WO 2005/110992 | 11/2005 |
| WO | WO 2005/121090 | 12/2005 |
| WO | WO 2006/105442 | 10/2006 |
| WO | WO 2006/117669 | 11/2006 |
| WO | WO 2007/011809 | 1/2007 |
| WO | WO 2007/011811 | 1/2007 |
| WO | WO 2007/050124 | 5/2007 |
| WO | WO 2007/124045 | 11/2007 |
| WO | WO 2007/128782 | 11/2007 |
| WO | WO 2007/136605 | 11/2007 |
| WO | WO 2008/045564 | 4/2008 |
| WO | WO 2008/065508 | 6/2008 |
| WO | WO 2008/088688 | 7/2008 |
| WO | WO 2008/088692 | 7/2008 |
| WO | WO 2009/127609 | 10/2009 |
| WO | WO 2009/144554 | 12/2009 |
| WO | WO 2010/002010 | 1/2010 |
| WO | WO 2010/009195 | 1/2010 |
| WO | WO 2010/027567 | 3/2010 |
| WO | WO 2010/051476 | 5/2010 |
| WO | WO 2010/051497 | 5/2010 |
| WO | WO 2010/114957 | 10/2010 |
| WO | WO 2010/151595 | 12/2010 |
| WO | WO 2010/151597 | 12/2010 |
| WO | WO 2011/025690 | 3/2011 |
| WO | WO 2011/092198 | 8/2011 |
| WO | WO 2011/140425 | 11/2011 |
| WO | WO 2012/106499 | * 8/2012 |
| WO | WO 2012/112743 | 8/2012 |
| WO | WO 2012/125613 | 9/2012 |

* cited by examiner

PYRROLOPYRAZINE-SPIROCYCLIC PIPERIDINE AMIDES AS MODULATORS OF ION CHANNELS

CROSS REFERENCE TO RELATED APPLICATIONS

This application claims priority to U.S. provisional patent application Ser. Nos. 61/438,685, filed Feb. 2, 2011, 61/440, 987, filed Feb. 9, 2011, and 61/495,538, filed Jun. 10, 2011, the entire contents of all applications are incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S, and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block of neural channels in the CNS (nausea, sedation, confusion, ataxia). Cardiac side effects can also occur, and indeed these compounds are also used as class 1 anti-arrhythmics, presumably due to block of NaV 1.5 channels in the heart. Other compounds that have proven effective at reducing pain have also been suggested to act by sodium channel blockade including carbamazepine, lamotragine, and tricyclic antidepressants (Soderpalm, B., Anticonvulsants: aspects of their mechanisms of action. *Eur J Pain* 6 Suppl A, 3 (2002); Wang, G. K., Mitchell, J., and Wang, S. Y., Block of persistent late Na+ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nocioception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nociceptive terminals to the central nervous. Like NaV 1.3, NaV 1.7 expression increases after nerve injury and may contribute to neuropathic pain states. The localization of NaV 1.7, 1.8, and 1.9 in nociceptors led to the hypothesis that reducing the sodium currents through these channels might alleviate pain. Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. *Hum Gene Ther* 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PN1) in acute and inflammatory pain. *Proc Natl Acad Sci USA* 101 (34), 12706 (2004)). Global knockouts of NaV 1.7 in mice lead to animals that die on the first day after birth. These mice fail to feed and this is the presumed cause of death.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. *Pain* 95 (1-2), 143 (2002); Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. *Pain* 95 (1-2), 143 (2002); Akopian, A. N. et al., The tetrodotoxin-resistant sodium channel SNS has a specialized function in pain pathways. *Nat Neurosci* 2 (6), 541 (1999); Abrahamsen, B. et al., The cell and molecular basis of mechanical, cold, and inflammatory pain. *Science* 321 (5889), 702 (2008); Laird, J. M., Souslova, V., Wood, J. N., and Cervero, F., Deficits in visceral pain and referred hyperalgesia in NaV 1.8 (SNS/PN3)-null mice. *J Neurosci* 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. *J Neurosci* 26 (50), 12852 (2006); Priest, B. T. et al., Contribution of the tetrodotoxin-resistant voltage-gated sodium channel NaV 1.9 to sensory transmission and nociceptive behavior. *Proc Natl Acad Sci USA* 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. *Proc Natl Acad Sci USA* 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. *Epilepsy Res* 70 Suppl 1, S223 (2006); George, A. L., Jr., Inherited disorders of voltage-gated sodium channels. *J Clin Invest* 115 (8), 1990 (2005); Misra, S, N., Kahlig, K. M., and George, A. L., Jr., Impaired NaV 1.2 function and reduced cell surface expression in benign familial neonatal-infantile seizures. *Epilepsia* 49 (9), 1535 (2008)). Mutations of the NaV 1.4 cause muscular disorders like paramyotonia congenita (Vicart, S., Sternberg, D., Fontaine, B., and Meola, G., Human skeletal muscle sodium channelopathies. *Neurol Sci* 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. *Nature* 376 (6542), 683 (1995); Darbar, D. et al., Cardiac sodium channel (SCN5A) variants associated with atrial fibrillation. *Circulation* 117 (15), 1927 (2008); Wang, Q. et al., SCN5A mutations associated with an inherited cardiac arrhythmia, long QT syndrome. *Cell* 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. *J Invest Dermatol* 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. *J Neurosci* 28 (43), 11079 (2008)).

NaV 1.7 null mutations in human patients were recently described by several groups (Ahmad, S. et al., A stop codon mutation in SCN9A causes lack of pain sensation. *Hum Mol Genet.* 16 (17), 2114 (2007); Cox, J. J. et al., An SCN9A channelopathy causes congenital inability to experience pain. *Nature* 444 (7121), 894 (2006); Goldberg, Y. P. et al., Loss-of-function mutations in the NaV 1.7 gene underlie congenital indifference to pain in multiple human populations. *Clin Genet.* 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent of smell (Goldberg, Y. P. et al., Loss-of-function mutations in the NaV 1.7 gene underlie congenital indifference to pain in multiple human populations. *Clin Genet.* 71 (4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromafin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. *EMBO J* 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

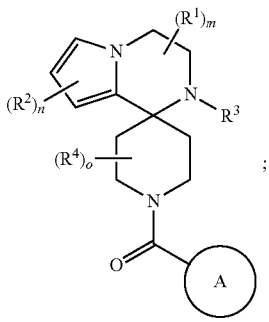

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one aspect, the invention provides compounds of formula I:

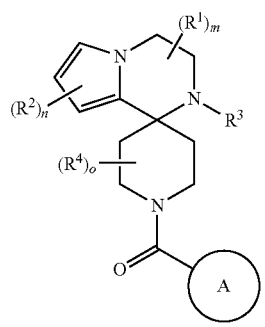

or a pharmaceutically acceptable salt thereof,
wherein, independently for each occurrence:
$R^1$ is H, C1-C8 alkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, heterocycloalkyl, or a straight chain, branched, or cyclic (C1-C8)-$R^1$ wherein up to two $CH_2$ units may be replaced with O, CO, S, SO, $SO_2$ or $NR^8$, or two $R^1$ taken together form an oxo group, or a 3 to 7 membered fused cycloalkyl ring, or a 3 to 7 membered spirocyclic ring;

$R^2$ is H, C1-C8 alkyl, halo, C1-C8 haloalkyl, CN, OH, $SO_2R^8$, $SR^8$, $SOR^8$, $CO_2R^8$, $CON(R^8)_2$, $COR^8$, $SO_2N(R^8)_2$, $CF_3$, $CHF_2$, or a straight chain, branched, or cyclic (C1-C8)-$R^9$ wherein up to two $CH_2$ units may be replaced with O, CO, S, SO, $SO_2$, $CF_2$, or $NR^8$;

$R^3$ is H, C1-C8 alkyl, C3-C8 cycloalkyl, $CO_2R^8$, $COR^8$, COH, $CON(R^8)_2$, $CF_3$, $CH_2CF_3$, $CH_2CHF_2$, or a straight chain, branched, or cyclic (C1-C8)-$R^9$ wherein up to two $CH_2$ units may be replaced with O, CO, S, SO, $SO_2$, $CF_2$, or $NR^8$;

$R^4$ is H, C1-C8 alkyl, halo, C3-C8 cycloalkyl, wherein up to two $CH_2$ units may be replaced by O, CO, S, SO, $SO_2$, or $NR^8$, or 2 $R^4$ taken together form a fused 3 to 7 membered cycloalkyl ring;

$R^8$ is H, C1-C8 alkyl, $CF_3$, C3-C8 cycloalkyl, fluoroalkyl, aryl, heteroaryl, or a straight chain, branched, or cyclic (C1-C8)-$R^9$ wherein up to two $CH_2$ units may be replaced with O, CO, S, SO, $SO_2$ or NR, or 2 $R^8$ taken together with the atoms to which they are attached form a ring;

$R^9$ is H, $CF_3$, $CO_2R$, OH, aryl, heteroaryl, C3-C8 cycloalkyl, heterocycloalkyl, $N(R)_2$, NRCOR, $CON(R)_2$, CN, halo, or $SO_2R$;

R is H, C1-C8 alkyl, aryl, heteroaryl, C3-C8 cycloalkyl, or heterocycloalkyl;

A is an optionally substituted aryl, heteroaryl or heterocyclic;
m is an integer from 0 to 4 inclusive;
n is an integer from 0 to 3 inclusive; and
o is an integer from 0 to 4 inclusive.

In another aspect, the invention provides compounds of formula I,
or a pharmaceutically acceptable salt thereof, wherein, independently for each occurrence:
$R^1$ is H, C1-C6 alkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, heterocycloalkyl, or a straight chain, branched, or cyclic (C1-C8)-$R^9$ wherein up to two $CH_2$ units may be replaced with O, CO, S, SO, $SO_2$ or $NR^8$, or two $R^1$ taken together form an oxo group, or a 3 to 7 membered fused cycloalkyl ring, or a 3 to 7 membered spirocyclic ring;

$R^2$ is H, C1-C6 alkyl, C1-C6 haloalkyl, CN, OH, $SO_2R^8$, $SR^8$, $SOR^8$, $CO_2R^8$, $CON(R^8)_2$, $SO_2N(R^8)_2$, $CF_3$, $CHF_2$, or a straight chain, branched, or cyclic (C1-C8)-$R^9$ wherein up to two $CH_2$ units may be replaced with O, CO, S, SO, $SO_2$, $CF_2$, or $NR^8$;

$R^3$ is H, C1-C6 alkyl, C3-C8 cycloalkyl, $CO_2R^8$, $COR^S$, COH, $CON(R^8)_2$, $CF_3$, $CH_2CF_3$, $CH_2CHF_2$, or a straight chain, branched, or cyclic (C1-C8)-$R^9$ wherein up to two $CH_2$ units may be replaced with O, CO, S, SO, $SO_2$ or $NR^8$;

$R^4$ is H, C1-C6 alkyl, halo, C3-C8 cycloalkyl, wherein up to two $CH_2$ units may be replaced by O, CO, S, SO, $SO_2$, or $NR^8$, or 2 $R^4$ taken together form a fused 3 to 7 membered cycloalkyl ring;

$R^8$ is H, C1-C6 alkyl, $CF_3$, C3-C8 cycloalkyl, or a straight chain, branched, or cyclic (C1-C8)-$R^9$ wherein up to two $CH_2$ units may be replaced with O, CO, S, SO, $SO_2$ or NR, or 2 $R^8$ taken together with the atoms to which they are attached form a ring;

$R^9$ is H, $CF_3$, $CO_2R$, OH, aryl, heteroaryl, C3-C8 cycloalkyl, heterocycloalkyl, $N(R)_2$, NRCOR, $CON(R)_2$, CN, or $SO_2R$;

R is H, C1-C6 alkyl, aryl, heteroaryl, C3-C8 cycloalkyl, or heterocycloalkyl;

A is an optionally substituted aryl, heteroaryl or heterocyclic;

m is an integer from 0 to 4 inclusive;

n is an integer from 0 to 3 inclusive; and o is an integer from 0 to 4 inclusive.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables $R^1$-$R^9$ in formula I encompass specific groups, such as, for example, alkyl and aryl. Unless otherwise noted, each of the specific groups for the variables $R^1$-$R^8$ can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members.

The term "electron withdrawing group", as used herein means an atom or a group that is electronegative relative to hydrogen. See, e.g., "Advanced Organic Chemistry: Reactions, Mechanisms, and Structure," Jerry March, 4th Ed., John Wiley & Sons (1992), e.g., pp. 14-16, 18-19, etc. Exemplary such substituents include halo such as Cl, Br, or F, CN, COOH, $CF_3$, etc.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated", as used herein, means that a moiety has one or more units of unsaturation but is not aromatic.

The term "alkoxy", or "thioalkyl", as used herein, refers to an aliphatic group, as previously defined, attached to the principal carbon chain through an oxygen ("alkoxy") or sulfur ("thioalkyl") atom. As used herein, alkoxy group includes alkenyloxy and aklkynyloxy groups.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms. For example, compounds of formula I, wherein one or more hydrogen atoms are replaced deuterium or tritium, or one or more carbon atoms are replaced by a $^{13}C$- or $^{14}C$-enriched carbon are within the scope of this invention. Such compounds are useful, for example, as analytical tools, probes in biological assays, or sodium channel blockers with improved therapeutic profile.

In the formulas and drawings, a line transversing a ring and bonded to an R group such as in

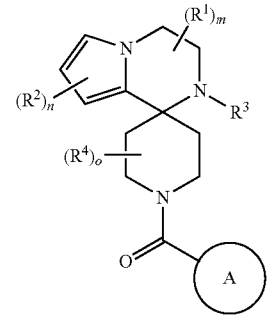

means that the R group can be bonded to any carbon, or if applicable, heteroatom such as N, of that ring as valency allows.

Within a definition of a term as for example, $R^1$, $R^2$, $R^3$, $R^4$, $R^5$, $R^6$, or $R^7$ when a $CH_2$ unit or, interchangeably, methylene unit may be replaced by O, CO, S, SO, $SO_2$ or $NR^8$, it is meant to include any $CH_2$ unit, including a $CH_2$ within a terminal methyl group. For example, —$CH_2CH_2CH_2SH$ is within the definition of C1-C8 alkyl wherein up to two $CH_2$ units may be replaced by S because the $CH_2$ unit of the terminal methyl group has been replaced by S.

In another embodiment, the invention features a compound of formula I and the attendant definitions, wherein $R^1$ is C1-C8 alkyl or two $R^1$ taken together with the atoms to which they are attached form a 3 to 7 membered fused cycloalkyl or spirocyclic ring. In another embodiment, $R^1$ is $CH_3$ or two $R^1$ taken together form a fused cyclohexyl ring.

In another embodiment, the invention features a compound of formula I and the attendant definitions, wherein $R^2$ is H, C1-C8 alkyl, halo, $CF_3$, CN, $CON(R^8)_2$, or a straight chain, branched, or cyclic (C1-C8)-$R^9$ wherein up to two $CH_2$ units may be replaced with O, CO, S, SO, $SO_2$, $CF_2$, or $NR^8$. In another embodiment, $R^2$ is $COCF_3$, COtBu, Cl, $COCH_3$, $CF_2CF_3$, $CH_2CF_3$, $CF_3$, CN, Br, $COCH(CH_3)_2$, $COCH_2CH_3$, $CH(OH)CF_3$, $SO_2CH_3$,

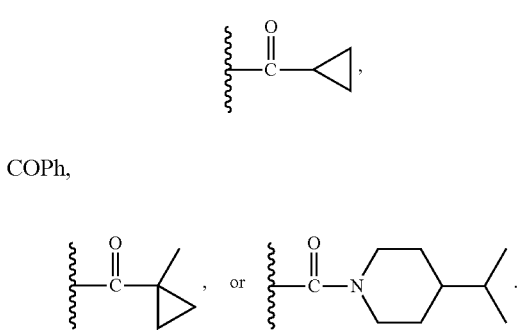

COPh,

In another embodiment, the invention features a compound of formula I and the attendant definitions, wherein $R^3$ is H, C1-C8 alkyl, $CO_2R^8$, $COR^8$, COH, $CON(R^8)_2$ or a straight chain, branched, or cyclic (C1-C8)-$R^9$ wherein up to two $CH_2$ units may be replaced with O, CO, $CF_2$, S, SO, $SO_2$ or $NR^8$. In another embodiment, $R^3$ is H, $CH_3$, $CH_2CH_3$, $CH_2CH_2OCH_3$, benzyl, $CH_2CH(CH_3)_2$, $CH(CH_3)_2$, cyclobutyl, $COCH_3$, $CO_2CH_3$, $CO_2CH_2CH_3$, $CH_2CF_3$, $CH_2CHF_2$, COH, $CON(CH_3)_2$, or $CONHCH_3$.

In another embodiment, the invention features a compound of formula I and the attendant definitions, wherein $R^4$ is H, halo, or C1-C8 alkyl. In another embodiment, $R^4$ is H, F, or $CH_3$.

In another embodiment, the invention features a compound of formula I and the attendant definitions, wherein m is 0, 1, or 2. In another embodiment, n is 0, 1 or 2. In another embodiment, o is 0 or 1.

In another embodiment, the invention features a compound of formula I and the attendant definitions, wherein A is

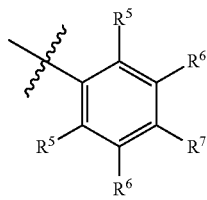

wherein:
$R^5$ is H, C1-C8 alkyl, C3-C8 cycloalkyl, C1-C8 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, or $NR^8$;

$R^6$ is H, C1-C8 alkyl, C3-C8 cycloalkyl, C1-C8 alkoxy, C3-C8 cycloalkoxy, halo, CN, OH, $OR^8N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, or $NR^8$;

$R^7$ is H, C1-C8 alkyl, C3-C8 cycloalkyl, C1-C8 alkoxy, halo, CN, OH, $OR^8$, $N(R^8)_2$, $NR^8SO_2R^8$, $SO_2R^8$, $OSO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$(R^9)_p$, wherein p is 1 or 2 and wherein up to three $CH_2$ units may be replaced with O, CO, S, SO, $SO_2$, or $NR^8$; or two occurrences of $R^5$ and $R^6$, or $R^6$ and $R^7$ are both C1-C8 alkyl and together with the carbons to which they are attached form an optionally substituted ring comprising up to 2 heteroatoms.

In another embodiment, the invention features a compound of formula I and the attendant definitions, wherein $R^5$ is H, C1-C8 alkyl, C1-C8 alkoxy, halo, $OCF_3$, $OCHF_2$, $R^9$, or a straight chain, branched, or cyclic (C1-C8)-$R^9$ wherein up to three $CH_2$ units may be replaced with O, CO, S, SO, $SO_2$, or $NR^7$. In another embodiment, $R^5$ is H, $CH_3$, $OCH_3$, $OCF_3$, OPh, Ph, $OCHF_2$, or F.

In another embodiment, the invention features a compound of formula I and the attendant definitions, wherein $R^6$ is H, C1-C8 alkyl, C1-C8 alkoxy, halo, $R^9$, or a straight chain, branched, or cyclic (C1-C8)-$R^9$ wherein up to three $CH_2$ units may be replaced with O, CO, S, SO, $SO_2$, or $NR^8$. In another embodiment, $R^6$ is H, $CH_3$, $OCH_3$, $OCH_2CH_3$, $OCH_2CH_2CH_3$, $OCH(CH_3)_2$, $CF_3$, CN, Ph, $SO_2CH_3$, OH, $CH(CH_3)_2$, $OCH_2CH_2CH_2CH_3$, F, Cl, or $CH_2OH$.

In another embodiment, the invention features a compound of formula I and the attendant definitions, wherein $R^7$ is H, C1-C8 alkyl, C1-C8 alkoxy, $SO_2R^8$, $OSO_2R^8$, $SO_2N(R^8)_2$, $R^9$, or a straight chain, branched, or cyclic (C1-C8)-$(R^9)_p$, wherein p is 1 or 2 and wherein up to three $CH_2$ units may be replaced with O, CO, S, SO, $SO_2$, or $NR^8$. In another embodiment, $R^7$ is H, $CH_2CH_3$, tBu, Cl, F, OH, $C(=CH_2)CH_3$, $OC(=CH_2)CH_3$, $OCH_3$, $OCH_2CH_2CH_3$, $CH_2OH$, $OCH_2CH_2OH$, $OCH_2CH_2CH_2OH$, OtBu, $OCH(CH_3)(CH_2CH_3)$, $OCH_2C(CH_3)_2OH$, $C(CH_3)_2OH$, $CH_2C(CH_3)_2OH$, $CH(OH)CH(CH_3)_2$, $C(CH_3)_2CH_2OH$, $OCH_2CH_2CH(CH_3)_2$, $OCH_2CH_2CH_3$, $OCH(CH_3)_2$, $OCH_2CH_2OCH_3$,

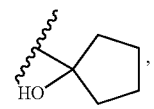 [SMILES: *C1(O)CCCC1]

$SO_2CH_3$, $SO_2tBu$, $SO_2CH_2CH_3$, $SO_2CH_2CH(CH_3)_2$, $SO_2CH(CH_3)_2$,

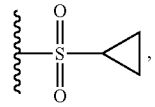

$SO_2NH(CH_3)$, $SO_2NH(CH(CH_2)_2)$, $SO_2NH(CH_2CH_3)$, $SO_2NH(CH(CH_3)_2)$, $SO_2N(CH_3)_2$,

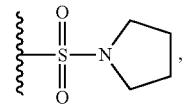 [SMILES: *S(=O)(=O)N1CCCC1]

Ph,

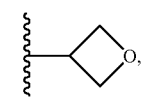

$OCH_2CH_2OCH_3$, $CH(CH_3)_2$, $SO_2N(CH_2CH_3)_2$, $CH_2CH_2CH_2CH_3$, $CH_2CH_2CH_3$, OPh, $OCH_2CH_2CH_3$, $CH_2OPh$,

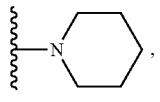

$OCH_2Ph$, $CH_2CH_2CH_2CH_2CH_3$, $OCH_2CH_3$, $OCH_2CH(CH_3)_2$, $CH_2CH_3$, $CH_2Ph$,

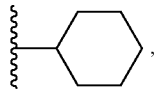

CCCH₂OCH₃, SO₂CHF₂, OCF₃,
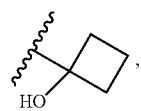
OCHF₂,
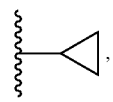
CH₂CH(CH₃)₂, OCH₂tBu,
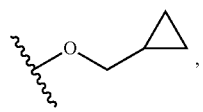
OCH₂CF₃,
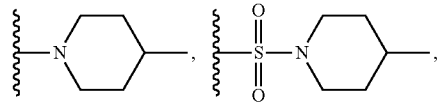
CH₂OCH₂CH₂CF₃, CH₂OCH₂CF₃, SO₂CF₃, C(CH₃)₂CH₂CH₃, C(CH₂CH₃)₃, CH(OCH₂CF₃)₂,
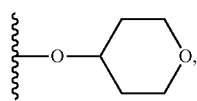
CF₃, OCH₂C(CH₃)₂F,
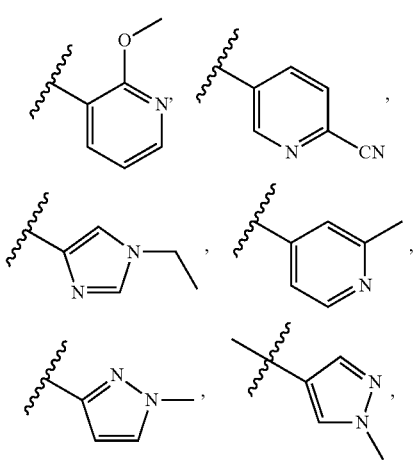
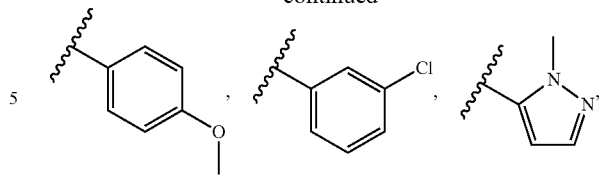
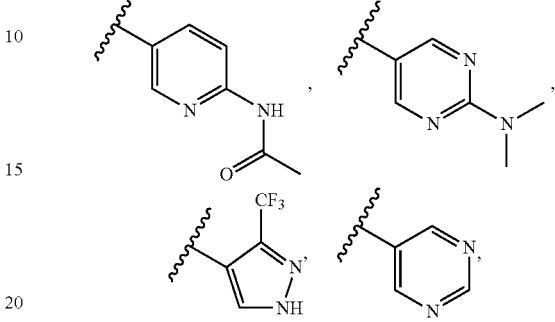
CH(OH)CH₂OCH₂CF₃, CH(OCH₂CF₃)CH₂OH, OSO₂CF₃,
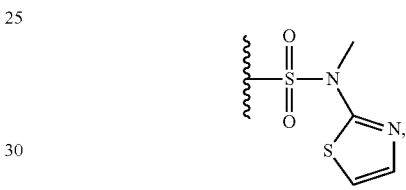
or OCH₂CH₂OCF₃.
In another embodiment, the invention features a compound of formula I and the attendant definitions, wherein A is
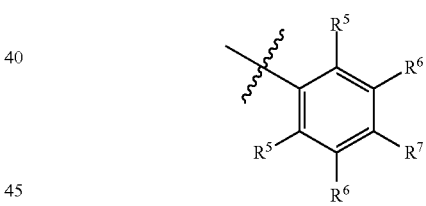
and is selected from:
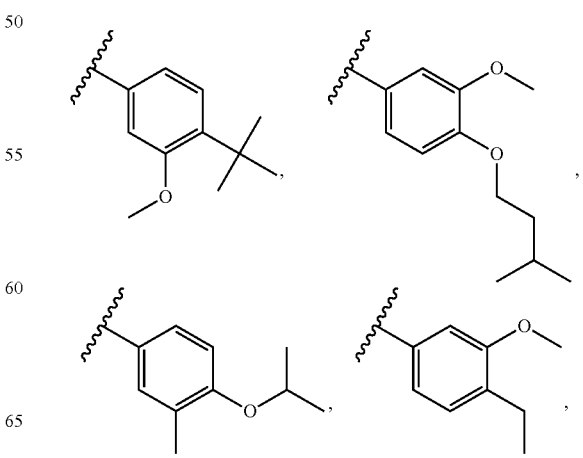

-continued

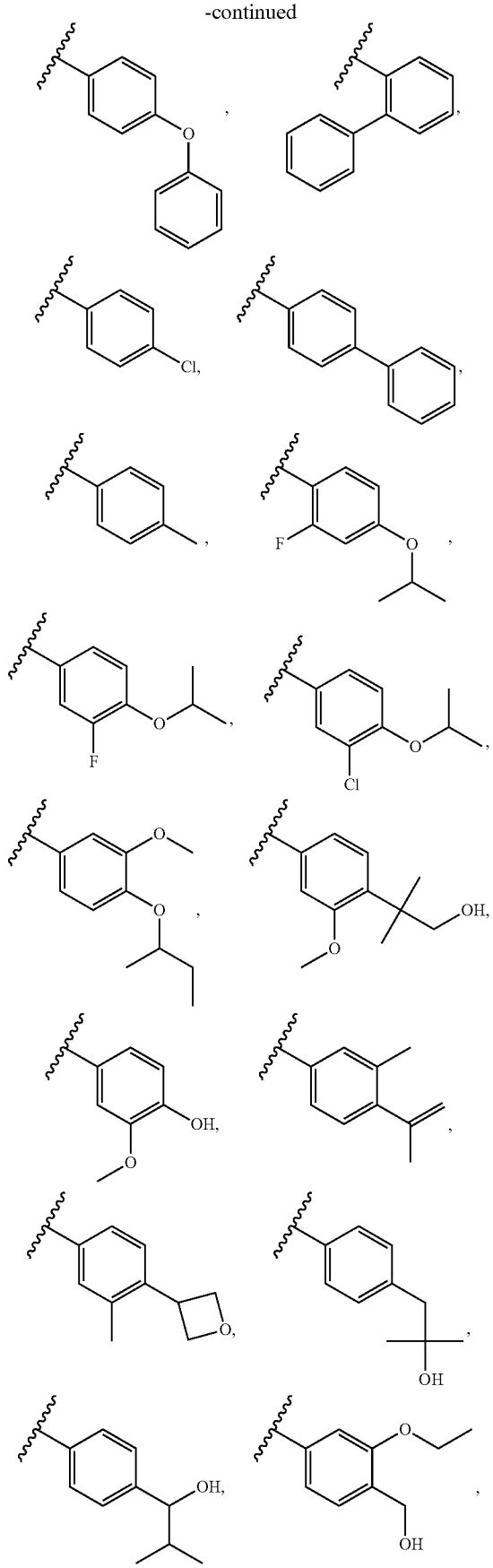
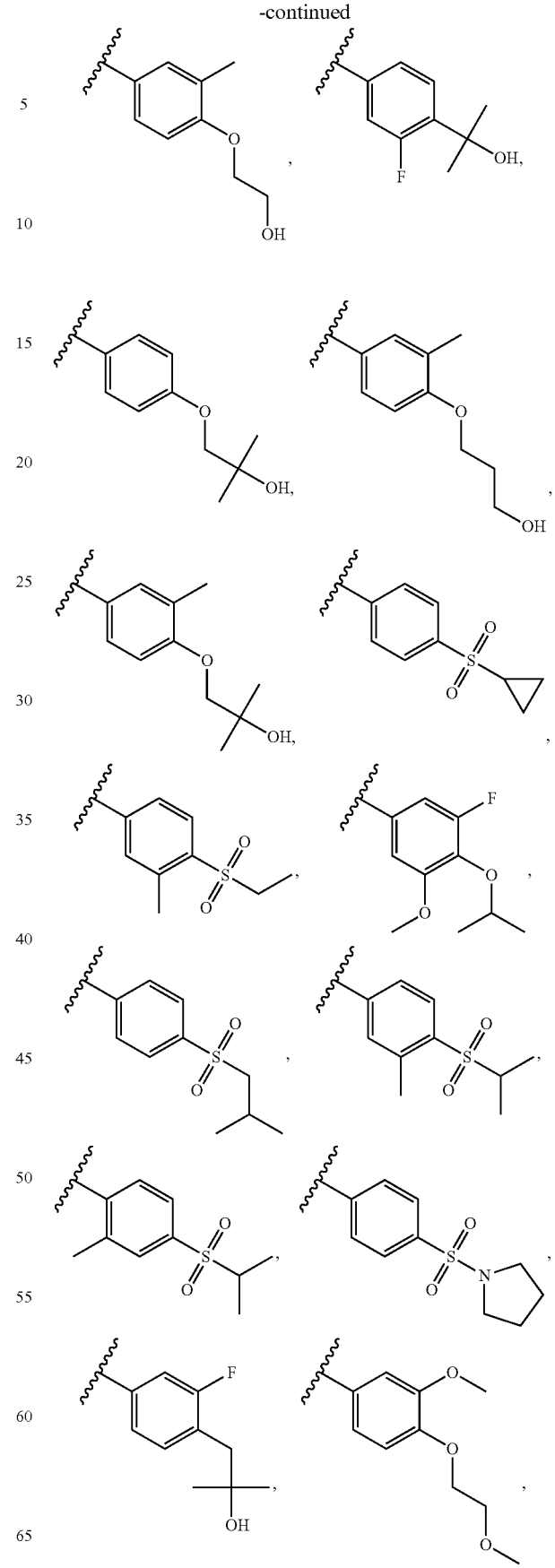

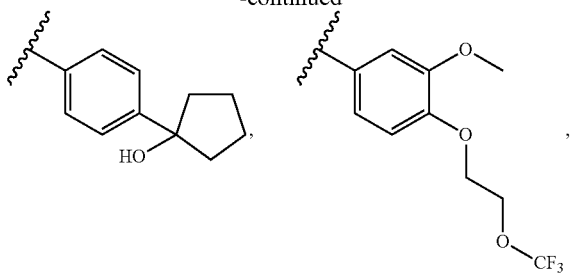
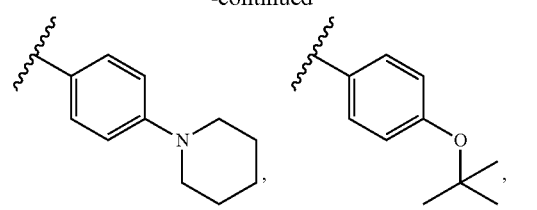
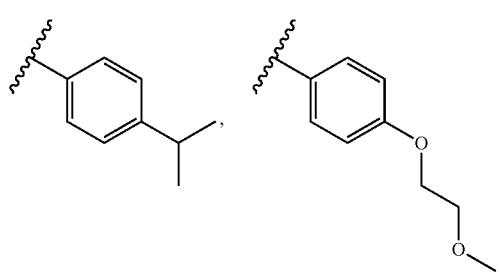
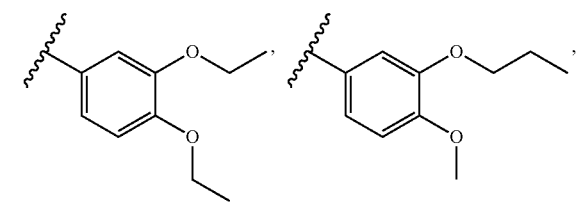
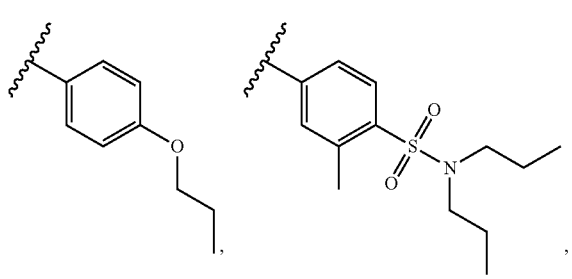
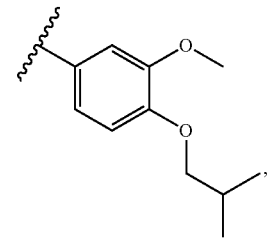
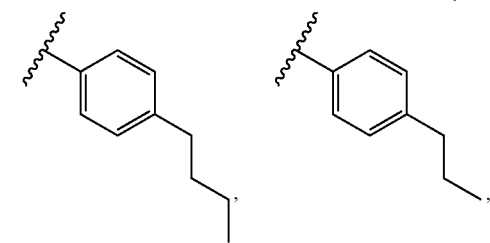
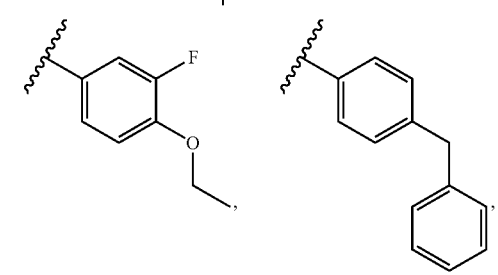
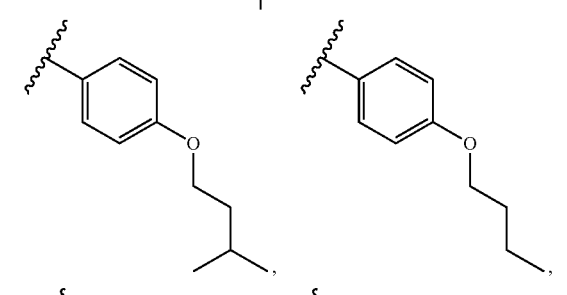
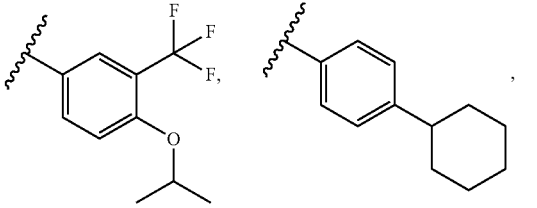
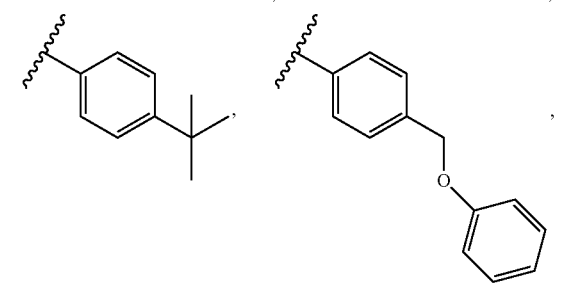
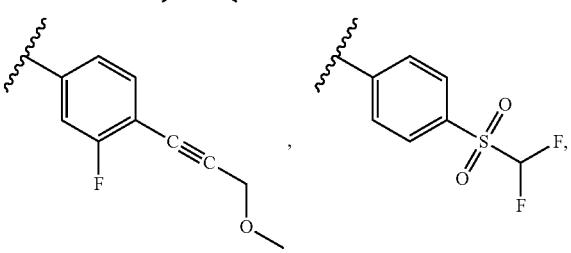

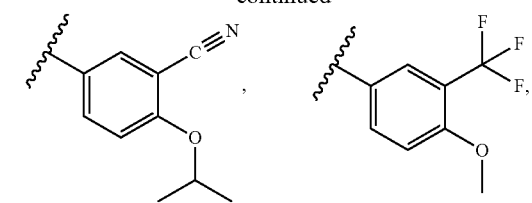
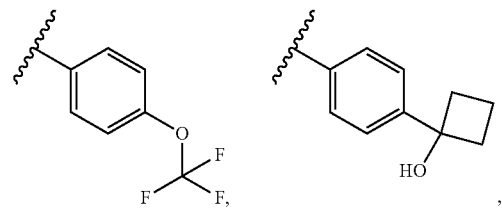
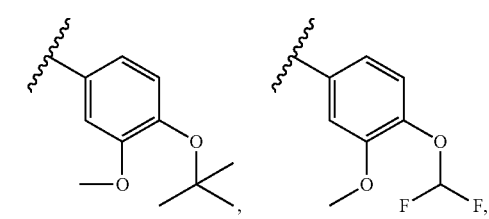
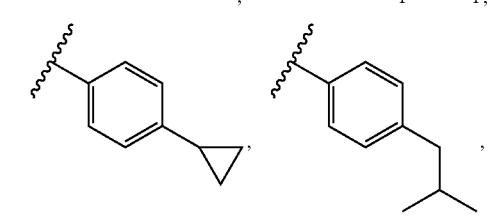
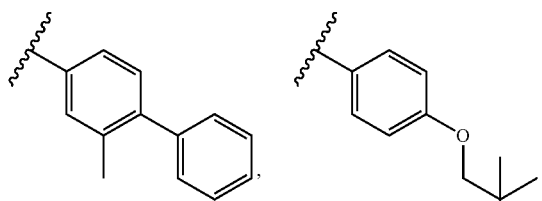
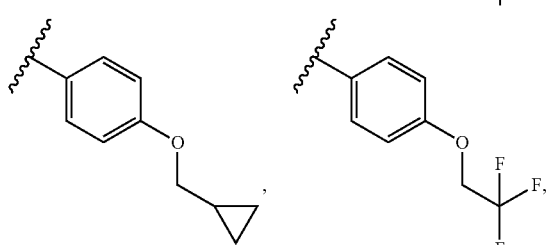
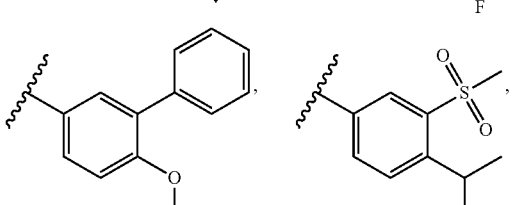
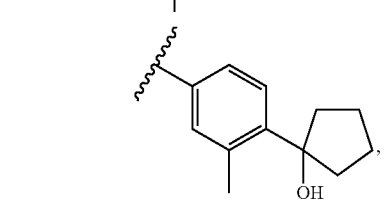
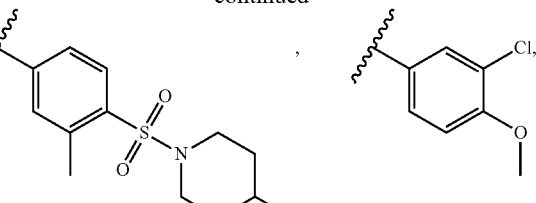
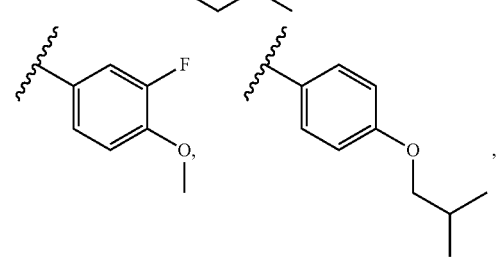
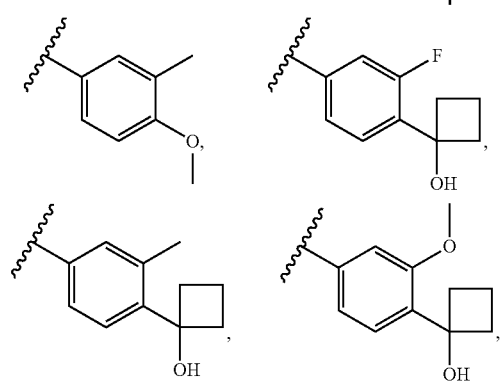
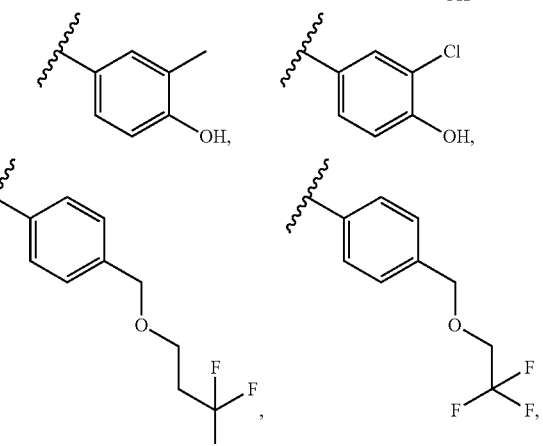
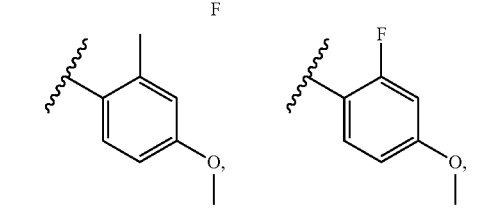
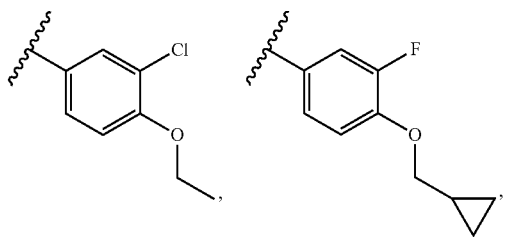

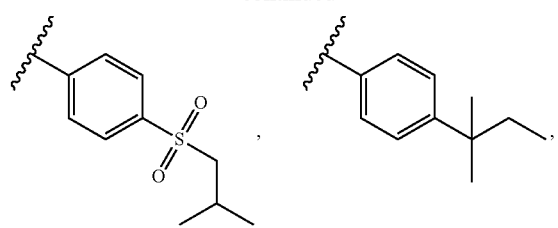
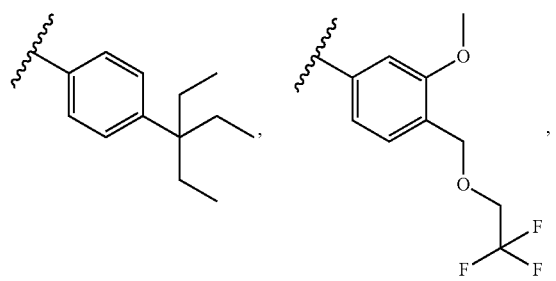
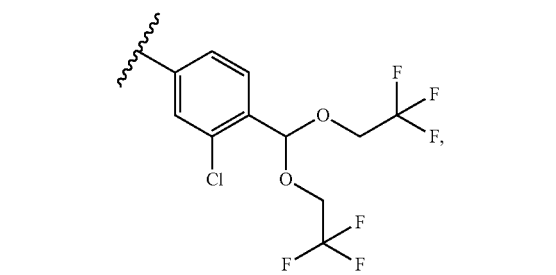
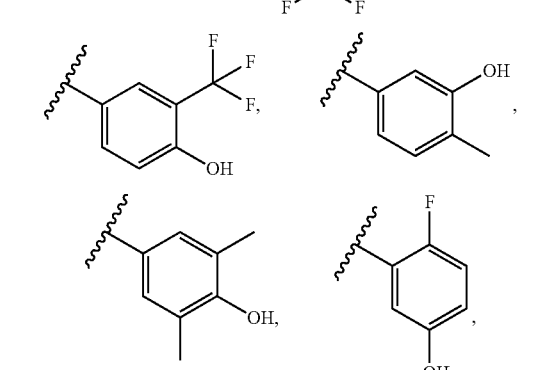
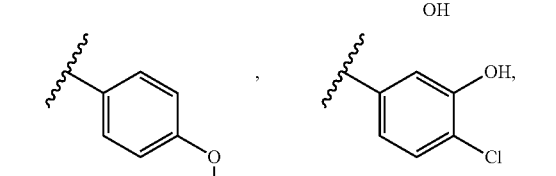
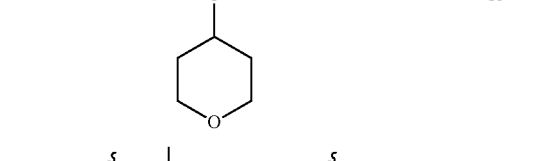
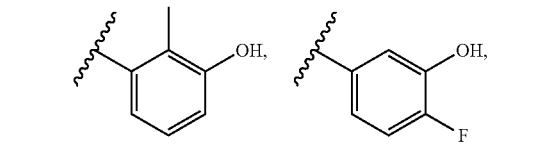
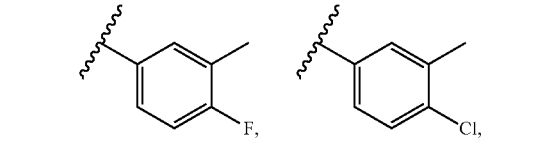
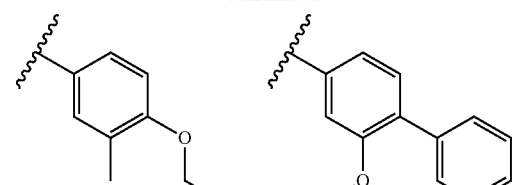
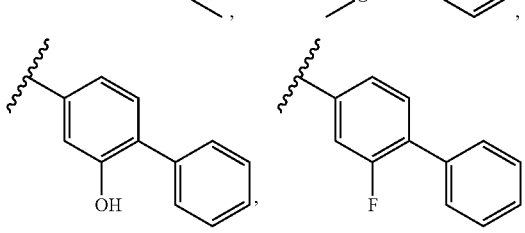
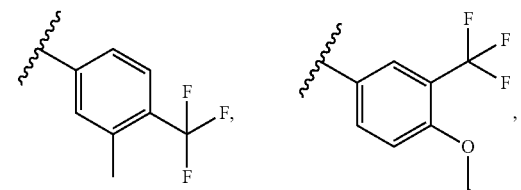
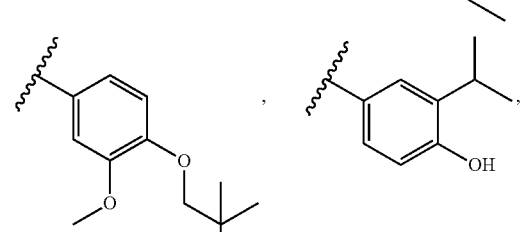
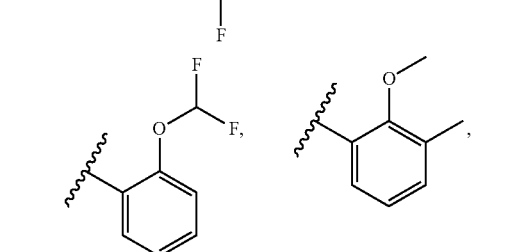
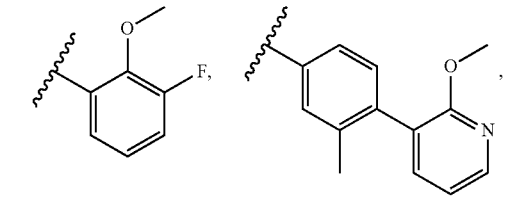
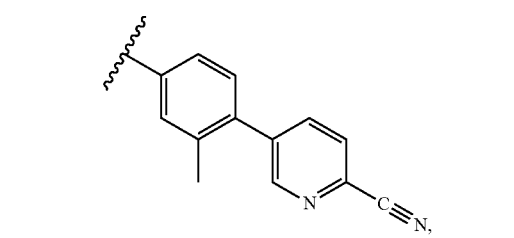
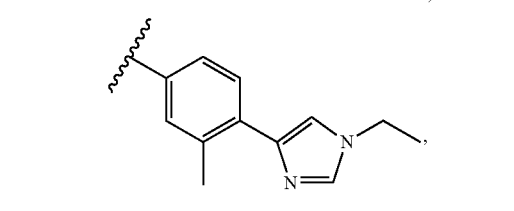

-continued
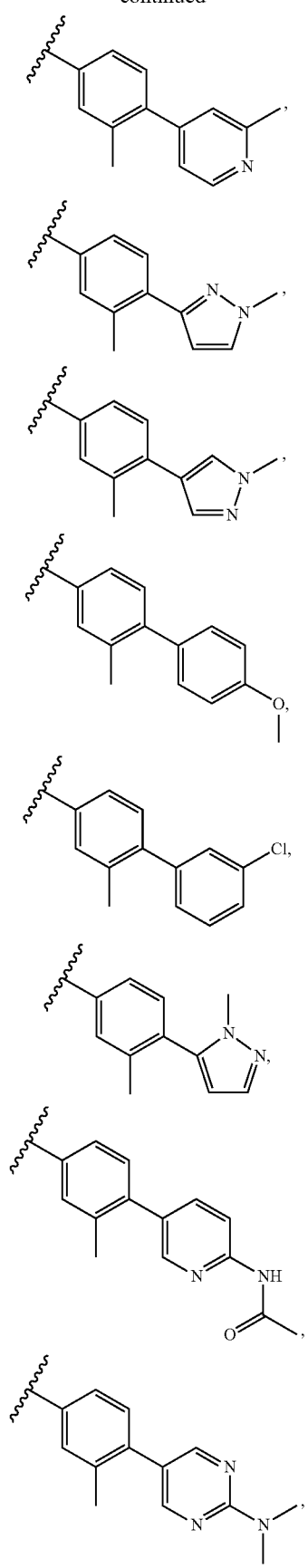
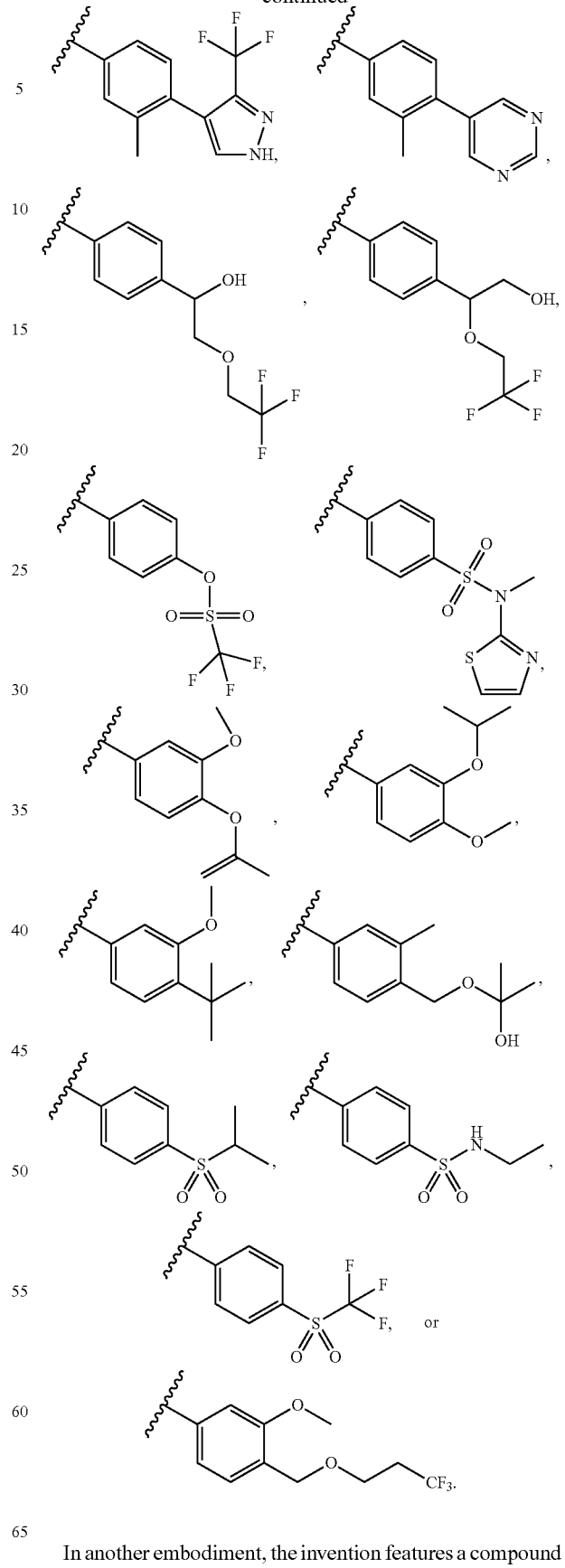
In another embodiment, the invention features a compound of formula I and the attendant definitions, wherein A is heteroaryl or heterocyclic. In another embodiment, A is a monocyclic heteroaryl comprising 1 to 3 heteroatoms independently selected from N, O, or S. In another embodiment, A is selected from a bicyclic heteroaryl comprising from 1 to 3 heteroatoms independently selected from N, O, or S.

In another embodiment, the invention features a compound of formula I and the attendant definitions, wherein A is selected from the following:

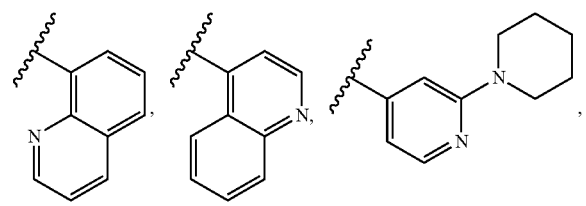

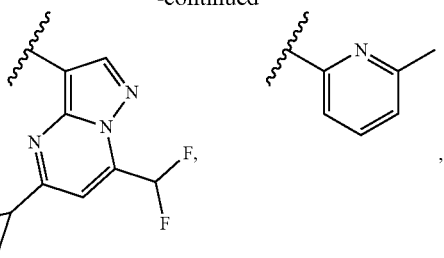

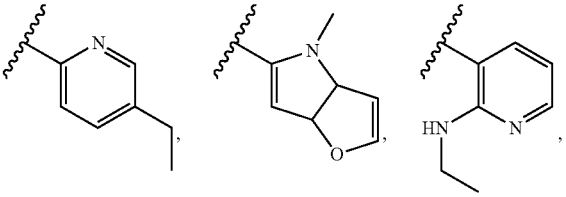

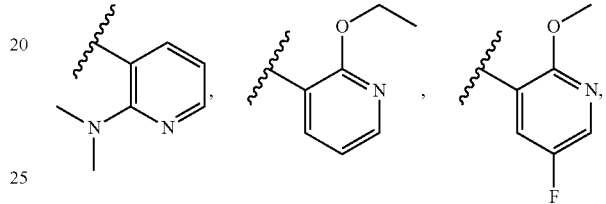

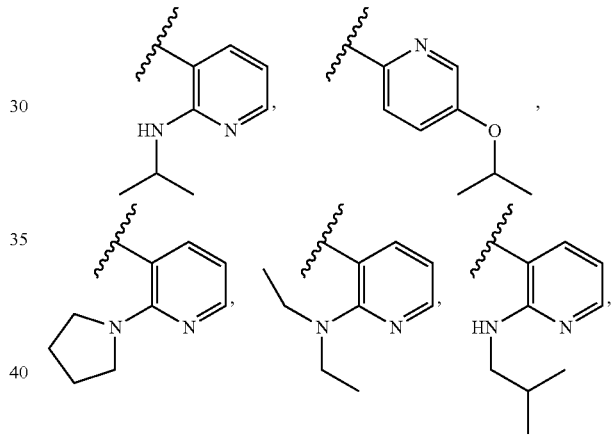

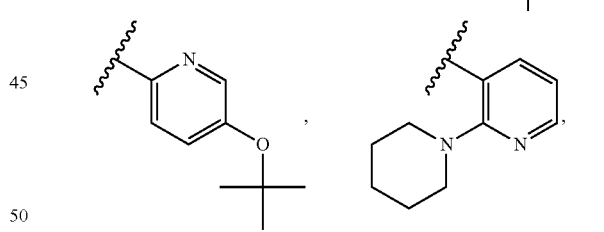

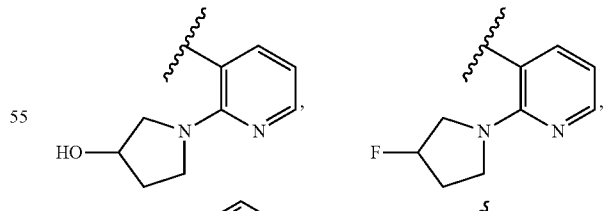

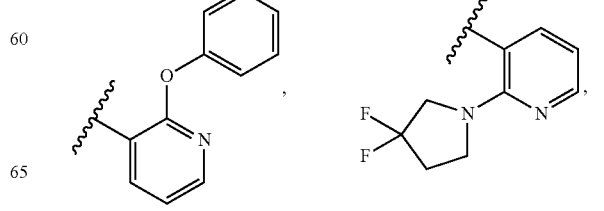

-continued

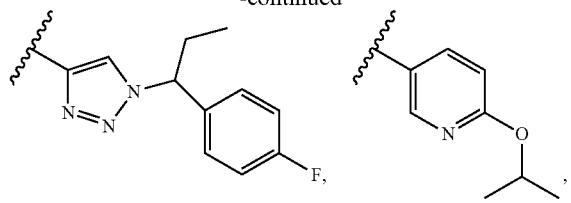

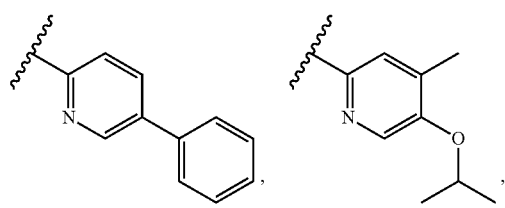

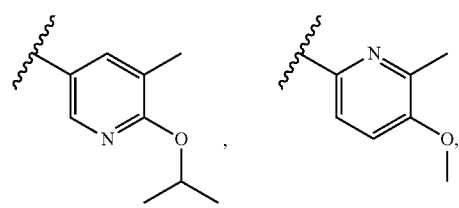

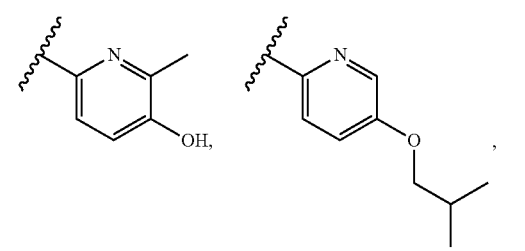

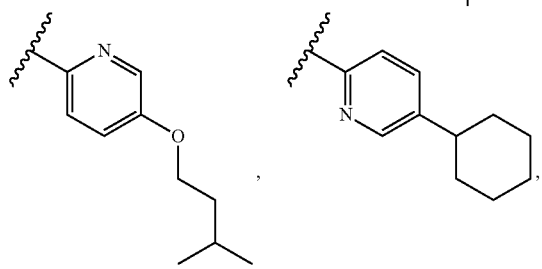

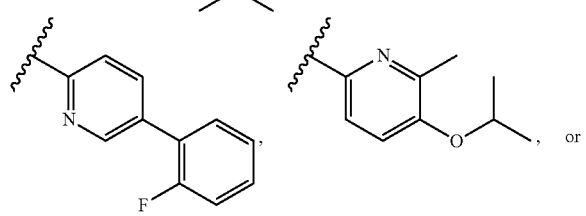

In another embodiment, the compounds of the invention have formula IA:

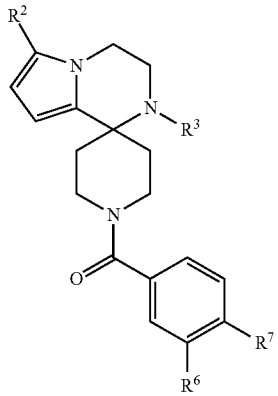

IA wherein:
$R^2$ is H, C1-C8 alkyl, halo, C1-C8 haloalkyl, CN, OH, $SO_2R^8$, $SR^8$, $SOR^8$, $COR^8$, $CO_2R^8$, $CON(R^8)_2$, $SO_2N(R^8)_2$, $CF_3$, $CHF_2$, or a straight chain, branched, or cyclic (C1-C8)-$R^9$ wherein up to two $CH_2$ units may be replaced with O, CO, S, SO, $SO_2$ $CF_2$, or $NR^8$;

$R^3$ is H, C1-C8 alkyl, $CO_2R^8$, $COR^8$, COH, $CON(R^8)_2$, $CF_3$, or a straight chain, branched, or cyclic (C1-C8)-$R^9$ wherein up to two $CH_2$ units may be replaced with O, CO, $CF_2$, S, SO, $SO_2$ or $NR^8$;

$R^6$ is H, C1-C8 alkyl, C3-C8 cycloalkyl, C1-C8 alkoxy, C3-C8 cycloalkoxy, halo, CN, OH, $OR^8N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, or $NR^8$;

$R^7$ is H, C1-C8 alkyl, C3-C8 cycloalkyl, C1-C8 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C1-C8)-$R^9$ wherein up to three $CH_2$ units may be replaced with O, CO, S, SO, $SO_2$, or $NR^8$.

In another embodiment, the invention features a compound of formula IA and the attendant definitions, wherein $R^2$ is H, $COCF_3$, COtBu, Cl, $COCH_3$, $CF_2CF_3$, $CH_2CF_3$, $CF_3$, CN, Br, $COCH(CH_3)_2$, $COCH_2CH_3$, $CH(OH)CF_3$, $SO_2CH_3$,

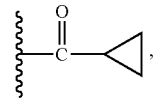 [SMILES: *C(=O)C1CC1]

COPh,

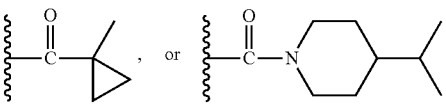

In another embodiment, the invention features a compound of formula IA and the attendant definitions, wherein $R^3$ is H, $CH_3$, $CH_2CH_3$, $CH_2CH_2OCH_3$, $CH_2CH_2OH$, $CH_2CO_2CH_2CH_3$, $CH_2CON(CH_3)_2$, $CH_2CONH_2$, $CH_2CN$, benzyl, cyclobutyl, $CH_2CH(CH_2)_2$, $CH(CH_2)_2$, $CH_2CF_3$, $CH_2CHF_2$, $COCH_3$, $COCH_2CH_3$, $CO_2CH_3$, $CO_2CH_2CH_3$, $COH$, $CONH(CH_3)_2$, or $CONHCH_3$.

In another embodiment, the invention features a compound of formula IA and the attendant definitions, wherein $R^6$ is H, $CH_3$, $OCH_3$, $OCH_2CH_3$, $OCH_2CH_2CH_3$, $OCH(CH_3)_2$, $CF_3$, $CN$, Ph, $SO_2CH_3$, OH, $CH(CH_3)_2$, $OCH_2CH_2CH_2CH_3$, F, Cl, or $CH_2OH$.

In another embodiment, the invention features a compound of formula IA and the attendant definitions, wherein $R^7$ is H, $CH_3$, $CH_2CH_3$, tBu, Cl, F, OH, $C(=CH_2)CH_3$, $OC(=CH_2)CH_3$, $OCH_3$, $OCH_2CH_2CH_3$, $CH_2OH$, $OCH_2CH_2OH$, $OCH_2CH_2CH_2OH$, OtBu, $OCH(CH_3)(CH_2CH_3)$, $OCH_2C(CH_3)_2OH$, $C(CH_3)_2OH$, $CH_2C(CH_3)_2OH$, $CH(OH)CH(CH_3)_2$, $C(CH_3)_2CH_2OH$, $OCH_2CH_2CH(CH_3)_2$, $OCH_2CH_3$, $OCH(CH_3)_2$, $OCH_2CH_2OCH_3$,

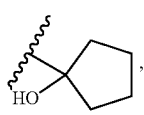, $SO_2CH_3$, $SO_2tBu$, $SO_2CH_2CH_3$, $SO_2CH_2CH(CH_3)_2$, $SO_2CH(CH_3)_2$,

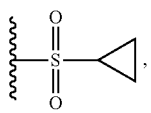 [SMILES: *S(=O)(=O)C1CC1], $SO_2NH(CH_3)$, $SO_2NH(CH(CH_2)_2)$, $SO_2NH(CH_2CH_3)$, $SO_2NH(CH(CH_3)_2)$, $SO_2N(CH_3)_2$,

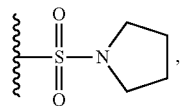,

OPh, Ph,

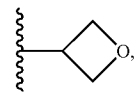, $OCH_2CH_2OCH_3$, $CH(CH_3)_2$, $SO_2N(CH_2CH_2CH_3)_2$, $CH_2CH_2CH_2CH_3$, $CH_2CH_2CH_3$, $OCH_2CH_2CH_2CH_3$, $CH_2OPh$,

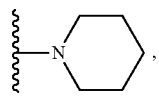, $OCH_2Ph$, $CH_2CH_2CH_2CH_3$, $OCH_2CH_3$, $OCH_2CH(CH_3)_2$, $CH_2Ph$,

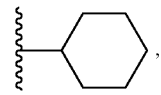, $CCCH_2OCH_3$, $SO_2CHF_2$, $OCF_3$,

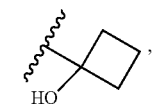 [SMILES: *C1(O)CCC1], $OCHF_2$,

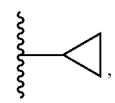, $CH_2CH(CH_3)_2$, $OCH_2tBu$,

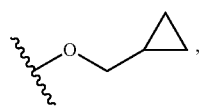 [SMILES: *OCC1CC1], $OCH_2CF_3$,

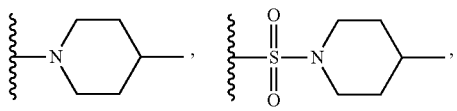, $CH_2OCH_2CH_2CF_3$, $CH_2OCH_2CF_3$, $SO_2CF_3$, $C(CH_3)_2CH_2CH_3$, $C(CH_2CH_3)_3$, $CH(OCH_2CF_3)_2$,

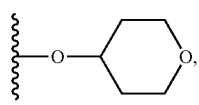, $CF_3$, $OCH_2C(CH_3)_2F$,

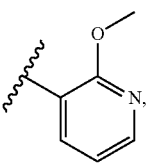 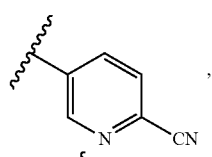

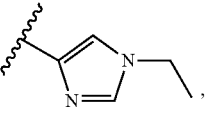 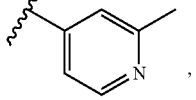

-continued

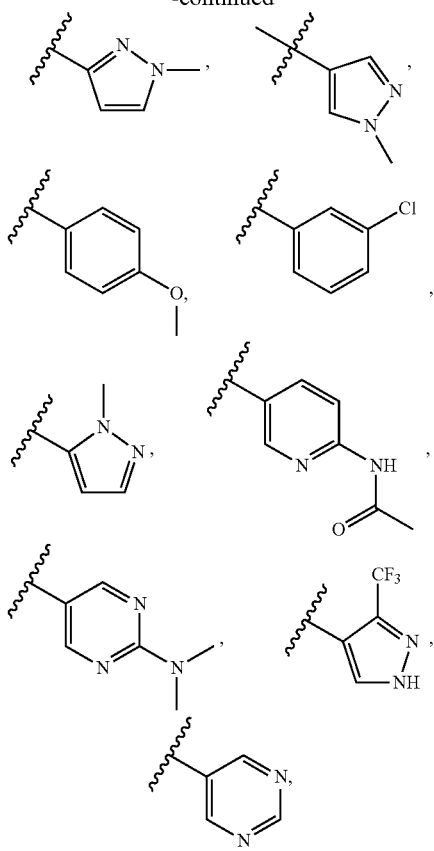

CH(OH)CH₂OCH₂CF₃, CH(OCH₂CF₃)CH₂OH, OSO₂CF₃,

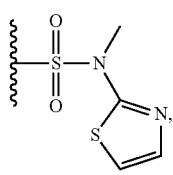

or OCH₂CH₂OCF₃.

In another embodiment, the invention features a compound of formula IA and the attendant definitions, wherein R² is H, CF₃, COCF₃, COtBu, Cl, COCH₃, CF₂CF₃, CH₂CF₃ or CN; R³ is H, CH₂CH₂OCH₃, benzyl, CH₃, CH₂CH₃, CH₂CH(CH₂)₂, cyclobutyl, COCH₃, CO₂CH₃, COH, CH(CH₂)₂, CH₂CF₃, CH₂CHF₂, CO₂CH₂CH₃, CON(CH₃)₂, or CONHCH₃; R⁶ is CH₃, OCH₃, OCH₂CH₃, OCH₂CH₂CH₂CH₃, CH₂OH, F, or Cl; and R⁷ is F, CH₂CH₃, tBu, OH, OCH₃, OCH₂CH₂CH₂CH₃, OtBu, OCH(CH₃)(CH₂CH₃), OCH₂CH₂OH, OCH₂CH₂CH₂OH, OCH₂C(CH₃)₂OH, C(CH₃)₂OH, C(=CH₂)CH₃, OC(=CH₂)CH₃, CH₂OH, C(CH₃)₂CH₂OH,

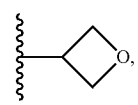

OCH₂CH₂CH(CH₃)₂, OCH₂CH₂CH₃, OCH(CH₃)₂, OCH₂CH₂OCH₃, SO₂CH₃, SO₂CH₂CH₃, SO₂CH(CH₃)₂,

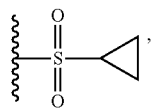

SO₂NH(CH₃), SO₂NH(CH(CH₂)₂), SO₂NH(CH₂CH₃), SO₂NH(CH(CH₃)₂), SO₂N(CH₃)₂, or OCH₂CH₂OCF₃.

In another embodiment, the invention features a compound of formula IA and the attendant definitions, wherein the

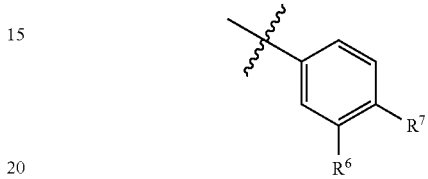

moiety is selected from:

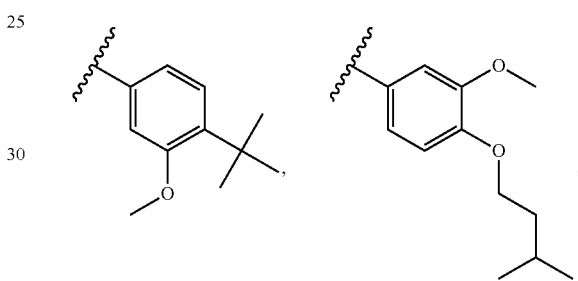

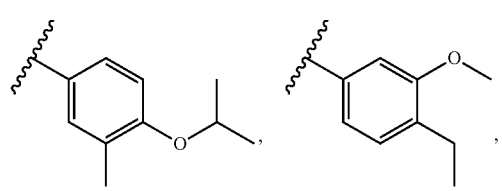

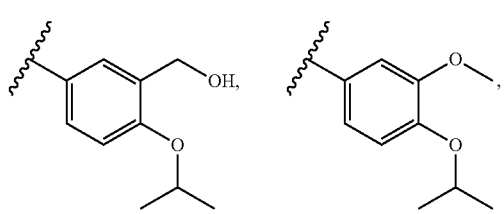

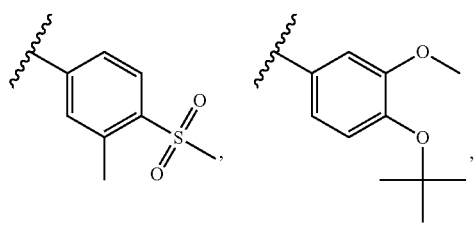

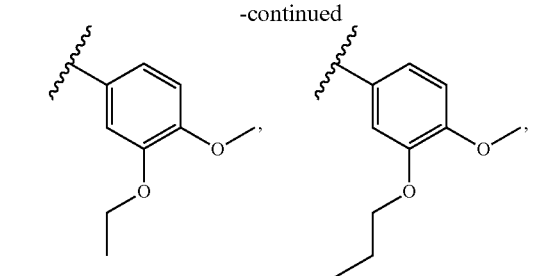 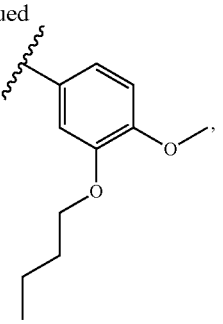 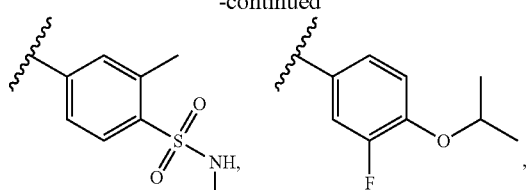 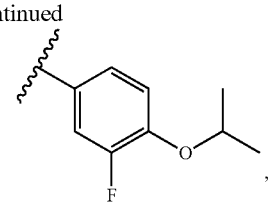
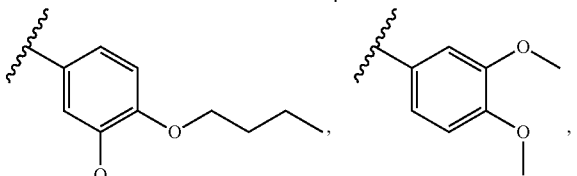 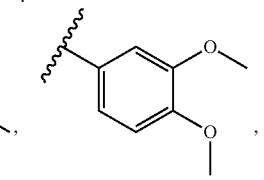 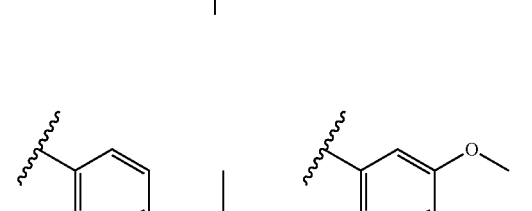 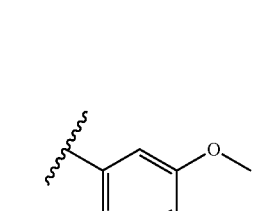
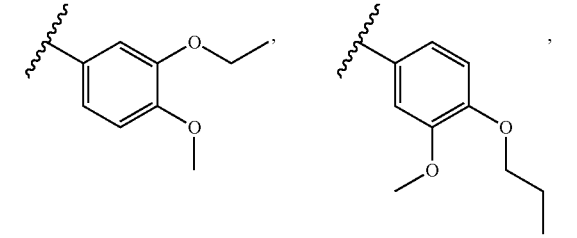 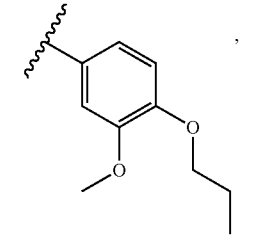 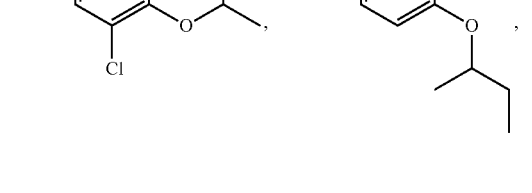 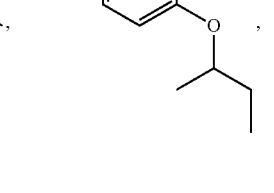
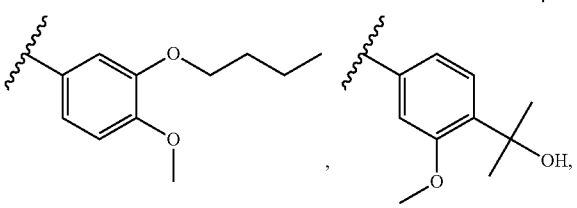 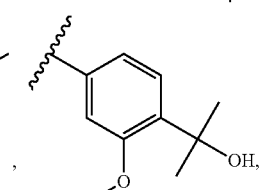 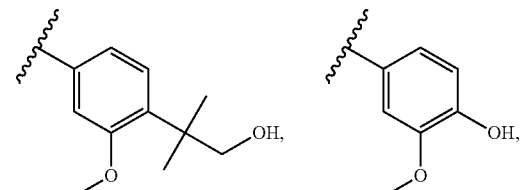 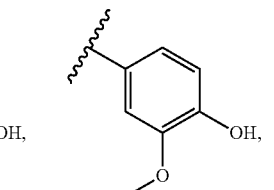
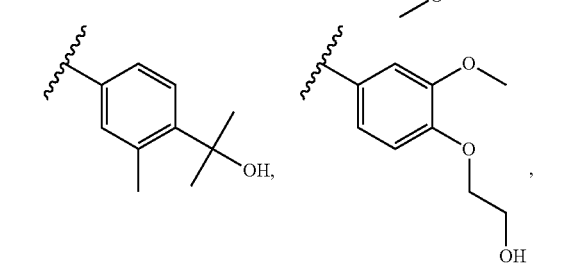 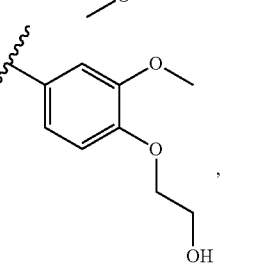 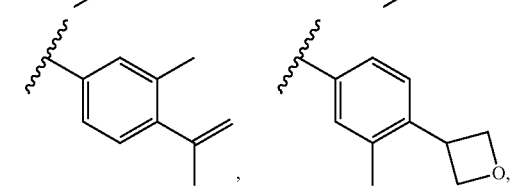 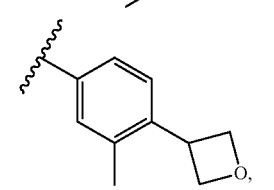
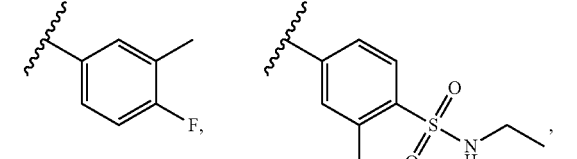 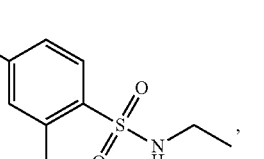 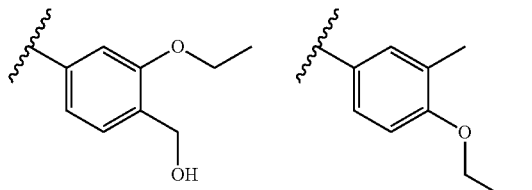 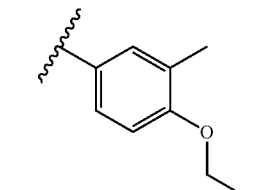
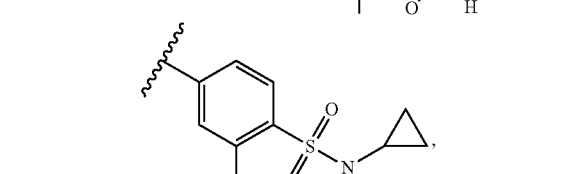 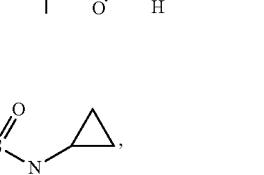 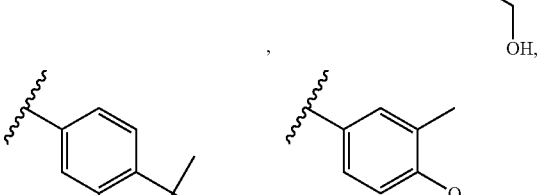 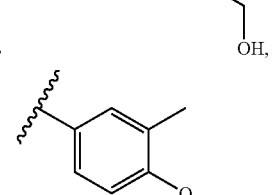
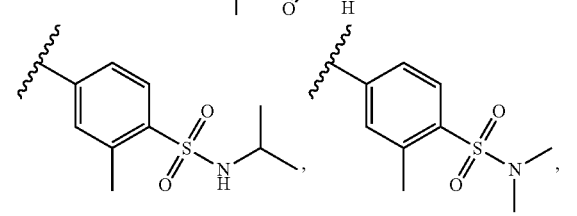 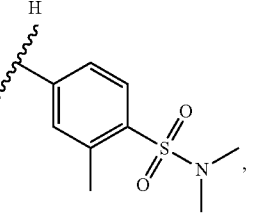 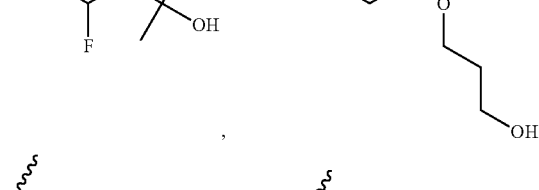 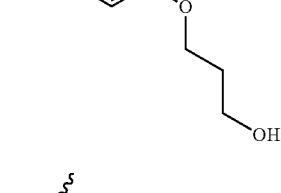
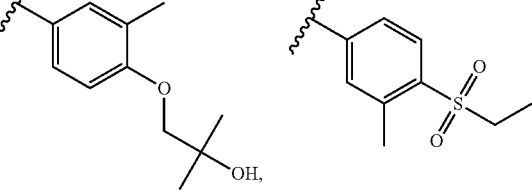 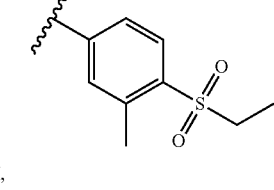

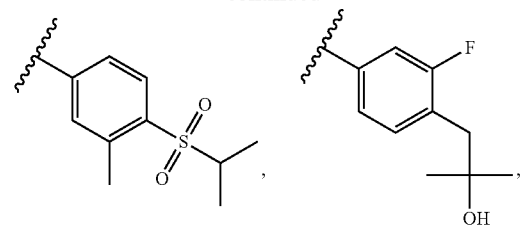
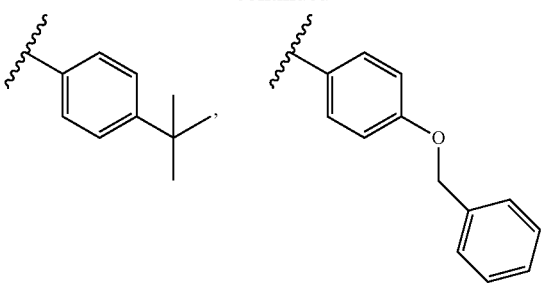
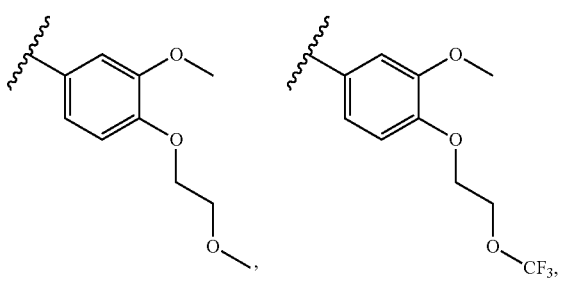
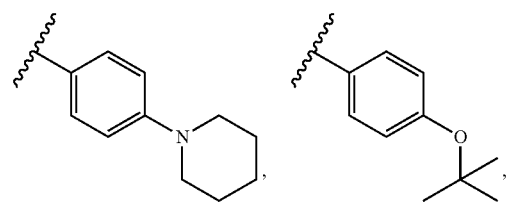
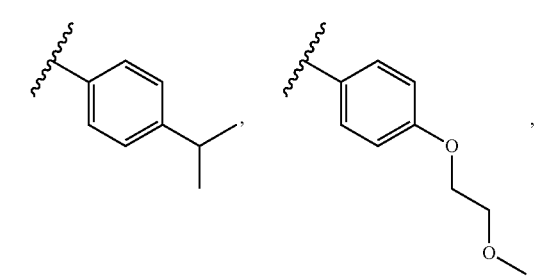
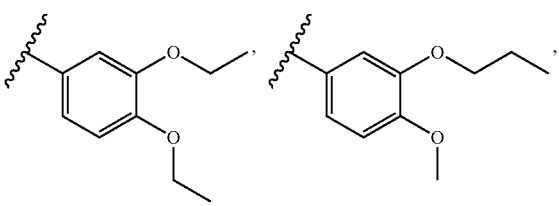
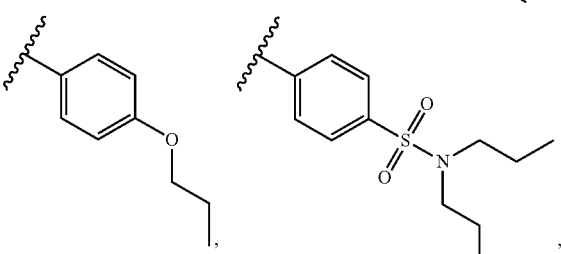
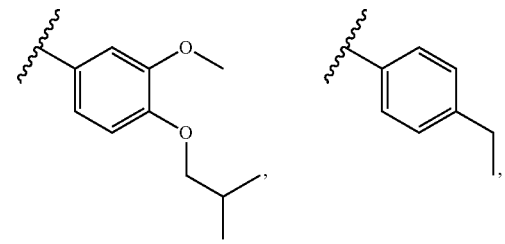
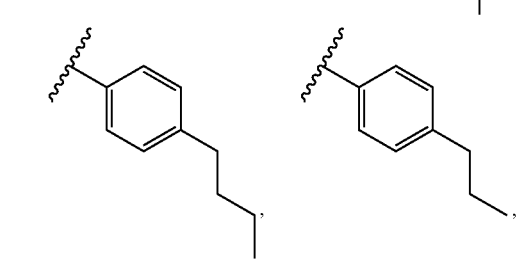
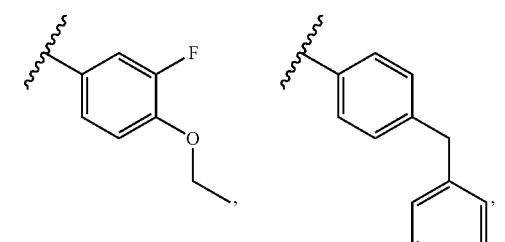
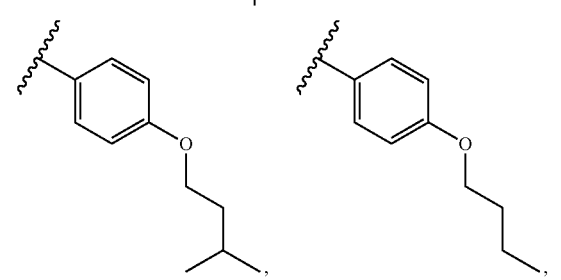
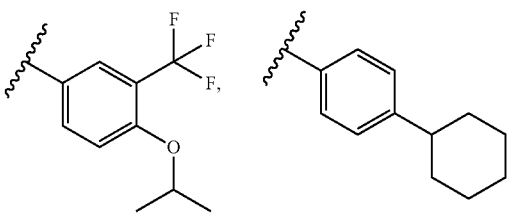

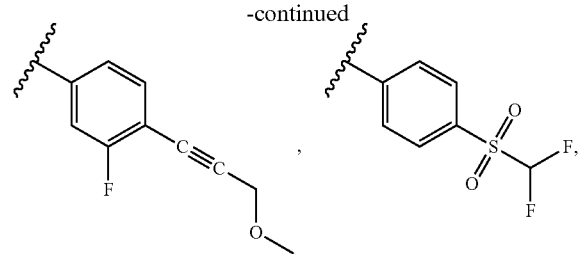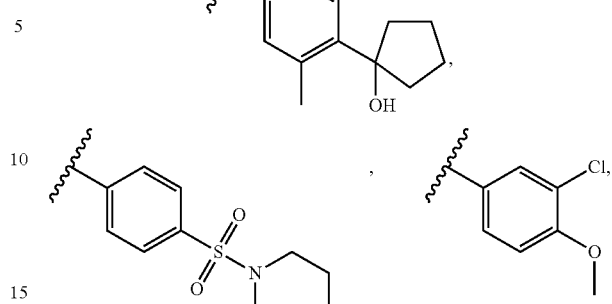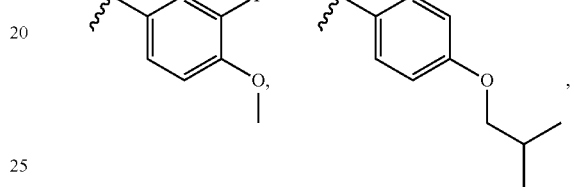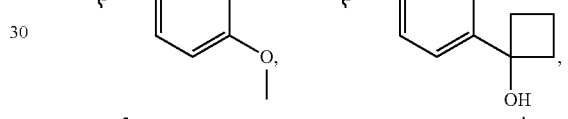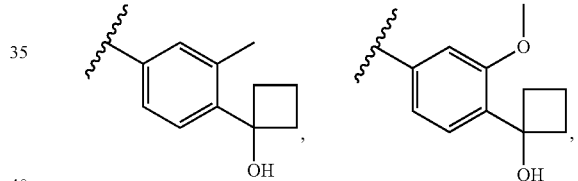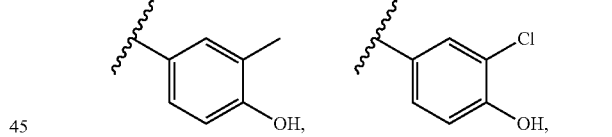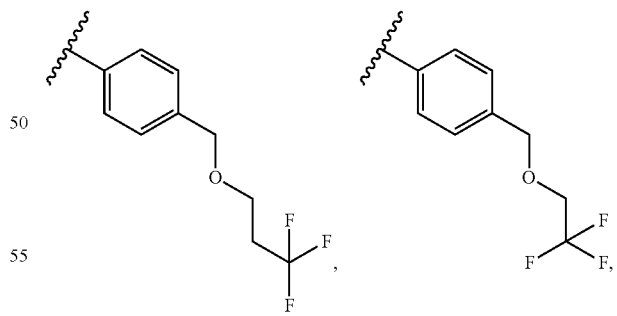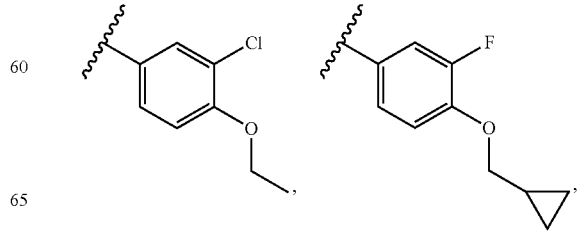

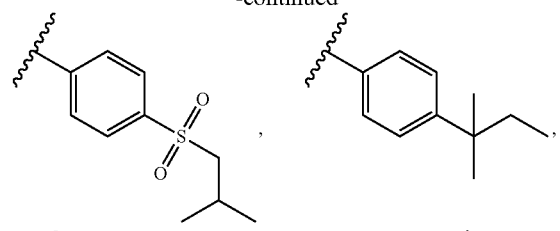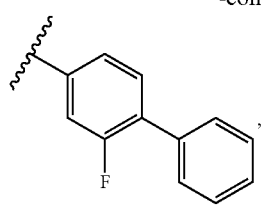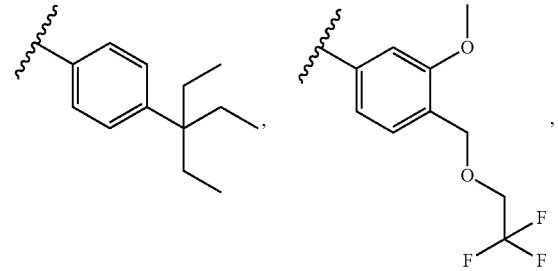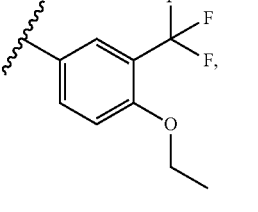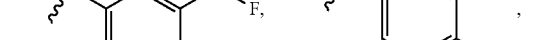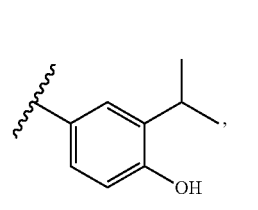

-continued
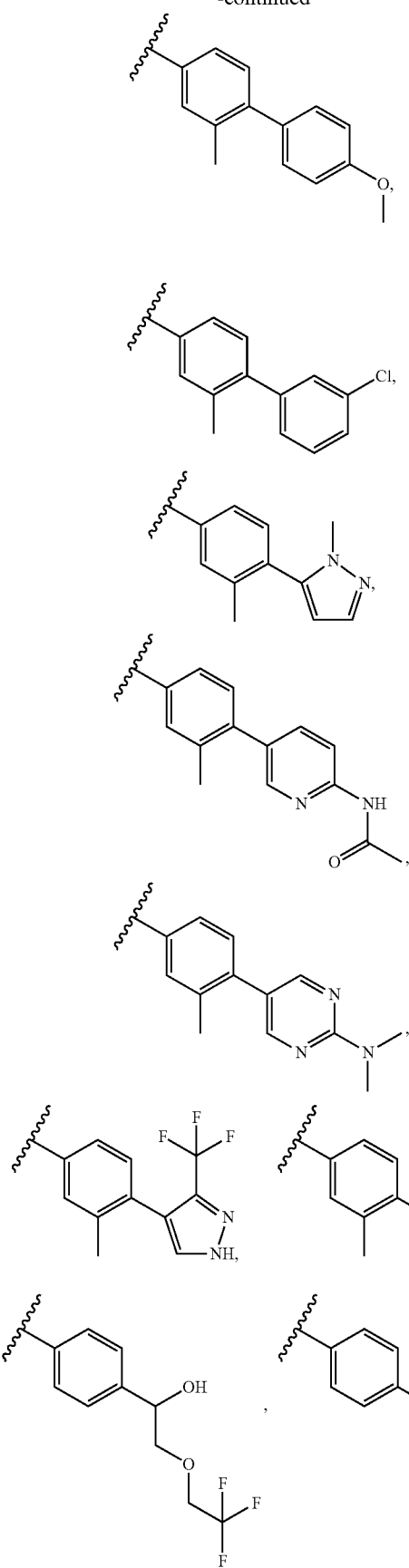
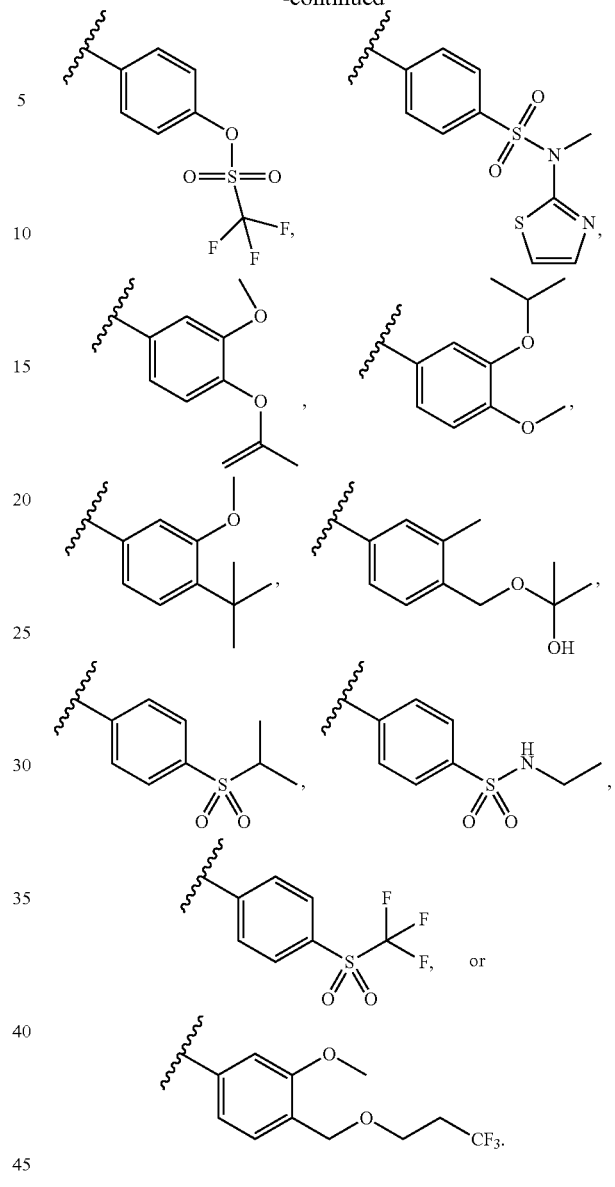
In another embodiment, the invention features a compound of formula I, wherein the compound is selected from Table 1:
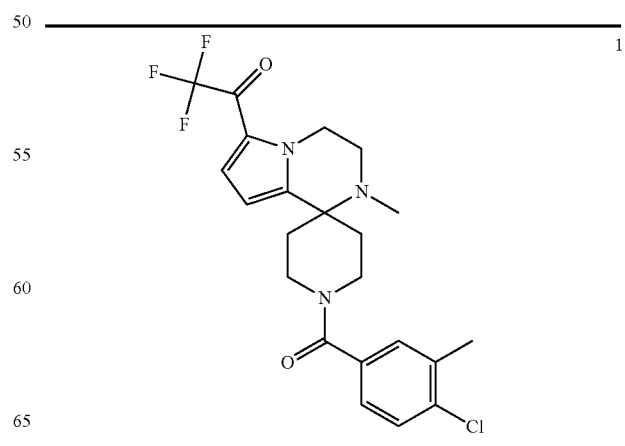

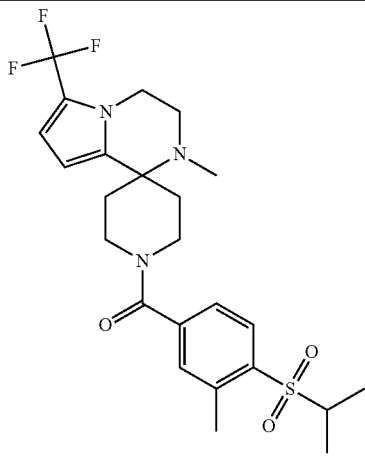
2
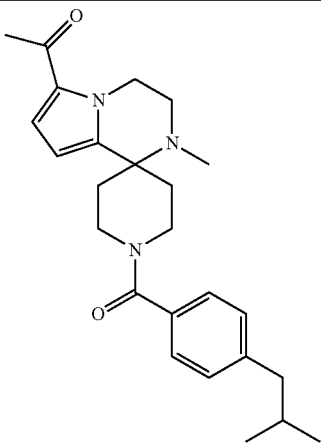
5
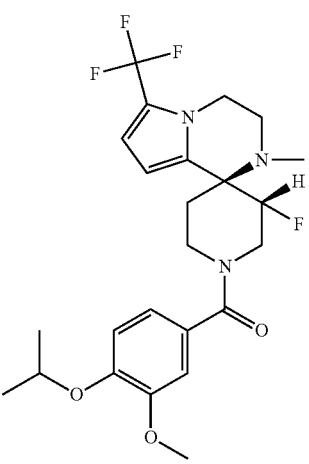 [SMILES: COc1cc(C(=O)N2CC[C@]3(c4ccc(C(F)(F)F)n4CCN3C)[C@H](F)C2)ccc1OC(C)C]
3
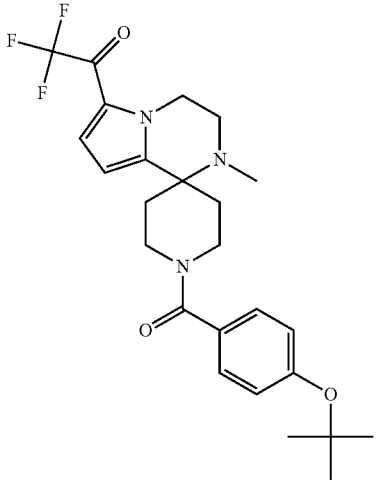
6
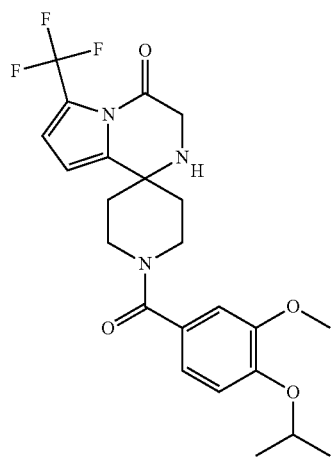
4
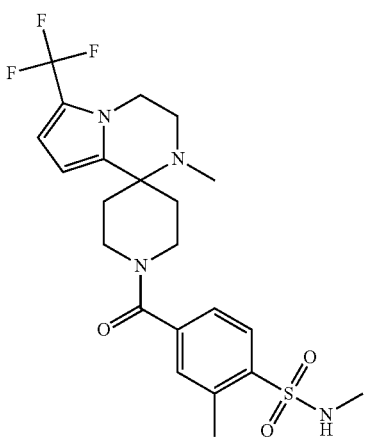
7

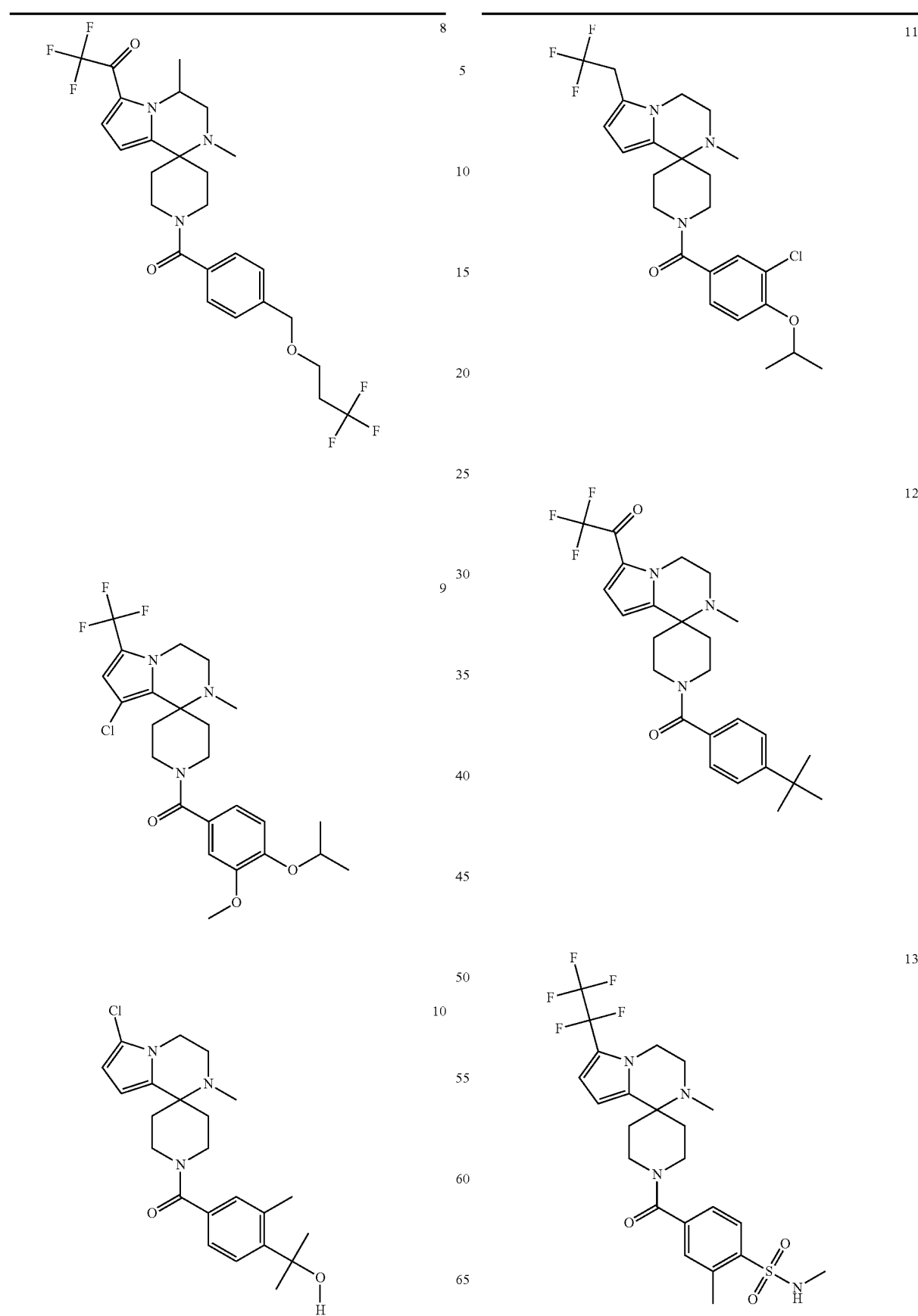

-continued
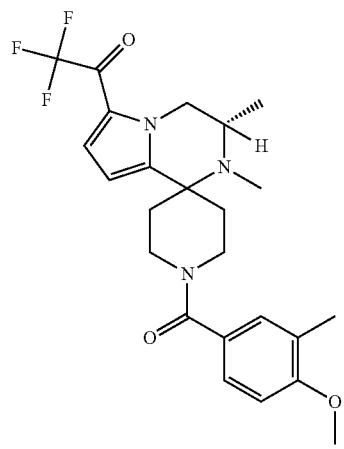 [SMILES: COc1ccc(C(=O)N2CCC3(CC2)c2ccc(C(=O)C(F)(F)F)n2C[C@H](C)N3C)cc1C]
14
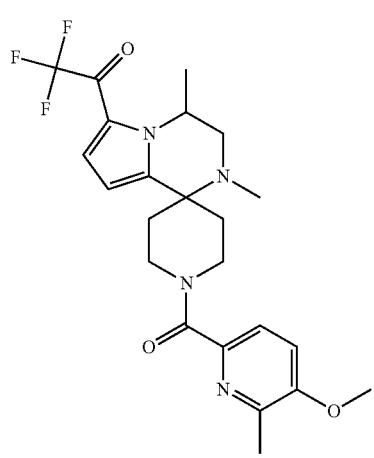 [SMILES: COc1ccc(C(=O)N2CCC3(CC2)c2ccc(C(=O)C(F)(F)F)n2C(C)CN3C)nc1C]
15
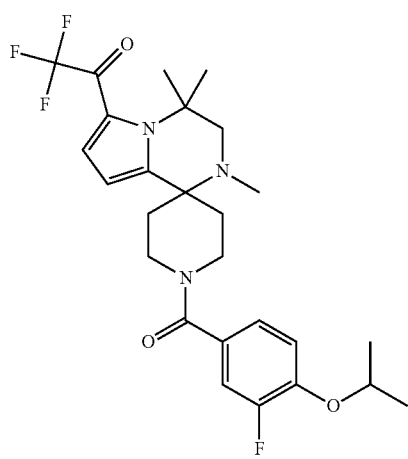 [SMILES: CC(C)Oc1ccc(C(=O)N2CCC3(CC2)c2ccc(C(=O)C(F)(F)F)n2C(C)(C)CN3C)cc1F]
16
-continued
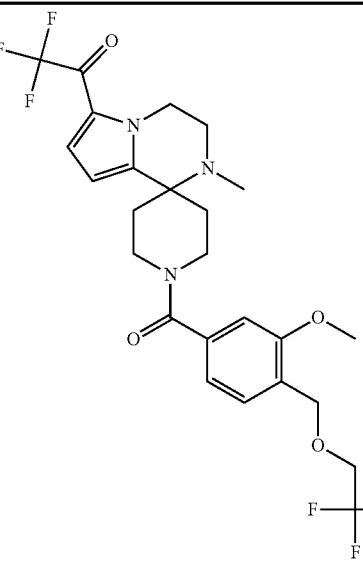
17
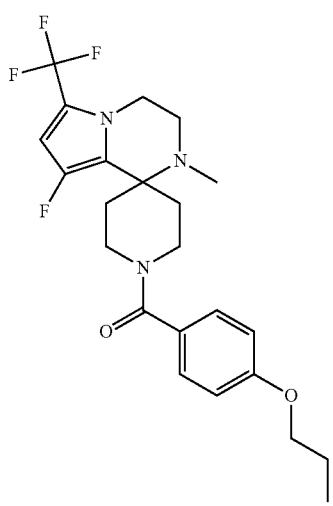 [SMILES: CCCOc1ccc(C(=O)N2CCC3(CC2)c2c(F)cc(C(F)(F)F)n2CCN3C)cc1]
18
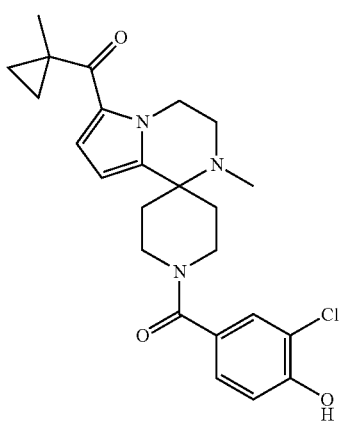 [SMILES: CN1CCn2c(C(=O)C3(C)CC3)ccc2C12CCN(C(=O)c1ccc(O)c(Cl)c1)CC2]
19

-continued
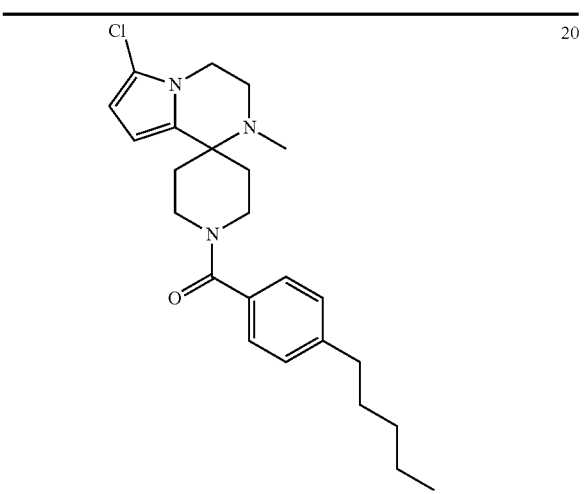
20
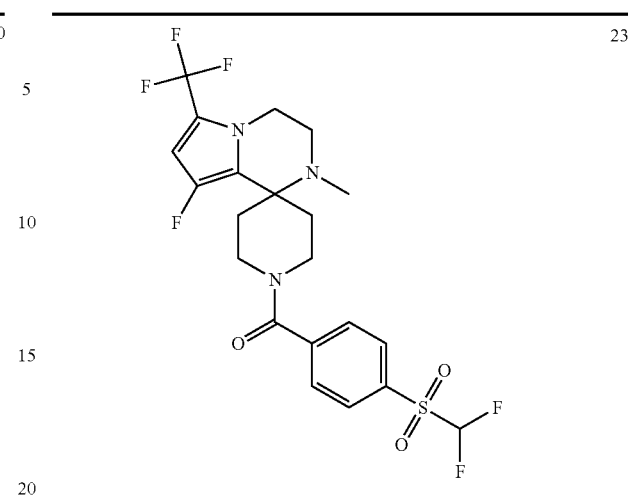
23
-continued
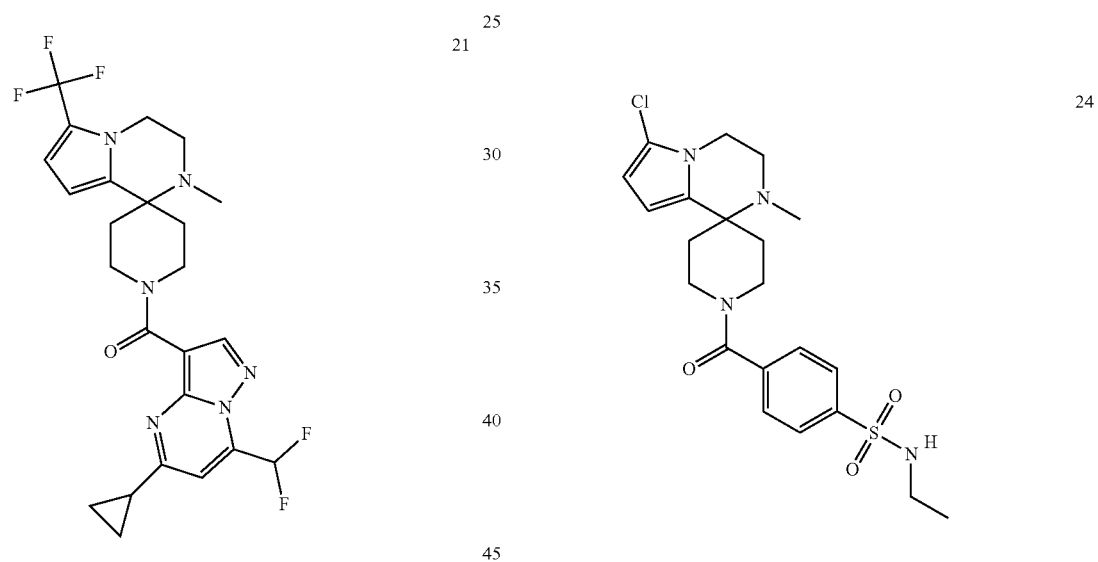
21
24
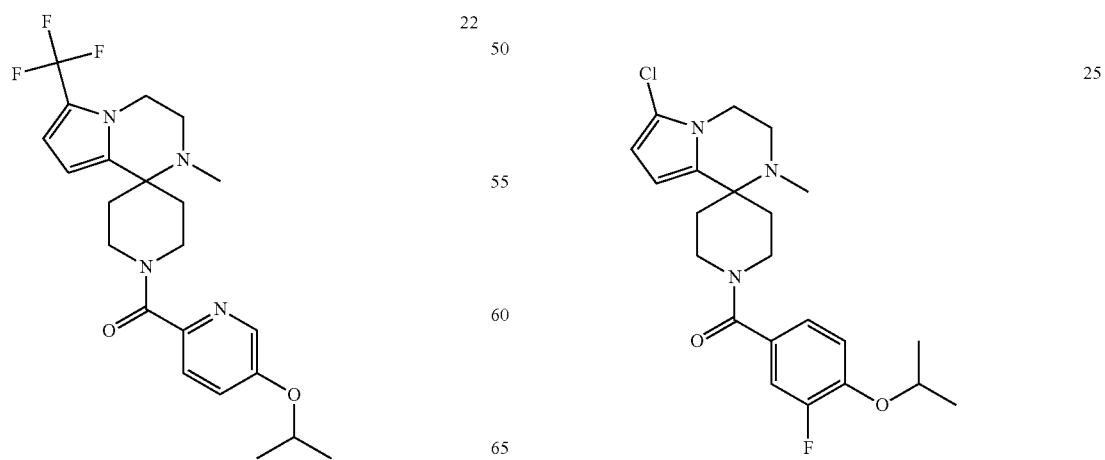
22
25

-continued
26
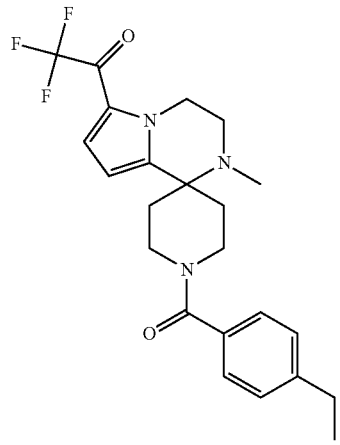 [SMILES: CCc1ccc(C(=O)N2CCC3(CC2)c2ccc(C(=O)C(F)(F)F)n2CCN3C)cc1]
27
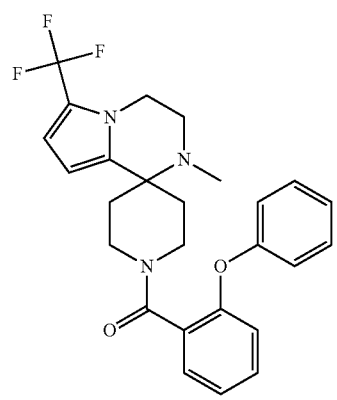 [SMILES: CN1CCn2c(C(F)(F)F)ccc2C12CCN(C(=O)c1ccccc1Oc1ccccc1)CC2]
28
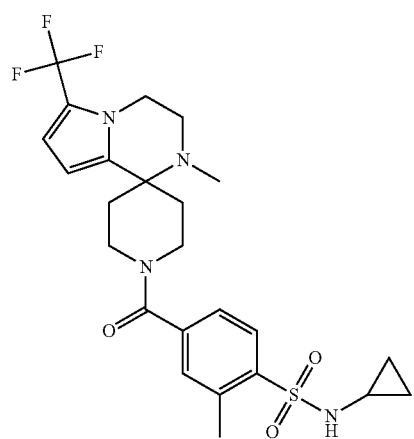
-continued
29
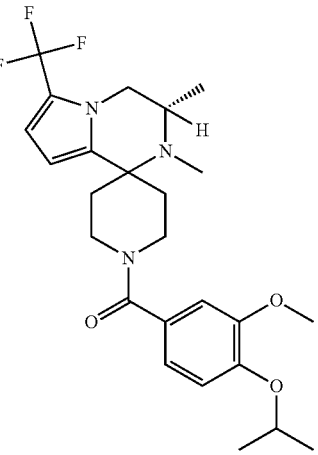
30
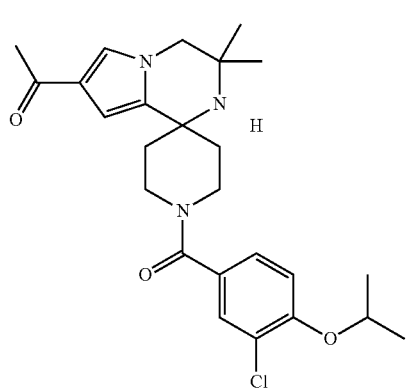
31
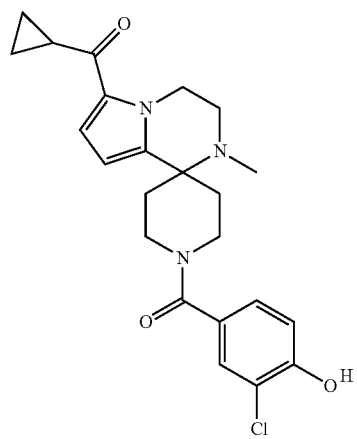

| 32 | 35 |
|---|---|
| 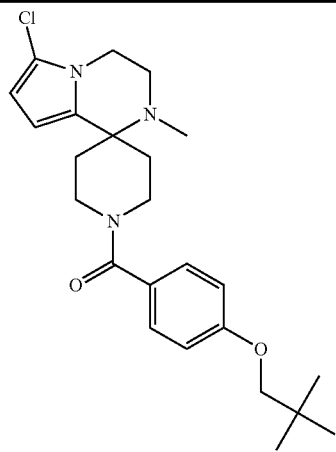 | 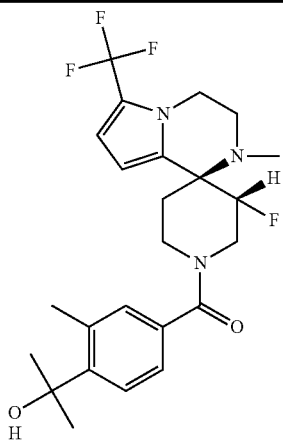 |
| 33 | 36 |
| 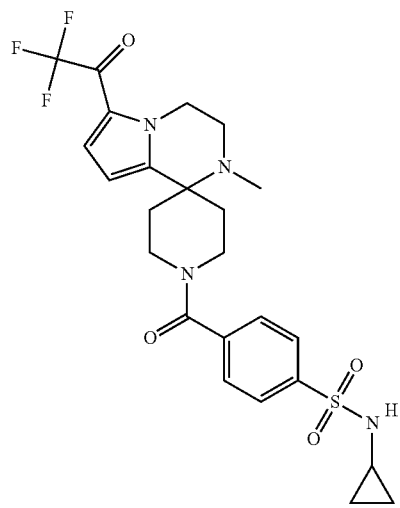 | 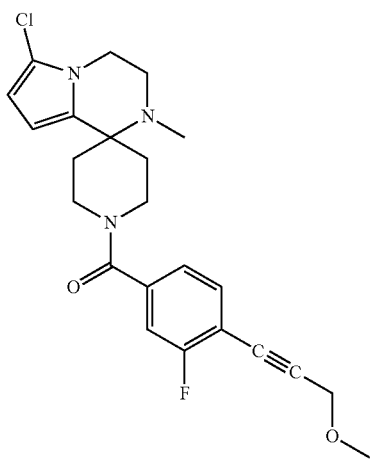 [SMILES: COCC#Cc1ccc(C(=O)N2CCC3(CC2)c2ccc(Cl)n2CCN3C)cc1F] |
| 34 | 37 |
| 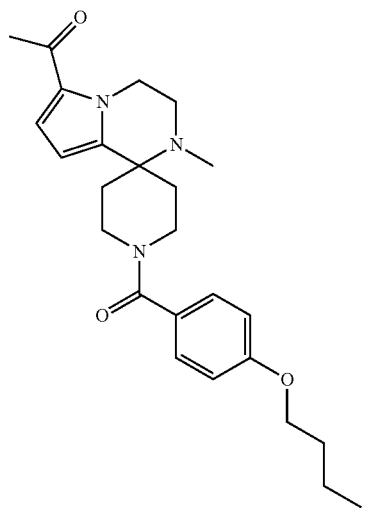 | 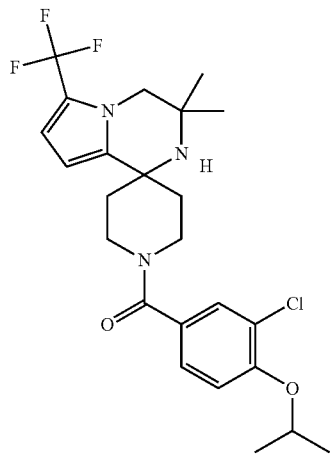 |

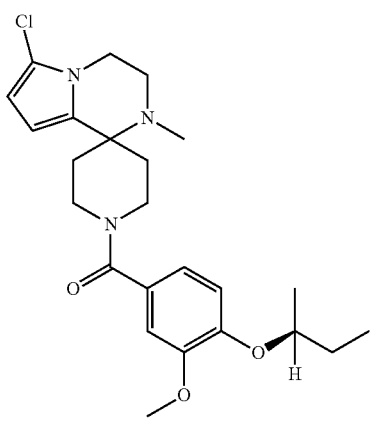 [SMILES: CC[C@H](C)Oc1ccc(C(=O)N2CCC3(CC2)c2ccc(Cl)n2CCN3C)cc1OC]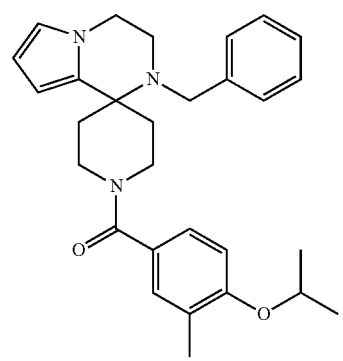 [SMILES: Cc1cc(C(=O)N2CCC3(CC2)c2cccn2CCN3Cc2ccccc2)ccc1OC(C)C]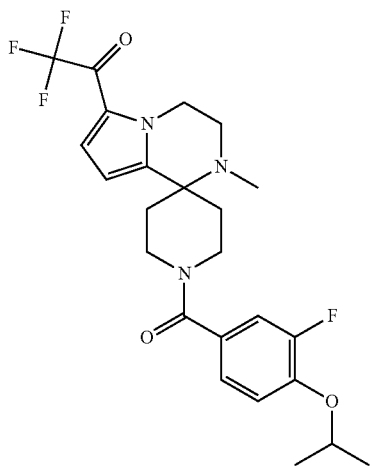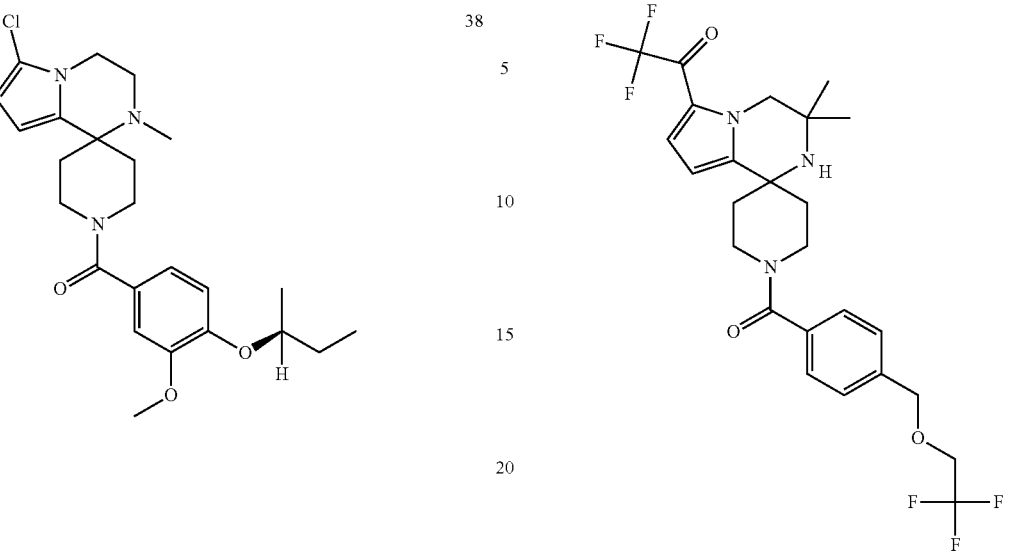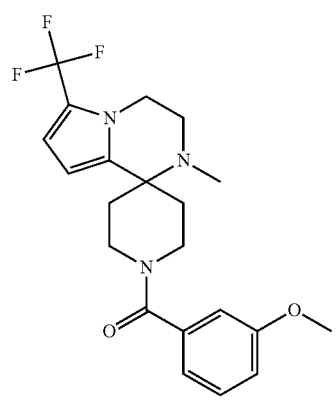 [SMILES: COc1cccc(C(=O)N2CCC3(CC2)c2ccc(C(F)(F)F)n2CCN3C)c1]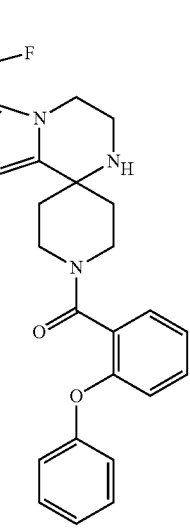

| 59 -continued | 60 -continued |
|---|---|
| 44 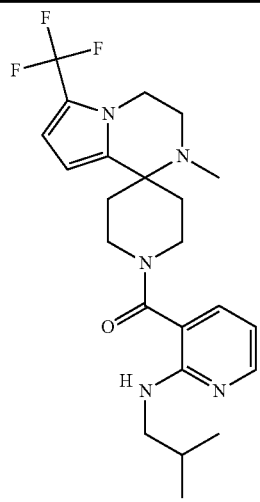 | 47 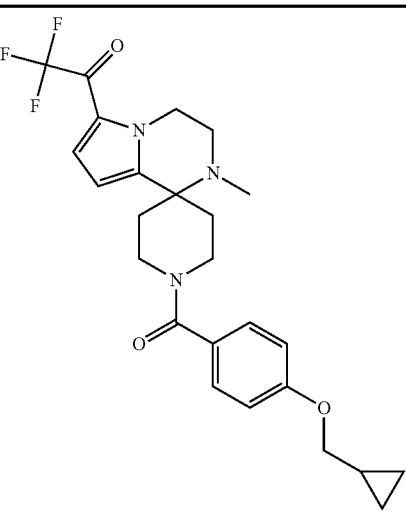 |
| 45 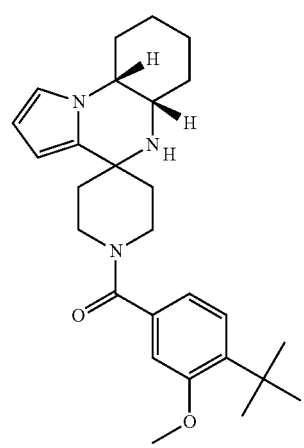 | 48 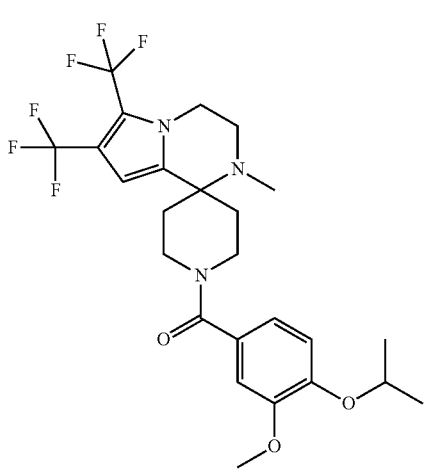 |
| 46 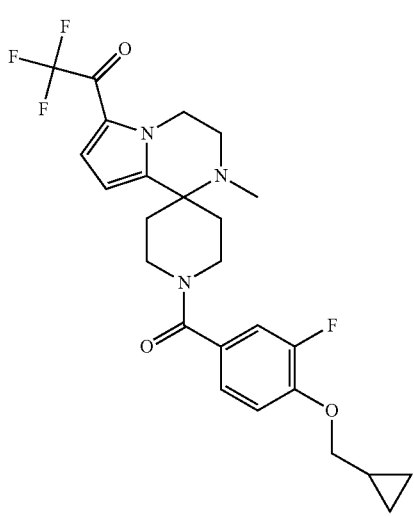 [SMILES: CN1CCn2c(C(=O)C(F)(F)F)ccc2C12CCN(C(=O)c1ccc(OCC3CC3)c(F)c1)CC2] | 49 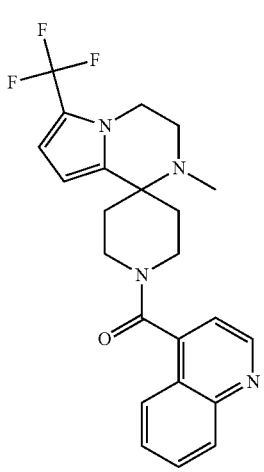 [SMILES: CN1CCn2c(C(F)(F)F)ccc2C12CCN(C(=O)c1ccnc3ccccc13)CC2] |

| 61 -continued | 62 -continued |
|---|---|
| 50 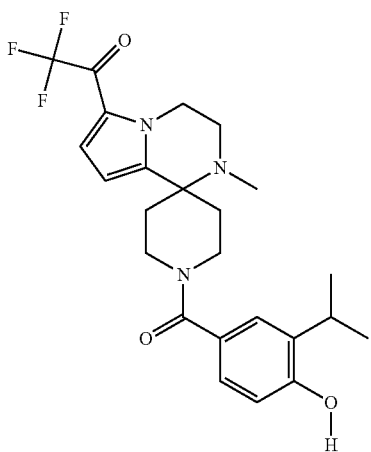 [SMILES: CC(C)c1cc(C(=O)N2CCC3(CC2)c2ccc(C(=O)C(F)(F)F)n2CCN3C)ccc1O] | 53 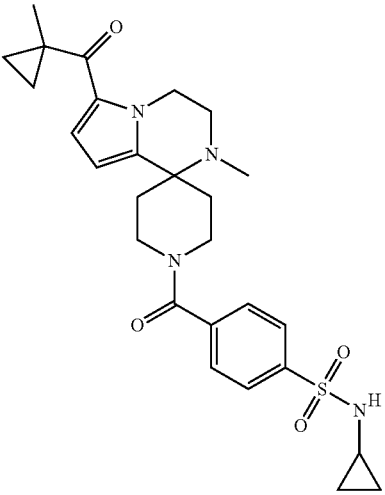 |
| 51 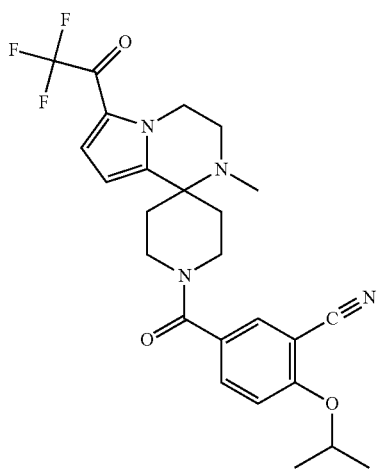 [SMILES: CC(C)Oc1ccc(C(=O)N2CCC3(CC2)c2ccc(C(=O)C(F)(F)F)n2CCN3C)cc1C#N] | 54 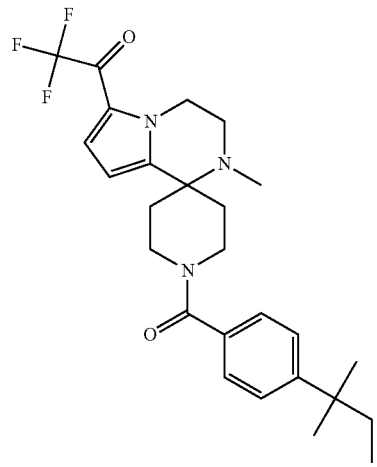 |
| 52 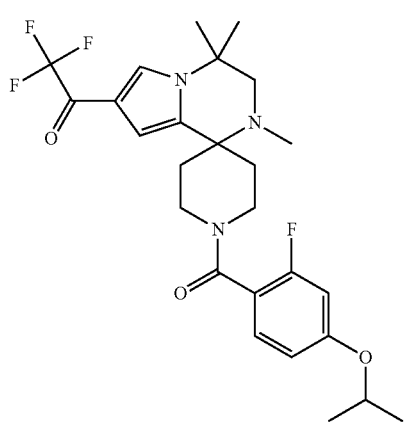 [SMILES: CC(C)Oc1ccc(C(=O)N2CCC3(CC2)c2cc(C(=O)C(F)(F)F)cn2C(C)(C)CN3C)c(F)c1] | 55 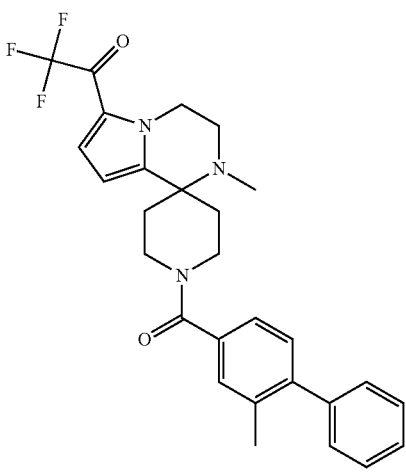 |

| 56 | 59 |
|---|---|
| 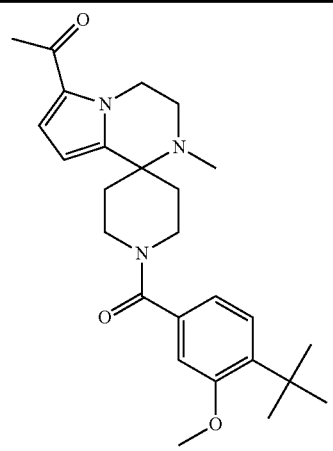 | 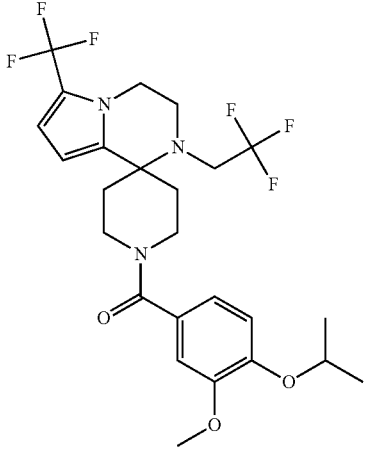 |
| 57 | 60 |
| 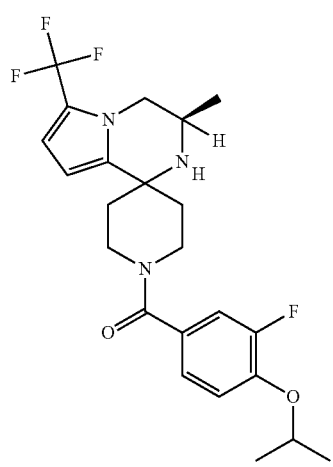 | 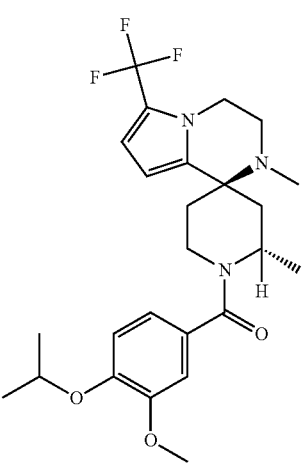 |
| 58 | 61 |
| 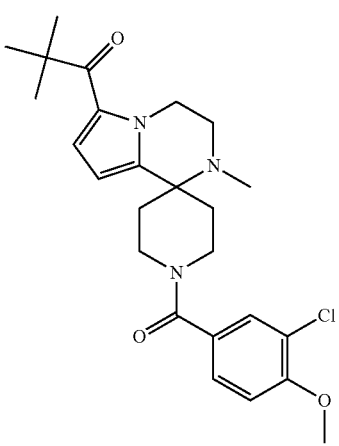 [SMILES: COc1ccc(C(=O)N2CCC3(CC2)c2ccc(C(=O)C(C)(C)C)n2CCN3C)cc1Cl] | 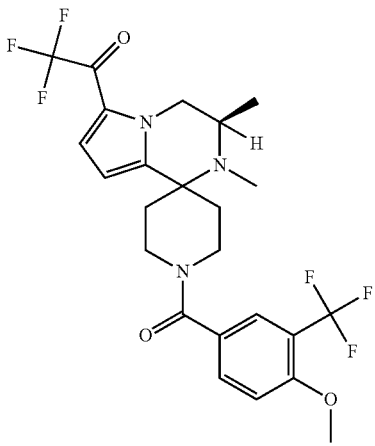 [SMILES: COc1ccc(C(=O)N2CCC3(CC2)c2ccc(C(=O)C(F)(F)F)n2C[C@@H](C)N3C)cc1C(F)(F)F] |

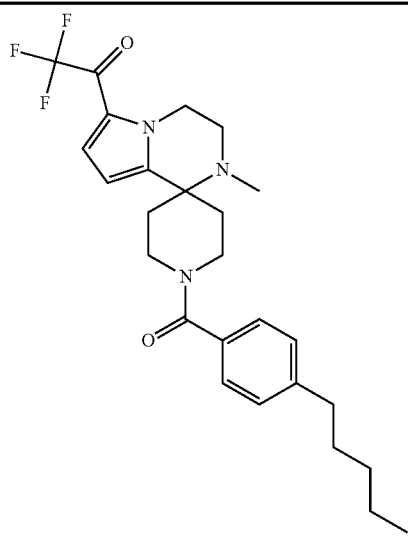
62
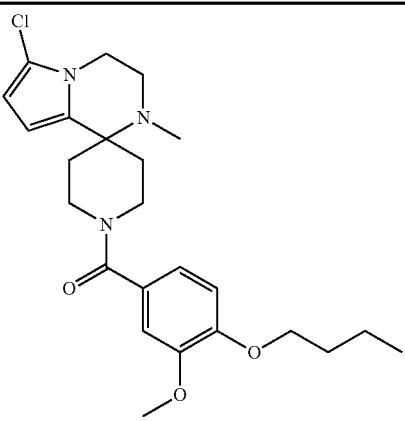
65
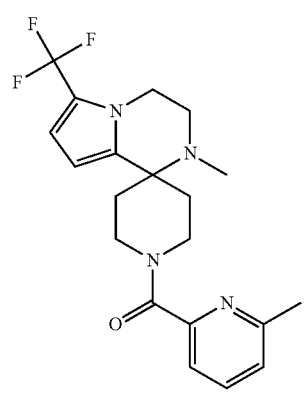
63
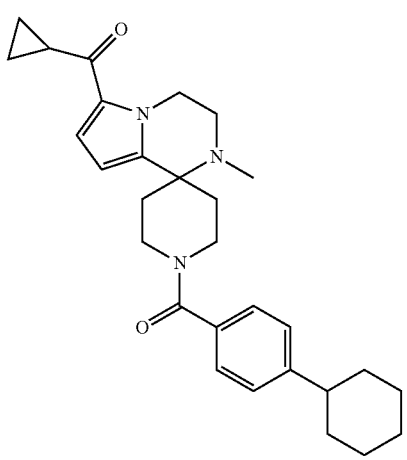
66
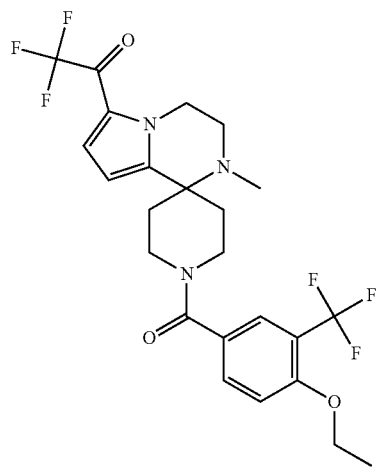 [SMILES: CCOc1ccc(C(=O)N2CCC3(CC2)c2ccc(C(=O)C(F)(F)F)n2CCN3C)cc1C(F)(F)F]
64
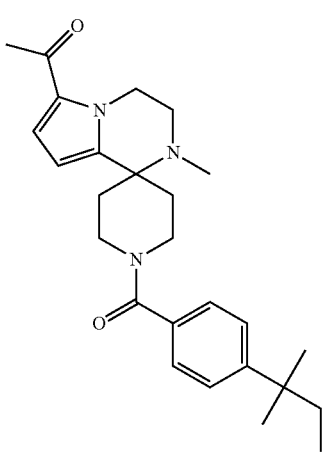 [SMILES: CCC(C)(C)c1ccc(C(=O)N2CCC3(CC2)c2ccc(C(C)=O)n2CCN3C)cc1]
67

-continued
68
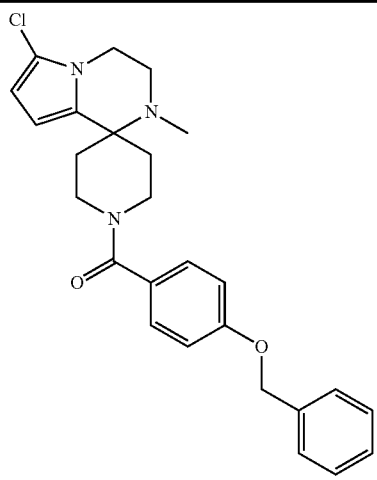
69
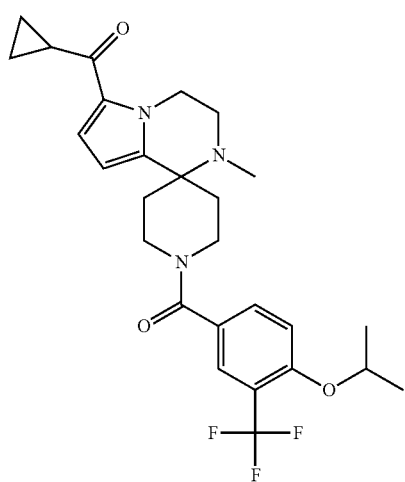 [SMILES: CC(C)Oc1ccc(C(=O)N2CCC3(CC2)c2ccc(C(=O)C4CC4)n2CCN3C)cc1C(F)(F)F]
70
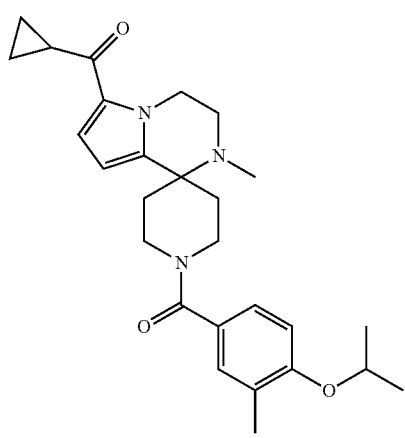 [SMILES: Cc1cc(C(=O)N2CCC3(CC2)c2ccc(C(=O)C4CC4)n2CCN3C)ccc1OC(C)C]
-continued
71
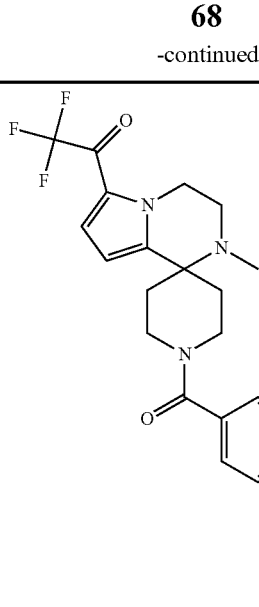
72
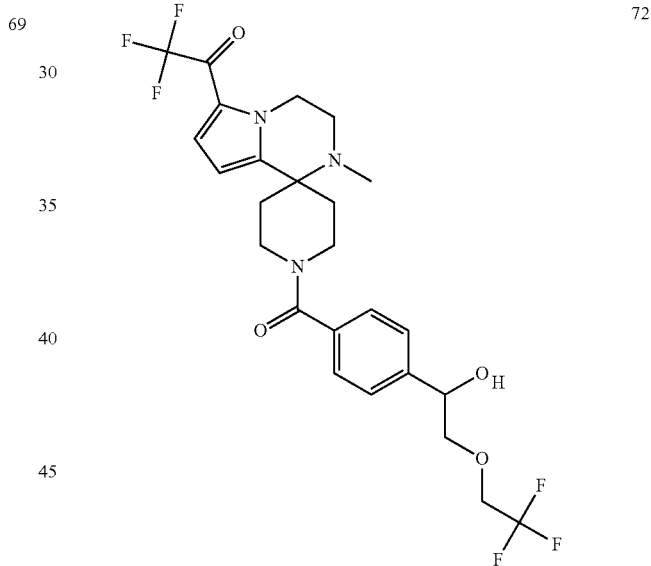
73
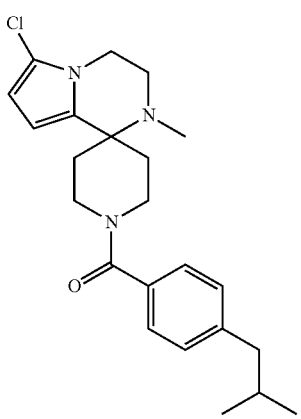 [SMILES: CC(C)Cc1ccc(C(=O)N2CCC3(CC2)c2ccc(Cl)n2CCN3C)cc1]

| 74 | 77 |
|---|---|
| 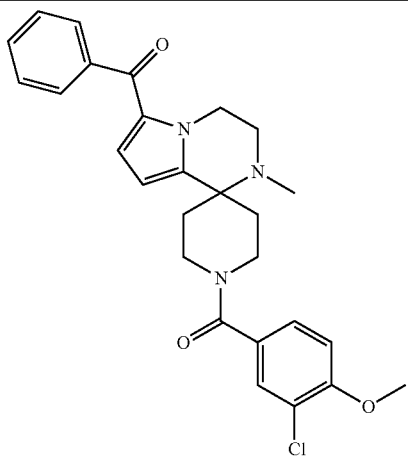 | 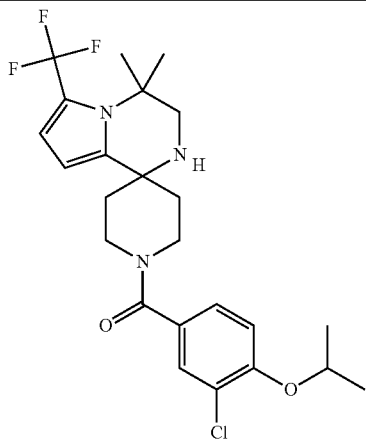 |
| 75 | 78 |
| 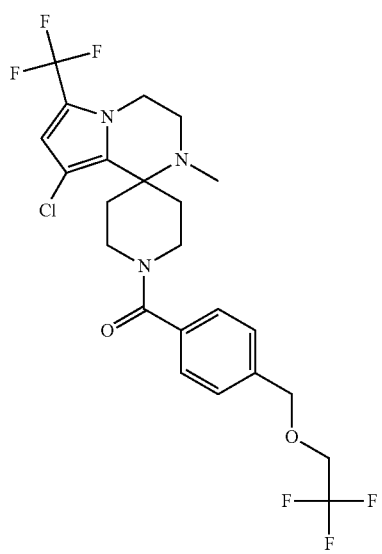 [SMILES: CN1CCn2c(C(F)(F)F)cc(Cl)c2C12CCN(C(=O)c1ccc(COCC(F)(F)F)cc1)CC2] | 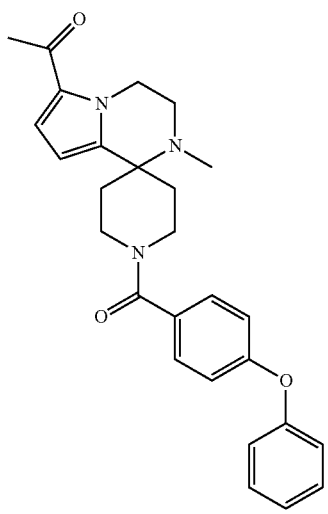 |
| 76 | 79 |
| 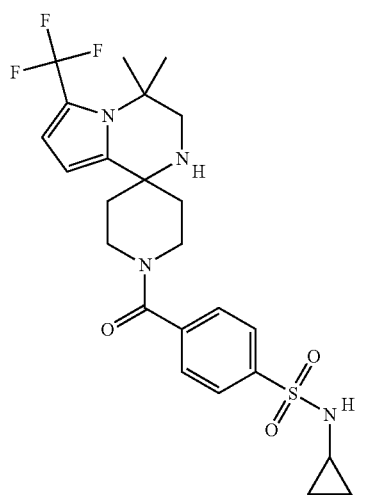 | 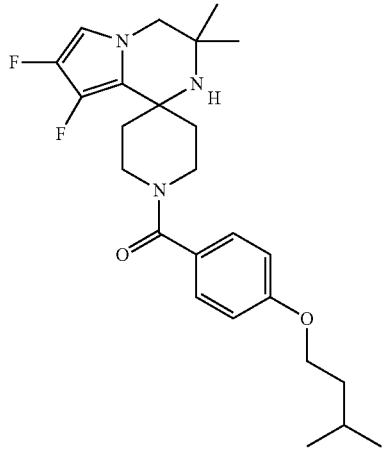 |

| 80 | 83 |
|---|---|
| 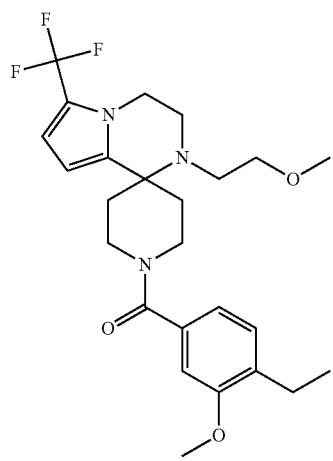 [SMILES: CCc1ccc(C(=O)N2CCC3(CC2)c2ccc(C(F)(F)F)n2CCN3CCOC)cc1OC] | 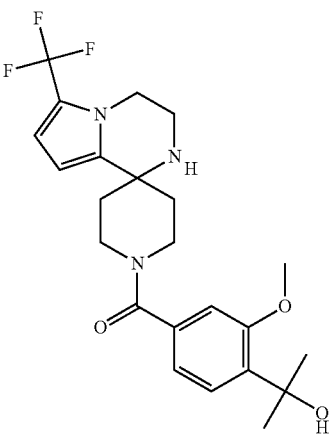 |
| 81 | 84 |
| 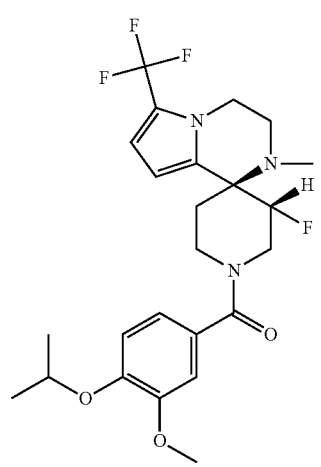 [SMILES: COc1cc(C(=O)N2CC[C@]3(c4ccc(C(F)(F)F)n4CCN3C)[C@H](F)C2)ccc1OC(C)C] | 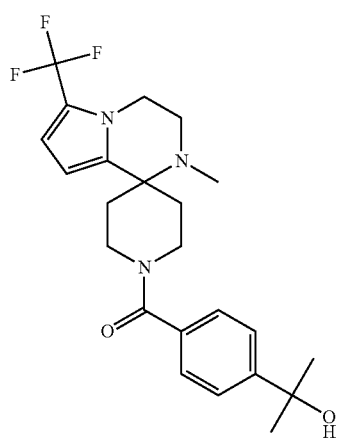 |
| 82 | 85 |
| 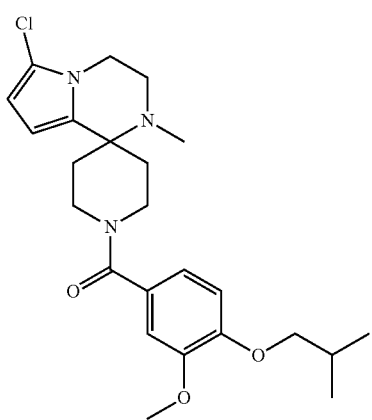 [SMILES: COc1cc(C(=O)N2CCC3(CC2)c2ccc(Cl)n2CCN3C)ccc1OCC(C)C] | 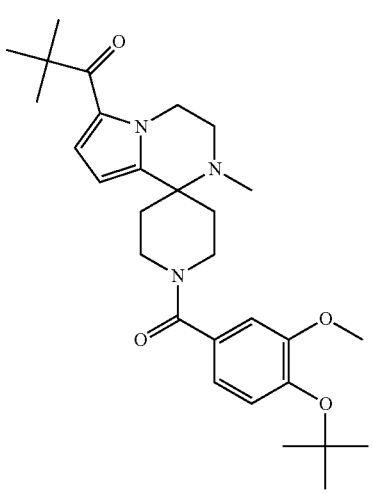 [SMILES: COc1cc(C(=O)N2CCC3(CC2)c2ccc(C(=O)C(C)(C)C)n2CCN3C)ccc1OC(C)(C)C] |

86 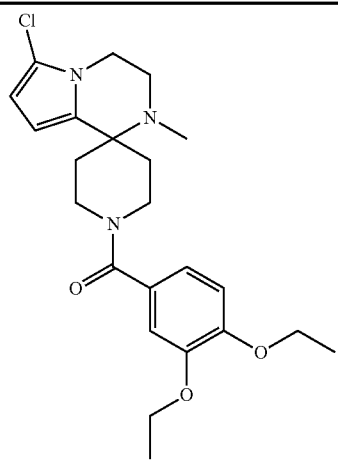
87 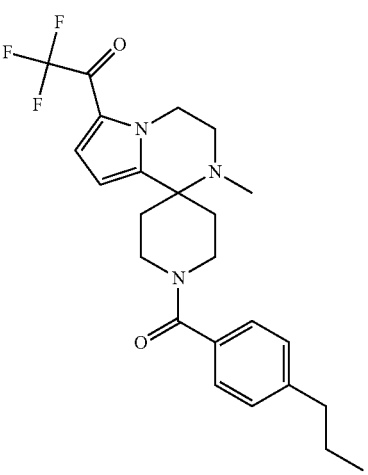 [SMILES: CCCc1ccc(C(=O)N2CCC3(CC2)c2ccc(C(=O)C(F)(F)F)n2CCN3C)cc1]
88 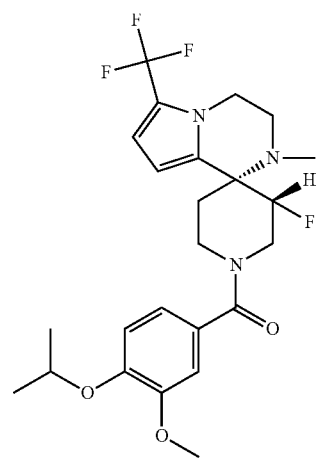 [SMILES: COc1cc(C(=O)N2CC[C@@]3(c4ccc(C(F)(F)F)n4CCN3C)[C@H](F)C2)ccc1OC(C)C]
89 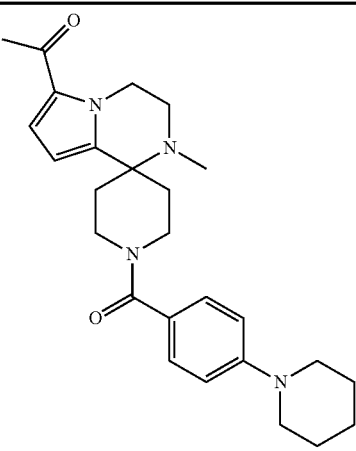
90 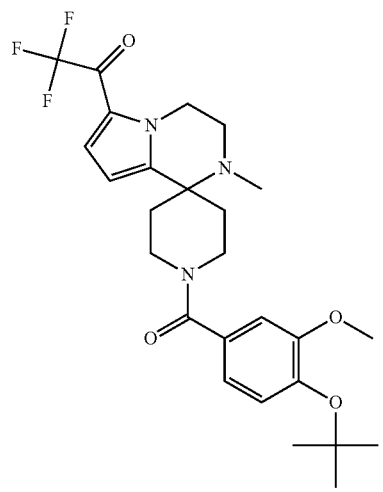 [SMILES: COc1cc(C(=O)N2CCC3(CC2)c2ccc(C(=O)C(F)(F)F)n2CCN3C)ccc1OC(C)(C)C]
91 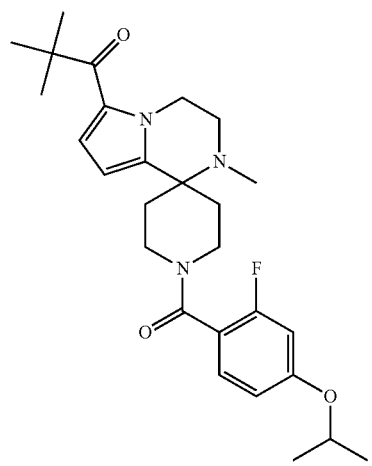 [SMILES: CC(C)Oc1ccc(C(=O)N2CCC3(CC2)c2ccc(C(=O)C(C)(C)C)n2CCN3C)c(F)c1]

| 75 -continued | | 76 -continued | |
|---|---|---|---|
| 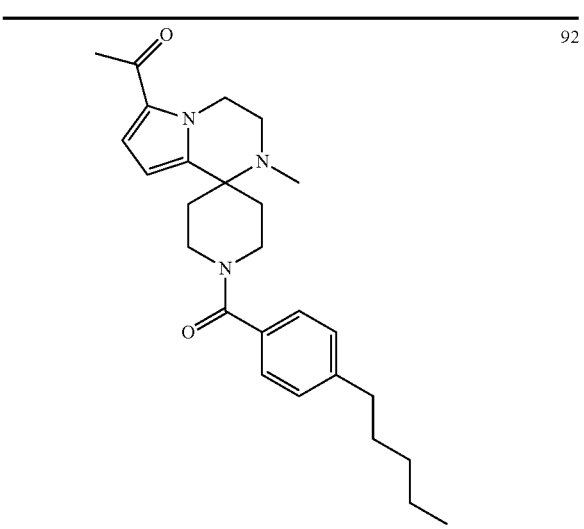 | 92 | 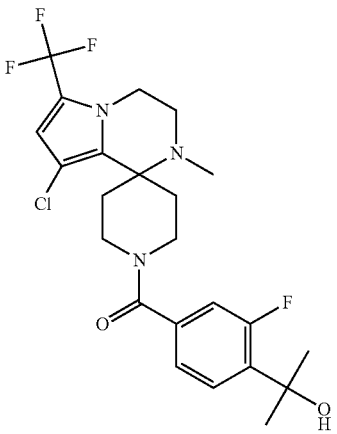 | 95 |
| 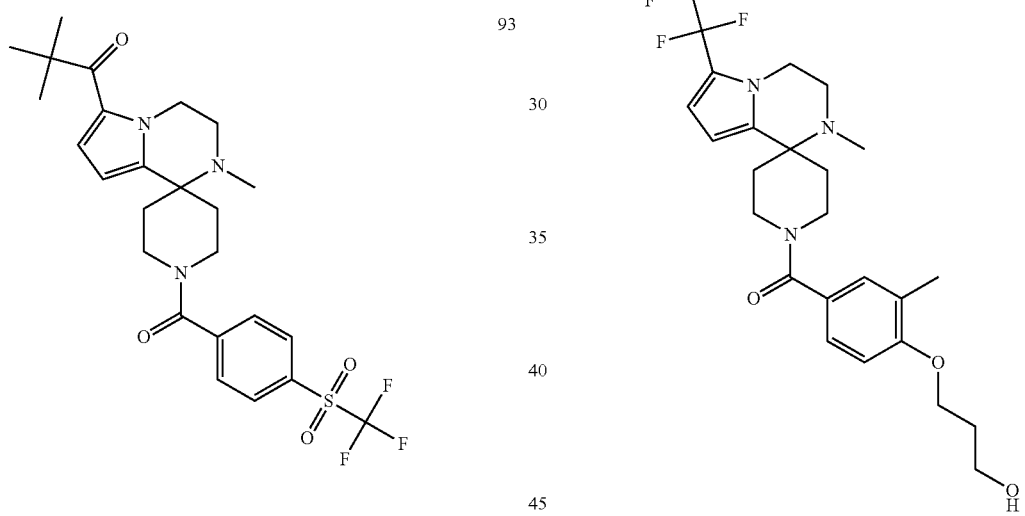 | 93 94 | 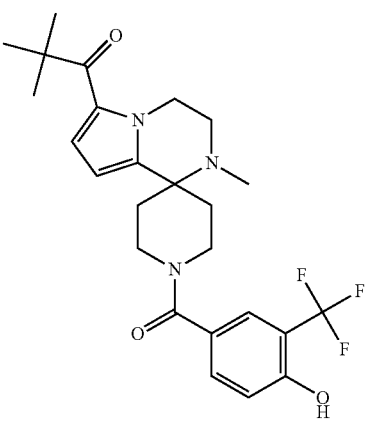 | 96 97 |
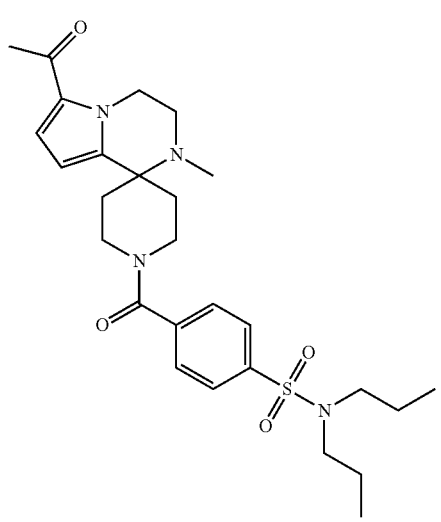 [SMILES: CCCN(CCC)S(=O)(=O)c1ccc(C(=O)N2CCC3(CC2)c2ccc(C(C)=O)n2CCN3C)cc1]

98 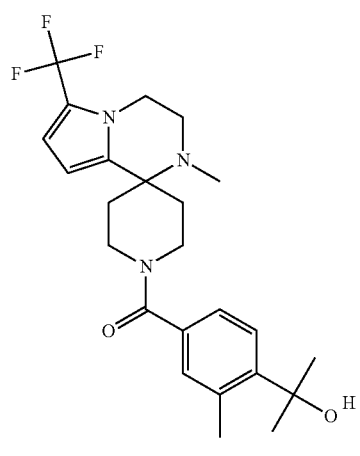
101 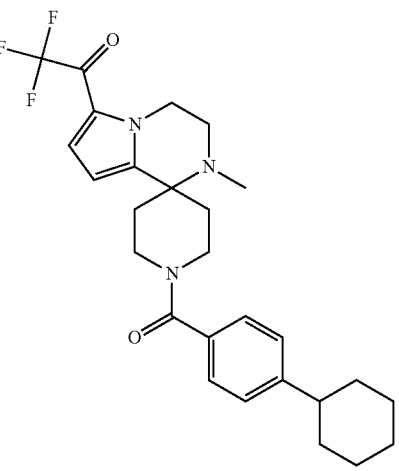
99 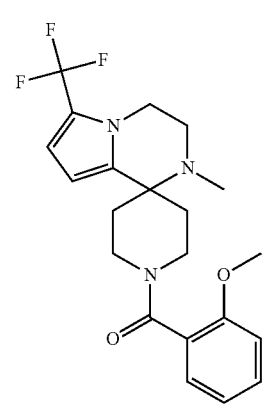 [SMILES: COc1ccccc1C(=O)N1CCC2(CC1)c1ccc(C(F)(F)F)n1CCN2C]
102 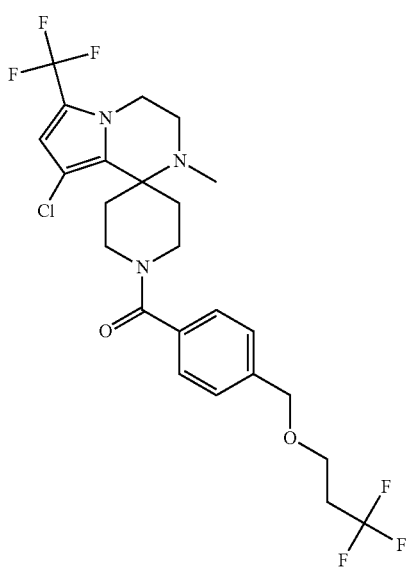
100 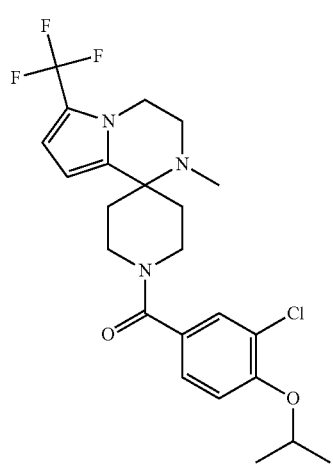 [SMILES: CC(C)Oc1ccc(C(=O)N2CCC3(CC2)c2ccc(C(F)(F)F)n2CCN3C)cc1Cl]
103 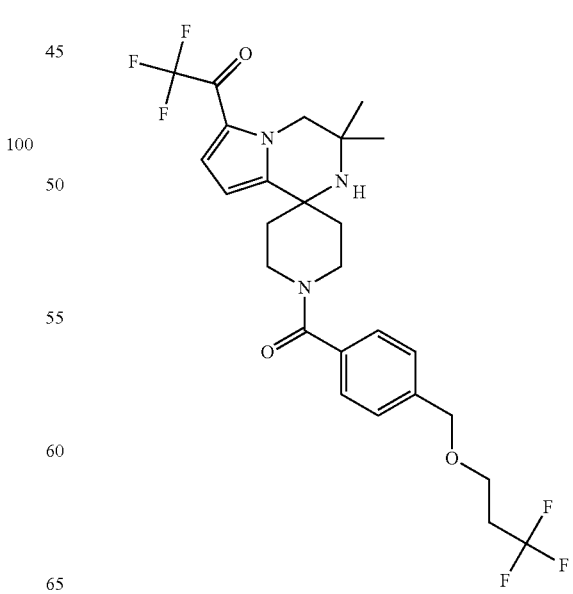

-continued
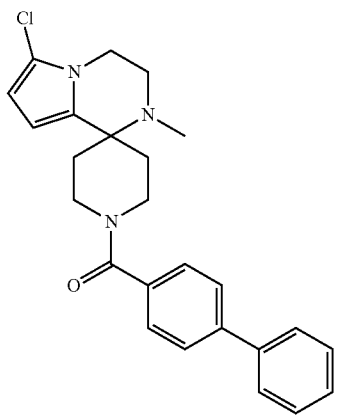 [SMILES: CN1CCn2c(Cl)ccc2C12CCN(C(=O)c1ccc(-c3ccccc3)cc1)CC2]
104
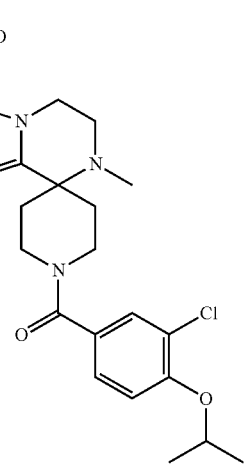
107
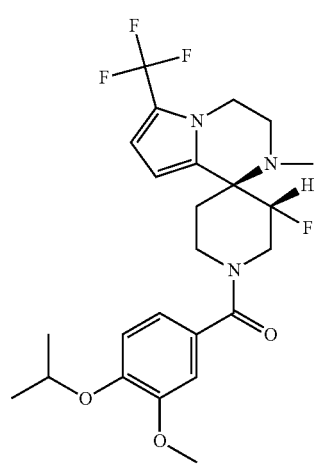 [SMILES: COc1cc(C(=O)N2CC[C@]3(c4ccc(C(F)(F)F)n4CCN3C)[C@H](F)C2)ccc1OC(C)C]
105
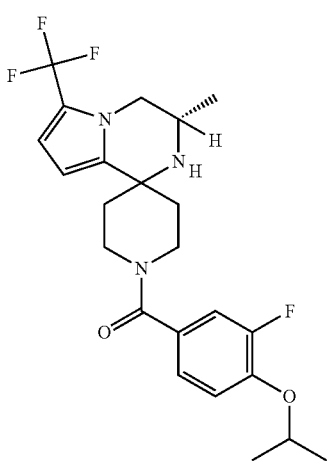
108
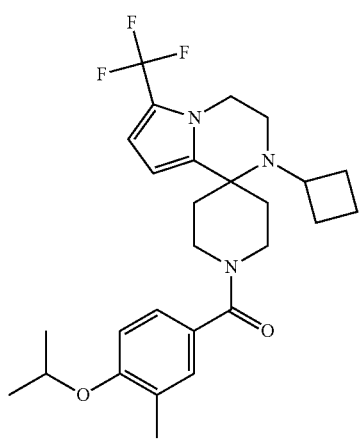 [SMILES: Cc1cc(C(=O)N2CCC3(CC2)c2ccc(C(F)(F)F)n2CCN3C2CCC2)ccc1OC(C)C]
106
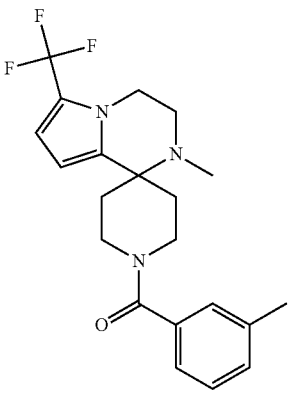 [SMILES: Cc1cccc(C(=O)N2CCC3(CC2)c2ccc(C(F)(F)F)n2CCN3C)c1]
109

110
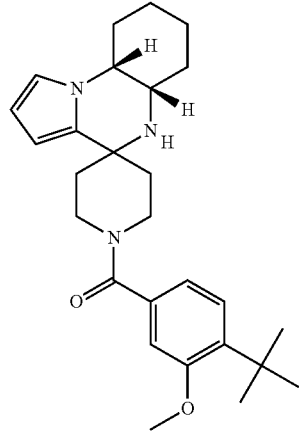
113
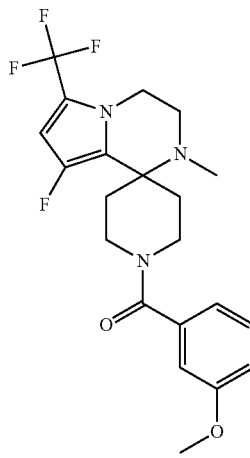
111
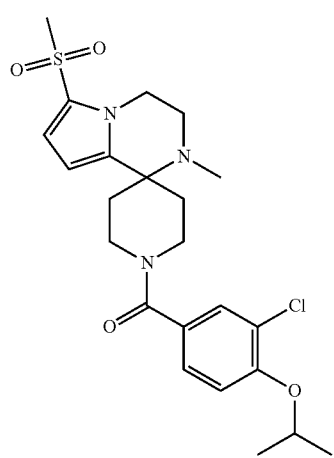 [SMILES: CC(C)Oc1ccc(C(=O)N2CCC3(CC2)c2ccc(S(C)(=O)=O)n2CCN3C)cc1Cl]
114
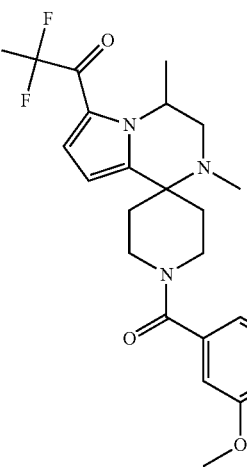
112
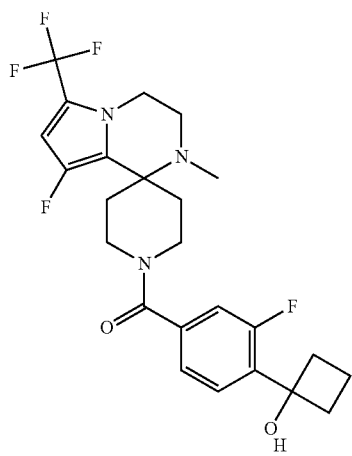
115
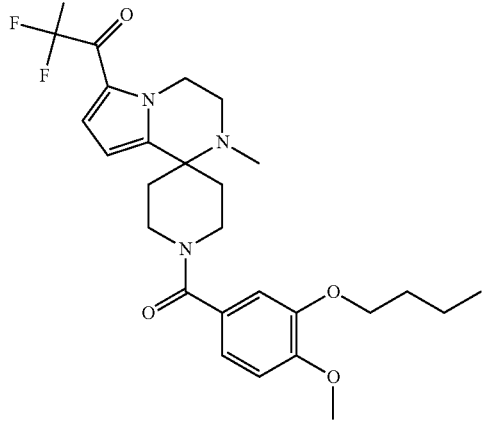

| 116 | 119 |
|---|---|
| 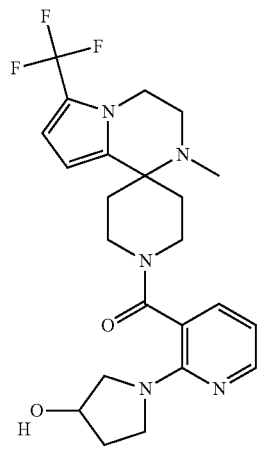 | 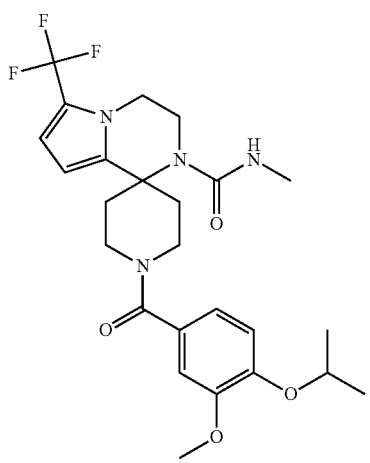 |
| 117 | 120 |
|---|---|
| 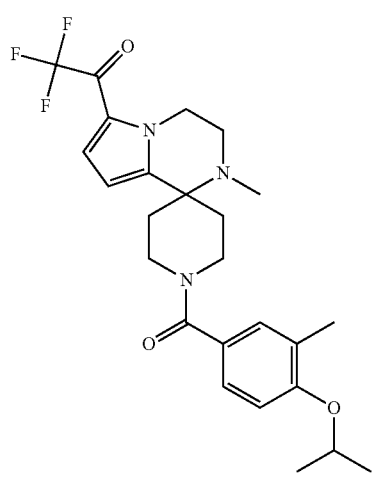 | 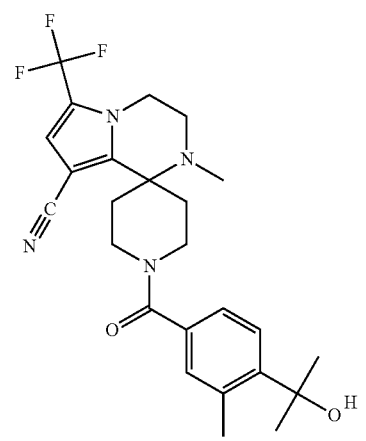 |
| 118 | 121 |
|---|---|
| 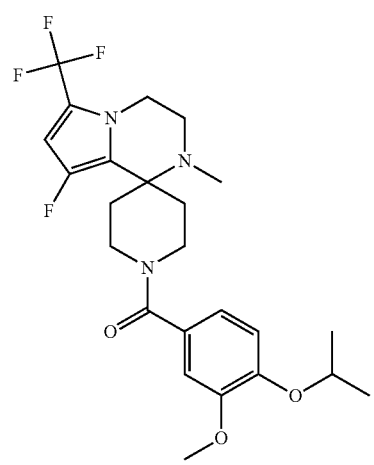 | 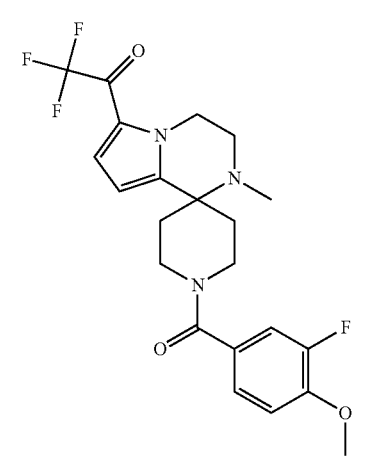 |

| 122 | 125 |
|---|---|
| 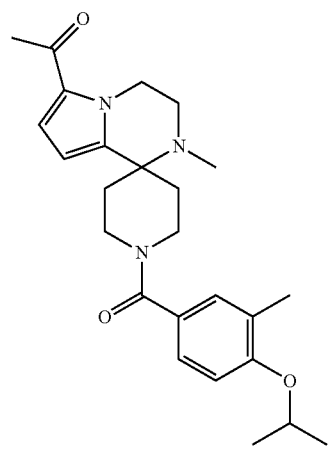 | 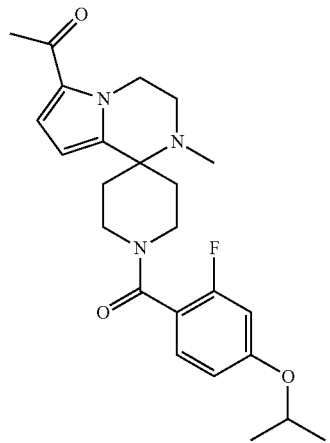 |
| 123 | 126 |
| 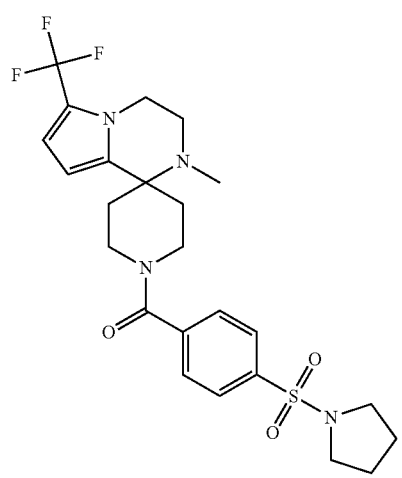 [SMILES: CN1CCn2c(C(F)(F)F)ccc2C12CCN(C(=O)c1ccc(S(=O)(=O)N3CCCC3)cc1)CC2] | 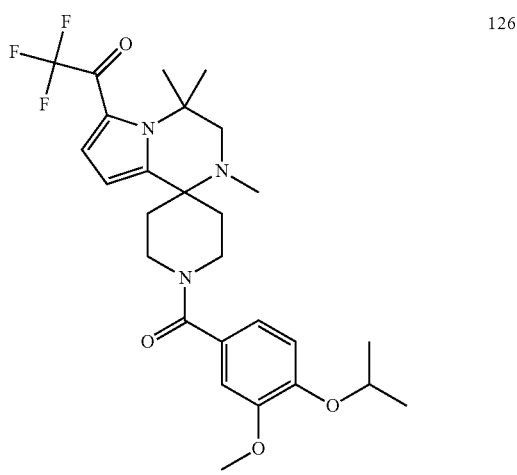 |
| 124 | 127 |
| 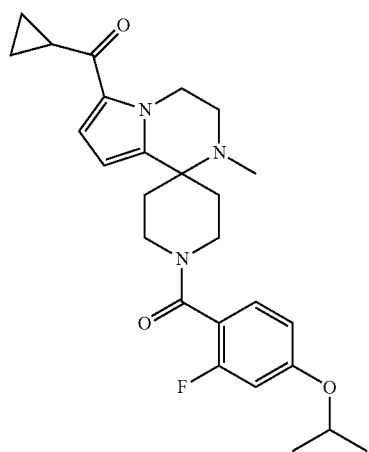 [SMILES: CC(C)Oc1ccc(C(=O)N2CCC3(CC2)c2ccc(C(=O)C4CC4)n2CCN3C)c(F)c1] | 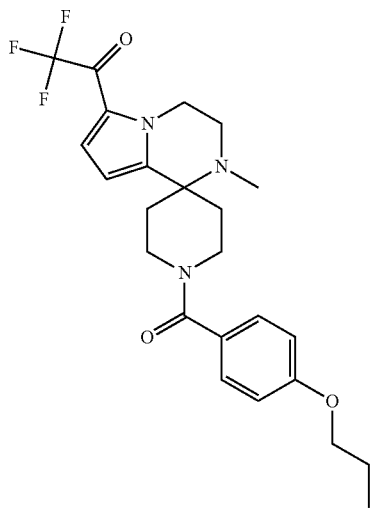 [SMILES: CCCOc1ccc(C(=O)N2CCC3(CC2)c2ccc(C(=O)C(F)(F)F)n2CCN3C)cc1] |

128 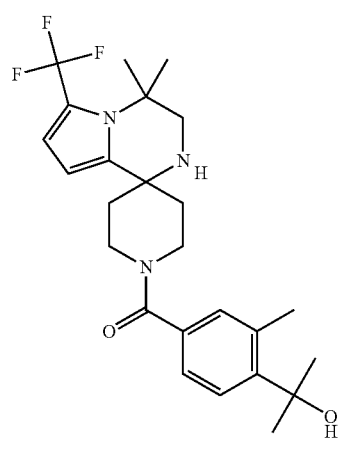
131 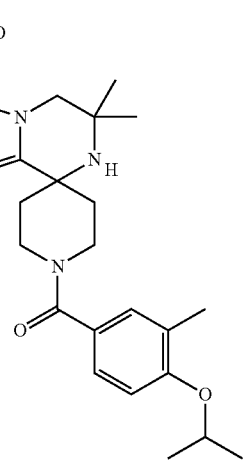
129 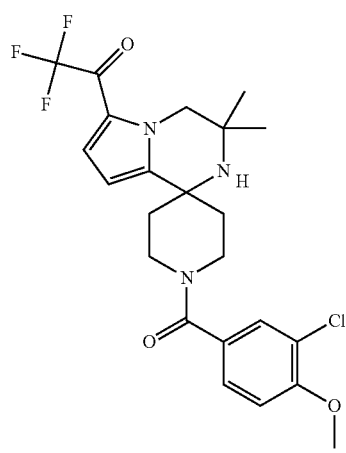
132 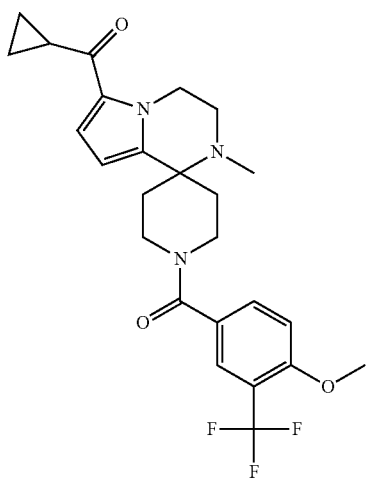
130 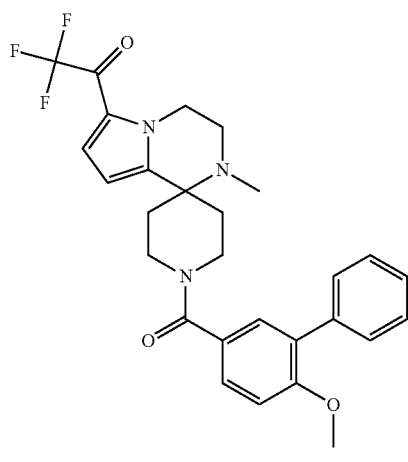 [SMILES: COc1ccc(C(=O)N2CCC3(CC2)c2ccc(C(=O)C(F)(F)F)n2CCN3C)cc1-c1ccccc1]
133 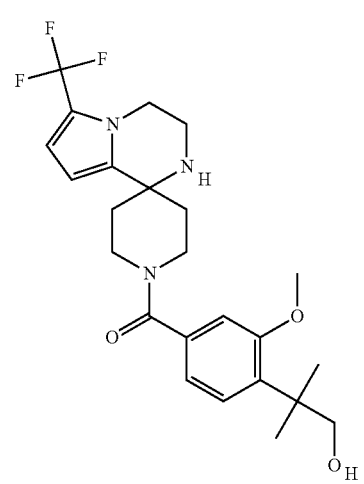

-continued
| | |
|---|---|
| 134 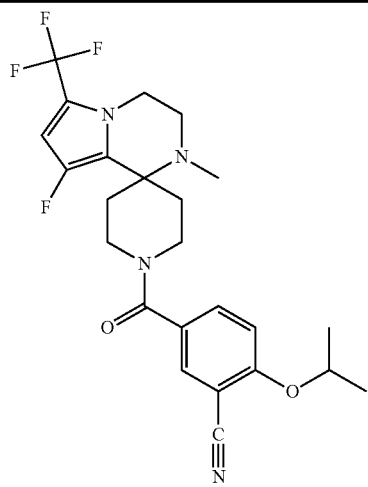 | 137 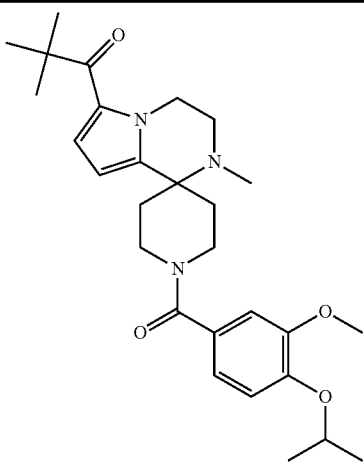 |
| 135 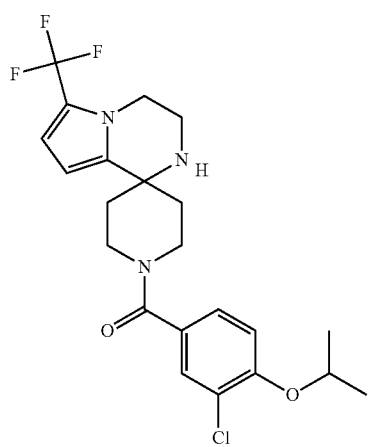 | 138 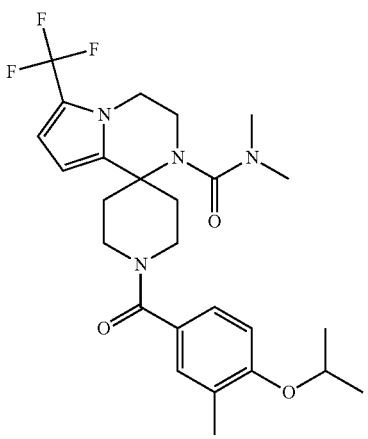 [SMILES: Cc1cc(C(=O)N2CCC3(CC2)c2ccc(C(F)(F)F)n2CCN3C(=O)N(C)C)ccc1OC(C)C] |
| 136 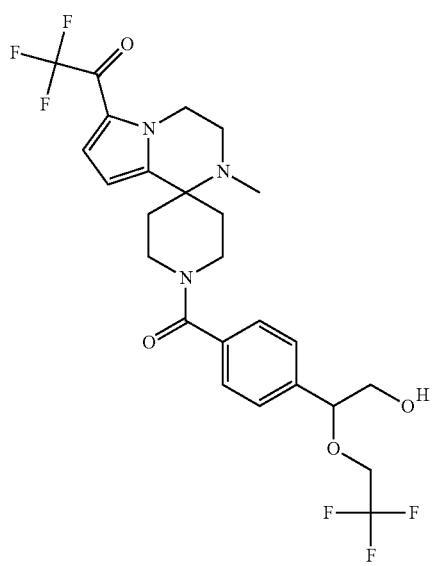 | 139 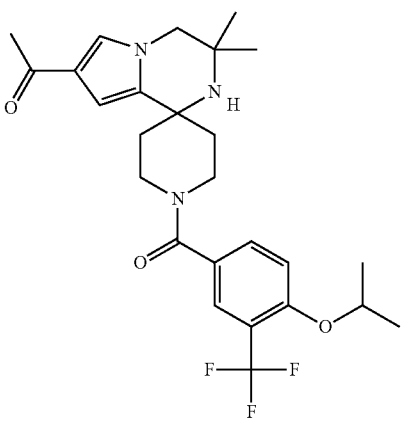 |

| 91 -continued | | 92 -continued | |
|---|---|---|---|
| 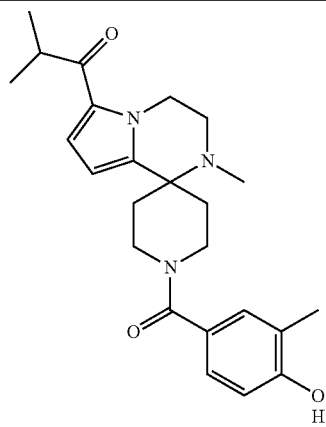 | 140 | 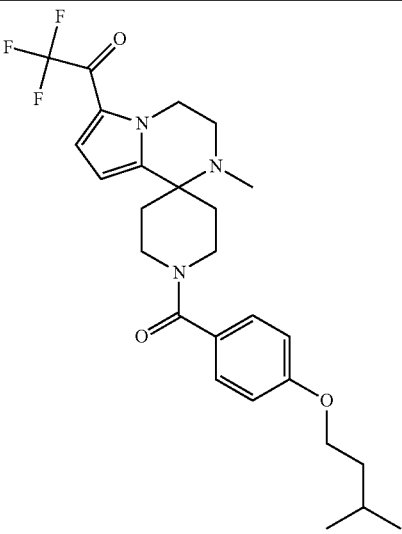 | 143 |
| 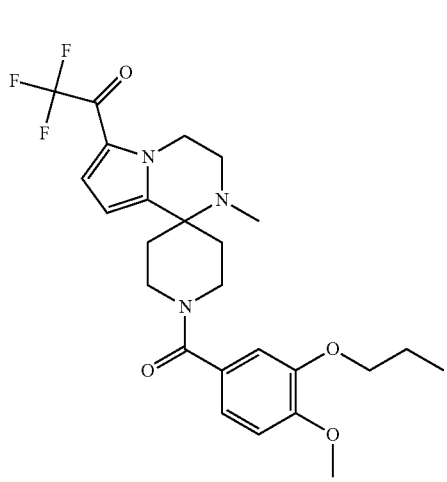 [SMILES: CCCOc1cc(C(=O)N2CCC3(CC2)c2ccc(C(=O)C(F)(F)F)n2CCN3C)ccc1OC] | 141 142 | 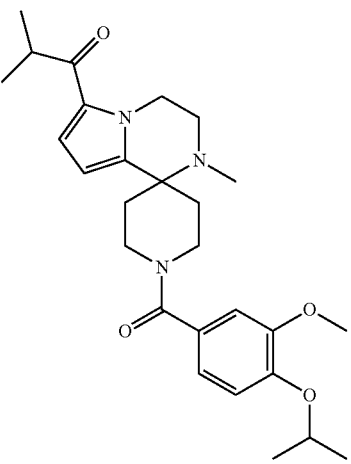 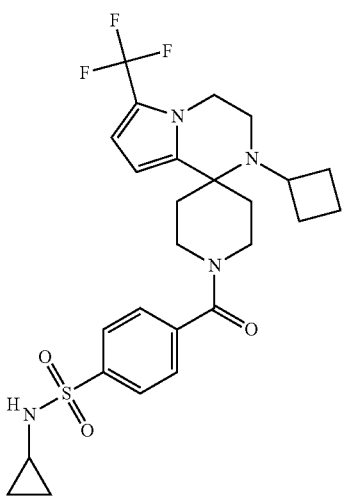 | 144 145 |

| 146 | 149 |
|---|---|
| 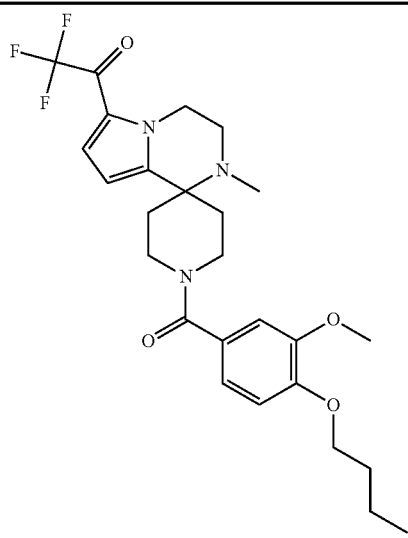 | 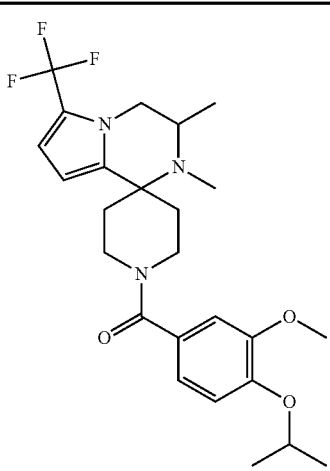 |
| 147 | 150 |
| 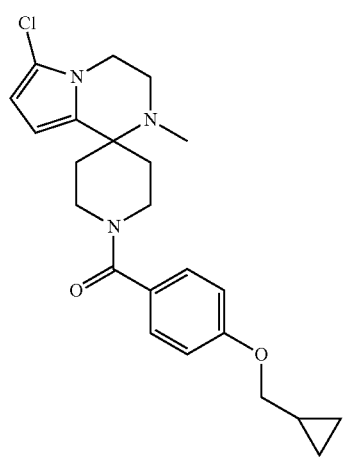 [SMILES: CN1CCn2c(Cl)ccc2C12CCN(C(=O)c1ccc(OCC3CC3)cc1)CC2] | 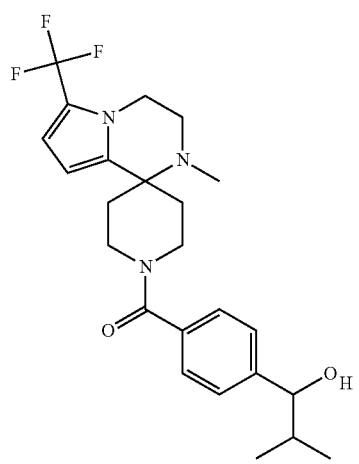 |
| 148 | 151 |
| 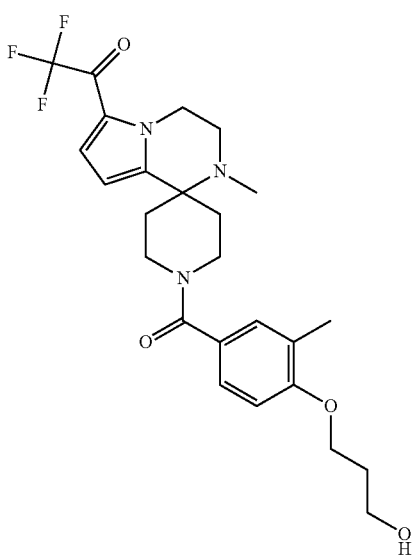 [SMILES: Cc1cc(C(=O)N2CCC3(CC2)c2ccc(C(=O)C(F)(F)F)n2CCN3C)ccc1OCCCO] | 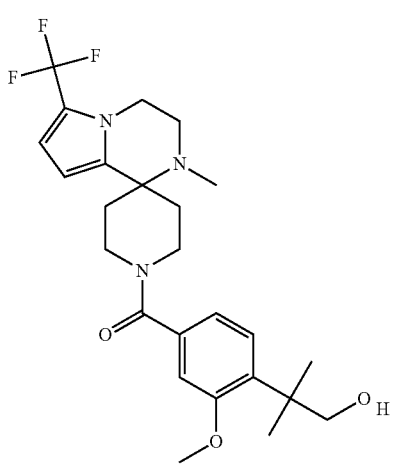 |

| 95 -continued | | 96 -continued | |
|---|---|---|---|
| 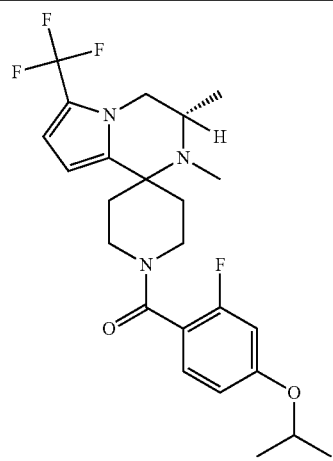 | 152 | 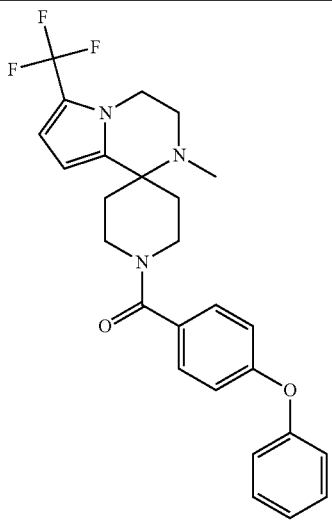 | 155 |
| 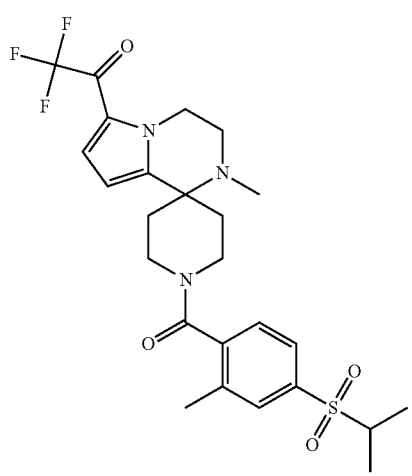 [SMILES: Cc1cc(S(=O)(=O)C(C)C)ccc1C(=O)N1CCC2(CC1)c1ccc(C(=O)C(F)(F)F)n1CCN2C] | 153 | 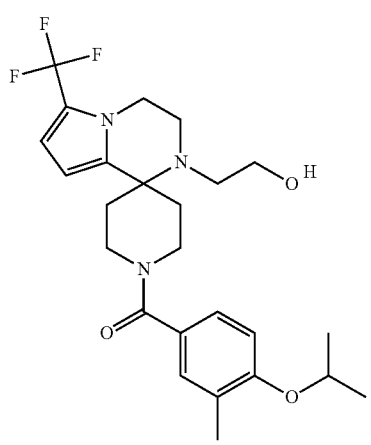 | 156 |
| 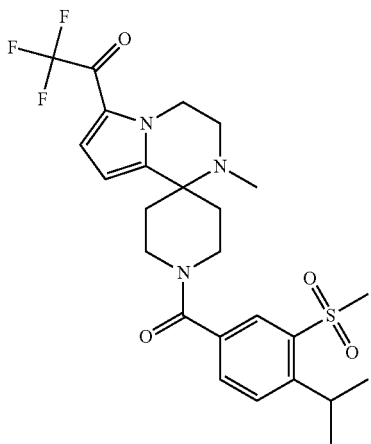 [SMILES: CC(C)c1ccc(C(=O)N2CCC3(CC2)c2ccc(C(=O)C(F)(F)F)n2CCN3C)cc1S(C)(=O)=O] | 154 | 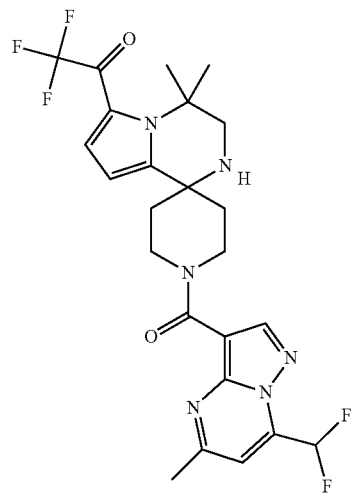 | 157 |

-continued
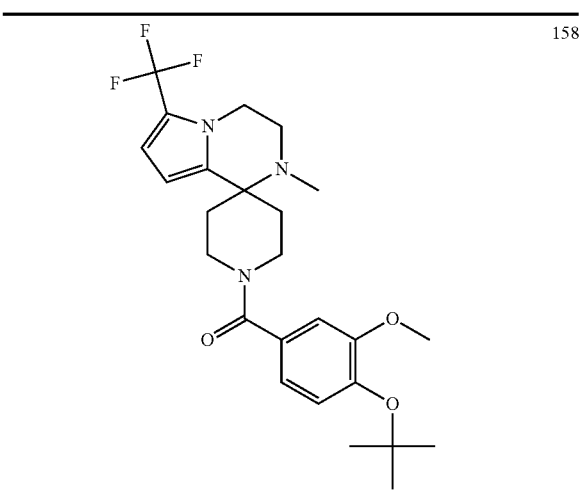
158
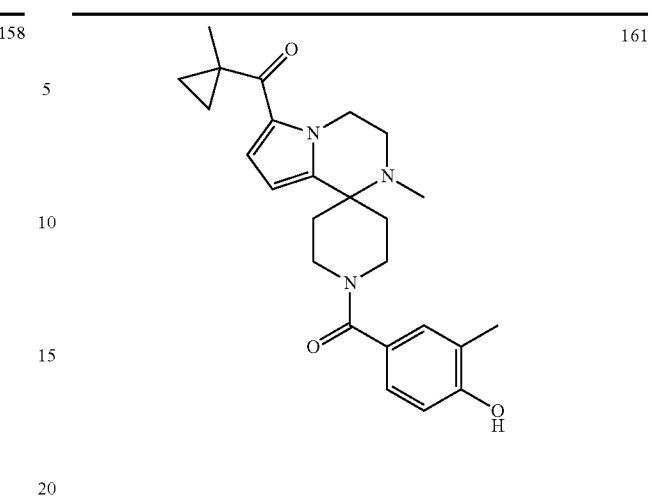
161
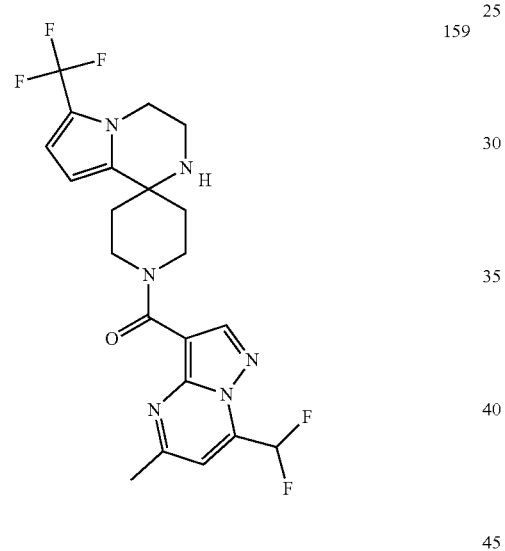
159
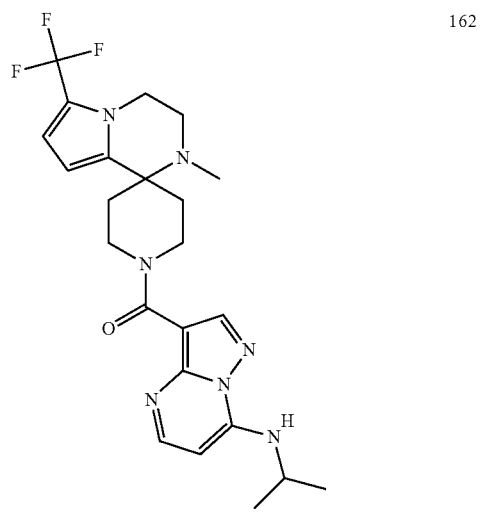
162
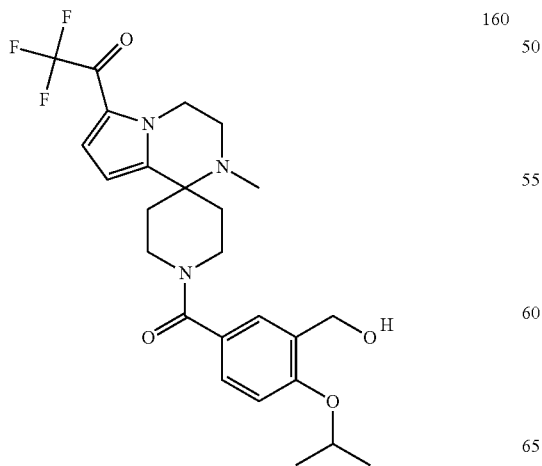
160
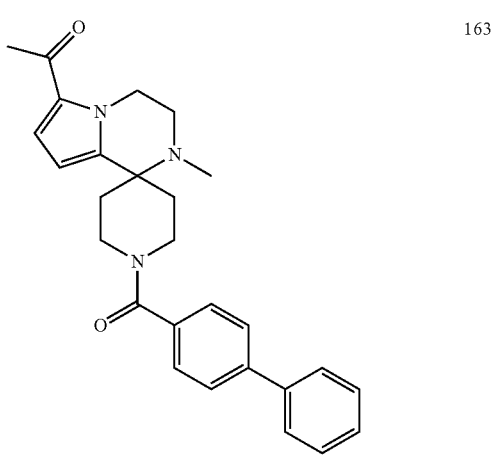
163

| 99 -continued | 100 -continued |
|---|---|
| 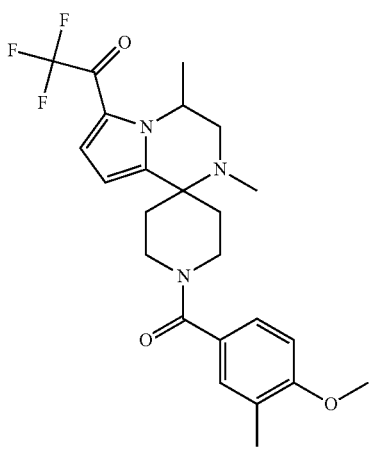 [SMILES: COc1ccc(C(=O)N2CCC3(CC2)c2ccc(C(=O)C(F)(F)F)n2C(C)CN3C)cc1C] 164 | 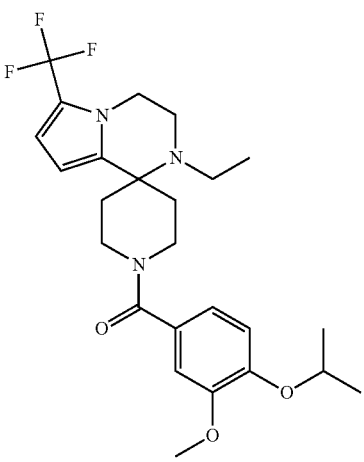 167 |
| 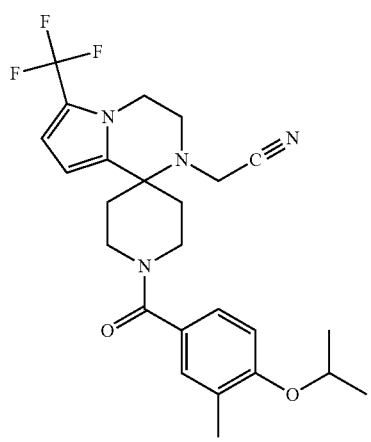 [SMILES: Cc1cc(C(=O)N2CCC3(CC2)c2ccc(C(F)(F)F)n2CCN3CC#N)ccc1OC(C)C] 165 | 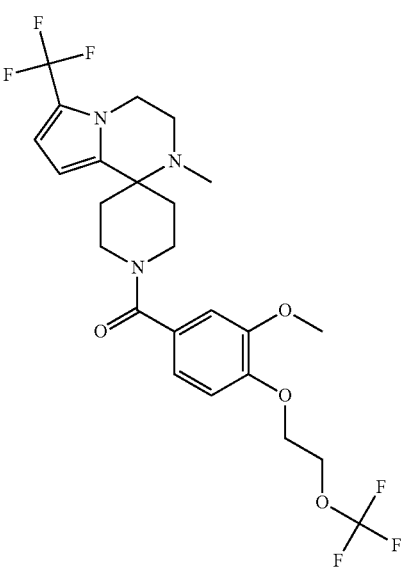 168 |
| 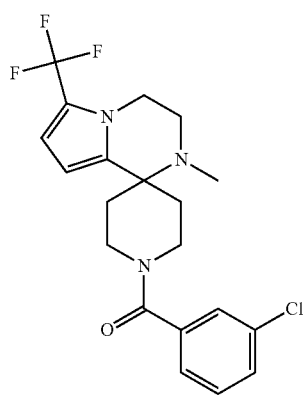 [SMILES: CN1CCn2c(C(F)(F)F)ccc2C12CCN(C(=O)c1cccc(Cl)c1)CC2] 166 | 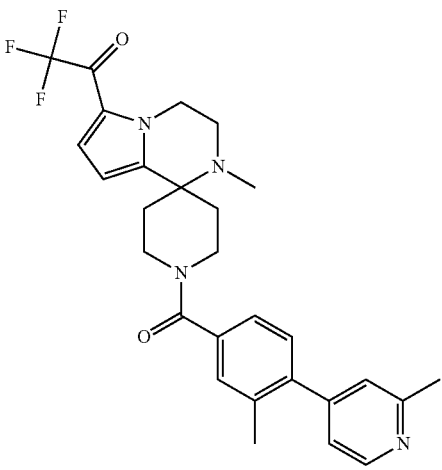 [SMILES: Cc1cc(-c2ccc(C(=O)N3CCC4(CC3)c3ccc(C(=O)C(F)(F)F)n3CCN4C)cc2C)ccn1] 169 |

| 101 -continued | 102 -continued |
|---|---|
| 170 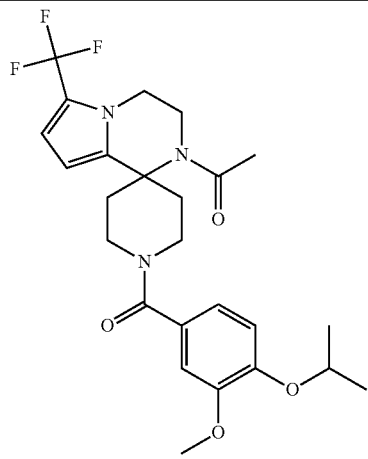 | 173 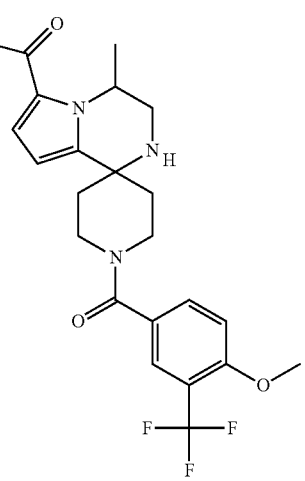 |
| 171 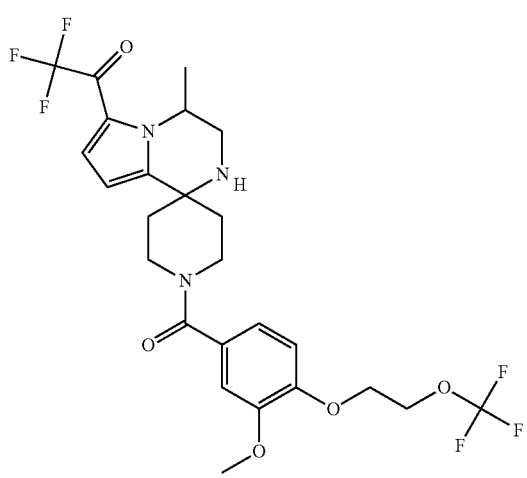 | 174 |
| 172 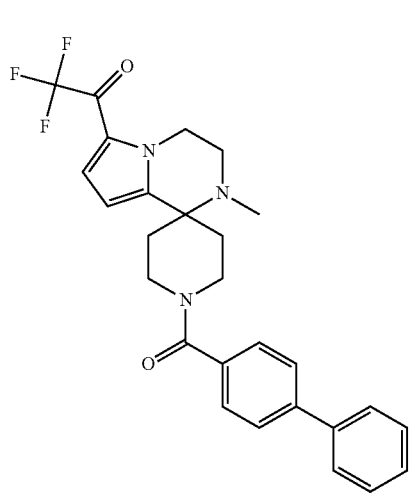 [SMILES: CN1CCn2c(C(=O)C(F)(F)F)ccc2C12CCN(C(=O)c1ccc(-c3ccccc3)cc1)CC2] | 175 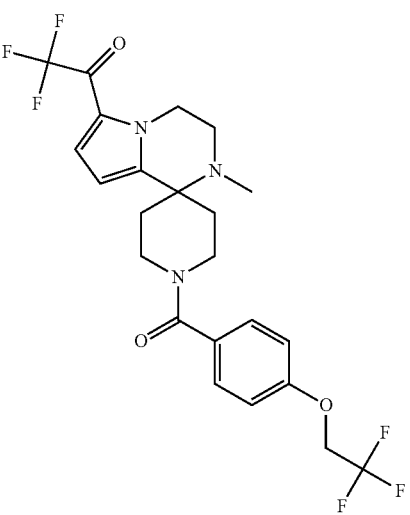 [SMILES: CN1CCn2c(C(=O)C(F)(F)F)ccc2C12CCN(C(=O)c1ccc(OCC(F)(F)F)cc1)CC2] |

-continued
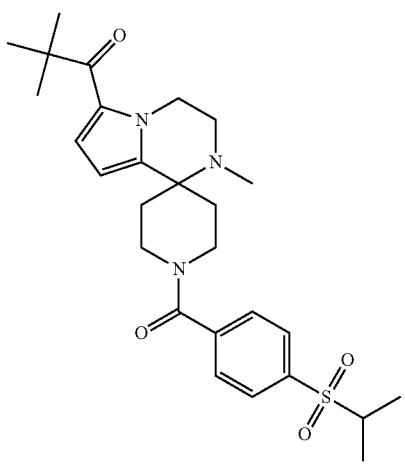 [SMILES: CC(C)S(=O)(=O)c1ccc(C(=O)N2CCC3(CC2)c2ccc(C(=O)C(C)(C)C)n2CCN3C)cc1]
176
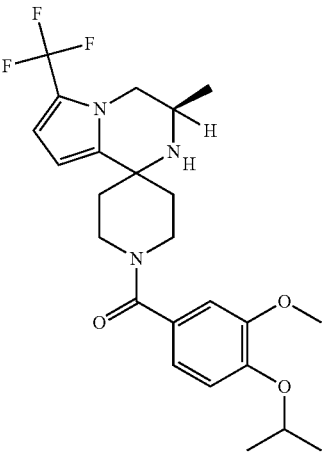
179
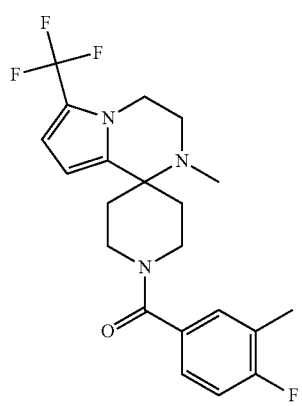 [SMILES: Cc1cc(C(=O)N2CCC3(CC2)c2ccc(C(F)(F)F)n2CCN3C)ccc1F]
177
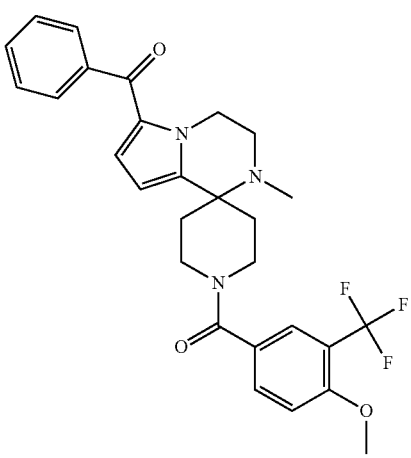
180
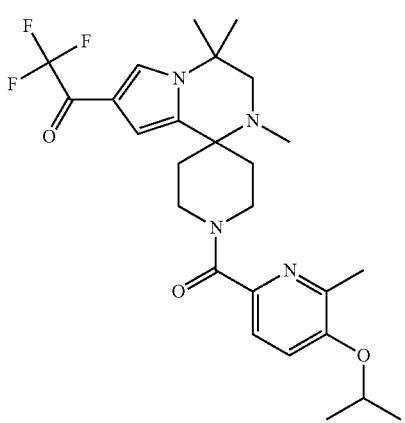 [SMILES: Cc1nc(C(=O)N2CCC3(CC2)c2cc(C(=O)C(F)(F)F)cn2C(C)(C)CN3C)ccc1OC(C)C]
178
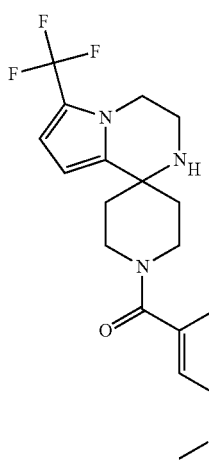
181

| 105 -continued | 106 -continued |
|---|---|
| 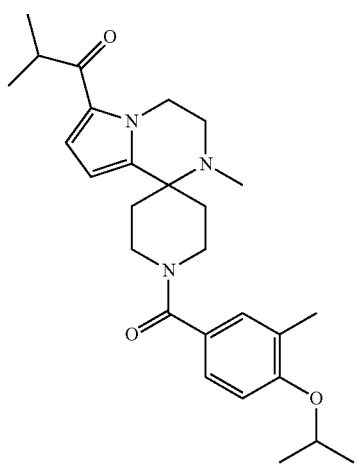 [SMILES: Cc1cc(C(=O)N2CCC3(CC2)c2ccc(C(=O)C(C)C)n2CCN3C)ccc1OC(C)C] 182 | 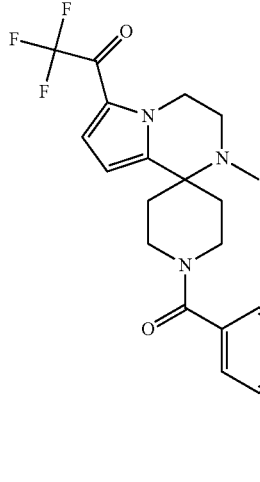 185 |
| 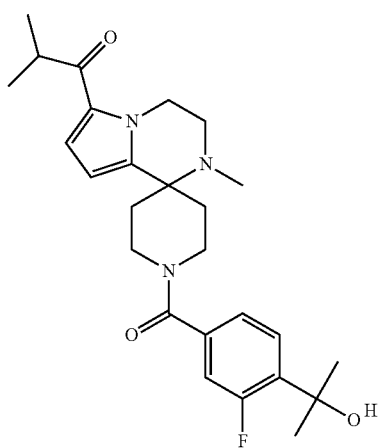 183 | 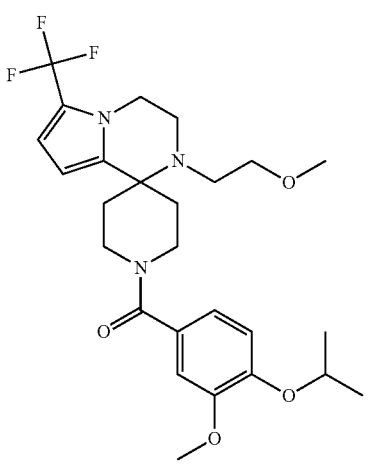 186 |
| 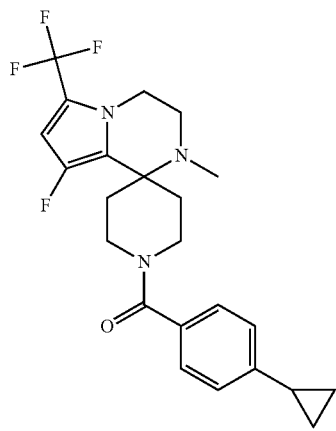 [SMILES: CN1CCn2c(C(F)(F)F)cc(F)c2C12CCN(C(=O)c1ccc(C3CC3)cc1)CC2] 184 | 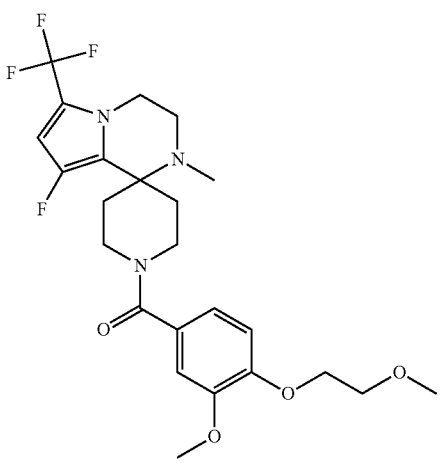 [SMILES: COCCOc1ccc(C(=O)N2CCC3(CC2)c2c(F)cc(C(F)(F)F)n2CCN3C)cc1OC] 187 |

| 107 -continued | 108 -continued |
|---|---|
| 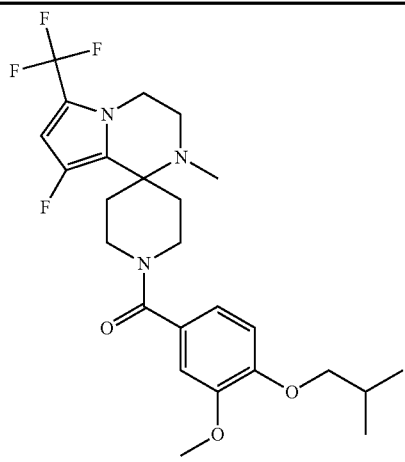 188 | 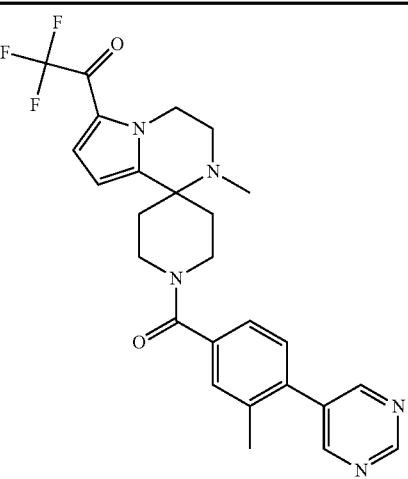 191 |
| 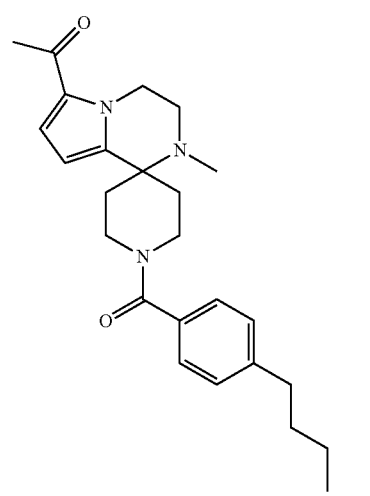 189 | 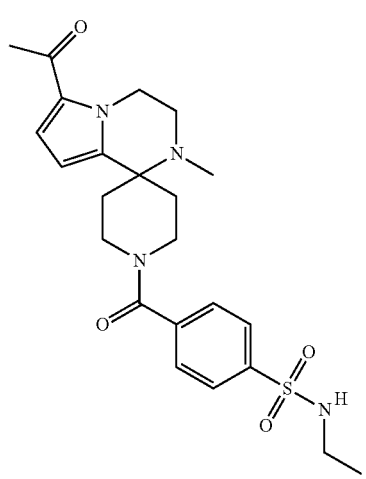 192 |
| 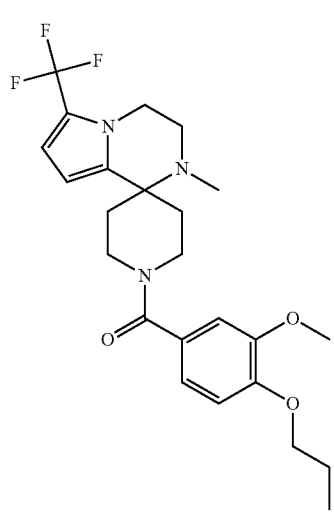 [SMILES: CCCOc1ccc(C(=O)N2CCC3(CC2)c2ccc(C(F)(F)F)n2CCN3C)cc1OC] 190 | 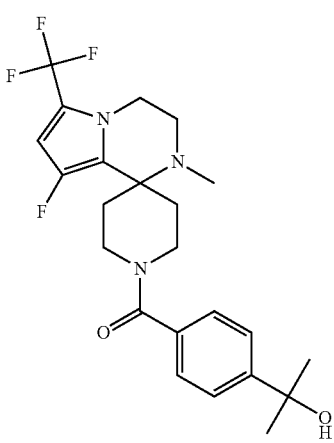 193 |

| 194 | 197 |
| --- | --- |
| 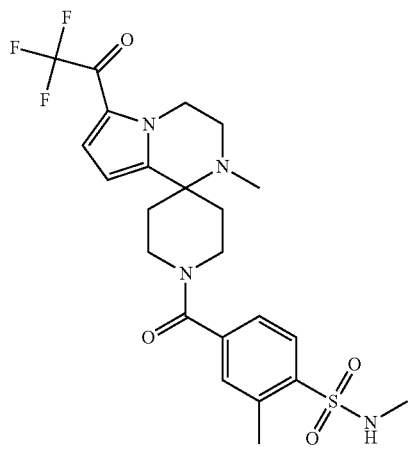 [SMILES: CNS(=O)(=O)c1ccc(C(=O)N2CCC3(CC2)c2ccc(C(=O)C(F)(F)F)n2CCN3C)cc1C] | 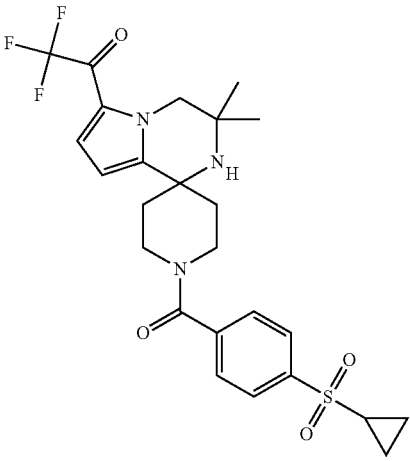 |
| 195 | 198 |
| 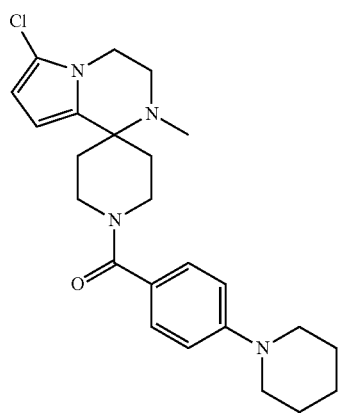 [SMILES: CN1CCn2c(Cl)ccc2C12CCN(C(=O)c1ccc(N3CCCCC3)cc1)CC2] | 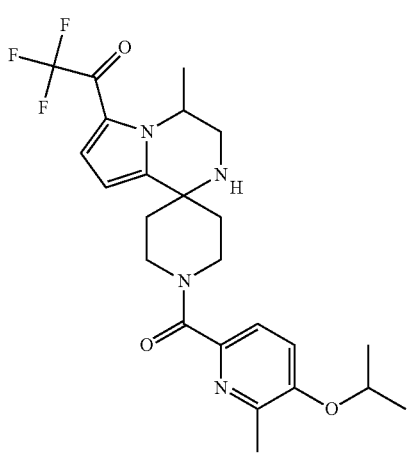 |
| 196 | 199 |
| 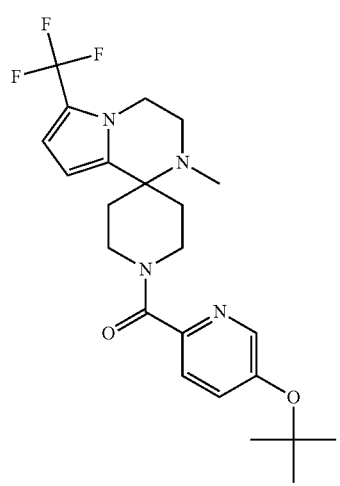 [SMILES: CN1CCn2c(C(F)(F)F)ccc2C12CCN(C(=O)c1ccc(OC(C)(C)C)cn1)CC2] | |

| 200 | 203 |
|---|---|
| 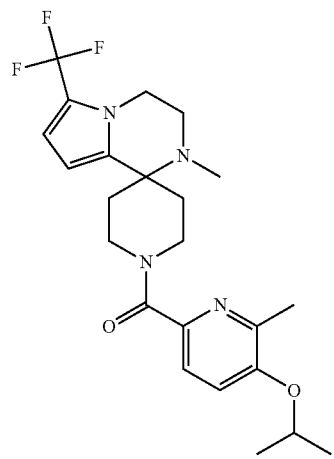 [SMILES: Cc1nc(C(=O)N2CCC3(CC2)c2ccc(C(F)(F)F)n2CCN3C)ccc1OC(C)C] | 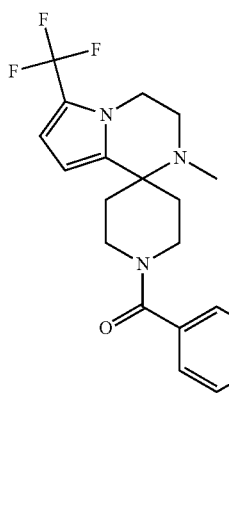 |
| 201 | 204 |
|---|---|
| 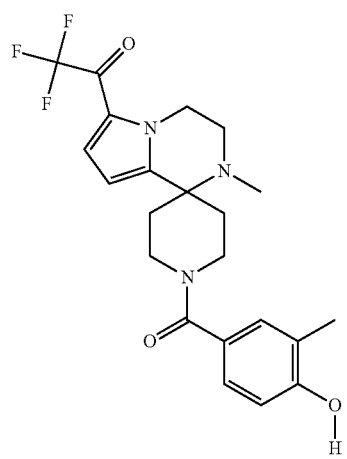 [SMILES: Cc1cc(C(=O)N2CCC3(CC2)c2ccc(C(=O)C(F)(F)F)n2CCN3C)ccc1O] | 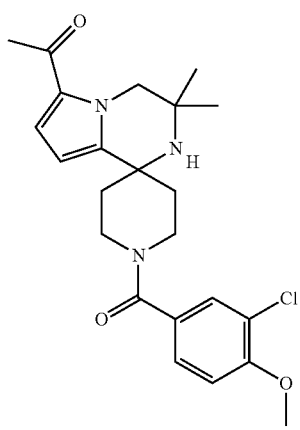 |
| 202 | 205 |
|---|---|
| 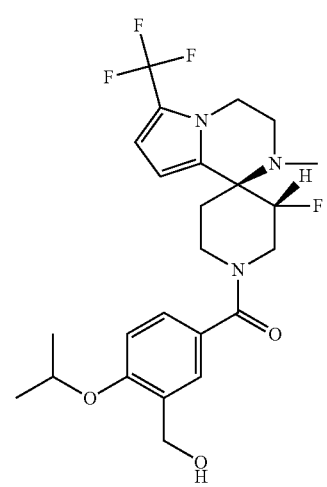 [SMILES: CC(C)Oc1ccc(C(=O)N2CC[C@]3(c4ccc(C(F)(F)F)n4CCN3C)[C@H](F)C2)cc1CO] | 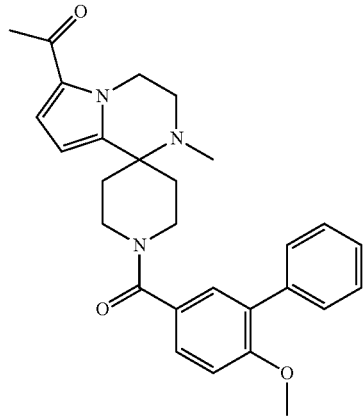 [SMILES: COc1ccc(C(=O)N2CCC3(CC2)c2ccc(C(C)=O)n2CCN3C)cc1-c1ccccc1] |

| 206 | 209 |
|---|---|
| 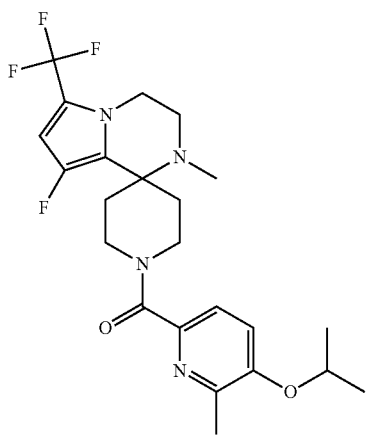 [SMILES: Cc1nc(C(=O)N2CCC3(CC2)c2c(F)cc(C(F)(F)F)n2CCN3C)ccc1OC(C)C] | 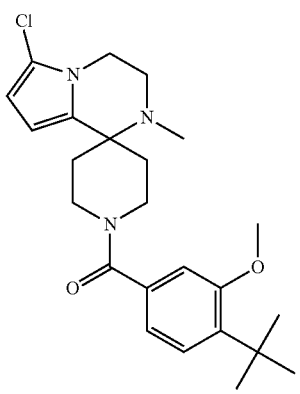 |
| 207 | 210 |
| 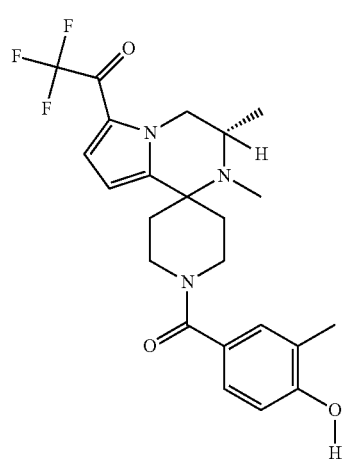 [SMILES: Cc1cc(C(=O)N2CCC3(CC2)c2ccc(C(=O)C(F)(F)F)n2C[C@H](C)N3C)ccc1O] | 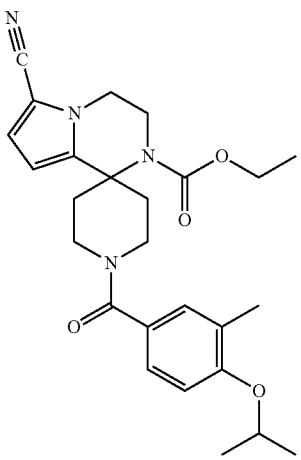 |
| 208 | 211 |
| 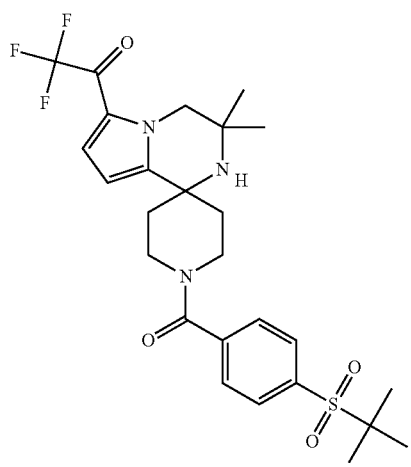 | 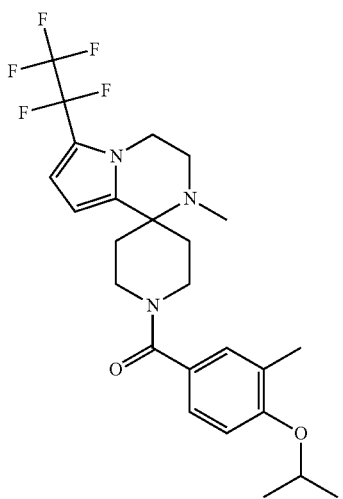 [SMILES: Cc1cc(C(=O)N2CCC3(CC2)c2ccc(C(F)(F)C(F)(F)F)n2CCN3C)ccc1OC(C)C] |

| 115 -continued | 116 -continued |
|---|---|
| 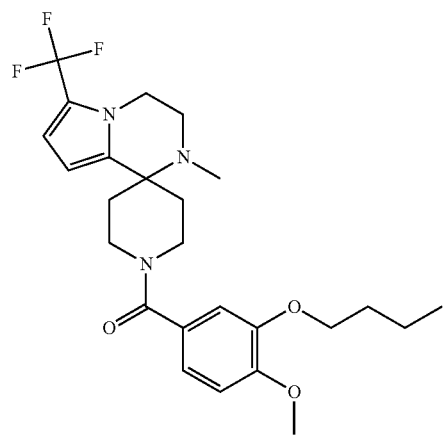 [SMILES: CCCCOc1cc(C(=O)N2CCC3(CC2)c2ccc(C(F)(F)F)n2CCN3C)ccc1OC] 212 | 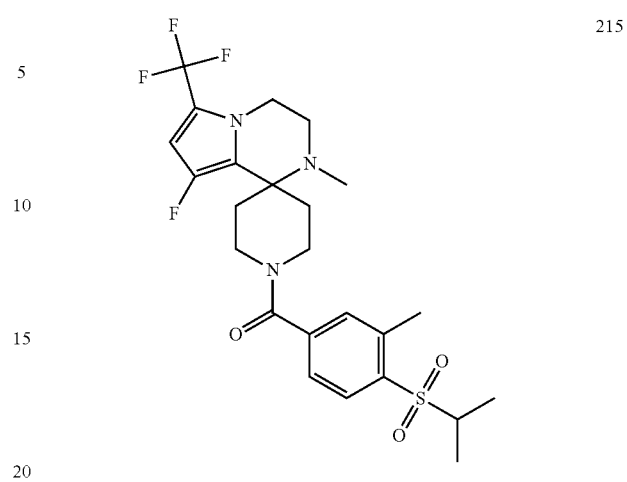 215 |
| 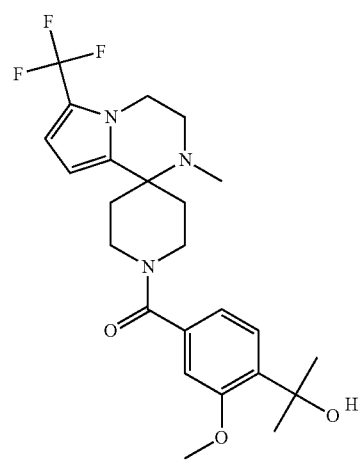 213 | 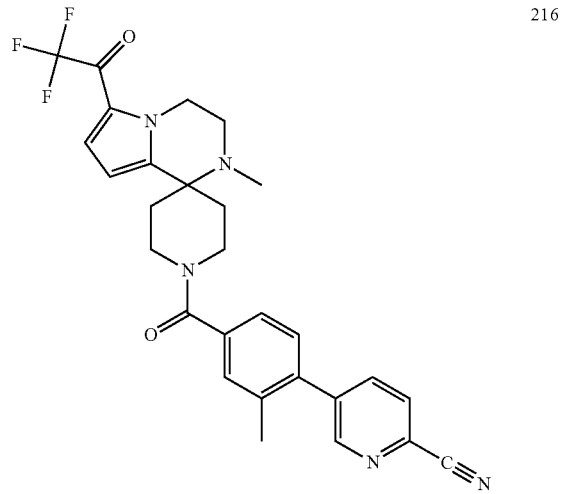 216 |
| 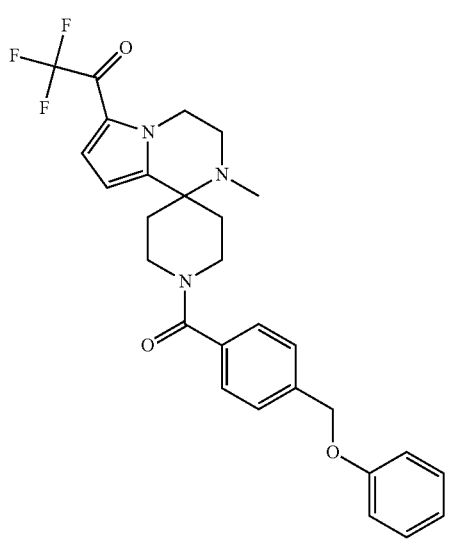 [SMILES: CN1CCn2c(C(=O)C(F)(F)F)ccc2C12CCN(C(=O)c1ccc(COc3ccccc3)cc1)CC2] 214 | 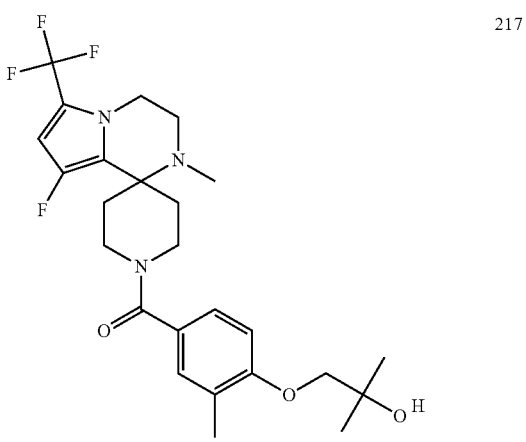 217 |

| 117 -continued | | 118 -continued | |
|---|---|---|---|
| 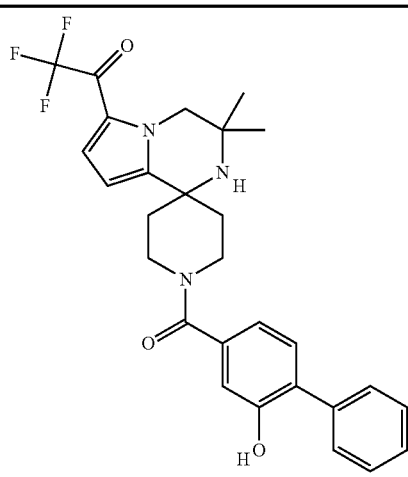 | 218 | 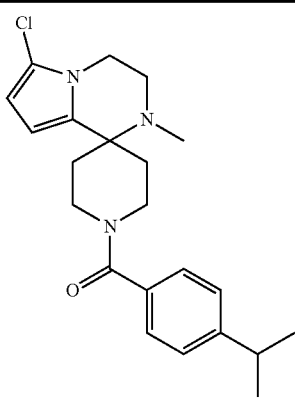 | 221 |
| 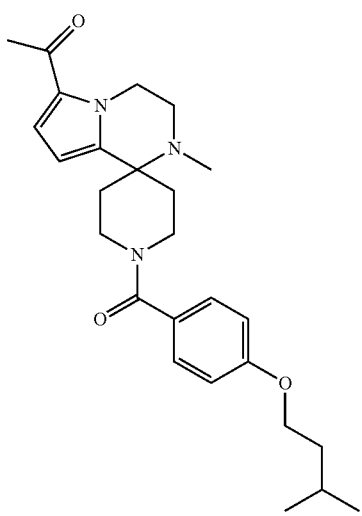 | 219 | 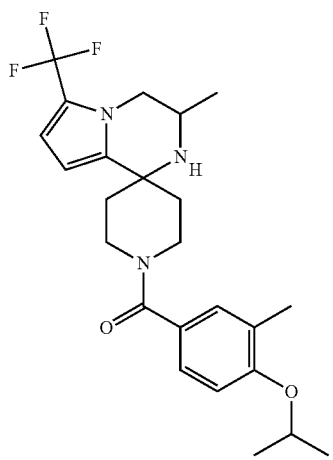 | 222 |
| 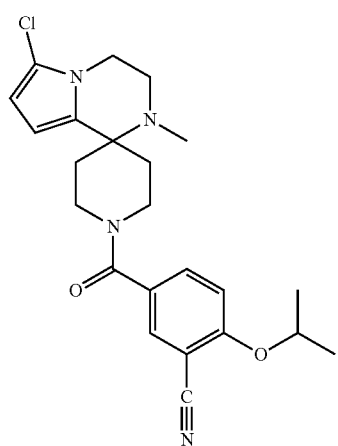 [SMILES: CC(C)Oc1ccc(C(=O)N2CCC3(CC2)c2ccc(Cl)n2CCN3C)cc1C#N] | 220 | 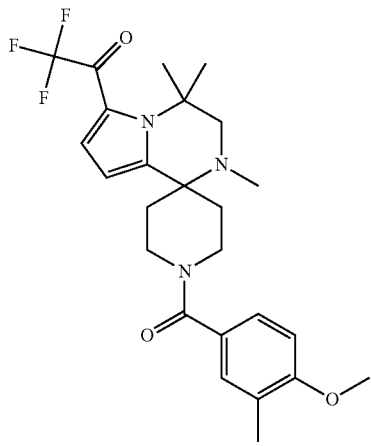 [SMILES: COc1ccc(C(=O)N2CCC3(CC2)c2ccc(C(=O)C(F)(F)F)n2C(C)(C)CN3C)cc1C] | 223 |

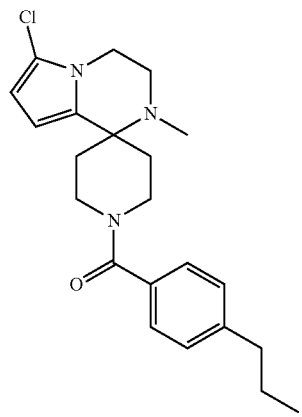 [SMILES: CCCc1ccc(C(=O)N2CCC3(CC2)c2ccc(Cl)n2CCN3C)cc1]
224
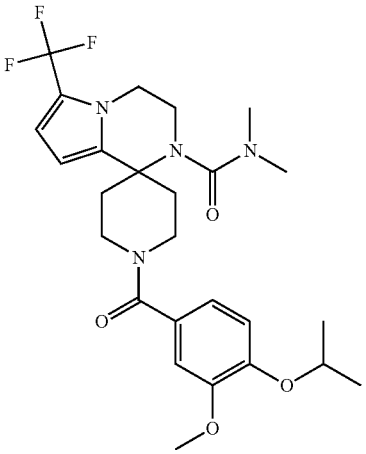
227
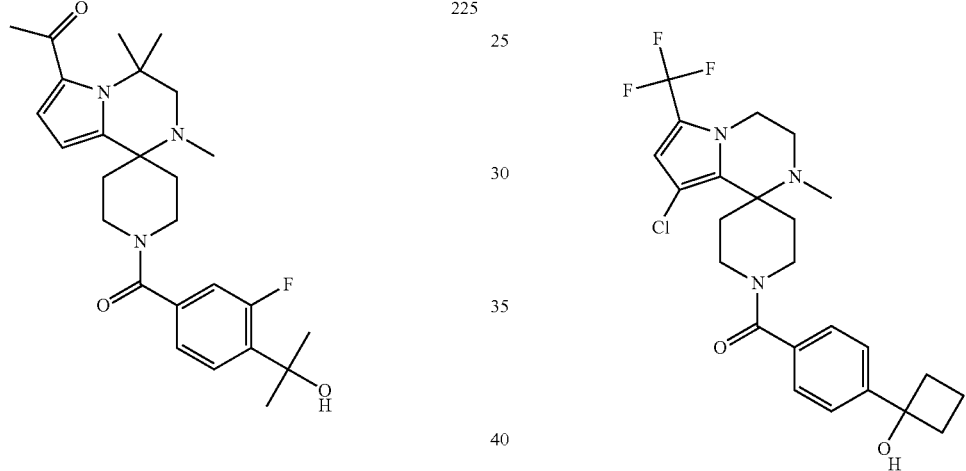
225
228
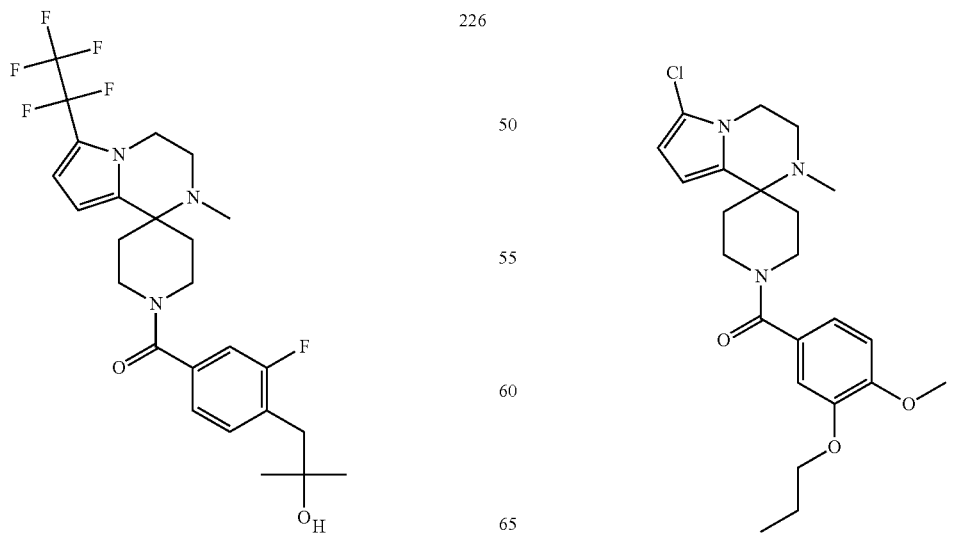
226
229

| 230 | 233 |
| --- | --- |
| 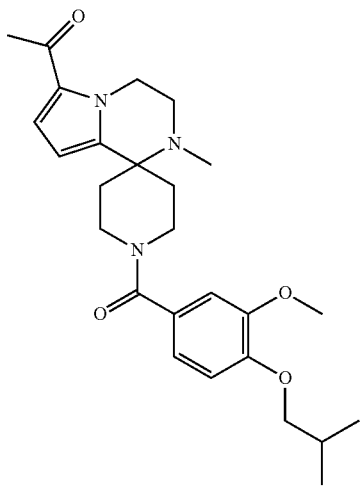 [SMILES: COc1cc(C(=O)N2CCC3(CC2)c2ccc(C(C)=O)n2CCN3C)ccc1OCC(C)C] | 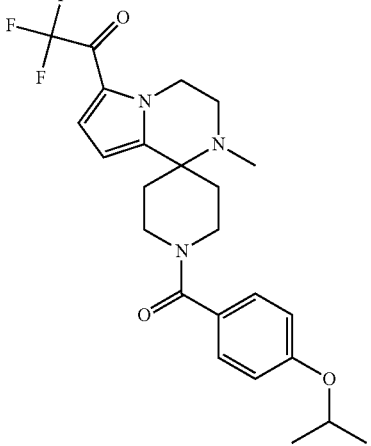 |
| 231 | 234 |
| | 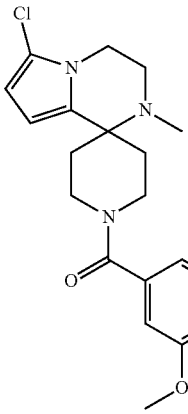 |
| 232 | 235 |
| | 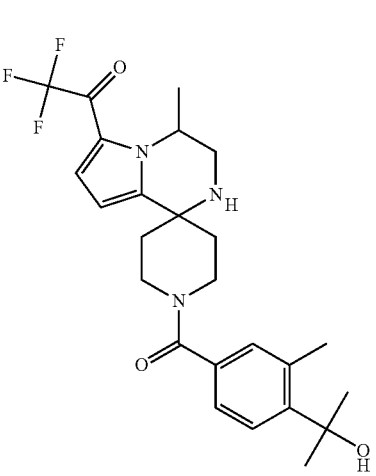 |

-continued
236
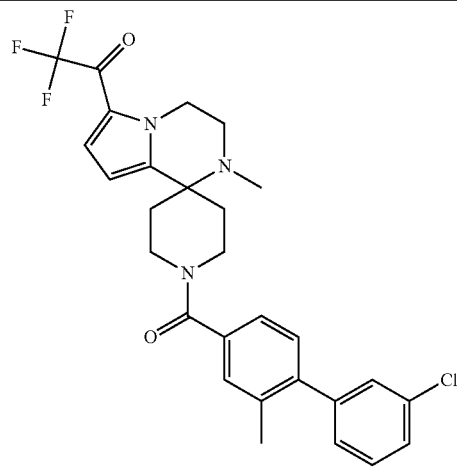
237
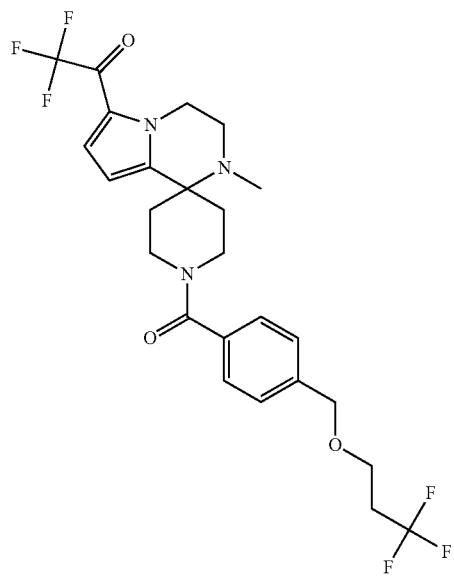 [SMILES: CN1CCn2c(C(=O)C(F)(F)F)ccc2C12CCN(C(=O)c1ccc(COCCC(F)(F)F)cc1)CC2]
238
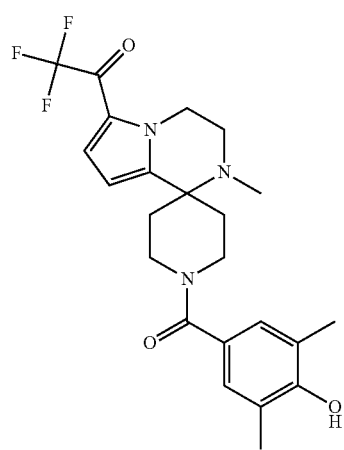 [SMILES: Cc1cc(C(=O)N2CCC3(CC2)c2ccc(C(=O)C(F)(F)F)n2CCN3C)cc(C)c1O]
-continued
239
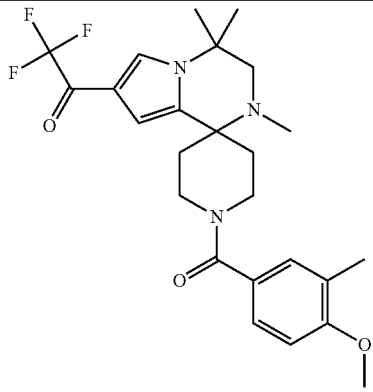
240
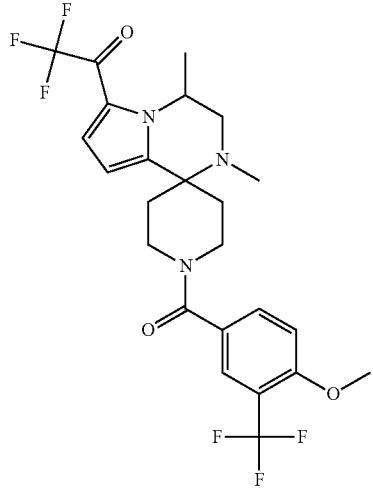 [SMILES: COc1ccc(C(=O)N2CCC3(CC2)c2ccc(C(=O)C(F)(F)F)n2C(C)CN3C)cc1C(F)(F)F]
241
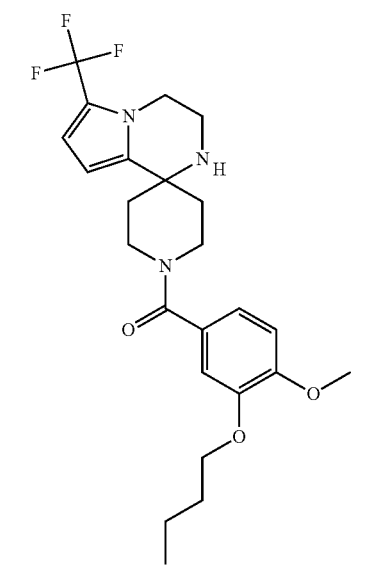

-continued
242
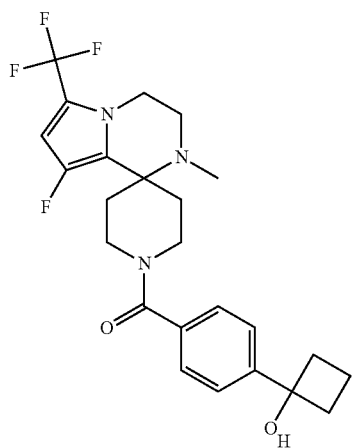
243
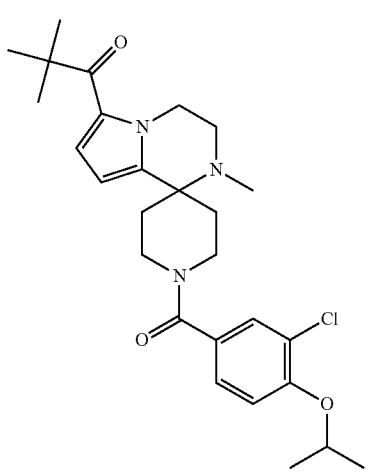
244
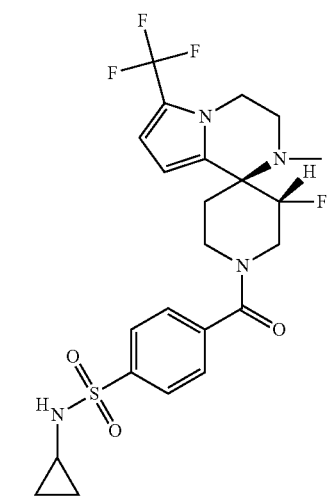
-continued
245
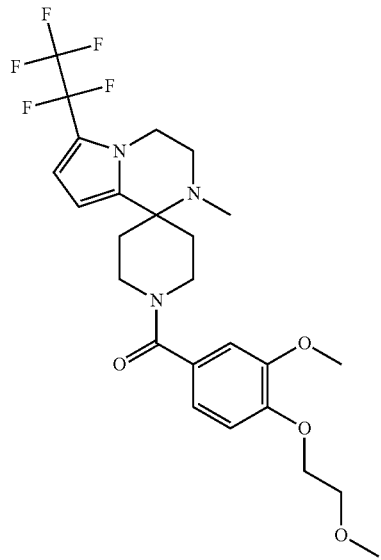 [SMILES: COCCOc1ccc(C(=O)N2CCC3(CC2)c2ccc(C(F)(F)C(F)(F)F)n2CCN3C)cc1OC]
246
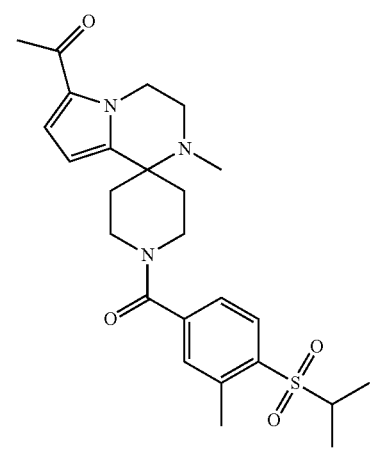 [SMILES: CC(=O)c1ccc2n1CCN(C)C21CCN(C(=O)c2ccc(S(=O)(=O)C(C)C)c(C)c2)CC1]
247
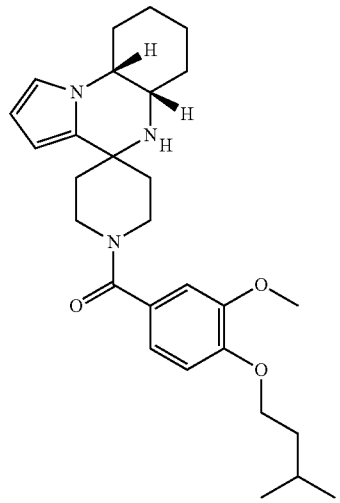

| 248 | 251 |
|---|---|
| 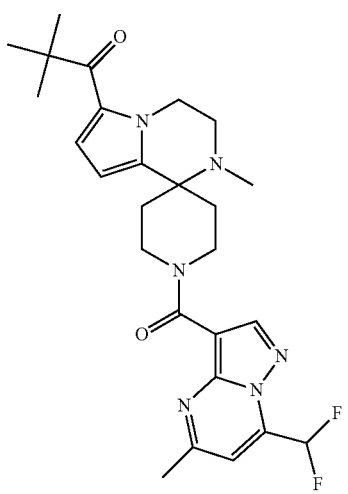 [SMILES: Cc1cc(C(F)F)n2ncc(C(=O)N3CCC4(CC3)c3ccc(C(=O)C(C)(C)C)n3CCN4C)c2n1] | 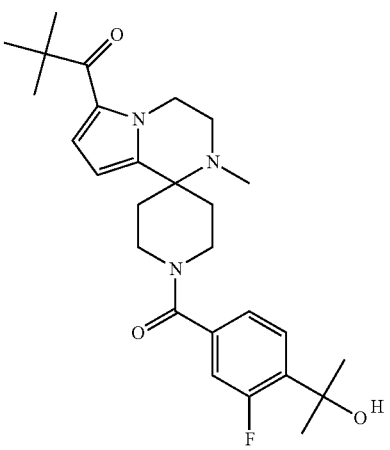 |
| 249 | 252 |
| 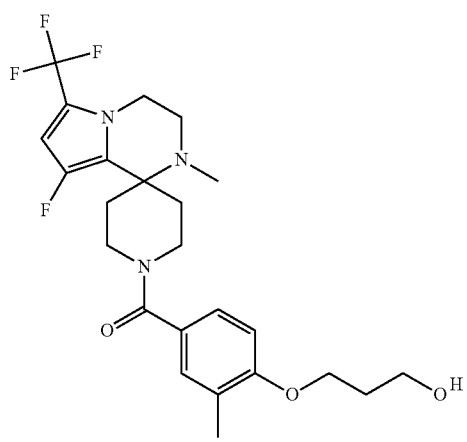 | 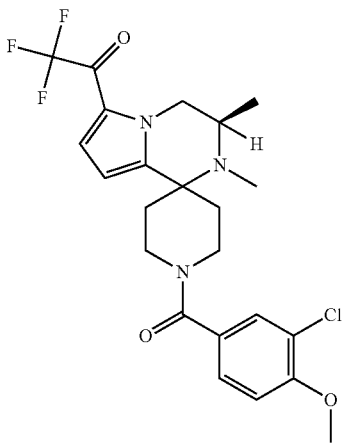 |
| 250 | 253 |
| 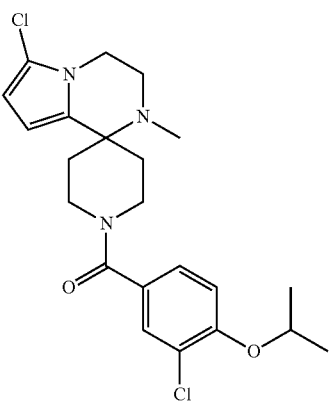 [SMILES: CC(C)Oc1ccc(C(=O)N2CCC3(CC2)c2ccc(Cl)n2CCN3C)cc1Cl] | 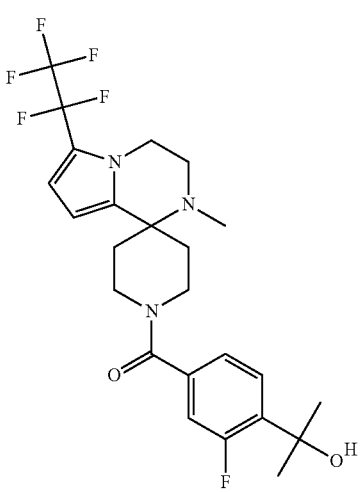 |

-continued
254
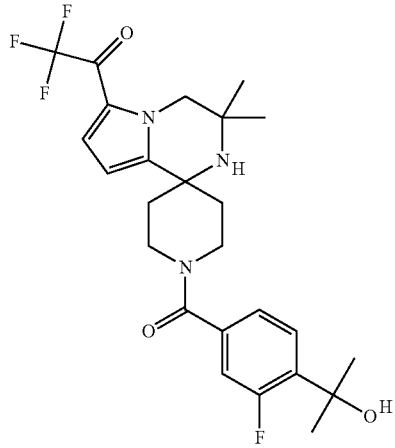
255
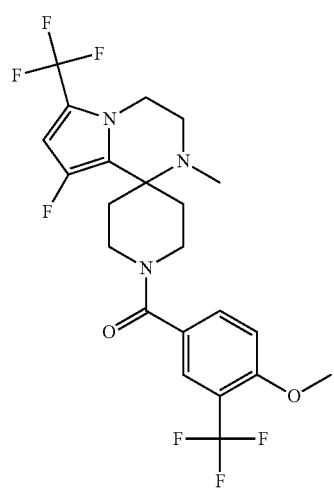 [SMILES: COc1ccc(C(=O)N2CCC3(CC2)c2c(F)cc(C(F)(F)F)n2CCN3C)cc1C(F)(F)F]
256
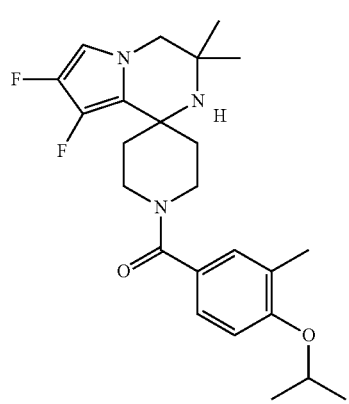
-continued
257
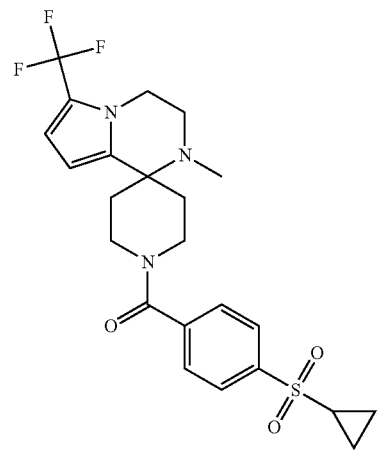 [SMILES: CN1CCn2c(C(F)(F)F)ccc2C12CCN(C(=O)c1ccc(S(=O)(=O)C3CC3)cc1)CC2]
258
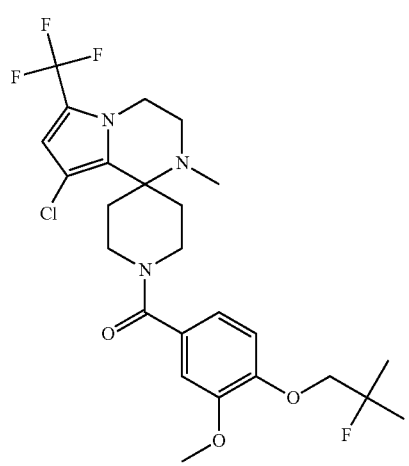 [SMILES: COc1cc(C(=O)N2CCC3(CC2)c2c(Cl)cc(C(F)(F)F)n2CCN3C)ccc1OCC(C)(C)F]
259
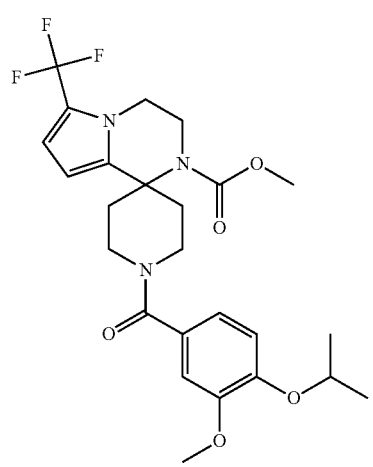 [SMILES: COC(=O)N1CCn2c(C(F)(F)F)ccc2C12CCN(C(=O)c1ccc(OC(C)C)c(OC)c1)CC2]

260
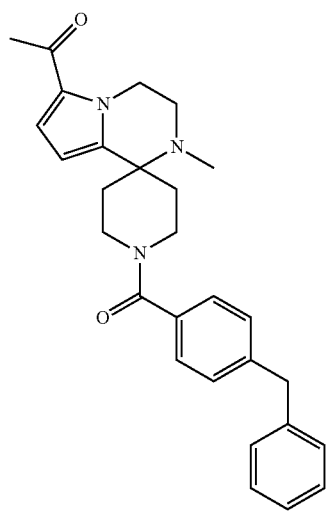 [SMILES: CC(=O)c1ccc2n1CCN(C)C21CCN(C(=O)c2ccc(Cc3ccccc3)cc2)CC1]
261
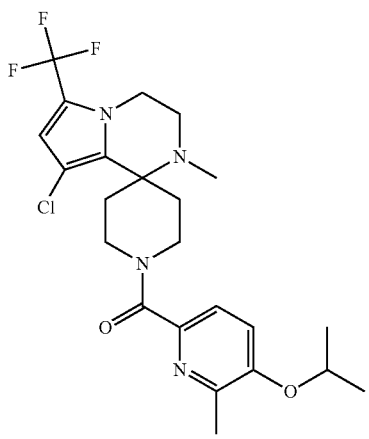 [SMILES: Cc1nc(C(=O)N2CCC3(CC2)c2c(Cl)cc(C(F)(F)F)n2CCN3C)ccc1OC(C)C]
262
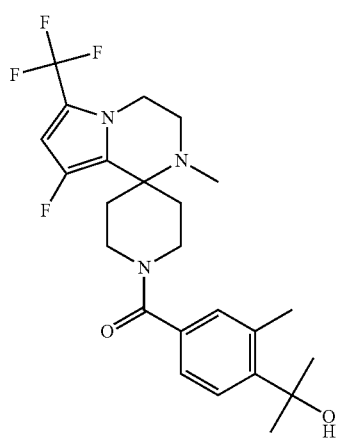
263
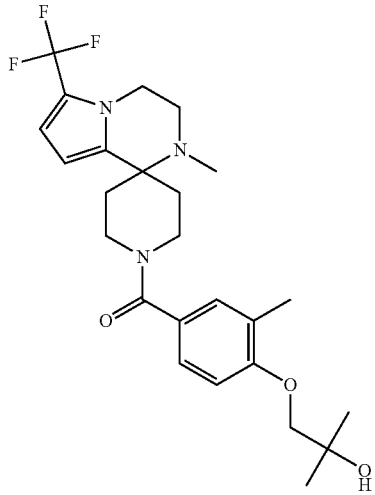
264
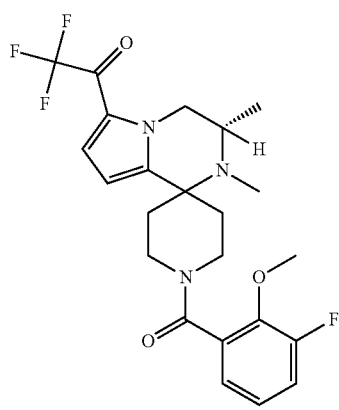 [SMILES: COc1c(F)cccc1C(=O)N1CCC2(CC1)c1ccc(C(=O)C(F)(F)F)n1C[C@H](C)N2C]
265
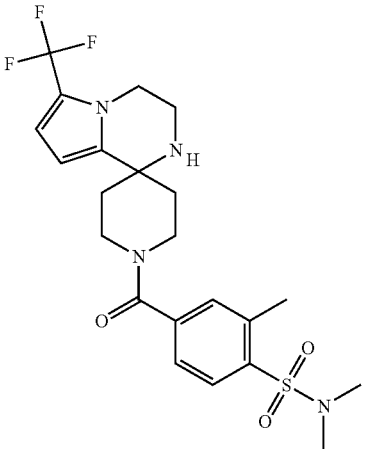

266 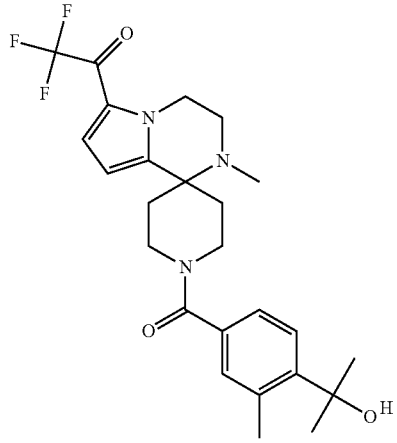
267 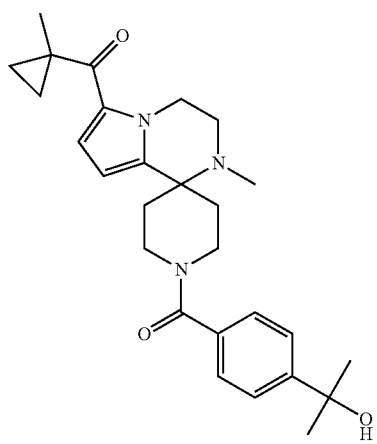 [SMILES: CN1CCn2c(C(=O)C3(C)CC3)ccc2C12CCN(C(=O)c1ccc(C(C)(C)O)cc1)CC2]
268 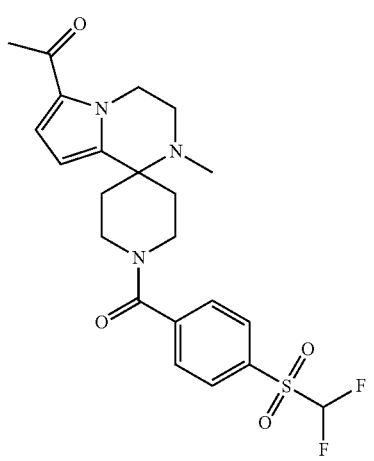 [SMILES: CC(=O)c1ccc2n1CCN(C)C21CCN(C(=O)c2ccc(S(=O)(=O)C(F)F)cc2)CC1]
269 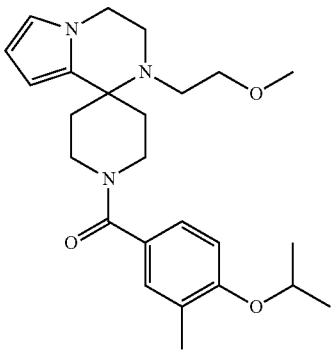 [SMILES: COCCN1CCn2cccc2C12CCN(C(=O)c1ccc(OC(C)C)c(C)c1)CC2]
270 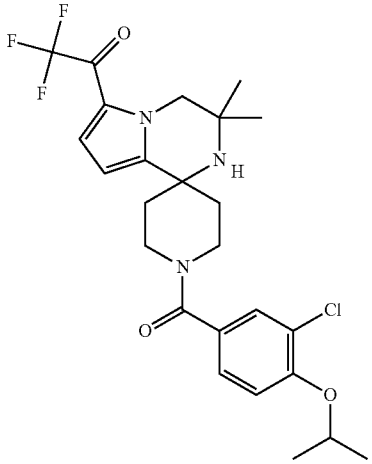
271 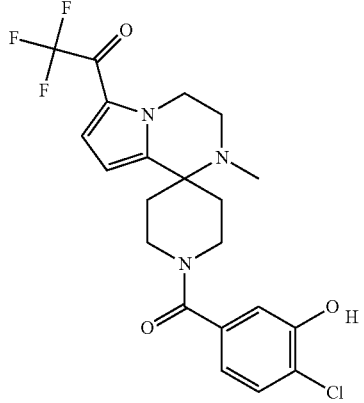
272 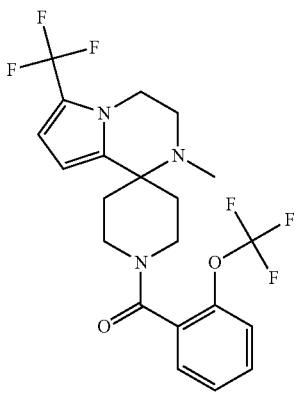 [SMILES: CN1CCn2c(C(F)(F)F)ccc2C12CCN(C(=O)c1ccccc1OC(F)(F)F)CC2]

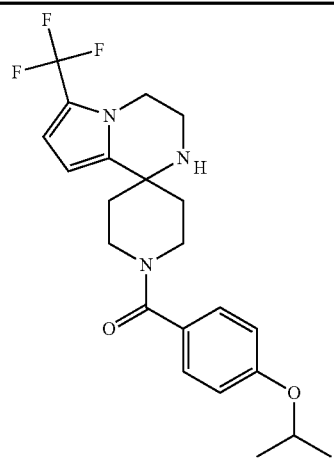
273
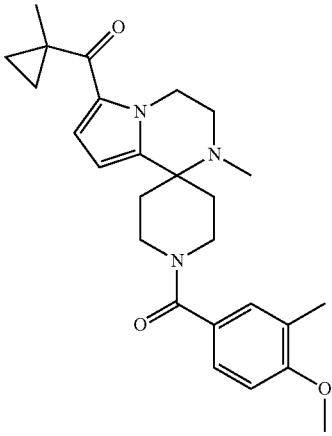
276
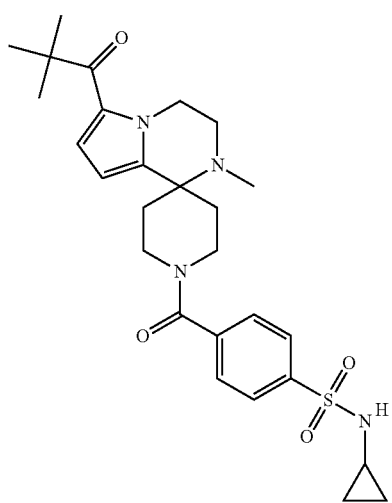
274
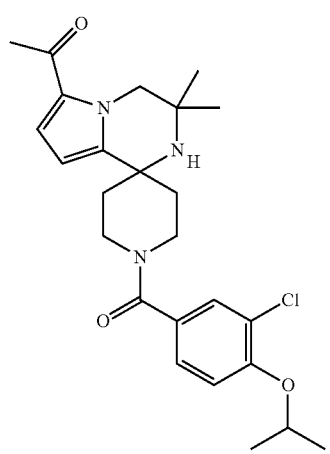
277
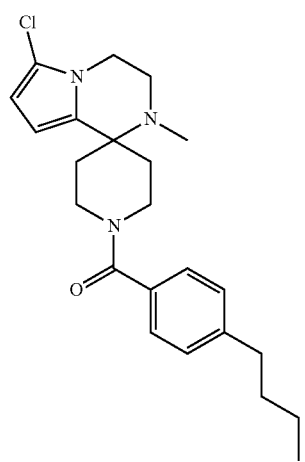 [SMILES: CCCCc1ccc(C(=O)N2CCC3(CC2)c2ccc(Cl)n2CCN3C)cc1]
275
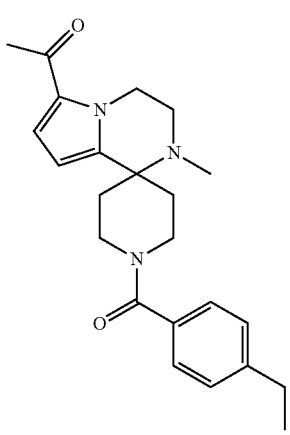 [SMILES: CCc1ccc(C(=O)N2CCC3(CC2)c2ccc(C(C)=O)n2CCN3C)cc1]
278

279 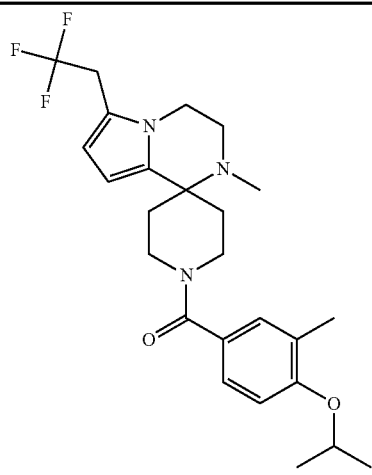
280 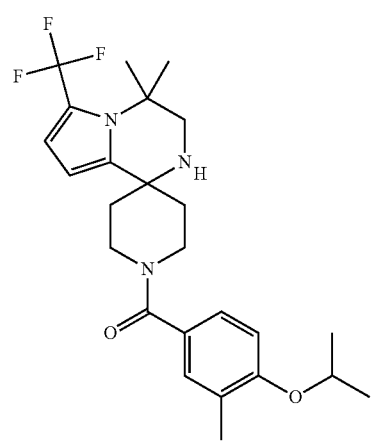
281 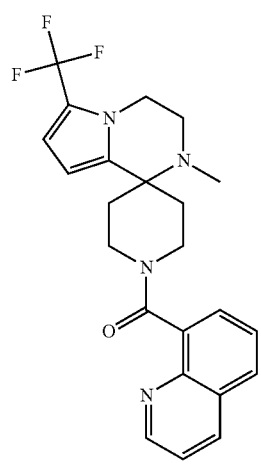 [SMILES: CN1CCn2c(C(F)(F)F)ccc2C12CCN(C(=O)c1cccc3cccnc13)CC2]
282 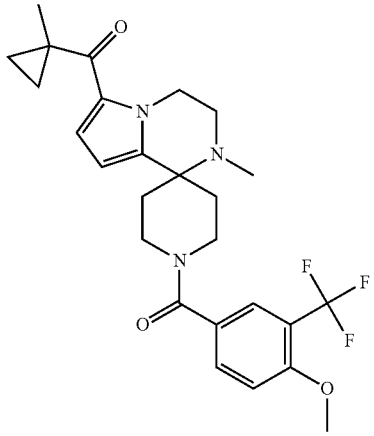 [SMILES: COc1ccc(C(=O)N2CCC3(CC2)c2ccc(C(=O)C4(C)CC4)n2CCN3C)cc1C(F)(F)F]
283 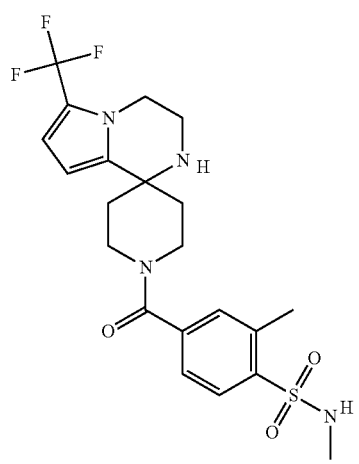
284 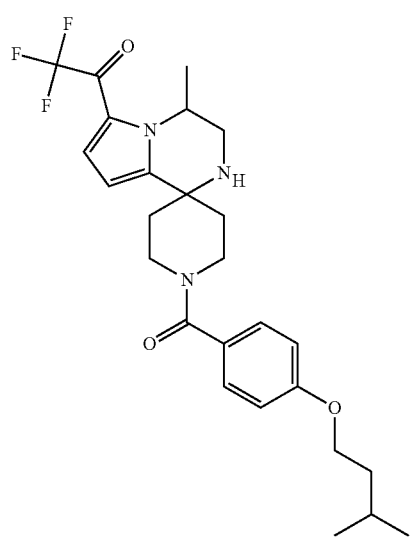

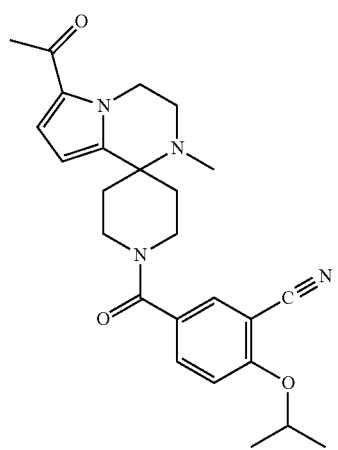 [SMILES: CC(=O)c1ccc2n1CCN(C)C21CCN(C(=O)c2ccc(OC(C)C)c(C#N)c2)CC1]
285
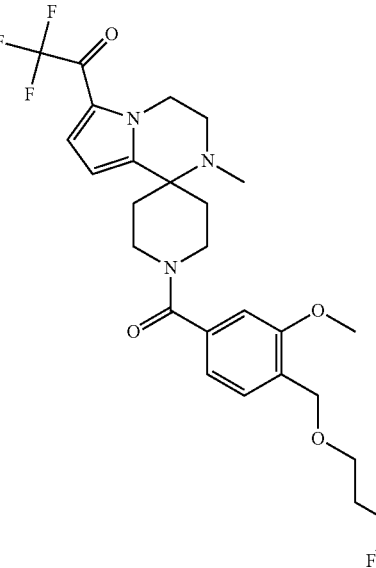
288
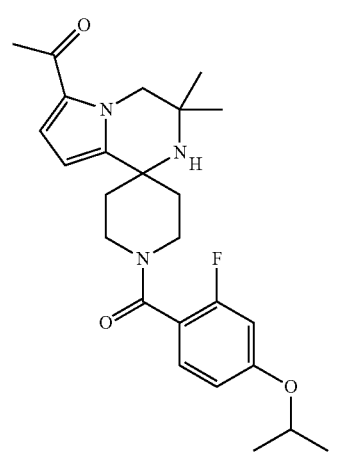
286
289
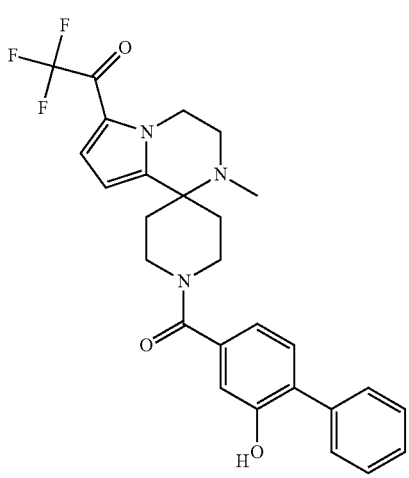
287
290

| 291 | 294 |
|---|---|
| 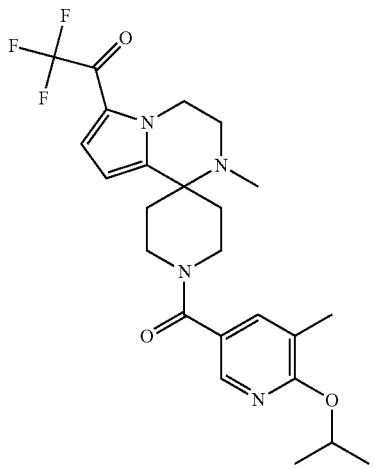 [SMILES: Cc1cc(C(=O)N2CCC3(CC2)c2ccc(C(=O)C(F)(F)F)n2CCN3C)cnc1OC(C)C] | 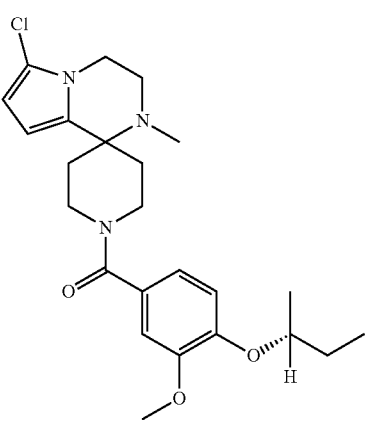 [SMILES: CC[C@@H](C)Oc1ccc(C(=O)N2CCC3(CC2)c2ccc(Cl)n2CCN3C)cc1OC] |
| 292 | 295 |
|---|---|
| 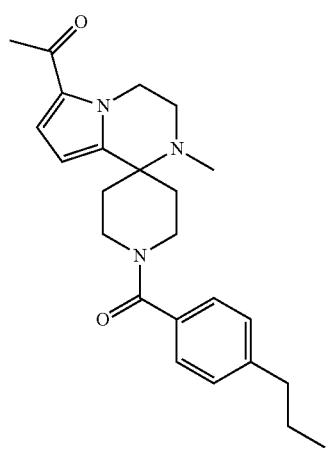 | 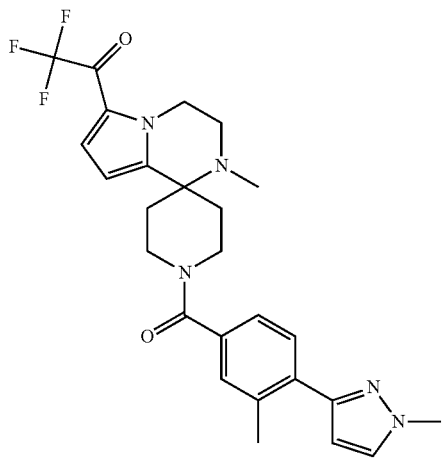 [SMILES: Cc1cc(C(=O)N2CCC3(CC2)c2ccc(C(=O)C(F)(F)F)n2CCN3C)ccc1-c1ccn(C)n1] |
| 293 | 296 |
|---|---|
| 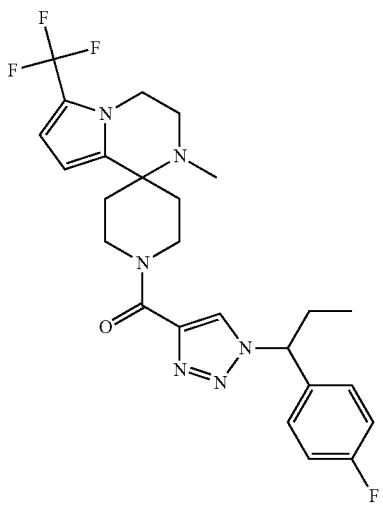 | 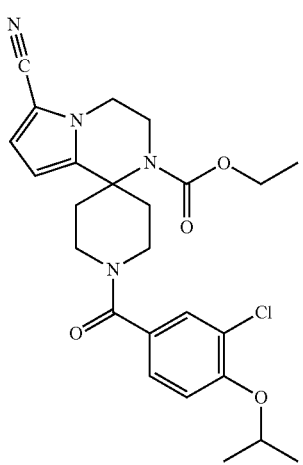 [SMILES: CCOC(=O)N1CCn2c(C#N)ccc2C12CCN(C(=O)c1ccc(OC(C)C)c(Cl)c1)CC2] |

| 143 -continued | 144 -continued |
|---|---|
| 297 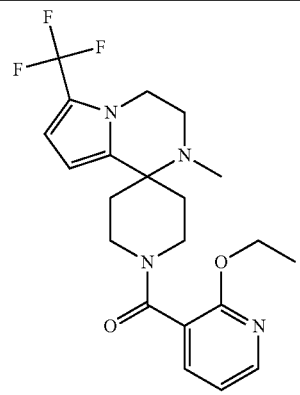 | 300 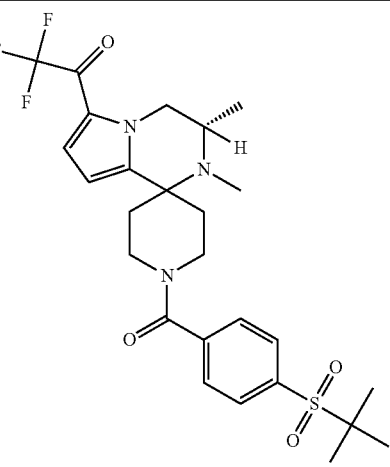 |
| 298 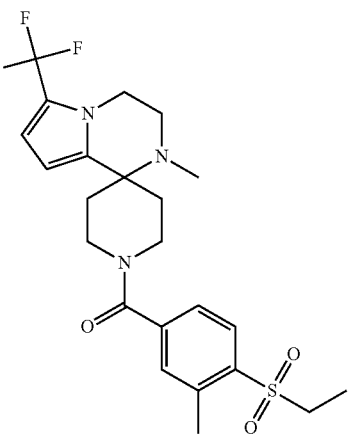 | 301 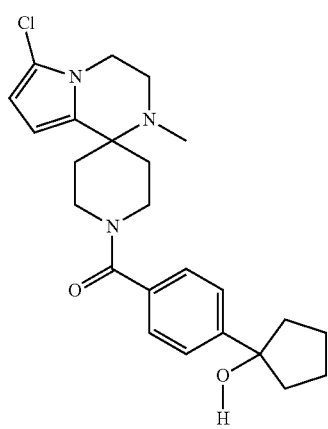 [SMILES: CN1CCn2c(Cl)ccc2C12CCN(C(=O)c1ccc(C3(O)CCCC3)cc1)CC2] |
| 299 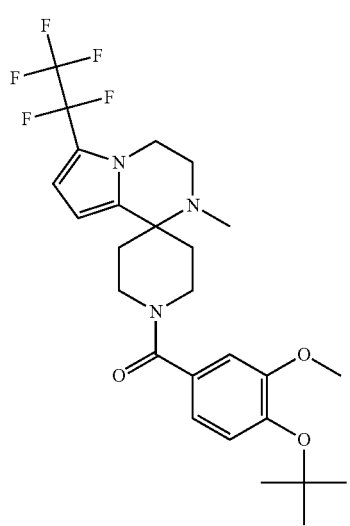 | 302 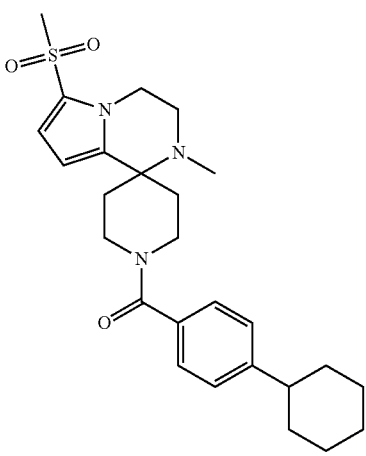 [SMILES: CN1CCn2c(ccc2S(C)(=O)=O)C12CCN(C(=O)c1ccc(C3CCCCC3)cc1)CC2] |

| 145 -continued | 146 -continued |
|---|---|
| 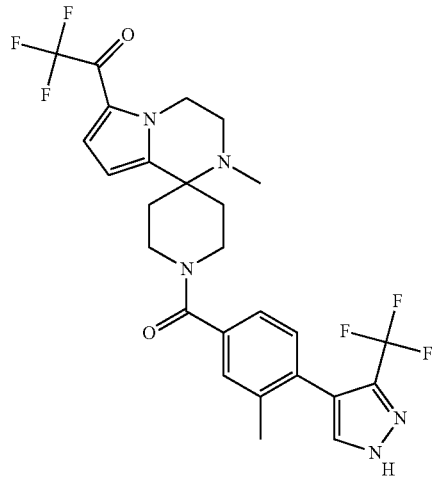 303 | 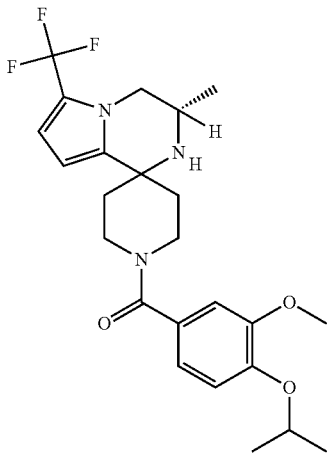 306 |
| 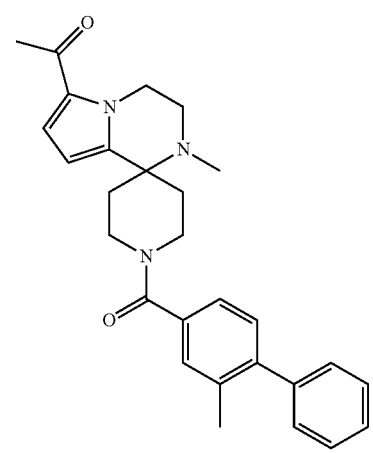 [SMILES: CC(=O)c1ccc2n1CCN(C)C21CCN(C(=O)c2ccc(-c3ccccc3)c(C)c2)CC1] 304 | 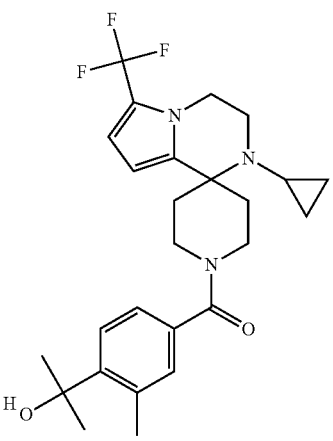 307 |
| 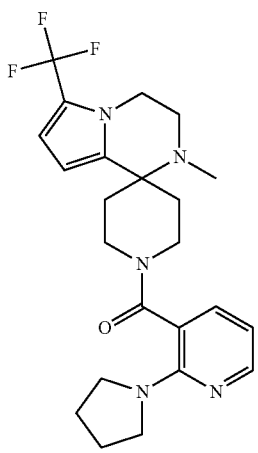 [SMILES: CN1CCn2c(C(F)(F)F)ccc2C12CCN(C(=O)c1cccnc1N1CCCC1)CC2] 305 | 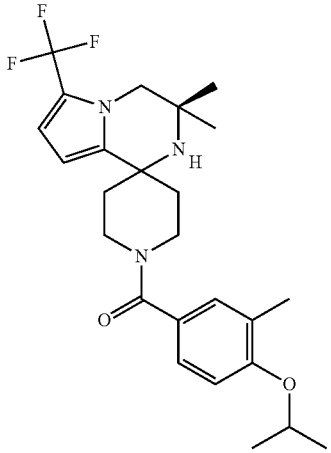 308 |

| 147 -continued | 148 -continued |
|---|---|
| 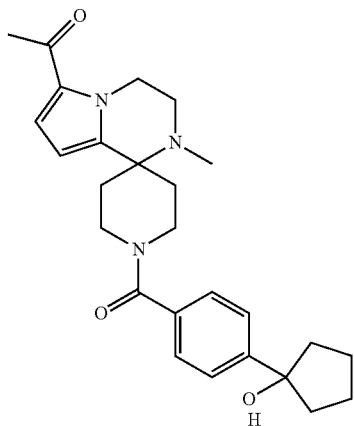 309 | 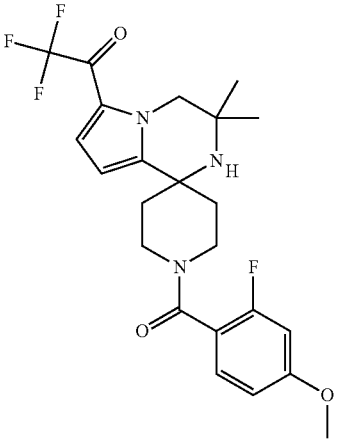 312 |
| 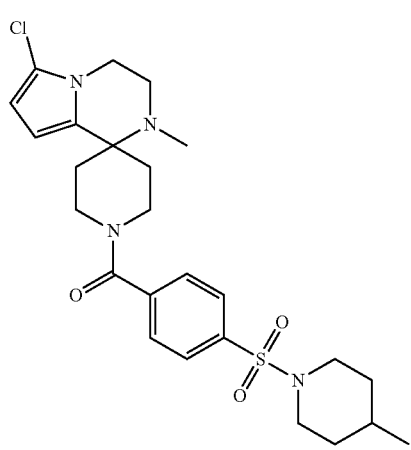 [SMILES: CC1CCN(S(=O)(=O)c2ccc(C(=O)N3CCC4(CC3)c3ccc(Cl)n3CCN4C)cc2)CC1] 310 | 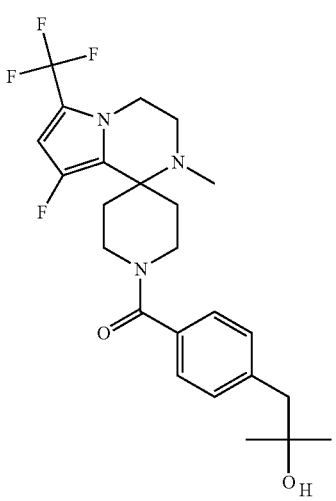 313 |
| 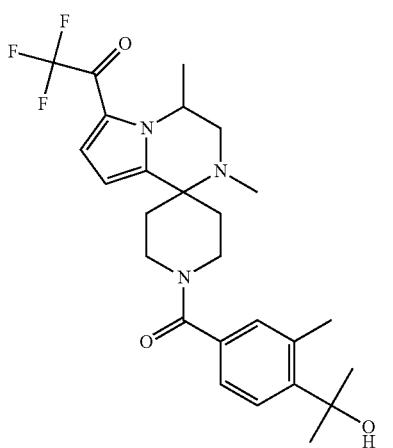 311 | 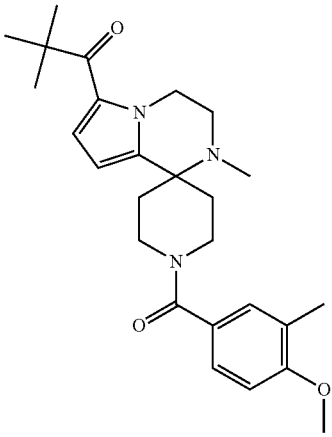 [SMILES: COc1ccc(C(=O)N2CCC3(CC2)c2ccc(C(=O)C(C)(C)C)n2CCN3C)cc1C] 314 |

| 149 -continued | 150 -continued |
|---|---|
| 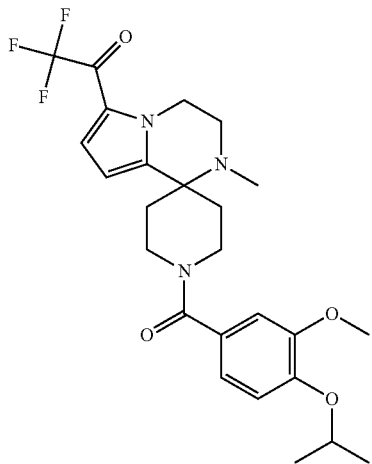 [SMILES: COc1cc(C(=O)N2CCC3(CC2)c2ccc(C(=O)C(F)(F)F)n2CCN3C)ccc1OC(C)C] 315 | 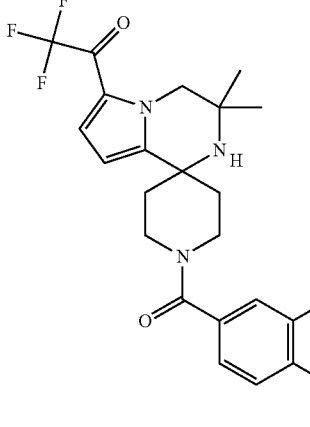 318 |
| 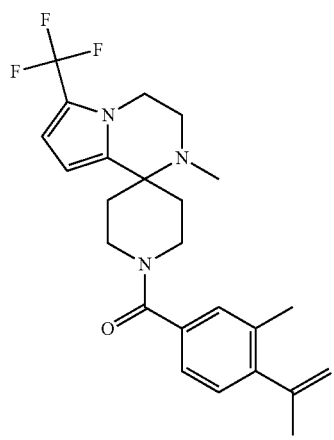 [SMILES: C=C(C)c1ccc(C(=O)N2CCC3(CC2)c2ccc(C(F)(F)F)n2CCN3C)cc1C] 316 | 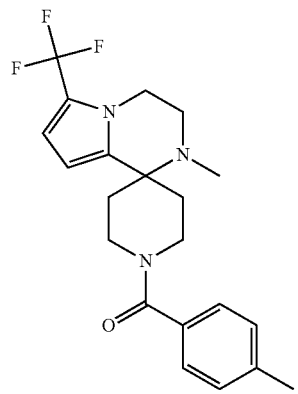 319 |
| 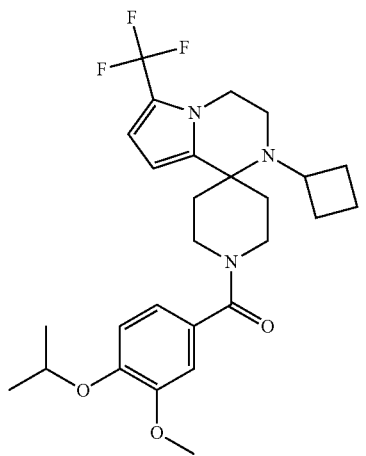 [SMILES: COc1cc(C(=O)N2CCC3(CC2)c2ccc(C(F)(F)F)n2CCN3C2CCC2)ccc1OC(C)C] 317 | 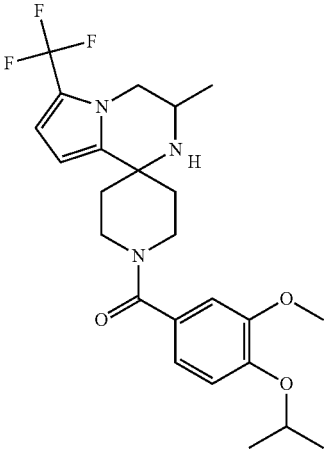 320 |

| 321 | 324 |
|---|---|
| 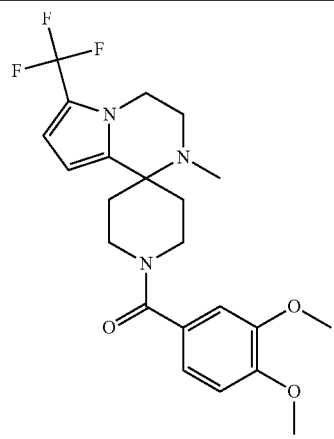 | 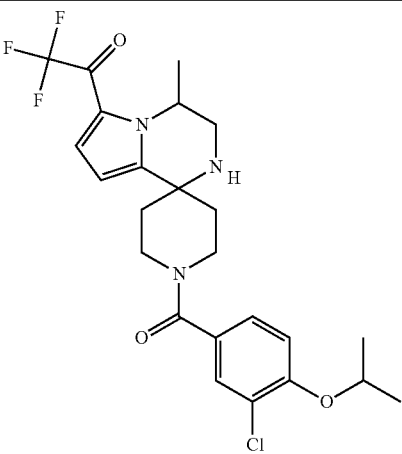 |
| 322 | 325 |
| 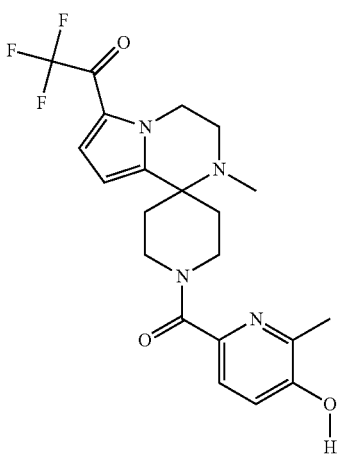 [SMILES: Cc1nc(C(=O)N2CCC3(CC2)c2ccc(C(=O)C(F)(F)F)n2CCN3C)ccc1O] | 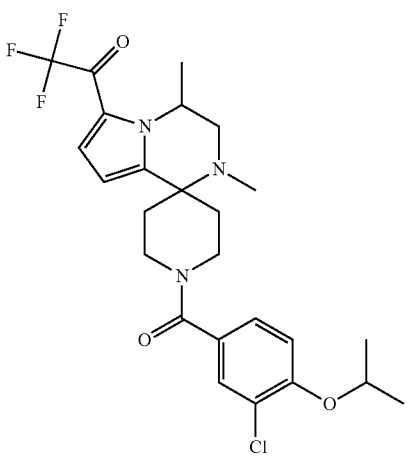 |
| 323 | 326 |
| 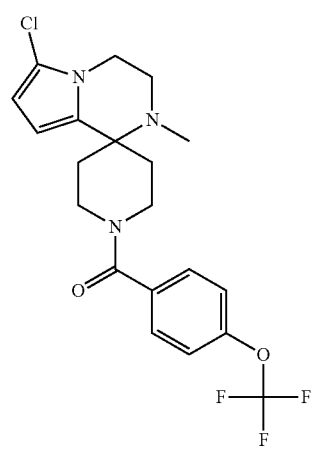 [SMILES: CN1CCn2c(Cl)ccc2C12CCN(C(=O)c1ccc(OC(F)(F)F)cc1)CC2] | 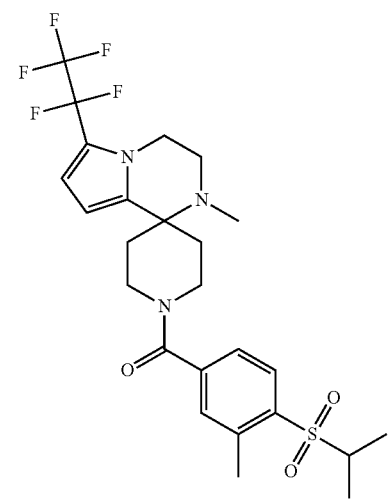 [SMILES: Cc1cc(C(=O)N2CCC3(CC2)c2ccc(C(F)(F)C(F)(F)F)n2CCN3C)ccc1S(=O)(=O)C(C)C] |

153
-continued
327 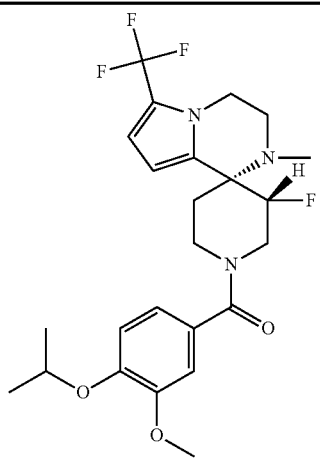
328 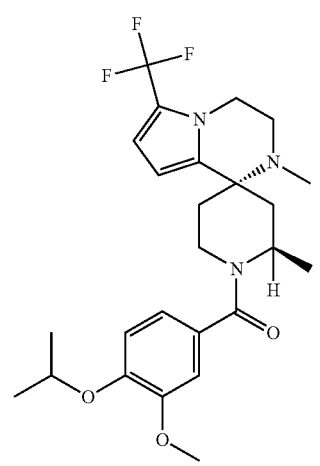 [SMILES: COc1cc(C(=O)N2CC[C@]3(C[C@H]2C)c2ccc(C(F)(F)F)n2CCN3C)ccc1OC(C)C]
329 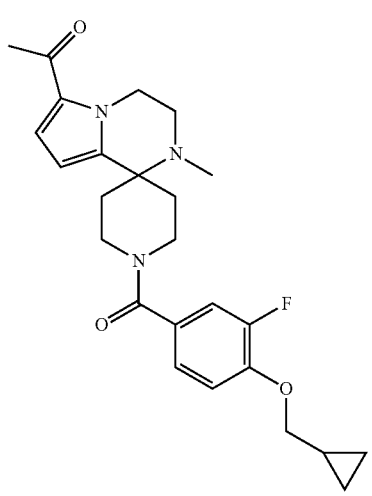 [SMILES: CC(=O)c1ccc2n1CCN(C)C21CCN(C(=O)c2ccc(OCC3CC3)c(F)c2)CC1]
154
-continued
330 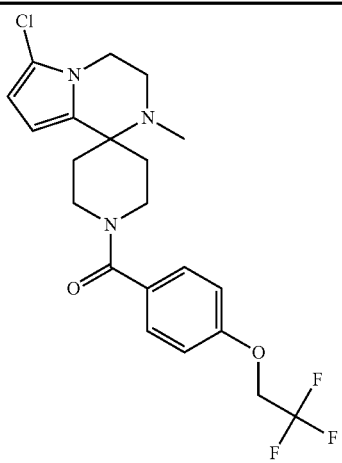
331 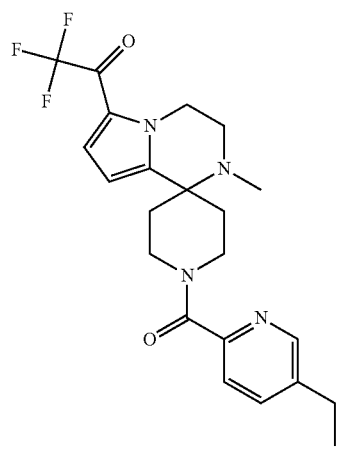 [SMILES: CCc1ccc(C(=O)N2CCC3(CC2)c2ccc(C(=O)C(F)(F)F)n2CCN3C)nc1]
332 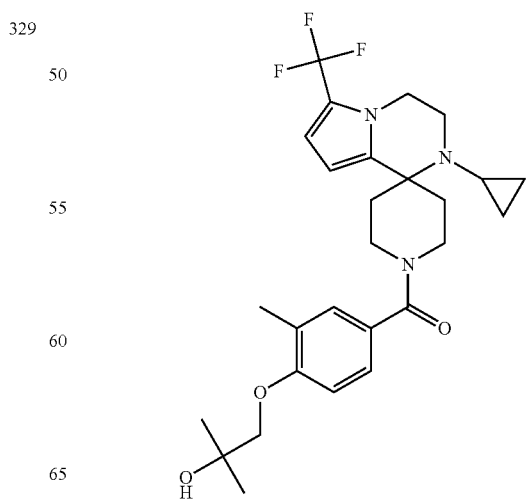

| 333 | 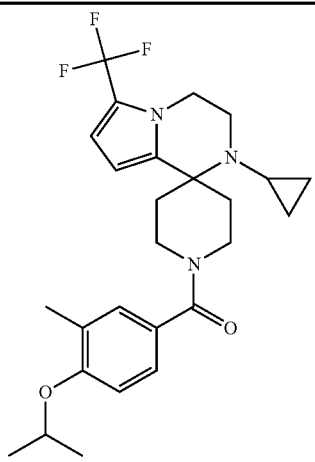 |
| 334 | 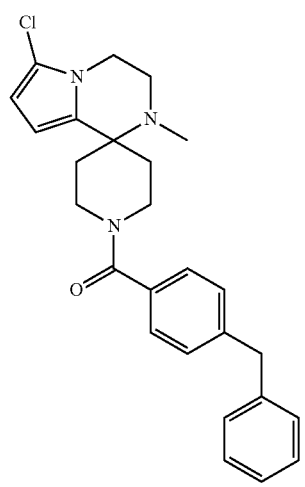 [SMILES: CN1CCn2c(Cl)ccc2C12CCN(C(=O)c1ccc(Cc3ccccc3)cc1)CC2] |
| 335 | 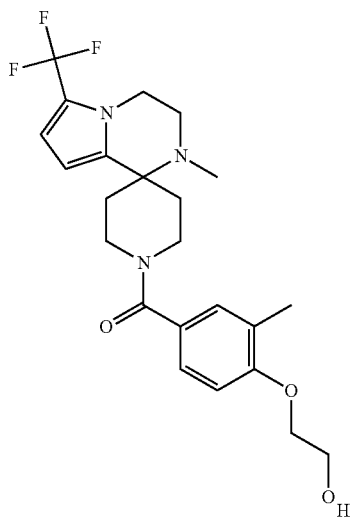 |
| 336 | 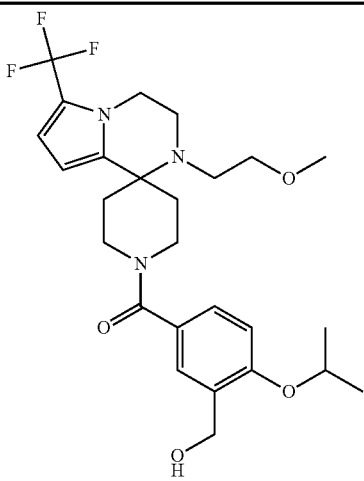 |
| 337 | 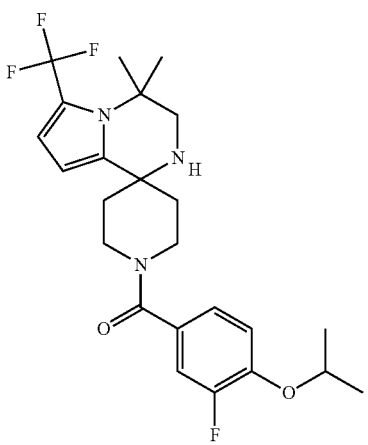 |
| 338 | 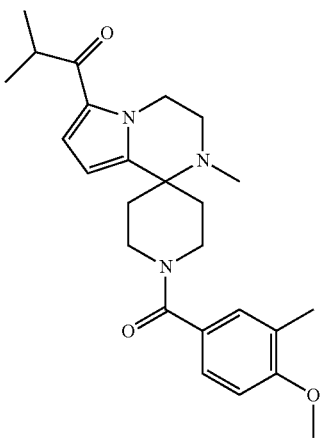 [SMILES: COc1ccc(C(=O)N2CCC3(CC2)c2ccc(C(=O)C(C)C)n2CCN3C)cc1C] |

339
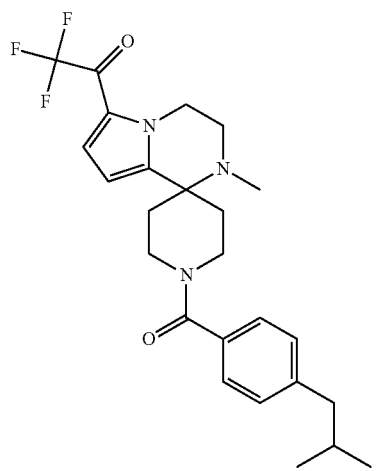 [SMILES: CC(C)Cc1ccc(C(=O)N2CCC3(CC2)c2ccc(C(=O)C(F)(F)F)n2CCN3C)cc1]
340
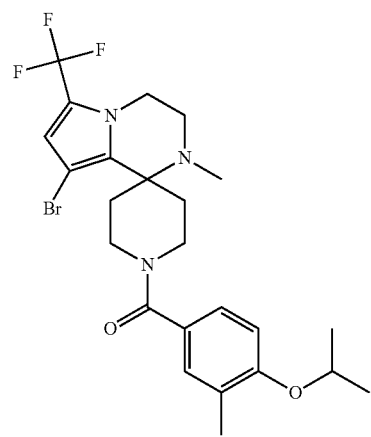
341
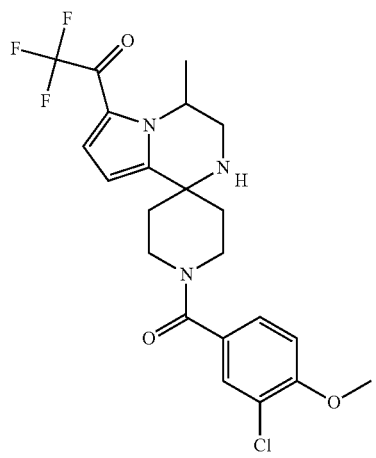
342
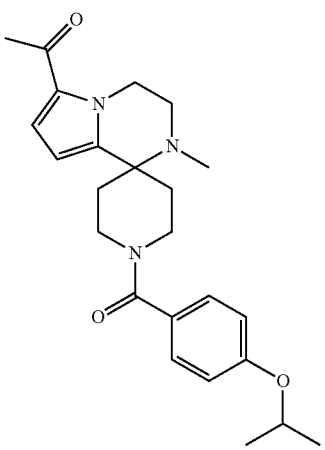 [SMILES: CC(=O)c1ccc2n1CCN(C)C21CCN(C(=O)c2ccc(OC(C)C)cc2)CC1]
343
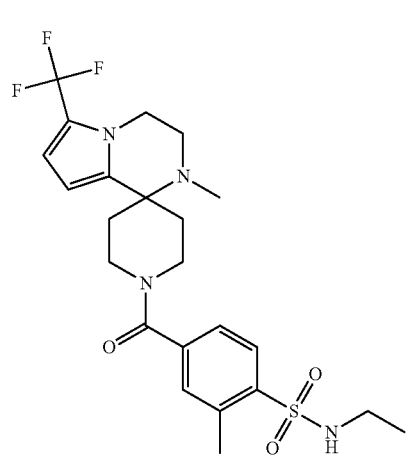 [SMILES: CCNS(=O)(=O)c1ccc(C(=O)N2CCC3(CC2)c2ccc(C(F)(F)F)n2CCN3C)cc1C]
344
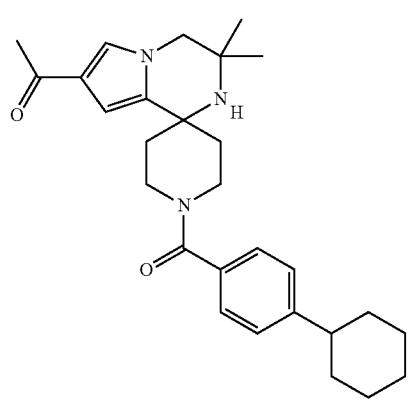

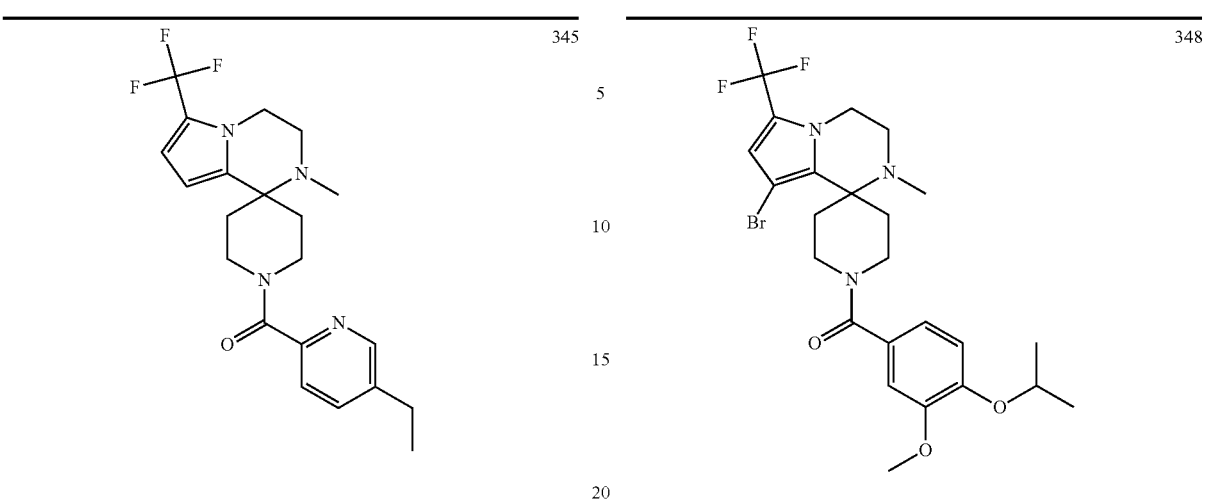
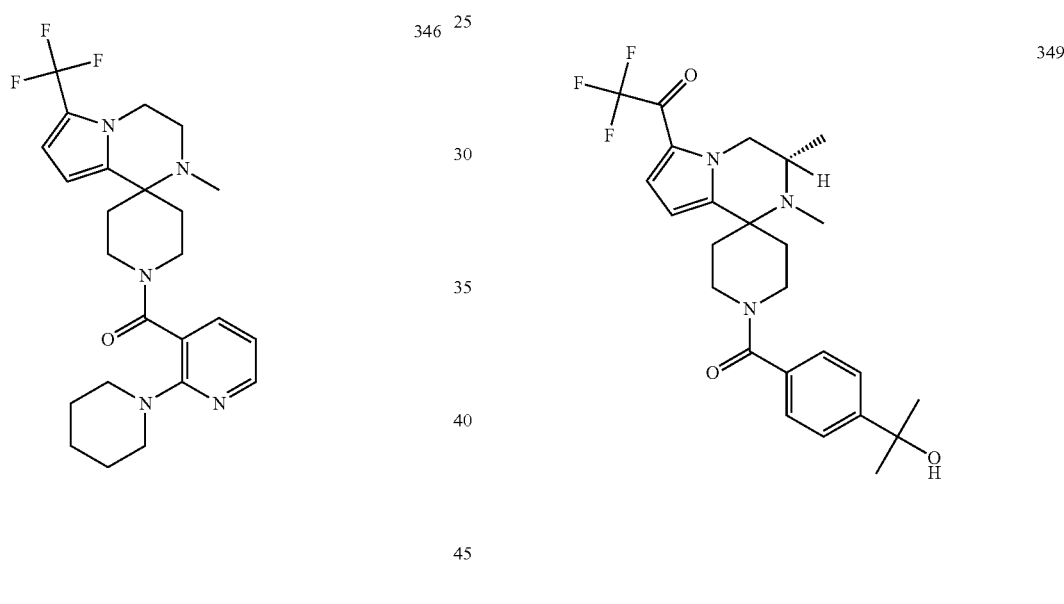
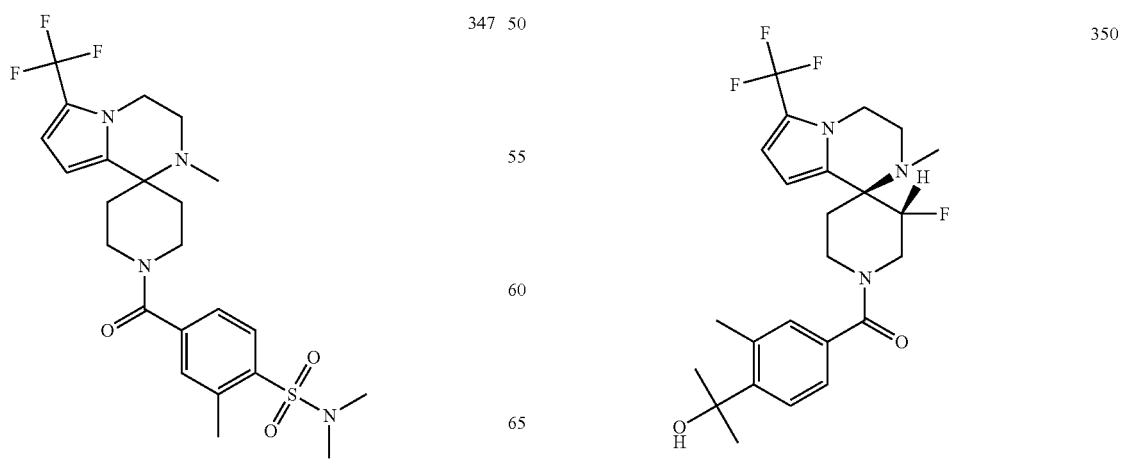

| | |
|---|---|
| 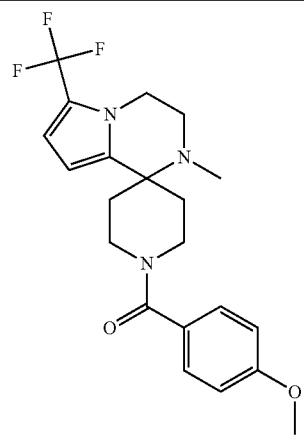 351 | 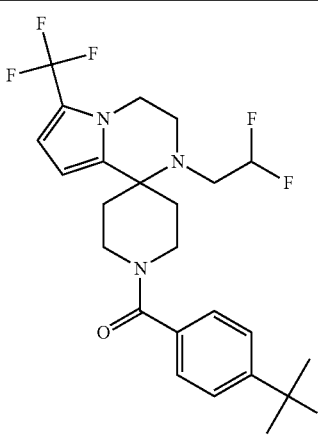 354 |
| 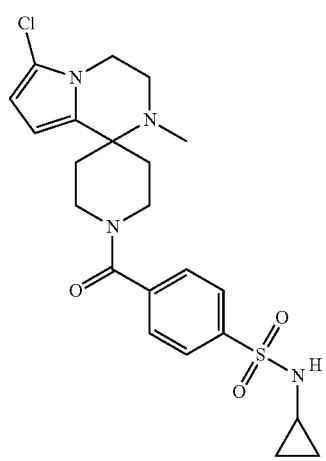 352 | 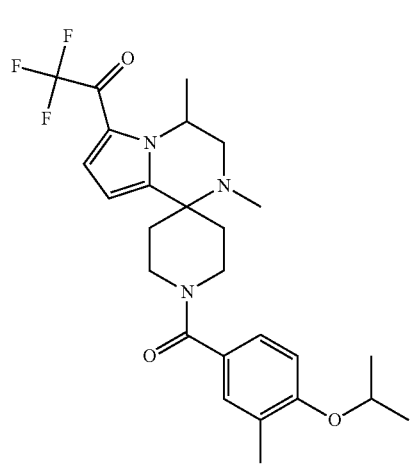 [SMILES: Cc1cc(C(=O)N2CCC3(CC2)c2ccc(C(=O)C(F)(F)F)n2C(C)CN3C)ccc1OC(C)C] 355 |
| 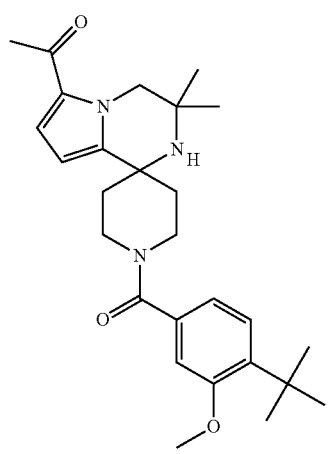 353 | 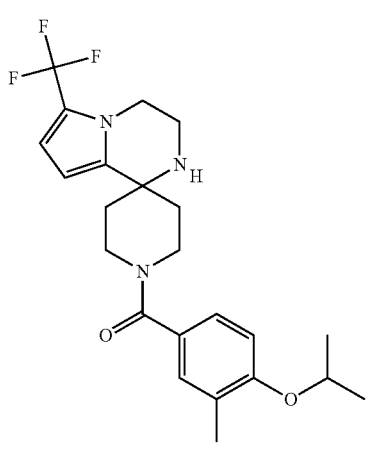 356 |

| 163 -continued | 164 -continued |
|---|---|
| 357 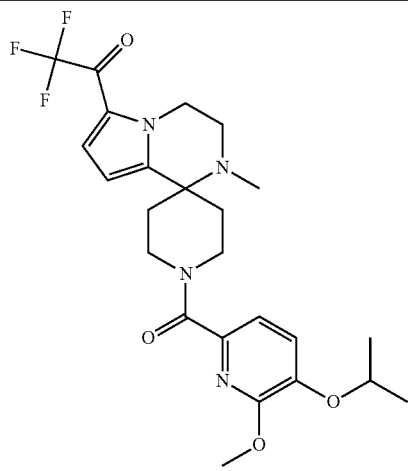 | 360 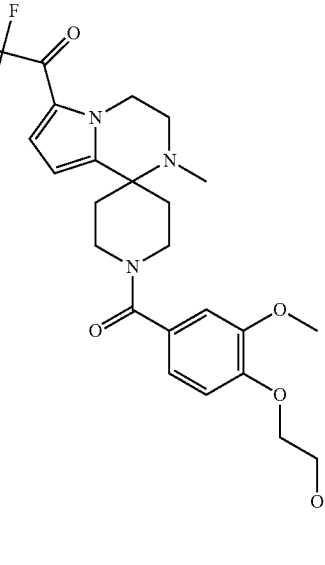 |
| 358 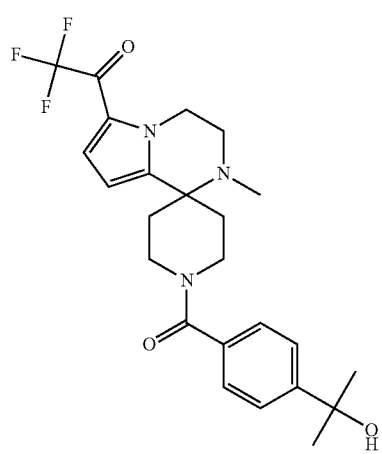 [SMILES: CN1CCn2c(C(=O)C(F)(F)F)ccc2C12CCN(C(=O)c1ccc(C(C)(C)O)cc1)CC2] | 361 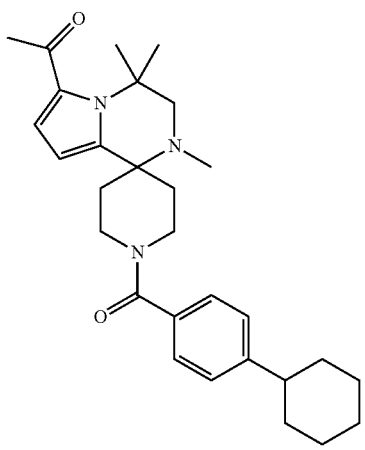 |
| 359 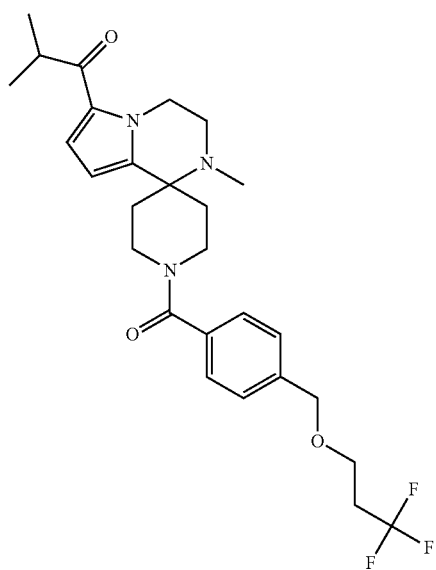 [SMILES: CC(C)C(=O)c1ccc2n1CCN(C)C21CCN(C(=O)c2ccc(COCCC(F)(F)F)cc2)CC1] | 362 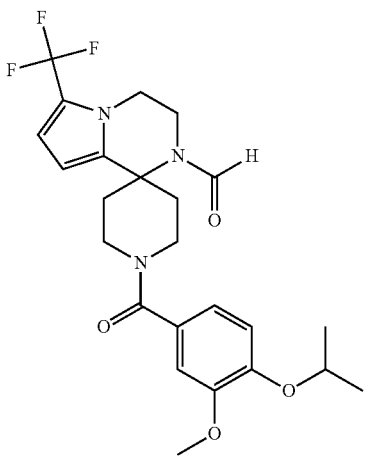 |

| 363 | 366 |
|---|---|
| 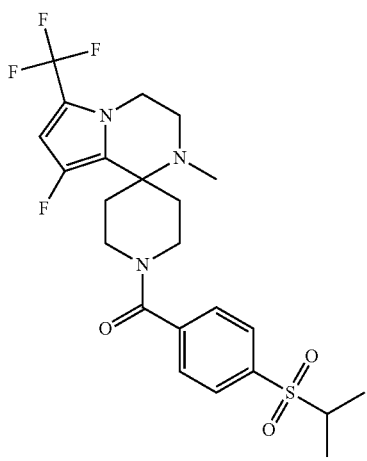 [SMILES: CC(C)S(=O)(=O)c1ccc(C(=O)N2CCC3(CC2)c2c(F)cc(C(F)(F)F)n2CCN3C)cc1] | 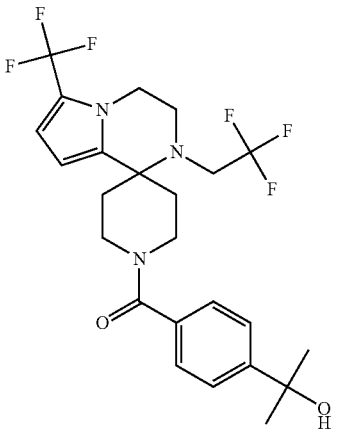 |
| 364 | 367 |
| 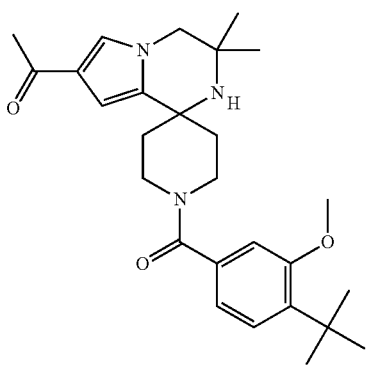 | |
| 365 | 368 |
| 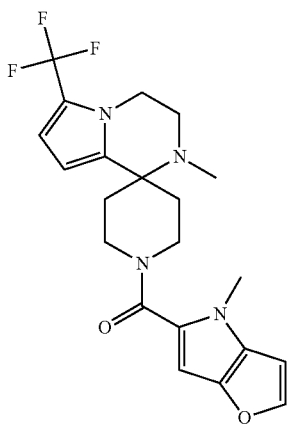 [SMILES: CN1CCn2c(C(F)(F)F)ccc2C12CCN(C(=O)c1cc3occc3n1C)CC2] | 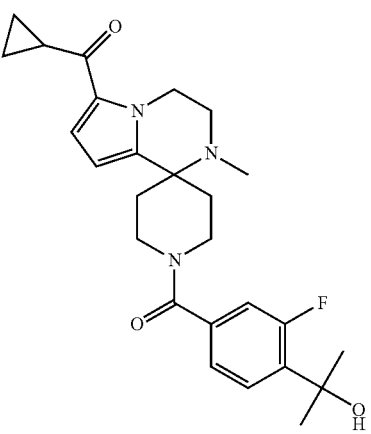 [SMILES: CN1CCn2c(C(=O)C3CC3)ccc2C12CCN(C(=O)c1ccc(C(C)(C)O)c(F)c1)CC2] |

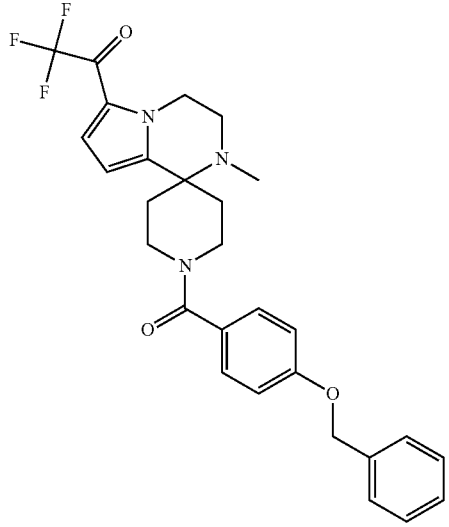 [SMILES: CN1CCn2c(C(=O)C(F)(F)F)ccc2C12CCN(C(=O)c1ccc(OCc3ccccc3)cc1)CC2]
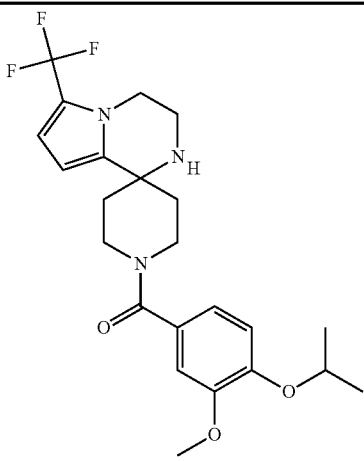
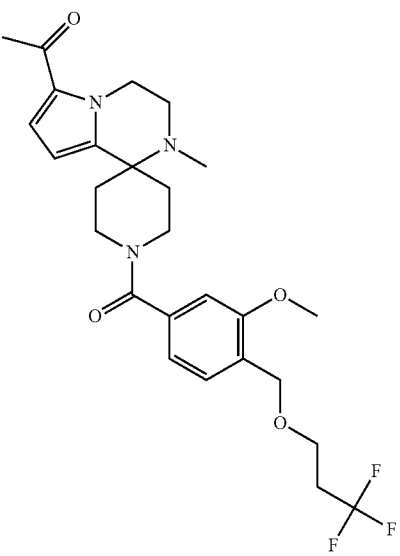 [SMILES: COc1cc(C(=O)N2CCC3(CC2)c2ccc(C(C)=O)n2CCN3C)ccc1COCCC(F)(F)F]
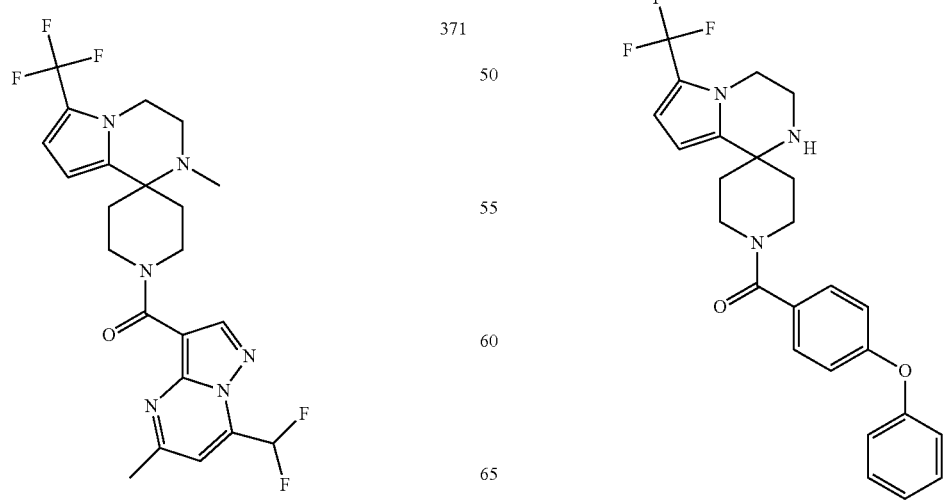

| 375 | 378 |
|---|---|
| 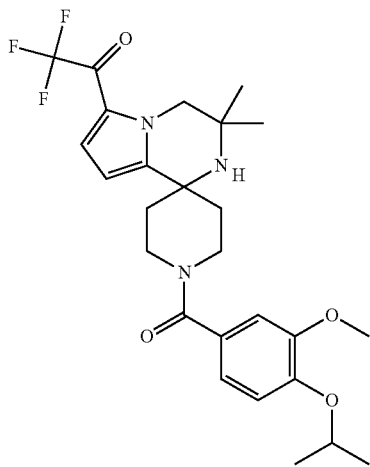 | 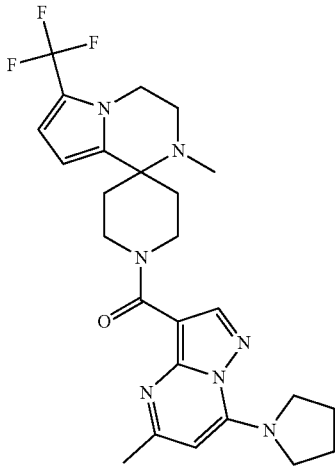 |
| 376 | 379 |
| 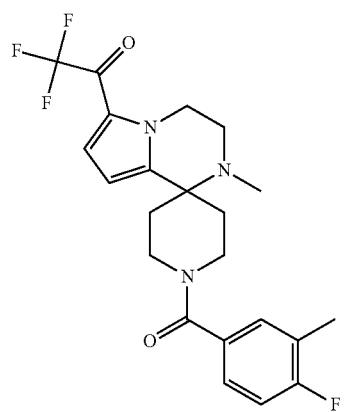 [SMILES: Cc1cc(C(=O)N2CCC3(CC2)c2ccc(C(=O)C(F)(F)F)n2CCN3C)ccc1F] | 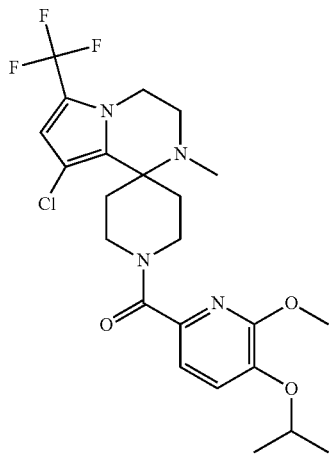 |
| 377 | 380 |
| 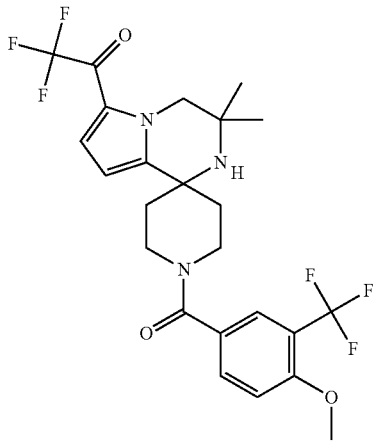 | 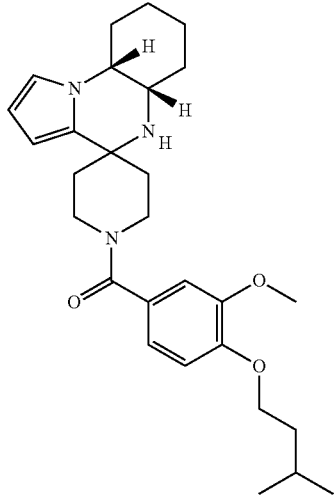 |

381
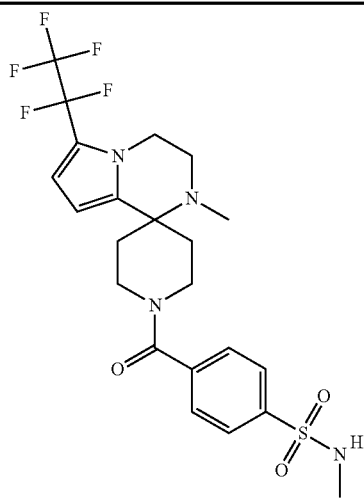
382
383
384
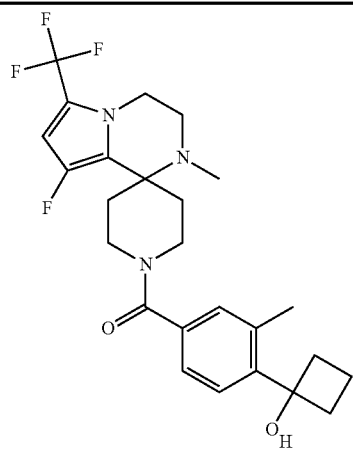
385
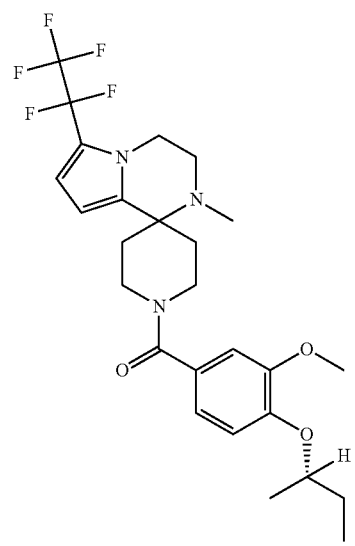 [SMILES: CC[C@H](C)Oc1ccc(C(=O)N2CCC3(CC2)c2ccc(C(F)(F)C(F)(F)F)n2CCN3C)cc1OC]
386
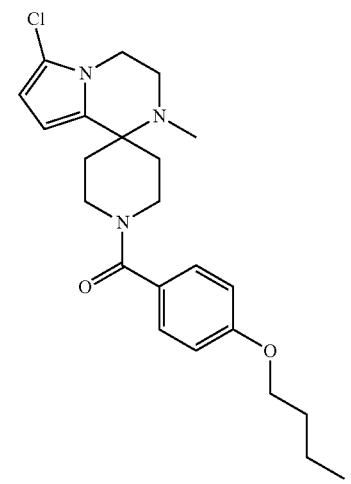 [SMILES: CCCCOc1ccc(C(=O)N2CCC3(CC2)c2ccc(Cl)n2CCN3C)cc1]

| 173 -continued | 174 -continued |
|---|---|
| 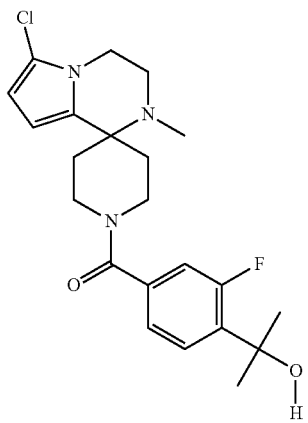 387 | 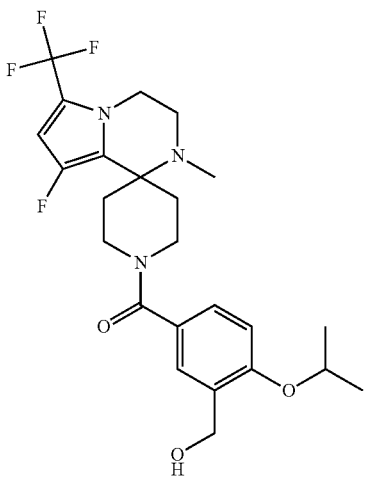 390 |
| 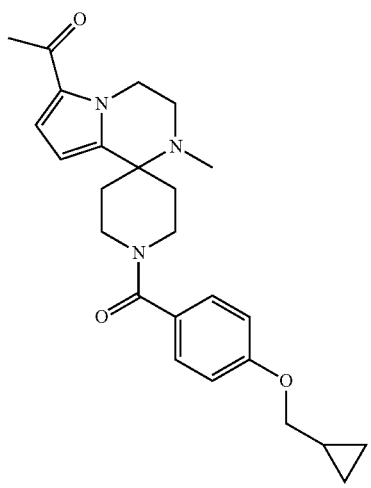 [SMILES: CC(=O)c1ccc2n1CCN(C)C21CCN(C(=O)c2ccc(OCC3CC3)cc2)CC1] 388 | 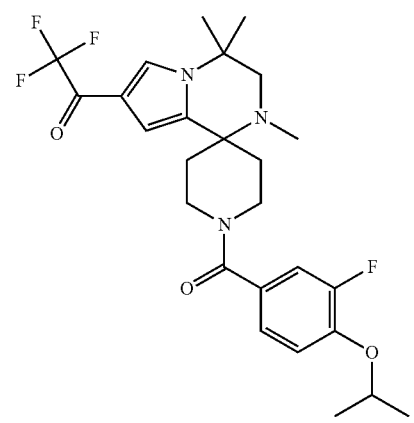 391 |
| 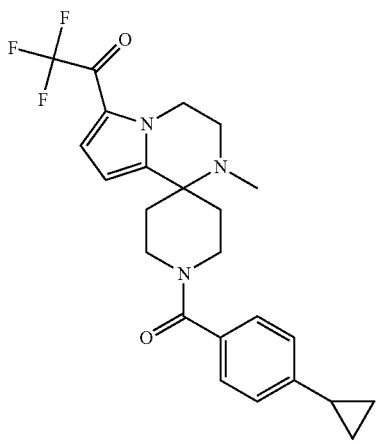 [SMILES: CN1CCn2c(C(=O)C(F)(F)F)ccc2C12CCN(C(=O)c1ccc(C3CC3)cc1)CC2] 389 | 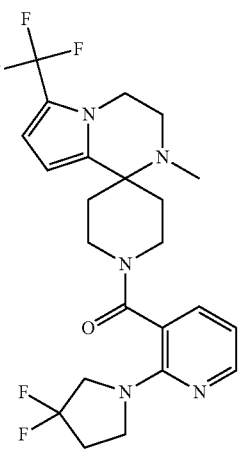 392 |

| 393 | 396 |
|---|---|
| 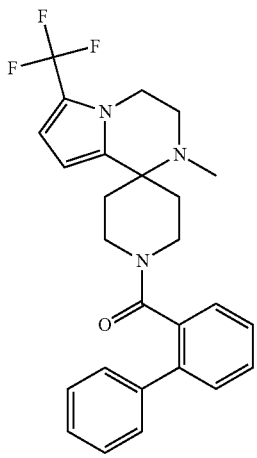 [SMILES: CN1CCn2c(C(F)(F)F)ccc2C12CCN(C(=O)c1ccccc1-c1ccccc1)CC2] | 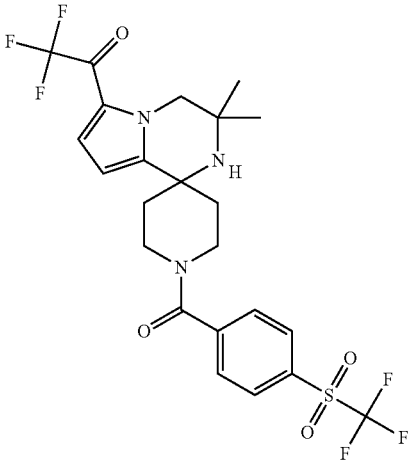 |
| 394 | 397 |
|---|---|
| 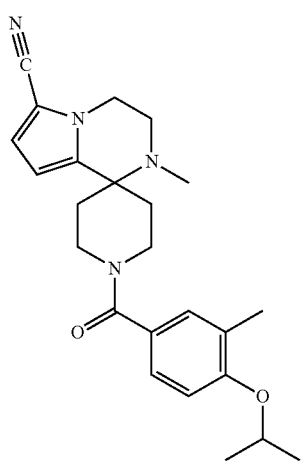 [SMILES: Cc1cc(C(=O)N2CCC3(CC2)c2ccc(C#N)n2CCN3C)ccc1OC(C)C] | 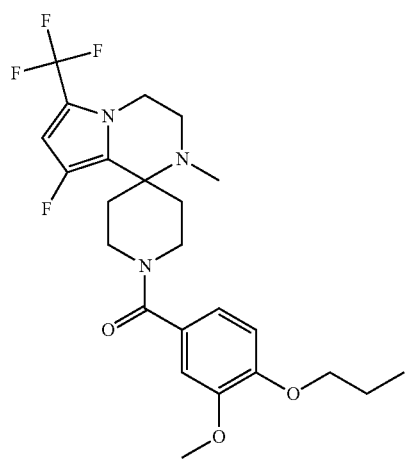 |
| 395 | 398 |
|---|---|
| 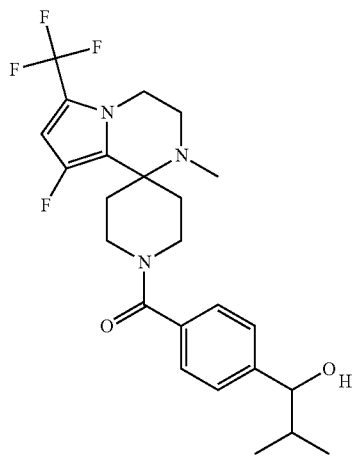 | 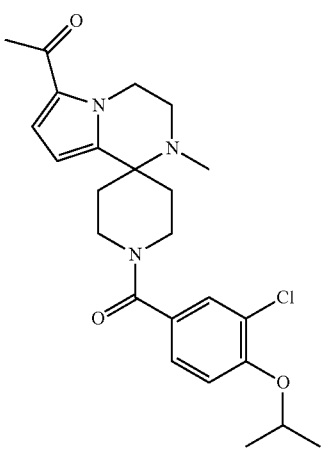 |

| 177 -continued | 178 -continued |
|---|---|
| 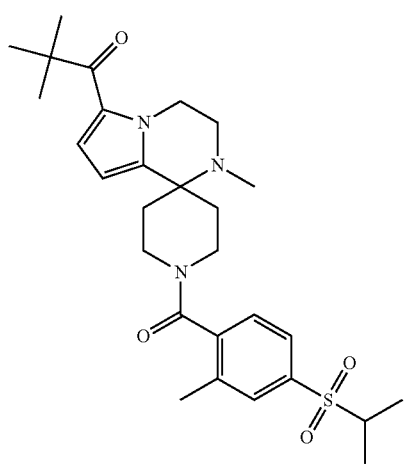 [SMILES: Cc1cc(S(=O)(=O)C(C)C)ccc1C(=O)N1CCC2(CC1)c1ccc(C(=O)C(C)(C)C)n1CCN2C] 399 | 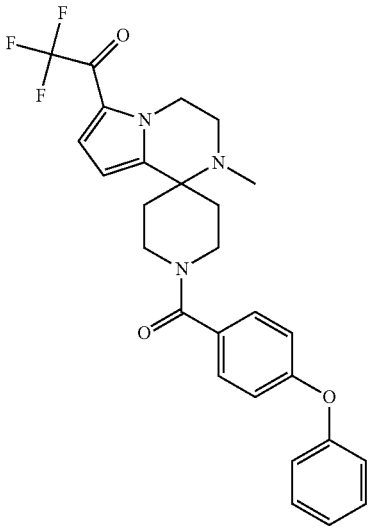 402 |
| 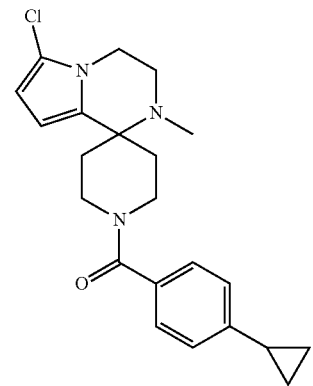 [SMILES: CN1CCn2c(Cl)ccc2C12CCN(C(=O)c1ccc(C3CC3)cc1)CC2] 400 | 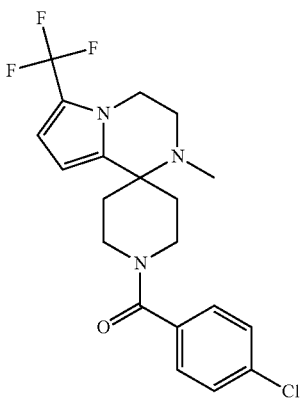 403 |
| 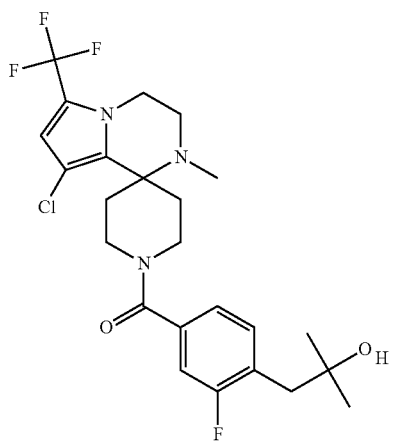 401 | 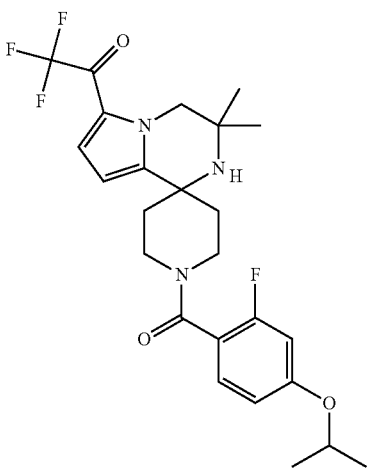 404 |

| 179 -continued | 180 -continued |
|---|---|
| 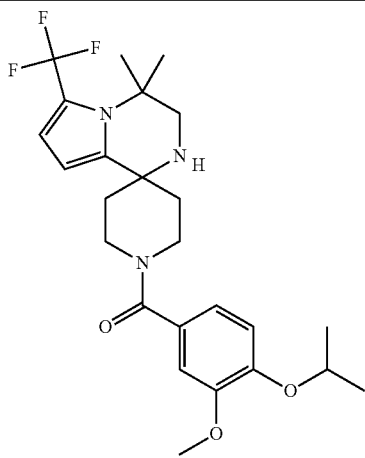 405 | 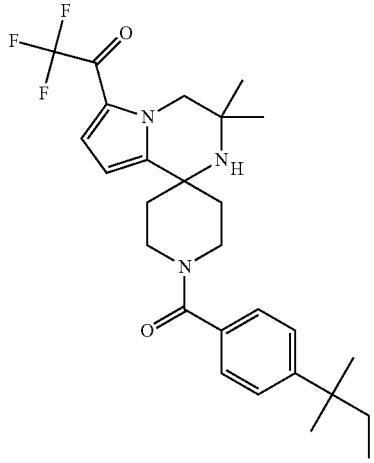 408 |
| 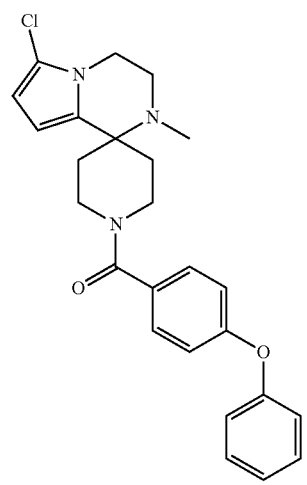 406 | 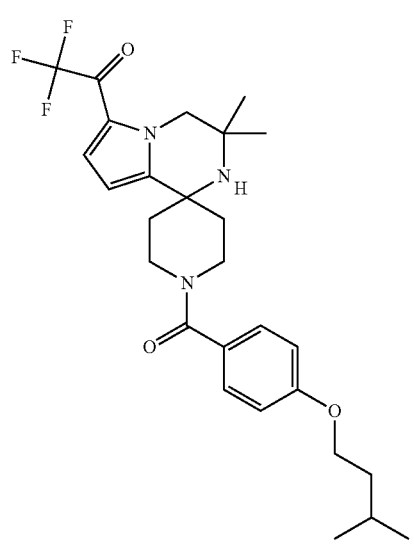 409 |
| 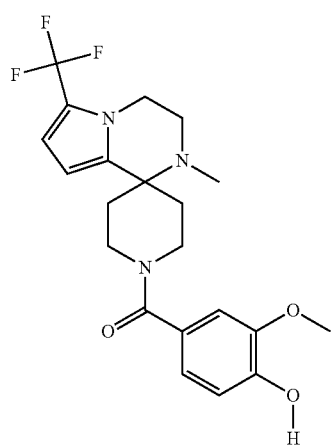 [SMILES: COc1cc(C(=O)N2CCC3(CC2)c2ccc(C(F)(F)F)n2CCN3C)ccc1O] 407 | 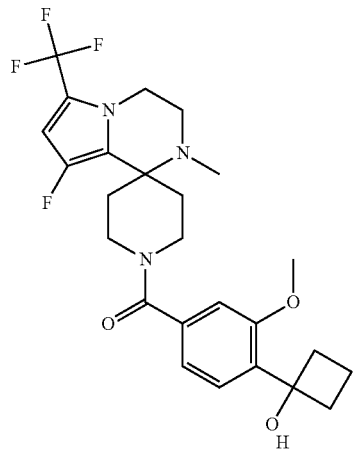 410 |

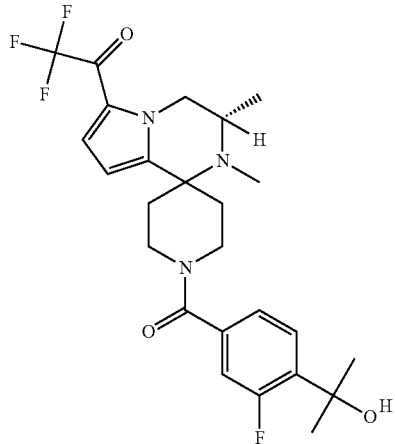
411
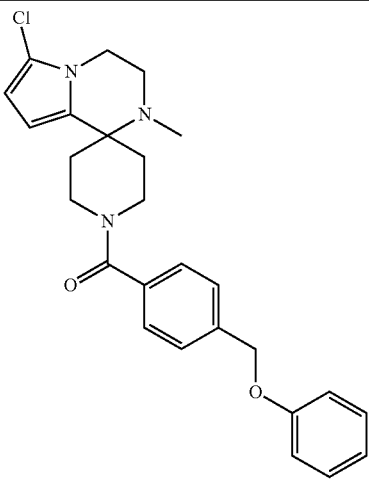
414
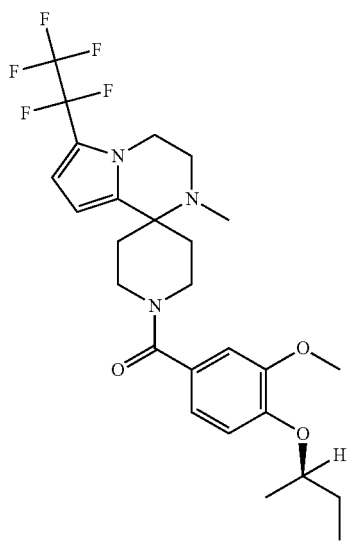 [SMILES: CC[C@@H](C)Oc1ccc(C(=O)N2CCC3(CC2)c2ccc(C(F)(F)C(F)(F)F)n2CCN3C)cc1OC]
412
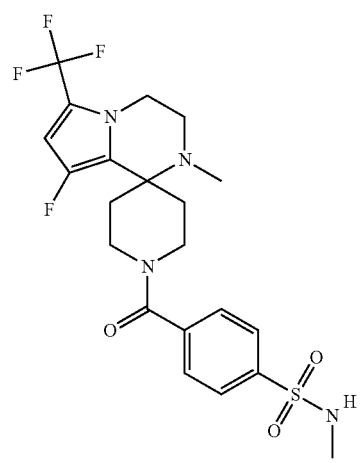
415
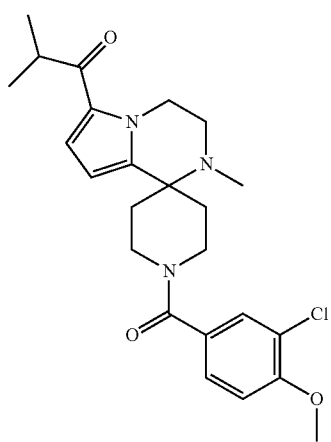 [SMILES: COc1ccc(C(=O)N2CCC3(CC2)c2ccc(C(=O)C(C)C)n2CCN3C)cc1Cl]
413
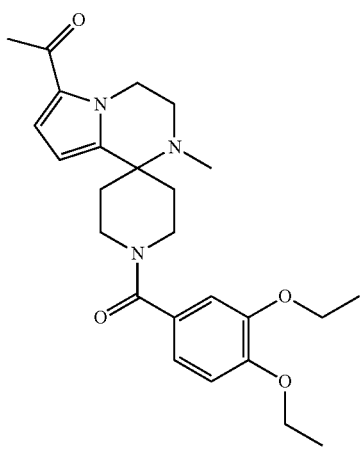 [SMILES: CCOc1ccc(C(=O)N2CCC3(CC2)c2ccc(C(C)=O)n2CCN3C)cc1OCC]
416

| 417 | 420 |
|---|---|
| 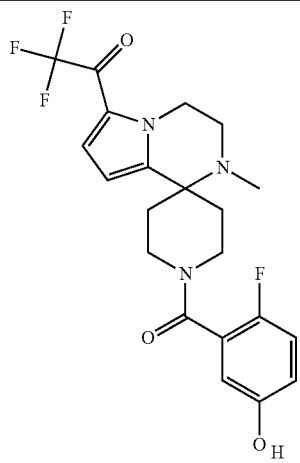 | 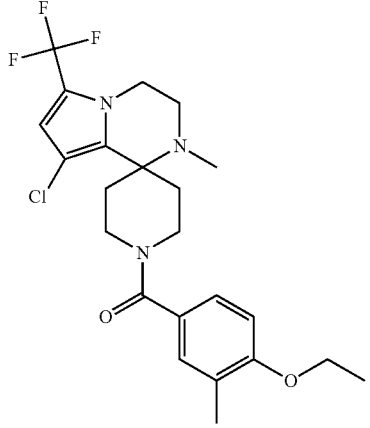 |
| 418 | 421 |
| 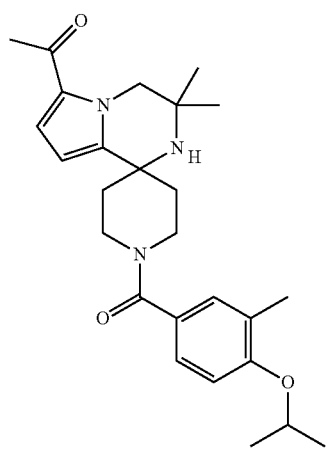 | 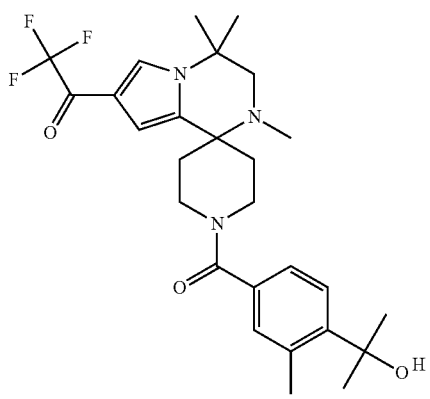 |
| 419 | 422 |
| 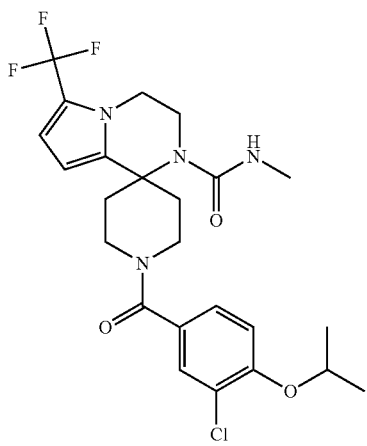 [SMILES: CNC(=O)N1CCn2c(C(F)(F)F)ccc2C12CCN(C(=O)c1ccc(OC(C)C)c(Cl)c1)CC2] | 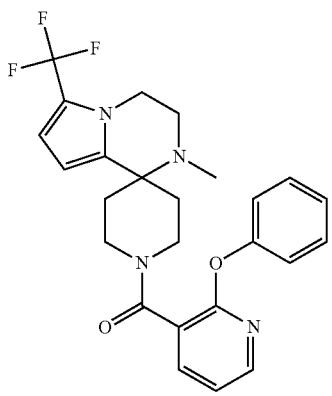 |

| 185 -continued | 186 -continued |
|---|---|
| 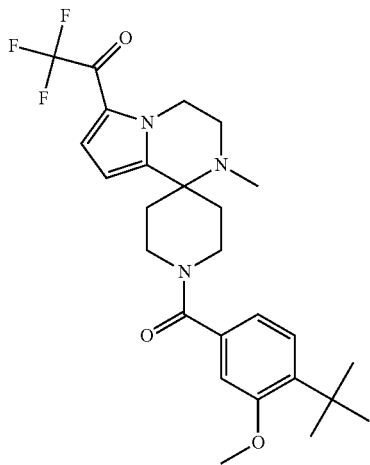 [SMILES: COc1cc(C(=O)N2CCC3(CC2)c2ccc(C(=O)C(F)(F)F)n2CCN3C)ccc1C(C)(C)C] 423 | 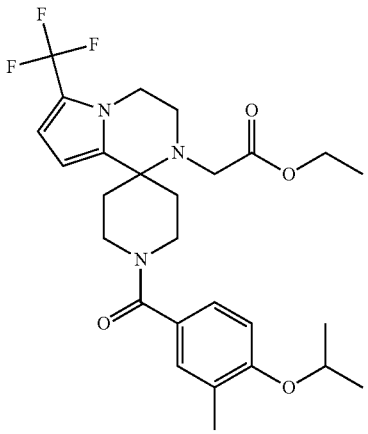 426 |
| 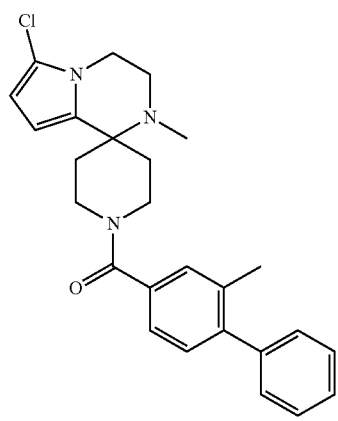 [SMILES: Cc1cc(C(=O)N2CCC3(CC2)c2ccc(Cl)n2CCN3C)ccc1-c1ccccc1] 424 | 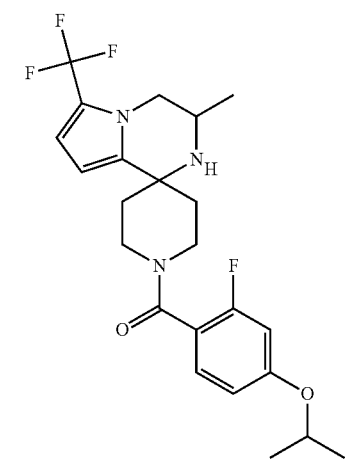 427 |
| 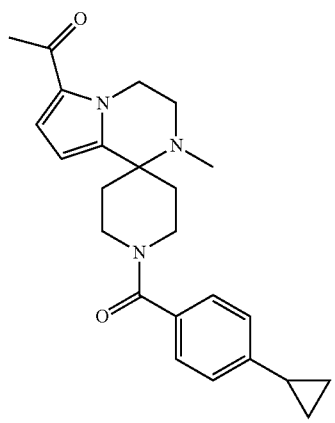 [SMILES: CC(=O)c1ccc2n1CCN(C)C21CCN(C(=O)c2ccc(C3CC3)cc2)CC1] 425 | 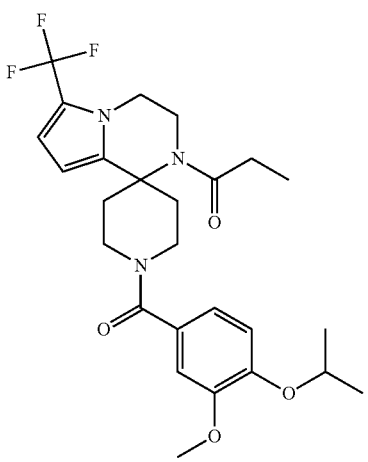 428 |

187
-continued
188
-continued
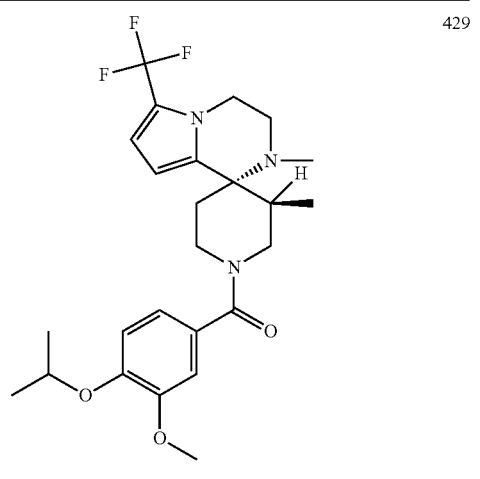
429
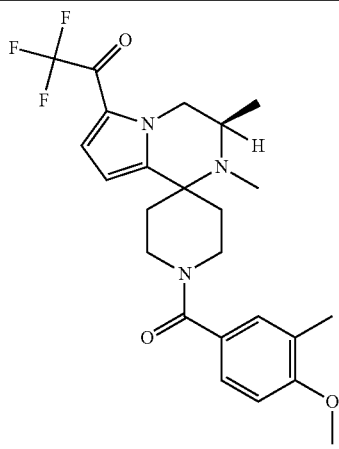
432
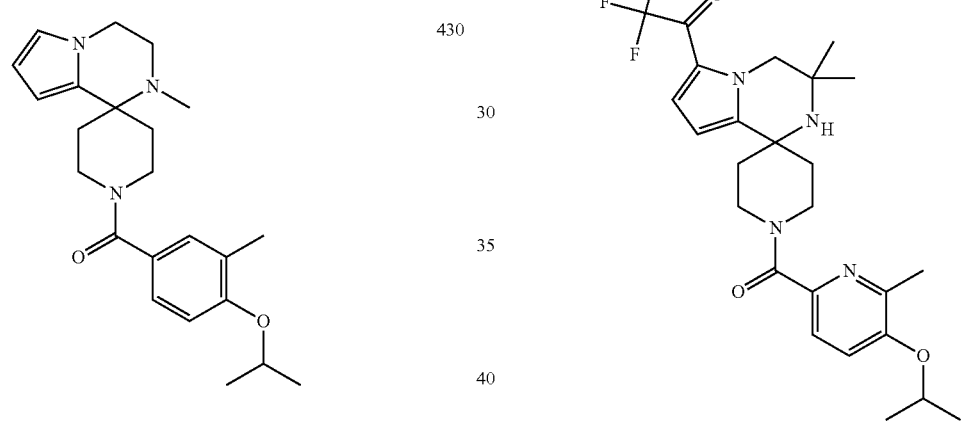
430
433
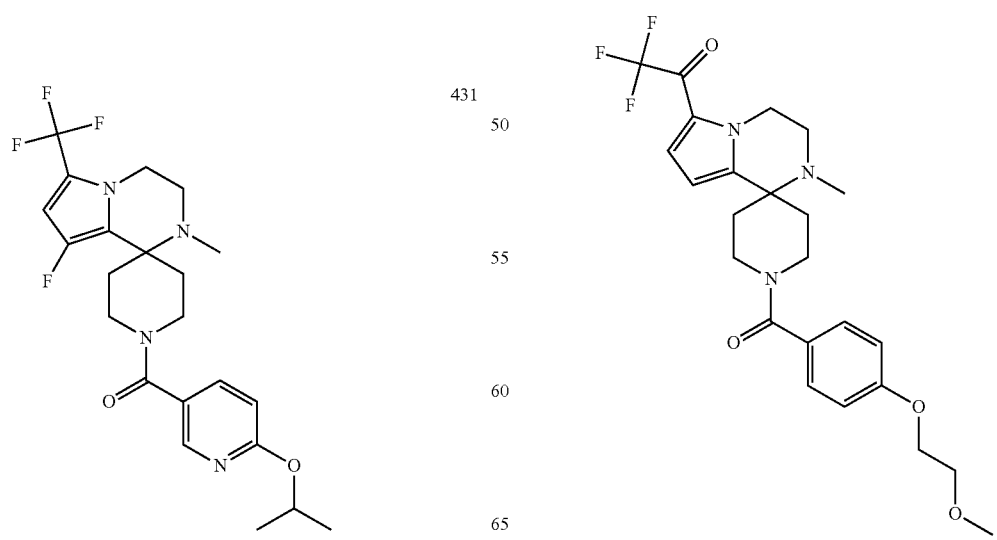
431
434

| 189 -continued | | 190 -continued | |
|---|---|---|---|
| 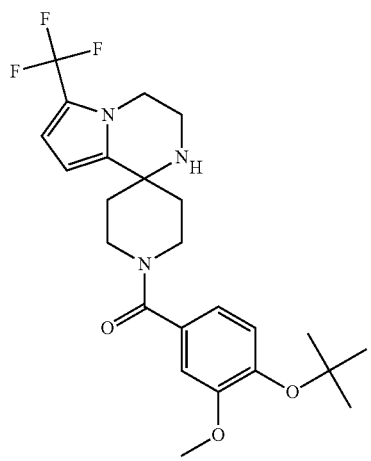 | 435 | 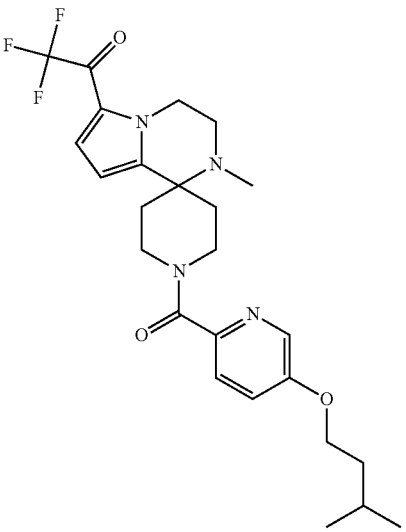 | 438 |
| | 436 | | 439 |
| 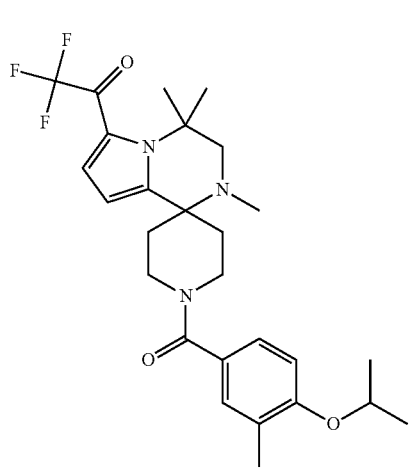 [SMILES: Cc1cc(C(=O)N2CCC3(CC2)c2ccc(C(=O)C(F)(F)F)n2C(C)(C)CN3C)ccc1OC(C)C] | 437 | | 440 |

| 441 | 444 |
|---|---|
| 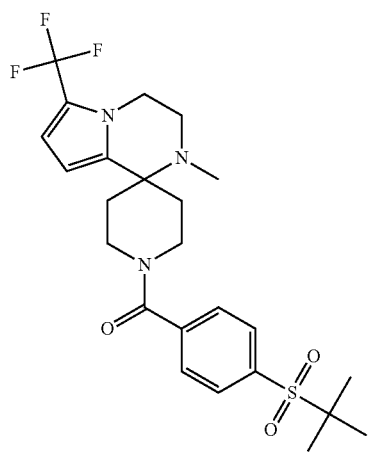 [SMILES: CN1CCn2c(C(F)(F)F)ccc2C12CCN(C(=O)c1ccc(S(=O)(=O)C(C)(C)C)cc1)CC2] | 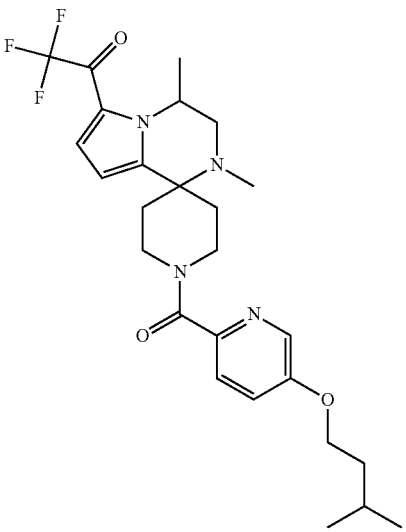 [SMILES: CC(C)CCOc1ccc(C(=O)N2CCC3(CC2)c2ccc(C(=O)C(F)(F)F)n2C(C)CN3C)nc1] |
| 442 | 445 |
|---|---|
| | 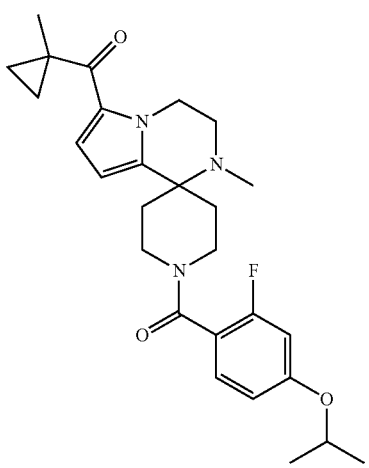 [SMILES: CC(C)Oc1ccc(C(=O)N2CCC3(CC2)c2ccc(C(=O)C4(C)CC4)n2CCN3C)c(F)c1] |
| 443 | 446 |
|---|---|
| 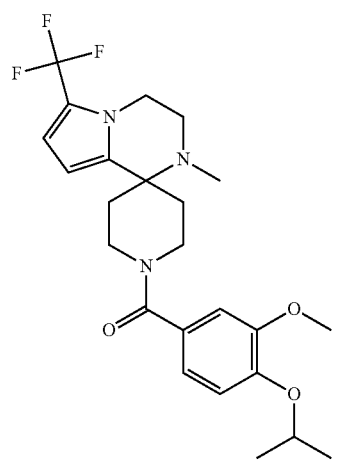 | 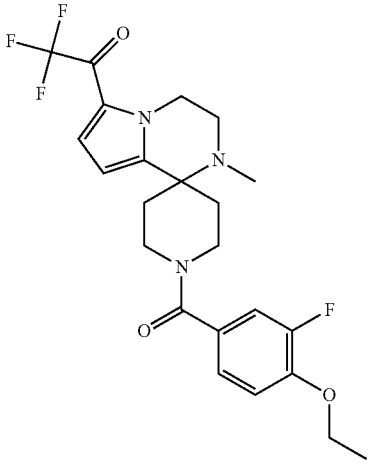 [SMILES: CCOc1ccc(C(=O)N2CCC3(CC2)c2ccc(C(=O)C(F)(F)F)n2CCN3C)cc1F] |

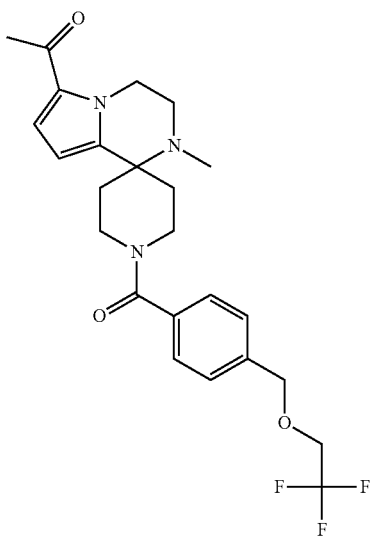 [SMILES: CC(=O)c1ccc2n1CCN(C)C21CCN(C(=O)c2ccc(COCC(F)(F)F)cc2)CC1]
447
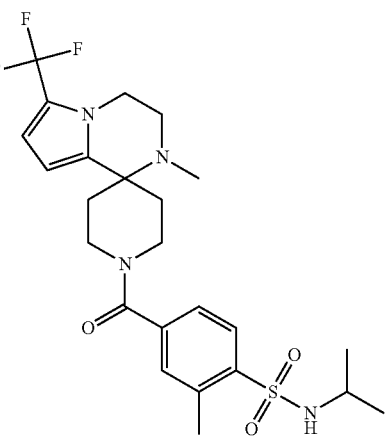
450
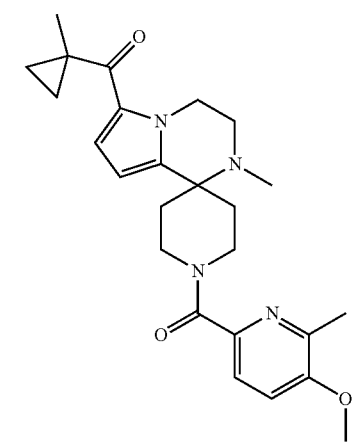 [SMILES: COc1ccc(C(=O)N2CCC3(CC2)c2ccc(C(=O)C4(C)CC4)n2CCN3C)nc1C]
448
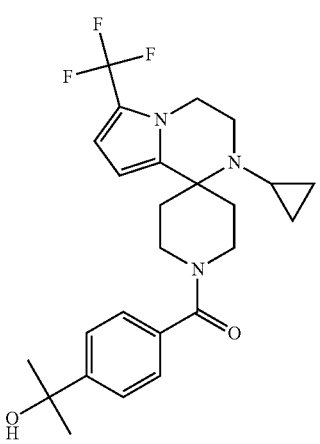
451
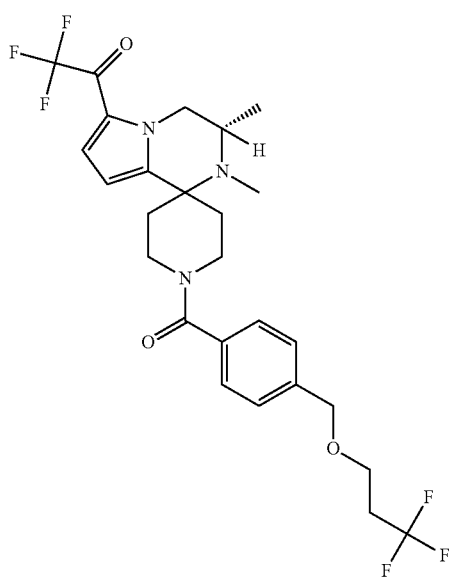 [SMILES: C[C@H]1Cn2c(C(=O)C(F)(F)F)ccc2C2(CCN(C(=O)c3ccc(COCCC(F)(F)F)cc3)CC2)N1C]
449
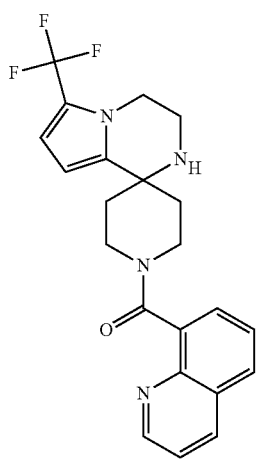
452

| 453 | 456 |
|---|---|
| 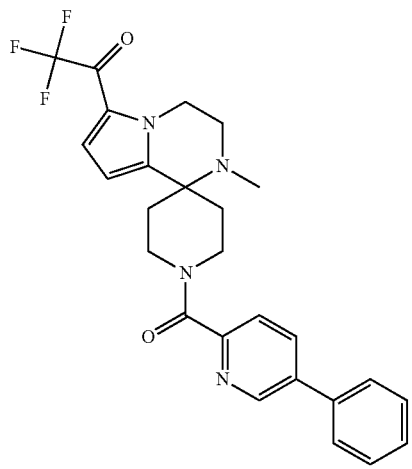 [SMILES: CN1CCn2c(C(=O)C(F)(F)F)ccc2C12CCN(C(=O)c1ccc(-c3ccccc3)cn1)CC2] | 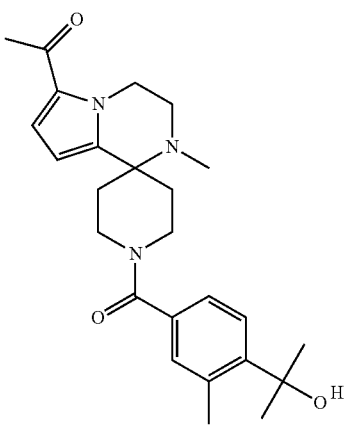 |
| 454 | 457 |
|---|---|
| 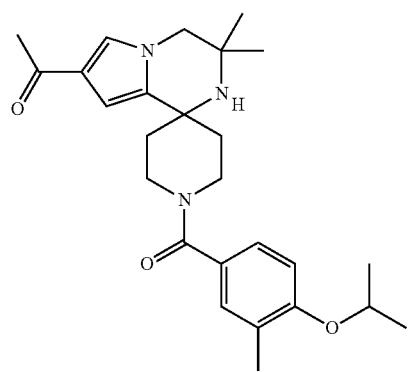 | 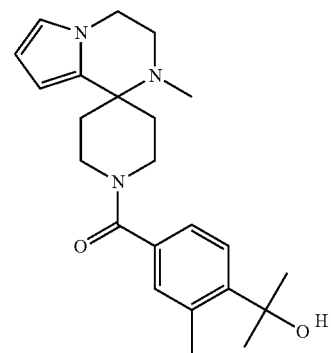 |
| 455 | 458 |
|---|---|
| 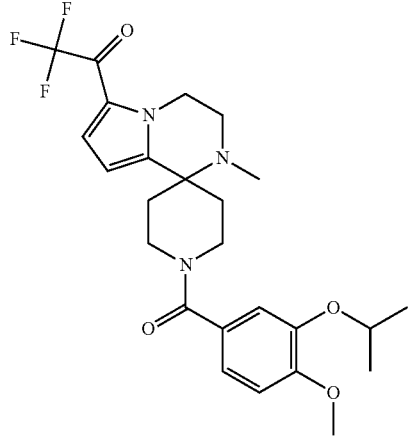 [SMILES: COc1ccc(C(=O)N2CCC3(CC2)c2ccc(C(=O)C(F)(F)F)n2CCN3C)cc1OC(C)C] | 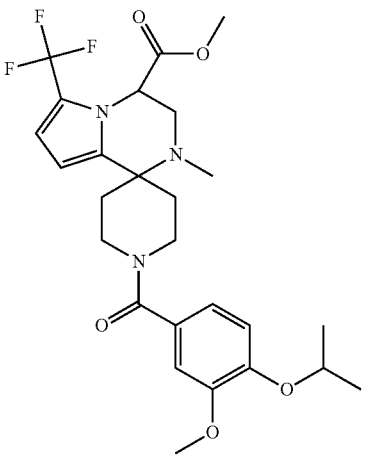 [SMILES: COC(=O)C1CN(C)C2(CCN(C(=O)c3ccc(OC(C)C)c(OC)c3)CC2)c2ccc(C(F)(F)F)n21] |

| 459 | 462 |
|---|---|
| 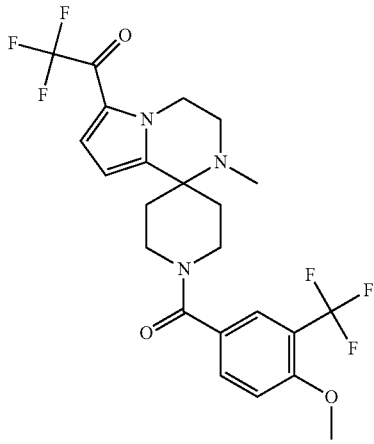 [SMILES: COc1ccc(C(=O)N2CCC3(CC2)c2ccc(C(=O)C(F)(F)F)n2CCN3C)cc1C(F)(F)F] | 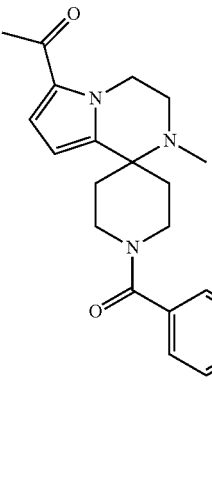 |
| 460 | 463 |
|---|---|
| 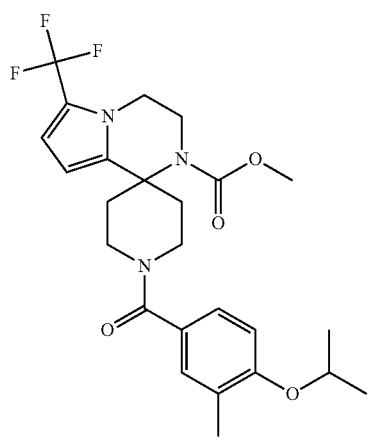 | 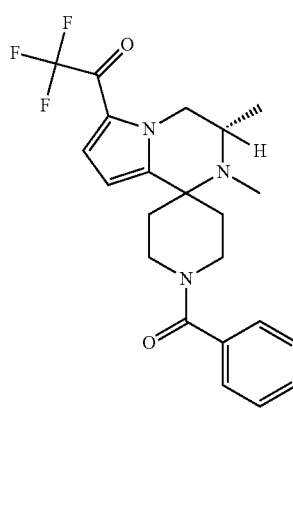 |
| 461 | 464 |
|---|---|
| 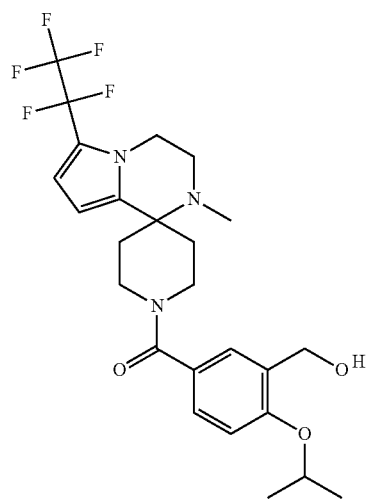 | 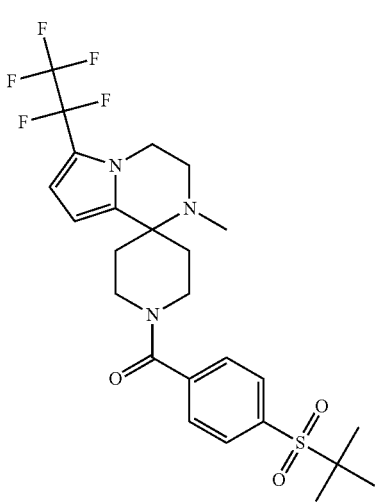 [SMILES: CN1CCn2c(ccc2C(F)(F)C(F)(F)F)C12CCN(C(=O)c1ccc(S(=O)(=O)C(C)(C)C)cc1)CC2] |

| 199 -continued | | 200 -continued | |
|---|---|---|---|
| 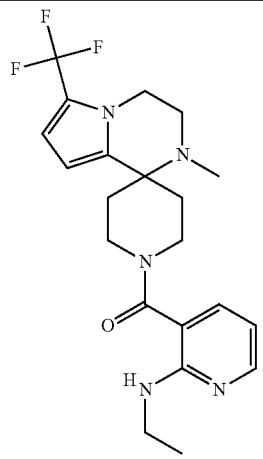 | 465 | 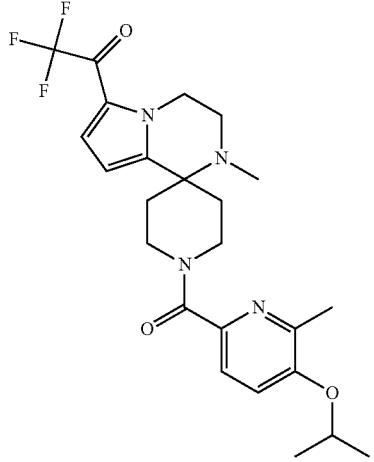 | 468 |
| 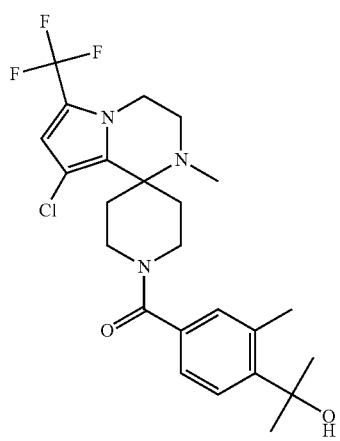 | 466 | 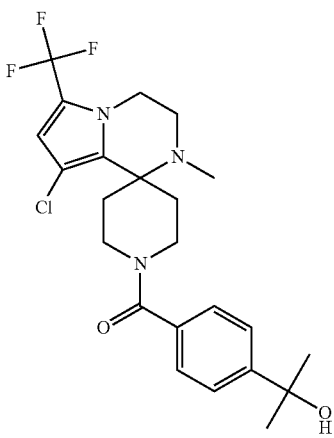 | 469 |
| 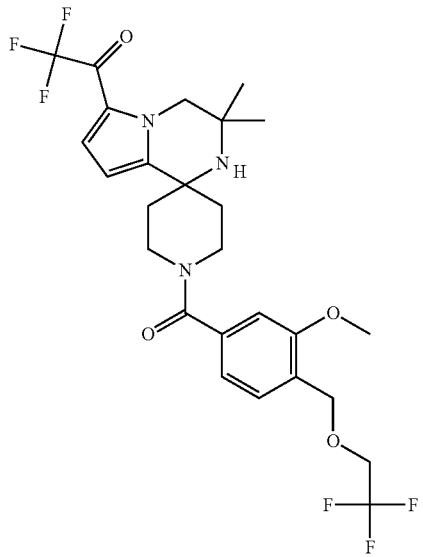 | 467 | 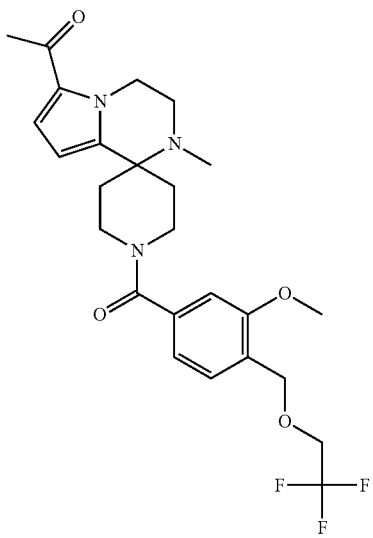 [SMILES: COc1cc(C(=O)N2CCC3(CC2)c2ccc(C(C)=O)n2CCN3C)ccc1COCC(F)(F)F] | 470 |

| 201 -continued | 202 -continued |
|---|---|
| 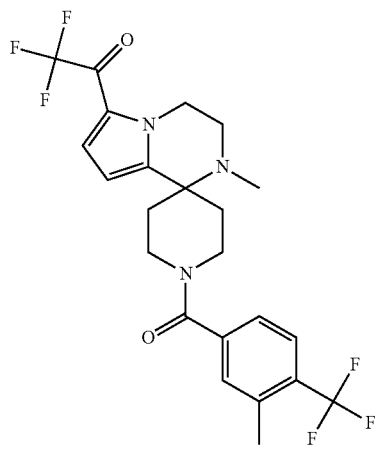 [SMILES: Cc1cc(C(=O)N2CCC3(CC2)c2ccc(C(=O)C(F)(F)F)n2CCN3C)ccc1C(F)(F)F] 471 | 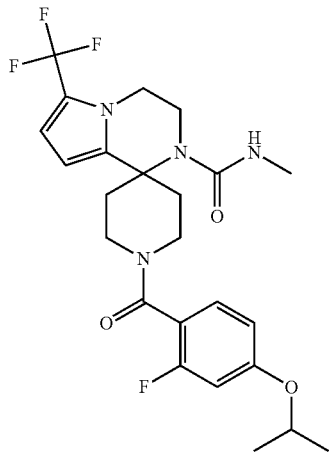 474 |
| 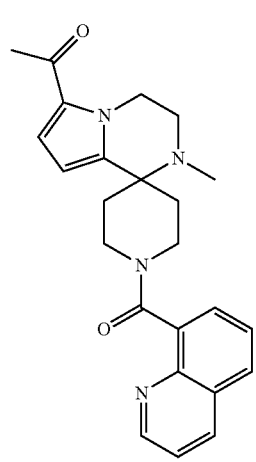 [SMILES: CC(=O)c1ccc2n1CCN(C)C21CCN(C(=O)c2cccc3cccnc23)CC1] 472 | 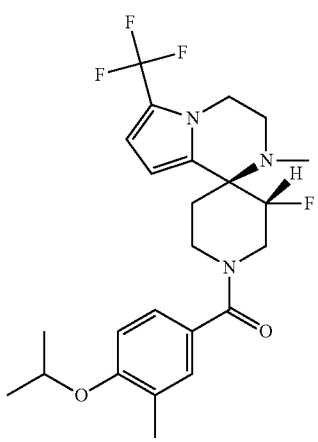 475 |
| 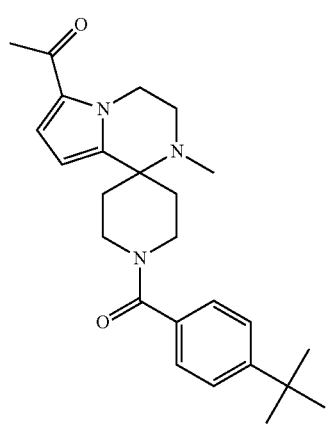 [SMILES: CC(=O)c1ccc2n1CCN(C)C21CCN(C(=O)c2ccc(C(C)(C)C)cc2)CC1] 473 | 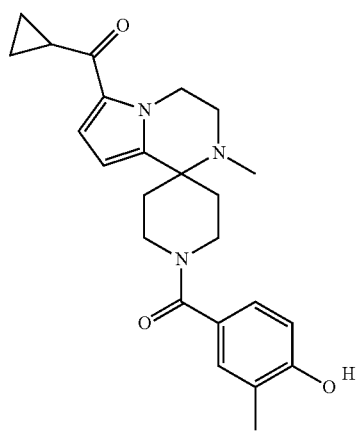 476 |

| 477 | 480 |
|---|---|
| 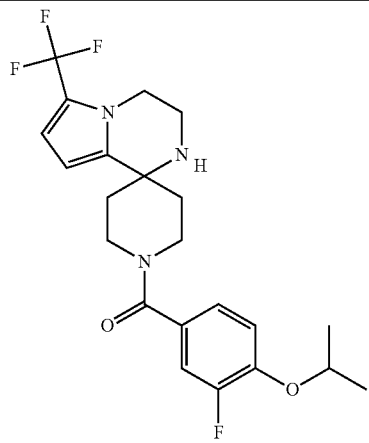 | 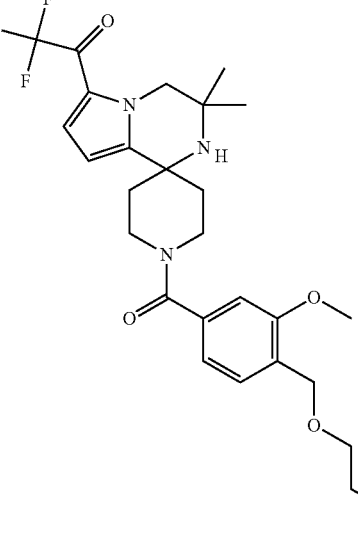 |
| 478 | 481 |
|---|---|
| 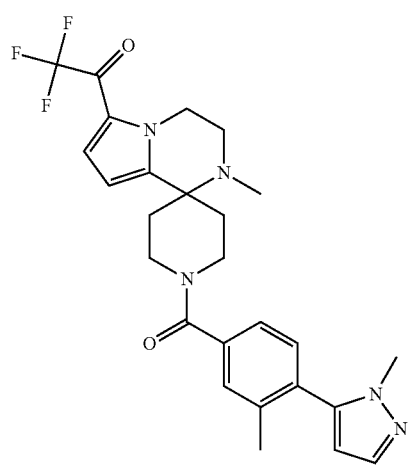 [SMILES: Cc1cc(C(=O)N2CCC3(CC2)c2ccc(C(=O)C(F)(F)F)n2CCN3C)ccc1-c1ccnn1C] | 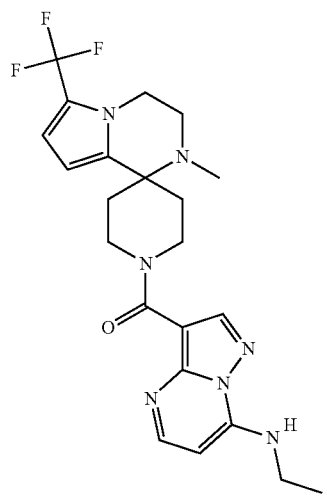 |
| 479 | 482 |
|---|---|
| 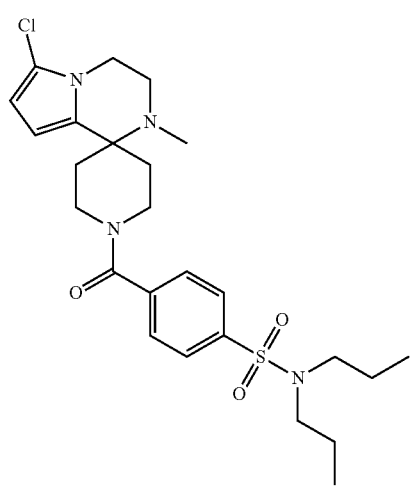 [SMILES: CCCN(CCC)S(=O)(=O)c1ccc(C(=O)N2CCC3(CC2)c2ccc(Cl)n2CCN3C)cc1] | 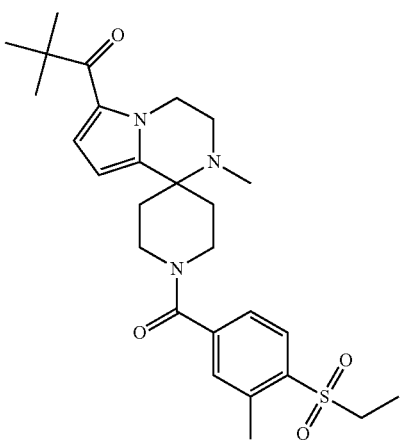 [SMILES: CCS(=O)(=O)c1ccc(C(=O)N2CCC3(CC2)c2ccc(C(=O)C(C)(C)C)n2CCN3C)cc1C] |

| 483 | 486 |
|---|---|
| 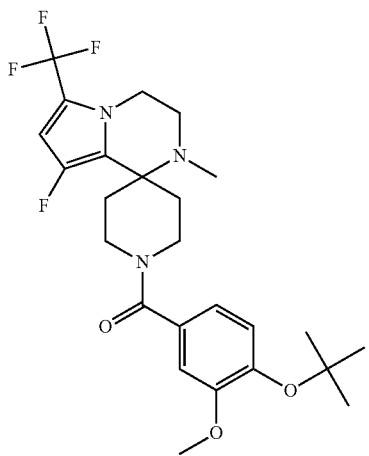 [SMILES: COc1cc(C(=O)N2CCC3(CC2)c2c(F)cc(C(F)(F)F)n2CCN3C)ccc1OC(C)(C)C] | 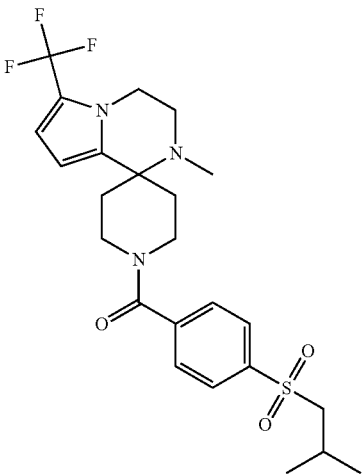 |
| 484 | 487 |
| 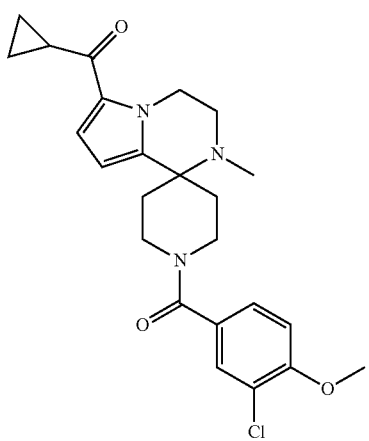 [SMILES: COc1ccc(C(=O)N2CCC3(CC2)c2ccc(C(=O)C4CC4)n2CCN3C)cc1Cl] | 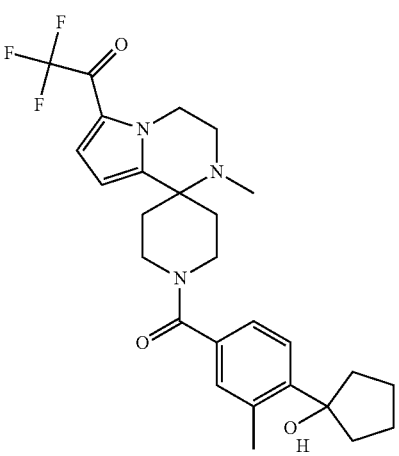 |
| 485 | 488 |
| 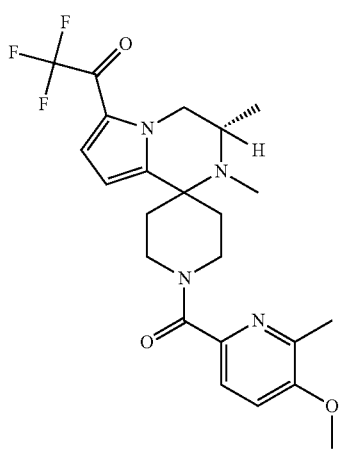 [SMILES: COc1ccc(C(=O)N2CCC3(CC2)c2ccc(C(=O)C(F)(F)F)n2C[C@H](C)N3C)nc1C] | 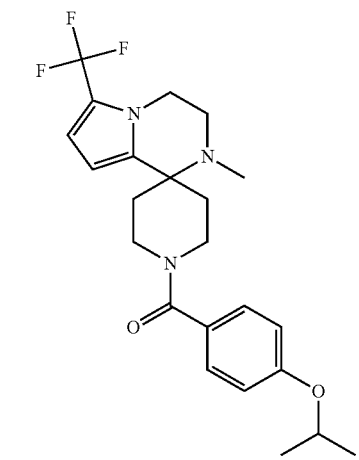 [SMILES: CC(C)Oc1ccc(C(=O)N2CCC3(CC2)c2ccc(C(F)(F)F)n2CCN3C)cc1] |

| 207 -continued | 208 -continued |
|---|---|
| 489 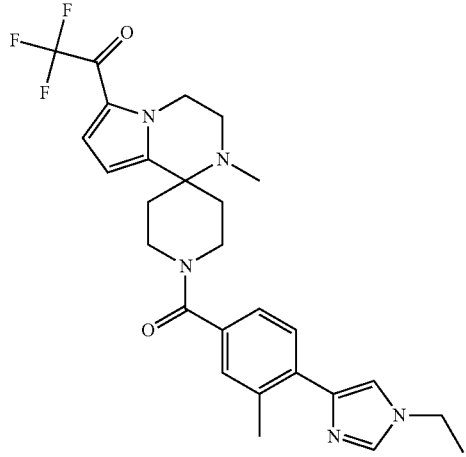 | 492 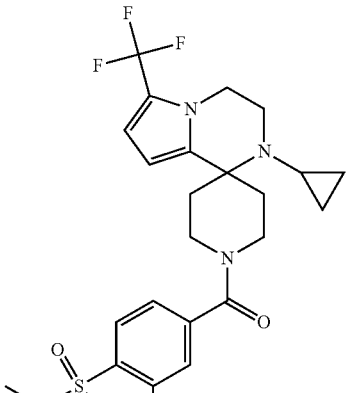 |
| 490 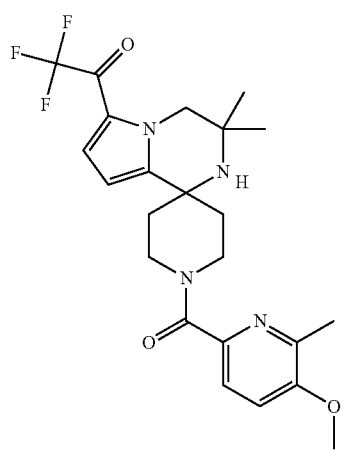 | 493 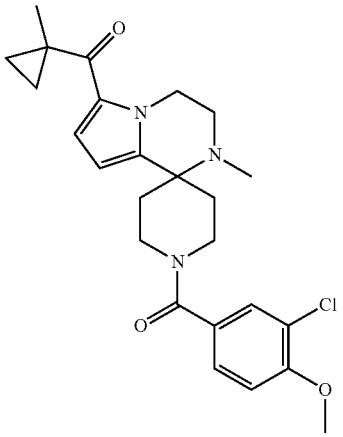 |
| 491 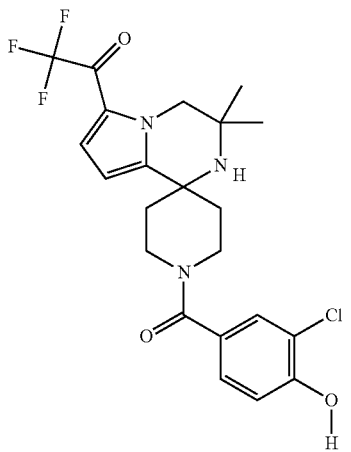 | 494 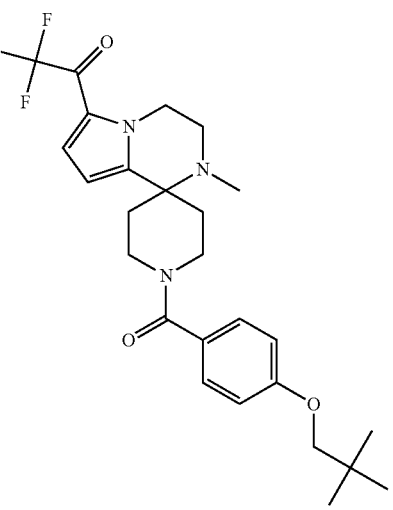 |

| 495 | 498 |
|---|---|
| 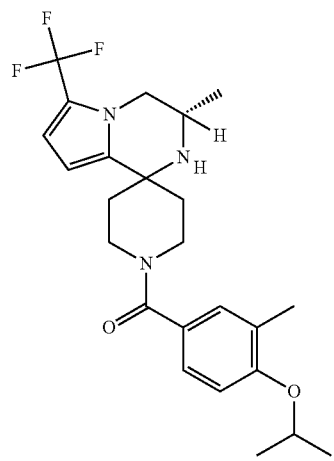 | 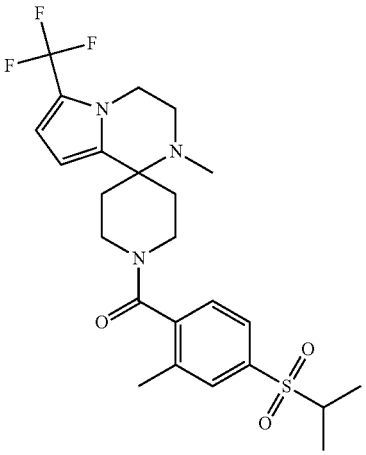 |
| 496 | 499 |
|---|---|
| 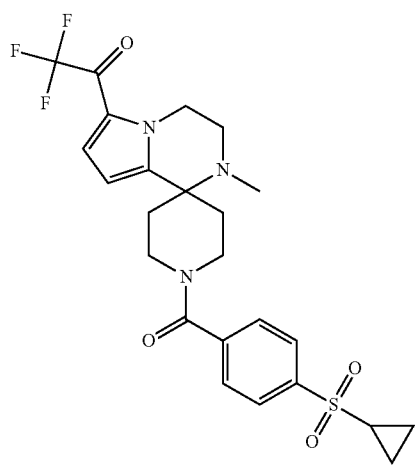 [SMILES: CN1CCn2c(C(=O)C(F)(F)F)ccc2C12CCN(C(=O)c1ccc(S(=O)(=O)C3CC3)cc1)CC2] | 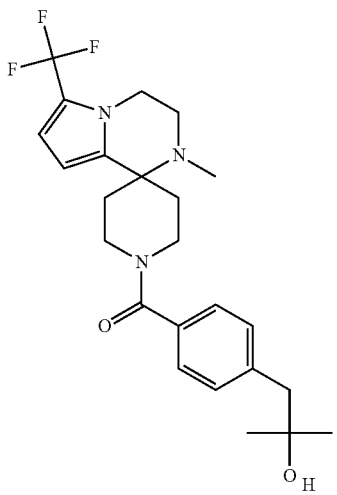 |
| 497 | 500 |
|---|---|
| 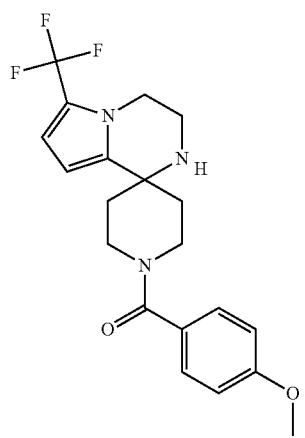 | 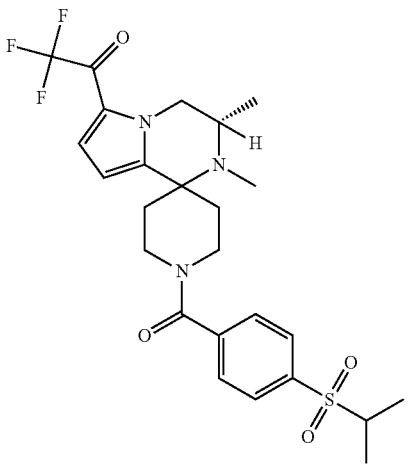 [SMILES: CC(C)S(=O)(=O)c1ccc(C(=O)N2CCC3(CC2)c2ccc(C(=O)C(F)(F)F)n2C[C@H](C)N3C)cc1] |

| 211 -continued | 212 -continued |
|---|---|
| 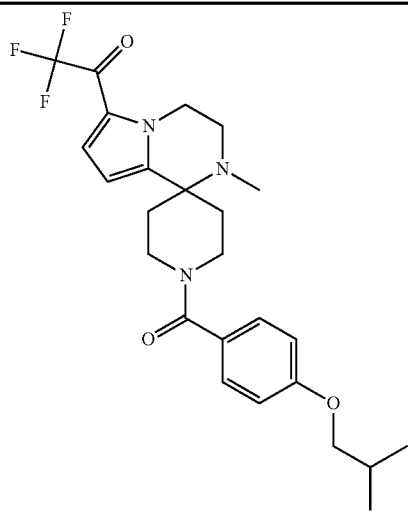 501 | 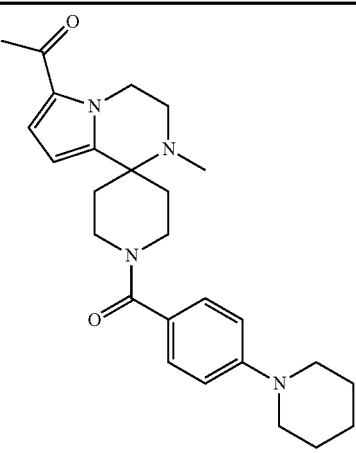 504 |
| 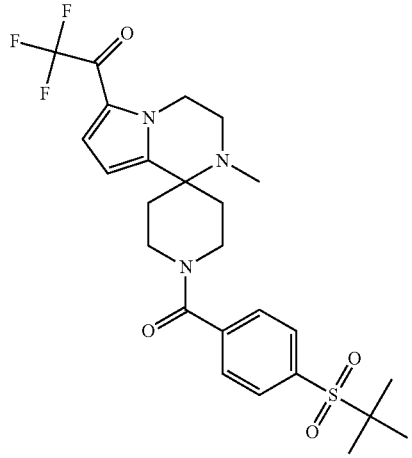 [SMILES: CN1CCn2c(C(=O)C(F)(F)F)ccc2C12CCN(C(=O)c1ccc(S(=O)(=O)C(C)(C)C)cc1)CC2] 502 | 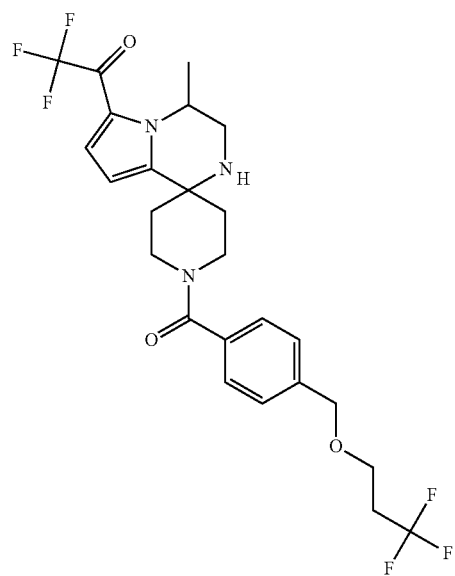 505 |
| 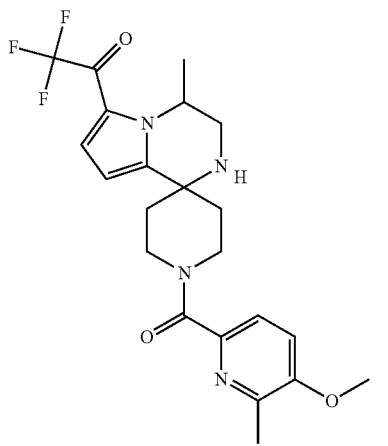 503 | 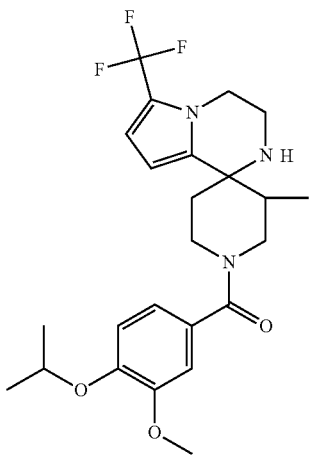 506 |

| 213 -continued | 214 -continued |
|---|---|
| 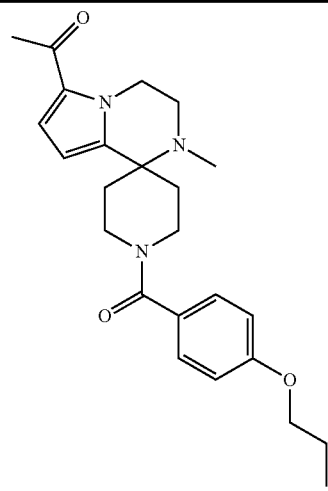 507 | 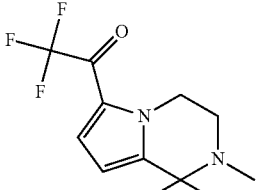 510 |
| 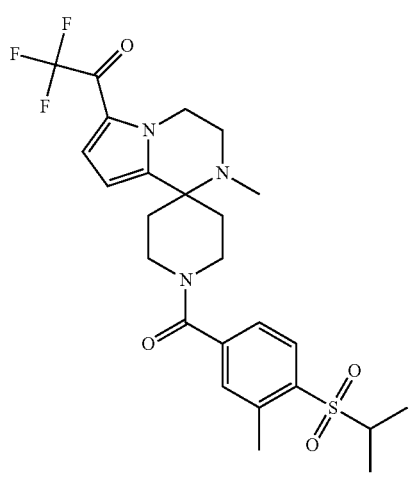 [SMILES: Cc1cc(C(=O)N2CCC3(CC2)c2ccc(C(=O)C(F)(F)F)n2CCN3C)ccc1S(=O)(=O)C(C)C] 508 | 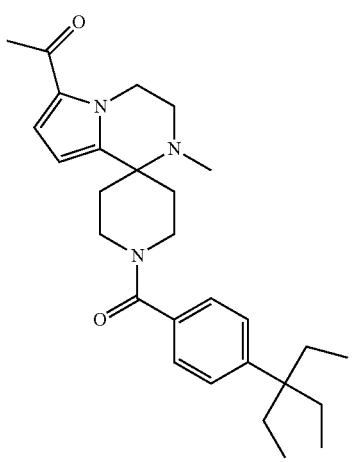 511 |
| 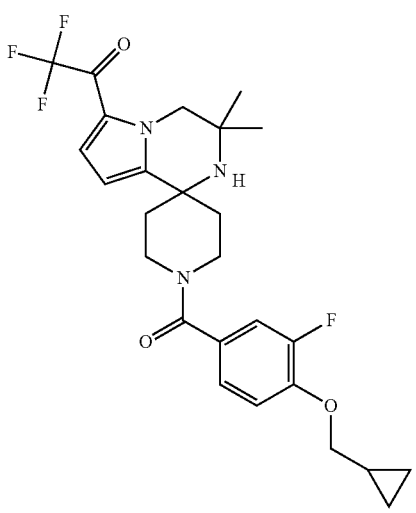 509 | 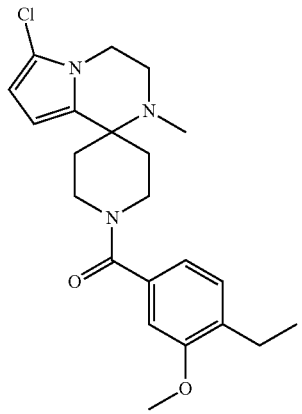 [SMILES: CCc1ccc(C(=O)N2CCC3(CC2)c2ccc(Cl)n2CCN3C)cc1OC] 512 |

| 513 | 516 |
|---|---|
| 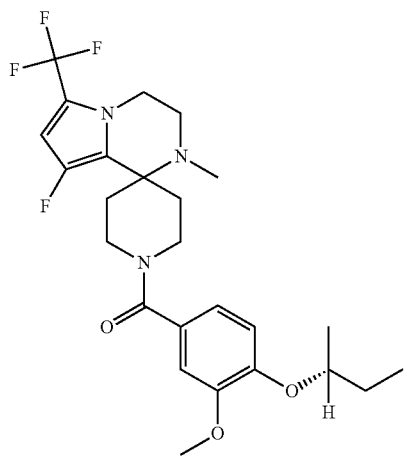 [SMILES: CC[C@@H](C)Oc1ccc(C(=O)N2CCC3(CC2)c2c(F)cc(C(F)(F)F)n2CCN3C)cc1OC] | 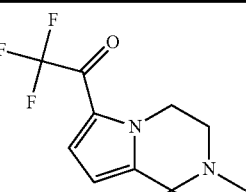 |
| 514 | 517 |
| 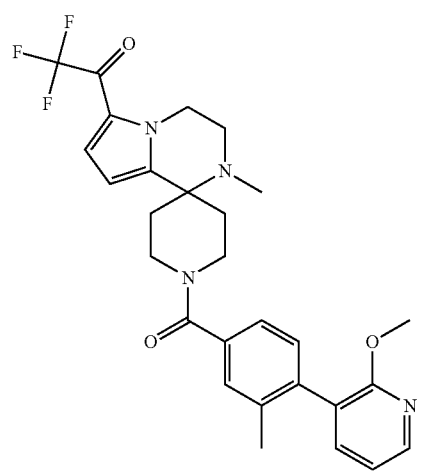 [SMILES: COc1ncccc1-c1ccc(C(=O)N2CCC3(CC2)c2ccc(C(=O)C(F)(F)F)n2CCN3C)cc1C] | |
| 515 | 518 |
| 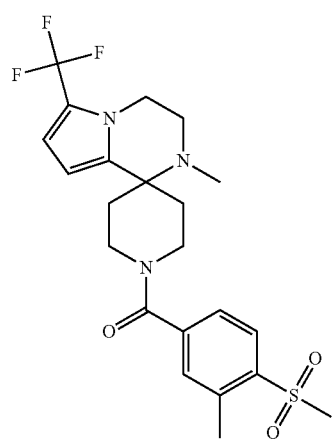 [SMILES: Cc1cc(C(=O)N2CCC3(CC2)c2ccc(C(F)(F)F)n2CCN3C)ccc1S(C)(=O)=O] | 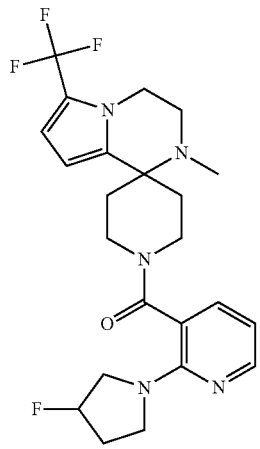 |

| 519 | 522 |
|---|---|
| 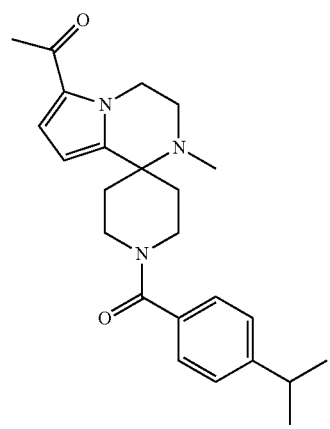 [SMILES: CC(=O)c1ccc2n1CCN(C)C21CCN(C(=O)c2ccc(C(C)C)cc2)CC1] | 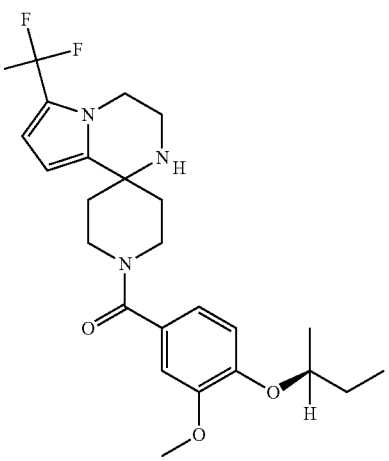 |
| 520 | 523 |
|---|---|
| 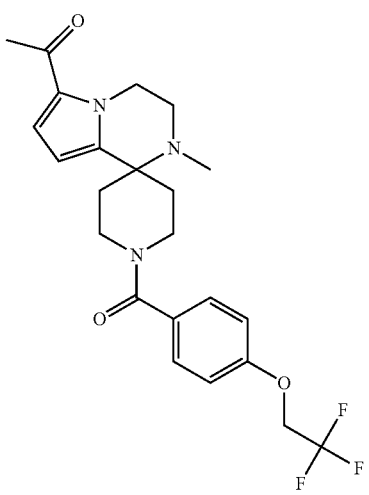 [SMILES: CC(=O)c1ccc2n1CCN(C)C21CCN(C(=O)c2ccc(OCC(F)(F)F)cc2)CC1] | 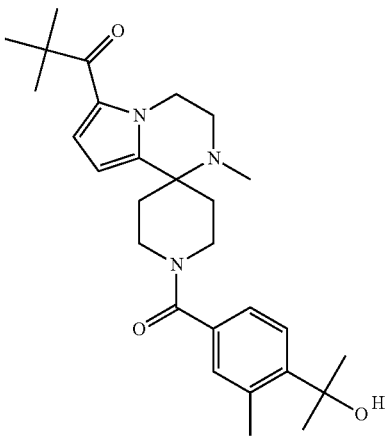 |
| 521 | 524 |
|---|---|
| 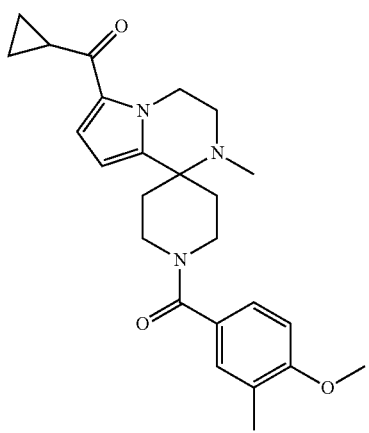 [SMILES: COc1ccc(C(=O)N2CCC3(CC2)c2ccc(C(=O)C4CC4)n2CCN3C)cc1C] | 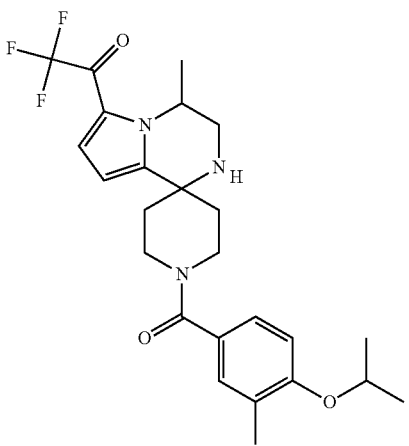 |

| 525 | 528 |
|---|---|
| 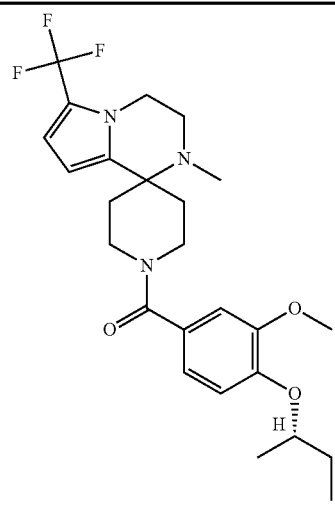 | 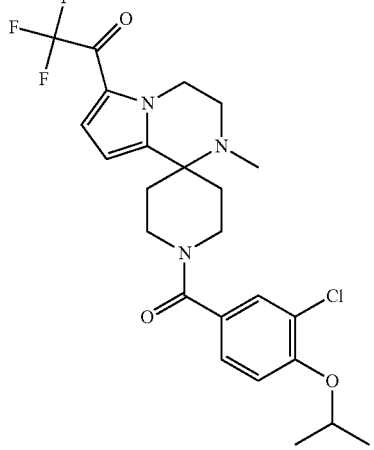 |
| 526 | 529 |
|---|---|
| 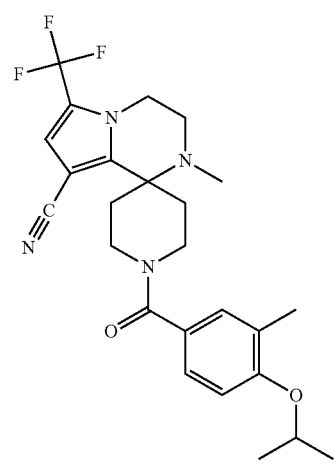 [SMILES: Cc1cc(C(=O)N2CCC3(CC2)c2c(C#N)cc(C(F)(F)F)n2CCN3C)ccc1OC(C)C] | 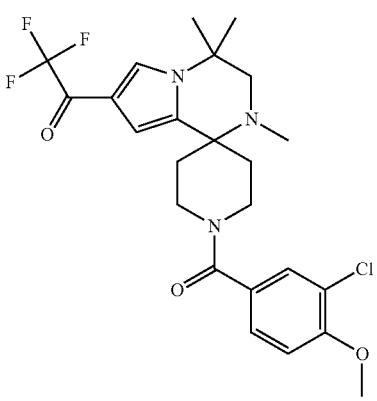 [SMILES: COc1ccc(C(=O)N2CCC3(CC2)c2cc(C(=O)C(F)(F)F)cn2C(C)(C)CN3C)cc1Cl] |
| 527 | 530 |
|---|---|
| 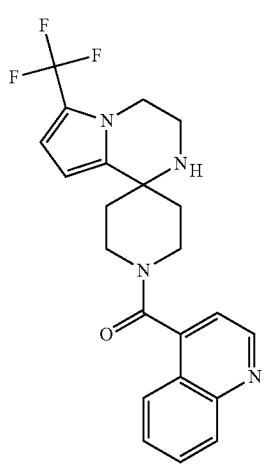 | 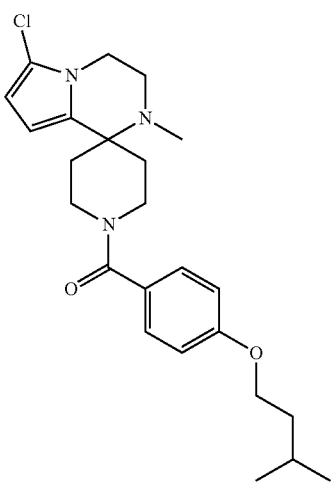 [SMILES: CC(C)CCOc1ccc(C(=O)N2CCC3(CC2)c2ccc(Cl)n2CCN3C)cc1] |

531 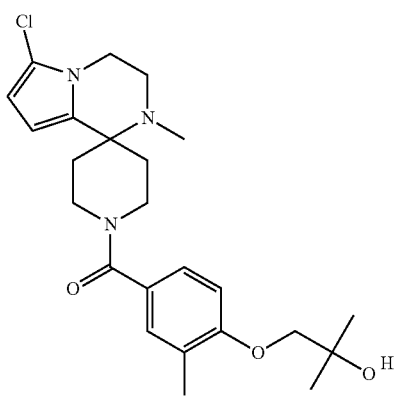
532 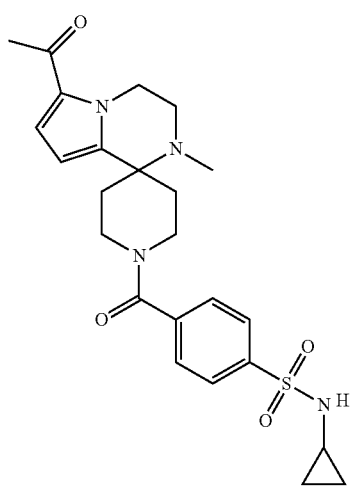
533 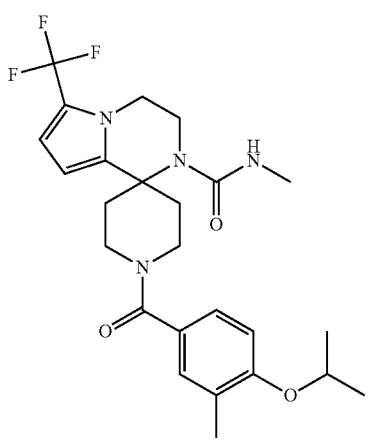
534 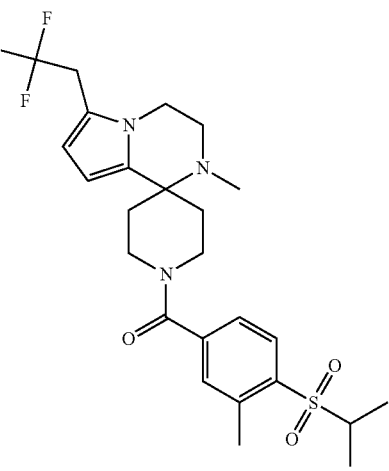
535 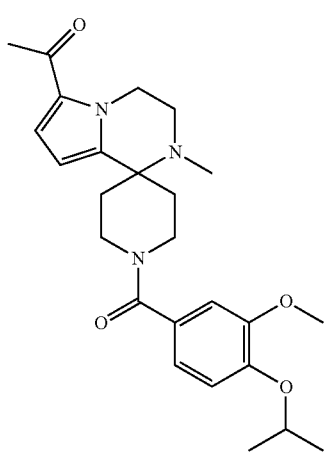
536 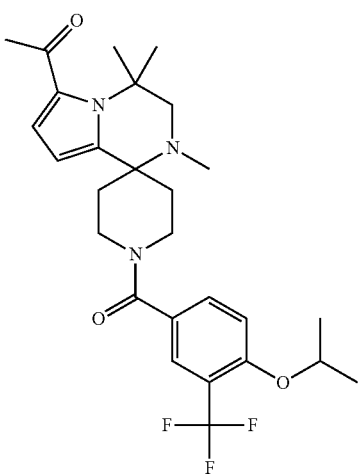 [SMILES: CC(=O)c1ccc2n1C(C)(C)CN(C)C21CCN(C(=O)c2ccc(OC(C)C)c(C(F)(F)F)c2)CC1]

223
-continued
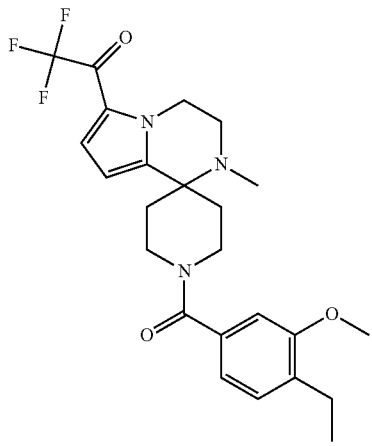 [SMILES: CCc1ccc(C(=O)N2CCC3(CC2)c2ccc(C(=O)C(F)(F)F)n2CCN3C)cc1OC]
537
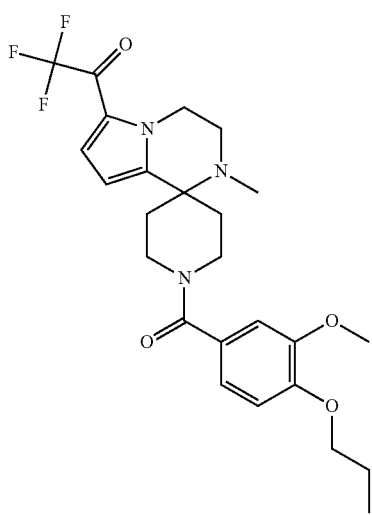 [SMILES: CCCOc1ccc(C(=O)N2CCC3(CC2)c2ccc(C(=O)C(F)(F)F)n2CCN3C)cc1OC]
538
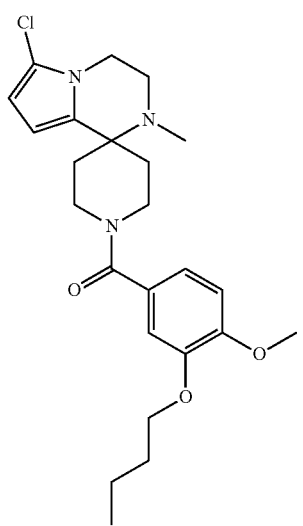 [SMILES: CCCCOc1cc(C(=O)N2CCC3(CC2)c2ccc(Cl)n2CCN3C)ccc1OC]
539
224
-continued
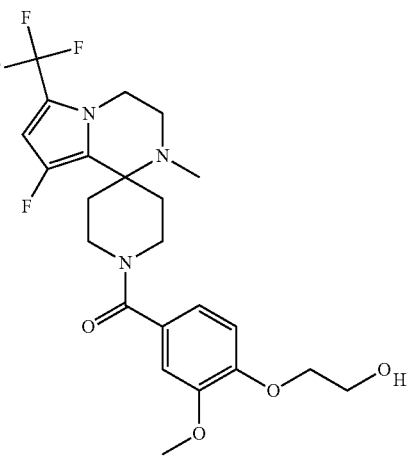
540
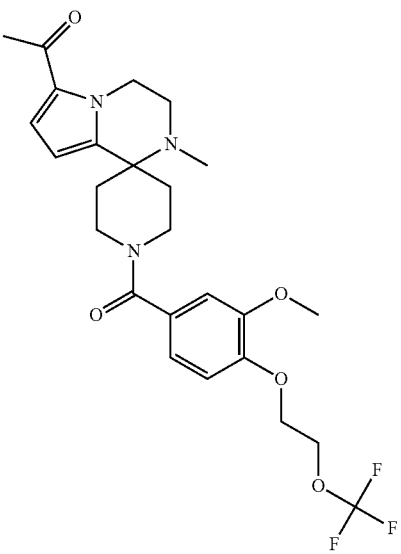 [SMILES: COc1cc(C(=O)N2CCC3(CC2)c2ccc(C(C)=O)n2CCN3C)ccc1OCCOC(F)(F)F]
541
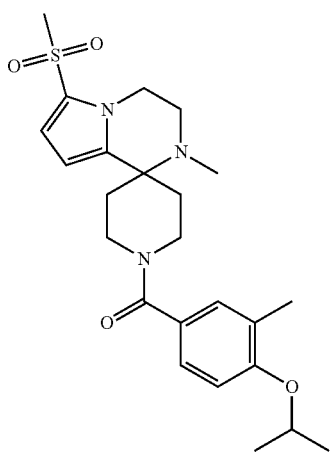 [SMILES: Cc1cc(C(=O)N2CCC3(CC2)c2ccc(S(C)(=O)=O)n2CCN3C)ccc1OC(C)C]
542

225
-continued
543
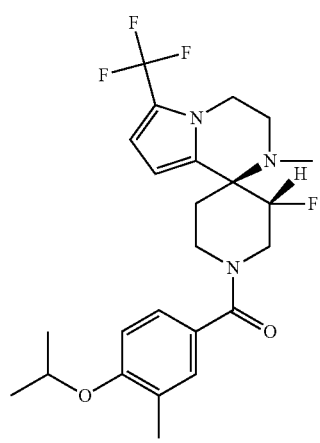
544
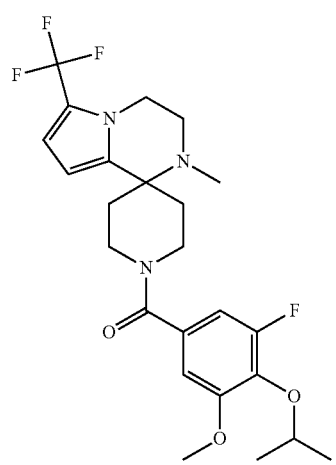 [SMILES: COc1cc(C(=O)N2CCC3(CC2)c2ccc(C(F)(F)F)n2CCN3C)cc(F)c1OC(C)C]
545
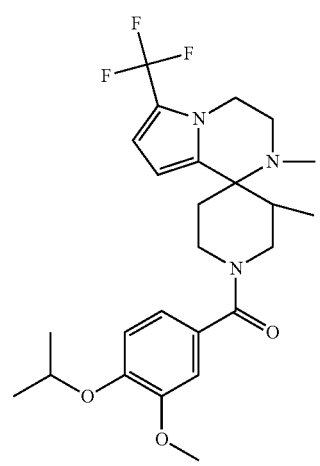 [SMILES: COc1cc(C(=O)N2CCC3(c4ccc(C(F)(F)F)n4CCN3C)C(C)C2)ccc1OC(C)C]
226
-continued
546
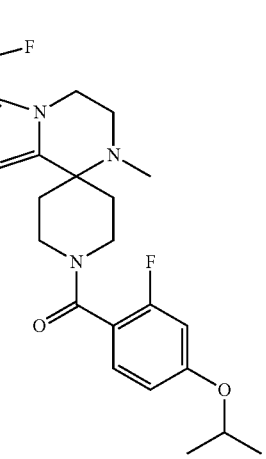
547
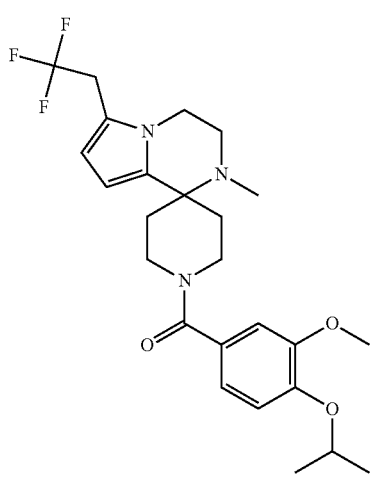 [SMILES: COc1cc(C(=O)N2CCC3(CC2)c2ccc(CC(F)(F)F)n2CCN3C)ccc1OC(C)C]
548
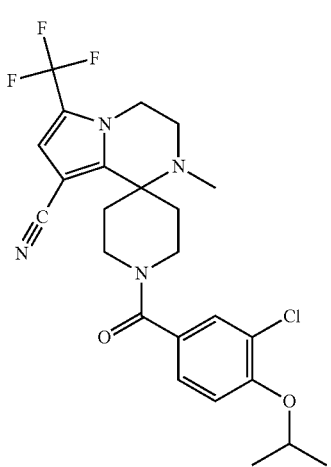 [SMILES: CC(C)Oc1ccc(C(=O)N2CCC3(CC2)c2c(C#N)cc(C(F)(F)F)n2CCN3C)cc1Cl]

| 227 -continued | 228 -continued |
|---|---|
| 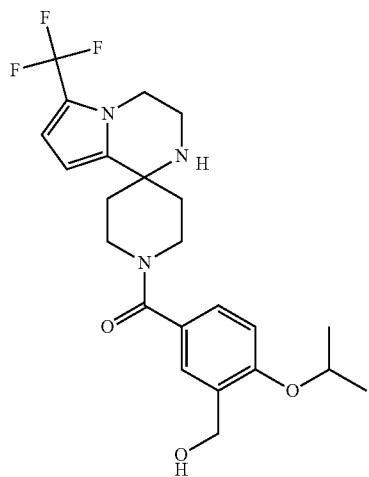 549 | 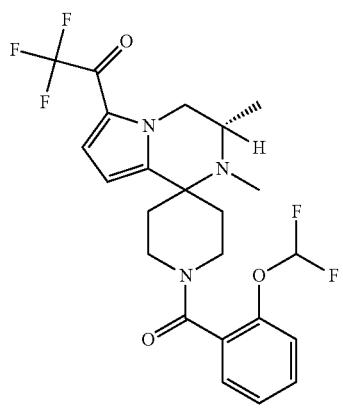 552 |
| 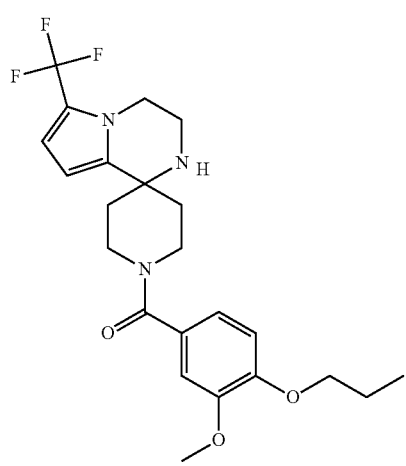 550 | 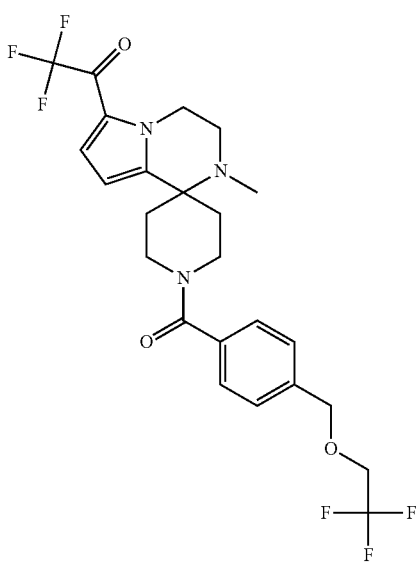 [SMILES: CN1CCn2c(C(=O)C(F)(F)F)ccc2C12CCN(C(=O)c1ccc(COCC(F)(F)F)cc1)CC2] 553 |
| 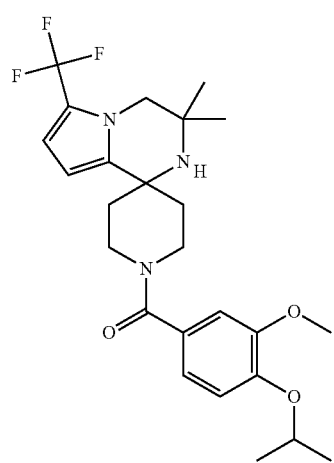 551 | 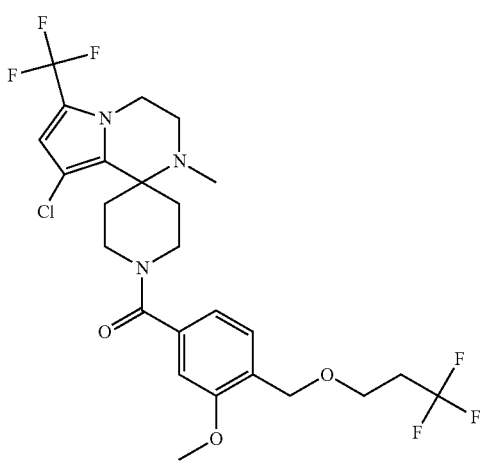 [SMILES: COc1cc(C(=O)N2CCC3(CC2)c2c(Cl)cc(C(F)(F)F)n2CCN3C)ccc1COCCC(F)(F)F] 554 |

| 555 | 558 |
|---|---|
| 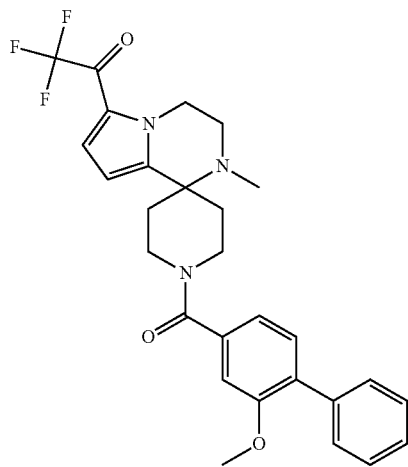 [SMILES: COc1cc(C(=O)N2CCC3(CC2)c2ccc(C(=O)C(F)(F)F)n2CCN3C)ccc1-c1ccccc1] | 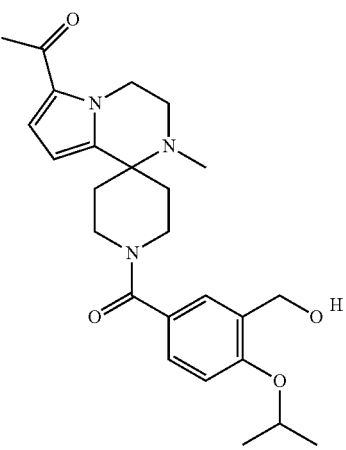 |
| 556 | 559 |
|---|---|
| 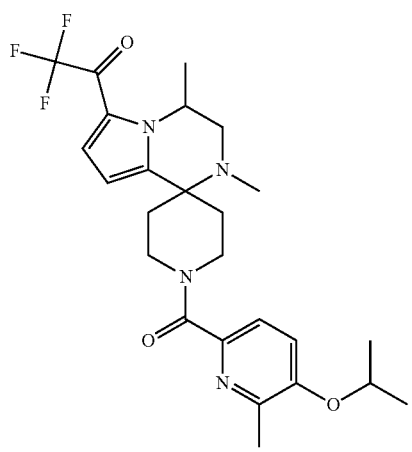 [SMILES: Cc1nc(C(=O)N2CCC3(CC2)c2ccc(C(=O)C(F)(F)F)n2C(C)CN3C)ccc1OC(C)C] | 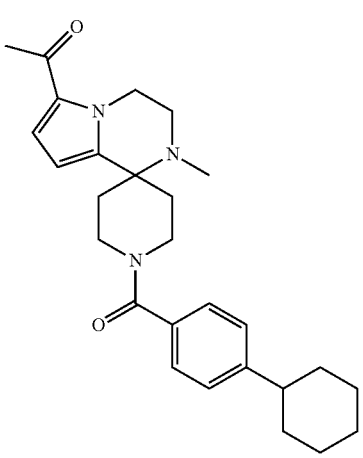 |
| 557 | 560 |
|---|---|
| 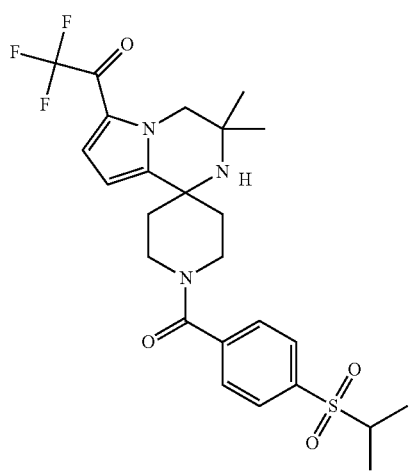 | 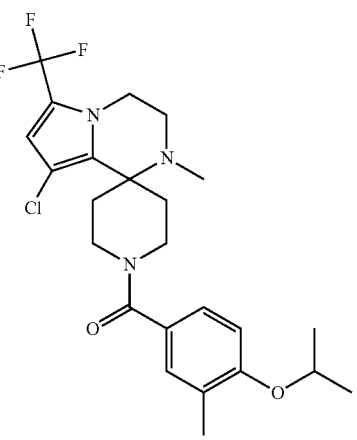 |

| 231 -continued | 232 -continued |
|---|---|
| 561 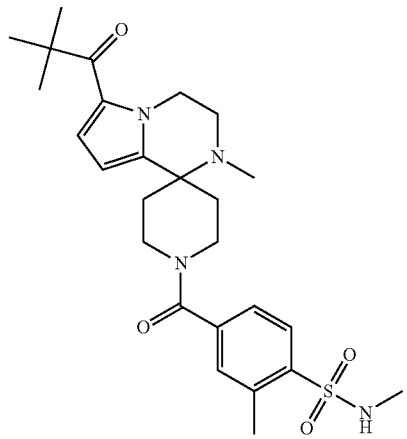 [SMILES: CNS(=O)(=O)c1ccc(C(=O)N2CCC3(CC2)c2ccc(C(=O)C(C)(C)C)n2CCN3C)cc1C] | 564 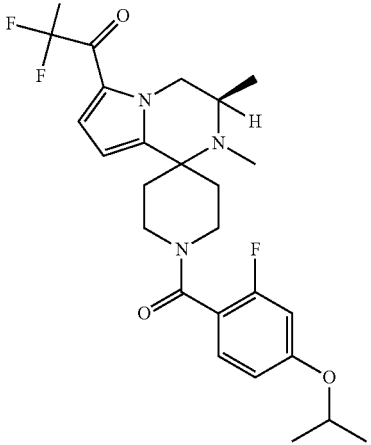 |
| 562 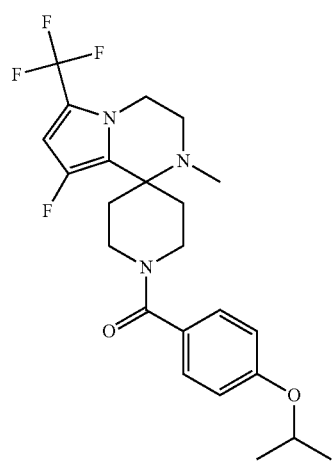 [SMILES: CC(C)Oc1ccc(C(=O)N2CCC3(CC2)c2c(F)cc(C(F)(F)F)n2CCN3C)cc1] | 565 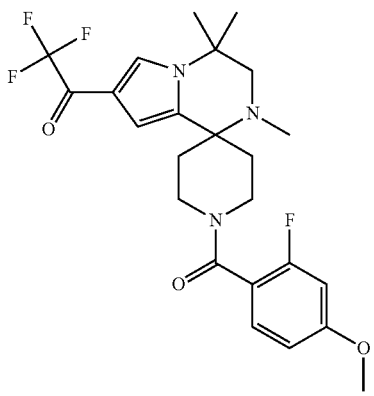 |
| 563 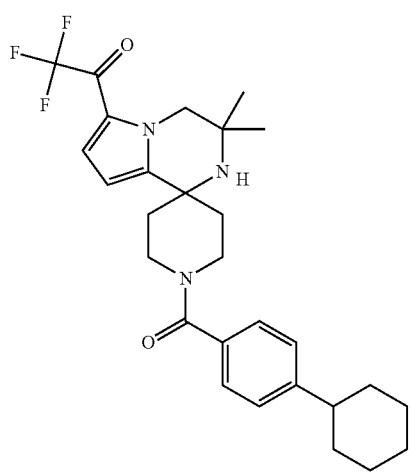 | 566 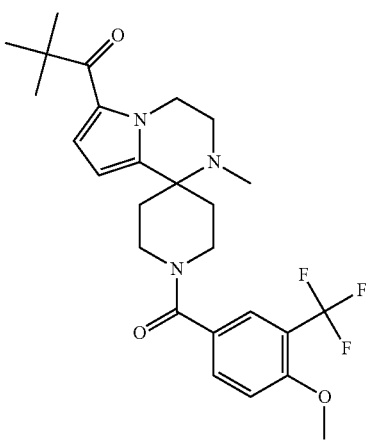 [SMILES: COc1ccc(C(=O)N2CCC3(CC2)c2ccc(C(=O)C(C)(C)C)n2CCN3C)cc1C(F)(F)F] |

233
-continued
567
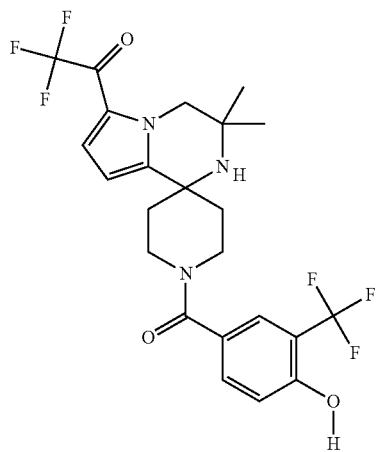
568
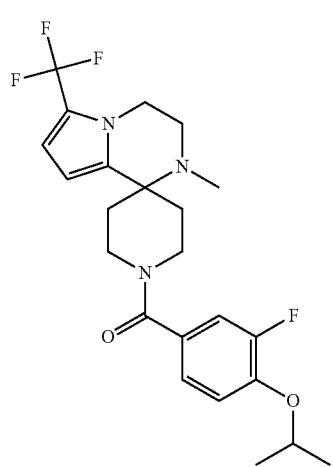 [SMILES: CC(C)Oc1ccc(C(=O)N2CCC3(CC2)c2ccc(C(F)(F)F)n2CCN3C)cc1F]
569
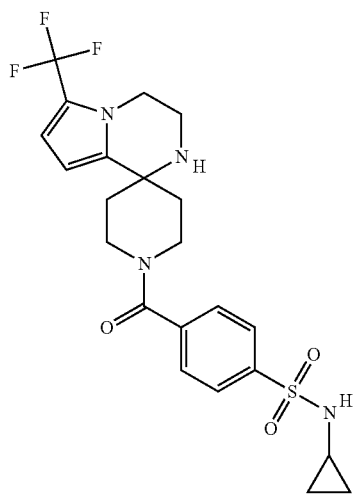
234
-continued
570
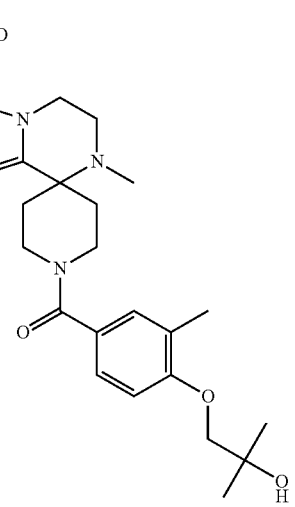
571
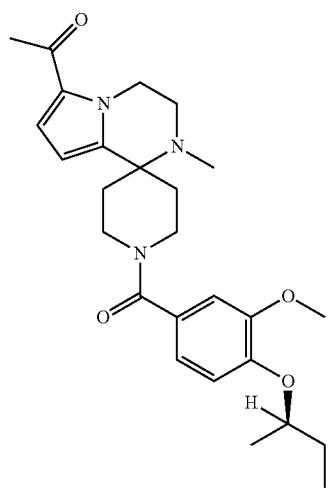
572

235
-continued
573
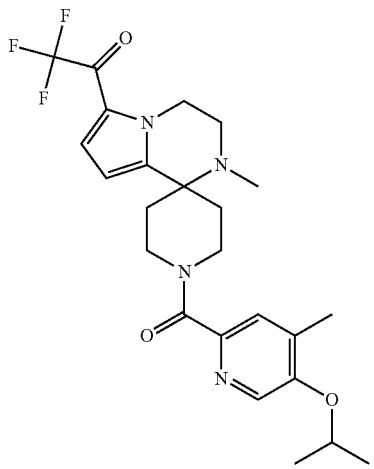 [SMILES: Cc1cc(C(=O)N2CCC3(CC2)c2ccc(C(=O)C(F)(F)F)n2CCN3C)ncc1OC(C)C]
574
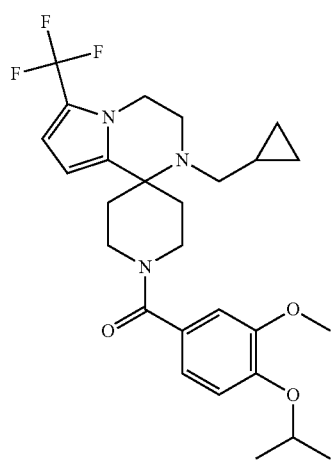 [SMILES: COc1cc(C(=O)N2CCC3(CC2)c2ccc(C(F)(F)F)n2CCN3CC2CC2)ccc1OC(C)C]
575
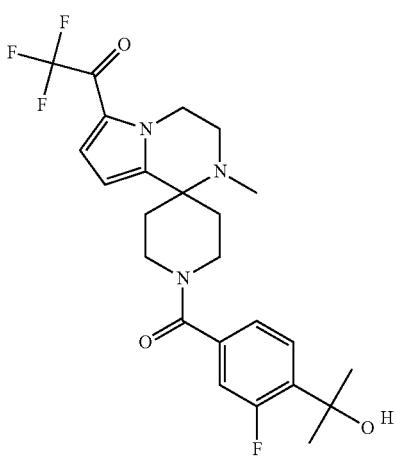
236
-continued
576
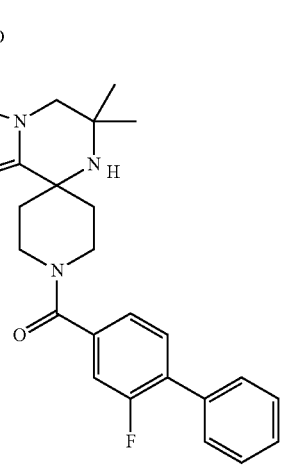
577
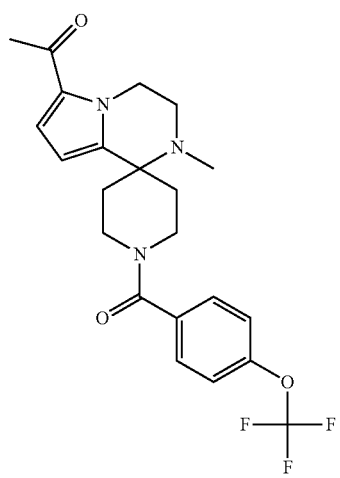 [SMILES: CC(=O)c1ccc2n1CCN(C)C21CCN(C(=O)c2ccc(OC(F)(F)F)cc2)CC1]
578
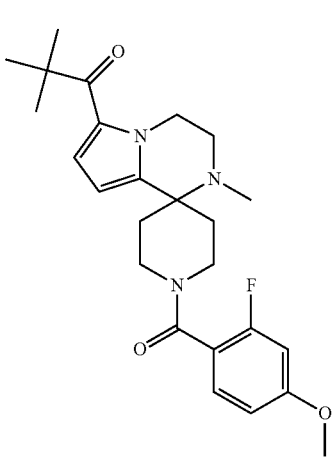 [SMILES: COc1ccc(C(=O)N2CCC3(CC2)c2ccc(C(=O)C(C)(C)C)n2CCN3C)c(F)c1]

| 237 -continued | 238 -continued |
|---|---|
| 579 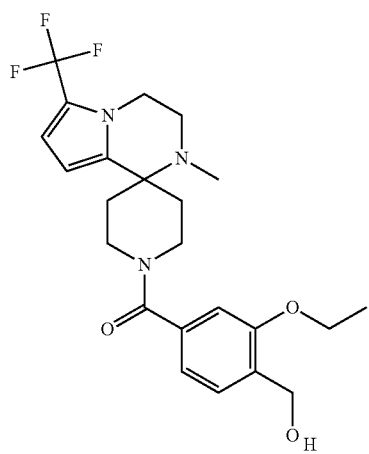 | 582 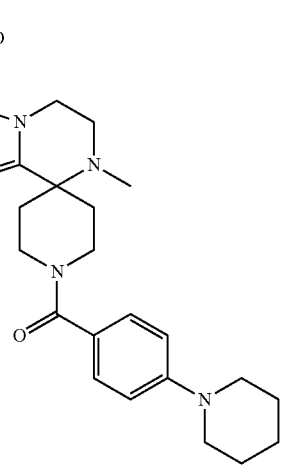 |
| 580 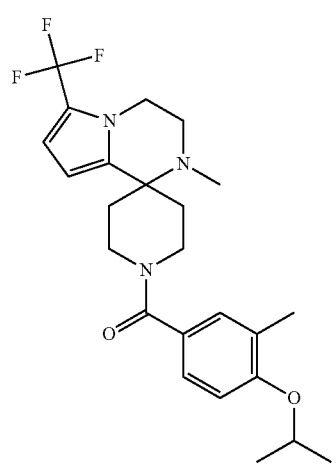 | 583 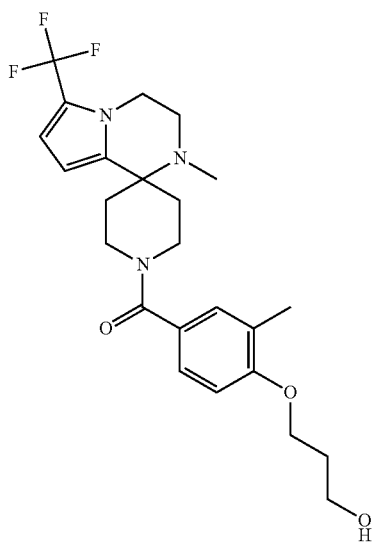 |
| 581 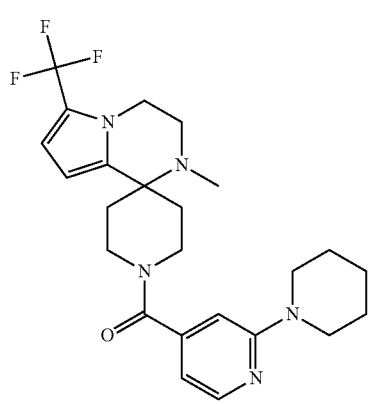 [SMILES: CN1CCn2c(C(F)(F)F)ccc2C12CCN(C(=O)c1ccnc(N3CCCCC3)c1)CC2] | 584 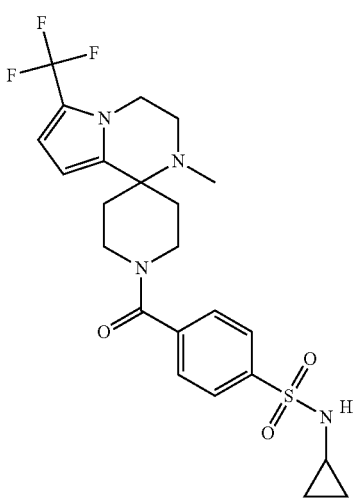 |

| 585 | 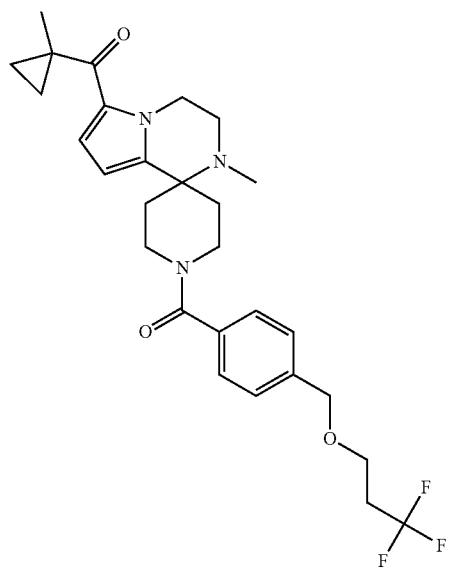 [SMILES: CN1CCn2c(C(=O)C3(C)CC3)ccc2C12CCN(C(=O)c1ccc(COCCC(F)(F)F)cc1)CC2] | 588 | 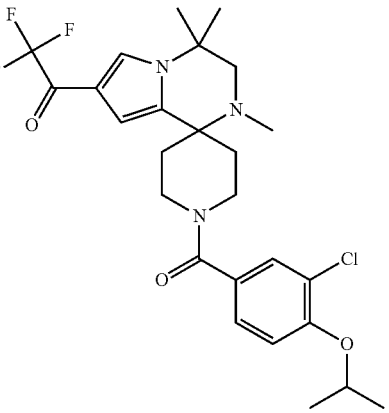 |
| 586 | 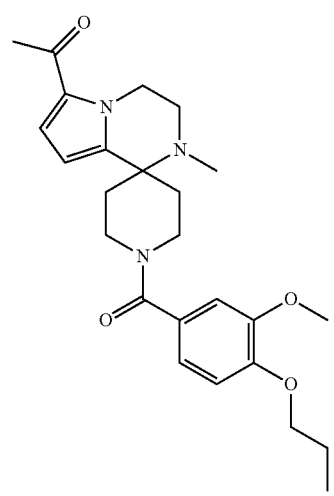 [SMILES: CCCOc1ccc(C(=O)N2CCC3(CC2)c2ccc(C(C)=O)n2CCN3C)cc1OC] | 589 | 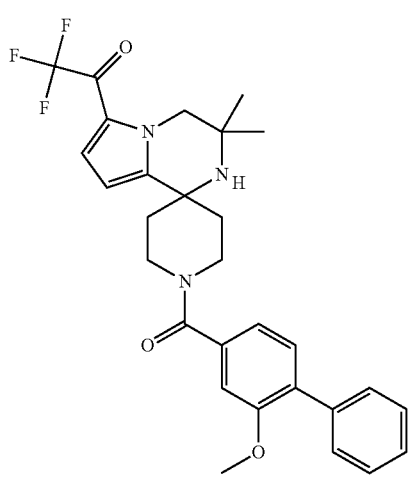 |
| 587 | 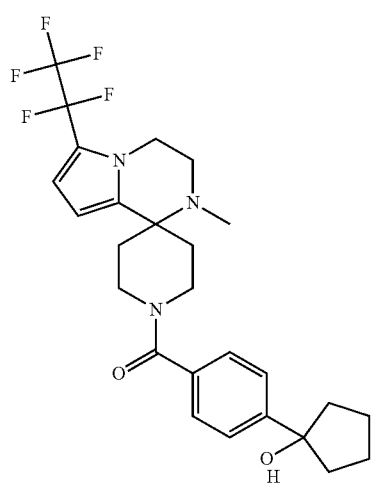 | 590 | 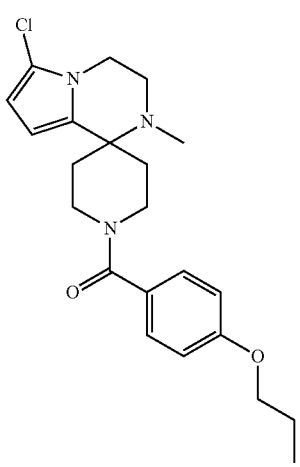 [SMILES: CCCOc1ccc(C(=O)N2CCC3(CC2)c2ccc(Cl)n2CCN3C)cc1] |

| 241 -continued | 242 -continued |
|---|---|
| 591 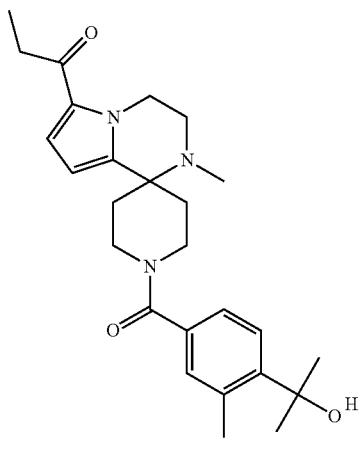 | 594 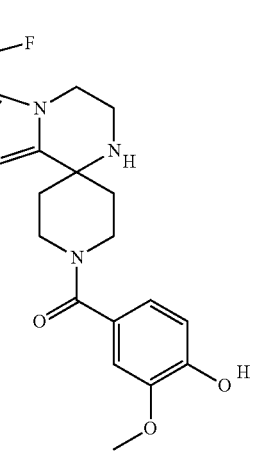 |
| 592 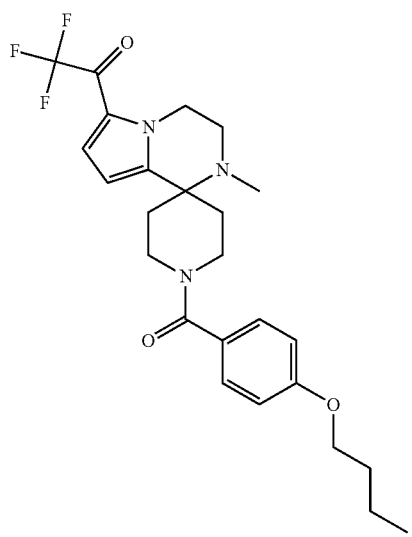 | 595 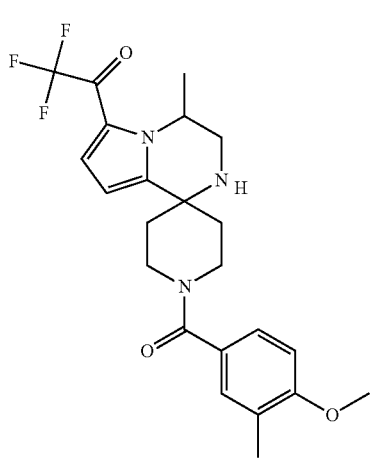 |
| 593 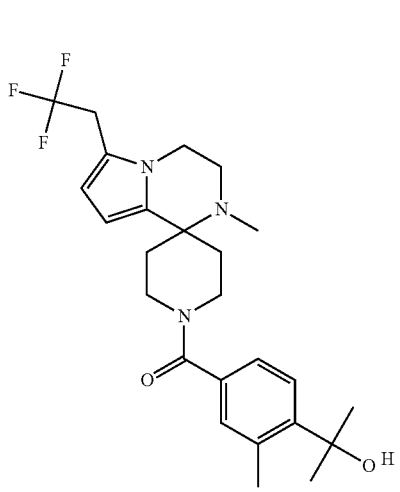 | 596 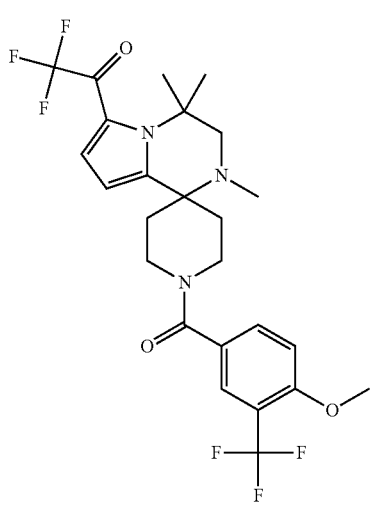 [SMILES: COc1ccc(C(=O)N2CCC3(CC2)c2ccc(C(=O)C(F)(F)F)n2C(C)(C)CN3C)cc1C(F)(F)F] |

| 243 -continued | 244 -continued |
|---|---|
| 597 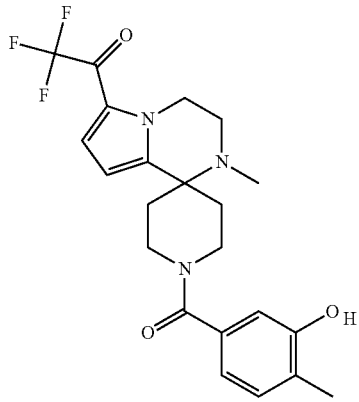 | 600 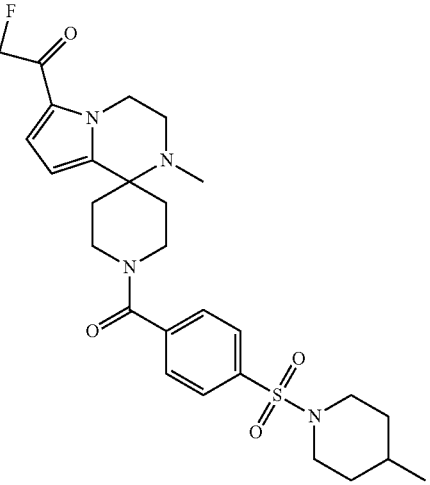 |
| 598 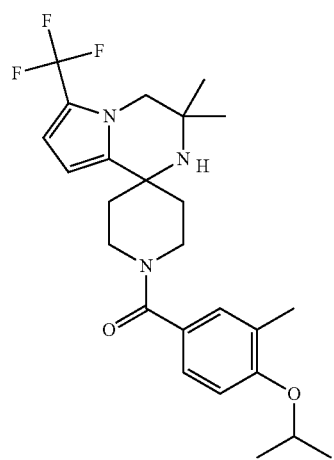 | 601 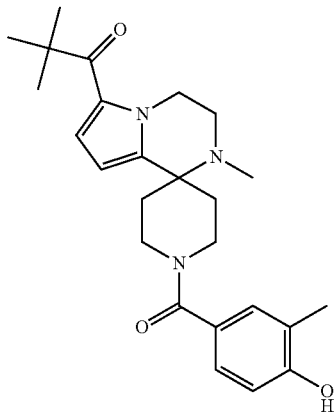 |
| 599 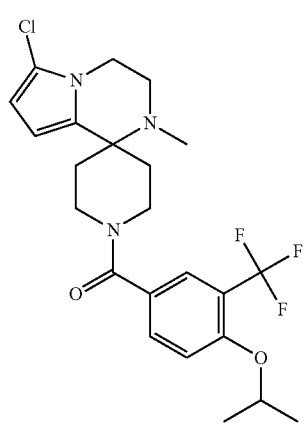 [SMILES: CC(C)Oc1ccc(C(=O)N2CCC3(CC2)c2ccc(Cl)n2CCN3C)cc1C(F)(F)F] | 602 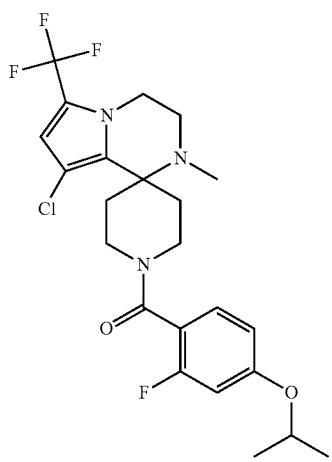 [SMILES: CC(C)Oc1ccc(C(=O)N2CCC3(CC2)c2c(Cl)cc(C(F)(F)F)n2CCN3C)c(F)c1] |

| 603 | 606 |
|---|---|
| 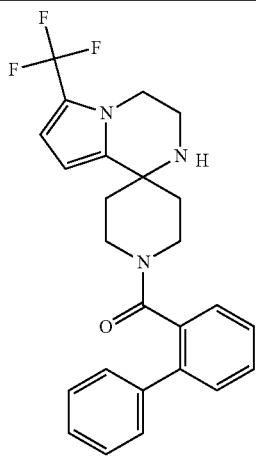 | 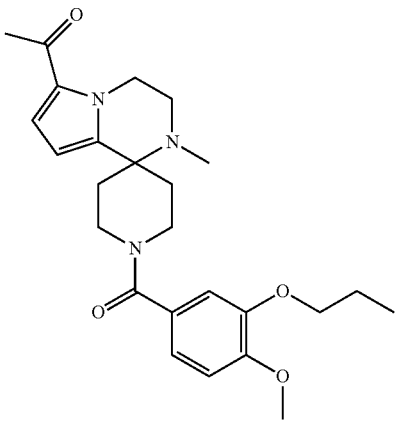 |
| 604 | 607 |
|---|---|
| 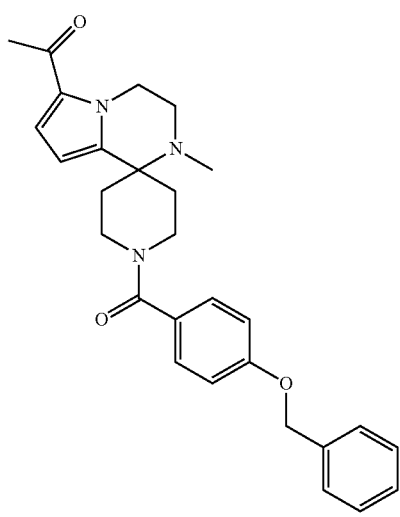 | 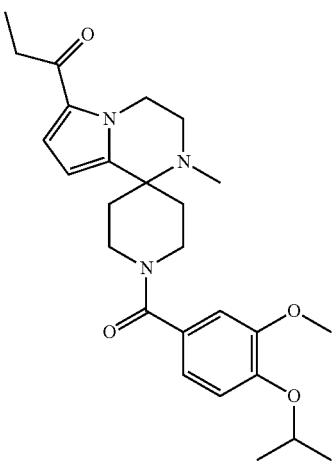 |
| 605 | 608 |
|---|---|
| 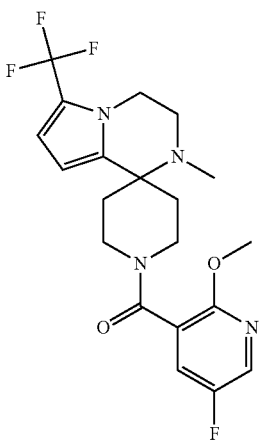 [SMILES: COc1ncc(F)cc1C(=O)N1CCC2(CC1)c1ccc(C(F)(F)F)n1CCN2C] | 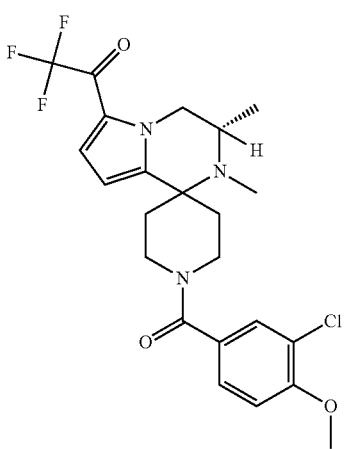 [SMILES: COc1ccc(C(=O)N2CCC3(CC2)c2ccc(C(=O)C(F)(F)F)n2C[C@H](C)N3C)cc1Cl] |

| 247 -continued | 248 -continued |
|---|---|
| 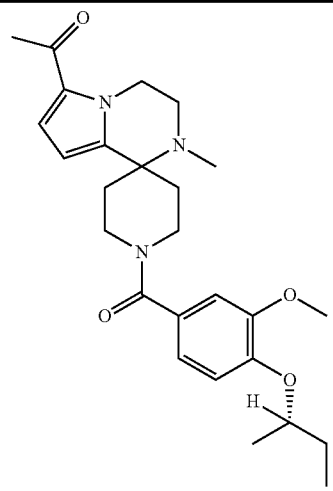 609 | 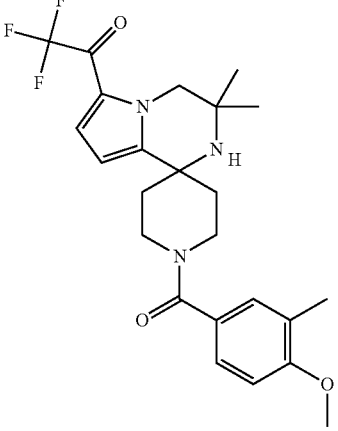 612 |
| 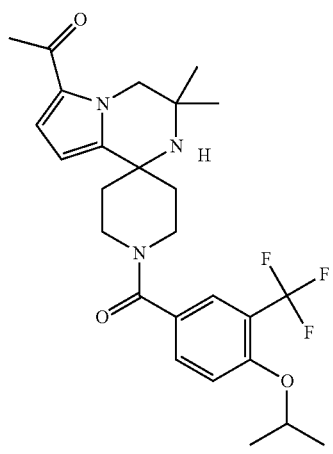 610 | 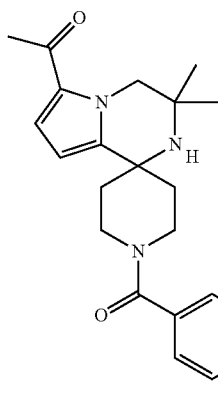 613 |
| 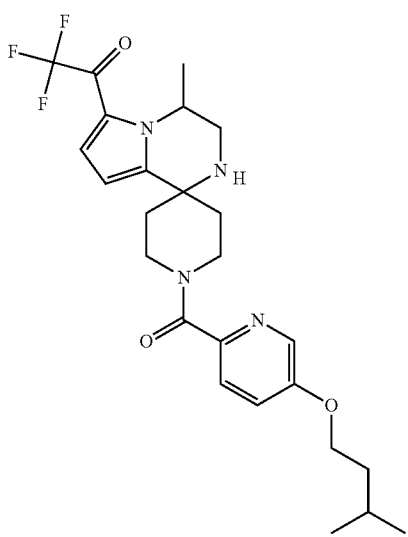 611 | 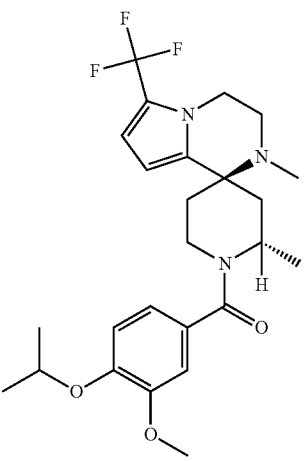 [SMILES: COc1cc(C(=O)N2CC[C@@]3(C[C@@H]2C)c2ccc(C(F)(F)F)n2CCN3C)ccc1OC(C)C] 614 |

| 249 -continued | 250 -continued |
|---|---|
| 615 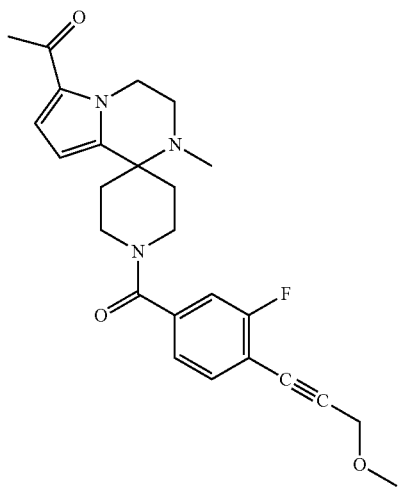 [SMILES: COCC#Cc1ccc(C(=O)N2CCC3(CC2)c2ccc(C(C)=O)n2CCN3C)cc1F] | 618 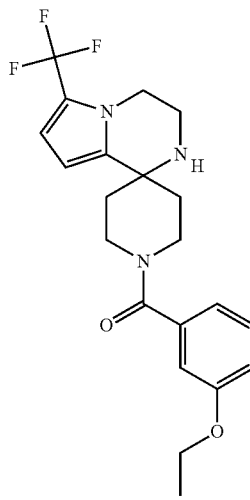 |
| 616 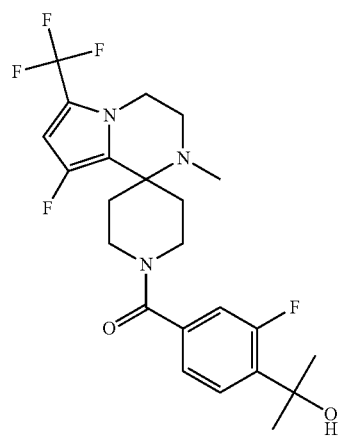 | 619 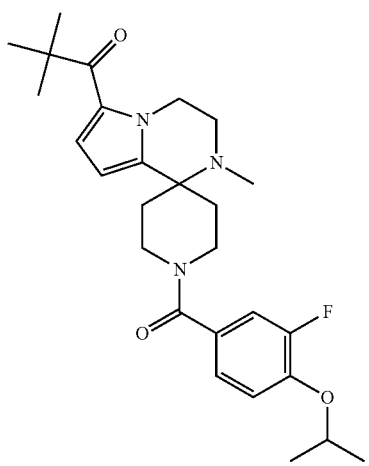 |
| 617 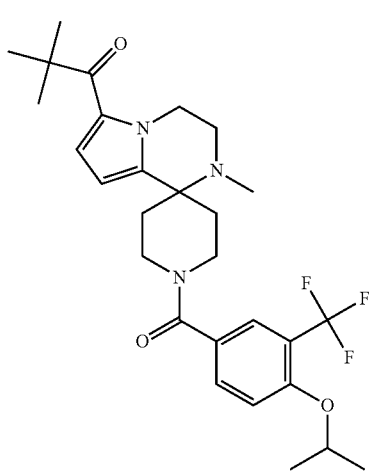 [SMILES: CC(C)Oc1ccc(C(=O)N2CCC3(CC2)c2ccc(C(=O)C(C)(C)C)n2CCN3C)cc1C(F)(F)F] | 620 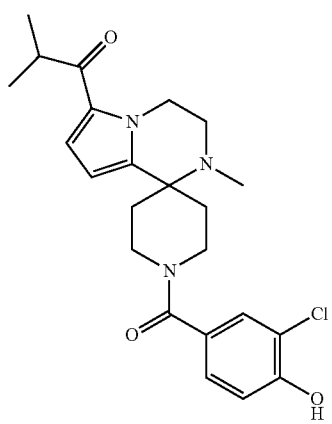 [SMILES: CC(C)C(=O)c1ccc2n1CCN(C)C21CCN(C(=O)c2ccc(O)c(Cl)c2)CC1] |

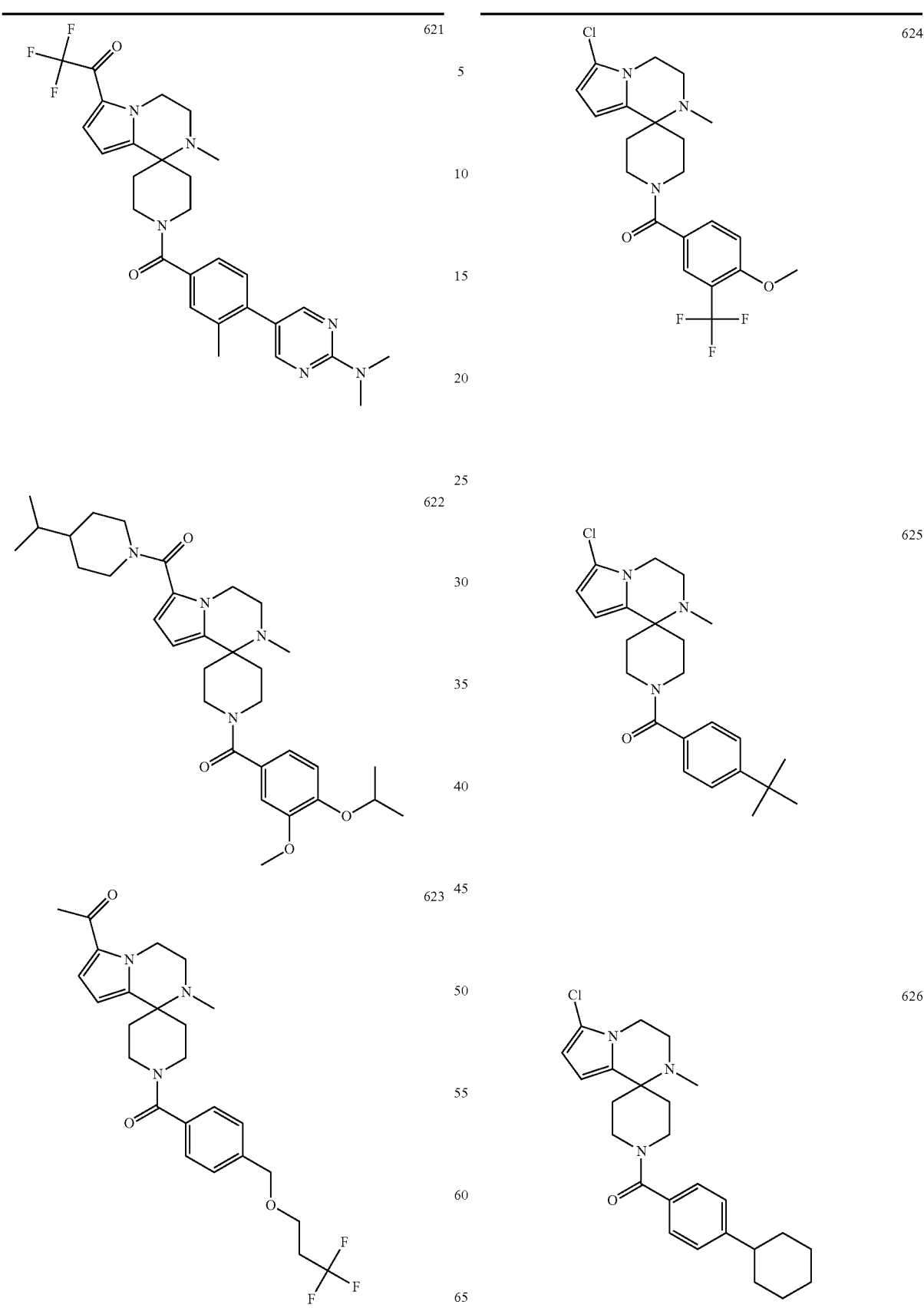

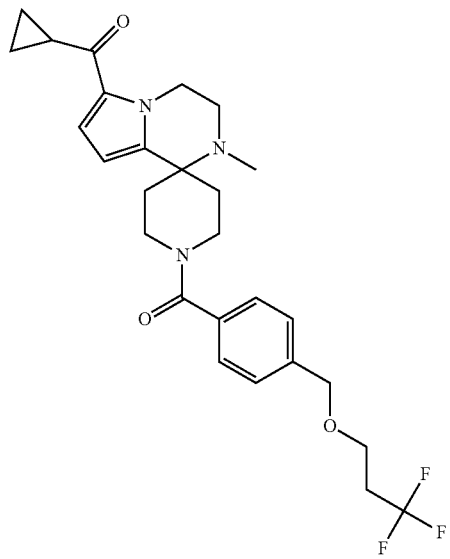 [SMILES: CN1CCn2c(C(=O)C3CC3)ccc2C12CCN(C(=O)c1ccc(COCCC(F)(F)F)cc1)CC2]
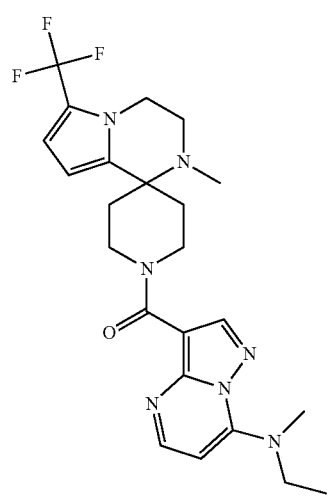 [SMILES: CCN(C)c1ccnc2c(C(=O)N3CCC4(CC3)c3ccc(C(F)(F)F)n3CCN4C)cnn12]
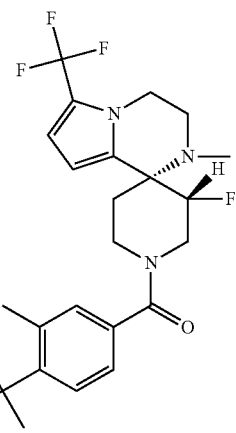
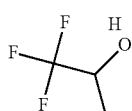
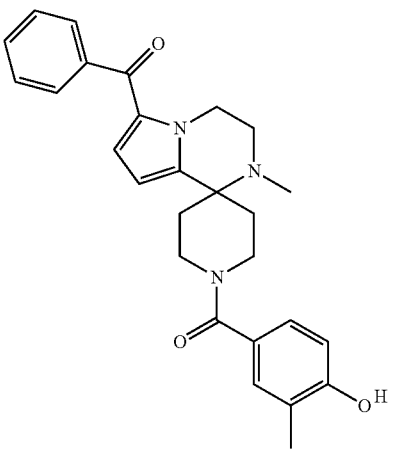

| 255 -continued | 256 -continued |
|---|---|
| 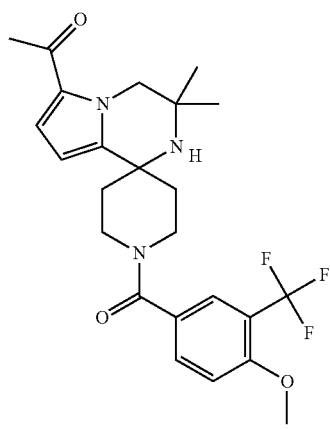 633 | 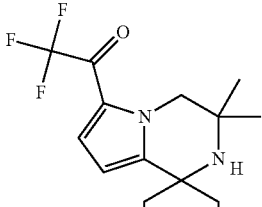 636 |
| 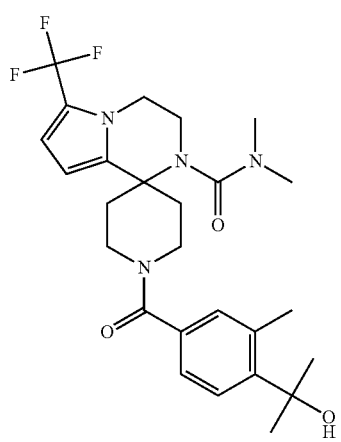 [SMILES: Cc1cc(C(=O)N2CCC3(CC2)c2ccc(C(F)(F)F)n2CCN3C(=O)N(C)C)ccc1C(C)(C)O] 634 | 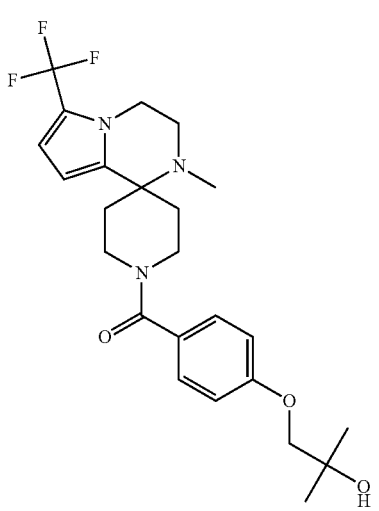 637 |
| 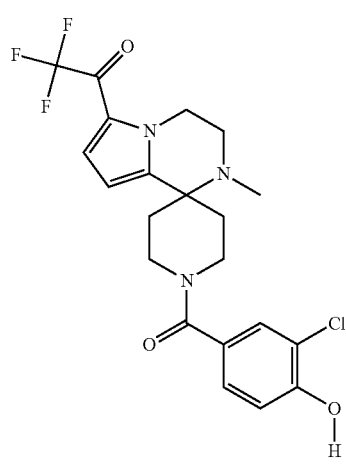 [SMILES: CN1CCn2c(C(=O)C(F)(F)F)ccc2C12CCN(C(=O)c1ccc(O)c(Cl)c1)CC2] 635 | 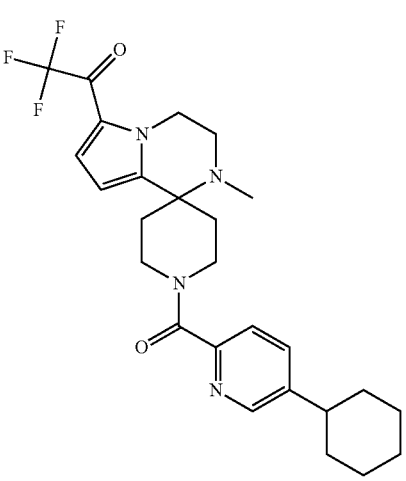 638 |

257
-continued
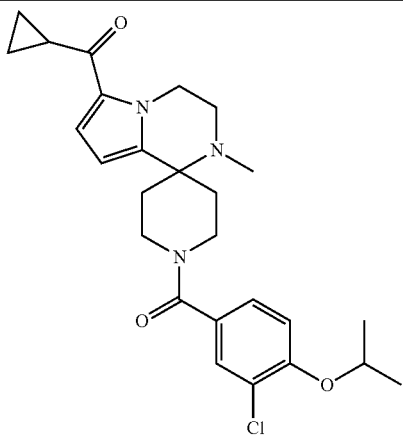
639
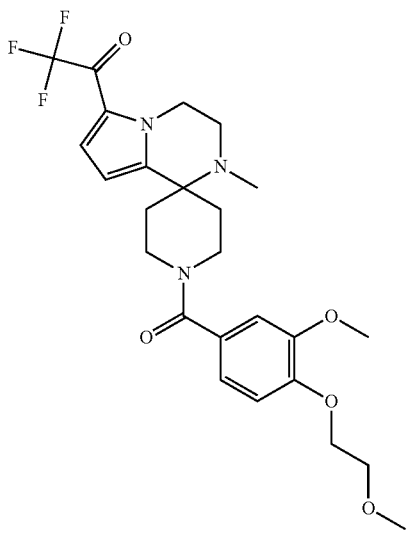 [SMILES: COCCOc1ccc(C(=O)N2CCC3(CC2)c2ccc(C(=O)C(F)(F)F)n2CCN3C)cc1OC]
640
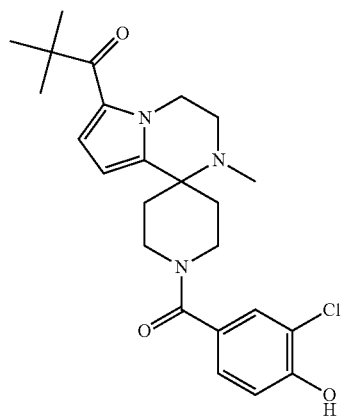 [SMILES: CN1CCn2c(C(=O)C(C)(C)C)ccc2C12CCN(C(=O)c1ccc(O)c(Cl)c1)CC2]
641
258
-continued
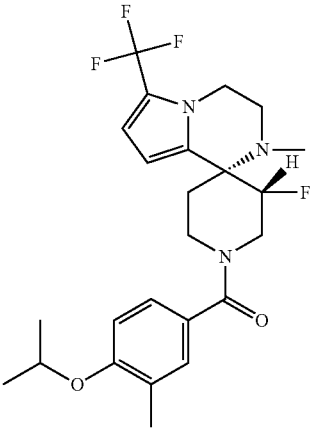 [SMILES: Cc1cc(C(=O)N2CC[C@@]3(c4ccc(C(F)(F)F)n4CCN3C)[C@H](F)C2)ccc1OC(C)C]
642
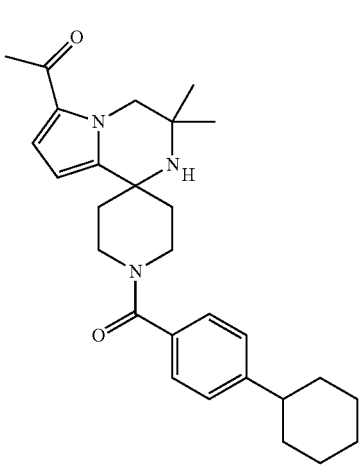
643
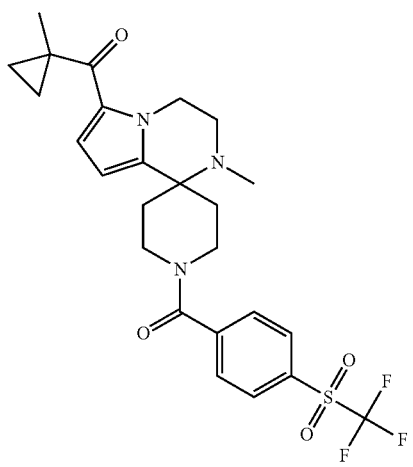 [SMILES: CN1CCn2c(C(=O)C3(C)CC3)ccc2C12CCN(C(=O)c1ccc(S(=O)(=O)C(F)(F)F)cc1)CC2]
644

259
-continued
645
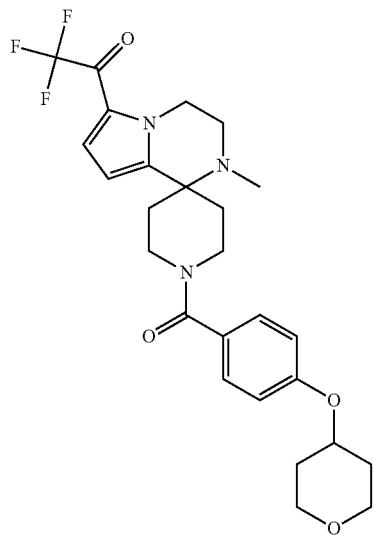 [SMILES: CN1CCn2c(C(=O)C(F)(F)F)ccc2C12CCN(C(=O)c1ccc(OC3CCOCC3)cc1)CC2]
646
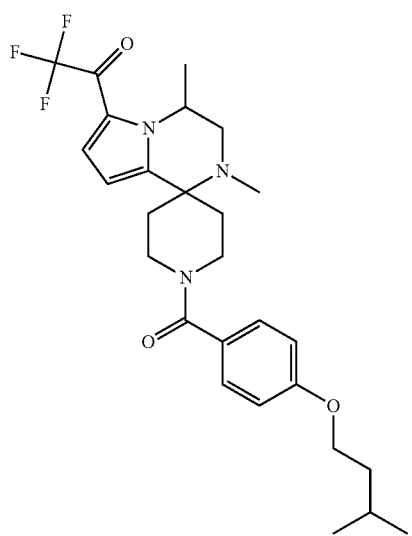 [SMILES: CC(C)CCOc1ccc(C(=O)N2CCC3(CC2)c2ccc(C(=O)C(F)(F)F)n2C(C)CN3C)cc1]
647
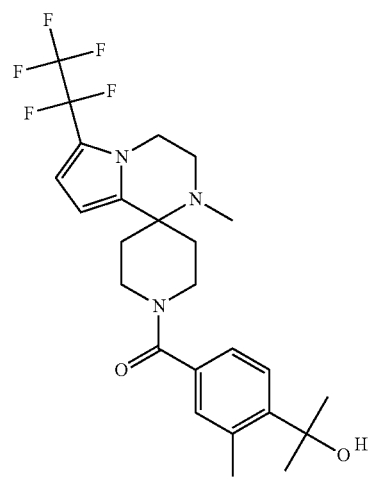
260
-continued
648
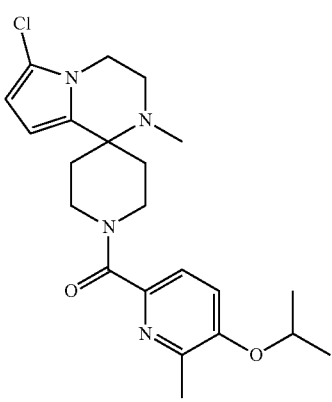 [SMILES: Cc1nc(C(=O)N2CCC3(CC2)c2ccc(Cl)n2CCN3C)ccc1OC(C)C]
649
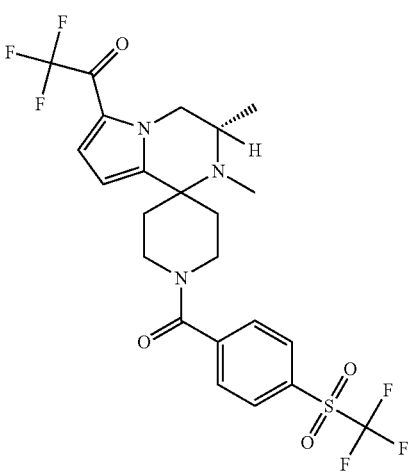 [SMILES: C[C@H]1Cn2c(C(=O)C(F)(F)F)ccc2C2(CCN(C(=O)c3ccc(S(=O)(=O)C(F)(F)F)cc3)CC2)N1C]
650
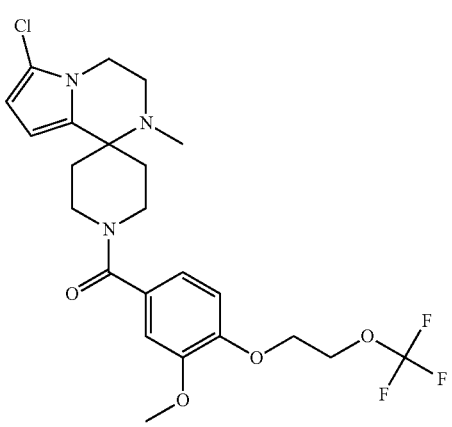 [SMILES: COc1cc(C(=O)N2CCC3(CC2)c2ccc(Cl)n2CCN3C)ccc1OCCOC(F)(F)F]

| 261 -continued | 262 -continued |
|---|---|
| 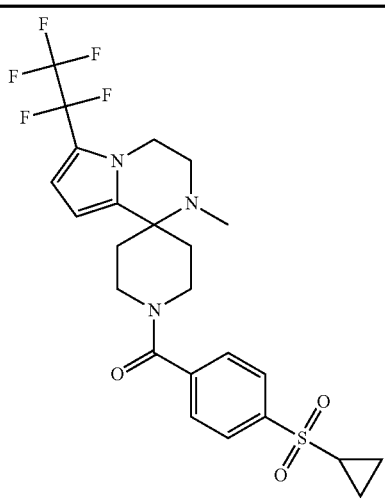 651 | 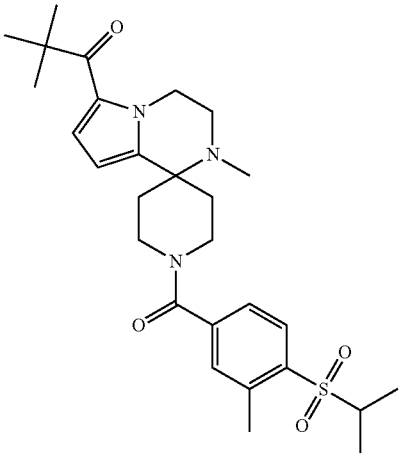 654 |
| 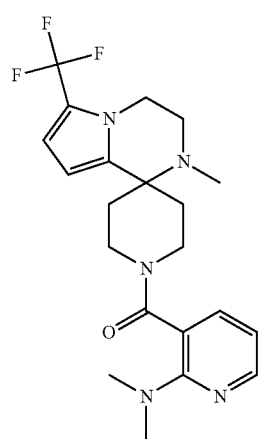 [SMILES: CN(C)c1ncccc1C(=O)N1CCC2(CC1)c1ccc(C(F)(F)F)n1CCN2C] 652 | 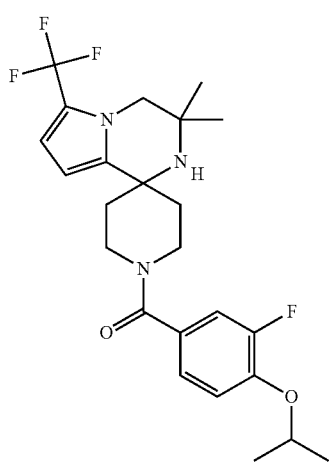 655 |
| 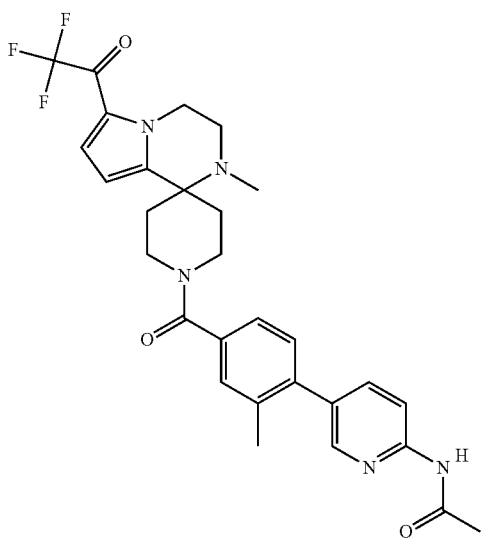 653 | 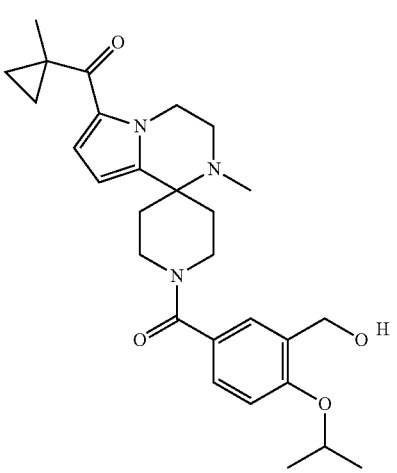 656 |

263
-continued
| | |
|---|---|
| 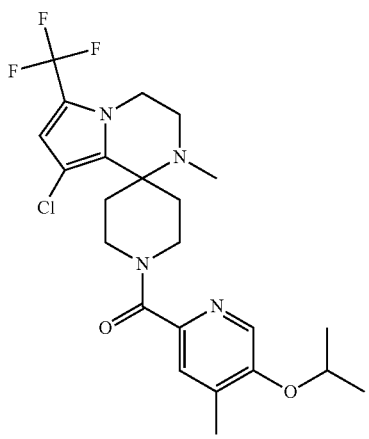 | 657 |
| 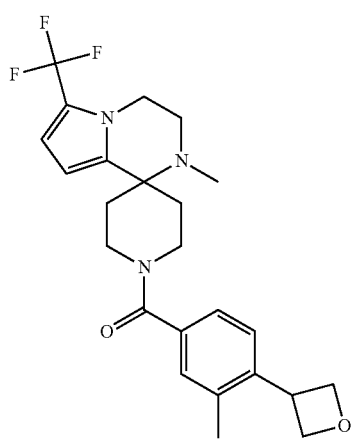 [SMILES: Cc1cc(C(=O)N2CCC3(CC2)c2ccc(C(F)(F)F)n2CCN3C)ccc1C1COC1] | 658 |
| 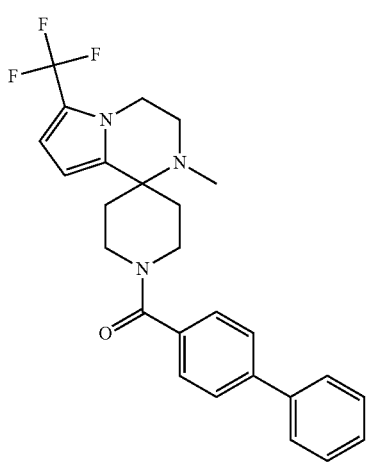 [SMILES: CN1CCn2c(C(F)(F)F)ccc2C12CCN(C(=O)c1ccc(-c3ccccc3)cc1)CC2] | 659 |
264
-continued
| | |
|---|---|
| 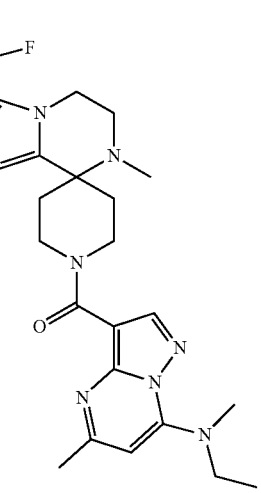 | 660 |
| 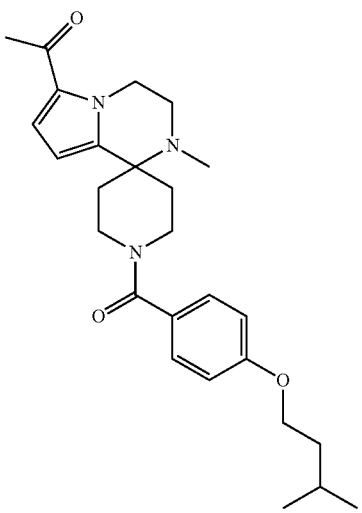 [SMILES: CC(=O)c1ccc2n1CCN(C)C21CCN(C(=O)c2ccc(OCCC(C)C)cc2)CC1] | 661 |
| 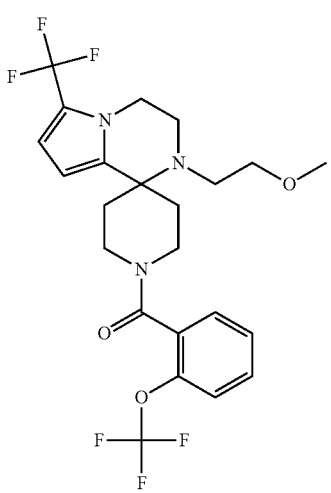 [SMILES: COCCN1CCn2c(C(F)(F)F)ccc2C12CCN(C(=O)c1ccccc1OC(F)(F)F)CC2] | 662 |

| 265 -continued | 266 -continued |
|---|---|
| 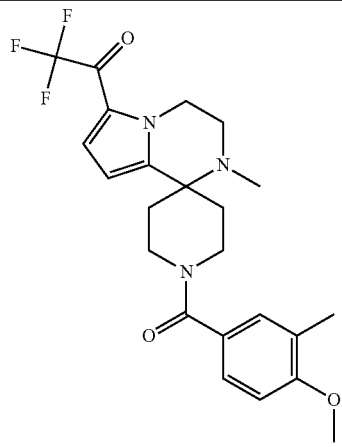 663 | 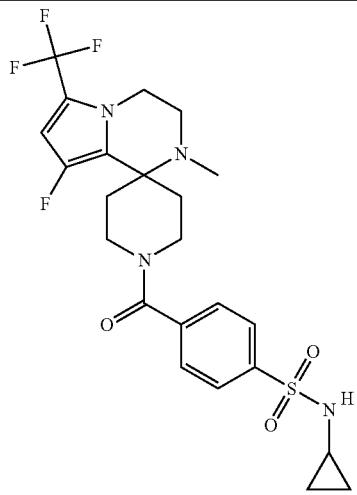 666 |
| 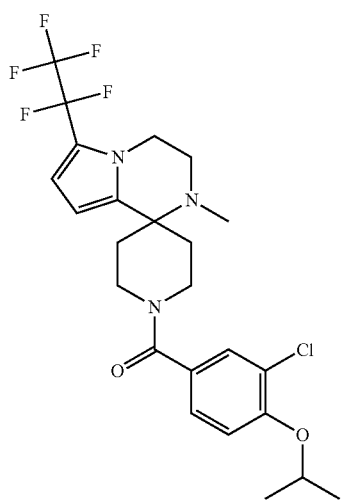 664 | 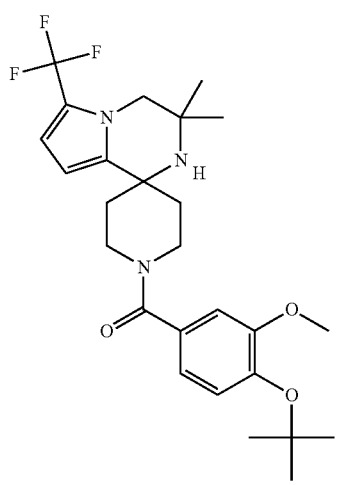 667 |
| 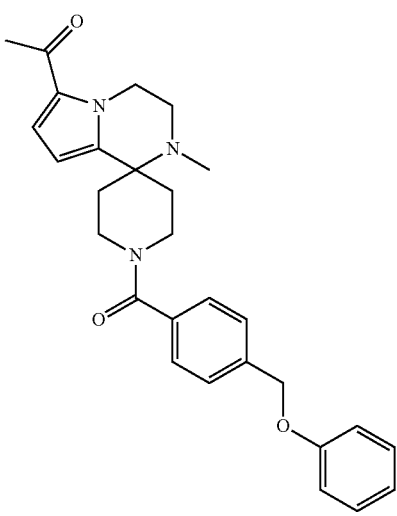 665 | 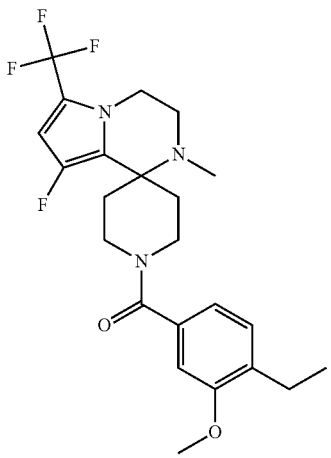 [SMILES: CCc1ccc(C(=O)N2CCC3(CC2)c2c(F)cc(C(F)(F)F)n2CCN3C)cc1OC] 668 |

| 267 -continued | 268 -continued |
|---|---|
| 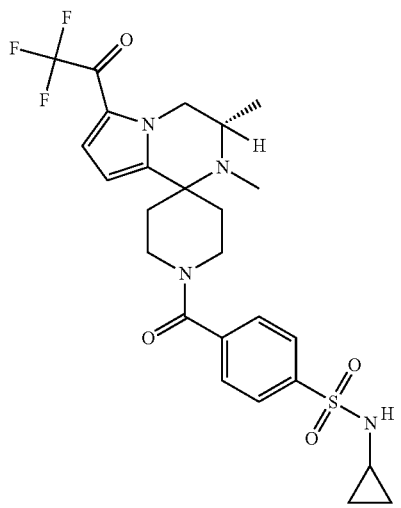 669 | 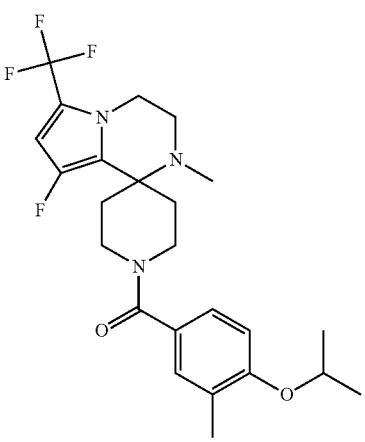 672 |
| 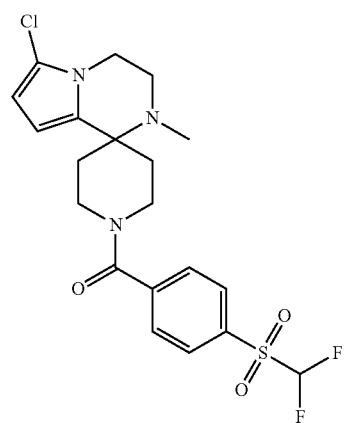 [SMILES: CN1CCn2c(Cl)ccc2C12CCN(C(=O)c1ccc(S(=O)(=O)C(F)F)cc1)CC2] 670 | 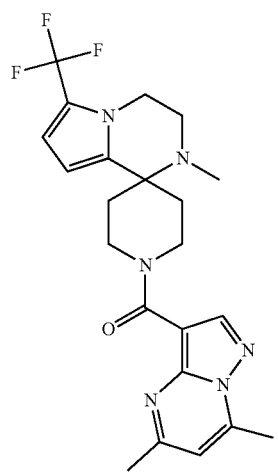 673 |
| 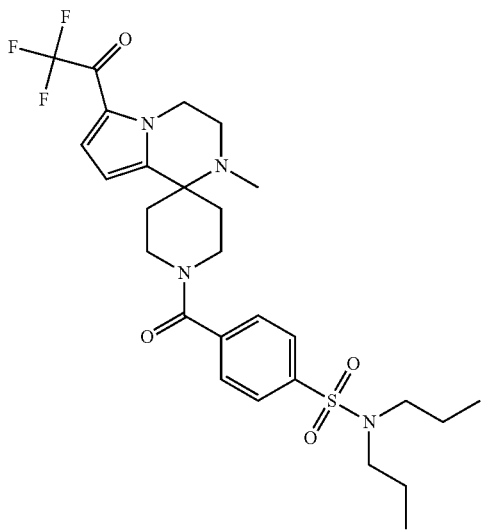 [SMILES: CCCN(CCC)S(=O)(=O)c1ccc(C(=O)N2CCC3(CC2)c2ccc(C(=O)C(F)(F)F)n2CCN3C)cc1] 671 | 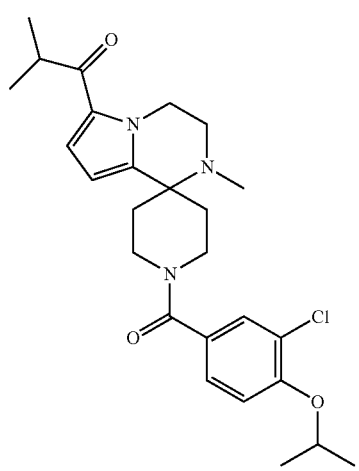 [SMILES: CC(C)Oc1ccc(C(=O)N2CCC3(CC2)c2ccc(C(=O)C(C)C)n2CCN3C)cc1Cl] 674 |

| 269 -continued | 270 -continued |
|---|---|
| 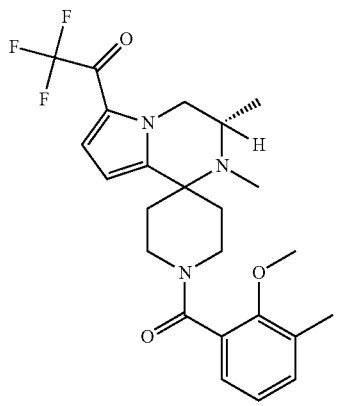 [SMILES: COc1c(C)cccc1C(=O)N1CCC2(CC1)c1ccc(C(=O)C(F)(F)F)n1C[C@H](C)N2C] 675 | 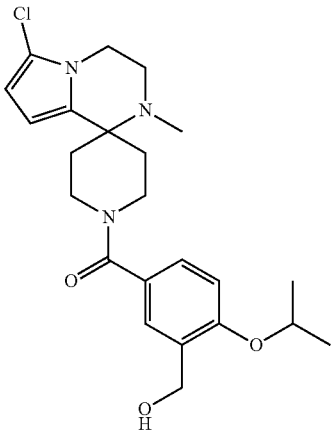 678 |
| 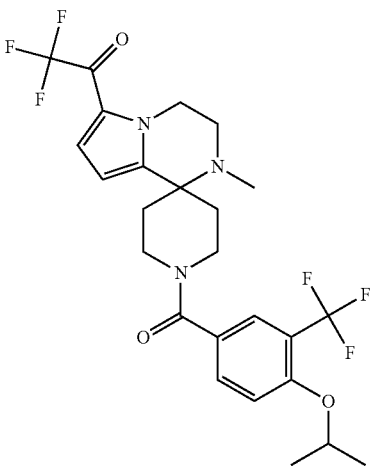 [SMILES: CC(C)Oc1ccc(C(=O)N2CCC3(CC2)c2ccc(C(=O)C(F)(F)F)n2CCN3C)cc1C(F)(F)F] 676 | 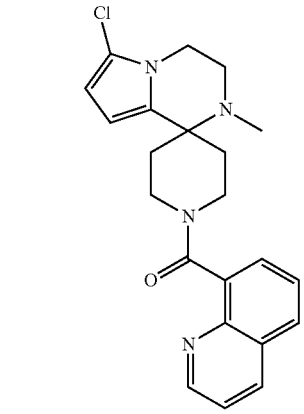 679 |
| 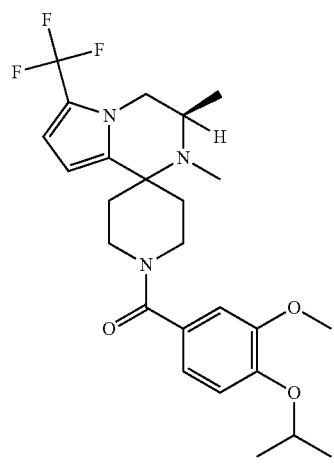 [SMILES: COc1cc(C(=O)N2CCC3(CC2)c2ccc(C(F)(F)F)n2C[C@@H](C)N3C)ccc1OC(C)C] 677 | 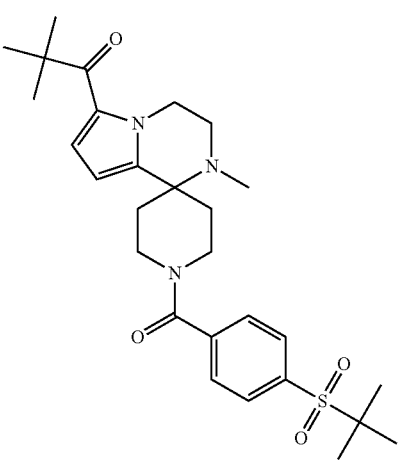 [SMILES: CN1CCn2c(C(=O)C(C)(C)C)ccc2C12CCN(C(=O)c1ccc(S(=O)(=O)C(C)(C)C)cc1)CC2] 680 |

271
-continued
681
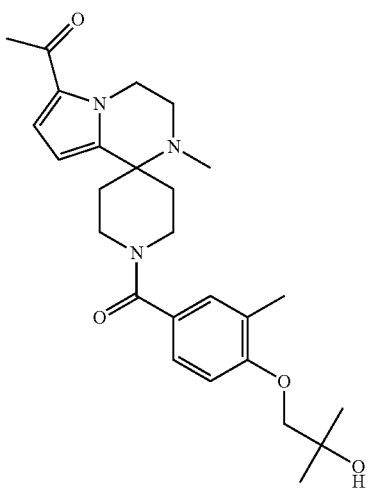 [SMILES: CC(=O)c1ccc2n1CCN(C)C21CCN(C(=O)c2ccc(OCC(C)(C)O)c(C)c2)CC1]
682
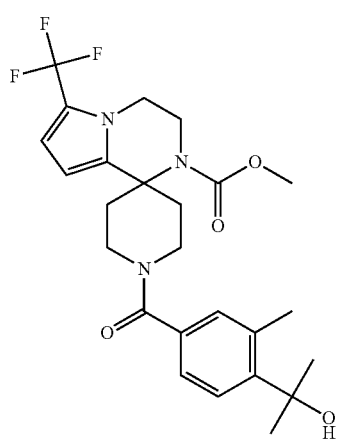 [SMILES: COC(=O)N1CCn2c(C(F)(F)F)ccc2C12CCN(C(=O)c1ccc(C(C)(C)O)c(C)c1)CC2]
683
272
-continued
684
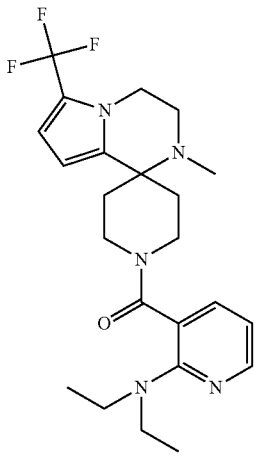 [SMILES: CCN(CC)c1ncccc1C(=O)N1CCC2(CC1)c1ccc(C(F)(F)F)n1CCN2C]
685
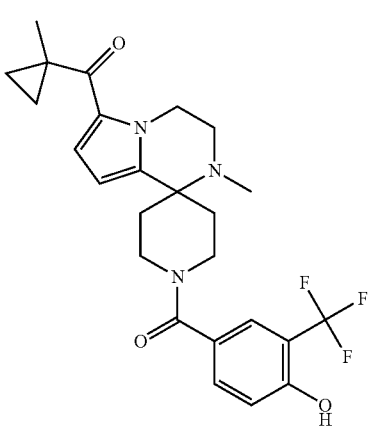 [SMILES: CN1CCn2c(C(=O)C3(C)CC3)ccc2C12CCN(C(=O)c1ccc(O)c(C(F)(F)F)c1)CC2]
686
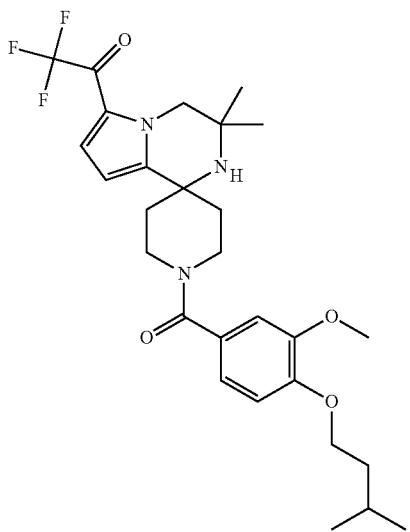

| 273 -continued | 274 -continued |
|---|---|
| 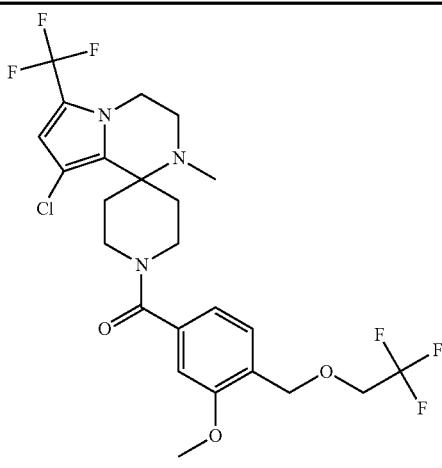 687 | 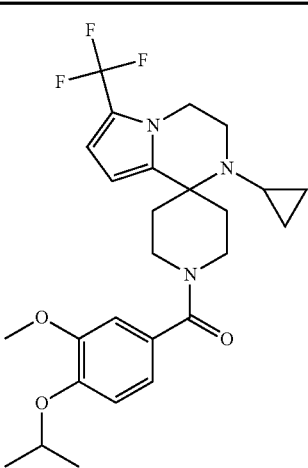 690 |
| 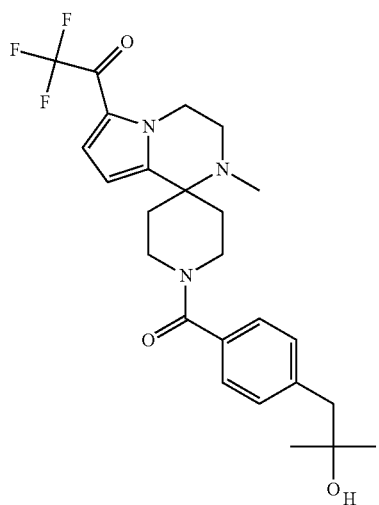 688 | 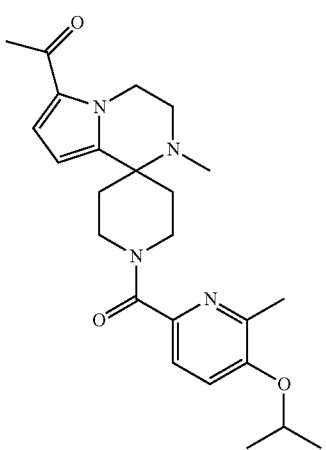 691 |
| 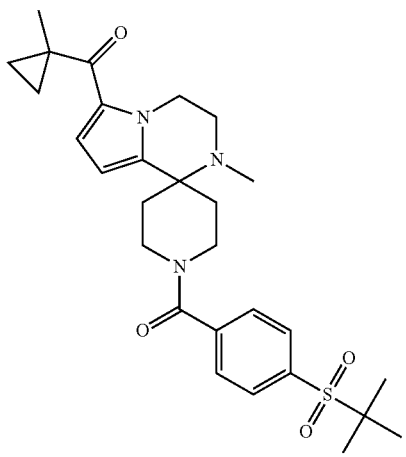 [SMILES: CN1CCn2c(C(=O)C3(C)CC3)ccc2C12CCN(C(=O)c1ccc(S(=O)(=O)C(C)(C)C)cc1)CC2] 689 | 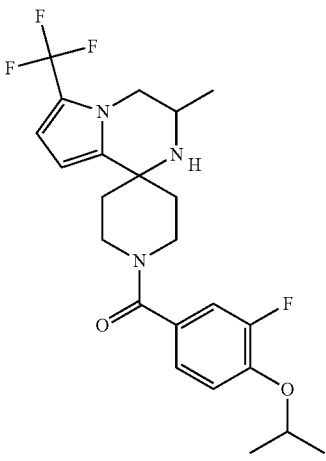 692 |

275 -continued

693

694

695

276 -continued

696

697

698

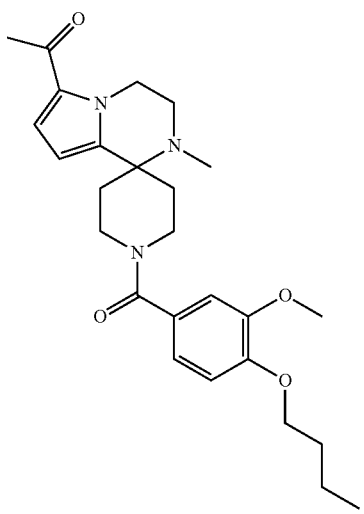 [SMILES: CCCCOc1ccc(C(=O)N2CCC3(CC2)c2ccc(C(C)=O)n2CCN3C)cc1OC]
699
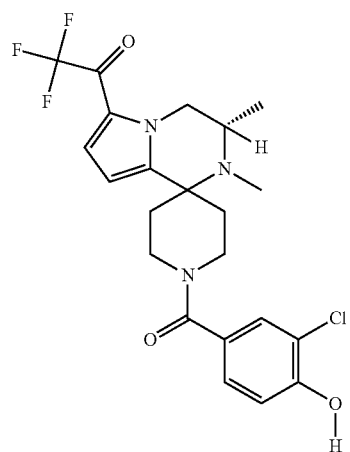 [SMILES: C[C@H]1Cn2c(C(=O)C(F)(F)F)ccc2C2(CCN(C(=O)c3ccc(O)c(Cl)c3)CC2)N1C]
700
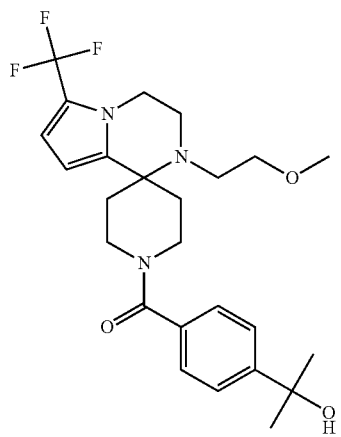 [SMILES: COCCN1CCn2c(C(F)(F)F)ccc2C12CCN(C(=O)c1ccc(C(C)(C)O)cc1)CC2]
701
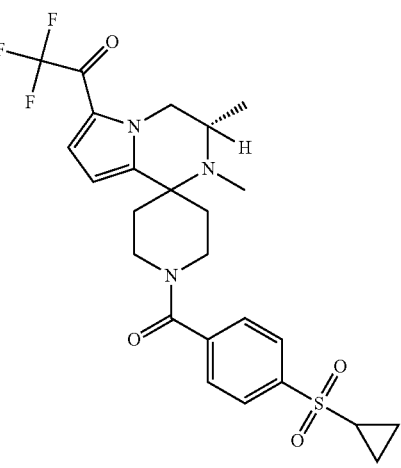
702
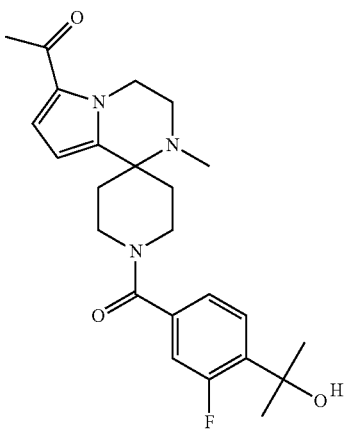
703
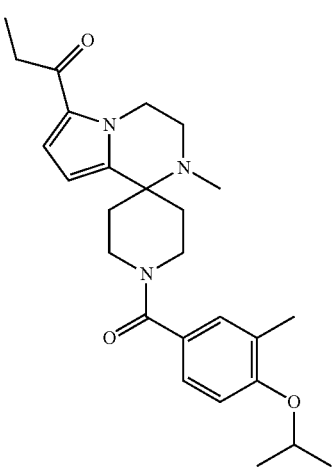 [SMILES: CCC(=O)c1ccc2n1CCN(C)C21CCN(C(=O)c2ccc(OC(C)C)c(C)c2)CC1]
704

279
-continued
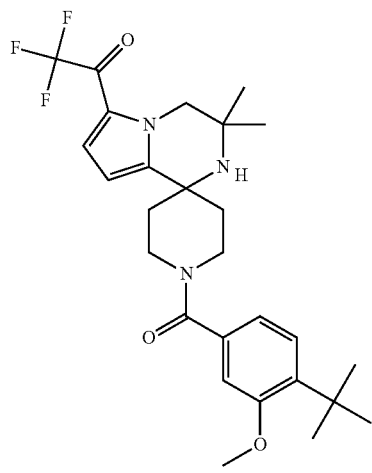
705
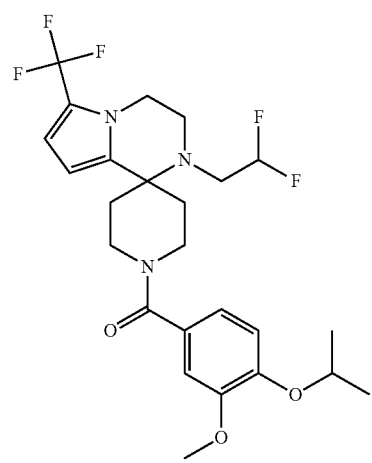 [SMILES: COc1cc(C(=O)N2CCC3(CC2)c2ccc(C(F)(F)F)n2CCN3CC(F)F)ccc1OC(C)C]
706
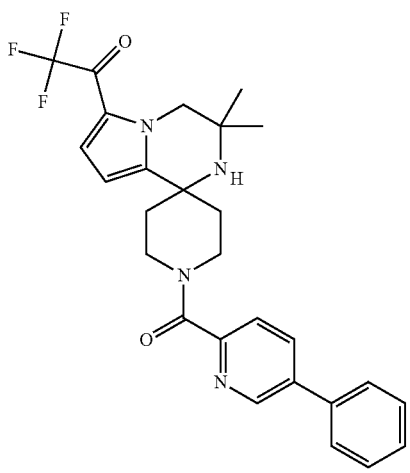
707
280
-continued
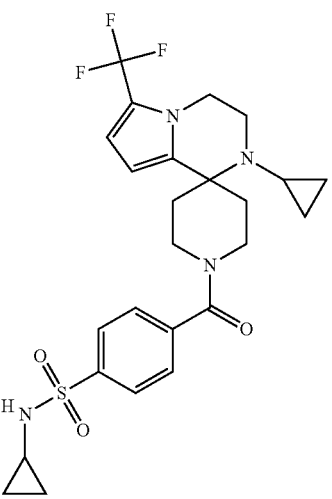
708
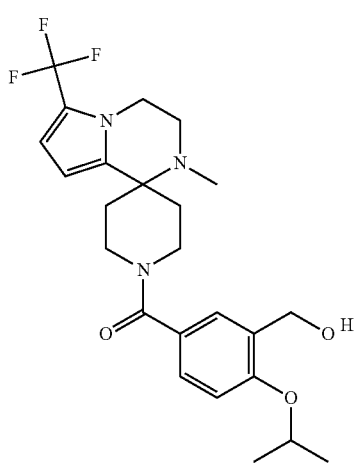
709
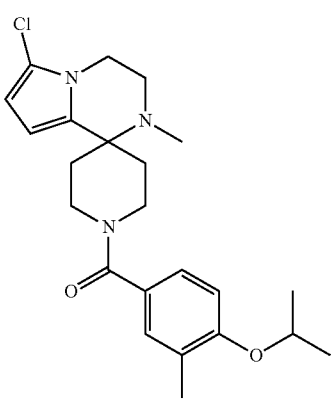 [SMILES: Cc1cc(C(=O)N2CCC3(CC2)c2ccc(Cl)n2CCN3C)ccc1OC(C)C]
710

| 281 -continued | 282 -continued |
|---|---|
| 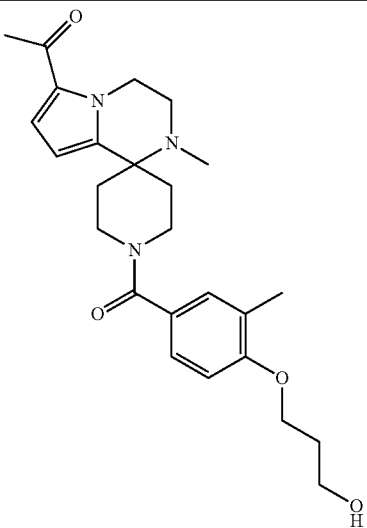 711 | 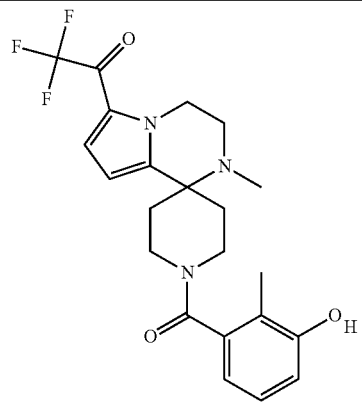 714 |
| 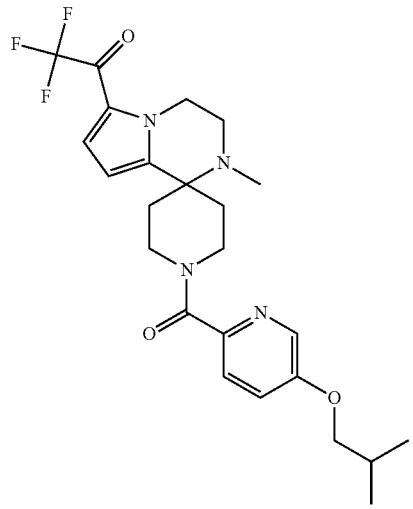 [SMILES: CC(C)COc1ccc(C(=O)N2CCC3(CC2)c2ccc(C(=O)C(F)(F)F)n2CCN3C)nc1] 712 | 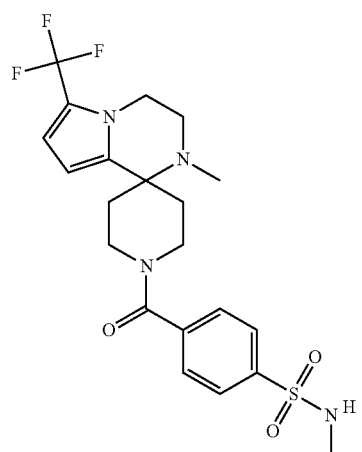 715 |
| 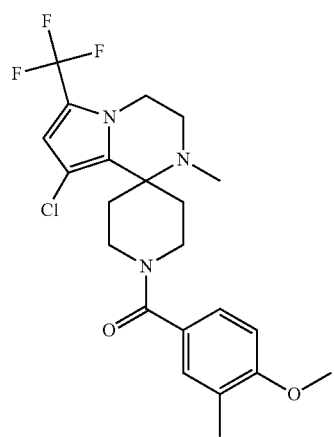 [SMILES: COc1ccc(C(=O)N2CCC3(CC2)c2c(Cl)cc(C(F)(F)F)n2CCN3C)cc1C] 713 | 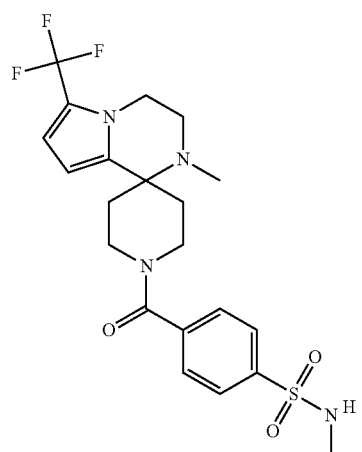 716 |

717
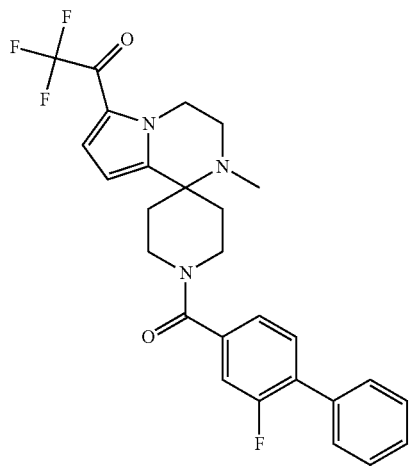
718
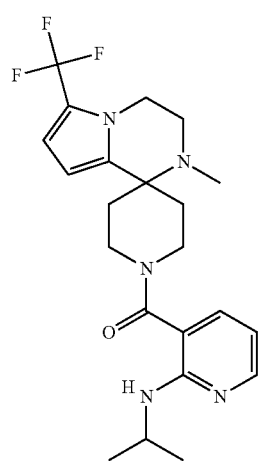
719
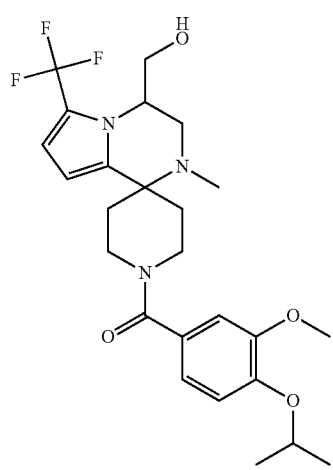 [SMILES: COc1cc(C(=O)N2CCC3(CC2)c2ccc(C(F)(F)F)n2C(CO)CN3C)ccc1OC(C)C]
720
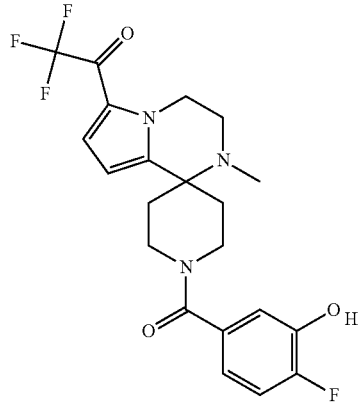
721
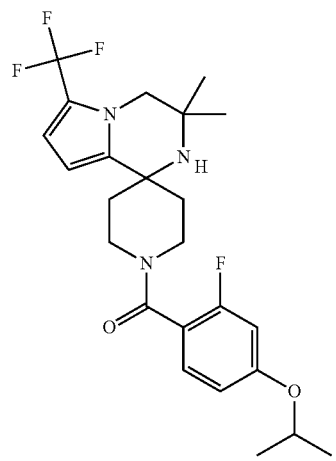
722
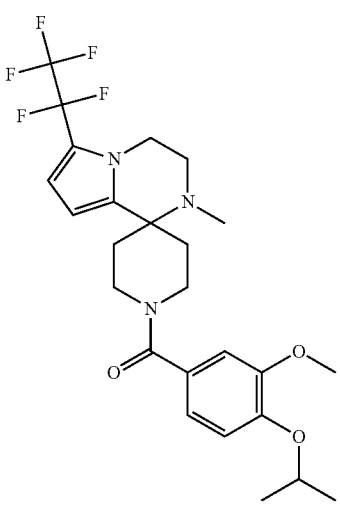 [SMILES: COc1cc(C(=O)N2CCC3(CC2)c2ccc(C(F)(F)C(F)(F)F)n2CCN3C)ccc1OC(C)C]

285
-continued
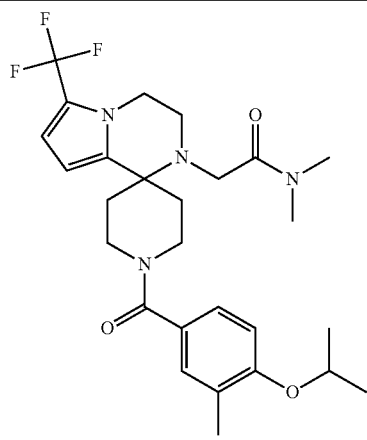
723
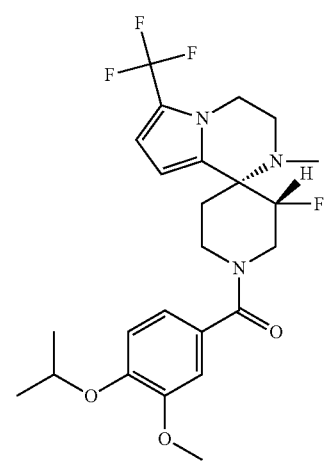 [SMILES: COc1cc(C(=O)N2CC[C@@]3(c4ccc(C(F)(F)F)n4CCN3C)[C@H](F)C2)ccc1OC(C)C]
724
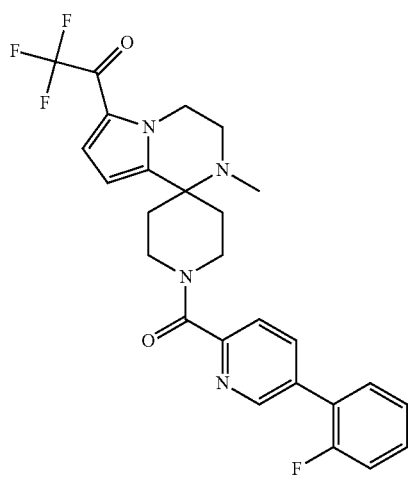 [SMILES: CN1CCn2c(C(=O)C(F)(F)F)ccc2C12CCN(C(=O)c1ccc(-c3ccccc3F)cn1)CC2]
725
286
-continued
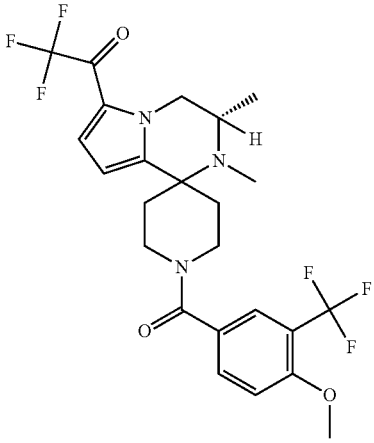 [SMILES: COc1ccc(C(=O)N2CCC3(CC2)c2ccc(C(=O)C(F)(F)F)n2C[C@H](C)N3C)cc1C(F)(F)F]
726
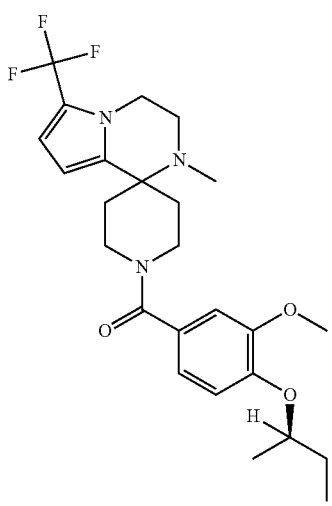 [SMILES: CC[C@@H](C)Oc1ccc(C(=O)N2CCC3(CC2)c2ccc(C(F)(F)F)n2CCN3C)cc1OC]
727
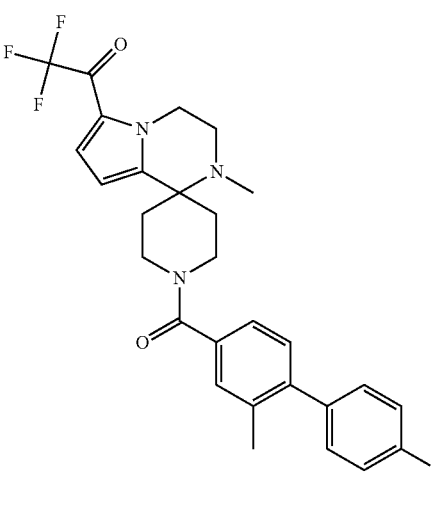
728

| 287 -continued | 288 -continued |
|---|---|
| 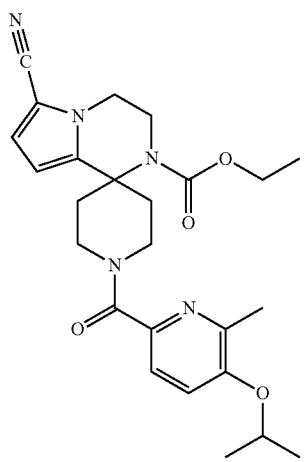 [SMILES: CCOC(=O)N1CCn2c(C#N)ccc2C12CCN(C(=O)c1ccc(OC(C)C)c(C)n1)CC2] 729 | 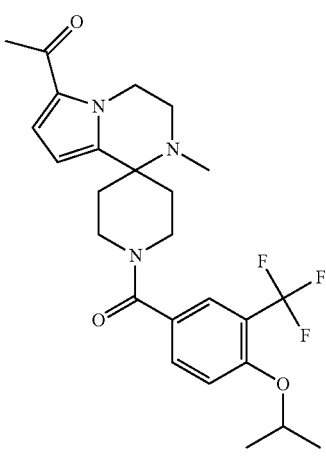 732 |
| 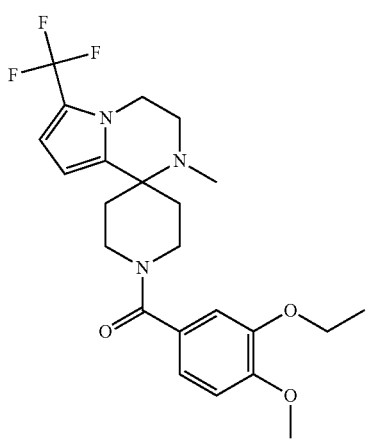 [SMILES: CCOc1cc(C(=O)N2CCC3(CC2)c2ccc(C(F)(F)F)n2CCN3C)ccc1OC] 730 | 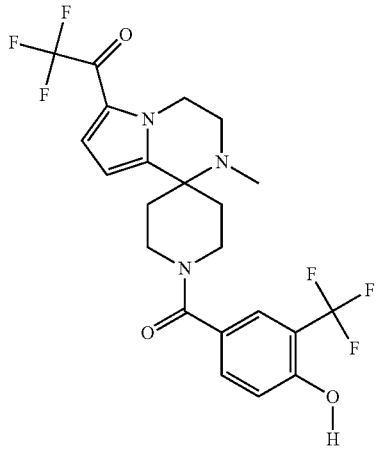 733 |
| 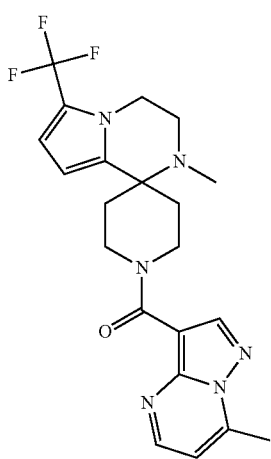 [SMILES: Cc1ccnc2c(C(=O)N3CCC4(CC3)c3ccc(C(F)(F)F)n3CCN4C)cnn12] 731 | 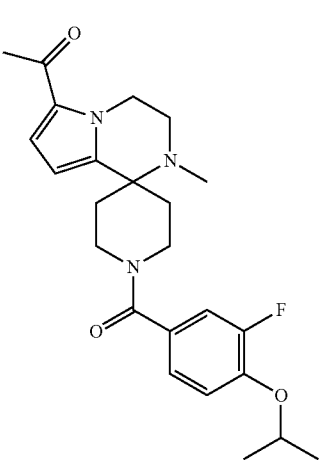 734 |

| 289 -continued | 290 -continued |
|---|---|
| 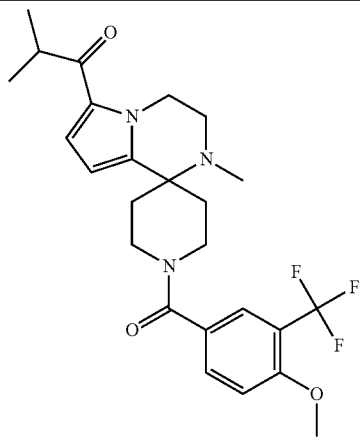 735 | 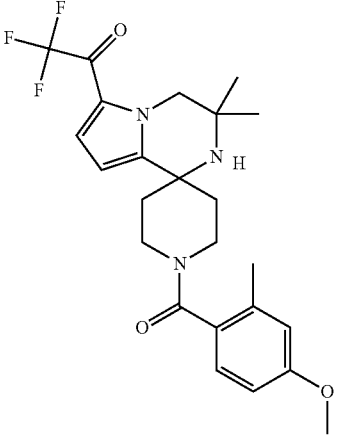 738 |
| 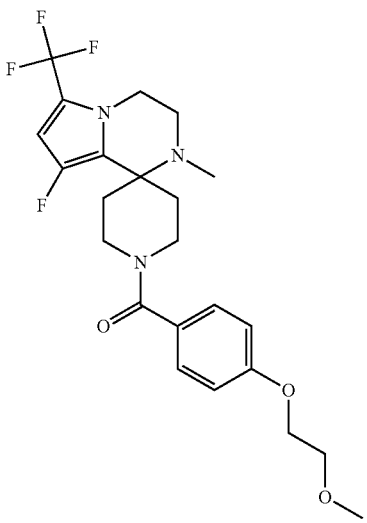 [SMILES: COCCOc1ccc(C(=O)N2CCC3(CC2)c2c(F)cc(C(F)(F)F)n2CCN3C)cc1] 736 | 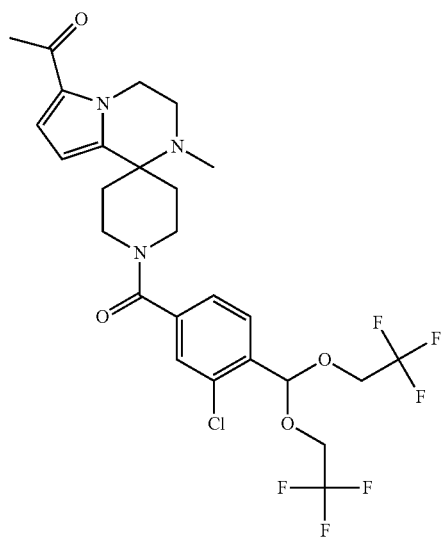 739 |
| 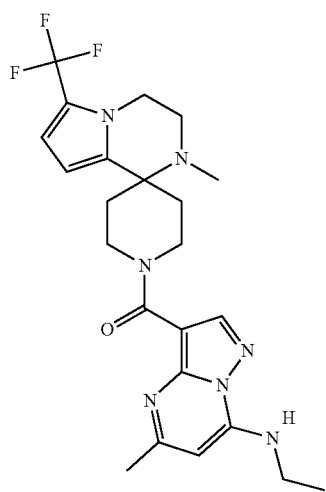 737 | 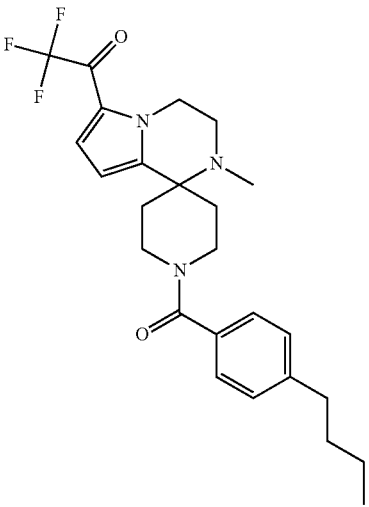 [SMILES: CCCCc1ccc(C(=O)N2CCC3(CC2)c2ccc(C(=O)C(F)(F)F)n2CCN3C)cc1] 740 |

291
-continued
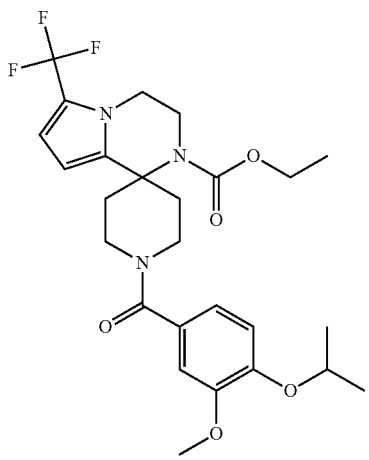
741
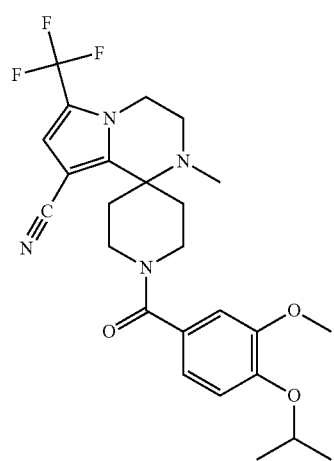 [SMILES: COc1cc(C(=O)N2CCC3(CC2)c2c(C#N)cc(C(F)(F)F)n2CCN3C)ccc1OC(C)C]
742
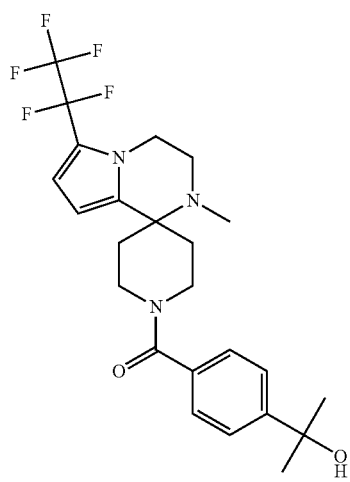 [SMILES: CN1CCn2c(ccc2C(F)(F)C(F)(F)F)C12CCN(C(=O)c1ccc(C(C)(C)O)cc1)CC2]
743
292
-continued
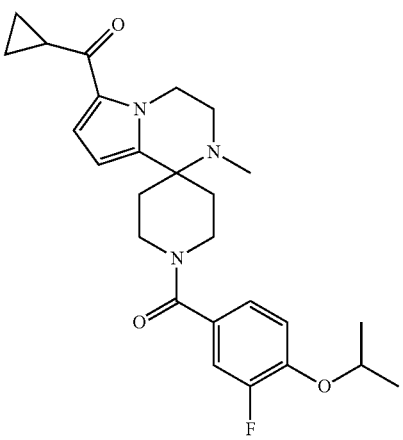 [SMILES: CC(C)Oc1ccc(C(=O)N2CCC3(CC2)c2ccc(C(=O)C4CC4)n2CCN3C)cc1F]
744
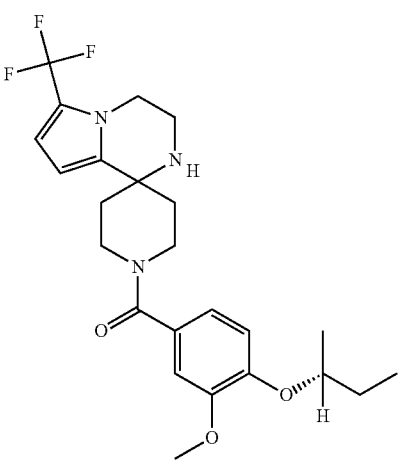
745
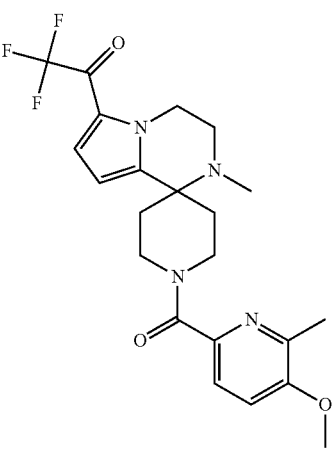 [SMILES: COc1ccc(C(=O)N2CCC3(CC2)c2ccc(C(=O)C(F)(F)F)n2CCN3C)nc1C]
746

| 747 | 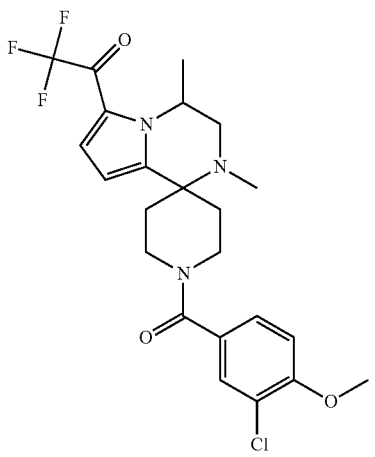 [SMILES: COc1ccc(C(=O)N2CCC3(CC2)c2ccc(C(=O)C(F)(F)F)n2C(C)CN3C)cc1Cl] |
| --- | --- |
| 748 | 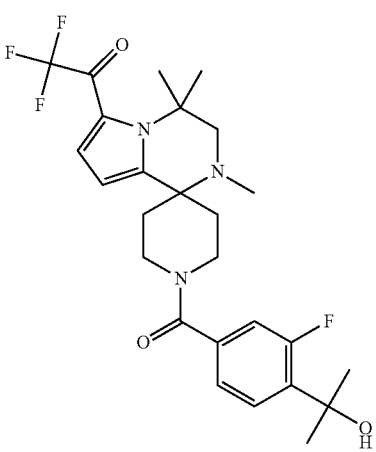 [SMILES: CN1CC(C)(C)n2c(C(=O)C(F)(F)F)ccc2C12CCN(C(=O)c1ccc(C(C)(C)O)c(F)c1)CC2] |
| 749 | 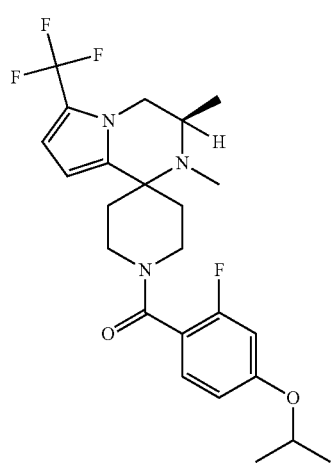 [SMILES: CC(C)Oc1ccc(C(=O)N2CCC3(CC2)c2ccc(C(F)(F)F)n2C[C@@H](C)N3C)c(F)c1] |
| 750 | 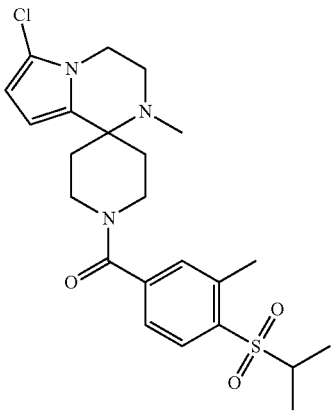 [SMILES: Cc1cc(C(=O)N2CCC3(CC2)c2ccc(Cl)n2CCN3C)ccc1S(=O)(=O)C(C)C] |
| --- | --- |
| 751 | 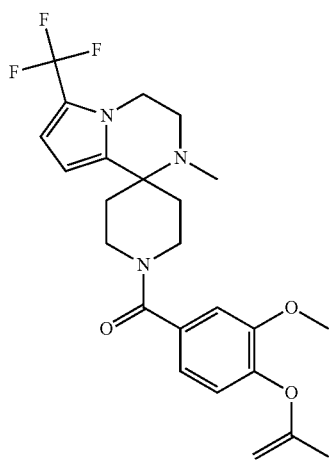 [SMILES: C=C(C)Oc1ccc(C(=O)N2CCC3(CC2)c2ccc(C(F)(F)F)n2CCN3C)cc1OC] |
| 752 | 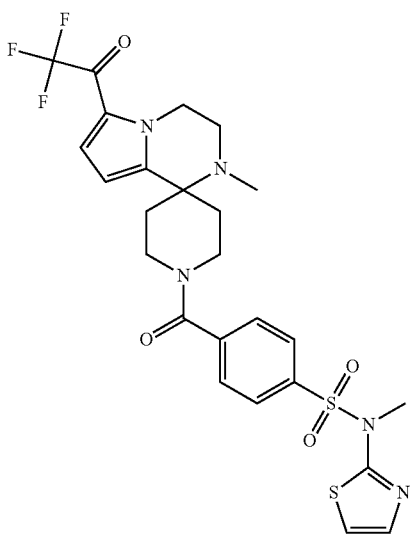 [SMILES: CN1CCn2c(C(=O)C(F)(F)F)ccc2C12CCN(C(=O)c1ccc(S(=O)(=O)N(C)c3nccs3)cc1)CC2] |
In another aspect, the invention features a pharmaceutical composition comprising the compound of the invention and a pharmaceutically acceptable carrier.
In another aspect, the invention features a method of inhibiting a voltage-gated sodium ion channel in:
a patient; or
a biological sample;

comprising administering to the patient, or contacting the biological sample, with the compound or composition of the invention. In another embodiment, the voltage-gated sodium ion channel is NaV 1.7.

In another aspect, the invention features a method of treating or lessening the severity in a subject of acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abnormal gastro-intestinal motility, comprising administering an effective amount of a compound or composition of the invention.

In another embodiment, the method is used for treating or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpatic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitus, or angina-induced pain.

The compounds of the invention may be prepared readily using the following methods. Illustrated below in Scheme 1 through Scheme 4 are methods for preparing the compounds of the invention.

Scheme 1

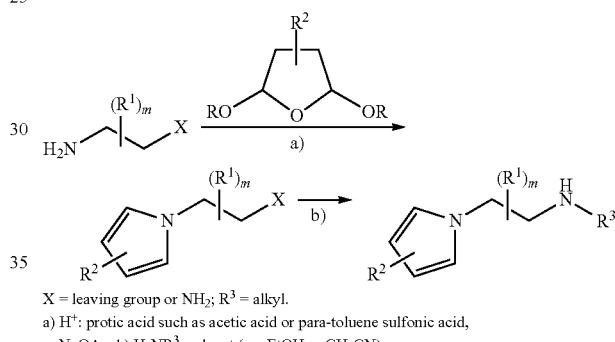

X = leaving group or NH$_2$; R$^3$ = alkyl.
a) H$^+$: protic acid such as acetic acid or para-toluene sulfonic acid, NaOAc; b) H$_2$NR$^3$, solvent (ex: EtOH or CH$_3$CN).

Scheme 2

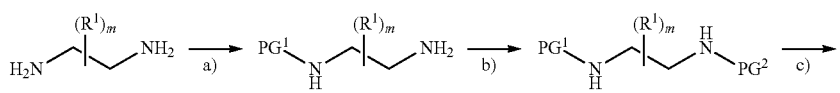

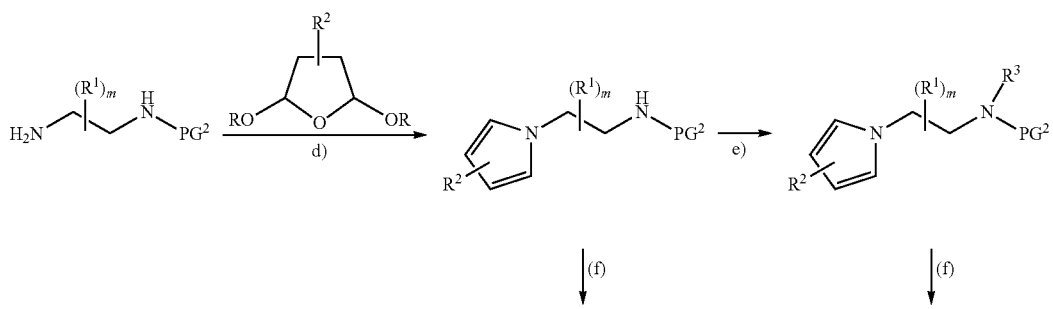

-continued

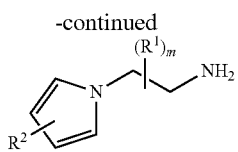 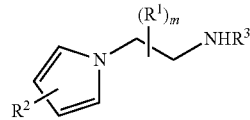

PG¹ = acid-labile protecting group (ex: Boc);
PG² = acid stable protecting group (ex: cbz, benzyl); R³ = alkyl.
a) PG¹ = Boc; Boc₂O, base (ex: Et₃N), solvent (ex: THF);
b) PG² = cbz; benzyl 2,5-dioxopyrrolidin-1-yl carbonate, base (ex: Et₃N), solvent (ex: THF);
c) PG¹ = Boc; H⁺ (ex: HCl or TFA), solvent (ex: iPrOH, EtOH, CH₃CN or CH₂Cl₂);
d) H⁺: protic acid such as acetic acid or para-toluene sulfonic acid, NaOAc;
e) R³—X, base (ex: NaH or K₂CO₃), solvent (ex: DMF, THF or CH₃CN);
f) PG² = cbz, Pd/C, H₂, solvent (ex: iPrOH, EtOH or CH₃CN).

Scheme 3

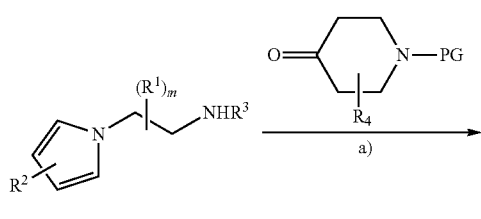 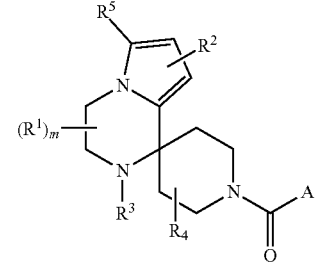

PG = protective group such as Boc, benzyl, cbz; R³ = H or alkyl.
a) cat. H⁺: protic acid such as trifluoroacetic acid, para-toluene sulfonic acid or dichloroacetic acid, solvent (ex: EtOH); b) R⁵ = CF₃, 5-(trifluoromethyl)-5H-dibenzo[b,d]thiophenium trifluoromethanesulfonate, base (ex: K₂CO₃), solvent (ex: CH₃CN) or R⁵ = haloakyl; haloalkyliodide (ex: CF₃I, CF₃CH₂I, or CF₃CF₂I), FeSO₄·6H₂O, H₂O₂, solvent (ex: DMSO); R⁵ = CN, chlorosulfonyl isocyanate, solvent (ex: THF or DMF); R⁵ = Cl, CF₃SO₂Cl, solvent (ex: CH₂Cl₂); R⁵ = R⁶C(O), acylating agent (ex: R⁶C(O)₂O, R⁶C(O)Cl), base (ex: pyridine, Et₃N, or DBN), solvent (ex: CH₂Cl₂, DCE, or THF) or i) NBS, CH₂Cl₂; ii) CH₃(CH₂)ₙOCH=CHR⁷, catalyst (ex: Pd₂dba₃·CHCl₃), solvent (ex: dioxane); PG = Boc, H⁺ (ex: HCl or TFA), solvent (ex: iPrOH, CH₃CN or CH₂Cl₂); PG = cbz; Pd/C, H₂, solvent (ex: iPrOH, EtOH or CH₃CN); d) A—CO₂H; coupling agent (ex: HATU or EDCI), base (ex: Et₃N or iPr₂NEt), solvent (ex: DMF, CH₃CN or CH₂Cl₂); or A—C(O)—Cl, NaOH, solvent (ex: water and MTBE).

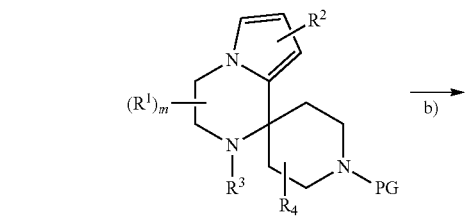

Scheme 4

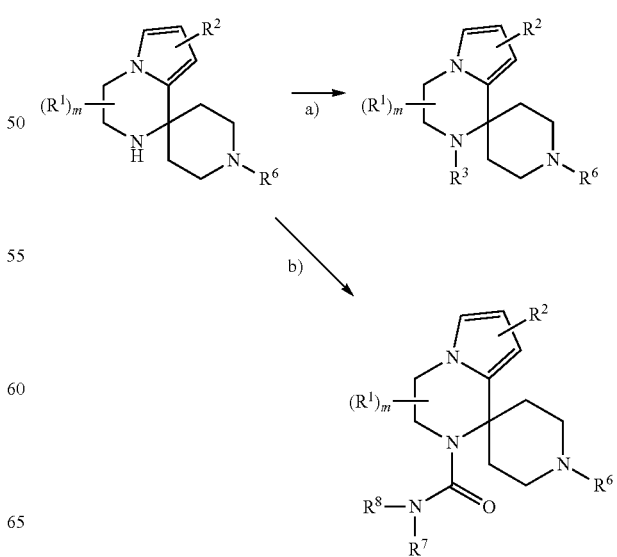

-continued $R^3$ = acyl; $R^6$ = PG or C(O)A; $R^7$ = alkyl.
a) $R^3$—X
(X = leaving group ex: halo, OTs), base (ex: $K_2CO_3$, $Et_3N$ or pyridine), solvent (ex: DMF, THF, ACN, $CH_2Cl_2$ or pyridine);
b) $R^8$ = H; $R^7$—NCO, base (ex: $Et_3N$), solvent (ex: THF) or ClC(O)$NR^7R^8$, base (ex: pyridine).

Uses, Formulation and Administration

Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abnormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitus or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts.

The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV1.1, NaV1.2, NaV1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an $H_1$ antagonist having a sedative action, e.g. diphenhydramine, pyrilamine, promethazine, chlorpheniramine or chlorocyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex(R), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-I antagonist, e.g. ([alpha]R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion(R) or sarizotan;

(17) a vanilloid receptor agonist (e.g. resiniferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HT$_{1B/1D}$ agonist such as eletriptan, sumatriptan, naratriptan, zolmitriptan or rizatriptan;

(22) a 5-HT2A receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®;

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin, pregabalin, 3-methyl gabapentin, (1[alpha],3[alpha],5[alpha])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl) bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan(R)), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, or guanidinoethyldisulfide;

(33) an acetylcholinesterase inhibitor such as donepezil;

(34) a prostaglandin E2 subtype 4 (EP4) antagonist such as 7V-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy) pyridin-3-yl]carbonyl}amino)ethyl]benzoic acid;

(35) a leukotriene B4 antagonist; such as 1-(3-biphenyl-4-ylmethyl-4-hydroxy -chroman-7-yl)-cyclopentanecarboxylic acid (CP-105696), 5-[2-(2-carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])

phenoxy-methyl]-1-methyl-2-quinolone (ZD-2138), or 2,3, 5-trimethyl-6-(3-pyridylmethyl),1,4-benzoquinone (CV-6504);

(37) a sodium channel blocker, such as lidocaine;

(38) a 5-HT3 antagonist, such as ondansetron; and the pharmaceutically acceptable salts and solvates thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General methods. $^1$H NMR (400 MHz) and $^{13}$C NMR (100 MHz) spectra were obtained as solutions in deuterioacetonitrile (CD$_3$CN), chloroform-d (CDCl$_3$) or dimethyl sulfoxide-D$_6$ (DMSO). Mass spectra (MS) were obtained using an Applied Biosystems API EX LC/MS system equipped with a Phenomenex 50×4.60 mm luna-5µ C18 column. The LC/MS eluting system was 1-99% or 10-99% acetonitrile in H$_2$O with 0.035% v/v trifluoroacetic acid, 0.035% v/v formic acid, 5 mM HCl or 5 mM ammonium formate using a 3 or 15 minute linear gradient and a flow rate of 12 mL/minute. Silica gel chromatography was performed using silica gel-60 with a particle size of 230-400 mesh. Pyridine, dichloromethane (CH$_2$Cl$_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

trans-5a',6',7',8',9',9a'-Hexahydro-5'H-spiro[piperidine-4,4'-pyrrolo[1,2-a]quinoxaline]dihydrochloride

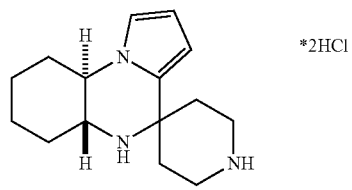 [SMILES: c1cc2n(c1)[C@@H]1CCCC[C@H]1NC21CCNCC1]

Step 1:

tert-Butyl N-[(1R,2R)-2-aminocyclohexyl]carbamate (1.06 g, 4.93 mmol), sodium acetate (1.70 g, 20.7 mmol) and 2,5-dimethoxytetrahydrofuran (764 µL, 5.91 mmol) were combined in acetic acid (10.6 mL). The reaction mixture was heated at 80° C. for 16 hours. The reaction mixture was then evaporated to dryness and the residue was partitioned between ethyl acetate and a saturated aqueous solution of sodium bicarbonate. The layers were separated, and the organic layer was washed twice with a saturated aqueous solution of sodium chloride, dried over sodium sulfate, and evaporated to dryness to yield a brown solid. This solid was then dissolved in HCl in dioxane (10.3 mL of 4.0 M, 41.1 mmol) and was allowed to stand for 3 hours. The solvent was then removed to yield trans-2-(1H-pyrrol-1-yl)cyclohexanamine hydrogen chloride (989 mg, 99%) as a brown solid. ESI-MS m/z calc. 164.1, found 165.2 (M+1)+; Retention time: 0.27 minutes (4 min run).

Step 2:

trans-2-(1H-Pyrrol-1-yl)cyclohexanamine hydrogen chloride (989 mg, 4.93 mmol), tert-butyl 4-oxopiperidine-1-carboxylate (982 mg, 4.93 mmol), and maleic acid (56.2 mg, 0.493 mmol) were combined in ethanol (12 mL). The reaction mixture was heated at 80° C. for 4 hours. The reaction mixture was cooled to room temperature and the solvent was evaporated. The residue was dissolved in dichloromethane and was then purified on 80 g of silica gel utilizing a gradient of 0-10% methanol in dichloromethane to give trans-tert-butyl 5a',6',7', 8',9',9a'-hexahydro-5'H-spiro[piperidine-4,4'-pyrrolo[1,2-a] quinoxaline]-1-carboxylate. ESI-MS m/z calc. 345.2, found 346.2 (M+1)+; Retention time: 1.63 minutes (4 min run).

Step 3:

trans-tert-Butyl 5a',6',7',8',9',9a'-hexahydro-5'H-spiro[piperidine-4,4'-pyrrolo[1,2-a]quinoxaline]-1-carboxylate (0.311 g, 0.901 mmol) was suspended in hydrogen chloride in dioxane (2.0 mL of 4.0 M, 8.0 mmol). The reaction mixture was allowed to stand for 2 hours. The reaction mixture was then evaporated to dryness to give trans-5a',6',7',8',9',9a'-hexahydro-5'H-spiro[piperidine-4,4'-pyrrolo[1,2-a]quinoxaline]. ESI-MS m/z calc. 245.2, found 246.3 (M+1)+; Retention time: 0.32 minutes (3 min run).

2'-Methyl-6'-(trifluoromethyl)-3',4'-dihydro-2'H-spiro[piperidine-4,1'-pyrrolo[1,2-a]pyrazine]dihydrochloride

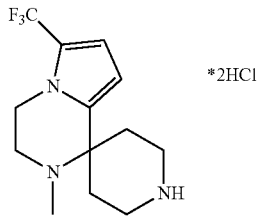 [SMILES: CN1CCn2c(C(F)(F)F)ccc2C12CCNCC2]

Step 1:
A mixture of 2,5-dimethoxytetrahydrofuran (15 g, 113.5 mmol), 2-chloroethanamine hydrochloride (44.76 g, 385.9 mmol), and sodium acetate (46.55 g, 567.5 mmol) in acetic acid (55 mL) was heated at 110° C. After 2 h, the reaction was poured into brine and the product was extracted with dichloromethane. The organics were washed with brine, saturated $Na_2CO_3$, and brine again. The organics were dried over sodium sulfate and evaporated. The crude material was filtered through a plug of Florisil (80 g) using hexane as the eluent to give 1-(2-chloroethyl)pyrrole (10.1 g, 69%). $^1$H NMR (400 MHz, $CDCl_3$) δ 6.70 (t, J=1.9 Hz, 2H), 6.18 (t, J=1.9 Hz, 2H), 4.20 (t, J=6.5 Hz, 2H), 3.73 (t, J=6.5 Hz, 2H).

Step 2:
1-(2-Chloroethyl)pyrrole (2.0 g, 15.43 mmol) was combined with a solution of 33% methylamine in ethanol (7.3 mL of 33% w/v, 77.15 mmol). The mixture was heated at 90° C. for 16 h before it was concentrated under reduced pressure to provide N-methyl-2-pyrrol-1-yl-ethanamine (2.19 g, 88%) which was used directly in next reaction. ESI-MS m/z calc. 124.1, found 125.3 (M+1)+; Retention time: 0.22 minutes (3 min run). $^1$H NMR (400 MHz, $CDCl_3$) δ 6.73-6.68 (m, 2H), 6.22-6.14 (m, 2H), 4.05 (t, J=5.9 Hz, 2H), 2.94 (t, J=5.9 Hz, 2H), 2.45 (s, 3H).

Step 3:
N-Methyl-2-pyrrol-1-yl-ethanamine (2.19 g, 17.64 mmol), tert-butyl 4-oxopiperidine-1-carboxylate (3.51 g, 17.64 mmol), and pTsOH.H$_2$O (0.334 g, 1.76 mmol) were combined in ethanol (87.60 mL) and heated at 70° C. for 4 h. The reaction was concentrated and the residue was dissolved in dichloromethane. The organics were washed with a saturated $NaHCO_3$ solution and brine. The organics were dried over sodium sulfate and evaporated. The crude material was purified by silica gel chromatography eluting with 0-10% methanol in dichloromethane with 2% triethylamine to give tert-butyl 2-methylspiro[3,4-dihydropyrrolo[1,2-a]pyrazine-1,4'-piperidine]-1'-carboxylate (4.2 g, 78%). ESI-MS m/z calc. 305.4, found 306.3 (M+1)+; Retention time: 0.97 minutes (3 min run). $^1$H NMR (400 MHz, $CDCl_3$) δ 6.55-6.52 (m, 1H), 6.15-6.11 (m, 1H), 5.92-5.89 (m, 1H), 3.92 (t, J=6.0 Hz, 2H), 3.91-3.75 (m, 2H), 3.29 (t, J=6.0 Hz, 2H), 3.26-3.12 (m, 2H), 2.36 (s, 3H), 2.10-1.99 (m, 2H), 1.83-1.69 (m, 2H), 1.47 (s, 9H).

Step 4:
Method A: tert-Butyl 2-methylspiro[3,4-dihydropyrrolo[1,2-a]pyrazine-1,4'-piperidine]-1'-carboxylate (1.0 g, 3.27 mmol), potassium carbonate (497.7 mg, 3.60 mmol) and trifluoromethanesulfonate; 5-(trifluoromethyl)dibenzothiophen-5-ium (1.32 g, 3.27 mmol) were combined in acetonitrile (10 mL). The reaction mixture was heated at 60° C. for 16 h. The reaction was evaporated to dryness and the residue was dissolved in dichloromethane. The organics were washed with water and brine, dried over sodium sulfate and evaporated. The crude material was purified by silica gel chromatography eluting with 0-50% ethyl acetate in hexanes to give tert-butyl 2-methyl-6-(trifluoromethyl)spiro[3,4-dihydropyrrolo[1,2-a]pyrazine-1,4'-piperidine]-1'-carboxylate (812 mg, 66%). ESI-MS m/z calc. 373.2, found 374.5 (M+1)+; Retention time: 1.21 minutes (3 min run). $^1$H NMR (400 MHz, $CDCl_3$) δ 6.52 (d, J=3.8 Hz, 1H), 5.91 (d, J=3.8 Hz, 1H), 3.98 (t, J=6.0 Hz, 2H), 3.93-3.76 (m, 2H), 3.32 (t, J=6.0 Hz, 2H), 3.26-3.08 (m, 2H), 2.36 (s, 3H), 2.11-1.99 (m, 2H), 1.81-1.65 (m, 2H), 1.47 (s, 9H).

Method B: To tert-butyl 2-methylspiro[3,4-dihydropyrrolo[1,2-a]pyrazine-1,4'-piperidine]-1'-carboxylate (10.0 g, 32.7 mmol) in DMSO (164 mL) was added ferrous sulfate heptahydrate (9.8 mL of 1.0 M, 9.8 mmol) followed by $CF_3I$ (6.41 g, 32.7 mmol) by slow bubbling through the solution and taking the weight difference of the canister. The mixture was cooled with a ice-water bath before $H_2O_2$ (3.71 mL of 30% w/v, 32.7 mmol) dropwise over 15 min keeping the internal temperature<20° C. The mixture was poured onto 300 mL of ice water and was extracted with EtOAc (2×400 mL). The combined organic phases were washed with brine, dried over $MgSO_4$, filtered and concentrated in vacuo. The crude material was purified column chromatography eluting with 0-10% methanol in dichloromethane with 2% $iPr_2NEt$ to give tert-butyl 2-methyl-6-(trifluoromethyl)spiro[3,4-dihydropyrrolo[1,2-a]pyrazine-1,4'-piperidine]-1'-carboxylate (7.8 g, 64%).

Step 5:
tert-Butyl 2-methyl-6-(trifluoromethyl)spiro[3,4-dihydropyrrolo[1,2-a]pyrazine-1,4'-piperidine]-1'-carboxylate (7.8 g, 20.89 mmol) was stirred in 4M HCl in dioxane (26.10 mL of 4 M, 104.4 mmol) and methanol (22 mL) at room temperature for 1 h. The reaction mixture was evaporated to dryness and the residue was co-evaporated with 100 mL of MTBE to afford 2'-methyl-6'-(trifluoromethyl)-3',4'-dihydro-2'H-spiro[piperidine-4,1'-pyrrolo[1,2-a]pyrazine]dihydrochloride as a yellow foam/solid (7.23 g, quantitative). ESI-MS m/z calc. 273.2, found 274.5 (M+1)+; Retention time: 0.44 minutes (3 min run).

2'-Methyl-3',4'-dihydro-2'H-spiro[piperidine-4,1'-pyrrolo[1,2-a]pyrazine]-6'-carbonitrile dihydrochloride

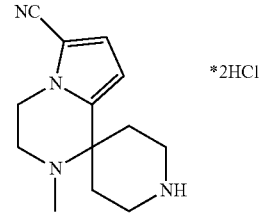 [SMILES: CN1CCn2c(C#N)ccc2C12CCNCC2]

Step 1:
A solution of chlorosulfonyl isocyanate (590.9 mg, 363.4 µL, 4.175 mmol) in tetrahydrofuran (2 mL) was slowly added to a solution of tert-butyl 2-methylspiro[3,4-dihydropyrrolo[1,2-a]pyrazine-1,4'-piperidine]-1'-carboxylate (1020 mg, 3.340 mmol) in tetrahydrofuran (9 mL) held at −78° C. (bath temperature) under an atmosphere of argon. The reaction mixture was allowed to stir for 1 hour at −78° C. N,N-dimethylformamide (732.4 mg, 775.8 μL, 10.02 mmol) was then slowly added to the cold reaction mixture. The reaction mixture was then allowed to slowly warm to room temperature. After stirring for 3 hours at room temperature the crude material was diluted with 25 mL of tetrahydrofuran, washed with a 1M solution of sodium hydroxide, followed by three washes of a saturated aqueous solution of sodium chloride. The organic layer was dried over sodium sulfate, filtered, and evaporated to dryness to yield the crude product. The crude material was purified on 80 g of silica gel utilizing a gradient of 0-70% ethyl acetate in hexanes to yield tert-butyl 6-cyano-2-methyl-spiro[3,4-dihydropyrrolo[1,2-a]pyrazine-1,4'-piperidine]-1'-carboxylate (280 mg, 25%) as a white solid. ESI-MS m/z calc. 330.2, found 331.1 (M+1)+; Retention time: 0.94 minutes. $^1$H NMR (400 MHz, CDCl$_3$) δ 6.76 (d, J=4.0 Hz, 1H), 5.97 (d, J=4.0 Hz, 1H), 4.01 (t, J=6.0 Hz, 2H), 3.98-3.76 (m, 2H), 3.36 (t, J=6.0 Hz, 2H), 3.30-3.08 (m, 2H), 2.36 (s, 3H), 2.09-1.98 (m, 2H), 1.84-1.66 (m, 2H), 1.47 (s, 9H).

Step 2:
tert-Butyl 6-cyano-2-methyl-spiro[3,4-dihydropyrrolo[1,2-a]pyrazine-1,4'-piperidine]-1'-carboxylate (280 mg, 0.8474 mmol) was dissolved in a mixture of hydrochloric acid in dioxane (8 mL of 4 M, 32.00 mmol) and dioxane (8 mL). The reaction mixture was allowed to stir for 30 minutes and then evaporated to dryness to yield 2-methylspiro[3,4-dihydropyrrolo[1,2-a]pyrazine-1,4'-piperidine]-6-carbonitrile dihydrochloride (258 mg, 99%) as a white solid. ESI-MS m/z calc. 230.2, found 231.5 (M+1)+; Retention time: 0.50 minutes (3 min run). $^1$H NMR (400 MHz, D$_2$O) δ 7.10 (d, J=4.2 Hz, 1H), 6.59 (d, J=4.3 Hz, 1H), 4.51 (t, J=6.4 Hz, 2H), 4.02 (t, J=6.3 Hz, 2H), 3.66-3.56 (m, 2H), 3.49-3.36 (m, 2H), 2.95 (s, 3H), 2.69-2.59 (m, 2H), 2.54-2.40 (m, 2H).

N-methyl-6'-(trifluoromethyl)-3',4'-dihydro-2'H-spiro[piperidine-4,1'-pyrrolo[1,2-a]pyrazine]-2'-carboxamide hydrochloride

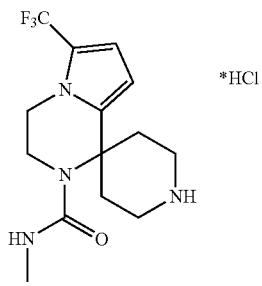 [SMILES: CNC(=O)N1CCn2c(C(F)(F)F)ccc2C12CCNCC2]

Step 1:
To tert-butyl 6-(trifluoromethyl)spiro[3,4-dihydro-2H-pyrrolo[1,2-a]pyrazine-1,4'-piperidine]-1'-carboxylate (600 mg, 1.67 mmol), THF (3 mL) and Et$_3$N (698 μL, 5.01 mmol) was added methyl isocyanate (199 μL, 3.34 mmol). The mixture was allowed to stir at room temperature for 2 h. The mixture was charged with additional Et$_3$N (698 μL, 5.01 mmol) and methyl isocyanate (199 μL, 3.34 mmol), and the reaction was stirred at room temperature for 3 d. The solvent was evaporated under reduced pressure. The residue was dissolved in ethyl acetate (40 mL) and washed with water (3×10 mL). The organic layer was dried over sodium sulfate, filtered, and concentrated in vacuo to yield tert-butyl 2-(methylcarbamoyl)-6-(trifluoromethyl)spiro[3,4-dihydropyrrolo[1,2-a]pyrazine-1,4'-piperidine]-1'-carboxylate (680 mg, 97%). ESI-MS m/z calc. 416.2, found 417.4 (M+1)+; Retention time: 1.73 minutes (3 min run). $^1$H NMR (400 MHz, DMSO) δ 7.14 (q, J=4.3 Hz, 1H), 6.56 (d, J=3.4 Hz, 1H), 6.03 (d, J=3.9 Hz, 1H), 3.88 (t, J=5.4 Hz, 2H), 3.73 (t, J=5.4 Hz, 2H), 3.69-3.55 (m, 2H), 3.23-3.03 (m, 2H), 2.78-2.62 (m, 2H), 2.56 (d, J=4.4 Hz, 3H), 1.76-1.60 (m, 2H), 1.40 (s, 9H).

Step 2:
To tert-butyl 2-(methylcarbamoyl)-6-(trifluoromethyl)spiro[3,4-dihydropyrrolo[1,2-a]pyrazine-1,4'-piperidine]-1'-carboxylate (0.66 g, 1.6 mmol) and acetonitrile (5 mL) was added a solution of HCl in dioxane (5.2 mL of 4.0 M, 21 mmol). The reaction mixture was stirred at room temperature for 60 minutes. The solvent was evaporated under reduced pressure to yield N-methyl-6-(trifluoromethyl)spiro[3,4-dihydropyrrolo[1,2-a]pyrazine-1,4'-piperidine]-2-carboxamide hydrochloride as a brown solid (99%). ESI-MS m/z calc. 316.2, found 317.2 (M+1)+; Retention time: 0.77 minutes (3 min run).

The following compounds were synthesized using the procedures described above:

2'-(2-methoxyethyl)-3',4'-dihydro-2'H-spiro[piperidine-4,1'-pyrrolo[1,2-a]pyrazine]dihydrochloride, 2'-benzyl-3',4'-dihydro-2'H-spiro[piperidine-4,1'-pyrrolo[1,2-a]pyrazine]dihydrochloride, 2'-(2-methoxyethyl)-6'-(trifluoromethyl)-3',4'-dihydro-2'H-spiro[piperidine-4,1'-pyrrolo[1,2-a]pyrazine]dihydrochloride, 6'-(trifluoromethyl)-3',4'-dihydro-2'H-spiro[piperidine-4,1'-pyrrolo[1,2-a]pyrazine]dihydrochloride, 2'-ethyl-6'-(trifluoromethyl)-3',4'-dihydro-2'H-spiro[piperidine-4,1'-pyrrolo[1,2-a]pyrazine]dihydrochloride, 3',3'-dimethyl-6'-(trifluoromethyl)-3',4'-dihydro-2'H-spiro[piperidine-4,1'-pyrrolo[1,2-a]pyrazine]dihydrochloride, 3'-methyl-6'-(trifluoromethyl)-3',4'-dihydro-2'H-spiro[piperidine-4,1'-pyrrolo[1,2-a]pyrazine]dihydrochloride, 4',4'-dimethyl-6'-(trifluoromethyl)-3',4'-dihydro-2'H-spiro[piperidine-4,1'-pyrrolo[1,2-a]pyrazine]dihydrochloride, 2',3'-dimethyl-6'-(trifluoromethyl)-3',4'-dihydro-2'H-spiro[piperidine-4,1'-pyrrolo[1,2-a]pyrazine]dihydrochloride, 3-methyl-6'-(trifluoromethyl)-3',4'-dihydro-2'H-spiro[piperidine-4,1'-pyrrolo[1,2-a]pyrazine]dihydrochloride, 2'-cyclopropyl-6'-(trifluoromethyl)-3',4'-dihydro-2'H-spiro[piperidine-4,1'-pyrrolo[1,2-a]pyrazine]dihydrochloride, 2'-(cyclopropylmethyl)-6'-(trifluoromethyl)-3',4'-dihydro-2'H-spiro[piperidine-4,1'-pyrrolo[1,2-a]pyrazine]dihydrochloride, 2',3-dimethyl-6'-(trifluoromethyl)-3',4'-dihydro-2'H-spiro[piperidine-4,1'-pyrrolo[1,2-a]pyrazine]dihydrochloride, 2'-methyl-6'-(2,2,2-trifluoroethyl)-3',4'-dihydro-2'H-spiro[piperidine-4,1'-pyrrolo[1,2-a]pyrazine]dihydrochloride, 2'-methyl-6'-(perfluoroethyl)-3',4'-dihydro-2'H-spiro[piperidine-4,1'-pyrrolo[1,2-a]pyrazine]dihydrochloride, 2'-methyl-3',4'-dihydro-2'H-spiro[piperidine-4,1'-pyrrolo[1,2-a]pyrazine]dihydrochloride, 3',4'-dihydro-2'H-spiro[piperidine-4,1'-pyrrolo[1,2-a]pyrazine]dihydrochloride, N,N-dimethyl-6'-(trifluoromethyl)-3',4'-dihydro-2'H-spiro[piperidine-4,1'-pyrrolo[1,2-a]pyrazine]-2'-carboxamide, 2'-(2,2,2-trifluoroethyl)-6'-(trifluoromethyl)-3',4'-dihydro-2'H-spiro[piperidine-4,1'-pyrrolo[1,2-a]pyrazine]hydrochloride, 3-fluoro-2'-methyl-6'-(trifluoromethyl)-3',4'-dihydro-2'H-spiro[piperidine-4,1'-pyrrolo[1,2-a]pyrazine]dihydrochloride, 2,2'-dimethyl-6'-(trifluoromethyl)-3',4'-dihydro-2'H-spiro[piperidine-4,1'-pyrrolo[1,2-a]pyrazine]dihydrochloride, methyl 2'-methyl-6'-(trifluoromethyl)-3',4'-dihydro-2'H-spiro[piperidine-4,1'-pyrrolo[1,2-a]pyrazine]-4'-carboxylate, 2'-(2,2-difluoroethyl)-6'-(trifluoromethyl)-3',4'-dihydro-2'H-spiro[piperidine-4,1'-pyrrolo[1,2-a]pyrazine]hydrochloride, 2'-cyclobutyl-6'-(trifluoromethyl)-3',4'-dihydro-2'H-spiro[piperidine-4,1'-pyrrolo[1,2-a]pyrazine]dihydrochloride, ethyl 2-(6'-(trifluoromethyl)-3',4'-dihydro-2'H-spiro[piperidine-4,1'-pyrrolo[1,2-a]pyrazine]-2'-yl)acetate, and methyl 6'-(trifluoromethyl)-3',4'-dihydro-2'H-spiro[piperidine-4,1'-pyrrolo[1,2-a]pyrazine]-2'-carboxylate.

2,2,2-Trifluoro-1-(2-methylspiro[3,4-dihydropyrrolo[1,2-a]pyrazine-1,4'-piperidine]-6-yl)ethanone dihydrochloride

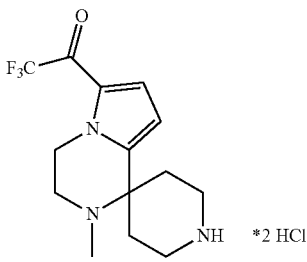 [SMILES: CN1CCn2c(C(=O)C(F)(F)F)ccc2C12CCNCC2]

Step 1:

(2,2,2-Trifluoroacetyl) 2,2,2-trifluoroacetate (910 μL, 6.55 mmol) was added dropwise to a solution of tert-butyl 2-methylspiro[3,4-dihydropyrrolo[1,2-a]pyrazine-1,4'-piperidine]-1'-carboxylate (1.0 g, 3.27 mmol), pyridine (1.06 mL, 13.10 mmol) and CH$_2$Cl$_2$ (6.5 mL) at room temperature. The mixture was heated at 35° C. for 2 h. The reaction mixture was partitioned between 1N HCl and CH$_2$Cl$_2$. The layers were separated and the aqueous layer was extracted with CH$_2$Cl$_2$ (2×). The combined organics were dried over sodium sulfate and filtered. The filtrate was concentrated to give tert-butyl 2-methyl-6-(2,2,2-trifluoroacetyl)spiro[3,4-dihydropyrrolo[1,2-a]pyrazine-1,4'-piperidine]-1'-carboxylate (1.38 g, 94%) as a yellowish solid. ESI-MS m/z calc. 401.2, found 402.5 (M+1)$^+$; Retention time: 1.36 minutes. $^1$H NMR (400 MHz, CDCl$_3$) δ 7.21 (dd, J=4.4, 2.1 Hz, 1H), 6.14 (d, J=4.5 Hz, 1H), 4.34 (t, J=6.0 Hz, 2H), 3.93 (s, 2H), 3.33 (t, J=6.0 Hz, 2H), 3.19 (s, 2H), 2.39 (s, 3H), 2.13-2.05 (m, 2H), 1.79 (t, J=11.6 Hz, 2H), 1.48 (s, 9H).

Step 2:

Hydrogen chloride (6.01 mL of 4 M, 24.07 mmol) was added to a solution of tert-butyl 2-methyl-6-(2,2,2-trifluoroacetyl)spiro[3,4-dihydropyrrolo[1,2-a]pyrazine-1,4'-piperidine]1'-carboxylate (1.38 g, 3.44 mmol) in CH$_2$Cl$_2$ (9.7 mL) at room temperature. The mixture was stirred at room temperature for 1.5 h. The reaction mixture was concentrated under reduced pressure to give 2,2,2-trifluoro-1-(2-methyl-spiro[3,4-dihydropyrrolo[1,2-a]pyrazine-1,4'-piperidine]-6-yl)ethanone dihydrochloride (1.34 g, 99%) as a tan solid. ESI-MS m/z calc. 301.1, found 302.5 (M+1)$^+$; Retention time: 1.02 minutes.

2,2-Dimethyl-1-(2-methylspiro[3,4-dihydropyrrolo[1,2-a]pyrazine-1,4'-piperidine]-6-yl)propan-1-one dihydrochloric acid

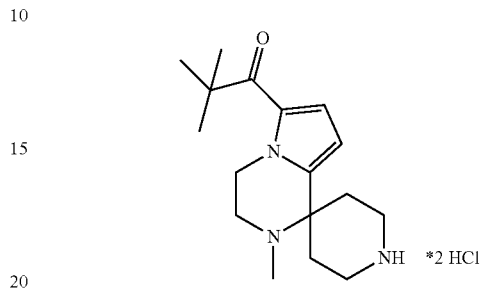

Step 1:

2,2-Dimethylpropanoyl chloride (1.22 mL, 9.90 mmol) was added to a mixture of tert-butyl 2-methylspiro[3,4-dihydropyrrolo[1,2-a]pyrazine-1,4'-piperidine]-1'-carboxylate (2.75 g, 9.0 mmol), DBN (1.22 mL, 9.90 mmol) and dichloroethane (6.9 mL) at room temperature. The mixture was allowed to stir for 18 h at 115° C. The mixture was cooled to room temperature before it was partitioned between CH$_2$Cl$_2$ and 1N HCl. The layers were separated and the organic layer was washed with 1N NaOH. The organic layer was dried over sodium sulfate, filtered and concentrated under reduced pressure. The residue was purified by column chromatography (0-100% ethyl acetate/hexanes) to give tert-butyl dimethylpropanoyl)-2-methyl-spiro[3,4-dihydropyrrolo[1,2-a]pyrazine-1,4'-piperidine]-1'-carboxylate (1.8 g, 41%) as an off-white solid. ESI-MS m/z calc. 389.3, found 390.5 (M+1)+; Retention time: 1.46 minutes.

Step 2:

Hydrogen chloride (5.1 mL of 4 M, 20.22 mmol) was added to a solution of tert-butyl 6-(2,2-dimethylpropanoyl)-2-methyl-spiro[3,4-dihydropyrrolo[1,2-a]pyrazine-1,4'-piperidine]-1'-carboxylate (1.75 g, 4.49 mmol) in CH$_2$Cl$_2$ (12.3 mL) at room temperature. The mixture was stirred at room temperature for 1.5 h. The reaction mixture was concentrated under reduced pressure to give 2,2-dimethyl-1-(2-methylspiro[3,4-dihydropyrrolo[1,2-a]pyrazine-1,4'-piperidine]-6-yl)propan-1-one dihydrochloride (1.8 g, 99%) as a tan solid. ESI-MS m/z calc. 289.2, found 290.5 (M+1)+; Retention time: 0.97 minutes.

1-(2'-Methyl-3',4'-dihydro-2'H-spiro[piperidine-4,1'-pyrrolo[1,2-a]pyrazine]-6'-yl)ethanone dihydrochloride

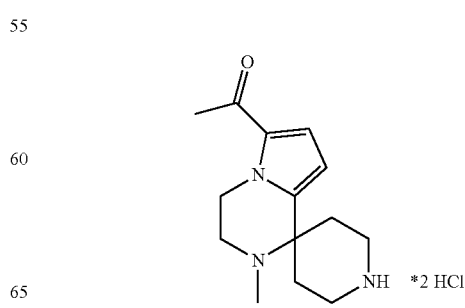

Step 1:

To tert-butyl 2-methylspiro[3,4-dihydropyrrolo[1,2-a]pyrazine-1,4'-piperidine]-1'-carboxylate (10 g, 32.74 mmol) in methylene chloride (73.5 mL) at 0° C. was added N-bromosuccinimide (5.53 g, 31.10 mmol) portionwise. The reaction was stirred at 0° C. After 30 minutes, additional N-bromosuccinimide (291.4 mg, 1.64 mmol) was added and the reaction was stirred for 1 hour. The reaction was diluted with 0.5 M $Na_2S_2O_3$ (135 mL) and the aqueous phase was removed. The organic layer was washed with brine (135 mL). The organic layer was dried over sodium sulfate, filtered and the solvent was evaporated under reduced pressure to yield tert-butyl 6-bromo-2-methyl-spiro[3,4-dihydropyrrolo[1,2-a]pyrazine-1,4'-piperidine]-1'-carboxylate as a red viscous liquid that was used in the next step without further purification. 1H NMR (400 MHz, DMSO) δ 6.09 (d, J=3.7 Hz, 1H), 5.99 (d, J=3.7 Hz, 1H), 3.78-3.65 (m, 4H), 3.27 (t, J=6.0 Hz, 2H), 3.17-2.92 (m, 2H), 2.21 (s, 3H), 2.03-1.93 (m, 2H), 1.65-1.53 (m, 2H), 1.40 (s, 9H). ESI-MS m/z calc. 383.1, found 386.0 (M+1)+; Retention time: 1.13 minutes (3 minute run).

Step 2:

A solution of tert-butyl 6-bromo-2-methyl-spiro[3,4-dihydropyrrolo[1,2-a]pyrazine-1,4'-piperidine]-1'-carboxylate (2 g, 5.2 mmol) and N-cyclohexyl-N-methyl-cyclohexanamine (1.67 mL, 7.81 mmol) in 1,4-dioxane (8.0 mL) was purged with $N_2$ for 5 minutes. 1-Vinyloxybutane (7.04 mL, 52.04 mmol), $Pd(dba)_3$ (1.078 g, 1.04 mmol) and tri tert-butylphosphane (642.0 μL, 2.60 mmol) were added and the reaction was heated at 80° C. for 5 hours in a pressure vessel. The reaction was filtered through a plug of celite using ethyl acetate. The solvent was evaporated under reduced pressure. The crude product was purified by silica gel chromatography utilizing a gradient of 1-100% ethyl acetate in hexane to yield tert-butyl 6-acetyl-2-methyl-spiro[3,4-dihydropyrrolo[1,2-a]pyrazine-1,4'-piperidine]-1'-carboxylate (672.1 mg, 1.93 mmol, 37%) as a yellow solid. $^1$H NMR (400 MHz, DMSO) δ 7.04 (d, J=4.1 Hz, 1H), 6.12 (d, J=4.2 Hz, 1H), 4.17 (t, J=6.0 Hz, 2H), 3.83-3.68 (m, 2H), 3.21 (t, J=6.0 Hz, 2H), 3.17-2.91 (m, 2H), 2.31 (s, 3H), 2.24 (s, 3H), 2.07-1.97 (m, 2H), 1.72-1.59 (m, 2H), 1.41 (s, 9H). ESI-MS m/z calc. 347.2, found 348.5 (M+1)+; Retention time: 0.95 minutes (3 minute run).

Step 3:

To tert-butyl 6-acetyl-2-methyl-Spiro[3,4-dihydropyrrolo[1,2-a]pyrazine-1,4'-piperidine]-1'-carboxylate (300 mg, 0.86 mmol) and methylene chloride (1.7 mL) was added hydrogen chloride in dioxane (1.60 mL of 4 M, 6.40 mmol) The reaction was stirred at room temperature for 0.5 hours. The solvent was evaporated under reduced pressure to yield 1-(2-methylspiro[3,4-dihydropyrrolo[1,2-a]pyrazine-1,4'-piperidine]-6-yl)ethanone dihydrochloride as a light green solid in quantitative yield. ESI-MS m/z calc. 247.2, found 248.2 (M+1)+; Retention time: 0.17 minutes (3 minute run).

The following compounds were synthesized using the procedures described above:

1-(2'-methyl-3',4'-dihydro-2'H-spiro[piperidine-4,1'-pyrrolo[1,2-a]pyrazine]-6'-yl)propan-1-one dihydrochloride,
2-methyl-1-(2'-methyl-3',4'-dihydro-2'H-spiro[piperidine-4,1'-pyrrolo[1,2-a]pyrazine]-6'-yl)propan-1-one dihydrochloride,
cyclopropyl(2'-methyl-3',4'-dihydro-2'H-spiro[piperidine-4,1'-pyrrolo[1,2-a]pyrazine]-6'-yl)methanone dihydrochloride,
(2'-methyl-3',4'-dihydro-2'H-spiro[piperidine-4,1'-pyrrolo[1,2-a]pyrazine]-6'-yl)(phenyl)methanone dihydrochloride,
1-(3',3'-dimethyl-3',4'-dihydro-2'H-spiro[piperidine-4,1'-pyrrolo[1,2-a]pyrazine]-6'-yl)-2,2,2-trifluoroethanone dihydrochloride,
1-(3',3'-dimethyl-3',4'-dihydro-2'H-spiro[piperidine-4,1'-pyrrolo[1,2-a]pyrazine]-6'-yl)ethanone dihydrochloride,
1-(3',3'-dimethyl-3',4'-dihydro-2'H-spiro[piperidine-4,1'-pyrrolo[1,2-a]pyrazine]-7'-yl)ethanone dihydrochloride,
2,2,2-trifluoro-1-(2',4',4'-trimethyl-3',4'-dihydro-2'H-spiro[piperidine-4,1'-pyrrolo[1,2-a]pyrazine]-6'-yl)ethanone dihydrochloride,
2,2,2-trifluoro-1-(2',4',4'-trimethyl-3',4'-dihydro-2'H-spiro[piperidine-4,1'-pyrrolo[1,2-a]pyrazine]-7'-yl)ethanone dihydrochloride,
1-(2',4',4'-trimethyl-3',4'-dihydro-2'H-spiro[piperidine-4,1'-pyrrolo[1,2-a]pyrazine]-6'-yl)ethanone dihydrochloride,
1-(2',3'-dimethyl-3',4'-dihydro-2'H-spiro[piperidine-4,1'-pyrrolo[1,2-a]pyrazine]-6'-yl)-2,2,2-trifluoroethanone dihydrochloride,
2,2,2-trifluoro-1-(3'-methyl-3',4'-dihydro-2'H-spiro[piperidine-4,1'-pyrrolo[1,2-a]pyrazine]-6'-yl)ethanone dihydrochloride,
2,2,2-trifluoro-1-(4'-methyl-3',4'-dihydro-2'H-spiro[piperidine-4,1'-pyrrolo[1,2-a]pyrazine]-6'-yl)ethanone dihydrochloride,
1-(2',4'-dimethyl-3',4'-dihydro-2'H-spiro[piperidine-4,1'-pyrrolo[1,2-a]pyrazine]-6'-yl)-2,2,2-trifluoroethanone dihydrochloride, and
(2'-methyl-3',4'-dihydro-2'H-spiro[piperidine-4,1'-pyrrolo[1,2-a]pyrazine]-6'-yl)(1-methylcyclopropyl)methanone.

2'-Methyl-6'-(trifluoromethyl)-3',4'-dihydro-2'H-spiro[piperidine-4,1'-pyrrolo[1,2-a]pyrazine]-8'-carbonitrile dihydrochloride

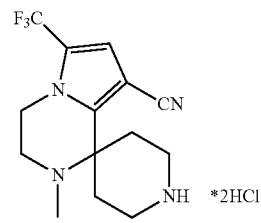 [SMILES: CN1CCn2c(C(F)(F)F)cc(C#N)c2C12CCNCC2]

Step 1:

To a solution of tert-butyl 2-methyl-6-(trifluoromethyl)spiro[3,4-dihydropyrrolo[1,2-a]pyrazine-1,4'-piperidine]-1'-carboxylate (1.86 g, 5.0 mmol) in acetonitrile (50 mL) was added N-bromosuccinimide (930.4 mg, 5.25 mmol). The mixture was stirred at room temperature overnight. The solvent was evaporated under reduced pressure. The residue was partitioned between ethyl acetate and water. The layers were separated and the aqueous layer was extracted with ethyl acetate (2×). The combined organic layers were washed with brine, dried over $MgSO_4$ and concentrated to dryness. The crude material was purified by column chromatography (10-20% Ethyl acetate-Hexanes) to provide a the product as light yellow solid (1.7 g, 75%). ESI-MS m/z calc. 451.1, found 452.1 (M+1)+; Retention time: 1.59 minutes (3 minute run).

Step 2:

A mixture of tert-butyl 8-bromo-2-methyl-6-(trifluoromethyl)spiro[3,4-dihydropyrrolo[1,2-a]pyrazine-1,4'-piperidine]-1'-carboxylate (1.67 g, 3.7 mmol) and dicyanozinc (234.9 μL, 3.7 mmol) in DMF (10 mL) was purged with $N_2$ for 5 min. $Pd(PPh_3)_4$ (427.6 mg, 0.37 mmol) was added. The mixture was heated in a sealed microwave vial at 150° C. overnight. The mixture was partitioned between ethyl acetate and water. The layers were separated. The aqueous layer was extracted with ethyl acetate (3×). All organic layers were combined, washed with water (3×), brine, dried over MgSO₄, filtered and concentrated to dryness. The crude material was purified by column chromatography (10-20% EtOAc/hexanes) to provide tert-butyl 8-cyano-2-methyl-6-(trifluoromethyl)spiro[3,4-dihydropyrrolo[1,2-a]pyrazine-1,4'-piperidine]-1'-carboxylate (510 mg, 35%) as a white solid. ESI-MS m/z calc. 398.2, found 399.3 (M+1)+; Retention time: 1.56 minutes (3 minute run).

Step 3:

To a solution of tert-butyl 8-cyano-2-methyl-6-(trifluoromethyl)spiro[3,4-dihydropyrrolo[1,2-a]pyrazine-1,4'-piperidine]-1'-carboxylate (278.9 mg, 0.7 mmol) in DCM (4 mL) was added HCl in dioxane (2 mL of 4 M, 8.0 mmol). The mixture was stirred at room temperature for 30 min. The solvent was evaporated and the crude material was used directly in next step without further purification. ESI-MS m/z calc. 298.1, found 299.5 (M+1)+; Retention time: 0.88 minutes (3 minute run).

6'-Chloro-2'-methyl-3',4'-dihydro-2'H-spiro[piperidine-4,1'-pyrrolo[1,2-a]pyrazine]dihydrochloride

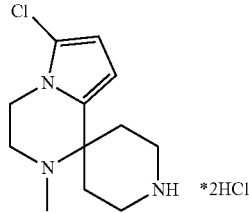 [SMILES: CN1CCn2c(Cl)ccc2C12CCNCC2]

Step 1:

To tert-butyl 2-methylspiro[3,4-dihydropyrrolo[1,2-a]pyrazine-1,4'-piperidine]-1'-carboxylate (5 g, 16.37 mmol) in dichloromethane (50.00 mL) at 0° C. was added trifluoromethanesulfonyl chloride (3.64 mL, 34.38 mmol) and the reaction was stirred from 0° C. to room temperature overnight. The reaction was diluted with dichloromethane and washed with water. The layers were separated and the organics were dried over sodium sulfate, filtered and concentrated. Purification of the residue by silica gel chromatography eluting with 10-100% ethylacetate in hexanes afforded tert-butyl 6-chloro-2-methyl-spiro[3,4-dihydropyrrolo[1,2-a]pyrazine-1,4'-piperidine]-1'-carboxylate (4.3 g, 77%) as a yellow solid. ESI-MS m/z calc. 339.2, found 340.3 (M+1)+; Retention time: 1.13 minutes (3 min run). ¹H NMR (400 MHz, CDCl₃) δ 6.01 (d, J=3.8 Hz, 1H), 5.91 (d, J=3.7 Hz, 1H), 3.77 (t, J=6.1 Hz, 2H), 3.34 (s, 2H), 3.24 (s, 2H), 2.34 (s, 3H), 2.03 (d, J=13.1 Hz, 2H), 1.74 (t, J=11.1 Hz, 2H), 1.47 (s, 9H).

Step 2:

HCl (1.84 mL of 4 M in dioxanes, 7.34 mmol) was added to a solution of tert-butyl 6-chloro-2-methyl-spiro[3,4-dihydropyrrolo[1,2-a]pyrazine-1,4'-piperidine]-1'-carboxylate (624 mg, 1.84 mmol) in dichloromethane (2 mL) and was stirred at 40° C. for 1 hour. The reaction was evaporated to dryness to yield 6'-chloro-2'-methyl-3',4'-dihydro-2'H-spiro[piperidine-4,1'-pyrrolo[1,2-a]pyrazine]dihydrochloride (quantitative) that was used without further purification. ESI-MS m/z calc. 239.1, found 240.3 (M+1)+; Retention time: 0.22 minutes (3 min run).

Ethyl 6'-cyano-3',4'-dihydro-2'H-spiro[piperidine-4,1'-pyrrolo[1,2-a]pyrazine]-2'-carboxylate hydrochloride

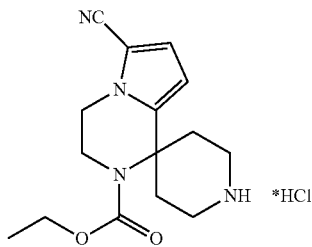 [SMILES: CCOC(=O)N1CCn2c(C#N)ccc2C12CCNCC2]

Step 1:

Ethyl chloroformate (328.2 μL, 3.43 mmol) was added to a solution of tert-butyl spiro[3,4-dihydro-2H-pyrrolo[1,2-a]pyrazine-1,4'-piperidine]-1'-carboxylate (500 mg, 1.72 mmol) and K₂CO₃ (474.3 mg, 3.43 mmol) in acetonitrile (5.0 mL) and the reaction was stirred at room temperature overnight. The reaction was filtered using acetonitrile and the solvent was evaporated under reduced pressure. The compound was dissolved in ethyl acetate and washed with 1N hydrochloric acid and brine. The organic layer was dried over sodium sulfate, filtered, and concentrated under reduced pressure to yield 1-tert-butyl 2'-ethyl 3',4'-dihydro-2'H-spiro[piperidine-4,1'-pyrrolo[1,2-a]pyrazine]-1,2'-dicarboxylate (395 mg, 63%) as an amber oil that was used in the next step without further purification. ESI-MS m/z calc. 363.2, found 364.3 (M+1)+; Retention time: 1.78 minutes (3 minute run).

Step 2:

A solution of N-(oxomethylene)sulfamoyl chloride (23.9 μL, 0.27 mmol) in THF (200.0 μL) was slowly added to a solution of 1-tert-butyl 2'-ethyl 3',4'-dihydro-2'H-spiro[piperidine-4,1'-pyrrolo[1,2-a]pyrazine]-1,2'-dicarboxylate (100 mg, 0.27 mmol) in THF (1.0 mL) at −78° C. under nitrogen. The reaction mixture was stirred for 1 hour at −78° C. N,N-dimethylformamide (39.9 μL, 0.51 mmol) was then slowly added to the cold reaction mixture. The reaction mixture was then allowed to slowly warm to room temperature. The reaction was filtered and purified by reverse phase preparatory-LC-MS (10-99% CH₃CN/H₂O) using HCl modifier to give 1-tert-butyl 2'-ethyl 6'-cyano-3',4'-dihydro-2'H-spiro[piperidine-4,1'-pyrrolo[1,2-a]pyrazine]-1,2'-dicarboxylate. ESI-MS m/z calc. 388.2, found 389.3 (M+1)+; Retention time: 1.82 minutes (3 minute run).

Step 3:

4 N HCl in dioxane (8.7 mL, 34.7 mmol) was added to a solution of 1-tert-butyl 2'-ethyl 6'-cyano-3',4'-dihydro-2'H-spiro[piperidine-4,1'-pyrrolo[1,2-a]pyrazine]-1,2'-dicarboxylate (0.27 mmol) in dichloromethane (5 mL) and the mixture was stirred at 40° C. for 1 hour. The reaction mixture was evaporated to dryness to give ethyl 6'-cyano-3',4'-dihydro-2'H-spiro[piperidine-4,1'-pyrrolo[1,2-a]pyrazine]-2'- carboxylate hydrochloride. ESI-MS m/z calc. 288.2, found 289.3 (M+1)+; Retention time: 0.75 minutes (3 minute run).

8'-Fluoro-2'-methyl-6'-(trifluoromethyl)-3',4'-dihydro-2'H-spiro[piperidine-4,1'-pyrrolo[1,2-a]pyrazine] dihydrochloride

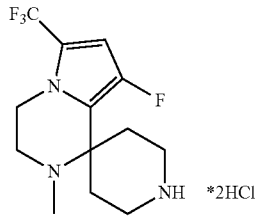 [SMILES: CN1CCn2c(C(F)(F)F)cc(F)c2C12CCNCC2]

Step 1:
To a solution of tert-butyl 2-methyl-6-(trifluoromethyl)spiro[3,4-dihydropyrrolo[1,2-a]pyrazine-1,4'-piperidine]-1'-carboxylate (5.60 g, 15.0 mmol) in acetonitrile (50 mL) was added NBS (2.80 g, 15.8 mmol). The mixture was stirred at room temperature overnight. The solvent was removed and the residue was partitioned between EtOAc and water. The aqueous layer was extracted with EtOAc (2×). The combined organic layers were washed with brine, dried over MgSO₄ and concentrated to dryness. The crude material was purified by column chromatography (10-20% EtOAc-Hex) to provide tert-butyl 8-bromo-2-methyl-6-(trifluoromethyl)spiro[3,4-dihydropyrrolo[1,2-a]pyrazine-1,4'-piperidine]-1'-carboxylate (5.40 g, 73%) as a light yellow solid. ESI-MS m/z calc. 452.3. found 454.5 (M+1)+; Retention time: 1.60 minutes (3 minute run).

Step 2:
A solution of tert-butyl 8-bromo-2-methyl-6-(trifluoromethyl)spiro[3,4-dihydropyrrolo[1,2-a]pyrazine-1,4'-piperidine]-1'-carboxylate (15.0 g, 33.2 mmol) in THF (200 mL) was purged with Argon for 5 min. The mixture was cooled to −78° C. before nBuLi (42.5 mL of 1.6 M, 68 mmol) was added dropwise. The mixture was stirred at −78° C. for 30 min before a solution of N-(benzenesulfonyl)-N-fluoro-benzenesulfonamide (20.9 g, 66.3 mmol) in THF (100 mL) was added dropwise. The mixture was allowed to warm to room temperature overnight. The reaction mixture was quenched with sat. aq. NH₄Cl. The layers were separated and the aqueous layer was extracted with EtOAc (2×). The organic layers were combined and washed with brine, dried over MgSO₄, filtered and concentrated to dryness. CH₂Cl₂ was added and the solid was removed via filtration. The filtrate was concentrated to dryness and the residue was purified by column chromatography (10-20% EtOAc-Hex) to provide tert-butyl 8-fluoro-2-methyl-6-(trifluoromethyl)spiro[3,4-dihydropyrrolo[1,2-a]pyrazine-1,4'-piperidine]-1'-carboxylate (5.52 g, 43%) as a light brown oil that solidified upon standing. ESI-MS m/z calc. 391.4, found 392.5 (M+1)+; Retention time: 1.35 minutes (3 minute run).

Step 3:
To tert-butyl 8-fluoro-2-methyl-6-(trifluoromethyl)spiro[3,4-dihydropyrrolo[1,2-a]pyrazine-1,4'-piperidine]-1'-carboxylate (310 mg, 0.80 mmol) in CH₂Cl₂ (2 mL) was added a solution of HCl (2.0 mL of 4 M, 8.0 mmol) in 1,4-dioxane. The reaction mixture was allowed to stir at room temperature for 1 hour. The volatiles were removed under reduced pressure providing 8-fluoro-2-methyl-6-(trifluoromethyl)spiro[3,4-dihydropyrrolo[1,2-a]pyrazine-1,4'-piperidine]dihydrochloride (290 mg, 99%) as a pink solid. ESI-MS m/z calc. 291.1, found 292.3 (M+1)+; Retention time: 0.75 minutes (3 minute run).

8'-Chloro-2'-methyl-6'-(trifluoromethyl)-3',4'-dihydro-2'H-spiro[piperidine-4,1'-pyrrolo[1,2-a]pyrazine] dihydrochloride

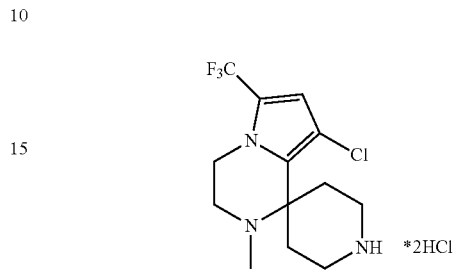

Step 1:
To a solution of tert-butyl 8-bromo-2-methyl-6-(trifluoromethyl)spiro[3,4-dihydropyrrolo[1,2-a]pyrazine-1,4'-piperidine]-1'-carboxylate (5.00 g, 11.1 mmol) in anhydrous THF (125 mL) at −78° C. was added nBuLi (8.84 mL of 2.5 M, 22.1 mmol) slowly. The reaction mixture was allowed to stir at −78 for 20 minutes before 1,1,1,2,2,2-hexachloroethane (5.36 g, 22.7 mmol) was added dropwise as a solution in THF (12 mL). The reaction mixture was allowed to slowly warm to room temperature and was stirred overnight. The reaction mixture was quenched with the addition of saturated aqueous ammonium chloride (100 mL). The volatiles were removed under reduced pressure to half volume. The remaining aqueous suspension was extracted with EtOAc (2×100 mL). The combined organic layers were dried over sodium sulfate, filtered and concentrated under reduced pressure to afford a thick brown oil. The crude product was purified by silica gel column chromatography: 10-20% EtOAc/hexane gradient to provide tert-butyl 8-chloro-2-methyl-6-(trifluoromethyl)spiro[3,4-dihydropyrrolo[1,2-a]pyrazine-1,4'-piperidine]-1'-carboxylate (2.40 g, 53%) as a yellow oil that crystallized upon standing. ESI-MS m/z calc. 407.2, found 407.9 (M+1)+; Retention time: 1.70 minutes (3 min run). ¹H NMR (400 MHz, CDCl₃) δ 6.47 (s, 1H), 3.97 (t, J=5.5 Hz, 4H), 3.28 (s, 2H), 3.13 (s, 2H), 2.51-2.28 (m, 5H), 1.93 (d, J=13.7 Hz, 2H), 1.47 (d, J=9.5 Hz, 9H).

Step 2:
To a solution of tert-butyl 8-chloro-2-methyl-6-(trifluoromethyl)spiro[3,4-dihydropyrrolo[1,2-a]pyrazine-1,4'-piperidine]-1'-carboxylate (750 mg, 1.84 mmol) in CH₂Cl₂ (2 mL) was added a prepared solution of 1:1 trifluoroacetic acid (2.0 mL, 26 mmol) in CH₂Cl₂ (2 mL). After stirring at room temperature for 2 hours, saturated aqueous sodium bicarbonate solution (75 mL) was slowly added. The mixture was extracted with EtOAc (2×75 mL). The organic layers were combined, dried over sodium sulfate, filtered and concentrated under reduced pressure to provide 8-chloro-2-methyl-6-(trifluoromethyl)spiro[3,4-dihydropyrrolo[1,2-a]pyrazine-1,4'-piperidine] (555 mg, 98%) as a yellow-brown solid. ESI-MS m/z calc. 307.1, found 307.9 (M+1)+; Retention time: 1.12 minutes (3 min run). ¹H NMR (400 MHz, CDCl₃) δ 9.72 (s, 1H), 9.38 (s, 1H), 6.49 (s, 1H), 3.98 (t, J=5.6 Hz, 2H), 3.36 (d, J=11.6 Hz, 2H), 3.26 (d, J=6.1 Hz, 4H), 2.78 (s, 2H), 2.40 (s, 3H), 2.11 (d, J=14.4 Hz, 2H), 1.69 (s, 2H).

2'-Methyl-6',7'-bis(trifluoromethyl)-3',4'-dihydro-2'H-spiro[piperidine-4,1'-pyrrolo[1,2-a]pyrazine]

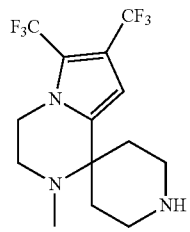 [SMILES: CN1CCn2c(cc(C(F)(F)F)c2C(F)(F)F)C12CCNCC2]

Step 1:

Ferrous sulfate heptahydrate (803 µL of 1.00 M, 0.803 mmol) was added to a mixture of tert-butyl 2-methyl-6-(trifluoromethyl)spiro[3,4-dihydropyrrolo[1,2-a]pyrazine-1,4'-piperidine]-1'-carboxylate (1.00 g, 2.68 mmol) and DMSO (15 mL) at room temperature. The vessel was then charged with CF$_3$I (gas) before H$_2$O$_2$ (304 µL of 30% w/v, 2.68 mmol) was added dropwise. The mixture was allowed to stir overnight at room temperature before it was partitioned between ethyl acetate and water. The layers were separated and the aqueous layer was extracted with ethyl acetate (3×). The combined organics were washed with brine, dried over sodium sulfate, filtered and concentrated. The reside was purified by column chromatography (0-100% ethyl acetate/hexanes) to give tert-butyl 2-methyl-6,7-bis(trifluoromethyl)spiro[3,4-dihydropyrrolo[1,2-a]pyrazine-1,4'-piperidine]-1'-carboxylate. ESI-MS m/z calc. 441.2, found 442.5 (M+1)+; Retention time: 1.36 minutes (3 min run).

Step 2:

tert-Butyl 2-methyl-6,7-bis(trifluoromethyl)spiro[3,4-dihydropyrrolo[1,2-a]pyrazine-1,4'-piperidine]-1'-carboxylate (from step 1) was taken up in CH$_2$Cl$_2$ (2 mL) and HCl (1.7 mL of 4 M, 6.8 mmol) was added. The mixture was allowed to stir for 30 min before it was concentrated under reduced pressure. The residue was taken up in ethyl acetate and was washed with sat. aq. NaHCO$_3$, then brine. The organic layer was dried over sodium sulfate, filtered and concentrated to give 2-methyl-6,7-bis(trifluoromethyl)spiro[3,4-dihydropyrrolo[1,2-a]pyrazine-1,4'-piperidine] (22 mg, 2% over 2 steps). ESI-MS m/z calc. 341.1, found 342.3 (M+1)+; Retention time: 1.29 minutes.

2'-Methyl-6'-(methylsulfonyl)-3',4'-dihydro-2'H-spiro[piperidine-4,1'-pyrrolo[1,2-a]pyrazine]

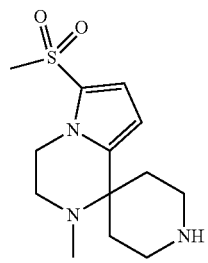 [SMILES: CN1CCn2c(ccc2S(C)(=O)=O)C12CCNCC2]

Step 1:

To benzyl 2-methylspiro[3,4-dihydropyrrolo[1,2-a]pyrazine-1,4'-piperidine]-1'-carboxylate (3.00 g, 8.84 mmol) in CH$_2$Cl$_2$ (30 mL) at 0° C. was added NBS (1.57 g, 8.84 mmol) portionwise. The reaction mixture was stirred at 0° C. for 2 h. Additional NBS (157 mg) was added and the reaction mixture was stirred at 0° C. for 15 minutes (repeated 6 additional times until starting material was consumed). The reaction mixture was diluted with 0.5 M Na$_2$S$_2$O$_3$ (30 mL) and the aqueous phase was removed. The organic phase was washed with brine (30 mL). The organic layer was dried over sodium sulfate, filtered and the solvent was evaporated under reduced pressure. The crude product was purified by column chromatography utilizing a gradient of 0-30% ethyl acetate in CH$_2$Cl$_2$ to yield benzyl 6-bromo-2-methyl-spiro[3,4-dihydropyrrolo[1,2-a]pyrazine-1,4'-piperidine]-1'-carboxylate (2.34 g, 63%) as a cream solid. ESI-MS m/z calc. 417.1, found 418.1 (M+1)+; Retention time: 1.49 minutes (3 min run). $^1$H NMR (400 MHz, DMSO) δ 7.43-7.26 (m, 5H), 6.09 (d, J=3.7 Hz, 1H), 5.99 (d, J=3.7 Hz, 1H), 5.08 (s, 2H), 3.89-3.74 (m, 2H), 3.68 (t, J=5.8 Hz, 2H), 3.27 (t, J=5.8 Hz, 2H), 3.22-2.99 (m, 2H), 2.21 (s, 3H), 2.09-1.94 (m, 2H), 1.73-1.52 (m, 2H).

Step 2:

A mixture of sodium methanesulfinate (293 mg, 2.87 mmol), benzyl 6-bromo-2-methyl-spiro[3,4-dihydropyrrolo[1,2-a]pyrazine-1,4'-piperidine]-1'-carboxylate (1.00 g, 2.39 mmol), CuI (296 mg, 1.55 mmol) and DMSO (5 mL) was heated at 90° C. in a pressure vessel for 20 hours. The mixture was cooled and was partitioned between ether (10 mL) and water (10 mL). The organic layer was separated and the aqueous layer was extracted with ether (3×5 mL). The combined organic layers were washed with brine (2×10 mL), dried over sodium sulfate, filtered and concentrated in vacuo. The crude product was purified by column chromatography utilizing a gradient of 0-50% ethyl acetate in CH$_2$Cl$_2$ to yield benzyl 2-methyl-6-methylsulfonyl-spiro[3,4-dihydropyrrolo[1,2-a]pyrazine-1,4'-piperidine]-1'-carboxylate (520 mg, 52%) as a white solid. ESI-MS m/z calc. 417.2, found 418.3 (M+1)+; Retention time: 1.27 minutes (3 min run). $^1$H NMR (400 MHz, CDCl$_3$) δ 7.45-7.30 (m, 5H), 6.88 (d, J=4.1 Hz, 1H), 6.01 (d, J=3.9 Hz, 1H), 5.15 (s, 2H), 4.28-4.15 (m, 2H), 4.09-3.89 (m, 2H), 3.40-3.16 (m, 4H), 3.10 (s, 3H), 2.37 (s, 3H), 2.20-2.02 (m, 2H), 1.89-1.66 (m, 2H).

Step 3:

To a solution of benzyl 2-methyl-6-methylsulfonyl-spiro[3,4-dihydropyrrolo[1,2-a]pyrazine-1,4'-piperidine]-1'-carboxylate (520 mg, 1.25 mmol) in EtOH (13 mL) was added 10% palladium-carbon (66 mg, 0.062 mmol) under nitrogen atmosphere. The reaction mixture was stirred at room temperature for 16 h under a hydrogen atmosphere. The mixture was filtered through a plug of celite and the solvent was evaporated under reduced pressure to yield 2-methyl-6-methylsulfonyl-spiro[3,4-dihydropyrrolo[1,2-a]pyrazine-1,4'-piperidine] (342 mg, 97%) as an off-white solid. ESI-MS m/z calc. 283.1, found 284.3 (M+1)+; Retention time: 0.30 minutes (3 min run).

3-Methyl-4-(methylsulfamoyl)benzoic acid

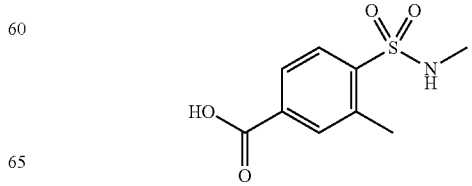

Step 1:

A solution of 4-amino-3-methyl-benzoic acid (4.00 g, 26.5 mmol) in conc. HCl (15 mL) was cooled to 0° C. in an ice bath before a solution of sodium nitrite (1.97 g, 910 μL, 28.6 mmol) in water (5 mL) was added dropwise while keeping the temperature below 5° C. $SO_2$ was bubbled through a solution of acetic acid (60 mL) and $CuCl_2$ (889 mg, 6.62 mmol) for 20 min before the cold diazonium solution was added. The reaction mixture was stirred for 1 h before it was poured onto ice. The solid was collected by filtration and was washed with water. The solid was further dried to give 4-chlorosulfonyl-3-methyl-benzoic acid (2.30 g, 37%). $^1$H NMR (400 MHz, DMSO) δ 7.81 (d, J=7.8 Hz, 1H), 7.74-7.66 (m, 2H), 2.57 (s, 3H).

Step 2:

4-Chlorosulfonyl-3-methyl-benzoic acid (0.99 g, 4.2 mmol), methanamine (2.0 mL of 33% w/v, 21 mmol), and triethylamine (1.8 mL, 13 mmol) were stirred for 45 min at rt. The reaction mixture was evaporated and the resultant oil was partitioned between ethyl acetate and 1N HCl. The organics were separated and washed with another portion of 1N HCl and then brine. The organics were dried over sodium sulfate and evaporated to give 3-methyl-4-(methylsulfamoyl)benzoic acid (841 mg, 87%). ESI-MS m/z calc. 229.0, found 230.5 (M+1)+; Retention time: 0.64 minutes (3 min run).

The following compounds were synthesized using the procedures described above:

4-(N-ethylsulfamoyl)-3-methylbenzoic acid, 4-(N-cyclopropylsulfamoyl)-3-methylbenzoic acid, 4-(N-isopropylsulfamoyl)-3-methylbenzoic acid, and 4-(N,N-dimethylsulfamoyl)-3-methylbenzoic acid.

7-(Ethyl(methyl)amino)pyrazolo[1,5-a]pyrimidine-3-carboxylic acid

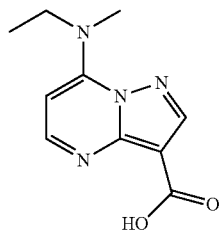 [SMILES: CCN(C)c1ccnc2c(C(=O)O)cnn12]

Step 1:

To a stirred suspension ethyl 7-hydroxypyrazolo[1,5-a]pyrimidine-3-carboxylate (0.95 g, 4.6 mmol) in $POCl_3$ (8.0 mL, 86 mmol) was added dimethyl aniline (0.8 μL, 0.006 mmol) and the mixture was heated at 80° C. for 2 hours. The mixture was slowly poured onto ice, and the pH was carefully adjusted to ~7 with 1N NaOH, then to pH 10 with solid $Na_2CO_3$. The mixture was then extracted with dichloromethane (3×). The organics were combined, washed with brine, dried ($MgSO_4$) and evaporated to dryness. Trituration of the solids with hexanes gave ethyl 7-chloropyrazolo[1,5-a]pyrimidine-3-carboxylate (260 mg, 25%) as a tan solid. ESI-MS m/z calc. 225.0, found 226.5 (M+1)+; Retention time: 0.87 minutes (3 min run).

Step 2:

To a solution of ethyl 7-chloropyrazolo[1,5-a]pyrimidine-3-carboxylate (68 mg, 0.30 mmol) in $CH_3CN$ (1 mL) was added N-methylethanamine (18 mg, 0.30 mmol) and the mixture was stirred at ambient temperature for 16 h. The mixture was evaporated and the residue was purified by column chromatography (0-10% MeOH in dichloromethane) to give a solid. The solid was taken up in EtOH (0.5 mL) and water (0.1 mL) before NaOH (12 mg, 0.30 mmol) was added. The mixture was stirred at 50° C. for 4 h. The pH of the mixture was adjusted to 4 with conc. HCl, and the solvents were removed. The residue was co-evaporated with MeOH (3×) to provide 7-(ethyl(methyl)amino)pyrazolo[1,5-a]pyrimidine-3-carboxylic acid. ESI-MS m/z calc. 220.1, found 221.5 (M+1)+; Retention time: 0.29 minutes (3 min run).

The following compounds were synthesized using the procedures described above:

7-(ethylamino)pyrazolo[1,5-a]pyrimidine-3-carboxylic acid, 7-(isopropylamino)pyrazolo[1,5-a]pyrimidine-3-carboxylic acid, 7-(ethyl(methyl)amino)-5-methylpyrazolo[1,5-a]pyrimidine-3-carboxylic acid, 5-methyl-7-(pyrrolidin-1-yl)pyrazolo[1,5-a]pyrimidine-3-carboxylic acid, and 7-(ethylamino)-5-methylpyrazolo[1,5-a]pyrimidine-3-carboxylic acid.

4-(1-Hydroxy-1-methyl-ethyl)-3-methyl-benzoic acid

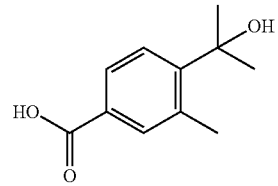

4-Bromo-3-methyl-benzoic acid (3.96 g, 18.4 mmol) was dissolved in tetrahydrofuran (100 mL) and the solution was cooled to −78° C. n-Butyllithium in hexanes (16.2 mL of 2.5 M, 41 mmol) was added dropwise over 20 minutes. The reaction mixture was allowed to stir for 30 minutes at −78° C. and then acetone (1.35 mL, 18.4 mmol) was added in a drop-wise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and then the aqueous layer was made acidic with 4M aqueous hydrochloric acid. The aqueous layer was then extracted 3 times with ethyl acetate. The combined extracts were dried over sodium sulfate and then evaporated to dryness. The crude material was further purified on silica gel utilizing a gradient of 0-10% methanol in dichloromethane to give 4-(1-hydroxy-1-methyl-ethyl)-3-methyl-benzoic acid (1.51 g, 42%). $^1$H NMR (400 MHz, DMSO) δ 12.74 (s, 1H), 7.68 (dd, J=3.9, 2.5 Hz, 2H), 7.55 (d, J=8.7 Hz, 1H), 5.06 (s, 1H), 2.56 (s, 3H), 1.51 (s, 6H).

The following compounds were synthesized using the procedures described above:

4-(1-hydroxycyclopentyl)-3-methylbenzoic acid, 4-(1-hydroxycyclopentyl)benzoic acid, 4-(1-hydroxycyclohexyl)-3-methylbenzoic acid, 4-(1-hydroxycyclohexyl)benzoic acid, 3-fluoro-4-(1-hydroxycyclohexyl)benzoic acid, and 4-(1-hydroxycyclohexyl)-3-methoxybenzoic acid.

5-Isopropoxy-6-methylpicolinic acid

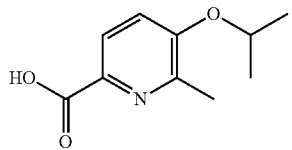

Step 1:
2-Methyl-3-pyridinol (8.3 g, 76.1 mmol) was suspended in acetonitrile (125 mL). A solution of NBS (27.7 g, 155.6 mmol, 2.05 equiv) in acetonitrile (275 mL) was added to the suspension drop-wise over 1 hour. The mixture was heated at reflux for 1.5 h. The mixture was concentrated and the residue was purified by column chromatography (DCM) to give 4,6-dibromo-2-methylpyridin-3-ol (15.8 g, 78%) as a yellow solid. $^1$H NMR (300 MHz, DMSO-$d_6$) 2.41 (s, 3H), 7.70 (s, 1H), 9.98 (s, 1H).

Step 2:
4,6-Dibromo-2-methylpyridin-3-ol (15.8 g, 59.4 mmol) was dissolved in THF (200 mL). The solution was cooled to −78° C. and n-BuLi (50 mL, 125 mmol, 2.5 M in hexane) was added drop-wise keeping the temperature below −78° C. The mixture was allowed to stir at that temperature for 2 h. The mixture was quenched with water (50 mL) and was neutralized with 2 N HCl. The aqueous mixture was extracted with dichloromethane (2×). The combined organic layers were dried ($Na_2SO_4$) and concentrated to give 6-bromo-2-methylpyridin-3-ol (10.5 g, 95%) as a yellow oil. $^1$H-NMR (300 MHz, DMSO-$d_6$) 2.29 (s, 3H), 7.08 (d, 1H), 7.26 (d, 1H), 10.08 (s, 1H).

Step 3:
6-Bromo-2-methylpyridin-3-ol (10.5 g, 55.9 mmol) was dissolved in DMF (100 mL). $K_2CO_3$ (19.3 g, 139.6 mmol) and 2-bromopropane (13.1 ml, 139.6 mmol) were added to the solution and the mixture was heated at 100° C. overnight. The mixture was poured into a mixture of water and EtOAc (200 mL). The layers were separated and the aqueous layer was extracted with EtOAc (2×). The combined organic layers were dried ($Na_2SO_4$) and concentrated. The crude oil was purified by column chromatography (0-20% ethyl acetate/heptanes) to give 6-bromo-3-isopropoxy-2-methylpyridine (10.9 g, 85) as a yellow oil. $^1$H-NMR (300 MHz, $CDCl_3$) 1.42 (d, 6H), 2.48 (s, 3H), 4.65 (m, 1H), 7.20 (d, 1H), 8.04 (d, 1H).

Step 4:
6-Bromo-3-isopropoxy-2-methylpyridine (2.00 g, 8.70 mmol), $PdCl_2(PPh_3)_2$ (0.18 g, 0.26 mmol) and $Et_3N$ (1.8 ml, 13.04 mmol) were added to MeOH (5.2 mL) and acetonitrile (20 mL) in a Berghoff reactor. The reactor was charged with 10 bar CO (g) and was heated at 60° C. overnight. The mixture was concentrated and the residue was partitioned between DCM and water. The layers were separated and the organic layer was washed with brine and dried ($Na_2SO_4$). The mixture was concentrated and purified by column chromatography to give methyl 5-isopropoxy-6-methylpicolinate (1.3 g, 71%) as a yellow oil. $^1$H-NMR (300 MHz, $CDCl_3$) 1.40 (d, 6H), 2.53 (s, 3H), 3.98 (s, 3H), 4.62 (m, 1H), 7.12 (d, 1H), 7.98 (d, 1H).

Step 5:
5-Isopropoxy-6-methylpicolinate (1.3 g, 6.22 mmol) was dissolved in THF/water 2:1 (9 mL). LiOH*$H_2O$ (0.26 g, 6.22 mmol) was added and the mixture was stirred at room temperature overnight. The mixture was poured into a mixture of water and EtOAc and the layers were separated. The aqueous layer was acidified to pH 4 with 2 N HCl and was extracted with EtOAc (2×). The combined organics were dried ($Na_2SO_4$) and concentrated to give 5-isopropoxy-6-methylpicolinic acid (860 mg, 74%) as a beige solid. $^1$H-NMR (300 MHz, DMSO-$d_6$) 1.31 (d, 6H), 4.73 (m, 1H), 7.44 (d, 1H), 7.86 (d, 1H). 1H NMR (400 MHz, DMSO) δ 12.61 (s, 1H), 7.88 (d, J=8.5 Hz, 1H), 7.44 (d, J=8.7 Hz, 1H), 4.74 (dt, J=12.0, 6.0 Hz, 1H), 2.37 (s, 3H), 1.32 (d, J=6.0 Hz, 6H).

The following compound was synthesized using the procedures described above:
5-methoxy-6-methylpicolinic acid.

4-Isopropoxy-3-methoxybenzoic acid

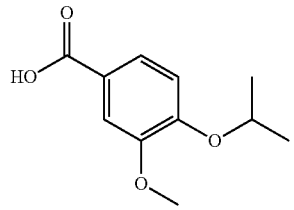

Step 1:
Under a balloon of $N_2$, tert-butyllithium (2.14 mL of 1.6 M, 3.43 mmol) was added drop-wise to a solution of 4-bromo-1-isopropoxy-2-methoxy-benzene (400 mg, 1.63 mmol) in THF (6.0 mL) at −78° C. The mixture was allowed to stir for 1 h at −78° C. before it was added drop-wise to a flask containing $CO_2$ (1.80 g, 40.8 mmol)(solid, dry ice) in THF (2.0 mL). The mixture was allowed to stir for 30 min as it warmed to room temperature (caution: $CO_2$ gas evolution). Water (20 mL) was added and the volatiles were removed under reduced pressure. The resultant aqueous layer was acidified with 1N HCl to pH ~1-2 and the mixture was extracted with ethyl acetate (3×15 mL). The combined organics were washed with brine, dried over sodium sulfate, filtered and concentrated to give 4-isopropoxy-3-methoxy-benzoic acid (≥94% pure, 310 mg, 85%) as a white solid. ESI-MS m/z calc. 210.1, found 210.9 (M+1)$^+$; Retention time: 1.23 min. $^1$H NMR (400 MHz, DMSO) δ 12.63 (s, 1H), 7.53 (dd, J=8.4, 2.0 Hz, 1H), 7.44 (d, J=2.0 Hz, 1H), 7.04 (d, J=8.7 Hz, 1H), 4.67 (dt, J=12.1, 6.0 Hz, 1H), 3.78 (s, 3H), 1.28 (d, J=6.0 Hz, 6H).

3-Methoxy-4-(2-(trifluoromethoxy)ethoxy)benzoic acid

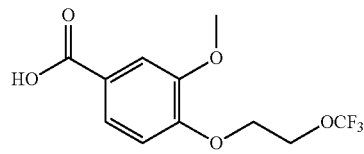 [SMILES: COc1cc(C(=O)O)ccc1OCCOC(F)(F)F]

Step 1:
To sodium hydride (200 mg, 5.0 mmol) in DMF (6 mL) under $N_2$ was added methyl 4-hydroxy-3-methoxy-benzoate (920 mg, 5.0 mmol) and the mixture was stirred for 10 min. 2-(trifluoromethoxy)ethyl trifluoromethanesulfonate (1.2 g, 4.6 mmol) was then added dropwise and the solution was stirred at room temperature for 2 h, then at 50° C. for 2 h. The mixture was concentrated to a solid, and the residue was taken up in 50 mL of CH₂Cl₂ before it was washed with brine (20 mL), dried over MgSO₄ and purified by column chromatography (0-25% EtOAc/hexane) to give methyl 3-methoxy-4-(2-(trifluoromethoxy)ethoxy)benzoate as a white solid. ESI-MS m/z calc. 294.1, found 295.3 (M+1)+; Retention time: 1.63 minutes (3 min run).

Step 2:

Methyl 3-methoxy-4-(2-(trifluoromethoxy)ethoxy)benzoate (obtained in Step 1) was dissolved in THF (5 mL) and a suspension of LiOH (550 mg, 23 mmol) in water (5 mL) was added. The mixture was stirred vigorously and heated at 60° C. for 6 h before it was concentrated to half volume. Water (5 mL) was added and the mixture was extracted with diethyl ether (1×10 mL). The aqueous layer was acidified with 4N HCl to pH 2. The resulting mixture was extracted with ethyl acetate (3×10 mL) and the combined organics were washed (1×10 mL H₂O, 1×10 mL brine), dried over MgSO₄ and evaporated to give 3-methoxy-4-(2-(trifluoromethoxy) ethoxy)benzoic acid (1.0 g, 82%) as a white solid. ESI-MS m/z calc. 280.1, found 281.3 (M+1)⁺; Retention time: 1.34 minutes (3 min run).

4-tert-Butoxy-3-methoxybenzoic acid

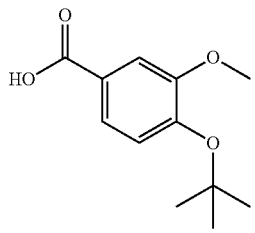 [SMILES: COc1cc(C(=O)O)ccc1OC(C)(C)C]

Step 1:

4-Hydroxy-3-methoxy-benzaldehyde (500 mg, 3.29 mmol), Boc₂O (1.74 g, 7.97 mmol), and Sc(OTf)₃ (0.080 g, 0.16 mmol) were combined in dichloromethane (5 mL). The reaction mixture was allowed to stir at room temperature for 24 h. Water (5 mL) and dichloromethane (5 mL) were added and the two phases were separated. The aqueous layer was extracted with dichloromethane (3×5 mL) and the combined organics were stirred with 10% aqueous potassium hydroxide until all remaining starting material was not observed in the organic phase (TLC, 40% ethyl acetate in hexanes). The two phases were separated and the dichloromethane layer was then washed twice with a saturated aqueous solution of sodium chloride, dried over sodium sulfate, filtered, and evaporated to dryness to give 4-tert-butoxy-3-methoxybenzaldehyde (130 mg, 19%) as a yellow oil. Rf=0.66 (SiO₂, 40% ethyl acetate in hexanes); ESI-MS m/z calc. 208.1, found 209.2 (M+1)⁺. Retention time: 0.96 minutes (6 min run).

Step 2:

4-tert-Butoxy-3-methoxybenzaldehyde (130 mg, 0.62 mmol) was suspended in a mixture of dioxane (520 µL) and potassium hydroxide (6.5 mL of 0.20 M, 1.3 mmol). KMnO₄ (150 mg, 0.93 mmol) was added and the reaction was stirred vigorously for 16 h. The reaction mixture was filtered and then concentrated to 3 mL. Hydrochloric acid (1M, 4 mL) was added and the resulting precipitate was filtered (after standing for 15 minutes) and washed with 1M HCl and a small amount of water to yield 4-tert-butoxy-3-methoxy-benzoic acid (68 mg, 49%) as a white solid. Rf=0.23 (SiO₂, 40% ethyl acetate in hexanes); ESI-MS m/z calc. 224.1, found 225.2 (M+1)⁺. Retention time: 1.66 minutes (3 min run). ¹H NMR (400 MHz, DMSO) δ 12.80 (s, 1H), 7.66-7.41 (m, 2H), 7.09 (d, J=8.8 Hz, 1H), 3.78 (s, 3H), 1.32 (s, 9H).

The following compounds were synthesized using the procedures described above:

4-tert-butoxy-3-methylbenzoic acid from 4-hydroxy-3-methylbenzaldehyde, 2-fluoro-4,5-dimethoxybenzoic acid from 2-fluoro-4,5-dimethoxybenzaldehyde, 4-tert-butoxy-2-methoxybenzoic acid from 4-hydroxy-2-methoxybenzaldehyde, 4-tert-butoxy-2-fluorobenzoic acid from 2-fluoro-4-hydroxybenzaldehyde, and 4-tert-butoxybenzoic acid from 4-hydroxybenzaldehyde.

4-Ethyl-3-methoxybenzoic acid

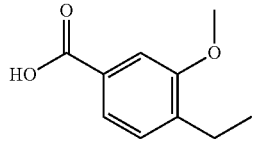

A mixture of 4-bromo-3-methoxy-benzoic acid (2.49 g, 10.9 mmol) and Pd(dppf)Cl₂ (158 mg, 0.216 mmol) were stirred in dioxane (25 mL) and Et₂Zn (22 mL, 1 M in hexanes, 22 mmol) was added. The reaction mixture was heated at 70° C. for 1 h. The mixture was cooled to room temperature and was quenched with MeOH (1.1 mL). The solution was diluted with ethyl acetate (20 mL) and was washed with 1 N HCl (10 mL). The combined organics were washed with brine, dried over sodium sulfate and evaporated to dryness to give 4-ethyl-3-methoxybenzoic acid. ESI-MS m/z calc. 180.1, found 179.1 (M−1)⁻; Retention time: 1.77 minutes (3 min run).

4-(Isopropylsulfonyl)-3-methylbenzoic acid

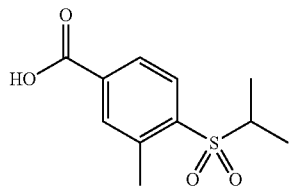 [SMILES: Cc1cc(C(=O)O)ccc1S(=O)(=O)C(C)C]

Step 1:

Butyllithium (16 mL of 1.6 M, 26 mmol) was added drop-wise to a mixture of 4-bromo-3-methyl-benzoic acid (2.5 g, 12 mmol) and THF (63 mL) at −78° C. The mixture was allowed to stir at −78° C. for 30 minutes before a solution of 2-isopropyldisulfanylpropane (1.7 g, 12 mmol) in THF (2 mL) was added drop-wise. The mixture was allowed to stir at −78° C. for 30 min, then 30 min at rt. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography using a gradient of 0-5% MeOH in dichloromethane to give 4-(isopropylthio)-3-methylbenzoic acid (870 mg, 18%). MS m/z calc. 210.3, found 211.2 (M+1)⁺. Retention time: 2.32 minutes (3 min run).

Step 2:

3-Chlorobenzenecarboperoxoic acid (930 mg, 4.2 mmol) was added to a mixture of 4-(isopropylthio)-3-methylbenzoic acid (250 mg, 1.2 mmol) and dichloromethane (5.0 mL) at 25° C. The mixture was allowed to stir at 25° C. for 2 h before it was concentrated in vacuo. The white solid material was taken up in dichloromethane and was subjected to column chromatography (0-2% MeOH/dichloromethane) to give 4-isopropylsulfonyl-3-methyl-benzoic acid (90 mg, 31%) as a white solid. ESI-MS m/z calc. 242.3, found 243.2 (M+1)⁺. Retention time: 1.57 minutes (3 min run). ¹H NMR (400 MHz, DMSO) δ 13.50 (s, 1H), 8.50-7.66 (m, 3H), 3.50-3.47 (m, 1H), 2.67 (s, 3H), 1.19 (d, J=1.16 Hz, 6H).

The following compounds were synthesized using the procedures described above:

4-(isopropylsulfonyl)-2-methylbenzoic acid and 4-(ethylsulfonyl)-3-methylbenzoic acid, 4-(2-Hydroxypropan-2-yl)-3-methoxybenzoic acid

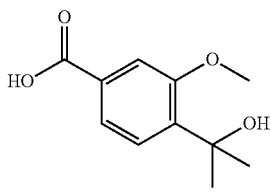

4-Bromo-3-methoxy-benzoic acid (2.00 g, 8.67 mmol) was dissolved in THF (50 mL) and the solution was cooled to −78° C. n-BuLi in hexanes (7.6 mL of 2.5 M, 19 mmol) was added dropwise over 15 minutes. The reaction mixture was allowed to stir for 30 minutes at −78° C. and then acetone (640 µL, 8.9 mmol) was added in a dropwise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography utilizing a gradient of 0-5% methanol in dichloromethane to give 4-(2-hydroxypropan-2-yl)-3-methoxybenzoic acid (618 mg, 34%). ESI-MS m/z calc. 210.1, found 209.1 (M−1)⁻; Retention time: 0.68 minutes (3 min run).

3-Fluoro-4-isopropoxybenzoic acid

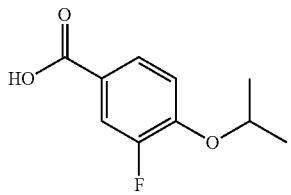

Step 1:

To methyl 3-fluoro-4-hydroxy-benzoate (2.00 g, 11.8 mmol) in DMF (12.5 mL) was added K₂CO₃ (6.50 g, 47.0 mmol) followed by 2-iodopropane (2.35 mL, 23.5 mmol). The mixture was heated at 60° C. for 1.5 h. The mixture was filtered using EtOAc and the filtrate was evaporated under reduced pressure. The residue was dissolved in EtOAc and was washed with water and brine. The organic layer was dried over sodium sulfate, filtered and concentrated under reduced pressure to give methyl 3-fluoro-4-isopropoxybenzoate. ESI-MS m/z calc 212.1, found 213.3 (M+1)⁺. Retention time: 1.70 minutes (3 min run).

Step 2:

Methyl 3-fluoro-4-isopropoxybenzoate (from step 1), 1,4-dioxane (31 mL), and NaOH (31 mL of 1.0 M, 31 mmol) were combined and the mixture was heated at 80° C. for 20 min. The solvent was evaporated under reduced pressure. The crude mixture was dissolved in water and was washed with EtOAc (3×). The combined organics were discarded. The aqueous layer was acidified and was extracted with EtOAc (3×). The organic layer was dried over sodium sulfate, filtered and the concentrated under reduced pressure to yield 3-fluoro-4-isopropoxy-benzoic acid (1.25 g, 72%) as a white solid. ESI-MS m/z calc 198.1, found 199.3 (M+1)⁺. Retention time: 1.34 minutes (3 min run).

The following compounds were synthesized using the procedures described above:

2-fluoro-4-isopropoxybenzoic acid and 4-isopropoxy-3-methylbenzoic acid, 3-cyano-4-isopropoxybenzoic acid and 4-isopropoxy-3-(trifluoromethyl)benzoic acid.

4-(tert-Butylsulfonyl)benzoic acid

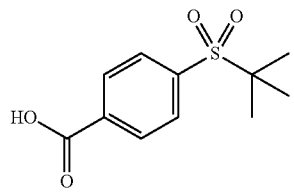 [SMILES: CC(C)(C)S(=O)(=O)c1ccc(C(=O)O)cc1]

Step 1:

Ethyl 4-fluorobenzoate (1.5 g, 8.9 mmol) and tert-butylsulfanylsodium (2.00 g, 17.8 mmol) were combined in DMF (10 mL). The reaction mixture was heated at 80° C. for 2 hours. A large amount of precipitate formed and an additional 15 mL of DMF was added and the reaction mixture was stirred for an additional 20 hours at 80° C. The reaction mixture was partitioned between ethyl acetate (100 mL) and water (100 mL). The organic layer was discarded, and the water layer was made acidic with 4M hydrochloric acid. The water layer was extracted two times with ethyl acetate. The combined extracts were dried over sodium sulfate, filtered, and evaporated to dryness to yield 4-(tert-butylthio)benzoic acid as a colorless oil. ESI-MS m/z calc. 210.3, found 211.1 (M+1)⁺. Retention time: 1.74 minutes (3 min run).

Step 2:

4-(tert-Butylthio)benzoic acid (from Step 1) was dissolved in AcOH (10 mL) and hydrogen peroxide (5.0 mL of 30% w/w, 52 mmol) was added to the reaction mixture. The resulting mixture was heated at 80° C. for 2 hours. The reaction mixture was then allowed to cool to room temperature, and was diluted with 50 mL of water and 100 mL of ethyl acetate. The layers were separated and the aqueous layer was extracted with ethyl acetate. The combined ethyl acetate extracts were dried over sodium sulfate, filtered, and evaporated to dryness to yield a white solid. The white solid was then dissolved in dichloromethane and was evaporated to dryness. The solid was then dried under vacuum for 16 hours to give 4-tert-butylsulfonylbenzoic acid (2.2 g, 92%) as a white solid. ESI-MS m/z calc. 242.1, found 243.1 (M+1)+. Retention time: 1.15 minutes (3 min run). $^1$H NMR (400 MHz, DMSO) δ 8.18 (d, J=8.0 Hz, 2H), 7.94 (d, J=7.6 Hz, 2H), 1.25 (s, 9H).

The following compound was synthesized using the procedures described above:

4-(ethylsulfonyl)benzoic acid.

4-(Isobutylsulfonyl)benzoic acid

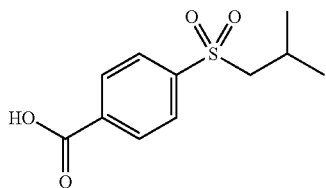 [SMILES: CC(C)CS(=O)(=O)c1ccc(C(=O)O)cc1]

Step 1:

$K_2CO_3$ (1.23 g, 8.92 mmol) was added to a mixture of methyl 4-sulfanylbenzoate (1.00 g, 5.95 mmol), 1-bromo-2-methyl-propane (970 μL, 8.92 mmol), and DMF (10 mL) at rt. The mixture was allowed to stir for 4 h at rt before the solids were filtered off. The solids were washed with ethyl acetate, and then were discarded. The combined filtrates were partitioned between ethyl acetate (100 mL) and water (100 mL). The layers were separated and the organic layer was washed with brine, dried over sodium sulfate, filtered and concentrated to give methyl 4-(isobutylthio)benzoate (82%) as a clear oil. ESI-MS m/z calc. 224.1, found 225.2 (M+1)+. Retention time: 1.59 minutes (3 min run).

Step 2:

m-CPBA (3.59 g, 15.6 mmol) was added to a solution of methyl 4-(isobutylsulfanyl)benzoate (1.00 g, 4.46 mmol) in $CH_2Cl_2$ (20 mL) at rt. The mixture was allowed to stir for 2 h before it was concentrated in vacuo. Column chromatography (0-100% ethyl acetate/hexanes) on the residue gave methyl 4-(isobutylsulfonyl)benzoate. ESI-MS m/z calc. 256.1, found 257.2 (M+1)+; Retention time: 1.96 minutes (3 min run). $^1$H NMR (400 MHz, $CDCl_3$) δ 8.23 (d, J=8.4 Hz, 2H), 8.00 (d, J=8.3 Hz, 2H), 3.98 (s, 3H), 3.02 (d, J=6.5 Hz, 2H), 2.25 (dp, J=13.3, 6.6 Hz, 1H), 1.07 (d, J=6.7 Hz, 6H).

Step 3:

A mixture of methyl 4-isobutylsulfonylbenzoate (1.00 g, 3.90 mmol), NaOH (10 mL of 1.0 M, 10 mmol), and 1,4-dioxane (10 mL) was heated at 80° C. for 1.5 h. The mixture was cooled to rt before it was concentrated in vacuo. The solid residue was taken up in water and was washed with ethyl acetate which was discarded. The aqueous layer was acidified with 1N HCl and was extracted with ethyl acetate (2×). The combined organics were washed with brine, dried over sodium sulfate, and were concentrated in vacuo. Column chromatography (0-100% ethyl acetate/hexanes) on the residue gave 4-(isobutylsulfonyl)benzoic acid (98%). ESI-MS m/z calc. 242.1, found 243.2 (M+1)+; Retention time: 1.73 minutes (3 min run). $^1$H NMR (400 MHz, $CDCl_3$) δ 8.30 (d, J=8.3 Hz, 2H), 8.05 (d, J=8.3 Hz, 2H), 3.03 (d, J=6.5 Hz, 2H), 2.27 (dt, J=13.3, 6.6 Hz, 1H), 1.08 (d, J=6.7 Hz, 6H).

3-(Hydroxymethyl)-4-isopropoxy-benzoic acid

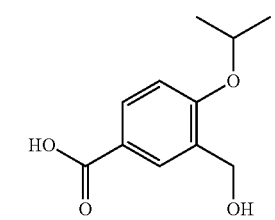

Step 1:

To methyl 3-formyl-4-hydroxy-benzoate (10.0 g, 55.5 mmol), potassium carbonate (30.7 g, 222 mmol) and DMF (63 mL) was added 2-iodopropane (11.1 mL, 111 mmol). The mixture was heated at 60° C. for 18 hours. The mixture was filtered using ethyl acetate (200 mL) and the solvent was evaporated under reduced pressure. The residue was dissolved in ethyl acetate (150 mL) and was washed with water (3×75 mL) and a saturated aqueous solution of sodium chloride (1×75 mL). The organic layer was dried over sodium sulfate, filtered and the solvent was evaporated under reduced pressure to yield methyl 3-formyl-4-isopropoxy-benzoate (98%) as a yellow viscous liquid. ESI-MS m/z calc. 222.2, found 223.3 (M+1)+; Retention time: 1.51 minutes (3 min run). $^1$H NMR (400 MHz, DMSO) δ 10.35 (s, 1H), 8.23 (d, J=2.3 Hz, 1H), 8.17 (dd, J=8.8, 2.3 Hz, 1H), 7.39 (d, J=8.9 Hz, 1H), 4.98-4.83 (m, 1H), 3.85 (s, 3H), 1.38 (d, J=6.0 Hz, 6H).

Step 2:

Methyl 3-formyl-4-isopropoxy-benzoate (180 mg, 0.81 mmol) was dissolved in tetrahydrofuran (4.8 mL) and $LiBH_4$ (35 mg, 1.6 mmol) was added. The reaction was stirred at room temperature for 30 minutes before it was quenched with methanol (3 mL). The reaction was neutralized by the addition of a saturated aqueous solution of sodium bicarbonate (3 mL) and was then extracted with ethyl acetate (3×10 mL). The combined organics were washed with a saturated aqueous solution of sodium chloride (1×10 mL), dried over sodium sulfate, filtered and the solvent was evaporated under reduced pressure to yield methyl 3-(hydroxymethyl)-4-isopropoxy-benzoate (99%) as a viscous liquid. ESI-MS m/z calc. 224.3, found 225.3 (M+1)+; Retention time: 1.26 minutes (3 min run). $^1$H NMR (400 MHz, DMSO) δ 8.09 (s, 1H), 7.89 (d, J=8.6 Hz, 1H), 7.13 (d, J=8.6 Hz, 1H), 5.25 (t, J=5.6 Hz, 1H), 4.86-4.68 (m, 1H), 4.54 (d, J=5.6 Hz, 2H), 3.87 (s, 3H), 1.35 (d, J=6.0 Hz, 6H).

Step 3:

To methyl 3-(hydroxymethyl)-4-isopropoxy-benzoate (180 mg, 0.80 mmol) and 1,4-dioxane (1.895 mL) was added sodium hydroxide (2.1 mL of 1.0 M, 2.1 mmol) and the mixture was heated at 80° C. for 50 minutes. The solvent was evaporated under reduced pressure. The crude mixture was dissolved in water (10 mL) and was washed with ethyl acetate (3×10 mL) which was discarded. The aqueous layer was acidified with hydrochloric acid. The aqueous layer was extracted with ethyl acetate (3×10 mL). The combined organics were dried over sodium sulfate, filtered and the solvent was evaporated under reduced pressure to yield 3-(hydroxymethyl)-4-isopropoxy-benzoic acid (89%) as a white solid. ESI-MS m/z calc. 210.2, found 211.3 (M+1)+; Retention time: 1.01 minutes (3 min run).

The following compounds were synthesized using the procedures described above:

4-ethoxy-3-(hydroxymethyl)benzoic acid, 4-(2-hydroxy-2-methylpropoxy)-3-methylbenzoic acid, 4-isopropoxy-3-methoxy-5-methylbenzoic acid, 5-isobutoxypicolinic acid, 5-(isopentyloxy)picolinic acid, 5-isopropoxy-4-methylpicolinic acid.

3-Methyl-4-(oxetan-3-yl)benzoic acid

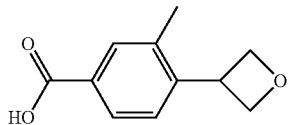

Step 1:
(4-Cyano-2-methyl-phenyl)boronic acid (1.75 g, 10.87 mmol), diiodonickel (102 mg, 0.326 mmol), (1S,2S)-2-aminocyclohexan-1-ol hydrochloride (50 mg, 0.33 mmol) and NaHMDS (2.01 g, 11.0 mmol) were combined in isopropanol (10 mL) under N2 in a pressure vial. A solution of 3-iodooxetane (1.00 g, 5.44 mmol) in isopropanol (1 mL) was added. The vial was immersed in a pre-heated 90° C. oil bath and stirred for 2 h, then cooled, diluted with ethanol (20 mL), filtered over Celite, concentrated, then absorbed onto Celite and purified by silica gel column chromatography (0-60% EtOAc/hexane) to give 3-methyl-4-(oxetan-3-yl)benzonitrile (616 mg, 3.556 mmol, 65.42%) as a white solid. ESI-MS m/z calc. 173.1, found 174.3 (M+1)+; Retention time: 1.09 minutes (3 min run).

Step 2:
To 3-methyl-4-(oxetan-3-yl)benzonitrile (500 mg, 2.89 mmol) in ethanol (7.5 mL) was added NaOH (3.0 mL of 5 M, 15 mmol) and the mixture immersed in a 85° C. oil bath. The mixture was heated and stirred for 1 h, concentrated, then diluted with ethyl acetate (20 mL). 6N HCl (~3 mL) was added to adjust pH to 6. The aqueous layer was extracted with ethyl acetate (2×20 mL), then the combined organics washed with brine (10 mL), dried over MgSO4 and concentrated to give a white solid, which was triturated with ether to give a mixture (2:3 by NMR) of acid 3-methyl-4-(oxetan-3-yl)benzoic acid (500 mg, 14%) and amide. ESI-MS m/z calc. 192.2, found 193.3 (M+1)+; Retention time: 0.87 minutes (3 min run).

5-Isopropoxy-6-methoxypicolinic acid

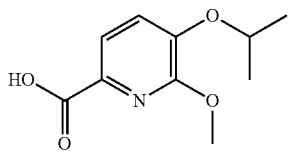

Step 1:
To a solution of 2-chloro-6-iodo-pyridin-3-ol (5.00 g, 19.57 mmol) in DMF was added finely ground potassium carbonate (5.409 g, 39.14 mmol) followed by 2-bromopropane (4.814 g, 3.675 mL, 39.14 mmol). The reaction mixture was allowed to stir at 70° C. overnight. The reaction mixture was concentrated under reduced pressure. The residue was dissolved/suspended in EtOAc (75 mL) and washed with water (1×75 mL). The aqueous layer was further extracted with EtOAc (1×75 mL). Both organic layers were combined, dried over sodium sulfate, filtered and concentrated under reduced pressure to obtain a yellow oil which was purified by silica gel column chromatography: 0-30% EtOAc/hexane gradient to provide 2-chloro-6-iodo-3-isopropoxy-pyridine (5.68 g, 97.%) as a clear colourless thin oil. ESI-MS m/z calc. 296.9, found 298.4 (M+1)+; Retention time: 1.74 minutes (3 min run). 1H NMR (400 MHz, CDCl3) δ 7.55 (d, J=8.3 Hz, 1H), 6.90 (d, J=8.3 Hz, 1H), 4.53 (dt, J=12.1, 6.1 Hz, 1H), 1.39 (d, J=6.1 Hz, 6H).

Step 2:
2-Chloro-6-iodo-3-isopropoxy-pyridine (2.00 g, 6.722 mmol) was dissolved in DMF (15 mL). Zn(CN)2 (592 mg, 5.04 mmol) was added, and the mixture was bubbled with nitrogen gas prior to the addition of Pd(PPh3)4 (600 mg, 0.519 mmol). The reaction system was sealed and heated under microwave irradiation at 100° C. for 30 minutes. The reaction mixture was diluted with EtOAc (75 mL) and washed with saturated aqueous sodium bicarbonate solution (75 mL) followed by brine (75 mL). The organic layer was dried over sodium sulfate, filtered and concentrated under reduced pressure to obtain a clear oil which was purified by silica gel column chromatography: 0-30% EtOAc/hexane gradient to provide 6-chloro-5-isopropoxy-pyridine-2-carbonitrile (1.17 g, 88%) as a clear colourless oil that crystallized upon standing. ESI-MS m/z calc. 196.0, found 197.3 (M+1)+; Retention time: 1.46 minutes (3 min run). 1H NMR (400 MHz, CDCl3) δ 7.61 (d, J=8.4 Hz, 1H), 7.21 (d, J=8.4 Hz, 1H), 4.67 (dt, J=12.1, 6.1 Hz, 1H), 1.45 (d, J=6.1 Hz, 6H).

Step 3:
6-Chloro-5-isopropoxy-pyridine-2-carbonitrile (1.10 g, 5.59 mmol) was dissolved in methanol (11 mL). To the solution was added a solution of HCl (11 mL of 4 M, 44.00 mmol) in 1,4-dioxane. The reaction mixture was allowed to stir at 70° C. overnight. The reaction mixture was cooled to room temperature and concentrated under reduced pressure. The remaining solids were suspended in EtOAc (75 mL) and washed with saturated aqueous sodium bicarbonate solution (1×75 mL). The organic layer was dried over sodium sulfate, filtered and concentrated under reduced pressure. It was purified by silica gel column chromatography: 0-50% EtOAc/hexane to provide methyl 6-chloro-5-isopropoxy-pyridine-2-carboxylate (894 mg, 69%) as a clear colourless oil that crystallized upon standing. ESI-MS m/z calc. 229.1, found 230.3 (M+1)+; Retention time: 1.23 minutes (3 min run). 1H NMR (400 MHz, CDCl3) δ 8.06 (d, J=8.4 Hz, 1H), 7.25 (d, J=8.5 Hz, 1H), 4.68 (dt, J=12.1, 6.1 Hz, 1H), 3.97 (s, 3H), 1.44 (d, J=6.1 Hz, 6H).

Step 4:
Methyl 6-chloro-5-isopropoxy-pyridine-2-carboxylate (330 mg, 1.44 mmol) was dissolved in dioxane (12 mL), and a solution of sodium methoxide (5.75 mL of 0.5 M, 2.87 mmol) in methanol was added. The reaction was heated under microwave irradiation at 140° C. for 1.5 hours. Water (52 µL, 2.9 mmol) was added, and the reaction mixture was heated by microwave irradiation at 100° C. for 30 minutes. The reaction mixture was diluted with 1 N HCl solution (50 mL) and extracted with EtOAc (2×50 mL). Organic layers were combined, dried over sodium sulfate, filtered and concentrated under reduced pressure to provide 5-isopropoxy-6-methoxy-pyridine-2-carboxylic acid (300 mg, 98%) as a beige solid. ESI-MS m/z calc. 211.1, found 211.9 (M+1)+; Retention time: 0.97 minutes (3 min run). 1H NMR (400 MHz, CDCl3)

δ 7.83 (d, J=8.1 Hz, 1H), 7.17 (d, J=8.1 Hz, 1H), 4.72-4.61 (m, 1H), 4.06 (s, 3H), 1.45 (t, J=7.4 Hz, 7H).

5-tert-Butoxypicolinic acid

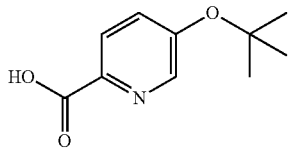

Step 1:

To NaOtBu (1.57 g, 16.4 mmol) in HMPA (6 mL) was added DMF (6 mL) (to facilitate stirring). 5-Fluoropyridine-2-carbonitrile (1.00 g, 8.19 mmol) was added and the dark mixture was stirred overnight. The mixture was diluted with water (100 mL), extracted with DCM (3×50 mL) and the organics were washed with water (50 mL) and sat. aq. NaHCO₃ (50 mL), dried over MgSO₄, evaporated and purified by column chromatography (0-50% EtOAc/hex) to give 5-tert-butoxypyridine-2-carbonitrile (0.90 g, 62%) as a yellow solid. ESI-MS m/z calc. 211.1, found 211.9 (M+1)+; Retention time: 0.97 minutes (3 min run). $^1$H NMR (400 MHz, CDCl₃) δ 8.38 (dd, J=2.7, 0.5 Hz, 1H), 7.67-7.56 (m, 1H), 7.41-7.31 (m, 1H), 1.52-1.38 (m, 10H).

Step 2:

To 5-tert-butoxypyridine-2-carbonitrile (751 mg, 4.26 mmol) in ethanol (10 mL) was added NaOH (4.262 mL of 5 M, 21.31 mmol) and the mixture immersed in a 85° C. heated bath. The mixture was heated and stirred for 1 h, concentrated, then diluted with ethyl acetate (50 mL). 10 mL brine and ~3 mL of 6N HCl (to adjust to pH 6) was added. The organic layer was separated, dried over MgSO₄ and concentrated to give 5-tert-butoxypyridine-2-carboxylic acid (820 mg, 98%) as a yellow solid. ESI-MS m/z calc. 195.1, found 196.1 (M+1)+; Retention time: 0.62 minutes (3 min run). $_1$H NMR (400 MHz, DMSO) δ 12.74 (s, 1H), 8.29 (d, J=32.6 Hz, 1H), 7.99 (s, 1H), 7.60 (d, J=6.5 Hz, 1H), 3.37 (s, 1H), 1.39 (s, 11H).

4-(N-Methyl-N-(thiazol-2-yl)sulfamoyl)benzoic acid

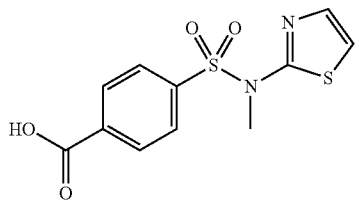 [SMILES: CN(c1nccs1)S(=O)(=O)c1ccc(C(=O)O)cc1]

Step 1:

To methyl 4-chlorosulfonylbenzoate (4 g, 17.05 mmol), N-methylthiazol-2-amine (1.95 g, 17.05 mmol), 1,2-dichloroethane (20 mL), and triethylamine (2.38 mL, 17.05 mmol) were added and the reaction was heated at 100° C. in a pressure vessel for 20.5 hours on a heat block. The solvent was evaporated under reduced pressure. The crude compound was dissolved in dichloromethane and filtered. The filtrate was purified by silica gel chromatography utilizing a gradient of 0-30% ethyl acetate in dichloromethane to yield methyl 4-[methyl(thiazol-2-yl)sulfamoyl]benzoate (4.22 g, 79.2%). 1H NMR (400 MHz, DMSO) δ 8.16 (d, J=8.5 Hz, 2H), 7.95 (d, J=8.5 Hz, 2H), 7.46 (d, J=3.6 Hz, 1H), 7.44 (d, J=3.6 Hz, 1H), 3.89 (s, 3H), 3.39 (s, 3H). ESI-MS m/z calc. 312.0, found 313.3 (M+1)+; Retention time: 1.52 minutes (3 min run).

Step 2:

To methyl 4-[methyl(thiazol-2-yl)sulfamoyl]benzoate (4.22 g, 13.5 mmol) and 1,4-dioxane (32 mL) was added aq. NaOH (62 mL of 2.5 M, 155 mmol) and the mixture was stirred at 50° C. for 1 hour. The reaction mixture was cooled to room temperature. Ethyl acetate (135 mL) was added before acidifying it to pH 1 with HCl (37%). The organic and aqueous layers were separated. The aqueous layer was extracted with ethyl acetate (1×50 mL). The organic layers were dried over sodium sulfate, filtered and the solvent was evaporated under reduced pressure to yield 4-[methyl(thiazol-2-yl)sulfamoyl]benzoic acid (3.63 g, 87%) as a white solid. ESI-MS m/z calc. 298.0, found 299.1 (M+1)+; Retention time: 1.31 minutes (3 minutes run). $^1$H NMR (400 MHz, DMSO) δ 13.56 (s, 1H), 8.14 (d, J=8.6 Hz, 2H), 7.92 (d, J=8.5 Hz, 2H), 7.46 (d, J=3.6 Hz, 1H), 7.44 (d, J=3.6 Hz, 1H), 3.39 (s, 3H).

4-(2-Fluoro-2-methylpropoxy)-3-methoxybenzoic acid

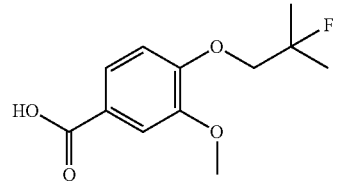 [SMILES: COc1cc(C(=O)O)ccc1OCC(C)(C)F]

Step 1:

To a solution of methyl 4-(2-hydroxy-2-methyl-propoxy)-3-methoxy-benzoate (509 mg, 2.00 mmol) in DCM (5 mL) at 0° C. was added 2-methoxy-N-(2-methoxyethyl)-N-(trifluoro-sulfanyl)ethanamine (406 µL, 2.20 mmol) dropwise. The mixture was stirred at 0° C. for 1 h before the cooling bath was removed and the mixture was stirred for 1 h at room temperature. The mixture was poured into water and was extracted with EtOAc (3×). The organics were combined, washed with water, brine, dried (Na₂SO₄) and evaporated to dryness. Purification of the residue by column chromatography (0-20% EtOAc in Hex) gave methyl 4-(2-fluoro-2-methyl-propoxy)-3-methoxy-benzoate (450 mg, 70%). ESI-MS m/z calc. 256.1, found 257.1 (M+1)+; Retention time: 1.57 minutes (3 min run).

Step 2:

To a solution of methyl 4-(2-fluoro-2-methyl-propoxy)-3-methoxy-benzoate (450 mg, 1.76 mmol) in MeOH (3.6 mL) and water (900 µL) was added NaOH (210 mg, 5.27 mmol) and the mixture was stirred at 40° C. for 1 hour. The MeOH was evaporated and the pH of the solution was adjusted to 3 with 1N HCl. The precipitate was filtered, washed with water, and desiccated to give 4-(2-fluoro-2-methylpropoxy)-3- methoxybenzoic acid. ESI-MS m/z calc. 242.2, found 243.7 (M+1)+; Retention time: 1.25 minutes (3 min run).

3-Methoxy-4-((2,2,2-trifluoroethoxy)methyl)benzoic acid

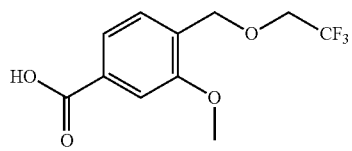 [SMILES: COc1cc(C(=O)O)ccc1COCC(F)(F)F]

To a solution of 2,2,2-trifluoroethanol (874 µL, 12.0 mmol) at 0° C. was added NaH (60%, 520 mg, 13.0 mmol) and the mixture was stirred at this temp for 10 min, then at room temperature for 10 min. The mixture was cooled to 0° C. before methyl 4-(bromomethyl)-3-methoxybenzoate (2.59 g, 10.0 mmol) was added. The cooling bath was removed and the mixture was stirred at room temperature for 3 hours. The mixture was poured into water and extracted with EtOAc (3×). The organics were combined, washed with water, brine, dried (MgSO$_4$) and evaporated to dryness. Crushed NaOH was added to the residue, followed by water (4 mL) and MeOH (20 mL). The mixture was stirred at room temperature for 1 hour. The MeOH was evaporated and the residue was taken up in 1N NaOH (30 ml) and the pH was adjusted to pH 2 with conc HCl. The precipitate was filtered, washed with water (2×) then hexanes (2×) and desiccated to give 3-methoxy-4-((2,2,2-trifluoroethoxy)methyl)benzoic acid. $^1$H NMR (400 MHz, CDCl$_3$) δ 7.79 (dd, J=7.8, 1.4 Hz, 1H), 7.61 (d, J=1.4 Hz, 1H), 7.53 (d, J=7.8 Hz, 1H), 4.80 (s, 2H), 4.00-3.91 (m, 5H).

The following compound was synthesized using the procedures described above:
methyl 3-methoxy-4-((3,3,3-trifluoropropoxy)methyl)benzoate.

4-(1-Hydroxy-2-methylpropan-2-yl)-3-methoxybenzoic acid

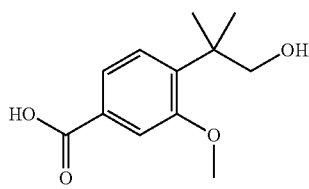 [SMILES: COc1cc(C(=O)O)ccc1C(C)(C)CO]

Step 1:
4-Bromo-3-methoxy-benzoic acid (1.50 g, 6.49 mmol), K$_2$CO$_3$ (2.69 g, 19.5 mmol), and DMF (10 mL) were combined and the mixture was allowed to stir for 10 minutes. Bromomethylbenzene (849 gL, 7.14 mmol) was added dropwise and the mixture was allowed to stir at room temperature for 1 h. The reaction mixture was quenched with brine and was extracted with EtOAc (3×). The organic layers were dried over sodium sulfate, filter and concentrated. The residue was purified using silica gel chromatography (5%-70% EtOAc in hexanes) to provide benzyl 4-bromo-3-methoxybenzoate (91%). ESI-MS m/z calc 320.0, found 321.0/323.0 (M+I)+. Retention time: 3.24 minutes (4 min run).

Step 2:
To a flask purged with nitrogen was added Pd(tBu$_3$P)$_2$ (26 mg, 0.050 mmol), ZnF$_2$ (52 mg, 0.50 mmol) and DMF (4 mL). The reaction mixture was allowed to stir for 10 minutes before benzyl 4-bromo-3-methoxy-benzoate (323 mg, 1.01 mmol) was added followed by trimethyl(2-methylprop-1-enoxy)silane (277 µL, 1.51 mmol). The reaction was heated at 80° C. overnight. The crude mixture was quenched with brine and extracted with EtOAc 3 times. The organic layer was dried over sodium sulfate and the solvent was evaporated to give benzyl 3-methoxy-4-(2-methyl-1-oxopropan-2-yl)benzoate. ESI-MS m/z calc. 312.4, found 313.4 (M+1)+; Retention time: 3.27 minutes (4 min run).

Step 3:
Benzyl 3-methoxy-4-(2-methyl-1-oxopropan-2-yl)benzoate (crude, from step 2) was then treated with MeOH (2 mL) followed by NaBH$_4$ (190 mg, 5.03 mmol). The reaction mixture was stirred for 1 h before it was quenched with brine and extracted with EtOAc. The organic layers were combined, dried over sodium sulfate, and evaporated to give benzyl 4-(1-hydroxy-2-methylpropan-2-yl)-3-methoxybenzoate.

Step 4:
To the crude benzyl 4-(1-hydroxy-2-methylpropan-2-yl)-3-methoxybenzoate (from step 3) was added THF (2 mL) followed by aqueous NaOH (1.7 mL of 3.0 M, 5.0 mmol). The reaction mixture was stirred for 3 h. The reaction mixture was acidified to pH 3 and was extracted with EtOAc 3 times. The organic layers were dried over sodium sulfate and the solvent was evaporated to give 4-(1-hydroxy-2-methylpropan-2-yl)-3-methoxybenzoic acid. ESI-MS m/z calc. 224.1, found 224.2 (M+1)+; Retention time: 2.46 minutes (4 min run).

3-Fluoro-4-(2-hydroxy-2-methylpropyl)benzoic acid

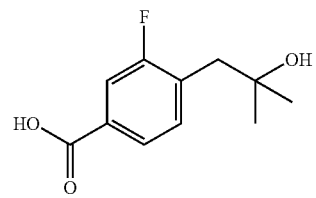

Step 1:
Diazomethyl-trimethyl-silane (11.6 mL of 2.0 M, 23.2 mmol) was added dropwise to a solution of 2-(4-bromo-2-fluoro-phenyl)acetic acid (4.50 g, 19.3 mmol) in toluene (7.7 mL) and MeOH (7.7 mL) under a nitrogen atmosphere at room temperature. A persistent yellow color remained after complete addition of diazomethane. The reaction was then quenched with a few drops of acetic acid and the solvents were removed under reduced pressure. The residue was purified by silica gel flash column chromatography using 0-10% EtOAc in hexanes to yield methyl 2-(4-bromo-2-fluoro-phenyl)acetate (4.32 g, 91%). $^1$H NMR (400 MHz, CDCl$_3$) δ 7.28-7.22 (m, 2H), 7.15 (t, J=8.0 Hz, 1H), 3.71 (s, 3H), 3.63 (d, J=1.0 Hz, 2H).

Step 2:
Methyl 2-(4-bromo-2-fluoro-phenyl)acetate (4.00 g, 16.2 mmol) in THF (56 mL) was cooled in an ice water bath under a nitrogen atmosphere upon which bromo-methyl-magnesium (16.2 mL of 3 M, 48.6 mmol) was added dropwise over 30 minutes. The reaction mixture was continued to stir for 2 hours under ice water bath cooling. The reaction mixture was then quenched with saturated aqueous ammonium chloride and diluted with EtOAc. The layers were separated, and the aqueous layer was extracted with EtOAc. The combined organics were dried over Na$_2$SO$_4$, filtered and concentrated under reduced pressure. The residue was purified by silica gel flash column chromatography using 0-15% EtOAc in hexanes to yield 1-(4-bromo-2-fluoro-phenyl)-2-methyl-propan-2-ol (3.0 g, 75%) as a clear colorless oil. ESI-MS m/z calc. 246.0, found 231.1 (M+1)+; Retention time: 1.53 minutes (3 min run). LC/MS observed m/z does not show parent mass, but the −17 fragment. $^1$H NMR (400 MHz, CDCl$_3$) δ 7.26-7.21 (m, 2H), 7.14 (t, J=8.1 Hz, 1H), 2.78 (d, J=1.4 Hz, 2H), 1.24 (d, J=0.8 Hz, 6H).

Step 3:

1-(4-Bromo-2-fluoro-phenyl)-2-methyl-propan-2-ol (2.35 g, 9.51 mmol), diacetoxypalladium (214 mg, 0.951 mmol), 3-diphenylphosphanylpropyl-diphenyl-phosphane (404 mg, 0.951 mmol), and Et$_3$N (4.24 mL, 30.4 mmol) in DMF (26 mL) were treated with MeOH (20.0 mL, 495 mmol). The vessel was charged to 50 psi with CO (266 mg, 9.51 mmol) and then vented. This operation was repeated twice. The reaction was charged to 50 psi and heated at 80° C. for 15 h. The reaction mixture was allowed to cool, vented and partitioned between EtOAc/brine. The layers were separated and the aqueous layer was extracted with EtOAc. The combined organics were washed twice with brine, dried over Na$_2$SO$_4$, filtered and concentrated to an orange oil. The residue was purified by silica gel flash column chromatography using 0-30% EtOAc in hexanes to yield methyl 3-fluoro-4-(2-hydroxy-2-methyl-propyl)benzoate (1.83 g, 85%) ESI-MS m/z calc. 226.1, found 227.5 (M+1)+; Retention time: 1.29 minutes (3 min run). $^1$H NMR (400 MHz, CDCl$_3$) δ 7.78 (dd, J=7.9, 1.7 Hz, 1H), 7.71 (dd, J=10.3, 1.6 Hz, 1H), 7.34 (t, J=7.6 Hz, 1H), 3.92 (s, 3H), 2.88 (d, J=1.3 Hz, 2H), 1.26 (s, 6H).

Step 4:

Methyl 3-fluoro-4-(2-hydroxy-2-methyl-propyl)benzoate (1.59 g, 7.03 mmol) was dissolved in THF (40 mL), water (200 mL) and MeOH (21 mL) before LiOH (1.01 g, 42.2 mmol) was added. The reaction mixture was heated at 55° C. for 30 minutes. The reaction mixture was cooled to room temperature and the solvents were removed under reduced pressure. The residue was dissolved in water and cooled in an ice water bath and treated with HCl 1M to pH 3. The resulting precipitate was collected by vacuum filtration, washed with water and dried under high vacuum to yield 3-fluoro-4-(2-hydroxy-2-methyl-propyl)benzoic acid (999 mg, 67%) as a white solid. ESI-MS m/z calc. 212.1, found 211.1 (M+1)+; Retention time: 0.98 minutes (3 min run, scanned using negative ionization mode). $^1$H NMR (400 MHz, CDCl$_3$) δ 7.84 (dd, J=7.9, 1.6 Hz, 1H), 7.77 (dd, J=10.1, 1.6 Hz, 1H), 7.39 (d, J=15.1 Hz, 1H), 2.91 (s, 2H), 1.28 (s, 6H).

3-Fluoro-4-(3-methoxyprop-1-ynyl)benzoic acid

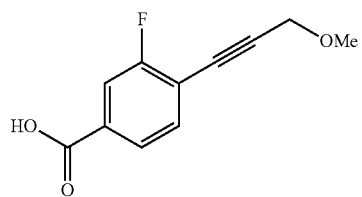 [SMILES: COCC#Cc1ccc(C(=O)O)cc1F]

Step 1:

To methyl 4-bromo-3-fluoro-benzoate (2.50 g, 10.7 mmol), copper (I) iodide (204 mg, 1.07 mmol) and Pd(PPh$_3$)$_2$Cl$_2$ (753 mg, 1.07 mmol) in a flask under Argon was added DMF (degassed for 30 min) and reaction cooled to 0 C. Et$_3$N (1.95 mL, 14.0 mmol) was added followed by 3-methoxyprop-1-yne (997 μL, 11.8 mmol) and the mixture was allowed to stir at 60° C. for 70 min. The mixture was cooled, diluted with ethyl acetate and filtered. The filtrate was washed sequentially with 1 M HCl, 10% NH$_4$OH and brine solutions. The organic layer was separated, dried and purified with silica gel using ethyl acetate-hexanes to give methyl 3-fluoro-4-(3-methoxyprop-1-ynyl)benzoate. ESI-MS m/z calc. 222.2, found 223.2 (M+1)+; Retention time: 1.53 minutes (3 min run). $^1$H NMR (400 MHz, CDCl$_3$) δ 7.75 (ddd, J=11.2, 8.8, 1.5 Hz, 2H), 7.50 (dd, J=7.9, 7.0 Hz, 1H), 4.37 (s, 2H), 3.92 (s, 3H), 3.47 (s, 3H).

Step 2:

To methyl 3-fluoro-4-(3-methoxyprop-1-ynyl)benzoate (1.40 g, 6.30 mmol) in 15 ml of 2:1 THF:MeOH at room temperature was added NaOH (1.89 mL of 4 M, 7.56 mmol). The mixture was stirred at room temperature for 1 h before the volatile solvents were removed. The remainder was extracted with ether. The aqueous layer was acidified with 1M HCl and was extracted with ether (3×). The combined ether extracts were dried and concentrated to give 3-fluoro-4-(3-methoxyprop-1-ynyl)benzoic acid as a white solid. ESI-MS m/z calc. 208.2, found 209.2 (M+1)+; Retention time: 1.22 minutes (3 min run). $^1$H NMR (400 MHz, CDCl$_3$) δ 7.85 (dd, J=8.0, 1.4 Hz, 1H), 7.80 (dd, J=9.5, 1.3 Hz, 1H), 7.59-7.49 (m, 1H), 4.39 (s, 2H), 3.48 (s, 3H).

4-(Bis(2,2,2-trifluoroethoxy)methyl)-3-chlorobenzoic acid

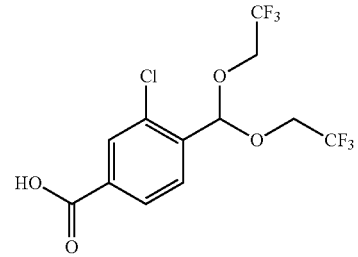 [SMILES: O=C(O)c1ccc(C(OCC(F)(F)F)OCC(F)(F)F)c(Cl)c1]

To a solution of methyl 3-chloro-4-methyl-benzoate (2.00 g, 10.8 mmol) and NBS (2.05 g, 11.5 mmol) in CCl$_4$ (9 mL) at reflux was added AIBN (178 mg, 1.08 mmol). The mixture was heated at reflux for 16 h before additional AIBN (178 mg, 1.08 mmol) was added. The mixture was heated at reflux for 72 h before it was cooled. The mixture was concentrated to dryness, the residue was partitioned between Et$_2$O and water, the layers were separated, and the aqueous layer was extracted with Et$_2$O (2×). The organics were combined, washed with water, brine, dried (MgSO$_4$) and concentrated to dryness. Purification of the residue by column chromatography (0-30% EtOAc in Hex) gave methyl 3-chloro-4-(dibromomethyl)benzoate. ESI-MS m/z calc. 342.5, found 342.9 (M+1)+; Retention time: 1.96 minutes (3 min run).

Step 2:

To a solution of 2,2,2-trifluoroethanol (109 μL, 1.50 mmol) in DMF (2.63 mL) was added NaH (64 mg, 1.6 mmol). The mixture was stirred at room temperature for 1 h before methyl 3-chloro-4-(dibromomethyl)benzoate (342 mg, 1.00 mol) was added. The mixture was stirred at room temperature for 2 h before it was poured into water and was extracted with EtOAc (3×). The organics were combined, washed with water, brine, dried (Na₂SO₄) and evaporated to dryness. The material was taken up in MeOH and powdered NaOH (160 mg, 4.00 mol) was added and the mixture was stirred at room temperature for 1 h. The mixture was evaporated and treated with 1N HCl (until the solution was strongly acidic). The precipitated product was washed with water and dried to give 4-(bis(2,2,2-trifluoroethoxy)methyl)-3-chlorobenzoic acid. ESI-MS m/z calc. 394.4, found 394.5 (M+1)+; Retention time: 1.74 minutes (3 min run).

4-(1-Hydroxy-2-(2,2,2-trifluoroethoxy)ethyl)benzoic acid and 4-(2-hydroxy-1-(2,2,2-trifluoroethoxy)ethyl)benzoic acid

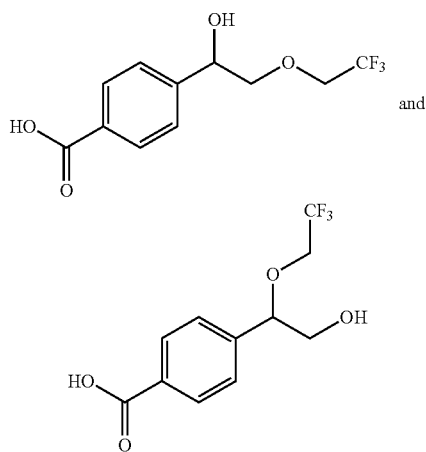

Step 1:
To a solution of methyl 4-acetylbenzoate (8.91 g, 50.0 mmol) in AcOH (80 mL) was added Br₂ (2.71 mL, 52.5 mmol) dropwise. The mixture was stirred at room temperature for 2 h. The mixture was cooled to 0° C. and the solid was filtered. The precipitate was washed with 1:1 MeOH in water and was desiccated to give methyl 4-(2-bromoacetyl)benzoate (10.6 g, 82%) as a tan solid. ¹H NMR (400 MHz, CDCl₃) δ 8.19-8.12 (m, 2H), 8.04 (d, J=8.5 Hz, 2H), 4.47 (s, 2H), 3.96 (s, 3H).

Step 2:
To a stirred solution of methyl 4-(2-bromoacetyl)benzoate (0.59 g, 2.3 mmol) in MeOH (6 mL) at 0° C. was added NaBH₄ (92 mg, 2.4 mmol) in portions. The cooling bath was removed and the mixture was stirred at room temperature for 1 h. K₂CO₃ (317 mg, 2.30 mmol) was added and the mixture was stirred at room temperature for 72 h. The mixture was poured into water and was extracted with Et₂O (3×). The organics were combined, washed with water, brine, dried (MgSO₄) and evaporated to dryness to give methyl 4-(oxiran-2-yl)benzoate (370 mg, 90%) as a white solid. ESI-MS m/z calc. 178.2, found 179.1 (M+1)+; Retention time: 1.14 minutes (3 min run).

Step 3:
To 2,2,2-trifluoroethanol (0.50 mL, 6.9 mmol) was added NaH (10 mg, 0.24 mmol). The mixture was stirred for 5 min before the addition of methyl 4-(oxiran-2-yl)benzoate (36 mg, 0.20 mmol) and heating at 70° C. for 2 h. Crushed NaOH (40 mg, 1.0 mmol) was added followed by water (0.1 mL) and the mixture was stirred at 40° C. for 3 h. The mixture was evaporated and the residue was partitioned between 1N HCl and EtOAc. The layers were separated, and aqueous layer was extracted with EtOAc (2×). The organics were combined and evaporated to dryness to give a mixture of 4-[1-hydroxy-2-(2,2,2-trifluoroethoxy)ethyl]benzoic acid and 4-(2-hydroxy-1-(2,2,2-trifluoroethoxy)ethyl)benzoic acid (30 mg, 57%) as an oil. ESI-MS m/z calc. 264.1, found 265.1 (M+1)+; Retention time: 1.07 minutes (3 min run).

(4-Isopropoxy-3-methoxyphenyl)(2'-methyl-6'-(trifluoromethyl)-3',4'-dihydro-2'H-spiro[piperidine-4,1'-pyrrolo[1,2-a]pyrazine]-1-yl)methanone

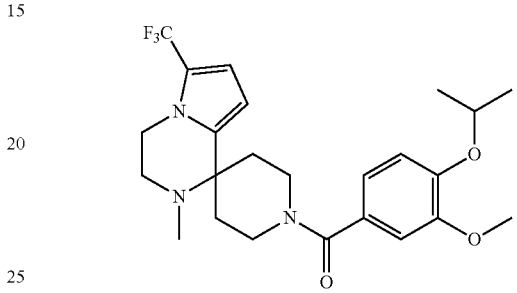

A mixture of 2'-methyl-6'-(trifluoromethyl)-3',4'-dihydro-2'H-spiro[piperidine-4,1'-pyrrolo[1,2-a]pyrazine]dihydrochloride (69 mg, 0.20 mmol), 4-isopropoxy-3-methoxybenzoic acid (42 mg, 0.20 mmol), HATU (76 mg, 0.20 mmol), Et₃N (112 µL, 0.80 mmol) and DMF (2 mL) was allowed to stir at room temperature for 3 h. The mixture was filtered and purified by reverse-phase preparatory HPLC (10-99% ACN/water). The desired fractions were concentrated to give (4-isopropoxy-3-methoxyphenyl)(2'-methyl-6'-(trifluoromethyl)-3',4'-dihydro-2'H-spiro[piperidine-4,1'-pyrrolo[1,2-a]pyrazine]-1-yl)methanone as an amorphous white solid. ESI-MS m/z calc. 465.2, found 466.3 (M+1)+; Retention time: 1.23 minutes (3 min run). ¹H NMR (400 MHz, CDCl₃) δ 7.01 (d, J=1.7 Hz, 1H), 6.97 (dd, J=8.2, 1.7 Hz, 1H), 6.88 (d, J=8.3 Hz, 1H), 6.53 (d, J=3.0 Hz, 1H), 5.94 (d, J=3.5 Hz, 1H), 4.57 (dt, J=12.2, 6.1 Hz, 1H), 4.52 (s, 1H), 3.99 (s, 2H), 3.87 (s, 3H), 3.69 (s, 1H), 3.40 (s, 1H), 3.34 (t, J=5.4 Hz, 3H), 2.39 (s, 3H), 2.11 (s, 2H), 1.82 (s, 2H), 1.38 (d, J=6.1 Hz, 6H).

(4-Isopropoxy-3-methoxyphenyl)(6'-(trifluoromethyl)-3',4'-dihydro-2'H-spiro[piperidine-4,1'-pyrrolo[1,2-a]pyrazine]-1-yl)methanone

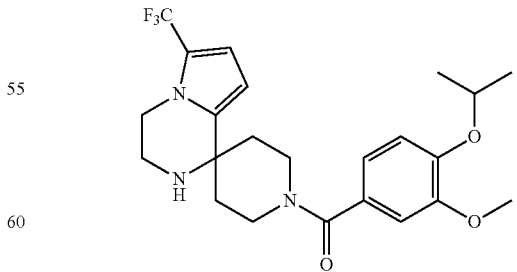

To a stirred solution of 6-(trifluoromethyl)spiro[3,4-dihydro-2H-pyrrolo[1,2-a]pyrazine-1,4'-piperidine]dihydrochloride (475 mg, 1.43 mmol), 4-isopropoxy-3-methoxy-benzoic acid (361 mg, 1.72 mmol) and 1-hydroxybenzotriazole (232 mg, 1.72 mmol) in CH$_2$Cl$_2$ (5.5 mL) at ambient temperature was added 3-(ethyliminomethyleneamino)-N,N-dimethylpropan-1-amine (266 mg, 1.72 mmol) followed by 4-methylmorpholine (786 µL, 7.15 mmol). The mixture was stirred for 16 h at room temperature. The mixture was poured into water and was extracted with EtOAc (3×). The organics were combined, washed with 0.1 N HCl, 1N NaOH, water, brine, dried (Na$_2$SO$_4$) and evaporated to dryness. The residue was purified by column chromatography (0-100% ethyl acetate/hexanes) to give (4-isopropoxy-3-methoxy-phenyl)-[6-(trifluoromethyl)spiro[3,4-dihydro-2H-pyrrolo[1,2-a]pyrazine-1,4'-piperidine]-1'-yl]methanone (623 mg, 96%). ESI-MS m/z calc. 451.2, found 452.3 (M+1)+; Retention time: 1.30 minutes (3 min run). $^1$H NMR (400 MHz, CDCl$_3$) δ 7.03 (d, J=1.9 Hz, 1H), 6.98 (dd, J=8.2, 1.9 Hz, 1H), 6.88 (d, J=8.3 Hz, 1H), 6.54 (d, J=3.7 Hz, 1H), 5.93 (d, J=3.8 Hz, 1H), 4.56 (dd, J=12.2, 6.1 Hz, 1H), 4.52 (s, 1H), 3.94 (s, 2H), 3.88 (s, 3H), 3.69 (s, 1H), 3.47 (s, 2H), 3.27 (s, 2H), 1.87 (s, 4H), 1.38 (d, J=6.1 Hz, 6H).

The following compounds were made using the procedures described above:

| Compound name | Amine name | Acid name |
|---|---|---|
| [(5aR,9aR)-spiro[5a,6,7,8,9,9a-hexahydro-5H-pyrrolo[1,2-a]quinoxaline-4,4'-piperidine]-1'-yl]-(4-tert-butyl-3-methoxy-phenyl)methanone | (5aR,9aR)-spiro[5a,6,7,8,9,9a-hexahydro-5H-pyrrolo[1,2-a]quinoxaline-4,4'-piperidine] | 4-tert-butyl-3-methoxy-benzoic acid |
| [(5aS,9aS)-spiro[5a,6,7,8,9,9a-hexahydro-5H-pyrrolo[1,2-a]quinoxaline-4,4'-piperidine]-1'-yl]-(4-tert-butyl-3-methoxy-phenyl)methanone | (5aS,9aS)-spiro[5a,6,7,8,9,9a-hexahydro-5H-pyrrolo[1,2-a]quinoxaline-4,4'-piperidine] | 4-tert-butyl-3-methoxy-benzoic acid |
| (4-isopropoxy-3-methyl-phenyl)-[2-(2-methoxyethyl)spiro[3,4-dihydropyrrolo[1,2-a]pyrazine-1,4'-piperidine]-1'-yl]methanone | 2-(2-methoxyethyl)spiro[3,4-dihydropyrrolo[1,2-a]pyrazine-1,4'-piperidine] | 4-isopropoxy-3-methyl-benzoic acid |
| (2-benzylspiro[3,4-dihydropyrrolo[1,2-a]pyrazine-1,4'-piperidine]-1'-yl)-(4-isopropoxy-3-methyl-phenyl)methanone | 2-benzylspiro[3,4-dihydropyrrolo[1,2-a]pyrazine-1,4'-piperidine] | 4-isopropoxy-3-methyl-benzoic acid |
| (4-ethyl-3-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-ethyl-3-methoxy-benzoic acid |
| [3-(hydroxymethyl)-4-isopropoxy-phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-(hydroxymethyl)-4-isopropoxy-benzoic acid |
| [2-methyl-6-(trifluoromethyl)spiro[3,4-dihydropyrrolo[1,2-a]pyrazine-1,4'-piperidine]-1'-yl]-[2-(trifluoromethoxy)phenyl]methanone | 2-methyl-6-(trifluoromethyl)spiro[3,4-dihydropyrrolo[1,2-a]pyrazine-1,4'-piperidine] | 2-(trifluoromethoxy)benzoic acid |
| (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-isopropoxy-3-methoxy-benzoic acid |
| [4-(1-hydroxy-1-methyl-ethyl)phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-(1-hydroxy-1-methyl-ethyl)benzoic acid |
| (4-ethyl-3-methoxy-phenyl)-[2-(2-methoxyethyl)-6-(trifluoromethyl)spiro[3,4-dihydropyrrolo[1,2-a]pyrazine-1,4'-piperidine]-1'-yl]methanone | 2-(2-methoxyethyl)-6-(trifluoromethyl)spiro[3,4-dihydropyrrolo[1,2-a]pyrazine-1,4'-piperidine] | 4-ethyl-3-methoxy-benzoic acid |
| [3-(hydroxymethyl)-4-isopropoxy-phenyl]-[2-(2-methoxyethyl)-6-(trifluoromethyl)spiro[3,4-dihydropyrrolo[1,2-a]pyrazine-1,4'-piperidine]-1'-yl]methanone | 2-(2-methoxyethyl)-6-(trifluoromethyl)spiro[3,4-dihydropyrrolo[1,2-a]pyrazine-1,4'-piperidine] | 3-(hydroxymethyl)-4-isopropoxy-benzoic acid |
| [2-(2-methoxyethyl)-6-(trifluoromethyl)spiro[3,4-dihydropyrrolo[1,2-a]pyrazine-1,4'-piperidine]-1'-yl]-[2-(trifluoromethoxy)phenyl]methanone | 2-(2-methoxyethyl)-6-(trifluoromethyl)spiro[3,4-dihydropyrrolo[1,2-a]pyrazine-1,4'-piperidine] | 2-(trifluoromethoxy)benzoic acid |
| (4-isopropoxy-3-methoxy-phenyl)-[2-(2-methoxyethyl)-6-(trifluoromethyl)spiro[3,4-dihydropyrrolo[1,2-a]pyrazine-1,4'-piperidine]-1'-yl]methanone | 2-(2-methoxyethyl)-6-(trifluoromethyl)spiro[3,4-dihydropyrrolo[1,2-a]pyrazine-1,4'-piperidine] | 4-isopropoxy-3-methoxy-benzoic acid |
| [4-(1-hydroxy-1-methyl-ethyl)phenyl]-[2-(2-methoxyethyl)-6-(trifluoromethyl)spiro[3,4-dihydropyrrolo[1,2- | 2-(2-methoxyethyl)-6-(trifluoromethyl)spiro[3,4-dihydropyrrolo[1,2- | 4-(1-hydroxy-1-methyl-ethyl)benzoic acid |

| Compound name | Amine name | Acid name |
|---|---|---|
| dihydropyrrolo[1,2-a]pyrazine-1,4'-piperidine]-1'-yl]methanone | a]pyrazine-1,4'-piperidine] | |
| (4-isopropoxy-3-methoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-isopropoxy-3-methoxy-benzoic acid |
| [3-(hydroxymethyl)-4-isopropoxy-phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-(hydroxymethyl)-4-isopropoxy-benzoic acid |
| [2-ethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 2-ethyl-6-(trifluoromethyl)spiro[3,4-dihydropyrrolo[1,2-a]pyrazine-1,4'-piperidine] | 4-isopropoxy-3-methoxy-benzoic acid |
| (3-methyl-4-methylsulfonyl-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-methyl-4-methylsulfonyl-benzoic acid |
| N-methyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(methylsulfamoyl)benzoic acid |
| (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-isopropoxy-3-methyl-benzoic acid |
| (4-tert-butoxy-3-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-tert-butoxy-3-methoxy-benzoic acid |
| (4-tert-butoxy-3-methoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-tert-butoxy-3-methoxy-benzoic acid |
| 1'-(4-isopropoxy-3-methyl-benzoyl)-2-methyl-spiro[3,4-dihydropyrrolo[1,2-a]pyrazine-1,4'-piperidine]-6-carbonitrile | 2-methylspiro[3,4-dihydropyrrolo[1,2-a]pyrazine-1,4'-piperidine]-6-carbonitrile | 4-isopropoxy-3-methyl-benzoic acid |
| (4-tert-butylsulfonylphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-tert-butylsulfonylbenzoic acid |
| N-cyclopropyl-4-[6-(trifluoromethyl)spiro[3,4-dihydro-2H-pyrrolo[1,2-a]pyrazine-1,4'-piperidine]-1'-carbonyl]benzenesulfonamide | 6-(trifluoromethyl)spiro[3,4-dihydro-2H-pyrrolo[1,2-a]pyrazine-1,4'-piperidine] | 4-(cyclopropylsulfamoyl)-benzoic acid |
| (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-isopropoxy-3-methyl-benzoic acid |
| N-cyclopropyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(cyclopropylsulfamoyl)-benzoic acid |
| N,2-dimethyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 3-methyl-4-(methylsulfamoyl)benzoic acid |
| (3-ethoxy-4-methoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-ethoxy-4-methoxy-benzoic acid |
| (4-isopropoxyphenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-isopropoxybenzoic acid |
| 8-quinolyl-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | quinoline-8-carboxylic acid |

-continued

| Compound name | Amine name | Acid name |
|---|---|---|
| (3-butoxy-4-methoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-butoxy-4-methoxy-benzoic acid |
| (4-butoxy-3-methoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-butoxy-3-methoxy-benzoic acid |
| (4-methoxyphenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-methoxybenzoic acid |
| 4-quinolyl-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | quinoline-4-carboxylic acid |
| (3,4-dimethoxyphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3,4-dimethoxybenzoic acid |
| (3-ethoxy-4-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-ethoxy-4-methoxy-benzoic acid |
| (3-methoxy-4-propoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-methoxy-4-propoxy-benzoic acid |
| (3-methoxyphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-methoxybenzoic acid |
| (4-isopropoxyphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-isopropoxybenzoic acid |
| [2-methyl-6-(trifluoromethyl)spiro[3,4-dihydropyrrolo[1,2-a]pyrazine-1,4'-piperidine]-1'-yl]-(8-quinolyl)methanone | 2-methyl-6-(trifluoromethyl)spiro[3,4-dihydropyrrolo[1,2-a]pyrazine-1,4'-piperidine] | quinoline-8-carboxylic acid |
| (3-butoxy-4-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-butoxy-4-methoxy-benzoic acid |
| [4-(1-hydroxy-1-methyl-ethyl)-3-methoxy-phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-(1-hydroxy-1-methyl-ethyl)-3-methoxy-benzoic acid |
| [4-(1-hydroxy-1-methyl-ethyl)-3-methyl-phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-butoxy-3-methoxy-benzoic acid |
| [2-methyl-6-(trifluoromethyl)spiro[3,4-dihydropyrrolo[1,2-a]pyrazine-1,4'-piperidine]-1'-yl]-(m-tolyl)methanone | 2-methyl-6-(trifluoromethyl)spiro[3,4-dihydropyrrolo[1,2-a]pyrazine-1,4'-piperidine] | 3-methylbenzoic acid |
| [2-methyl-6-(trifluoromethyl)spiro[3,4-dihydropyrrolo[1,2-a]pyrazine-1,4'-piperidine]-1'-yl]-[2-(1-piperidyl)-4-pyridyl]methanone | 2-methyl-6-(trifluoromethyl)spiro[3,4-dihydropyrrolo[1,2-a]pyrazine-1,4'-piperidine] | 2-(1-piperidyl)pyridine-4-carboxylic acid |
| (3-chlorophenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-chlorobenzoic acid |
| (2-methoxyphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 2-methoxybenzoic acid |

| Compound name | Amine name | Acid name |
|---|---|---|
| [4-(2-hydroxyethoxy)-3-methoxy-phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-(2-hydroxyethoxy)-3-methoxy-benzoic acid |
| (4-methoxyphenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-methoxybenzoic acid |
| (4-fluoro-3-methyl-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-fluoro-3-methyl-benzoic acid |
| [2-methyl-6-(trifluoromethyl)spiro[3,4-dihydropyrrolo[1,2-a]pyrazine-1,4'-piperidine]-1'-yl]-(4-quinolyl)methanone | 2-methyl-6-(trifluoromethyl)spiro[3,4-dihydropyrrolo[1,2-a]pyrazine-1,4'-piperidine] | quinoline-4-carboxylic acid |
| [4-(1-hydroxy-1-methyl-ethyl)-3-methoxy-phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-(1-hydroxy-1-methyl-ethyl)-3-methoxy-benzoic acid |
| (3-methoxy-4-propoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-methoxy-4-propoxy-benzoic acid |
| [4-(1-hydroxy-1-methyl-ethyl)-3-methyl-phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-(1-hydroxy-1-methyl-ethyl)-3-methyl-benzoic acid |
| N-ethyl-2-methyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(ethylsulfamoyl)-3-methyl-benzoic acid |
| N-cyclopropyl-2-methyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(cyclopropylsulfamoyl)-3-methyl-benzoic acid |
| N-isopropyl-2-methyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(isopropylsulfamoyl)-3-methyl-benzoic acid |
| N,N,2-trimethyl-4-[2-methyl-6-(trifluoromethyl)spiro[3,4-dihydropyrrolo[1,2-a]pyrazine-1,4'-piperidine]-1'-carbonyl]benzenesulfonamide | 2-methyl-6-(trifluoromethyl)spiro[3,4-dihydropyrrolo[1,2-a]pyrazine-1,4'-piperidine] | 4-(dimethylsulfamoyl)-3-methyl-benzoic acid |
| N,2-dimethyl-4-[6-(trifluoromethyl)spiro[3,4-dihydro-2H-pyrrolo[1,2-a]pyrazine-1,4'-piperidine]-1'-carbonyl]benzenesulfonamide | 6-(trifluoromethyl)spiro[3,4-dihydro-2H-pyrrolo[1,2-a]pyrazine-1,4'-piperidine] | 3-methyl-4-(methylsulfamoyl)benzoic acid |
| (2-phenoxyphenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 2-phenoxybenzoic acid |
| (4-phenoxyphenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-phenoxybenzoic acid |
| (2-phenylphenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 2-phenylbenzoic acid |
| [2-methyl-6-(trifluoromethyl)spiro[3,4-dihydropyrrolo[1,2-a]pyrazine-1,4'-piperidine]-1'-yl]-(2-phenoxyphenyl)methanone | 2-methyl-6-(trifluoromethyl)spiro[3,4-dihydropyrrolo[1,2-a]pyrazine-1,4'-piperidine] | 2-phenoxybenzoic acid |
| (4-chlorophenyl)-[2-methyl-6-(trifluoromethyl)spiro[3,4-dihydropyrrolo[1,2-a]pyrazine-1,4'- | 2-methyl-6-(trifluoromethyl)spiro[3,4-dihydropyrrolo[1,2- | 4-chlorobenzoic acid |

| Compound name | Amine name | Acid name |
| --- | --- | --- |
| piperidine]-1'-yl]methanone [2-methyl-6-(trifluoromethyl)spiro[3,4-dihydropyrrolo[1,2-a]pyrazine-1,4'-piperidine]-1'-yl]-(4-phenoxyphenyl)methanone | a]pyrazine-1,4'-piperidine] 2-methyl-6-(trifluoromethyl)spiro[3,4-dihydropyrrolo[1,2-a]pyrazine-1,4'-piperidine] | 4-phenoxybenzoic acid |
| [2-methyl-6-(trifluoromethyl)spiro[3,4-dihydropyrrolo[1,2-a]pyrazine-1,4'-piperidine]-1'-yl]-(4-phenylphenyl)methanone | 2-methyl-6-(trifluoromethyl)spiro[3,4-dihydropyrrolo[1,2-a]pyrazine-1,4'-piperidine] | 4-phenylbenzoic acid |
| [2-methyl-6-(trifluoromethyl)spiro[3,4-dihydropyrrolo[1,2-a]pyrazine-1,4'-piperidine]-1'-yl]-(2-phenylphenyl)methanone | 2-methyl-6-(trifluoromethyl)spiro[3,4-dihydropyrrolo[1,2-a]pyrazine-1,4'-piperidine] | 2-phenylbenzoic acid |
| [2-methyl-6-(trifluoromethyl)spiro[3,4-dihydropyrrolo[1,2-a]pyrazine-1,4'-piperidine]-1'-yl]-(p-tolyl)methanone | 2-methyl-6-(trifluoromethyl)spiro[3,4-dihydropyrrolo[1,2-a]pyrazine-1,4'-piperidine] | 4-methylbenzoic acid |
| N,N,2-trimethyl-4-[6-(trifluoromethyl)spiro[3,4-dihydro-2H-pyrrolo[1,2-a]pyrazine-1,4'-piperidine]-1'-carbonyl]benzenesulfonamide | 6-(trifluoromethyl)spiro[3,4-dihydro-2H-pyrrolo[1,2-a]pyrazine-1,4'-piperidine] | 4-(dimethylsulfamoyl)-3-methyl-benzoic acid |
| (2'-(cyclopropylmethyl)-6'-(trifluoromethyl)-3',4'-dihydro-2'H-spiro[piperidine-4,1'-pyrrolo[1,2-a]pyrazine]-1-yl)(4-isopropoxy-3-methoxyphenyl)methanone | 2'-(cyclopropylmethyl)-6'-(trifluoromethyl)-3',4'-dihydro-2'H-spiro[piperidine-4,1'-pyrrolo[1,2-a]pyrazine] | 4-isopropoxy-3-methoxy-benzoic acid |
| (2-fluoro-4-isopropoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 2-fluoro-4-isopropoxy-benzoic acid |
| (3-fluoro-4-isopropoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-fluoro-4-isopropoxy-benzoic acid |
| (3-chloro-4-isopropoxy-phenyl)-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-chloro-4-isopropoxy-benzoic acid |
| (2-fluoro-4-isopropoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 2-fluoro-4-isopropoxy-benzoic acid |
| (3-fluoro-4-isopropoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-fluoro-4-isopropoxy-benzoic acid |
| (3-chloro-4-isopropoxy-phenyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-chloro-4-isopropoxy-benzoic acid |
| [3,3-dimethyl-6-(trifluoromethyl)spiro[2,4-dihydropyrrolo[1,2-a]pyrazine-1,4'-piperidine]-1'-yl]-(4-isopropoxy-3-methyl-phenyl)methanone | 3,3-dimethyl-6-(trifluoromethyl)spiro[2,4-dihydropyrrolo[1,2-a]pyrazine-1,4'-piperidine] | 4-isopropoxy-3-methyl-benzoic acid |
| [3,3-dimethyl-6-(trifluoromethyl)spiro[2,4-dihydropyrrolo[1,2-a]pyrazine-1,4'-piperidine]-1'-yl]-(4-isopropoxy-3-methoxy-phenyl)methanone | 3,3-dimethyl-6-(trifluoromethyl)spiro[2,4-dihydropyrrolo[1,2-a]pyrazine-1,4'-piperidine] | 4-isopropoxy-3-methoxy-benzoic acid |
| [3,3-dimethyl-6-(trifluoromethyl)spiro[2,4-dihydropyrrolo[1,2-a]pyrazine-1,4'-piperidine]-1'-yl]-(2-fluoro-4-isopropoxy-phenyl)methanone | 3,3-dimethyl-6-(trifluoromethyl)spiro[2,4-dihydropyrrolo[1,2-a]pyrazine-1,4'-piperidine] | 2-fluoro-4-isopropoxy-benzoic acid |
| (3-chloro-4-isopropoxy-phenyl)-[3,3-dimethyl-6-(trifluoromethyl)spiro[2,4-dihydropyrrolo[1,2-a]pyrazine-1,4'-piperidine]-1'-yl]methanone | 3,3-dimethyl-6-(trifluoromethyl)spiro[2,4-dihydropyrrolo[1,2-a]pyrazine-1,4'-piperidine] | 3-chloro-4-isopropoxy-benzoic acid |
| (4-tert-butoxy-3-methoxy-phenyl)-[3,3-dimethyl-6-(trifluoromethyl)spiro[2,4-dihydropyrrolo[1,2- | 3,3-dimethyl-6-(trifluoromethyl)spiro[2,4-dihydropyrrolo[1,2- | 4-tert-butoxy-3-methoxy-benzoic acid |

| Compound name | Amine name | Acid name |
| --- | --- | --- |
| dihydropyrrolo[1,2-a]pyrazine-1,4'-piperidine]-1'-yl]methanone | a]pyrazine-1,4'-piperidine] | |
| [3,3-dimethyl-6-(trifluoromethyl)spiro[2,4-dihydropyrrolo[1,2-a]pyrazine-1,4'-piperidine]-1'-yl]-(3-fluoro-4-isopropoxy-phenyl)methanone | 3,3-dimethyl-6-(trifluoromethyl)spiro[2,4-dihydropyrrolo[1,2-a]pyrazine-1,4'-piperidine] | 3-fluoro-4-isopropoxy-benzoic acid |
| (2-fluoro-4-isopropoxy-phenyl)-[3-methyl-6-(trifluoromethyl)spiro[3,4-dihydro-2H-pyrrolo[1,2-a]pyrazine-1,4'-piperidine]-1'-yl]methanone | 3-methyl-6-(trifluoromethyl)spiro[3,4-dihydro-2H-pyrrolo[1,2-a]pyrazine-1,4'-piperidine] | 2-fluoro-4-isopropoxy-benzoic acid |
| (4-isopropoxy-3-methoxy-phenyl)-[3-methyl-6-(trifluoromethyl)spiro[3,4-dihydro-2H-pyrrolo[1,2-a]pyrazine-1,4'-piperidine]-1'-yl]methanone | 3-methyl-6-(trifluoromethyl)spiro[3,4-dihydro-2H-pyrrolo[1,2-a]pyrazine-1,4'-piperidine] | 4-isopropoxy-3-methoxy-benzoic acid |
| (4-isopropoxy-3-methyl-phenyl)-[3-methyl-6-(trifluoromethyl)spiro[3,4-dihydro-2H-pyrrolo[1,2-a]pyrazine-1,4'-piperidine]-1'-yl]methanone | 3-methyl-6-(trifluoromethyl)spiro[3,4-dihydro-2H-pyrrolo[1,2-a]pyrazine-1,4'-piperidine] | 4-isopropoxy-3-methyl-benzoic acid |
| (3-fluoro-4-isopropoxy-phenyl)-[3-methyl-6-(trifluoromethyl)spiro[3,4-dihydro-2H-pyrrolo[1,2-a]pyrazine-1,4'-piperidine]-1'-yl]methanone | 3-methyl-6-(trifluoromethyl)spiro[3,4-dihydro-2H-pyrrolo[1,2-a]pyrazine-1,4'-piperidine] | 3-fluoro-4-isopropoxy-benzoic acid |
| [4,4-dimethyl-6-(trifluoromethyl)spiro[2,3-dihydropyrrolo[1,2-a]pyrazine-1,4'-piperidine]-1'-yl]-(4-isopropoxy-3-methoxy-phenyl)methanone | 4,4-dimethyl-6-(trifluoromethyl)spiro[2,3-dihydropyrrolo[1,2-a]pyrazine-1,4'-piperidine] | 4-isopropoxy-3-methoxy-benzoic acid |
| [7-(difluoromethyl)-5-methyl-pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-(difluoromethyl)-5-methyl-pyrazolo[1,5-a]pyrimidine-3-carboxylic acid |
| [7-(difluoromethyl)-5-methyl-pyrazolo[1,5-a]pyrimidin-3-yl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 7-(difluoromethyl)-5-methyl-pyrazolo[1,5-a]pyrimidine-3-carboxylic acid |
| [2,3-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 2,3-dimethyl-6-(trifluoromethyl)spiro[3,4-dihydropyrrolo[1,2-a]pyrazine-1,4'-piperidine] | 4-isopropoxy-3-methoxy-benzoic acid |
| [4,4-dimethyl-6-(trifluoromethyl)spiro[2,3-dihydropyrrolo[1,2-a]pyrazine-1,4'-piperidine]-1'-yl]-(3-fluoro-4-isopropoxy-phenyl)methanone | 4,4-dimethyl-6-(trifluoromethyl)spiro[2,3-dihydropyrrolo[1,2-a]pyrazine-1,4'-piperidine] | 3-fluoro-4-isopropoxy-benzoic acid |
| [4,4-dimethyl-6-(trifluoromethyl)spiro[2,3-dihydropyrrolo[1,2-a]pyrazine-1,4'-piperidine]-1'-yl]-(4-isopropoxy-3-methyl-phenyl)methanone | 4,4-dimethyl-6-(trifluoromethyl)spiro[2,3-dihydropyrrolo[1,2-a]pyrazine-1,4'-piperidine] | 4-isopropoxy-3-methyl-benzoic acid |
| (3-chloro-4-isopropoxy-phenyl)-[4,4-dimethyl-6-(trifluoromethyl)spiro[2,3-dihydropyrrolo[1,2-a]pyrazine-1,4'-piperidine]-1'-yl]methanone | 4,4-dimethyl-6-(trifluoromethyl)spiro[2,3-dihydropyrrolo[1,2-a]pyrazine-1,4'-piperidine] | 3-chloro-4-isopropoxy-benzoic acid |
| N-cyclopropyl-4-[4,4-dimethyl-6-(trifluoromethyl)spiro[2,3-dihydropyrrolo[1,2-a]pyrazine-1,4'-piperidine]-1'-carbonyl]benzenesulfonamide | 4,4-dimethyl-6-(trifluoromethyl)spiro[2,3-dihydropyrrolo[1,2-a]pyrazine-1,4'-piperidine] | 4-(cyclopropylsulfamoyl)-benzoic acid |
| [7-(difluoromethyl)-5-methyl-pyrazolo[1,5-a]pyrimidin-3-yl]-[4,4-dimethyl-6-(trifluoromethyl)spiro[2,3-dihydropyrrolo[1,2-a]pyrazine-1,4'-piperidine]-1'-yl]methanone | 4,4-dimethyl-6-(trifluoromethyl)spiro[2,3-dihydropyrrolo[1,2-a]pyrazine-1,4'-piperidine] | 7-(difluoromethyl)-5-methyl-pyrazolo[1,5-a]pyrimidine-3-carboxylic acid |
| [7-[ethyl(methyl)amino]-5-methyl-pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-[ethyl(methyl)amino]-5-methyl-pyrazolo[1,5-a]pyrimidine-3-carboxylic acid |
| [4,4-dimethyl-6-(trifluoromethyl)spiro[2,3- | 4,4-dimethyl-6-(trifluoromethyl)spiro[2,3- | 4-(1-hydroxy-1-methyl-ethyl)-3-methyl-benzoic |

| Compound name | Amine name | Acid name |
| --- | --- | --- |
| dihydropyrrolo[1,2-a]pyrazine-1,4'-piperidine]-1'-yl]-[4-(1-hydroxy-1-methyl-ethyl)-3-methyl-phenyl]methanone | dihydropyrrolo[1,2-a]pyrazine-1,4'-piperidine] | acid |
| [3-methoxy-4-[(1S)-1-methylpropoxy]phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-methoxy-4-[(1S)-1-methylpropoxy]benzoic acid |
| [3-methoxy-4-[(1R)-1-methylpropoxy]phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 3-methoxy-4-[(1R)-1-methylpropoxy]benzoic acid |
| [3-methoxy-4-[(1S)-1-methylpropoxy]phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-methoxy-4-[(1S)-1-methylpropoxy]benzoic acid |
| [3-methoxy-4-[(1R)-1-methylpropoxy]phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 3-methoxy-4-[(1R)-1-methylpropoxy]benzoic acid |
| (5,7-dimethylpyrazolo[1,5-a]pyrimidin-3-yl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 5,7-dimethylpyrazolo[1,5-a]pyrimidine-3-carboxylic acid |
| [7-[ethyl(methyl)amino]pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-[ethyl(methyl)amino]-pyrazolo[1,5-a]pyrimidine-3-carboxylic acid |
| (5-methyl-7-pyrrolidin-1-yl-pyrazolo[1,5-a]pyrimidin-3-yl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 5-methyl-7-pyrrolidin-1-yl-pyrazolo[1,5-a]pyrimidine-3-carboxylic acid |
| [7-(ethylamino)-5-methyl-pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-(ethylamino)-5-methyl-pyrazolo[1,5-a]pyrimidine-3-carboxylic acid |
| (4-isopropoxy-3-methoxy-phenyl)-[3'-methyl-6-(trifluoromethyl)spiro[3,4-dihydro-2H-pyrrolo[1,2-a]pyrazine-1,4'-piperidine]-1'-yl]methanone | 3'-methyl-6-(trifluoromethyl)spiro[3,4-dihydro-2H-pyrrolo[1,2-a]pyrazine-1,4'-piperidine] | 4-isopropoxy-3-methoxy-benzoic acid |
| (7-methylpyrazolo[1,5-a]pyrimidin-3-yl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-methylpyrazolo[1,5-a]pyrimidine-3-carboxylic acid |
| [7-(ethylamino)pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-(ethylamino)pyrazolo[1,5-a]pyrimidine-3-carboxylic acid |
| [7-(isopropylamino)pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 7-(isopropylamino)pyrazolo[1,5-a]pyrimidine-3-carboxylic acid |
| [5-cyclopropyl-7-(difluoromethyl)pyrazolo[1,5-a]pyrimidin-3-yl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 5-cyclopropyl-7-(difluoromethyl)pyrazolo[1,5-a]pyrimidine-3-carboxylic acid |
| [2-cyclopropyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 2-cyclopropyl-6-(trifluoromethyl)spiro[3,4-dihydropyrrolo[1,2-a]pyrazine-1,4'-piperidine] | 4-isopropoxy-3-methoxy-benzoic acid |
| [2-cyclopropyl-6-(trifluoromethyl)spiro[3,4- | 2-cyclopropyl-6-(trifluoromethyl)spiro[3,4- | 4-isopropoxy-3-methyl-benzoic acid |

| Compound name | Amine name | Acid name |
|---|---|---|
| dihydropyrrolo[1,2-a]pyrazine-1,4'-piperidine]-1'-yl]-(4-isopropoxy-3-methyl-phenyl)methanone | dihydropyrrolo[1,2-a]pyrazine-1,4'-piperidine] | |
| [2,3'-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 2,3'-dimethyl-6-(trifluoromethyl)spiro[3,4-dihydropyrrolo[1,2-a]pyrazine-1,4'-piperidine] | 4-isopropoxy-3-methoxy-benzoic acid |
| [4-(2-hydroxy-1,1-dimethyl-ethyl)-3-methoxy-phenyl]-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 4-(2-hydroxy-1,1-dimethyl-ethyl)-3-methoxy-benzoic acid |
| [4-(2-hydroxy-1,1-dimethyl-ethyl)-3-methoxy-phenyl]-[6-(trifluoromethyl)spiro[3,4-dihydro-2H-pyrrolo[1,2-a]pyrazine-1,4'-piperidine]-1'-yl]methanone | 6-(trifluoromethyl)spiro[3,4-dihydro-2H-pyrrolo[1,2-a]pyrazine-1,4'-piperidine] | 4-(2-hydroxy-1,1-dimethyl-ethyl)-3-methoxy-benzoic acid |
| 1'-(4-isopropoxy-3-methoxy-benzoyl)-N-methyl-6-(trifluoromethyl)spiro[3,4-dihydropyrrolo[1,2-a]pyrazine-1,4'-piperidine]-2-carboxamide | N-methyl-6-(trifluoromethyl)spiro[3,4-dihydropyrrolo[1,2-a]pyrazine-1,4'-piperidine]-2-carboxamide | 4-isopropoxy-3-methoxy-benzoic acid |
| 1'-(4-isopropoxy-3-methyl-benzoyl)-N-methyl-6-(trifluoromethyl)spiro[3,4-dihydropyrrolo[1,2-a]pyrazine-1,4'-piperidine]-2-carboxamide | N-methyl-6-(trifluoromethyl)spiro[3,4-dihydropyrrolo[1,2-a]pyrazine-1,4'-piperidine]-2-carboxamide | 4-isopropoxy-3-methyl-benzoic acid |
| 1'-(3-chloro-4-isopropoxy-benzoyl)-N-methyl-6-(trifluoromethyl)spiro[3,4-dihydropyrrolo[1,2-a]pyrazine-1,4'-piperidine]-2-carboxamide | N-methyl-6-(trifluoromethyl)spiro[3,4-dihydropyrrolo[1,2-a]pyrazine-1,4'-piperidine]-2-carboxamide | 3-chloro-4-isopropoxy-benzoic acid |
| 1'-(2-fluoro-4-isopropoxy-benzoyl)-N-methyl-6-(trifluoromethyl)spiro[3,4-dihydropyrrolo[1,2-a]pyrazine-1,4'-piperidine]-2-carboxamide | N-methyl-6-(trifluoromethyl)spiro[3,4-dihydropyrrolo[1,2-a]pyrazine-1,4'-piperidine]-2-carboxamide | 2-fluoro-4-isopropoxy-benzoic acid |
| (5-isopropoxy-6-methyl-2-pyridyl)-[2-methyl-6-(trifluoromethyl)spiro[3,4-dihydropyrrolo[1,2-a]pyrazine-1,4'-piperidine]-1'-yl]methanone | 2-methyl-6-(trifluoromethyl)spiro[3,4-dihydropyrrolo[1,2-a]pyrazine-1,4'-piperidine] | 5-isopropoxy-6-methyl-pyridine-2-carboxylic acid |
| 2,2,2-trifluoro-1-[1'-(4-isopropylsulfonyl-3-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropylsulfonyl-3-methyl-benzoic acid |
| 2,2,2-trifluoro-1-[1'-(4-isopropylsulfonyl-2-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropylsulfonyl-2-methyl-benzoic acid |
| 2,2,2-trifluoro-1-[1'-[3-fluoro-4-(1-hydroxy-1-methyl-ethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-fluoro-4-(1-hydroxy-1-methyl-ethyl)benzoic acid |
| 2,2,2-trifluoro-1-[1'-[4-(3-hydroxypropoxy)-3-methyl-benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(3-hydroxypropoxy)-3-methyl-benzoic acid |
| 1-[1'-(4-tert-butoxy-3-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-tert-butoxy-3-methoxy-benzoic acid |
| N,2-dimethyl-4-[2-methyl-6-(2,2,2-trifluoroacetyl)spiro[3,4-dihydropyrrolo[1,2-a]pyrazine-1,4'-piperidine]-1'-carbonyl]benzenesulfonamide | 2,2,2-trifluoro-1-(2-methylspiro[3,4-dihydropyrrolo[1,2-a]pyrazine-1,4'-piperidine]-6-yl)ethanone | 3-methyl-4-(methylsulfamoyl)benzoic acid |
| N-cyclopropyl-4-[2-methyl-6-(2,2,2-trifluoroacetyl)spiro[3,4- | 2,2,2-trifluoro-1-(2-methylspiro[3,4- | 4-(cyclopropylsulfamoyl)-benzoic acid |

| Compound name | Amine name | Acid name |
|---|---|---|
| dihydropyrrolo[1,2-a]pyrazine-1,4'-piperidine]-1'-carbonyl]benzenesulfonamide | dihydropyrrolo[1,2-a]pyrazine-1,4'-piperidine]-6-yl)ethanone | |
| 2,2,2-trifluoro-1-[1'-[4-(1-hydroxy-1-methyl-ethyl)-3-methyl-benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(1-hydroxy-1-methyl-ethyl)-3-methyl-benzoic acid |
| 1-[1'-(4-tert-butylsulfonylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-tert-butylsulfonylbenzoic acid |
| 2,2,2-trifluoro-1-[1'-(4-isopropoxy-3-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropoxy-3-methyl-benzoic acid |
| 2,2,2-trifluoro-1-[1'-(4-isopropoxy-3-methoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropoxy-3-methoxy-benzoic acid |
| 1-[1'-(4-isopropylsulfonyl-2-methyl-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropylsulfonyl-2-methyl-benzoic acid |
| 1-[1'-[3-fluoro-4-(1-hydroxy-1-methyl-ethyl)benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 3-fluoro-4-(1-hydroxy-1-methyl-ethyl)benzoic acid |
| 1-[1'-[4-(3-hydroxypropoxy)-3-methyl-benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-(3-hydroxypropoxy)-3-methyl-benzoic acid |
| 1-[1'-(4-tert-butoxy-3-methoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-tert-butoxy-3-methoxy-benzoic acid |
| 4-[6-(2,2-dimethylpropanoyl)-2-methyl-spiro[3,4-dihydropyrrolo[1,2-a]pyrazine-1,4'-piperidine]-1'-carbonyl]-N,2-dimethyl-benzenesulfonamide | 2,2-dimethyl-1-(2-methylspiro[3,4-dihydropyrrolo[1,2-a]pyrazine-1,4'-piperidine]-6-yl)propan-1-one | 3-methyl-4-(methylsulfamoyl)benzoic acid |
| 1-[1'-[4-(1-hydroxy-1-methyl-ethyl)-3-methyl-benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-(1-hydroxy-1-methyl-ethyl)-3-methyl-benzoic acid |
| 1-[1'-(4-isopropoxy-3-methyl-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropoxy-3-methyl-benzoic acid |
| 1-[1'-(4-isopropoxy-3-methoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropoxy-3-methoxy-benzoic acid |
| 1-[1'-(3-chloro-4-isopropoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 3-chloro-4-isopropoxy-benzoic acid |

| Compound name | Amine name | Acid name |
|---|---|---|
| 1-[1'-(4-isopropylsulfonyl-3-methyl-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropylsulfonyl-3-methyl-benzoic acid |
| N-cyclopropyl-4-[6-(2,2-dimethylpropanoyl)-2-methyl-spiro[3,4-dihydropyrrolo[1,2-a]pyrazine-1,4'-piperidine]-1'-carbonyl]benzenesulfonamide | 2,2-dimethyl-1-(2-methylspiro[3,4-dihydropyrrolo[1,2-a]pyrazine-1,4'-piperidine]-6-yl)propan-1-one | 4-(cyclopropylsulfamoyl)-benzoic acid |
| 1-[1'-(4-tert-butylsulfonylbenzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-tert-butylsulfonylbenzoic acid |
| 1-[1'-(3-chloro-4-isopropoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 3-chloro-4-isopropoxy-benzoic acid |
| (6-chloro-2-methyl-spiro[3,4-dihydropyrrolo[1,2-a]pyrazine-1,4'-piperidine]-1'-yl)-(4-isopropylsulfonyl-3-methyl-phenyl)methanone | 6-chloro-2-methyl-spiro[3,4-dihydropyrrolo[1,2-a]pyrazine-1,4'-piperidine] | 4-isopropylsulfonyl-3-methyl-benzoic acid |
| (6-chloro-2-methyl-spiro[3,4-dihydropyrrolo[1,2-a]pyrazine-1,4'-piperidine]-1'-yl)-[4-(1-hydroxy-1-methyl-ethyl)-3-methyl-phenyl]methanone | 6-chloro-2-methyl-spiro[3,4-dihydropyrrolo[1,2-a]pyrazine-1,4'-piperidine] | 4-(1-hydroxy-1-methyl-ethyl)-3-methyl-benzoic acid |
| (3-chloro-4-isopropoxy-phenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 3-chloro-4-isopropoxy-benzoic acid |
| 4-(6-chloro-2-methyl-spiro[3,4-dihydropyrrolo[1,2-a]pyrazine-1,4'-piperidine]-1'-carbonyl)-N-cyclopropyl-benzenesulfonamide | 6-chloro-2-methyl-spiro[3,4-dihydropyrrolo[1,2-a]pyrazine-1,4'-piperidine] | 4-(cyclopropylsulfamoyl)-benzoic acid |
| (6-chloro-2-methyl-spiro[3,4-dihydropyrrolo[1,2-a]pyrazine-1,4'-piperidine]-1'-yl)-(5-isopropoxy-6-methyl-2-pyridyl)methanone | 6-chloro-2-methyl-spiro[3,4-dihydropyrrolo[1,2-a]pyrazine-1,4'-piperidine] | 5-isopropoxy-6-methyl-pyridine-2-carboxylic acid |
| (6-chloro-2-methyl-spiro[3,4-dihydropyrrolo[1,2-a]pyrazine-1,4'-piperidine]-1'-yl)-(4-isopropoxy-3-methoxy-phenyl)methanone | 6-chloro-2-methyl-spiro[3,4-dihydropyrrolo[1,2-a]pyrazine-1,4'-piperidine] | 4-isopropoxy-3-methoxy-benzoic acid |
| (6-chloro-2-methyl-spiro[3,4-dihydropyrrolo[1,2-a]pyrazine-1,4'-piperidine]-1'-yl)-(4-isopropoxy-3-methyl-phenyl)methanone | 6-chloro-2-methyl-spiro[3,4-dihydropyrrolo[1,2-a]pyrazine-1,4'-piperidine] | 4-isopropoxy-3-methyl-benzoic acid |
| [3-methoxy-4-[(1R)-1-methylpropoxy]phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-methoxy-4-[(1R)-1-methylpropoxy]benzoic acid |
| N,2-dimethyl-4-[2-methyl-6-(1,1,2,2,2-pentafluoroethyl)spiro[3,4-dihydropyrrolo[1,2-a]pyrazine-1,4'-piperidine]-1'-carbonyl]benzenesulfonamide | 2-methyl-6-(1,1,2,2,2-pentafluoroethyl)spiro[3,4-dihydropyrrolo[1,2-a]pyrazine-1,4'-piperidine] | 3-methyl-4-(methylsulfamoyl)benzoic acid |
| [4-(3-hydroxypropoxy)-3-methyl-phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-(3-hydroxypropoxy)-3-methyl-benzoic acid |
| [3-fluoro-4-(2-hydroxy-2-methyl-propyl)phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-fluoro-4-(2-hydroxy-2-methyl-propyl)benzoic acid |

| Compound name | Amine name | Acid name |
| --- | --- | --- |
| N-methyl-4-[2-methyl-6-(1,1,2,2,2-pentafluoroethyl)spiro[3,4-dihydropyrrolo[1,2-a]pyrazine-1,4'-piperidine]-1'-carbonyl]benzenesulfonamide | 2-methyl-6-(1,1,2,2,2-pentafluoroethyl)spiro[3,4-dihydropyrrolo[1,2-a]pyrazine-1,4'-piperidine] | 4-(methylsulfamoyl)benzoic acid |
| [3-methoxy-4-[(1S)-1-methylpropoxy]phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-methoxy-4-[(1S)-1-methylpropoxy]benzoic acid |
| (4-tert-butoxy-3-methoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-tert-butoxy-3-methoxy-benzoic acid |
| (4-cyclopropylsulfonylphenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-cyclopropylsulfonyl-benzoic acid |
| (4-tert-butylsulfonylphenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-tert-butylsulfonylbenzoic acid |
| [3-methoxy-4-(2-methoxyethoxy)phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-methoxy-4-(2-methoxyethoxy)benzoic acid |
| [3-(hydroxymethyl)-4-isopropoxy-phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-(hydroxymethyl)-4-isopropoxy-benzoic acid |
| [4-(1-hydroxycyclopentyl)phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-(1-hydroxycyclopentyl)-benzoic acid |
| [3-fluoro-4-(1-hydroxy-1-methyl-ethyl)phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-fluoro-4-(1-hydroxy-1-methyl-ethyl)benzoic acid |
| [4-(1-hydroxy-1-methyl-ethyl)phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-(1-hydroxy-1-methyl-ethyl)benzoic acid |
| N-cyclopropyl-4-[2-methyl-6-(1,1,2,2,2-pentafluoroethyl)spiro[3,4-dihydropyrrolo[1,2-a]pyrazine-1,4'-piperidine]-1'-carbonyl]benzenesulfonamide | 2-methyl-6-(1,1,2,2,2-pentafluoroethyl)spiro[3,4-dihydropyrrolo[1,2-a]pyrazine-1,4'-piperidine] | 4-(cyclopropylsulfamoyl)-benzoic acid |
| (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 3-chloro-4-isopropoxy-benzoic acid |
| [4-(1-hydroxy-1-methyl-ethyl)-3-methyl-phenyl]-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-(1-hydroxy-1-methyl-ethyl)-3-methyl-benzoic acid |
| (4-isopropylsulfonyl-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-isopropylsulfonyl-3-methyl-benzoic acid |
| (4-isopropoxy-3-methoxy-phenyl)-[2-methyl-6-(1,1,2,2,2-pentafluoroethyl)spiro[3,4-dihydropyrrolo[1,2- | 2-methyl-6-(1,1,2,2,2-pentafluoroethyl)spiro[3,4-dihydropyrrolo[1,2- | 4-isopropoxy-3-methoxy-benzoic acid |

| Compound name | Amine name | Acid name |
| --- | --- | --- |
| dihydropyrrolo[1,2-a]pyrazine-1,4'-piperidine]-1'-yl]methanone | a]pyrazine-1,4'-piperidine] | |
| (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone | 2-methyl-6-(1,1,2,2,2-pentafluoroethyl)spiro[3,4-dihydropyrrolo[1,2-a]pyrazine-1,4'-piperidine] | 4-isopropoxy-3-methyl-benzoic acid |
| ethyl 1'-(3-chloro-4-isopropoxy-benzoyl)-6-cyano-spiro[3,4-dihydropyrrolo[1,2-a]pyrazine-1,4'-piperidine]-2-carboxylate | ethyl 6-cyanospiro[3,4-dihydropyrrolo[1,2-a]pyrazine-1,4'-piperidine]-2-carboxylate | 3-chloro-4-isopropoxy-benzoic acid |
| ethyl 6-cyano-1'-(4-isopropoxy-3-methyl-benzoyl)spiro[3,4-dihydropyrrolo[1,2-a]pyrazine-1,4'-piperidine]-2-carboxylate | ethyl 6-cyanospiro[3,4-dihydropyrrolo[1,2-a]pyrazine-1,4'-piperidine]-2-carboxylate | 4-isopropoxy-3-methyl-benzoic acid |
| ethyl 6-cyano-1'-(5-isopropoxy-6-methyl-pyridine-2-carbonyl)spiro[3,4-dihydropyrrolo[1,2-a]pyrazine-1,4'-piperidine]-2-carboxylate | ethyl 6-cyanospiro[3,4-dihydropyrrolo[1,2-a]pyrazine-1,4'-piperidine]-2-carboxylate | 5-isopropoxy-6-methyl-pyridine-2-carboxylic acid |
| 4-(6-acetyl-2-methyl-spiro[3,4-dihydropyrrolo[1,2-a]pyrazine-1,4'-piperidine]-1'-carbonyl)-N-cyclopropyl-benzenesulfonamide | 1-(2-methylspiro[3,4-dihydropyrrolo[1,2-a]pyrazine-1,4'-piperidine]-6-yl)ethanone | 4-(cyclopropylsulfamoyl)-benzoic acid |
| 1-[1'-(4-isopropylsulfonyl-3-methyl-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropylsulfonyl-3-methyl-benzoic acid |
| 1-[1'-(4-isopropoxy-3-methyl-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropoxy-3-methyl-benzoic acid |
| 1-[1'-(3-chloro-4-isopropoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-chloro-4-isopropoxy-benzoic acid |
| 1-[1'-[4-(1-hydroxy-1-methyl-ethyl)-3-methyl-benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(1-hydroxy-1-methyl-ethyl)-3-methyl-benzoic acid |
| 1-[1'-(4-isopropoxy-3-methoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropoxy-3-methoxy-benzoic acid |
| [4-(1-hydroxy-1-methyl-ethyl)-3-methyl-phenyl]-(2-methylspiro[3,4-dihydropyrrolo[1,2-a]pyrazine-1,4'-piperidine]-1'-yl)methanone | 2-methylspiro[3,4-dihydropyrrolo[1,2-a]pyrazine-1,4'-piperidine] | 4-(1-hydroxy-1-methyl-ethyl)-3-methyl-benzoic acid |
| (4-isopropoxy-3-methyl-phenyl)-(2-methylspiro[3,4-dihydropyrrolo[1,2-a]pyrazine-1,4'-piperidine]-1'-yl)methanone | 2-methylspiro[3,4-dihydropyrrolo[1,2-a]pyrazine-1,4'-piperidine] | 4-isopropoxy-3-methyl-benzoic acid |
| (3-chloro-4-isopropoxy-phenyl)-[2-methyl-6-(2,2,2-trifluoroethyl)spiro[3,4-dihydropyrrolo[1,2-a]pyrazine-1,4'-piperidine]-1'-yl]methanone | 2-methyl-6-(2,2,2-trifluoroethyl)spiro[3,4-dihydropyrrolo[1,2-a]pyrazine-1,4'-piperidine] | 3-chloro-4-isopropoxy-benzoic acid |
| [4-(1-hydroxy-1-methyl-ethyl)-3-methyl-phenyl]-[2-methyl-6-(2,2,2-trifluoroethyl)spiro[3,4-dihydropyrrolo[1,2-a]pyrazine-1,4'-piperidine]-1'-yl]methanone | 2-methyl-6-(2,2,2-trifluoroethyl)spiro[3,4-dihydropyrrolo[1,2-a]pyrazine-1,4'-piperidine] | 4-(1-hydroxy-1-methyl-ethyl)-3-methyl-benzoic acid |
| (4-isopropylsulfonyl-3-methyl-phenyl)-[2-methyl-6-(2,2,2-trifluoroethyl)spiro[3,4-dihydropyrrolo[1,2-a]pyrazine-1,4'-piperidine]-1'-yl]methanone | 2-methyl-6-(2,2,2-trifluoroethyl)spiro[3,4-dihydropyrrolo[1,2-a]pyrazine-1,4'-piperidine] | 4-isopropylsulfonyl-3-methyl-benzoic acid |
| (4-isopropoxy-3-methoxy-phenyl)-[2-methyl-6-(2,2,2-trifluoroethyl)spiro[3,4-dihydropyrrolo[1,2-a]pyrazine-1,4'-piperidine]-1'-yl]methanone | 2-methyl-6-(2,2,2-trifluoroethyl)spiro[3,4-dihydropyrrolo[1,2-a]pyrazine-1,4'-piperidine] | 4-isopropoxy-3-methoxy-benzoic acid |
| (4-isopropoxy-3-methyl-phenyl)-[2-methyl-6-(2,2,2-trifluoroethyl)spiro[3,4- | 2-methyl-6-(2,2,2-trifluoroethyl)spiro[3,4-dihydropyrrolo[1,2- | 4-isopropoxy-3-methyl-benzoic acid |

| Compound name | Amine name | Acid name |
|---|---|---|
| dihydropyrrolo[1,2-a]pyrazine-1,4'-piperidine]-1'-yl]methanone | a]pyrazine-1,4'-piperidine] | |
| 1'-(4-isopropoxy-3-methoxy-benzoyl)-2-methyl-6-(trifluoromethyl)spiro[3,4-dihydropyrrolo[1,2-a]pyrazine-1,4'-piperidine]-8-carbonitrile | 2-methyl-6-(trifluoromethyl)spiro[3,4-dihydropyrrolo[1,2-a]pyrazine-1,4'-piperidine]-8-carbonitrile | 4-isopropoxy-3-methoxy-benzoic acid |
| [(5aR,9aR)-spiro[5a,6,7,8,9,9a-hexahydro-5H-pyrrolo[1,2-a]quinoxaline-4,4'-piperidine]-1'-yl]-(4-isopentyloxy-3-methoxy-phenyl)methanone | (5aR,9aR)-spiro[5a,6,7,8,9,9a-hexahydro-5H-pyrrolo[1,2-a]quinoxaline-4,4'-piperidine] | 4-isopentyloxy-3-methoxy-benzoic acid |
| [(5aS,9aS)-spiro[5a,6,7,8,9,9a-hexahydro-5H-pyrrolo[1,2-a]quinoxaline-4,4'-piperidine]-1'-yl]-(4-isopentyloxy-3-methoxy-phenyl)methanone | (5aS,9aS)-spiro[5a,6,7,8,9,9a-hexahydro-5H-pyrrolo[1,2-a]quinoxaline-4,4'-piperidine] | 4-isopentyloxy-3-methoxy-benzoic acid |
| (4-isopropoxy-3-methoxy-phenyl)-[(3S)-3-methyl-6-(trifluoromethyl)spiro[3,4-dihydro-2H-pyrrolo[1,2-a]pyrazine-1,4'-piperidine]-1'-yl]methanone | (3S)-3-methyl-6-(trifluoromethyl)spiro[3,4-dihydro-2H-pyrrolo[1,2-a]pyrazine-1,4'-piperidine] | 4-isopropoxy-3-methoxy-benzoic acid |
| (4-isopropoxy-3-methoxy-phenyl)-[(3R)-3-methyl-6-(trifluoromethyl)spiro[3,4-dihydro-2H-pyrrolo[1,2-a]pyrazine-1,4'-piperidine]-1'-yl]methanone | (3R)-3-methyl-6-(trifluoromethyl)spiro[3,4-dihydro-2H-pyrrolo[1,2-a]pyrazine-1,4'-piperidine] | 4-isopropoxy-3-methoxy-benzoic acid |
| [(3S)-2,3-dimethyl-6-(trifluoromethyl)spiro[3,4-dihydropyrrolo[1,2-a]pyrazine-1,4'-piperidine]-1'-yl]-(2-fluoro-4-isopropoxy-phenyl)methanone | (3S)-2,3-dimethyl-6-(trifluoromethyl)spiro[3,4-dihydropyrrolo[1,2-a]pyrazine-1,4'-piperidine] | 2-fluoro-4-isopropoxy-benzoic acid |
| [(3R)-2,3-dimethyl-6-(trifluoromethyl)spiro[3,4-dihydropyrrolo[1,2-a]pyrazine-1,4'-piperidine]-1'-yl]-(2-fluoro-4-isopropoxy-phenyl)methanone | (3R)-2,3-dimethyl-6-(trifluoromethyl)spiro[3,4-dihydropyrrolo[1,2-a]pyrazine-1,4'-piperidine] | 2-fluoro-4-isopropoxy-benzoic acid |
| [(3S)-2,3-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (3S)-2,3-dimethyl-6-(trifluoromethyl)spiro[3,4-dihydropyrrolo[1,2-a]pyrazine-1,4'-piperidine] | 4-isopropoxy-3-methoxy-benzoic acid |
| [(3R)-2,3-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (3R)-2,3-dimethyl-6-(trifluoromethyl)spiro[3,4-dihydropyrrolo[1,2-a]pyrazine-1,4'-piperidine] | 4-isopropoxy-3-methoxy-benzoic acid |
| (4-isopropoxy-3-methyl-phenyl)-[(3S)-3-methyl-6-(trifluoromethyl)spiro[3,4-dihydro-2H-pyrrolo[1,2-a]pyrazine-1,4'-piperidine]-1'-yl]methanone | (3S)-3-methyl-6-(trifluoromethyl)spiro[3,4-dihydro-2H-pyrrolo[1,2-a]pyrazine-1,4'-piperidine] | 4-isopropoxy-3-methyl-benzoic acid |
| (4-isopropoxy-3-methyl-phenyl)-[(3R)-3-methyl-6-(trifluoromethyl)spiro[3,4-dihydro-2H-pyrrolo[1,2-a]pyrazine-1,4'-piperidine]-1'-yl]methanone | (3R)-3-methyl-6-(trifluoromethyl)spiro[3,4-dihydro-2H-pyrrolo[1,2-a]pyrazine-1,4'-piperidine] | 4-isopropoxy-3-methyl-benzoic acid |
| (3-fluoro-4-isopropoxy-phenyl)-[(3S)-3-methyl-6-(trifluoromethyl)spiro[3,4-dihydro-2H-pyrrolo[1,2-a]pyrazine-1,4'-piperidine]-1'-yl]methanone | (3S)-3-methyl-6-(trifluoromethyl)spiro[3,4-dihydro-2H-pyrrolo[1,2-a]pyrazine-1,4'-piperidine] | 3-fluoro-4-isopropoxy-benzoic acid |
| (3-fluoro-4-isopropoxy-phenyl)-[(3R)-3-methyl-6-(trifluoromethyl)spiro[3,4-dihydro-2H-pyrrolo[1,2-a]pyrazine-1,4'-piperidine]-1'-yl]methanone | (3R)-3-methyl-6-(trifluoromethyl)spiro[3,4-dihydro-2H-pyrrolo[1,2-a]pyrazine-1,4'-piperidine] | 3-fluoro-4-isopropoxy-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1S,3'R)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [(1R,3'R)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1R,3'R)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |

| Compound name | Amine name | Acid name |
| --- | --- | --- |
| [(1R,2'S)-2,2'-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1R,2'S)-2,2'-dimethyl-6-(trifluoromethyl)spiro[3,4-dihydropyrrolo[1,2-a]pyrazine-1,4'-piperidine] | 4-isopropoxy-3-methoxy-benzoic acid |
| [(1R,3'R)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1R,3'R)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [(1R,3'S)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1R,3'S)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1S,3'R)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [(1S,3'S)-2,3'-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1S,3'S)-2,3'-dimethyl-6-(trifluoromethyl)spiro[3,4-dihydropyrrolo[1,2-a]pyrazine-1,4'-piperidine] | 4-isopropoxy-3-methoxy-benzoic acid |
| [(1S,3'S)-3'-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1S,3'S)-3'-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)-3-methyl-phenyl]methanone | (1S,3'R)-3'-fluoro-2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-[3-(hydroxymethyl)-4-isopropoxy-phenyl]methanone | (1S,3'R)-3'-fluoro-2-methyl-6-(trifluoromethyl)spiro[3,4-dihydropyrrolo[1,2-a]pyrazine-1,4'-piperidine] | 3-(hydroxymethyl)-4-isopropoxy-benzoic acid |
| N-cyclopropyl-4-[(1S,3'R)-3'-fluoro-2-methyl-6-(trifluoromethyl)spiro[3,4-dihydropyrrolo[1,2-a]pyrazine-1,4'-piperidine]-1'-carbonyl]benzenesulfonamide | (1S,3'R)-3'-fluoro-2-methyl-6-(trifluoromethyl)spiro[3,4-dihydropyrrolo[1,2-a]pyrazine-1,4'-piperidine] | 4-(cyclopropylsulfamoyl)-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-(4-isopropoxy-3-methyl-phenyl)methanone | (1S,3'R)-3'-fluoro-2-methyl-6-(trifluoromethyl)spiro[3,4-dihydropyrrolo[1,2-a]pyrazine-1,4'-piperidine] | 4-isopropoxy-3-methyl-benzoic acid |
| [(1R,2'S)-2,2'-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1R,2'S)-2,2'-dimethyl-6-(trifluoromethyl)spiro[3,4-dihydropyrrolo[1,2-a]pyrazine-1,4'-piperidine] | 4-isopropoxy-3-methoxy-benzoic acid |
| [(1S,2'R)-2,2'-dimethyl-6-(trifluoromethyl)spiro[3,4-dihydropyrrolo[1,2-a]pyrazine-1,4'-piperidine]-1'-yl]-(4-isopropoxy-3-methoxy-phenyl)methanone | (1S,2'R)-2,2'-dimethyl-6-(trifluoromethyl)spiro[3,4-dihydropyrrolo[1,2-a]pyrazine-1,4'-piperidine] | 4-isopropoxy-3-methoxy-benzoic acid |
| [(1S,3'R)-3'-fluoro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)-3-methyl-phenyl]methanone | (1S,3'R)-3'-fluoro-2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| [(1R,3'S)-3'-fluoro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)-3-methyl-phenyl]methanone | (1R,3'S)-3'-fluoro-2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| [(1S,3'R)-3'-fluoro-2-methyl-6-(trifluoromethyl)spiro[3,4- | (1S,3'R)-3'-fluoro-2-methyl-6- | 4-isopropoxy-3-methyl-benzoic acid |

| Compound name | Amine name | Acid name |
| --- | --- | --- |
| dihydropyrrolo[1,2-a]pyrazine-1,4'-piperidine]-1'-yl]-(4-isopropoxy-3-methyl-phenyl)methanone [(1R,3'S)-3'-fluoro-2-methyl-6-(trifluoromethyl)spiro[3,4-dihydropyrrolo[1,2-a]pyrazine-1,4'-piperidine]-1'-yl]-(4-isopropoxy-3-methyl-phenyl)methanone | (trifluoromethyl)spiro[3,4-dihydropyrrolo[1,2-a]pyrazine-1,4'-piperidine] (1R,3'S)-3'-fluoro-2-methyl-6-(trifluoromethyl)spiro[3,4-dihydropyrrolo[1,2-a]pyrazine-1,4'-piperidine] | 4-isopropoxy-3-methyl-benzoic acid |
| ethyl 2-[1'-(4-isopropoxy-3-methoxy-benzoyl)-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 4-isopropoxy-3-methoxy-benzoic acid |
| ethyl 2-[1'-(4-isopropoxy-3-methyl-benzoyl)-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 4-isopropoxy-3-methyl-benzoic acid |
| ethyl 2-[1'-[4-(1-hydroxy-1-methyl-ethyl)-3-methyl-benzoyl]-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 4-(1-hydroxy-1-methyl-ethyl)-3-methyl-benzoic acid |
| ethyl 2-[1'-(3-chloro-4-isopropoxy-benzoyl)-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 3-chloro-4-isopropoxy-benzoic acid |
| ethyl 2-[1'-(4-isopropylsulfonyl-3-methyl-benzoyl)-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 4-isopropylsulfonyl-3-methyl-benzoic acid |
| ethyl 2-[1'-[4-(cyclopropylsulfamoyl)benzoyl]-2-methyl-spiro[3,4-dihydropyrrolo[1,2-a]pyrazine-1,4'-piperidine]-6-yl]-2-oxo-acetate | ethyl 2-(2-methylspiro[3,4-dihydropyrrolo[1,2-a]pyrazine-1,4'-piperidine]-6-yl)-2-oxo-acetate | 4-(cyclopropylsulfamoyl)-benzoic acid |
| [8-bromo-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 8-bromo-2-methyl-6-(trifluoromethyl)spiro[3,4-dihydropyrrolo[1,2-a]pyrazine-1,4'-piperidine] | 4-isopropoxy-3-methoxy-benzoic acid |
| [8-bromo-2-methyl-6-(trifluoromethyl)spiro[3,4-dihydropyrrolo[1,2-a]pyrazine-1,4'-piperidine]-1'-yl]-(4-isopropoxy-3-methyl-phenyl)methanone | 8-bromo-2-methyl-6-(trifluoromethyl)spiro[3,4-dihydropyrrolo[1,2-a]pyrazine-1,4'-piperidine] | 4-isopropoxy-3-methyl-benzoic acid |
| 1'-(4-isopropoxy-3-methyl-benzoyl)-2-methyl-6-(trifluoromethyl)spiro[3,4-dihydropyrrolo[1,2-a]pyrazine-1,4'-piperidine]-8-carbonitrile | 2-methyl-6-(trifluoromethyl)spiro[3,4-dihydropyrrolo[1,2-a]pyrazine-1,4'-piperidine]-8-carbonitrile | 4-isopropoxy-3-methyl-benzoic acid |
| 1'-(3-chloro-4-isopropoxy-benzoyl)-2-methyl-6-(trifluoromethyl)spiro[3,4-dihydropyrrolo[1,2-a]pyrazine-1,4'-piperidine]-8-carbonitrile | 2-methyl-6-(trifluoromethyl)spiro[3,4-dihydropyrrolo[1,2-a]pyrazine-1,4'-piperidine]-8-carbonitrile | 3-chloro-4-isopropoxy-benzoic acid |
| 1'-[4-(1-hydroxy-1-methyl-ethyl)-3-methyl-benzoyl]-2-methyl-6-(trifluoromethyl)spiro[3,4-dihydropyrrolo[1,2-a]pyrazine-1,4'-piperidine]-8-carbonitrile | 2-methyl-6-(trifluoromethyl)spiro[3,4-dihydropyrrolo[1,2-a]pyrazine-1,4'-piperidine]-8-carbonitrile | 4-(1-hydroxy-1-methyl-ethyl)-3-methyl-benzoic acid |
| [8-chloro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)-3-methyl-phenyl]methanone | 8-chloro-2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| [8-chloro-2-methyl-6-(trifluoromethyl)spiro[3,4- | 8-chloro-2-methyl-6-(trifluoromethyl)spiro[3,4- | 5-isopropoxy-6-methyl-pyridine-2-carboxylic acid |

| Compound name | Amine name | Acid name |
| --- | --- | --- |
| dihydropyrrolo[1,2-a]pyrazine-1,4'-piperidine]-1'-yl]-(5-isopropoxy-6-methyl-2-pyridyl)methanone | dihydropyrrolo[1,2-a]pyrazine-1,4'-piperidine] | |
| [8-chloro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 8-chloro-2-methyl-6-(trifluoromethyl)spiro[3,4-dihydropyrrolo[1,2-a]pyrazine-1,4'-piperidine] | 4-isopropoxy-3-methoxy-benzoic acid |
| [8-fluoro-2-methyl-6-(trifluoromethyl)spiro[3,4-dihydropyrrolo[1,2-a]pyrazine-1,4'-piperidine]-1'-yl]-(4-isopropoxy-3-methoxy-phenyl)methanone | 8-fluoro-2-methyl-6-(trifluoromethyl)spiro[3,4-dihydropyrrolo[1,2-a]pyrazine-1,4'-piperidine] | 4-isopropoxy-3-methoxy-benzoic acid |
| [8-chloro-2-methyl-6-(trifluoromethyl)spiro[3,4-dihydropyrrolo[1,2-a]pyrazine-1,4'-piperidine]-1'-yl]-(4-isopropoxy-3-methyl-phenyl)methanone | 8-chloro-2-methyl-6-(trifluoromethyl)spiro[3,4-dihydropyrrolo[1,2-a]pyrazine-1,4'-piperidine] | 4-isopropoxy-3-methyl-benzoic acid |
| [8-fluoro-2-methyl-6-(trifluoromethyl)spiro[3,4-dihydropyrrolo[1,2-a]pyrazine-1,4'-piperidine]-1'-yl]-(4-isopropoxy-3-methyl-phenyl)methanone | 8-fluoro-2-methyl-6-(trifluoromethyl)spiro[3,4-dihydropyrrolo[1,2-a]pyrazine-1,4'-piperidine] | 4-isopropoxy-3-methyl-benzoic acid |
| 2,2,2-trifluoro-1-[1'-(4-isopropylbenzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropylbenzoic acid |
| 2,2,2-trifluoro-1-[1'-[4-(2-methoxyethoxy)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(2-methoxyethoxy)benzoic acid |
| 2,2,2-trifluoro-1-[2-methyl-1'-(4-propoxybenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-propoxybenzoic acid |
| 4-[2-methyl-6-(2,2,2-trifluoroacetyl)spiro[3,4-dihydropyrrolo[1,2-a]pyrazine-1,4'-piperidine]-1'-carbonyl]-N,N-dipropyl-benzenesulfonamide | 2,2,2-trifluoro-1-(2-methylspiro[3,4-dihydropyrrolo[1,2-a]pyrazine-1,4'-piperidine]-6-yl)ethanone | 4-(dipropylsulfamoyl)-benzoic acid |
| 1-[1'-(4-butylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-butylbenzoic acid |
| 2,2,2-trifluoro-1-[2-methyl-1'-(4-phenylbenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-phenylbenzoic acid |
| 2,2,2-trifluoro-1-[2-methyl-1'-(4-propylbenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-propylbenzoic acid |
| 2,2,2-trifluoro-1-[2-methyl-1'-(4-phenoxybenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-phenoxybenzoic acid |
| 2,2,2-trifluoro-1-[1'-(4-isopentyloxybenzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopentyloxybenzoic acid |
| 1-[1'-(4-butoxybenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-butoxybenzoic acid |
| 1-[1'-(4-tert-butylbenzoyl)-2-methyl-spiro[3,4-dihydropyrrolo[1,2- | 2,2,2-trifluoro-1-(2-methylspiro[3,4- | 4-tert-butylbenzoic acid |

| Compound name | Amine name | Acid name |
|---|---|---|
| a]pyrazine-1,4'-piperidine]-6-yl]-2,2,2-trifluoro-ethanone | dihydropyrrolo[1,2-a]pyrazine-1,4'-piperidine]-6-yl)ethanone | |
| 2,2,2-trifluoro-1-[2-methyl-1'-[4-(phenoxymethyl)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(phenoxymethyl)benzoic acid |
| 2,2,2-trifluoro-1-[2-methyl-1'-[4-(1-piperidyl)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(1-piperidyl)benzoic acid |
| 1-[1'-(4-tert-butoxybenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-tert-butoxybenzoic acid |
| 1-[1'-(4-benzyloxybenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-benzyloxybenzoic acid |
| 1-[1'-(3-chloro-4-isopropoxy-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 3-chloro-4-isopropoxy-benzoic acid |
| 1-[1'-(4-isopropoxy-3-methyl-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 4-isopropoxy-3-methyl-benzoic acid |
| 1-[1'-(4-isopropoxy-3-methoxy-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 4-isopropoxy-3-methoxy-benzoic acid |
| 2,2,2-trifluoro-1-[2-methyl-1'-(4-pentylbenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-pentylbenzoic acid |
| 1-[1'-(3,4-diethoxybenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 3,4-diethoxybenzoic acid |
| 1-[1'-(4-tert-butyl-3-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-tert-butyl-3-methoxy-benzoic acid |
| 2,2,2-trifluoro-1-[1'-(4-methoxy-3-propoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-methoxy-3-propoxy-benzoic acid |
| 1-[1'-(4-butoxy-3-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-butoxy-3-methoxy-benzoic acid |
| 2,2,2-trifluoro-1-[1'-(3-methoxy-4-propoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methoxy-4-propoxy-benzoic acid |
| 2,2,2-trifluoro-1-[1'-(3-isopropoxy-4-methoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-isopropoxy-4-methoxy-benzoic acid |

| Compound name | Amine name | Acid name |
| --- | --- | --- |
| 2,2,2-trifluoro-1-[1'-[4-(2-hydroxy-2-methyl-propoxy)-3-methyl-benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(2-hydroxy-2-methyl-propoxy)-3-methyl-benzoic acid |
| 1-[1'-(3-butoxy-4-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 3-butoxy-4-methoxy-benzoic acid |
| 2,2,2-trifluoro-1-[1'-[4-(1-hydroxy-1-methyl-ethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(1-hydroxy-1-methyl-ethyl)benzoic acid |
| 2,2,2-trifluoro-1-[1'-(4-isobutoxy-3-methoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isobutoxy-3-methoxy-benzoic acid |
| 1-[1'-(4-ethylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-ethylbenzoic acid |
| 2,2,2-trifluoro-1-[1'-(3-fluoro-4-isopropoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-fluoro-4-isopropoxy-benzoic acid |
| 1-[1'-(4-ethoxy-3-fluoro-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-ethoxy-3-fluoro-benzoic acid |
| 1-[1'-(4-ethyl-3-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-ethyl-3-methoxy-benzoic acid |
| 2,2,2-trifluoro-1-[1'-(4-isopropoxybenzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropoxybenzoic acid |
| 1-[1'-(4-benzylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-benzylbenzoic acid |
| 2,2,2-trifluoro-1-[1'-[4-isopropoxy-3-(trifluoromethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropoxy-3-(trifluoromethyl)benzoic acid |
| (6-chloro-2-methyl-spiro[3,4-dihydropyrrolo[1,2-a]pyrazine-1,4'-piperidine]-1'-yl)-(4-isopropylphenyl)methanone | 6-chloro-2-methyl-spiro[3,4-dihydropyrrolo[1,2-a]pyrazine-1,4'-piperidine] | 4-isopropylbenzoic acid |
| (6-chloro-2-methyl-spiro[3,4-dihydropyrrolo[1,2-a]pyrazine-1,4'-piperidine]-1'-yl)-(4-propoxyphenyl)methanone | 6-chloro-2-methyl-spiro[3,4-dihydropyrrolo[1,2-a]pyrazine-1,4'-piperidine] | 4-propoxybenzoic acid |
| 4-(6-chloro-2-methyl-spiro[3,4-dihydropyrrolo[1,2-a]pyrazine-1,4'-piperidine]-1'-carbonyl)-N,N-dipropyl-benzenesulfonamide | 6-chloro-2-methyl-spiro[3,4-dihydropyrrolo[1,2-a]pyrazine-1,4'-piperidine] | 4-(dipropylsulfamoyl)-benzoic acid |
| (4-butylphenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-butylbenzoic acid |
| (6-chloro-2-methyl-spiro[3,4-dihydropyrrolo[1,2-a]pyrazine-1,4'-piperidine]-1'-yl)-(4-phenylphenyl)methanone | 6-chloro-2-methyl-spiro[3,4-dihydropyrrolo[1,2-a]pyrazine-1,4'-piperidine] | 4-phenylbenzoic acid |

| Compound name | Amine name | Acid name |
|---|---|---|
| (6-chloro-2-methyl-spiro[3,4-dihydropyrrolo[1,2-a]pyrazine-1,4'-piperidine]-1'-yl)-(4-propylphenyl)methanone | 6-chloro-2-methyl-spiro[3,4-dihydropyrrolo[1,2-a]pyrazine-1,4'-piperidine] | 4-propylbenzoic acid |
| (6-chloro-2-methyl-spiro[3,4-dihydropyrrolo[1,2-a]pyrazine-1,4'-piperidine]-1'-yl)-(4-phenoxyphenyl)methanone | 6-chloro-2-methyl-spiro[3,4-dihydropyrrolo[1,2-a]pyrazine-1,4'-piperidine] | 4-phenoxybenzoic acid |
| (6-chloro-2-methyl-spiro[3,4-dihydropyrrolo[1,2-a]pyrazine-1,4'-piperidine]-1'-yl)-(4-isopentyloxyphenyl)methanone | 6-chloro-2-methyl-spiro[3,4-dihydropyrrolo[1,2-a]pyrazine-1,4'-piperidine] | 4-isopentyloxybenzoic acid |
| (4-butoxyphenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-butoxybenzoic acid |
| (4-tert-butylphenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-tert-butylbenzoic acid |
| (6-chloro-2-methyl-spiro[3,4-dihydropyrrolo[1,2-a]pyrazine-1,4'-piperidine]-1'-yl)-[4-(phenoxymethyl)phenyl]methanone | 6-chloro-2-methyl-spiro[3,4-dihydropyrrolo[1,2-a]pyrazine-1,4'-piperidine] | 4-(phenoxymethyl)benzoic acid |
| (6-chloro-2-methyl-spiro[3,4-dihydropyrrolo[1,2-a]pyrazine-1,4'-piperidine]-1'-yl)-[4-(1-piperidyl)phenyl]methanone | 6-chloro-2-methyl-spiro[3,4-dihydropyrrolo[1,2-a]pyrazine-1,4'-piperidine] | 4-(1-piperidyl)benzoic acid |
| (4-benzyloxyphenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-benzyloxybenzoic acid |
| (6-chloro-2-methyl-spiro[3,4-dihydropyrrolo[1,2-a]pyrazine-1,4'-piperidine]-1'-yl)-(4-pentylphenyl)methanone | 6-chloro-2-methyl-spiro[3,4-dihydropyrrolo[1,2-a]pyrazine-1,4'-piperidine] | 4-pentylbenzoic acid |
| (6-chloro-2-methyl-spiro[3,4-dihydropyrrolo[1,2-a]pyrazine-1,4'-piperidine]-1'-yl)-(4-cyclohexylphenyl)methanone | 6-chloro-2-methyl-spiro[3,4-dihydropyrrolo[1,2-a]pyrazine-1,4'-piperidine] | 4-cyclohexylbenzoic acid |
| (4-tert-butyl-3-methoxy-phenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-tert-butyl-3-methoxy-benzoic acid |
| (6-chloro-2-methyl-spiro[3,4-dihydropyrrolo[1,2-a]pyrazine-1,4'-piperidine]-1'-yl)-(4-methoxy-3-propoxy-phenyl)methanone | 6-chloro-2-methyl-spiro[3,4-dihydropyrrolo[1,2-a]pyrazine-1,4'-piperidine] | 4-methoxy-3-propoxy-benzoic acid |
| (4-butoxy-3-methoxy-phenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-butoxy-3-methoxy-benzoic acid |
| (6-chloro-2-methyl-spiro[3,4-dihydropyrrolo[1,2-a]pyrazine-1,4'-piperidine]-1'-yl)-(3-methoxy-4-propoxy-phenyl)methanone | 6-chloro-2-methyl-spiro[3,4-dihydropyrrolo[1,2-a]pyrazine-1,4'-piperidine] | 3-methoxy-4-propoxy-benzoic acid |
| (3-butoxy-4-methoxy-phenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 3-butoxy-4-methoxy-benzoic acid |
| (6-chloro-2-methyl-spiro[3,4-dihydropyrrolo[1,2-a]pyrazine-1,4'-piperidine]-1'-yl)-[3-methoxy-4-[2-(trifluoromethoxy)ethoxy]phenyl]methanone | 6-chloro-2-methyl-spiro[3,4-dihydropyrrolo[1,2-a]pyrazine-1,4'-piperidine] | 3-methoxy-4-[2-(trifluoromethoxy)ethoxy]benzoic acid |
| (6-chloro-2-methyl-spiro[3,4-dihydropyrrolo[1,2-a]pyrazine-1,4'-piperidine]-1'-yl)-[3-fluoro-4-(3-methoxyprop-1-ynyl)phenyl]methanone | 6-chloro-2-methyl-spiro[3,4-dihydropyrrolo[1,2-a]pyrazine-1,4'-piperidine] | 3-fluoro-4-(3-methoxyprop-1-ynyl)benzoic acid |
| (6-chloro-2-methyl-spiro[3,4-dihydropyrrolo[1,2-a]pyrazine-1,4'-piperidine]-1'-yl)-(3-fluoro-4-isopropoxy-phenyl)methanone | 6-chloro-2-methyl-spiro[3,4-dihydropyrrolo[1,2-a]pyrazine-1,4'-piperidine] | 3-fluoro-4-isopropoxy-benzoic acid |
| 4-(6-chloro-2-methyl-spiro[3,4-dihydropyrrolo[1,2-a]pyrazine-1,4'-piperidine]-1'-carbonyl)-N-ethyl-benzenesulfonamide | 6-chloro-2-methyl-spiro[3,4-dihydropyrrolo[1,2-a]pyrazine-1,4'-piperidine] | 4-(ethylsulfamoyl)benzoic acid |

| Compound name | Amine name | Acid name |
|---|---|---|
| (6-chloro-2-methyl-spiro[3,4-dihydropyrrolo[1,2-a]pyrazine-1,4'-piperidine]-1'-yl)-[3-fluoro-4-(1-hydroxyl-1-methyl-ethyl)phenyl]methanone | 6-chloro-2-methyl-spiro[3,4-dihydropyrrolo[1,2-a]pyrazine-1,4'-piperidine] | 3-fluoro-4-(1-hydroxy-1-methyl-ethyl)benzoic acid |
| (6-chloro-2-methyl-spiro[3,4-dihydropyrrolo[1,2-a]pyrazine-1,4'-piperidine]-1'-yl)-[4-isopropoxy-3-(trifluoromethyl)phenyl]methanone | 6-chloro-2-methyl-spiro[3,4-dihydropyrrolo[1,2-a]pyrazine-1,4'-piperidine] | 4-isopropoxy-3-(trifluoromethyl)benzoic acid |
| (6-chloro-2-methyl-spiro[3,4-dihydropyrrolo[1,2-a]pyrazine-1,4'-piperidine]-1'-yl)-(4-isopropoxyphenyl)methanone | 6-chloro-2-methyl-spiro[3,4-dihydropyrrolo[1,2-a]pyrazine-1,4'-piperidine] | 4-isopropoxybenzoic acid |
| (6-chloro-2-methyl-spiro[3,4-dihydropyrrolo[1,2-a]pyrazine-1,4'-piperidine]-1'-yl)-(4-isobutoxy-3-methoxy-phenyl)methanone | 6-chloro-2-methyl-spiro[3,4-dihydropyrrolo[1,2-a]pyrazine-1,4'-piperidine] | 4-isobutoxy-3-methoxy-benzoic acid |
| (6-chloro-2-methyl-spiro[3,4-dihydropyrrolo[1,2-a]pyrazine-1,4'-piperidine]-1'-yl)-[4-(difluoromethylsulfonyl)phenyl]methanone | 6-chloro-2-methyl-spiro[3,4-dihydropyrrolo[1,2-a]pyrazine-1,4'-piperidine] | 4-(difluoromethylsulfonyl)-benzoic acid |
| (6-chloro-2-methyl-spiro[3,4-dihydropyrrolo[1,2-a]pyrazine-1,4'-piperidine]-1'-yl)-(8-quinolyl)methanone | 6-chloro-2-methyl-spiro[3,4-dihydropyrrolo[1,2-a]pyrazine-1,4'-piperidine] | quinoline-8-carboxylic acid |
| (6-chloro-2-methyl-spiro[3,4-dihydropyrrolo[1,2-a]pyrazine-1,4'-piperidine]-1'-yl)-[4-(1-hydroxycyclopentyl)phenyl]methanone | 6-chloro-2-methyl-spiro[3,4-dihydropyrrolo[1,2-a]pyrazine-1,4'-piperidine] | 4-(1-hydroxycyclopentyl)-benzoic acid |
| (6-chloro-2-methyl-spiro[3,4-dihydropyrrolo[1,2-a]pyrazine-1,4'-piperidine]-1'-yl)-[3-methoxy-4-[(1S)-1-methylpropoxy]phenyl]methanone | 6-chloro-2-methyl-spiro[3,4-dihydropyrrolo[1,2-a]pyrazine-1,4'-piperidine] | 3-methoxy-4-[(1S)-1-methylpropoxy]benzoic acid |
| (6-chloro-2-methyl-spiro[3,4-dihydropyrrolo[1,2-a]pyrazine-1,4'-piperidine]-1'-yl)-(4-ethyl-3-methoxy-phenyl)methanone | 6-chloro-2-methyl-spiro[3,4-dihydropyrrolo[1,2-a]pyrazine-1,4'-piperidine] | 4-ethyl-3-methoxy-benzoic acid |
| (4-benzylphenyl)-(6-chloro-2-methyl-spiro[3,4-dihydropyrrolo[1,2-a]pyrazine-1,4'-piperidine]-1'-yl)methanone | 6-chloro-2-methyl-spiro[3,4-dihydropyrrolo[1,2-a]pyrazine-1,4'-piperidine] | 4-benzylbenzoic acid |
| (6-chloro-2-methyl-spiro[3,4-dihydropyrrolo[1,2-a]pyrazine-1,4'-piperidine]-1'-yl)-(3,4-diethoxyphenyl)methanone | 6-chloro-2-methyl-spiro[3,4-dihydropyrrolo[1,2-a]pyrazine-1,4'-piperidine] | 3,4-diethoxybenzoic acid |
| (6-chloro-2-methyl-spiro[3,4-dihydropyrrolo[1,2-a]pyrazine-1,4'-piperidine]-1'-yl)-[4-(2-hydroxy-2-methyl-propoxy)-3-methyl-phenyl]methanone | 6-chloro-2-methyl-spiro[3,4-dihydropyrrolo[1,2-a]pyrazine-1,4'-piperidine] | 4-(2-hydroxy-2-methyl-propoxy)-3-methyl-benzoic acid |
| 1-[1'-(4-isopropylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropylbenzoic acid |
| 1-[2-methyl-1'-(4-propoxybenzoyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-propoxybenzoic acid |
| 4-(6-acetyl-2-methyl-spiro[3,4-dihydropyrrolo[1,2-a]pyrazine-1,4'-piperidine]-1'-carbonyl)-N,N-dipropyl-benzenesulfonamide | 1-(2-methylspiro[3,4-dihydropyrrolo[1,2-a]pyrazine-1,4'-piperidine]-6-yl)ethanone | 4-(dipropylsulfamoyl)-benzoic acid |
| 1-[1'-(4-butylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-butylbenzoic acid |
| 1-[2-methyl-1'-(4-phenylbenzoyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-phenylbenzoic acid |
| 1-[2-methyl-1'-(4-propylbenzoyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-propylbenzoic acid |
| 1-[2-methyl-1'-(4-phenoxybenzoyl)spiro[3,4- | 1-(2-methylspiro[3,4-dihydropyrrolo[1,2- | 4-phenoxybenzoic acid |

| Compound name | Amine name | Acid name |
| --- | --- | --- |
| dihydropyrrolo[1,2-a]pyrazine-1,4'-piperidine]-6-yl]ethanone | a]pyrazine-1,4'-piperidine]-6-yl]ethanone | |
| 1-[1'-(4-isopentyloxybenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopentyloxybenzoic acid |
| 1-[1'-(4-butoxybenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-butoxybenzoic acid |
| 1-[1'-(4-tert-butylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-tert-butylbenzoic acid |
| 1-[2-methyl-1'-[4-(phenoxymethyl)benzoyl]spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(phenoxymethyl)benzoic acid |
| 1-[2-methyl-1'-[4-(1-piperidyl)benzoyl]spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(1-piperidyl)benzoic acid |
| 1-[1'-(4-benzyloxybenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-benzyloxybenzoic acid |
| 1-[2-methyl-1'-(4-pentylbenzoyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-pentylbenzoic acid |
| 1-[1'-(4-cyclohexylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-cyclohexylbenzoic acid |
| 1-[1'-(4-tert-butyl-3-methoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-tert-butyl-3-methoxy-benzoic acid |
| 1-[1'-(4-methoxy-3-propoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-methoxy-3-propoxy-benzoic acid |
| 1-[1'-(4-butoxy-3-methoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-butoxy-3-methoxy-benzoic acid |
| 1-[1'-(3-methoxy-4-propoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-propoxy-benzoic acid |
| 1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-[2-(trifluoromethoxy)ethoxy]benzoic acid |
| 1-[1'-[3-fluoro-4-(3-methoxyprop-1-ynyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-fluoro-4-(3-methoxyprop-1-ynyl)benzoic acid |
| 1-[1'-(4-ethylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-ethylbenzoic acid |
| 1-[1'-(3-fluoro-4-isopropoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-fluoro-4-isopropoxy-benzoic acid |
| 4-(6-acetyl-2-methyl-spiro[3,4-dihydropyrrolo[1,2-a]pyrazine-1,4'-piperidine]-1'-carbonyl)-N-ethyl-benzenesulfonamide | 1-(2-methylspiro[3,4-dihydropyrrolo[1,2-a]pyrazine-1,4'-piperidine]-6-yl)ethanone | 4-(ethylsulfamoyl)benzoic acid |
| 1-[1'-[3-fluoro-4-(1-hydroxy-1-methyl-ethyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-fluoro-4-(1-hydroxy-1-methyl-ethyl)benzoic acid |

| Compound name | Amine name | Acid name |
| --- | --- | --- |
| 1-[1'-[4-isopropoxy-3-(trifluoromethyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropoxy-3-(trifluoromethyl)benzoic acid |
| 1-[1'-(4-isopropoxybenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isopropoxybenzoic acid |
| 1-[1'-(4-isobutoxy-3-methoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isobutoxy-3-methoxy-benzoic acid |
| 1-[1'-[4-(difluoromethylsulfonyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(difluoromethylsulfonyl)-benzoic acid |
| 1-[2-methyl-1'-(quinoline-8-carbonyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | quinoline-8-carboxylic acid |
| 1-[1'-[4-(1-hydroxycyclopentyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(1-hydroxycyclopentyl)-benzoic acid |
| 1-[1'-[3-methoxy-4-[(1S)-1-methylpropoxy]benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-[(1S)-1-methylpropoxy]benzoic acid |
| 1-[1'-(4-ethyl-3-methoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-ethyl-3-methoxy-benzoic acid |
| 1-[1'-(4-benzylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-benzylbenzoic acid |
| 1-[1'-(3,4-diethoxybenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3,4-diethoxybenzoic acid |
| 1-[1'-[4-(2-hydroxy-2-methyl-propoxy)-3-methyl-benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(2-hydroxy-2-methyl-propoxy)-3-methyl-benzoic acid |
| (6-chloro-2-methyl-spiro[3,4-dihydropyrrolo[1,2-a]pyrazine-1,4'-piperidine]-1'-yl)-[3-methoxy-4-[(1R)-1-methylpropoxy]phenyl]methanone | 6-chloro-2-methyl-spiro[3,4-dihydropyrrolo[1,2-a]pyrazine-1,4'-piperidine] | 3-methoxy-4-[(1R)-1-methylpropoxy]benzoic acid |
| 1-[1'-[3-methoxy-4-[(1R)-1-methylpropoxy]benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-[(1R)-1-methylpropoxy]benzoic acid |
| 2-isopropoxy-5-[2-methyl-6-(2,2,2-trifluoroacetyl)spiro[3,4-dihydropyrrolo[1,2-a]pyrazine-1,4'-piperidine]-1'-carbonyl]benzonitrile | 2,2,2-trifluoro-1-(2-methylspiro[3,4-dihydropyrrolo[1,2-a]pyrazine-1,4'-piperidine]-6-yl)ethanone | 3-cyano-4-isopropoxy-benzoic acid |
| 2,2,2-trifluoro-1-[1'-[4-methoxy-3-(trifluoromethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-methoxy-3-(trifluoromethyl)benzoic acid |
| 2,2,2-trifluoro-1-[2-methyl-1'-[4-(trifluoromethoxy)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(trifluoromethoxy)benzoic acid |
| 2,2,2-trifluoro-1-[1'-[3-(hydroxymethyl)-4-isopropoxy-benzoyl]-2-methyl-spiro[3,4- | 2,2,2-trifluoro-1-(2-methylspiro[3,4-dihydropyrrolo[1,2- | 3-(hydroxymethyl)-4-isopropoxy-benzoic acid |

| Compound name | Amine name | Acid name |
| --- | --- | --- |
| dihydropyrrolo[1,2-a]pyrazine-1,4'-piperidine]-6-yl]ethanone | a]pyrazine-1,4'-piperidine]-6-yl]ethanone | |
| 2,2,2-trifluoro-1-[1'-[4-(2-hydroxy-2-methyl-propyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(2-hydroxy-2-methyl-propyl)benzoic acid |
| 2,2,2-trifluoro-1-[1'-[3-methoxy-4-(2-methoxyethoxy)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methoxy-4-(2-methoxyethoxy)benzoic acid |
| [8-fluoro-2-methyl-6-(trifluoromethyl)spiro[3,4-dihydropyrrolo[1,2-a]pyrazine-1,4'-piperidine]-1'-yl]-(4-isopropoxyphenyl)methanone | 8-fluoro-2-methyl-6-(trifluoromethyl)spiro[3,4-dihydropyrrolo[1,2-a]pyrazine-1,4'-piperidine] | 4-isopropoxybenzoic acid |
| [8-fluoro-2-methyl-6-(trifluoromethyl)spiro[3,4-dihydropyrrolo[1,2-a]pyrazine-1,4'-piperidine]-1'-yl]-(4-propoxyphenyl)methanone | 8-fluoro-2-methyl-6-(trifluoromethyl)spiro[3,4-dihydropyrrolo[1,2-a]pyrazine-1,4'-piperidine] | 4-propoxybenzoic acid |
| [8-fluoro-2-methyl-6-(trifluoromethyl)spiro[3,4-dihydropyrrolo[1,2-a]pyrazine-1,4'-piperidine]-1'-yl]-[4-(2-methoxyethoxy)phenyl]methanone | 8-fluoro-2-methyl-6-(trifluoromethyl)spiro[3,4-dihydropyrrolo[1,2-a]pyrazine-1,4'-piperidine] | 4-(2-methoxyethoxy)benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)phenyl]methanone | 8-fluoro-2-methyl-6-(trifluoromethyl)spiro[3,4-dihydropyrrolo[1,2-a]pyrazine-1,4'-piperidine] | 4-(1-hydroxy-1-methyl-ethyl)benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxy-2-methyl-propyl)phenyl]methanone | 8-fluoro-2-methyl-6-(trifluoromethyl)spiro[3,4-dihydropyrrolo[1,2-a]pyrazine-1,4'-piperidine] | 4-(1-hydroxy-2-methyl-propyl)benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)-3-methyl-phenyl]methanone | 8-fluoro-2-methyl-6-(trifluoromethyl)spiro[3,4-dihydropyrrolo[1,2-a]pyrazine-1,4'-piperidine] | 4-(1-hydroxy-1-methyl-ethyl)-3-methyl-benzoic acid |
| [3-fluoro-4-(1-hydroxy-1-methyl-ethyl)phenyl]-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 3-fluoro-4-(1-hydroxy-1-methyl-ethyl)benzoic acid |
| [8-fluoro-2-methyl-6-(trifluoromethyl)spiro[3,4-dihydropyrrolo[1,2-a]pyrazine-1,4'-piperidine]-1'-yl]-[4-(2-hydroxy-2-methyl-propoxy)-3-methyl-phenyl]methanone | 8-fluoro-2-methyl-6-(trifluoromethyl)spiro[3,4-dihydropyrrolo[1,2-a]pyrazine-1,4'-piperidine] | 4-(2-hydroxy-2-methyl-propoxy)-3-methyl-benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxycyclobutyl)phenyl]methanone | 8-fluoro-2-methyl-6-(trifluoromethyl)spiro[3,4-dihydropyrrolo[1,2-a]pyrazine-1,4'-piperidine] | 4-(1-hydroxycyclobutyl)-benzoic acid |
| (3-fluoro-4-isopropoxy-phenyl)-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 3-fluoro-4-isopropoxy-benzoic acid |
| [8-fluoro-2-methyl-6-(trifluoromethyl)spiro[3,4-dihydropyrrolo[1,2-a]pyrazine-1,4'-piperidine]-1'-yl]-(3-methoxy-4-propoxy-phenyl)methanone | 8-fluoro-2-methyl-6-(trifluoromethyl)spiro[3,4-dihydropyrrolo[1,2-a]pyrazine-1,4'-piperidine] | 3-methoxy-4-propoxy-benzoic acid |
| [8-fluoro-2-methyl-6-(trifluoromethyl)spiro[3,4-dihydropyrrolo[1,2-a]pyrazine-1,4'-piperidine]-1'-yl]-[3-methoxy-4-[(1S)-1-methylpropoxy]phenyl]methanone | 8-fluoro-2-methyl-6-(trifluoromethyl)spiro[3,4-dihydropyrrolo[1,2-a]pyrazine-1,4'-piperidine] | 3-methoxy-4-[(1S)-1-methylpropoxy]benzoic acid |
| [8-fluoro-2-methyl-6-(trifluoromethyl)spiro[3,4- | 8-fluoro-2-methyl-6-(trifluoromethyl)spiro[3,4- | 3-methoxy-4-(2-methoxyethoxy)benzoic |

| Compound name | Amine name | Acid name |
| --- | --- | --- |
| dihydropyrrolo[1,2-a]pyrazine-1,4'-piperidine]-1'-yl]-[3-methoxy-4-(2-methoxyethoxy)phenyl]methanone | dihydropyrrolo[1,2-a]pyrazine-1,4'-piperidine] | acid |
| (4-tert-butoxy-3-methoxy-phenyl)-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 4-tert-butoxy-3-methoxy-benzoic acid |
| [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone | 8-fluoro-2-methyl-6-(trifluoromethyl)spiro[3,4-dihydropyrrolo[1,2-a]pyrazine-1,4'-piperidine] | 4-isobutoxy-3-methoxy-benzoic acid |
| [4-(difluoromethoxy)-3-methoxy-phenyl]-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 4-(difluoromethoxy)-3-methoxy-benzoic acid |
| [8-fluoro-2-methyl-6-(trifluoromethyl)spiro[3,4-dihydropyrrolo[1,2-a]pyrazine-1,4'-piperidine]-1'-yl]-[4-(3-hydroxypropoxy)-3-methyl-phenyl]methanone | 8-fluoro-2-methyl-6-(trifluoromethyl)spiro[3,4-dihydropyrrolo[1,2-a]pyrazine-1,4'-piperidine] | 4-(3-hydroxypropoxy)-3-methyl-benzoic acid |
| [8-fluoro-2-methyl-6-(trifluoromethyl)spiro[3,4-dihydropyrrolo[1,2-a]pyrazine-1,4'-piperidine]-1'-yl]-[3-(hydroxymethyl)-4-isopropoxy-phenyl]methanone | 8-fluoro-2-methyl-6-(trifluoromethyl)spiro[3,4-dihydropyrrolo[1,2-a]pyrazine-1,4'-piperidine] | 3-(hydroxymethyl)-4-isopropoxy-benzoic acid |
| [8-fluoro-2-methyl-6-(trifluoromethyl)spiro[3,4-dihydropyrrolo[1,2-a]pyrazine-1,4'-piperidine]-1'-yl]-[4-methoxy-3-(trifluoromethyl)phenyl]methanone | 8-fluoro-2-methyl-6-(trifluoromethyl)spiro[3,4-dihydropyrrolo[1,2-a]pyrazine-1,4'-piperidine] | 4-methoxy-3-(trifluoromethyl)benzoic acid |
| [8-fluoro-2-methyl-6-(trifluoromethyl)spiro[3,4-dihydropyrrolo[1,2-a]pyrazine-1,4'-piperidine]-1'-yl]-[4-(2-hydroxyethoxy)-3-methoxy-phenyl]methanone | 8-fluoro-2-methyl-6-(trifluoromethyl)spiro[3,4-dihydropyrrolo[1,2-a]pyrazine-1,4'-piperidine] | 4-(2-hydroxyethoxy)-3-methoxy-benzoic acid |
| [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone | 8-fluoro-2-methyl-6-(trifluoromethyl)spiro[3,4-dihydropyrrolo[1,2-a]pyrazine-1,4'-piperidine] | 5-isopropoxy-6-methyl-pyridine-2-carboxylic acid |
| N-cyclopropyl-4-[8-fluoro-2-methyl-6-(trifluoromethyl)spiro[3,4-dihydropyrrolo[1,2-a]pyrazine-1,4'-piperidine]-1'-carbonyl]benzenesulfonamide | 8-fluoro-2-methyl-6-(trifluoromethyl)spiro[3,4-dihydropyrrolo[1,2-a]pyrazine-1,4'-piperidine] | 4-(cyclopropylsulfamoyl)-benzoic acid |
| 4-[8-fluoro-2-methyl-6-(trifluoromethyl)spiro[3,4-dihydropyrrolo[1,2-a]pyrazine-1,4'-piperidine]-1'-carbonyl]-N-methyl-benzenesulfonamide | 8-fluoro-2-methyl-6-(trifluoromethyl)spiro[3,4-dihydropyrrolo[1,2-a]pyrazine-1,4'-piperidine] | 4-(methylsulfamoyl)benzoic acid |
| [4-(difluoromethylsulfonyl)phenyl]-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 4-(difluoromethylsulfonyl)-benzoic acid |
| [8-fluoro-2-methyl-6-(trifluoromethyl)spiro[3,4-dihydropyrrolo[1,2-a]pyrazine-1,4'-piperidine]-1'-yl]-(4-isopropylsulfonylphenyl)methanone | 8-fluoro-2-methyl-6-(trifluoromethyl)spiro[3,4-dihydropyrrolo[1,2-a]pyrazine-1,4'-piperidine] | 4-isopropylsulfonylbenzoic acid |
| [8-fluoro-2-methyl-6-(trifluoromethyl)spiro[3,4-dihydropyrrolo[1,2-a]pyrazine-1,4'-piperidine]-1'-yl]-(4-isopropylsulfonyl-3-methyl-phenyl)methanone | 8-fluoro-2-methyl-6-(trifluoromethyl)spiro[3,4-dihydropyrrolo[1,2-a]pyrazine-1,4'-piperidine] | 4-isopropylsulfonyl-3-methyl-benzoic acid |
| [8-fluoro-2-methyl-6-(trifluoromethyl)spiro[3,4-dihydropyrrolo[1,2-a]pyrazine-1,4'-piperidine]-1'-yl]-(6-isopropoxy-3-pyridyl)methanone | 8-fluoro-2-methyl-6-(trifluoromethyl)spiro[3,4-dihydropyrrolo[1,2-a]pyrazine-1,4'-piperidine] | 6-isopropoxypyridine-3-carboxylic acid |

| Compound name | Amine name | Acid name |
|---|---|---|
| [8-fluoro-2-methyl-6-(trifluoromethyl)spiro[3,4-dihydropyrrolo[1,2-a]pyrazine-1,4'-piperidine]-1'-yl]-[4-(2-hydroxy-2-methyl-propyl)phenyl]methanone | 8-fluoro-2-methyl-6-(trifluoromethyl)spiro[3,4-dihydropyrrolo[1,2-a]pyrazine-1,4'-piperidine] | 4-(2-hydroxy-2-methyl-propyl)benzoic acid |
| [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone | 8-fluoro-2-methyl-6-(trifluoromethyl)spiro[3,4-dihydropyrrolo[1,2-a]pyrazine-1,4'-piperidine] | 3-methoxy-4-[(1R)-1-methylpropoxy]benzoic acid |
| 1-[1'-[4-(1-hydroxy-1-methyl-ethyl)-3-methyl-benzoyl]-2-methyl-spiro[3,4-dihydropyrrolo[1,2-a]pyrazine-1,4'-piperidine]-6-yl]propan-1-one | 1-(2-methylspiro[3,4-dihydropyrrolo[1,2-a]pyrazine-1,4'-piperidine]-6-yl)propan-1-one | 4-(1-hydroxy-1-methyl-ethyl)-3-methyl-benzoic acid |
| 1-[1'-(4-isopropoxy-3-methoxy-benzoyl)-2-methyl-spiro[3,4-dihydropyrrolo[1,2-a]pyrazine-1,4'-piperidine]-6-yl]propan-1-one | 1-(2-methylspiro[3,4-dihydropyrrolo[1,2-a]pyrazine-1,4'-piperidine]-6-yl)propan-1-one | 4-isopropoxy-3-methoxy-benzoic acid |
| 1-[1'-(3-chloro-4-isopropoxy-benzoyl)-2-methyl-spiro[3,4-dihydropyrrolo[1,2-a]pyrazine-1,4'-piperidine]-6-yl]propan-1-one | 1-(2-methylspiro[3,4-dihydropyrrolo[1,2-a]pyrazine-1,4'-piperidine]-6-yl)propan-1-one | 3-chloro-4-isopropoxy-benzoic acid |
| 1-[1'-(4-isopropoxy-3-methyl-benzoyl)-2-methyl-spiro[3,4-dihydropyrrolo[1,2-a]pyrazine-1,4'-piperidine]-6-yl]propan-1-one | 1-(2-methylspiro[3,4-dihydropyrrolo[1,2-a]pyrazine-1,4'-piperidine]-6-yl)propan-1-one | 4-isopropoxy-3-methyl-benzoic acid |
| 1-[2-methyl-1'-[4-(1-piperidyl)benzoyl]spiro[3,4-dihydropyrrolo[1,2-a]pyrazine-1,4'-piperidine]-6-yl]propan-1-one | 1-(2-methylspiro[3,4-dihydropyrrolo[1,2-a]pyrazine-1,4'-piperidine]-6-yl)propan-1-one | 4-(1-piperidyl)benzoic acid |
| 1-[1'-(4-cyclopropylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-cyclopropylbenzoic acid |
| 2,2,2-trifluoro-1-[1'-(4-isobutylbenzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isobutylbenzoic acid |
| 2,2,2-trifluoro-1-[2-methyl-1'-(3-methyl-4-phenyl-benzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methyl-4-phenyl-benzoic acid |
| 1-[1'-[4-(2,2-dimethylpropoxy)benzoyl]-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-(2,2-dimethylpropoxy)benzoic acid |
| 5-[8-fluoro-2-methyl-6-(trifluoromethyl)spiro[3,4-dihydropyrrolo[1,2-a]pyrazine-1,4'-piperidine]-1'-carbonyl]-2-isopropoxy-benzonitrile | 8-fluoro-2-methyl-6-(trifluoromethyl)spiro[3,4-dihydropyrrolo[1,2-a]pyrazine-1,4'-piperidine] | 3-cyano-4-isopropoxy-benzoic acid |
| (4-ethyl-3-methoxy-phenyl)-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 4-ethyl-3-methoxy-benzoic acid |
| (4-cyclopropylphenyl)-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 4-cyclopropylbenzoic acid |
| 1-[1'-[4-(cyclopropylmethoxy)benzoyl]-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-(cyclopropylmethoxy)-benzoic acid |
| 2,2,2-trifluoro-1-[2-methyl-1'-[4-(2,2,2- | 2,2,2-trifluoro-1-(2-methylspiro[3,4- | 4-(2,2,2-trifluoroethoxy)benzoic |

| Compound name | Amine name | Acid name |
|---|---|---|
| trifluoroethoxy)benzoyl]spiro[3,4-dihydropyrrolo[1,2-a]pyrazine-1,4'-piperidine]-6-yl]ethanone | dihydropyrrolo[1,2-a]pyrazine-1,4'-piperidine]-6-yl]ethanone | acid |
| 2,2,2-trifluoro-1-[1'-(4-methoxy-3-phenyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-methoxy-3-phenyl-benzoic acid |
| 2,2,2-trifluoro-1-[1'-(4-isopropyl-3-methylsulfonyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isopropyl-3-methylsulfonyl-benzoic acid |
| 1-[1'-(4-cyclohexylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-cyclohexylbenzoic acid |
| 2,2,2-trifluoro-1-[1'-[4-(1-hydroxycyclopentyl)-3-methyl-benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(1-hydroxycyclopentyl)-3-methyl-benzoic acid |
| (6-chloro-2-methyl-spiro[3,4-dihydropyrrolo[1,2-a]pyrazine-1,4'-piperidine]-1'-yl)-[3-(hydroxymethyl)-4-isopropoxy-phenyl]methanone | 6-chloro-2-methyl-spiro[3,4-dihydropyrrolo[1,2-a]pyrazine-1,4'-piperidine] | 3-(hydroxymethyl)-4-isopropoxy-benzoic acid |
| (6-chloro-2-methyl-spiro[3,4-dihydropyrrolo[1,2-a]pyrazine-1,4'-piperidine]-1'-yl)-[4-(cyclopropylmethoxy)phenyl]methanone | 6-chloro-2-methyl-spiro[3,4-dihydropyrrolo[1,2-a]pyrazine-1,4'-piperidine] | 4-(cyclopropylmethoxy)benzoic acid |
| (6-chloro-2-methyl-spiro[3,4-dihydropyrrolo[1,2-a]pyrazine-1,4'-piperidine]-1'-yl)-[4-(2,2,2-trifluoroethoxy)phenyl]methanone | 6-chloro-2-methyl-spiro[3,4-dihydropyrrolo[1,2-a]pyrazine-1,4'-piperidine] | 4-(2,2,2-trifluoroethoxy)benzoic acid |
| (6-chloro-2-methyl-spiro[3,4-dihydropyrrolo[1,2-a]pyrazine-1,4'-piperidine]-1'-yl)-[4-(2,2-dimethylpropoxy)phenyl]methanone | 6-chloro-2-methyl-spiro[3,4-dihydropyrrolo[1,2-a]pyrazine-1,4'-piperidine] | 4-(2,2-dimethylpropoxy)benzoic acid |
| 5-(6-chloro-2-methyl-spiro[3,4-dihydropyrrolo[1,2-a]pyrazine-1,4'-piperidine]-1'-carbonyl)-2-isopropoxy-benzonitrile | 6-chloro-2-methyl-spiro[3,4-dihydropyrrolo[1,2-a]pyrazine-1,4'-piperidine] | 3-cyano-4-isopropoxy-benzoic acid |
| (6-chloro-2-methyl-spiro[3,4-dihydropyrrolo[1,2-a]pyrazine-1,4'-piperidine]-1'-yl)-(3-methyl-4-phenyl-phenyl)methanone | 6-chloro-2-methyl-spiro[3,4-dihydropyrrolo[1,2-a]pyrazine-1,4'-piperidine] | 3-methyl-4-phenyl-benzoic acid |
| (6-chloro-2-methyl-spiro[3,4-dihydropyrrolo[1,2-a]pyrazine-1,4'-piperidine]-1'-yl)-[4-(trifluoromethoxy)phenyl]methanone | 6-chloro-2-methyl-spiro[3,4-dihydropyrrolo[1,2-a]pyrazine-1,4'-piperidine] | 4-(trifluoromethoxy)benzoic acid |
| (6-chloro-2-methyl-spiro[3,4-dihydropyrrolo[1,2-a]pyrazine-1,4'-piperidine]-1'-yl)-(4-cyclopropylphenyl)methanone | 6-chloro-2-methyl-spiro[3,4-dihydropyrrolo[1,2-a]pyrazine-1,4'-piperidine] | 4-cyclopropylbenzoic acid |
| (6-chloro-2-methyl-spiro[3,4-dihydropyrrolo[1,2-a]pyrazine-1,4'-piperidine]-1'-yl)-(4-isobutylphenyl)methanone | 6-chloro-2-methyl-spiro[3,4-dihydropyrrolo[1,2-a]pyrazine-1,4'-piperidine] | 4-isobutylbenzoic acid |
| (6-chloro-2-methyl-spiro[3,4-dihydropyrrolo[1,2-a]pyrazine-1,4'-piperidine]-1'-yl)-[4-methoxy-3-(trifluoromethyl)phenyl]methanone | 6-chloro-2-methyl-spiro[3,4-dihydropyrrolo[1,2-a]pyrazine-1,4'-piperidine] | 4-methoxy-3-(trifluoromethyl)benzoic acid |
| 1-[1'-[3-(hydroxymethyl)-4-isopropoxy-benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-(hydroxymethyl)-4-isopropoxy-benzoic acid |
| 1-[1'-[4-(cyclopropylmethoxy)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(cyclopropylmethoxy)benzoic acid |
| 1-[1'-(4-methoxy-3-phenyl-benzoyl)-2-methyl-spiro[3,4- | 1-(2-methylspiro[3,4-dihydropyrrolo[1,2- | 4-methoxy-3-phenyl-benzoic acid |

| Compound name | Amine name | Acid name |
|---|---|---|
| dihydropyrrolo[1,2-a]pyrazine-1,4'-piperidine]-6-yl]ethanone | a]pyrazine-1,4'-piperidine]-6-yl]ethanone | |
| 1-(2-methyl-1'-[4-(2,2,2-trifluoroethoxy)benzoyl]spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(2,2,2-trifluoroethoxy)benzoic acid |
| 1-[1'-[4-(2,2-dimethylpropoxy)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(2,2-dimethylpropoxy)benzoic acid |
| 5-(6-acetyl-2-methyl-spiro[3,4-dihydropyrrolo[1,2-a]pyrazine-1,4'-piperidine]-1'-carbonyl)-2-isopropoxy-benzonitrile | 1-(2-methylspiro[3,4-dihydropyrrolo[1,2-a]pyrazine-1,4'-piperidine]-6-yl)ethanone | 3-cyano-4-isopropoxy-benzoic acid |
| 1-[2-methyl-1'-(3-methyl-4-phenyl-benzoyl)spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methyl-4-phenyl-benzoic acid |
| 1-[2-methyl-1'-[4-(trifluoromethoxy)benzoyl]spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(trifluoromethoxy)benzoic acid |
| 1-[1'-(4-cyclopropylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-cyclopropylbenzoic acid |
| 1-[1'-(4-isobutylbenzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-isobutylbenzoic acid |
| (6-chloro-2-methyl-spiro[3,4-dihydropyrrolo[1,2-a]pyrazine-1,4'-piperidine]-1'-yl)-[4-[(4-methyl-1-piperidyl)sulfonyl]phenyl]methanone | 6-chloro-2-methyl-spiro[3,4-dihydropyrrolo[1,2-a]pyrazine-1,4'-piperidine] | 4-[(4-methyl-1-piperidyl)sulfonyl]benzoic acid |
| 2,2,2-trifluoro-1-[1'-(5-isopropoxy-6-methyl-pyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-isopropoxy-6-methyl-pyridine-2-carboxylic acid |
| 2,2,2-trifluoro-1-[2-methyl-1'-[4-[(4-methyl-1-piperidyl)sulfonyl]benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-[(4-methyl-1-piperidyl)sulfonyl]benzoic acid |
| 1-[1'-(3-chloro-4-methoxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 3-chloro-4-methoxy-benzoic acid |
| 2,2,2-trifluoro-1-[1'-(3-fluoro-4-methoxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-fluoro-4-methoxy-benzoic acid |
| 2,2,2-trifluoro-1-[1'-(4-isobutoxybenzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-isobutoxybenzoic acid |
| (4-cyclohexylphenyl)-[2-methyl-6-(2,2,2-trifluoro-1-hydroxy-ethyl)spiro[3,4-dihydropyrrolo[1,2-a]pyrazine-1,4'-piperidine]-1'-yl]methanone | 2,2,2-trifluoro-1-(2-methylspiro[3,4-dihydropyrrolo[1,2-a]pyrazine-1,4'-piperidine]-6-yl)ethanol | 4-cyclohexylbenzoic acid |
| 2,2,2-trifluoro-1-[1'-(4-methoxy-3-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-methoxy-3-methyl-benzoic acid |
| 1-[1'-(4-cyclohexylbenzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-cyclohexylbenzoic acid |
| 2,2,2-trifluoro-1-[1'-(3-fluoro-4- | 1-(3,3-dimethylspiro[2,4- | 3-fluoro-4-isopropoxy- |

| Compound name | Amine name | Acid name |
|---|---|---|
| isopropoxy-benzoyl)-3,3-dimethyl-spiro[2,4-dihydropyrrolo[1,2-a]pyrazine-1,4'-piperidine]-6-yl]ethanone | dihydropyrrolo[1,2-a]pyrazine-1,4'-piperidine]-6-yl)-2,2,2-trifluoro-ethanone | benzoic acid |
| 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 5-isopropoxy-6-methyl-pyridine-2-carboxylic acid |
| 2,2,2-trifluoro-1-[1'-(4-isopropoxy-3-methoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-isopropoxy-3-methoxy-benzoic acid |
| 2,2,2-trifluoro-1-[1'-(2-fluoro-4-isopropoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 2-fluoro-4-isopropoxy-benzoic acid |
| 1-[1'-(3-chloro-4-isopropoxy-benzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 3-chloro-4-isopropoxy-benzoic acid |
| 2,2,2-trifluoro-1-[1'-(4-isopentyloxy-3-methoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-isopentyloxy-3-methoxy-benzoic acid |
| 2,2,2-trifluoro-1-[1'-(4-isopropoxy-3-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-isopropoxy-3-methyl-benzoic acid |
| 2,2,2-trifluoro-1-[1'-(4-isopentyloxybenzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-isopentyloxybenzoic acid |
| [3-fluoro-4-(1-hydroxycyclobutyl)phenyl]-[8-fluoro-2-methyl-6-(trifluoromethyl)spiro[3,4-dihydropyrrolo[1,2-a]pyrazine-1,4'-piperidine]-1'-yl]methanone | 8-fluoro-2-methyl-6-(trifluoromethyl)spiro[3,4-dihydropyrrolo[1,2-a]pyrazine-1,4'-piperidine] | 3-fluoro-4-(1-hydroxycyclobutyl)-benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxycyclobutyl)-3-methyl-phenyl]methanone | 8-fluoro-2-methyl-6-(trifluoromethyl)spiro[3,4-dihydropyrrolo[1,2-a]pyrazine-1,4'-piperidine] | 4-(1-hydroxycyclobutyl)-3-methyl-benzoic acid |
| [8-fluoro-2-methyl-6-(trifluoromethyl)spiro[3,4-dihydropyrrolo[1,2-a]pyrazine-1,4'-piperidine]-1'-yl]-[4-(1-hydroxycyclobutyl)-3-methoxy-phenyl]methanone | 8-fluoro-2-methyl-6-(trifluoromethyl)spiro[3,4-dihydropyrrolo[1,2-a]pyrazine-1,4'-piperidine] | 4-(1-hydroxycyclobutyl)-3-methoxy-benzoic acid |
| 2,2,2-trifluoro-1-[1'-(4-hydroxy-3-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-hydroxy-3-methyl-benzoic acid |
| 1-[1'-(3-chloro-4-hydroxy-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 3-chloro-4-hydroxy-benzoic acid |
| (4-isopropoxy-3-methoxy-phenyl)-[2-methyl-6,7-bis(trifluoromethyl)spiro[3,4-dihydropyrrolo[1,2-a]pyrazine-1,4'-piperidine]-1'-yl]methanone | 2-methyl-6,7-bis(trifluoromethyl)spiro[3,4-dihydropyrrolo[1,2-a]pyrazine-1,4'-piperidine] | 4-isopropoxy-3-methoxy-benzoic acid |
| 1-[2-methyl-1'-[4-(3,3,3-trifluoropropoxymethyl)benzoyl]spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(3,3,3-trifluoropropoxymethyl)-benzoic acid |
| 1-[2-methyl-1'-[4-(2,2,2- | 1-(2-methylspiro[3,4- | 4-(2,2,2- |

| Compound name | Amine name | Acid name |
|---|---|---|
| trifluoroethoxymethyl)benzoyl]spiro[3,4-dihydropyrrolo[1,2-a]pyrazine-1,4'-piperidine]-6-yl]ethanone | dihydropyrrolo[1,2-a]pyrazine-1,4'-piperidine-6-yl)ethanone | trifluoroethoxymethyl)-benzoic acid |
| (4-isopropoxy-3-methyl-phenyl)-(2-methyl-6-methylsulfonyl-spiro[3,4-dihydropyrrolo[1,2-a]pyrazine-1,4'-piperidine]-1'-yl)methanone | 2-methyl-6-methylsulfonyl-spiro[3,4-dihydropyrrolo[1,2-a]pyrazine-1,4'-piperidine] | 4-isopropoxy-3-methyl-benzoic acid |
| (4-cyclohexylphenyl)-(2-methyl-6-methylsulfonyl-spiro[3,4-dihydropyrrolo[1,2-a]pyrazine-1,4'-piperidine]-1'-yl)methanone | 2-methyl-6-methylsulfonyl-spiro[3,4-dihydropyrrolo[1,2-a]pyrazine-1,4'-piperidine] | 4-cyclohexylbenzoic acid |
| (3-chloro-4-isopropoxy-phenyl)-(2-methyl-6-methylsulfonyl-spiro[3,4-dihydropyrrolo[1,2-a]pyrazine-1,4'-piperidine]-1'-yl)methanone | 2-methyl-6-methylsulfonyl-spiro[3,4-dihydropyrrolo[1,2-a]pyrazine-1,4'-piperidine] | 3-chloro-4-isopropoxy-benzoic acid |
| 2,2,2-trifluoro-1-[1'-(4-methoxy-3-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-methoxy-3-methyl-benzoic acid |
| 2,2,2-trifluoro-1-[1'-[4-methoxy-3-(trifluoromethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-methoxy-3-(trifluoromethyl)benzoic acid |
| 2,2,2-trifluoro-1-[1'-[3-fluoro-4-(1-hydroxy-1-methyl-ethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-fluoro-4-(1-hydroxy-1-methyl-ethyl)benzoic acid |
| 1-[1'-(3-chloro-4-methoxy-benzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 3-chloro-4-methoxy-benzoic acid |
| 2,2,2-trifluoro-1-[1'-(4-methoxy-2-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-methoxy-2-methyl-benzoic acid |
| 2,2,2-trifluoro-1-[1'-(2-fluoro-4-methoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 2-fluoro-4-methoxy-benzoic acid |
| 1-[1'-(3-chloro-4-ethoxy-benzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 3-chloro-4-ethoxy-benzoic acid |
| 1-[1'-(4-tert-butyl-3-methoxy-benzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-tert-butyl-3-methoxy-benzoic acid |
| 1-[1'-(4-isopropoxy-3-methyl-benzoyl)-3,3-dimethyl-spiro[2,4-dihydropyrrolo[1,2-a]pyrazine-1,4'-piperidine]-7-yl]ethanone | 1-(3,3-dimethylspiro[2,4-dihydropyrrolo[1,2-a]pyrazine-1,4'-piperidine]-7-yl)ethanone | 4-isopropoxy-3-methyl-benzoic acid |
| 1-[1'-(4-isopropoxy-3-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)ethanone | 4-isopropoxy-3-methyl-benzoic acid |
| 1-[1'-(4-cyclohexylbenzoyl)-3,3-dimethyl-spiro[2,4-dihydropyrrolo[1,2-a]pyrazine-1,4'-piperidine]-7-yl]ethanone | 1-(3,3-dimethylspiro[2,4-dihydropyrrolo[1,2-a]pyrazine-1,4'-piperidine]-7-yl)ethanone | 4-cyclohexylbenzoic acid |
| 1-[1'-(4-cyclohexylbenzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)ethanone | 4-cyclohexylbenzoic acid |
| 1-[1'-(4-methoxy-3-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)ethanone | 4-methoxy-3-methyl-benzoic acid |
| 1-[1'-[4-methoxy-3-(trifluoromethyl)benzoyl]-3,3- | 1-(3,3-dimethylspiro[2,4-dihydropyrrolo[1,2- | 4-methoxy-3-(trifluoromethyl)benzoic |

| Compound name | Amine name | Acid name |
| --- | --- | --- |
| dimethyl-spiro[2,4-dihydropyrrolo[1,2-a]pyrazine-1,4'-piperidine]-6-yl]ethanone | a]pyrazine-1,4'-piperidine-6-yl)ethanone | acid |
| 1-[1'-(3-chloro-4-methoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine-6-yl)ethanone | 3-chloro-4-methoxy-benzoic acid |
| 1-[1'-(2-fluoro-4-isopropoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine-6-yl)ethanone | 2-fluoro-4-isopropoxy-benzoic acid |
| 1-[1'-[4-isopropoxy-3-(trifluoromethyl)benzoyl]-3,3-dimethyl-spiro[2,4-dihydropyrrolo[1,2-a]pyrazine-1,4'-piperidine]-7-yl]ethanone | 1-(3,3-dimethylspiro[2,4-dihydropyrrolo[1,2-a]pyrazine-1,4'-piperidine-7-yl)ethanone | 4-isopropoxy-3-(trifluoromethyl)benzoic acid |
| 1-[1'-[4-isopropoxy-3-(trifluoromethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine-6-yl)ethanone | 4-isopropoxy-3-(trifluoromethyl)benzoic acid |
| 1-[1'-(3-chloro-4-isopropoxy-benzoyl)-3,3-dimethyl-spiro[2,4-dihydropyrrolo[1,2-a]pyrazine-1,4'-piperidine]-7-yl]ethanone | 1-(3,3-dimethylspiro[2,4-dihydropyrrolo[1,2-a]pyrazine-1,4'-piperidine-7-yl)ethanone | 3-chloro-4-isopropoxy-benzoic acid |
| 1-[1'-(3-chloro-4-isopropoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine-6-yl)ethanone | 3-chloro-4-isopropoxy-benzoic acid |
| 1-[1'-(4-tert-butyl-3-methoxy-benzoyl)-3,3-dimethyl-spiro[2,4-dihydropyrrolo[1,2-a]pyrazine-1,4'-piperidine]-7-yl]ethanone | 1-(3,3-dimethylspiro[2,4-dihydropyrrolo[1,2-a]pyrazine-1,4'-piperidine-7-yl)ethanone | 4-tert-butyl-3-methoxy-benzoic acid |
| 1-[1'-(4-tert-butyl-3-methoxy-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine-6-yl)ethanone | 4-tert-butyl-3-methoxy-benzoic acid |
| 2,2,2-trifluoro-1-[1'-(2-fluoro-4-methoxy-benzoyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 2-fluoro-4-methoxy-benzoic acid |
| 2,2,2-trifluoro-1-[1'-[4-(1-hydroxy-1-methyl-ethyl)-3-methyl-benzoyl]-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 4-(1-hydroxy-1-methyl-ethyl)-3-methyl-benzoic acid |
| 2,2,2-trifluoro-1-[1'-(4-isopropoxy-3-methyl-benzoyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 4-isopropoxy-3-methyl-benzoic acid |
| 1-[1'-(3-chloro-4-methoxy-benzoyl)-2,4,4-trimethyl-spiro[3H-pyrrolo[1,2-a]pyrazine-1,4'-piperidine]-7-yl]-2,2,2-trifluoro-ethanone | 2,2,2-trifluoro-1-(2,4,4-trimethylspiro[3H-pyrrolo[1,2-a]pyrazine-1,4'-piperidine]-7-yl)ethanone | 3-chloro-4-methoxy-benzoic acid |
| 2,2,2-trifluoro-1-[1'-(2-fluoro-4-isopropoxy-benzoyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 2-fluoro-4-isopropoxy-benzoic acid |
| 2,2,2-trifluoro-1-[1'-(4-methoxy-3-methyl-benzoyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 4-methoxy-3-methyl-benzoic acid |
| 2,2,2-trifluoro-1-[1'-(5-isopropoxy-6-methyl-pyridine-2-carbonyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 5-isopropoxy-6-methyl-pyridine-2-carboxylic acid |
| 1-[1'-(3-chloro-4-isopropoxy-benzoyl)-2,4,4-trimethyl-spiro[3H-pyrrolo[1,2-a]pyrazine-1,4'- | 2,2,2-trifluoro-1-(2,4,4-trimethylspiro[3H-pyrrolo[1,2-a]pyrazine- | 3-chloro-4-isopropoxy-benzoic acid |

| Compound name | Amine name | Acid name |
|---|---|---|
| piperidine]-7-yl]-2,2,2-trifluoro-ethanone | 1,4'-piperidine]-7-yl)ethanone | |
| 2,2,2-trifluoro-1-[1'-(3-fluoro-4-isopropoxy-benzoyl)-2,4,4-trimethyl-spiro[3H-pyrrolo[1,2-a]pyrazine-1,4'-piperidine]-7-yl]ethanone | 2,2,2-trifluoro-1-(2,4,4-trimethylspiro[3H-pyrrolo[1,2-a]pyrazine-1,4'-piperidine]-7-yl)ethanone | 3-fluoro-4-isopropoxy-benzoic acid |
| 1-[1'-[4-(cyclopropylmethoxy)-3-fluoro-benzoyl]-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-(cyclopropylmethoxy)-3-fluoro-benzoic acid |
| 1-[1'-[4-(cyclopropylmethoxy)-3-fluoro-benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(cyclopropylmethoxy)-3-fluoro-benzoic acid |
| 1-[1'-[4-(cyclopropylmethoxy)-3-fluoro-benzoyl]-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-(cyclopropylmethoxy)-3-fluoro-benzoic acid |
| 2,2,2-trifluoro-1-[1'-(4-isopropoxy-3-methyl-benzoyl)-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 4-isopropoxy-3-methyl-benzoic acid |
| 2,2,2-trifluoro-1-[1'-[4-methoxy-3-(trifluoromethyl)benzoyl]-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 4-methoxy-3-(trifluoromethyl)benzoic acid |
| 2,2,2-trifluoro-1-[1'-(3-fluoro-4-isopropoxy-benzoyl)-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 3-fluoro-4-isopropoxy-benzoic acid |
| (7,8-difluoro-3,3-dimethyl-spiro[2,4-dihydropyrrolo[1,2-a]pyrazine-1,4'-piperidine]-1'-yl)-(4-isopropoxy-3-methyl-phenyl)methanone | 7,8-difluoro-3,3-dimethyl-spiro[2,4-dihydropyrrolo[1,2-a]pyrazine-1,4'-piperidine] | 4-isopropoxy-3-methyl-benzoic acid |
| (7,8-difluoro-3,3-dimethyl-spiro[2,4-dihydropyrrolo[1,2-a]pyrazine-1,4'-piperidine]-1'-yl)-(4-isopentyloxyphenyl)methanone | 7,8-difluoro-3,3-dimethyl-spiro[2,4-dihydropyrrolo[1,2-a]pyrazine-1,4'-piperidine] | 4-isopentyloxybenzoic acid |
| 2,2,2-trifluoro-1-[1'-(4-methoxy-3-methyl-benzoyl)-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 4-methoxy-3-methyl-benzoic acid |
| 1-[1'-[4-isopropoxy-3-(trifluoromethyl)benzoyl]-2,4,4-trimethyl-spiro[3H-pyrrolo[1,2-a]pyrazine-1,4'-piperidine]-6-yl]ethanone | 1-(2,4,4-trimethylspiro[3H-pyrrolo[1,2-a]pyrazine-1,4'-piperidine]-6-yl)ethanone | 4-isopropoxy-3-(trifluoromethyl)benzoic acid |
| 1-[1'-[3-fluoro-4-(1-hydroxy-1-methyl-ethyl)benzoyl]-2,4,4-trimethyl-spiro[3H-pyrrolo[1,2-a]pyrazine-1,4'-piperidine]-6-yl]ethanone | 1-(2,4,4-trimethylspiro[3H-pyrrolo[1,2-a]pyrazine-1,4'-piperidine]-6-yl)ethanone | 3-fluoro-4-(1-hydroxy-1-methyl-ethyl)benzoic acid |
| 2,2,2-trifluoro-1-[1'-(4-isopropoxy-3-methoxy-benzoyl)-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 4-isopropoxy-3-methoxy-benzoic acid |
| 2,2,2-trifluoro-1-[1'-[3-fluoro-4-(1-hydroxy-1-methyl-ethyl)benzoyl]-2,4,4-trimethyl-spiro[3H-pyrrolo[1,2-a]pyrazine-1,4'-piperidine]-6-yl]ethanone | 2,2,2-trifluoro-1-(2,4,4-trimethylspiro[3H-pyrrolo[1,2-a]pyrazine-1,4'-piperidine]-6-yl)ethanone | 3-fluoro-4-(1-hydroxy-1-methyl-ethyl)benzoic acid |
| 1-[1'-(4-isopropoxy-3-methyl-benzoyl)-2,4,4-trimethyl-spiro[3H-pyrrolo[1,2-a]pyrazine-1,4'-piperidine]-6-yl]ethanone | 1-(2,4,4-trimethylspiro[3H-pyrrolo[1,2-a]pyrazine-1,4'-piperidine]-6-yl)ethanone | 4-isopropoxy-3-methyl-benzoic acid |
| 1-[1'-(4-cyclohexylbenzoyl)-2,4,4-trimethyl-spiro[3H-pyrrolo[1,2- | 1-(2,4,4-trimethylspiro[3H- | 4-cyclohexylbenzoic acid |

| Compound name | Amine name | Acid name |
|---|---|---|
| a]pyrazine-1,4'-piperidine]-6-yl]ethanone | pyrrolo[1,2-a]pyrazine-1,4'-piperidine]-6-yl)ethanone | |
| 1-[1'-(4-hydroxy-3-methyl-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-hydroxy-3-methyl-benzoic acid |
| 1-[1'-(3-chloro-4-hydroxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 3-chloro-4-hydroxy-benzoic acid |
| 1-[1'-(4-methoxy-3-methyl-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-methoxy-3-methyl-benzoic acid |
| 1-[1'-(3-chloro-4-methoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 3-chloro-4-methoxy-benzoic acid |
| 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-methoxy-3-(trifluoromethyl)benzoic acid |
| 1-[1'-[4-isopropoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropoxy-3-(trifluoromethyl)benzoic acid |
| 1-[1'-(2-fluoro-4-isopropoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 2-fluoro-4-isopropoxy-benzoic acid |
| 1-[1'-(2-fluoro-4-methoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 2-fluoro-4-methoxy-benzoic acid |
| 2,2-dimethyl-1-[2-methyl-1'-(3-methyl-4-methylsulfonyl-benzoyl)spiro[3,4-dihydropyrrolo[1,2-a]pyrazine-1,4'-piperidine]-6-yl]propan-1-one | 2,2-dimethyl-1-(2-methylspiro[3,4-dihydropyrrolo[1,2-a]pyrazine-1,4'-piperidine]-6-yl)propan-1-one | 3-methyl-4-methylsulfonyl-benzoic acid |
| 1-[1'-(3-fluoro-4-isopropoxy-benzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 3-fluoro-4-isopropoxy-benzoic acid |
| 1-[1'-(4-isopropylsulfonylbenzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopropylsulfonylbenzoic acid |
| 1-[1'-(4-isopentyloxybenzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isopentyloxybenzoic acid |
| 1-[1'-(4-ethylsulfonyl-3-methyl-benzoyl)-2-methyl-spiro[3,4- | 2,2-dimethyl-1-(2-methylspiro[3,4- | 4-ethylsulfonyl-3-methyl-benzoic acid |

| Compound name | Amine name | Acid name |
|---|---|---|
| dihydropyrrolo[1,2-a]pyrazine-1,4'-piperidine]-6-yl]-2,2-dimethyl-propan-1-one | dihydropyrrolo[1,2-a]pyrazine-1,4'-piperidine]-6-yl)propan-1-one | |
| 2,2-dimethyl-1-[2-methyl-1'-[4-(trifluoromethylsulfonyl)benzoyl]spiro[3,4-dihydropyrrolo[1,2-a]pyrazine-1,4'-piperidine]-6-yl]propan-1-one | 2,2-dimethyl-1-(2-methylspiro[3,4-dihydropyrrolo[1,2-a]pyrazine-1,4'-piperidine]-6-yl)propan-1-one | 4-(trifluoromethylsulfonyl)-benzoic acid |
| 1-[1'-[7-(difluoromethyl)-5-methyl-pyrazolo[1,5-a]pyrimidine-3-carbonyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 7-(difluoromethyl)-5-methyl-pyrazolo[1,5-a]pyrimidine-3-carboxylic acid |
| 1-[1'-(4-isobutylsulfonylbenzoyl)-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-isobutylsulfonylbenzoic acid |
| 1-[1'-[4-(1,1-dimethylpropyl)benzoyl]-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-(1,1-dimethylpropyl)benzoic acid |
| 1-[1'-[4-(1,1-dimethylpropyl)benzoyl]-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-(1,1-dimethylpropyl)benzoic acid |
| 1-[1'-[4-(1,1-diethylpropyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(1,1-diethylpropyl)benzoic acid |
| 1-[1'-[4-(1,1-dimethylpropyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-(1,1-dimethylpropyl)benzoic acid |
| 1-[1'-[3-methoxy-4-(3,3,3-trifluoropropoxymethyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-(3,3,3-trifluoropropoxymethyl)-benzoic acid |
| 1-[1'-[3-methoxy-4-(2,2,2-trifluoroethoxymethyl)benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 3-methoxy-4-(2,2,2-trifluoroethoxymethyl)-benzoic acid |
| 2,2,2-trifluoro-1-[2-methyl-1'-[4-(3,3,3-trifluoropropoxymethyl)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(3,3,3-trifluoropropoxymethyl)-benzoic acid |
| 2,2,2-trifluoro-1-[2-methyl-1'-[4-(2,2,2-trifluoroethoxymethyl)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-(2,2,2-trifluoroethoxymethyl)-benzoic acid |
| 2,2,2-trifluoro-1-[1'-[3-methoxy-4-(3,3,3-trifluoropropoxymethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methoxy-4-(3,3,3-trifluoropropoxymethyl)-benzoic acid |
| 2,2,2-trifluoro-1-[1'-[3-methoxy-4-(2,2,2-trifluoroethoxymethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methoxy-4-(2,2,2-trifluoroethoxymethyl)-benzoic acid |
| 1-[3,3-dimethyl-1'-[4-(3,3,3-trifluoropropoxymethyl)benzoyl]spiro[2,4-dihydropyrrolo[1,2-a]pyrazine- | 1-(3,3-dimethylspiro[2,4-dihydropyrrolo[1,2-a]pyrazine-1,4'- | 4-(3,3,3-trifluoropropoxymethyl)-benzoic acid |

| Compound name | Amine name | Acid name |
| --- | --- | --- |
| 1,4'-piperidine]-6-yl]-2,2,2-trifluoro-ethanone | piperidine]-6-yl)-2,2,2-trifluoro-ethanone | |
| 1-(3,3-dimethyl-1'-[4-(2,2,2-trifluoroethoxymethyl)benzoyl]spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-(2,2,2-trifluoroethoxymethyl)-benzoic acid |
| 2,2,2-trifluoro-1-[1'-[3-methoxy-4-(3,3,3-trifluoropropoxymethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-methoxy-4-(3,3,3-trifluoropropoxymethyl)-benzoic acid |
| 2,2,2-trifluoro-1-[1'-[3-methoxy-4-(2,2,2-trifluoroethoxymethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-methoxy-4-(2,2,2-trifluoroethoxymethyl)-benzoic acid |
| 1-[1'-[4-[bis(2,2,2-trifluoroethoxy)methyl]-3-chloro-benzoyl]-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 4-[bis(2,2,2-trifluoroethoxy)methyl]-3-chloro-benzoic acid |
| 2,2,2-trifluoro-1-[1'-(4-hydroxy-3-methyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-hydroxy-3-methyl-benzoic acid |
| 1-[1'-(3-chloro-4-hydroxy-benzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 3-chloro-4-hydroxy-benzoic acid |
| 2,2,2-trifluoro-1-[1'-[4-hydroxy-3-(trifluoromethyl)benzoyl]-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-hydroxy-3-(trifluoromethyl)benzoic acid |
| 2,2,2-trifluoro-1-[1'-[4-hydroxy-3-(trifluoromethyl)benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-hydroxy-3-(trifluoromethyl)benzoic acid |
| 1-[1'-[4-hydroxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one | 2,2-dimethyl-1-(2-methylspiro[3,4-dihydropyrrolo[1,2-a]pyrazine-1,4'-piperidine]-6-yl)propan-1-one | 4-hydroxy-3-(trifluoromethyl)benzoic acid |
| 2,2,2-trifluoro-1-[1'-(3-hydroxy-4-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-hydroxy-4-methyl-benzoic acid |
| 2,2,2-trifluoro-1-[1'-(4-hydroxy-3,5-dimethyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-hydroxy-3,5-dimethyl-benzoic acid |
| 2,2,2-trifluoro-1-[1'-(2-fluoro-5-hydroxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 2-fluoro-5-hydroxy-benzoic acid |
| 2,2,2-trifluoro-1-[2-methyl-1'-(4-tetrahydropyran-4-yloxybenzoyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-tetrahydropyran-4-yloxybenzoic acid |
| 1-[1'-(4-chloro-3-hydroxy-benzoyl)-2-methylspiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-chloro-3-hydroxy-benzoic acid |
| 2,2,2-trifluoro-1-[1'-(3-hydroxy-2-methyl-benzoyl)-2-methyl-spiro[3,4- | 2,2,2-trifluoro-1-(2-methylspiro[3,4- | 3-hydroxy-2-methyl-benzoic acid |

| Compound name | Amine name | Acid name |
|---|---|---|
| dihydropyrrolo[1,2-a]pyrazine-1,4'-piperidine]-6-yl]ethanone | dihydropyrrolo[1,2-a]pyrazine-1,4'-piperidine]-6-yl)ethanone | |
| 2,2,2-trifluoro-1-[1'-(4-fluoro-3-hydroxy-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-fluoro-3-hydroxy-benzoic acid |
| 2,2,2-trifluoro-1-[1'-(4-fluoro-3-methyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-fluoro-3-methyl-benzoic acid |
| 1-[1'-(4-chloro-3-methyl-benzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3 4-dihydropyrrolo[1,2-a]pyrazine-1,4'-piperidine]-6-yl)ethanone | 4-chloro-3-methyl-benzoic acid |
| [8-chloro-2-methyl-6-(trifluoromethyl)spiro[3,4-dihydropyrrolo[1,2-a]pyrazine-1,4'-piperidine]-1'-yl]-[4-(1-hydroxy-1-methyl-ethyl)phenyl]methanone | 8-chloro-2-methyl-6-(trifluoromethyl)spiro[3,4-dihydropyrrolo[1,2-a]pyrazine-1,4'-piperidine] | 4-(1-hydroxy-1-methyl-ethyl)benzoic acid |
| [8-chloro-2-methyl-6-(trifluoromethyl)spiro[3,4-dihydropyrrolo[1,2-a]pyrazine-1,4'-piperidine]-1'-yl]-[3-fluoro-4-(1-hydroxy-1-methyl-ethyl)phenyl]methanone | 8-chloro-2-methyl-6-(trifluoromethyl)spiro[3,4-dihydropyrrolo[1,2-a]pyrazine-1,4'-piperidine] | 3-fluoro-4-(1-hydroxy-1-methyl-ethyl)benzoic acid |
| [8-chloro-2-methyl-6-(trifluoromethyl)spiro[3,4-dihydropyrrolo[1,2-a]pyrazine-1,4'-piperidine]-1'-yl]-[4-(1-hydroxycyclobutyl)phenyl]methanone | 8-chloro-2-methyl-6-(trifluoromethyl)spiro[3,4-dihydropyrrolo[1,2-a]pyrazine-1,4'-piperidine] | 4-(1-hydroxycyclobutyl)-benzoic acid |
| [8-chloro-2-methyl-6-(trifluoromethyl)spiro[3,4-dihydropyrrolo[1,2-a]pyrazine-1,4'-piperidine]-1'-yl]-[3-fluoro-4-(2-hydroxy-2-methyl-propyl)phenyl]methanone | 8-chloro-2-methyl-6-(trifluoromethyl)spiro[3,4-dihydropyrrolo[1,2-a]pyrazine-1,4'-piperidine] | 3-fluoro-4-(2-hydroxy-2-methyl-propyl)benzoic acid |
| [8-chloro-2-methyl-6-(trifluoromethyl)spiro[3,4-dihydropyrrolo[1,2-a]pyrazine-1,4'-piperidine]-1'-yl]-(4-methoxy-3-methyl-phenyl)methanone | 8-chloro-2-methyl-6-(trifluoromethyl)spiro[3,4-dihydropyrrolo[1,2-a]pyrazine-1,4'-piperidine] | 4-methoxy-3-methyl-benzoic acid |
| [8-chloro-2-methyl-6-(trifluoromethyl)spiro[3,4-dihydropyrrolo[1,2-a]pyrazine-1,4'-piperidine]-1'-yl]-(4-ethoxy-3-methyl-phenyl)methanone | 8-chloro-2-methyl-6-(trifluoromethyl)spiro[3,4-dihydropyrrolo[1,2-a]pyrazine-1,4'-piperidine] | 4-ethoxy-3-methyl-benzoic acid |
| [8-chloro-2-methyl-6-(trifluoromethyl)spiro[3,4-dihydropyrrolo[1,2-a]pyrazine-1,4'-piperidine]-1'-yl]-(2-fluoro-4-isopropoxy-phenyl)methanone | 8-chloro-2-methyl-6-(trifluoromethyl)spiro[3,4-dihydropyrrolo[1,2-a]pyrazine-1,4'-piperidine] | 2-fluoro-4-isopropoxy-benzoic acid |
| [8-chloro-2-methyl-6-(trifluoromethyl)spiro[3,4-dihydropyrrolo[1,2-a]pyrazine-1,4'-piperidine]-1'-yl]-[4-(2,2,2-trifluoroethoxymethyl)phenyl]methanone | 8-chloro-2-methyl-6-(trifluoromethyl)spiro[3,4-dihydropyrrolo[1,2-a]pyrazine-1,4'-piperidine] | 4-(2,2,2-trifluoroethoxymethyl)-benzoic acid |
| 2,2,2-trifluoro-1-[2-methyl-1'-(5-phenylpyridine-2-carbonyl)spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-phenylpyridine-2-carboxylic acid |
| 1-(3,3-dimethyl-1'-(5-phenylpyridine-2-carbonyl)spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 5-phenylpyridine-2-carboxylic acid |
| 2,2,2-trifluoro-1-[1'-(3-methoxy-4-phenyl-benzoyl)-2-methyl-spiro[3,4-dihydropyrrolo[1,2-a]pyrazine-1,4'- | 2,2,2-trifluoro-1-(2-methylspiro[3,4-dihydropyrrolo[1,2- | 3-methoxy-4-phenyl-benzoic acid |

| Compound name | Amine name | Acid name |
|---|---|---|
| piperidine]-6-yl]ethanone | a]pyrazine-1,4'-piperidine]-6-yl)ethanone | |
| 2,2,2-trifluoro-1-[1'-(3-methoxy-4-phenyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-methoxy-4-phenyl-benzoic acid |
| 2,2,2-trifluoro-1-[1'-(3-hydroxy-4-phenyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-hydroxy-4-phenyl-benzoic acid |
| 2,2,2-trifluoro-1-[1'-(3-hydroxy-4-phenyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-hydroxy-4-phenyl-benzoic acid |
| 2,2,2-trifluoro-1-[1'-(3-fluoro-4-phenyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-fluoro-4-phenyl-benzoic acid |
| 2,2,2-trifluoro-1-[1'-(3-fluoro-4-phenyl-benzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 3-fluoro-4-phenyl-benzoic acid |
| 2,2,2-trifluoro-1-[(3R)-1'-(2-fluoro-4-isopropoxy-benzoyl)-2,3-dimethyl-spiro[3,4-dihydropyrrolo[1,2-a]pyrazine-1,4'-piperidine]-6-yl]ethanone | 1-[(3R)-2,3-dimethylspiro[3,4-dihydropyrrolo[1,2-a]pyrazine-1,4'-piperidine]-6-yl]-2,2,2-trifluoro-ethanone | 2-fluoro-4-isopropoxy-benzoic acid |
| 1-[(3R)-1'-(3-chloro-4-methoxy-benzoyl)-2,3-dimethyl-spiro[3,4-dihydropyrrolo[1,2-a]pyrazine-1,4'-piperidine]-6-yl]-2,2,2-trifluoro-ethanone | 1-[(3R)-2,3-dimethylspiro[3,4-dihydropyrrolo[1,2-a]pyrazine-1,4'-piperidine]-6-yl]-2,2,2-trifluoro-ethanone | 3-chloro-4-methoxy-benzoic acid |
| 2,2,2-trifluoro-1-[(3R)-1'-(4-methoxy-3-methyl-benzoyl)-2,3-dimethyl-spiro[3,4-dihydropyrrolo[1,2-a]pyrazine-1,4'-piperidine]-6-yl]ethanone | 1-[(3R)-2,3-dimethylspiro[3,4-dihydropyrrolo[1,2-a]pyrazine-1,4'-piperidine]-6-yl]-2,2,2-trifluoro-ethanone | 4-methoxy-3-methyl-benzoic acid |
| 2,2,2-trifluoro-1-[(3R)-1'-[4-methoxy-3-(trifluoromethyl)benzoyl]-2,3-dimethyl-spiro[3,4-dihydropyrrolo[1,2-a]pyrazine-1,4'-piperidine]-6-yl]ethanone | 1-[(3R)-2,3-dimethylspiro[3,4-dihydropyrrolo[1,2-a]pyrazine-1,4'-piperidine]-6-yl]-2,2,2-trifluoro-ethanone | 4-methoxy-3-(trifluoromethyl)benzoic acid |
| 2,2,2-trifluoro-1-[2-methyl-1'-[3-methyl-4-(trifluoromethyl)benzoyl]spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methyl-4-(trifluoromethyl)benzoic acid |
| 1-[1'-[4-ethoxy-3-(trifluoromethyl)benzoyl]-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-ethoxy-3-(trifluoromethyl)benzoic acid |
| 2,2,2-trifluoro-1-[1'-(5-isopropoxy-4-methyl-pyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-isopropoxy-4-methyl-pyridine-2-carboxylic acid |
| [6-(cyclopropanecarbonyl)-2-methyl-spiro[3,4-dihydropyrrolo[1,2-a]pyrazine-1,4'-piperidine]-1'-yl]-[4-methoxy-3-(trifluoromethyl)phenyl]methanone | cyclopropyl-(2-methylspiro[3,4-dihydropyrrolo[1,2-a]pyrazine-1,4'-piperidine]-6-yl)methanone | 4-methoxy-3-(trifluoromethyl)benzoic acid |
| (3-chloro-4-methoxy-phenyl)-[6-(cyclopropanecarbonyl)-2-methyl-spiro[3,4-dihydropyrrolo[1,2- | cyclopropyl-(2-methylspiro[3,4-dihydropyrrolo[1,2- | 3-chloro-4-methoxy-benzoic acid |

| Compound name | Amine name | Acid name |
|---|---|---|
| a]pyrazine-1,4'-piperidine]-1'-yl]methanone | a]pyrazine-1,4'-piperidine]-6-yl)methanone | |
| (4-cyclohexylphenyl)-[6-(cyclopropanecarbonyl)-2-methyl-spiro[3,4-dihydropyrrolo[1,2-a]pyrazine-1,4'-piperidine]-1'-yl]methanone | cyclopropyl-(2-methylspiro[3,4-dihydropyrrolo[1,2-a]pyrazine-1,4'-piperidine]-6-yl)methanone | 4-cyclohexylbenzoic acid |
| [6-(cyclopropanecarbonyl)-2-methyl-spiro[3,4-dihydropyrrolo[1,2-a]pyrazine-1,4'-piperidine]-1'-yl]-[4-isopropoxy-3-(trifluoromethyl)phenyl]methanone | cyclopropyl-(2-methylspiro[3,4-dihydropyrrolo[1,2-a]pyrazine-1,4'-piperidine]-6-yl)methanone | 4-isopropoxy-3-(trifluoromethyl)benzoic acid |
| 2,2,2-trifluoro-1-[(3S)-1'-[4-methoxy-3-(trifluoromethyl)benzoyl]-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 4-methoxy-3-(trifluoromethyl)benzoic acid |
| 2,2,2-trifluoro-1-[(3S)-1'-(4-methoxy-3-methyl-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 4-methoxy-3-methyl-benzoic acid |
| 1-[(3S)-1'-(3-chloro-4-methoxy-benzoyl)-2,3-dimethyl-spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 3-chloro-4-methoxy-benzoic acid |
| 2,2,2-trifluoro-1-[(3S)-1'-(2-fluoro-4-isopropoxy-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 2-fluoro-4-isopropoxy-benzoic acid |
| [8-chloro-2-methyl-6-(trifluoromethyl)spiro[3,4-dihydropyrrolo[1,2-a]pyrazine-1,4'-piperidine]-1'-yl]-[4-(3,3,3-trifluoropropoxymethyl)phenyl]methanone | 8-chloro-2-methyl-6-(trifluoromethyl)spiro[3,4-dihydropyrrolo[1,2-a]pyrazine-1,4'-piperidine] | 4-(3,3,3-trifluoropropoxymethyl)-benzoic acid |
| [8-chloro-2-methyl-6-(trifluoromethyl)spiro[3,4-dihydropyrrolo[1,2-a]pyrazine-1,4'-piperidine]-1'-yl]-[3-methoxy-4-(2,2,2-trifluoroethoxymethyl)phenyl]methanone | 8-chloro-2-methyl-6-(trifluoromethyl)spiro[3,4-dihydropyrrolo[1,2-a]pyrazine-1,4'-piperidine] | 3-methoxy-4-(2,2,2-trifluoroethoxymethyl)-benzoic acid |
| [8-chloro-2-methyl-6-(trifluoromethyl)spiro[3,4-dihydropyrrolo[1,2-a]pyrazine-1,4'-piperidine]-1'-yl]-[3-methoxy-4-(3,3,3-trifluoropropoxymethyl)phenyl]methanone | 8-chloro-2-methyl-6-(trifluoromethyl)spiro[3,4-dihydropyrrolo[1,2-a]pyrazine-1,4'-piperidine] | 3-methoxy-4-(3,3,3-trifluoropropoxymethyl)-benzoic acid |
| [8-chloro-2-methyl-6-(trifluoromethyl)spiro[3,4-dihydropyrrolo[1,2-a]pyrazine-1,4'-piperidine]-1'-yl]-[4-(2-fluoro-2-methyl-propoxy)-3-methoxy-phenyl]methanone | 8-chloro-2-methyl-6-(trifluoromethyl)spiro[3,4-dihydropyrrolo[1,2-a]pyrazine-1,4'-piperidine] | 4-(2-fluoro-2-methyl-propoxy)-3-methoxy-benzoic acid |
| [8-chloro-2-methyl-6-(trifluoromethyl)spiro[3,4-dihydropyrrolo[1,2-a]pyrazine-1,4'-piperidine]-1'-yl]-(5-isopropoxy-4-methyl-2-pyridyl)methanone | 8-chloro-2-methyl-6-(trifluoromethyl)spiro[3,4-dihydropyrrolo[1,2-a]pyrazine-1,4'-piperidine] | 5-isopropoxy-4-methyl-pyridine-2-carboxylic acid |
| [6-(cyclopropanecarbonyl)-2-methyl-spiro[3,4-dihydropyrrolo[1,2-a]pyrazine-1,4'-piperidine]-1'-yl]-(4-methoxy-3-methyl-phenyl)methanone | cyclopropyl-(2-methylspiro[3,4-dihydropyrrolo[1,2-a]pyrazine-1,4'-piperidine]-6-yl)methanone | 4-methoxy-3-methyl-benzoic acid |
| [6-(cyclopropanecarbonyl)-2-methyl-spiro[3,4-dihydropyrrolo[1,2-a]pyrazine-1,4'-piperidine]-1'-yl]-(2-fluoro-4-isopropoxy- | cyclopropyl-(2-methylspiro[3,4-dihydropyrrolo[1,2-a]pyrazine-1,4'- | 2-fluoro-4-isopropoxy-benzoic acid |

| Compound name | Amine name | Acid name |
| --- | --- | --- |
| phenyl)methanone | piperidine]-6-yl)methanone | |
| [6-(cyclopropanecarbonyl)-2-methyl-spiro[3,4-dihydropyrrolo[1,2-a]pyrazine-1,4'-piperidine]-1'-yl]-[3-fluoro-4-(1-hydroxy-1-methyl-ethyl)phenyl]methanone | cyclopropyl-(2-methylspiro[3,4-dihydropyrrolo[1,2-a]pyrazine-1,4'-piperidine]-6-yl)methanone | 3-fluoro-4-(1-hydroxy-1-methyl-ethyl)benzoic acid |
| [6-(cyclopropanecarbonyl)-2-methyl-spiro[3,4-dihydropyrrolo[1,2-a]pyrazine-1,4'-piperidine]-1'-yl-[4-(3,3,3-trifluoropropoxymethyl)phenyl]methanone | cyclopropyl-(2-methylspiro[3,4-dihydropyrrolo[1,2-a]pyrazine-1,4'-piperidine]-6-yl)methanone | 4-(3,3,3-trifluoropropoxymethyl)-benzoic acid |
| [6-(cyclopropanecarbonyl)-2-methyl-spiro[3,4-dihydropyrrolo[1,2-a]pyrazine-1,4'-piperidine]-1'-yl]-(4-isopropoxy-3-methyl-phenyl)methanone | cyclopropyl-(2-methylspiro[3,4-dihydropyrrolo[1,2-a]pyrazine-1,4'-piperidine]-6-yl)methanone | 4-isopropoxy-3-methyl-benzoic acid |
| [6-(cyclopropanecarbonyl)-2-methyl-spiro[3,4-dihydropyrrolo[1,2-a]pyrazine-1,4'-piperidine]-1'-yl]-(3-fluoro-4-isopropoxy-phenyl)methanone | cyclopropyl-(2-methylspiro[3,4-dihydropyrrolo[1,2-a]pyrazine-1,4'-piperidine]-6-yl)methanone | 3-fluoro-4-isopropoxy-benzoic acid |
| (3-chloro-4-hydroxy-phenyl)-[6-(cyclopropanecarbonyl)-2-methyl-spiro[3,4-dihydropyrrolo[1,2-a]pyrazine-1,4'-piperidine]-1'-yl]methanone | cyclopropyl-(2-methylspiro[3,4-dihydropyrrolo[1,2-a]pyrazine-1,4'-piperidine]-6-yl)methanone | 3-chloro-4-hydroxy-benzoic acid |
| (3-chloro-4-isopropoxy-phenyl)-[6-(cyclopropanecarbonyl)-2-methyl-spiro[3,4-dihydropyrrolo[1,2-a]pyrazine-1,4'-piperidine]-1'-yl]methanone | cyclopropyl-(2-methylspiro[3,4-dihydropyrrolo[1,2-a]pyrazine-1,4'-piperidine]-6-yl)methanone | 3-chloro-4-isopropoxy-benzoic acid |
| [6-(cyclopropanecarbonyl)-2-methyl-spiro[3,4-dihydropyrrolo[1,2-a]pyrazine-1,4'-piperidine]-1'-yl]-(4-hydroxy-3-methyl-phenyl)methanone | cyclopropyl-(2-methylspiro[3,4-dihydropyrrolo[1,2-a]pyrazine-1,4'-piperidine]-6-yl)methanone | 4-hydroxy-3-methyl-benzoic acid |
| 1-[1'-(4-methoxy-3-methyl-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 4-methoxy-3-methyl-benzoic acid |
| 1-[1'-[4-methoxy-3-(trifluoromethyl)benzoyl]-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 4-methoxy-3-(trifluoromethyl)benzoic acid |
| 1-[1'-(3-chloro-4-methoxy-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 3-chloro-4-methoxy-benzoic acid |
| 1-[1'-(4-hydroxy-3-methyl-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 4-hydroxy-3-methyl-benzoic acid |
| 1-[1'-(3-chloro-4-hydroxy-benzoyl)-2-methyl-spiro[3,4-dihydropyrrolo[1,2-a]pyrazine-1,4'-piperidine]-6-yl]-2-methyl-propan-1-one | 2-methyl-1-(2-methylspiro[3,4-dihydropyrrolo[1,2-a]pyrazine-1,4'-piperidine]-6-yl)propan-1-one | 3-chloro-4-hydroxy-benzoic acid |
| 1-[1'-[3-fluoro-4-(1-hydroxy-1-methyl-ethyl)benzoyl]-2-methyl-spiro[3,4-dihydropyrrolo[1,2- | 2-methyl-1-(2-methylspiro[3,4-dihydropyrrolo[1,2- | 3-fluoro-4-(1-hydroxy-1-methyl-ethyl)benzoic acid |

| Compound name | Amine name | Acid name |
|---|---|---|
| a]pyrazine-1,4'-piperidine]-6-yl]-2-methyl-propan-1-one | a]pyrazine-1,4'-piperidine]-6-yl)propan-1-one | |
| 2-methyl-1-[2-methyl-1'-[4-(3,3,3-trifluoropropoxymethyl)benzoyl]spiro[3,4-dihydropyrrolo[1,2-a]pyrazine-1,4'-piperidine]-6-yl]propan-1-one | 2-methyl-1-(2-methylspiro[3,4-dihydropyrrolo[1,2-a]pyrazine-1,4'-piperidine]-6-yl)propan-1-one | 4-(3,3,3-trifluoropropoxymethyl)-benzoic acid |
| [1'-(4-methoxy-3-methyl-benzoyl)-2-methyl-spiro[3,4-dihydropyrrolo[1,2-a]pyrazine-1,4'-piperidine]-6-yl]-phenyl-methanone | (2-methylspiro[3,4-dihydropyrrolo[1,2-a]pyrazine-1,4'-piperidine]-6-yl)-phenyl-methanone | 4-methoxy-3-methyl-benzoic acid |
| [1'-[4-methoxy-3-(trifluoromethyl)benzoyl]-2-methyl-spiro[3,4-dihydropyrrolo[1,2-a]pyrazine-1,4'-piperidine]-6-yl]-phenyl-methanone | (2-methylspiro[3,4-dihydropyrrolo[1,2-a]pyrazine-1,4'-piperidine]-6-yl)-phenyl-methanone | 4-methoxy-3-(trifluoromethyl)benzoic acid |
| [1'-(3-chloro-4-methoxy-benzoyl)-2-methyl-spiro[3,4-dihydropyrrolo[1,2-a]pyrazine-1,4'-piperidine]-6-yl]-phenyl-methanone | (2-methylspiro[3,4-dihydropyrrolo[1,2-a]pyrazine-1,4'-piperidine]-6-yl)-phenyl-methanone | 3-chloro-4-methoxy-benzoic acid |
| [1'-(4-hydroxy-3-methyl-benzoyl)-2-methyl-spiro[3,4-dihydropyrrolo[1,2-a]pyrazine-1,4'-piperidine]-6-yl]-phenyl-methanone | (2-methylspiro[3,4-dihydropyrrolo[1,2-a]pyrazine-1,4'-piperidine]-6-yl)-phenyl-methanone | 4-hydroxy-3-methyl-benzoic acid |
| 2,2,2-trifluoro-1-[1'-(6-isopropoxy-5-methyl-pyridine-3-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 6-isopropoxy-5-methyl-pyridine-3-carboxylic acid |
| 2,2,2-trifluoro-1-[1'-(4-hydroxy-3-isopropyl-benzoyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-hydroxy-3-isopropyl-benzoic acid |
| 1-[1'-(5-ethylpyridine-2-carbonyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 5-ethylpyridine-2-carboxylic acid |
| 1-[(3S)-1'-(3-chloro-4-hydroxy-benzoyl)-2,3-dimethyl-spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 3-chloro-4-hydroxy-benzoic acid |
| 2,2,2-trifluoro-1-[(3S)-1'-(4-hydroxy-3-methyl-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 4-hydroxy-3-methyl-benzoic acid |
| 2,2,2-trifluoro-1-[(3S)-1'-[3-fluoro-4-(1-hydroxy-1-methyl-ethyl)benzoyl]-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 3-fluoro-4-(1-hydroxy-1-methyl-ethyl)benzoic acid |
| 1-[(3S)-1'-(4-tert-butylsulfonylbenzoyl)-2,3-dimethyl-spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 4-tert-butylsulfonylbenzoic acid |
| 1-[(3S)-1'-[2-(difluoromethoxy)benzoyl]-2,3-dimethyl-spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 2-(difluoromethoxy)benzoic acid |

| Compound name | Amine name | Acid name |
| --- | --- | --- |
| 2,2,2-trifluoro-1-[(3S)-1'-(3-fluoro-4-isopropoxy-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 3-fluoro-4-isopropoxy-benzoic acid |
| 2,2,2-trifluoro-1-[(3S)-1'-(2-methoxy-3-methyl-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 2-methoxy-3-methyl-benzoic acid |
| 1-[(3S)-2,3-dimethyl-1'-[4-(2,2,2-trifluoroethoxy)benzoyl]spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 4-(2,2,2-trifluoroethoxy)benzoic acid |
| 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 4-(3,3,3-trifluoropropoxymethyl)-benzoic acid |
| 2,2,2-trifluoro-1-[(3S)-1'-(3-fluoro-2-methoxy-benzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 3-fluoro-2-methoxy-benzoic acid |
| 2,2,2-trifluoro-1-[(3S)-1'-(5-methoxy-6-methyl-pyridine-2-carbonyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 5-methoxy-6-methyl-pyridine-2-carboxylic acid |
| 2,2,2-trifluoro-1-[1'-(5-methoxy-6-methyl-pyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-methoxy-6-methyl-pyridine-2-carboxylic acid |
| 2,2,2-trifluoro-1-[1'-(5-hydroxy-6-methyl-pyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-hydroxy-6-methyl-pyridine-2-carboxylic acid |
| 1-[1'-(5-isopropoxy-6-methyl-pyridine-2-carbonyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 5-isopropoxy-6-methyl-pyridine-2-carboxylic acid |
| 1-[1'-(2-fluoro-4-isopropoxy-benzoyl)-2-methyl-spiro[3,4-dihydropyrrolo[1,2-a]pyrazine-1,4'-piperidine]-6-yl]ethanone | 1-(2-methylspiro[3,4-dihydropyrrolo[1,2-a]pyrazine-1,4'-piperidine]-6-yl)ethanone | 2-fluoro-4-isopropoxy-benzoic acid |
| 2,2,2-trifluoro-1-[1'-(5-isobutoxypyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-isobutoxypyridine-2-carboxylic acid |
| 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-isopentyloxypyridine-2-carboxylic acid |
| [4-methoxy-3-(trifluoromethyl)phenyl]-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-methoxy-3-(trifluoromethyl)benzoic acid |
| [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone | (1-methylcyclopropyl)-(2-methylspiro[3,4-dihydropyrrolo[1,2-a]pyrazine-1,4'-piperidine]-6-yl)methanone | 4-(3,3,3-trifluoropropoxymethyl)-benzoic acid |

| Compound name | Amine name | Acid name |
|---|---|---|
| 2,2,2-trifluoro-1-[1'-[4-[1-hydroxy-2-(2,2,2-trifluoroethoxy)ethyl]benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-[1-hydroxy-2-(2,2,2-trifluoroethoxy)ethyl]-benzoic acid |
| 2,2,2-trifluoro-1-[1'-[4-[2-hydroxy-1-(2,2,2-trifluoroethoxy)ethyl]benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 4-[2-hydroxy-1-(2,2,2-trifluoroethoxy)ethyl]-benzoic acid |
| 2,2,2-trifluoro-1-[1'-(4-isopropylsulfonylbenzoyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 4-isopropylsulfonylbenzoic acid |
| 1-[3,3-dimethyl-1'-[4-(trifluoromethylsulfonyl)benzoyl]spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-(trifluoromethylsulfonyl)-benzoic acid |
| N-cyclopropyl-4-[3,3-dimethyl-6-(2,2,2-trifluoroacetyl)spiro[2,4-dihydropyrrolo[1,2-a]pyrazine-1,4'-piperidine]-1'-carbonyl]benzenesulfonamide | 1-(3,3-dimethylspiro[2,4-dihydropyrrolo[1,2-a]pyrazine-1,4'-piperidine]-6-yl)-2,2,2-trifluoro-ethanone | 4-(cyclopropylsulfamoyl)-benzoic acid |
| 1-[1'-(4-tert-butylsulfonylbenzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-tert-butylsulfonylbenzoic acid |
| 2,2,2-trifluoro-1-[(3S)-1'-(4-isopropylsulfonylbenzoyl)-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 4-isopropylsulfonylbenzoic acid |
| 1-[(3S)-2,3-dimethyl-1'-[4-(trifluoromethylsulfonyl)benzoyl]spiro[3,4-dihydropyrrolo[1,2-a]pyrazine-1,4'-piperidine]-6-yl]-2,2,2-trifluoro-ethanone | 1-[(3S)-2,3-dimethylspiro[3,4-dihydropyrrolo[1,2-a]pyrazine-1,4'-piperidine]-6-yl]-2,2,2-trifluoro-ethanone | 4-(trifluoromethylsulfonyl)-benzoic acid |
| N-cyclopropyl-4-[(3S)-2,3-dimethyl-6-(2,2,2-trifluoroacetyl)spiro[3,4-dihydropyrrolo[1,2-a]pyrazine-1,4'-piperidine]-1'-carbonyl]benzenesulfonamide | 1-[(3S)-2,3-dimethylspiro[3,4-dihydropyrrolo[1,2-a]pyrazine-1,4'-piperidine]-6-yl]-2,2,2-trifluoro-ethanone | 4-(cyclopropylsulfamoyl)-benzoic acid |
| 1-[1'-(5-cyclohexylpyridine-2-carbonyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 5-cyclohexylpyridine-2-carboxylic acid |
| 2,2,2-trifluoro-1-[1'-[5-(2-fluorophenyl)pyridine-2-carbonyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-(2-fluorophenyl)pyridine-2-carboxylic acid |
| 2,2,2-trifluoro-1-[(3S)-1'-[4-(1-hydroxy-1-methyl-ethyl)benzoyl]-2,3-dimethyl-spiro[3,4-dihydropyrrolo[1,2-a]pyrazine-1,4'-piperidine]-6-yl]ethanone | 1-[(3S)-2,3-dimethylspiro[3,4-dihydropyrrolo[1,2-a]pyrazine-1,4'-piperidine]-6-yl]-2,2,2-trifluoro-ethanone | 4-(1-hydroxy-1-methyl-ethyl)benzoic acid |
| [4-(1-hydroxy-1-methyl-ethyl)phenyl]-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-(1-hydroxy-1-methyl-ethyl)benzoic acid |
| (5-methoxy-6-methyl-2-pyridyl)-[2-methyl-6-(1-methylcyclopropanecarbonyl)spiro[3,4-dihydropyrrolo[1,2-a]pyrazine- | (1-methylcyclopropyl)-(2-methylspiro[3,4-dihydropyrrolo[1,2-a]pyrazine-1,4'- | 5-methoxy-6-methyl-pyridine-2-carboxylic acid |

| Compound name | Amine name | Acid name |
|---|---|---|
| 1,4'-piperidine]-1'-yl]methanone | piperidine]-6-yl)methanone | |
| (3-chloro-4-methoxy-phenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 3-chloro-4-methoxy-benzoic acid |
| (4-hydroxy-3-methyl-phenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-hydroxy-3-methyl-benzoic acid |
| N-cyclopropyl-4-[2-methyl-6-(1-methylcyclopropanecarbonyl)spiro[3,4-dihydropyrrolo[1,2-a]pyrazine-1,4'-piperidine]-1'-carbonyl]benzenesulfonamide | (1-methylcyclopropyl)-(2-methylspiro[3,4-dihydropyrrolo[1,2-a]pyrazine-1,4'-piperidine]-6-yl)methanone | 4-(cyclopropylsulfamoyl)-benzoic acid |
| (3-chloro-4-hydroxy-phenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 3-chloro-4-hydroxy-benzoic acid |
| [2-methyl-6-(1-methylcyclopropanecarbonyl)spiro[3,4-dihydropyrrolo[1,2-a]pyrazine-1,4'-piperidine]-1'-yl]-[4-(trifluoromethylsulfonyl)phenyl]methanone | (1-methylcyclopropyl)-(2-methylspiro[3,4-dihydropyrrolo[1,2-a]pyrazine-1,4'-piperidine]-6-yl)methanone | 4-(trifluoromethylsulfonyl)-benzoic acid |
| [3-(hydroxymethyl)-4-isopropoxy-phenyl]-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 3-(hydroxymethyl)-4-isopropoxy-benzoic acid |
| (2-fluoro-4-isopropoxy-phenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 2-fluoro-4-isopropoxy-benzoic acid |
| (4-methoxy-3-methyl-phenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-methoxy-3-methyl-benzoic acid |
| [4-hydroxy-3-(trifluoromethyl)phenyl]-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-hydroxy-3-(trifluoromethyl)benzoic acid |
| 2,2,2-trifluoro-1-[1'-(5-methoxy-6-methyl-pyridine-2-carbonyl)-3,3-dimethyl-spiro[2,4-dihydropyrrolo[1,2-a]pyrazine-1,4'-piperidine]-6-yl]ethanone | 1-(3,3-dimethylspiro[2,4-dihydropyrrolo[1,2-a]pyrazine-1,4'-piperidine]-6-yl)-2,2,2-trifluoro-ethanone | 5-methoxy-6-methyl-pyridine-2-carboxylic acid |
| (4-tert-butylsulfonylphenyl)-[2-methyl-6-(1-methylcyclopropanecarbonyl)spiro[3,4-dihydropyrrolo[1,2-a]pyrazine-1,4'-piperidine]-1'-yl]methanone | (1-methylcyclopropyl)-(2-methylspiro[3,4-dihydropyrrolo[1,2-a]pyrazine-1,4'-piperidine]-6-yl)methanone | 4-tert-butylsulfonylbenzoic acid |
| 1-[1'-(4-cyclopropylsulfonylbenzoyl)-2-methyl-spiro[3,4-dihydropyrrolo[1,2-a]pyrazine-1,4'-piperidine]-6-yl]-2,2,2-trifluoro-ethanone | 2,2,2-trifluoro-1-(2-methylspiro[3,4-dihydropyrrolo[1,2-a]pyrazine-1,4'-piperidine]-6-yl)ethanone | 4-cyclopropylsulfonyl-benzoic acid |
| 1-[(3S)-1'-(4-cyclopropylsulfonylbenzoyl)-2,3-dimethyl-spiro[3,4-dihydropyrrolo[1,2-a]pyrazine-1,4'- | 1-[(3S)-2,3-dimethylspiro[3,4-dihydropyrrolo[1,2-a]pyrazine-1,4'- | 4-cyclopropylsulfonyl-benzoic acid |

| Compound name | Amine name | Acid name |
|---|---|---|
| piperidine]-6-yl]-2,2,2-trifluoro-ethanone | piperidine]-6-yl]-2,2,2-trifluoro-ethanone | |
| 1-[1'-(4-cyclopropylsulfonylbenzoyl)-3,3-dimethyl-spiro[2,4-dihydropyrrolo[1,2-a]pyrazine-1,4'-piperidine]-6-yl]-2,2,2-trifluoro-ethanone | 1-(3,3-dimethylspiro[2,4-dihydropyrrolo[1,2-a]pyrazine-1,4'-piperidine]-6-yl)-2,2,2-trifluoro-ethanone | 4-cyclopropylsulfonyl-benzoic acid |
| [4-[2-methyl-6-(2,2,2-trifluoroacetyl)spiro[3,4-dihydropyrrolo[1,2-a]pyrazine-1,4'-piperidine]-1'-carbonyl]phenyl]trifluoromethanesulfonate | 2,2,2-trifluoro-1-(2-methylspiro[3,4-dihydropyrrolo[1,2-a]pyrazine-1,4'-piperidine]-6-yl)ethanone | 4-(trifluoromethyl-sulfonyloxy)benzoic acid |
| 2,2,2-trifluoro-1-[1'-(4-methoxy-3-methyl-benzoyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 4-methoxy-3-methyl-benzoic acid |
| 1-[1'-(3-chloro-4-methoxy-benzoyl)-2,4-dimethyl-spiro[3,4-dihydropyrrolo[1,2-a]pyrazine-1,4'-piperidine]-6-yl]-2,2,2-trifluoro-ethanone | 1-(2,4-dimethylspiro[3,4-dihydropyrrolo[1,2-a]pyrazine-1,4'-piperidine]-6-yl)-2,2,2-trifluoro-ethanone | 3-chloro-4-methoxy-benzoic acid |
| 2,2,2-trifluoro-1-[1'-[4-methoxy-3-(trifluoromethyl)benzoyl]-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 4-methoxy-3-(trifluoromethyl)benzoic acid |
| 2,2,2-trifluoro-1-[1'-(4-isopentyloxybenzoyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 4-isopentyloxybenzoic acid |
| 2,2,2-trifluoro-1-[1'-(4-isopropoxy-3-methyl-benzoyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 4-isopropoxy-3-methyl-benzoic acid |
| 1-[2,4-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone | 1-(2,4-dimethylspiro[3,4-dihydropyrrolo[1,2-a]pyrazine-1,4'-piperidine]-6-yl)-2,2,2-trifluoro-ethanone | 4-(3,3,3-trifluoropropoxymethyl)-benzoic acid |
| 1-[1'-(3-chloro-4-isopropoxy-benzoyl)-2,4-dimethyl-spiro[3,4-dihydropyrrolo[1,2-a]pyrazine-1,4'-piperidine]-6-yl]-2,2,2-trifluoro-ethanone | 1-(2,4-dimethylspiro[3,4-dihydropyrrolo[1,2-a]pyrazine-1,4'-piperidine]-6-yl)-2,2,2-trifluoro-ethanone | 3-chloro-4-isopropoxy-benzoic acid |
| 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 5-isopropoxy-6-methyl-pyridine-2-carboxylic acid |
| 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 5-isopentyloxypyridine-2-carboxylic acid |
| 2,2,2-trifluoro-1-[1'-(4-methoxy-3-methyl-benzoyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-methoxy-3-methyl-benzoic acid |
| 1-[1'-(3-chloro-4-methoxy-benzoyl)-4-methyl-spiro[3,4-dihydro-2H-pyrrolo[1,2-a]pyrazine-1,4'-piperidine]-6-yl]-2,2,2-trifluoro-ethanone | 2,2,2-trifluoro-1-(4-methylspiro[3,4-dihydro-2H-pyrrolo[1,2-a]pyrazine-1,4'-piperidine]-6-yl)ethanone | 3-chloro-4-methoxy-benzoic acid |
| 2,2,2-trifluoro-1-[1'-(4-isopentyloxybenzoyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-isopentyloxybenzoic acid |
| 2,2,2-trifluoro-1-[1'-(4-isopropoxy-3-methyl-benzoyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-isopropoxy-3-methyl-benzoic acid |

-continued

| Compound name | Amine name | Acid name |
|---|---|---|
| 2,2,2-trifluoro-1-[4-methyl-1'-[4-(3,3,3-trifluoropropoxymethyl)benzoyl]spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-(3,3,3-trifluoropropoxymethyl)-benzoic acid |
| 2,2,2-trifluoro-1-[1'-(5-methoxy-6-methyl-pyridine-2-carbonyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 5-methoxy-6-methyl-pyridine-2-carboxylic acid |
| 1-[1'-(3-chloro-4-isopropoxy-benzoyl)-4-methyl-spiro[3,4-dihydro-2H-pyrrolo[1,2-a]pyrazine-1,4'-piperidine]-6-yl]-2,2,2-trifluoro-ethanone | 2,2,2-trifluoro-1-(4-methylspiro[3,4-dihydro-2H-pyrrolo[1,2-a]pyrazine-1,4'-piperidine]-6-yl)ethanone | 3-chloro-4-isopropoxy-benzoic acid |
| 2,2,2-trifluoro-1-[1'-(5-isopentyloxypyridine-2-carbonyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 5-isopentyloxypyridine-2-carboxylic acid |
| 2,2,2-trifluoro-1-[1'-(5-methoxy-6-methyl-pyridine-2-carbonyl)-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 5-methoxy-6-methyl-pyridine-2-carboxylic acid |
| 2,2,2-trifluoro-1-[1'-[4-methoxy-3-(trifluoromethyl)benzoyl]-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-methoxy-3-(trifluoromethyl)benzoic acid |
| 2,2,2-trifluoro-1-[1'-(5-isopropoxy-6-methyl-pyridine-2-carbonyl)-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 5-isopropoxy-6-methyl-pyridine-2-carboxylic acid |
| 2,2,2-trifluoro-1-[1'-[4-(1-hydroxy-1-methyl-ethyl)-3-methyl-benzoyl]-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 4-(1-hydroxy-1-methyl-ethyl)-3-methyl-benzoic acid |
| 2,2,2-trifluoro-1-[1'-[4-(1-hydroxy-1-methyl-ethyl)-3-methyl-benzoyl]-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 4-(1-hydroxy-1-methyl-ethyl)-3-methyl-benzoic acid |
| 2,2,2-trifluoro-1-[1'-(5-isopropoxy-6-methoxy-pyridine-2-carbonyl)-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 5-isopropoxy-6-methoxy-pyridine-2-carboxylic acid |
| [8-chloro-2-methyl-6-(trifluoromethyl)spiro[3,4-dihydropyrrolo[1,2-a]pyrazine-1,4'-piperidine]-1'-yl]-(5-isopropoxy-6-methoxy-2-pyridyl)methanone | 8-chloro-2-methyl-6-(trifluoromethyl)spiro[3,4-dihydropyrrolo[1,2-a]pyrazine-1,4'-piperidine] | 5-isopropoxy-6-methoxy-pyridine-2-carboxylic acid |
| 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone | 1-(2,4-dimethylspiro[3,4-dihydropyrrolo[1,2-a]pyrazine-1,4'-piperidine]-6-yl)-2,2,2-trifluoro-ethanone | 3-methoxy-4-[2-(trifluoromethoxy)ethoxy]benzoic acid |
| 2,2,2-trifluoro-1-[1'-[3-methoxy-4-[2-(trifluoromethoxy)ethoxy]benzoyl]-4-methyl-spiro[3,4-dihydro-2H-pyrrolo[1,2-a]pyrazine-1,4'-piperidine]-6-yl]ethanone | 2,2,2-trifluoro-1-(4-methylspiro[3,4-dihydro-2H-pyrrolo[1,2-a]pyrazine-1,4'-piperidine]-6-yl)ethanone | 3-methoxy-4-[2-(trifluoromethoxy)ethoxy]benzoic acid |
| 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone | 2,2,2-trifluoro-1-(2-methylspiro[3,4-dihydropyrrolo[1,2-a]pyrazine-1,4'-piperidine]-6-yl)ethanone | 3-methoxy-4-[2-(trifluoromethoxy)ethoxy]benzoic acid |
| [4-[2,4-dimethyl-6-(2,2,2-trifluoroacetyl)spiro[3,4-dihydropyrrolo[1,2-a]pyrazine-1,4'- | 1-(2,4-dimethylspiro[3,4-dihydropyrrolo[1,2-a]pyrazine-1,4'- | 4-(trifluoromethyl-sulfonyloxy)benzoic acid |

| Compound name | Amine name | Acid name |
|---|---|---|
| piperidine]-1'-carbonyl]phenyl]trifluoromethanesulfonate | piperidine]-6-yl)-2,2,2-trifluoro-ethanone | |
| 2,2,2-trifluoro-1-[(3S)-1'-(4-methoxy-3-methyl-benzoyl)-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 4-methoxy-3-methyl-benzoic acid |
| 1-[(3S)-1'-(3-chloro-4-methoxy-benzoyl)-3-methyl-spiro[3,4-dihydro-2H-pyrrolo[1,2-a]pyrazine-1,4'-piperidine]-6-yl]-2,2,2-trifluoro-ethanone | 2,2,2-trifluoro-1-[(3S)-3-methylspiro[3,4-dihydro-2H-pyrrolo[1,2-a]pyrazine-1,4'-piperidine]-6-yl]ethanone | 3-chloro-4-methoxy-benzoic acid |
| 2,2,2-trifluoro-1-[(3S)-1'-[4-methoxy-3-(trifluoromethyl)benzoyl]-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 4-methoxy-3-(trifluoromethyl)benzoic acid |
| 2,2,2-trifluoro-1-[(3S)-1'-(3-fluoro-4-isopropoxy-benzoyl)-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 3-fluoro-4-isopropoxy-benzoic acid |
| 1-[(3S)-1'-(4-tert-butylsulfonylbenzoyl)-3-methyl-spiro[3,4-dihydro-2H-pyrrolo[1,2-a]pyrazine-1,4'-piperidine]-6-yl]-2,2,2-trifluoro-ethanone | 2,2,2-trifluoro-1-[(3S)-3-methylspiro[3,4-dihydro-2H-pyrrolo[1,2-a]pyrazine-1,4'-piperidine]-6-yl]ethanone | 4-tert-butylsulfonylbenzoic acid |
| 2,2,2-trifluoro-1-[(3S)-3-methyl-1'-[4-(3,3,3-trifluoropropoxymethyl)benzoyl]spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 4-(3,3,3-trifluoropropoxymethyl)-benzoic acid |
| 2,2,2-trifluoro-1-[(3S)-1'-(5-methoxy-6-methyl-pyridine-2-carbonyl)-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 5-methoxy-6-methyl-pyridine-2-carboxylic acid |
| 2,2,2-trifluoro-1-[(3S)-1'-(2-fluoro-4-isopropoxy-benzoyl)-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 2-fluoro-4-isopropoxy-benzoic acid |
| 2,2,2-trifluoro-1-[(3S)-1'-(5-isopentyloxypyridine-2-carbonyl)-3-methyl-spiro[3,4-dihydro-2H-pyrrolo[1,2-a]pyrazine-1,4'-piperidine]-6-yl]ethanone | 2,2,2-trifluoro-1-[(3S)-3-methylspiro[3,4-dihydro-2H-pyrrolo[1,2-a]pyrazine-1,4'-piperidine]-6-yl]ethanone | 5-isopentyloxypyridine-2-carboxylic acid |
| N-methyl-4-[2-methyl-6-(2,2,2-trifluoroacetyl)spiro[3,4-dihydropyrrolo[1,2-a]pyrazine-1,4'-piperidine]-1'-carbonyl]-N-thiazol-2-yl-benzenesulfonamide | 2,2,2-trifluoro-1-(2-methylspiro[3,4-dihydropyrrolo[1,2-a]pyrazine-1,4'-piperidine]-6-yl)ethanone | 4-[methyl(thiazol-2-yl)sulfamoyl]benzoic acid |
| 1-(1-(4-bromo-3-methylbenzoyl)-2'-methyl-3',4'-dihydro-2'H-spiro[piperidine-4,1'-pyrrolo[1,2-a]pyrazine]-6'-yl)-2,2,2-trifluoroethanone | 2,2,2-trifluoro-1-(2'-methyl-3',4'-dihydro-2'H-spiro[piperidine-4,1'-pyrrolo[1,2-a]pyrazine]-6'-yl)ethanone | 4-bromo-3-methylbenzoic acid |
| (2-chloropyridin-3-yl)(2'-methyl-6'-(trifluoromethyl)-3',4'-dihydro-2'H-spiro[piperidine-4,1'-pyrrolo[1,2-a]pyrazine]-1-yl)methanone | 2'-methyl-6'-(trifluoromethyl)-3',4'-dihydro-2'H-spiro[piperidine-4,1'-pyrrolo[1,2-a]pyrazine] | 2-chloronicotinic acid |

1-(1-(4-Isopropoxy-3-methoxybenzoyl)-6'-(trifluoromethyl)-3',4'-dihydro-2'H-spiro[piperidine-4,1'-pyrrolo[1,2-a]pyrazine]-2'-yl)ethanone

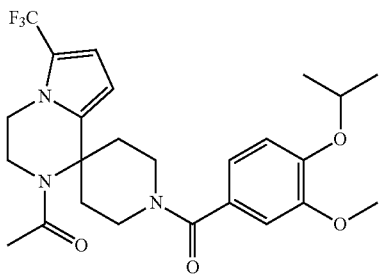 [SMILES: COc1cc(C(=O)N2CCC3(CC2)c2ccc(C(F)(F)F)n2CCN3C(C)=O)ccc1OC(C)C]

Acetyl chloride (158 μL, 2.22 mmol) was added drop-wise to a mixture of (4-isopropoxy-3-methoxy-phenyl)-[6-(trifluoromethyl)spiro[3,4-dihydro-2H-pyrrolo[1,2-a]pyrazine-1,4'-piperidine]-1'-yl]methanone (100 mg, 0.222 mmol) and pyridine (1 mL) at room temperature. The mixture was allowed to stir for 16 h at room temperature before it was partitioned between ethyl acetate and 1N HCl. The layers were separated and the organic layer was washed with 1N HCl, water, and then brine. The organic layer was dried over sodium sulfate and concentrated under reduced pressure. The residue was taken up in DMF and was purified by preparatory-HPLC (10-99% ACN/water with ammonium formate modifier) to give 1-[1'-(4-isopropoxy-3-methoxy-benzoyl)-6-(trifluoromethyl)spiro[3,4-dihydropyrrolo[1,2-a]pyrazine-1,4'-piperidine]-2'-yl]ethanone (60 mg, 53%) as a white solid. ESI-MS m/z calc. 493.2, found 494.7 (M+1)+; Retention time: 1.70 minutes (3 min run). $^1$H NMR (400 MHz, CDCl$_3$) δ 7.06 (d, J=1.8 Hz, 1H), 7.05-6.98 (m, 1H), 6.88 (d, J=8.2 Hz, 1H), 6.55 (d, J=3.3 Hz, 1H), 6.15 (d, J=3.9 Hz, 1H), 4.57 (d, J=6.1 Hz, 1H), 4.19-4.10 (m, 2H), 3.88 (m, s, 5H), 3.79 (s, 2H), 3.70-3.52 (m, J=31.5 Hz, 2H), 3.11 (s, 2H), 2.24 (s, 3H), 1.92-1.75 (m, 2H), 1.38 (d, J=6.1 Hz, 6H).

The following compounds were synthesized using the procedure described above: methyl 1-(4-isopropoxy-3-methoxy-benzoyl)-6'-(trifluoromethyl)-3',4'-dihydro-2'H -spiro[piperidine-4,1'-pyrrolo[1,2-a]pyrazine]-2'-carboxylate and ethyl 1-(4-isopropoxy-3-methoxybenzoyl)-6'-(trifluoromethyl)-3',4'-dihydro-2'H-spiro[piperidine-4,1'-pyrrolo[1,2-a]pyrazine]-2'-carboxylate.

2,2,2-Trifluoro-1-[1'-[4-(2-methoxy-3-pyridyl)-3-methyl-benzoyl]-2-methyl-spiro[3,4-dihydropyrrolo[1,2-a]pyrazine-1,4'-piperidine]-6-yl]ethanone

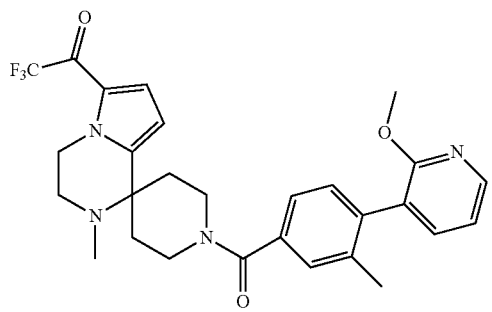 [SMILES: COc1ncccc1-c1ccc(C(=O)N2CCC3(CC2)c2ccc(C(=O)C(F)(F)F)n2CCN3C)cc1C]

To a microtube with Pd(dppf)Cl$_2$ (5.5 mg, 0.075 mmol) was added 2-methoxypyridin-3-ylboronic acid (0.10 mmol) in NMP (0.2 mL), followed by a solution of 1-(1-(4-bromo-3-methylbenzoyl)-2'-methyl-3',4'-dihydro-2'H-spiro[piperidine-4,1'-pyrrolo[1,2-a]pyrazine]-6'-yl)-2,2,2-trifluoroethanone (0.75 mmol) in DMF (0.3 mL) and aq. Na$_2$CO$_3$ (2M, 4 mmol). The reaction mixture was shaken at 80° C. for 16 h. Filtration followed by purification using preparatory-HPLC (1-99% ACN in water (HCl modifier)) gave 2,2,2-trifluoro-1-[1'-[4-(2-methoxy-3-pyridyl)-3-methyl-benzoyl]-2-methyl-spiro[3,4-dihydropyrrolo[1,2-a]pyrazine-1,4'-piperidine]-6-yl]ethanone. ESI-MS m/z calc. 526.2, found 527.3 (M+1)+; Retention time: 1.38 minutes (3 min run).

The following compounds were synthesized using the procedure described above:
5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile,
1-[1'-[4-(1-ethylimidazol-4-yl)-3-methyl-benzoyl]-2-methyl-spiro[3,4-dihydropyrrolo[1,2-a]pyrazine-1,4'-piperidine]-6-yl]-2,2,2-trifluoro-ethanone,
2,2,2-trifluoro-1-[2-methyl-1'-[3-methyl-4-(2-methyl-4-pyridyl)benzoyl]spiro[3,4-dihydropyrrolo[1,2-a]pyrazine-1,4'-piperidine]-6-yl]ethanone,
2,2,2-trifluoro-1-[2-methyl-1'-[3-methyl-4-(1-methylpyrazol-3-yl)benzoyl]spiro[3,4-dihydropyrrolo[1,2-a]pyrazine-1,4'-piperidine]-6-yl]ethanone,
2,2,2-trifluoro-1-[2-methyl-1'-[3-methyl-4-(1-methylpyrazol-4-yl)benzoyl]spiro[3,4-dihydropyrrolo[1,2-a]pyrazine-1,4'-piperidine]-6-yl]ethanone,
2,2,2-trifluoro-1-[1'-[4-(4-methoxyphenyl)-3-methyl-benzoyl]-2-methyl-spiro[3,4-dihydropyrrolo[1,2-a]pyrazine-1,4'-piperidine]-6-yl]ethanone,
1-[1'-[4-(3-chlorophenyl)-3-methyl-benzoyl]-2-methyl-spiro[3,4-dihydropyrrolo[1,2-a]pyrazine-1,4'-piperidine]-6-yl]-2,2,2-trifluoro-ethanone,
2,2,2-trifluoro-1-[2-methyl-1'-[3-methyl-4-(2-methylpyrazol-3-yl)benzoyl]spiro[3,4-dihydropyrrolo[1,2-a]pyrazine-1,4'-piperidine]-6-yl]ethanone,
N-[5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]-2-pyridyl]acetamide,
1-[1'-[4-[2-(dimethylamino)pyrimidin-5-yl]-3-methyl-benzoyl]-2-methyl-spiro[3,4-dihydropyrrolo[1,2-a]pyrazine-1,4'-piperidine]-6-yl]-2,2,2-trifluoro-ethanone,
2,2,2-trifluoro-1-[2-methyl-1'-[3-methyl-4-[3-(trifluoromethyl)-1H-pyrazol-4-yl]benzoyl]spiro[3,4-dihydropyrrolo[1,2-a]pyrazine-1,4'-piperidine]-6-yl]ethanone, and
2,2,2-trifluoro-1-[2-methyl-1'-(3-methyl-4-pyrimidin-5-yl-benzoyl)spiro[3,4-dihydropyrrolo[1,2-a]pyrazine-1,4'-piperidine]-6-yl]ethanone.

(2-(3-Hydroxypyrrolidin-1-yl)pyridin-3-yl)(2'-methyl-6'-(trifluoromethyl)-3',4'-dihydro-2'H-spiro[piperidine-4,1'-pyrrolo[1,2-a]pyrazine]-1-yl)methanone

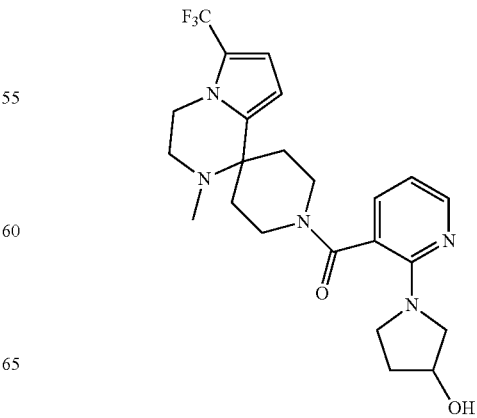

A mixture of (2-Chloro-3-pyridyl)-[2-methyl-6-(trifluoromethyl)spiro[3,4-dihydropyrrolo[1,2-a]pyrazine-1,4'-piperidine]-1'-yl]methanone (0.1 mol) and pyrrolidin-3-ol (0.3 mmol) DMF (0.5 mL) was stirred at 80° C. for 16 h. Additional pyrrolidin-3-ol (0.5 mmol) was added and the mixture was stirred at 150° C. for 16 h. The mixture was filtered and was subjected to preparatory-HPLC (10-90% ACN in water) to give (2-(3-hydroxypyrrolidin-1-yl)pyridin-3-yl)(2'-methyl-6'-(trifluoromethyl)-3',4'-dihydro-2'H-spiro[piperidine-4,1'-pyrrolo[1,2-a]pyrazine]-1-yl)methanone. ESI-MS m/z calc. 463.5, found 464.3 (M+1)+; Retention time: 0.75 minutes (3 min run).

The following compounds were synthesized using the procedure described above:

(2-(3-fluoropyrrolidin-1-yl)pyridin-3-yl)(2'-methyl-6'-(trifluoromethyl)-3',4'-dihydro-2'H-spiro[piperidine-4,1'-pyrrolo[1,2-a]pyrazine]-1-yl)methanone and (2-(3,3-difluoropyrrolidin-1-yl)pyridin-3-yl)(2'-methyl-6'-(trifluoromethyl)-3',4'-dihydro-2'H -spiro[piperidine-4,1'-pyrrolo[1,2-a]pyrazine]-1-yl)methanone.

2,2,2-Trifluoro-1-(1-(3-methoxy-4-(prop-1-en-2-yloxy)benzoyl)-2'-methyl-3',4'-dihydro-2'H-spiro[piperidine-4,1'-pyrrolo[1,2-a]pyrazine]-6'-yl)ethanone

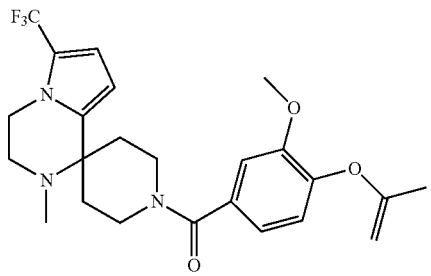 [SMILES: C=C(C)Oc1ccc(C(=O)N2CCC3(CC2)c2ccc(C(F)(F)F)n2CCN3C)cc1OC]

Step 1:

4-Methyl morpholine (1.59 mL, 14.4 mmol) was added to a mixture of 2-methyl-6-(trifluoromethyl)spiro[3,4-dihydropyrrolo[1,2-a]pyrazine-1,4'-piperidine]dihydrochloride (1.00 g, 2.89 mmol), 4-hydroxy-3-methoxy-benzoic acid (486 mg, 2.89 mmol), EDCI (831 mg, 4.33 mmol), HOBt (585 mg, 4.33 mmol) and DMF (10 mL) at room temperature. The mixture was heated at 60° C. overnight before it was cooled to room temperature and partitioned between ethyl acetate and 1N HCl. The layers were separated and the aqueous layer was extracted with ethyl acetate (3×). The combined organics were washed with brine, dried over sodium sulfate, filtered and concentrated. The residue was subjected to column chromatography (0-100% ethyl acetate/hexanes) to give (4-hydroxy-3-methoxy-phenyl)-[2-methyl-6-(trifluoromethyl)spiro[3,4-dihydropyrrolo[1,2-a]pyrazine-1,4'-piperidine]-1'-yl]methanone (690 mg, 58%). ESI-MS m/z calc. 423.2, found 424.1 (M+1)+; Retention time: 1.16 minutes (3 min run). $^1$H NMR (400 MHz, CD$_3$CN) δ 7.04 (d, J=1.8 Hz, 1H), 6.94 (dd, J=8.1, 1.9 Hz, 1H), 6.87 (d, J=8.1 Hz, 1H), 6.82 (s, 1H), 6.62-6.56 (m, 1H), 6.05 (d, J =3.9 Hz, 1H), 4.35 (s, 1H), 4.00 (t, J=6.0 Hz, 2H), 3.89 (s, 3H), 3.64 (s, 2H), 3.36 (t, J=6.0 Hz, 2H), 3.29 (s, 1H), 2.36 (s, 3H), 2.16-2.04 (m, 2H), 1.81 (dd, J=17.1, 7.3 Hz, 2H).26-7.21 (m, 2H), 7.14 (t, J=8.1 Hz, 1H), 2.78 (d, J=1.4 Hz, 2H), 1.24 (d, J=0.8 Hz, 6H).

Step 2:

A mixture of Cs$_2$CO$_3$ (115 mg, 0.354 mmol), acetylacetone (12 μL, 0.12 mmol), CuCl (5.8 mg, 0.059 mmol) and THF (2.5 mL) in a vial was stirred at room temperature for 5 min before (4-hydroxy-3-methoxy-phenyl)-[2-methyl-6-(trifluoromethyl)spiro[3,4-dihydropyrrolo[1,2-a]pyrazine-1,4'-piperidine]-1'-yl]methanone (100 mg, 0.236 mmol) then 2-bromoprop-1-ene (27 μL, 0.31 mmol) were added. The vial was capped and heated at 70° C. overnight. The mixture was cooled to room temperature, filtered and concentrated under reduced pressure. The residue was subjected to column chromatography (0-100% ethyl acetate/hexanes) to give (4-isopropenyloxy-3-methoxy-phenyl)-[2-methyl-6-(trifluoromethyl)spiro[3,4-dihydropyrrolo[1,2-a]pyrazine-1,4'-piperidine]-1'-yl]methanone (8.9 mg, 8%). ESI-MS m/z calc. 463.2, found 464.3 (M+1)+; Retention time: 1.47 minutes (3 min run). $^1$H NMR (400 MHz, CD$_3$CN) δ 7.12 (d, J=1.8 Hz, 1H), 7.07 (d, J=8.0 Hz, 1H), 7.01 (dd, J=8.0, 1.8 Hz, 1H), 6.60 (d, J=3.4 Hz, 1H), 6.07 (d, J=3.7 Hz, 1H), 4.42 (s, 1H), 4.12 (dd, J=1.6, 0.9 Hz, 1H), 4.01 (t, J=6.0 Hz, 2H), 3.85 (s, 3H), 3.79 (d, J=1.7 Hz, 1H), 3.67-3.40 (m, 2H), 3.36 (t, J=5.6 Hz, 2H), 3.20 (s, 1H), 2.36 (s, 3H), 2.18 (s, 2H), 2.00 (d, J=0.7 Hz, 3H), 1.83 (s, 2H).

Table 2 below recites the analytical data for the compounds of Table 1.

TABLE 2

| Cmpd. No. | LC/MS M + 1 | LC/RT min | NMR |
|---|---|---|---|
| 1 | 454.50 | 1.61 | 1H NMR (400 MHz, DMSO) δ 7.89 (d, J = 8.0 Hz, 1H), 7.59-7.45 (m, 2H), 6.58 (d, J = 3.7 Hz, 1H), 6.12 (d, J = 3.9 Hz, 1H), 4.45-4.27 (m, 1H), 3.93 (t, J = 5.8 Hz, 2H), 3.57-3.43 (m, 1H), 3.43-3.01 (m, 5H), 2.65 (s, 3H), 2.27 (s, 3H), 2.23-1.65 (m, 4H), 1.17 (d, J = 6.8 Hz, 6H). |
| 2 | 498.20 | 2.57 | 1H NMR (400 MHz, DMSO) δ 7.11-6.97 (m, 3H), 6.65 (d, J = 3.5 Hz, 1H), 6.33 (d, J = 3.9 Hz, 1H), 4.98-4.69 (m, 1H), 4.67-4.54 (m, 1H), 4.09-3.98 (m, 1H), 3.90-3.81 (m, 1H), 3.77 (s, 3H), 3.74-3.52 (m, 2H), 3.46-3.35 (m, 1H), 3.34-3.30 (m, 2H), 3.26-3.08 (m, 1H), 2.32 (s, 3H), 2.14-1.82 (m, 2H), 1.27 (d, J = 6.0 Hz, 6H). |
| 3 | 484.40 | 2.83 | |
| 4 | 466.30 | 1.63 | |
| 5 | 408.20 | 2.38 | |
| 6 | 478.50 | 1.55 | 1H NMR (400 MHz, DMSO) δ 7.83 (d, J = 8.0 Hz, 1H), 7.63-7.54 (m, 1H), 7.52-7.39 (m, 2H), 6.58 (d, J = 3.7 Hz, 1H), 6.12 (d, J = 3.9 Hz, 1H), 4.43-4.26 (m, 1H), 3.93 (t, J = 5.6 Hz, 2H), 3.48-3.19 (m, 4H), |

TABLE 2-continued

| Cmpd. No. | LC/MS M + 1 | LC/RT min | NMR |
|---|---|---|---|
| | | | 3.19-3.01 (m, 1H), 2.59 (s, 3H), 2.45 (d, J = 4.6 Hz, 3H), 2.27 (s, 3H), 2.23-2.12 (m, 1H), 2.06-1.96 (m, 1H), 1.85-1.70 (m, 2H). |
| 7 | 485.50 | 1.24 | |
| 8 | 546.70 | 1.64 | |
| 9 | 500.50 | 1.51 | |
| 10 | 416.50 | 1.05 | 1H NMR (400 MHz, DMSO) δ 7.50 (d, J = 2.1 Hz, 1H), 7.36 (dd, J = 8.5, 2.1 Hz, 1H), 7.20 (d, J = 8.7 Hz, 1H), 5.99 (d, J = 3.5 Hz, 1H), 5.93 (d, J = 3.6 Hz, 1H), 4.78-4.64 (m, 1H), 4.38-4.03 (m, 1H), 3.78 (t, J = 5.8 Hz, 2H), 3.63 (q, J = 11.2 Hz, 2H), 3.55-3.03 (m, 5H), 2.24 (s, 3H), 2.12-1.91 (m, 2H), 1.79-1.62 (m, 2H), 1.31 (d, J = 6.0 Hz, 6H). |
| 11 | 484.50 | 1.32 | |
| 12 | 462.50 | 1.64 | 1H NMR (400 MHz, DMSO) δ 7.83 (d, J = 8.0 Hz, 1H), 7.57 (q, J = 4.9 Hz, 1H), 7.50-7.41 (m, 2H), 6.57 (s, 1H), 6.19 (d, J = 4.0 Hz, 1H), 4.36 (d, J = 12.5 Hz, 1H), 3.98 (t, J = 5.7 Hz, 2H), 3.44-3.33 (m, 2H), 3.31-3.22 (m, 2H), 3.11 (t, J = 12.6 Hz, 1H), 2.59 (s, 3H), 2.45 (d, J = 4.9 Hz, 3H), 2.28 (s, 3H), 2.19 (d, J = 12.9 Hz, 1H), 2.06-1.99 (m, 1H), 1.80 (t, J = 12.6 Hz, 2H). |
| 13 | 535.50 | 1.40 | |
| 14 | 464.50 | 1.47 | |
| 15 | 465.50 | 1.35 | |
| 16 | 510.70 | 1.74 | |
| 17 | 548.50 | 1.73 | |
| 18 | 454.50 | 2.97 | |
| 19 | 442.50 | 1.26 | |
| 20 | 414.18 | 2.84 | |
| 21 | 509.50 | 1.36 | |
| 22 | 437.10 | 1.27 | |
| 23 | 510.50 | 2.68 | |
| 24 | 451.20 | 1.73 | |
| 25 | 420.22 | 2.21 | |
| 26 | 434.50 | 1.54 | |
| 27 | 470.50 | 1.70 | 1H NMR (400 MHz, DMSO) δ 8.10 (d, J = 1.7 Hz, 1H), 7.91 (d, J = 7.9 Hz, 1H), 7.50-7.39 (m, 2H), 6.59 (d, J = 3.6 Hz, 1H), 6.13 (d, J = 3.8 Hz, 1H), 4.36 (d, J = 12.3 Hz, 1H), 3.93 (t, J = 5.2 Hz, 2H), 3.48-3.25 (m, 4H), 3.12 (t, J = 11.7 Hz, 1H), 2.59 (s, 3H), 2.28 (s, 3H), 2.23-2.10 (m, 2H), 2.07-1.95 (m, 1H), 1.86-1.68 (m, 2H), 0.51-0.42 (m, 2H), 0.38-0.30 (m, 2H). |
| 28 | 511.70 | 1.23 | 1H NMR (400 MHz, CDCl3) δ 7.04-7.00 (m, 1H), 6.97 (dd, J = 8.2, 1.6 Hz, 1H), 6.88 (d, J = 8.2 Hz, 1H), 6.52 (d, J = 3.6 Hz, 1H), 5.98-5.86 (m, 1H), 4.72-4.26 (m, 2H), 3.88 (s, 3H), 3.86-3.07 (m, 6H), 2.46-1.88 (m, 6H), 1.71-1.46 (m, 1H), 1.38 (d, J = 6.1 Hz, 6H), 1.34-1.12 (m, 3H). |
| 29 | 480.30 | 1.70 | |
| 30 | 458.30 | 1.45 | |
| 31 | 428.50 | 1.22 | |
| 32 | 430.23 | 2.75 | 1H NMR (400 MHz, CDCl3) δ 8.00-7.94 (m, 2H), 7.61-7.55 (m, 2H), 7.22 (dd, J = 4.3, 2.1 Hz, 1H), 6.17 (d, J = 4.4 Hz, 1H), 4.91 (s, 1H), 4.63 (d, J = 12.5 Hz, 1H), 4.36 (t, J = 5.8 Hz, 2H), 3.64-3.41 (m, 2H), 3.34 (t, J = 5.7 Hz, 2H), 3.31-3.21 (m, 1H), 2.41 (s, 3H), 2.32-2.18 (m, 2H), 2.08 (d, J = 10.2 Hz, 1H), 1.95 (t, J = 12.2 Hz, 1H), 1.74 (t, J = 11.1 Hz, 1H), 0.68-0.60 (m, 4H). |
| 33 | 525.50 | 1.41 | |
| 34 | 424.24 | 2.33 | 1H NMR (400 MHz, DMSO) δ 7.54-7.39 (m, 1H), 7.22-7.09 (m, 2H), 6.60 (d, J = 3.6 Hz, 1H), 6.10 (s, 1H), 5.20-4.36 (m, 3H), 4.19-3.99 (m, 1H), 3.92-3.37 (m, 4H), 3.20-2.93 (m, 2H), 2.54 (s, 3H), 2.35-2.14 (m, 4H), 1.95-1.64 (m, 1H), 1.51 (s, 6H). |
| 35 | 468.20 | 4.64 | |
| 36 | 430.19 | 2.11 | 1H NMR (400 MHz, DMSO) δ 7.51 (d, J = 2.0 Hz, 1H), 7.37 (dd, J = 8.5, 2.0 Hz, 1H), 7.21 (d, J = 8.6 Hz, 1H), 6.60 (d, J = 3.8 Hz, 1H), 6.16 (d, J = 3.9 Hz, 1H), 4.86-4.60 (m, 1H), 4.48-4.08 (m, 1H), 3.70 (s, 2H), 3.62-2.81 (m, 3H), 2.09 (s, 1H), 1.89-1.61 (m, 4H), 1.31 (d, J = 6.0 Hz, 6H), 1.09 (s, 6H). |
| 37 | 484.40 | 1.54 | |
| 38 | 446.26 | 2.26 | |
| 39 | 458.70 | 1.53 | |
| 40 | 482.50 | 1.56 | |
| 41 | 532.50 | 1.62 | |
| 42 | 408.50 | 1.24 | |

TABLE 2-continued

| Cmpd. No. | LC/MS M + 1 | LC/RT min | NMR |
|---|---|---|---|
| 43 | 456.50 | 1.42 | |
| 44 | 450.30 | 1.10 | |
| 45 | 436.20 | 2.13 | |
| 46 | 494.30 | 1.69 | |
| 47 | 476.50 | 1.52 | |
| 48 | 534.20 | 1.25 | |
| 49 | 429.70 | 1.17 | |
| 50 | 464.50 | 1.42 | |
| 51 | 489.50 | 1.54 | |
| 52 | 510.70 | 1.64 | |
| 53 | 511.70 | 1.28 | |
| 54 | 476.50 | 1.76 | |
| 55 | 496.20 | 1.79 | |
| 56 | 438.28 | 2.52 | |
| 57 | 454.50 | 1.51 | |
| 58 | 458.40 | 1.55 | |
| 59 | 534.50 | 2.04 | 1H NMR (400 MHz, DMSO) δ 7.04-6.87 (m, 3H), 6.57 (d, J = 3.5 Hz, 1H), 6.07 (d, J = 3.9 Hz, 1H), 4.66-4.52 (m, 1H), 4.04-3.83 (m, 2H), 3.77 (s, 3H), 3.60-3.12 (m, 5H), 2.33-2.21 (m, 4H), 2.17-1.65 (m, 3H), 1.42 (d, J = 7.0 Hz, 3H), 1.26 (d, J = 6.0 Hz, 6H). |
| 60 | 480.40 | 3.01 | |
| 61 | 518.20 | 1.17 | |
| 62 | 476.50 | 1.81 | |
| 63 | 393.50 | 0.99 | |
| 64 | 518.30 | 1.66 | |
| 65 | 446.17 | 2.37 | |
| 66 | 460.50 | 1.64 | |
| 67 | 422.50 | 1.51 | |
| 68 | 450.14 | 2.52 | |
| 69 | 504.50 | 1.54 | |
| 70 | 450.50 | 1.46 | |
| 71 | 496.70 | 1.69 | |
| 72 | 548.30 | 1.28 | |
| 73 | 400.20 | 2.57 | |
| 74 | 478.20 | 0.98 | 1H NMR (400 MHz, CDCl3) δ 7.45 (d, J = 8.2 Hz, 2H), 7.40 (d, J = 8.2 Hz, 2H), 6.49 (s, 1H), 4.71 (s, 2H), 4.63 (s, 1H), 3.98 (s, 2H), 3.86 (q, J = 8.7 Hz, 2H), 3.57 (s, 1H), 3.47 (s, 1H), 3.30 (s, 2H), 3.19 (s, 1H), 2.47 (s, 1H), 2.41 (d, J = 24.3 Hz, 4H), 2.16-2.02 (m, 1H), 2.01 (s, 1H), 1.91 (s, 1H), 1.56 (s, 2H), 1.25 (s, 1H). |
| 75 | 524.00 | 1.69 | 1H NMR (400 MHz, DMSO) δ 8.07-7.95 (m, 1H), 7.95-7.81 (m, 2H), 7.76-7.61 (m, 2H), 6.62 (d, J = 4.0 Hz, 1H), 6.12 (d, J = 4.0 Hz, 1H), 4.45-4.30 (m, 1H), 3.57-3.08 (m, 3H), 2.97-2.85 (m, 2H), 2.85-2.74 (m, 1H), 2.20-2.07 (m, 1H), 2.01-1.66 (m, 4H), 1.43 (d, J = 6.7 Hz, 6H), 0.56-0.32 (m, 4H). |
| 76 | 511.50 | 4.41 | 1H NMR (400 MHz, DMSO) δ 7.51 (d, J = 2.0 Hz, 1H), 7.37 (dd, J = 8.5, 2.0 Hz, 1H), 7.21 (d, J = 8.6 Hz, 1H), 6.61 (d, J = 4.0 Hz, 1H), 6.11 (d, J = 4.0 Hz, 1H), 4.81-4.66 (m, 1H), 4.41-4.16 (m, 1H), 3.58-2.99 (m, 3H), 2.91 (d, J = 5.8 Hz, 2H), 2.77 (t, J = 7.1 Hz, 1H), 1.99-1.68 (m, 4H), 1.43 (s, 6H), 1.31 (d, J = 6.0 Hz, 6H). |
| 77 | 484.50 | 6.20 | |
| 78 | 444.20 | 2.34 | |
| 79 | 446.50 | 1.59 | 1H NMR (400 MHz, DMSO) δ 7.19 (d, J = 7.6 Hz, 1H), 6.96 (s, 1H), 6.93 (d, J = 7.8 Hz, 1H), 6.56 (d, J = 3.7 Hz, 1H), 6.09 (d, J = 3.9 Hz, 1H), 4.33-4.15 (m, 1H), 3.97-3.87 (m, 2H), 3.81 (s, 3H), 3.48 (t, J = 5.5 Hz, 2H), 3.46-3.32 (m, 4H), 3.25 (s, 3H), 3.23-3.08 (m, 1H), 2.70-2.61 (m, 2H), 2.57 (q, J = 7.5 Hz, 2H), 2.29-1.98 (m, 2H), 1.90-1.63 (m, 2H), 1.13 (t, J = 7.5 Hz, 3H). |
| 80 | 480.50 | 1.57 | 1H NMR (400 MHz, DMSO) δ 7.07-6.91 (m, 3H), 6.60 (d, J = 3.7 Hz, 1H), 6.18-6.04 (m, 1H), 5.14-4.73 (m, 1H), 4.66-4.58 (m, 1H), 4.57-4.19 (m, 1H), 4.19-3.99 (m, 1H), 3.93-3.71 (m, 5H), 3.59-3.43 (m, 1H), 3.40-3.26 (m, 2H), 3.14-2.97 (m, 1H), 2.30 (s, 3H), 2.26-2.12 (m, 1H), 1.94-1.75 (m, 1H), 1.27 (d, J = 6.0 Hz, 6H). |
| 81 | 484.40 | 5.39 | |
| 82 | 446.26 | 2.37 | |
| 83 | 452.20 | 1.16 | |
| 84 | 436.50 | 1.06 | 1H NMR (400 MHz, CDCl3) δ 7.06-6.98 (m, 3H), 6.91 (dd, J = 8.1, 1.9 Hz, 1H), 6.00 (d, J = 4.3 Hz, 1H), 4.57 (s, 1H), 4.31 (t, J = 6.0 Hz, 2H), 3.83 (s, 3H), 3.65 (s, 1H), 3.53 (s, 1H), 3.26 (t, J = 6.0 Hz, 2H), 3.26 (s, 1H), |

TABLE 2-continued

| Cmpd. No. | LC/MS M + 1 | LC/RT min | NMR |
|---|---|---|---|
| | | | 2.42-2.37 (m, 3H), 2.27-2.00 (m, 2H), 1.90 (s, 1H), 1.73 (s, 1H), 1.36 (s, 9H), 1.35 (s, 9H). |
| 85 | 496.70 | 1.51 | |
| 86 | 432.26 | 2.02 | |
| 87 | 448.20 | 1.69 | 1H NMR (400 MHz, DMSO) δ 7.07-6.90 (m, 3H), 6.60 (d, J = 3.8 Hz, 1H), 6.18-6.03 (m, 1H), 5.14-4.74 (m, 1H), 4.67-4.52 (m, 1H), 4.54-4.14 (m, 1H), 4.18-3.94 (m, 1H), 3.89-3.69 (m, 5H), 3.60-3.37 (m, 1H), 3.37-3.27 (m, 2H), 3.17-2.99 (m, 1H), 2.30 (s, 3H), 2.25-2.08 (m, 1H), 1.96-1.71 (m, 1H), 1.27 (d, J = 6.0 Hz, 6H). |
| 88 | 484.40 | 5.32 | 1H NMR (400 MHz, DMSO) δ 7.30 (d, J = 8.8 Hz, 2H), 7.05 (d, J = 4.2 Hz, 1H), 6.92 (d, J = 8.8 Hz, 2H), 6.16 (d, J = 4.2 Hz, 1H), 4.19 (t, J = 5.9 Hz, 2H), 4.12-3.56 (m, 1H), 3.38-3.29 (m, 2H), 3.27-3.16 (m, 7H), 2.73 (q, J = 7.4 Hz, 2H), 2.27 (s, 3H), 2.15-1.98 (m, 2H), 1.85-1.66 (m, 2H), 1.66-1.50 (m, 6H), 1.04 (t, J = 7.4 Hz, 3H). |
| 89 | 449.20 | 1.07 | 1H NMR (400 MHz, CDCl3) δ 7.25-7.18 (m, 1H), 7.08-6.98 (m, 2H), 6.97-6.88 (m, 1H), 6.25-6.10 (m, 1H), 4.59 (s, 1H), 4.37 (s, 2H), 3.84 (s, 3H), 3.75 (s, 1H), 3.51 (s, 1H), 3.35 (s, 1H), 3.35 (s, 2H), 2.42 (s, 3H), 2.16 (s, 2H), 1.87 (s, 2H), 1.37 (s, 9H). |
| 90 | 508.70 | 1.52 | |
| 91 | 470.50 | 1.49 | |
| 92 | 422.29 | 2.67 | |
| 93 | 526.30 | 1.65 | |
| 94 | 515.29 | 2.43 | 1H NMR (400 MHz, CDCl3) δ 7.63 (t, J = 8.1 Hz, 1H), 7.19 (dd, J = 8.0, 1.6 Hz, 1H), 7.12 (dd, J = 11.9, 1.6 Hz, 1H), 6.49 (s, 1H), 4.60 (s, 1H), 3.99 (s, 2H), 3.72 (q, J = 7.0 Hz, 3H), 3.37 (t, J = 80.3 Hz, 5H), 2.43 (d, J = 16.6 Hz, 5H), 2.25-1.83 (m, 3H), 1.65 (d, J = 0.8 Hz, 7H), 1.29-1.20 (m, 5H). |
| 95 | 488.50 | 1.46 | 1H NMR (400 MHz, DMSO) δ 7.28-7.22 (m, 2H), 6.95 (d, J = 8.5 Hz, 1H), 6.58-6.52 (m, 1H), 6.18 (d, J = 4.0 Hz, 1H), 4.54 (t, J = 5.2 Hz, 1H), 4.47-4.13 (m, 1H), 4.07 (t, J = 6.2 Hz, 2H), 3.97 (t, J = 5.7 Hz, 2H), 3.62 (s, 1H), 3.62-3.54 (m, 2H), 3.33 (s, 2H), 3.30-3.03 (m, 2H), 2.28 (s, 3H), 2.16 (s, 3H), 2.14-2.00 (m, 2H), 1.88 (q, J = 6.2 Hz, 2H), 1.81-1.67 (m, 2H). |
| 96 | 516.50 | 1.44 | |
| 97 | 478.20 | 1.01 | 1H NMR (400 MHz, DMSO) δ 7.47 (d, J = 8.7 Hz, 1H), 7.24-7.09 (m, 2H), 6.57 (d, J = 3.2 Hz, 1H), 6.12 (d, J = 3.9 Hz, 1H), 4.97 (s, 1H), 4.45-4.25 (m, 1H), 3.92 (t, J = 5.2 Hz, 2H), 3.60-2.97 (m, 5H), 2.54 (s, 3H), 2.27 (s, 3H), 2.21-1.95 (m, 2H), 1.85-1.63 (m, 2H), 1.50 (s, 6H). |
| 98 | 450.50 | 1.21 | |
| 99 | 408.10 | 1.20 | |
| 100 | 470.50 | 1.58 | 1H NMR (400 MHz, DMSO) δ 7.36 (d, J = 8.2 Hz, 2H), 7.28 (d, J = 8.2 Hz, 2H), 7.27-7.18 (m, 1H), 6.49 (d, J = 4.6 Hz, 1H), 4.50-4.18 (m, 3H), 3.54-2.99 (m, 5H), 2.58-2.47 (m, 1H), 2.30 (s, 3H), 2.26-1.91 (m, 2H), 1.91-1.65 (m, 7H), 1.50-1.16 (m, 5H). |
| 101 | 488.50 | 1.84 | 1H NMR (400 MHz, CDCl3) δ 7.47-7.41 (m, 2H), 7.38 (d, J = 8.2 Hz, 2H), 6.48 (s, 1H), 4.64 (d, J = 10.0 Hz, 1H), 4.56 (s, 2H), 3.98 (s, 2H), 3.71 (t, J = 6.6 Hz, 2H), 3.58 (s, 1H), 3.46 (s, 1H), 3.29 (s, 2H), 3.18 (s, 1H), 2.61-2.28 (m, 7H), 2.17-2.02 (m, 1H), 2.01 (s, 1H), 1.88 (d, J = 12.1 Hz, 1H), 1.60 (s, 1H). |
| 102 | 538.00 | 1.81 | |
| 103 | 546.70 | 1.63 | |
| 104 | 420.10 | 2.45 | 1H NMR (400 MHz, DMSO) δ 7.06-6.90 (m, 3H), 6.60 (d, J = 3.5 Hz, 1H), 6.17-6.05 (m, 1H), 5.11-4.71 (m, 1H), 4.65-4.55 (m, 1H), 4.53-4.25 (m, 1H), 4.14-4.03 (m, 1H), 3.88-3.69 (m, 5H), 3.58-3.43 (m, 1H), 3.41-3.28 (m, 2H), 3.15-3.06 (m, 1H), 2.30 (s, 3H), 2.27-2.10 (m, 1H), 2.00-1.69 (m, 1H), 1.27 (d, J = 6.0 Hz, 6H). |
| 105 | 484.60 | 4.79 | 1H NMR (400 MHz, DMSO) δ 7.26-7.19 (m, 2H), 6.96 (d, J = 9.2 Hz, 1H), 6.57 (d, J = 3.8 Hz, 1H), 6.13 (d, J = 3.9 Hz, 1H), 4.71-4.56 (m, 1H), 4.32-3.90 (m, 1H), 3.79 (t, J = 6.0 Hz, 2H), 3.70-3.18 (m, 5H), 3.18-3.02 (m, 1H), 2.19-1.68 (m, 11H), 1.57-1.36 (m, 2H), 1.29 (d, J = 6.0 Hz, 6H). |
| 106 | 490.40 | 4.35 | 1H NMR (400 MHz, DMSO) δ 7.51 (d, J = 2.1 Hz, 1H), 7.38 (dd, J = 8.5, 2.1 Hz, 1H), 7.20 (d, J = 8.7 Hz, 1H), |

TABLE 2-continued

| Cmpd. No. | LC/MS M + 1 | LC/RT min | NMR |
|---|---|---|---|
| | | | 7.06 (d, J = 4.2 Hz, 1H), 6.17 (d, J = 4.2 Hz, 1H), 4.74 (hept, J = 6.0 Hz, 1H), 4.48-4.12 (m, 3H), 3.65-3.28 (m, 2H), 3.28-2.94 (m, 3H), 2.73 (q, J = 7.4 Hz, 2H), 2.27 (s, 3H), 2.17-1.90 (m, 2H), 1.86-1.68 (m, 2H), 1.31 (d, J = 6.0 Hz, 6H), 1.04 (t, J = 7.4 Hz, 3H). |
| 107 | 458.20 | 1.49 | |
| 108 | 454.50 | 1.51 | |
| 109 | 392.50 | 1.31 | |
| 110 | 436.20 | 1.92 | 1H NMR (400 MHz, DMSO) δ 7.51 (d, J = 2.1 Hz, 1H), 7.38 (dd, J = 8.5, 2.1 Hz, 1H), 7.20 (d, J = 8.7 Hz, 1H), 6.73 (d, J = 4.0 Hz, 1H), 6.22 (d, J = 4.1 Hz, 1H), 4.80-4.65 (m, 1H), 4.46-4.20 (m, 1H), 4.13 (t, J = 5.8 Hz, 2H), 3.62-3.24 (m, 4H), 3.20 (s, 3H), 3.18-2.93 (m, 1H), 2.29 (s, 3H), 2.23-1.90 (m, 2H), 1.87-1.70 (m, 2H), 1.31 (d, J = 6.0 Hz, 6H). |
| 111 | 480.30 | 1.37 | 1H NMR (400 MHz, CDCl3) δ 7.42 (t, J = 7.8 Hz, 1H), 7.17 (ddd, J = 12.5, 9.5, 1.5 Hz, 2H), 6.29 (s, 1H), 4.57 (s, 1H), 3.93 (s, 2H), 3.53 (d, J = 31.9 Hz, 2H), 3.25 (d, J = 38.8 Hz, 3H), 2.65 (dt, J = 11.8, 8.8 Hz, 2H), 2.50-2.33 (m, 6H), 2.27-2.07 (m, 3H), 2.01 (s, 2H), 1.84-1.67 (m, 1H). |
| 112 | 484.30 | 1.34 | |
| 113 | 492.50 | 2.82 | |
| 114 | 578.50 | 1.62 | |
| 115 | 508.70 | 1.58 | |
| 116 | 464.30 | 0.75 | 1H NMR (400 MHz, CDCl3) δ 7.28-7.20 (m, 3H), 6.82 (d, J = 8.1 Hz, 1H), 6.16 (d, J = 4.5 Hz, 1H), 4.56 (dt, J = 12.1, 6.0 Hz, 1H), 4.56 (s, 1H), 4.35 (t, J = 5.9 Hz, 2H), 3.80 (s, 1H), 3.37 (s, 2H), 3.34 (t, J = 5.9 Hz, 2H), 2.41 (s, 3H), 2.21 (s, 3H), 2.11 (s, 3H), 1.84 (s, 2H), 1.35 (d, J = 6.0 Hz, 6H). |
| 117 | 478.30 | 1.64 | |
| 118 | 484.70 | 1.32 | 1H NMR (400 MHz, CDCl3) δ 7.19-7.00 (m, 2H), 6.91 (d, J = 8.0 Hz, 1H), 6.56 (d, J = 3.8 Hz, 1H), 6.02 (d, J = 3.8 Hz, 1H), 5.92 (s, 1H), 4.71-4.50 (m, 1H), 4.46-4.23 (m, 2H), 4.16 (t, J = 6.5 Hz, 2H), 3.88 (s, 3H), 3.88-3.62 (m, 2H), 3.41 (t, J = 6.4 Hz, 2H), 2.71 (s, 3H), 2.59-2.44 (m, 2H), 2.36-1.61 (m, 2H), 1.39 (d, J = 6.1 Hz, 6H). |
| 119 | 509.60 | 4.60 | |
| 120 | 475.12 | 2.82 | |
| 121 | 454.50 | 1.42 | 1H NMR (400 MHz, DMSO) δ 7.28-7.20 (m, 2H), 7.05 (d, J = 4.1 Hz, 1H), 6.97 (d, J = 9.1 Hz, 1H), 6.17 (d, J = 4.2 Hz, 1H), 4.73-4.55 (m, 1H), 4.47-4.11 (m, 3H), 3.72-3.28 (m, 2H), 3.28-2.98 (m, 3H), 2.31 (s, 3H), 2.26 (s, 3H), 2.14 (s, 3H), 2.12-1.96 (m, 2H), 1.85-1.64 (m, 2H), 1.29 (d, J = 6.0 Hz, 6H). |
| 122 | 424.20 | 1.22 | 1H NMR (400 MHz, DMSO) δ 7.86 (d, J = 8.4 Hz, 2H), 7.68 (d, J = 8.4 Hz, 2H), 6.58 (d, J = 3.8 Hz, 1H), 6.12 (d, J = 3.9 Hz, 1H), 4.47-4.28 (m, 1H), 3.93 (t, J = 5.8 Hz, 2H), 3.48-3.25 (m, 4H), 3.25-3.07 (m, 5H), 2.27 (s, 3H), 2.23-1.96 (m, 2H), 1.86-1.73 (m, 2H), 1.71-1.63 (m, 4H). |
| 123 | 511.40 | 2.70 | |
| 124 | 454.50 | 1.37 | |
| 125 | 428.20 | 0.96 | |
| 126 | 522.70 | 1.64 | |
| 127 | 464.50 | 1.54 | 1H NMR (400 MHz, DMSO) δ 7.53-7.41 (m, 1H), 7.22-7.10 (m, 2H), 6.61 (d, J = 4.1 Hz, 1H), 6.09 (d, J = 4.0 Hz, 1H), 4.97 (s, 1H), 4.49-4.19 (m, 1H), 3.53-3.01 (m, 3H), 2.96-2.83 (m, 2H), 2.83-2.70 (m, 1H), 2.55 (s, 3H), 2.01-1.61 (m, 4H), 1.51 (s, 6H), 1.43 (s, 6H). |
| 128 | 464.50 | 4.17 | 1H NMR (400 MHz, CDCl3) δ 7.50 (d, J = 2.1 Hz, 1H), 7.37 (dd, J = 8.4, 2.1 Hz, 1H), 7.27-7.24 (m, 1H), 6.96 (d, J = 8.5 Hz, 1H), 6.20 (d, J = 4.5 Hz, 1H), 4.57 (s, 1H), 4.20 (s, 2H), 3.94 (s, 3H), 3.63 (s, 2H), 3.32 (s, 1H), 1.92 (s, 2H), 1.78 (s, 2H), 1.18 (s, 6H), 0.97 (s, 1H). |
| 129 | 484.50 | 1.50 | |
| 130 | 512.40 | 1.68 | |
| 131 | 492.20 | 1.84 | |
| 132 | 476.50 | 1.39 | 1H NMR (400 MHz, DMSO) δ 7.27 (d, J = 7.9 Hz, 1H), 6.99 (d, J = 1.4 Hz, 1H), 6.97-6.90 (m, 1H), 6.62-6.53 (m, 1H), 6.18-6.05 (m, 1H), 4.58-4.18 (m, 2H), 3.93-3.76 (m, 5H), 3.62 (d, J = 4.2 Hz, 2H), 3.54-3.02 (m, 5H), 2.49-2.26 (m, 1H), 2.01-1.63 (m, 4H), 1.27 (s, 6H). |

TABLE 2-continued

| Cmpd. No. | LC/MS M + 1 | LC/RT min | NMR |
|---|---|---|---|
| 133 | 466.40 | 2.99 | 1H NMR (400 MHz, CDCl3) δ 7.68-7.61 (m, 2H), 7.04-6.97 (m, 1H), 6.29 (s, 1H), 4.70 (dt, J = 12.1, 6.1 Hz, 1H), 4.53 (s, 1H), 3.93 (t, J = 5.7 Hz, 2H), 3.55 (s, 2H), 3.30 (s, 3H), 2.42 (s, 3H), 2.23-1.92 (m, 4H), 1.43 (d, J = 6.1 Hz, 6H). |
| 134 | 479.50 | 1.42 | |
| 135 | 456.50 | 1.45 | |
| 136 | 548.30 | 1.30 | 1H NMR (400 MHz, DMSO) δ 7.09 (d, J = 4.3 Hz, 1H), 7.05-6.92 (m, 3H), 6.17 (d, J = 4.3 Hz, 1H), 4.67-4.51 (m, 1H), 4.47-4.02 (m, 3H), 3.77 (s, 3H), 3.65-3.28 (m, 2H), 3.28-2.95 (m, 3H), 2.28 (s, 3H), 2.17-1.97 (m, 2H), 1.86-1.67 (m, 2H), 1.31-1.24 (m, 15H). |
| 137 | 482.40 | 1.28 | 1H NMR (400 MHz, CDCl3) δ 7.34-7.29 (m, 2H), 6.84 (d, J = 9.0 Hz, 1H), 6.56 (d, J = 3.7 Hz, 1H), 6.02 (d, J = 3.9 Hz, 1H), 4.62-4.52 (m, 1H), 4.51-4.40 (m, 1H), 4.34-4.23 (m, 2H), 4.18 (t, J = 6.5 Hz, 2H), 3.88-3.64 (m, 1H), 3.55-3.31 (m, 2H), 2.85 (s, 6H), 2.62-2.42 (m, 2H), 2.22 (s, 3H), 1.70-1.54 (m, 2H), 1.35 (d, J = 6.0 Hz, 6H). |
| 138 | 507.40 | 6.05 | |
| 139 | 492.30 | 1.55 | |
| 140 | 410.20 | 0.80 | |
| 141 | 498.70 | 2.97 | |
| 142 | 494.50 | 1.50 | 1H NMR (400 MHz, DMSO) δ 7.39 (d, J = 8.7 Hz, 2H), 7.27-7.17 (m, 1H), 6.97 (d, J = 8.7 Hz, 2H), 6.49 (d, J = 4.6 Hz, 1H), 4.55-4.15 (m, 3H), 4.03 (t, J = 6.6 Hz, 2H), 3.76-2.94 (m, 5H), 2.30 (s, 3H), 2.21-1.97 (m, 2H), 1.94-1.69 (m, 3H), 1.62 (q, J = 6.7 Hz, 2H), 0.93 (d, J = 6.6 Hz, 6H). |
| 143 | 492.50 | 1.73 | |
| 144 | 468.70 | 1.42 | 1H NMR (400 MHz, DMSO) δ 8.02 (d, J = 1.1 Hz, 1H), 7.86 (d, J = 8.4 Hz, 2H), 7.67 (d, J = 8.4 Hz, 2H), 6.58 (d, J = 3.4 Hz, 1H), 6.14 (d, J = 3.9 Hz, 1H), 4.26-4.14 (m, 1H), 3.79 (t, J = 5.9 Hz, 2H), 3.50-3.23 (m, 5H), 3.18-3.04 (m, 1H), 2.26-1.76 (m, 9H), 1.60-1.36 (m, 2H), 0.56-0.35 (m, 4H). |
| 145 | 537.40 | 2.89 | |
| 146 | 508.70 | 1.61 | |
| 147 | 414.17 | 2.22 | |
| 148 | 494.50 | 1.36 | 1H NMR (400 MHz, DMSO) δ 7.06-6.90 (m, 3H), 6.57 (d, J = 3.6 Hz, 1H), 6.11 (d, J = 3.9 Hz, 1H), 4.68-4.50 (m, 1H), 3.83-3.63 (m, 5H), 3.18-2.78 (m, 4H), 2.41-2.20 (m, 1H), 2.13-1.87 (m, 5H), 1.61-1.34 (m, 2H), 1.26 (d, J = 6.0 Hz, 6H), 1.24-1.19 (m, 3H). |
| 149 | 480.30 | 1.76 | |
| 150 | 450.50 | 1.28 | 1H NMR (400 MHz, DMSO) δ 7.27 (d, J = 7.9 Hz, 1H), 6.98 (d, J = 1.2 Hz, 1H), 6.96-6.87 (m, 1H), 6.58 (s, 1H), 6.12 (s, 1H), 4.62-4.19 (m, 2H), 4.01-3.85 (m, 2H), 3.81 (s, 3H), 3.62 (s, 2H), 3.55-2.94 (m, 5H), 2.36-2.01 (m, 5H), 1.86-1.59 (m, 2H), 1.27 (s, 6H). |
| 151 | 480.40 | 2.97 | |
| 152 | 468.30 | 1.91 | |
| 153 | 526.50 | 1.42 | |
| 154 | 526.20 | 1.50 | |
| 155 | 470.50 | 1.70 | |
| 156 | 480.50 | 0.65 | 1H NMR (400 MHz, DMSO) δ 8.46 (s, 1H), 7.61 (t, J = 52.4 Hz, 1H), 7.42 (s, 1H), 6.63 (d, J = 4.0 Hz, 1H), 6.03 (d, J = 4.0 Hz, 1H), 4.50-4.29 (m, 1H), 3.76-3.39 (m, 2H), 3.27-3.07 (m, 1H), 3.03-2.88 (m, 2H), 2.88-2.76 (m, 1H), 2.65 (s, 3H), 2.08-1.66 (m, 4H), 1.44 (s, 6H). |
| 157 | 497.50 | 4.05 | 1H NMR (400 MHz, DMSO) δ 7.05 (d, J = 1.7 Hz, 1H), 7.01 (d, J = 8.0 Hz, 1H), 6.93 (dd, J = 8.0, 1.8 Hz, 1H), 6.58 (d, J = 3.1 Hz, 1H), 6.12 (d, J = 3.9 Hz, 1H), 4.32 (s, 1H), 3.93 (t, J = 5.5 Hz, 2H), 3.76 (s, 3H), 3.58-3.35 (m, 2H), 3.35-3.29 (m, 2H), 3.22-3.02 (m, 1H), 2.28 (s, 3H), 2.11 (s, 2H), 1.76 (t, J = 11.1 Hz, 2H), 1.29 (s, 9H). |
| 158 | 480.50 | 1.36 | 1H NMR (400 MHz, CDCl3) δ 8.41 (s, 1H), 7.35 (t, J = 40.0 Hz, 1H), 7.09 (s, 1H), 6.55 (d, J = 3.7 Hz, 1H), 5.97 (d, J = 3.9 Hz, 1H), 4.63 (s, 1H), 3.95 (t, J = 5.3 Hz, 2H), 3.83 (s, 1H), 3.62 (s, 1H), 3.28 (s, 2H), 2.71 (s, 3H), 2.12 (s, 2H), 2.03-1.76 (m, 4H). |
| 159 | 469.50 | 1.12 | 1H NMR (400 MHz, DMSO) δ 7.47 (d, J = 2.1 Hz, 1H), 7.30 (dd, J = 8.4, 2.2 Hz, 1H), 7.26-7.18 (m, 1H), 6.99 (d, J = 8.6 Hz, 1H), 6.49 (d, J = 4.6 Hz, 1H), 5.06 (t, J = 5.7 Hz, 1H), 4.75-4.59 (m, 1H), 4.48 (d, J = 5.7 Hz, |

TABLE 2-continued

| Cmpd. No. | LC/MS M + 1 | LC/RT min | NMR |
|---|---|---|---|
| | | | 2H), 4.44-4.15 (m, 3H), 3.83-2.94 (m, 5H), 2.31 (s, 3H), 2.21-2.00 (m, 2H), 1.94-1.72 (m, 2H), 1.28 (d, J = 6.0 Hz, 6H). |
| 160 | 494.50 | 1.44 | |
| 161 | 422.50 | 1.21 | |
| 162 | 476.50 | 1.04 | |
| 163 | 428.21 | 2.32 | 1H NMR (400 MHz, DMSO) δ 7.36-7.22 (m, 3H), 6.97 (d, J = 8.4 Hz, 1H), 6.48 (d, J = 4.6 Hz, 1H), 4.86-4.72 (m, 1H), 4.43-4.02 (m, 1H), 3.82 (s, 3H), 3.76-3.39 (m, 1H), 3.40-3.29 (m, 2H), 3.29-2.97 (m, 2H), 2.34-2.13 (m, 7H), 2.06-1.88 (m, 2H), 1.81-1.61 (m, 1H), 1.30 (d, J = 6.0 Hz, 3H). |
| 164 | 464.50 | 1.53 | 1H NMR (400 MHz, DMSO) δ 7.24 (d, J = 6.6 Hz, 2H), 6.97 (d, J = 9.2 Hz, 1H), 6.58 (d, J = 3.8 Hz, 1H), 6.14 (d, J = 3.9 Hz, 1H), 4.64 (dt, J = 12.1, 6.1 Hz, 1H), 4.06 (t, J = 5.9 Hz, 2H), 3.90 (s, 2H), 3.51 (t, J = 6.0 Hz, 2H), 2.14 (s, 3H), 1.83 (t, J = 11.8 Hz, 2H), 1.29 (d, J = 6.0 Hz, 6H). |
| 165 | 475.30 | 2.04 | |
| 166 | 412.10 | 1.41 | |
| 167 | 480.30 | 1.49 | 1H NMR (400 MHz, CDCl3) δ 7.06 (d, J = 1.8 Hz, 1H), 7.00 (dd, J = 8.2, 1.9 Hz, 1H), 6.93 (d, J = 8.2 Hz, 1H), 6.56 (d, J = 3.8 Hz, 1H), 5.96 (d, J = 3.9 Hz, 1H), 4.53 (s br, 1H), 4.42-4.23 (m, 4H), 4.06 (s br, 2H), 3.91 (s, 3H), 3.71 (s br, 1H), 3.54 (s br, 1H), 3.43-3.25 (m, 3H), 2.42 (s, 3H), 2.15 (s br, 2H), 1.86 (s br, 2H). |
| 168 | 536.10 | 1.58 | |
| 169 | 511.26 | 1.00 | 1H NMR (400 MHz, CDCl3) δ 7.06 (d, J = 1.8 Hz, 1H), 7.05-6.98 (m, 1H), 6.88 (d, J = 8.2 Hz, 1H), 6.55 (d, J = 3.3 Hz, 1H), 6.15 (d, J = 3.9 Hz, 1H), 4.57 (d, J = 6.1 Hz, 1H), 4.19-4.10 (m, 2H), 3.88 (m, s, 5H), 3.79 (s, 2H), 3.70-3.52 (m, J = 31.5 Hz, 2H), 3.11 (s, 2H), 2.24 (s, 3H), 1.92-1.75 (m, 2H), 1.38 (d, J = 6.1 Hz, 6H). |
| 170 | 494.70 | 1.70 | 1H NMR (400 MHz, DMSO) δ 7.27-7.19 (m, 1H), 7.12-6.98 (m, 3H), 6.51 (d, J = 4.6 Hz, 1H), 4.82-4.69 (m, 1H), 4.46-4.38 (m, 2H), 4.31-4.23 (m, 2H), 3.80 (s, 3H), 3.62-3.39 (m, 1H), 3.38-3.30 (m, 2H), 3.30-3.08 (m, 2H), 2.94-2.72 (m, 2H), 2.17-2.07 (m, 1H), 2.05-1.51 (m, 3H), 1.35 (d, J = 6.4 Hz, 3H). |
| 171 | 564.70 | 1.60 | 1H NMR (400 MHz, DMSO) δ 7.77-7.68 (m, 4H), 7.58-7.46 (m, 4H), 7.43-7.37 (m, 1H), 7.29-7.18 (m, 1H), 6.51 (d, J = 4.6 Hz, 1H), 4.56-4.32 (m, 1H), 4.25 (t, J = 5.6 Hz, 2H), 3.63-3.21 (m, 4H), 3.21-2.98 (m, 1H), 2.31 (s, 3H), 2.27-1.98 (m, 2H), 1.95-1.78 (m, 2H). |
| 172 | 482.50 | 1.63 | |
| 173 | 504.50 | 1.58 | 1H NMR (400 MHz, DMSO) δ 7.30-7.19 (m, 3H), 6.97 (d, J = 9.0 Hz, 1H), 6.21 (d, J = 4.3 Hz, 1H), 4.73-4.55 (m, 1H), 4.36-3.82 (m, 1H), 3.82-3.42 (m, 1H), 3.42-3.15 (m, 2H), 3.08 (s, 2H), 2.41 (s, 3H), 2.40 (s, 3H), 2.14 (s, 3H), 2.13-1.95 (m, 2H), 1.86-1.66 (m, 2H), 1.59 (s, 6H), 1.29 (d, J = 6.0 Hz, 6H). |
| 174 | 452.50 | 1.53 | 1H NMR (400 MHz, DMSO) δ 7.45 (d, J = 8.7 Hz, 2H), 7.30-7.18 (m, 1H), 7.11 (d, J = 8.8 Hz, 2H), 6.49 (d, J = 4.6 Hz, 1H), 4.82 (q, J = 8.9 Hz, 2H), 4.54-4.12 (m, 3H), 3.61-2.95 (m, 5H), 2.30 (s, 3H), 2.26-1.77 (m, 4H). |
| 175 | 504.50 | 1.55 | |
| 176 | 500.50 | 1.34 | |
| 177 | 410.50 | 1.38 | |
| 178 | 507.50 | 1.54 | |
| 179 | 466.50 | 1.41 | |
| 180 | 512.20 | 1.07 | |
| 181 | 466.50 | 1.46 | 1H NMR (400 MHz, DMSO) δ 7.27-7.20 (m, 2H), 7.10 (d, J = 4.2 Hz, 1H), 6.97 (d, J = 9.2 Hz, 1H), 6.18 (d, J = 4.2 Hz, 1H), 4.71-4.59 (m, 1H), 4.48-4.09 (m, 3H), 3.72-3.28 (m, 3H), 3.28-2.95 (m, 3H), 2.27 (s, 3H), 2.14 (s, 3H), 2.13-1.93 (m, 2H), 1.81-1.64 (m, 2H), 1.29 (d, J = 6.0 Hz, 6H), 1.05 (d, J = 6.8 Hz, 6H). |
| 182 | 452.70 | 1.58 | |
| 183 | 456.30 | 0.87 | 1H NMR (400 MHz, CDCl3) δ 7.37-7.29 (m, 2H), 7.14-7.06 (m, 2H), 6.29 (s, 1H), 4.59 (s, 1H), 3.92 (t, J = 5.7 Hz, 2H), 3.64 (s, 1H), 3.45 (s, 1H), 3.25 (d, J = 39.3 Hz, 3H), 2.41 (s, 3H), 2.27-1.86 (m, 5H), 1.63 (s, 1H), 1.06-0.93 (m, 2H), 0.72 (dt, J = 6.6, 4.7 Hz, 2H). |
| 184 | 436.30 | 1.44 | |
| 185 | 490.30 | 1.61 | |
| 186 | 510.70 | 1.39 | |

TABLE 2-continued

| Cmpd. No. | LC/MS M + 1 | LC/RT min | NMR |
|---|---|---|---|
| 187 | 500.50 | 2.44 | |
| 188 | 498.50 | 3.07 | |
| 189 | 408.26 | 2.48 | |
| 190 | 466.50 | 1.41 | |
| 191 | 498.23 | 1.14 | |
| 192 | 459.15 | 1.58 | |
| 193 | 454.50 | 2.30 | |
| 194 | 513.50 | 1.32 | |
| 195 | 427.21 | 1.42 | 1H NMR (400 MHz, CDCl3) δ 8.27 (d, J = 2.3 Hz, 1H), 7.62 (d, J = 9.0 Hz, 1H), 7.52 (s, 1H), 7.39 (dd, J = 8.5, 2.7 Hz, 1H), 7.00 (s, 1H), 6.53 (d, J = 4.1 Hz, 2H), 5.95 (d, J = 3.8 Hz, 2H), 4.52 (s, 2H), 3.95 (dd, J = 23.5, 10.2 Hz, 4H), 3.63-3.44 (m, 4H), 3.40-3.16 (m, 4H), 2.80 (s, 3H), 2.39 (s, 4H), 2.28-2.15 (m, 2H), 2.06 (s, 2H), 1.92 (s, 3H), 1.40 (s, 10H), 1.25 (s, 2H). |
| 196 | 451.30 | 1.32 | |
| 197 | 524.50 | 1.38 | |
| 198 | 479.50 | 1.49 | 1H NMR (400 MHz, DMSO) δ 7.28-7.19 (m, 2H), 7.09 (d, J = 4.3 Hz, 1H), 6.97 (d, J = 9.2 Hz, 1H), 6.17 (d, J = 4.3 Hz, 1H), 4.70-4.56 (m, 1H), 4.51-4.04 (m, 3H), 3.83-3.28 (m, 2H), 3.28-2.91 (m, 3H), 2.27 (s, 3H), 2.14 (s, 3H), 2.13-1.96 (m, 2H), 1.84-1.66 (m, 2H), 1.29 (d, J = 6.0 Hz, 6H), 1.27 (s, 9H). |
| 199 | 466.40 | 1.48 | |
| 200 | 451.50 | 1.31 | 1H NMR (400 MHz, CDCl3) δ 7.21 (dt, J = 4.2, 2.1 Hz, 1H), 7.19 (d, J = 1.4 Hz, 1H), 7.08 (dd, J = 8.2, 2.0 Hz, 1H), 6.67 (d, J = 8.2 Hz, 1H), 6.16 (d, J = 4.5 Hz, 1H), 4.57 (s, 1H), 4.35 (t, J = 6.0 Hz, 2H), 3.76 (s, 1H), 3.52 (s, 1H), 3.32 (t, J = 6.0 Hz, 2H), 3.28 (s, 1H), 2.40 (s, 3H), 2.21 (s, 3H), 2.19-2.02 (m, 2H), 2.00 (s, 1H), 1.97-1.64 (m, 2H). |
| 201 | 436.30 | 1.30 | 1H NMR (400 MHz, DMSO) δ 7.47 (d, J = 2.1 Hz, 1H), 7.28 (dd, J = 8.4, 2.1 Hz, 1H), 6.99 (d, J = 8.6 Hz, 1H), 6.60 (d, J = 3.5 Hz, 1H), 6.16-6.03 (m, 1H), 5.07 (t, J = 5.6 Hz, 1H), 5.02-4.72 (m, 1H), 4.72-4.59 (m, 1H), 4.48 (d, J = 5.6 Hz, 2H), 4.18-4.01 (m, 1H), 3.96-3.26 (m, 5H), 3.21-2.90 (m, 2H), 2.30 (s, 3H), 2.26-2.12 (m, 1H), 1.98-1.75 (m, 1H), 1.28 (d, J = 6.0 Hz, 6H). |
| 202 | 484.40 | 4.78 | |
| 203 | 480.30 | 1.55 | |
| 204 | 430.50 | 1.28 | |
| 205 | 458.10 | 2.27 | |
| 206 | 469.50 | 2.74 | |
| 207 | 450.50 | 1.29 | |
| 208 | 540.50 | 1.44 | |
| 209 | 430.17 | 2.69 | |
| 210 | 465.14 | 3.62 | |
| 211 | 500.50 | 1.46 | |
| 212 | 480.30 | 1.52 | 1H NMR (400 MHz, DMSO) δ 7.61 (d, J = 7.8 Hz, 1H), 7.03-6.92 (m, 2H), 6.58 (d, J = 3.9 Hz, 1H), 6.12 (d, J = 3.9 Hz, 1H), 5.00 (s, 1H), 4.45-4.22 (m, 1H), 3.93 (t, J = 5.8 Hz, 2H), 3.82 (s, 3H), 3.57-3.02 (m, 5H), 2.27 (s, 3H), 2.24-1.98 (m, 2H), 1.86-1.67 (m, 2H), 1.48 (s, 6H). |
| 213 | 466.20 | 1.24 | |
| 214 | 512.70 | 1.65 | |
| 215 | 516.50 | 2.62 | |
| 216 | 522.22 | 1.33 | |
| 217 | 498.70 | 2.62 | |
| 218 | 512.20 | 1.15 | |
| 219 | 438.28 | 2.55 | |
| 220 | 427.20 | 2.15 | |
| 221 | 386.15 | 2.32 | 1H NMR (400 MHz, CDCl3) δ 7.28-7.20 (m, 2H), 6.82 (d, J = 8.0 Hz, 1H), 6.53 (d, J = 3.7 Hz, 1H), 5.97-5.86 (m, 1H), 4.56 (dt, J = 12.1, 6.0 Hz, 1H), 4.08 (d, J = 8.9 Hz, 1H), 3.62-3.13 (m, 4H), 2.21 (s, 3H), 2.18-1.84 (m, 2H), 1.78-1.40 (m, 4H), 1.35 (d, J = 6.0 Hz, 6H), 1.27 (d, J = 3.9 Hz, 3H), 0.87 (s, 1H). |
| 222 | 450.40 | 1.50 | |
| 223 | 478.50 | 1.65 | |
| 224 | 386.15 | 2.36 | |
| 225 | 456.70 | 1.29 | 1H NMR (400 MHz, DMSO) δ 7.37 (t, J = 7.7 Hz, 1H), 7.26-7.15 (m, 2H), 6.56 (s, 1H), 6.19 (d, J = 4.0 Hz, 1H), 4.44 (s, 1H), 4.42-4.21 (m, 1H), 3.97 (t, J = 5.7 Hz, 2H), 3.41 (s, 2H), 3.30-3.21 (m, 1H), 3.10 (s, 1H), 2.71 (s, 2H), 2.28 (s, 3H), 2.22-2.10 (m, 1H), |

TABLE 2-continued

| Cmpd. No. | LC/MS M + 1 | LC/RT min | NMR |
|---|---|---|---|
| | | | 2.10-1.95 (m, 1H), 1.86-1.71 (m, 2H), 1.25 (s, 1H), 1.09 (s, 6H). |
| 226 | 518.30 | 1.46 | 1H NMR (400 MHz, CDCl3) δ 7.12-7.03 (m, 2H), 6.91 (d, J = 8.6 Hz, 1H), 6.56 (d, J = 3.8 Hz, 1H), 6.03 (d, J = 3.9 Hz, 1H), 4.67-4.54 (m, 1H), 4.54-4.39 (m, 1H), 4.38-4.23 (m, 2H), 4.18 (t, J = 6.5 Hz, 2H), 3.89 (s, 3H), 3.84-3.63 (m, 1H), 3.50-3.32 (m, 2H), 2.85 (s, 6H), 2.66-2.44 (m, 2H), 1.72-1.48 (m, 2H), 1.39 (d, J = 6.1 Hz, 6H). |
| 227 | 523.60 | 4.94 | 1H NMR (400 MHz, CDCl3) δ 7.57 (d, J = 8.3 Hz, 2H), 7.45 (d, J = 8.3 Hz, 2H), 6.51 (s, 1H), 4.03 (s, 2H), 3.51 (d, J = 111.0 Hz, 5H), 2.65-2.45 (m, 6H), 2.39 (ddd, J = 12.6, 9.5, 7.5 Hz, 3H), 2.19-1.86 (m, 4H), 1.72 (dt, J = 10.1, 7.5 Hz, 1H), 1.55 (s, 5H). |
| 228 | 482.40 | 1.43 | |
| 229 | 432.13 | 2.06 | |
| 230 | 454.23 | 2.22 | 1H NMR (400 MHz, DMSO) δ 8.13-8.00 (m, 1H), 7.32-7.19 (m, 2H), 6.97 (d, J = 9.1 Hz, 1H), 6.60-6.51 (m, 1H), 4.69-4.57 (m, 1H), 4.32-3.38 (m, 2H), 3.38-3.20 (m, 2H), 3.14 (s, 2H), 2.39 (s, 3H), 2.14 (s, 3H), 2.13-1.94 (m, 2H), 1.89-1.68 (m, 2H), 1.53 (s, 6H), 1.29 (d, J = 6.0 Hz, 6H). |
| 231 | 506.50 | 1.67 | |
| 232 | 496.40 | 1.74 | 1H NMR (400 MHz, DMSO) δ 7.39 (d, J = 8.7 Hz, 2H), 7.30-7.17 (m, 1H), 6.95 (d, J = 8.7 Hz, 2H), 6.49 (d, J = 4.6 Hz, 1H), 4.74-4.59 (m, 1H), 4.50-4.04 (m, 3H), 3.76-2.94 (m, 5H), 2.30 (s, 3H), 2.22-1.94 (m, 2H), 1.94-1.74 (m, 2H), 1.28 (d, J = 6.0 Hz, 6H). |
| 233 | 464.50 | 1.52 | |
| 234 | 432.50 | 1.15 | |
| 235 | 478.50 | 1.41 | |
| 236 | 530.15 | 1.66 | 1H NMR (400 MHz, DMSO) δ 7.44 (d, J = 8.1 Hz, 2H), 7.39 (d, J = 8.1 Hz, 2H), 7.26-7.20 (m, 1H), 6.50 (d, J = 4.6 Hz, 1H), 4.55 (s, 2H), 4.47-4.30 (m, 1H), 4.29-4.19 (m, 2H), 3.67 (t, J = 6.1 Hz, 2H), 3.46-3.24 (m, 4H), 3.18-3.00 (m, 1H), 2.70-2.53 (m, 2H), 2.30 (s, 3H), 2.25-1.76 (m, 4H). |
| 237 | 532.30 | 1.70 | |
| 238 | 450.50 | 1.40 | |
| 239 | 478.50 | 1.53 | |
| 240 | 518.30 | 1.64 | |
| 241 | 466.50 | 1.42 | 1H NMR (400 MHz, CDCl3) δ 7.59-7.53 (m, 2H), 7.47-7.42 (m, 2H), 6.30 (s, 1H), 4.61 (s, 1H), 3.93 (s, 2H), 3.62 (s, 1H), 3.49 (s, 2H), 3.31 (s, 3H), 2.64-2.51 (m, 2H), 2.51-2.31 (m, 5H), 2.17 (s, 2H), 2.11-1.89 (m, 4H), 1.80-1.64 (m, 1H), 1.56 (s, 1H). |
| 242 | 466.50 | 2.45 | 1H NMR (400 MHz, DMSO) δ 7.51 (d, J = 2.1 Hz, 1H), 7.38 (dd, J = 8.5, 2.1 Hz, 1H), 7.20 (d, J = 8.7 Hz, 1H), 7.09 (d, J = 4.3 Hz, 1H), 6.17 (d, J = 4.3 Hz, 1H), 4.81-4.67 (m, 1H), 4.45-4.20 (m, 1H), 4.15 (t, J = 5.8 Hz, 2H), 3.60-3.28 (m, 2H), 3.27-2.96 (m, 3H), 2.27 (s, 3H), 2.17-1.94 (m, 2H), 1.87-1.72 (m, 2H), 1.31 (d, J = 6.0 Hz, 6H), 1.27 (s, 9H). |
| 243 | 486.40 | 1.44 | |
| 244 | 515.40 | 4.81 | |
| 245 | 532.50 | 1.19 | 1H NMR (400 MHz, CDCl3) δ 8.02 (d, J = 7.9 Hz, 1H), 7.48-7.35 (m, 2H), 6.95 (d, J = 4.1 Hz, 1H), 6.01 (d, J = 4.0 Hz, 1H), 4.67-4.49 (m, 1H), 4.35 (t, J = 5.9 Hz, 2H), 3.64-3.37 (m, 2H), 3.37-3.20 (m, 4H), 2.72 (s, 3H), 2.40 (s, 3H), 2.38 (s, 3H), 2.31-2.14 (m, 1H), 2.14-2.02 (m, 1H), 1.99-1.83 (m, 1H), 1.78-1.64 (m, 1H), 1.32 (d, J = 6.8 Hz, 6H). |
| 246 | 472.20 | 0.96 | |
| 247 | 466.20 | 1.96 | |
| 248 | 499.20 | 1.43 | |
| 249 | 484.70 | 2.50 | |
| 250 | 436.50 | 1.38 | |
| 251 | 470.50 | 1.34 | |
| 252 | 484.20 | 1.08 | |
| 253 | 504.50 | 1.22 | 1H NMR (400 MHz, CDCl3) δ 7.64 (t, J = 8.0 Hz, 1H), 7.29-7.26 (m, 1H), 7.20 (d, J = 8.0 Hz, 1H), 7.13 (d, J = 11.9 Hz, 1H), 6.21 (s, 1H), 4.60 (s, 1H), 4.43-4.01 (m, 2H), 3.65 (s, 2H), 3.28 (s, 1H), 2.04 (s, 2H), 1.92-1.72 (m, 2H), 1.65 (s, 6H), 1.19 (s, 6H), 0.99 (s, 1H). (OH not observed). |

TABLE 2-continued

| Cmpd. No. | LC/MS M + 1 | LC/RT min | NMR |
|---|---|---|---|
| 254 | 496.70 | 1.41 | |
| 255 | 494.50 | 2.99 | |
| 256 | 432.50 | 1.49 | |
| 257 | 482.50 | 1.20 | 1H NMR (400 MHz, CDCl3) δ 7.02 (d, J = 1.8 Hz, 1H), 6.98 (dd, J = 8.2, 1.8 Hz, 1H), 6.92 (d, J = 8.2 Hz, 1H), 6.49 (s, 1H), 4.61 (s, 1H), 4.04 (d, J = 10.3 Hz, 1H), 4.02-3.94 (m, 3H), 3.88 (s, 3H), 3.75 (d, J = 43.7 Hz, 1H), 3.43 (s, 1H), 3.30 (s, 2H), 3.25-3.07 (m, 1H), 2.44 (s, 5H), 2.01 (s, 2H), 1.56 (d, J = 13.8 Hz, 4H), 1.49 (s, 3H). |
| 258 | 532.50 | 1.73 | 1H NMR (400 MHz, CDCl3) δ 7.06 (d, J = 1.9 Hz, 1H), 7.00 (dd, J = 8.2, 1.9 Hz, 1H), 6.88 (d, J = 8.3 Hz, 1H), 6.54 (d, J = 3.3 Hz, 1H), 6.11 (d, J = 4.0 Hz, 1H), 4.57 (dt, J = 12.2, 6.1 Hz, 1H), 4.09-4.02 (m, 2H), 3.97-3.90 (m, 2H), 3.88 (s, 3H), 3.83-3.75 (m, 3H), 3.74 (s, 3H), 3.04-2.89 (m, 2H), 1.87 (dt, J = 14.0, 5.8 Hz, 2H), 1.38 (d, J = 6.1 Hz, 6H), 1.30-1.23 (m, 1H). |
| 259 | 510.70 | 1.89 | |
| 260 | 442.20 | 2.40 | 1H NMR (400 MHz, CDCl3) δ 7.50 (d, J = 8.4 Hz, 1H), 7.13 (d, J = 8.5 Hz, 1H), 6.47 (s, 1H), 4.68-4.51 (m, 2H), 3.99 (dd, J = 16.4, 10.5 Hz, 3H), 3.54 (t, J = 12.8 Hz, 1H), 3.27 (ddd, J = 36.4, 19.3, 9.5 Hz, 3H), 2.48 (dd, J = 28.6, 8.7 Hz, 8H), 2.06 (d, J = 13.3 Hz, 1H), 1.89 (d, J = 14.8 Hz, 1H), 1.59 (s, 1H), 1.37 (d, J = 6.0 Hz, 6H). |
| 261 | 485.05 | 3.02 | |
| 262 | 468.70 | 2.48 | 1H NMR (400 MHz, CDCl3) δ 7.29 (s, 1H), 7.27 (d, J = 2.1 Hz, 1H), 6.83 (d, J = 8.0 Hz, 1H), 6.56 (d, J = 3.8 Hz, 1H), 5.97 (d, J = 3.9 Hz, 1H), 4.53 (s br, 1H, OH), 4.10-3.94 (m, 2H), 3.84 (s, 2H), 3.62 (m br, J = 74.5 Hz, 2H), 3.37 (t, J = 6.0 Hz, 3H), 2.41 (s, 3H), 2.30 (s, 3H), 2.17 (m br, J = 15.0 Hz, 2H), 1.85 (s br, 3H), 1.40 (s, 6H). |
| 263 | 480.70 | 1.33 | |
| 264 | 468.50 | 1.37 | |
| 265 | 485.50 | 1.17 | 1H NMR (400 MHz, CDCl3) δ 7.49 (d, J = 8.1 Hz, 1H), 7.25-7.16 (m, 3H), 6.17 (d, J = 4.5 Hz, 1H), 4.68-4.53 (m, 1H), 4.35 (t, J = 5.9 Hz, 2H), 3.65 (s, 1H), 3.51 (n, 1H), 3.34 (t, J = 5.6 Hz, 2H), 3.24 (s, 1H), 2.61 (s, 3H), 2.41 (s, 3H), 2.18 (s, 1H), 2.06 (s, 1H), 1.93 (s, 1H), 1.73 (s, 1H), 1.70 (s, 1H), 1.66 (s, 6H). |
| 266 | 478.30 | 1.38 | |
| 267 | 450.50 | 1.25 | |
| 268 | 466.14 | 1.74 | |
| 269 | 426.50 | 1.27 | |
| 270 | 512.20 | 1.84 | 1H NMR (400 MHz, DMSO) δ 10.48 (s, 1H), 7.39 (d, J = 8.1 Hz, 1H), 7.30-7.16 (m, 1H), 6.99 (d, J = 1.8 Hz, 1H), 6.88 (dd, J = 8.1, 1.9 Hz, 1H), 6.48 (d, J = 4.6 Hz, 1H), 4.45-4.29 (m, 1H), 4.29-4.16 (m, 2H), 3.58-2.96 (m, 5H), 2.30 (s, 3H), 2.25-1.68 (m, 4H). |
| 271 | 456.50 | 1.44 | |
| 272 | 462.50 | 1.32 | |
| 273 | 422.50 | 1.32 | |
| 274 | 513.70 | 1.36 | |
| 275 | 400.13 | 2.61 | |
| 276 | 436.50 | 1.37 | |
| 277 | 458.50 | 1.46 | |
| 278 | 380.17 | 1.97 | 1H NMR (400 MHz, DMSO) δ 7.29-7.17 (m, 2H), 6.96 (d, J = 9.1 Hz, 1H), 6.04-5.88 (m, 2H), 4.69-4.57 (m, 1H), 4.46-3.92 (m, 1H), 3.86-3.72 (m, 2H), 3.72-3.55 (m, 2H), 3.42-2.95 (m, 5H), 2.24 (s, 3H), 2.14 (s, 3H), 2.11-1.91 (m, 2H), 1.78-1.57 (m, 2H), 1.29 (d, J = 6.0 Hz, 6H). |
| 279 | 464.50 | 1.32 | 1H NMR (400 MHz, DMSO) δ 7.29-7.19 (m, 2H), 7.02-6.92 (m, 1H), 6.61 (d, J = 4.0 Hz, 1H), 6.08 (d, J = 4.0 Hz, 1H), 4.71-4.58 (m, 1H), 4.46-4.08 (m, 1H), 3.65-3.00 (m, 3H), 2.91 (d, J = 6.7 Hz, 2H), 2.77 (t, J = 7.2 Hz, 1H), 2.14 (s, 3H), 1.98-1.63 (m, 4H), 1.43 (s, 6H), 1.29 (d, J = 6.0 Hz, 6H). |
| 280 | 464.50 | 6.18 | |
| 281 | 429.50 | 1.12 | 1H NMR (400 MHz, DMSO) δ 7.76 (dd, J = 8.6, 2.0 Hz, 1H), 7.69 (d, J = 1.9 Hz, 1H), 7.32 (d, J = 8.7 Hz, 1H), 7.08 (d, J = 4.1 Hz, 1H), 6.20 (d, J = 4.2 Hz, 1H), 4.48-4.23 (m, 1H), 4.14 (t, J = 5.8 Hz, 2H), 3.94 (s, 3H), 3.53-3.29 (m, 2H), 3.23 (t, J = 5.5 Hz, 2H), 3.19-2.96 (m, 1H), 2.28 (s, 3H), 2.23-1.89 (m, 2H), 1.89-1.70 (m, |

TABLE 2-continued

| Cmpd. No. | LC/MS M + 1 | LC/RT min | NMR |
|---|---|---|---|
| | | | 2H), 1.43 (s, 3H), ? 0.99-0.94 (m, 2H), 0.66-0.61 (m, 2H). |
| 282 | 490.50 | 1.47 | |
| 283 | 471.50 | 1.06 | |
| 284 | 492.30 | 1.78 | |
| 285 | 435.20 | 2.02 | |
| 286 | 442.40 | 1.45 | |
| 287 | 498.20 | 1.09 | |
| 288 | 561.80 | 1.76 | |
| 289 | 547.50 | 1.22 | |
| 290 | 448.50 | 1.57 | |
| 291 | 479.30 | 1.53 | |
| 292 | 394.22 | 2.22 | |
| 293 | 505.50 | 1.39 | |
| 294 | 446.26 | 2.27 | |
| 295 | 500.24 | 1.22 | |
| 296 | 485.05 | 3.58 | |
| 297 | 423.30 | 1.19 | 1H NMR (400 MHz, DMSO) δ 7.91 (d, J = 8.0 Hz, 1H), 7.58-7.46 (m, 2H), 6.58 (d, J = 3.4 Hz, 1H), 6.12 (d, J = 3.9 Hz, 1H), 4.43-4.29 (m, 1H), 3.93 (t, J = 5.8 Hz, 2H), 3.46-3.21 (m, 6H), 3.18-3.05 (m, 1H), 2.65 (s, 3H), 2.27 (s, 3H), 2.23-1.70 (m, 4H), 1.12 (t, J = 7.4 Hz, 3H). |
| 298 | 484.40 | 2.46 | 1H NMR (400 MHz, DMSO) δ 7.05 (d, J = 1.9 Hz, 1H), 7.01 (d, J = 8.1 Hz, 1H), 6.92 (dd, J = 8.1, 1.9 Hz, 1H), 6.59-6.53 (m, 1H), 6.19 (d, J = 4.0 Hz, 1H), 4.33 (s, 1H), 3.97 (t, J = 5.7 Hz, 2H), 3.76 (s, 3H), 3.62-3.34 (m, 2H), 3.31-2.99 (m, 3H), 2.28 (s, 3H), 2.11 (s, 2H), 1.84-1.71 (m, 2H), 1.29 (s, 9H). |
| 299 | 530.50 | 1.56 | |
| 300 | 540.50 | 1.41 | |
| 301 | 428.23 | 1.93 | 1H NMR (400 MHz, DMSO) δ 7.35 (d, J = 8.2 Hz, 2H), 7.28 (d, J = 8.2 Hz, 2H), 6.73 (d, J = 4.0 Hz, 1H), 6.22 (d, J = 4.1 Hz, 1H), 4.47-4.24 (m, 1H), 4.12 (t, J = 5.8 Hz, 2H), 3.55-3.37 (m, 1H), 3.37-3.26 (m, 3H), 3.20 (s, 3H), 3.18-2.98 (m, 1H), 2.58-2.51 (m, 1H), 2.29 (s, 3H), 2.25-1.91 (m, 2H), 1.88-1.63 (m, 7H), 1.53-1.14 (m, 5H). |
| 302 | 470.50 | 1.55 | |
| 303 | 554.20 | 1.34 | |
| 304 | 442.10 | 2.47 | |
| 305 | 448.50 | 0.83 | |
| 306 | 466.50 | 1.41 | 1H NMR (400 MHz, DMSO) δ 7.47 (d, J = 7.9 Hz, 1H), 7.24-7.12 (m, 2H), 6.60 (d, J = 3.7 Hz, 1H), 6.20 (d, J = 3.9 Hz, 1H), 4.97 (s, 1H), 4.27-4.08 (m, 1H), 4.08-3.93 (m, 2H), 3.51-3.13 (m, 5H), 2.54 (s, 3H), 2.42-2.13 (m, 2H), 1.97-1.68 (m, 3H), 1.51 (s, 6H), 0.68-0.47 (m, 4H). |
| 307 | 476.40 | 3.77 | |
| 308 | 450.50 | 1.61 | |
| 309 | 436.22 | 1.75 | |
| 310 | 505.30 | 1.55 | |
| 311 | 492.30 | 1.44 | 1H NMR (400 MHz, CDCl3) δ 7.36 (t, J = 8.2 Hz, 1H), 7.25 (dd, J = 4.9, 2.7 Hz, 1H), 6.76 (dd, J = 8.6, 2.3 Hz, 1H), 6.62 (dd, J = 11.5, 2.4 Hz, 1H), 6.19 (d, J = 4.5 Hz, 1H), 4.66 (d, J = 13.4 Hz, 1H), 4.30-4.08 (m, 2H), 3.83 (s, 3H), 3.68-3.54 (m, 1H), 3.49 (d, J = 13.0 Hz, 1H), 3.25 (t, J = 13.0 Hz, 1H), 2.07-1.96 (m, 1H), 1.85 (t, J = 16.3 Hz, 2H), 1.70 (d, J = 12.7 Hz, 1H), 1.21 (s, 3H), 1.14 (s, 3H), 0.96 (s, 1H). |
| 312 | 468.30 | 1.45 | |
| 313 | 468.70 | 2.38 | |
| 314 | 438.50 | 1.43 | 1H NMR (400 MHz, CDCl3) δ 7.25-7.19 (m, 1H), 7.02 (d, J = 1.8 Hz, 1H), 6.98 (dd, J = 8.2, 1.9 Hz, 1H), 6.88 (d, J = 8.2 Hz, 1H), 6.17 (d, J = 4.2 Hz, 1H), 4.57 (s, 1H), 4.56 (dd, J = 12.2, 6.1 Hz, 1H), 4.35 (t, J = 5.5 Hz, 2H), 3.88 (s, 3H), 3.74 (s, 1H), 3.34 (t, J = 5.2 Hz, 2H), 3.34 (s, 2H), 2.42 (s, 3H), 2.14 (s, 2H), 1.84 (s, 2H), 1.38 (d, J = 6.1 Hz, 6H). |
| 315 | 494.50 | 1.45 | 1H NMR (400 MHz, DMSO) δ 7.26 (s, 1H), 7.18 (dd, J = 23.4, 7.8 Hz, 2H), 6.57 (s, 1H), 6.12 (d, J = 3.0 Hz, 1H), 5.25 (s, 1H), 4.85 (d, J = 1.1 Hz, 1H), 4.33 (s, 1H), 3.93 (s, 2H), 3.09 (s, 1H), 2.30 (s, 3H), 2.27 (s, 3H), 2.01 (s, 3H), 1.75 (s, 2H). |
| 316 | 432.70 | 1.68 | 1H NMR (400 MHz, DMSO) δ 7.05-6.93 (m, 3H), 6.58 (d, J = 3.8 Hz, 1H), 6.13 (d, J = 3.9 Hz, 1H), 4.65-4.53 (m, 1H), 4.31-3.92 (m, 1H), 3.84-3.73 (m, 5H), |

TABLE 2-continued

| Cmpd. No. | LC/MS M + 1 | LC/RT min | NMR |
|---|---|---|---|
| | | | 3.60-3.20 (m, 5H), 3.16-3.03 (m, 1H), 2.17-1.69 (m, 8H), 1.58-1.35 (m, 2H), 1.26 (d, J = 6.0 Hz, 6H). |
| 317 | 506.40 | 3.47 | |
| 318 | 450.20 | 0.99 | |
| 319 | 392.50 | 1.37 | 1H NMR (400 MHz, CDCl3) δ 7.02 (d, J = 1.9 Hz, 1H), 6.98 (dd, J = 8.2, 1.9 Hz, 1H), 6.88 (d, J = 8.2 Hz, 1H), 6.53 (d, J = 3.8 Hz, 1H), 5.91 (d, J = 3.8 Hz, 1H), 4.57 (dt, J = 12.2, 6.1 Hz, 1H), 4.08 (d, J = 8.8 Hz, 1H), 3.88 (s, 3H), 3.67-3.18 (m, 5H), 2.27-1.86 (m, 2H), 1.65 (s, 3H), 1.38 (d, J = 6.1 Hz, 6H), 1.27 (d, J = 5.9 Hz, 3H), 0.79 (s, 1H). |
| 320 | 466.30 | 1.24 | |
| 321 | 438.20 | 1.16 | |
| 322 | 437.20 | 0.89 | |
| 323 | 428.15 | 2.27 | |
| 324 | 498.50 | 1.66 | |
| 325 | 512.50 | 1.71 | |
| 326 | 548.70 | 1.24 | 1H NMR (400 MHz, DMSO) δ 7.08-6.95 (m, 3H), 6.65 (d, J = 3.7 Hz, 1H), 6.33 (d, J = 3.9 Hz, 1H), 4.96-4.68 (m, 1H), 4.68-4.53 (m, 1H), 4.08-3.98 (m, 1H), 3.90-3.84 (m, 1H), 3.77 (s, 3H), 3.74-3.51 (m, 2H), 3.47-3.35 (m, 1H), 3.35-3.28 (m, 2H), 3.28-3.11 (m, 1H), 2.32 (s, 3H), 2.13-1.86 (m, 2H), 1.27 (d, J = 6.0 Hz, 6H). |
| 327 | 484.60 | 2.75 | 1H NMR (400 MHz, DMSO) δ 7.04-6.90 (m, 3H), 6.57 (d, J = 3.5 Hz, 1H), 6.07 (d, J = 3.9 Hz, 1H), 4.66-4.52 (m, 1H), 4.06-3.82 (m, 2H), 3.77 (s, 3H), 3.61-3.11 (m, 5H), 2.30-2.21 (m, 4H), 2.17-1.66 (m, 3H), 1.42 (d, J = 7.0 Hz, 3H), 1.26 (d, J = 6.0 Hz, 6H). |
| 328 | 480.20 | 3.02 | |
| 329 | 440.30 | 1.41 | |
| 330 | 442.12 | 2.25 | |
| 331 | 435.50 | 1.28 | 1H NMR (400 MHz, DMSO) δ 7.28-7.20 (m, 2H), 6.91 (d, J = 9.0 Hz, 1H), 6.59 (d, J = 3.6 Hz, 1H), 6.20 (d, J = 3.9 Hz, 1H), 4.65 (s, 1H), 4.25-3.91 (m, 3H), 3.73 (s, 2H), 3.65-3.09 (m, 5H), 2.36-2.14 (m, 5H), 1.92-1.68 (m, 3H), 1.23 (s, 6H), 0.66-0.46 (m, 4H). |
| 332 | 506.20 | 3.81 | 1H NMR (400 MHz, DMSO) δ 7.29-7.18 (m, 2H), 7.02-6.92 (m, 1H), 6.60 (d, J = 3.5 Hz, 1H), 6.20 (d, J = 3.9 Hz, 1H), 4.70-4.53 (m, 1H), 4.27-3.90 (m, 3H), 3.72-3.04 (m, 5H), 2.42-2.18 (m, 2H), 2.14 (s, 3H), 1.90-1.64 (m, 3H), 1.29 (d, J = 6.0 Hz, 6H), 0.68-0.48 (m, 4H). |
| 333 | 476.30 | 7.37 | |
| 334 | 434.25 | 2.57 | |
| 335 | 452.10 | 1.15 | |
| 336 | 510.70 | 1.32 | 1H NMR (400 MHz, DMSO) δ 7.38-7.27 (m, 1H), 7.27-7.16 (m, 2H), 6.62 (d, J = 4.1 Hz, 1H), 6.11 (d, J = 4.0 Hz, 1H), 4.75-4.63 (m, 1H), 4.41-4.13 (m, 1H), 3.59-2.99 (m, 3H), 2.90 (d, J = 6.3 Hz, 2H), 2.77 (t, J = 7.2 Hz, 1H), 1.99-1.69 (m, 4H), 1.43 (s, 6H), 1.30 (d, J = 6.0 Hz, 6H). |
| 337 | 468.70 | 5.63 | |
| 338 | 424.20 | 0.95 | 1H NMR (400 MHz, DMSO) δ 7.36 (d, J = 8.1 Hz, 2H), 7.29-7.14 (m, 3H), 6.50 (d, J = 4.6 Hz, 1H), 4.53-4.13 (m, 3H), 3.62-2.96 (m, 5H), 2.53-2.46 (m, 2H), 2.30 (s, 3H), 2.25-1.93 (m, 2H), 1.93-1.74 (m, 3H), 0.87 (d, J = 6.6 Hz, 6H). |
| 339 | 462.20 | 1.78 | |
| 340 | 528.06 | 3.63 | |
| 341 | 470.50 | 1.51 | |
| 342 | 410.14 | 1.98 | |
| 343 | 499.30 | 1.27 | |
| 344 | 448.50 | 1.53 | 1H NMR (400 MHz, CDCl3) δ 8.43 (d, J = 1.5 Hz, 1H), 7.69-7.51 (m, 2H), 6.53 (d, J = 3.4 Hz, 1H), 5.95 (d, J = 3.5 Hz, 1H), 4.64-4.45 (m, 1H), 4.08-3.92 (m, 2H), 3.92-3.74 (m, 1H), 3.61-3.25 (m, 4H), 2.70 (q, J = 7.6 Hz, 2H), 2.39 (s, 3H), 2.28-1.82 (m, 4H), 1.28 (t, J = 7.6 Hz, 3H). |
| 345 | 407.00 | 2.23 | |
| 346 | 462.50 | 1.20 | 1H NMR (400 MHz, DMSO) δ 7.80 (d, J = 8.1 Hz, 1H), 7.51 (s, 1H), 7.46 (d, J = 8.4 Hz, 1H), 6.58 (d, J = 3.7 Hz, 1H), 6.12 (d, J = 3.9 Hz, 1H), 4.35 (d, J = 12.4 Hz, 1H), 3.93 (t, J = 5.5 Hz, 2H), 3.47-3.31 (m, 4H), 3.11 (t, J = 12.8 Hz, 1H), 2.76 (s, 6H), 2.58 (s, 3H), 2.27 (s, 3H), 2.18 (d, J = 12.5 Hz, 1H), 2.01 (d, J = 13.8 Hz, 1H), 1.84-1.69 (m, 2H). |

TABLE 2-continued

| Cmpd. No. | LC/MS M + 1 | LC/RT min | NMR |
|---|---|---|---|
| 347 | 499.30 | 1.36 | |
| 348 | 544.02 | 3.17 | |
| 349 | 478.50 | 1.29 | 1H NMR (400 MHz, DMSO) δ 7.59-7.40 (m, 1H), 7.24-7.08 (m, 2H), 6.60 (d, J = 3.5 Hz, 1H), 6.10 (s, 1H), 5.21-4.36 (m, 3H), 4.18-3.97 (m, 1H), 3.91-3.64 (m, 2H), 3.63-2.93 (m, 4H), 2.54 (s, 3H), 2.38-2.11 (m, 4H), 1.93-1.68 (m, 1H), 1.51 (s, 6H). |
| 350 | 468.20 | 4.52 | |
| 351 | 408.10 | 1.24 | |
| 352 | 463.10 | 1.07 | |
| 353 | 452.20 | 1.69 | |
| 354 | 486.30 | 1.78 | |
| 355 | 492.50 | 1.70 | 1H NMR (400 MHz, DMSO) δ 10.44 (s, 2H), 7.30-7.23 (m, 2H), 7.04-6.97 (m, 1H), 6.74 (d, J = 3.5 Hz, 1H), 6.50 (s, 1H), 4.66 (sept, J = 6.0 Hz, 1H), 4.32-4.17 (m, 2H), 4.18-3.88 (m, 1H), 3.81-3.60 (m, 5H), 2.35-2.19 (m, 2H), 2.19-2.07 (m, 2H), 2.16 (s, 3H), 1.30 (d, J = 6.0 Hz, 6H). |
| 356 | 436.50 | 1.39 | |
| 357 | 495.50 | 1.43 | 1H NMR (400 MHz, DMSO) δ 7.52 (d, J = 8.3 Hz, 2H), 7.38 (d, J = 8.3 Hz, 2H), 7.28-7.19 (m, 1H), 6.50 (d, J = 4.6 Hz, 1H), 5.08 (s, 1H), 4.49-4.30 (m, 1H), 4.24 (t, J = 5.6 Hz, 2H), 3.55-3.23 (m, 4H), 3.21-3.00 (m, 1H), 2.30 (s, 3H), 2.25-1.96 (m, 2H), 1.95-1.77 (m, 2H), 1.43 (s, 6H). |
| 358 | 464.50 | 1.29 | |
| 359 | 506.20 | 1.05 | |
| 360 | 564.70 | 1.54 | |
| 361 | 462.70 | 1.69 | 1H NMR (400 MHz, CDCl3) δ 8.62 (s, 1H), 7.03 (d, J = 1.9 Hz, 1H), 6.98 (dd, J = 8.2, 1.9 Hz, 1H), 6.89 (d, J = 8.3, 2.4 Hz, 1H), 6.59 (d, J = 28.9, 3.6 Hz, 1H), 6.17 (dd, J = 112.7, 4.0 Hz, 1H), 4.59 (dt, J = 12.1, 6.1 Hz, 1H), 4.08 (dd, J = 18.9, 5.5 Hz, 3H), 3.88 (d, J = 1.9 Hz, 3H), 3.36 (s, 2H), 2.41 (s, 2H), 2.14 (d, J = 49.0 Hz, 2H), 1.39 (d, J = 6.1 Hz, 6H). |
| 362 | 480.30 | 4.65 | |
| 363 | 502.30 | 2.46 | |
| 364 | 452.50 | 1.52 | |
| 365 | 421.30 | 1.20 | |
| 366 | 504.50 | 1.85 | |
| 367 | 440.50 | 1.31 | 1H NMR (400 MHz, DMSO) δ 7.77-7.58 (m, 1H), 7.36-7.10 (m, 3H), 6.22 (d, J = 4.2 Hz, 1H), 5.35 (s, 1H), 4.43-4.24 (m, 1H), 4.22-4.09 (m, 2H), 3.46-3.27 (m, 2H), 3.27-2.94 (m, 3H), 2.62-2.53 (m, 1H), 2.26 (s, 3H), 2.21-1.88 (m, 2H), 1.88-1.68 (m, 2H), 1.49 (s, 6H), 0.95-0.67 (m, 4H). |
| 368 | 454.50 | 1.22 | |
| 369 | 512.40 | 1.74 | 1H NMR (400 MHz, CDCl3) δ 7.62 (t, J = 8.1 Hz, 1H), 7.18 (dd, J = 8.0, 1.5 Hz, 1H), 7.12 (dd, J = 11.9, 1.5 Hz, 1H), 6.53 (d, J = 3.8 Hz, 1H), 5.94 (d, J = 3.9 Hz, 1H), 4.54 (s br, 1H), 3.99 (d br, J = 5.9 Hz, 2H), 3.57 (s br, 2H), 3.33 (t, J = 6.0 Hz, 2H), 3.27 (s br, 1H), 2.38 (s, 3H), 2.19 (s br, 1H), 2.14-2.01 (m, 2H), 1.90 (s br, 1H), 1.72 (s br, 1H), 1.65 (s, 6H). |
| 370 | 454.30 | 1.23 | 1H NMR (400 MHz, CDCl3) δ 8.40 (s, 1H), 7.45-7.20 (m, 1H), 7.08 (s, 1H), 6.55 (d, J = 3.4 Hz, 1H), 5.98 (d, J = 3.8 Hz, 1H), 4.58 (s, 1H), 4.00 (s, 3H), 3.81 (s, 1H), 3.62 (s, 1H), 3.37 (t, J = 5.8 Hz, 2H), 2.72 (s, 3H), 2.41 (s, 3H), 2.28-2.06 (m, 2H), 1.99 (t, J = 11.6 Hz, 2H). |
| 371 | 483.70 | 1.22 | 1H NMR (400 MHz, CDCl3) δ 7.03 (d, J = 1.9 Hz, 1H), 6.98 (dd, J = 8.2, 1.9 Hz, 1H), 6.88 (d, J = 8.3 Hz, 1H), 6.54 (d, J = 3.7 Hz, 1H), 5.93 (d, J = 3.8 Hz, 1H), 4.56 (dd, J = 12.2, 6.1 Hz, 1H), 4.52 (s, 1H), 3.94 (s, 2H), 3.88 (s, 3H), 3.69 (s, 1H), 3.47 (s, 2H), 3.27 (s, 2H), 1.87 (s, 4H), 1.38 (d, J = 6.1 Hz, 6H). (NH is not observed.) |
| 372 | 452.50 | 1.21 | |
| 373 | 508.40 | 1.47 | |
| 374 | 456.50 | 1.47 | |
| 375 | 508.40 | 1.66 | |
| 376 | 438.50 | 1.54 | 1H NMR (400 MHz, CDCl3) δ 7.70 (d, J = 1.9 Hz, 1H), 7.64 (dd, J = 8.5, 2.1 Hz, 1H), 7.28-7.22 (m, 1H), 7.05 (d, J = 8.6 Hz, 1H), 6.20 (d, J = 4.5 Hz, 1H), 4.61 (s, 1H), 4.20 (s, 2H), 3.95 (s, 3H), 3.70 (s, 2H), 3.34 (s, 1H), 1.97 (s, 2H), 1.79 (s, 2H), 1.18 (s, 6H), 0.97 (s, 1H). |

TABLE 2-continued

| Cmpd. No. | LC/MS M + 1 | LC/RT min | NMR |
|---|---|---|---|
| 377 | 518.20 | 1.69 | |
| 378 | 502.50 | 1.03 | |
| 379 | 501.30 | 1.60 | |
| 380 | 466.20 | 1.92 | 1H NMR (400 MHz, DMSO) δ 7.86-7.81 (m, 2H), 7.69-7.64 (m, 2H), 7.55 (q, J = 4.8 Hz, 1H), 6.59-6.55 (m, 1H), 6.19 (d, J = 4.0 Hz, 1H), 4.37 (d, J = 12.5 Hz, 1H), 3.97 (t, J = 5.8 Hz, 2H), 3.46-3.33 (m, 2H), 3.31-3.23 (m, 2H), 3.12 (t, J = 12.6 Hz, 1H), 2.44 (d, J = 4.9 Hz, 3H), 2.28 (s, 3H), 2.23-2.14 (m, 1H), 2.06-1.98 (m, 1H), 1.80 (t, J = 13.3 Hz, 2H). |
| 381 | 521.50 | 1.35 | |
| 382 | 410.21 | 2.12 | |
| 383 | 500.24 | 1.24 | 1H NMR (400 MHz, CDCl3) δ 7.32 (d, J = 7.8 Hz, 1H), 7.21 (dd, J = 12.0, 4.2 Hz, 2H), 6.29 (s, 1H), 4.59 (s, 1H), 3.92 (s, 2H), 3.72 (q, J = 7.0 Hz, 3H), 3.61 (s, 1H), 3.46 (s, 1H), 3.30 (s, 2H), 3.19 (s, 1H), 2.75-2.61 (m, 2H), 2.48-2.35 (m, 8H), 2.25-2.06 (m, 3H), 1.99 (s, 2H), 1.72 (dtt, J = 10.7, 8.9, 5.2 Hz, 2H), 1.24 (t, J = 7.0 Hz, 5H). |
| 384 | 480.20 | 1.34 | 1H NMR (400 MHz, DMSO) δ 7.01 (d, J = 1.4 Hz, 1H), 7.00-6.93 (m, 2H), 6.56 (s, 1H), 6.18 (d, J = 4.0 Hz, 1H), 4.42-4.33 (m, 1H), 4.26 (s, 1H), 3.97 (t, J = 5.8 Hz, 2H), 3.77 (s, 3H), 3.59 (s, 2H), 3.31-2.85 (m, 3H), 2.28 (s, 3H), 2.10 (s, 2H), 1.76 (t, J = 13.3 Hz, 2H), 1.71-1.50 (m, 2H), 1.22 (d, J = 6.1 Hz, 3H), 0.92 (t, J = 7.4 Hz, 3H). |
| 385 | 530.50 | 1.56 | |
| 386 | 416.13 | 2.51 | |
| 387 | 420.22 | 1.81 | |
| 388 | 422.20 | 2.02 | |
| 389 | 446.20 | 1.59 | |
| 390 | 484.70 | 2.55 | |
| 391 | 510.70 | 1.63 | |
| 392 | 484.30 | 1.33 | |
| 393 | 454.30 | 1.72 | 1H NMR (400 MHz, DMSO) δ 7.26-7.19 (m, 2H), 6.96 (d, J = 9.1 Hz, 1H), 6.90 (d, J = 4.0 Hz, 1H), 6.20 (d, J = 4.0 Hz, 1H), 4.63 (hept, J = 6.0 Hz, 1H), 4.53-4.06 (m, 1H), 3.97 (t, J = 5.6 Hz, 2H), 3.38-2.87 (m, 5H), 2.27 (s, 3H), 2.14 (s, 3H), 2.11-1.95 (m, 2H), 1.83-1.65 (m, 2H), 1.28 (d, J = 6.0 Hz, 6H). |
| 394 | 407.70 | 1.32 | |
| 395 | 468.70 | 2.61 | |
| 396 | 552.50 | 1.56 | |
| 397 | 484.70 | 2.82 | 1H NMR (400 MHz, DMSO) δ 7.51 (d, J = 2.0 Hz, 1H), 7.38 (dd, J = 8.5, 2.0 Hz, 1H), 7.20 (d, J = 8.5 Hz, 1H), 7.05 (d, J = 4.1 Hz, 1H), 6.18 (d, J = 4.1 Hz, 1H), 4.80-4.67 (m, 1H), 4.46-4.08 (m, 3H), 3.62-3.30 (m, 2H), 3.30-2.97 (m, 3H), 2.31 (s, 3H), 2.27 (s, 3H), 2.21-1.91 (m, 2H), 1.89-1.69 (m, 2H), 1.31 (d, J = 6.0 Hz, 6H). |
| 398 | 444.40 | 1.21 | |
| 399 | 514.70 | 1.37 | |
| 400 | 384.21 | 2.16 | 1H NMR (400 MHz, CDCl3) δ 7.32 (t, J = 7.5 Hz, 1H), 7.20-7.12 (m, 2H), 6.49 (s, 1H), 4.61 (s, 1H), 3.99 (s, 2H), 3.72 (q, J = 7.0 Hz, 3H), 3.68-3.09 (m, 5H), 2.85 (s, 2H), 2.43 (d, J = 17.8 Hz, 5H), 2.07 (s, 1H), 1.94 (s, 1H), 1.60 (s, 1H), 1.47-1.30 (m, 2H), 1.25 (dd, J = 11.5, 4.4 Hz, 11H). |
| 401 | 502.10 | 1.48 | 1H NMR (400 MHz, DMSO) δ 7.53-7.38 (m, 4H), 7.27-7.14 (m, 2H), 7.14-6.96 (m, 4H), 6.49 (d, J = 4.6 Hz, 1H), 4.48-4.28 (m, 1H), 4.24 (t, J = 5.8 Hz, 2H), 3.65-3.23 (m, 4H), 3.23-2.94 (m, 1H), 2.31 (s, 3H), 2.23-1.95 (m, 2H), 1.95-1.75 (m, 2H). |
| 402 | 498.30 | 1.63 | |
| 403 | 412.50 | 1.45 | |
| 404 | 496.40 | 1.79 | 1H NMR (400 MHz, CDCl3) δ 7.06-6.95 (m, 2H), 6.93-6.85 (m, 1H), 6.63 (d, J = 4.0 Hz, 1H), 5.91 (d, J = 4.0 Hz, 1H), 4.57 (dt, J = 12.1, 6.1 Hz, 1H), 3.88 (s, 3H), 3.49 (s, 3H), 2.96 (s, 2H), 1.84 (s, 4H), 1.59 (s, 2H), 1.51 (s, 6H), 1.38 (d, J = 6.1 Hz, 6H). |
| 405 | 480.30 | 1.78 | |
| 406 | 436.09 | 2.50 | |
| 407 | 424.50 | 1.03 | |
| 408 | 490.50 | 1.79 | 1H NMR (400 MHz, DMSO) δ 7.39 (d, J = 8.7 Hz, 2H), 7.26 (dd, J = 4.4, 2.2 Hz, 1H), 6.97 (d, J = 8.7 Hz, 2H), 6.55 (d, J = 4.6 Hz, 1H), 4.33 (s, 1H), 4.11 (s, 2H), 4.03 (t, J = 6.6 Hz, 2H), 3.52 (s, 2H), 3.24 (s, 1H), 2.27 (s, |

TABLE 2-continued

| Cmpd. No. | LC/MS M + 1 | LC/RT min | NMR |
|---|---|---|---|
| | | | 1H), 1.94-1.83 (m, 2H), 1.83-1.67 (m, 3H), 1.62 (q, J = 6.7 Hz, 2H), 1.08 (s, 6H), 0.93 (d, J = 6.6 Hz, 6H). |
| 409 | 506.00 | 1.94 | 1H NMR (400 MHz, CDCl3) δ 7.33 (d, J = 7.7 Hz, 1H), 7.07-6.96 (m, 2H), 6.29 (s, 1H), 5.30 (s, 0H), 4.62 (s, 1H), 3.90 (d, J = 10.6 Hz, 5H), 3.50 (dd, J = 80.7, 48.4 Hz, 6H), 2.50 (ddd, J = 13.9, 8.6, 5.6 Hz, 2H), 2.45-2.32 (m, 5H), 2.17 (s, 2H), 2.12-1.91 (m, 8H), 1.63 (dt, J = 15.7, 8.6 Hz, 2H). |
| 410 | 496.30 | 1.36 | |
| 411 | 496.70 | 1.34 | 1H NMR (400 MHz, DMSO) δ 7.01 (d, J = 1.2 Hz, 1H), 7.00-6.93 (m, 2H), 6.56 (s, 1H), 6.18 (d, J = 4.0 Hz, 1H), 4.42-4.33 (m, 1H), 4.33-4.02 (m, 1H), 3.97 (t, J = 5.7 Hz, 2H), 3.77 (s, 3H), 3.59 (s, 2H), 3.20 (t, J = 20.2 Hz, 3H), 2.28 (s, 3H), 2.10 (s, 2H), 1.76 (t, J = 13.5 Hz, 2H), 1.71-1.51 (m, 2H), 1.22 (d, J = 6.1 Hz, 3H), 0.92 (t, J = 7.4 Hz, 3H). |
| 412 | 530.50 | 1.57 | |
| 413 | 444.20 | 0.94 | |
| 414 | 450.14 | 2.53 | |
| 415 | 489.50 | 2.26 | |
| 416 | 440.19 | 1.82 | |
| 417 | 440.50 | 1.38 | |
| 418 | 438.50 | 1.44 | 1H NMR (400 MHz, CDCl3) δ 7.55 (d, J = 2.0 Hz, 1H), 7.40 (dd, J = 8.5, 2.1 Hz, 1H), 6.97 (d, J = 8.5 Hz, 1H), 6.56 (d, J = 3.8 Hz, 1H), 6.02 (d, J = 3.8 Hz, 1H), 5.92 (s, 1H), 4.69-4.54 (m, 1H), 4.41-4.20 (m, 2H), 4.15 (t, J = 6.6 Hz, 2H), 4.06-3.56 (m, 2H), 3.41 (t, J = 6.5 Hz, 2H), 2.72 (s, 3H), 2.56-2.44 (m, 2H), 2.44-1.48 (m, 2H), 1.40 (d, J = 6.1 Hz, 6H). |
| 419 | 513.20 | 5.54 | 1H NMR (400 MHz, CDCl3) δ 7.25 (dd, J = 9.6, 2.6 Hz, 3H), 6.80 (d, J = 9.0 Hz, 1H), 6.49 (s, 1H), 4.60 (s, 1H), 4.06 (q, J = 7.0 Hz, 2H), 3.99 (s, 2H), 3.72 (q, J = 7.0 Hz, 2H), 3.32 (s, 4H), 2.43 (d, J = 20.3 Hz, 5H), 2.23 (s, 3H), 2.01 (s, 2H), 1.58 (s, 1H), 1.44 (t, J = 7.0 Hz, 3H), 1.25 (dd, J = 8.8, 5.2 Hz, 4H). |
| 420 | 470.50 | 1.71 | |
| 421 | 506.50 | 1.41 | |
| 422 | 471.10 | 1.42 | |
| 423 | 492.50 | 1.77 | |
| 424 | 434.19 | 2.62 | |
| 425 | 392.20 | 1.97 | |
| 426 | 522.50 | 2.19 | 1H NMR (400 MHz, CDCl3) δ 7.38-7.28 (m, 1H), 6.72 (d, J = 8.3 Hz, 1H), 6.59 (d, J = 11.7 Hz, 1H), 6.53 (d, J = 3.7 Hz, 1H), 5.95-5.84 (m, 1H), 4.68-4.46 (m, 2H), 4.07 (dd, J = 11.6, 5.2 Hz, 1H), 3.66-3.14 (m, 5H), 2.29-1.47 (m, 4H), 1.35 (d, J = 5.9 Hz, 6H), 1.31-1.22 (m, J = 6.1 Hz, 3H), 1.19-0.77 (m, 1H). |
| 427 | 454.40 | 1.36 | 1H NMR (400 MHz, CDCl3) δ 7.08 (d, J = 1.9 Hz, 1H), 7.02 (dd, J = 8.2, 1.9 Hz, 1H), 6.87 (d, J = 8.3 Hz, 1H), 6.55 (d, J = 3.1 Hz, 1H), 6.15 (d, J = 3.9 Hz, 1H), 4.56 (dt, J = 12.2, 6.1 Hz, 1H), 4.13 (t, J = 4.4 Hz, 2H), 3.88 (s, 3H), 3.92-3.84 (m, 2H), 3.79 (s, 2H), 3.63 (s, 2H), 3.22-2.96 (m, 2H), 2.46 (dd, J = 14.4, 7.5 Hz, 2H), 1.82 (s, 2H), 1.38 (d, J = 6.1 Hz, 6H), 1.17 (t, J = 7.3 Hz, 3H). |
| 428 | 508.70 | 1.83 | 1H NMR (400 MHz, DMSO) δ 6.97 (q, J = 8.3 Hz, 3H), 6.62 (d, J = 3.6 Hz, 1H), 6.37 (d, J = 3.9 Hz, 1H), 4.59 (dt, J = 12.1, 6.0 Hz, 1H), 4.09-3.97 (m, 1H), 3.84 (s, 1H), 3.76 (s, 3H), 3.06 (s, 1H), 2.69 (s, 2H), 2.19 (s, 3H), 2.07 (s, 1H), 1.87 (d, J = 27.8 Hz, 2H), 1.26 (d, J = 6.0 Hz, 6H), 1.11 (t, J = 7.2 Hz, 3H), 0.88 (s, 3H). |
| 429 | 480.50 | 1.28 | |
| 430 | 382.16 | 2.33 | |
| 431 | 455.50 | 2.70 | |
| 432 | 464.20 | 1.08 | 1H NMR (400 MHz, DMSO) δ 7.43 (s, 2H), 7.25 (dd, J = 4.5, 2.2 Hz, 1H), 6.50 (d, J = 4.6 Hz, 1H), 4.73-4.64 (m, 1H), 4.39 (d, J = 12.7 Hz, 1H), 4.11 (s, 2H), 3.76 (d, J = 12.7 Hz, 1H), 3.51 (t, J = 12.3 Hz, 1H), 3.21 (t, J = 11.2 Hz, 1H), 2.34 (s, 3H), 2.29 (s, 1H), 1.94-1.78 (m, 3H), 1.68 (d, J = 12.4 Hz, 1H), 1.31 (d, J = 6.0 Hz, 6H), 1.09 (d, J = 12.1 Hz, 6H). |
| 433 | 493.30 | 1.67 | |
| 434 | 480.30 | 1.36 | |
| 435 | 466.50 | 1.34 | |
| 436 | 472.30 | 2.95 | |
| 437 | 506.50 | 1.84 | |
| 438 | 493.20 | 1.26 | |

TABLE 2-continued

| Cmpd. No. | LC/MS M + 1 | LC/RT min | NMR |
|---|---|---|---|
| 439 | 496.70 | 1.52 | |
| 440 | 468.20 | 1.03 | |
| 441 | 498.50 | 1.26 | |
| 442 | 539.50 | 1.38 | 1H NMR (400 MHz, CDCl3) δ 7.01 (d, J = 1.9 Hz, 1H), 6.97 (dd, J = 8.2, 1.9 Hz, 1H), 6.88 (d, J = 8.3 Hz, 1H), 6.53 (d, J = 3.5 Hz, 1H), 5.94 (d, J = 3.7 Hz, 1H), 4.56 (dq, J = 12.2, 6.1 Hz, 1H), 4.52-4.34 (m, 1H), 4.05-3.94 (m, 2H), 3.87 (s, 3H), 3.69 (s, 1H), 3.50 (s, 1H), 3.34 (s, 1H), 3.34 (t, J = 5.7 Hz, 2H), 2.39 (s, 3H), 2.13 (s, 2H), 1.84 (s, 2H), 1.38 (d, J = 6.1 Hz, 6H). |
| 443 | 466.50 | 1.23 | |
| 444 | 507.50 | 1.68 | |
| 445 | 468.70 | 1.42 | |
| 446 | 468.70 | 1.47 | |
| 447 | 464.30 | 1.18 | |
| 448 | 437.50 | 1.21 | |
| 449 | 546.70 | 1.55 | 1H NMR (400 MHz, DMSO) δ 7.88 (d, J = 7.9 Hz, 1H), 7.71 (d, J = 8.0 Hz, 1H), 7.45 (s, 1H), 7.42 (d, J = 8.1 Hz, 1H), 6.58 (d, J = 3.6 Hz, 1H), 6.12 (d, J = 3.8 Hz, 1H), 4.35 (d, J = 11.4 Hz, 1H), 3.96-3.86 (m, 2H), 3.45-3.34 (m, 2H), 3.29-3.19 (m, 3H), 3.17-3.01 (m, 1H), 2.60 (s, 3H), 2.27 (s, 3H), 2.22-2.10 (m, 1H), 2.06-1.95 (m, 1H), 1.84-1.67 (m, 2H), 0.97 (d, J = 6.5 Hz, 6H). |
| 450 | 513.30 | 1.37 | 1H NMR (400 MHz, DMSO) δ 7.52 (d, J = 8.3 Hz, 2H), 7.36 (d, J = 8.3 Hz, 2H), 6.60 (d, J = 3.8 Hz, 1H), 6.20 (d, J = 3.9 Hz, 1H), 5.07 (s, 1H), 4.26-4.09 (m, 1H), 3.98 (t, J = 5.8 Hz, 2H), 3.51-3.13 (m, 5H), 2.43-2.12 (m, 2H), 1.95-1.69 (m, 3H), 1.43 (s, 6H), 0.63-0.50 (m, 4H). |
| 451 | 462.20 | 3.29 | |
| 452 | 415.50 | 1.06 | |
| 453 | 483.20 | 1.12 | |
| 454 | 438.50 | 1.36 | 1H NMR (400 MHz, DMSO) δ 7.28-7.17 (m, 1H), 7.06-6.95 (m, 3H), 6.50 (d, J = 4.6 Hz, 1H), 4.65-4.51 (m, 1H), 4.48-4.05 (m, 3H), 3.78 (s, 3H), 3.67-2.99 (m, 5H), 2.30 (s, 3H), 2.18-1.98 (m, 2H), 1.94-1.75 (m, 2H), 1.25 (d, J = 6.0 Hz, 6H). |
| 455 | 494.50 | 1.44 | 1H NMR (400 MHz, DMSO) δ 7.47 (d, J = 8.7 Hz, 1H), 7.21-7.14 (m, 2H), 7.05 (d, J = 4.1 Hz, 1H), 6.18 (d, J = 4.2 Hz, 1H), 4.97 (s, 1H), 4.43-4.25 (m, 1H), 4.18 (t, J = 5.8 Hz, 2H), 3.54-3.29 (m, 2H), 3.29-3.19 (m, 2H), 3.18-2.99 (m, 1H), 2.54 (s, 3H), 2.31 (s, 3H), 2.26 (s, 3H), 2.19-1.94 (m, 2H), 1.86-1.66 (m, 2H), 1.51 (s, 6H). |
| 456 | 424.20 | 0.90 | |
| 457 | 382.50 | 0.91 | 1H NMR (400 MHz, CDCl3) δ 7.01 (d, J = 1.8 Hz, 1H), 6.96 (dd, J = 8.2, 1.9 Hz, 1H), 6.87 (d, J = 8.3 Hz, 1H), 6.63 (d, J = 3.5 Hz, 1H), 6.06 (d, J = 2.2 Hz, 1H), 4.92 (t, J = 6.3 Hz, 1H), 4.56 (dt, J = 12.1, 6.1 Hz, 1H), 4.36 (s, 1H), 3.87 (s, 3H), 3.76 (s, 3H), 3.50 (d, J = 50.0 Hz, 5H), 2.33 (s, 3H), 2.28 (s, 1H), 2.06 (s, 1H), 1.86 (s, 2H), 1.38 (d, J = 6.1 Hz, 6H). |
| 458 | 524.70 | 1.87 | 1H NMR (400 MHz, DMSO) δ 7.76 (dd, J = 8.6, 2.0 Hz, 1H), 7.70 (d, J = 1.9 Hz, 1H), 7.33 (d, J = 8.7 Hz, 1H), 7.28-7.19 (m, 1H), 6.49 (d, J = 4.6 Hz, 1H), 4.52-4.15 (m, 3H), 3.94 (s, 3H), 3.59-2.96 (m, 5H), 2.31 (s, 3H), 2.26-1.78 (m, 4H). |
| 459 | 504.50 | 1.59 | 1H NMR (400 MHz, DMSO) δ 7.29-7.19 (m, 2H), 6.98 (d, J = 9.1 Hz, 1H), 6.63 (d, J = 3.9 Hz, 1H), 6.29 (d, J = 4.0 Hz, 1H), 4.71-4.56 (m, 1H), 4.05 (t, J = 5.0 Hz, 2H), 3.99-3.79 (m, 2H), 3.78-3.44 (m, 7H), 2.98-2.73 (m, 2H), 2.14 (s, 3H), 1.91-1.72 (m, 2H), 1.29 (d, J = 6.0 Hz, 6H). |
| 460 | 494.20 | 6.64 | 1H NMR (400 MHz, DMSO) δ 7.46 (d, J = 2.1 Hz, 1H), 7.29 (dd, J = 8.4, 2.2 Hz, 1H), 6.98 (d, J = 8.6 Hz, 1H), 6.60-6.50 (m, 1H), 6.18 (d, J = 4.0 Hz, 1H), 5.05 (t, J = 5.7 Hz, 1H), 4.72-4.58 (m, 1H), 4.48 (d, J = 5.7 Hz, 2H), 4.43-4.14 (m, 1H), 3.97 (t, J = 5.7 Hz, 2H), 3.82-3.42 (m, 1H), 3.40-2.91 (m, 4H), 2.29 (s, 3H), 2.22-2.01 (m, 2H), 1.86-1.65 (m, 2H), 1.27 (d, J = 6.0 Hz, 6H). |
| 461 | 516.50 | 1.26 | |
| 462 | 438.20 | 2.57 | |
| 463 | 518.30 | 1.51 | 1H NMR (400 MHz, Acetone) δ 7.99-7.93 (m, 2H), 7.76-7.70 (m, 2H), 6.61-6.54 (m, 1H), 6.18 (d, J = 4.1 Hz, 1H), 4.52 (d, J = 10.5 Hz, 1H), 4.10 (t, J = 5.9 Hz, |

TABLE 2-continued

| Cmpd. No. | LC/MS M + 1 | LC/RT min | NMR |
|---|---|---|---|
| | | | 2H), 3.63-3.41 (m, 4H), 3.24 (t, J = 11.3 Hz, 1H), 2.43 (s, 3H), 2.38-2.11 (m, 2H), 1.99-1.84 (m, 2H), 1.33 (s, 9H). |
| 464 | 548.70 | 1.46 | |
| 465 | 422.30 | 0.80 | |
| 466 | 484.07 | 2.75 | |
| 467 | 562.70 | 1.67 | 1H NMR (400 MHz, DMSO) δ 7.47-7.38 (m, 2H), 7.27-7.19 (m, 1H), 6.46 (d, J = 4.6 Hz, 1H), 4.76-4.62 (m, 1H), 4.46-4.30 (m, 1H), 4.24 (t, J = 5.9 Hz, 2H), 3.87-3.68 (m, 1H), 3.46-3.25 (m, 3H), 3.19-2.98 (m, 1H), 2.35 (s, 3H), 2.31 (s, 3H), 2.26-1.97 (m, 2H), 1.95-1.72 (m, 2H), 1.30 (d, J = 6.0 Hz, 6H). |
| 468 | 479.50 | 1.47 | 1H NMR (400 MHz, CDCl3) δ 7.59-7.49 (m, 2H), 7.48-7.37 (m, 2H), 6.50 (s, 1H), 4.64 (s, 1H), 4.00 (s, 2H), 3.72 (q, J = 7.0 Hz, 2H), 3.48 (d, J = 126.2 Hz, 5H), 2.46 (s, 5H), 2.07 (s, 1H), 1.88 (d, J = 33.9 Hz, 2H), 1.59 (s, 7H), 1.24 (dd, J = 9.2, 4.8 Hz, 4H). |
| 469 | 470.50 | 1.36 | |
| 470 | 494.50 | 1.48 | |
| 471 | 488.50 | 1.65 | |
| 472 | 403.15 | 1.35 | |
| 473 | 408.26 | 2.32 | 1H NMR (400 MHz, CDCl3) δ 7.38 (t, J = 8.2 Hz, 1H), 6.73 (d, J = 8.5 Hz, 1H), 6.68-6.50 (m, 2H), 6.06-5.71 (m, 2H), 4.61-4.50 (m, 1H), 4.46-4.30 (m, 1H), 4.15 (t, J = 6.3 Hz, 2H), 4.11-3.93 (m, 1H), 3.59 (t, J = 5.2 Hz, 1H), 3.50-3.33 (m, 2H), 2.79-2.65 (m, 3H), 2.58-2.39 (m, 2H), 2.36-1.47 (m, 2H), 1.35 (d, J = 6.0 Hz, 6H). |
| 474 | 497.40 | 5.17 | |
| 475 | 468.60 | 6.38 | |
| 476 | 408.50 | 1.20 | |
| 477 | 440.50 | 1.28 | |
| 478 | 500.24 | 1.24 | |
| 479 | 507.14 | 2.56 | |
| 480 | 576.70 | 1.69 | |
| 481 | 462.50 | 0.94 | |
| 482 | 500.50 | 1.45 | |
| 483 | 498.70 | 2.94 | |
| 484 | 442.70 | 1.28 | |
| 485 | 465.50 | 1.29 | |
| 486 | 498.50 | 1.39 | 1H NMR (400 MHz, DMSO) δ 7.44 (d, J = 8.0 Hz, 1H), 7.29-7.12 (m, 3H), 6.50 (d, J = 4.6 Hz, 1H), 4.69 (s, 1H), 4.49-4.17 (m, 3H), 3.61-2.94 (m, 5H), 2.53 (s, 3H), 2.30 (s, 3H), 2.24-1.59 (m, 12H). |
| 487 | 504.50 | 1.49 | |
| 488 | 436.50 | 1.42 | |
| 489 | 514.22 | 1.27 | |
| 490 | 465.50 | 1.34 | 1H NMR (400 MHz, DMSO) δ 10.67 (s, 1H), 7.44 (d, J = 2.0 Hz, 1H), 7.32-7.21 (m, 2H), 6.99 (d, J = 8.3 Hz, 1H), 6.56 (d, J = 4.6 Hz, 1H), 5.76 (s, 1H), 4.14 (s, 1H), 4.10 (s, 2H), 3.53 (s, 1H), 2.26 (s, 1H), 1.88 (td, J = 13.1, 4.4 Hz, 2H), 1.73 (d, J = 13.9 Hz, 2H), 1.08 (s, 6H). |
| 491 | 470.20 | 0.96 | 1H NMR (400 MHz, DMSO) δ 7.89 (d, J = 8.0 Hz, 1H), 7.58-7.47 (m, 2H), 6.60 (d, J = 3.4 Hz, 1H), 6.21 (d, J = 3.9 Hz, 1H), 4.29-4.14 (m, 1H), 3.98 (t, J = 5.8 Hz, 2H), 3.55-3.44 (m, 1H), 3.44-3.16 (m, 5H), 2.65 (s, 3H), 2.43-2.14 (m, 2H), 1.94-1.68 (m, 3H), 1.17 (d, J = 6.8 Hz, 6H), 0.65-0.48 (m, 4H). |
| 492 | 524.20 | 3.40 | |
| 493 | 456.50 | 1.34 | |
| 494 | 492.40 | 1.86 | |
| 495 | 450.30 | 1.64 | |
| 496 | 510.70 | 1.31 | |
| 497 | 394.30 | 1.08 | 1H NMR (400 MHz, DMSO) δ 7.85-7.39 (m, 3H), 6.65-6.51 (m, 1H), 6.17-6.05 (m, 1H), 4.51-4.32 (m, 1H), 3.92 (t, J = 5.7 Hz, 2H), 3.55-3.38 (m, 1H), 3.41-3.24 (m, 3H), 3.25-2.97 (m, 2H), 2.42-2.29 (m, 3H), 2.26 (s, 3H), 2.24-2.15 (m, 1H), 2.13-1.51 (m, 3H), 1.17 (d, J = 6.8 Hz, 6H). |
| 498 | 498.20 | 2.37 | 1H NMR (400 MHz, DMSO) δ 7.29 (dd, J = 24.6, 8.1 Hz, 4H), 6.58 (d, J = 3.7 Hz, 1H), 6.12 (d, J = 3.9 Hz, 1H), 4.35 (s, 1H), 3.92 (t, J = 5.8 Hz, 2H), 3.42 (s, 1H), |

TABLE 2-continued

| Cmpd. No. | LC/MS M + 1 | LC/RT min | NMR |
|---|---|---|---|
| | | | 3.10 (s, 1H), 2.68 (s, 2H), 2.27 (s, 3H), 2.07 (s, 1H), 1.75 (s, 2H), 1.07 (s, 6H). |
| 499 | 450.50 | 1.18 | |
| 500 | 526.50 | 1.35 | 1H NMR (400 MHz, DMSO) δ 7.39 (d, J = 8.7 Hz, 2H), 7.28-7.17 (m, 1H), 6.97 (d, J = 8.7 Hz, 2H), 6.49 (d, J = 4.6 Hz, 1H), 4.50-4.04 (m, 3H), 3.78 (d, J = 6.5 Hz, 2H), 3.68-2.91 (m, 5H), 2.30 (s, 3H), 2.19-1.93 (m, 3H), 1.91-1.75 (m, 2H), 0.98 (d, J = 6.7 Hz, 6H). |
| 501 | 478.50 | 1.67 | 1H NMR (400 MHz, CDCl3) δ 7.98-7.93 (m, 2H), 7.63-7.57 (m, 2H), 7.22 (dd, J = 4.3, 2.1 Hz, 1H), 6.17 (d, J = 4.4 Hz, 1H), 4.69-4.57 (m, 1H), 4.36 (t, J = 5.7 Hz, 2H), 3.57 (t, J = 10.0 Hz, 1H), 3.49-3.39 (m, 1H), 3.34 (t, J = 5.3 Hz, 2H), 3.29 (s, 1H), 2.41 (s, 3H), 2.25 (d, J = 13.3 Hz, 1H), 2.08 (d, J = 16.5 Hz, 1H), 1.95 (t, J = 13.8 Hz, 1H), 1.72 (t, J = 13.9 Hz, 1H), 1.36 (s, 9H). |
| 502 | 526.30 | 1.45 | |
| 503 | 451.30 | 1.34 | |
| 504 | 435.26 | 1.19 | |
| 505 | 532.50 | 1.61 | |
| 506 | 466.50 | 1.53 | |
| 507 | 410.21 | 2.09 | |
| 508 | 526.50 | 1.40 | |
| 509 | 508.50 | 1.74 | 1H NMR (400 MHz, DMSO) δ 7.28-7.18 (m, 1H), 7.06-6.93 (m, 3H), 6.49 (d, J = 4.6 Hz, 1H), 4.49-4.16 (m, 3H), 4.11-4.00 (m, 4H), 3.77-3.39 (m, 1H), 3.38-3.26 (m, 3H), 3.24-2.88 (m, 1H), 2.30 (s, 3H), 2.21-1.95 (m, 2H), 1.93-1.73 (m, 2H), 1.40-1.26 (m, 6H). |
| 510 | 494.70 | 1.48 | |
| 511 | 450.50 | 1.67 | |
| 512 | 402.25 | 2.29 | |
| 513 | 498.30 | 2.96 | |
| 514 | 527.25 | 1.38 | 1H NMR (400 MHz, DMSO) δ 7.95 (d, J = 8.0 Hz, 1H), 7.54-7.48 (m, 2H), 6.58 (d, J = 3.4 Hz, 1H), 6.12 (d, J = 3.9 Hz, 1H), 4.36 (d, J = 12.9 Hz, 1H), 3.93 (t, J = 5.6 Hz, 2H), 3.46-3.32 (m, 2H), 3.31-3.27 (m, 2H), 3.25 (s, 3H), 3.12 (t, J = 11.9 Hz, 1H), 2.67 (s, 3H), 2.27 (s, 3H), 2.18 (d, J = 13.7 Hz, 1H), 2.01 (d, J = 14.5 Hz, 1H), 1.85-1.69 (m, 2H). |
| 515 | 470.50 | 1.13 | 1H NMR (400 MHz, DMSO) δ 7.34-7.12 (m, 1H), 7.12-6.93 (m, 3H), 6.50 (d, J = 4.5 Hz, 1H), 4.52-4.14 (m, 3H), 3.89-3.71 (m, 5H), 3.69-2.94 (m, 5H), 2.31 (s, 3H), 2.24-1.95 (m, 3H), 1.95-1.72 (m, 2H), 0.98 (d, J = 6.7 Hz, 6H). |
| 516 | 508.70 | 1.61 | |
| 517 | 554.10 | 1.52 | |
| 518 | 466.30 | 0.99 | |
| 519 | 394.22 | 2.19 | |
| 520 | 450.10 | 2.03 | |
| 521 | 422.50 | 1.30 | |
| 522 | 466.50 | 3.36 | 1H NMR (400 MHz, DMSO) δ 7.47 (d, J = 8.7 Hz, 1H), 7.22-7.13 (m, 2H), 7.09 (d, J = 4.3 Hz, 1H), 6.17 (d, J = 4.3 Hz, 1H), 4.97 (s, 1H), 4.47-4.24 (m, 1H), 4.15 (t, J = 5.9 Hz, 2H), 3.53-3.29 (m, 2H), 3.28-3.18 (m, 2H), 3.16-2.97 (m, 1H), 2.54 (s, 3H), 2.27 (s, 3H), 2.19-1.93 (m, 2H), 1.88-1.62 (m, 2H), 1.51 (s, 6H), 1.27 (s, 9H). |
| 523 | 466.40 | 1.18 | |
| 524 | 478.50 | 1.66 | |
| 525 | 480.50 | 4.06 | |
| 526 | 475.12 | 3.70 | |
| 527 | 415.50 | 1.03 | 1H NMR (400 MHz, CDCl3) δ 7.48 (d, J = 2.1 Hz, 1H), 7.32 (dd, J = 8.4, 2.1 Hz, 1H), 7.22 (dd, J = 4.3, 2.1 Hz, 1H), 6.96 (d, J = 8.6 Hz, 1H), 6.16 (d, J = 4.4 Hz, 1H), 4.61 (dt, J = 12.2, 6.1 Hz, 1H), 4.56 (s, 1H), 4.35 (t, J = 5.8 Hz, 2H), 3.78-3.40 (m, 2H), 3.34 (s, 1H), 3.34 (t, J = 5.4 Hz, 2H), 2.41 (s, 3H), 2.14 (s, 2H), 1.83 (s, 2H), 1.40 (d, J = 6.1 Hz, 6H). |
| 528 | 498.30 | 1.61 | |
| 529 | 498.30 | 1.53 | |
| 530 | 430.17 | 2.69 | |
| 531 | 446.22 | 2.08 | 1H NMR (400 MHz, CDCl3) δ 7.96 (d, J = 8.5 Hz, 2H), 7.58 (d, J = 8.4 Hz, 2H), 6.95 (d, J = 4.2 Hz, 1H), 6.02 (d, J = 4.1 Hz, 1H), 5.02 (s, 1H), 4.67-4.48 (m, 1H), 4.35 (t, J = 5.9 Hz, 2H), 3.66-3.36 (m, 2H), 3.36-3.21 (m, 3H), 2.40 (s, 3H), 2.38 (s, 3H), 2.32-2.16 (m, 2H), 2.16-2.00 (m, 1H), 2.00-1.84 (m, 1H), 1.82-1.66 (m, 1H), 0.71-0.57 (m, 4H). |

TABLE 2-continued

| Cmpd. No. | LC/MS M + 1 | LC/RT min | NMR |
|---|---|---|---|
| 532 | 471.40 | 0.88 | 1H NMR (400 MHz, CDCl3) δ 7.32-7.28 (m, 2H), 6.92-6.79 (m, 1H), 6.55 (d, J = 3.8 Hz, 1H), 6.02 (d, J = 3.9 Hz, 1H), 5.90 (s, 1H), 4.63-4.51 (m, 1H), 4.35-4.19 (m, 2H), 4.15 (t, J = 6.6 Hz, 2H), 4.00-3.56 (m, 2H), 3.41 (t, J = 6.5 Hz, 2H), 2.71 (s, 3H), 2.53-2.44 (m, 2H), 2.22 (s, 3H), 2.18-1.38 (m, 2H), 1.35 (d, J = 6.0 Hz, 6H). |
| 533 | 493.40 | 5.60 | 1H NMR (400 MHz, DMSO) δ 7.89 (d, J = 8.0 Hz, 1H), 7.55-7.46 (m, 2H), 5.99 (d, J = 3.5 Hz, 1H), 5.93 (d, J = 3.6 Hz, 1H), 4.39-4.24 (m, 1H), 3.83-3.72 (m, 2H), 3.71-3.56 (m, 2H), 3.55-3.42 (m, 1H), 3.42-3.20 (m, 4H), 3.20-3.05 (m, 1H), 2.64 (s, 3H), 2.24 (s, 3H), 2.19-2.09 (m, 1H), 2.02-1.91 (m, 1H), 1.79-1.62 (m, 2H), 1.17 (d, J = 6.8 Hz, 6H). |
| 534 | 512.70 | 1.11 | 1H NMR (400 MHz, DMSO) δ 7.05 (d, J = 4.2 Hz, 1H), 7.03-6.94 (m, 3H), 6.18 (d, J = 4.1 Hz, 1H), 4.66-4.53 (m, 1H), 4.50-4.11 (m, 3H), 3.77 (s, 3H), 3.70-3.29 (m, 2H), 3.28-3.02 (m, 3H), 2.31 (s, 3H), 2.27 (s, 3H), 2.18-1.96 (m, 2H), 1.86-1.67 (m, 2H), 1.26 (d, J = 6.0 Hz, 6H). |
| 535 | 440.60 | 1.00 | |
| 536 | 506.50 | 1.62 | |
| 537 | 464.50 | 1.59 | |
| 538 | 494.70 | 1.51 | |
| 539 | 446.17 | 2.28 | |
| 540 | 486.50 | 2.17 | |
| 541 | 510.17 | 2.18 | 1H NMR (400 MHz, DMSO) δ 7.27-7.18 (m, 2H), 6.97 (d, J = 9.1 Hz, 1H), 6.73 (d, J = 4.0 Hz, 1H), 6.21 (d, J = 4.1 Hz, 1H), 4.72-4.54 (m, 1H), 4.46-4.01 (m, 3H), 3.80-3.37 (m, 1H), 3.36-3.26 (m, 3H), 3.20 (s, 3H), 3.17-2.89 (m, 1H), 2.29 (s, 3H), 2.14 (s, 3H), 2.14-1.96 (m, 2H), 1.84-1.64 (m, 2H), 1.29 (d, J = 6.0 Hz, 6H). |
| 542 | 460.50 | 1.36 | 1H NMR (400 MHz, DMSO) δ 7.28-7.18 (m, 2H), 6.98 (d, J = 9.1 Hz, 1H), 6.60 (d, J = 3.8 Hz, 1H), 6.10 (s, 1H), 5.15-4.76 (m, 1H), 4.68-4.57 (m, 1H), 4.52-4.19 (m, 1H), 4.17-4.00 (m, 1H), 3.90-3.73 (m, 2H), 3.60-2.96 (m, 4H), 2.30 (s, 3H), 2.26-2.18 (m, 1H), 2.14 (s, 3H), 1.93-1.75 (m, 1H), 1.29 (d, J = 6.0 Hz, 6H). |
| 543 | 468.20 | 6.35 | 1H NMR (400 MHz, CDCl3) δ 6.89-6.73 (m, 2H), 6.56 (d, J = 3.1 Hz, 1H), 5.96 (d, J = 3.9 Hz, 1H), 4.53 (s br, 1H), 4.50-4.41 (m, 1H), 4.02 (s, 2H), 3.89 (s, 3H), 3.60 (d, J = 45.1 Hz, 2H), 3.36 (t, J = 6.0 Hz, 2H), 3.34-3.19 (m, 1H), 2.41 (s, 3H), 2.18 (s, 2H), 1.83 (d, J = 51.6 Hz, 2H), 1.34 (d, J = 6.1 Hz, 6H). |
| 544 | 484.30 | 1.59 | |
| 545 | 480.50 | 1.30 | |
| 546 | 454.50 | 1.49 | 1H NMR (400 MHz, DMSO) δ 7.04-6.91 (m, 3H), 5.99 (d, J = 3.5 Hz, 1H), 5.92 (d, J = 3.6 Hz, 1H), 4.65-4.52 (m, 1H), 4.44-3.95 (m, 1H), 3.82-3.71 (m, 5H), 3.71-3.55 (m, 2H), 3.43-2.97 (m, 5H), 2.24 (s, 3H), 2.13-1.92 (m, 2H), 1.78-1.59 (m, 2H), 1.26 (d, J = 6.0 Hz, 6H). |
| 547 | 480.30 | 1.17 | |
| 548 | 495.06 | 3.68 | |
| 549 | 452.50 | 1.16 | |
| 550 | 452.30 | 1.32 | 1H NMR (400 MHz, DMSO) δ 7.06-6.89 (m, 3H), 6.60 (d, J = 3.8 Hz, 1H), 6.15 (d, J = 3.9 Hz, 1H), 4.68-4.47 (m, 1H), 4.46-3.89 (m, 1H), 3.77 (s, 3H), 3.70 (s, 2H), 3.66-2.78 (m, 3H), 2.09 (s, 1H), 1.95-1.52 (m, 4H), 1.26 (d, J = 6.0 Hz, 6H), 1.09 (s, 6H). |
| 551 | 480.40 | 1.35 | |
| 552 | 486.50 | 1.40 | |
| 553 | 518.20 | 1.67 | 1H NMR (400 MHz, CDCl3) δ 7.39 (d, J = 7.6 Hz, 1H), 6.99 (dd, J = 7.6, 1.4 Hz, 1H), 6.97 (d, J = 1.2 Hz, 1H), 6.48 (s, 1H), 4.63 (d, J = 11.1 Hz, 1H), 4.58 (s, 2H), 3.98 (t, J = 5.4 Hz, 2H), 3.86 (s, 3H), 3.75 (t, J = 6.7 Hz, 2H), 3.62 (s, 1H), 3.45 (s, 1H), 3.37-3.24 (m, 2H), 3.18 (s, 1H), 2.58-2.33 (m, 8H), 2.08 (d, J = 12.8 Hz, 1H), 2.01 (d, J = 4.6 Hz, 2H), 1.89 (d, J = 12.4 Hz, 1H). |
| 554 | 568.40 | 1.86 | |
| 555 | 512.20 | 1.27 | |
| 556 | 493.50 | 1.52 | 1H NMR (400 MHz, DMSO) δ 7.92 (d, J = 8.3 Hz, 2H), 7.73 (d, J = 8.2 Hz, 2H), 7.32-7.23 (m, 1H), 6.57 (d, J = 4.6 Hz, 1H), 4.51-4.32 (m, 1H), 4.18-4.00 (m, 2H), 3.63-3.38 (m, 2H), 3.38-3.15 (m, 2H), 2.29 (s, 1H), |

TABLE 2-continued

| Cmpd. No. | LC/MS M + 1 | LC/RT min | NMR |
|---|---|---|---|
| | | | 2.01-1.57 (m, 4H), 1.17 (d, J = 6.8 Hz, 6H), 1.12 (s, 3H), 1.04 (s, 3H). |
| 557 | 526.50 | 1.38 | |
| 558 | 440.20 | 1.76 | |
| 559 | 434.25 | 2.64 | |
| 560 | 484.70 | 1.71 | |
| 561 | 501.50 | 1.31 | 1H NMR (400 MHz, CDCl3) δ 7.42-7.35 (m, 2H), 6.92-6.86 (m, 2H), 6.29 (s, 1H), 4.58 (dt, J = 12.1, 6.1 Hz, 1H), 3.93 (s, 2H), 3.30 (s, 3H), 2.42 (s, 3H), 2.09 (s, 4H), 1.56 (s, 1H), 1.35 (d, J = 6.1 Hz, 7H). |
| 562 | 454.50 | 2.85 | |
| 563 | 502.10 | 2.01 | |
| 564 | 496.20 | 1.20 | |
| 565 | 482.50 | 1.46 | |
| 566 | 492.50 | 1.61 | |
| 567 | 504.20 | 1.11 | |
| 568 | 454.50 | 1.44 | 1H NMR (400 MHz, DMSO) δ 10.45 (s, 2H), 8.06 (d, J = 2.4 Hz, 1H), 7.90 (d, J = 8.3 Hz, 2H), 7.71 (d, J = 8.2 Hz, 2H), 6.79-6.73 (m, 1H), 6.51 (s, 1H), 4.32-4.15 (m, 3H), 3.80-3.59 (m, 4H), 3.57-3.42 (m, J = 37.6 Hz, 1H), 2.44-2.28 (m, 1H), 2.28-2.10 (m, 4H), 0.54-0.47 (m, 2H), 0.44-0.36 (m, 2H). |
| 569 | 483.50 | 1.12 | 1H NMR (400 MHz, DMSO) δ 7.34-7.17 (m, 3H), 6.92 (d, J = 9.0 Hz, 1H), 6.49 (d, J = 4.6 Hz, 1H), 4.65 (s, 1H), 4.49-4.10 (m, 3H), 3.73 (s, 2H), 3.69-2.93 (m, 5H), 2.30 (s, 3H), 2.21 (s, 3H), 2.18-1.94 (m, 2H), 1.93-1.73 (m, 2H), 1.23 (s, 6H). |
| 570 | 508.70 | 1.42 | 1H NMR (400 MHz, DMSO) δ 7.43 (s, 1H), 7.24 (t, J = 8.8 Hz, 3H), 7.02-6.93 (m, 1H), 6.58 (d, J = 3.7 Hz, 1H), 6.14 (d, J = 3.9 Hz, 1H), 4.64 (dt, J = 12.1, 6.0 Hz, 1H), 3.97 (s, 2H), 3.57 (s, 4H), 3.32 (s, 3H), 3.08 (s, 2H), 2.14 (s, 4H), 1.80 (s, 2H), 1.29 (d, J = 6.0 Hz, 6H). |
| 571 | 493.30 | 1.79 | |
| 572 | 454.23 | 2.08 | 1H NMR (400 MHz, DMSO) δ 8.24 (s, 1H), 7.47 (s, 1H), 7.26-7.17 (m, 1H), 6.45 (d, J = 4.6 Hz, 1H), 4.86-4.73 (m, 1H), 4.43-4.29 (m, 1H), 4.29-4.18 (m, 2H), 3.89-3.72 (m, 1H), 3.45-3.21 (m, 3H), 3.18-3.00 (m, 1H), 2.31 (s, 3H), 2.25-2.13 (m, 4H), 2.07-2.00 (m, 1H), 1.90-1.74 (m, 2H), 1.32 (d, J = 6.0 Hz, 6H). |
| 573 | 479.50 | 1.49 | |
| 574 | 506.30 | 1.50 | |
| 575 | 482.50 | 1.37 | |
| 576 | 514.20 | 1.34 | |
| 577 | 436.10 | 2.08 | |
| 578 | 442.70 | 1.38 | 1H NMR (400 MHz, DMSO) δ 7.42 (d, J = 7.6 Hz, 1H), 7.05-6.92 (m, 2H), 6.58 (d, J = 3.8 Hz, 1H), 6.12 (d, J = 4.0 Hz, 1H), 5.06 (d, J = 5.2 Hz, 1H), 4.51 (d, J = 4.8 Hz, 2H), 4.34 (s, 1H), 4.06 (q, J = 6.8 Hz, 2H), 3.93 (s, 2H), 3.10 (s, 1H), 2.27 (s, 3H), 2.05 (d, J = 19.9 Hz, 3H), 1.76 (s, 2H), 1.33 (t, J = 6.9 Hz, 3H). |
| 579 | 452.50 | 1.17 | 1H NMR (400 MHz, DMSO) δ 7.26-7.19 (m, 2H), 6.97 (d, J = 9.1 Hz, 1H), 6.57 (d, J = 3.5 Hz, 1H), 6.11 (d, J = 3.9 Hz, 1H), 4.64 (sept, J = 6.0 Hz, 1H), 4.51-4.07 (m, 1H), 3.92 (t, J = 5.8 Hz, 2H), 3.80-3.40 (m, 1H), 3.34-3.28 (m, 2H), 3.26-3.00 (m, 2H), 2.28 (s, 3H), 2.14 (s, 3H), 2.13-1.98 (m, 2H), 1.73 (t, J = 11.5 Hz, 2H), 1.29 (d, J = 6.0 Hz, 6H). |
| 580 | 450.50 | 1.47 | |
| 581 | 462.20 | 1.07 | 1H NMR (400 MHz, DMSO) δ 7.31 (d, J = 8.8 Hz, 2H), 7.27-7.17 (m, 1H), 6.92 (d, J = 8.9 Hz, 2H), 6.49 (d, J = 4.6 Hz, 1H), 4.36-3.57 (m, 4H), 3.35-3.27 (m, 3H), 3.27-3.16 (m, 5H), 2.30 (s, 3H), 2.20-1.99 (m, 2H), 1.93-1.75 (m, 2H), 1.69-1.49 (m, 6H). |
| 582 | 489.50 | 1.20 | 1H NMR (400 MHz, DMSO) δ 7.28-7.22 (m, 2H), 6.95 (d, J = 8.8 Hz, 1H), 6.57 (d, J = 3.8 Hz, 1H), 6.11 (d, J = 3.9 Hz, 1H), 4.54 (t, J = 5.2 Hz, 1H), 4.07 (t, J = 6.2 Hz, 2H), 3.92 (t, J = 5.7 Hz, 2H), 3.58 (dd, J = 11.5, 6.2 Hz, 2H), 2.28 (s, 3H), 2.16 (s, 3H), 2.07 (s, 1H), 1.88 (p, J = 6.2 Hz, 2H), 1.75 (d, J = 10.7 Hz, 2H). |
| 583 | 466.10 | 1.22 | 1H NMR (400 MHz, DMSO) δ 12.01 (s, 1H), 8.06 (s, 1H), 7.90 (d, J = 8.0 Hz, 2H), 7.75-7.63 (m, 2H), 6.78 (s, 1H), 6.55 (s, 1H), 4.42-4.18 (m, 2H), 4.18-3.85 (m, 2H), 3.70-3.52 (m, 3H), 3.36-3.16 (m, 1H), 2.90-2.63 (m, 3H), 2.37-1.96 (m, 5H), 0.54-0.46 (m, 2H), 0.43-0.35 (m, 2H). |
| 584 | 497.50 | 1.16 | |
| 585 | 518.30 | 1.47 | |

TABLE 2-continued

| Cmpd. No. | LC/MS M + 1 | LC/RT min | NMR |
|---|---|---|---|
| 586 | 440.24 | 1.87 | |
| 587 | 512.50 | 1.26 | |
| 588 | 526.50 | 1.72 | |
| 589 | 526.20 | 1.33 | |
| 590 | 402.15 | 2.25 | 1H NMR (400 MHz, DMSO) δ 7.47 (d, J = 8.7 Hz, 1H), 7.22-7.12 (m, 2H), 7.06 (d, J = 4.2 Hz, 1H), 6.17 (d, J = 4.2 Hz, 1H), 4.97 (s, 1H), 4.43-4.25 (m, 1H), 4.19 (t, J = 5.9 Hz, 2H), 3.52-3.29 (m, 2H), 3.27-3.19 (m, 2H), 3.19-2.97 (m, 1H), 2.73 (q, J = 7.4 Hz, 2H), 2.54 (s, 3H), 2.26 (s, 3H), 2.20-1.93 (m, 2H), 1.87-1.61 (m, 2H), 1.51 (s, 6H), 1.04 (t, J = 7.4 Hz, 3H). |
| 591 | 438.40 | 1.24 | |
| 592 | 478.50 | 1.67 | 1H NMR (400 MHz, DMSO) δ 7.47 (d, J = 8.7 Hz, 1H), 7.19-7.12 (m, 2H), 5.99 (d, J = 3.5 Hz, 1H), 5.93 (d, J = 3.6 Hz, 1H), 4.96 (s, 1H), 4.39-4.18 (m, 1H), 3.77 (t, J = 5.8 Hz, 2H), 3.63 (q, J = 11.2 Hz, 2H), 3.49-3.30 (m, 2H), 3.29-3.22 (m, 2H), 3.20-2.99 (m, 1H), 2.54 (s, 3H), 2.24 (s, 3H), 2.16-1.91 (m, 2H), 1.77-1.56 (m, 2H), 1.50 (s, 6H). |
| 593 | 464.50 | 1.04 | 1H NMR (400 MHz, DMSO) δ 10.45 (s, 2H), 9.47 (s, 1H), 7.02 (s, 1H), 6.92 (d, J = 7.5 Hz, 1H), 6.83 (d, J = 8.1 Hz, 1H), 6.75 (s, 1H), 6.51 (s, 1H), 4.24 (s, 2H), 3.80 (s, 4H), 3.69 (s, 4H), 2.20 (d, J = 40.3 Hz, 4H). |
| 594 | 410.50 | 0.95 | |
| 595 | 450.50 | 1.50 | |
| 596 | 532.50 | 1.76 | 1H NMR (400 MHz, DMSO) δ 9.54 (s, 1H), 7.29-7.16 (m, 1H), 7.10 (d, J = 7.9 Hz, 1H), 6.81 (d, J = 1.4 Hz, 1H), 6.76 (dd, J = 7.5, 1.5 Hz, 1H), 6.48 (d, J = 4.6 Hz, 1H), 4.48-4.27 (m, 1H), 4.27-4.17 (m, 2H), 3.67-3.41 (m, 1H), 3.41-3.21 (m, 3H), 3.21-2.93 (m, 1H), 2.30 (s, 3H), 2.19-1.97 (m, 5H), 1.93-1.68 (m, 2H). |
| 597 | 436.30 | 1.32 | 1H NMR (400 MHz, DMSO) δ 7.29-7.15 (m, 2H), 6.97 (d, J = 9.1 Hz, 1H), 6.60 (d, J = 3.8 Hz, 1H), 6.14 (d, J = 3.9 Hz, 1H), 4.71-4.54 (m, 1H), 4.42-3.97 (m, 1H), 3.70 (s, 2H), 3.61-3.38 (m, 1H), 3.26-3.15 (m, 1H), 3.06-2.73 (m, 1H), 2.14 (s, 3H), 2.08 (s, 1H), 1.88-1.56 (m, 4H), 1.29 (d, J = 6.0 Hz, 6H), 1.09 (s, 6H). |
| 598 | 464.40 | 1.53 | |
| 599 | 470.24 | 2.68 | |
| 600 | 567.50 | 1.65 | |
| 601 | 424.50 | 1.35 | |
| 602 | 488.30 | 1.72 | |
| 603 | 440.50 | 1.47 | |
| 604 | 458.24 | 2.34 | |
| 605 | 427.30 | 1.18 | |
| 606 | 440.24 | 1.82 | 1H NMR (400 MHz, DMSO) δ 7.06 (d, J = 4.2 Hz, 1H), 7.03-6.93 (m, 3H), 6.17 (d, J = 4.2 Hz, 1H), 4.66-4.53 (m, 1H), 4.45-4.11 (m, 3H), 3.77 (s, 3H), 3.69-3.29 (m, 2H), 3.29-2.94 (m, 3H), 2.73 (q, J = 7.4 Hz, 2H), 2.27 (s, 3H), 2.18-1.92 (m, 2H), 1.86-1.67 (m, 2H), 1.26 (d, J = 6.0 Hz, 6H), 1.04 (t, J = 7.4 Hz, 3H). |
| 607 | 454.20 | 1.32 | |
| 608 | 484.50 | 1.48 | |
| 609 | 454.23 | 2.08 | |
| 610 | 492.30 | 1.60 | |
| 611 | 493.50 | 1.65 | 1H NMR (400 MHz, CDCl3) δ 7.28-7.22 (m, 3H), 6.83 (d, J = 8.2 Hz, 1H), 6.20 (d, J = 4.5 Hz, 1H), 4.57 (s, 1H), 4.19 (s, 2H), 3.86 (s, 3H), 3.77 (s, 1H), 3.38 (n, 2H), 2.23 (s, 3H), 1.97 (s, 2H), 1.76 (s, 2H), 1.18 (s, 6H), 0.98 (s, 1H). |
| 612 | 464.50 | 1.50 | |
| 613 | 410.50 | 1.31 | 1H NMR (400 MHz, DMSO) δ 7.04-6.88 (m, 3H), 6.57 (d, J = 3.4 Hz, 1H), 6.07 (d, J = 3.9 Hz, 1H), 4.66-4.50 (m, 1H), 4.06-3.81 (m, 2H), 3.77 (s, 3H), 3.63-3.43 (m, 1H), 3.35-3.28 (m, 3H), 3.27-3.09 (m, 1H), 2.34-2.20 (m, 4H), 2.20-1.64 (m, 3H), 1.42 (d, J = 7.0 Hz, 3H), 1.26 (d, J = 6.0 Hz, 6H). |
| 614 | 480.40 | 3.08 | |
| 615 | 438.17 | 1.97 | 1H NMR (400 MHz, CDCl3) δ 7.62 (t, J = 8.1 Hz, 1H), 7.19 (dd, J = 8.0, 1.6 Hz, 1H), 7.12 (dd, J = 11.9, 1.6 Hz, 1H), 6.29 (s, 1H), 4.57 (s, 1H), 3.92 (d, J = 5.5 Hz, 2H), 3.59 (s, 1H), 3.48 (s, 1H), 3.30 (s, 3H), 2.42 (s, 3H), 2.16 (s, 2H), 2.07 (d, J = 2.8 Hz, 1H), 2.01 (s, 2H), 1.65 (d, J = 0.8 Hz, 6H), 1.55 (s, 1H). |
| 616 | 472.50 | 2.50 | |
| 617 | 520.50 | 1.65 | |
| 618 | 438.40 | 1.12 | |

TABLE 2-continued

| Cmpd. No. | LC/MS M + 1 | LC/RT min | NMR |
|---|---|---|---|
| 619 | 470.50 | 1.51 | |
| 620 | 430.20 | 0.81 | |
| 621 | 541.29 | 1.25 | 1H NMR (400 MHz, CDCl3) δ 7.01 (d, J = 1.9 Hz, 1H), 6.97 (dd, J = 8.2, 1.9 Hz, 1H), 6.88 (d, J = 8.3 Hz, 1H), 6.31 (d, J = 3.9 Hz, 1H), 5.91 (d, J = 3.8 Hz, 1H), 4.61-4.49 (m, 3H), 4.16 (t, J = 5.1 Hz, 2H), 3.87 (s, 3H), 3.69 (s, 1H), 3.49 (s, 1H), 3.37-3.18 (m, 2H), 2.82 (t, J = 12.9 Hz, 2H), 2.40 (s, 3H), 2.13 (s, 2H), 1.86 (s, 1H), 1.73 (d, J = 12.0 Hz, 3H), 1.50-1.42 (m, 1H), 1.38 (d, J = 6.1 Hz, 6H), 1.34-1.14 (m, 5H), 0.90 (d, J = 6.8 Hz, 6H). |
| 622 | 551.70 | 1.61 | |
| 623 | 478.30 | 1.20 | |
| 624 | 442.12 | 2.26 | |
| 625 | 400.13 | 2.49 | |
| 626 | 426.21 | 2.81 | |
| 627 | 504.50 | 1.41 | |
| 628 | 476.30 | 0.92 | |
| 629 | 436.50 | 1.41 | 1H NMR (400 MHz, DMSO) δ 7.57-7.40 (m, 1H), 7.23-7.09 (m, 2H), 6.60 (d, J = 3.5 Hz, 1H), 6.10 (s, 1H), 5.15-4.35 (m, 3H), 4.15-4.05 (m, 1H), 3.90-3.67 (m, 2H), 3.61-2.96 (m, 4H), 2.55 (s, 3H), 2.39-2.14 (m, 4H), 1.97-1.68 (m, 1H), 1.51 (s, 6H). |
| 630 | 468.40 | 4.54 | 1H NMR (400 MHz, DMSO) δ 7.34 (d, J = 8.0 Hz, 2H), 7.27 (d, J = 8.1 Hz, 2H), 6.47 (s, 1H), 6.15-6.00 (m, 1H), 5.94 (d, J = 3.7 Hz, 1H), 5.28-5.06 (m, 1H), 4.42-4.17 (m, 1H), 3.86 (t, J = 5.8 Hz, 2H), 3.50-3.30 (m, 2H), 3.29-3.21 (m, 2H), 3.20-2.98 (m, 1H), 2.58-2.45 (m, 1H), 2.25 (s, 3H), 2.18-1.89 (m, 2H), 1.88-1.57 (m, 7H), 1.53-1.12 (m, 5H). |
| 631 | 490.20 | 1.72 | |
| 632 | 444.20 | 0.86 | |
| 633 | 464.50 | 1.37 | |
| 634 | 507.40 | 4.29 | 1H NMR (400 MHz, CDCl3) δ 7.47 (d, J = 2.0 Hz, 1H), 7.32-7.25 (m, 1H), 7.22 (dd, J = 4.4, 2.1 Hz, 1H), 7.04 (d, J = 8.4 Hz, 1H), 6.16 (d, J = 4.5 Hz, 1H), 5.94 (s, 1H), 4.53 (s, 1H), 4.35 (t, J = 6.0 Hz, 2H), 3.82-3.38 (m, 2H), 3.34 (t, J = 6.0 Hz, 2H), 3.29 (s, 1H), 2.41 (s, 3H), 2.13 (s, 2H), 1.81 (s, 2H). |
| 635 | 456.50 | 1.34 | 1H NMR (400 MHz, CDCl3) δ 7.49 (d, J = 2.1 Hz, 1H), 7.34 (dd, J = 8.4, 2.1 Hz, 1H), 7.26 (dd, J = 4.0, 1.7 Hz, 1H), 6.94 (d, J = 8.5 Hz, 1H), 6.19 (d, J = 4.5 Hz, 1H), 4.57 (s, 1H), 4.19 (s, 2H), 4.14 (q, J = 7.0 Hz, 2H), 3.92-3.09 (m, 3H), 1.96 (s, 2H), 1.83-1.67 (m, 2H), 1.49 (t, J = 7.0 Hz, 3H), 1.18 (s, 6H), 0.96 (s, 1H). |
| 636 | 498.30 | 1.61 | 1H NMR (400 MHz, CDCl3) δ 7.48-7.35 (m, 2H), 7.02-6.87 (m, 2H), 6.53 (d, J = 3.8 Hz, 1H), 5.94 (d, J = 3.9 Hz, 1H), 5.30 (s, 1H), 4.49 (s, 1H), 4.17-3.93 (m, 2H), 3.82 (s, 2H), 3.76-3.13 (m, 5H), 2.39 (s, 3H), 2.28-1.95 (m, 3H), 1.80 (s, 2H), 1.43-1.25 (m, 6H). |
| 637 | 466.30 | 1.18 | |
| 638 | 489.50 | 1.57 | |
| 639 | 470.50 | 1.45 | |
| 640 | 510.70 | 1.37 | |
| 641 | 444.50 | 1.33 | 1H NMR (400 MHz, DMSO) δ 7.29-7.17 (m, 2H), 6.98 (d, J = 9.1 Hz, 1H), 6.60 (d, J = 3.8 Hz, 1H), 6.10 (s, 1H), 5.18-4.74 (m, 1H), 4.73-4.59 (m, 1H), 4.59-4.17 (m, 1H), 4.17-4.03 (m, 1H), 3.90-3.75 (m, 2H), 3.62-2.95 (m, 4H), 2.30 (s, 3H), 2.25-2.16 (m, 1H), 2.14 (s, 3H), 1.94-1.74 (m, 1H), 1.29 (d, J = 6.0 Hz, 6H). |
| 642 | 468.40 | 6.38 | |
| 643 | 448.50 | 1.61 | |
| 644 | 524.50 | 1.46 | |
| 645 | 506.50 | 1.48 | |
| 646 | 506.50 | 1.81 | 1H NMR (400 MHz, DMSO) δ 7.47 (d, J = 8.7 Hz, 1H), 7.21-7.13 (m, 2H), 6.60-6.51 (m, 1H), 6.19 (d, J = 4.0 Hz, 1H), 4.97 (s, 1H), 4.46-4.23 (m, 1H), 3.97 (t, J = 5.5 Hz, 2H), 3.55-3.22 (m, 4H), 3.20-2.96 (m, 1H), 2.54 (s, 3H), 2.28 (s, 3H), 2.23-1.95 (m, 2H), 1.84-1.63 (m, 2H), 1.51 (s, 6H). |
| 647 | 500.50 | 2.74 | |
| 648 | 417.30 | 1.17 | |
| 649 | 552.50 | 1.54 | |
| 650 | 502.10 | 2.31 | 1H NMR (400 MHz, Acetone) δ 8.05-7.94 (m, 2H), 7.77-7.68 (m, 2H), 6.62-6.53 (m, 1H), 6.18 (d, J = 4.0 Hz, 1H), 4.51 (d, J = 8.8 Hz, 1H), 4.16-4.03 (m, 2H), |

TABLE 2-continued

| Cmpd. No. | LC/MS M + 1 | LC/RT min | NMR |
|---|---|---|---|
| | | | 3.62-3.41 (m, 4H), 3.30-3.16 (m, 1H), 2.75 (ddd, J = 9.6, 6.4, 4.0 Hz, 1H), 2.43 (s, 3H), 2.36-2.11 (m, 2H), 1.92 (t, J = 13.9 Hz, 2H), 1.23 (dd, J = 4.5, 2.4 Hz, 2H), 1.10 (dd, J = 7.9, 2.6 Hz, 2H). |
| 651 | 535.50 | 1.41 | |
| 652 | 422.10 | 0.88 | |
| 653 | 554.20 | 1.13 | |
| 654 | 514.70 | 1.41 | 1H NMR (400 MHz, DMSO) δ 7.41-7.26 (m, 1H), 7.26-7.13 (m, 2H), 6.60 (d, J = 3.8 Hz, 1H), 6.16 (d, J = 3.9 Hz, 1H), 4.80-4.56 (m, 1H), 4.46-4.12 (m, 1H), 3.70 (s, 2H), 3.64-2.81 (m, 3H), 2.09 (s, 1H), 1.93-1.53 (m, 4H), 1.30 (d, J = 6.0 Hz, 6H), 1.09 (s, 6H). |
| 655 | 468.20 | 1.45 | |
| 656 | 480.50 | 1.31 | 1H NMR (400 MHz, CDCl3) δ 8.11 (s, 1H), 7.50 (s, 1H), 6.47 (s, 1H), 4.73-4.59 (m, 2H), 4.03 (d, J = 13.4 Hz, 1H), 3.97 (t, J = 5.8 Hz, 2H), 3.55 (t, J = 12.7 Hz, 1H), 3.39-3.16 (m, 3H), 2.56-2.41 (m, 5H), 2.25 (s, 3H), 2.07 (d, J = 14.2 Hz, 1H), 1.90 (d, J = 14.5 Hz, 1H), 1.68 (s, 1H), 1.39 (d, J = 6.0 Hz, 6H). |
| 657 | 485.40 | 1.66 | 1H NMR (400 MHz, CDCl3) δ 7.43 (d, J = 7.9 Hz, 1H), 7.30 (dd, J = 7.9, 1.6 Hz, 1H), 7.24 (s, 1H), 6.53 (d, J = 3.2 Hz, 1H), 5.94 (d, J = 3.9 Hz, 1H), 5.05 (dd, J = 8.4, 5.9 Hz, 2H), 4.84 (dd, J = 7.4, 5.9 Hz, 2H), 4.61-4.41 (m, J = 15.8, 7.9 Hz, 2H), 3.99 (s br, 2H), 3.55 (d br, J = 35.9 Hz, 2H), 3.34 (t, J = 6.0 Hz, 2H), 3.27 (s, 1H), 2.36 (d, J = 20.1 Hz, 3H), 2.26-2.13 (m, 4H), 2.15-2.00 (m, 1H), 1.91 (s, 1H), 1.72 (s, 1H). |
| 658 | 448.10 | 1.26 | |
| 659 | 454.50 | 1.71 | |
| 660 | 490.50 | 1.10 | |
| 661 | 480.50 | 1.69 | |
| 662 | 506.50 | 1.55 | 1H NMR (400 MHz, DMSO) δ 7.34-7.17 (m, 3H), 6.97 (d, J = 8.4 Hz, 1H), 6.49 (d, J = 4.6 Hz, 1H), 4.51-4.09 (m, 3H), 3.82 (s, 3H), 3.69-2.96 (m, 5H), 2.30 (s, 3H), 2.17 (s, 3H), 2.15-1.97 (m, 2H), 1.93-1.74 (m, 2H). |
| 663 | 450.30 | 1.49 | |
| 664 | 520.50 | 1.51 | |
| 665 | 458.24 | 2.37 | |
| 666 | 515.50 | 2.49 | 1H NMR (400 MHz, DMSO) δ 7.05 (d, J = 1.8 Hz, 1H), 7.01 (d, J = 8.1 Hz, 1H), 6.92 (dd, J = 8.1, 1.9 Hz, 1H), 6.60 (d, J = 3.7 Hz, 1H), 6.16 (d, J = 3.9 Hz, 1H), 4.50-4.08 (m, 1H), 3.77 (s, 3H), 3.70 (s, 2H), 3.63-2.76 (m, 3H), 2.09 (s, 1H), 1.92-1.57 (m, 4H), 1.29 (s, 9H), 1.09 (s, 6H). |
| 667 | 494.40 | 1.45 | 1H NMR (400 MHz, CDCl3) δ 7.15 (d, J = 7.7 Hz, 1H), 6.95-6.89 (m, 2H), 6.29 (s, 1H), 4.60 (s, 1H), 3.92 (t, J = 5.7 Hz, 2H), 3.86 (d, J = 11.1 Hz, 3H), 3.67 (s, 1H), 3.46 (s, 1H), 3.30 (s, 3H), 2.64 (q, J = 7.5 Hz, 2H), 2.42 (s, 3H), 2.08 (d, J = 57.9 Hz, 4H), 1.60 (s, 1H), 1.19 (t, J = 7.5 Hz, 3H). |
| 668 | 454.50 | 1.52 | |
| 669 | 539.50 | 1.35 | |
| 670 | 458.13 | 1.91 | |
| 671 | 569.20 | 1.76 | |
| 672 | 468.70 | 1.54 | |
| 673 | 447.30 | 2.07 | 1H NMR (400 MHz, DMSO) δ 7.51 (d, J = 2.1 Hz, 1H), 7.38 (dd, J = 8.5, 2.1 Hz, 1H), 7.20 (d, J = 8.7 Hz, 1H), 7.11 (d, J = 4.3 Hz, 1H), 6.19 (d, J = 4.2 Hz, 1H), 4.79-4.69 (m, 1H), 4.44-4.13 (m, 3H), 3.61-3.29 (m, 3H), 3.27-2.98 (m, 3H), 2.27 (s, 3H), 2.23-1.90 (m, 2H), 1.85-1.71 (m, 2H), 1.31 (d, J = 6.0 Hz, 6H), 1.05 (d, J = 6.8 Hz, 6H). |
| 674 | 472.50 | 1.56 | |
| 675 | 464.50 | 1.39 | |
| 676 | 532.50 | 1.73 | |
| 677 | 480.30 | 1.71 | |
| 678 | 432.18 | 1.94 | |
| 679 | 395.18 | 1.56 | |
| 680 | 514.70 | 1.42 | |
| 681 | 454.23 | 1.81 | |
| 682 | 486.30 | 1.40 | 1H NMR (400 MHz, DMSO) δ 7.48 (d, J = 8.6 Hz, 1H), 7.22-7.14 (m, 2H), 6.64 (d, J = 3.5 Hz, 1H), 6.30 (d, J = 4.0 Hz, 1H), 4.97 (s, 1H), 4.08-4.00 (m, 2H), 3.98-3.42 (m, 9H), 2.98-2.71 (m, 2H), 2.55 (s, 3H), 1.93-1.71 (m, 2H), 1.51 (s, 6H). |
| 683 | 494.20 | 4.87 | |
| 684 | 450.30 | 1.17 | |

TABLE 2-continued

| Cmpd. No. | LC/MS M + 1 | LC/RT min | NMR |
|---|---|---|---|
| 685 | 476.50 | 1.36 | 1H NMR (400 MHz, DMSO) δ 7.26 (dd, J = 4.5, 2.2 Hz, 1H), 7.02 (d, J = 1.5 Hz, 1H), 7.01-6.95 (m, 2H), 6.56 (d, J = 4.6 Hz, 1H), 4.33 (s, 1H), 4.10 (s, 2H), 4.01 (t, J = 6.7 Hz, 2H), 3.78 (s, 3H), 3.57 (s, 2H), 3.27 (s, 1H), 2.26 (s, 1H), 1.95-1.83 (m, 2H), 1.83-1.66 (m, 3H), 1.62 (q, J = 6.7 Hz, 2H), 1.08 (s, 6H), 0.93 (d, J = 6.6 Hz, 6H). |
| 686 | 536.40 | 1.88 | 1H NMR (400 MHz, CDCl3) δ 7.40 (d, J = 7.5 Hz, 1H), 7.03-6.95 (m, 2H), 6.49 (s, 1H), 4.73 (s, 2H), 4.64 (d, J = 10.9 Hz, 1H), 3.98 (t, J = 5.5 Hz, 2H), 3.95-3.82 (m, 5H), 3.60 (s, 1H), 3.47 (d, J = 11.9 Hz, 1H), 3.37-3.26 (m, 2H), 3.20 (d, J = 11.6 Hz, 1H), 2.58-2.31 (m, 5H), 2.08 (d, J = 13.6 Hz, 1H), 2.02-1.99 (m, 2H), 1.90 (d, J = 13.3 Hz, 1H), 1.62 (s, 1H). |
| 687 | 553.80 | 1.85 | 1H NMR (400 MHz, DMSO) δ 7.34 (d, J = 8.1 Hz, 2H), 7.27 (d, J = 8.1 Hz, 2H), 7.25-7.20 (m, 1H), 6.50 (d, J = 4.6 Hz, 1H), 4.49-4.29 (m, 2H), 4.24 (t, J = 5.7 Hz, 2H), 3.54-3.24 (m, 4H), 3.20-2.97 (m, 1H), 2.68 (s, 2H), 2.30 (s, 3H), 2.25-1.73 (m, 4H), 1.07 (s, 6H). |
| 688 | 478.50 | 1.38 | |
| 689 | 512.70 | 1.33 | 1H NMR (400 MHz, DMSO) δ 7.02-6.93 (m, 3H), 6.60 (d, J = 3.4 Hz, 1H), 6.20 (d, J = 3.9 Hz, 1H), 4.67-4.51 (m, 1H), 4.24-3.91 (m, 3H), 3.77 (s, 3H), 3.69-3.12 (m, 5H), 2.38-2.11 (m, 2H), 1.93-1.68 (m, 3H), 1.26 (d, J = 6.0 Hz, 6H), 0.64-0.49 (m, 4H). |
| 690 | 492.50 | 6.09 | |
| 691 | 425.30 | 0.91 | 1H NMR (400 MHz, CDCl3) δ 7.24-7.14 (m, 2H), 6.99 (t, J = 8.4 Hz, 1H), 6.53 (d, J = 3.8 Hz, 1H), 5.91 (d, J = 3.5 Hz, 1H), 4.59 (dt, J = 12.1, 6.1 Hz, 1H), 4.09 (d, J = 8.9 Hz, 1H), 3.78-3.17 (m, 5H), 2.28-1.86 (m, 2H), 1.63 (s, 3H), 1.38 (d, J = 6.1 Hz, 6H), 1.28 (d, J = 4.8 Hz, 3H), 0.78 (s, 1H). |
| 692 | 454.50 | 1.52 | |
| 693 | 514.50 | 1.53 | |
| 694 | 458.20 | 1.00 | |
| 695 | 496.70 | 1.58 | |
| 696 | 402.25 | 2.15 | 1H NMR (400 MHz, DMSO) δ 7.54 (d, J = 2.0 Hz, 1H), 7.43 (dd, J = 8.5, 2.1 Hz, 1H), 7.25-7.21 (m, 1H), 7.20 (d, J = 8.6 Hz, 1H), 6.49 (d, J = 4.6 Hz, 1H), 4.47-4.16 (m, 3H), 3.90 (s, 3H), 3.69-2.92 (m, 5H), 2.30 (s, 3H), 2.19-1.95 (m, 2H), 1.95-1.74 (m, 2H). |
| 697 | 470.50 | 1.47 | |
| 698 | 432.13 | 2.12 | |
| 699 | 454.28 | 2.12 | |
| 700 | 470.50 | 1.31 | |
| 701 | 480.50 | 1.19 | |
| 702 | 524.50 | 1.33 | |
| 703 | 428.16 | 1.66 | 1H NMR (400 MHz, DMSO) δ 7.27-7.19 (m, 2H), 7.05 (d, J = 4.2 Hz, 1H), 6.97 (d, J = 9.2 Hz, 1H), 6.16 (d, J = 4.2 Hz, 1H), 4.64 (hept, J = 5.9 Hz, 1H), 4.50-4.01 (m, 3H), 3.74-3.28 (m, 2H), 3.28-2.90 (m, 3H), 2.73 (q, J = 7.4 Hz, 2H), 2.27 (s, 3H), 2.14 (s, 3H), 2.12-1.95 (m, 2H), 1.85-1.63 (m, 2H), 1.29 (d, J = 6.0 Hz, 6H), 1.04 (t, J = 7.4 Hz, 3H). |
| 704 | 438.40 | 1.48 | 1H NMR (400 MHz, CDCl3) δ 7.26 (dd, J = 5.4, 1.8 Hz, 2H), 6.97 (d, J = 1.6 Hz, 1H), 6.92 (dd, J = 7.9, 1.6 Hz, 1H), 6.19 (d, J = 4.5 Hz, 1H), 4.64 (s, 1H), 4.34-4.04 (m, 2H), 3.88 (s, 3H), 3.77 (s, 1H), 3.57 (s, 1H), 3.27 (s, 1H), 2.01 (s, 1H), 1.93-1.62 (m, 3H), 1.37 (s, 9H), 1.18 (s, 6H), 0.98 (s, 1H). |
| 705 | 506.50 | 1.80 | |
| 706 | 516.30 | 2.02 | |
| 707 | 497.20 | 1.18 | 1H NMR (400 MHz, DMSO) δ 8.02 (s, 1H), 7.86 (d, J = 8.3 Hz, 2H), 7.67 (d, J = 8.3 Hz, 2H), 6.61 (d, J = 3.9 Hz, 1H), 6.21 (d, J = 3.9 Hz, 1H), 4.29-4.12 (m, 1H), 3.98 (t, J = 5.8 Hz, 2H), 3.50-3.17 (m, 5H), 2.43-2.09 (m, 3H), 1.99-1.68 (m, 3H), 0.65-0.35 (m, 8H). |
| 708 | 523.40 | 3.83 | |
| 709 | 466.50 | 1.22 | |
| 710 | 416.50 | 1.35 | |
| 711 | 482.70 | 1.35 | |
| 712 | 479.20 | 1.14 | 1H NMR (400 MHz, CDCl3) δ 7.27 (dd, J = 8.6, 2.3 Hz, 2H), 6.83 (d, J = 8.1 Hz, 1H), 6.48 (s, 1H), 4.60 (s, 1H), 3.98 (t, J = 5.7 Hz, 2H), 3.85 (s, 3H), 3.72 (dd, J = 13.8, 7.0 Hz, 2H), 3.30 (s, 5H), 2.42 (d, J = 14.8 Hz, 5H), 2.23 (s, 3H), 2.15-1.82 (m, 2H), 1.58 (s, 2H), 1.25 (dd, J = 8.8, 5.2 Hz, 4H). |

TABLE 2-continued

| Cmpd. No. | LC/MS M + 1 | LC/RT min | NMR |
|---|---|---|---|
| 713 | 456.40 | 1.59 | |
| 714 | 436.30 | 1.24 | |
| 715 | 436.30 | 1.09 | 1H NMR (400 MHz, DMSO) δ 7.83 (d, J = 8.4 Hz, 2H), 7.66 (d, J = 8.4 Hz, 2H), 7.55 (s, 1H), 6.58 (d, J = 3.2 Hz, 1H), 6.12 (d, J = 3.9 Hz, 1H), 4.36 (d, J = 12.8 Hz, 1H), 3.93 (t, J = 5.7 Hz, 2H), 3.46-3.33 (m, 2H), 3.31-3.24 (m, 2H), 3.19-3.05 (m, 1H), 2.44 (s, 3H), 2.27 (s, 3H), 2.18 (d, J = 12.9 Hz, 1H), 2.02 (d, J = 13.9 Hz, 1H), 1.87-1.70 (m, 2H). |
| 716 | 471.50 | 1.07 | |
| 717 | 500.20 | 1.28 | |
| 718 | 436.30 | 0.98 | 1H NMR (400 MHz, CDCl3) δ 7.02 (d, J = 1.8 Hz, 1H), 6.98 (dd, J = 8.2, 1.9 Hz, 1H), 6.88 (d, J = 8.2 Hz, 1H), 6.66 (d, J = 3.8 Hz, 1H), 6.15 (d, J = 3.9 Hz, 1H), 4.57 (dt, J = 12.1, 6.0 Hz, 1H), 4.40-4.30 (m, 1H), 4.19 (dd, J = 11.9, 3.8 Hz, 1H), 3.88 (s, 3H), 4.03-3.56 (m, 5H), 3.40 (s, 2H), 3.28 (dd, J = 13.5, 5.2 Hz, 1H), 2.37 (s, J = 20.5 Hz, 3H), 2.34 (s, 1H), 2.04 (s, 1H), 1.86 (s, 2H), 1.38 (d, J = 6.1 Hz, 6H). |
| 719 | 496.40 | 2.65 | |
| 720 | 440.50 | 1.36 | 1H NMR (400 MHz, DMSO) δ 7.34 (t, J = 8.2 Hz, 1H), 6.90-6.79 (m, 2H), 6.59 (d, J = 3.8 Hz, 1H), 6.09 (d, J = 3.6 Hz, 1H), 4.79-4.53 (m, 1H), 4.48-4.21 (m, 1H), 3.70 (s, 2H), 3.61-3.42 (m, 1H), 3.28-2.84 (m, 2H), 2.13 (s, 1H), 1.87-1.55 (m, 4H), 1.27 (d, J = 6.0 Hz, 6H), 1.11 (s, 3H), 1.06 (s, 3H). |
| 721 | 468.40 | 1.49 | H NMR (400.0 MHz, CDCl3) δ 7.02-6.97 (m, 2H), 6.87 (d, J = 8.2 Hz, 1H), 6.53 (s, 1H), 5.99 (s, 1H), 4.54 (qn, J = 6.1 Hz, 1H), 4.04 (s, 2H), 3.88 (s, 3H), 3.34 (s, 2H), 2.92 (d, J = 5.3 Hz, 4H), 2.40 (s, 3H), 2.14 (s, 2H), 1.82 (s, 2H) and 1.41-1.35 (m, 6H) ppm. |
| 722 | 516.50 | 1.28 | 1H NMR (400 MHz, DMSO) δ 7.28-7.19 (m, 2H), 7.01-6.93 (m, 1H), 6.62 (d, J = 3.6 Hz, 1H), 6.22 (d, J = 3.0 Hz, 1H), 4.64 (dt, J = 12.1, 6.1 Hz, 1H), 4.01 (s, 2H), 3.41 (d, J = 37.7 Hz, 11H), 3.14 (d, J = 20.8 Hz, 3H), 2.87 (s, 3H), 2.14 (s, 4H), 1.86 (s, 2H), 1.29 (d, J = 6.0 Hz, 6H). |
| 723 | 521.50 | 1.87 | 1H NMR (400 MHz, DMSO) δ 7.09-6.96 (m, 3H), 6.65 (d, J = 3.5 Hz, 1H), 6.33 (d, J = 3.3 Hz, 1H), 4.94-4.72 (m, 1H), 4.70-4.54 (m, 1H), 4.07-3.82 (m, 2H), 3.77 (s, 3H), 3.75-3.46 (m, 2H), 3.48-3.29 (m, 3H), 3.24-3.13 (m, 1H), 2.32 (s, 3H), 2.17-1.85 (m, 2H), 1.27 (d, J = 6.0 Hz, 6H). |
| 724 | 484.60 | 2.73 | |
| 725 | 501.50 | 1.47 | |
| 726 | 518.30 | 1.58 | |
| 727 | 480.50 | 4.03 | |
| 728 | 526.25 | 1.59 | |
| 729 | 466.12 | 2.80 | |
| 730 | 452.20 | 1.23 | |
| 731 | 433.70 | 0.92 | |
| 732 | 478.17 | 2.53 | |
| 733 | 490.20 | 1.00 | |
| 734 | 428.16 | 2.06 | |
| 735 | 478.20 | 1.03 | |
| 736 | 470.50 | 2.46 | |
| 737 | 476.50 | 0.98 | 1H NMR (400 MHz, CDCl3) δ 7.26-7.22 (m, 1H), 7.22-7.02 (m, 1H), 6.79-6.70 (m, 2H), 6.17 (s, 1H), 4.70 (d, J = 11.6 Hz, 1H), 4.30-4.07 (m, 2H), 3.81 (s, 3H), 3.56-3.45 (m, 1H), 3.45-3.34 (m, 1H), 3.31-3.15 (m, 1H), 2.44-2.23 (m, 3H), 2.02-1.93 (m, 1H), 1.89-1.71 (m, 2H), 1.71-1.60 (m, 1H), 1.21 (s, 3H), 1.13 (s, 3H), 0.96 (s, 1H). |
| 738 | 464.50 | 1.49 | |
| 739 | 596.50 | 1.71 | |
| 740 | 462.50 | 1.71 | 1H NMR (400 MHz, CDCl3) δ 7.06 (d, J = 1.8 Hz, 1H), 7.00 (dd, J = 8.2, 1.9 Hz, 1H), 6.88 (d, J = 8.3 Hz, 1H), 6.54 (d, J = 3.2 Hz, 1H), 6.11 (d, J = 4.0 Hz, 1H), 4.57 (dt, J = 12.2, 6.1 Hz, 1H), 4.18 (q, J = 7.1 Hz, 2H), 4.09-4.03 (m, 2H), 3.97-3.91 (m, 2H), 3.88 (s, 3H), 3.85-3.71 (m, 3H), 2.97 (s, 2H), 1.91-1.82 (m, 2H), 1.77-1.66 (m, 1H), 1.38 (d, J = 6.1 Hz, 6H), 1.32 (t, J = 7.1 Hz, 3H). |
| 741 | 524.40 | 1.96 | |
| 742 | 491.50 | 1.56 | 1H NMR (400 MHz, DMSO) δ 7.52 (d, J = 8.3 Hz, 2H), 7.36 (d, J = 8.3 Hz, 2H), 6.60-6.53 (m, 1H), 6.19 (d, J = 4.0 Hz, 1H), 5.07 (s, 1H), 4.44-4.24 (m, 1H), 3.97 (t, |

TABLE 2-continued

| Cmpd. No. | LC/MS M + 1 | LC/RT min | NMR |
|---|---|---|---|
| | | | J = 5.7 Hz, 2H), 3.52-3.22 (m, 4H), 3.22-2.98 (m, 1H), 2.28 (s, 3H), 2.23-1.95 (m, 2H), 1.85-1.67 (m, 2H), 1.43 (s, 6H). |
| 743 | 486.50 | 1.14 | |
| 744 | 454.70 | 1.36 | |
| 745 | 466.50 | 3.47 | 1H NMR (400 MHz, DMSO) δ 7.48 (d, J = 8.5 Hz, 1H), 7.42 (d, J = 8.5 Hz, 1H), 7.26-7.14 (m, 1H), 6.47 (d, J = 4.6 Hz, 1H), 4.47-4.28 (m, 1H), 4.24 (t, J = 5.9 Hz, 2H), 3.86 (s, 3H), 3.81-3.67 (m, 1H), 3.42-3.35 (m, 1H), 3.35-3.29 (m, 2H), 3.21-2.99 (m, 1H), 2.37 (s, 3H), 2.31 (s, 3H), 2.24-2.12 (m, 1H), 2.12-1.98 (m, 1H), 1.98-1.70 (m, 2H). |
| 746 | 451.30 | 1.28 | |
| 747 | 484.50 | 1.54 | 1H NMR (400 MHz, DMSO) δ 7.87-7.60 (m, 1H), 7.60-7.33 (m, 1H), 7.33-7.06 (m, 2H), 6.54 (d, J = 4.8 Hz, 1H), 5.35 (s, 1H), 4.30-4.06 (m, 1H), 3.62-3.03 (m, 5H), 2.46 (s, 3H), 2.24-1.77 (m, 4H), 1.62 (s, 6H), 1.49 (s, 6H). |
| 748 | 510.70 | 1.65 | |
| 749 | 468.30 | 1.91 | |
| 750 | 464.30 | 1.11 | 1H NMR (400 MHz, DMSO) δ 7.89 (d, J = 8.0 Hz, 1H), 7.59-7.45 (m, 2H), 6.58 (d, J = 3.7 Hz, 1H), 6.12 (d, J = 3.9 Hz, 1H), 4.45-4.27 (m, 1H), 3.93 (t, J = 5.8 Hz, 2H), 3.57-3.43 (m, 1H), 3.43-3.01 (m, 5H), 2.65 (s, 3H), 2.27 (s, 3H), 2.23-1.65 (m, 4H), 1.17 (d, J = 6.8 Hz, 6H). |
| 751 | 454.30 | 1.47 | 1H NMR (400 MHz, CD$_3$CN) d 7.12 (d, J = 1.8 Hz, 1H), 7.07 (d, J = 8.0 Hz, 1H), 7.01 (dd, J = 8.0, 1.8 Hz, 1H), 6.60 (d, J = 3.4 Hz, 1H), 6.07 (d, J = 3.7 Hz, 1H), 4.42 (s, 1H), 4.12 (dd, J = 1.6, 0.9 Hz, 1H), 4.01 (t, J = 6.0 Hz, 2H), 3.85 (s, 3H), 3.79 (d, J = 1.7 Hz, 1H), 3.67-3.40 (m, 2H), 3.36 (t, J = 5.6 Hz, 2H), 3.20 (s, 1H), 2.36 (s, 3H), 2.18 (s, 2H), 2.00 (d, J = 0.7 Hz, 3H), 1.83 (s, 2H). |
| 752 | 582.20 | 1.66 | |

Assays for Detecting and Measuring NaV Inhibition Properties of Compound

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO
Compound Plates: 384-well round bottom plate, e.g. Corning 384-well Polypropylene Round Bottom #3656
Cell Plates: 384-well tissue culture treated plate, e.g. Greiner #781091-1B
10 mM DiSBAC$_6$(3) (Aurora #00-100-010) in dry DMSO
10 mM CC2-DMPE (Aurora #00-100-008) in dry DMSO
200 mM ABSC1 in H$_2$O
Bath 1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).
Hexyl Dye Solution: Bath 1 Buffer+0.5% β-cyclodextrin (make this prior to use, Sigma #C4767), 8 µM CC2-DMPE+ 2.5 µM DiSBAC$_6$(3). To make the solution Add volume of 10% Pluronic F127 stock equal to volumes of CC2-DMPE+ DiSBAC$_6$(3). The order of preparation is first mix Pluronic and CC2-DMPE, then add DiSBAC$_6$(3) while vortexing, then add Bath 1+β-Cyclodextrin.

Assay Protocol

1) Pre-spot compounds (in neat DMSO) into compound plates. Vehicle control (neat DMSO), the positive control (20 mM DMSO stock tetracaine, 125 µM final in assay) and test compounds are added to each well at 160× desired final concentration in neat DMSO. Final compound plate volume will be 80 µL (80-fold intermediate dilution from 1 µL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 μL of Bath 1 Solution, maintaining 25 μL residual volume in each well.

4) Dispense 25 μL per well of Hexyl Dye Solution into cell plates. Incubate for 20-35 minutes at room temp or ambient conditions.

5) Dispense 80 μL per well of Bath 1 into compound plates. Acid Yellow-17 (1 mM) is added and Potassium Chloride can be altered from 4.5 to 20 mM depending on the NaV subtype and assay sensitivity.

6) Wash cell plates three times with 100 μL per well of Bath1, leaving 25 μL of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - background_{460\,nm})}{(intensity_{580\,nm} - background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks Assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath 1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-One Binding Assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry*, 2007, 46, 14693-14703, the entire contents of which are incorporated herein by reference.

The exemplified compounds of Table 1 herein are active against one or more sodium channels as measured using the assays described herein above as presented in Table 3.

TABLE 3

| IC50: +++ <= 2.0 μM< ++ <= 5.0 μM < + |  |
|---|---|
| Cmpd. No. | Binned Activity Data |
| 1 | ++ |
| 2 | +++ |
| 3 | + |
| 4 | + |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | ++ |
| 17 | +++ |
| 18 | +++ |
| 19 | +++ |
| 20 | +++ |
| 21 | + |
| 22 | + |
| 23 | +++ |
| 24 | ++ |
| 25 | + |

TABLE 3-continued

IC50: +++ <= 2.0 μM< ++ <= 5.0 μM < +

| Cmpd. No. | Binned Activity Data |
|---|---|
| 26 | ++ |
| 27 | +++ |
| 28 | +++ |
| 29 | +++ |
| 30 | + |
| 31 | ++ |
| 32 | +++ |
| 33 | +++ |
| 34 | +++ |
| 35 | +++ |
| 36 | + |
| 37 | +++ |
| 38 | ++ |
| 39 | +++ |
| 40 | +++ |
| 41 | +++ |
| 42 | + |
| 43 | + |
| 44 | ++ |
| 45 | +++ |
| 46 | +++ |
| 47 | +++ |
| 48 | +++ |
| 49 | +++ |
| 50 | +++ |
| 51 | +++ |
| 52 | + |
| 53 | +++ |
| 54 | ++ |
| 55 | +++ |
| 56 | +++ |
| 57 | +++ |
| 58 | +++ |
| 59 | +++ |
| 60 | + |
| 61 | ++ |
| 62 | +++ |
| 63 | + |
| 64 | +++ |
| 65 | +++ |
| 66 | +++ |
| 67 | + |
| 68 | ++ |
| 69 | +++ |
| 70 | +++ |
| 71 | +++ |
| 72 | +++ |
| 73 | ++ |
| 74 | ++ |
| 75 | +++ |
| 76 | + |
| 77 | +++ |
| 78 | ++ |
| 79 | + |
| 80 | +++ |
| 81 | +++ |
| 82 | +++ |
| 83 | +++ |
| 84 | +++ |
| 85 | +++ |
| 86 | + |
| 87 | +++ |
| 88 | ++ |
| 89 | +++ |
| 90 | +++ |
| 91 | +++ |
| 92 | +++ |
| 93 | +++ |
| 94 | ++ |
| 95 | +++ |
| 96 | +++ |
| 97 | +++ |
| 98 | +++ |
| 99 | ++ |
| 100 | +++ |
| 101 | +++ |
| 102 | +++ |
| 103 | +++ |
| 104 | + |
| 105 | +++ |
| 106 | +++ |
| 107 | +++ |
| 108 | ++ |
| 109 | + |
| 110 | +++ |
| 111 | + |
| 112 | +++ |
| 113 | +++ |
| 114 | +++ |
| 115 | +++ |
| 116 | + |
| 117 | +++ |
| 118 | +++ |
| 119 | +++ |
| 120 | ++ |
| 121 | + |
| 122 | +++ |
| 123 | +++ |
| 124 | +++ |
| 125 | ++ |
| 126 | ++ |
| 127 | +++ |
| 128 | +++ |
| 129 | +++ |
| 130 | ++ |
| 131 | +++ |
| 132 | +++ |
| 133 | +++ |
| 134 | +++ |
| 135 | +++ |
| 136 | +++ |
| 137 | +++ |
| 138 | +++ |
| 139 | + |
| 140 | +++ |
| 141 | +++ |
| 142 | +++ |
| 143 | +++ |
| 144 | +++ |
| 145 | + |
| 146 | +++ |
| 147 | ++ |
| 148 | +++ |
| 149 | +++ |
| 150 | +++ |
| 151 | +++ |
| 152 | +++ |
| 153 | + |
| 154 | ++ |
| 155 | + |
| 156 | +++ |
| 157 | + |
| 158 | +++ |
| 159 | ++ |
| 160 | +++ |
| 161 | +++ |
| 162 | +++ |
| 163 | + |
| 164 | +++ |
| 165 | +++ |
| 166 | + |
| 167 | +++ |
| 168 | +++ |
| 169 | +++ |
| 170 | + |
| 171 | +++ |
| 172 | +++ |
| 173 | +++ |
| 174 | +++ |
| 175 | +++ |

TABLE 3-continued

IC50: +++ <= 2.0 μM< ++ <= 5.0 μM < +

| Cmpd. No. | Binned Activity Data |
|---|---|
| 176 | ++ |
| 177 | + |
| 178 | + |
| 179 | ++ |
| 180 | +++ |
| 181 | +++ |
| 182 | +++ |
| 183 | +++ |
| 184 | ++ |
| 185 | +++ |
| 186 | +++ |
| 187 | +++ |
| 188 | +++ |
| 189 | +++ |
| 190 | +++ |
| 191 | +++ |
| 192 | + |
| 193 | +++ |
| 194 | +++ |
| 195 | + |
| 196 | + |
| 197 | +++ |
| 198 | +++ |
| 199 | +++ |
| 200 | +++ |
| 201 | +++ |
| 202 | ++ |
| 203 | +++ |
| 204 | + |
| 205 | + |
| 206 | +++ |
| 207 | +++ |
| 208 | +++ |
| 209 | +++ |
| 210 | ++ |
| 211 | +++ |
| 212 | +++ |
| 213 | +++ |
| 214 | +++ |
| 215 | +++ |
| 216 | +++ |
| 217 | +++ |
| 218 | + |
| 219 | +++ |
| 220 | ++ |
| 221 | + |
| 222 | +++ |
| 223 | ++ |
| 224 | + |
| 225 | + |
| 226 | +++ |
| 227 | + |
| 228 | +++ |
| 229 | ++ |
| 230 | +++ |
| 231 | + |
| 232 | +++ |
| 233 | +++ |
| 234 | + |
| 235 | +++ |
| 236 | +++ |
| 237 | +++ |
| 238 | +++ |
| 239 | + |
| 240 | +++ |
| 241 | + |
| 242 | +++ |
| 243 | +++ |
| 244 | +++ |
| 245 | +++ |
| 246 | + |
| 247 | +++ |
| 248 | +++ |
| 249 | +++ |
| 250 | +++ |

TABLE 3-continued

IC50: +++ <= 2.0 μM< ++ <= 5.0 μM < +

| Cmpd. No. | Binned Activity Data |
|---|---|
| 251 | +++ |
| 252 | + |
| 253 | +++ |
| 254 | +++ |
| 255 | +++ |
| 256 | + |
| 257 | +++ |
| 258 | +++ |
| 259 | +++ |
| 260 | ++ |
| 261 | +++ |
| 262 | +++ |
| 263 | +++ |
| 264 | +++ |
| 265 | +++ |
| 266 | +++ |
| 267 | ++ |
| 268 | + |
| 269 | +++ |
| 270 | +++ |
| 271 | + |
| 272 | ++ |
| 273 | ++ |
| 274 | +++ |
| 275 | ++ |
| 276 | +++ |
| 277 | +++ |
| 278 | + |
| 279 | +++ |
| 280 | +++ |
| 281 | +++ |
| 282 | +++ |
| 283 | ++ |
| 284 | +++ |
| 285 | ++ |
| 286 | +++ |
| 287 | ++ |
| 288 | +++ |
| 289 | +++ |
| 290 | +++ |
| 291 | +++ |
| 292 | + |
| 293 | + |
| 294 | +++ |
| 295 | + |
| 296 | +++ |
| 297 | +++ |
| 298 | +++ |
| 299 | +++ |
| 300 | +++ |
| 301 | + |
| 302 | ++ |
| 303 | + |
| 304 | +++ |
| 305 | +++ |
| 306 | ++ |
| 307 | +++ |
| 308 | +++ |
| 309 | + |
| 310 | + |
| 311 | +++ |
| 312 | +++ |
| 313 | +++ |
| 314 | +++ |
| 315 | +++ |
| 316 | +++ |
| 317 | ++ |
| 318 | +++ |
| 319 | + |
| 320 | +++ |
| 321 | + |
| 322 | +++ |
| 323 | + |
| 324 | +++ |
| 325 | +++ |

TABLE 3-continued

IC50: +++ <= 2.0 μM < ++ <= 5.0 μM < +

| Cmpd. No. | Binned Activity Data |
|---|---|
| 326 | +++ |
| 327 | +++ |
| 328 | + |
| 329 | ++ |
| 330 | ++ |
| 331 | + |
| 332 | +++ |
| 333 | +++ |
| 334 | + |
| 335 | +++ |
| 336 | +++ |
| 337 | +++ |
| 338 | +++ |
| 339 | +++ |
| 340 | +++ |
| 341 | +++ |
| 342 | + |
| 343 | +++ |
| 344 | ++ |
| 345 | + |
| 346 | +++ |
| 347 | +++ |
| 348 | +++ |
| 349 | +++ |
| 350 | +++ |
| 351 | + |
| 352 | ++ |
| 353 | +++ |
| 354 | +++ |
| 355 | +++ |
| 356 | +++ |
| 357 | +++ |
| 358 | ++ |
| 359 | +++ |
| 360 | +++ |
| 361 | +++ |
| 362 | + |
| 363 | +++ |
| 364 | + |
| 365 | +++ |
| 366 | +++ |
| 367 | +++ |
| 368 | +++ |
| 369 | +++ |
| 370 | +++ |
| 371 | +++ |
| 372 | +++ |
| 373 | +++ |
| 374 | + |
| 375 | +++ |
| 376 | ++ |
| 377 | +++ |
| 378 | +++ |
| 379 | +++ |
| 380 | +++ |
| 381 | +++ |
| 382 | ++ |
| 383 | ++ |
| 384 | +++ |
| 385 | +++ |
| 386 | +++ |
| 387 | +++ |
| 388 | + |
| 389 | +++ |
| 390 | +++ |
| 391 | + |
| 392 | ++ |
| 393 | + |
| 394 | ++ |
| 395 | +++ |
| 396 | +++ |
| 397 | +++ |
| 398 | +++ |
| 399 | ++ |
| 400 | + |

TABLE 3-continued

IC50: +++ <= 2.0 μM < ++ <= 5.0 μM < +

| Cmpd. No. | Binned Activity Data |
|---|---|
| 401 | +++ |
| 402 | ++ |
| 403 | + |
| 404 | +++ |
| 405 | +++ |
| 406 | ++ |
| 407 | ++ |
| 408 | +++ |
| 409 | +++ |
| 410 | +++ |
| 411 | +++ |
| 412 | +++ |
| 413 | +++ |
| 414 | ++ |
| 415 | +++ |
| 416 | + |
| 417 | + |
| 418 | +++ |
| 419 | +++ |
| 420 | +++ |
| 421 | + |
| 422 | +++ |
| 423 | +++ |
| 424 | +++ |
| 425 | + |
| 426 | +++ |
| 427 | +++ |
| 428 | +++ |
| 429 | ++ |
| 430 | + |
| 431 | ++ |
| 432 | ++ |
| 433 | +++ |
| 434 | + |
| 435 | ++ |
| 436 | +++ |
| 437 | +++ |
| 438 | +++ |
| 439 | +++ |
| 440 | + |
| 441 | +++ |
| 442 | +++ |
| 443 | +++ |
| 444 | +++ |
| 445 | +++ |
| 446 | ++ |
| 447 | + |
| 448 | +++ |
| 449 | +++ |
| 450 | +++ |
| 451 | + |
| 452 | ++ |
| 453 | ++ |
| 454 | + |
| 455 | +++ |
| 456 | ++ |
| 457 | + |
| 458 | ++ |
| 459 | +++ |
| 460 | +++ |
| 461 | +++ |
| 462 | +++ |
| 463 | +++ |
| 464 | +++ |
| 465 | + |
| 466 | +++ |
| 467 | +++ |
| 468 | +++ |
| 469 | ++ |
| 470 | +++ |
| 471 | +++ |
| 472 | + |
| 473 | + |
| 474 | ++ |
| 475 | +++ |

TABLE 3-continued

IC50: +++ <= 2.0 μM< ++ <= 5.0 μM < +

| Cmpd. No. | Binned Activity Data |
|---|---|
| 476 | +++ |
| 477 | +++ |
| 478 | + |
| 479 | ++ |
| 480 | +++ |
| 481 | +++ |
| 482 | ++ |
| 483 | +++ |
| 484 | +++ |
| 485 | +++ |
| 486 | +++ |
| 487 | +++ |
| 488 | +++ |
| 489 | +++ |
| 490 | +++ |
| 491 | +++ |
| 492 | +++ |
| 493 | +++ |
| 494 | +++ |
| 495 | +++ |
| 496 | ++ |
| 497 | + |
| 498 | +++ |
| 499 | +++ |
| 500 | +++ |
| 501 | +++ |
| 502 | + |
| 503 | +++ |
| 504 | + |
| 505 | +++ |
| 506 | ++ |
| 507 | + |
| 508 | +++ |
| 509 | +++ |
| 510 | +++ |
| 511 | + |
| 512 | ++ |
| 513 | +++ |
| 514 | + |
| 515 | + |
| 516 | +++ |
| 517 | +++ |
| 518 | +++ |
| 519 | + |
| 520 | +++ |
| 521 | +++ |
| 522 | +++ |
| 523 | +++ |
| 524 | +++ |
| 525 | +++ |
| 526 | +++ |
| 527 | + |
| 528 | +++ |
| 529 | + |
| 530 | +++ |
| 531 | +++ |
| 532 | + |
| 533 | +++ |
| 534 | + |
| 535 | + |
| 536 | ++ |
| 537 | +++ |
| 538 | +++ |
| 539 | + |
| 540 | + |
| 541 | +++ |
| 542 | + |
| 543 | +++ |
| 544 | +++ |
| 545 | ++ |
| 546 | +++ |
| 547 | + |
| 548 | +++ |
| 549 | +++ |
| 550 | +++ |

TABLE 3-continued

IC50: +++ <= 2.0 μM< ++ <= 5.0 μM < +

| Cmpd. No. | Binned Activity Data |
|---|---|
| 551 | +++ |
| 552 | +++ |
| 553 | +++ |
| 554 | +++ |
| 555 | +++ |
| 556 | +++ |
| 557 | +++ |
| 558 | + |
| 559 | +++ |
| 560 | +++ |
| 561 | +++ |
| 562 | +++ |
| 563 | +++ |
| 564 | +++ |
| 565 | ++ |
| 566 | +++ |
| 567 | +++ |
| 568 | +++ |
| 569 | +++ |
| 570 | +++ |
| 571 | ++ |
| 572 | +++ |
| 573 | +++ |
| 574 | +++ |
| 575 | +++ |
| 576 | +++ |
| 577 | + |
| 578 | ++ |
| 579 | +++ |
| 580 | +++ |
| 581 | ++ |
| 582 | +++ |
| 583 | +++ |
| 584 | +++ |
| 585 | +++ |
| 586 | ++ |
| 587 | +++ |
| 588 | + |
| 589 | +++ |
| 590 | ++ |
| 591 | +++ |
| 592 | +++ |
| 593 | +++ |
| 594 | + |
| 595 | +++ |
| 596 | + |
| 597 | + |
| 598 | +++ |
| 599 | +++ |
| 600 | +++ |
| 601 | +++ |
| 602 | +++ |
| 603 | + |
| 604 | +++ |
| 605 | + |
| 606 | + |
| 607 | ++ |
| 608 | +++ |
| 609 | ++ |
| 610 | +++ |
| 611 | +++ |
| 612 | +++ |
| 613 | + |
| 614 | + |
| 615 | + |
| 616 | +++ |
| 617 | +++ |
| 618 | + |
| 619 | +++ |
| 620 | ++ |
| 621 | +++ |
| 622 | ++ |
| 623 | +++ |
| 624 | ++ |
| 625 | + |

TABLE 3-continued

IC50: +++ <= 2.0 µM< ++ <= 5.0 µM < +

| Cmpd. No. | Binned Activity Data |
|---|---|
| 626 | +++ |
| 627 | +++ |
| 628 | +++ |
| 629 | +++ |
| 630 | +++ |
| 631 | + |
| 632 | +++ |
| 633 | + |
| 634 | + |
| 635 | ++ |
| 636 | +++ |
| 637 | ++ |
| 638 | +++ |
| 639 | +++ |
| 640 | ++ |
| 641 | +++ |
| 642 | +++ |
| 643 | +++ |
| 644 | +++ |
| 645 | +++ |
| 646 | +++ |
| 647 | +++ |
| 648 | +++ |
| 649 | +++ |
| 650 | +++ |
| 651 | +++ |
| 652 | + |
| 653 | ++ |
| 654 | +++ |
| 655 | +++ |
| 656 | +++ |
| 657 | +++ |
| 658 | +++ |
| 659 | + |
| 660 | +++ |
| 661 | +++ |
| 662 | +++ |
| 663 | +++ |
| 664 | +++ |
| 665 | +++ |
| 666 | +++ |
| 667 | +++ |
| 668 | +++ |
| 669 | +++ |
| 670 | + |
| 671 | +++ |
| 672 | +++ |
| 673 | +++ |
| 674 | +++ |
| 675 | +++ |
| 676 | +++ |
| 677 | + |
| 678 | ++ |
| 679 | ++ |
| 680 | +++ |
| 681 | ++ |
| 682 | + |
| 683 | +++ |
| 684 | + |
| 685 | +++ |
| 686 | +++ |
| 687 | +++ |
| 688 | +++ |
| 689 | + |
| 690 | +++ |
| 691 | +++ |
| 692 | +++ |
| 693 | +++ |
| 694 | ++ |
| 695 | +++ |
| 696 | + |
| 697 | +++ |
| 698 | ++ |
| 699 | +++ |
| 700 | +++ |

TABLE 3-continued

IC50: +++ <= 2.0 µM< ++ <= 5.0 µM < +

| Cmpd. No. | Binned Activity Data |
|---|---|
| 701 | +++ |
| 702 | +++ |
| 703 | + |
| 704 | +++ |
| 705 | +++ |
| 706 | +++ |
| 707 | +++ |
| 708 | +++ |
| 709 | +++ |
| 710 | +++ |
| 711 | +++ |
| 712 | +++ |
| 713 | ++ |
| 714 | + |
| 715 | +++ |
| 716 | +++ |
| 717 | +++ |
| 718 | ++ |
| 719 | ++ |
| 720 | + |
| 721 | +++ |
| 722 | +++ |
| 723 | +++ |
| 724 | +++ |
| 725 | + |
| 726 | +++ |
| 727 | +++ |
| 728 | +++ |
| 729 | +++ |
| 730 | +++ |
| 731 | ++ |
| 732 | +++ |
| 733 | +++ |
| 734 | + |
| 735 | +++ |
| 736 | +++ |
| 737 | +++ |
| 738 | +++ |
| 739 | + |
| 740 | +++ |
| 741 | +++ |
| 742 | ++ |
| 743 | +++ |
| 744 | +++ |
| 745 | +++ |
| 746 | +++ |
| 747 | +++ |
| 748 | + |
| 749 | ++ |
| 750 | + |
| 751 | +++ |
| 752 | +++ |

Many modifications and variations of the embodiments described herein may be made without departing from the scope, as is apparent to those skilled in the art. The specific embodiments described herein are offered by way of example only.

We claim:
1. A compound of formula I:

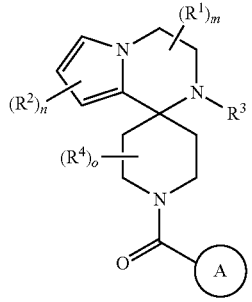

or a pharmaceutically acceptable salt thereof,
wherein, independently for each occurrence:
- $R^1$ is H, C1-C8 alkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, heterocycloalkyl, or a straight chain, branched, or cyclic (C3-C8)-$R^9$ wherein up to two $CH_2$ units may be replaced with O, CO, S, SO, $SO_2$ or $NR^8$, or two $R^1$ taken together form an oxo group;
- $R^2$ is H, C1-C8 alkyl, halo, C1-C8 haloalkyl, CN, OH, $SO_2R^8$, $SR^8$, $SOR^8$, $COR^8$, $CO_2R^8$, $CON(R^8)_2$, $SO_2N(R^8)_2$, $CF_3$, $CHF_2$, or a straight chain, branched, or cyclic (C3-C8)-$R^9$ wherein up to two $CH_2$ units may be replaced with O, CO, S, SO, $SO_2$, $CF_2$, or $NR^8$;
- $R^3$ is H, C1-C8 alkyl, C3-C8 cycloalkyl, $CO_2R^8$, $COR^8$, COH, $CON(R^8)_2$, $CF_3$, $CH_2CF_3$, $CH_2CHF_2$, or a straight chain, branched, or cyclic (C3-C8)-$R^9$ wherein up to two $CH_2$ units may be replaced with O, CO, S, SO, $SO_2$ or $NR^8$;
- $R^4$ is H, C1-C8 alkyl, halo, C3-C8 cycloalkyl, wherein up to two $CH_2$ units may be replaced by O, CO, S, SO, $SO_2$, or $NR^8$, or 2 $R^4$ taken together form a fused 3 to 7 membered cycloalkyl ring;
- $R^8$ is H, C1-C8 alkyl, $CF_3$, C3-C8 cycloalkyl, fluoroalkyl, aryl, heteroaryl, or a straight chain, branched, or cyclic (C3-C8)-$R^9$ wherein up to two $CH_2$ units may be replaced with O, CO, S, SO, $SO_2$ or NR, or 2 $R^8$ taken together with the atoms to which they are attached form a ring;
- $R^9$ is H, $CF_3$, $CO_2R$, OH, aryl, heteroaryl, C3-C8 cycloalkyl, heterocycloalkyl, $N(R)_2$, NRCOR, $CON(R)_2$, CN, halo, or $SO_2R$;
- R is H, C1-C8 alkyl, aryl, heteroaryl, C3-C8 cycloalkyl, or heterocycloalkyl;
- A is an aryl optionally substituted with one or more of C1-C8 alkyl, C3-C8 cycloalkyl, C1-C8 alkoxy, C3-C8 cycloalkoxy, halo, CN, OH, $OR^8$, $N(R^8)_2$, $NR^8SO_2R^8$, $OSO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$(R^9)_p$ wherein p is 1 or 2 and wherein up to three $CH_2$ units may be replaced with O, CO, S, SO, $SO_2$, or $NR^8$;
- or wherein two adjacent substituents on A together with the carbons to which they are attached form a ring comprising up to 2 heteroatoms;
- m is 0, 1, 2, 3, or 4;
- n is 0, 1, 2, or 3; and
- o is 0, 1, 2, 3, or 4.

2. The compound of claim 1, wherein A is

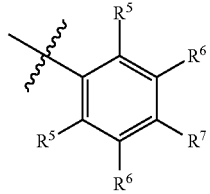

wherein:
- $R^5$ is H, C1-C8 alkyl, C3-C8 cycloalkyl, C1-C8 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$R^9$ wherein up to three $CH_2$ units may be replaced with O, CO, S, SO, $SO_2$, or $NR^8$;
- $R^6$ is H, C1-C8 alkyl, C3-C8 cycloalkyl, C1-C8 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$R^9$ wherein up to three $CH_2$ units may be replaced with O, CO, S, SO, $SO_2$, or $NR^8$;
- $R^7$ is H, C1-C8 alkyl, C3-C8 cycloalkyl, C1-C8 alkoxy, halo, CN, OH, $OR^8$, $N(R^8)_2$, $NR^8SO_2R^8$, $SO_2R^8$, $OSO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$(R^9)_p$, wherein p is 1 or 2 and wherein up to three $CH_2$ units may be replaced with O, CO, S, SO, $SO_2$, or $NR^8$; or
- two occurrences of $R^5$ and $R^6$, or $R^6$ and $R^7$ are both C1-C8 alkyl and together with the carbons to which they are attached form an optionally substituted ring comprising up to 2 heteroatoms.

3. The compound of claim 2, wherein $R^5$ is H, C1-C8 alkyl, C1-C8 alkoxy, halo, $OCF_3$, $OCHF_2$, $R^9$, or a straight chain, branched, or cyclic (C3-C8)-$R^9$ wherein up to three $CH_2$ units may be replaced with O, CO, S, SO, $SO_2$, or $NR^7$.

4. The compound of claim 2, wherein $R^5$ is H, $CH_3$, $OCH_3$, $OCF_3$, OPh, Ph, $OCHF_2$, or F.

5. The compound of claim 2, wherein $R^6$ is H, C1-C8 alkyl, C1-C8 alkoxy, halo, $R^9$, or a straight chain, branched, or cyclic (C3-C8)-$R^9$ wherein up to three $CH_2$ units may be replaced with O, CO, S, SO, $SO_2$, or $NR^8$.

6. The compound of claim 2, wherein $R^6$ is H, $CH_3$, $OCH_3$, $OCH_2CH_3$, $OCH_2CH_2CH_3$, $OCH(CH_3)_2$, $CF_3$, CN, Ph, $SO_2CH_3$, OH, $CH(CH_3)_2$, $OCH_2CH_2CH_2CH_3$, F, Cl, or $CH_2OH$.

7. The compound of claim 2, wherein $R^7$ is H, C1-C8 alkyl, C1-C8 alkoxy, $SO_2R^8$, $OSO_2R^8$, $SO_2N(R^8)_2$, $R^9$, $OCHF_2$, $OCF_3$, or a straight chain, branched, or cyclic (C3-C8)-$(R^9)_p$, wherein p is 1 or 2 and wherein up to three $CH_2$ units may be replaced with O, CO, S, SO, $SO_2$, or $NR^8$.

8. The compound of claim 2, wherein $R^7$ is H, $CH_3$, $CH_2CH_3$, tBu, Cl, F, OH, C(=$CH_2$)$CH_3$, OC(=$CH_2$)$CH_3$, $OCH_3$, $OCH_2CH_2CH_3$, $CH_2OH$, $OCH_2OH$, $OCH_2CH_2CH_2OH$, OtBu, $OCH(CH_3)(CH_2CH_3)$, $OCH_2C(CH_3)_2OH$, $C(CH_3)_2OH$, $CH_2C(CH_3)_2OH$, CH(OH)CH (CH₃)₂, C(CH₃)₂CH₂OH, OCH₂CH₂CH(CH₃)₂, OCH₂CH₂CH₃, OCH(CH₃)₂, OCH₂CH₂OCH₃,

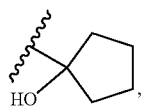 [SMILES: *C1(O)CCCC1],

SO₂CH₃, SO₂tBu, SO₂CH₂CH₃, SO₂CH₂CH(CH₃)₂, SO₂CH(CH₃)₂,

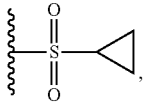,

SO₂NH(CH₃), SO₂NH(CH(CH₃)₂), SO₂NH(CH₂CH₃), SO₂NH(CH(CH₃)₂), SO₂N(CH₃)₂,

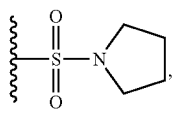,

OPh, Ph,

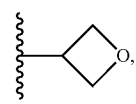

OCH₂CH₂OCH₃, CH(CH₃)₂, SO₂N(CH₂CH₂CH₃)₂, CH₂CH₂CH₂CH₃, CH₂CH₂CH₃, OCH₂CH₂CH₃, CH₂OPh,

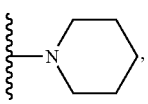,

OCH₂Ph, CH₂CH₂CH₂CH₂CH₃, OCH₂CH₃, OCH₂CH(CH₃)₂, CH₂Ph,

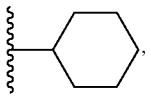,

CCCH₂OCH₃, SO₂CHF₂, OCF₃,

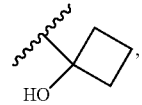,

OCHF₂,

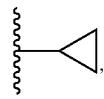,

CH₂CH(CH₃)₂, OCH₂tBu,

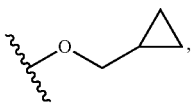 [SMILES: *OCC1CC1],

OCH₂CF₃,

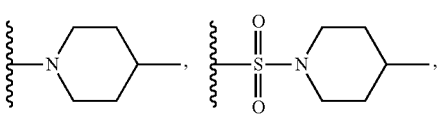,

CH₂OCH₂CH₂CF₃, CH₂OCH₂CF₃, SO₂CF₃, C(CH₃)₂CH₂CH₃, C(CH₂CH₃)₃, CH(OCH₂CF₃)₂,

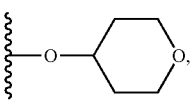,

CF₃, OCH₂C(CH₃)₂F,

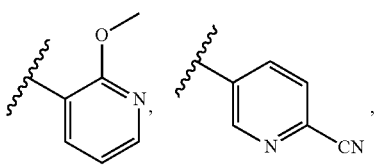

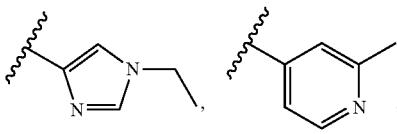

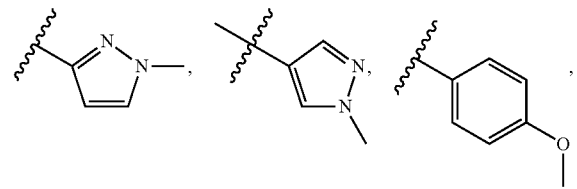

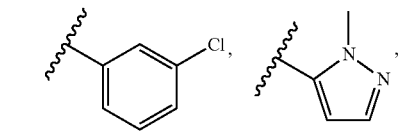

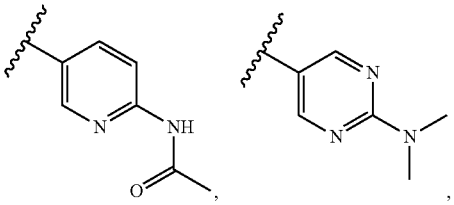

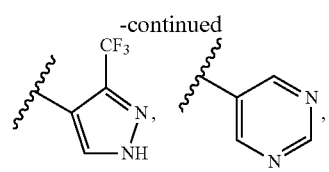
CH(OH)CH$_2$OCH$_2$CF$_3$, CH(OCH$_2$CF$_3$)CH$_2$OH, OSO$_2$CF$_3$,
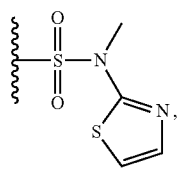
or OCH$_2$CH$_2$OCF$_3$.
9. The compound of claim 2, wherein
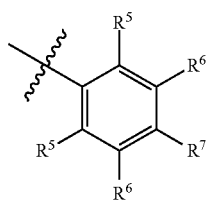
is:
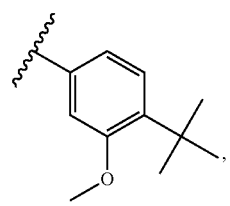 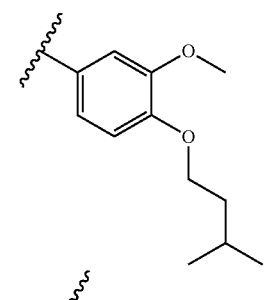
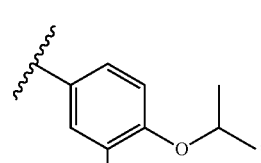 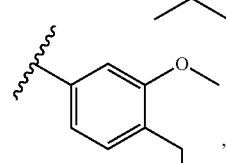
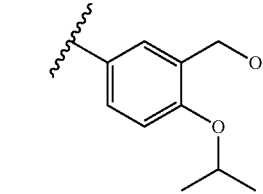 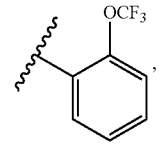
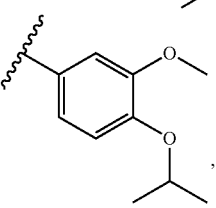 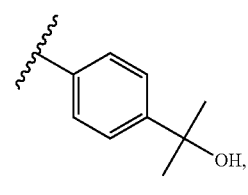
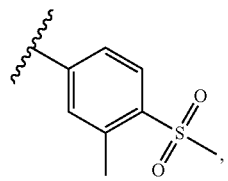 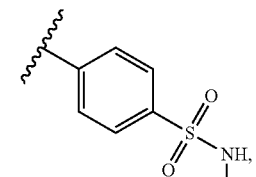
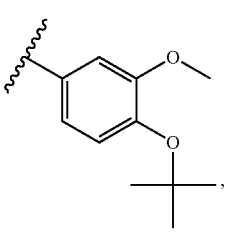 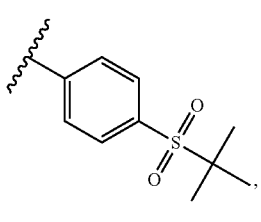
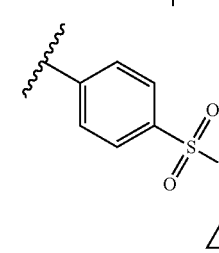 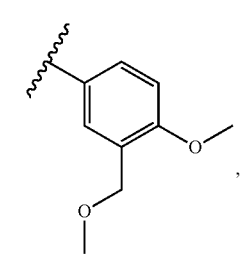
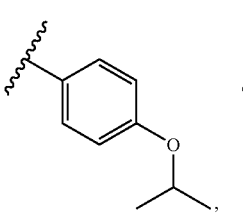 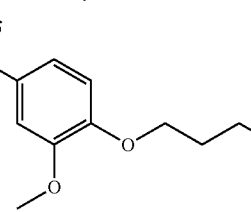
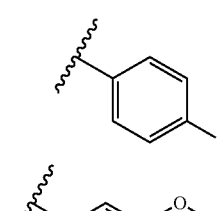 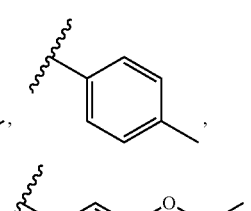
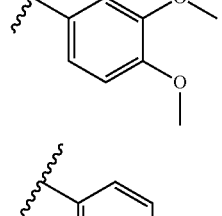 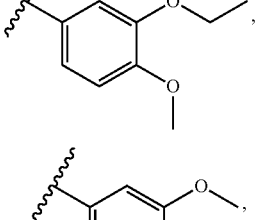
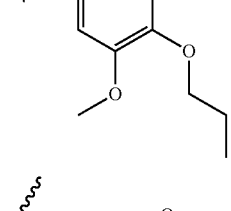 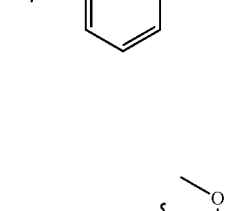
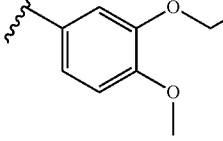 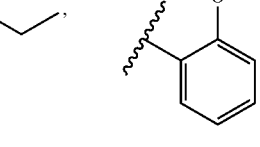

507
-continued
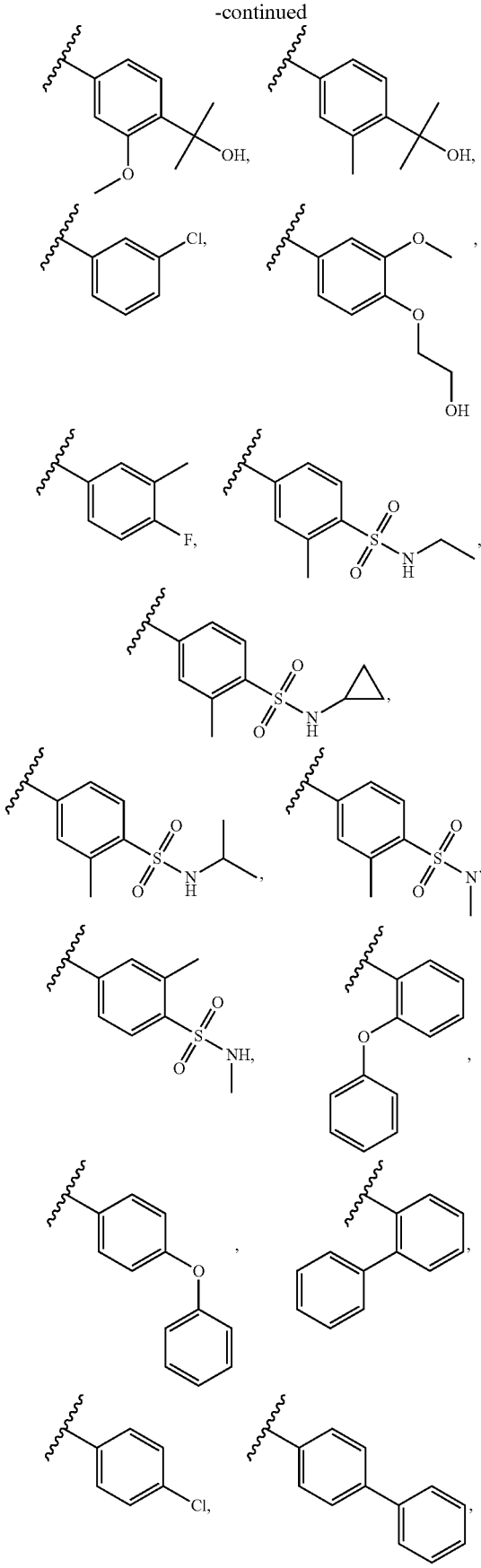
508
-continued
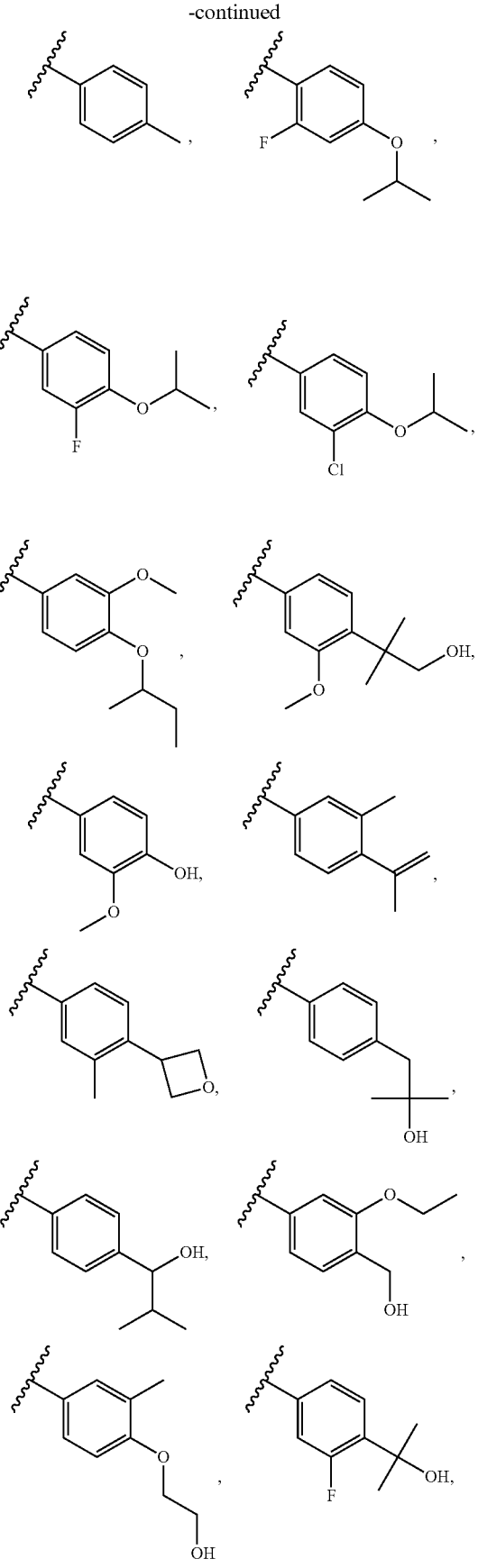

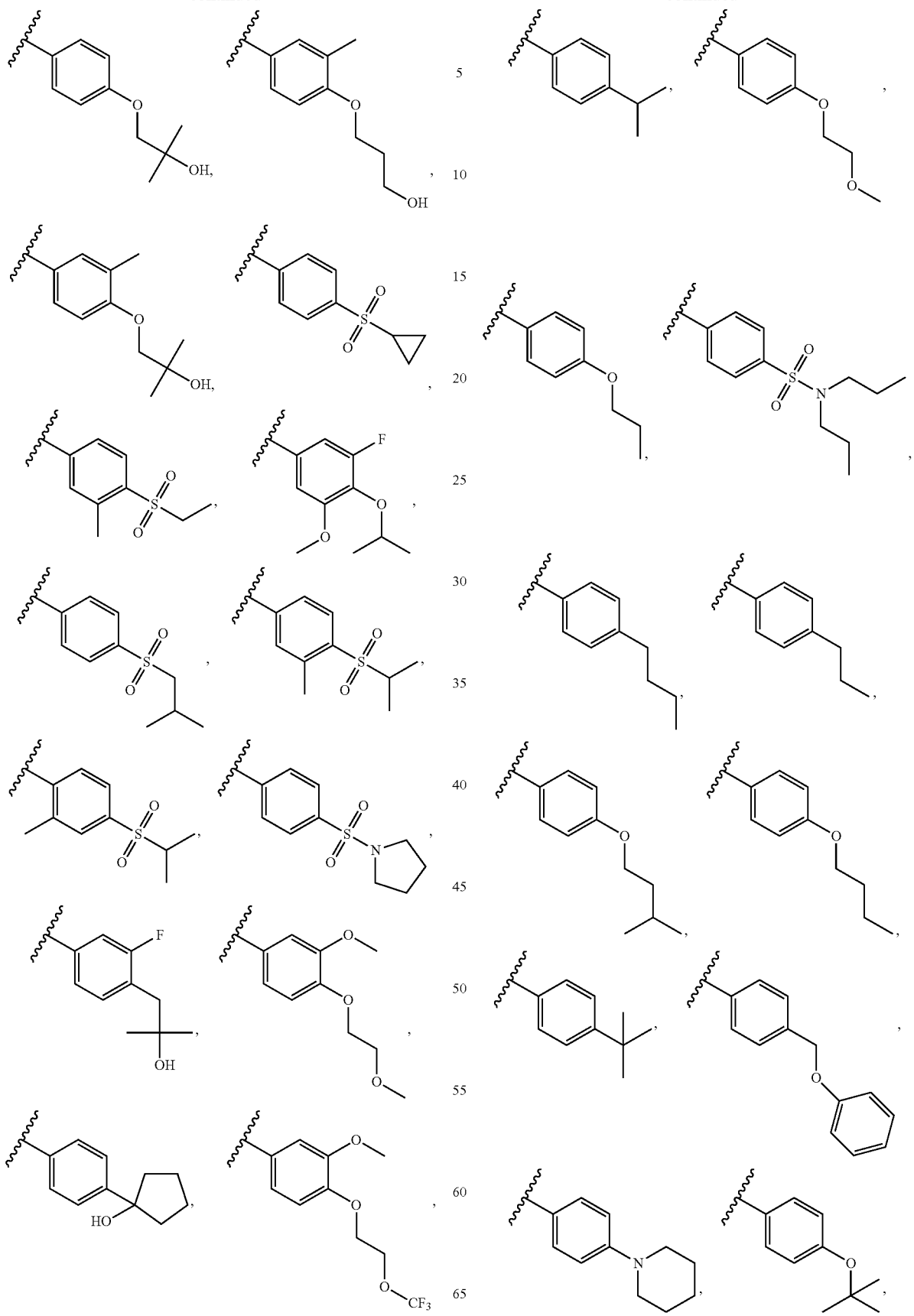

511
-continued
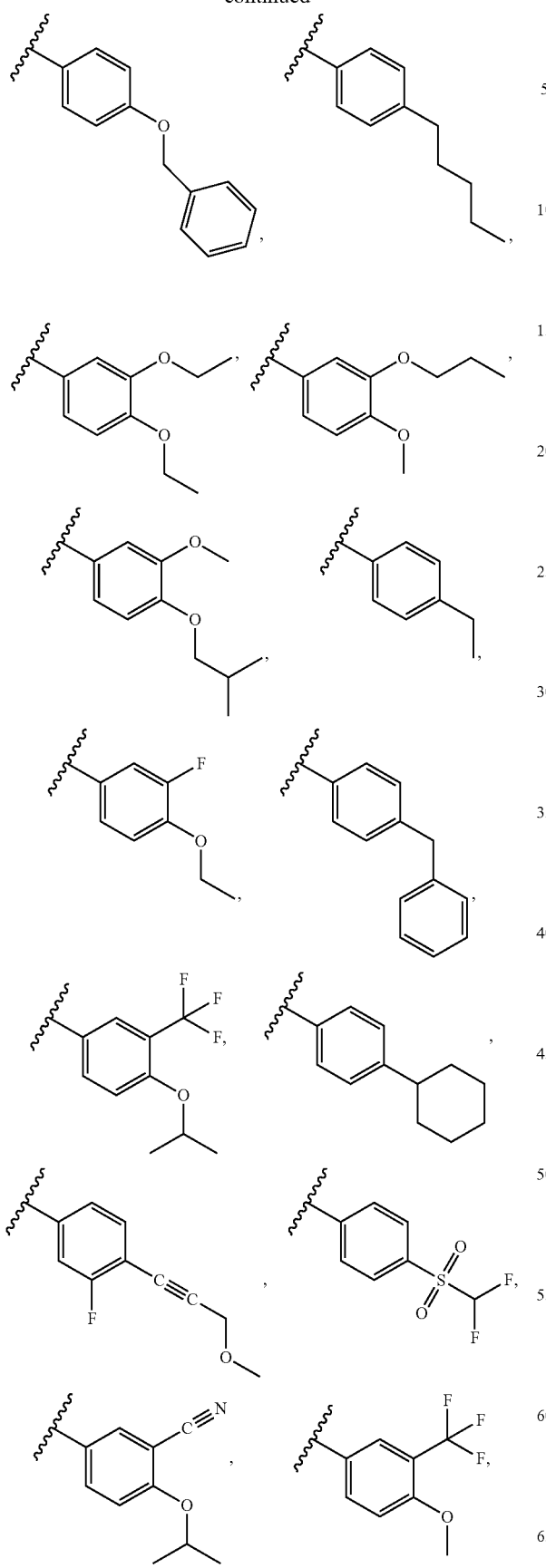
512
-continued
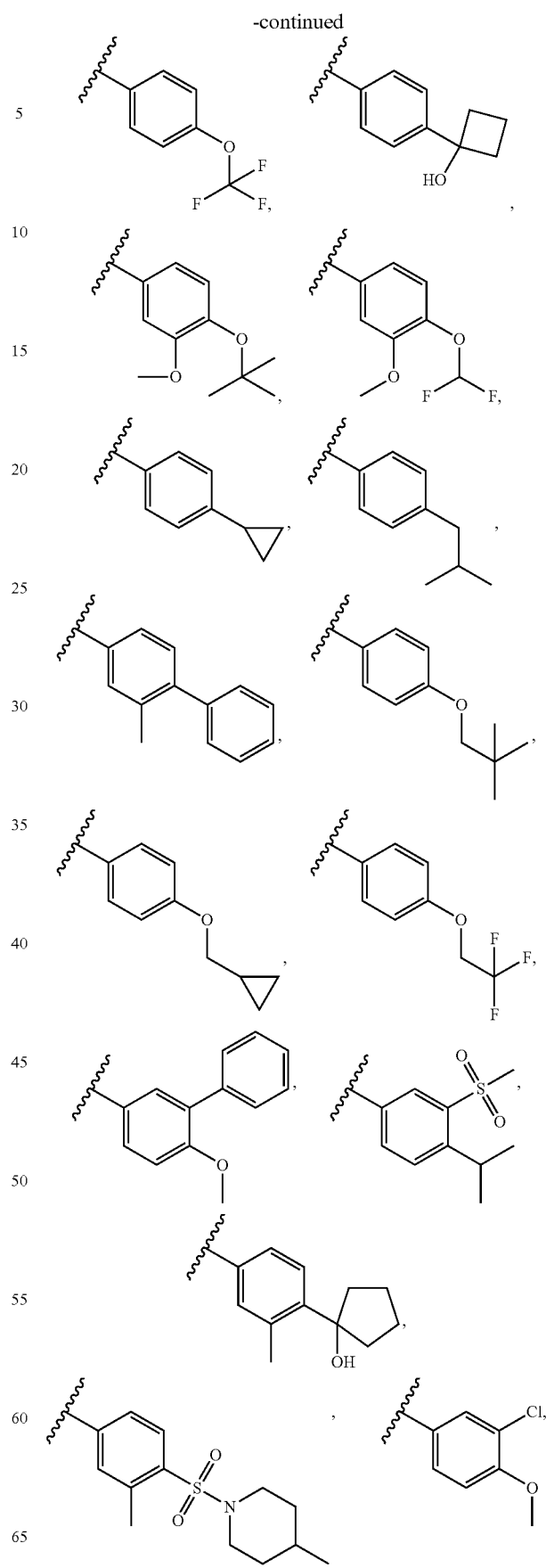

513
-continued
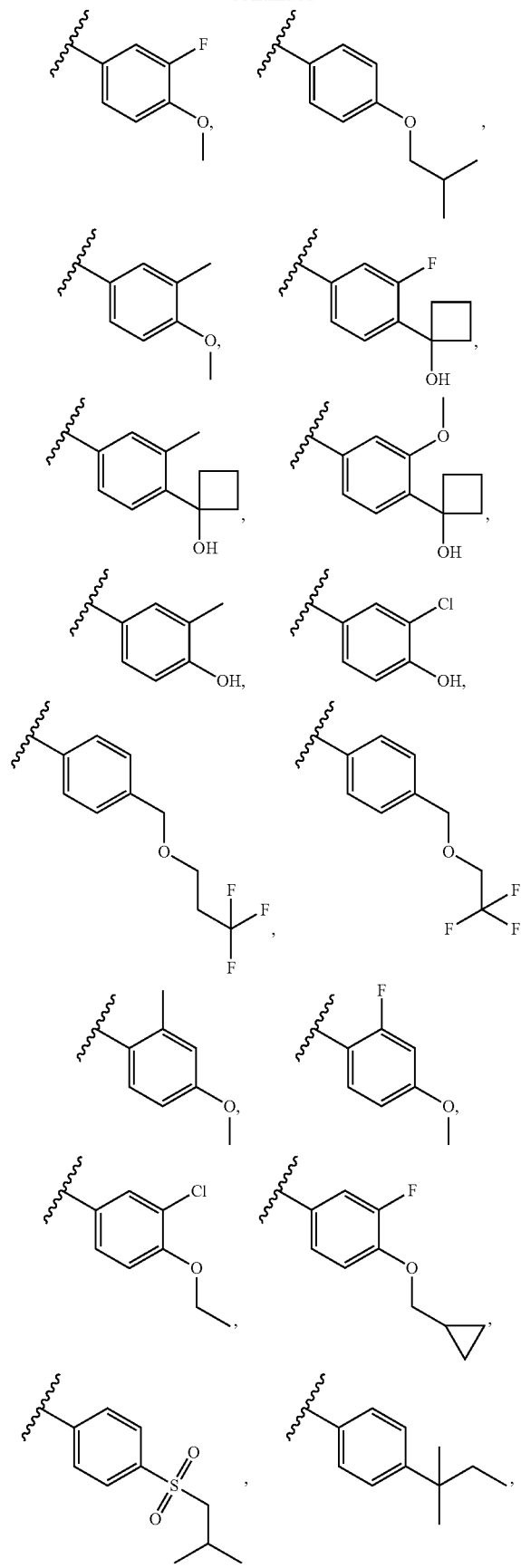
514
-continued
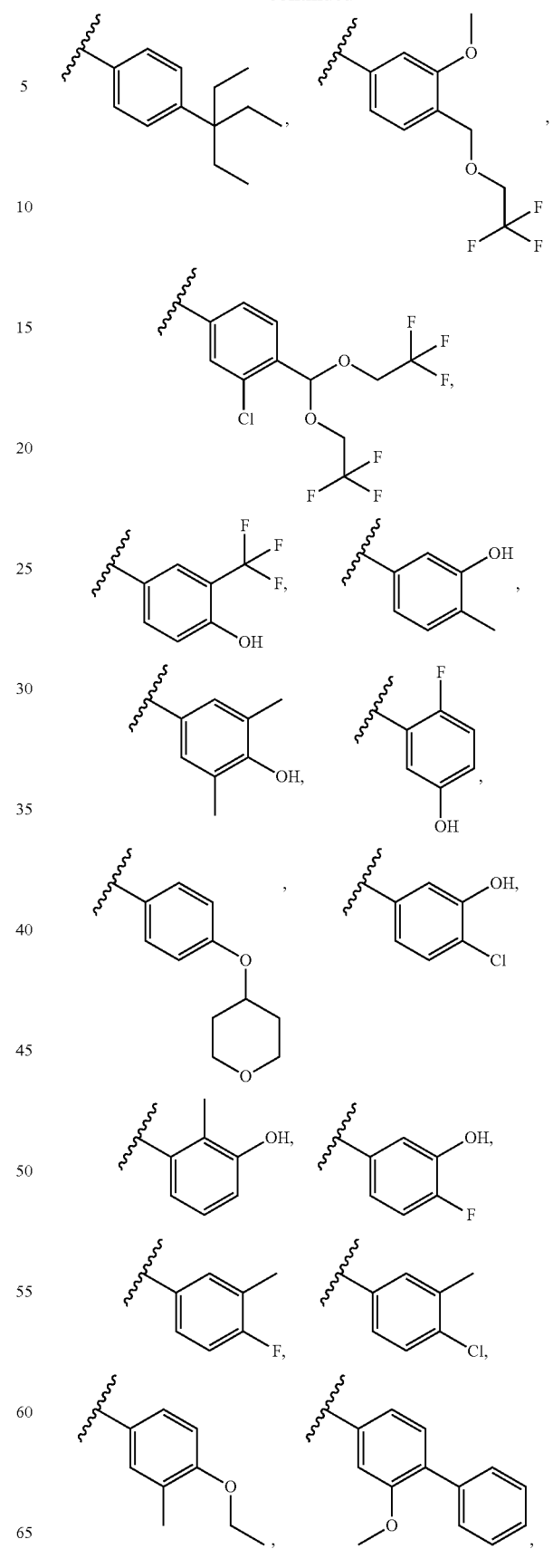

515
-continued
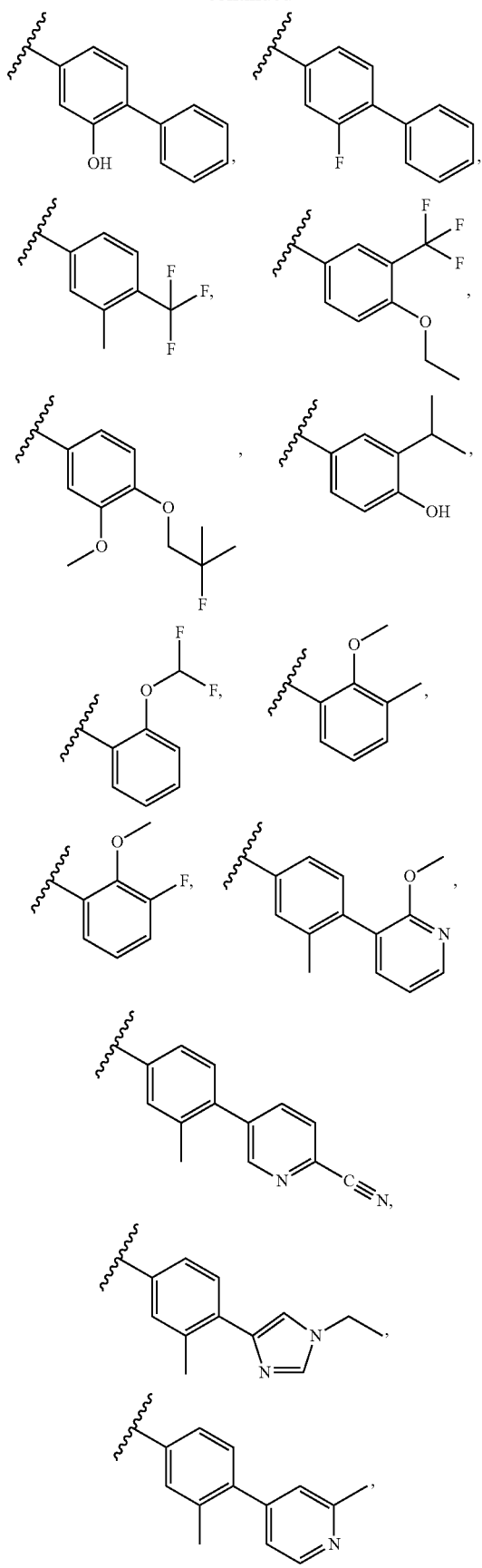
516
-continued
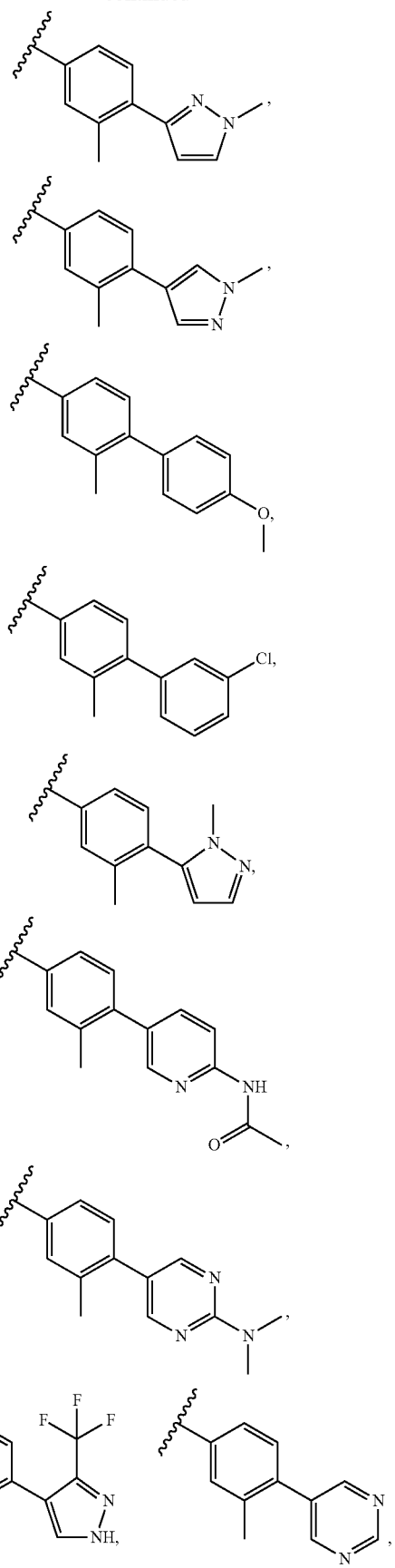

-continued

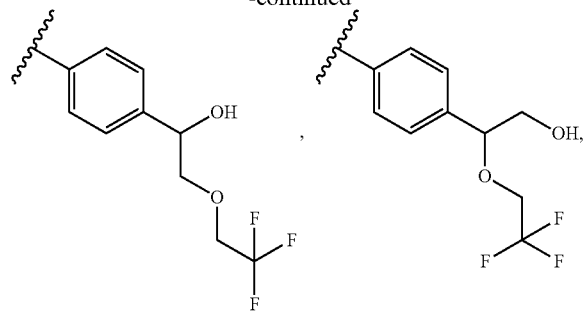

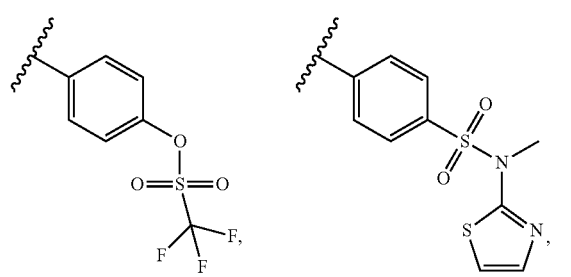

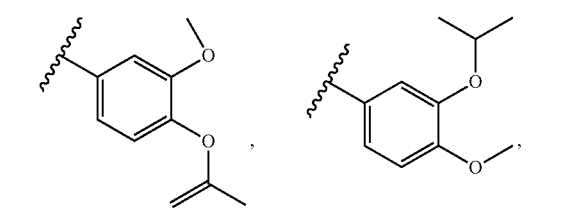

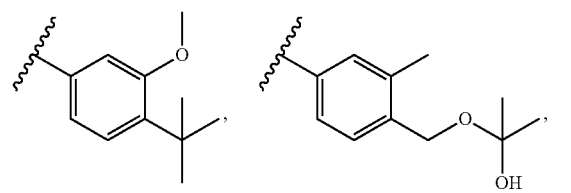

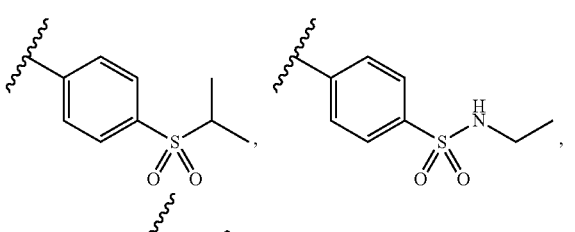

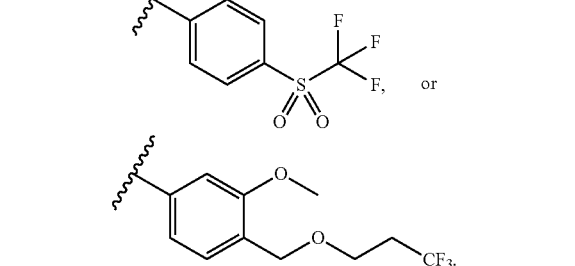

10. The compound of claim 1, wherein the compound has formula IA:

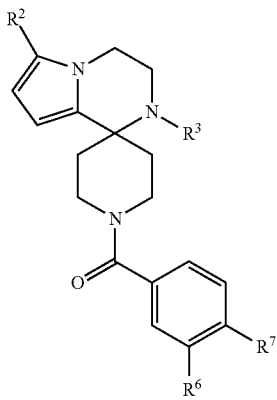

IA wherein:
R² is H, C1-C8 alkyl, halo, C1-C8 haloalkyl, CN, OH, SO₂R⁸, SR⁸, SOR⁸, COR⁸, CO₂R⁸, CON(R⁸)₂, SO₂N(R⁸)₂, CF₃, CHF₂, or a straight chain, branched, or cyclic (C3-C8)-R⁹ wherein up to two CH₂ units may be replaced with O, CO, S, SO, SO₂, CF₂, or NR⁸;

R³ is H, C1-C8 alkyl, CO₂R⁸, COR⁸, COH, CON(R⁸)₂, CF₃, or a straight chain, branched, or cyclic (C3-C8)-R⁹ wherein up to two CH₂ units may be replaced with CF₂, O, CO, S, SO, SO₂ or NR⁸;

R⁶ is H, C1-C8 alkyl, C3-C8 cycloalkyl, C1-C8 alkoxy, C3-C8 cycloalkoxy, halo, CN, OH, OR⁸, N(R⁸)₂, NR⁸SO₂R⁸, SO₂R⁸, SOR⁸, SR⁸, CO₂R⁸, NR⁸COR⁸, NR⁸CO₂R⁸, CON(R⁸)₂, SO₂N(R⁸)₂, CF₃, OCF₃, OCHF₂, R⁹, heterocycloalkyl, heterocycloalkoxy, aryl, heteroaryl, or a straight chain, branched, or cyclic (C3-C8)-R⁹ wherein up to three CH₂ units may be replaced with O, CO, S, SO, SO₂, or NR⁸;

R⁷ is H, C1-C8 alkyl, C3-C8 cycloalkyl, C1-C8 alkoxy, halo, CN, OH, OR⁸, N(R⁸)₂, NR⁸SO₂R⁸, SO₂R⁸, SOR⁸, SR⁸, CO₂R⁸, NR⁸COR⁸, NR⁸CO₂R⁸, CON(R⁸)₂, SO₂N(R⁸)₂, CF₃, OCF₃, OCHF₂, R⁹, heterocycloalkyl, heterocycloalkoxy, aryl, heteroaryl, or a straight chain, branched, or cyclic (C3-C8)-R⁹ wherein up to three CH₂ units may be replaced with O, CO, S, SO, SO₂, or NR⁸.

11. The compound of claim 10, wherein R² is H, COCF₃, COtBu, Cl, COCH₃, CF₂CF₃, CH₂CF₃, CF₃, CN, Br, COCH(CH₃)₂, COCH₂CH₃, CH(OH)CF₃, SO₂CH₃,

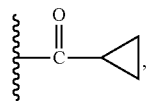

COPh,

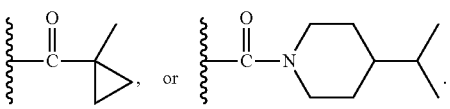

12. The compound of claim 10, wherein R³ is H, CH₃, CH₂CH₃, CH₂CH₂OCH₃, CH₂CH₂OH, CH₂CO₂CH₂CH₃, CH₂CON(CH₃)₂, CH₂CONH₂, CH₂CN, benzyl, cyclobutyl, CH₂CH(CH₂)₂, CH(CH₂)₂, CH₂CF₃, CH₂CHF₂, COCH₃, COCH₂CH₃, CO₂CH₃, CO₂CH₂CH₃, COH, CONH(CH₃)₂, or CONHCH₃.

13. The compound of claim 10, wherein R⁶ is H, CH₃, OCH₃, OCH₂CH₃, OCH₂CH₂CH₃, OCH(CH₃)₂, CF₃, CN, Ph, SO₂CH₃, OH, CH(CH₃)₂, OCH₂CH₂CH₂CH₃, F, Cl, or CH₂OH.

14. The compound of claim 10, wherein R⁷ is H, CH₃, CH₂CH₃, tBu, Cl, F, OH, C(=CH₂)CH₃, OC(=CH₂)CH₃, OCH₃, OCH₂CH₂CH₃, CH₂OH, OCH₂CH₂OH, OCH₂CH₂CH₂OH, OtBu, OCH(CH₃)(CH₂CH₃), OCH₂C(CH₃)₂OH, C(CH₃)₂OH, CH₂C(CH₃)₂OH, CH(OH)CH(CH₃)₂, C(CH₃)₂CH₂OH, OCH₂CH₂CH(CH₃)₂, OCH₂CH₂CH₃, OCH(CH₃)₂, OCH₂CH₂OCH₃,

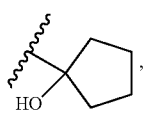,

SO₂CH₃, SO₂tBu, SO₂CH₂CH₃, SO₂CH₂CH(CH₃)₂, SO₂CH(CH₃)₂,

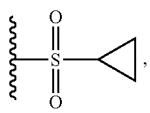 [SMILES: *S(=O)(=O)C1CC1],

SO₂NH(CH₃),), SO₂NH(CH(CH₃)₂), SO₂NH(CH₂CH₃), SO₂NH(CH(CH₃)₂), SO₂N(CH₃)₂,

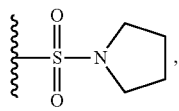,

OPh, Ph,

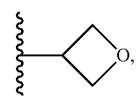,

OCH₂CH₂OCH₃, CH(CH₃)₂, SO₂N(CH₂CH₂CH₃)₂, CH₂CH₂CH₂CH₃, CH₂CH₂CH₃, OCH₂CH₂CH₂CH₃, CH₂OPh,

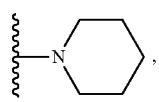,

OCH₂Ph, CH₂CH₂CH₂CH₂CH₃, OCH₂CH₃, OCH₂CH₂CH₂CH₃, CH₂Ph

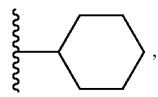,

CCCH₂OCH₃, SO₂CHF₂, OCF₃,

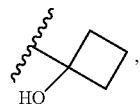 [SMILES: *C1(O)CCC1],

OCHF₂,

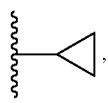,

CH₂CH(CH₃)₂, OCH₂tBu,

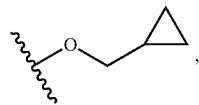,

OCH₂CF₃,

, 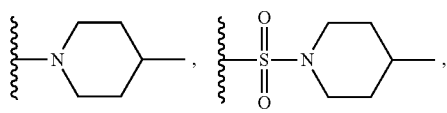,

CH₂OCH₂CH₂CF₃, CH₂OCH₂CF₃, SO₂CF₃, C(CH₃)₂CH₂CH₃, C(CH₂CH₃)₃, CH(OCH₂CF₃)₂,

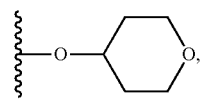,

CF₃, OCH₂C(CH₃)₂F,

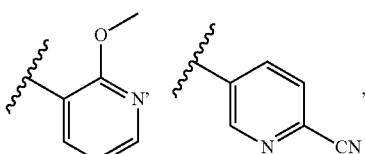

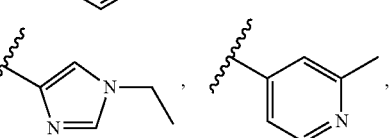

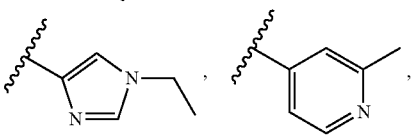

521
-continued
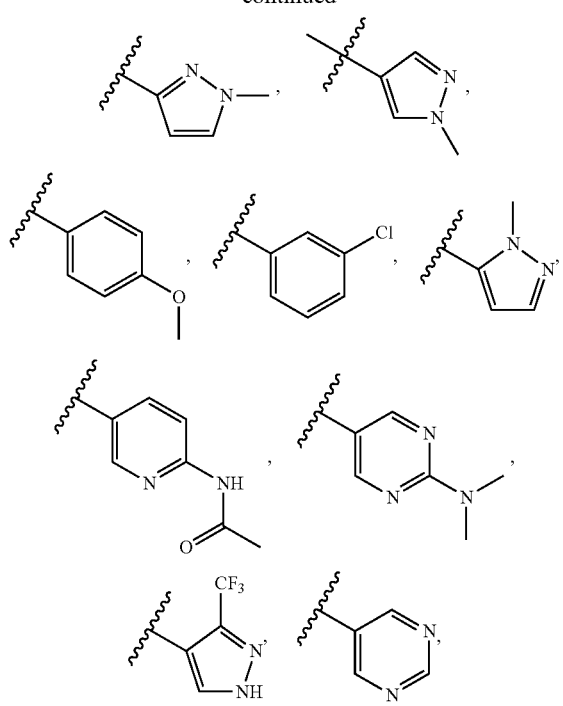
CH(OH)CH$_2$OCH$_2$CF$_3$, CH(OCH$_2$CF$_3$)CH$_2$OH, OSO$_2$CF$_3$,
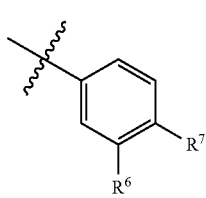
or OCH$_2$CH$_2$OCF$_3$.
15. The compound of claim 10, wherein the
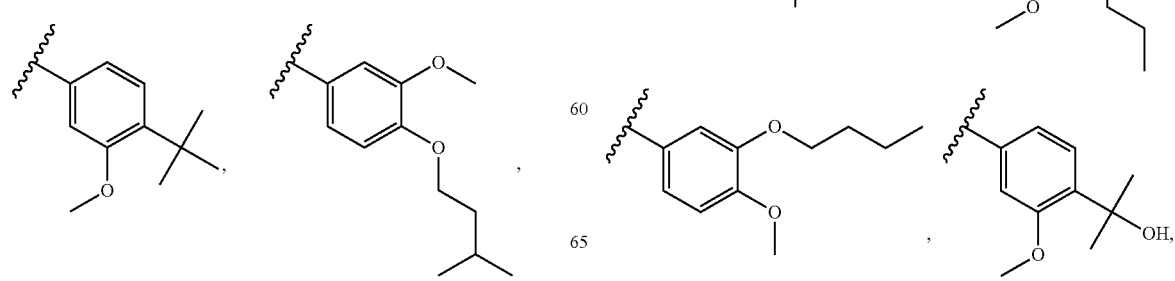
moiety is:
522
-continued
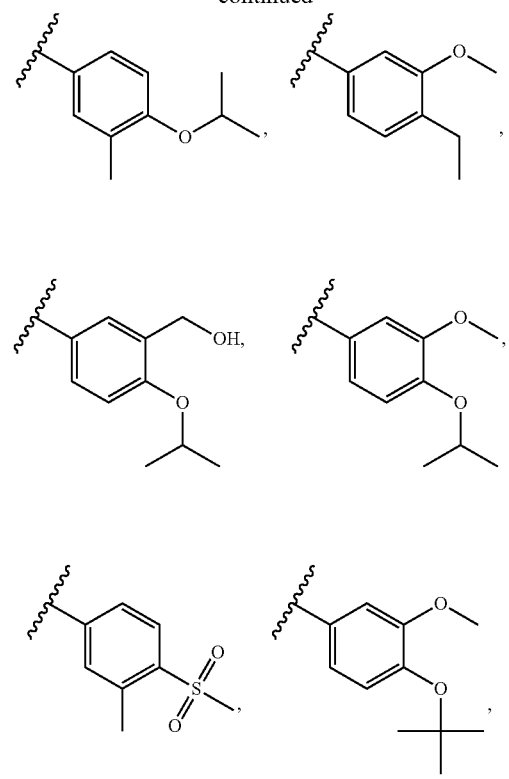
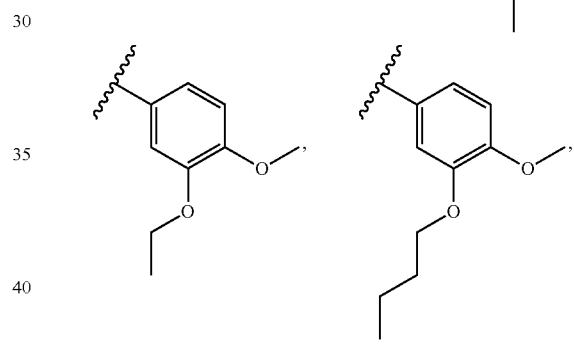
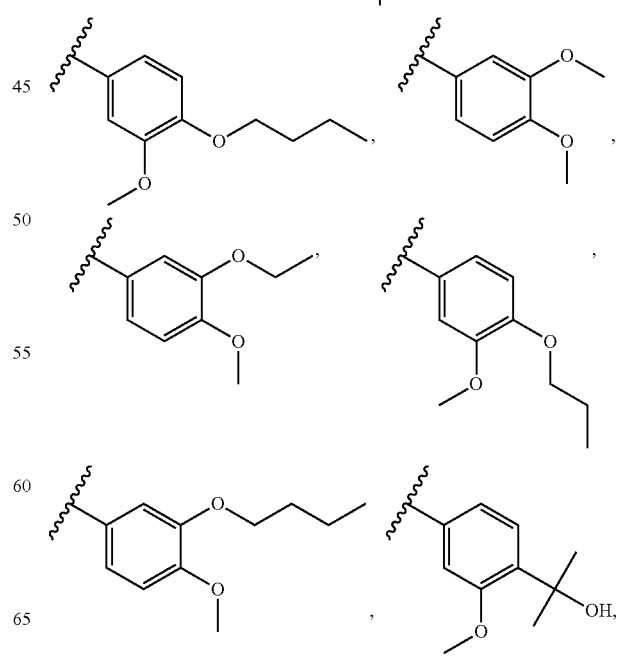

523
-continued
524
-continued
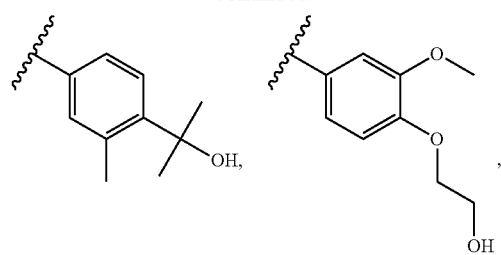
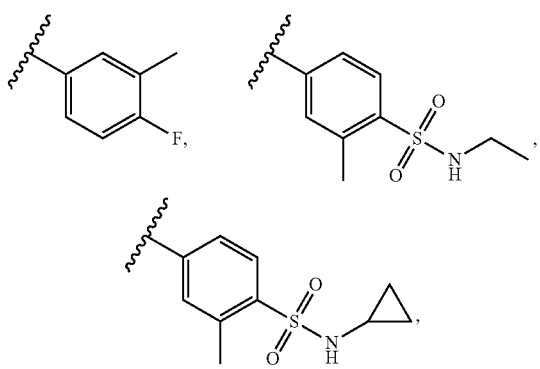
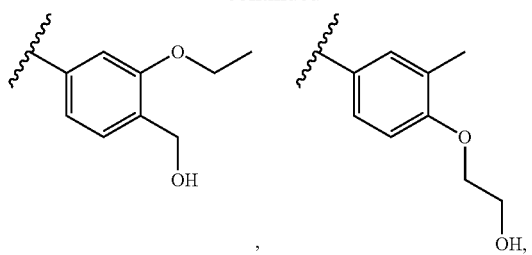

525
-continued
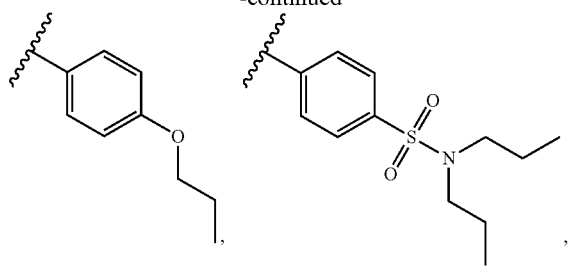
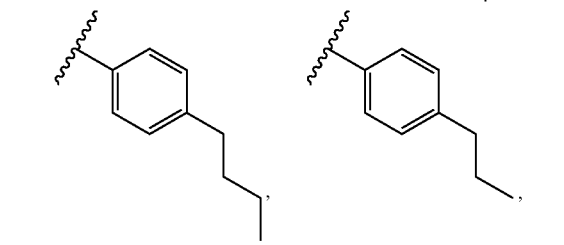
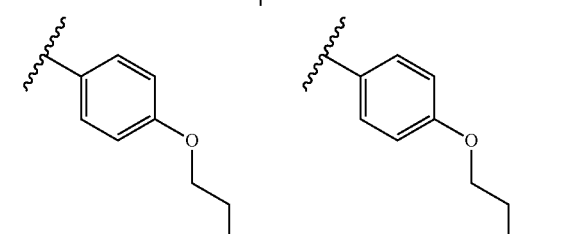
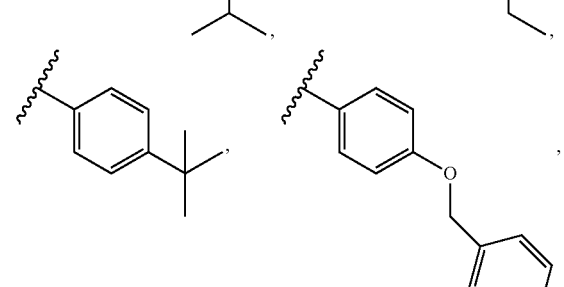
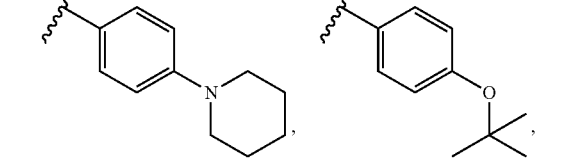
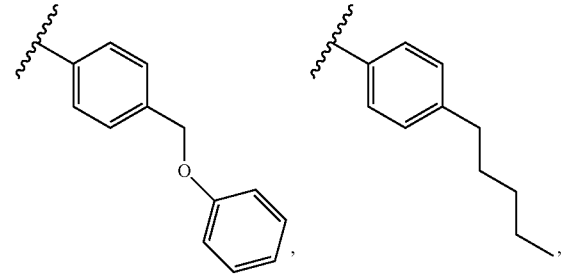
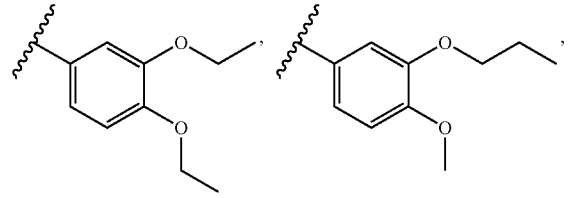
526
-continued
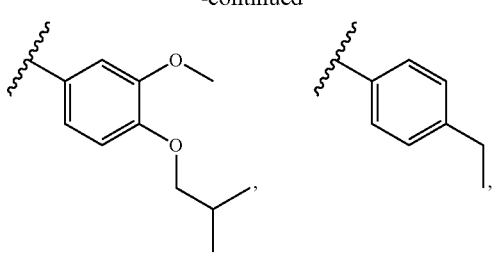
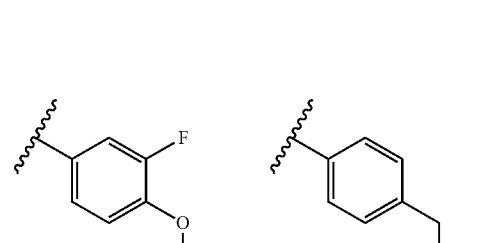
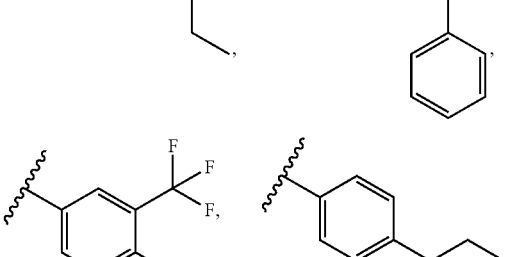
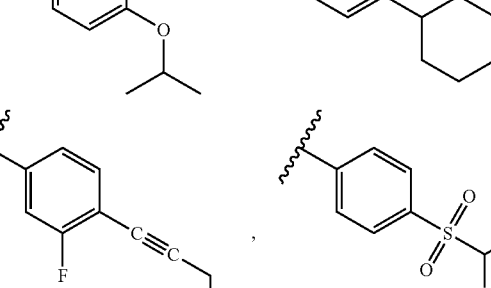
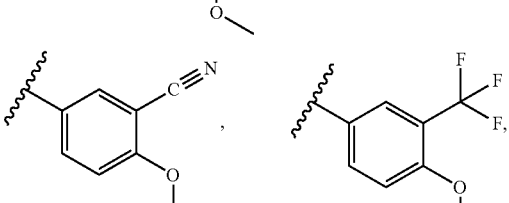
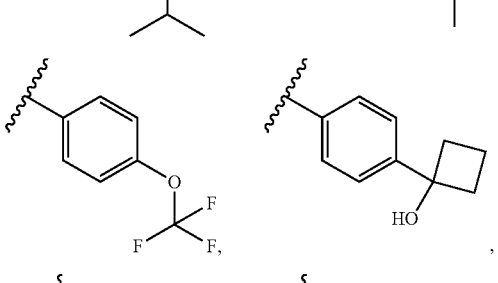
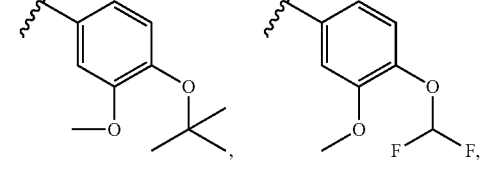

527
-continued
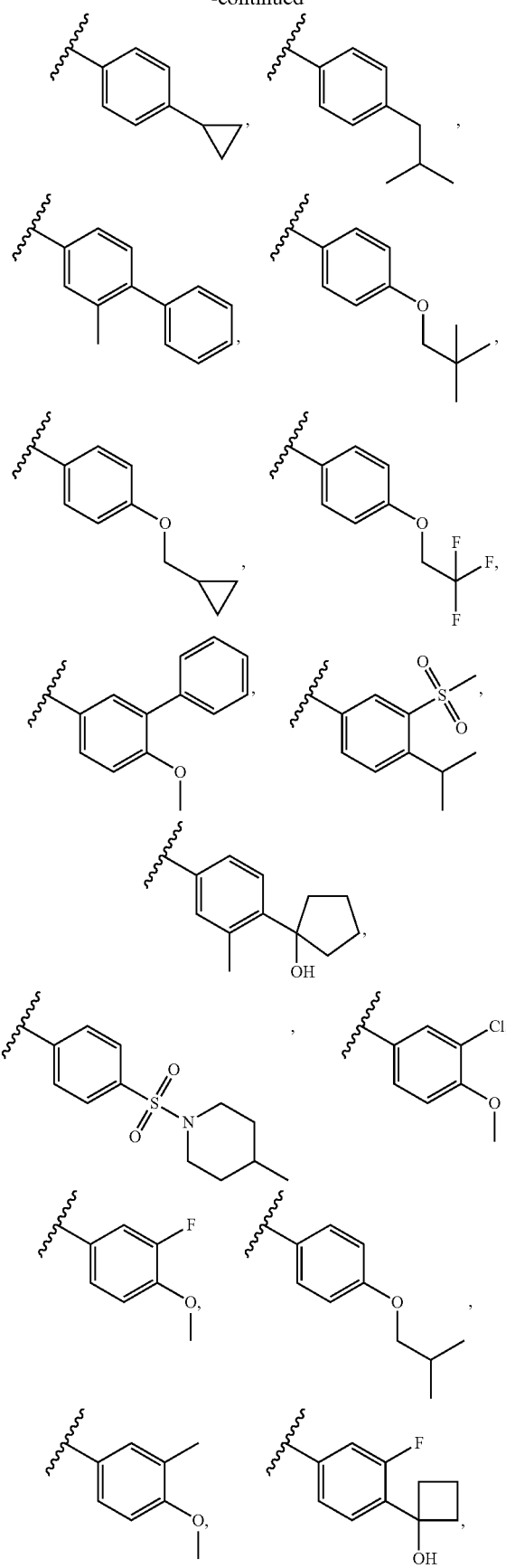
528
-continued
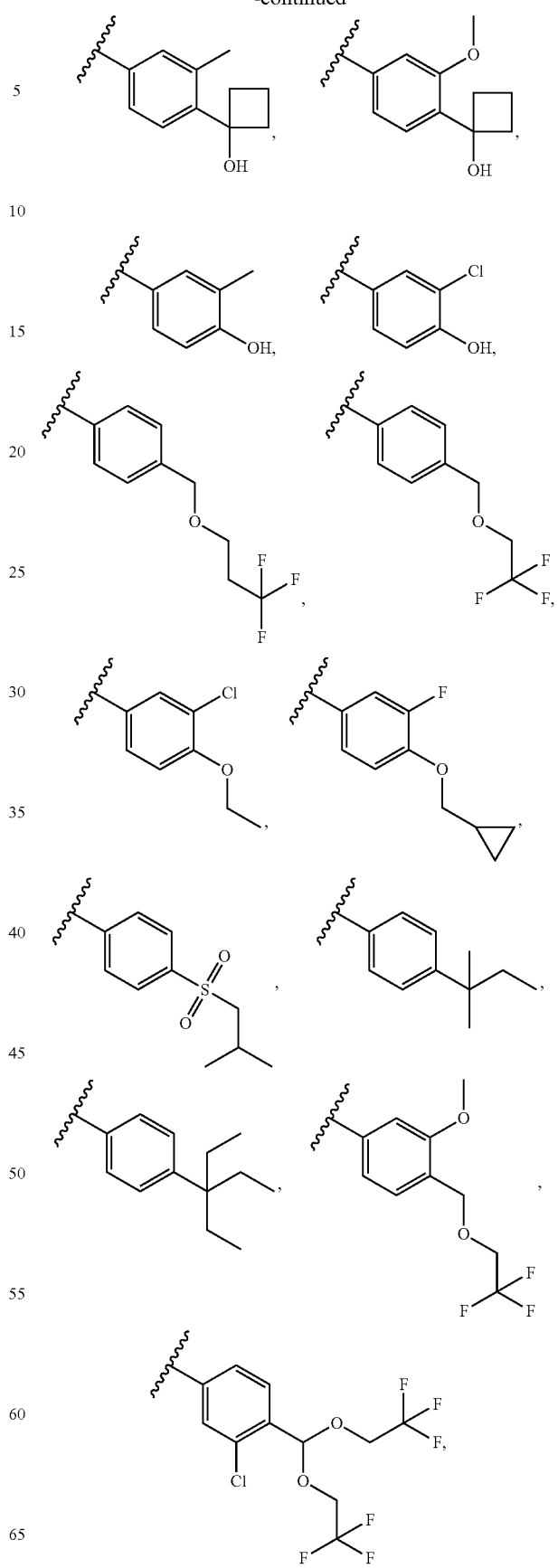

529
-continued
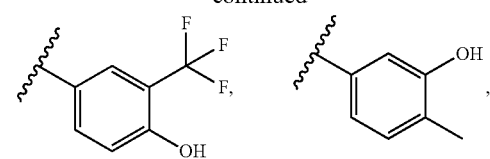
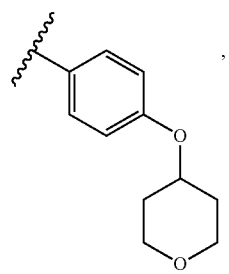
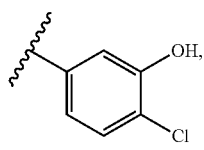
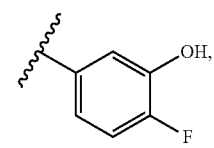
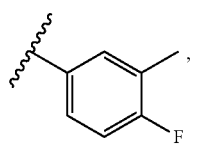
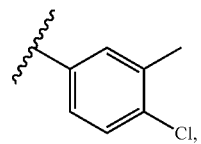
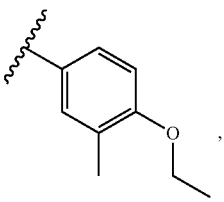
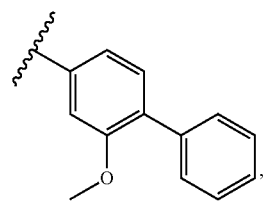
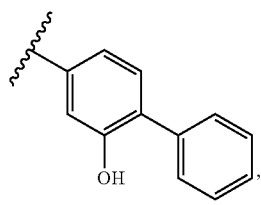
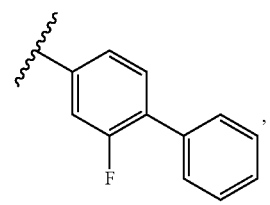
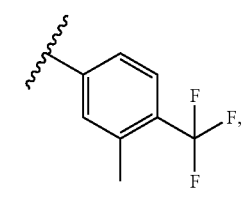
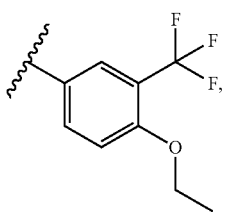
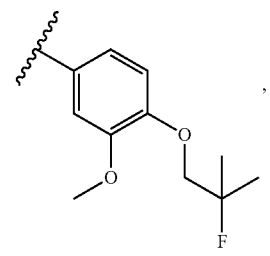
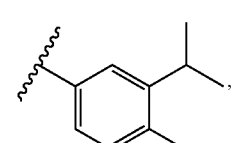
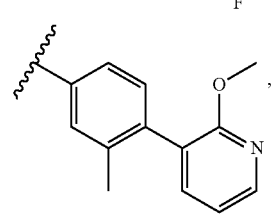
530
-continued
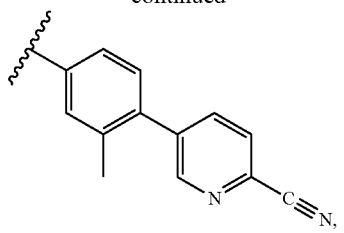
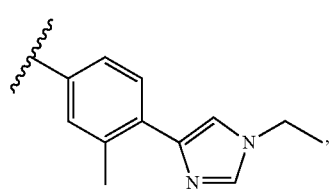
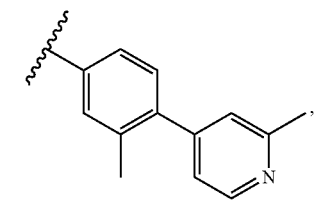
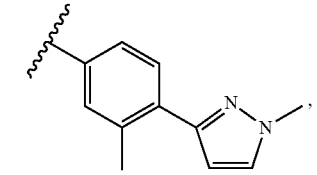
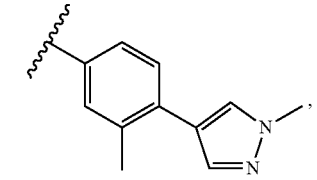
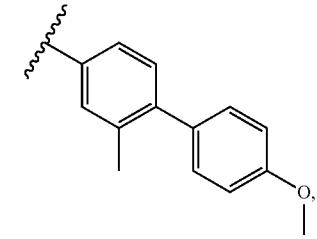
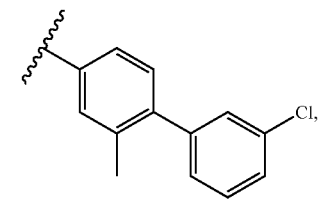
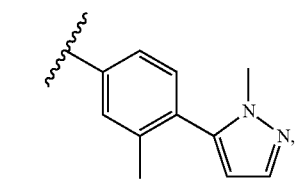

-continued

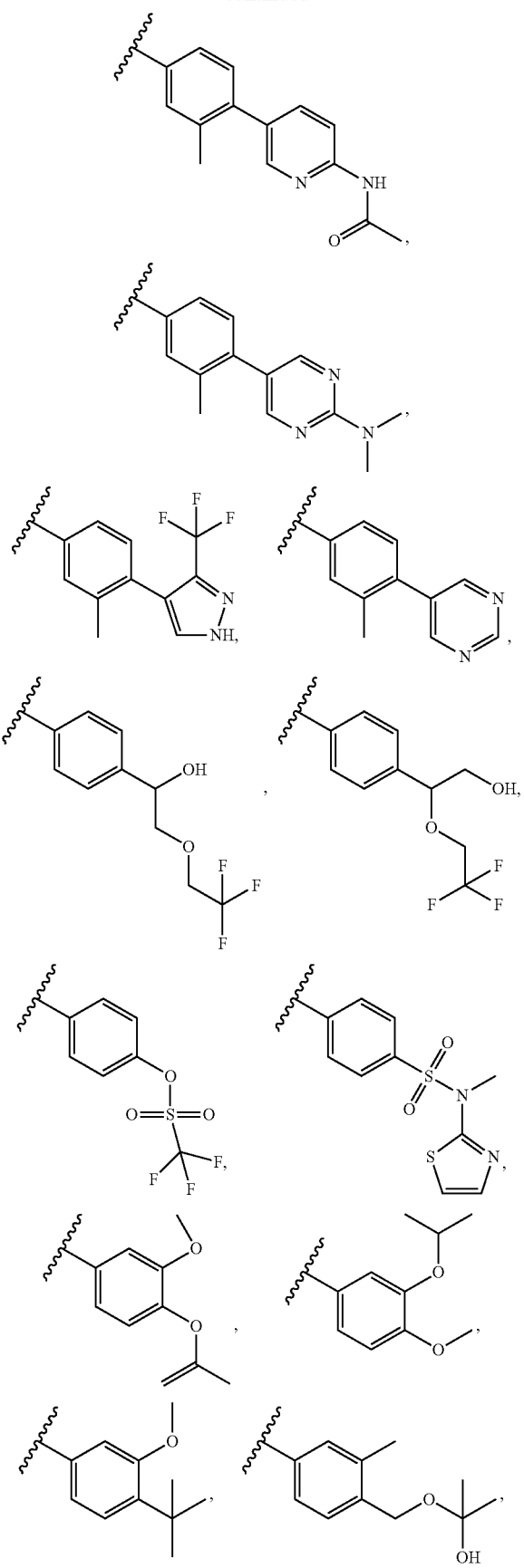

16. The compound of claim 1, wherein, independently for each occurrence:

$R^1$ is H, C1-C6 alkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, heterocycloalkyl, or a straight chain, branched, or cyclic (C3-C8)-$R^9$ wherein up to two $CH_2$ units may be replaced with O, CO, S, SO, $SO_2$ or $NR^8$, or two $R^1$ taken together form an oxo group, or a 3 to 7 membered fused cycloalkyl ring, or a 3 to 7 membered spirocyclic ring;

$R^2$ is H, C1-C6 alkyl, C1-C6 haloalkyl, CN, OH, $SO_2R^8$, $SR^8$, $SOR^8$, $CO_2R^8$, $CON(R^8)_2$, $SO_2N(R^8)_2$, $CF_3$, $CHF_2$, or a straight chain, branched, or cyclic (C3-C8)-$R^9$ wherein up to two $CH_2$ units may be replaced with O, CO, S, SO, $SO_2$, $CF_2$, or $NR^8$;

$R^3$ is H, C1-C6 alkyl, C3-C8 cycloalkyl, $CO_2R^8$, $COR^8$, COH, $CON(R^8)_2$, $CF_3$, $CH_2CF_3$, $CH_2CHF_2$, or a straight chain, branched, or cyclic (C3-C8)-$R^9$ wherein up to two $CH_2$ units may be replaced with O, CO, S, SO, $SO_2$ or $NR^8$;

$R^4$ is H, C1-C6 alkyl, halo, C3-C8 cycloalkyl, wherein up to two $CH_2$ units may be replaced by O, CO, S, SO, $SO_2$, or $NR^8$, or 2 $R^4$ taken together form a fused 3 to 7 membered cycloalkyl ring;

$R^8$ is H, C1-C6 alkyl, $CF_3$, C3-C8 cycloalkyl, or a straight chain, branched, or cyclic (C3-C8)-$R^9$ wherein up to two $CH_2$ units may be replaced with O, CO, S, SO, $SO_2$ or NR, or 2 $R^8$ taken together with the atoms to which they are attached form a ring;

$R^9$ is H, $CF_3$, $CO_2R$, OH, aryl, heteroaryl, C3-C8 cycloalkyl, heterocycloalkyl, $N(R)_2$, NRCOR, $CON(R)_2$, CN, or $SO_2R$;

R is H, C1-C6 alkyl, aryl, heteroaryl, C3-C8 cycloalkyl, or heterocycloalkyl.

17. The compound of claim 1, wherein $R^1$ is C1-C8 alkyl or two $R^1$ taken together with the atoms to which they are attached form a 3 to 7 membered fused cycloalkyl or spirocyclic ring.

18. The compound of claim 1, wherein $R^1$ is $CH_3$ or two $R^1$ taken together form a fused cyclohexyl ring.

19. The compound claim 1, wherein $R^2$ is H, C1-C8 alkyl, halo, $CF_3$, CN, $COR^8$, $CON(R^8)_2$, or a straight chain, branched, or cyclic (C3-C8)-$R^9$ wherein up to two $CH_2$ units may be replaced with O, CO, S, SO, $SO_2$, $CF_2$, or $NR^8$.

20. The compound of claim 1, wherein $R^2$ is $COCF_3$, $COtBu$, $Cl$, $COCH_3$, $CF_2CF_3$, $CH_2CF_3$, $CF_3$, $CN$, $Br$, $COCH(CH_3)_2$, $COCH_2CH_3$, $CH(OH)CF_3$, $SO_2CH_3$,

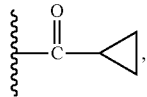

COPh,

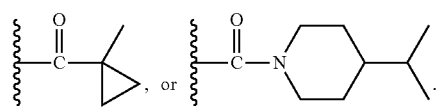

21. The compound of claim 1, wherein $R^3$ is H, C1-C8 alkyl, $CO_2R^8$, $COR^8$, $COH$, $CON(R^8)_2$ or a straight chain, branched, or cyclic (C3-C8)-$R^9$ wherein up to two $CH_2$ units may be replaced with O, CO, S, SO, $SO_2$ or $NR^8$.

22. The compound of claim 1, wherein $R^3$ is H, $CH_3$, $CH_2CH_3$, $CH_2CH_2OCH_3$, $CH_2CH_2OH$, $CH_2CO_2CH_2CH_3$, $CH_2CON(CH_3)_2$, $CH_2CONH_2$, $CH_2CN$, benzyl, cyclobutyl, $CH_2CH(CH_2)_2$, $CH(CH_2)_2$, $CH_2CF_3$, $CH_2CHF_2$, $COCH_3$, $COCH_2CH_3$, $CO_2CH_3$, $CO_2CH_2CH_3$, COH, $CONH(CH_3)_2$, or $CONHCH_3$.

23. The compound of claim 1, wherein $R^4$ is H, halo, or C1-C8 alkyl.

24. The compound of claim 1, wherein $R^4$ is H, F, or $CH_3$.

25. The compound of claim 1, wherein m is 0, 1, or 2.

26. The compound of claim 1, wherein n is 0, 1, or 2.

27. The compound of claim 1, wherein o is 0 or 1.

28. The compound of claim 1, wherein the compound is selected from the following table:

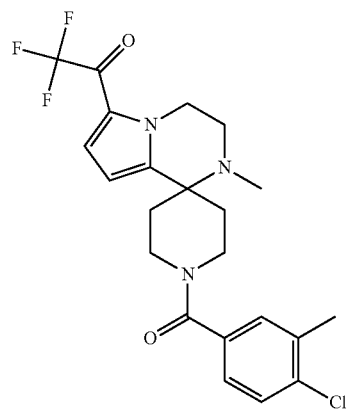 [SMILES: Cc1cc(C(=O)N2CCC3(CC2)c2ccc(C(=O)C(F)(F)F)n2CCN3C)ccc1Cl]

1

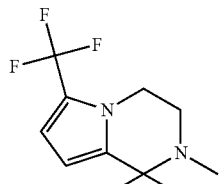

2

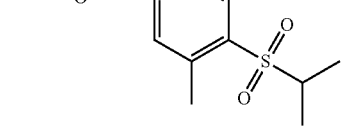

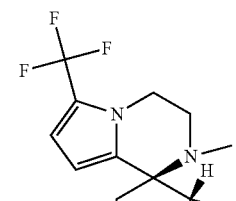

3

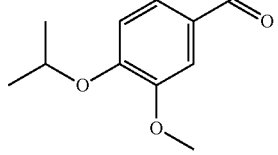

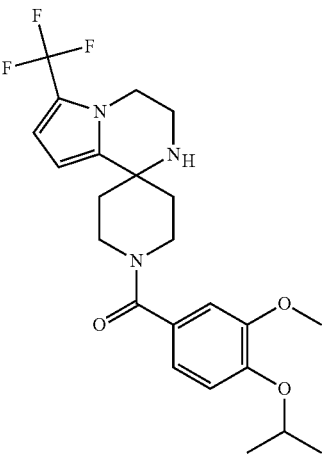

4

| 5 | 8 |
|---|---|
| 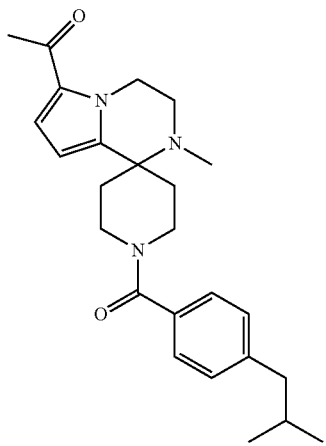 [SMILES: CC(=O)c1ccc2n1CCN(C)C21CCN(C(=O)c2ccc(CC(C)C)cc2)CC1] | 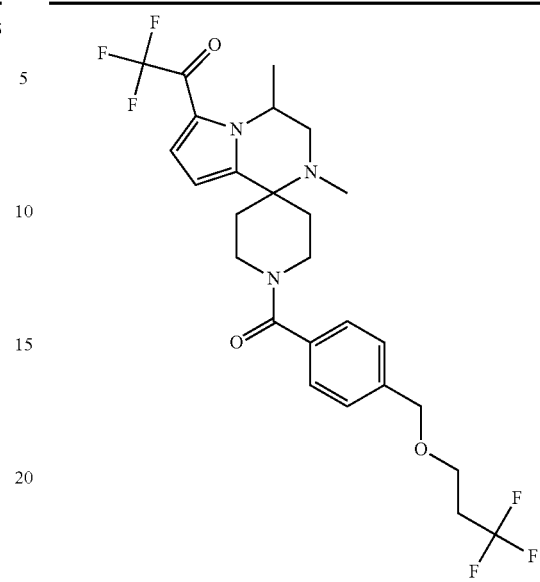 |
| 6 | 9 |
| 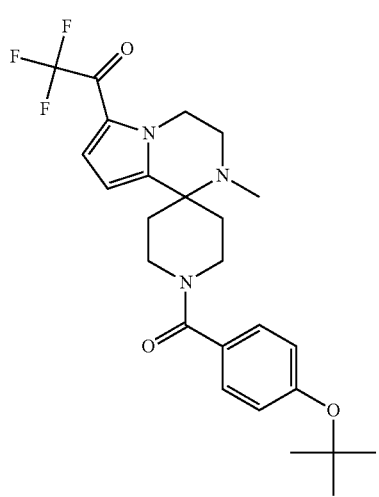 [SMILES: CN1CCn2c(C(=O)C(F)(F)F)ccc2C12CCN(C(=O)c1ccc(OC(C)(C)C)cc1)CC2] | 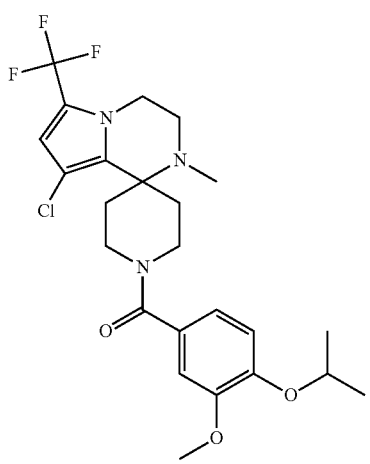 |
| 7 | 10 |
| 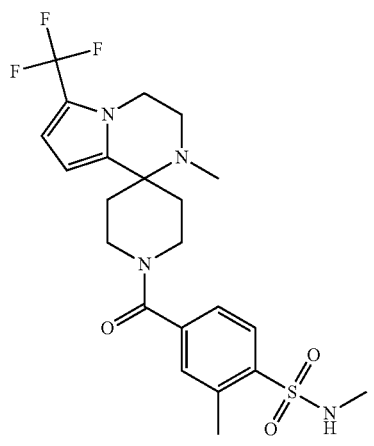 [SMILES: CNS(=O)(=O)c1ccc(C(=O)N2CCC3(CC2)c2ccc(C(F)(F)F)n2CCN3C)cc1C] | 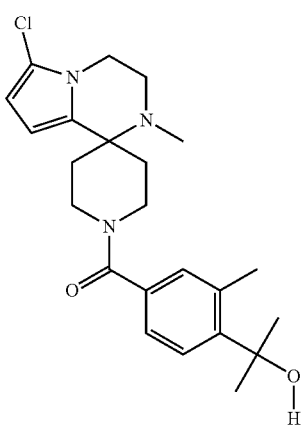 |

| 537 | 538 |
|---|---|
| 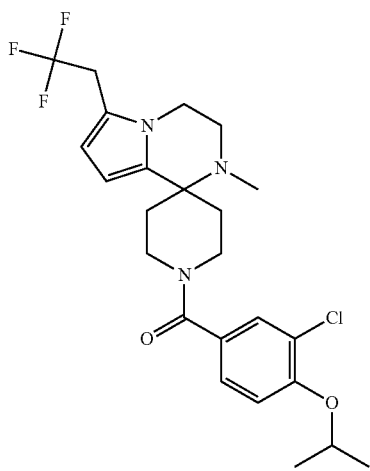 11 | 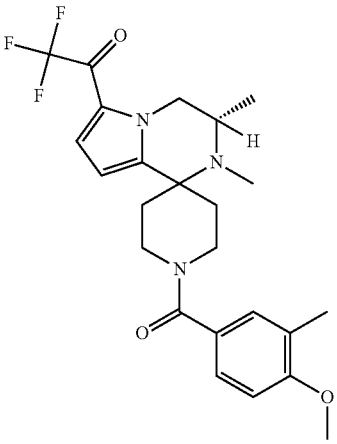 14 |
| 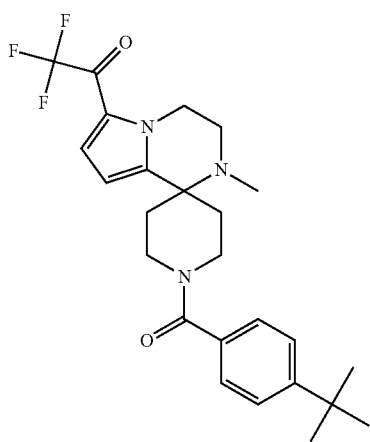 [SMILES: CN1CCn2c(C(=O)C(F)(F)F)ccc2C12CCN(C(=O)c1ccc(C(C)(C)C)cc1)CC2] 12 | 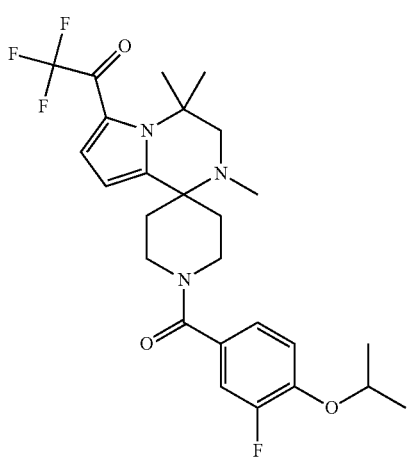 16 |
| 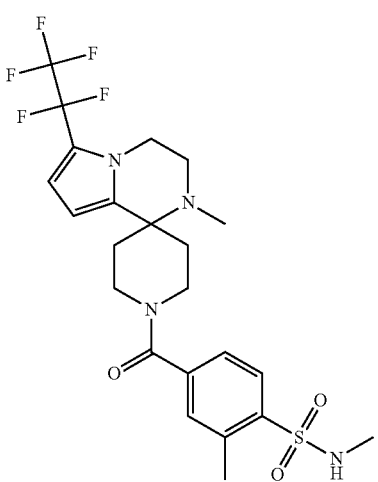 [SMILES: CNS(=O)(=O)c1ccc(C(=O)N2CCC3(CC2)c2ccc(C(F)(F)C(F)(F)F)n2CCN3C)cc1C] 13 | 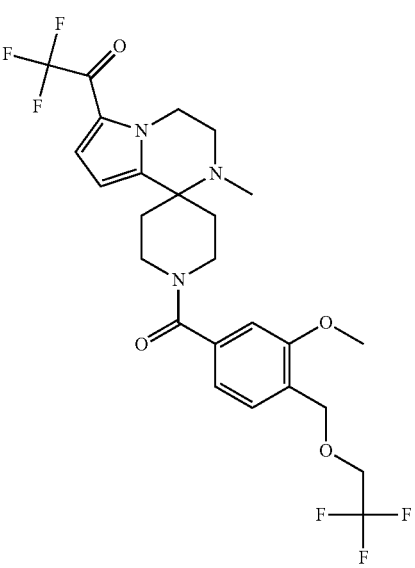 [SMILES: COc1cc(C(=O)N2CCC3(CC2)c2ccc(C(=O)C(F)(F)F)n2CCN3C)ccc1COCC(F)(F)F] 17 |

| 539 -continued | 540 -continued |
|---|---|
| 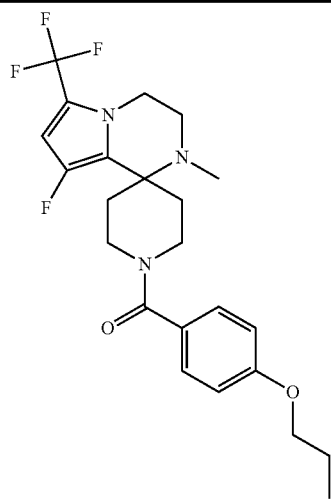 18 | 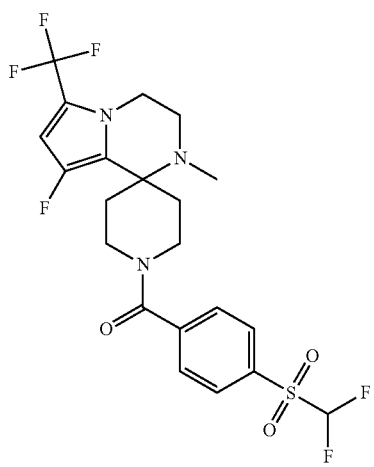 23 |
| 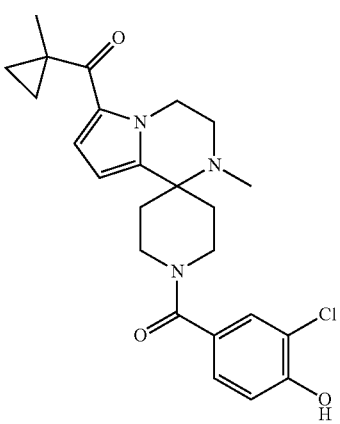 [SMILES: CN1CCn2c(C(=O)C3(C)CC3)ccc2C12CCN(C(=O)c1ccc(O)c(Cl)c1)CC2] 19 | 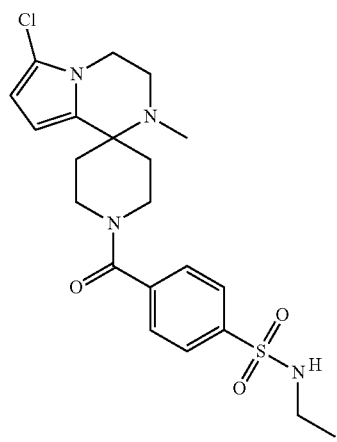 24 |
| 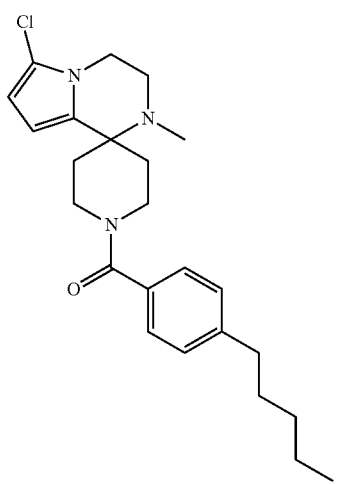 20 | 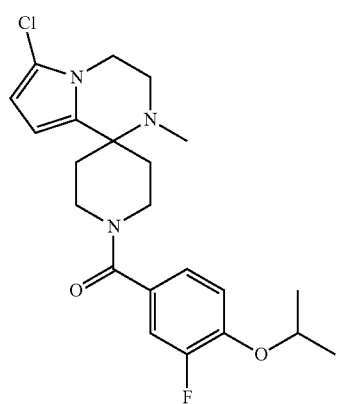 25 |

| 541 -continued | 542 -continued |
|---|---|
| 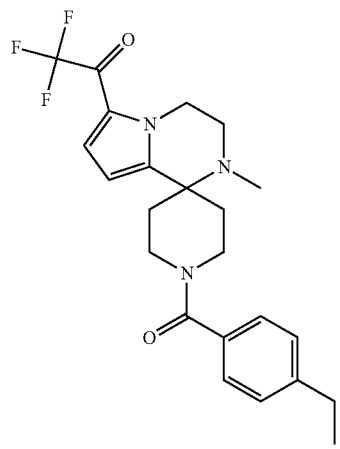 26 | 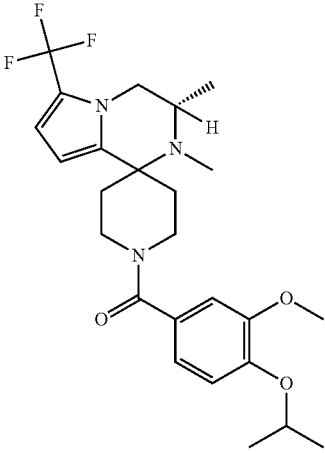 29 |
| 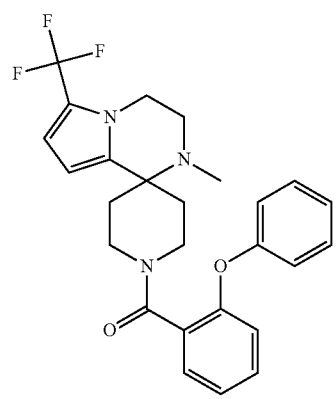 [SMILES: CN1CCn2c(C(F)(F)F)ccc2C12CCN(C(=O)c1ccccc1Oc1ccccc1)CC2] 27 | 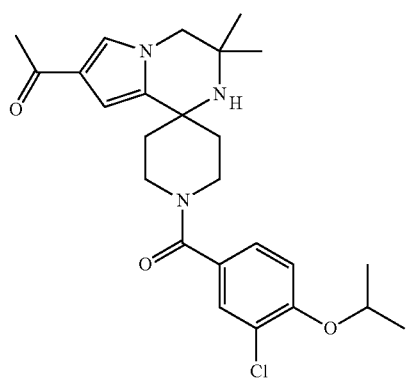 30 |
| 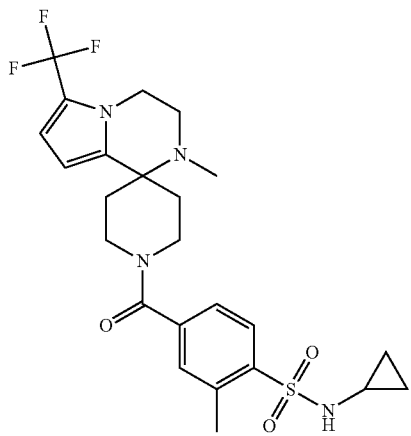 [SMILES: Cc1cc(C(=O)N2CCC3(CC2)c2ccc(C(F)(F)F)n2CCN3C)ccc1S(=O)(=O)NC1CC1] 28 | 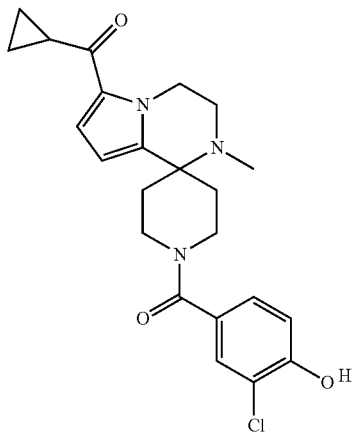 31 |

| 543 -continued | 544 -continued |
|---|---|
| 32 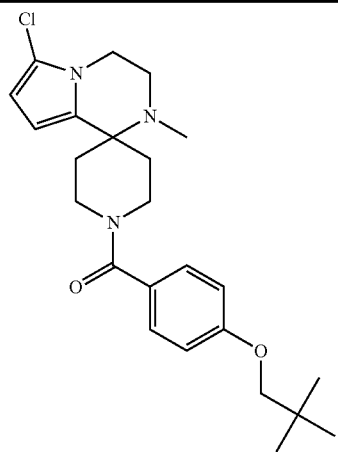 | 35 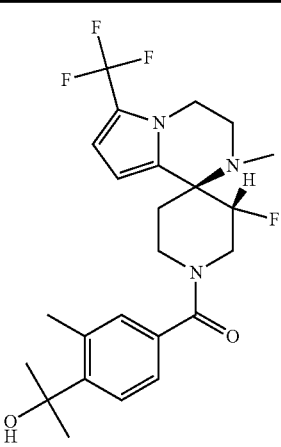 |
| 33 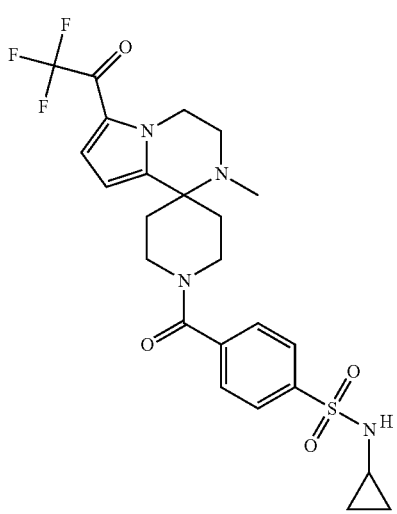 | 36 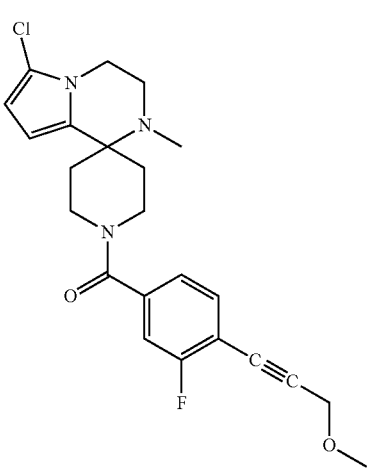 |
| 34 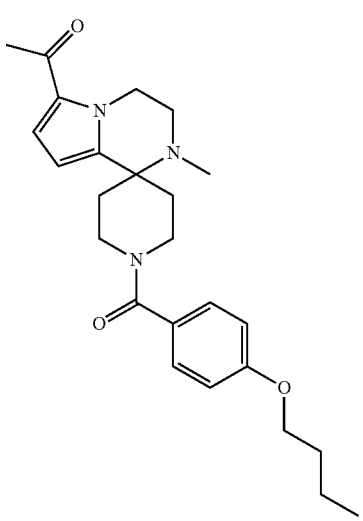 [SMILES: CCCCOc1ccc(C(=O)N2CCC3(CC2)c2ccc(C(C)=O)n2CCN3C)cc1] | 37 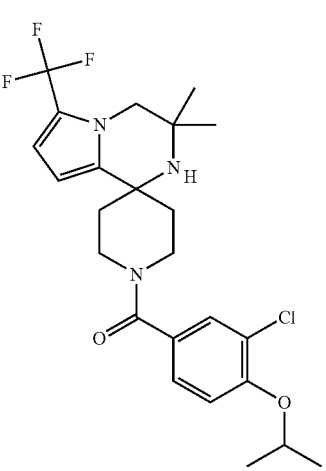 |

| 545 -continued | 546 -continued |
|---|---|
| 38 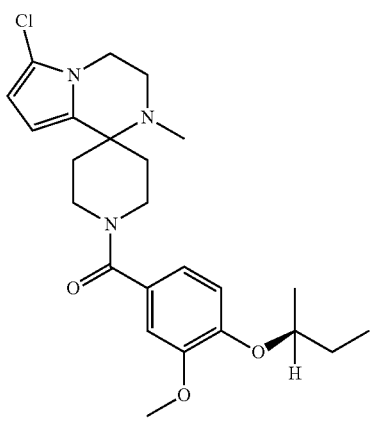 [SMILES: CC[C@H](C)Oc1ccc(C(=O)N2CCC3(CC2)c2ccc(Cl)n2CCN3C)cc1OC] | 41 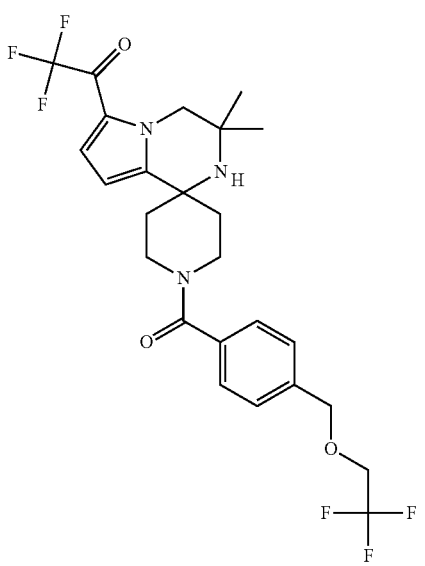 |
| 39 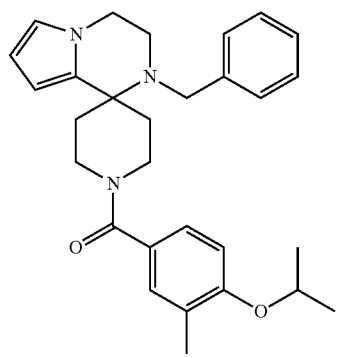 [SMILES: Cc1cc(C(=O)N2CCC3(CC2)c2cccn2CCN3Cc2ccccc2)ccc1OC(C)C] | 42 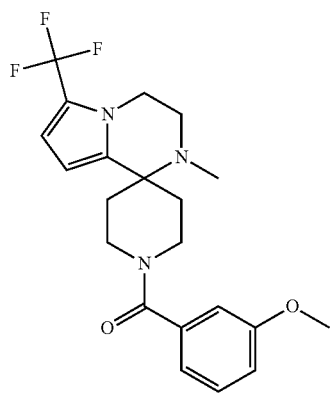 |
| 40 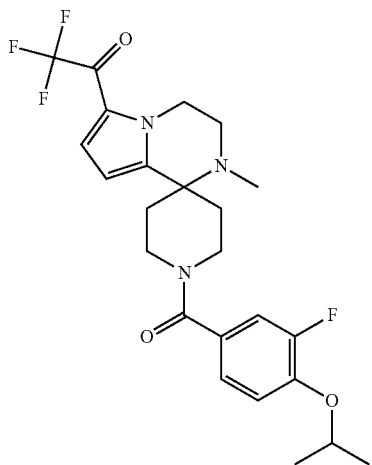 | 43 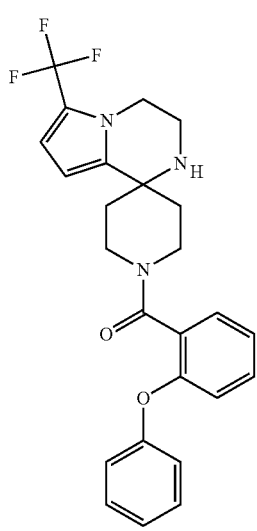 |

| 547 -continued | 548 -continued |
|---|---|
| 45 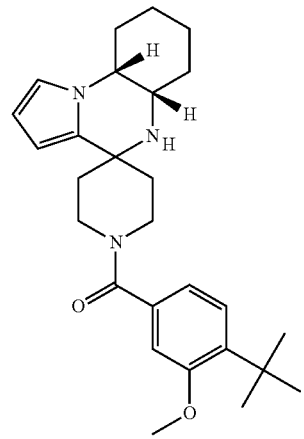 | 48 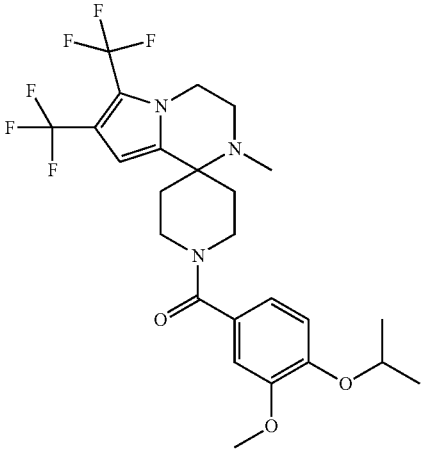 |
| 46 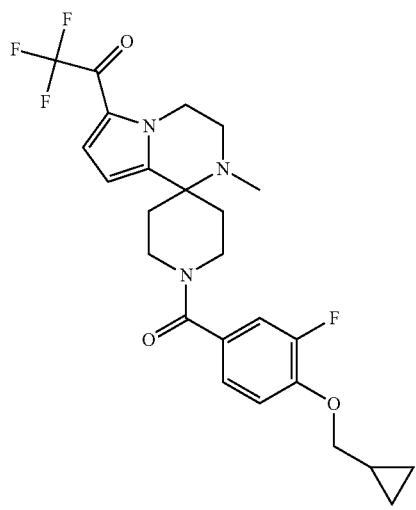 [SMILES: CN1CCn2c(C(=O)C(F)(F)F)ccc2C12CCN(C(=O)c1ccc(OCC3CC3)c(F)c1)CC2] | 50 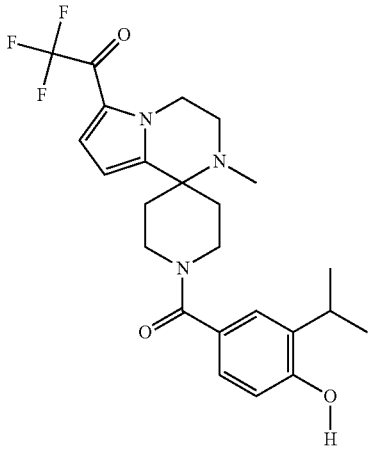 |
| 47 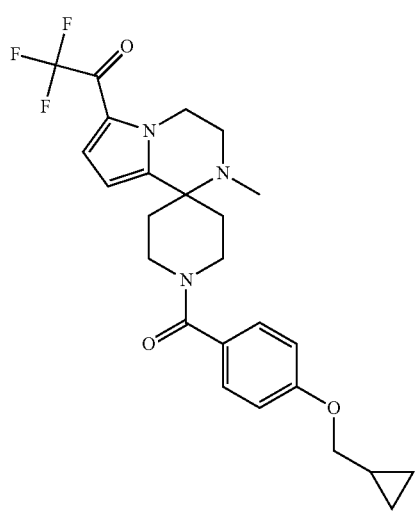 [SMILES: CN1CCn2c(C(=O)C(F)(F)F)ccc2C12CCN(C(=O)c1ccc(OCC3CC3)cc1)CC2] | 51 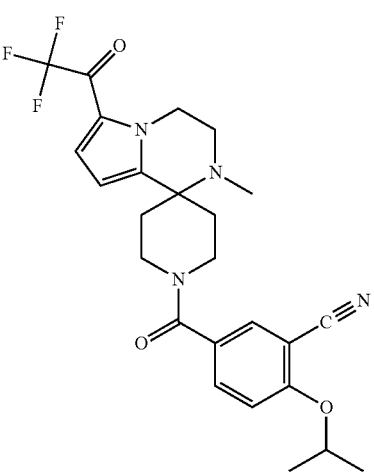 [SMILES: CC(C)Oc1ccc(C(=O)N2CCC3(CC2)c2ccc(C(=O)C(F)(F)F)n2CCN3C)cc1C#N] |

| 549 -continued | | 550 -continued | |
|---|---|---|---|
| 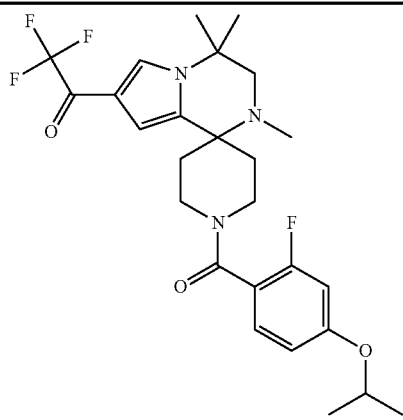 | 52 | 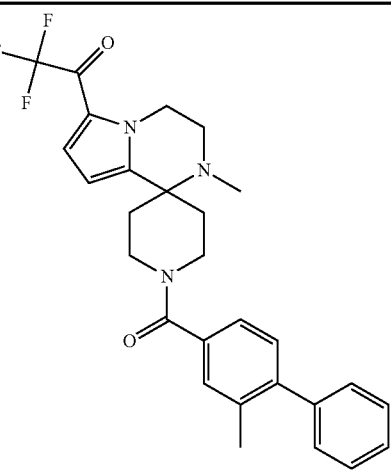 | 55 |
| 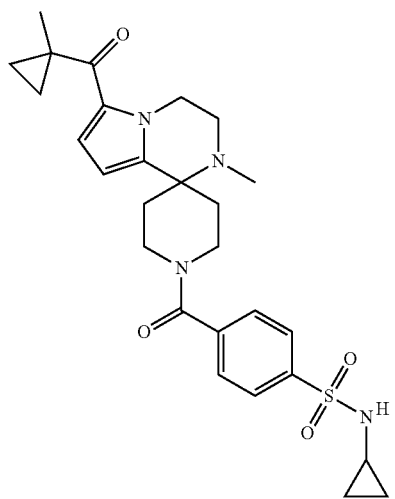 | 53 | 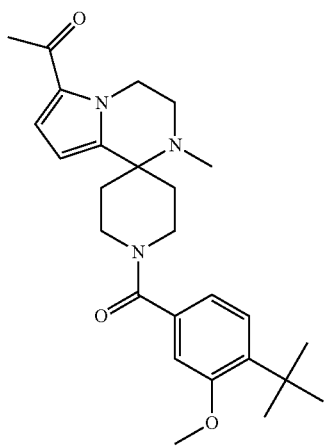 [SMILES: COc1cc(C(=O)N2CCC3(CC2)c2ccc(C(C)=O)n2CCN3C)ccc1C(C)(C)C] | 56 |
| 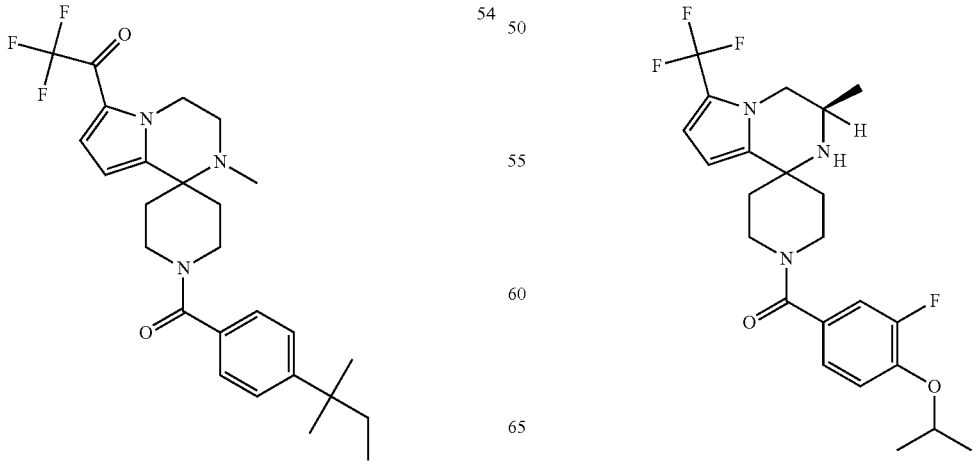 | 54 | | 57 |

| 551 -continued | 552 -continued |
|---|---|
| 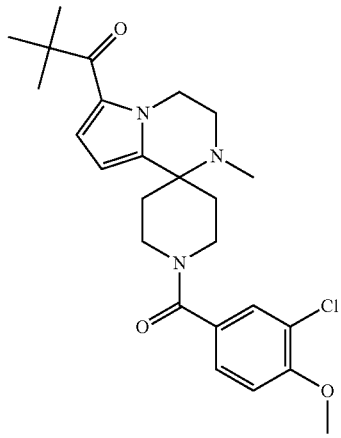 [SMILES: COc1ccc(C(=O)N2CCC3(CC2)c2ccc(C(=O)C(C)(C)C)n2CCN3C)cc1Cl] 58 | 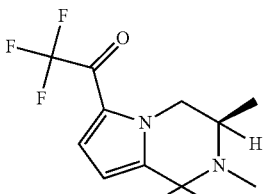 61 |
| 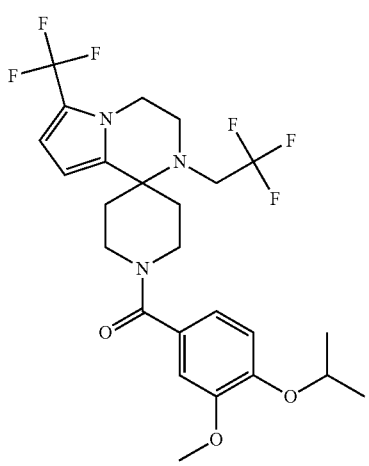 [SMILES: COc1cc(C(=O)N2CCC3(CC2)c2ccc(C(F)(F)F)n2CCN3CC(F)(F)F)ccc1OC(C)C] 59 | 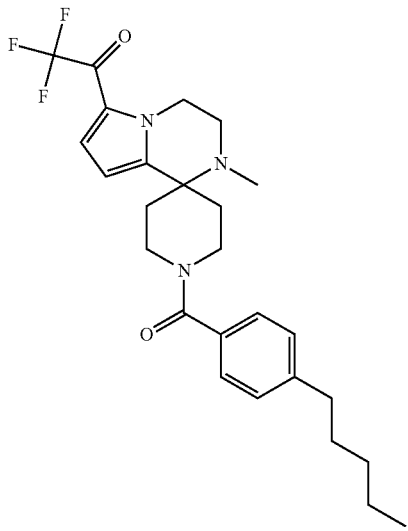 62 |
| 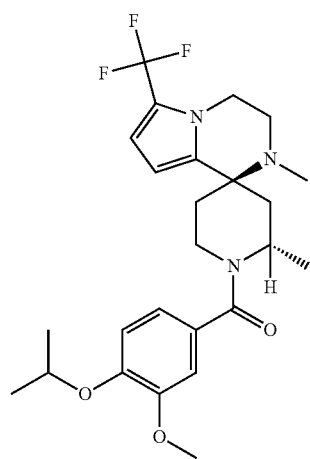 [SMILES: COc1cc(C(=O)N2CC[C@@]3(C[C@@H]2C)c2ccc(C(F)(F)F)n2CCN3C)ccc1OC(C)C] 60 | 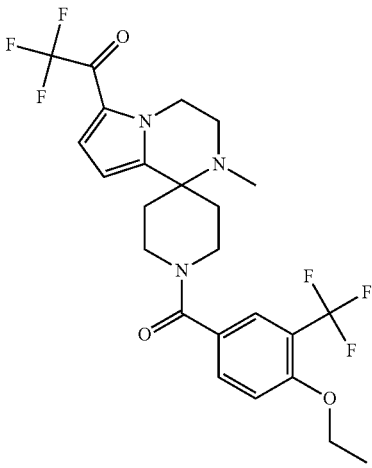 [SMILES: CCOc1ccc(C(=O)N2CCC3(CC2)c2ccc(C(=O)C(F)(F)F)n2CCN3C)cc1C(F)(F)F] 64 |

| 553 -continued | 554 -continued |
|---|---|
| 65 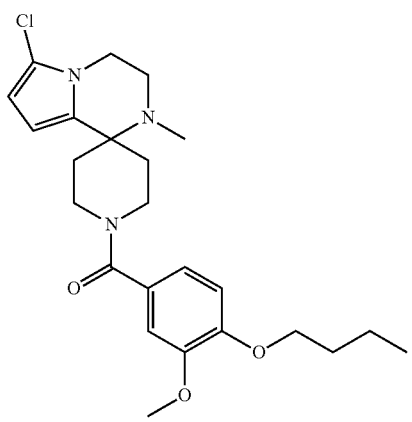 [SMILES: CCCCOc1ccc(C(=O)N2CCC3(CC2)c2ccc(Cl)n2CCN3C)cc1OC] | 68 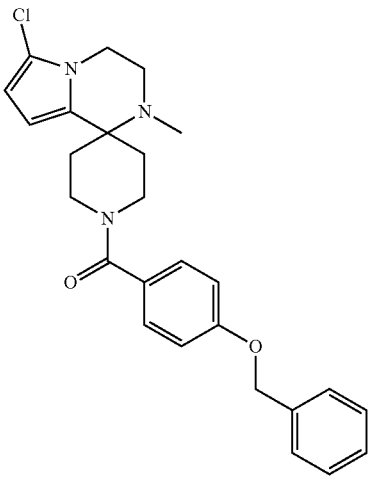 |
| 66 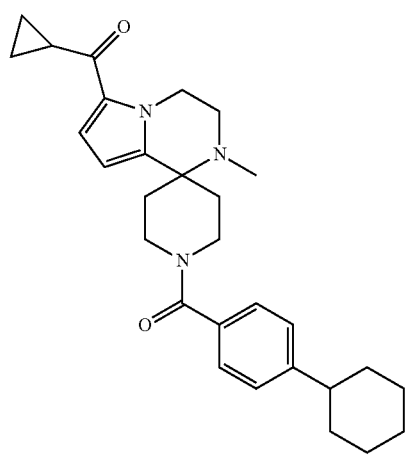 [SMILES: CN1CCn2c(C(=O)C3CC3)ccc2C12CCN(C(=O)c1ccc(C3CCCCC3)cc1)CC2] | 69 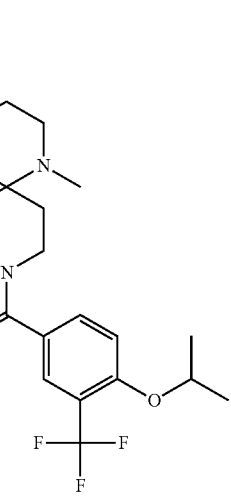 |
| 67 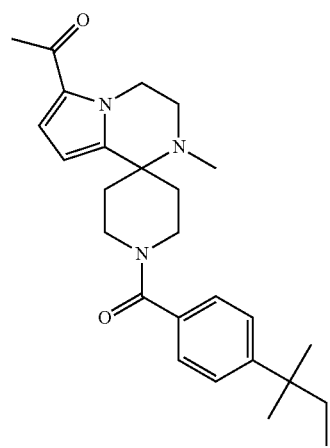 [SMILES: CCC(C)(C)c1ccc(C(=O)N2CCC3(CC2)c2ccc(C(C)=O)n2CCN3C)cc1] | 70 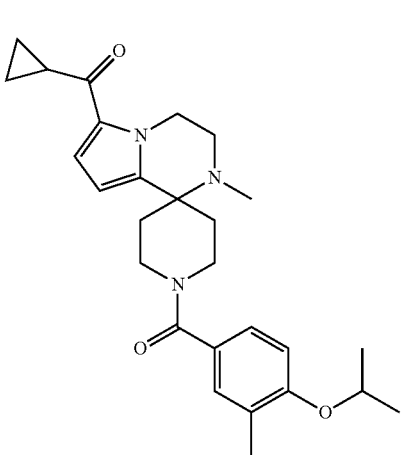 [SMILES: Cc1cc(C(=O)N2CCC3(CC2)c2ccc(C(=O)C4CC4)n2CCN3C)ccc1OC(C)C] |

| 71 | 74 |
|---|---|
| 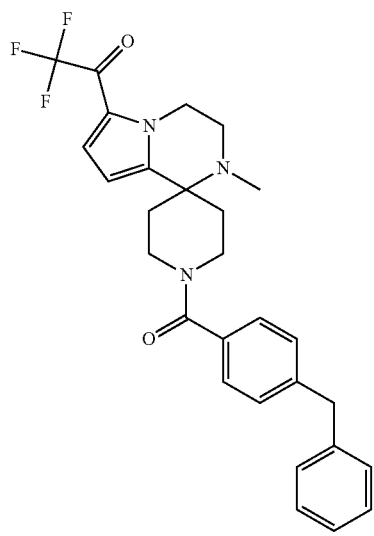 | 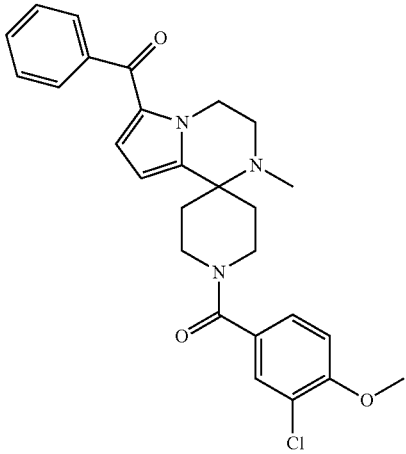 [SMILES: COc1ccc(C(=O)N2CCC3(CC2)c2ccc(C(=O)c4ccccc4)n2CCN3C)cc1Cl] |
| 72 | 75 |
| 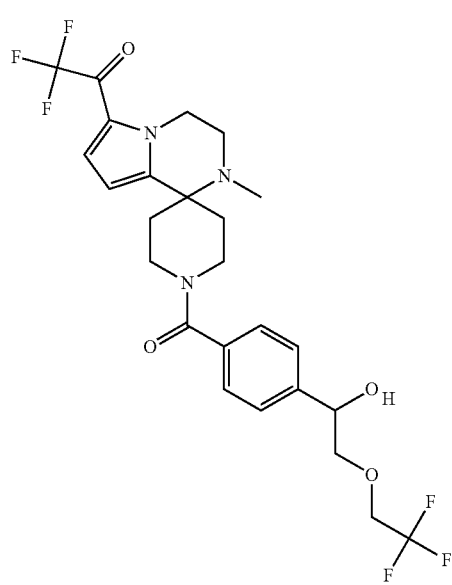 | 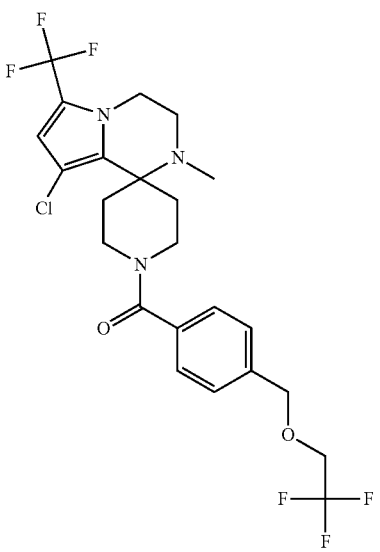 [SMILES: CN1CCn2c(C(F)(F)F)cc(Cl)c2C12CCN(C(=O)c1ccc(COCC(F)(F)F)cc1)CC2] |
| 73 | 76 |
| 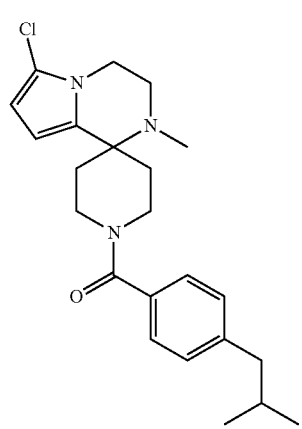 | 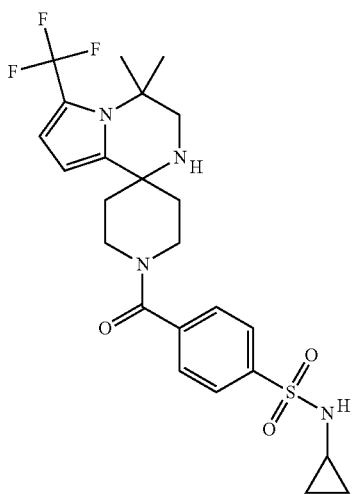 |

| 557 -continued | 558 -continued |
|---|---|
| 77 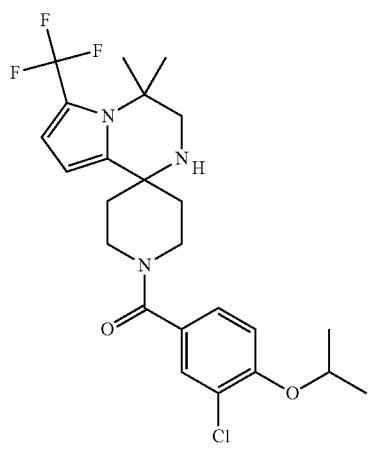 | 80 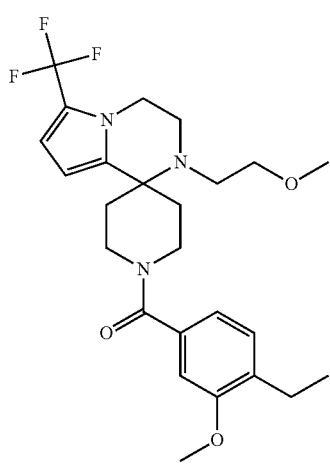 |
| 78 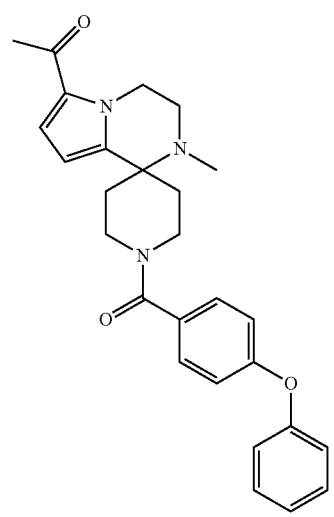 [SMILES: CC(=O)c1ccc2n1CCN(C)C21CCN(C(=O)c2ccc(Oc3ccccc3)cc2)CC1] | 81 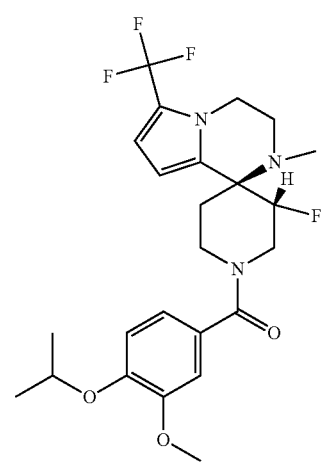 |
| 79 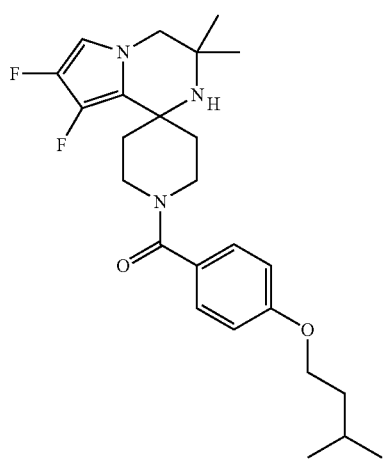 | 82 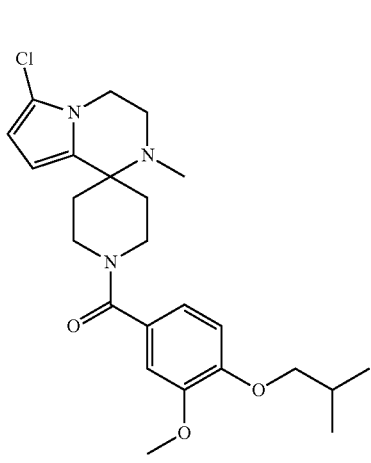 [SMILES: COc1cc(C(=O)N2CCC3(CC2)c2ccc(Cl)n2CCN3C)ccc1OCC(C)C] |

| 559 -continued | 560 -continued |
|---|---|
| 83 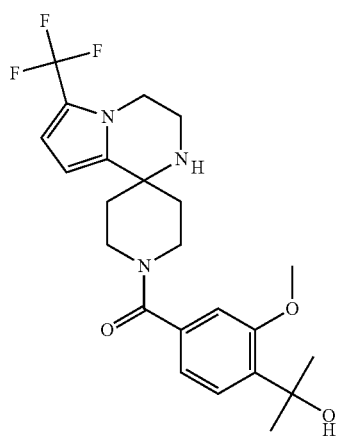 | 86 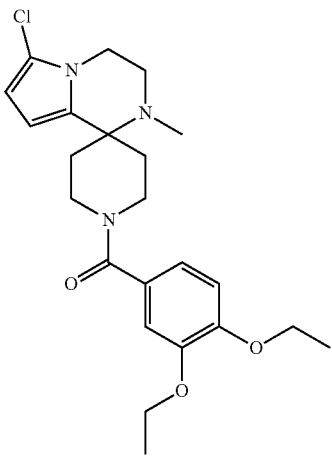 |
| 84 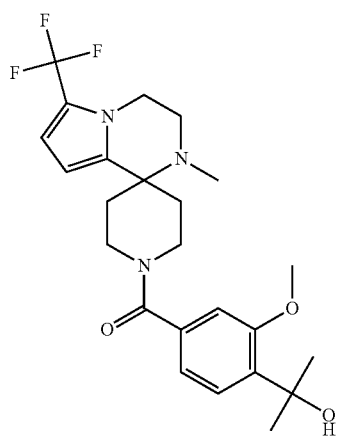 [SMILES: COc1cc(C(=O)N2CCC3(CC2)c2ccc(C(F)(F)F)n2CCN3C)ccc1C(C)(C)O] | 87 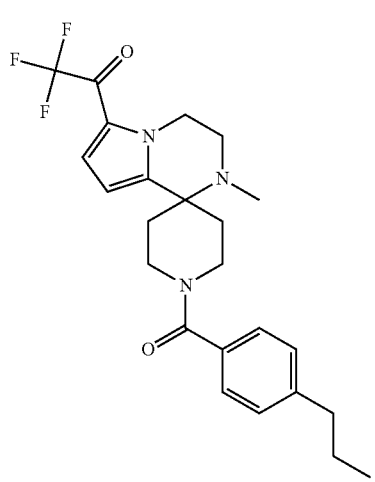 |
| 85 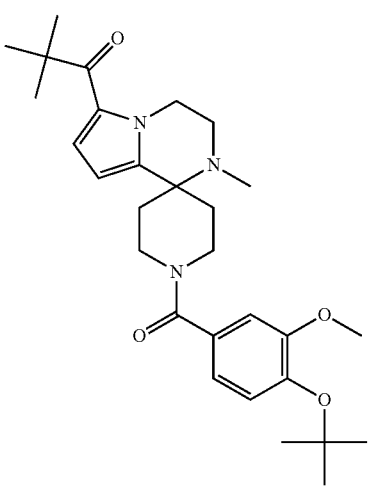 [SMILES: COc1cc(C(=O)N2CCC3(CC2)c2ccc(C(=O)C(C)(C)C)n2CCN3C)ccc1OC(C)(C)C] | 88 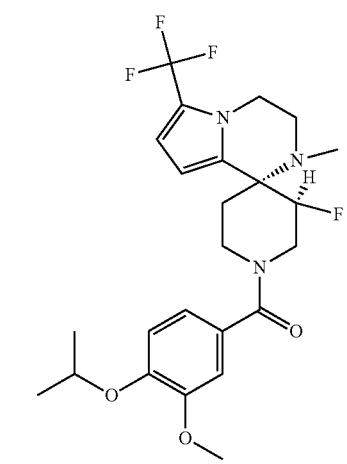 [SMILES: COc1cc(C(=O)N2CC[C@@]3(c4ccc(C(F)(F)F)n4CCN3C)[C@@H](F)C2)ccc1OC(C)C] |

| 561 -continued | 562 -continued |
|---|---|
| 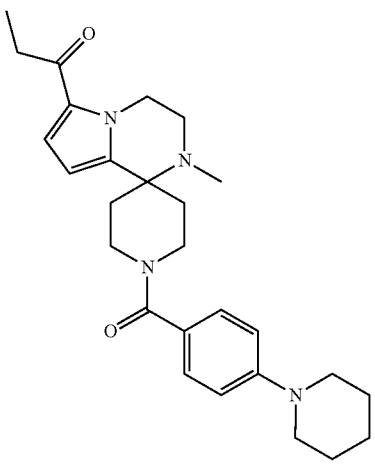 [SMILES: CCC(=O)c1ccc2n1CCN(C)C21CCN(C(=O)c2ccc(N3CCCCC3)cc2)CC1] 89 | 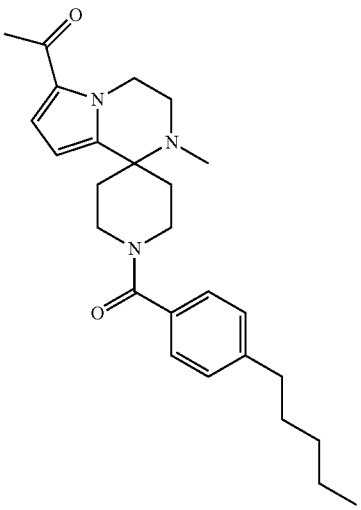 92 |
| 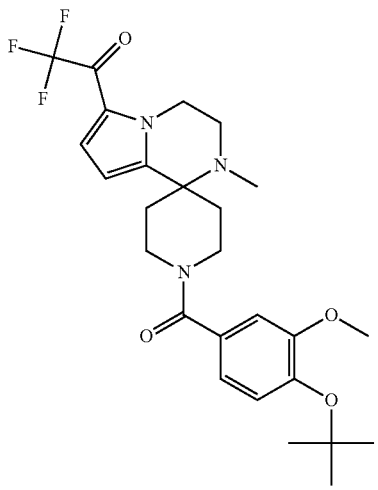 [SMILES: COc1cc(C(=O)N2CCC3(CC2)c2ccc(C(=O)C(F)(F)F)n2CCN3C)ccc1OC(C)(C)C] 90 | 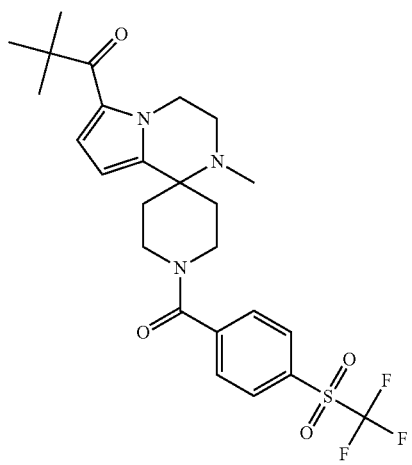 93 |
| 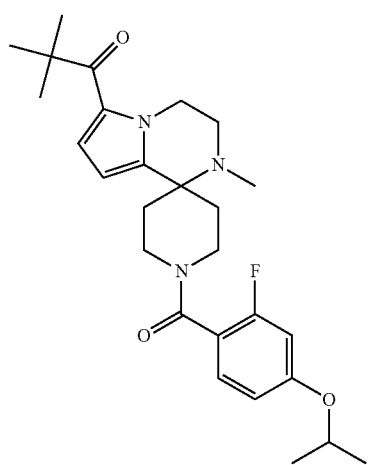 [SMILES: CC(C)Oc1ccc(C(=O)N2CCC3(CC2)c2ccc(C(=O)C(C)(C)C)n2CCN3C)c(F)c1] 91 | 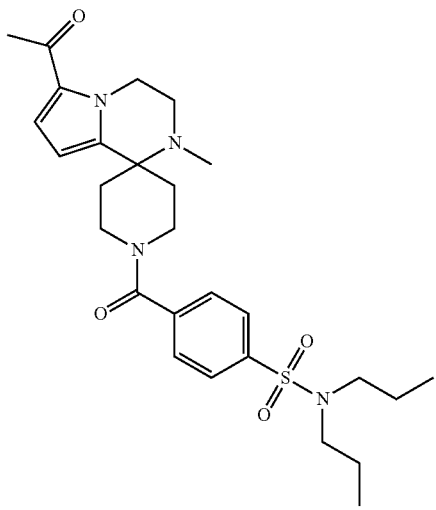 [SMILES: CCCN(CCC)S(=O)(=O)c1ccc(C(=O)N2CCC3(CC2)c2ccc(C(C)=O)n2CCN3C)cc1] 94 |

| 563 -continued | 564 -continued |
|---|---|
| 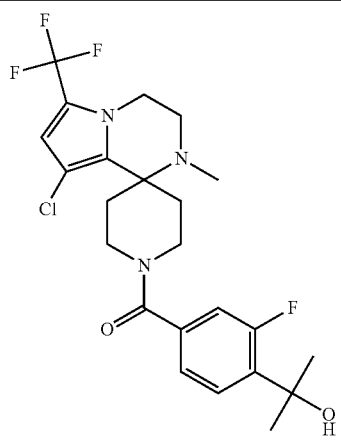 95 | 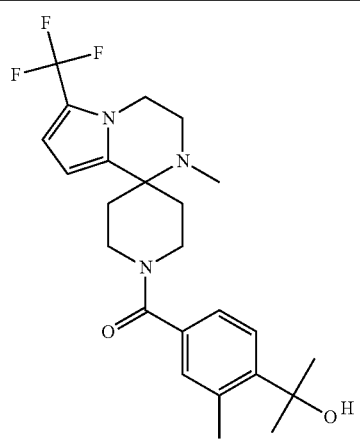 98 |
| 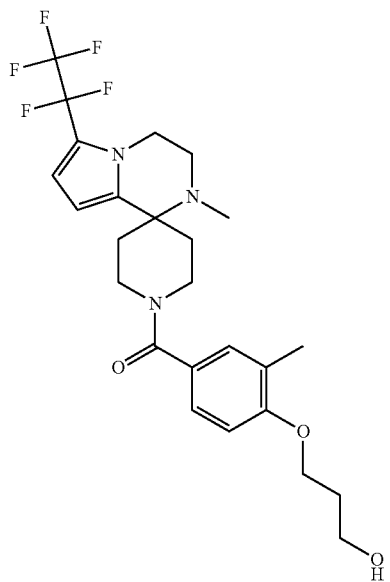 [SMILES: Cc1cc(C(=O)N2CCC3(CC2)c2ccc(C(F)(F)C(F)(F)F)n2CCN3C)ccc1OCCCO] 96 | 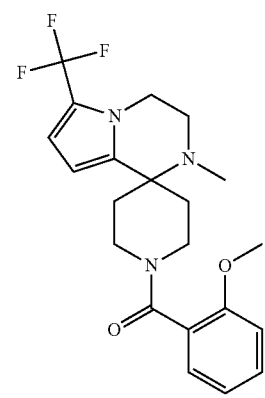 99 |
| 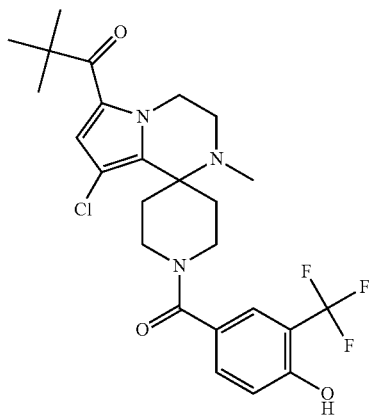 [SMILES: CN1CCn2c(C(=O)C(C)(C)C)cc(Cl)c2C12CCN(C(=O)c1ccc(O)c(C(F)(F)F)c1)CC2] 97 | 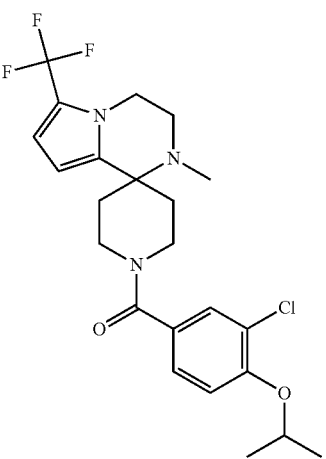 [SMILES: CC(C)Oc1ccc(C(=O)N2CCC3(CC2)c2ccc(C(F)(F)F)n2CCN3C)cc1Cl] 100 |

| 565 -continued | | 566 -continued | |
|---|---|---|---|
| 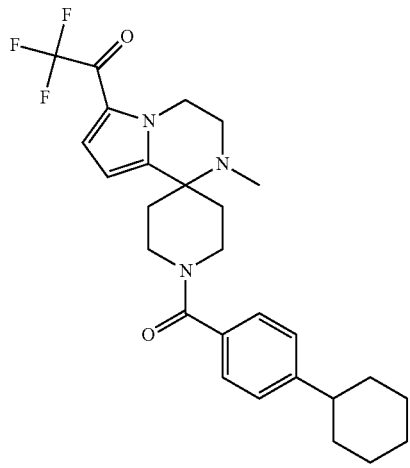 | 101 | 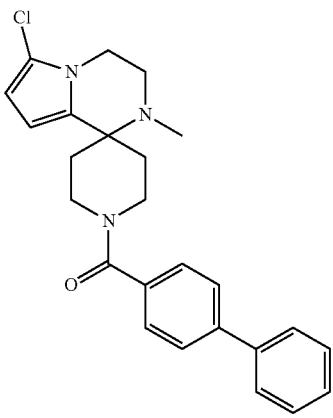 | 104 |
| 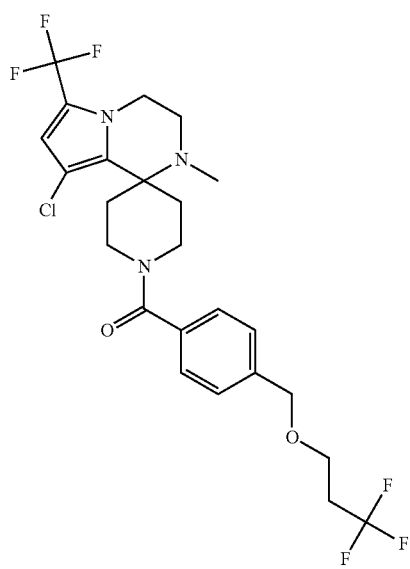 [SMILES: CN1CCn2c(C(F)(F)F)cc(Cl)c2C12CCN(C(=O)c1ccc(COCCC(F)(F)F)cc1)CC2] | 102 | 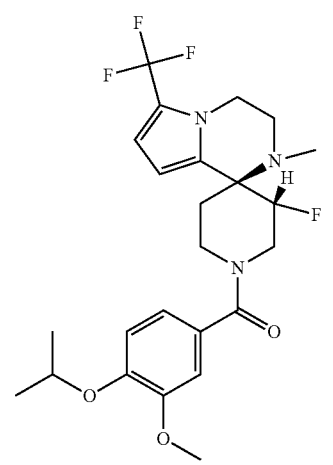 [SMILES: COc1cc(C(=O)N2CC[C@]3(c4ccc(C(F)(F)F)n4CCN3C)[C@H](F)C2)ccc1OC(C)C] | 105 |
| 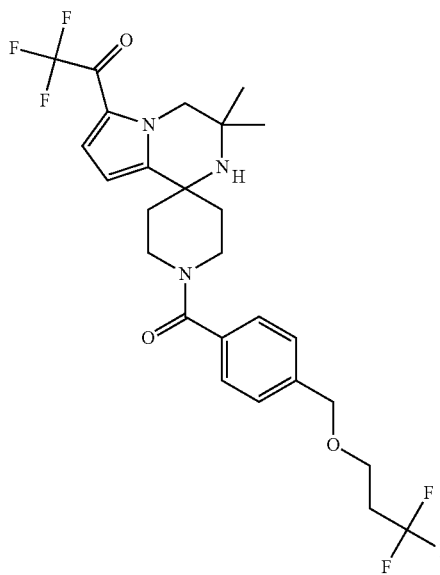 | 103 | 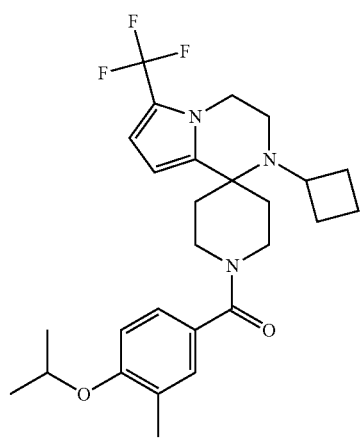 [SMILES: Cc1cc(C(=O)N2CCC3(CC2)c2ccc(C(F)(F)F)n2CCN3C2CCC2)ccc1OC(C)C] | 106 |

| 567 -continued | 568 -continued |
|---|---|
| 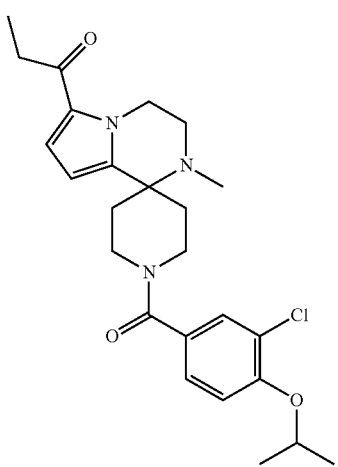 [SMILES: CCC(=O)c1ccc2n1CCN(C)C21CCN(C(=O)c2ccc(OC(C)C)c(Cl)c2)CC1] 107 | 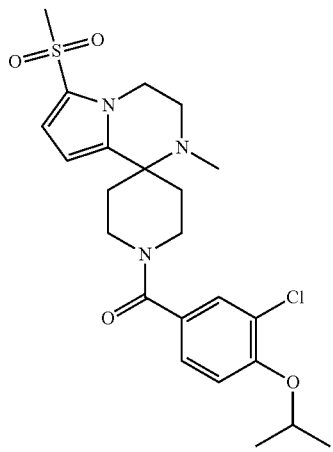 111 |
| 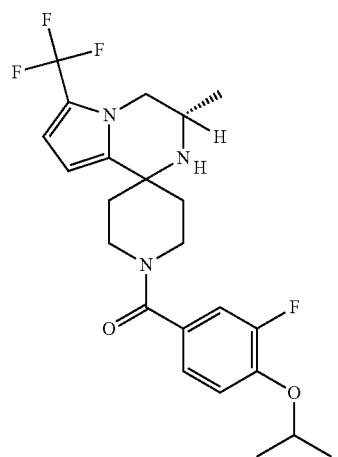 108 | 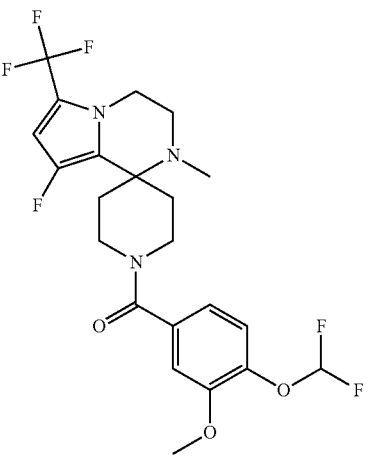 112 |
| 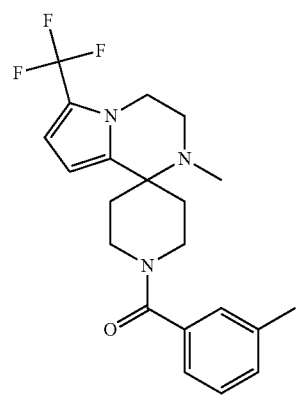 [SMILES: Cc1cccc(C(=O)N2CCC3(CC2)c2ccc(C(F)(F)F)n2CCN3C)c1] 109 | 113 |

| 569 -continued | | 570 -continued | |
|---|---|---|---|
| 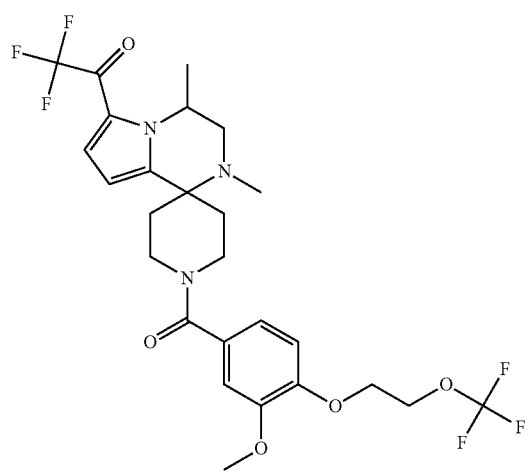 | 114 | 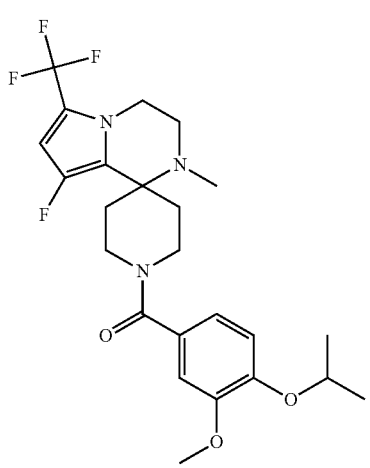 [SMILES: COc1cc(C(=O)N2CCC3(CC2)c2c(F)cc(C(F)(F)F)n2CCN3C)ccc1OC(F)F] | 118 |
| 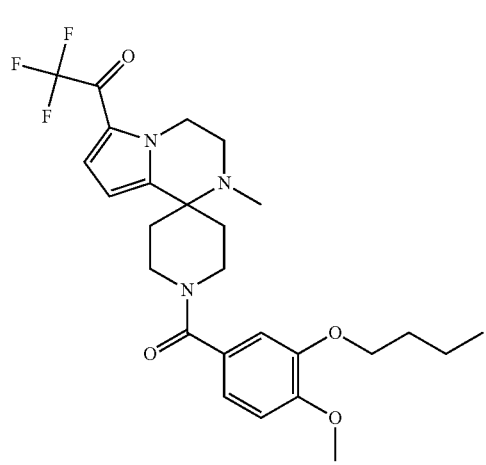 [SMILES: CCCCOc1cc(C(=O)N2CCC3(CC2)c2ccc(C(=O)C(F)(F)F)n2CCN3C)ccc1OC] | 115 | 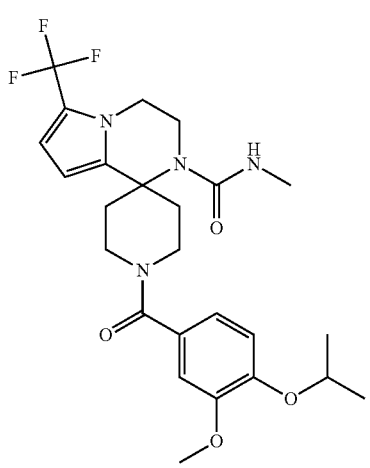 | 119 |
| 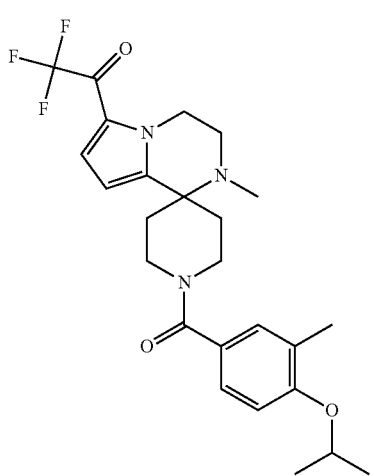 | 117 | 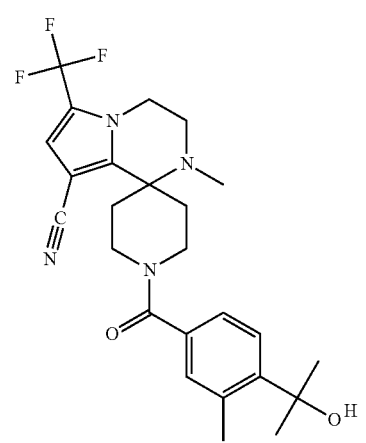 | 120 |

| 571 -continued | 572 -continued |
|---|---|
| 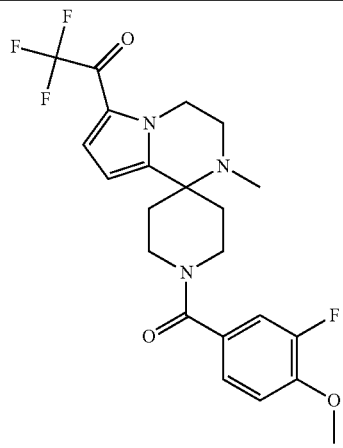 121 | 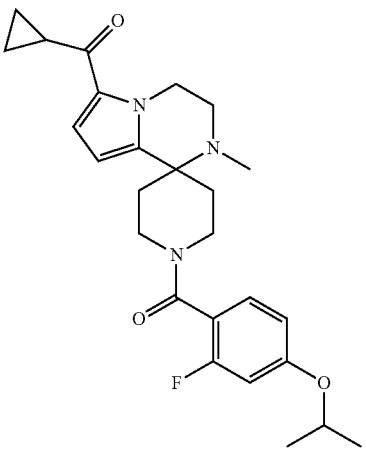 124 |
| 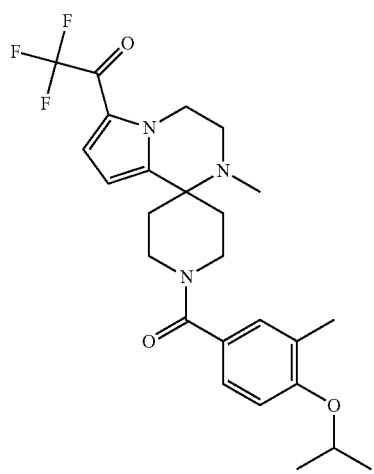 122 | 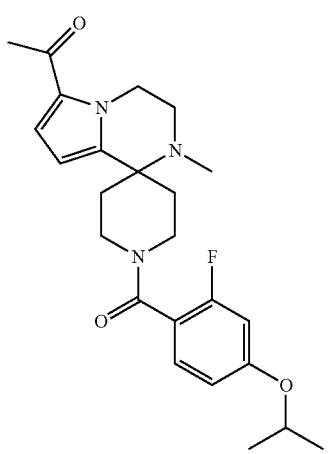 125 |
| 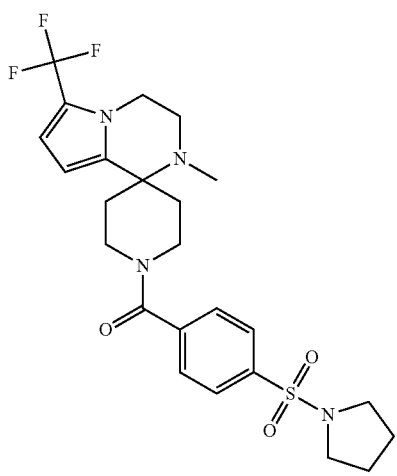 [SMILES: CN1CCn2c(C(F)(F)F)ccc2C12CCN(C(=O)c1ccc(S(=O)(=O)N3CCCC3)cc1)CC2] 123 | 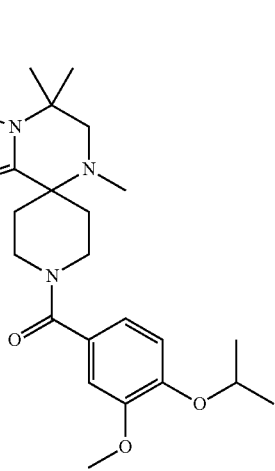 126 |

127 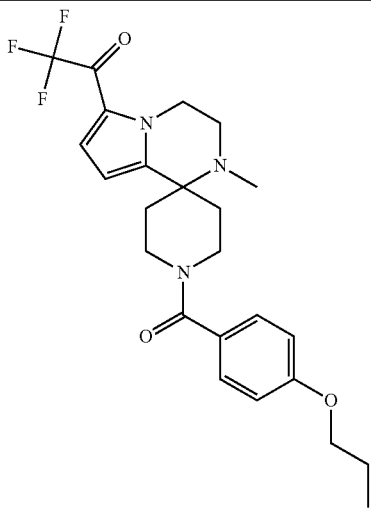
130 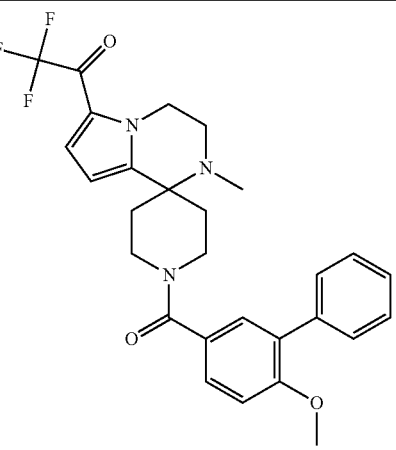
128 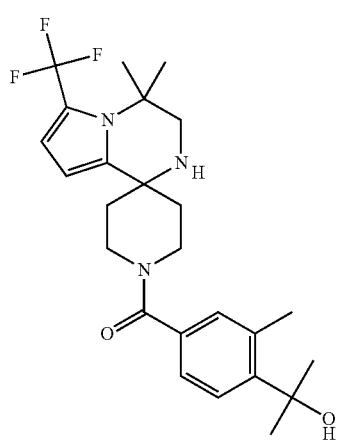
131 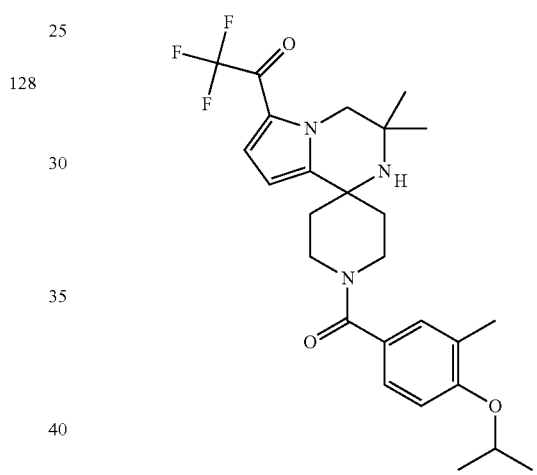
129 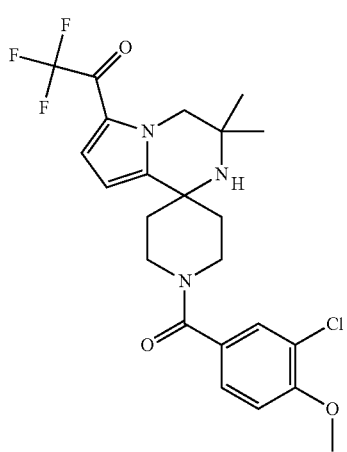
132 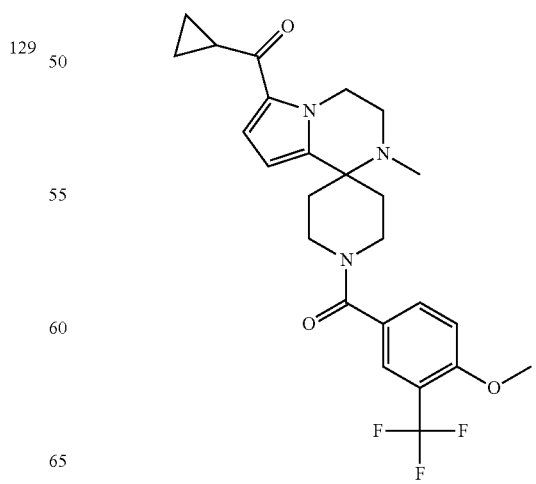

| 575 -continued | | 576 -continued | |
|---|---|---|---|
| 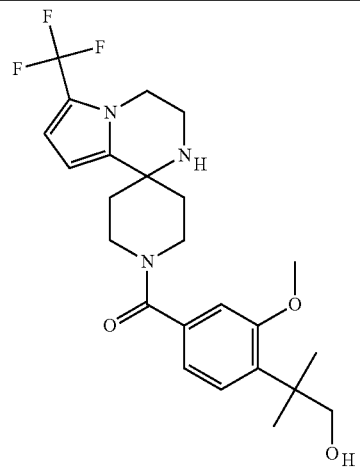 | 133 | 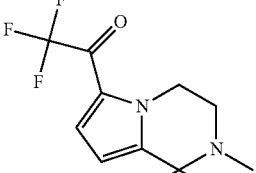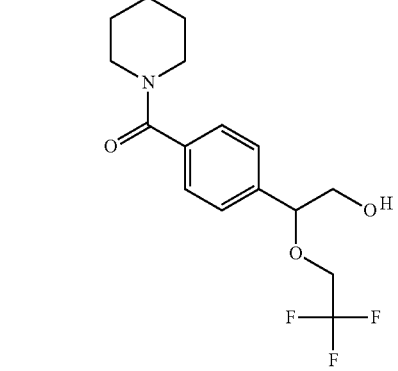 | 136 |
| 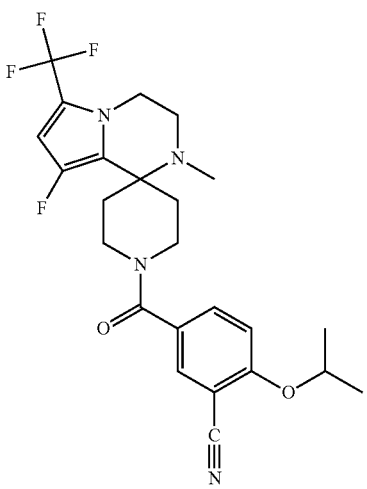 [SMILES: CC(C)Oc1ccc(C(=O)N2CCC3(CC2)c2c(F)cc(C(F)(F)F)n2CCN3C)cc1C#N] | 134 | | 137 |
| | | 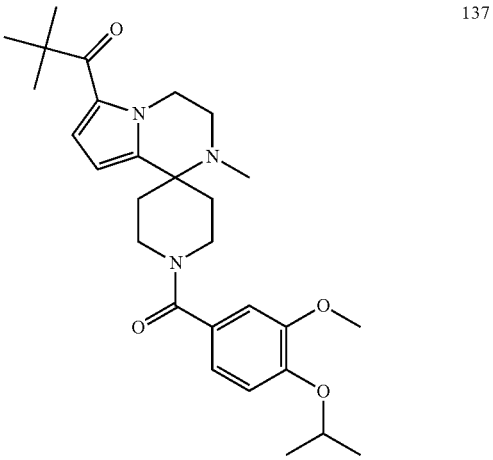 | |
| 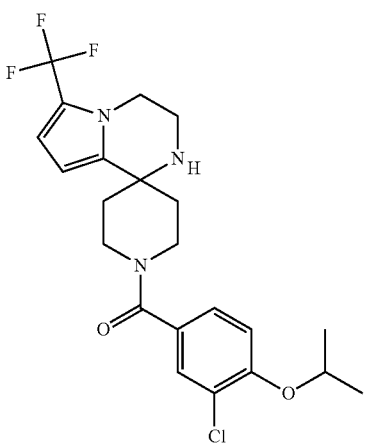 | 135 | 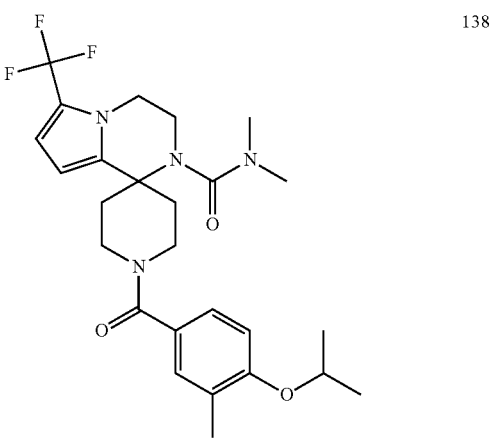 | 138 |

| 577 -continued | 578 -continued |
|---|---|
| 139 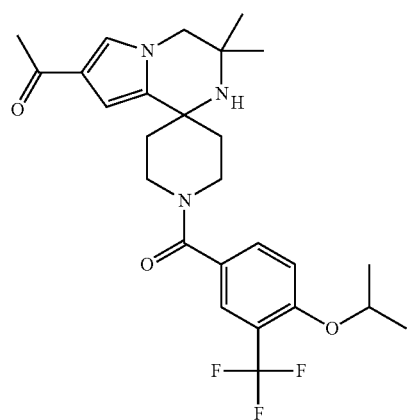 | 142 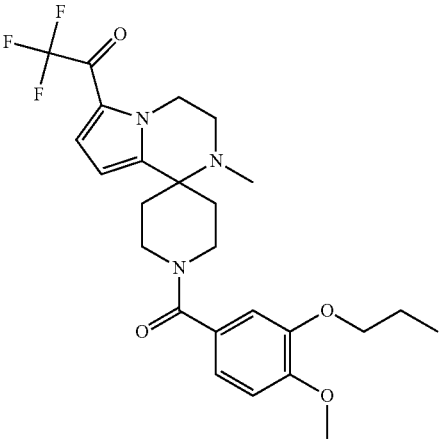 |
| 140 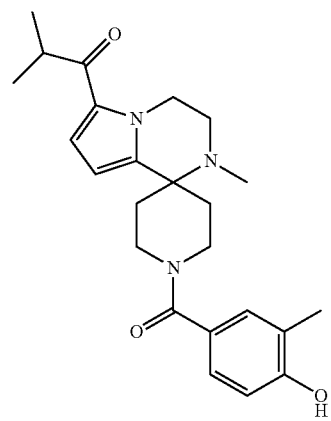 [SMILES: Cc1cc(C(=O)N2CCC3(CC2)c2ccc(C(=O)C(C)C)n2CCN3C)ccc1O] | 143 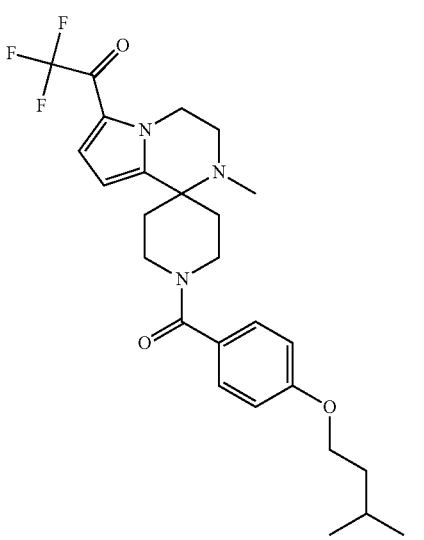 |
| 141 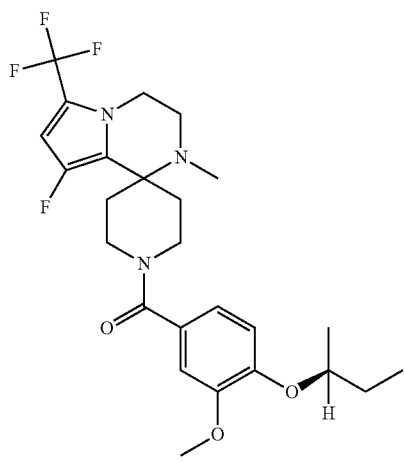 [SMILES: CC[C@H](C)Oc1ccc(C(=O)N2CCC3(CC2)c2c(F)cc(C(F)(F)F)n2CCN3C)cc1OC] | 144 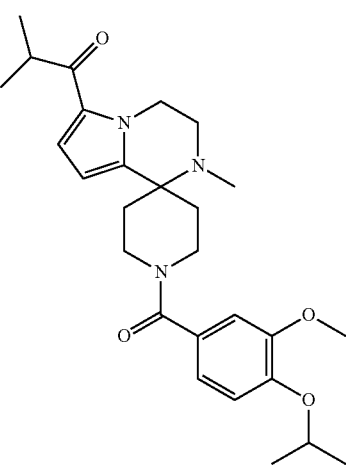 |

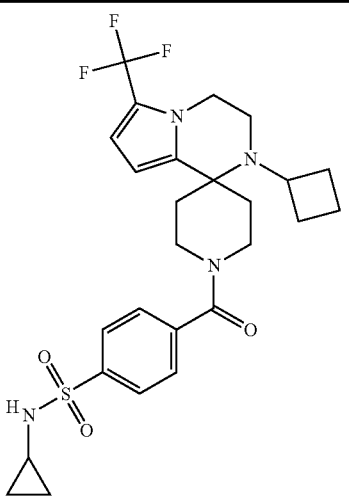
145
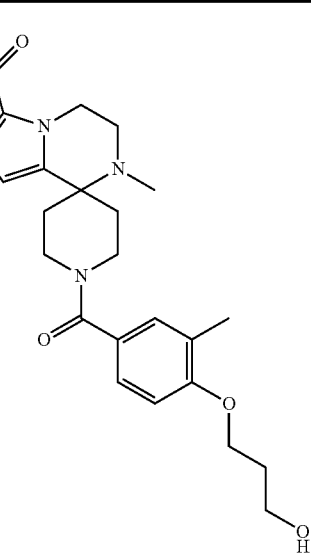
148
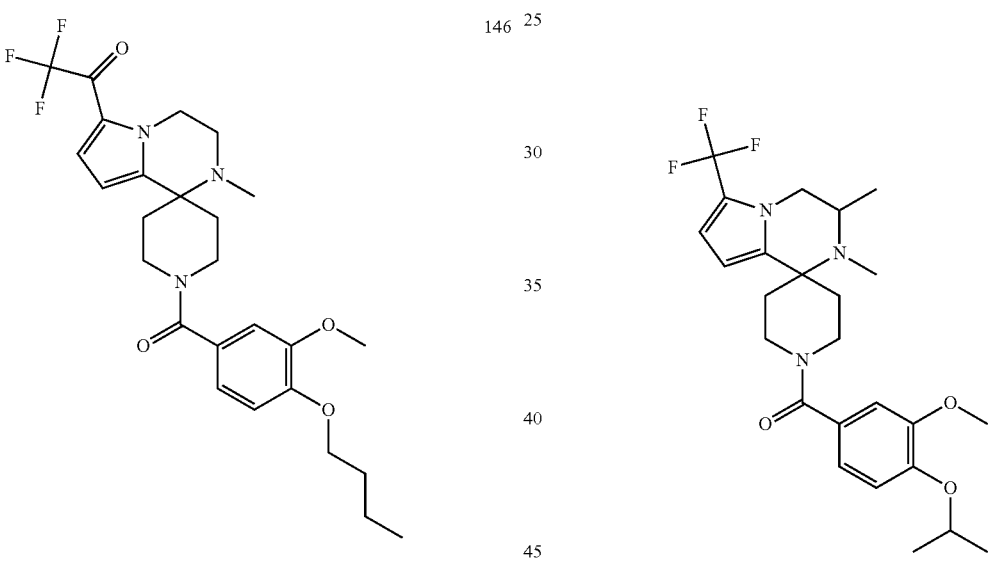
146
149
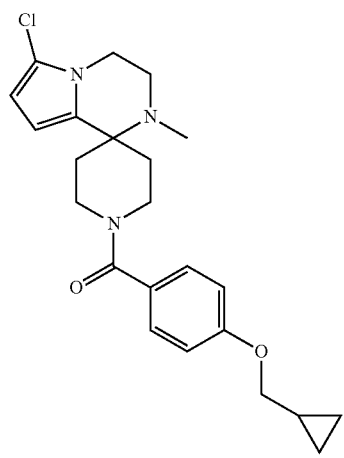 [SMILES: CN1CCn2c(Cl)ccc2C12CCN(C(=O)c1ccc(OCC3CC3)cc1)CC2]
147
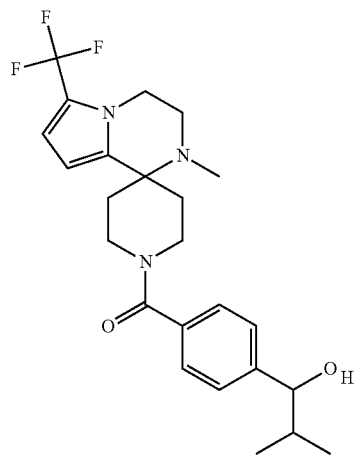
150

| 581 -continued | 582 -continued |
|---|---|
| 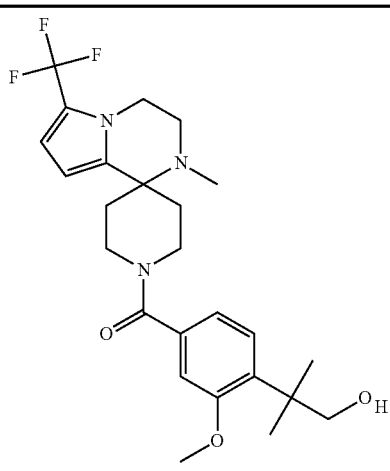 151 | 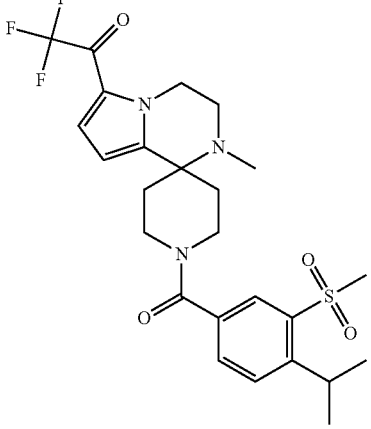 154 |
| 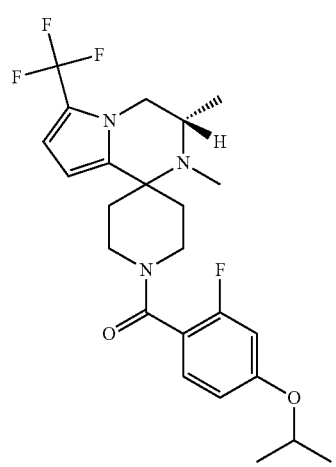 [SMILES: CC(C)Oc1ccc(C(=O)N2CCC3(CC2)c2ccc(C(F)(F)F)n2C[C@H](C)N3C)c(F)c1] 152 | 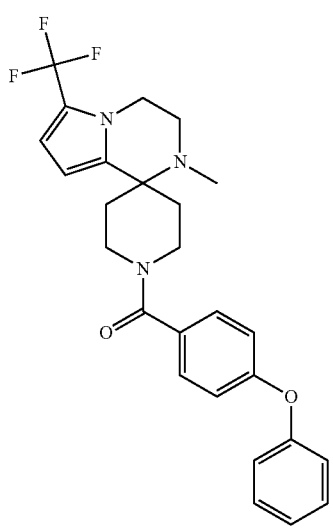 155 |
| 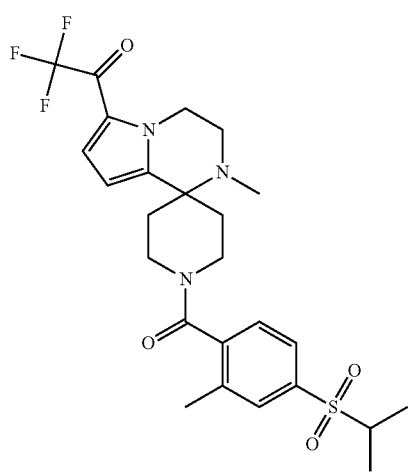 [SMILES: Cc1cc(S(=O)(=O)C(C)C)ccc1C(=O)N1CCC2(CC1)c1ccc(C(=O)C(F)(F)F)n1CCN2C] 153 | 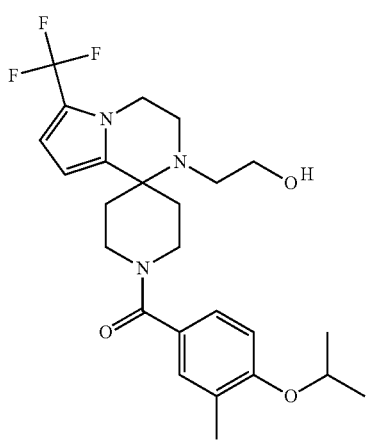 156 |

| 158 | 163 |
|---|---|
| 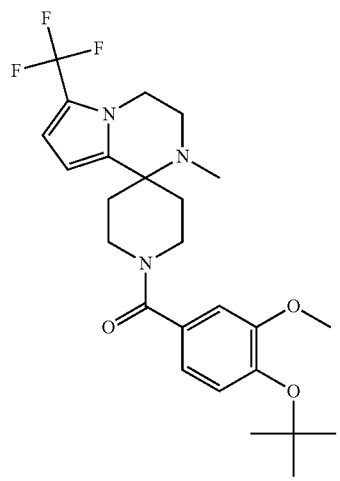 [SMILES: COc1cc(C(=O)N2CCC3(CC2)c2ccc(C(F)(F)F)n2CCN3C)ccc1OC(C)(C)C] | 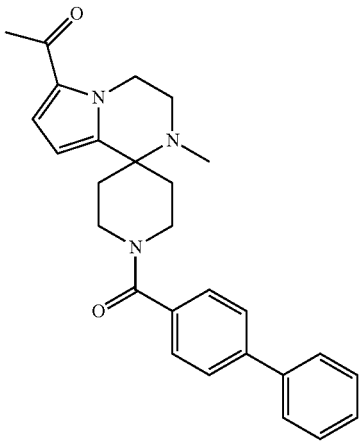 [SMILES: CC(=O)c1ccc2n1CCN(C)C21CCN(C(=O)c2ccc(-c3ccccc3)cc2)CC1] |
| 160 | 164 |
| 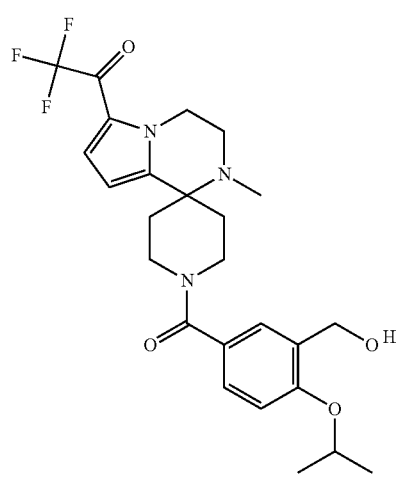 | 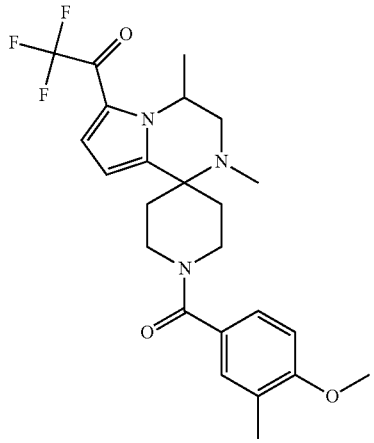 |
| 161 | 165 |
| 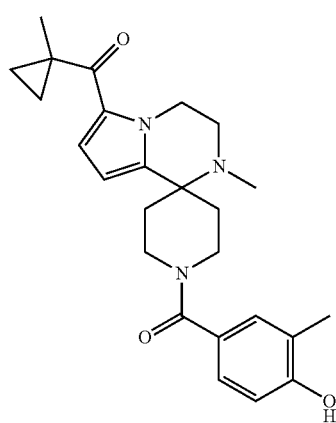 | 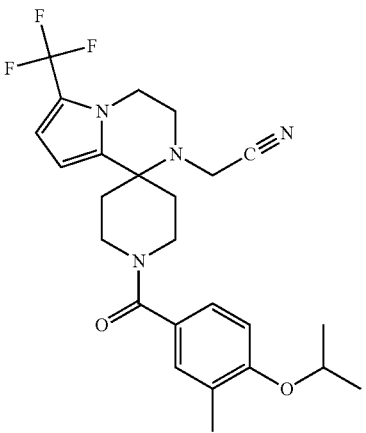 |

166 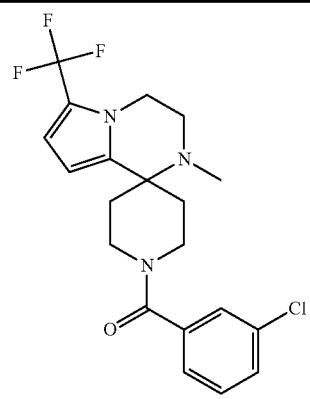
167 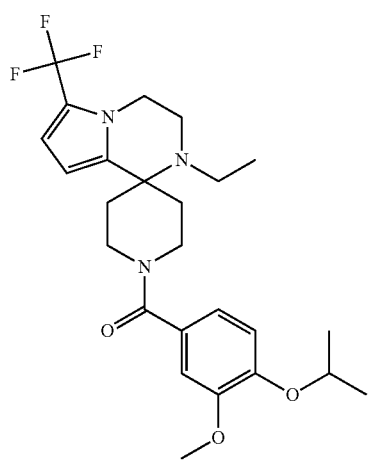 [SMILES: CCN1CCn2c(C(F)(F)F)ccc2C12CCN(C(=O)c1ccc(OC(C)C)c(OC)c1)CC2]
168 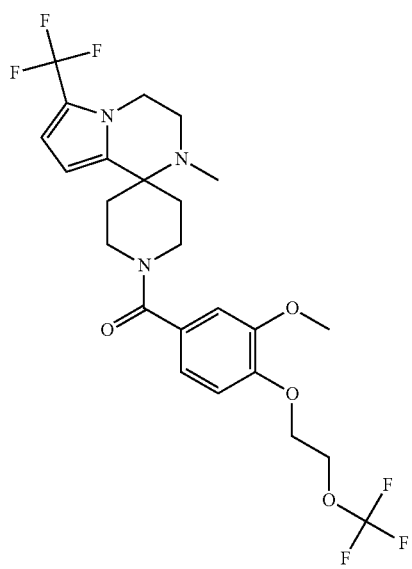 [SMILES: COc1cc(C(=O)N2CCC3(CC2)c2ccc(C(F)(F)F)n2CCN3C)ccc1OCCOC(F)(F)F]
169 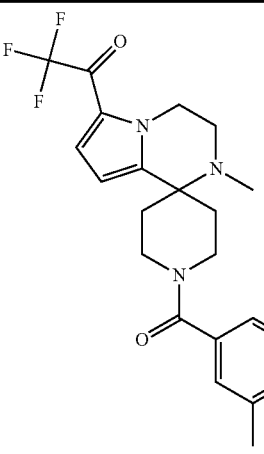
170 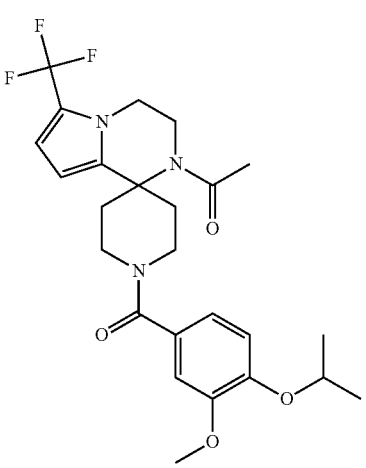 [SMILES: COc1cc(C(=O)N2CCC3(CC2)c2ccc(C(F)(F)F)n2CCN3C(C)=O)ccc1OC(C)C]
171 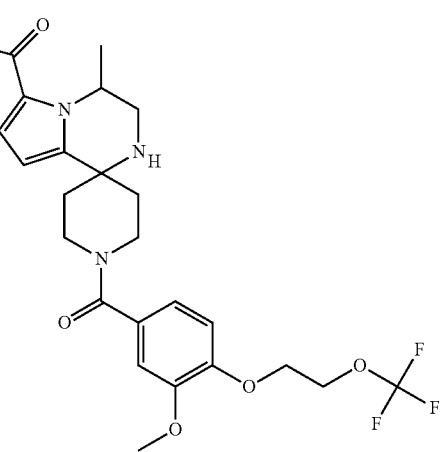

172 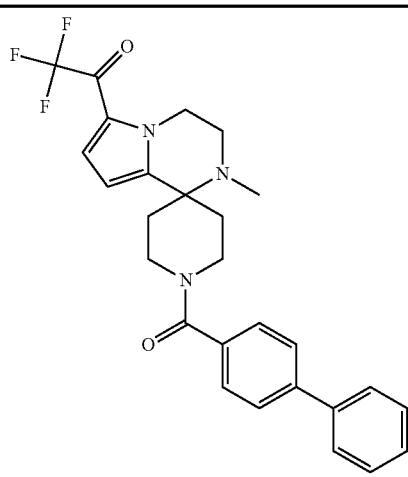
173 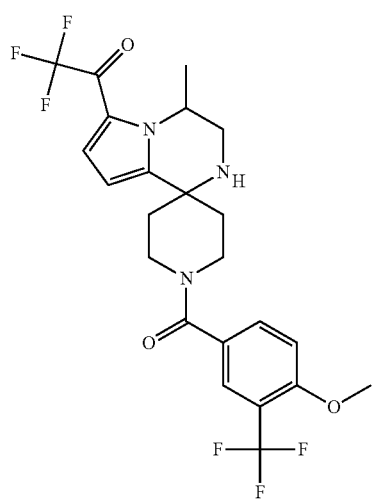
174 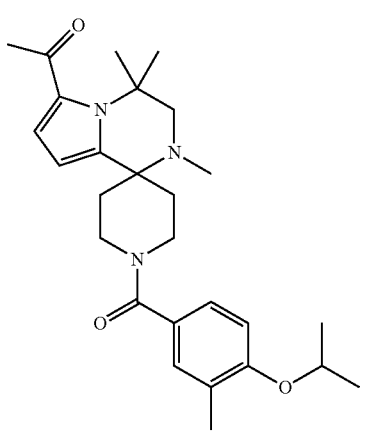 [SMILES: CC(=O)c1ccc2n1C(C)(C)CN(C)C21CCN(C(=O)c2ccc(OC(C)C)c(C)c2)CC1]
175 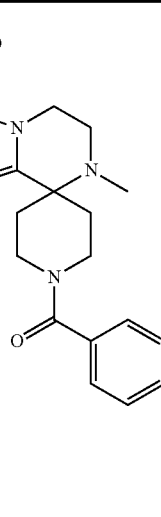
176 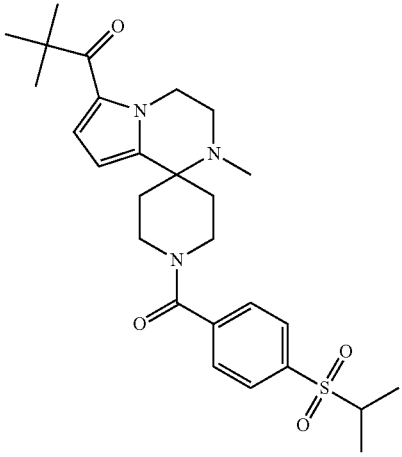 [SMILES: CC(C)S(=O)(=O)c1ccc(C(=O)N2CCC3(CC2)c2ccc(C(=O)C(C)(C)C)n2CCN3C)cc1]
177 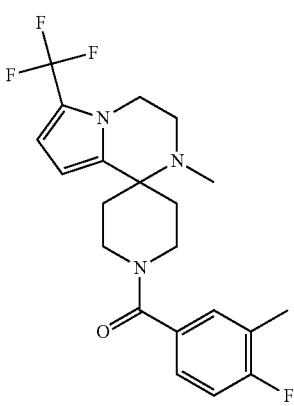 [SMILES: Cc1cc(C(=O)N2CCC3(CC2)c2ccc(C(F)(F)F)n2CCN3C)ccc1F]

| 589 -continued | 590 -continued |
|---|---|
| 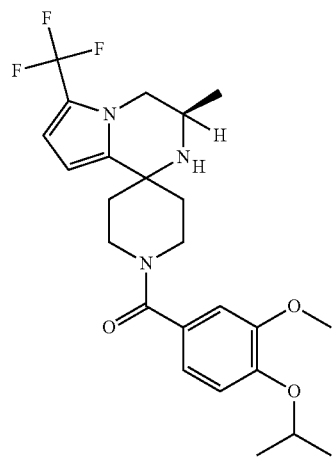 179 | 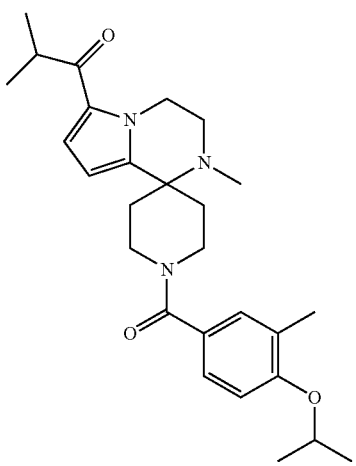 182 |
| 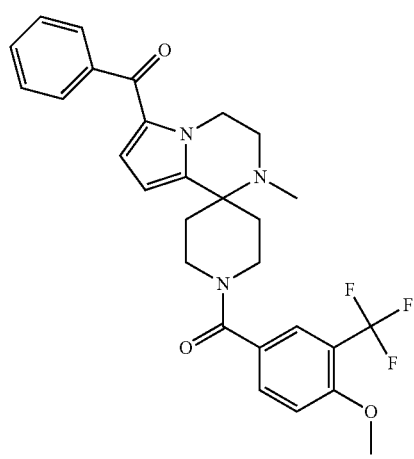 [SMILES: COc1ccc(C(=O)N2CCC3(CC2)c2ccc(C(=O)c4ccccc4)n2CCN3C)cc1C(F)(F)F] 180 | 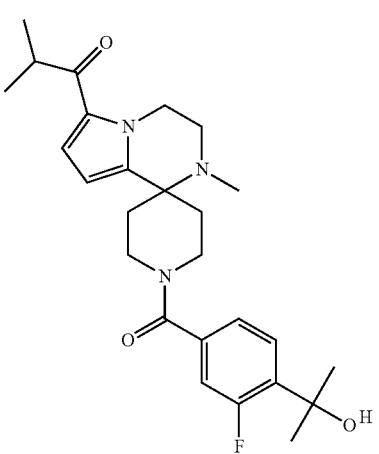 183 |
| 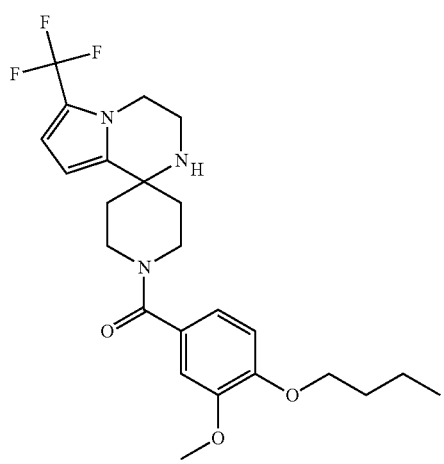 181 | 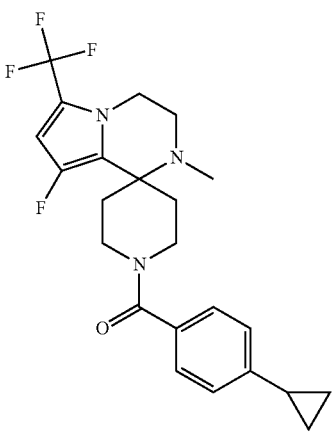 [SMILES: CN1CCn2c(C(F)(F)F)cc(F)c2C12CCN(C(=O)c1ccc(C3CC3)cc1)CC2] 184 |

| 185 | 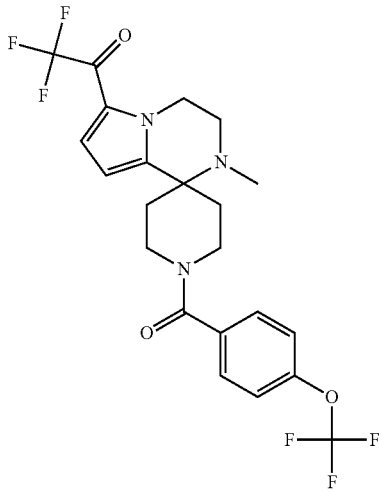 [SMILES: CN1CCn2c(C(=O)C(F)(F)F)ccc2C12CCN(C(=O)c1ccc(OC(F)(F)F)cc1)CC2] |
| 186 | 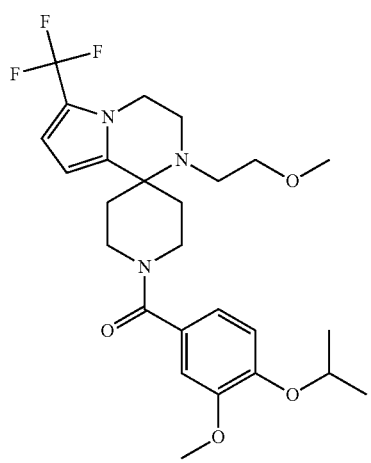 [SMILES: COCCN1CCn2c(C(F)(F)F)ccc2C12CCN(C(=O)c1ccc(OC(C)C)c(OC)c1)CC2] |
| 187 | 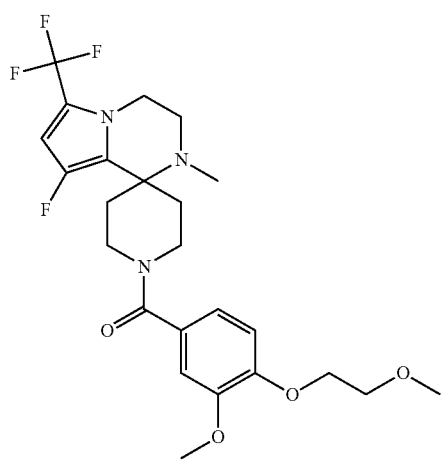 [SMILES: COCCOc1ccc(C(=O)N2CCC3(CC2)c2c(F)cc(C(F)(F)F)n2CCN3C)cc1OC] |
| 188 | 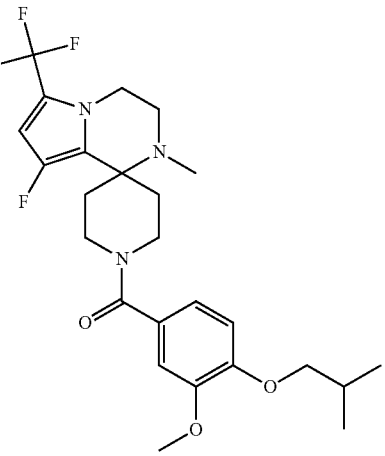 |
| 189 | 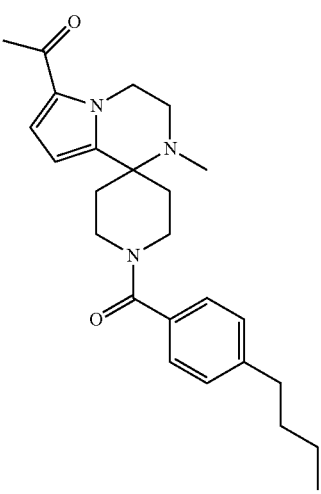 [SMILES: CCCCc1ccc(C(=O)N2CCC3(CC2)c2ccc(C(C)=O)n2CCN3C)cc1] |
| 190 | 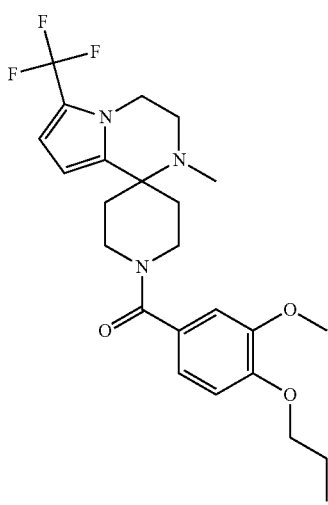 [SMILES: CCCOc1ccc(C(=O)N2CCC3(CC2)c2ccc(C(F)(F)F)n2CCN3C)cc1OC] |

| 593 -continued | | 594 -continued | |
|---|---|---|---|
| 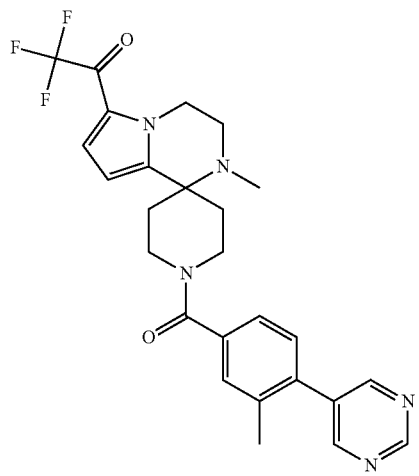 [SMILES: Cc1cc(C(=O)N2CCC3(CC2)c2ccc(C(=O)C(F)(F)F)n2CCN3C)ccc1-c1cncnc1] | 191 | 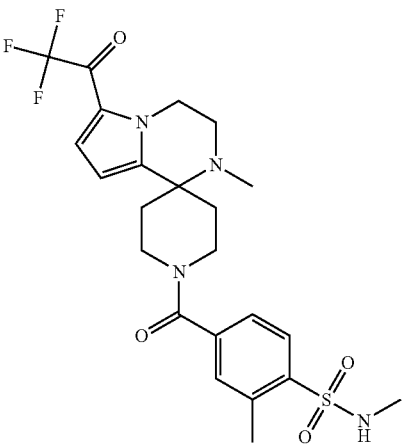 | 194 |
| 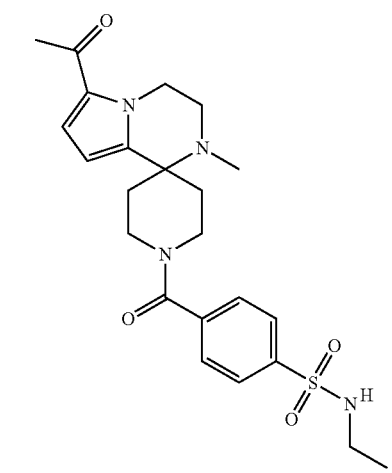 | 192 | 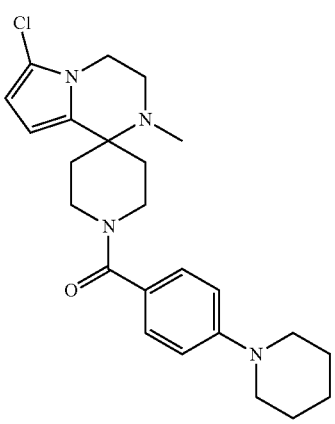 | 195 |
| 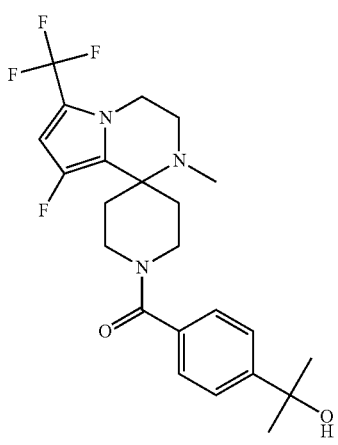 [SMILES: CN1CCn2c(C(F)(F)F)cc(F)c2C12CCN(C(=O)c1ccc(C(C)(C)O)cc1)CC2] | 193 | 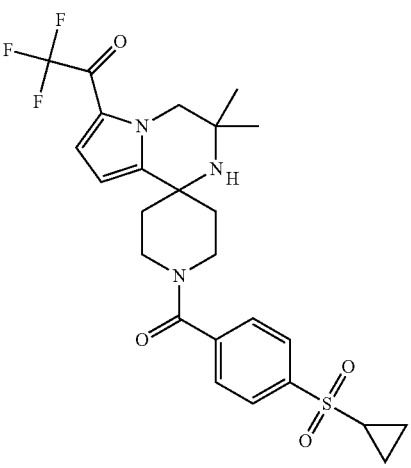 | 197 |

| 595 -continued | 596 -continued |
|---|---|
| 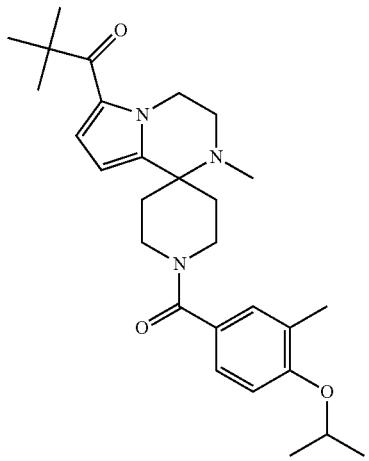 199 | 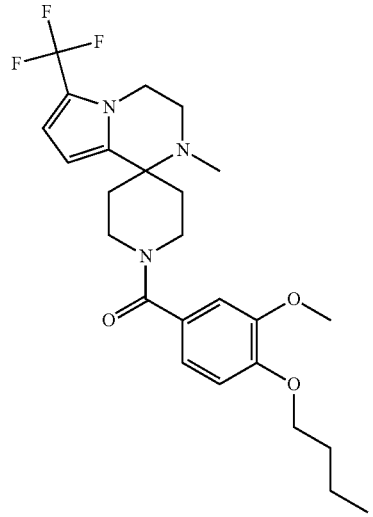 203 |
| 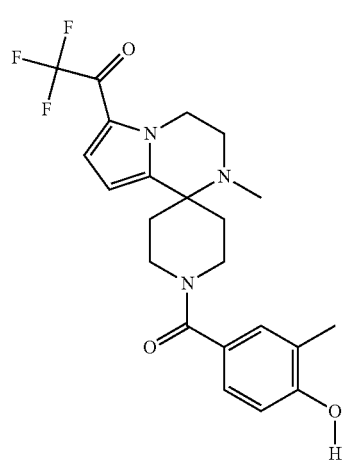 201 | 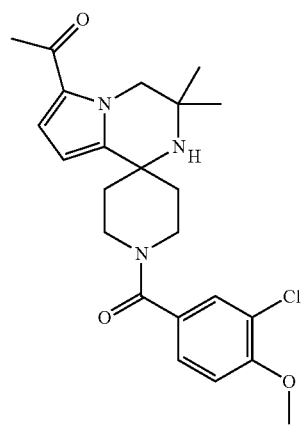 204 |
| 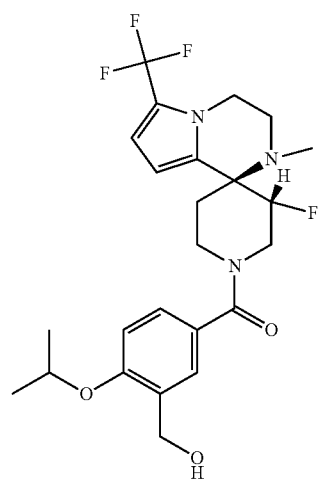 [SMILES: CC(C)Oc1ccc(C(=O)N2CC[C@]3(c4ccc(C(F)(F)F)n4CCN3C)[C@H](F)C2)cc1CO] 202 | 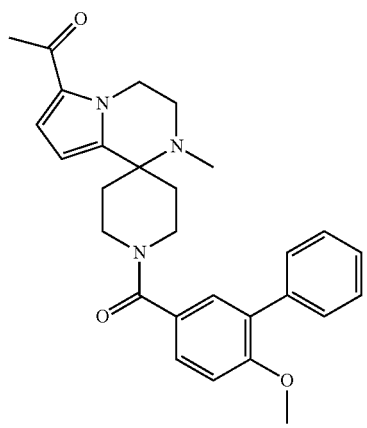 [SMILES: COc1ccc(C(=O)N2CCC3(CC2)c2ccc(C(C)=O)n2CCN3C)cc1-c1ccccc1] 205 |

597
-continued
207
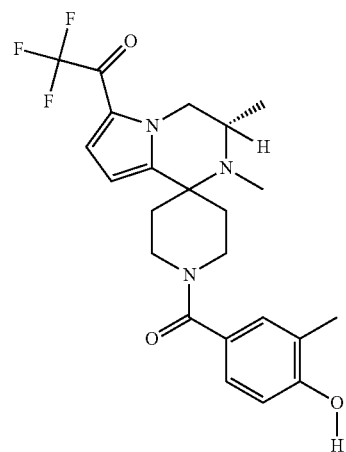
208
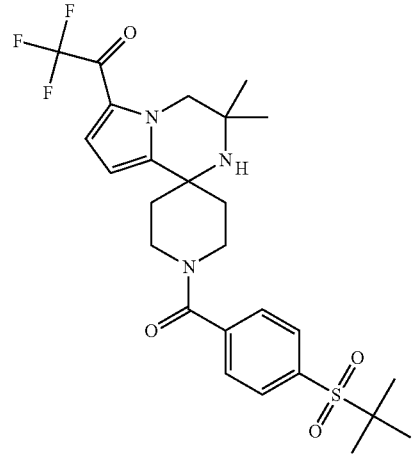
209
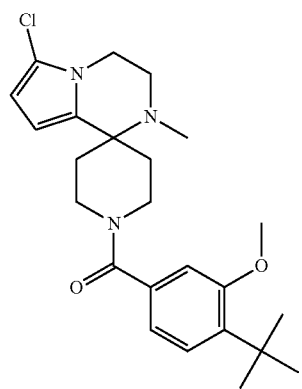 [SMILES: COc1cc(C(=O)N2CCC3(CC2)c2ccc(Cl)n2CCN3C)ccc1C(C)(C)C]
598
-continued
210
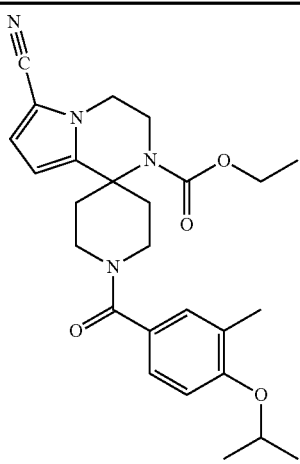
211
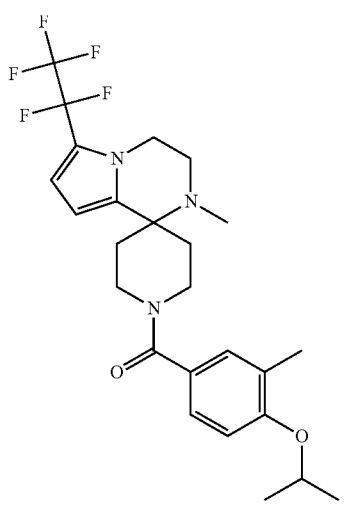
212
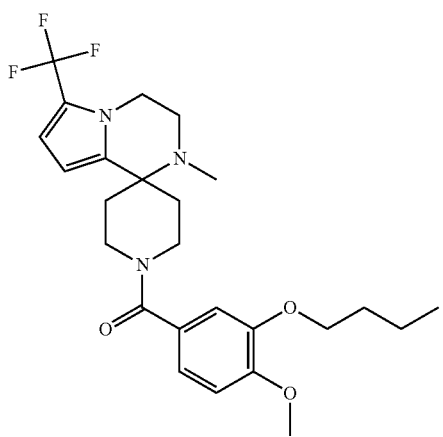 [SMILES: CCCCOc1cc(C(=O)N2CCC3(CC2)c2ccc(C(F)(F)F)n2CCN3C)ccc1OC]

| 599 -continued | 600 -continued |
|---|---|
| 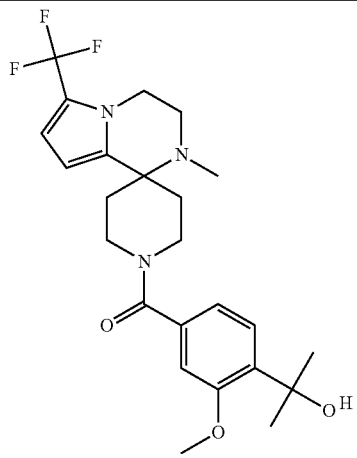 213 | 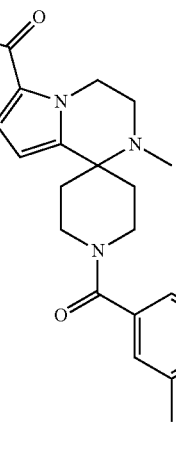 216 |
| 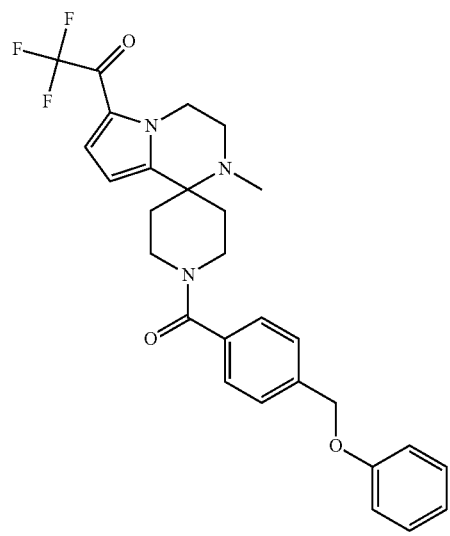 214 | 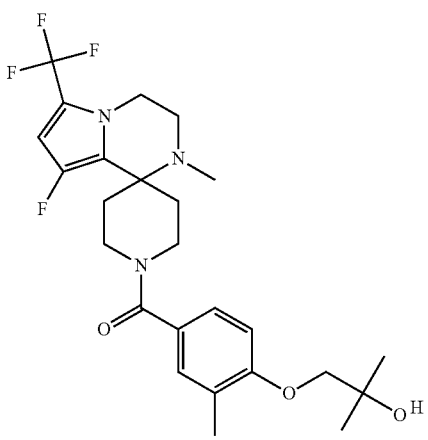 217 |
| 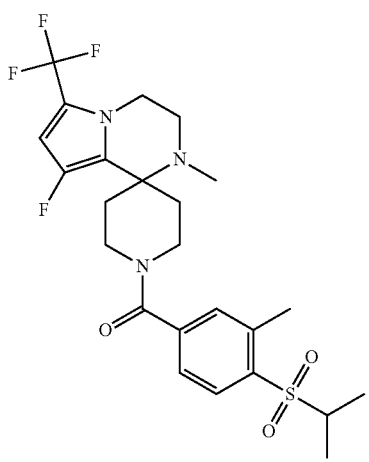 [SMILES: Cc1cc(C(=O)N2CCC3(CC2)c2c(F)cc(C(F)(F)F)n2CCN3C)ccc1S(=O)(=O)C(C)C] 215 | 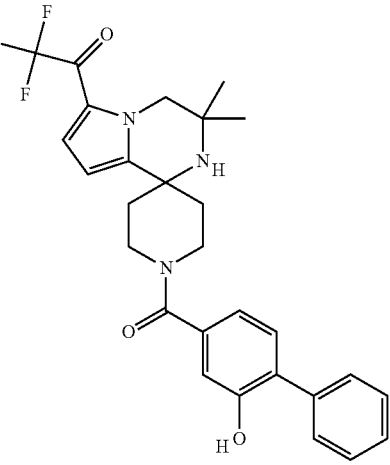 218 |

| 601 -continued | 602 -continued |
|---|---|
| 219 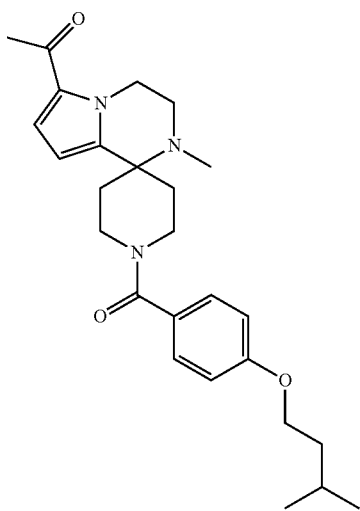 [SMILES: CC(=O)c1ccc2n1CCN(C)C21CCN(C(=O)c2ccc(OCCC(C)C)cc2)CC1] | 222 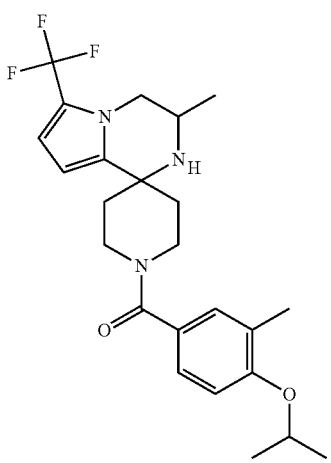 |
| 220 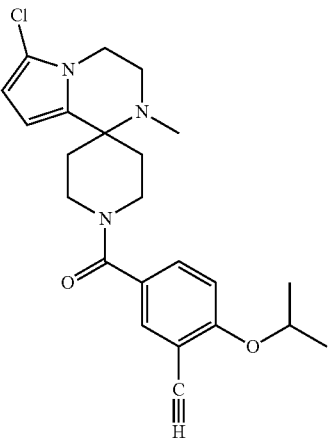 | 223 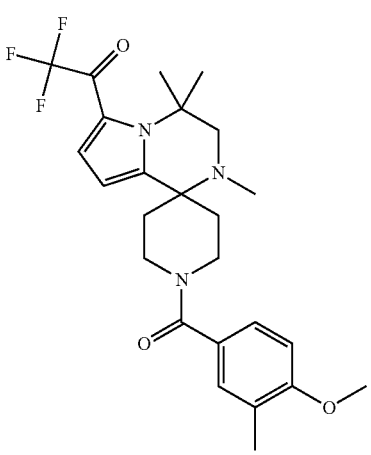 |
| 221 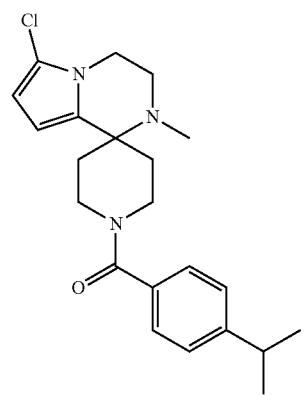 [SMILES: CC(C)c1ccc(C(=O)N2CCC3(CC2)c2ccc(Cl)n2CCN3C)cc1] | 224 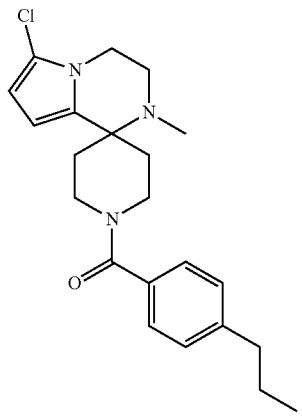 [SMILES: CCCc1ccc(C(=O)N2CCC3(CC2)c2ccc(Cl)n2CCN3C)cc1] |

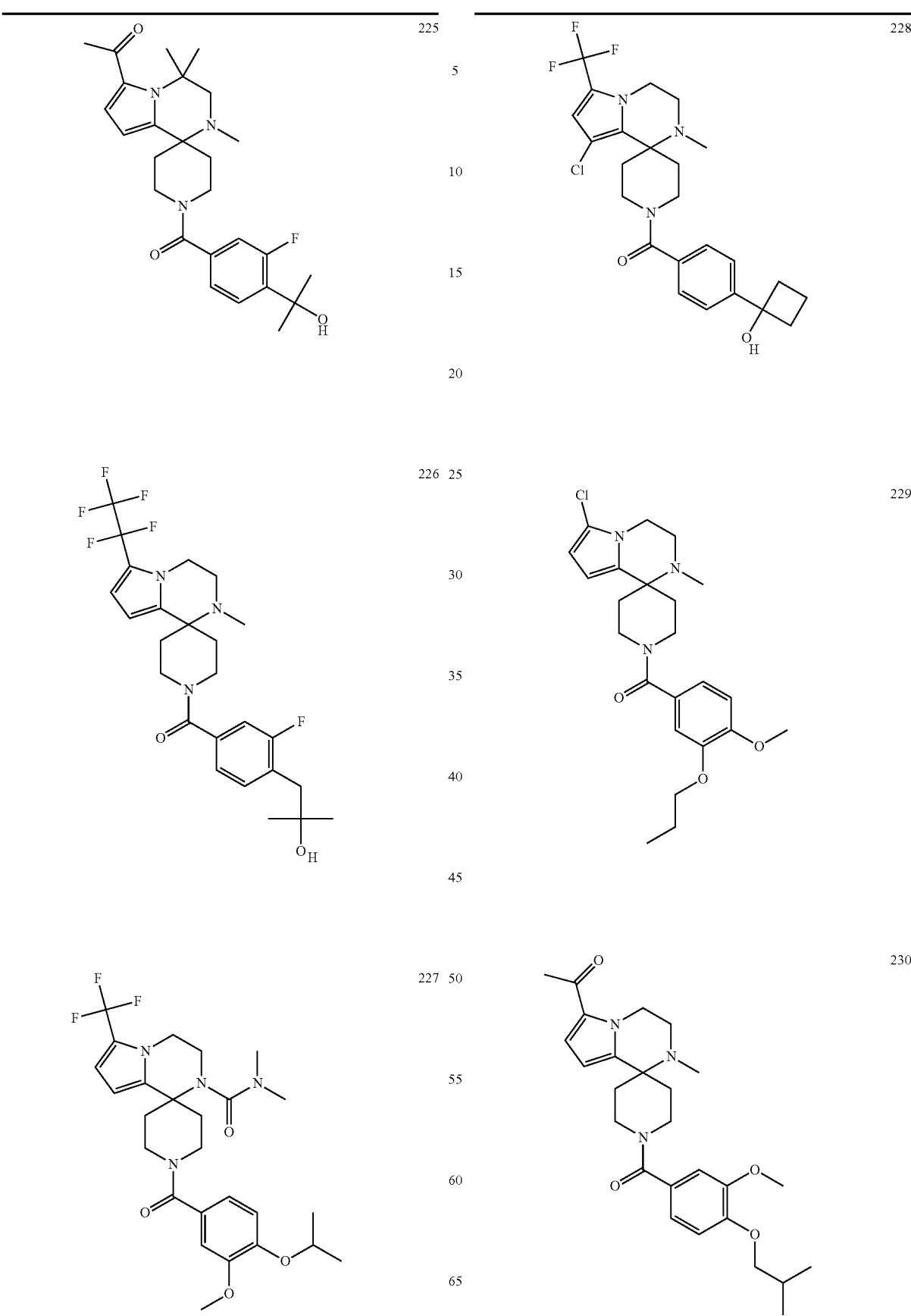

| 605 -continued | 606 -continued |
|---|---|
| 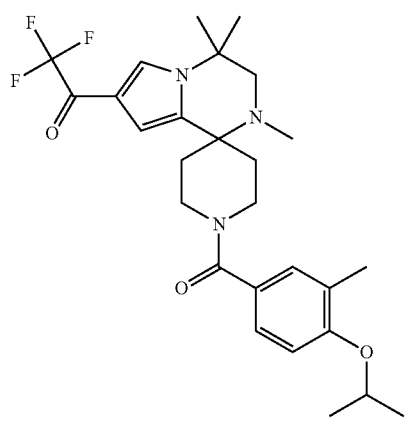 231 | 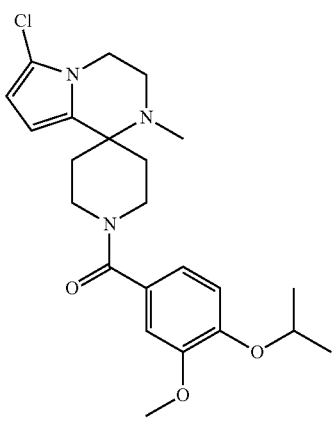 234 |
| 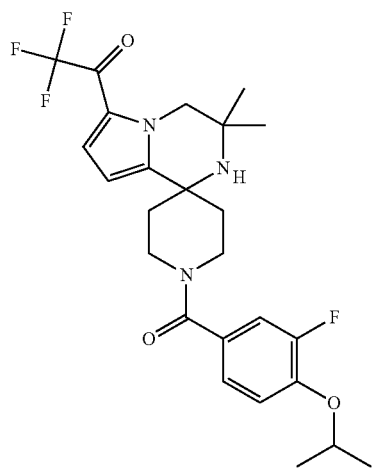 232 | 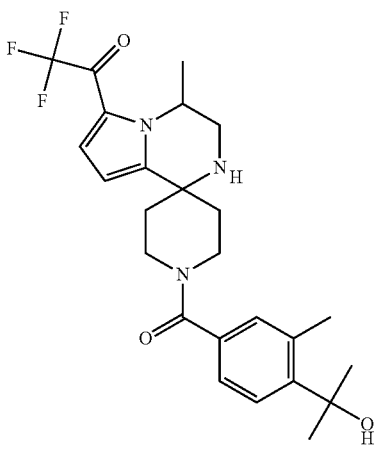 235 |
| 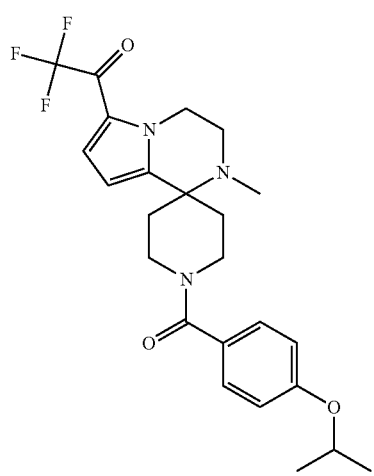 233 | 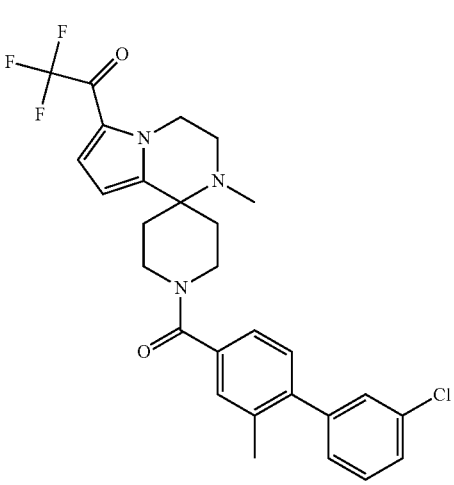 [SMILES: Cc1cc(C(=O)N2CCC3(CC2)c2ccc(C(=O)C(F)(F)F)n2CCN3C)ccc1-c1cccc(Cl)c1] 236 |

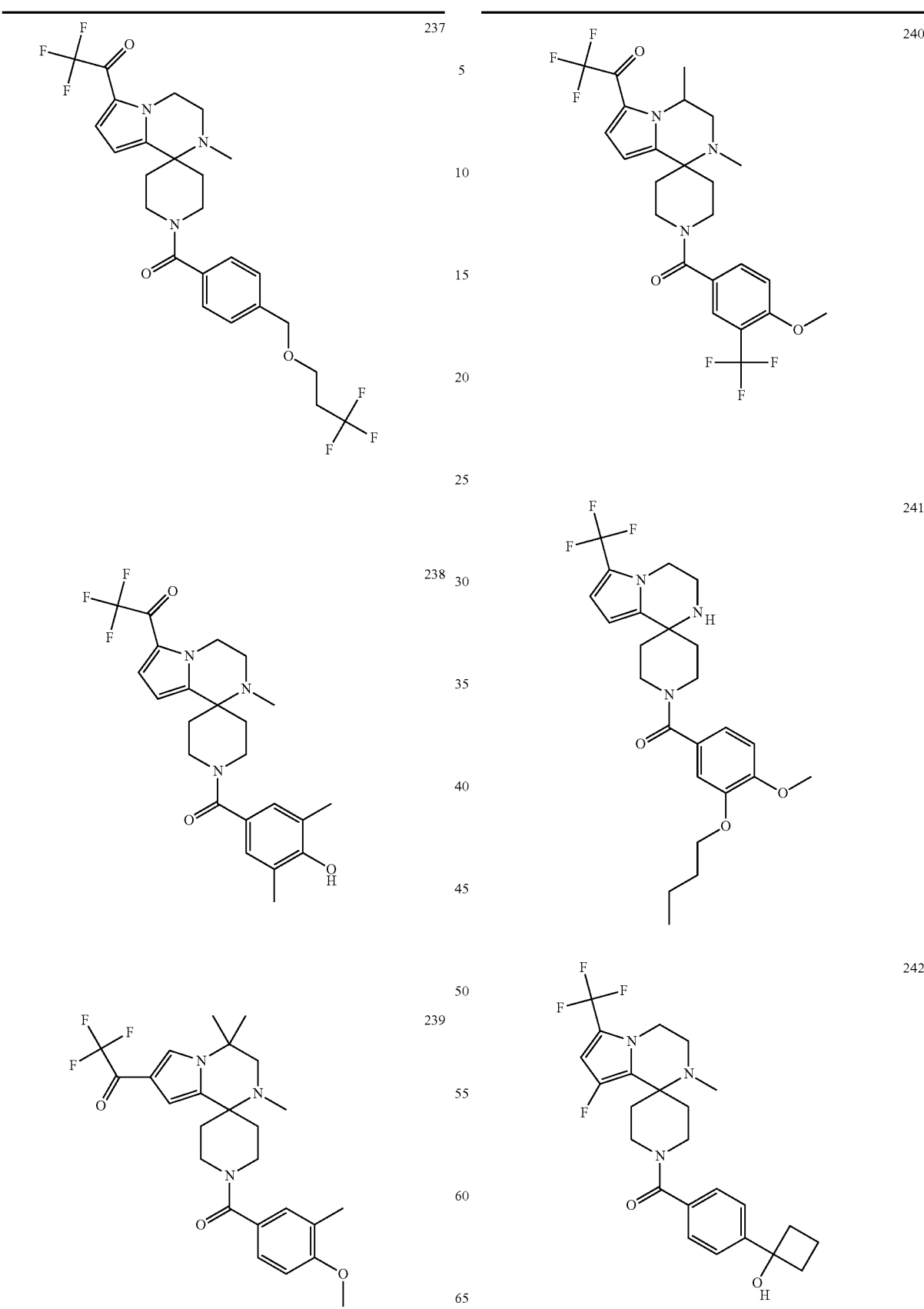

| 243 | 246 |
| --- | --- |
| 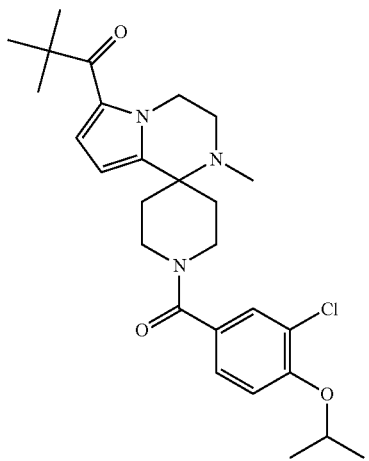 | 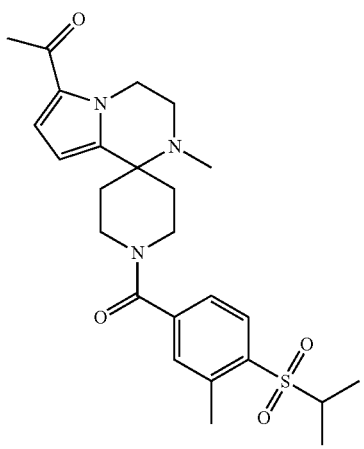 |
| 244 | 247 |
| --- | --- |
| 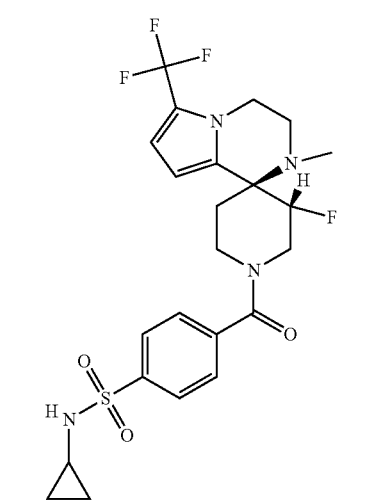 | 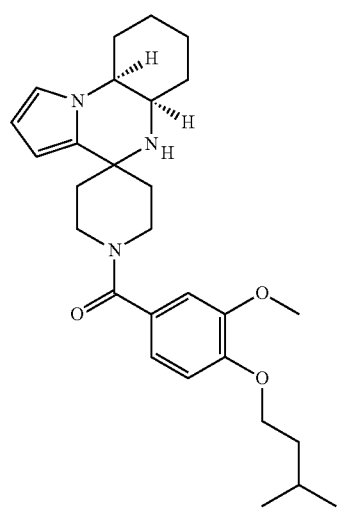 |
| 245 | 249 |
| --- | --- |
| 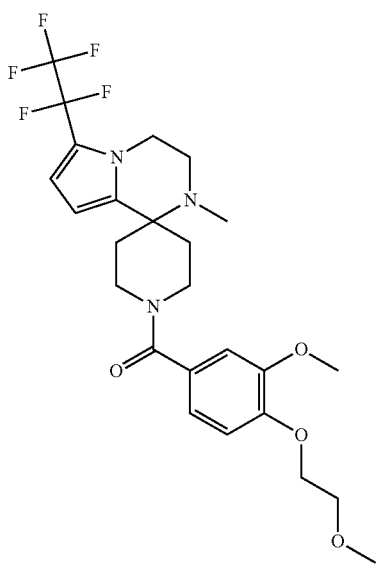 [SMILES: COCCOc1ccc(C(=O)N2CCC3(CC2)c2ccc(C(F)(F)C(F)(F)F)n2CCN3C)cc1OC] | 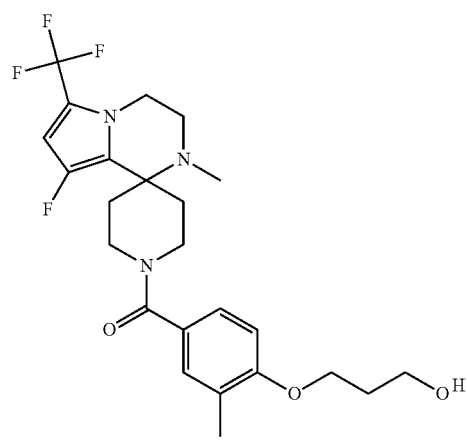 |

| 611 -continued | | 612 -continued | |
|---|---|---|---|
| 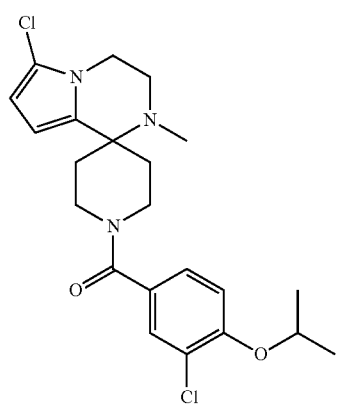 | 250 | 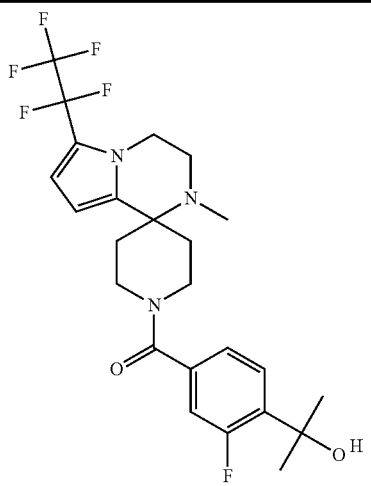 | 253 |
| 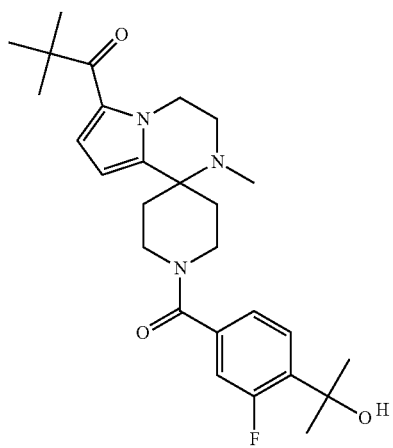 | 251 | 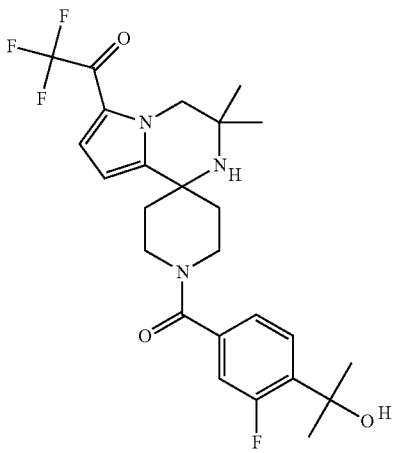 | 254 |
| 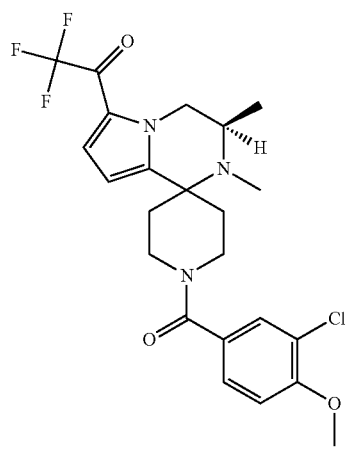 [SMILES: COc1ccc(C(=O)N2CCC3(CC2)c2ccc(C(=O)C(F)(F)F)n2C[C@@H](C)N3C)cc1Cl] | 252 | 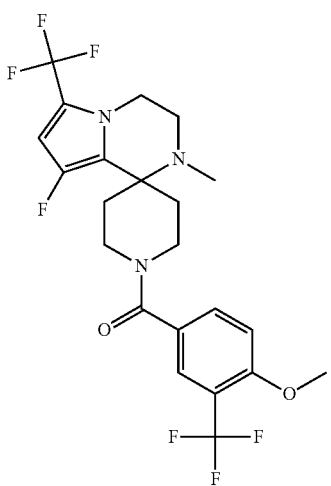 [SMILES: COc1ccc(C(=O)N2CCC3(CC2)c2c(F)cc(C(F)(F)F)n2CCN3C)cc1C(F)(F)F] | 255 |

| 256 | 259 |
|---|---|
| 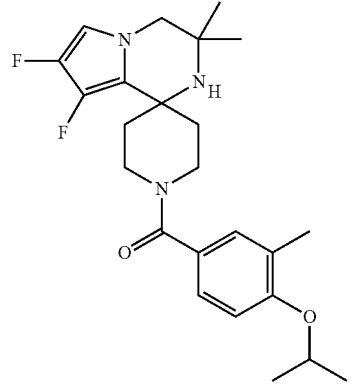 | 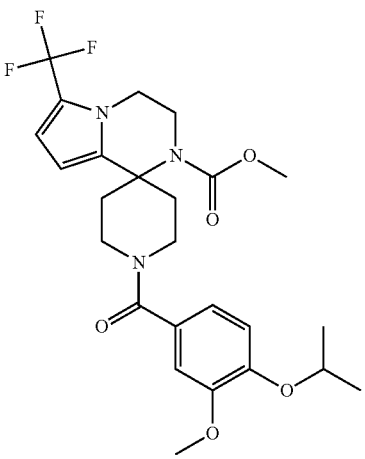 |
| 257 | 260 |
|---|---|
| 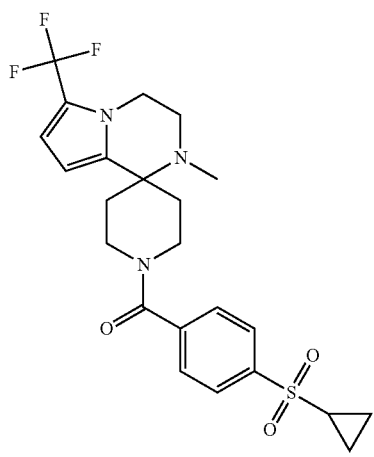 [SMILES: CN1CCn2c(C(F)(F)F)ccc2C12CCN(C(=O)c1ccc(S(=O)(=O)C3CC3)cc1)CC2] | 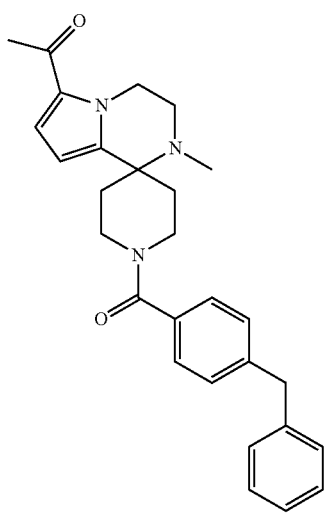 |
| 258 | 262 |
|---|---|
| 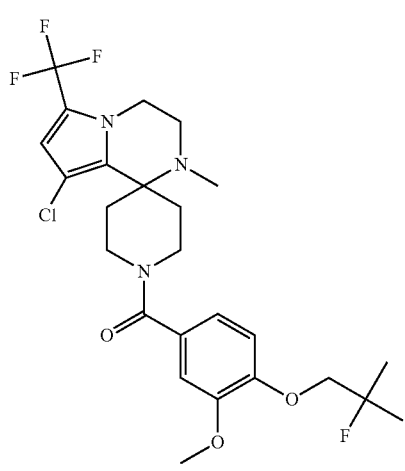 [SMILES: COc1cc(C(=O)N2CCC3(CC2)c2c(Cl)cc(C(F)(F)F)n2CCN3C)ccc1OCC(C)(C)F] | 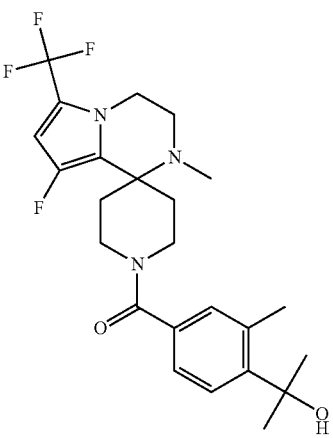 |

| 615 -continued | 616 -continued |
|---|---|
| 263 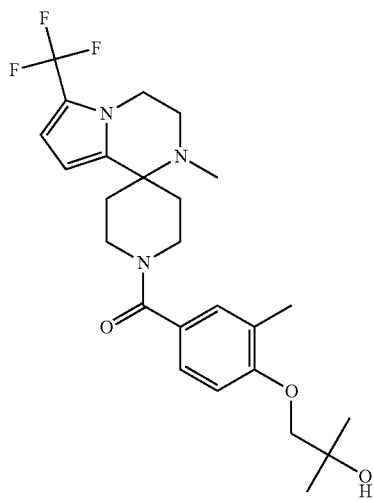 [SMILES: Cc1cc(C(=O)N2CCC3(CC2)c2ccc(C(F)(F)F)n2CCN3C)ccc1OCC(C)(C)O] | 266 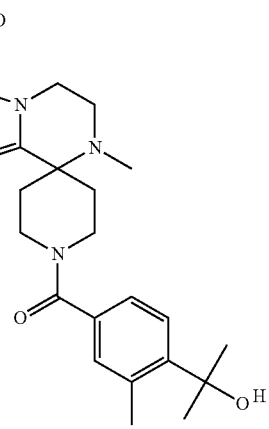 |
| 264 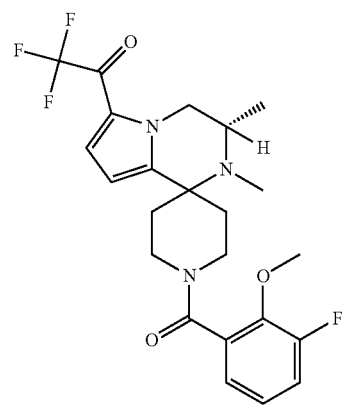 [SMILES: COc1c(F)cccc1C(=O)N1CCC2(CC1)c1ccc(C(=O)C(F)(F)F)n1C[C@H](C)N2C] | 267 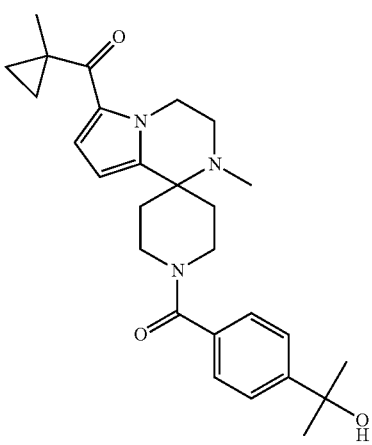 |
| 265 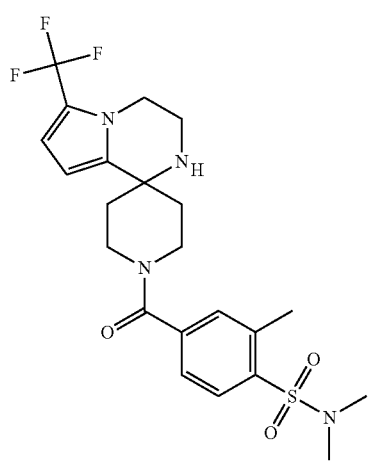 | 268 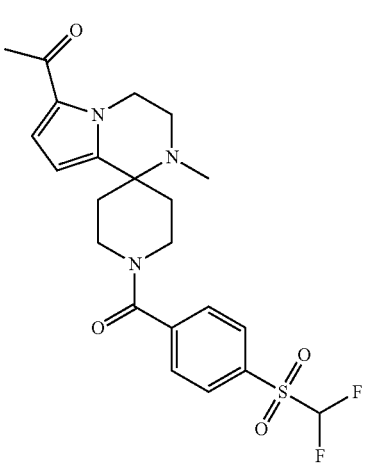 [SMILES: CC(=O)c1ccc2n1CCN(C)C21CCN(C(=O)c2ccc(S(=O)(=O)C(F)F)cc2)CC1] |

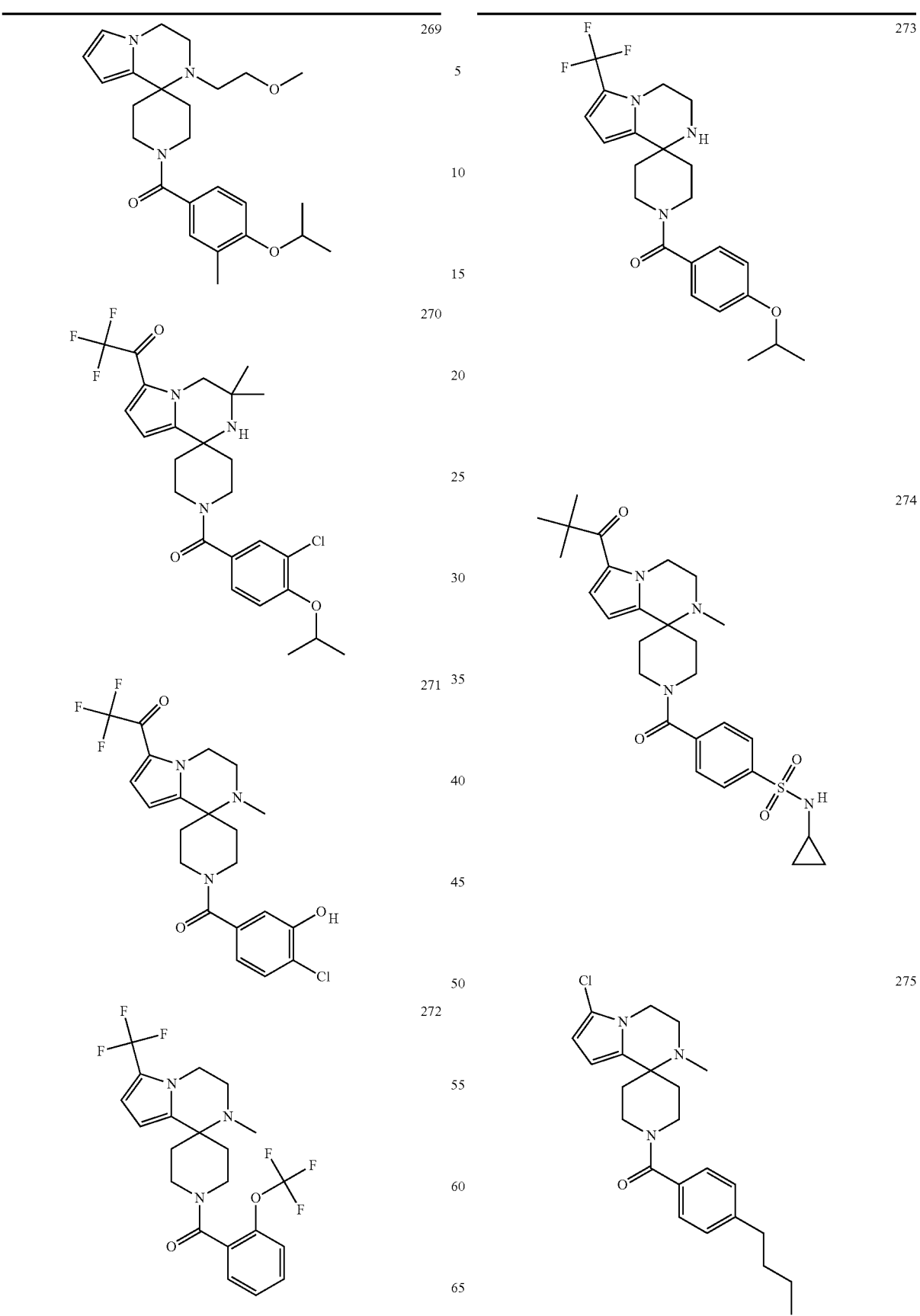

| 276 | 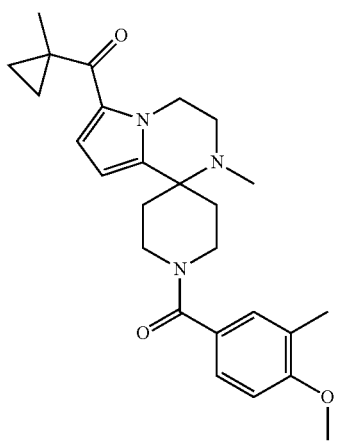 [SMILES: COc1ccc(C(=O)N2CCC3(CC2)c2ccc(C(=O)C4(C)CC4)n2CCN3C)cc1C] |
| 277 | 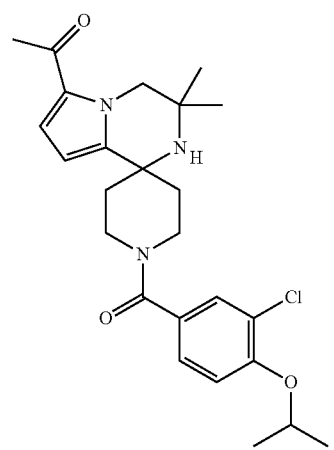 |
| 278 | 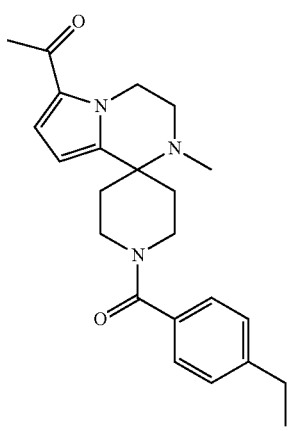 [SMILES: CCc1ccc(C(=O)N2CCC3(CC2)c2ccc(C(C)=O)n2CCN3C)cc1] |
| 279 | 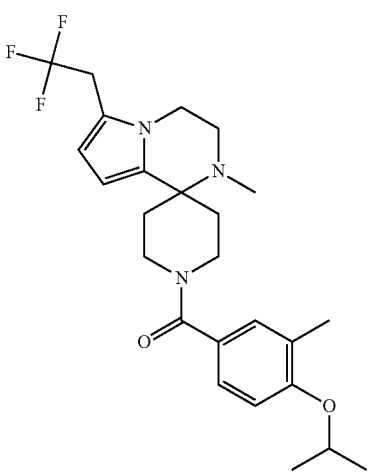 |
| 280 | 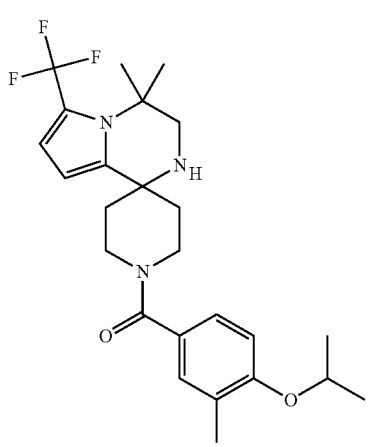 |
| 281 | 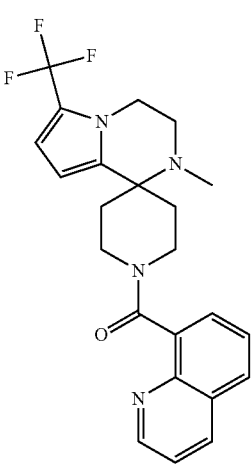 [SMILES: CN1CCn2c(C(F)(F)F)ccc2C12CCN(C(=O)c1cccc3cccnc13)CC2] |

| 621 -continued | 622 -continued |
|---|---|
| 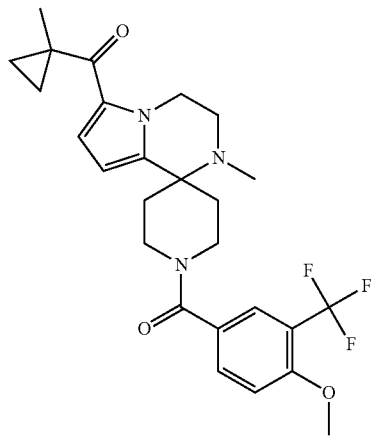 [SMILES: COc1ccc(C(=O)N2CCC3(CC2)c2ccc(C(=O)C4(C)CC4)n2CCN3C)cc1C(F)(F)F] 282 | 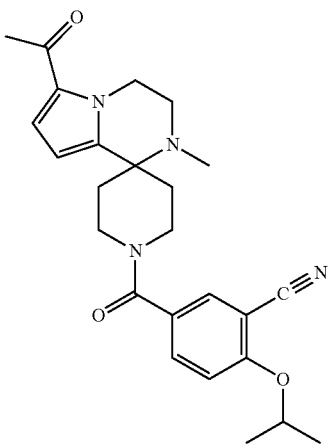 285 |
| 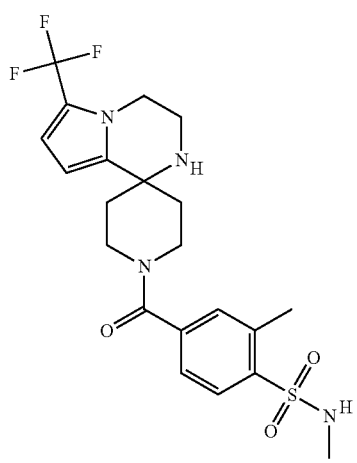 283 | 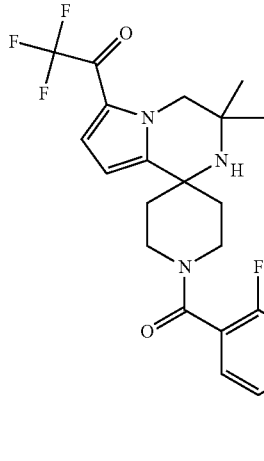 286 |
| 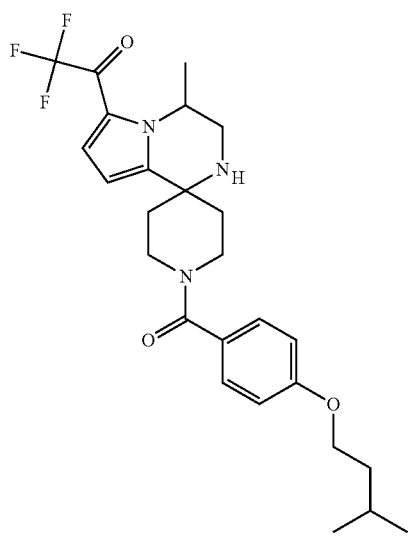 284 | 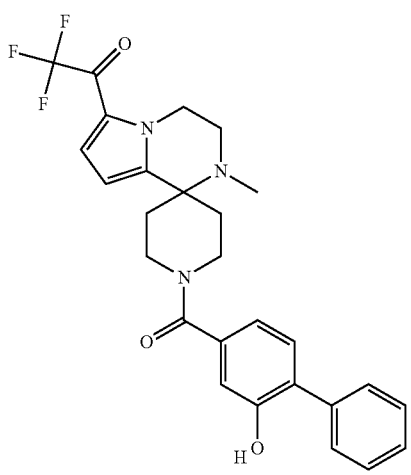 287 |

| 623 -continued | 288 | 624 -continued | 292 |
|---|---|---|---|
| 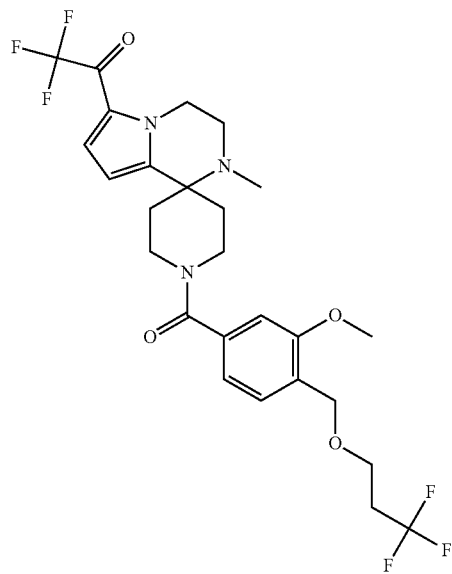 | | 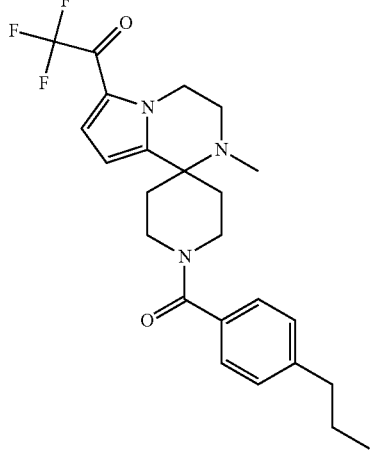 | |
| 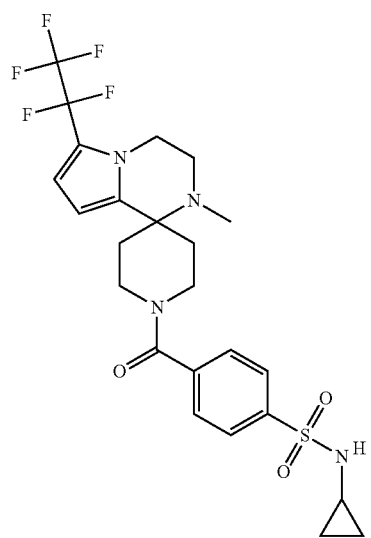 | 289 | 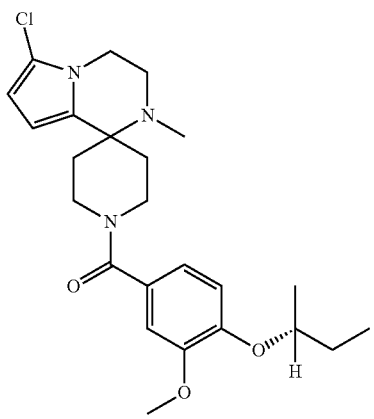 | 294 |
| 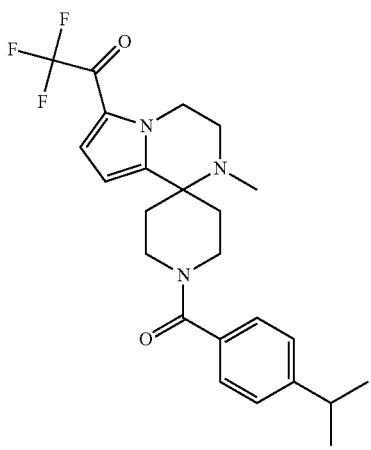 | 290 | 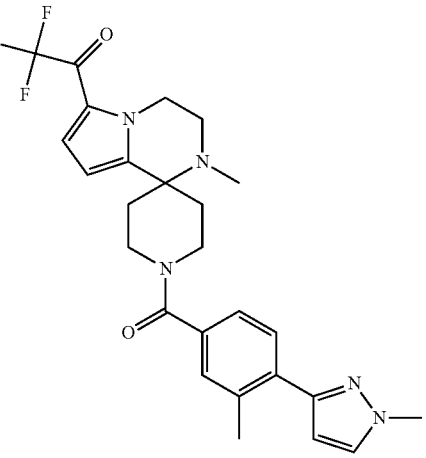 | 295 |

| 625 -continued | 626 -continued |
|---|---|
| 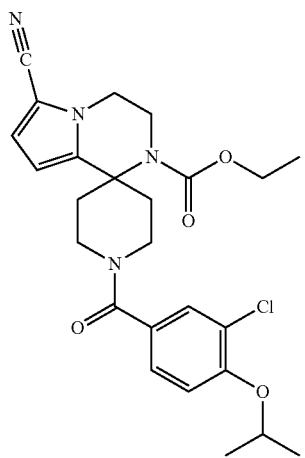 296 | 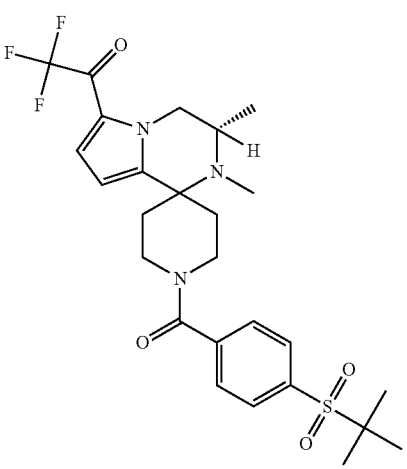 300 |
| 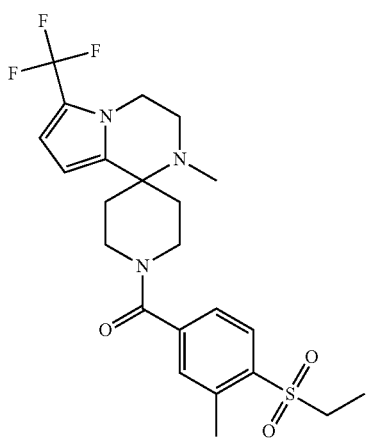 [SMILES: CCS(=O)(=O)c1ccc(C(=O)N2CCC3(CC2)c2ccc(C(F)(F)F)n2CCN3C)cc1C] 298 | 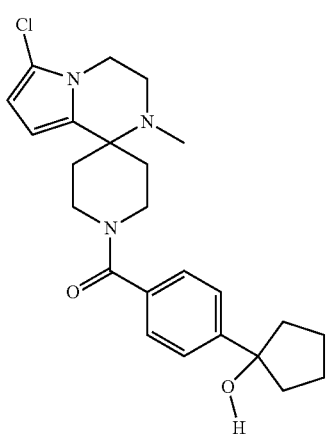 301 |
| 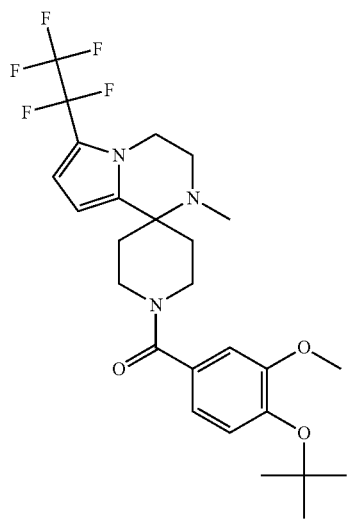 [SMILES: COc1cc(C(=O)N2CCC3(CC2)c2ccc(C(F)(F)C(F)(F)F)n2CCN3C)ccc1OC(C)(C)C] 299 | 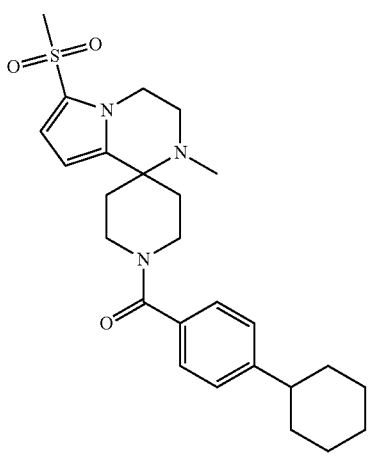 [SMILES: CN1CCn2c(ccc2S(C)(=O)=O)C12CCN(C(=O)c1ccc(C3CCCCC3)cc1)CC2] 302 |

| 627 -continued | 628 -continued |
|---|---|
| 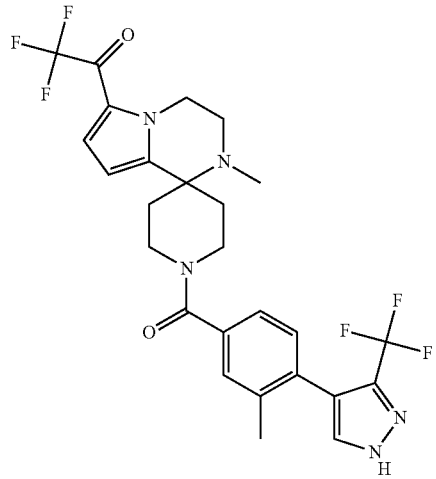 303 | 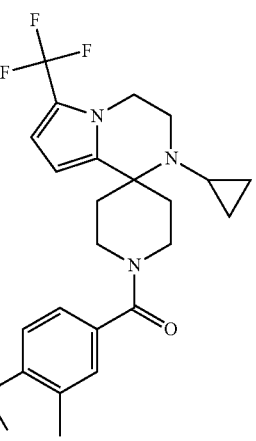 307 |
| 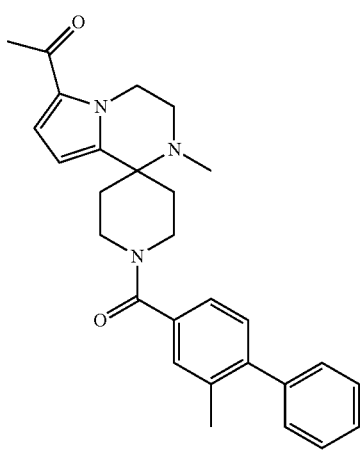 [SMILES: CC(=O)c1ccc2n1CCN(C)C21CCN(C(=O)c2ccc(-c3ccccc3)c(C)c2)CC1] 304 | 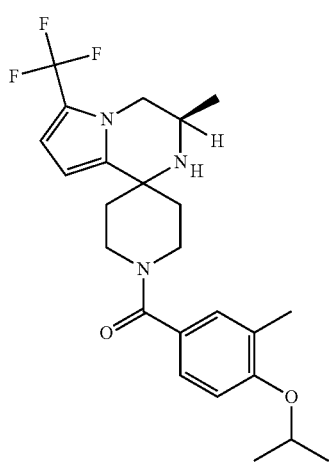 308 |
| 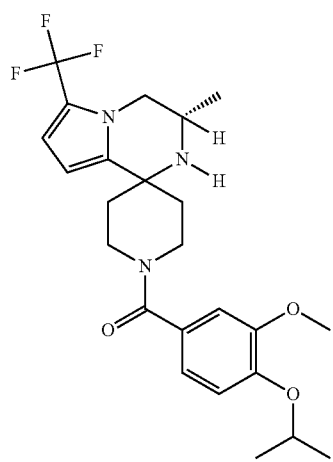 306 | 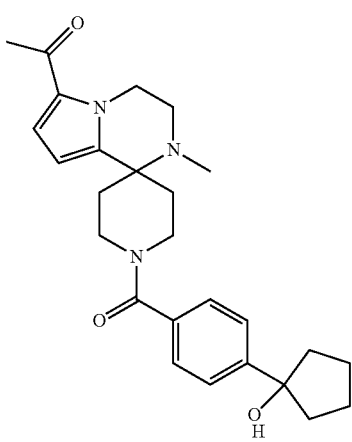 309 |

| 310 | 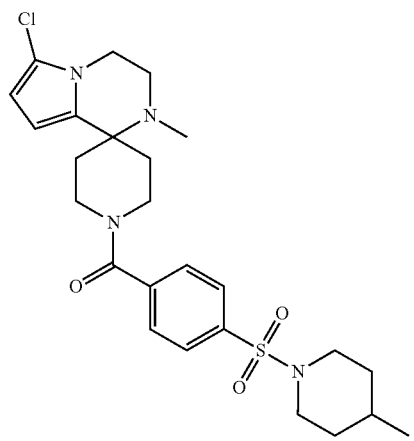 [SMILES: CC1CCN(S(=O)(=O)c2ccc(C(=O)N3CCC4(CC3)c3ccc(Cl)n3CCN4C)cc2)CC1] | 313 | 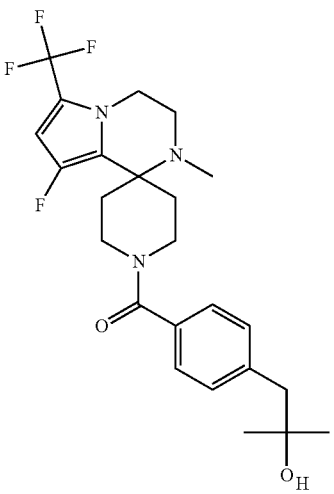 |
| 311 | 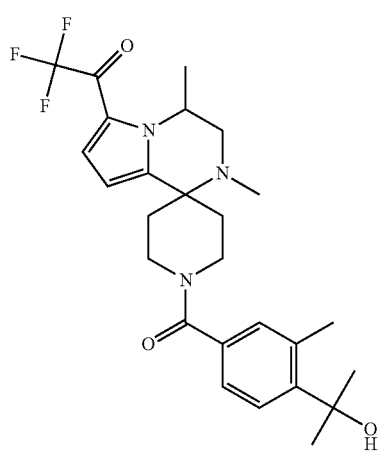 | 314 | 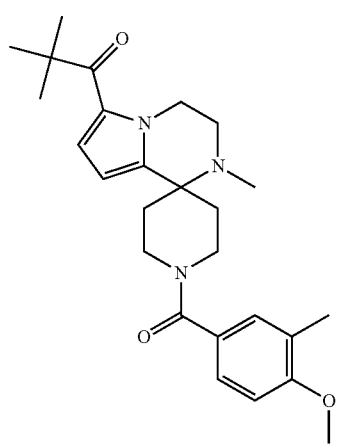 [SMILES: COc1ccc(C(=O)N2CCC3(CC2)c2ccc(C(=O)C(C)(C)C)n2CCN3C)cc1C] |
| 312 | 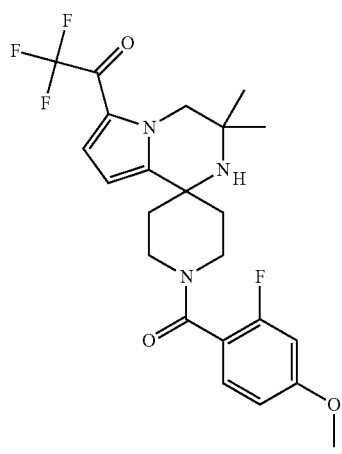 | 315 | 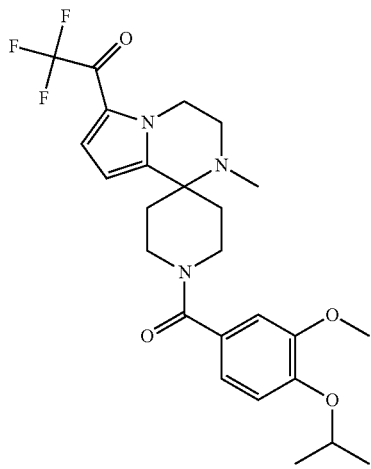 |

| 631 -continued | 632 -continued |
|---|---|
| 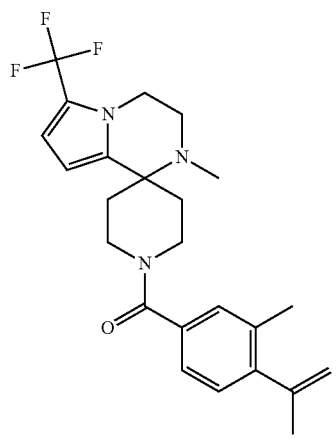 [SMILES: C=C(C)c1ccc(C(=O)N2CCC3(CC2)c2ccc(C(F)(F)F)n2CCN3C)cc1C] 316 | 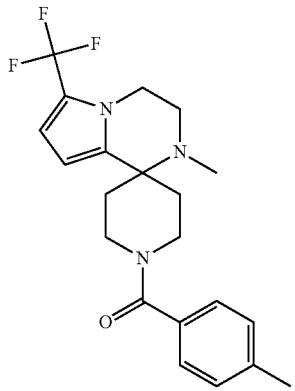 319 |
| 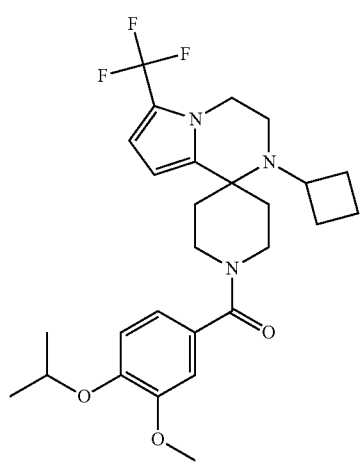 [SMILES: COc1cc(C(=O)N2CCC3(CC2)c2ccc(C(F)(F)F)n2CCN3C2CCC2)ccc1OC(C)C] 317 | 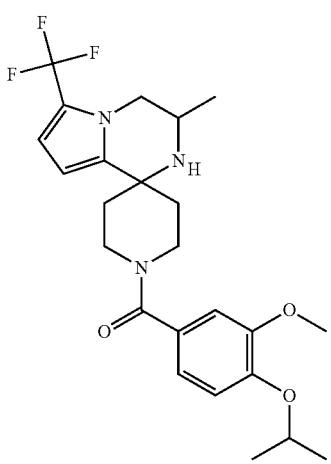 320 |
| 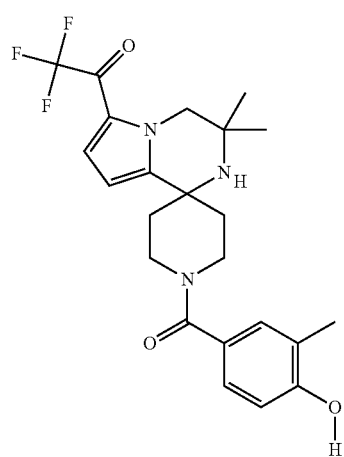 318 | 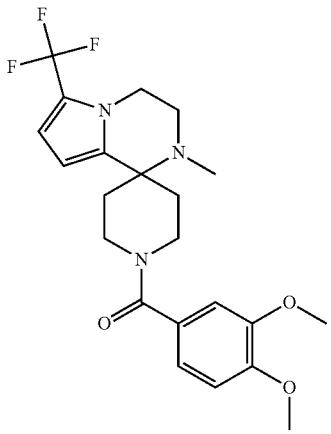 321 |

| 323 | 326 |
|---|---|
| 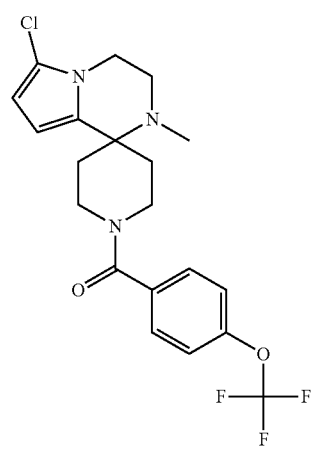 [SMILES: CN1CCn2c(Cl)ccc2C12CCN(C(=O)c1ccc(OC(F)(F)F)cc1)CC2] | 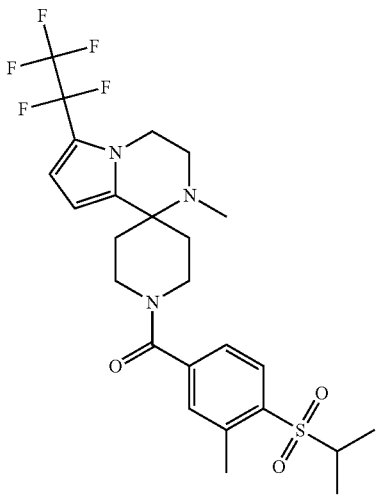 [SMILES: Cc1cc(C(=O)N2CCC3(CC2)c2ccc(C(F)(F)C(F)(F)F)n2CCN3C)ccc1S(=O)(=O)C(C)C] |
| 324 | 327 |
|---|---|
| 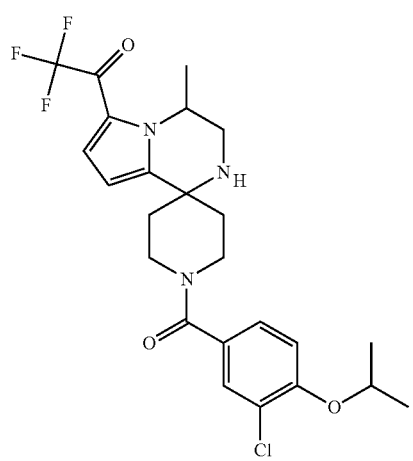 | 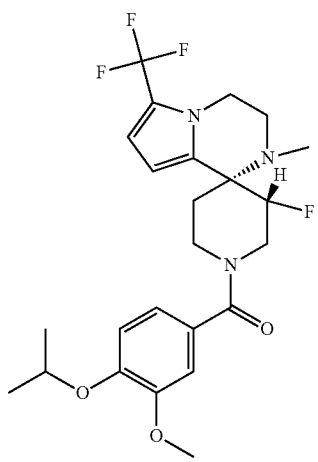 [SMILES: COc1cc(C(=O)N2CC[C@@]3(c4ccc(C(F)(F)F)n4CCN3C)[C@H](F)C2)ccc1OC(C)C] |
| 325 | 328 |
|---|---|
| 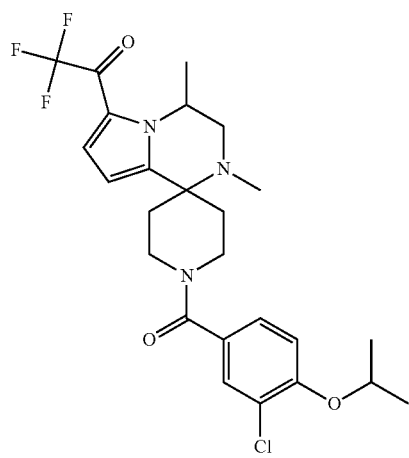 | 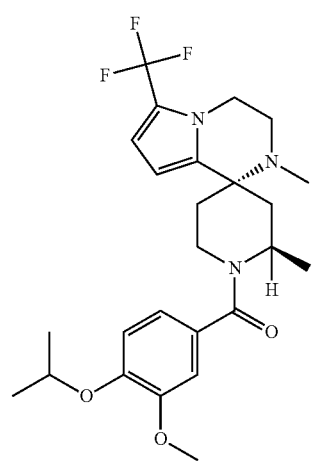 [SMILES: COc1cc(C(=O)N2CC[C@]3(C[C@H]2C)c2ccc(C(F)(F)F)n2CCN3C)ccc1OC(C)C] |

| 635 -continued | 636 -continued |
|---|---|
| 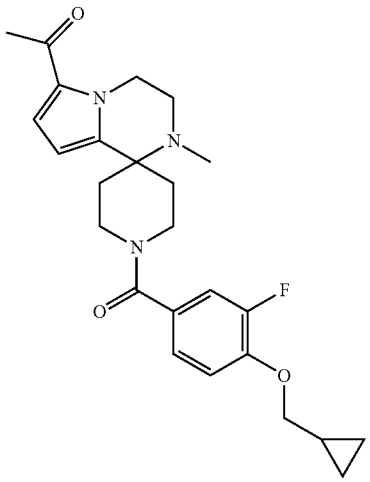 [SMILES: CC(=O)c1ccc2n1CCN(C)C21CCN(C(=O)c2ccc(OCC3CC3)c(F)c2)CC1] 329 | 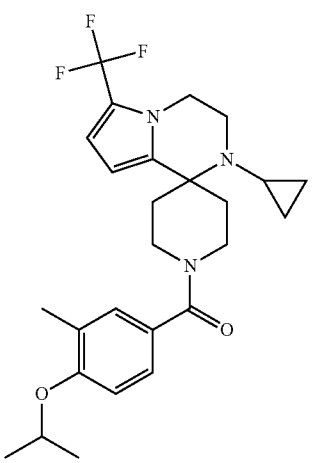 333 |
| 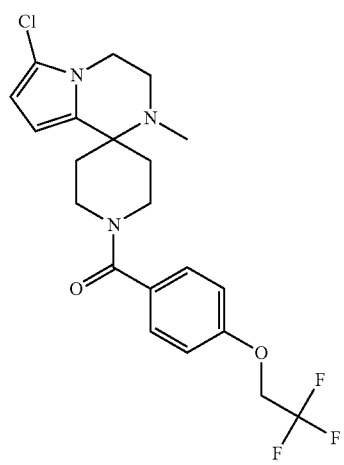 [SMILES: CN1CCn2c(Cl)ccc2C12CCN(C(=O)c1ccc(OCC(F)(F)F)cc1)CC2] 330 | 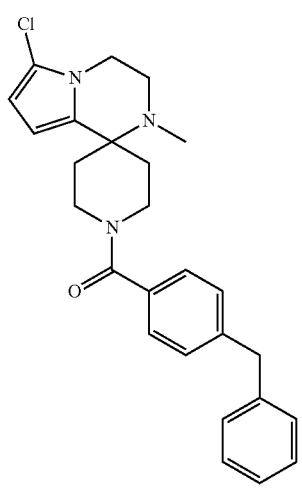 [SMILES: CN1CCn2c(Cl)ccc2C12CCN(C(=O)c1ccc(Cc3ccccc3)cc1)CC2] 334 |
|  | 1p;4p |
| 332 | 335 |
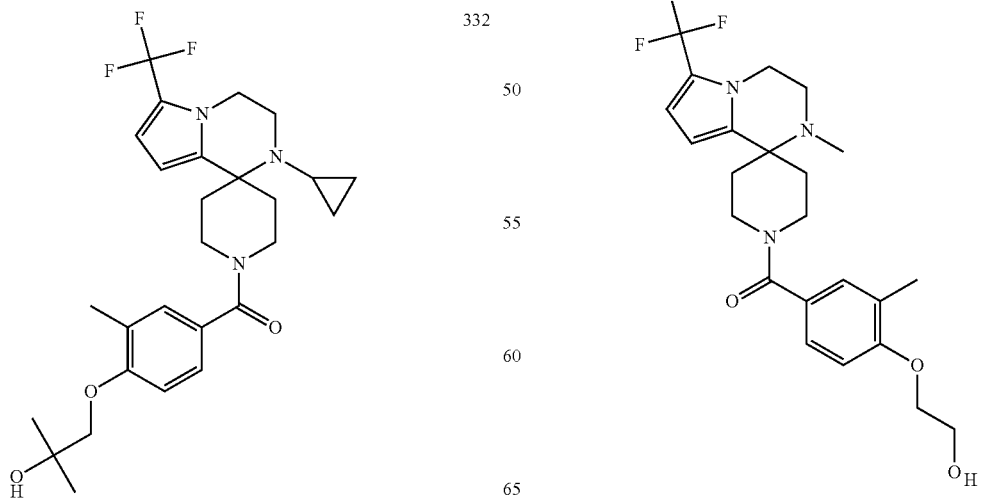

| 637 | 638 |
|---|---|
| 336 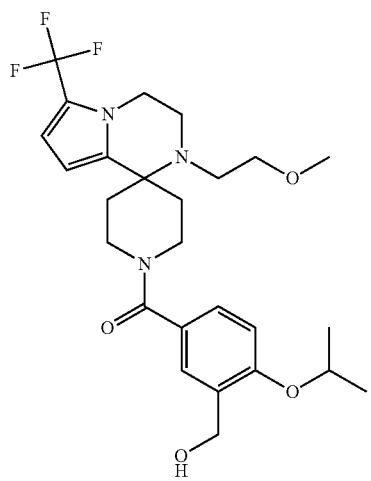 [SMILES: COCCN1CCn2c(C(F)(F)F)ccc2C12CCN(C(=O)c1ccc(OC(C)C)c(CO)c1)CC2] | 339 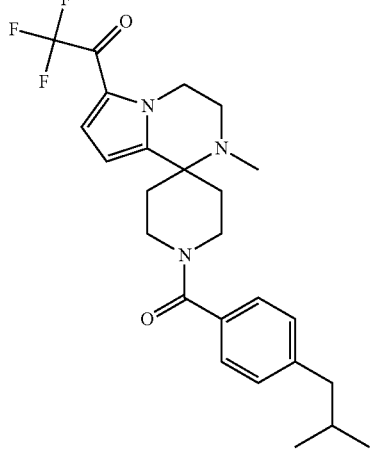 |
| 337 | 340 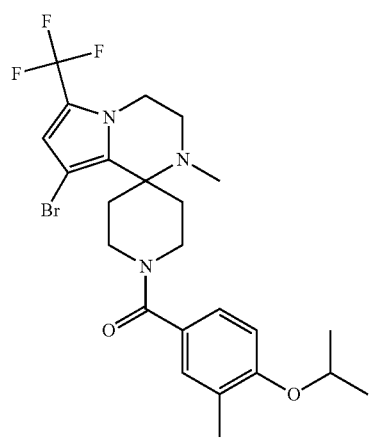 |
| 338 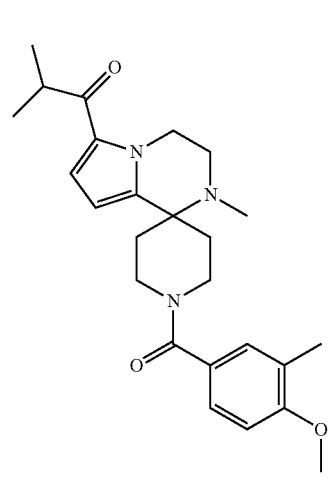 [SMILES: COc1ccc(C(=O)N2CCC3(CC2)c2ccc(C(=O)C(C)C)n2CCN3C)cc1C] | 341 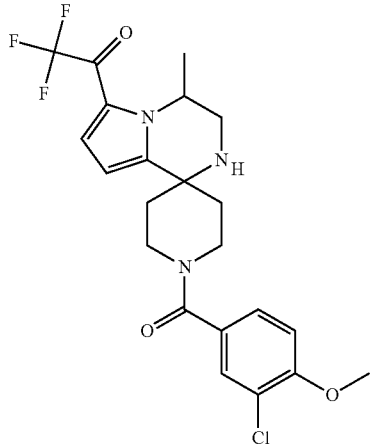 |

| 342 | 347 |
|---|---|
| 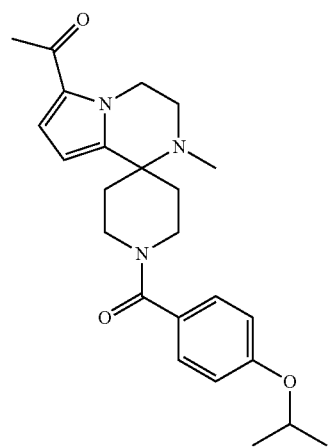 [SMILES: CC(=O)c1ccc2n1CCN(C)C21CCN(C(=O)c2ccc(OC(C)C)cc2)CC1] | 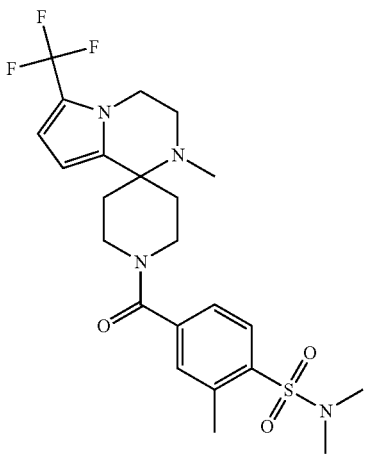 |
| 343 | 348 |
| 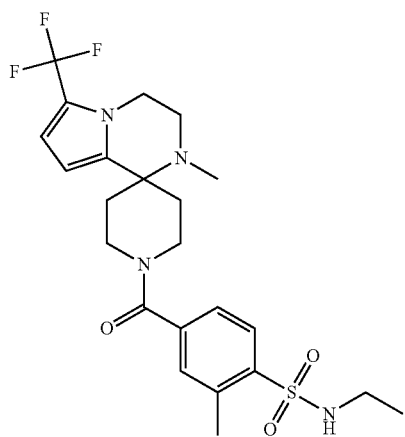 | 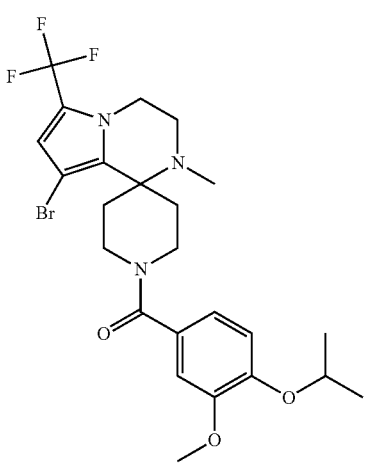 |
| 344 | 349 |
| 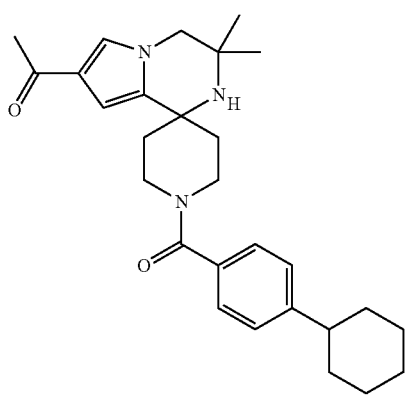 | 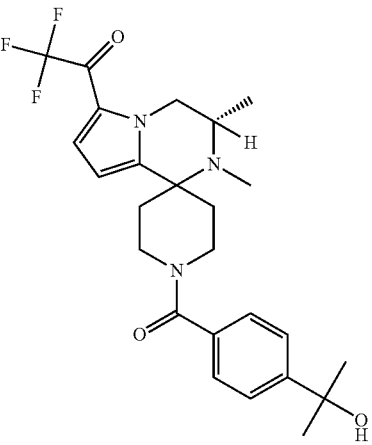 [SMILES: C[C@H]1Cn2c(C(=O)C(F)(F)F)ccc2C2(CCN(C(=O)c3ccc(C(C)(C)O)cc3)CC2)N1C] |

| 350 | 353 |
|---|---|
| 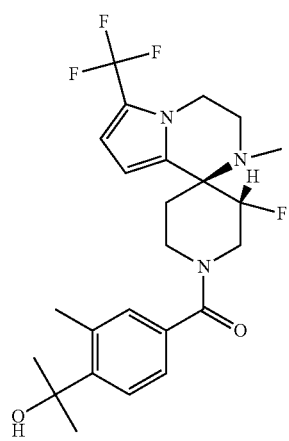 [SMILES: Cc1cc(C(=O)N2CC[C@]3(c4ccc(C(F)(F)F)n4CCN3C)[C@H](F)C2)ccc1C(C)(C)O] | 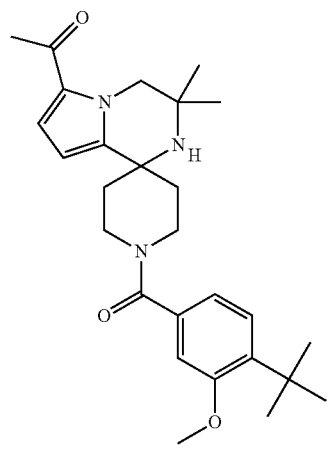 |
| 351 | 354 |
|---|---|
| 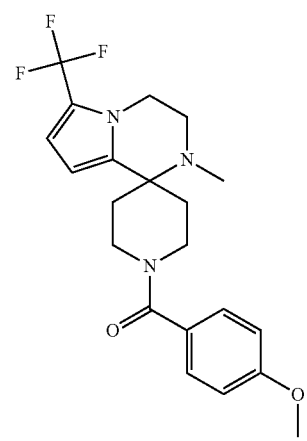 [SMILES: COc1ccc(C(=O)N2CCC3(CC2)c2ccc(C(F)(F)F)n2CCN3C)cc1] | 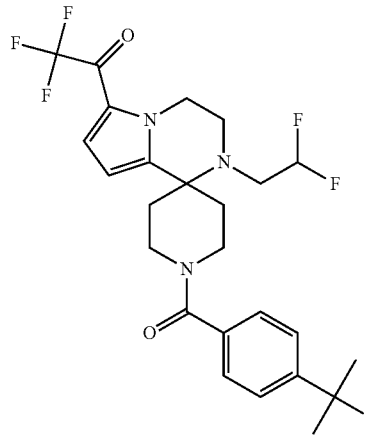 |
| 352 | 355 |
|---|---|
| 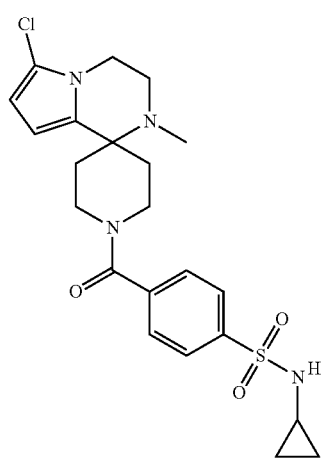 | 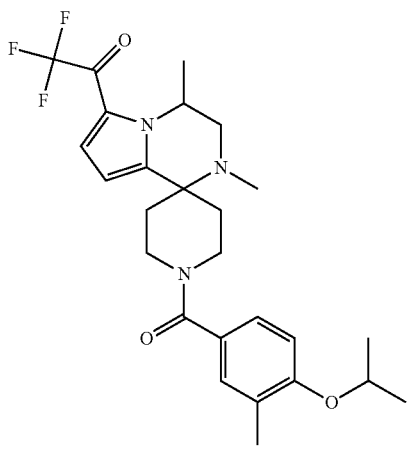 [SMILES: Cc1cc(C(=O)N2CCC3(CC2)c2ccc(C(=O)C(F)(F)F)n2C(C)CN3C)ccc1OC(C)C] |

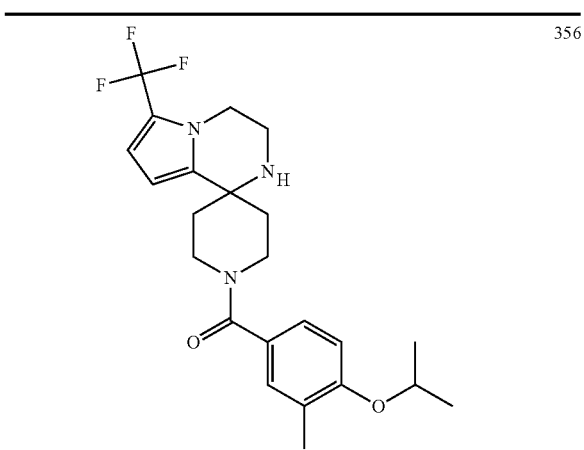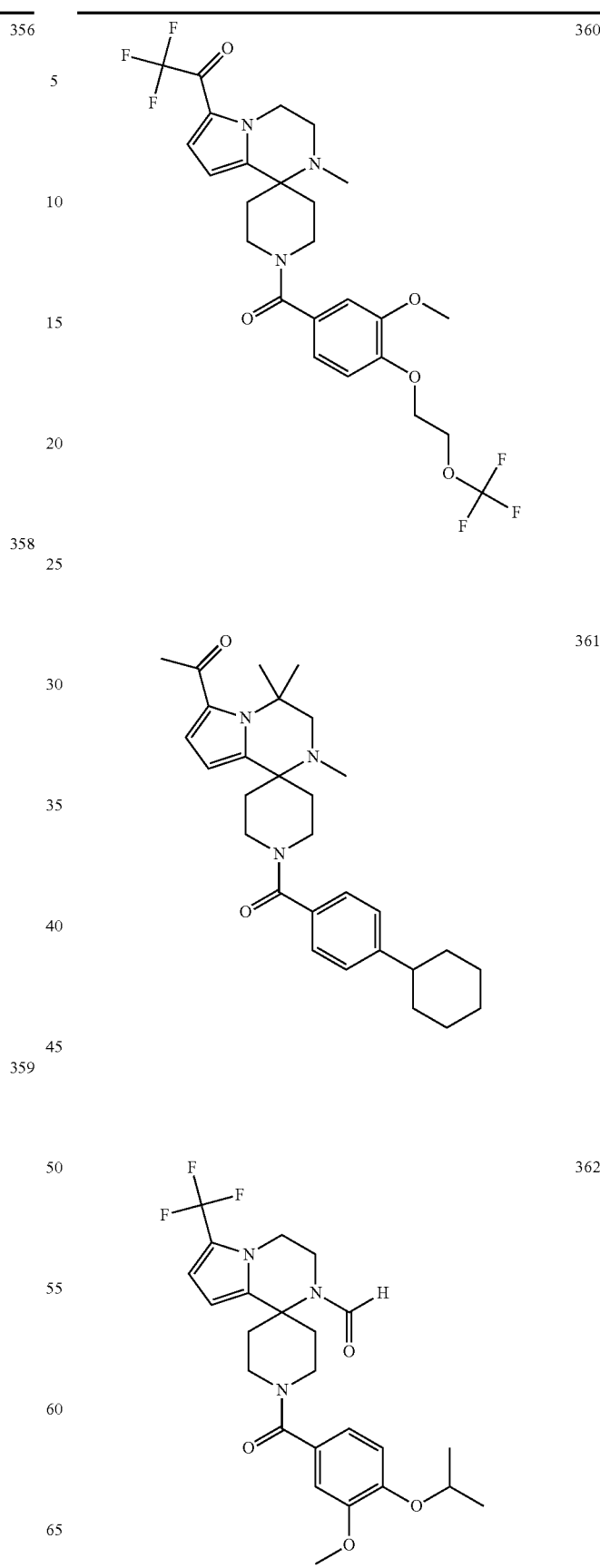

| 645 -continued | 646 -continued |
|---|---|
| 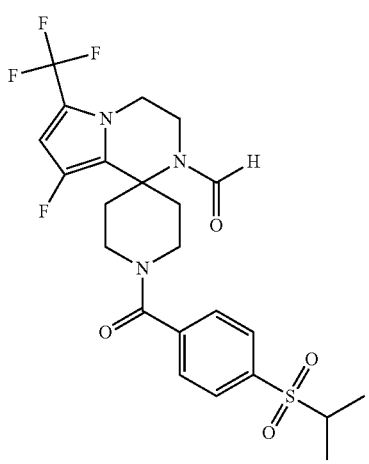 [SMILES: CC(C)S(=O)(=O)c1ccc(C(=O)N2CCC3(CC2)c2c(F)cc(C(F)(F)F)n2CCN3C=O)cc1] 363 | 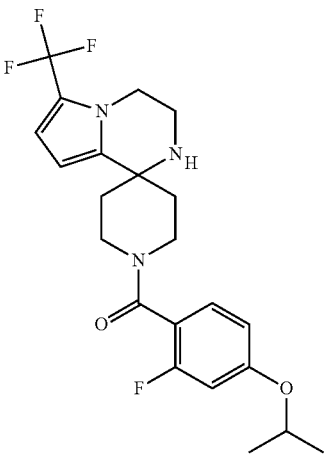 367 |
| 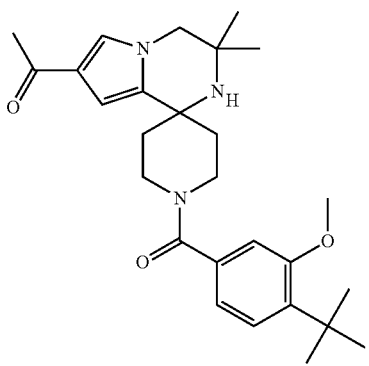 364 | 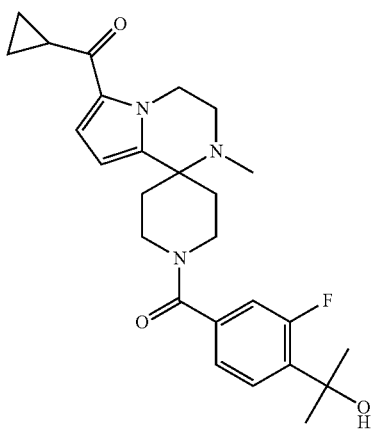 368 |
| 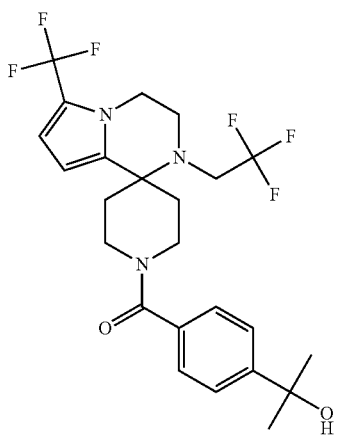 [SMILES: CC(C)(O)c1ccc(C(=O)N2CCC3(CC2)c2ccc(C(F)(F)F)n2CCN3CC(F)(F)F)cc1] 366 | 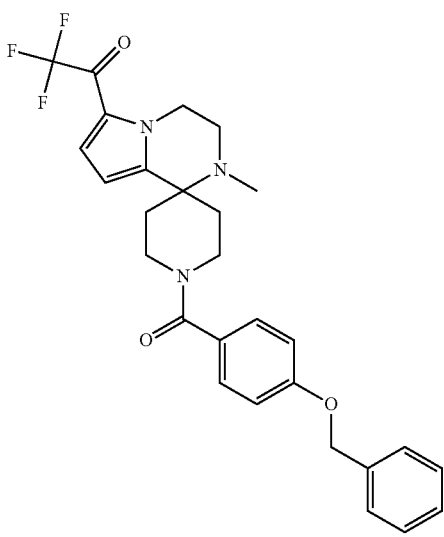 369 |

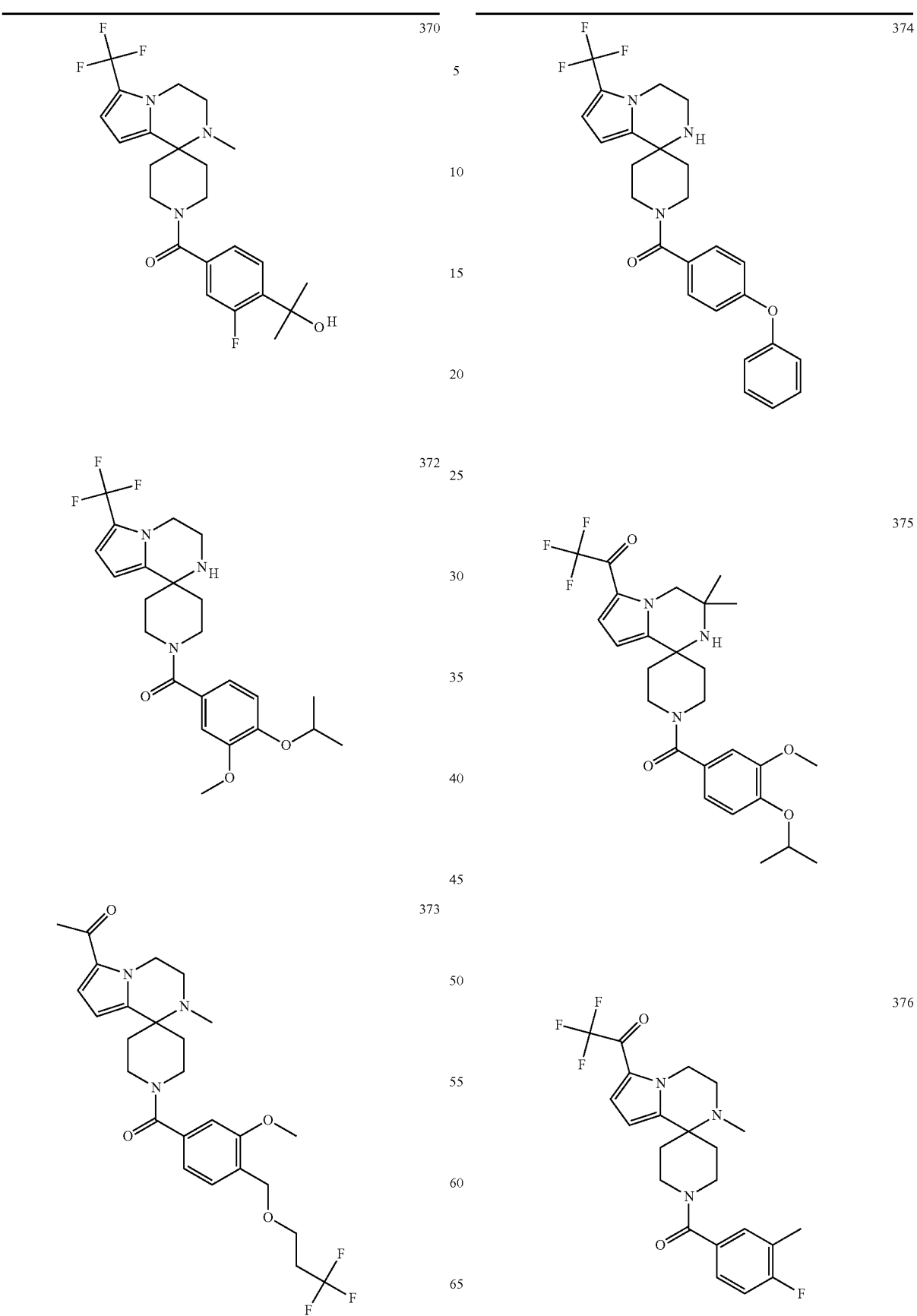

| 649 -continued | 650 -continued |
|---|---|
| 377 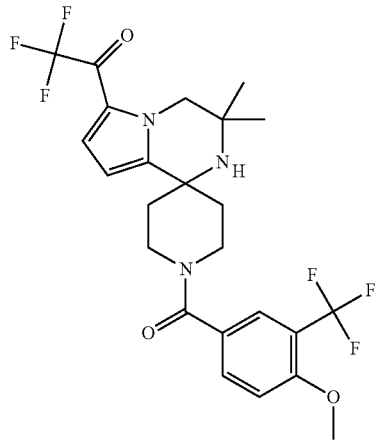 | 382 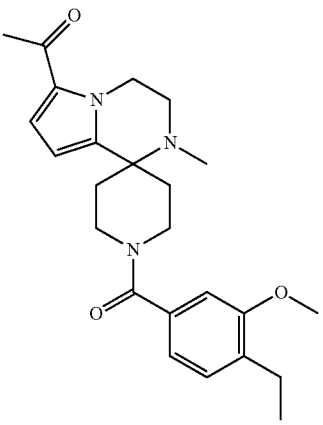 |
| 380 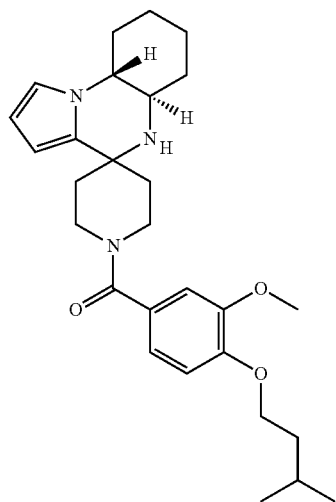 | 383 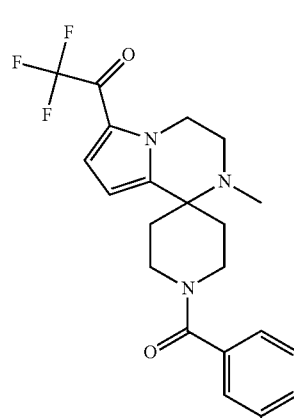 |
| 381 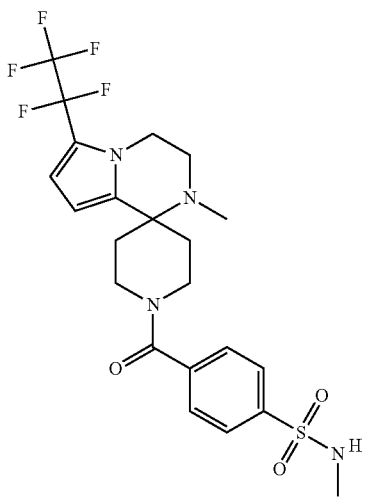 | 384 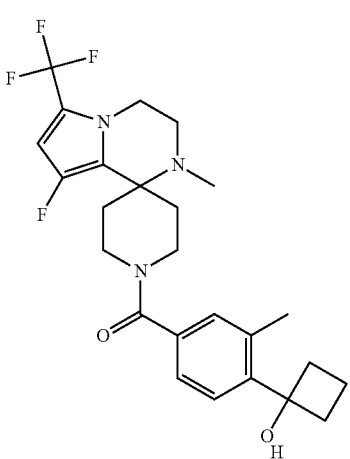 |

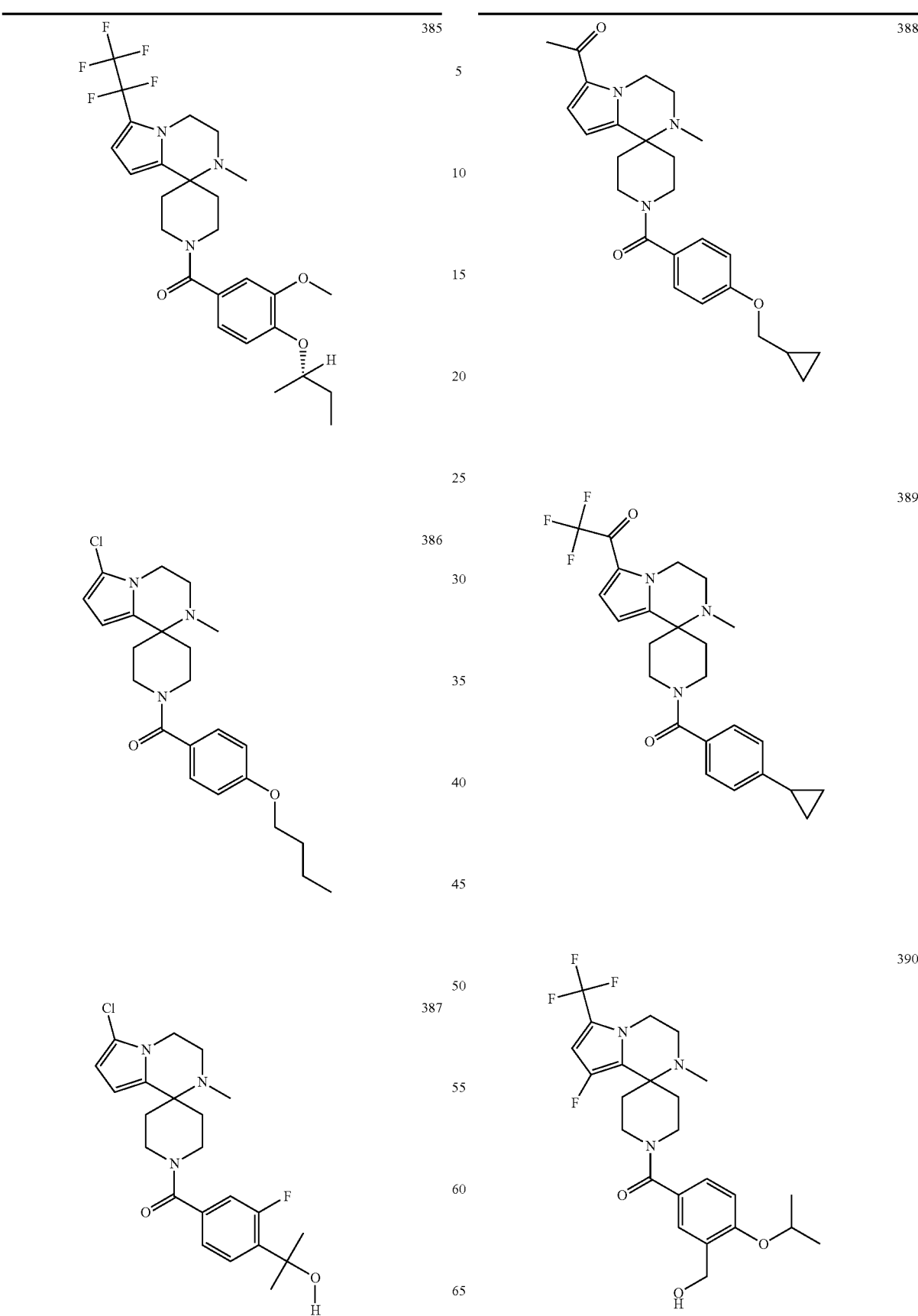

| 653 -continued | 654 -continued |
|---|---|
| 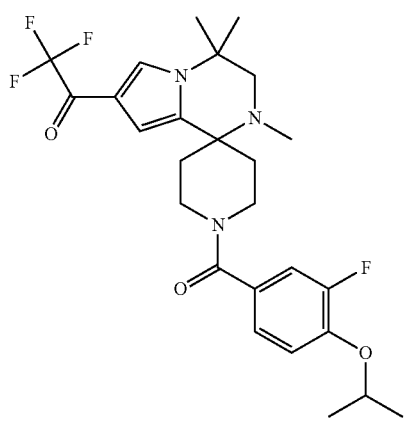 391 | 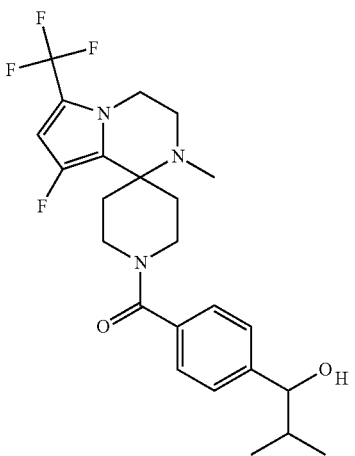 395 |
| 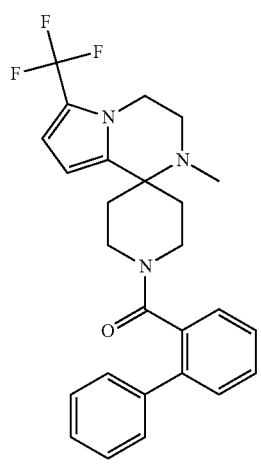 [SMILES: CN1CCn2c(C(F)(F)F)ccc2C12CCN(C(=O)c1ccccc1-c1ccccc1)CC2] 393 | 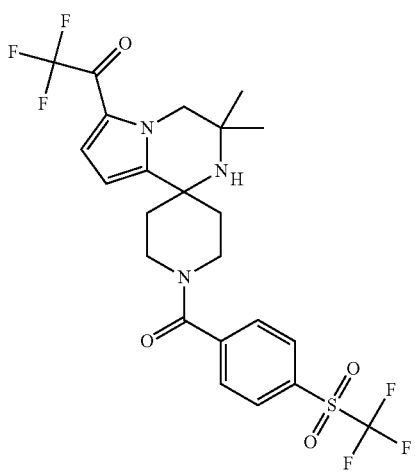 396 |
| 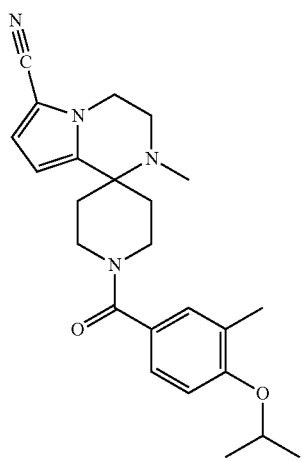 [SMILES: Cc1cc(C(=O)N2CCC3(CC2)c2ccc(C#N)n2CCN3C)ccc1OC(C)C] 394 | 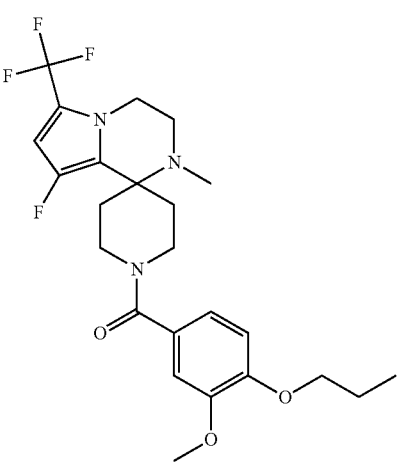 397 |

| 655 -continued | 656 -continued |
|---|---|
| 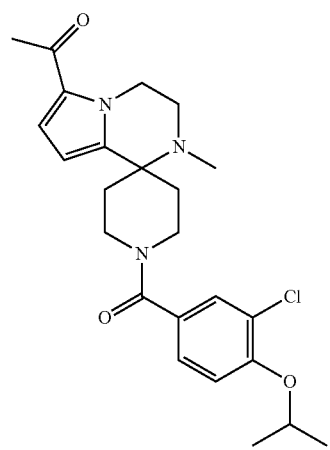 [SMILES: CC(=O)c1ccc2n1CCN(C)C21CCN(C(=O)c2ccc(OC(C)C)c(Cl)c2)CC1] 398 | 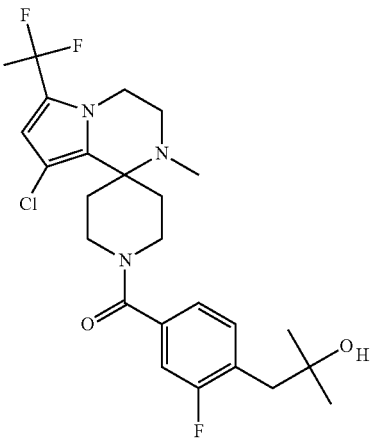 401 |
| 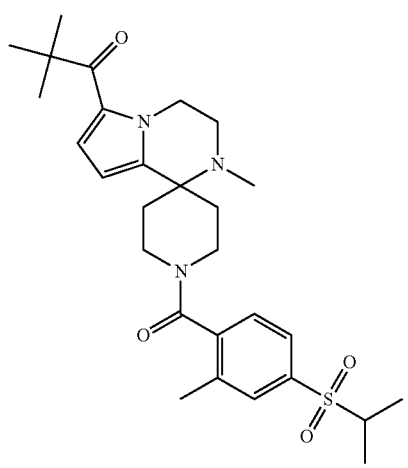 [SMILES: Cc1cc(S(=O)(=O)C(C)C)ccc1C(=O)N1CCC2(CC1)c1ccc(C(=O)C(C)(C)C)n1CCN2C] 399 | 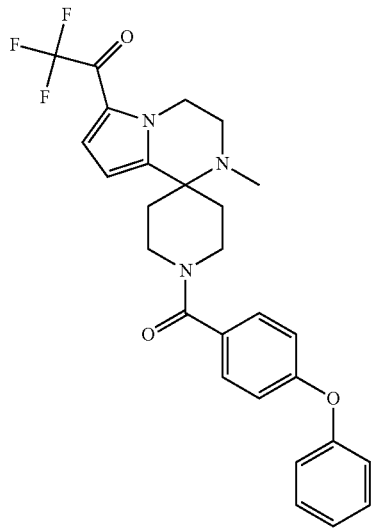 402 |
| 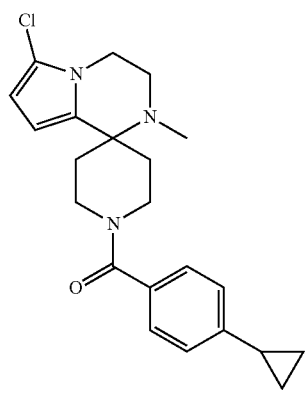 [SMILES: CN1CCn2c(Cl)ccc2C12CCN(C(=O)c1ccc(C3CC3)cc1)CC2] 400 | 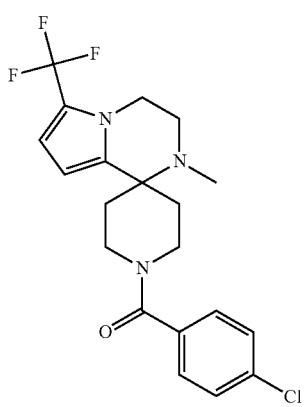 [SMILES: CN1CCn2c(C(F)(F)F)ccc2C12CCN(C(=O)c1ccc(Cl)cc1)CC2] 403 |

404 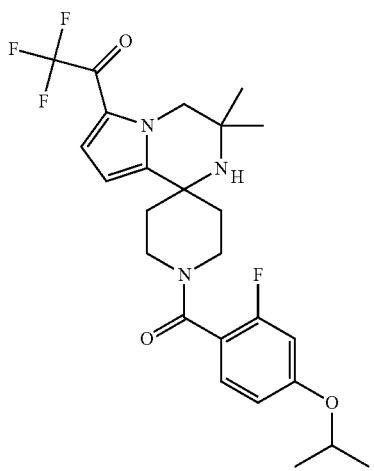
405 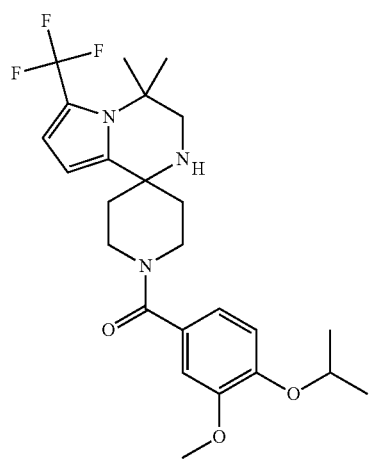
406 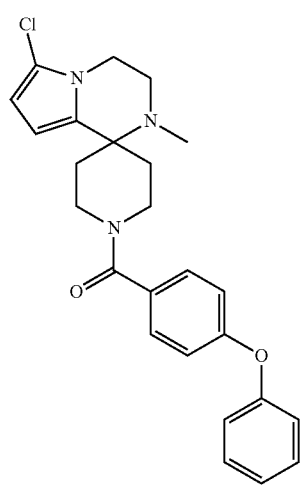 [SMILES: CN1CCn2c(Cl)ccc2C12CCN(C(=O)c1ccc(Oc3ccccc3)cc1)CC2]
407 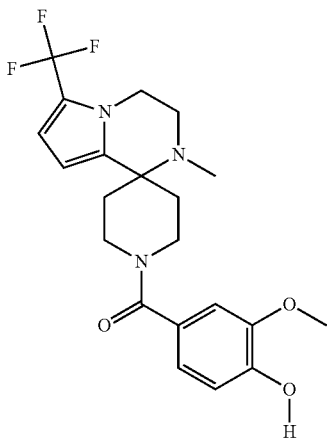 [SMILES: COc1cc(C(=O)N2CCC3(CC2)c2ccc(C(F)(F)F)n2CCN3C)ccc1O]
408 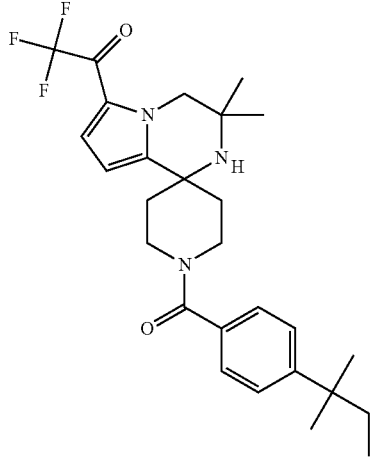
409 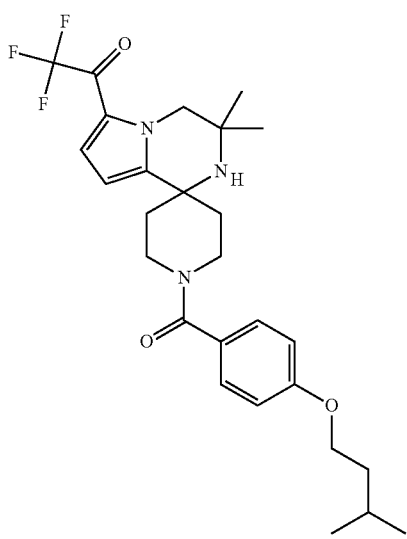

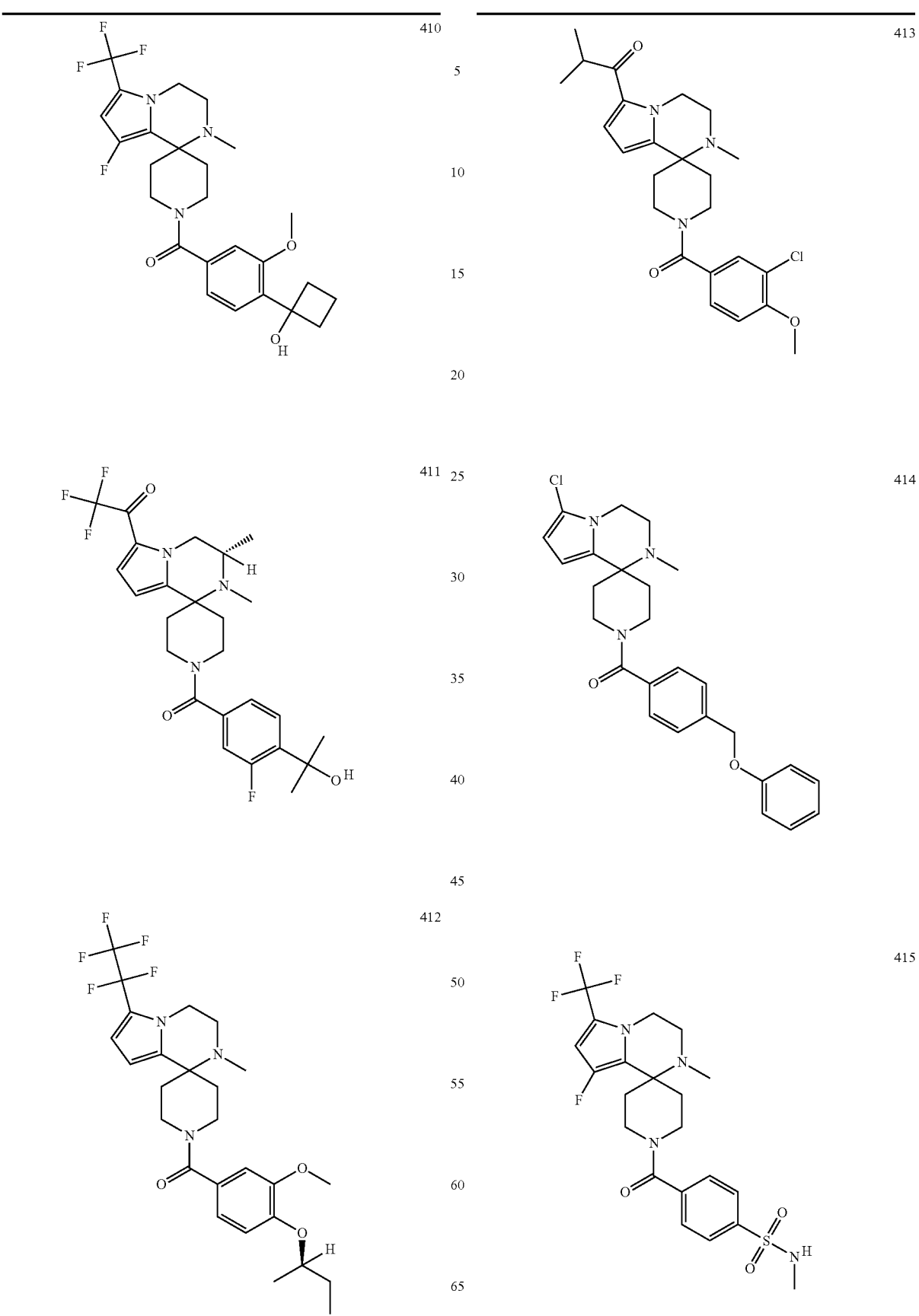

| 661 -continued | | 662 -continued | |
|---|---|---|---|
| 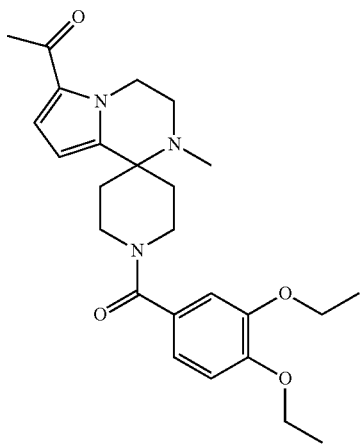 [SMILES: CCOc1ccc(C(=O)N2CCC3(CC2)c2ccc(C(C)=O)n2CCN3C)cc1OCC] | 416 | 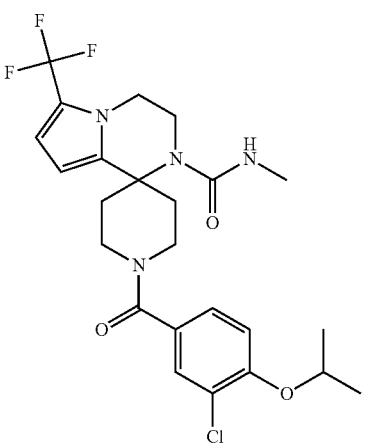 | 419 |
| 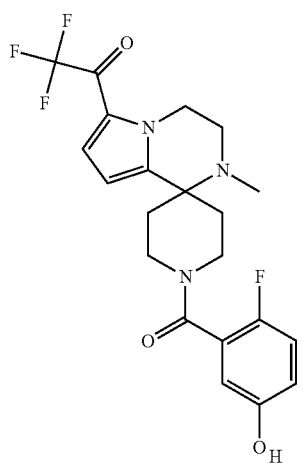 | 417 | 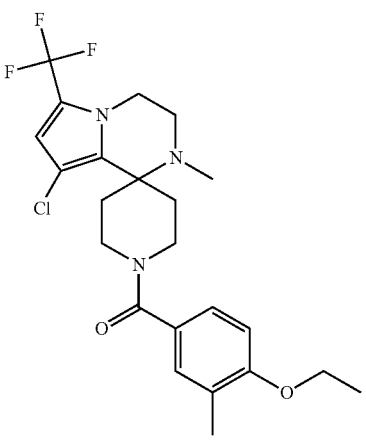 | 420 |
| 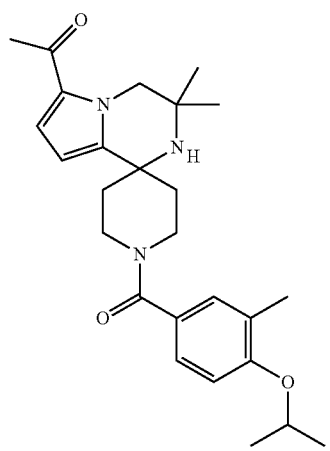 | 418 | 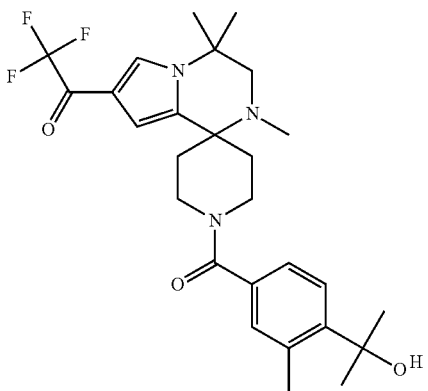 | 421 |

| 663 -continued | 664 -continued |
|---|---|
| 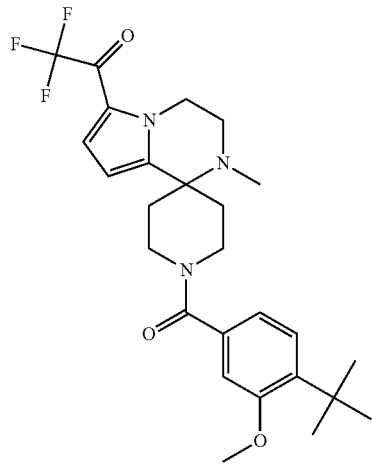 [SMILES: COc1cc(C(=O)N2CCC3(CC2)c2ccc(C(=O)C(F)(F)F)n2CCN3C)ccc1C(C)(C)C] 423 | 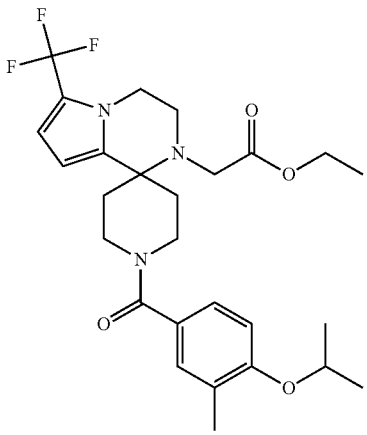 426 |
| 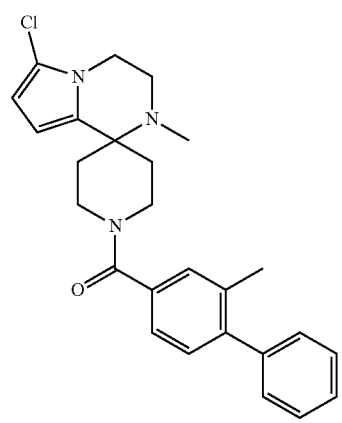 [SMILES: Cc1cc(C(=O)N2CCC3(CC2)c2ccc(Cl)n2CCN3C)ccc1-c1ccccc1] 424 | 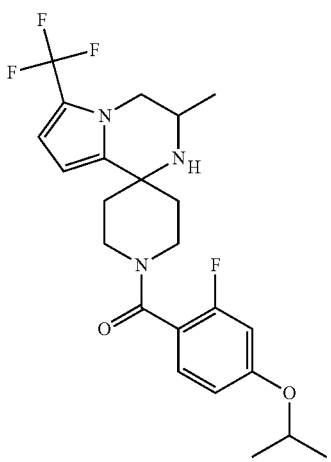 427 |
| 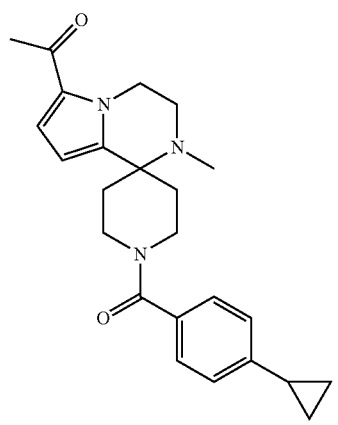 [SMILES: CC(=O)c1ccc2n1CCN(C)C21CCN(C(=O)c2ccc(C3CC3)cc2)CC1] 425 | 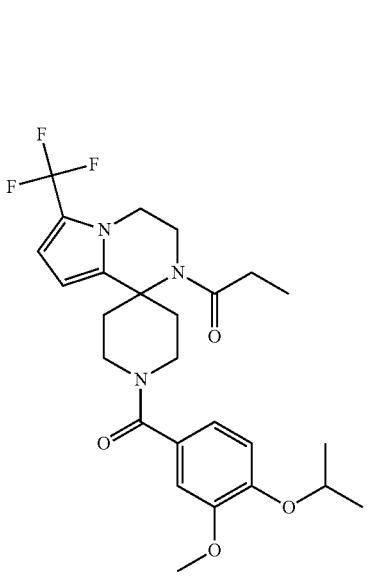 428 |

| 665 -continued | | 666 -continued | |
|---|---|---|---|
| 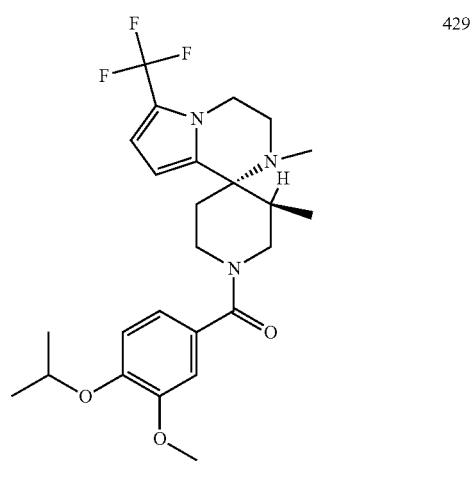 | 429 | 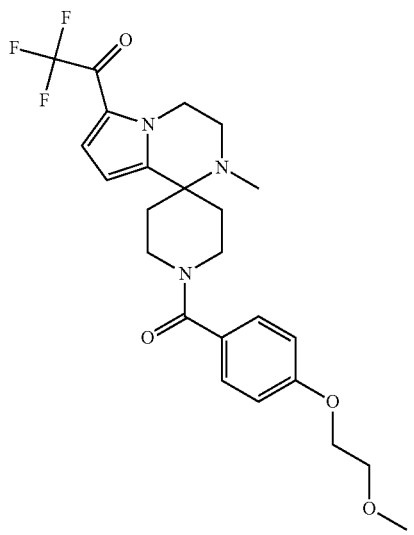 [SMILES: COCCOc1ccc(C(=O)N2CCC3(CC2)c2ccc(C(=O)C(F)(F)F)n2CCN3C)cc1] | 434 |
| 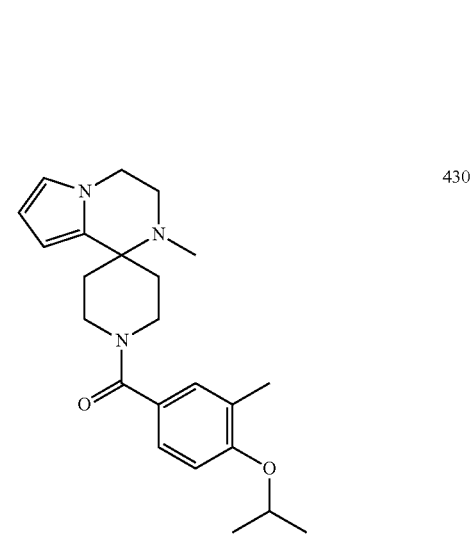 | 430 | 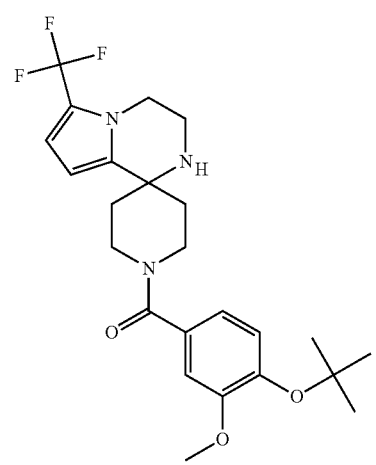 | 435 |
| 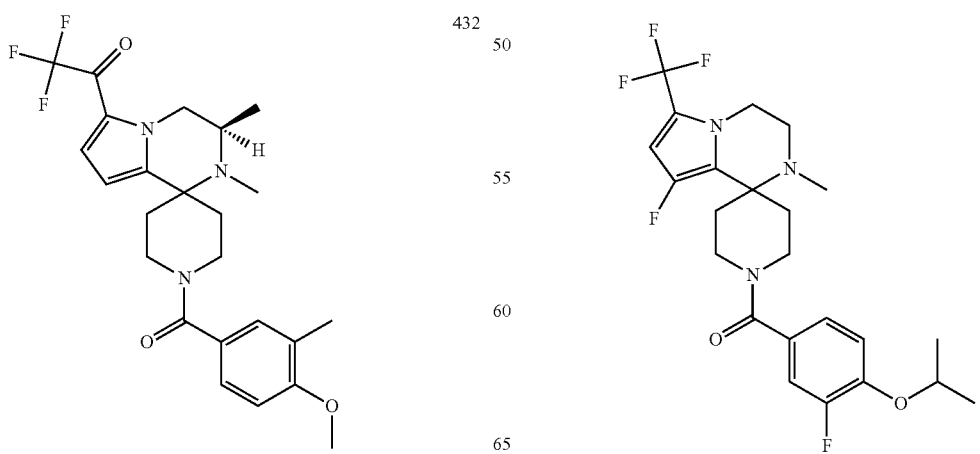 | 432 | | 436 |

667
-continued
| 437 | 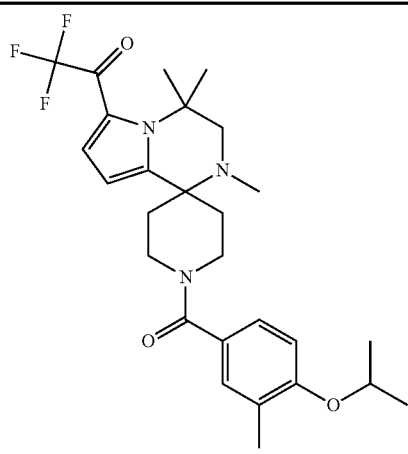 |
| 439 | 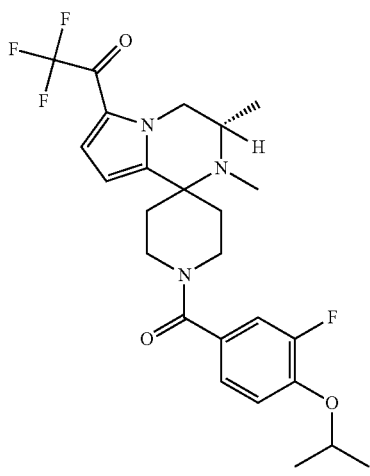 |
| 440 | 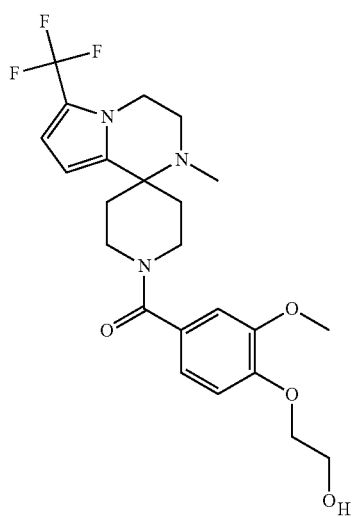 |
668
-continued
| 441 | 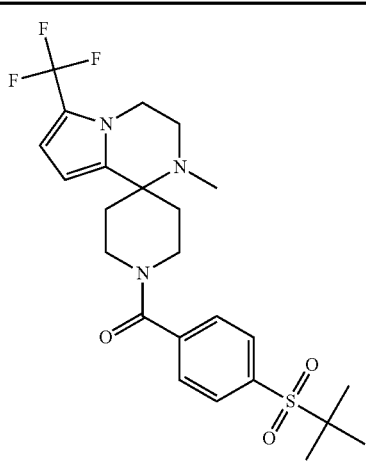 |
| 442 | 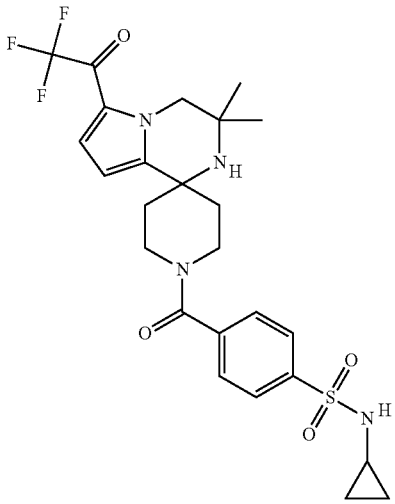 |
| 443 | 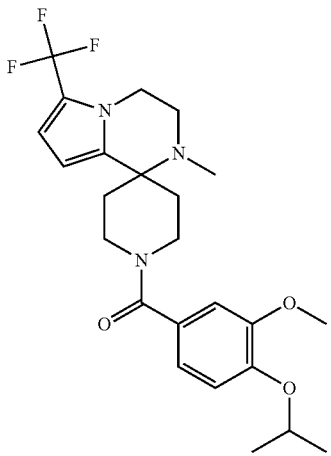 [SMILES: COc1cc(C(=O)N2CCC3(CC2)c2ccc(C(F)(F)F)n2CCN3C)ccc1OC(C)C] |

| 669 -continued | 670 -continued |
|---|---|
| 445 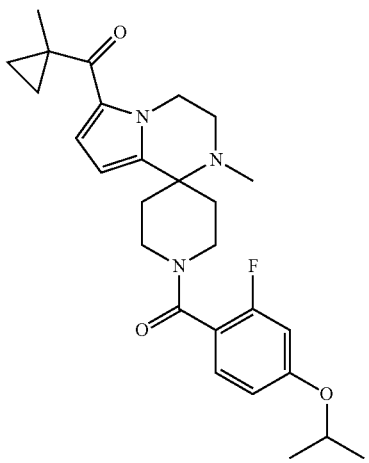 [SMILES: CC(C)Oc1ccc(C(=O)N2CCC3(CC2)c2ccc(C(=O)C4(C)CC4)n2CCN3C)c(F)c1] | 449 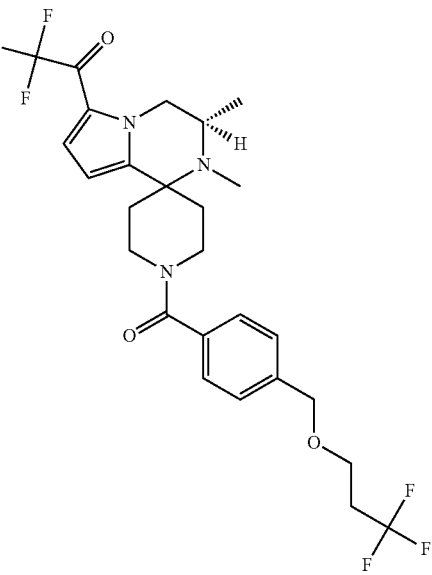 |
| 446 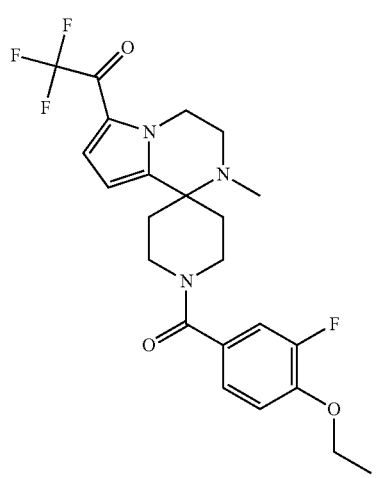 [SMILES: CCOc1ccc(C(=O)N2CCC3(CC2)c2ccc(C(=O)C(F)(F)F)n2CCN3C)cc1F] | 450 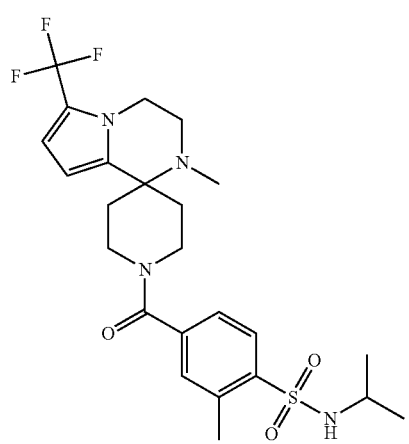 |
| 447 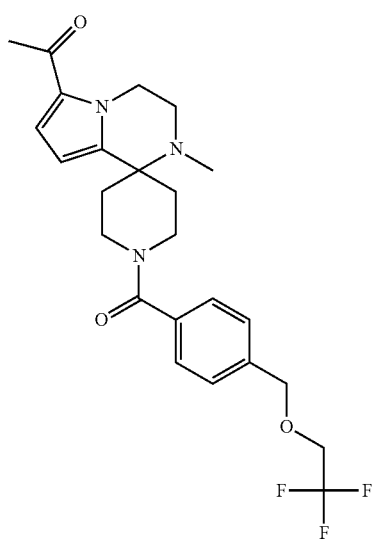 [SMILES: CC(=O)c1ccc2n1CCN(C)C21CCN(C(=O)c2ccc(COCC(F)(F)F)cc2)CC1] | 451 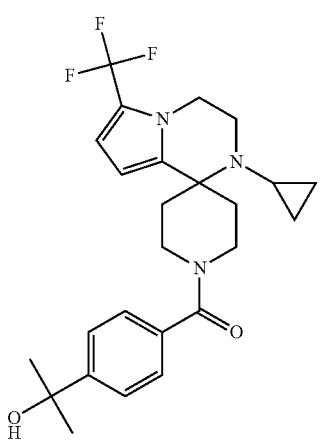 [SMILES: CC(C)(O)c1ccc(C(=O)N2CCC3(CC2)c2ccc(C(F)(F)F)n2CCN3C2CC2)cc1] |

| 452 | 456 |
|---|---|
| 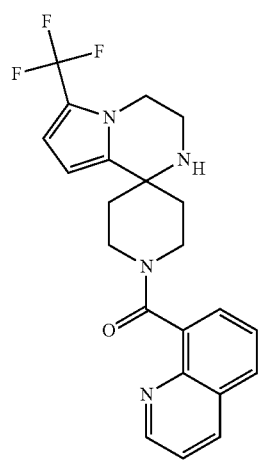 | 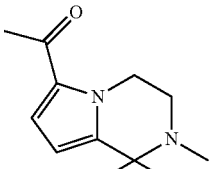 |
| 454 | 457 |
|---|---|
| 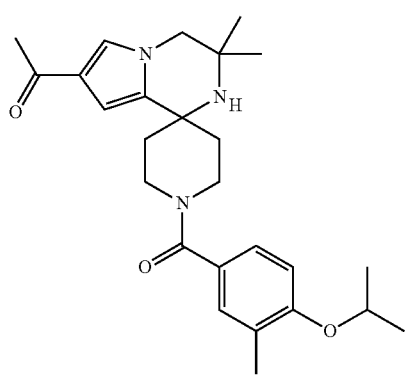 | 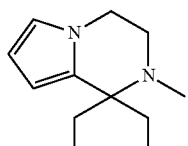 |
| 455 | 458 |
|---|---|
| 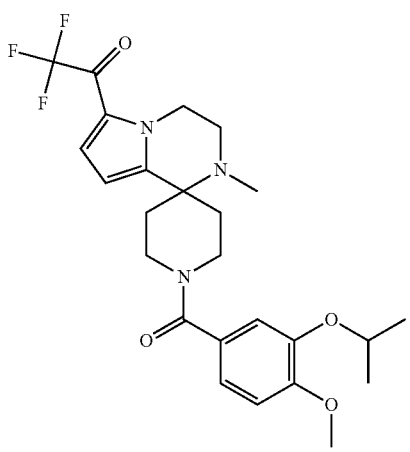 [SMILES: COc1ccc(C(=O)N2CCC3(CC2)c2ccc(C(=O)C(F)(F)F)n2CCN3C)cc1OC(C)C] | 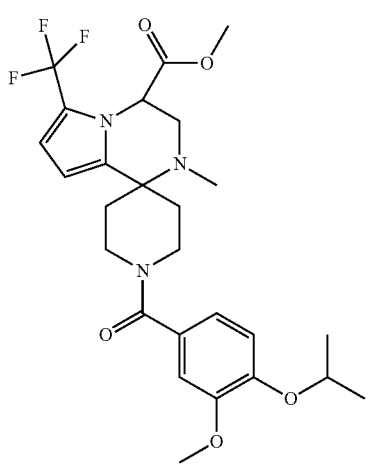 [SMILES: COC(=O)C1CN(C)C2(CCN(C(=O)c3ccc(OC(C)C)c(OC)c3)CC2)c2ccc(C(F)(F)F)n21] |

| 673 -continued | 674 -continued |
|---|---|
| 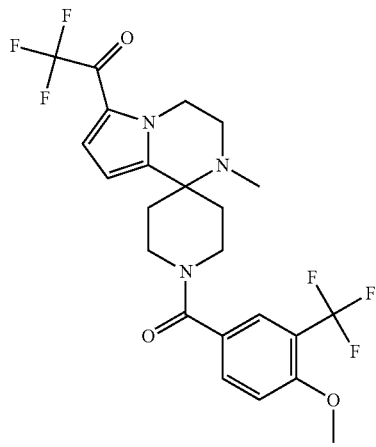 [SMILES: COc1ccc(C(=O)N2CCC3(CC2)c2ccc(C(=O)C(F)(F)F)n2CCN3C)cc1C(F)(F)F] 459 | 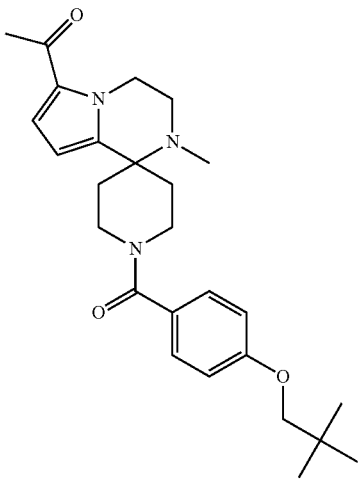 462 |
| 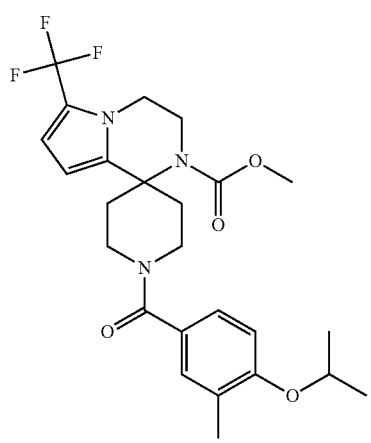 [SMILES: COC(=O)N1CCn2c(C(F)(F)F)ccc2C12CCN(C(=O)c1ccc(OC(C)C)c(C)c1)CC2] 460 | 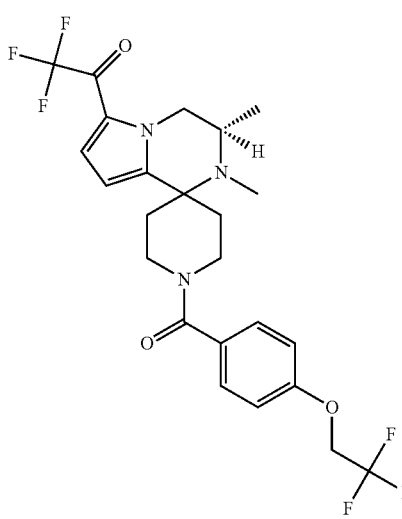 463 |
| 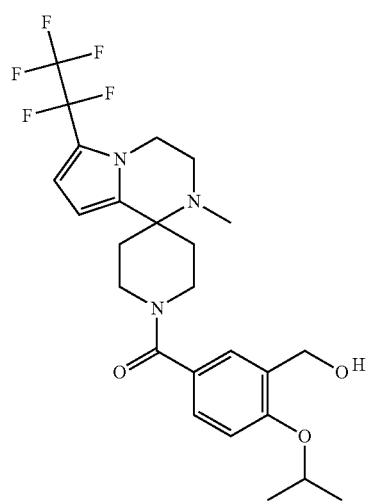 461 | 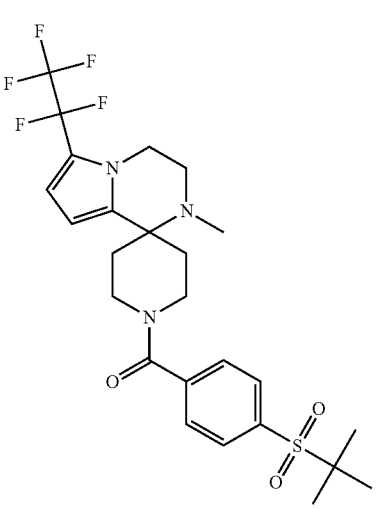 [SMILES: CN1CCn2c(ccc2C(F)(F)C(F)(F)F)C12CCN(C(=O)c1ccc(S(=O)(=O)C(C)(C)C)cc1)CC2] 464 |

| 675 -continued | 676 -continued |
|---|---|
| 466 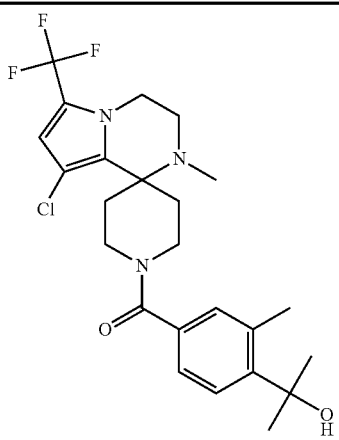 | 470 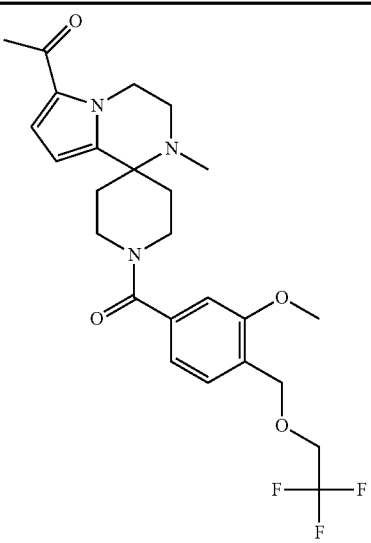 |
| 467 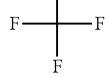 | 471 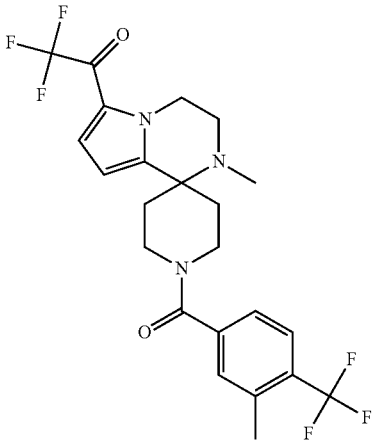 |
| 469 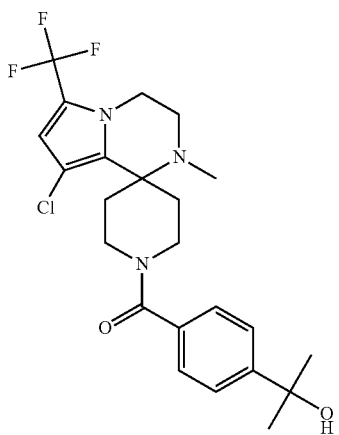 [SMILES: CN1CCn2c(C(F)(F)F)cc(Cl)c2C12CCN(C(=O)c1ccc(C(C)(C)O)cc1)CC2] | 472 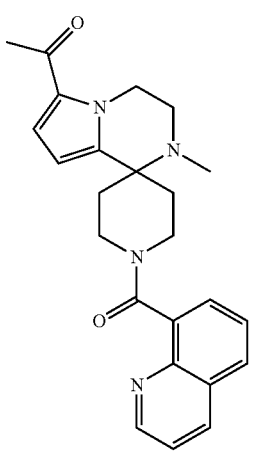 [SMILES: CC(=O)c1ccc2n1CCN(C)C21CCN(C(=O)c2cccc3cccnc23)CC1] |

| 677 -continued | 678 -continued |
|---|---|
| 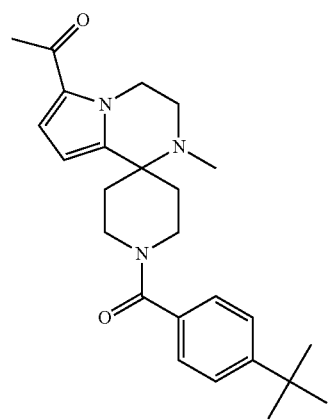 [SMILES: CC(=O)c1ccc2n1CCN(C)C21CCN(C(=O)c2ccc(C(C)(C)C)cc2)CC1] 473 | 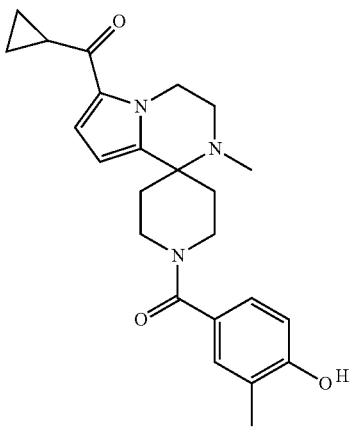 476 |
| 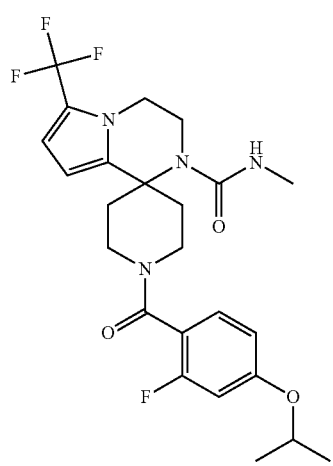 474 | 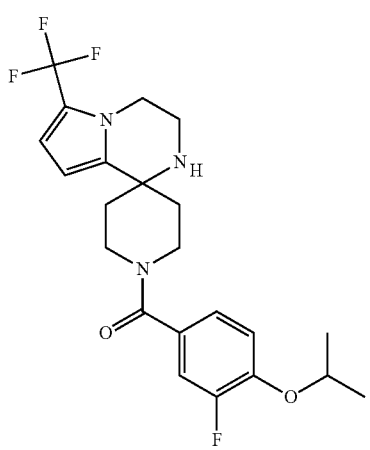 477 |
| 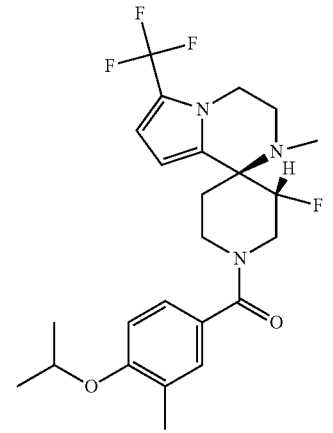 [SMILES: Cc1cc(C(=O)N2CC[C@]3(c4ccc(C(F)(F)F)n4CCN3C)[C@H](F)C2)ccc1OC(C)C] 475 | 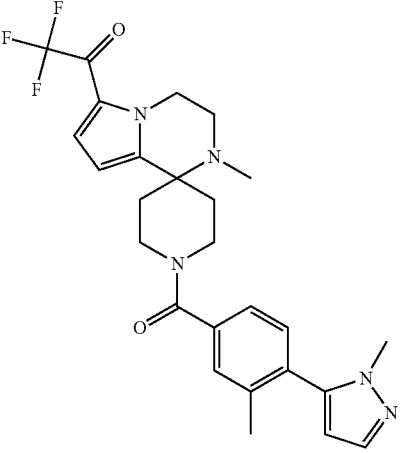 [SMILES: Cc1cc(C(=O)N2CCC3(CC2)c2ccc(C(=O)C(F)(F)F)n2CCN3C)ccc1-c1ccnn1C] 478 |

| 679 -continued | 680 -continued |
|---|---|
| 479 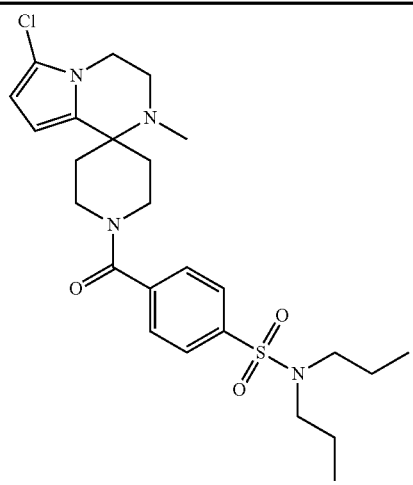 | 483 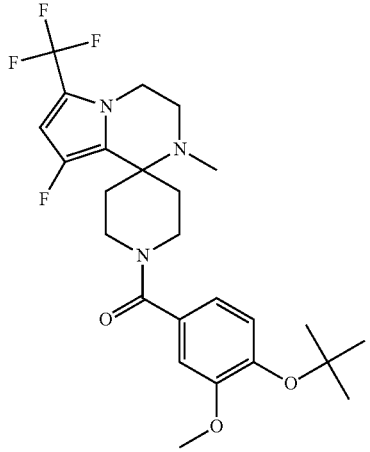 [SMILES: COc1cc(C(=O)N2CCC3(CC2)c2c(F)cc(C(F)(F)F)n2CCN3C)ccc1OC(C)(C)C] |
| 480 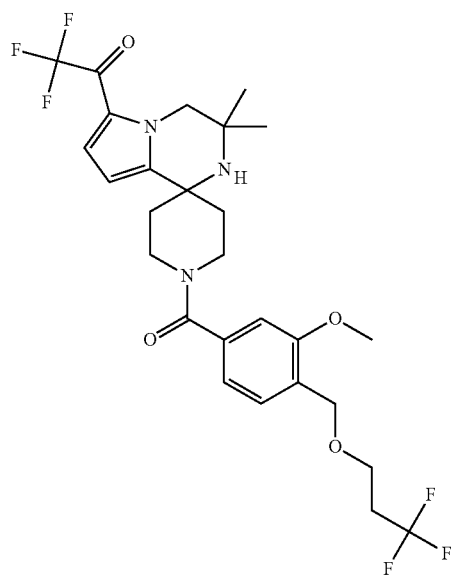 | 484 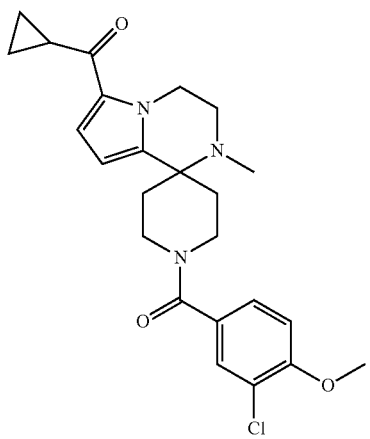 [SMILES: COc1ccc(C(=O)N2CCC3(CC2)c2ccc(C(=O)C4CC4)n2CCN3C)cc1Cl] |
| 482 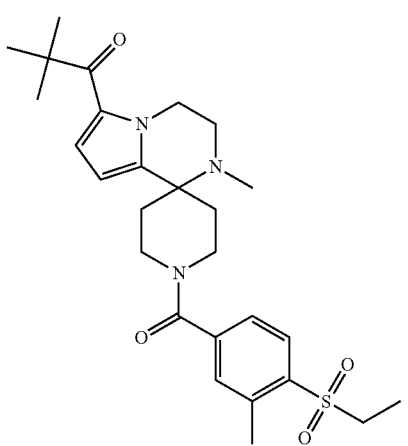 | 486 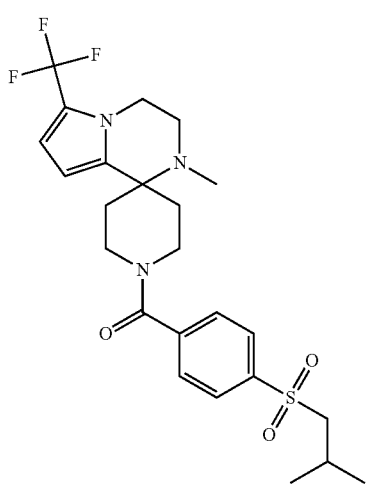 [SMILES: CC(C)CS(=O)(=O)c1ccc(C(=O)N2CCC3(CC2)c2ccc(C(F)(F)F)n2CCN3C)cc1] |

| 681 -continued | 682 -continued |
|---|---|
| 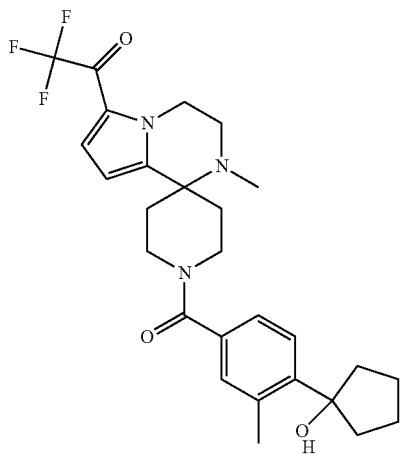 487 | 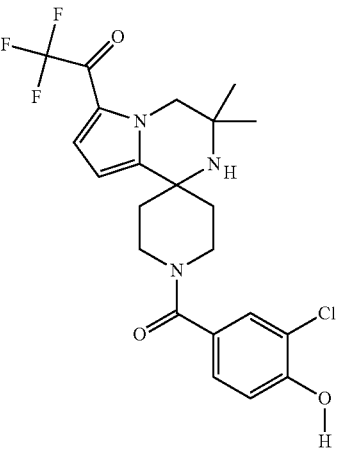 491 |
| 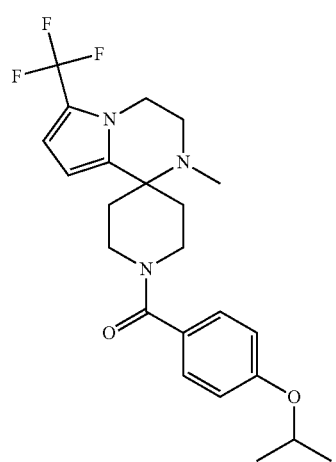 [SMILES: CC(C)Oc1ccc(C(=O)N2CCC3(CC2)c2ccc(C(F)(F)F)n2CCN3C)cc1] 488 | 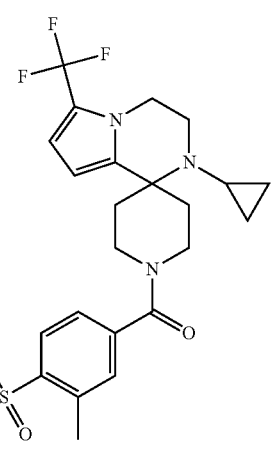 492 |
| 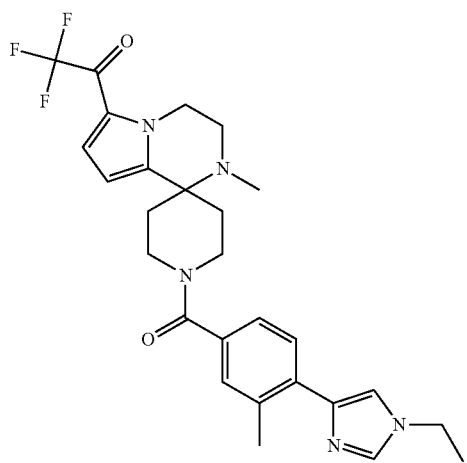 [SMILES: CCn1cnc(-c2ccc(C(=O)N3CCC4(CC3)c3ccc(C(=O)C(F)(F)F)n3CCN4C)cc2C)c1] 489 | 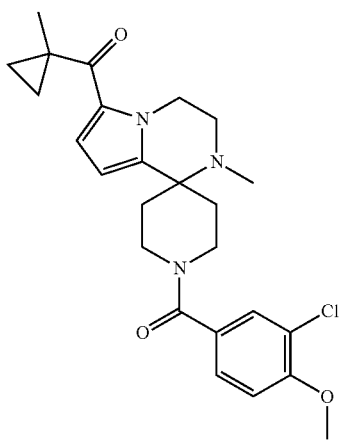 [SMILES: COc1ccc(C(=O)N2CCC3(CC2)c2ccc(C(=O)C4(C)CC4)n2CCN3C)cc1Cl] 493 |

| 683 | 684 |
|---|---|
| 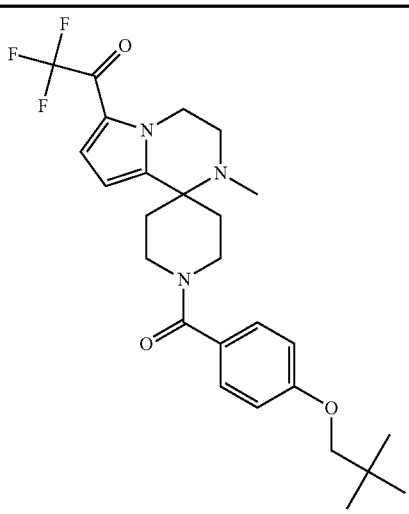 494 | 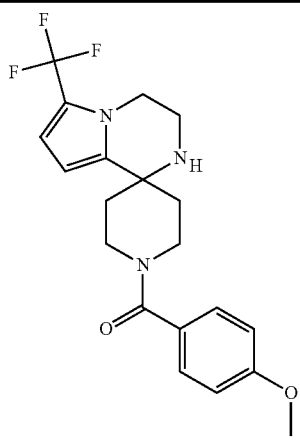 497 |
| 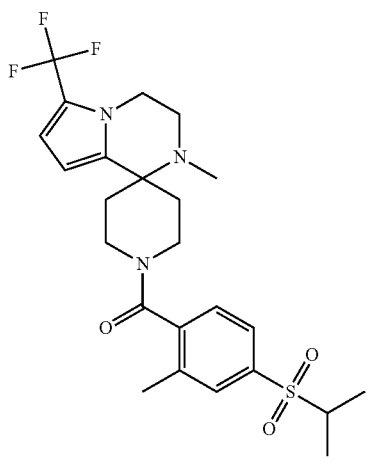 495 | 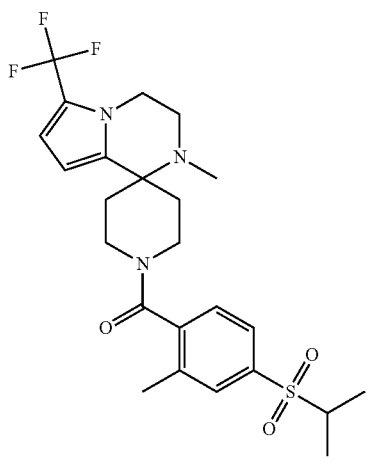 498 |
| 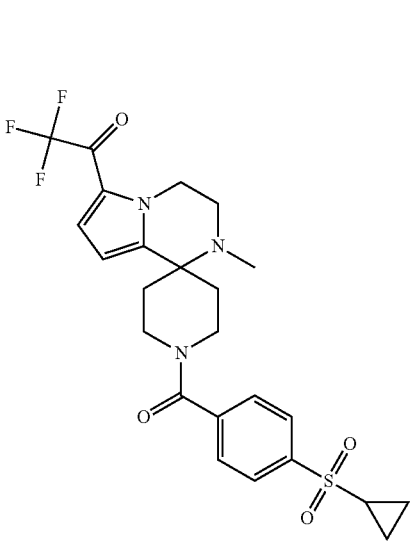 [SMILES: CN1CCn2c(C(=O)C(F)(F)F)ccc2C12CCN(C(=O)c1ccc(S(=O)(=O)C3CC3)cc1)CC2] 496 | 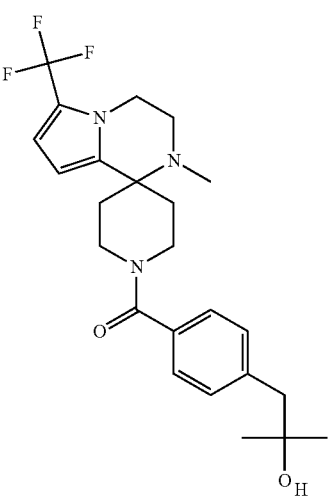 499 |

| 685 -continued | 686 -continued |
|---|---|
| 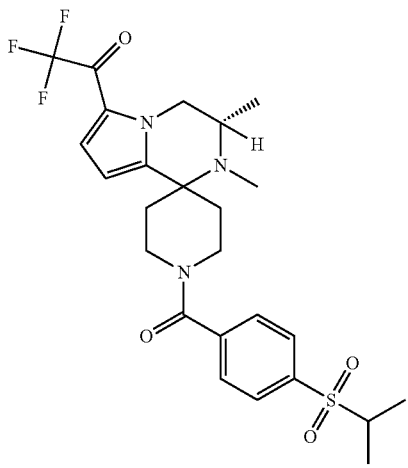 [SMILES: CC(C)S(=O)(=O)c1ccc(C(=O)N2CCC3(CC2)c2ccc(C(=O)C(F)(F)F)n2C[C@H](C)N3C)cc1] 500 | 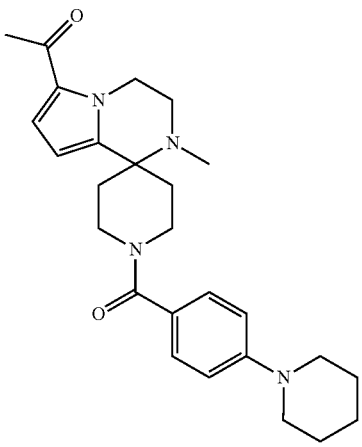 504 |
| 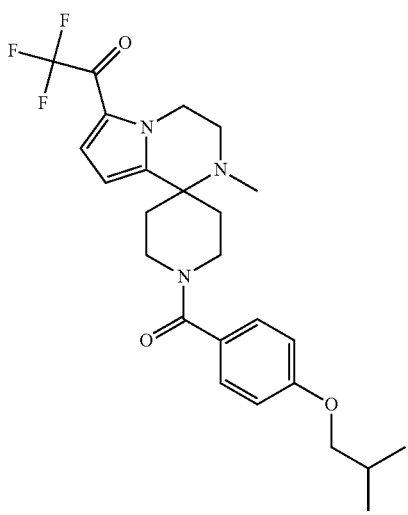 501 | 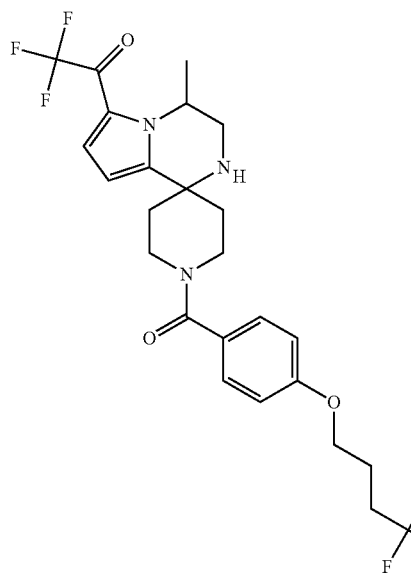 505 |
| 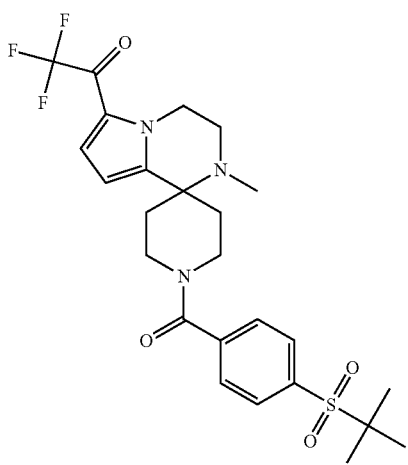 [SMILES: CN1CCn2c(C(=O)C(F)(F)F)ccc2C12CCN(C(=O)c1ccc(S(=O)(=O)C(C)(C)C)cc1)CC2] 502 | 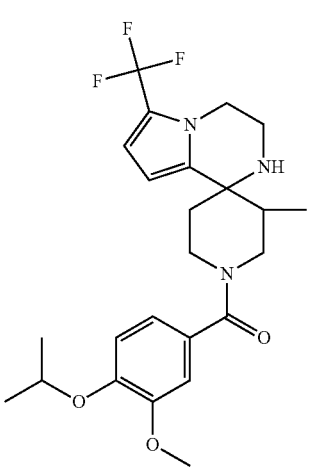 [SMILES: COc1cc(C(=O)N2CCC3(NCCn4c(C(F)(F)F)ccc43)C(C)C2)ccc1OC(C)C] 506 |

| 687 -continued | 688 -continued |
|---|---|
| 507 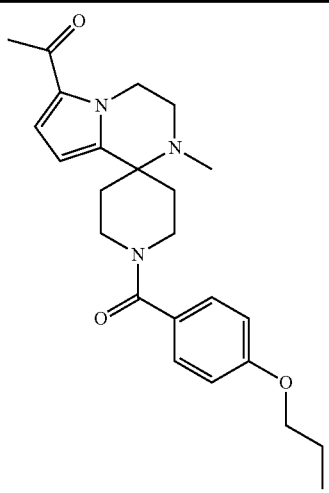 | 510 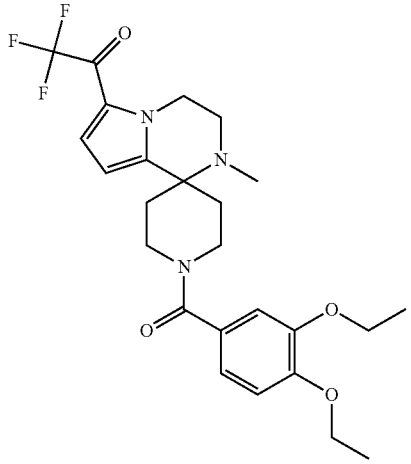 |
| 508 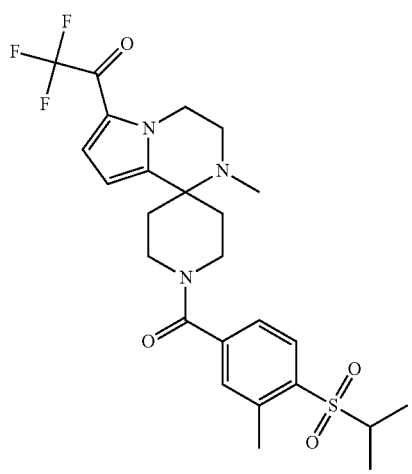 [SMILES: Cc1cc(C(=O)N2CCC3(CC2)c2ccc(C(=O)C(F)(F)F)n2CCN3C)ccc1S(=O)(=O)C(C)C] | 511 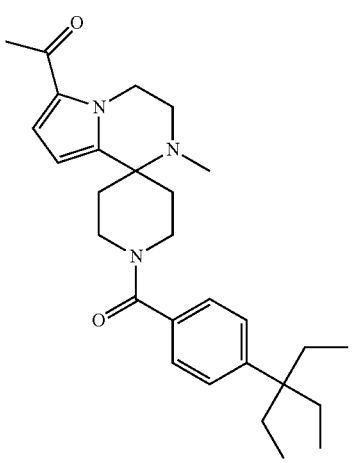 [SMILES: CCC(CC)(CC)c1ccc(C(=O)N2CCC3(CC2)c2ccc(C(C)=O)n2CCN3C)cc1] |
| 509 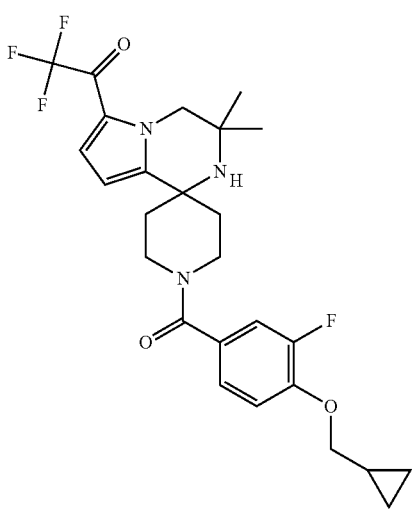 | 512 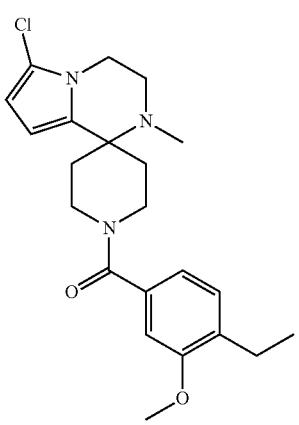 [SMILES: CCc1ccc(C(=O)N2CCC3(CC2)c2ccc(Cl)n2CCN3C)cc1OC] |

| 689 -continued | 690 -continued |
|---|---|
| 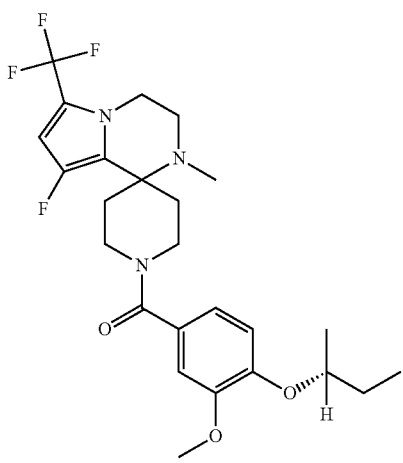 [SMILES: CC[C@@H](C)Oc1ccc(C(=O)N2CCC3(CC2)c2c(F)cc(C(F)(F)F)n2CCN3C)cc1OC] 513 | 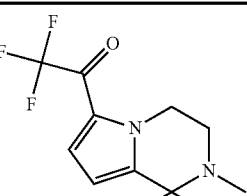 516 |
| 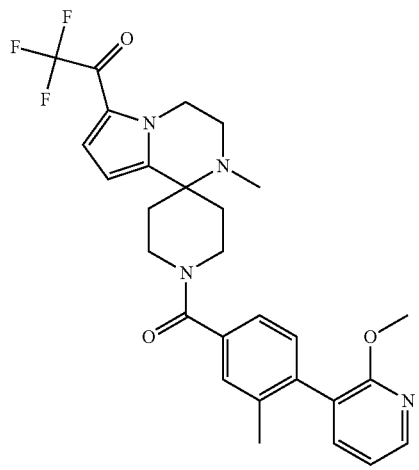 [SMILES: COc1ncccc1-c1ccc(C(=O)N2CCC3(CC2)c2ccc(C(=O)C(F)(F)F)n2CCN3C)cc1C] 514 | 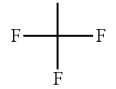 517 |
| 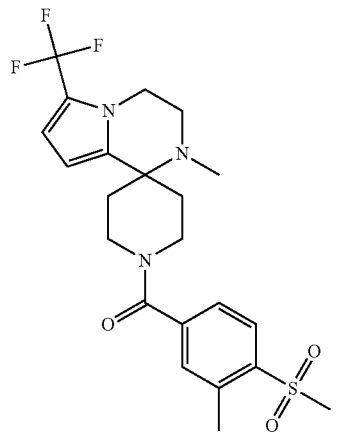 [SMILES: Cc1cc(C(=O)N2CCC3(CC2)c2ccc(C(F)(F)F)n2CCN3C)ccc1S(C)(=O)=O] 515 | 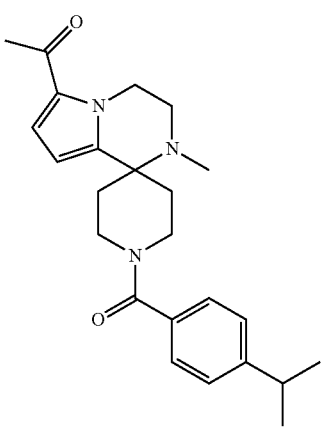 [SMILES: CC(=O)c1ccc2n1CCN(C)C21CCN(C(=O)c2ccc(C(C)C)cc2)CC1] 519 |

| 691 -continued | 692 -continued |
|---|---|
| 520 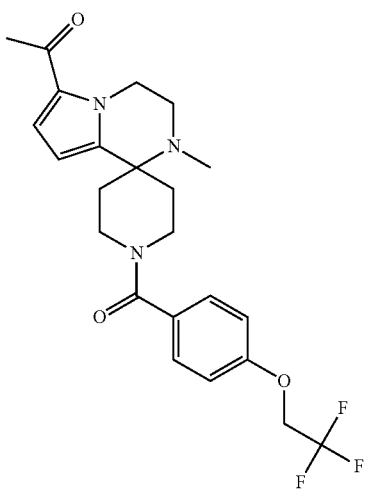 [SMILES: CC(=O)c1ccc2n1CCN(C)C21CCN(C(=O)c2ccc(OCC(F)(F)F)cc2)CC1] | 523 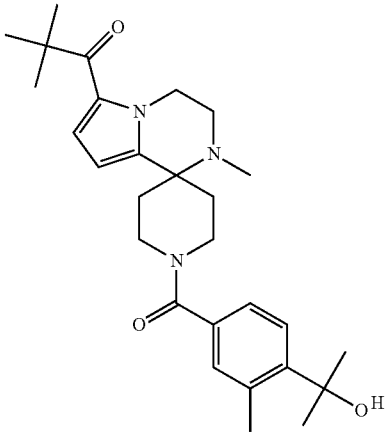 |
| 521 | 524 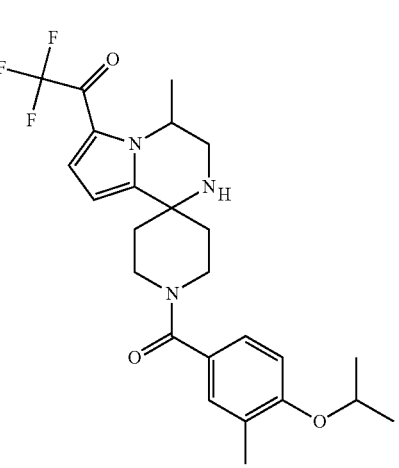 |
| 522 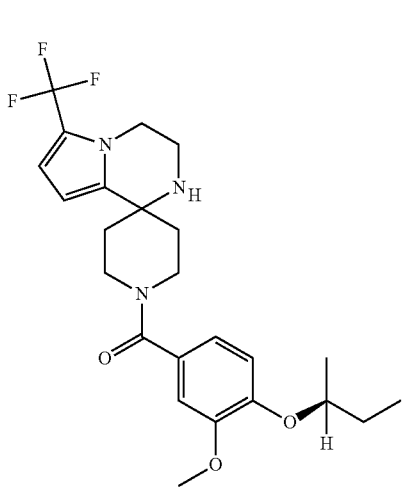 | 525 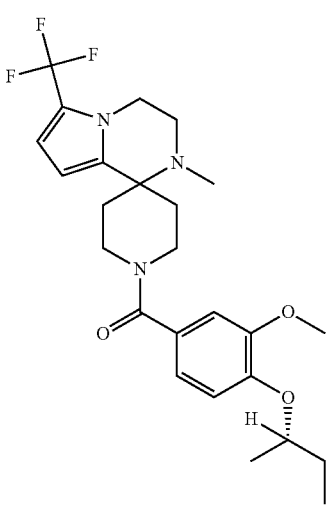 [SMILES: CC[C@H](C)Oc1ccc(C(=O)N2CCC3(CC2)c2ccc(C(F)(F)F)n2CCN3C)cc1OC] |

| 526 | 530 |
|---|---|
| 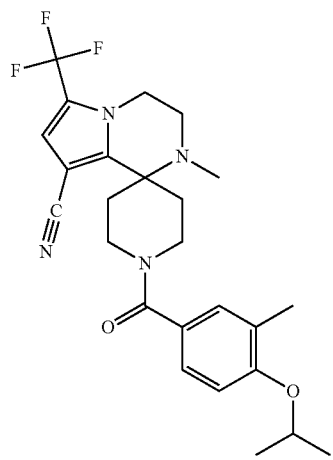 [SMILES: Cc1cc(C(=O)N2CCC3(CC2)c2c(C#N)cc(C(F)(F)F)n2CCN3C)ccc1OC(C)C] | 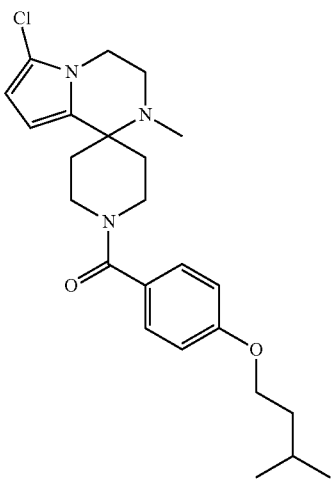 |
| 528 | 531 |
| 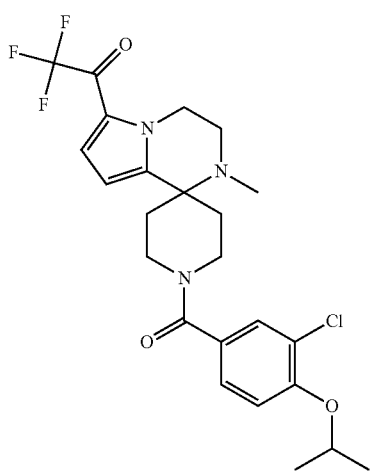 | 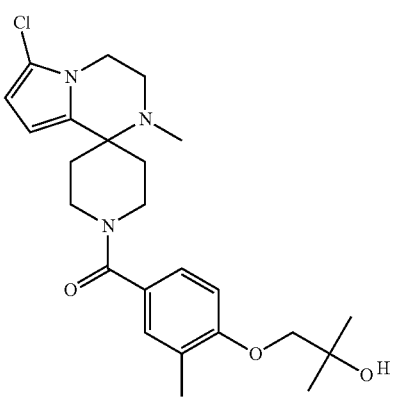 |
| 529 | 532 |
| 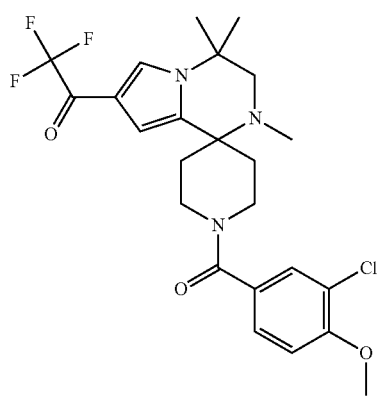 [SMILES: COc1ccc(C(=O)N2CCC3(CC2)c2cc(C(=O)C(F)(F)F)cn2C(C)(C)CN3C)cc1Cl] | 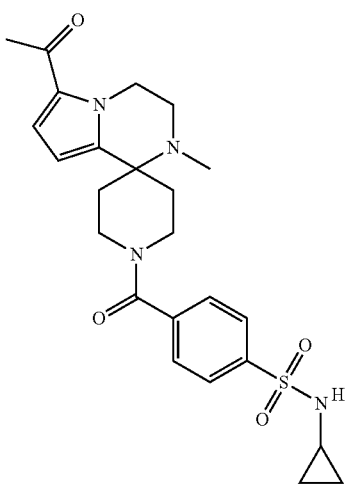 |

| 533 | 536 |
|---|---|
| 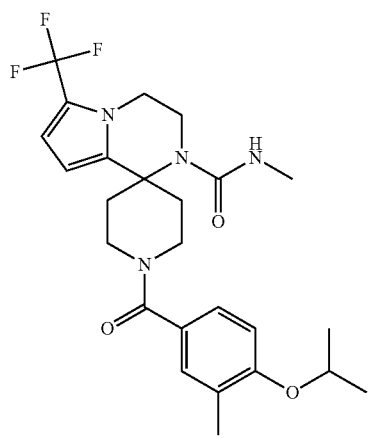 [SMILES: CNC(=O)N1CCn2c(C(F)(F)F)ccc2C12CCN(C(=O)c1ccc(OC(C)C)c(C)c1)CC2] | 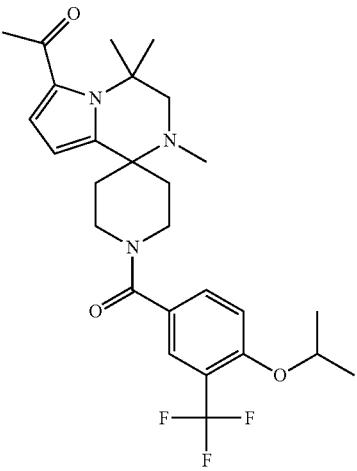 |
| 534 | 537 |
| 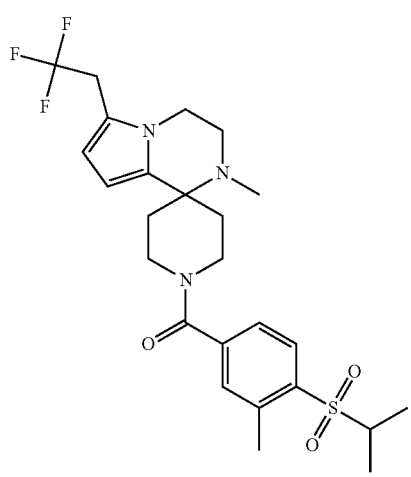 [SMILES: Cc1cc(C(=O)N2CCC3(CC2)c2ccc(CC(F)(F)F)n2CCN3C)ccc1S(=O)(=O)C(C)C] | 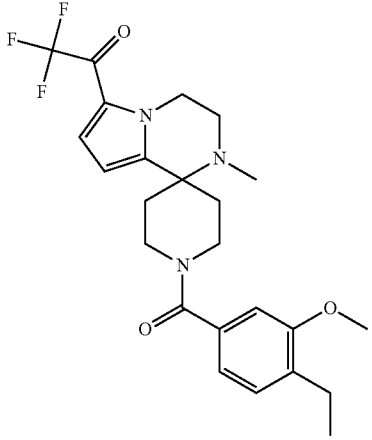 |
| 535 | 538 |
| 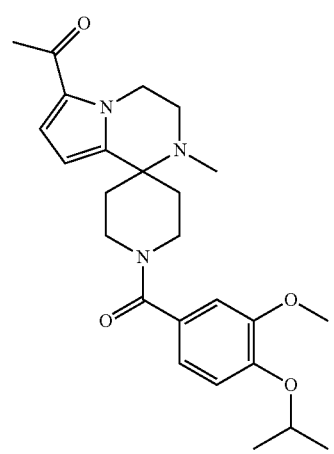 [SMILES: COc1cc(C(=O)N2CCC3(CC2)c2ccc(C(C)=O)n2CCN3C)ccc1OC(C)C] | 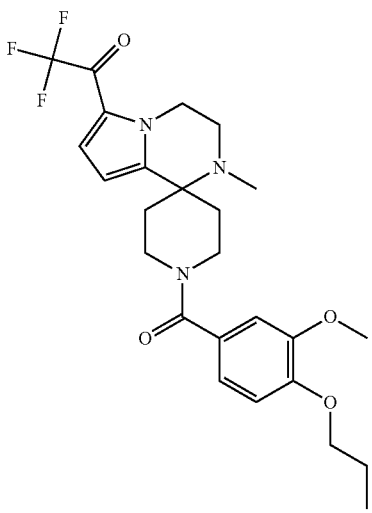 |

| 697 -continued | 698 -continued |
|---|---|
| 539 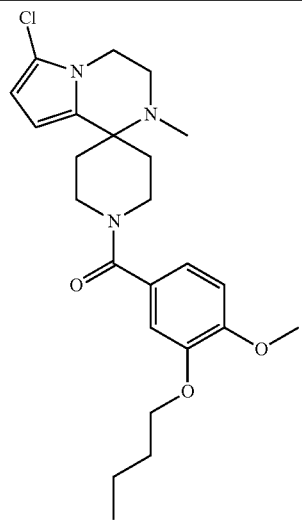 | 542 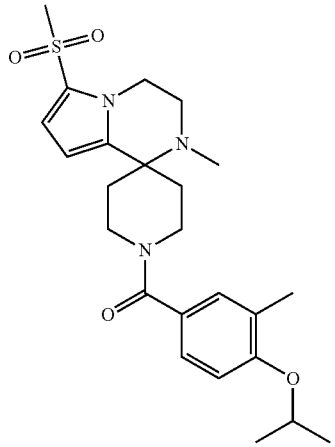 |
| 540 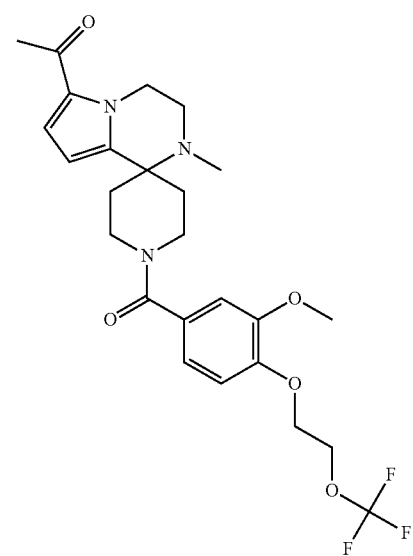 [SMILES: COc1cc(C(=O)N2CCC3(CC2)c2ccc(C(C)=O)n2CCN3C)ccc1OCCOC(F)(F)F](top) | 543 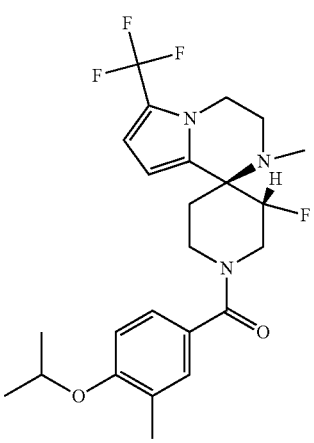 [SMILES: Cc1cc(C(=O)N2CC[C@]3(c4ccc(C(F)(F)F)n4CCN3C)[C@H](F)C2)ccc1OC(C)C] |
| 541 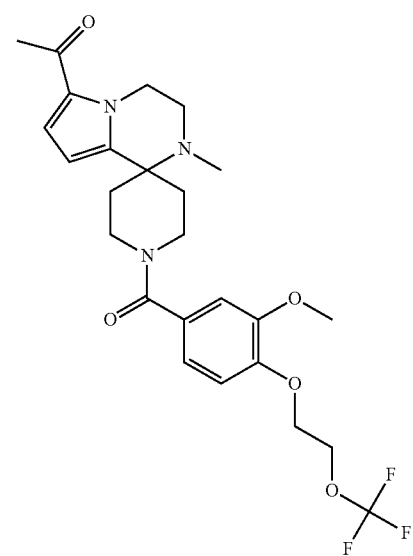 [SMILES: COc1cc(C(=O)N2CCC3(CC2)c2ccc(C(C)=O)n2CCN3C)ccc1OCCOC(F)(F)F](bottom) | 544 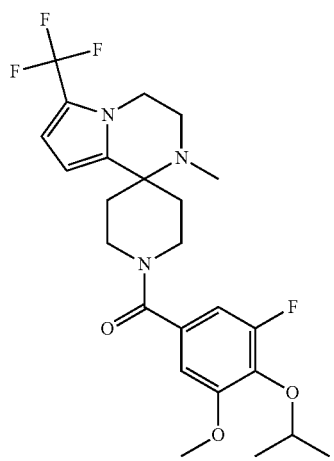 [SMILES: COc1cc(C(=O)N2CCC3(CC2)c2ccc(C(F)(F)F)n2CCN3C)cc(F)c1OC(C)C] |

-continued
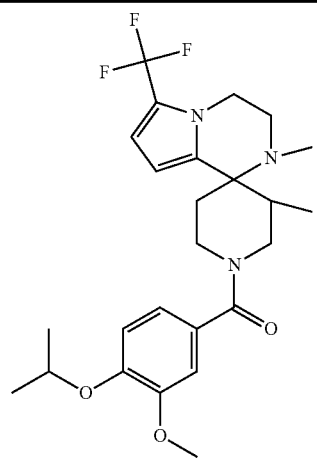
545
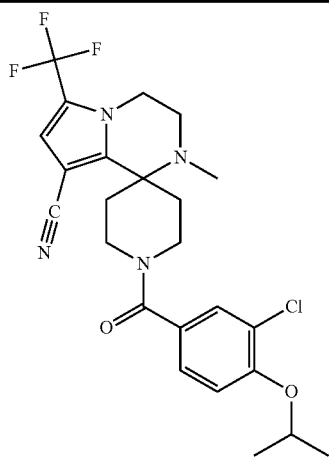
548
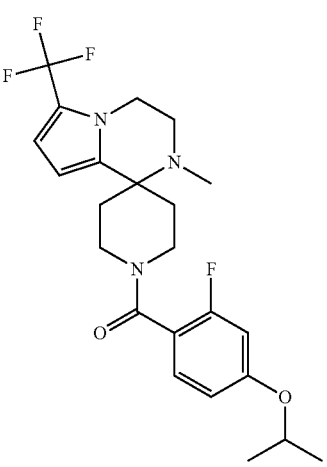 [SMILES: CC(C)Oc1ccc(C(=O)N2CCC3(CC2)c2ccc(C(F)(F)F)n2CCN3C)c(F)c1]
546
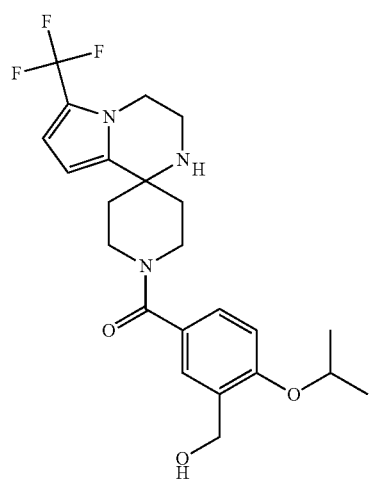
549
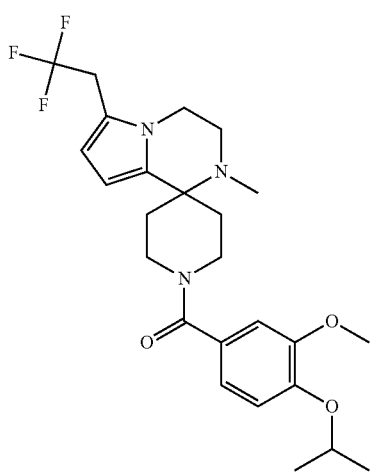
547
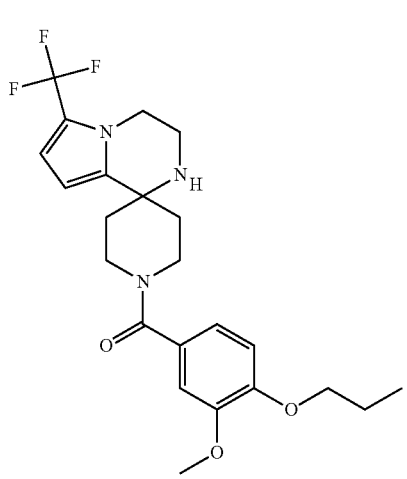
550

| 701 -continued | 702 -continued |
|---|---|
| 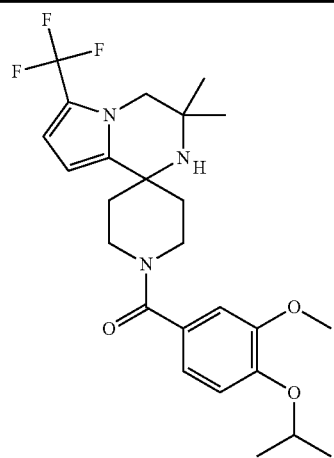 551 | 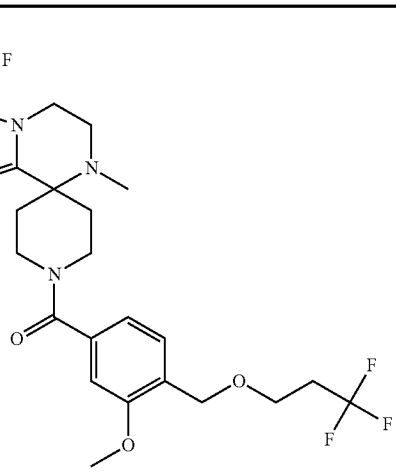 554 |
| 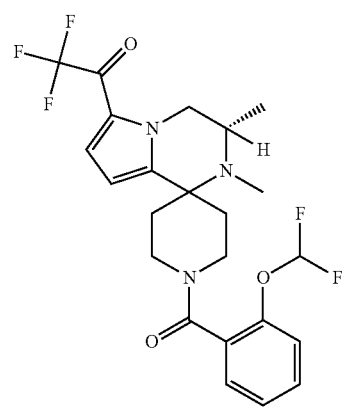 [SMILES: C[C@H]1Cn2c(C(=O)C(F)(F)F)ccc2C2(CCN(C(=O)c3ccccc3OC(F)F)CC2)N1C] 552 | 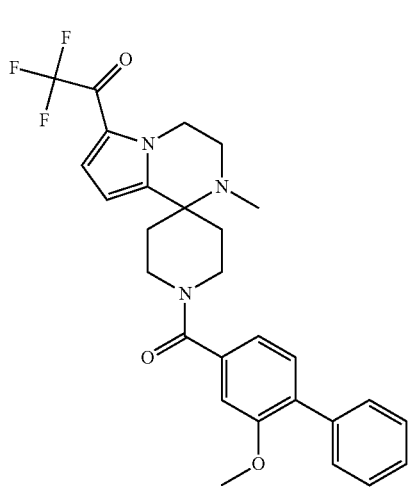 [SMILES: COc1cc(C(=O)N2CCC3(CC2)c2ccc(C(=O)C(F)(F)F)n2CCN3C)ccc1-c1ccccc1] 555 |
| 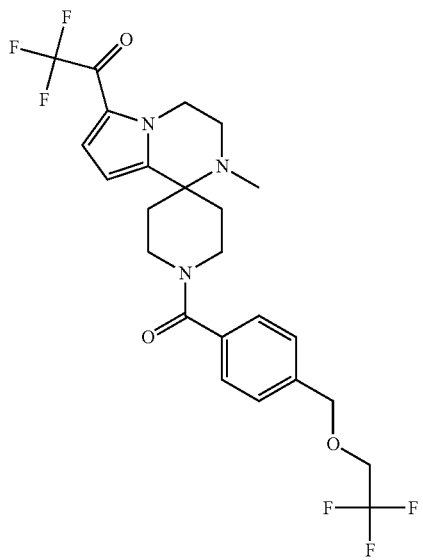 553 | 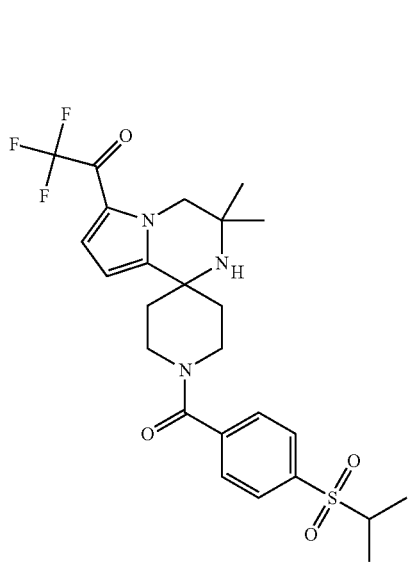 557 |

| 703 -continued | 704 -continued |
|---|---|
| 558 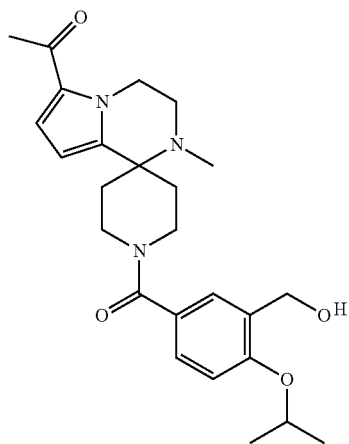 | 561 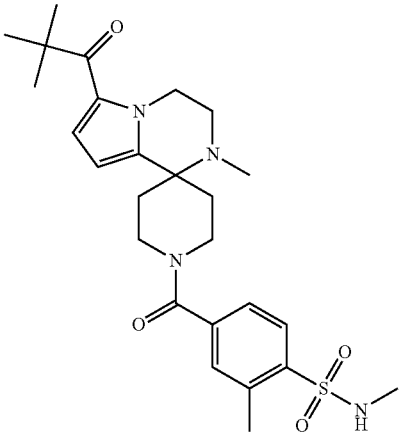 |
| 559 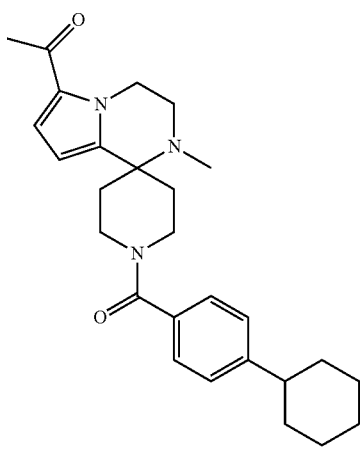 [SMILES: CC(=O)c1ccc2n1CCN(C)C21CCN(C(=O)c2ccc(C3CCCCC3)cc2)CC1] | 562 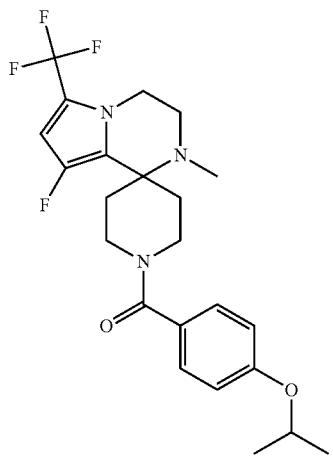 |
| 560 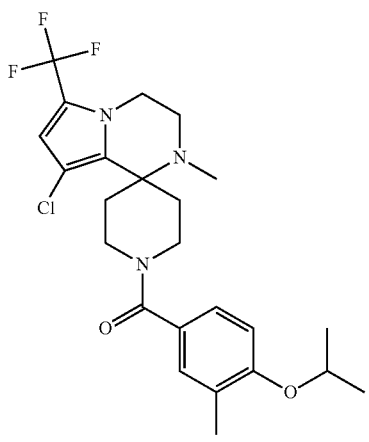 [SMILES: Cc1cc(C(=O)N2CCC3(CC2)c2c(Cl)cc(C(F)(F)F)n2CCN3C)ccc1OC(C)C] | 563 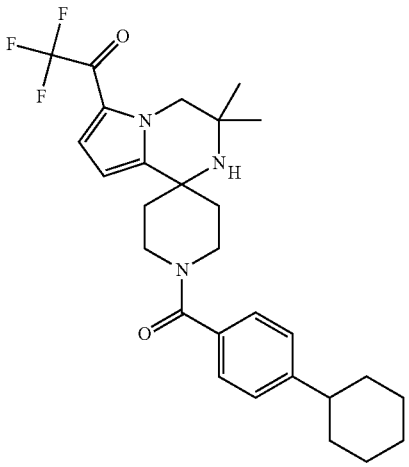 |

| 705 -continued | 706 -continued |
|---|---|
| 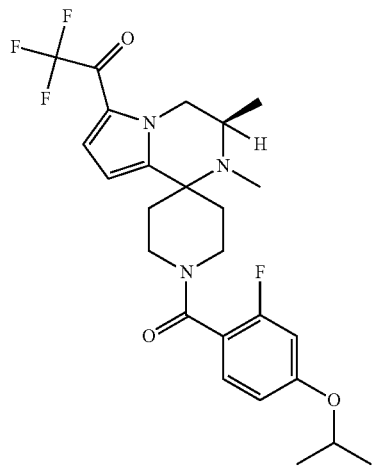 564 | 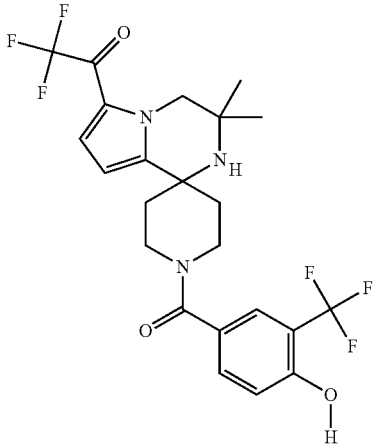 567 |
| 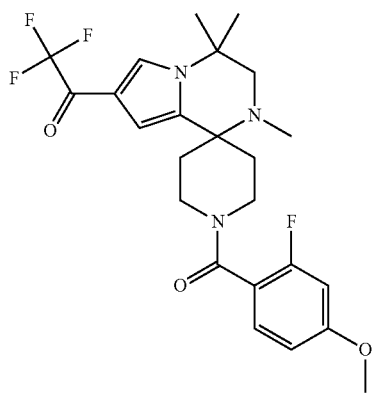 [SMILES: COc1ccc(C(=O)N2CCC3(CC2)c2cc(C(=O)C(F)(F)F)cn2C(C)(C)CN3C)c(F)c1] 565 | 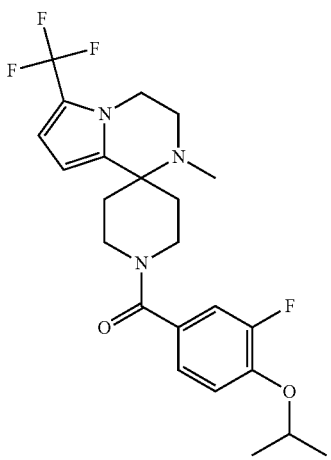 568 |
| 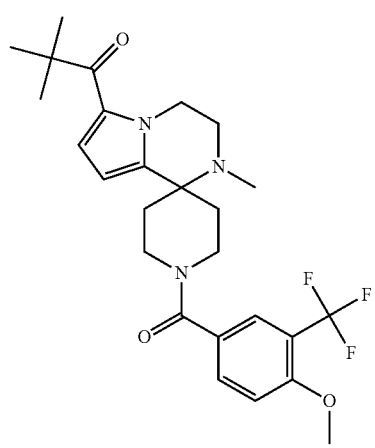 [SMILES: COc1ccc(C(=O)N2CCC3(CC2)c2ccc(C(=O)C(C)(C)C)n2CCN3C)cc1C(F)(F)F] 566 | 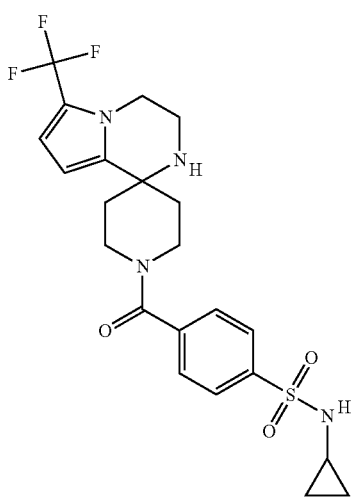 569 |

| 707 | 708 |
|---|---|
| 570 | 574 |
| 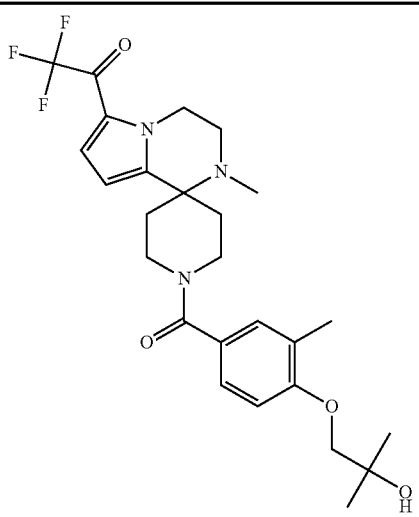 | 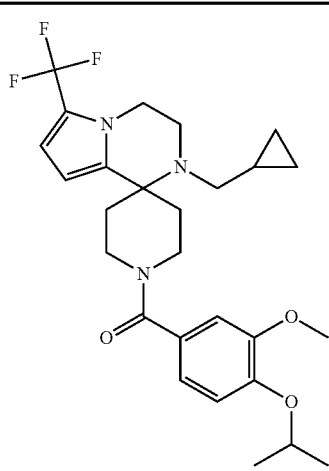 |
| 571 | 575 |
| 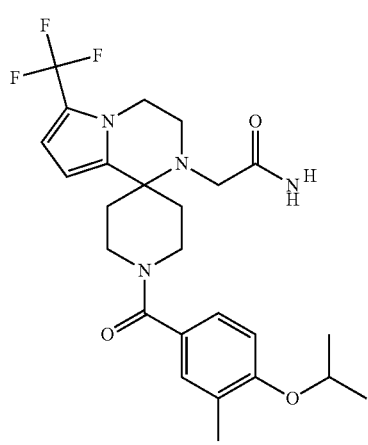 | 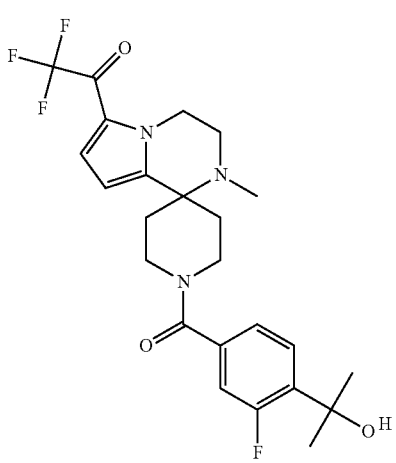 |
| 572 | 576 |
| 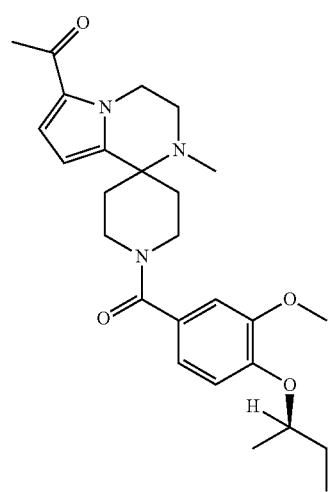 [SMILES: CC[C@@H](C)Oc1ccc(C(=O)N2CCC3(CC2)c2ccc(C(C)=O)n2CCN3C)cc1OC] | 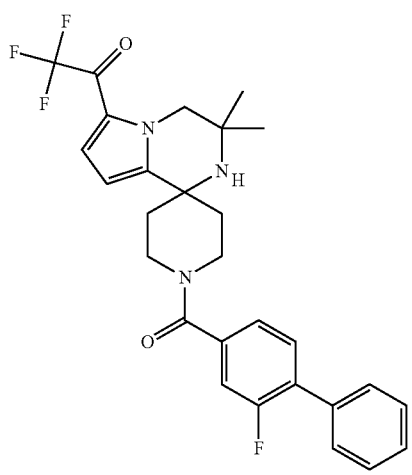 |

| 709 -continued | 710 -continued |
|---|---|
| 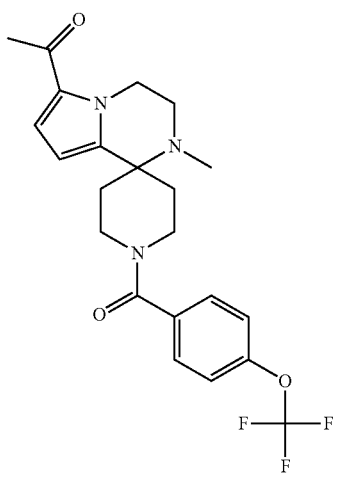 [SMILES: CC(=O)c1ccc2n1CCN(C)C21CCN(C(=O)c2ccc(OC(F)(F)F)cc2)CC1] 577 | 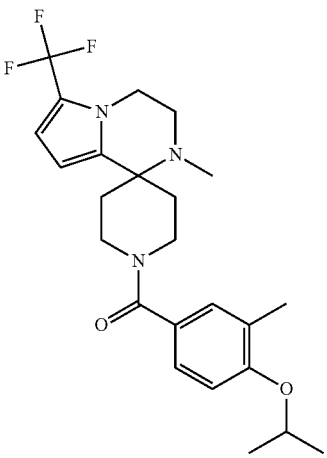 580 |
| 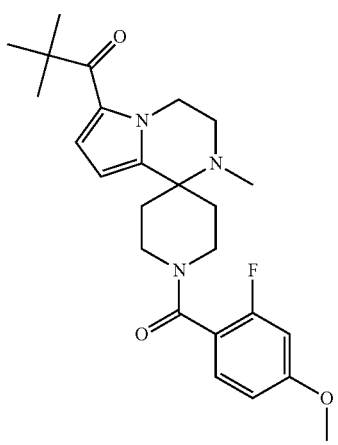 [SMILES: COc1ccc(C(=O)N2CCC3(CC2)c2ccc(C(=O)C(C)(C)C)n2CCN3C)c(F)c1] 578 | 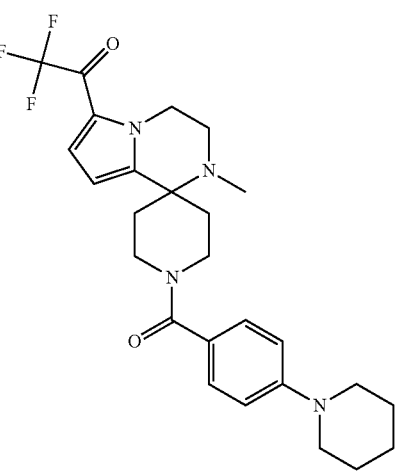 582 |
| 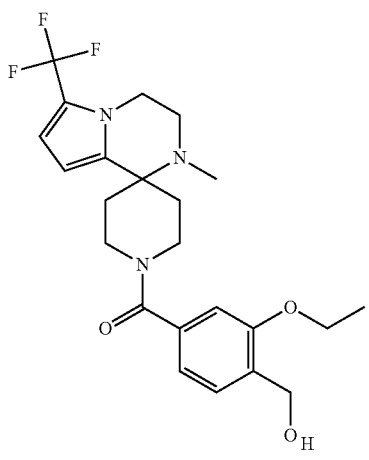 579 | 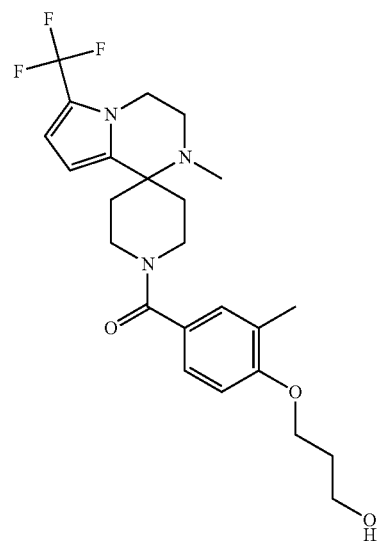 [SMILES: Cc1cc(C(=O)N2CCC3(CC2)c2ccc(C(F)(F)F)n2CCN3C)ccc1OCCCO] 583 |

| 711 -continued | 712 -continued |
|---|---|
| 584 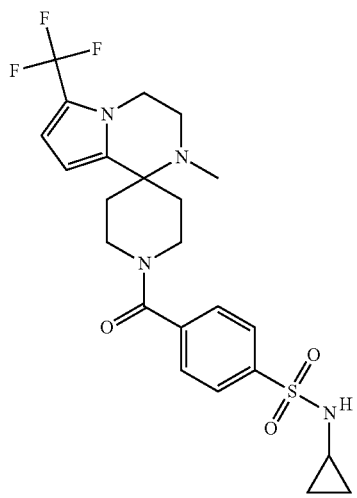 | 587 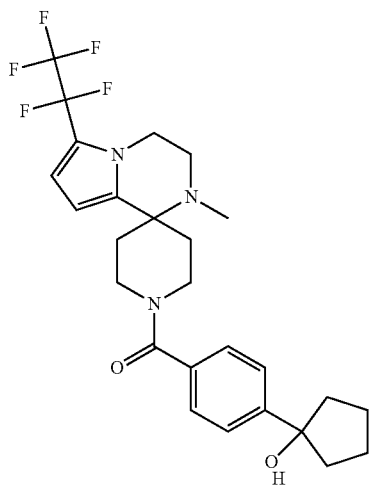 |
| 585 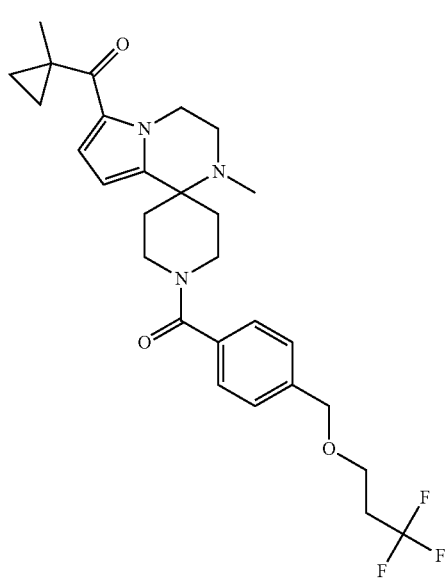 [SMILES: CN1CCn2c(C(=O)C3(C)CC3)ccc2C12CCN(C(=O)c1ccc(COCCC(F)(F)F)cc1)CC2] | 588 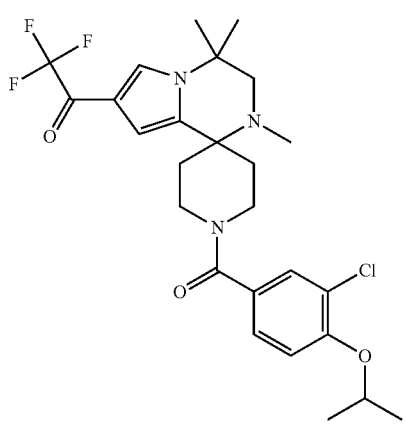 |
| 586 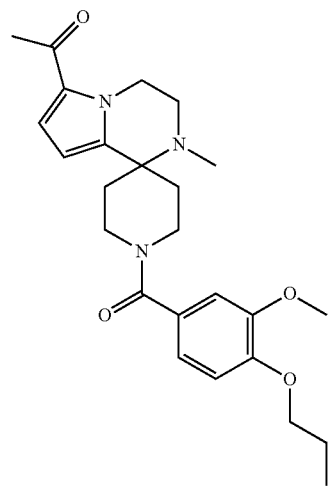 [SMILES: CCCOc1ccc(C(=O)N2CCC3(CC2)c2ccc(C(C)=O)n2CCN3C)cc1OC] | 589 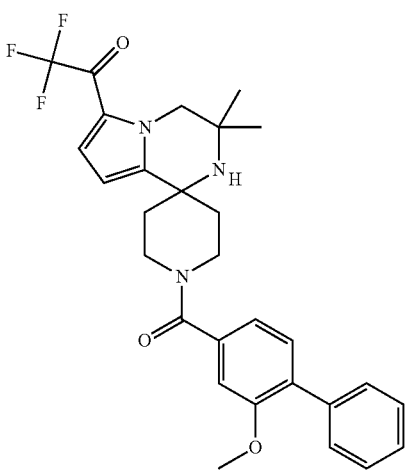 |

| 713 -continued | 714 -continued |
|---|---|
| 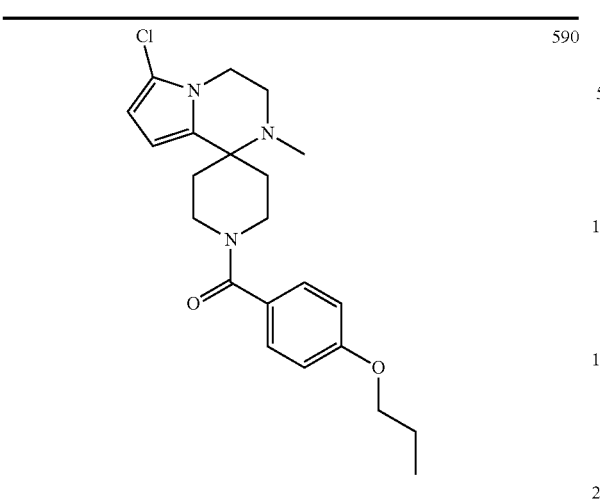 590 | 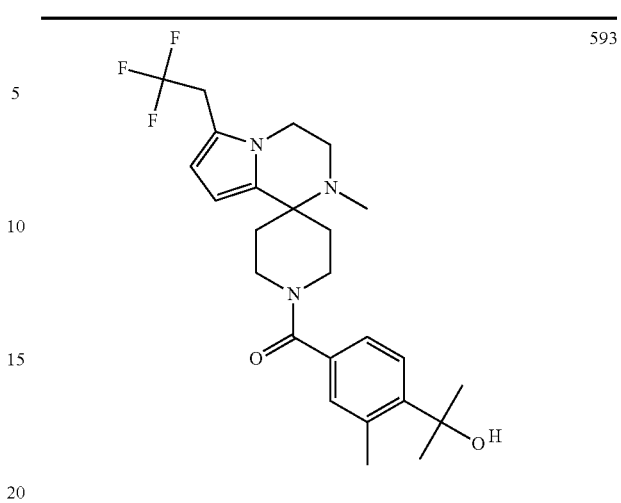 593 |
| 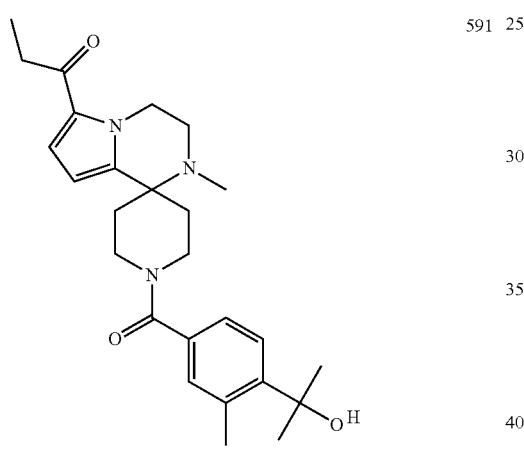 591 | 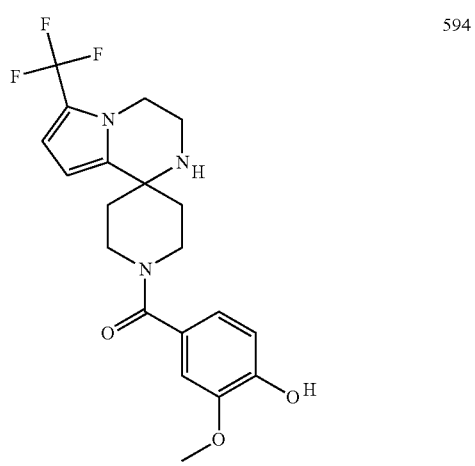 594 |
| 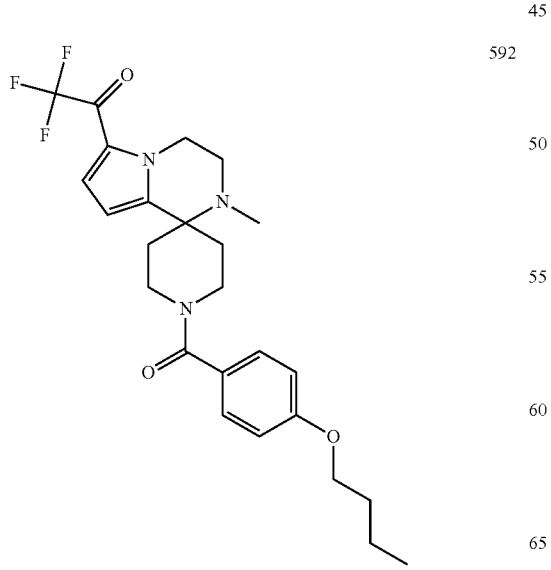 592 | 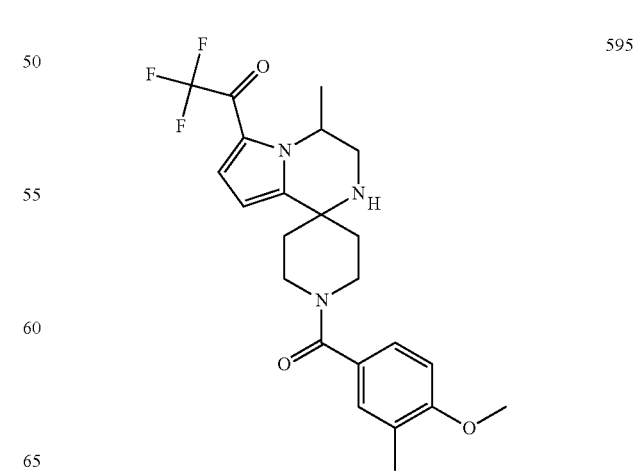 595 |

| 715 -continued | 716 -continued |
|---|---|
| 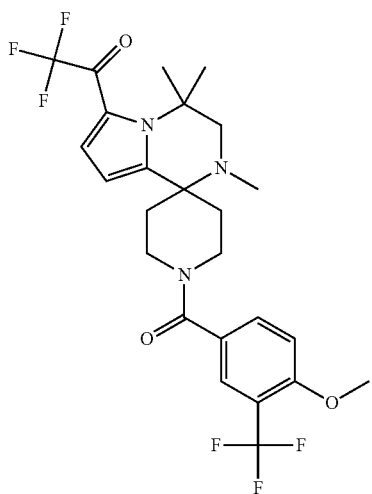 596 | 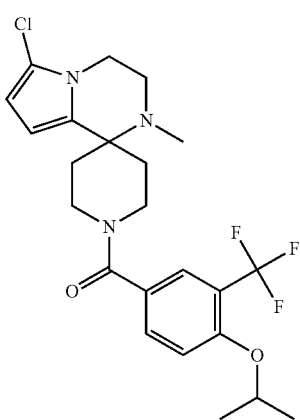 599 |
| 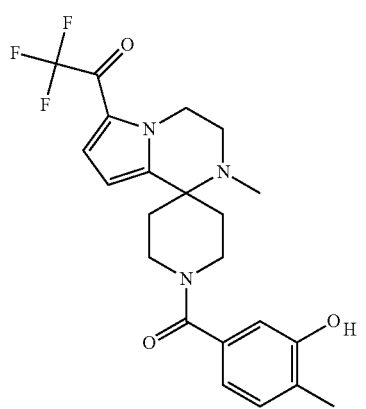 597 | 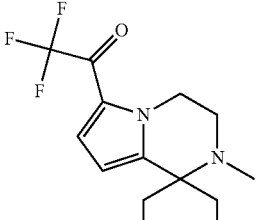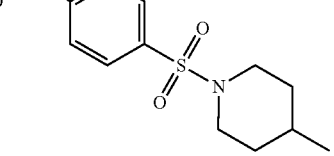 600 |
| 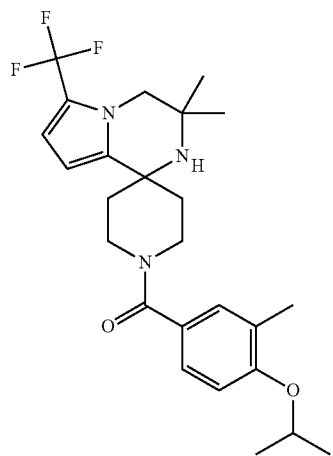 598 | 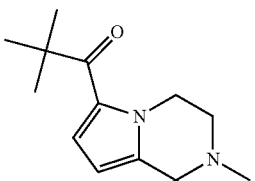 601 |

US 8,916,565 B2
717
-continued
602
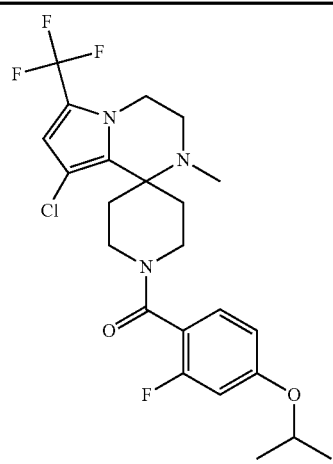
603
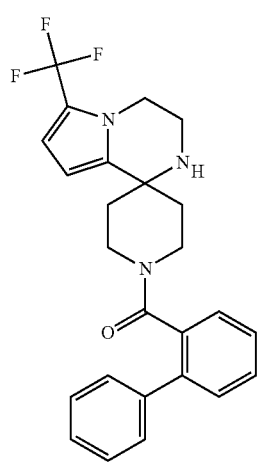
604
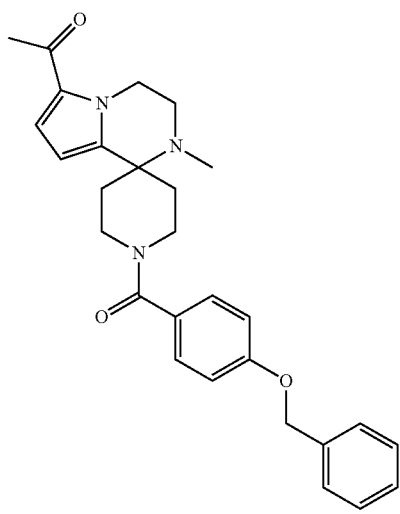 [SMILES: CC(=O)c1ccc2n1CCN(C)C21CCN(C(=O)c2ccc(OCc3ccccc3)cc2)CC1]
718
-continued
606
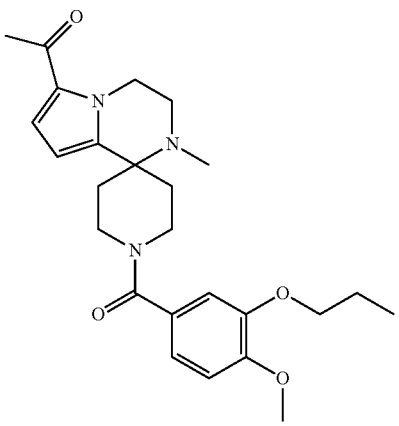 [SMILES: CCCOc1cc(C(=O)N2CCC3(CC2)c2ccc(C(C)=O)n2CCN3C)ccc1OC]
607
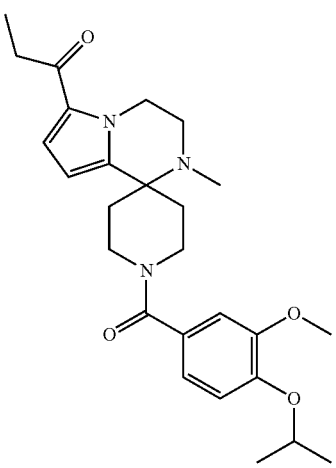 [SMILES: CCC(=O)c1ccc2n1CCN(C)C21CCN(C(=O)c2ccc(OC(C)C)c(OC)c2)CC1]
608
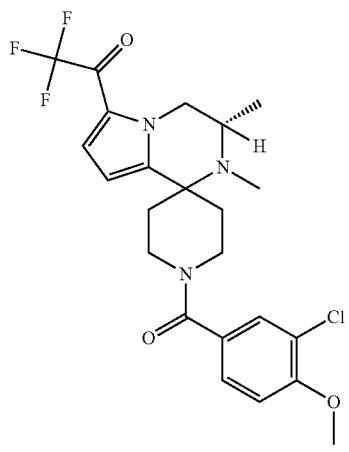 [SMILES: COc1ccc(C(=O)N2CCC3(CC2)c2ccc(C(=O)C(F)(F)F)n2C[C@H](C)N3C)cc1Cl]

| 719 -continued | 720 -continued |
|---|---|
| 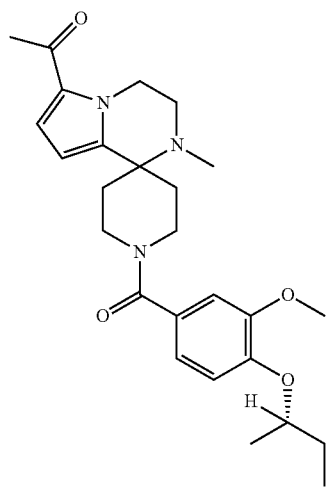 [SMILES: CC[C@H](C)Oc1ccc(C(=O)N2CCC3(CC2)c2ccc(C(C)=O)n2CCN3C)cc1OC] 609 | 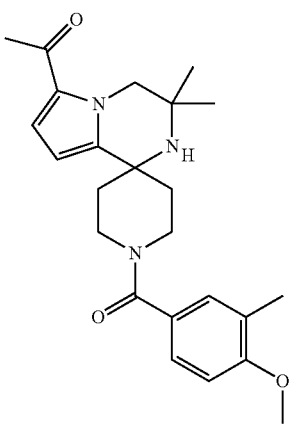 613 |
| 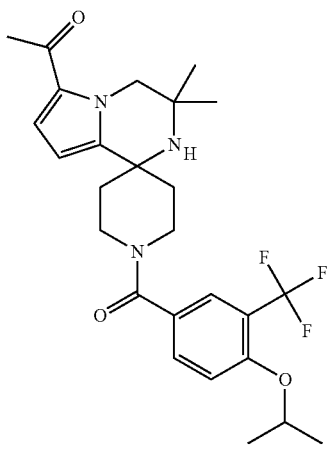 610 | 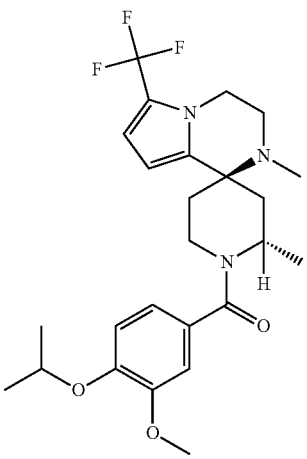 [SMILES: COc1cc(C(=O)N2CC[C@@]3(C[C@@H]2C)c2ccc(C(F)(F)F)n2CCN3C)ccc1OC(C)C] 614 |
| 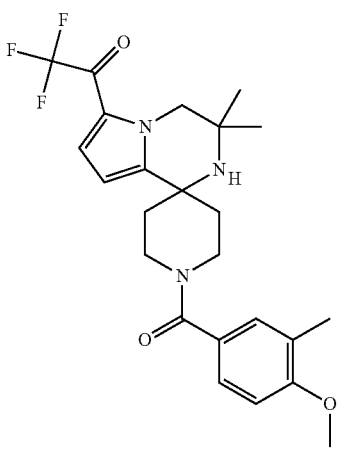 612 | 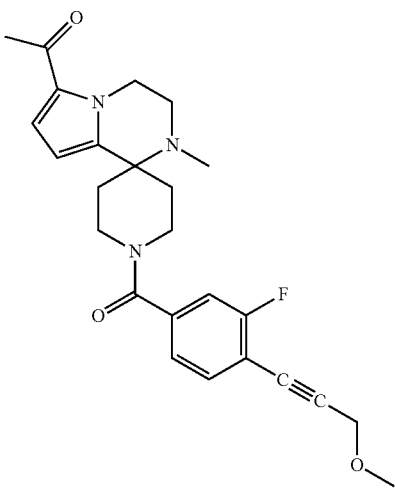 [SMILES: COCC#Cc1ccc(C(=O)N2CCC3(CC2)c2ccc(C(C)=O)n2CCN3C)cc1F] 615 |

| 721 -continued | 722 -continued |
|---|---|
| 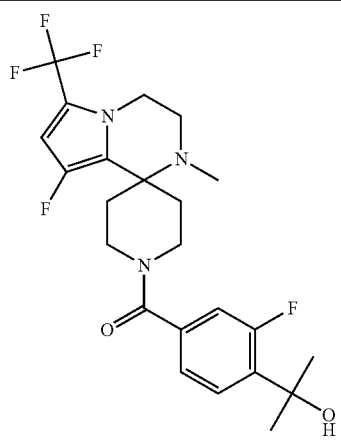 616 | 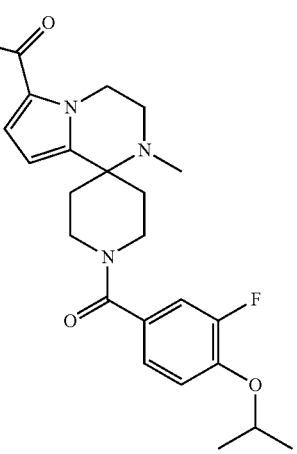 619 |
| 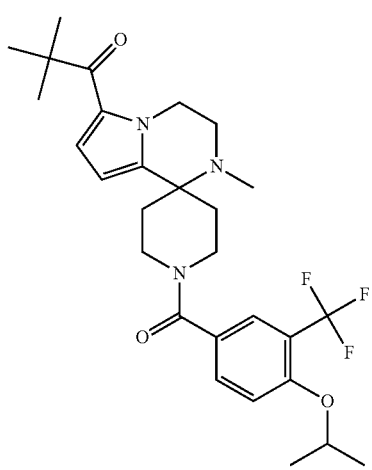 [SMILES: CC(C)Oc1ccc(C(=O)N2CCC3(CC2)c2ccc(C(=O)C(C)(C)C)n2CCN3C)cc1C(F)(F)F] 617 | 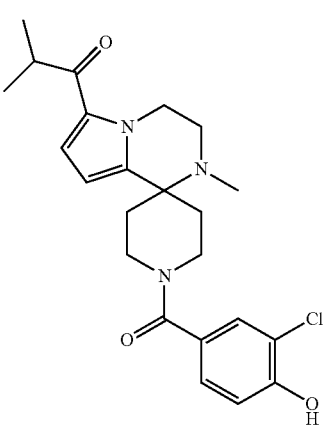 [SMILES: CC(C)C(=O)c1ccc2n1CCN(C)C21CCN(C(=O)c2ccc(O)c(Cl)c2)CC1] 620 |
| 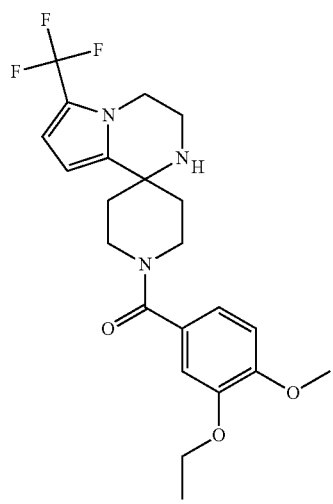 618 | 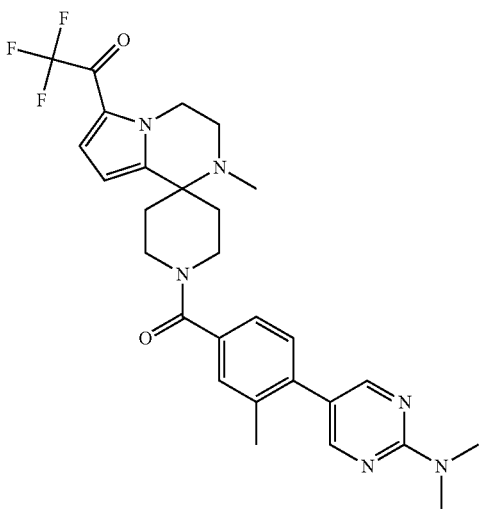 [SMILES: Cc1cc(C(=O)N2CCC3(CC2)c2ccc(C(=O)C(F)(F)F)n2CCN3C)ccc1-c1cnc(N(C)C)nc1] 621 |

| 723 -continued | 724 -continued |
|---|---|
| 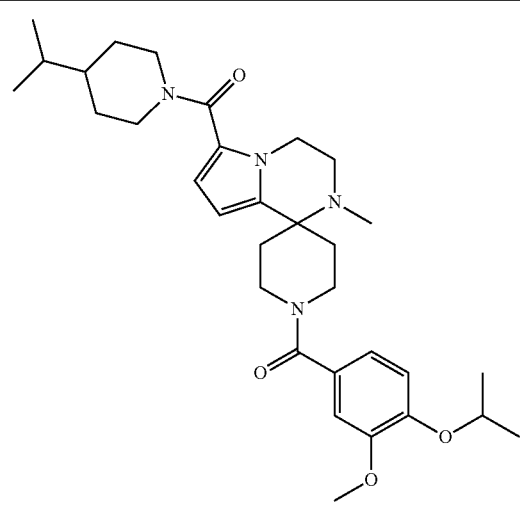 622 | 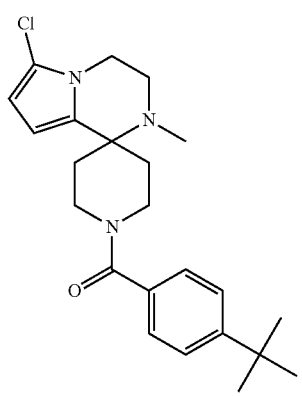 625 |
| 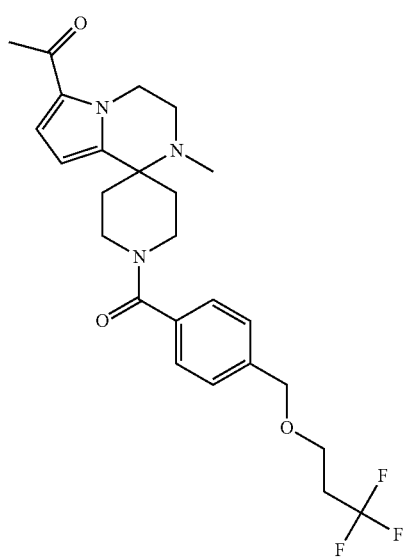 [SMILES: CC(=O)c1ccc2n1CCN(C)C21CCN(C(=O)c2ccc(COCCC(F)(F)F)cc2)CC1] 623 | 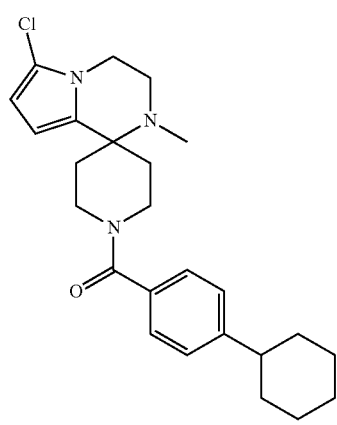 626 |
| 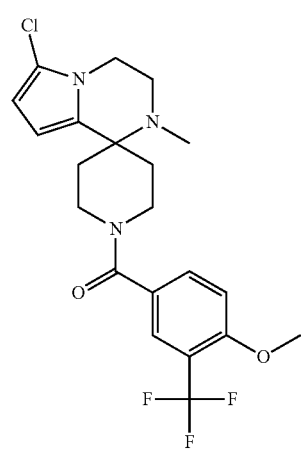 [SMILES: COc1ccc(C(=O)N2CCC3(CC2)c2ccc(Cl)n2CCN3C)cc1C(F)(F)F] 624 | 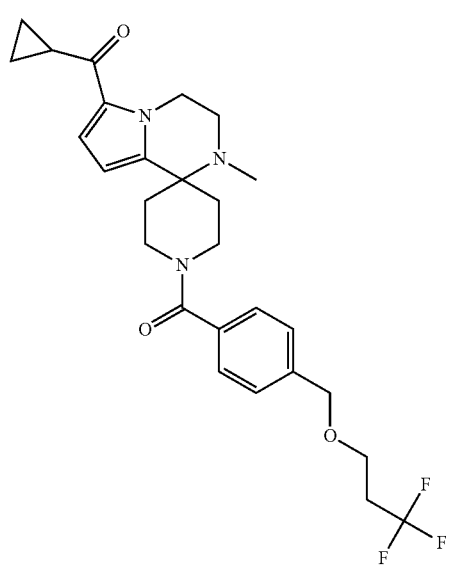 [SMILES: CN1CCn2c(C(=O)C3CC3)ccc2C12CCN(C(=O)c1ccc(COCCC(F)(F)F)cc1)CC2] 627 |

-continued
| 725 | 726 |
|---|---|
| 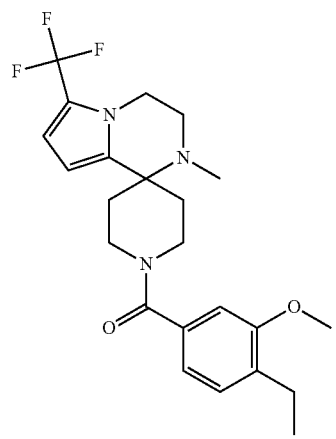 [SMILES: CCc1ccc(C(=O)N2CCC3(CC2)c2ccc(C(F)(F)F)n2CCN3C)cc1OC] 629 | 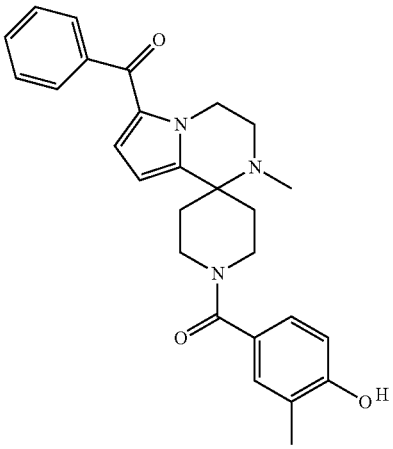 632 |
| 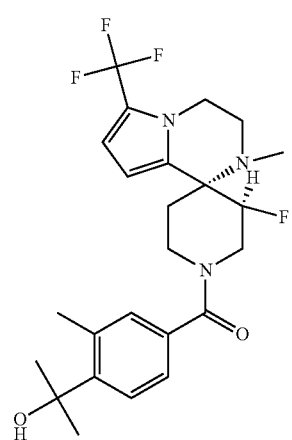 [SMILES: Cc1cc(C(=O)N2CC[C@@]3(c4ccc(C(F)(F)F)n4CCN3C)[C@@H](F)C2)ccc1C(C)(C)O] 630 | 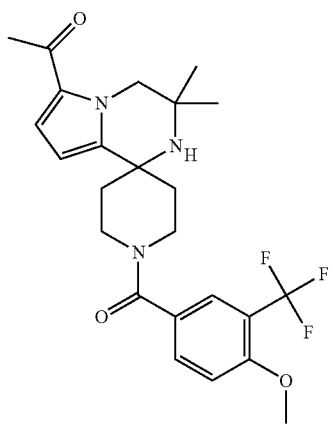 633 |
| 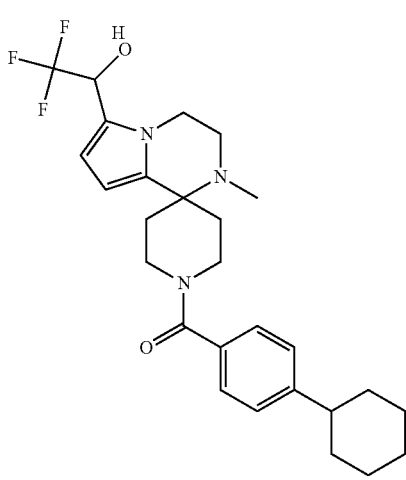 631 | 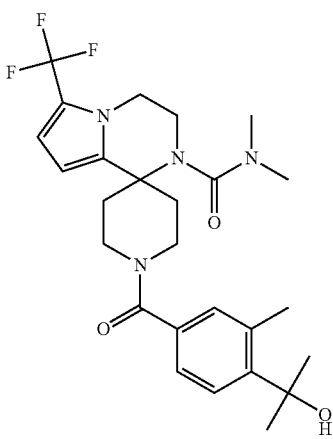 634 |

727
-continued
635
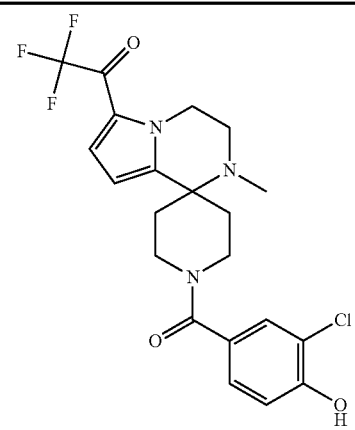
636
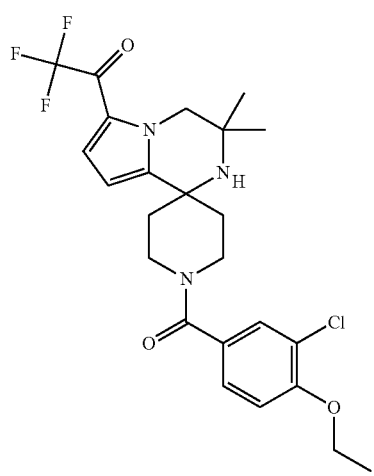
637
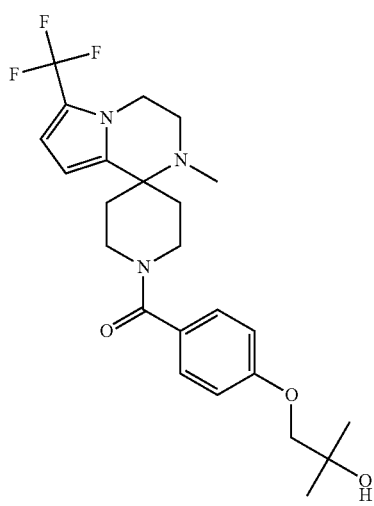 [SMILES: CN1CCn2c(C(F)(F)F)ccc2C12CCN(C(=O)c1ccc(OCC(C)(C)O)cc1)CC2]
728
-continued
639
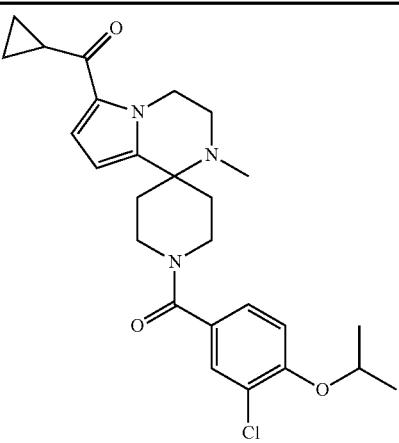
640
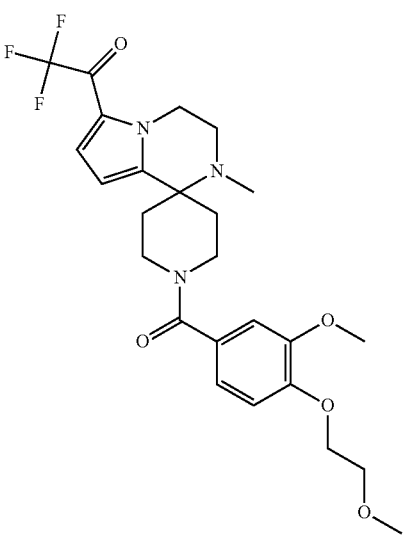 [SMILES: COCCOc1ccc(C(=O)N2CCC3(CC2)c2ccc(C(=O)C(F)(F)F)n2CCN3C)cc1OC]
641
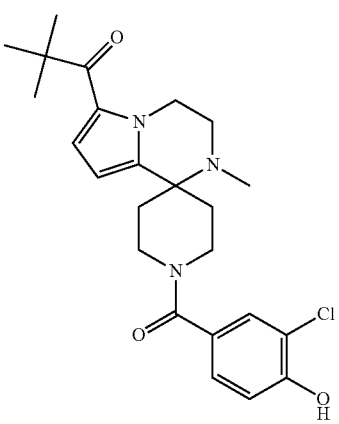 [SMILES: CN1CCn2c(C(=O)C(C)(C)C)ccc2C12CCN(C(=O)c1ccc(O)c(Cl)c1)CC2]

| 729 -continued | 730 -continued |
|---|---|
| 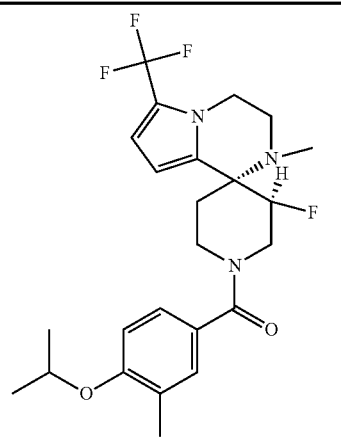 642 | 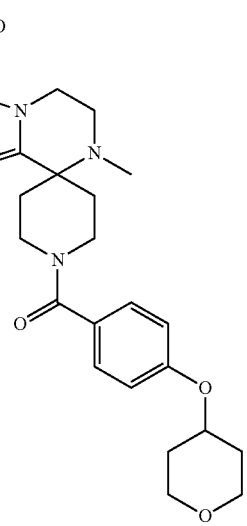 645 |
| 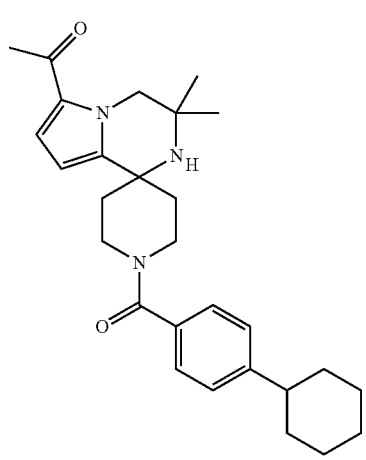 643 | 646 |
| 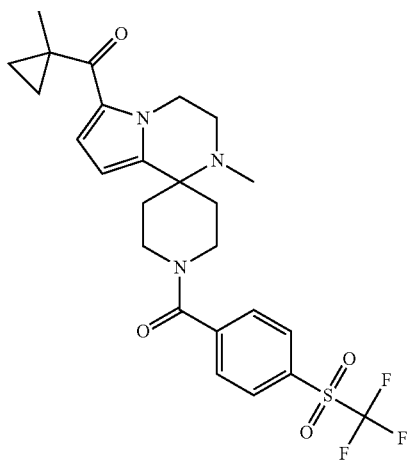 [SMILES: CN1CCn2c(C(=O)C3(C)CC3)ccc2C12CCN(C(=O)c1ccc(S(=O)(=O)C(F)(F)F)cc1)CC2] 644 | 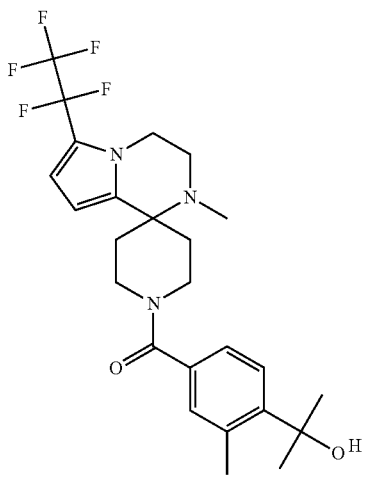 647 |

| 731 -continued | 732 -continued |
|---|---|
| 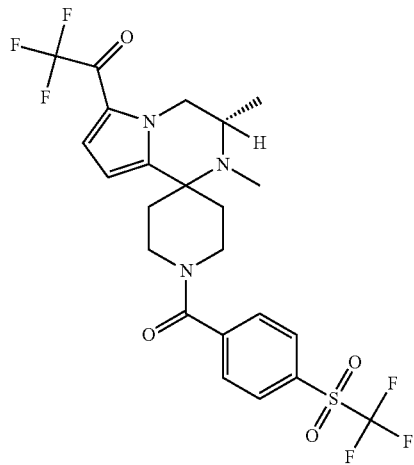 [SMILES: C[C@H]1Cn2c(C(=O)C(F)(F)F)ccc2C2(CCN(C(=O)c3ccc(S(=O)(=O)C(F)(F)F)cc3)CC2)N1C] 649 | 653 |
| 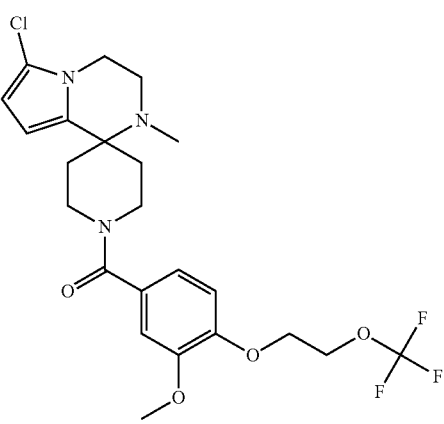 [SMILES: COc1cc(C(=O)N2CCC3(CC2)c2ccc(Cl)n2CCN3C)ccc1OCCOC(F)(F)F] 650 | 654 |
| 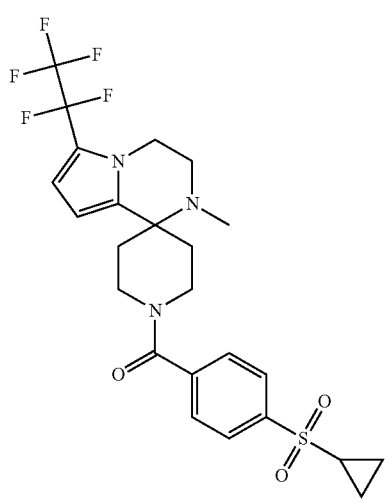 [SMILES: CN1CCn2c(ccc2C(F)(F)C(F)(F)F)C12CCN(C(=O)c1ccc(S(=O)(=O)C3CC3)cc1)CC2] 651 | 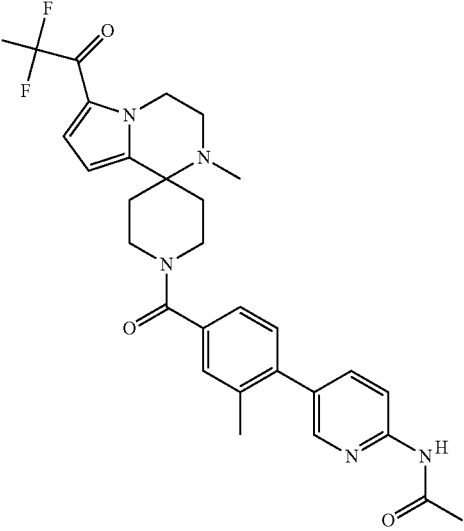 655 |

| 656 | 661 |
|---|---|
| 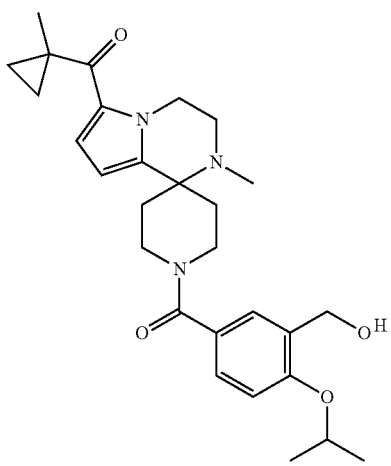 | 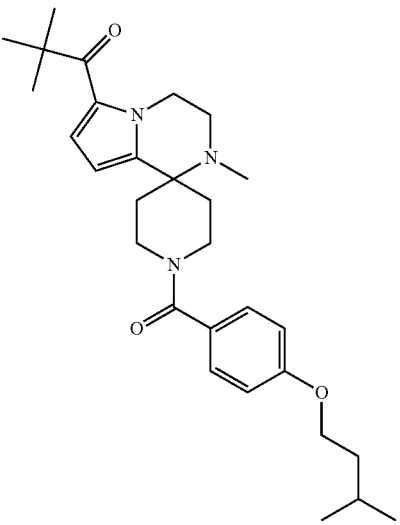 |
| 658 | 662 |
|---|---|
| 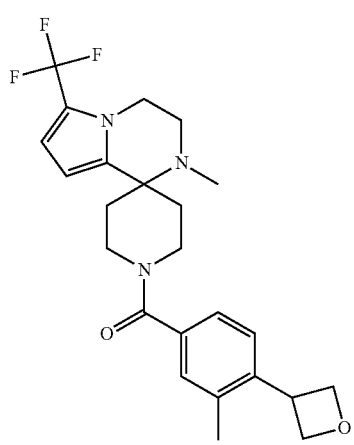 [SMILES: Cc1cc(C(=O)N2CCC3(CC2)c2ccc(C(F)(F)F)n2CCN3C)ccc1C1COC1] | 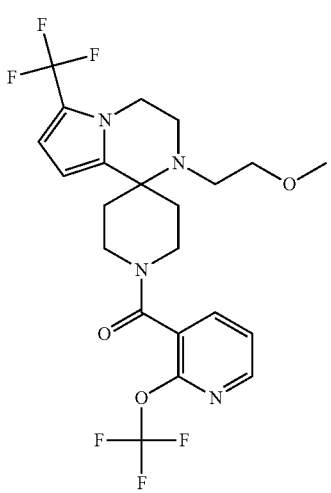 |
| 659 | 663 |
|---|---|
| 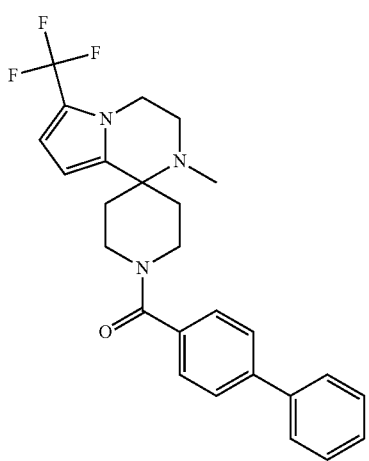 [SMILES: CN1CCn2c(C(F)(F)F)ccc2C12CCN(C(=O)c1ccc(-c3ccccc3)cc1)CC2] | 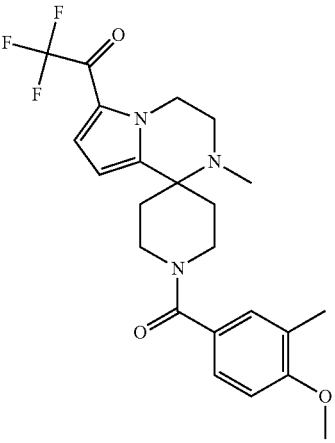 |

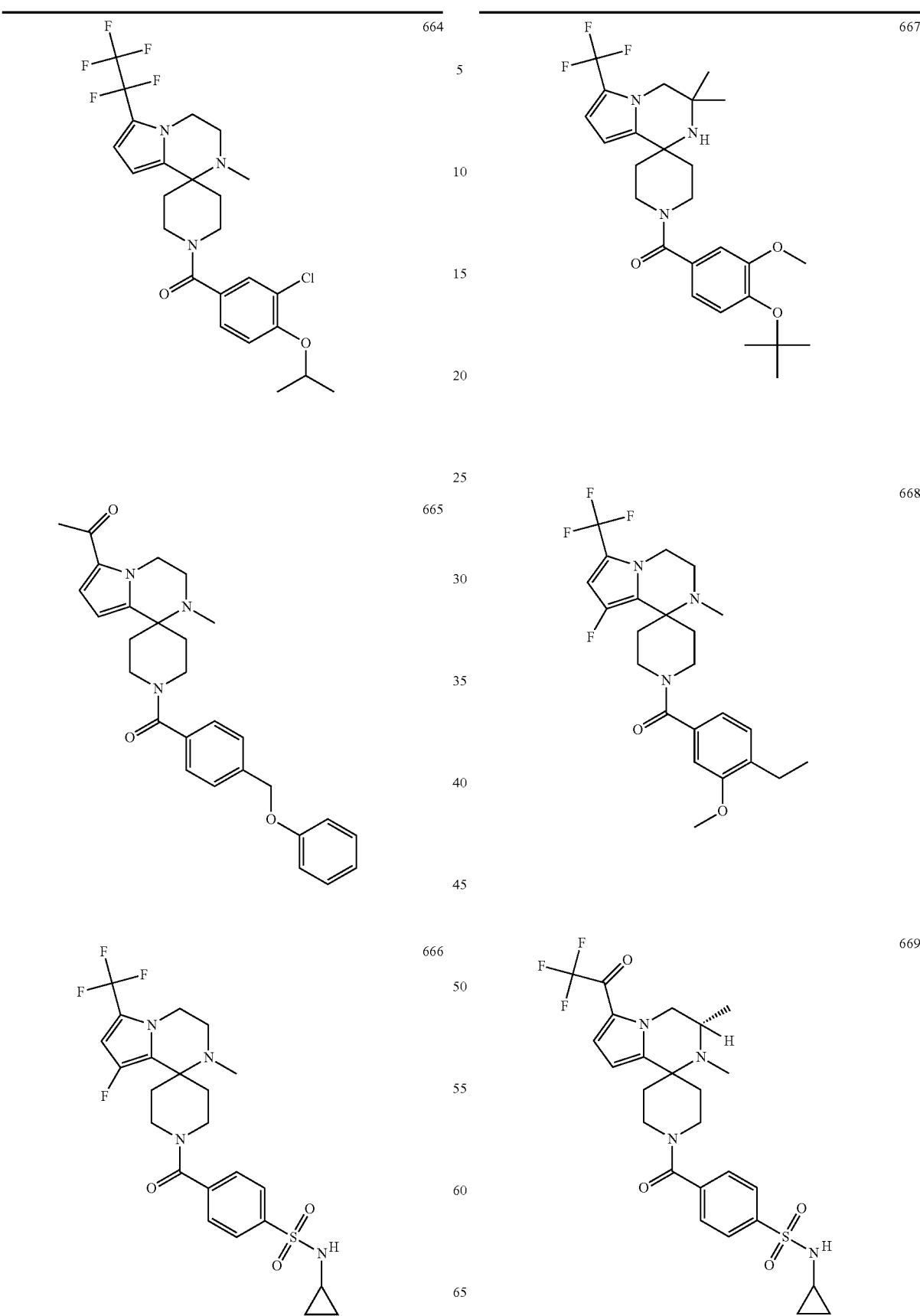

| 737 -continued | 738 -continued |
|---|---|
| 670 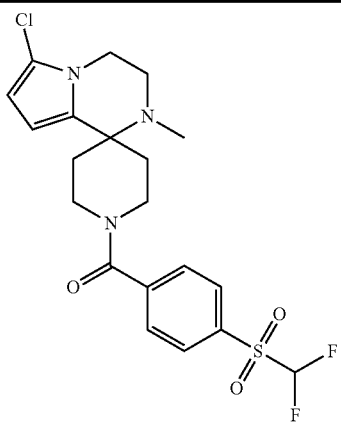 | 674 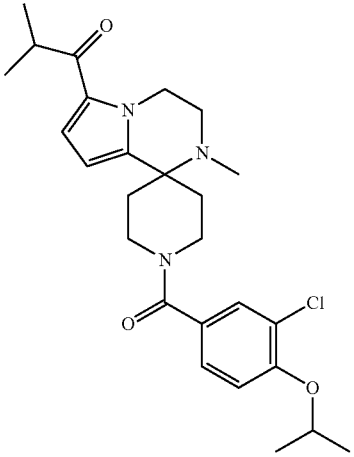 |
| 671 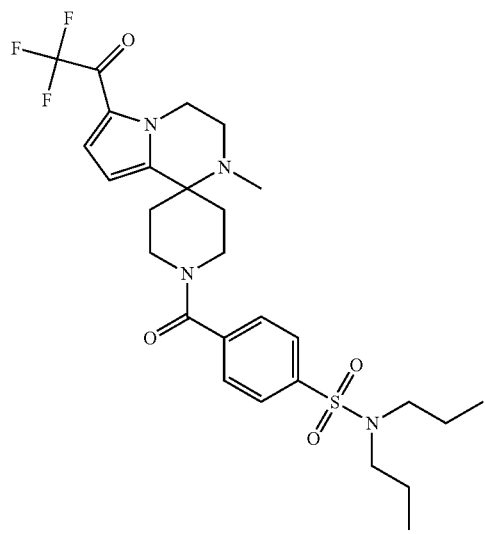 [SMILES: CCCN(CCC)S(=O)(=O)c1ccc(C(=O)N2CCC3(CC2)c2ccc(C(=O)C(F)(F)F)n2CCN3C)cc1] | 675 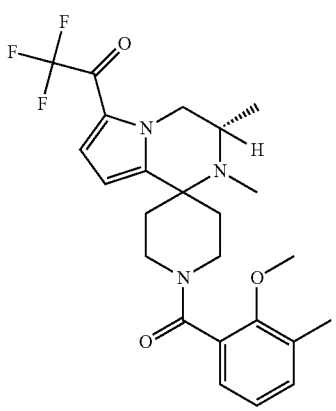 |
| 672 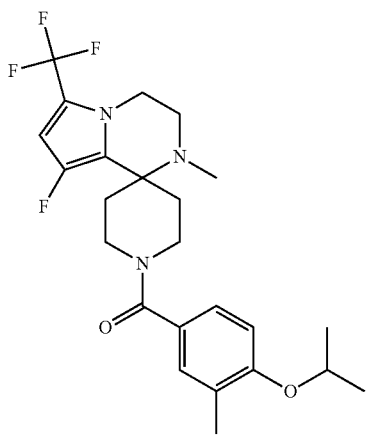 [SMILES: Cc1cc(C(=O)N2CCC3(CC2)c2c(F)cc(C(F)(F)F)n2CCN3C)ccc1OC(C)C] | 676 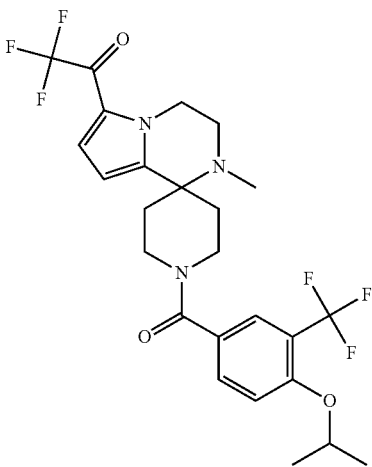 [SMILES: CC(C)Oc1ccc(C(=O)N2CCC3(CC2)c2ccc(C(=O)C(F)(F)F)n2CCN3C)cc1C(F)(F)F] |

| 739 -continued | | 740 -continued | |
|---|---|---|---|
| 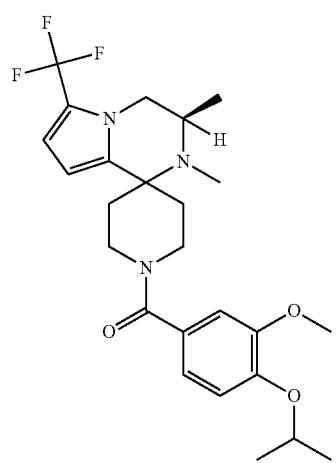 [SMILES: COc1cc(C(=O)N2CCC3(CC2)c2ccc(C(F)(F)F)n2C[C@@H](C)N3C)ccc1OC(C)C] | 677 | 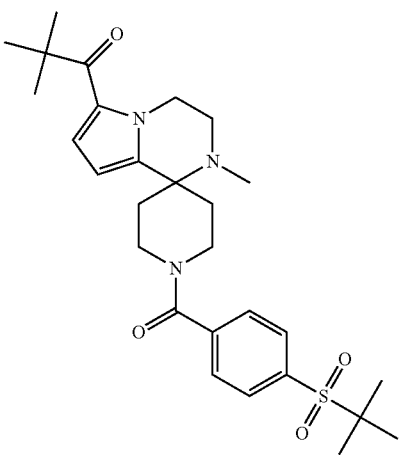 | 680 |
| 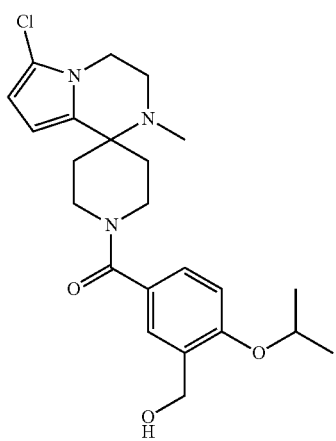 [SMILES: CC(C)Oc1ccc(C(=O)N2CCC3(CC2)c2ccc(Cl)n2CCN3C)cc1CO] | 678 | 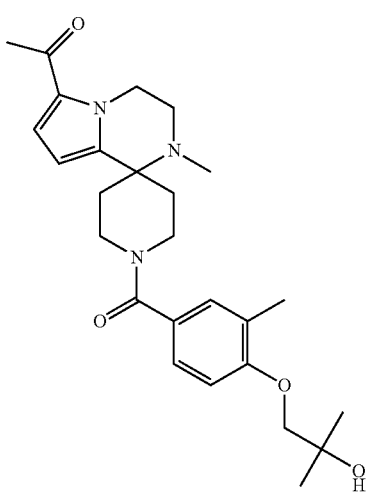 | 681 |
| 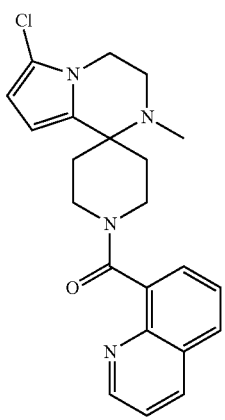 [SMILES: CN1CCn2c(Cl)ccc2C12CCN(C(=O)c1cccc3cccnc13)CC2] | 679 | 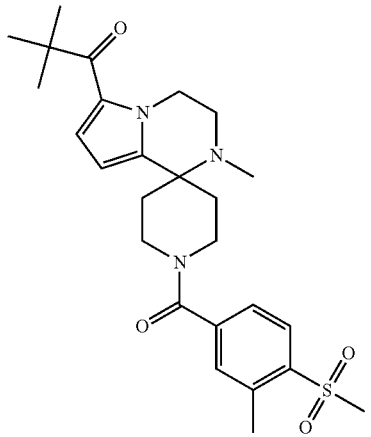 [SMILES: Cc1cc(C(=O)N2CCC3(CC2)c2ccc(C(=O)C(C)(C)C)n2CCN3C)ccc1S(C)(=O)=O] | 682 |

| 741 -continued | 742 -continued |
|---|---|
| 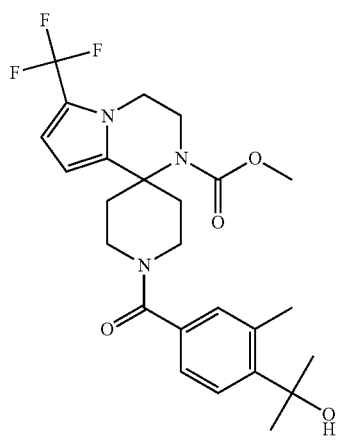 [SMILES: COC(=O)N1CCn2c(C(F)(F)F)ccc2C12CCN(C(=O)c1ccc(C(C)(C)O)c(C)c1)CC2] 683 | 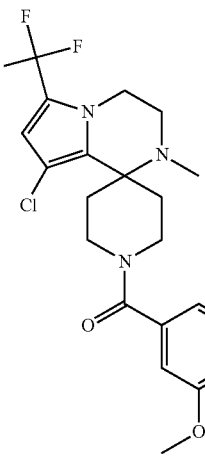 687 |
| 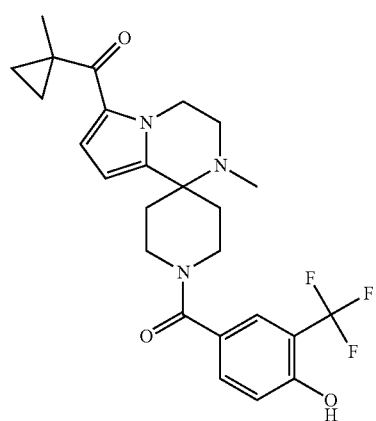 [SMILES: CN1CCn2c(C(=O)C3(C)CC3)ccc2C12CCN(C(=O)c1ccc(O)c(C(F)(F)F)c1)CC2] 685 | 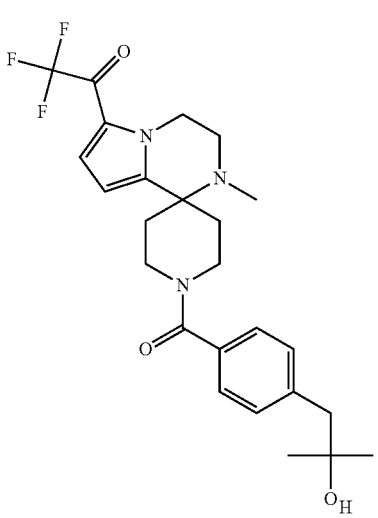 688 |
| 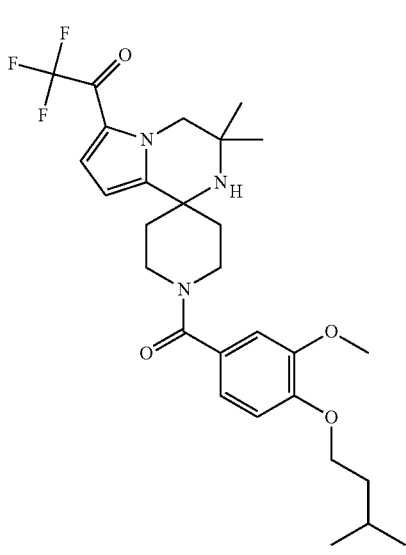 686 | 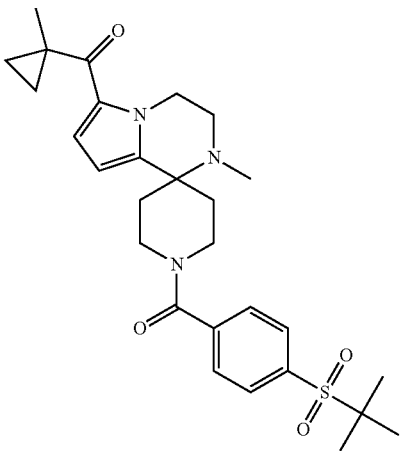 [SMILES: CN1CCn2c(C(=O)C3(C)CC3)ccc2C12CCN(C(=O)c1ccc(S(=O)(=O)C(C)(C)C)cc1)CC2] 689 |

| 743 -continued | 744 -continued |
|---|---|
| 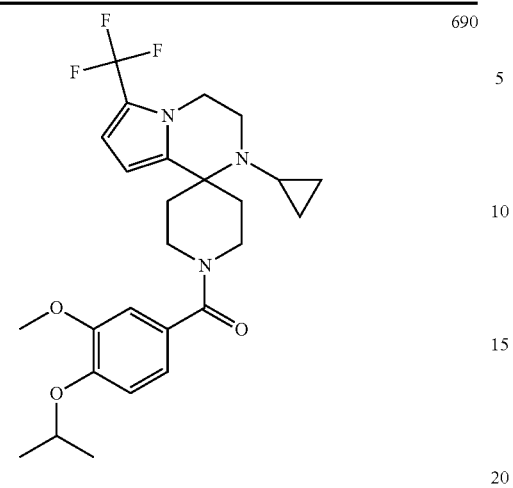 690 | 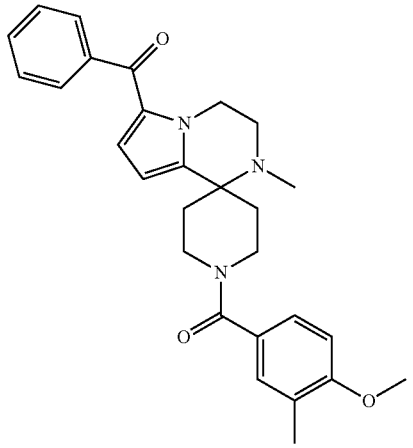 [SMILES: COc1ccc(C(=O)N2CCC3(CC2)c2ccc(C(=O)c4ccccc4)n2CCN3C)cc1C] 694 |
| 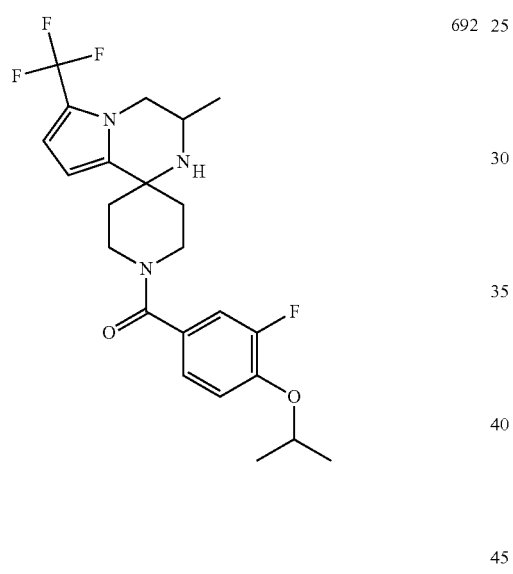 692 | 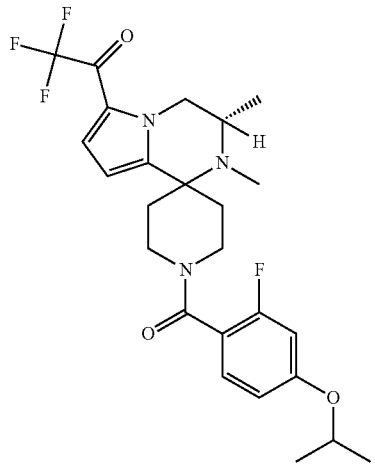 695 |
| 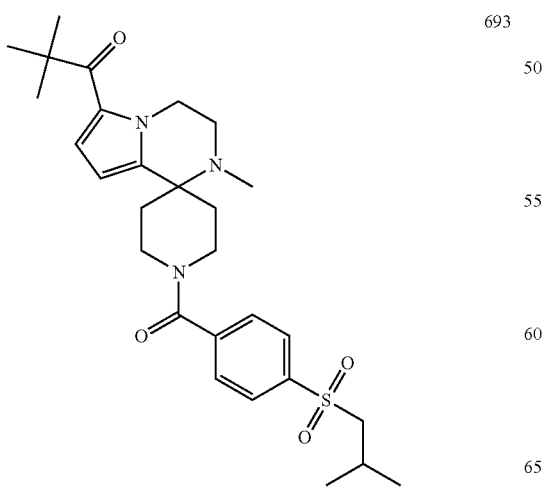 693 | 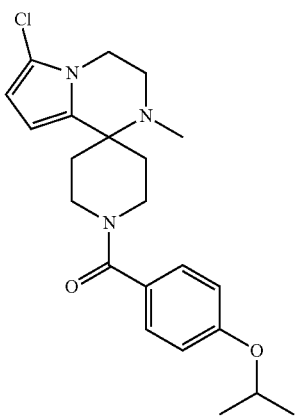 [SMILES: CC(C)Oc1ccc(C(=O)N2CCC3(CC2)c2ccc(Cl)n2CCN3C)cc1] 696 |

| 697 | 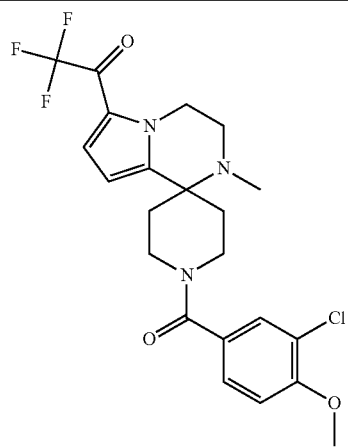 | 700 | 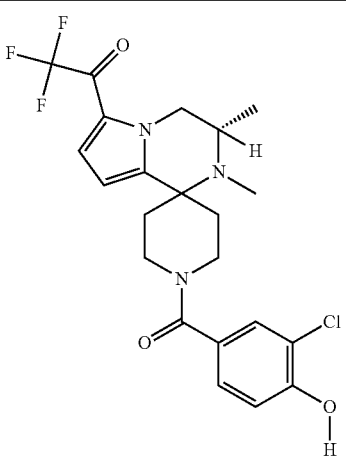 |
| 698 | 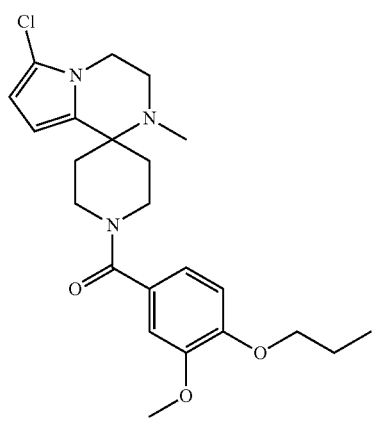 [SMILES: CCCOc1ccc(C(=O)N2CCC3(CC2)c2ccc(Cl)n2CCN3C)cc1OC] | 701 | 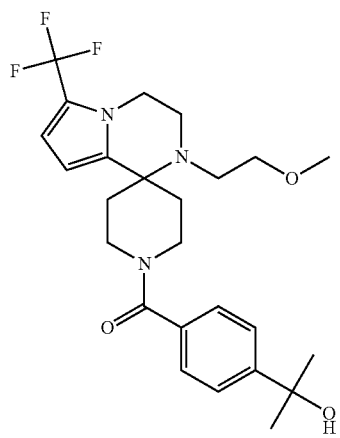 |
| 699 | 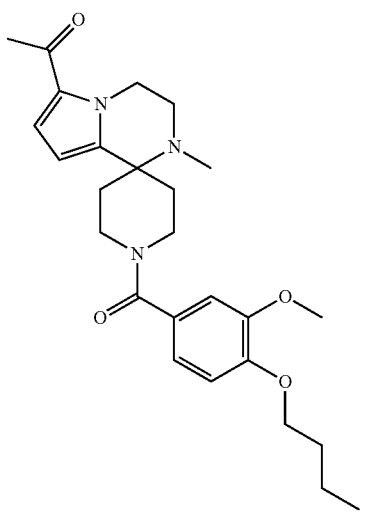 [SMILES: CCCCOc1ccc(C(=O)N2CCC3(CC2)c2ccc(C(C)=O)n2CCN3C)cc1OC] | 702 | 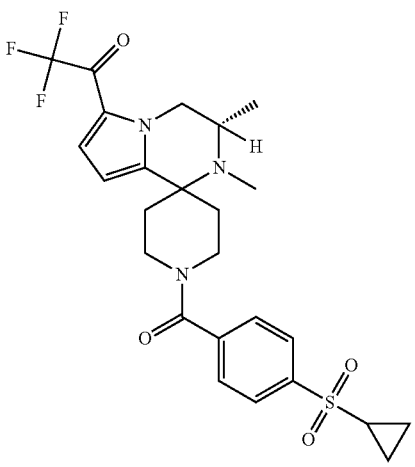 [SMILES: C[C@H]1Cn2c(C(=O)C(F)(F)F)ccc2C2(CCN(C(=O)c3ccc(S(=O)(=O)C4CC4)cc3)CC2)N1C] |

| 747 -continued | 748 -continued |
|---|---|
| 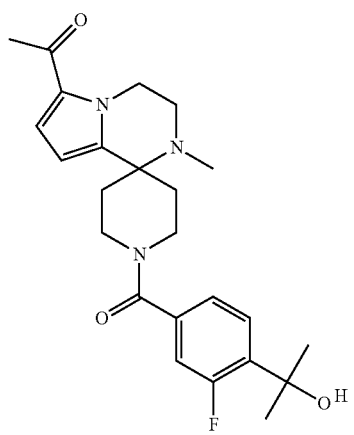 703 | 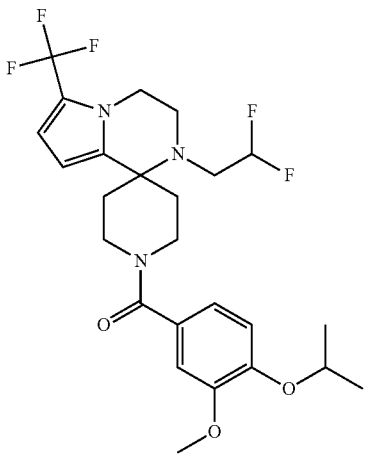 706 |
| 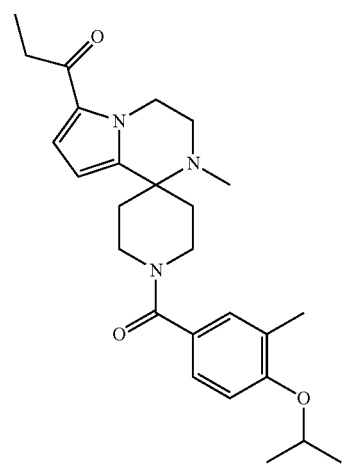 [SMILES: CCC(=O)c1ccc2n1CCN(C)C21CCN(C(=O)c2ccc(OC(C)C)c(C)c2)CC1] 704 | 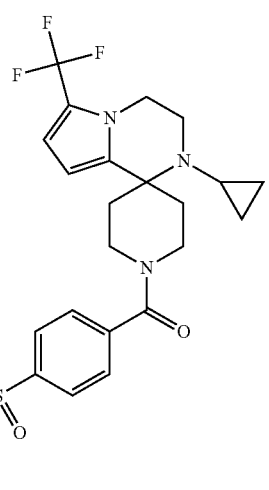 708 |
| 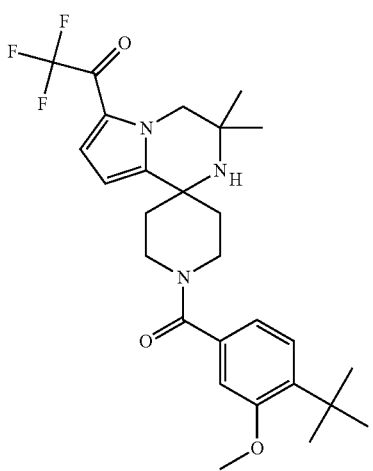 705 | 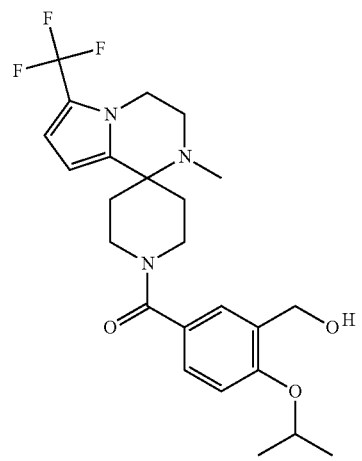 709 |

| 749 -continued | 750 -continued |
|---|---|
| 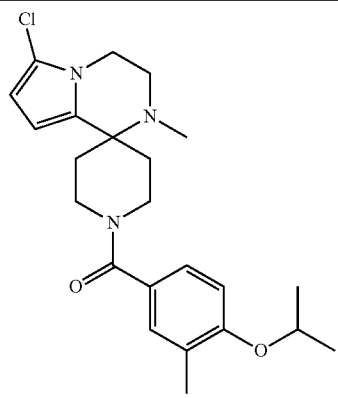 710 | 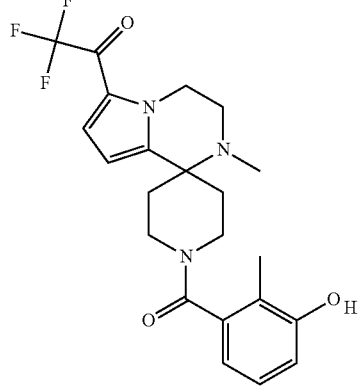 714 |
| 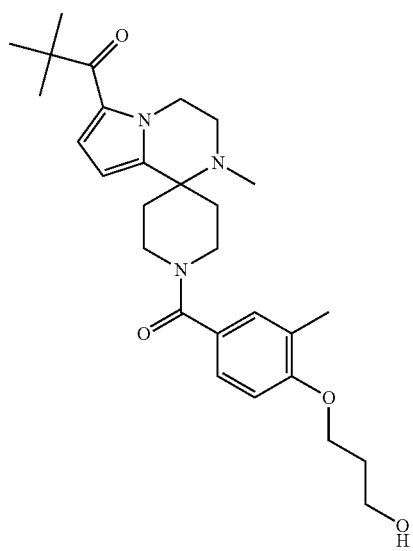 [SMILES: Cc1cc(C(=O)N2CCC3(CC2)c2ccc(C(=O)C(C)(C)C)n2CCN3C)ccc1OCCCO] 711 | 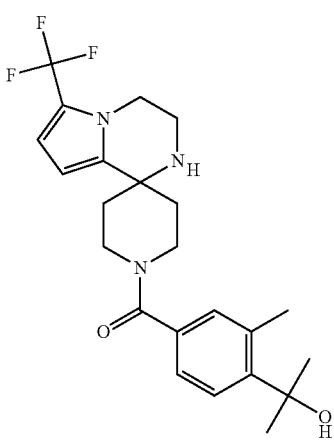 715 |
| 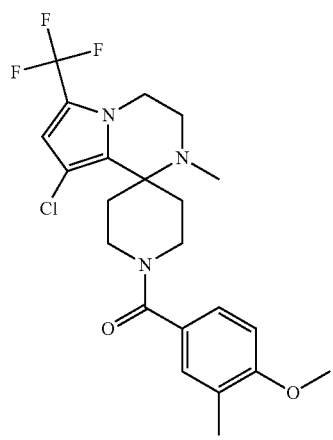 [SMILES: COc1ccc(C(=O)N2CCC3(CC2)c2c(Cl)cc(C(F)(F)F)n2CCN3C)cc1C] 713 | 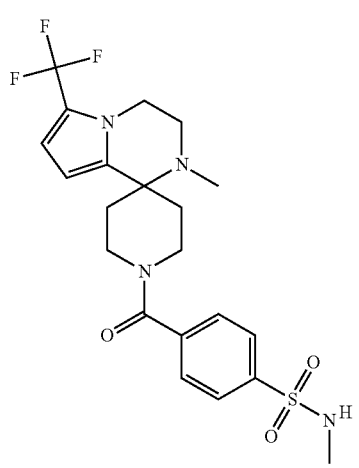 716 |

| 751 -continued | 752 -continued |
|---|---|
| 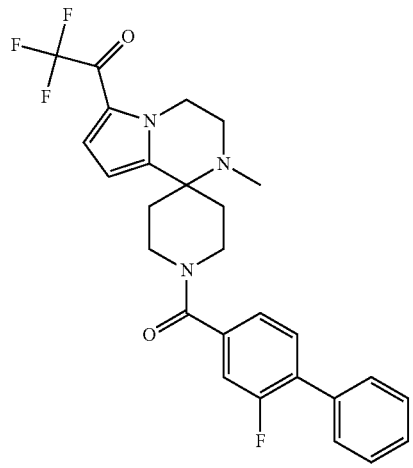 [SMILES: CN1CCn2c(C(=O)C(F)(F)F)ccc2C12CCN(C(=O)c1ccc(-c3ccccc3)c(F)c1)CC2] 717 | 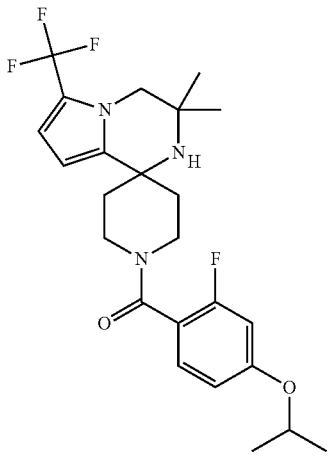 721 |
| 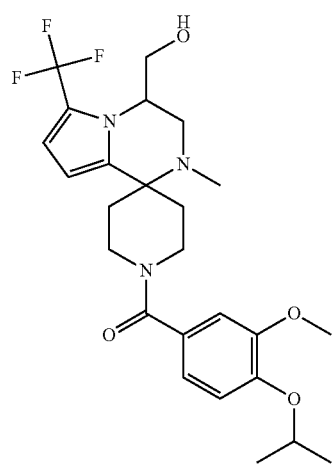 [SMILES: COc1cc(C(=O)N2CCC3(CC2)c2ccc(C(F)(F)F)n2C(CO)CN3C)ccc1OC(C)C] 719 | 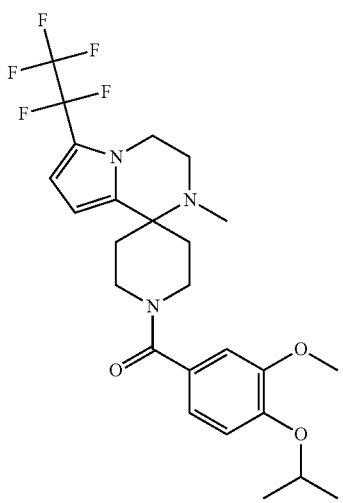 722 |
| 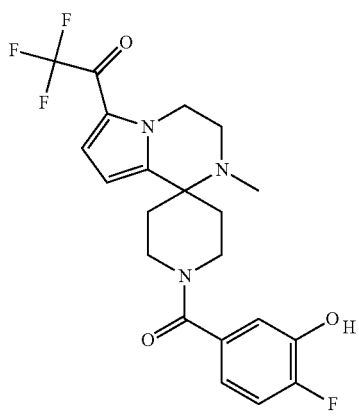 720 | 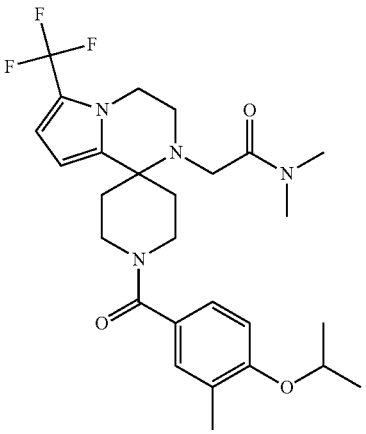 [SMILES: Cc1cc(C(=O)N2CCC3(CC2)c2ccc(C(F)(F)F)n2CCN3CC(=O)N(C)C)ccc1OC(C)C] 723 |

| 753 -continued | 754 -continued |
|---|---|
| 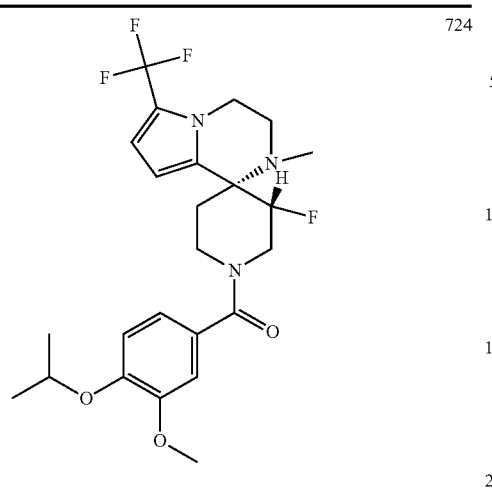 724 | 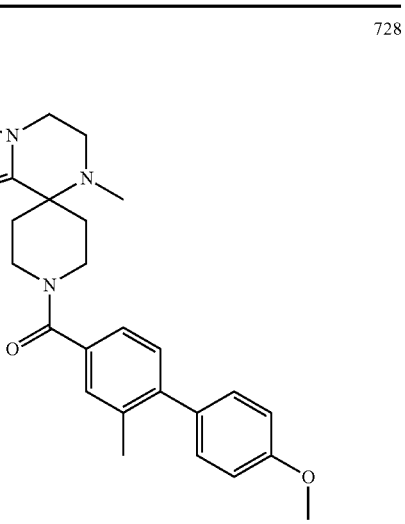 728 |
| 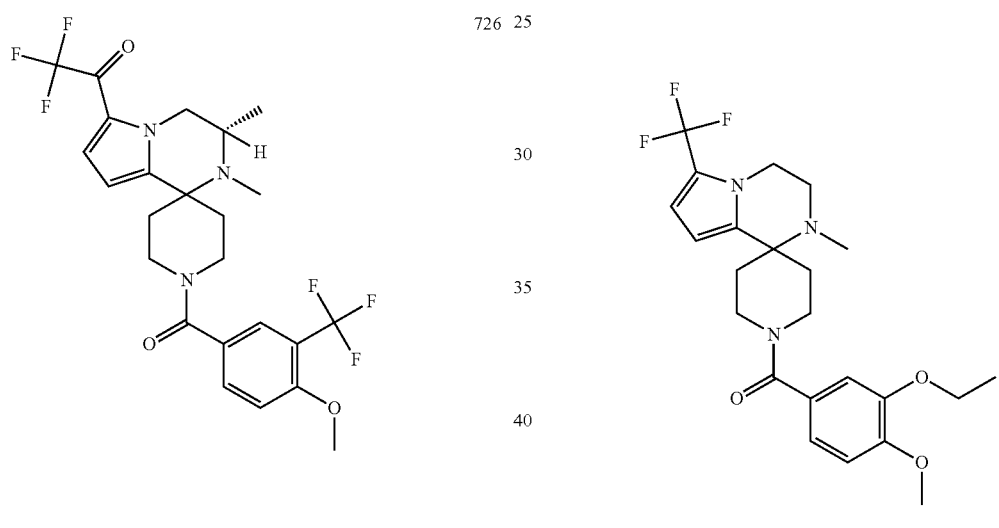 726 727 | 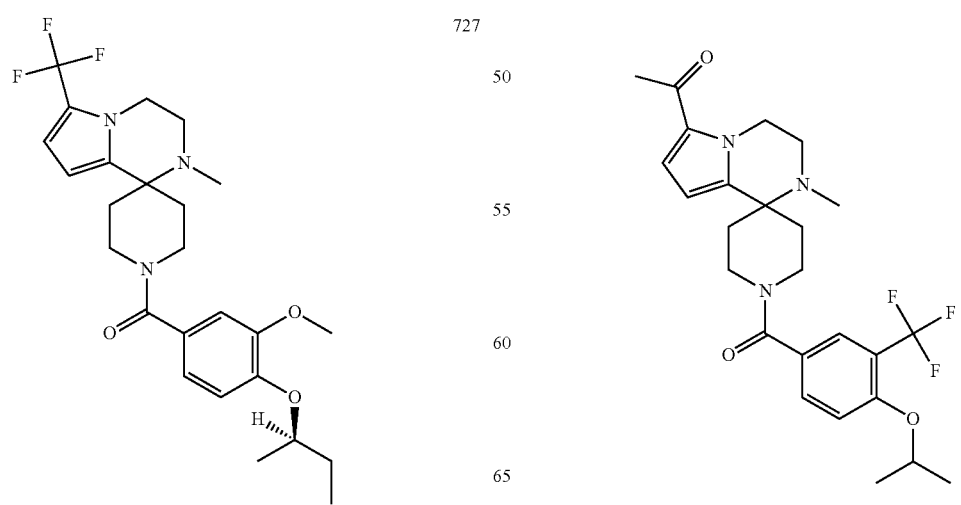 730 732 |

| 755 -continued | 756 -continued |
|---|---|
| 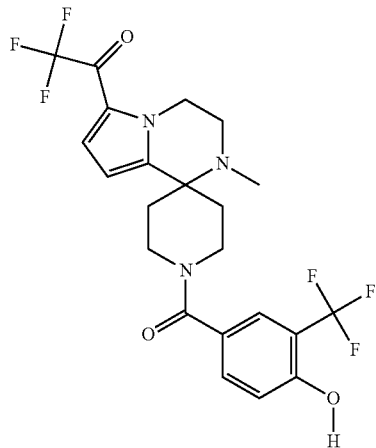 [SMILES: CN1CCn2c(C(=O)C(F)(F)F)ccc2C12CCN(C(=O)c1ccc(O)c(C(F)(F)F)c1)CC2] 733 | 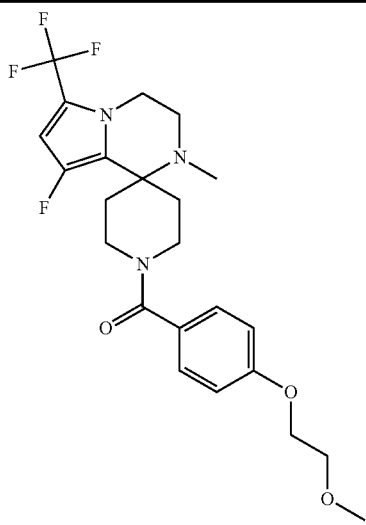 736 |
| 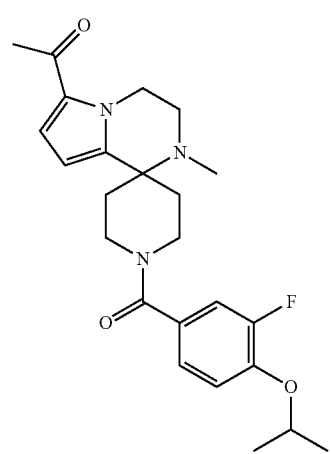 [SMILES: CC(=O)c1ccc2n1CCN(C)C21CCN(C(=O)c2ccc(OC(C)C)c(F)c2)CC1] 734 | 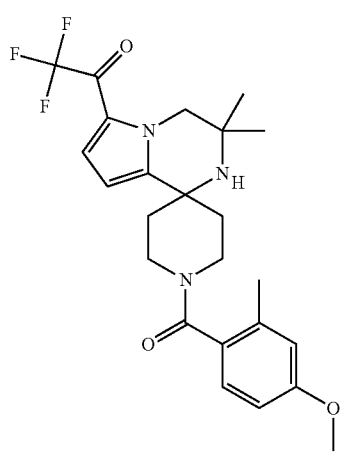 738 |
| 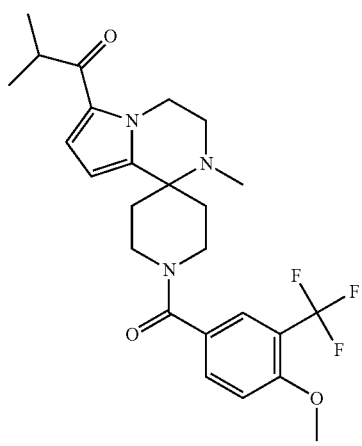 [SMILES: COc1ccc(C(=O)N2CCC3(CC2)c2ccc(C(=O)C(C)C)n2CCN3C)cc1C(F)(F)F] 735 | 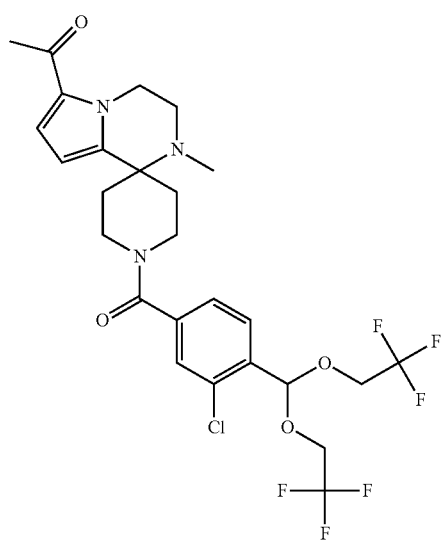 [SMILES: CC(=O)c1ccc2n1CCN(C)C21CCN(C(=O)c2ccc(C(OCC(F)(F)F)OCC(F)(F)F)c(Cl)c2)CC1] 739 |

| 757 -continued | 758 -continued |
|---|---|
| 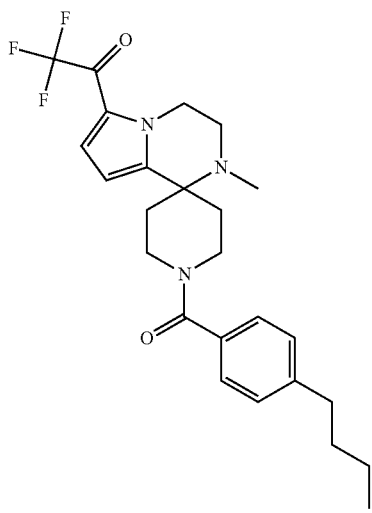 740 | 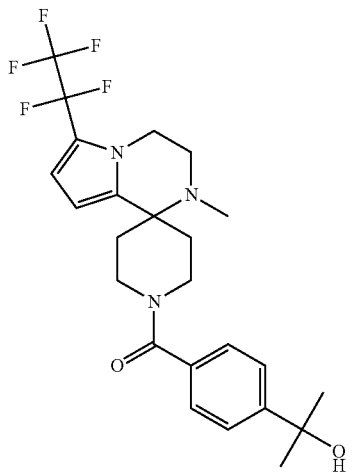 743 |
| 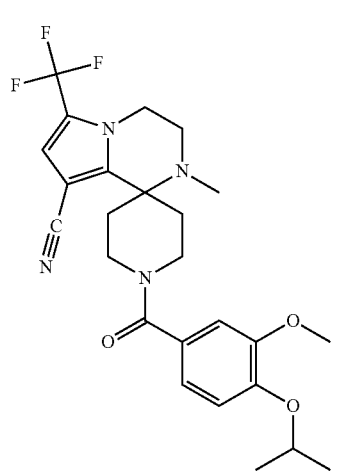 [SMILES: COc1cc(C(=O)N2CCC3(CC2)c2c(C#N)cc(C(F)(F)F)n2CCN3C)ccc1OC(C)C] 741 742 | 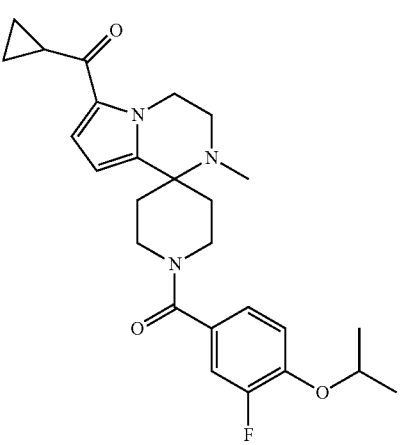 744 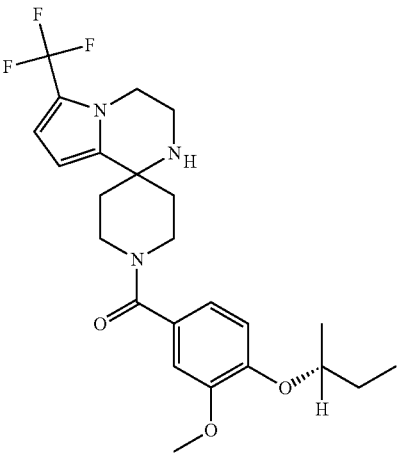 745 |

747 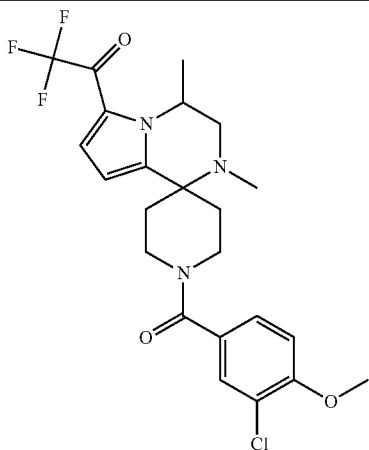
748 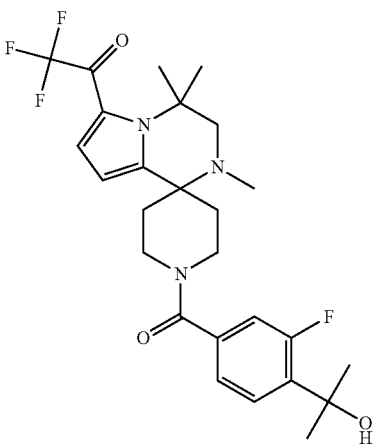 [SMILES: CN1CC(C)(C)n2c(C(=O)C(F)(F)F)ccc2C12CCN(C(=O)c1ccc(C(C)(C)O)c(F)c1)CC2]
749 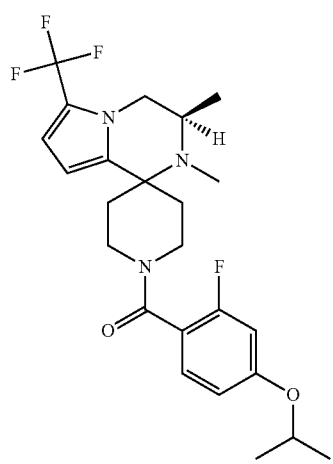 [SMILES: CC(C)Oc1ccc(C(=O)N2CCC3(CC2)c2ccc(C(F)(F)F)n2C[C@@H](C)N3C)c(F)c1]
750 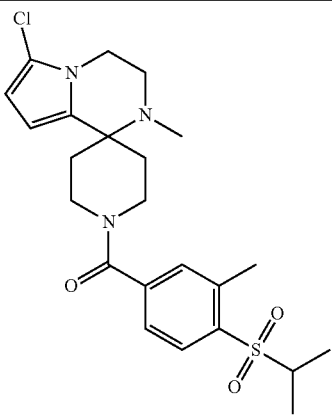
751 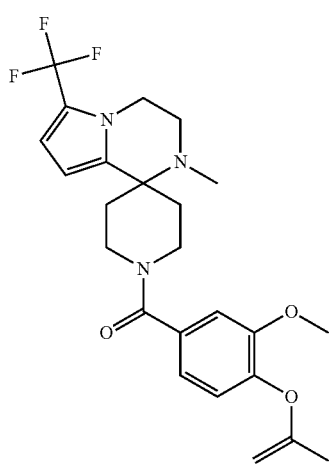 [SMILES: C=C(C)Oc1ccc(C(=O)N2CCC3(CC2)c2ccc(C(F)(F)F)n2CCN3C)cc1OC]
752 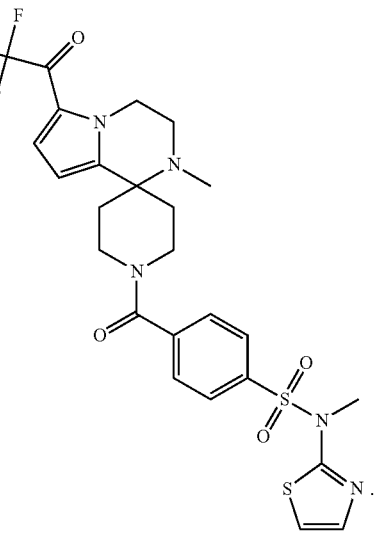
29. A pharmaceutical composition comprising the compound of claim 1 and a pharmaceutically acceptable carrier.
30. A method of inhibiting a voltage-gated sodium ion channel in:
   a patient; or
   a biological sample;
   comprising administering to the patient, or contacting the biological sample, with the compound of claim 1.

31. The method of claim 30, wherein the voltage-gated sodium ion channel is NaV 1.7.

32. A compound of formula I:

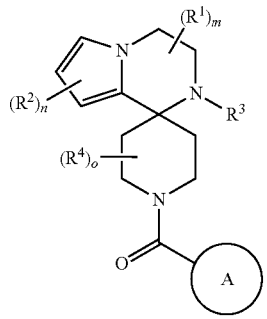

or a pharmaceutically acceptable salt thereof,
wherein, independently for each occurrence:
$R^1$ is H, C1-C6 alkyl, C3-C8 cycloalkyl, halo, CN, $NR^8SO_2R^8$, $SO_2R^8$, $SR^8$, $SOR^8$, $NR^8COR^8$, $NR^8CO_2R^8$, $CON(R^8)_2$, $SO_2N(R^8)_2$, $CF_3$, heterocycloalkyl, or a straight chain, branched, or cyclic (C3-C8)-$R^9$ wherein up to two $CH_2$ units may be replaced with O, CO, S, SO, $SO_2$ or $NR^8$, or two $R^1$ taken together form an oxo group;

$R^2$ is H, C1-C6 alkyl, C1-C6 haloalkyl, CN, OH, $SO_2R^8$, $SR^8$, $SOR^8$, $CO_2R^8$, $CON(R^8)_2$, $SO_2N(R^8)_2$, $CF_3$, $CHF_2$, or a straight chain, branched, or cyclic (C3-C8)-$R^9$ wherein up to two $CH_2$ units may be replaced with O, CO, S, SO, $SO_2$, $CF_2$, or $NR^8$;

$R^3$ is H, C1-C6 alkyl, C3-C8 cycloalkyl, $CO_2R^8$, $COR^8$, COH, $CON(R^8)_2$, $CF_3$, $CH_2CF_3$, $CH_2CHF_2$, or a straight chain, branched, or cyclic (C3-C8)-$R^9$ wherein up to two $CH_2$ units may be replaced with O, CO, S, SO, $SO_2$ or $NR^8$;

$R^4$ is H, C1-C6 alkyl, halo, C3-C8 cycloalkyl, wherein up to two $CH_2$ units may be replaced by O, CO, S, SO, $SO_2$, or $NR^8$, or 2 $R^4$ taken together form a fused 3 to 7 membered cycloalkyl ring;

$R^8$ is H, C1-C6 alkyl, $CF_3$, C3-C8 cycloalkyl, or a straight chain, branched, or cyclic (C3-C8)-$R^9$ wherein up to two $CH_2$ units may be replaced with O, CO, S, SO, $SO_2$ or NR, or 2 $R^8$ taken together with the atoms to which they are attached form a ring;

$R^9$ is H, $CF_3$, $CO_2R$, OH, aryl, heteroaryl, C3-C8 cycloalkyl, heterocycloalkyl, $N(R)_2$, NRCOR, CON(R)$_2$, CN, or $SO_2R$;

R is H, C1-C6 alkyl, aryl, heteroaryl, C3-C8 cycloalkyl, or heterocycloalkyl;

A is an aryl optionally substituted with one or more of C1-C6 alkyl, C3-C8 cycloalkyl, C1-C6 alkoxy, C3-C8 cycloalkoxy halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CHF_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$R^9$ wherein up to three $CH_2$ units may be replaced with O, CO, S, SO, $SO_2$, or $NR^8$;

or wherein two substituents on A together with the carbon atoms to which they are attached form a ring comprising up to 2 heteroatoms;

m is 0, 1, 2, 3, or 4;
n is 0, 1, 2, or 3; and
o is 0, 1, 2, 3, or 4.

33. The compound of claim 32, wherein the compound has formula IA:

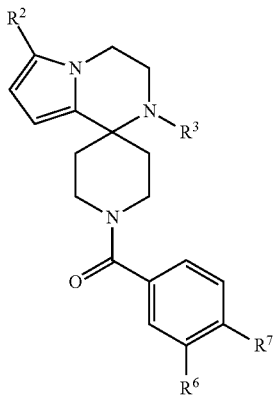

wherein:
$R^2$ is C1-C6 alkyl, C1-C6 haloalkyl, CN, OH, $SO_2R^8$, $SR^8$, $SOR^8$, $CO_2R^8$, $CON(R^8)_2$, $SO_2N(R^8)_2$, $CF_3$, $CHF_2$, or a straight chain, branched, or cyclic (C3-C8)-$R^9$ wherein up to two $CH_2$ units may be replaced with O, CO, S, SO, $SO_2$, $CF_2$, or $NR^8$;

$R^3$ is H, C1-C6 alkyl, $CO_2R^8$, $COR^8$, COH, $CON(R^8)_2$, $CF_3$, or a straight chain, branched, or cyclic (C1-C8)-$R^9$ wherein up to two $CH_2$ units may be replaced with O, CO, S, SO, $SO_2$ or $NR^8$;

$R^6$ is H, C1-C6 alkyl, C3-C8 cycloalkyl, C1-C6 alkoxy, C3-C8 cycloalkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$R^9$ wherein up to three $CH_2$ units may be replaced with O, CO, S, SO, $SO_2$, or $NR^8$;

$R^7$ is H, C1-C6 alkyl, C3-C8 cycloalkyl, C1-C6 alkoxy, halo, CN, OH, $OR^8$, $N(R^8)_2$, $NR^8SO_2R^8$, $SO_2R^8$, $SOR^8$, $SR^8$, $CO_2R^8$, $NR^8COR^8$, $NR^8CO_2R^8$, $CON(R^8)_2$, $SO_2N(R^8)_2$, $CF_3$, $OCF_3$, $OCHF_2$, $R^9$, heterocycloalkyl, heterocycloalkoxy, aryl, heteroaryl, or a straight chain, branched, or cyclic (C3-C8)-$R^9$ wherein up to three $CH_2$ units may be replaced with O, CO, S, SO, $SO_2$, or $NR^8$.

34. The compound of claim 32, wherein the

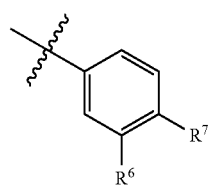

moiety is selected from:

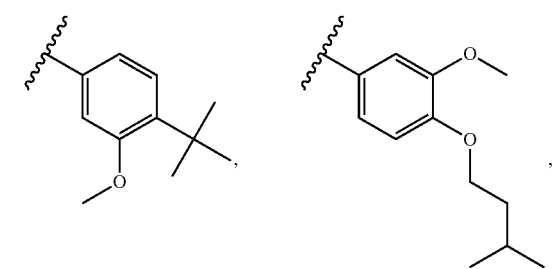
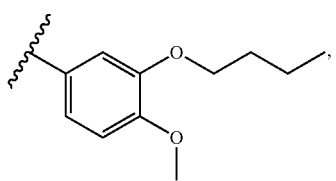
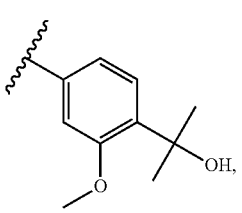
-continued
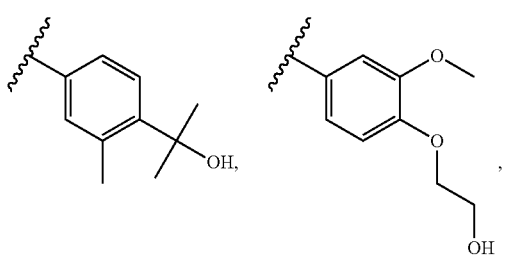
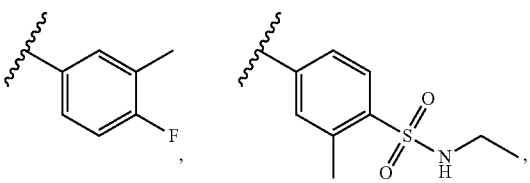
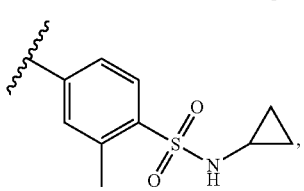
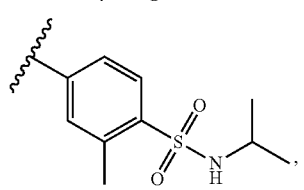
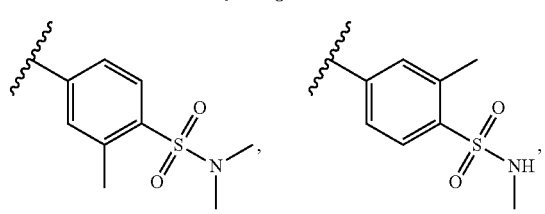
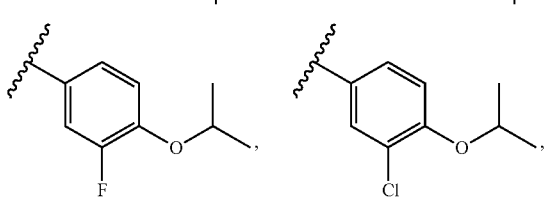

-continued
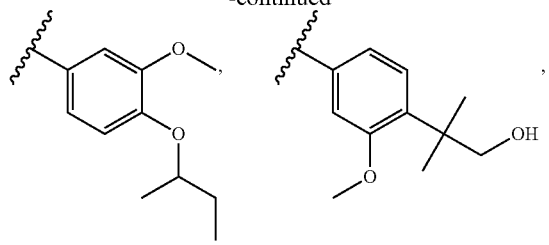
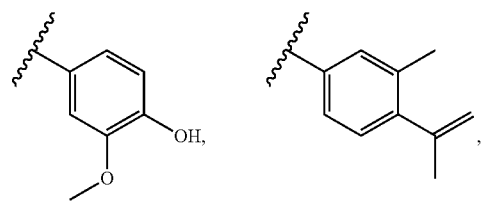
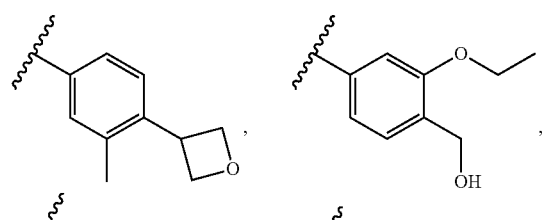
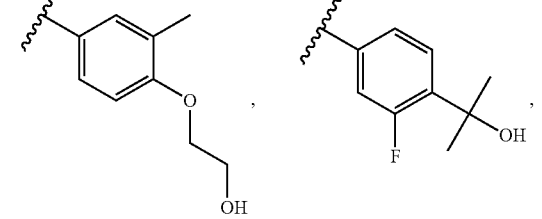
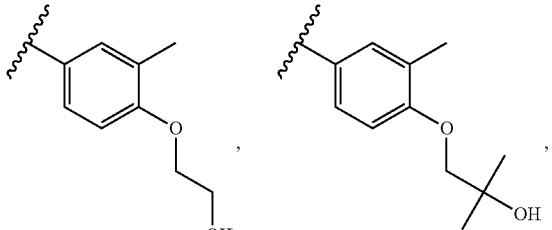
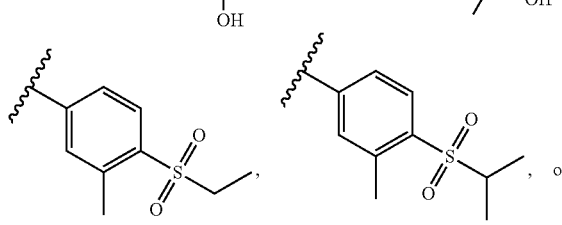, or
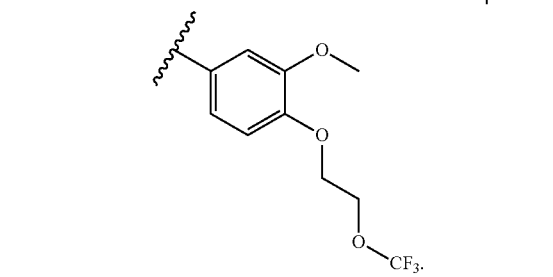
35. The compound of claim 32, wherein the compound is selected from the following table:
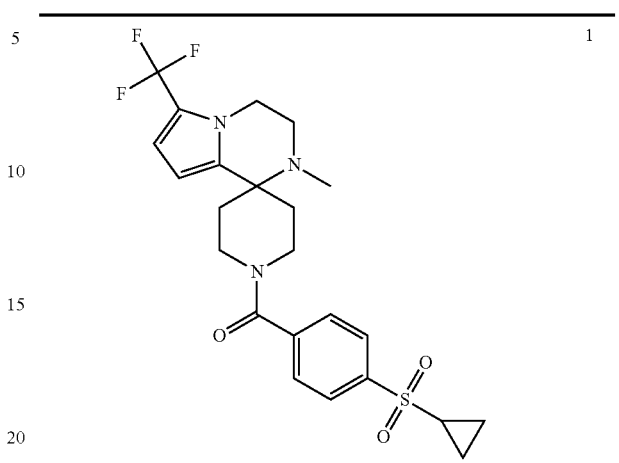
1
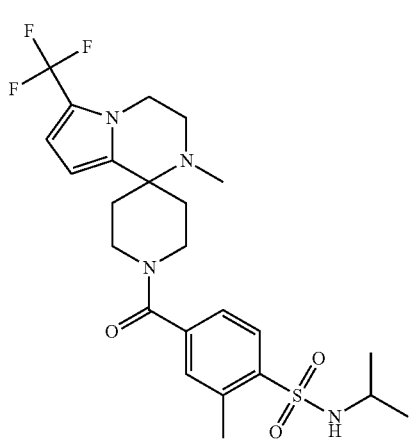 [SMILES: Cc1cc(C(=O)N2CCC3(CC2)c2ccc(C(F)(F)F)n2CCN3C)ccc1S(=O)(=O)NC(C)C]
2
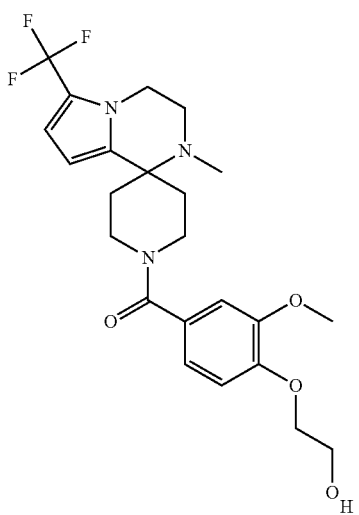
3

| 767 -continued | | 768 -continued | |
|---|---|---|---|
| 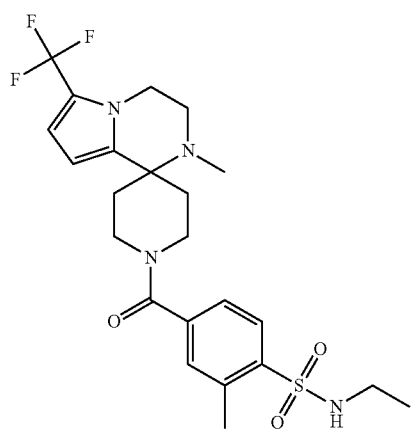 [SMILES: CCNS(=O)(=O)c1ccc(C(=O)N2CCC3(CC2)c2ccc(C(F)(F)F)n2CCN3C)cc1C] | 4 | 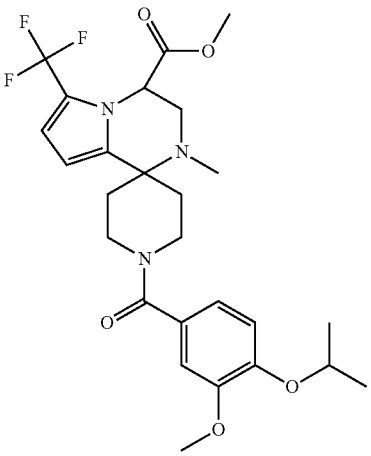 | 8 |
| 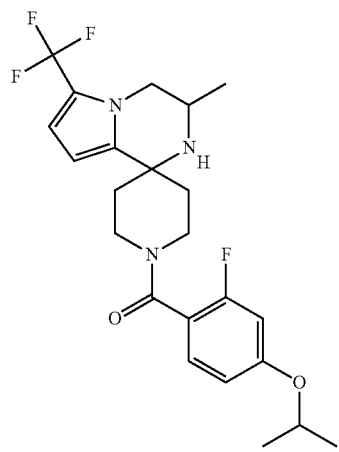 | 6 | 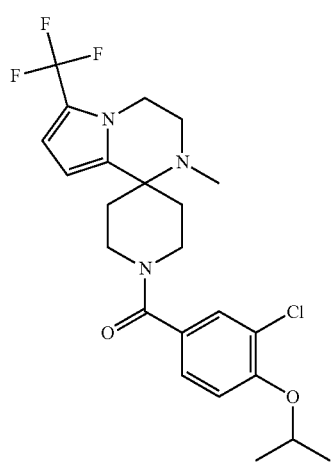 | 9 |
| 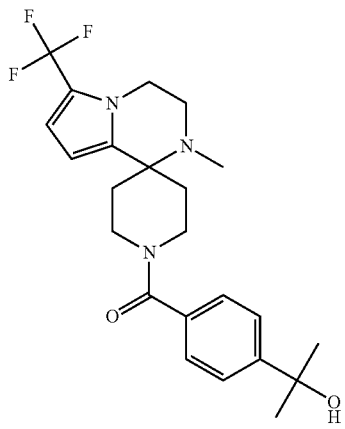 [SMILES: CN1CCn2c(C(F)(F)F)ccc2C12CCN(C(=O)c1ccc(C(C)(C)O)cc1)CC2] | 7 | 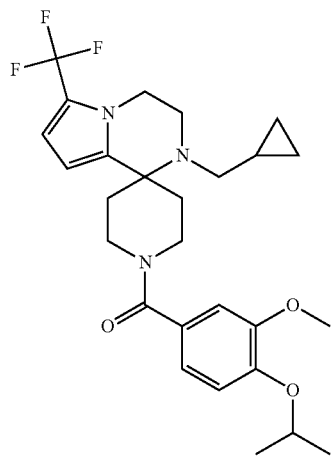 [SMILES: COc1cc(C(=O)N2CCC3(CC2)c2ccc(C(F)(F)F)n2CCN3CC2CC2)ccc1OC(C)C] | 10 |

| 769 -continued | 770 -continued |
|---|---|
| 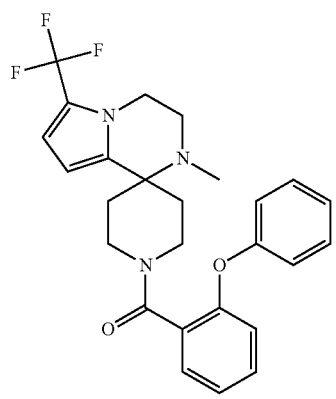 [SMILES: CN1CCn2c(C(F)(F)F)ccc2C12CCN(C(=O)c1ccccc1Oc1ccccc1)CC2] 11 | 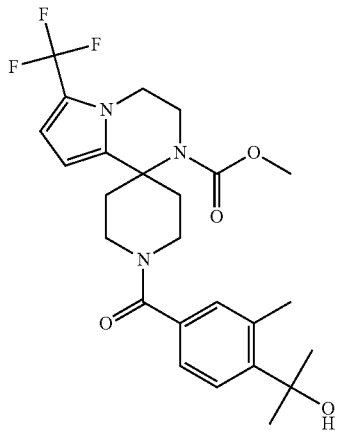 14 |
| 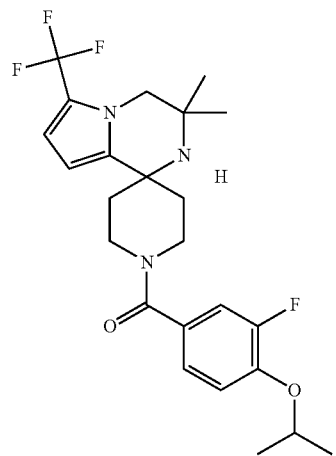 12 | 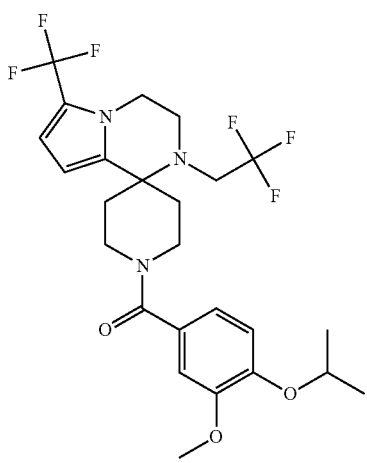 15 |
| 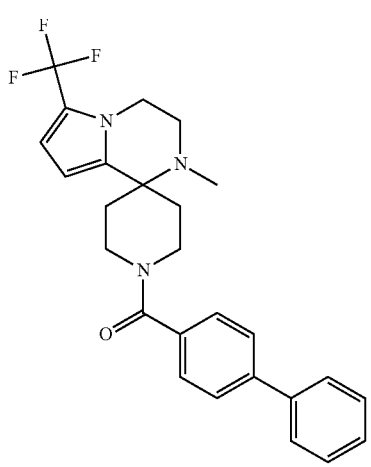 [SMILES: CN1CCn2c(C(F)(F)F)ccc2C12CCN(C(=O)c1ccc(-c3ccccc3)cc1)CC2] 13 | 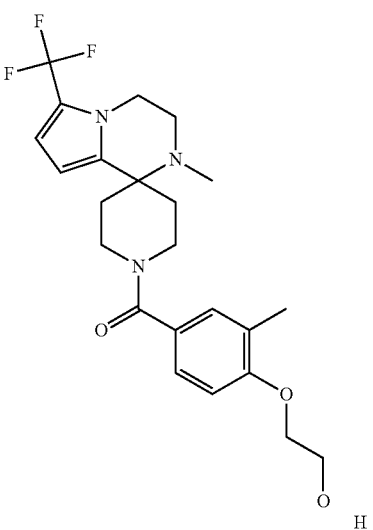 16 |

| 771 -continued | 772 -continued |
|---|---|
| 17 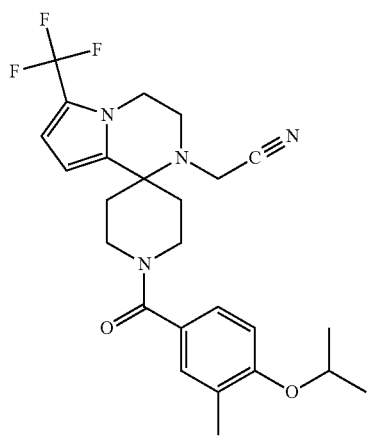 [SMILES: Cc1cc(C(=O)N2CCC3(CC2)c2ccc(C(F)(F)F)n2CCN3CC#N)ccc1OC(C)C] | 21 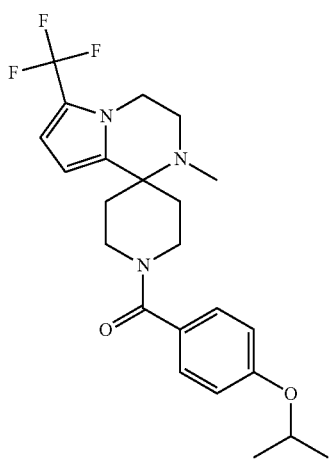 |
| 18 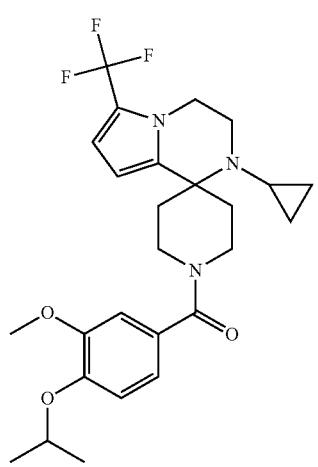 [SMILES: COc1cc(C(=O)N2CCC3(CC2)c2ccc(C(F)(F)F)n2CCN3C2CC2)ccc1OC(C)C] | 22 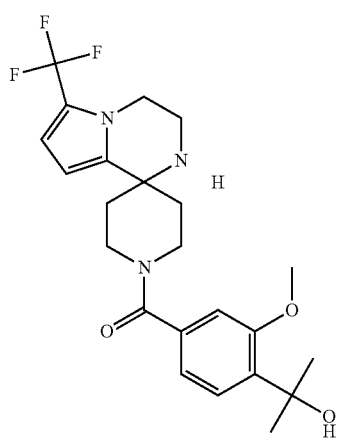 |
| 19 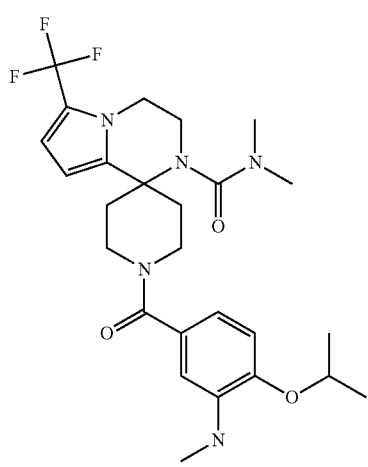 | 23 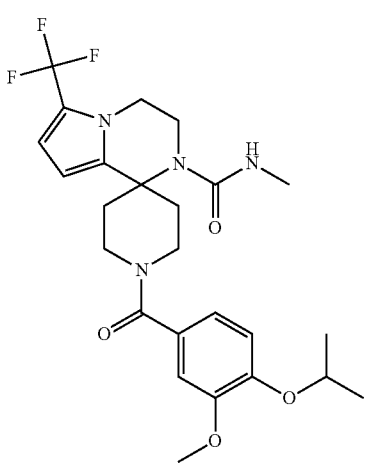 |

| 773 -continued | 774 -continued |
|---|---|
| 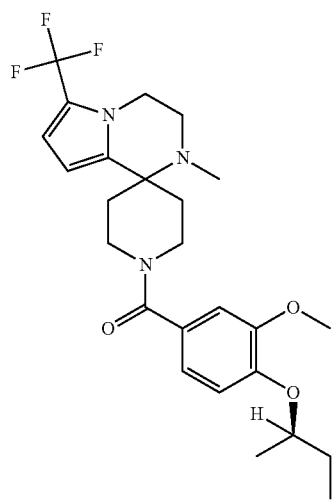 [SMILES: CC[C@@H](C)Oc1ccc(C(=O)N2CCC3(CC2)c2ccc(C(F)(F)F)n2CCN3C)cc1OC] 24 | 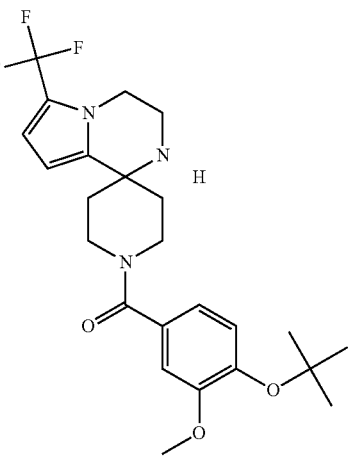 27 |
| 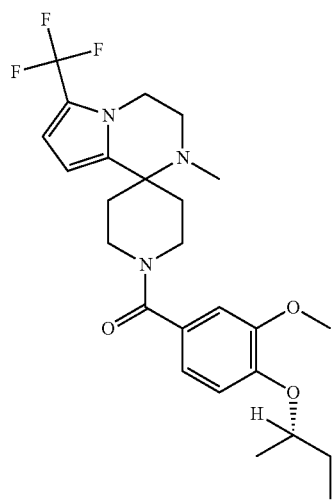 [SMILES: CC[C@H](C)Oc1ccc(C(=O)N2CCC3(CC2)c2ccc(C(F)(F)F)n2CCN3C)cc1OC] 25 | 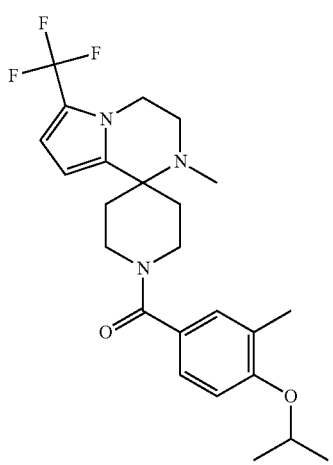 28 |
| 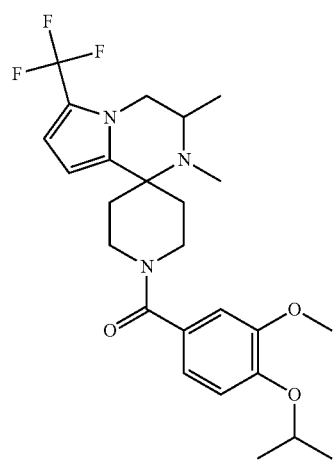 [SMILES: COc1cc(C(=O)N2CCC3(CC2)c2ccc(C(F)(F)F)n2CC(C)N3C)ccc1OC(C)C] 26 | 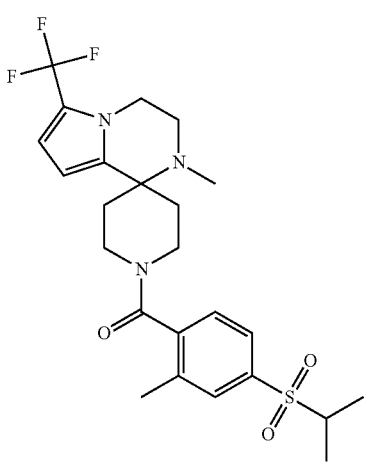 [SMILES: Cc1cc(S(=O)(=O)C(C)C)ccc1C(=O)N1CCC2(CC1)c1ccc(C(F)(F)F)n1CCN2C] 31 |

| | |
|---|---|
| 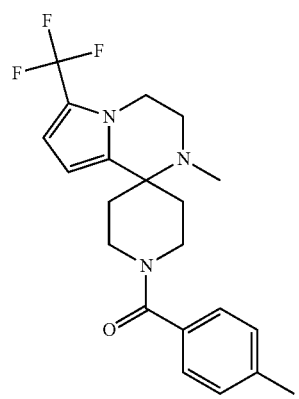 33 | 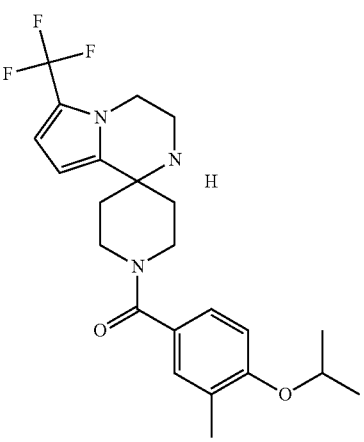 37 |
| 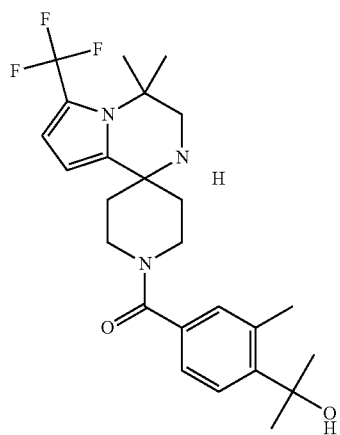 35 | 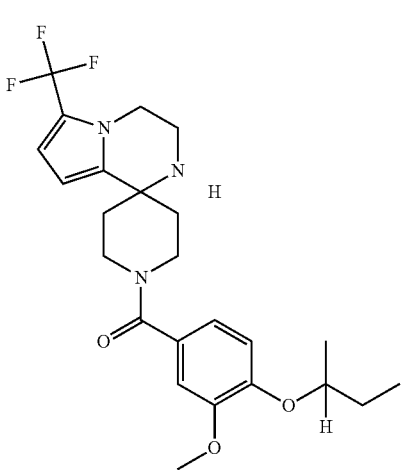 38 |
| 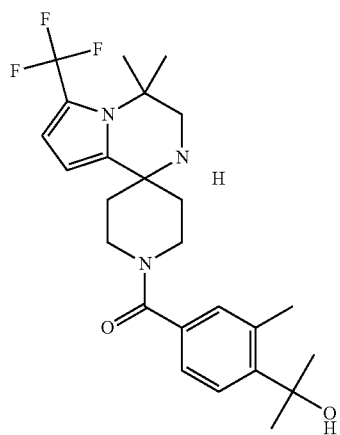 36 | 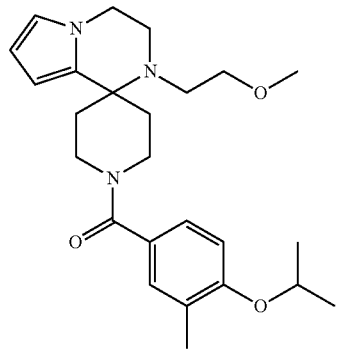 [SMILES: COCCN1CCn2cccc2C12CCN(C(=O)c1ccc(OC(C)C)c(C)c1)CC2] 39 |

| 777 -continued | 778 -continued |
|---|---|
| 40 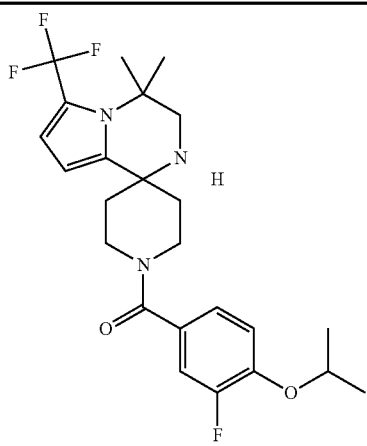 | 43 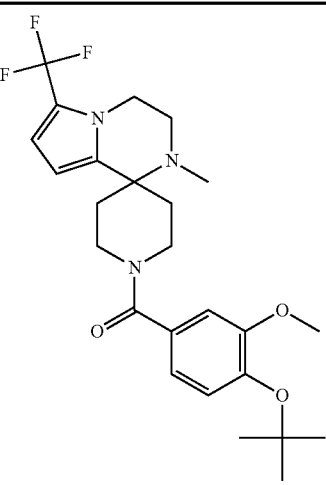 |
| 41 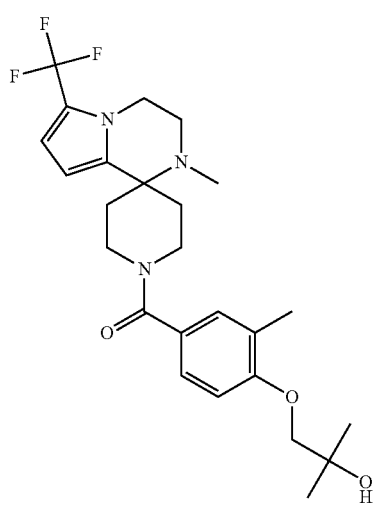 [SMILES: Cc1cc(C(=O)N2CCC3(CC2)c2ccc(C(F)(F)F)n2CCN3C)ccc1OCC(C)(C)O] | 44 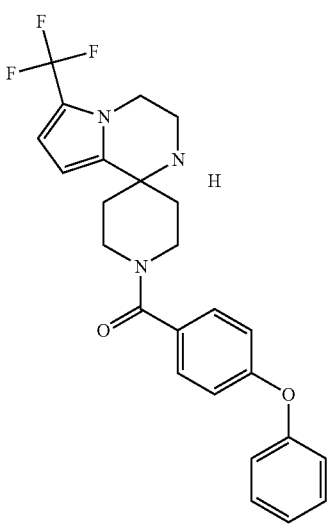 |
| 42 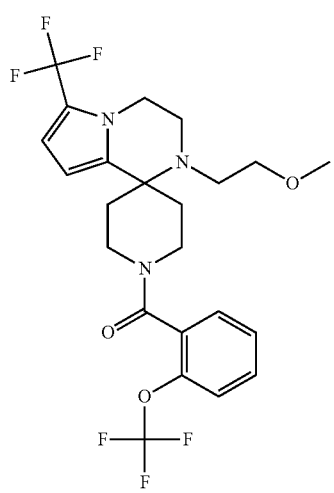 | 45 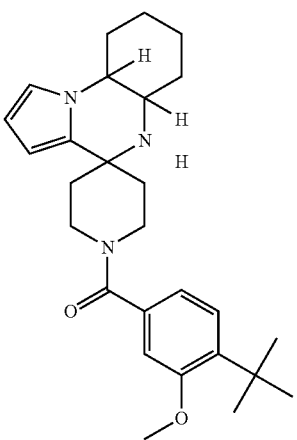 |

| 779 -continued | 780 -continued |
|---|---|
| 46 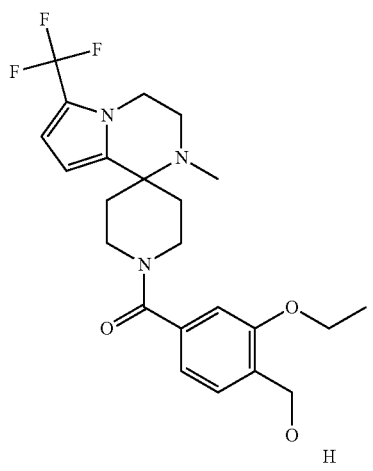 | 50 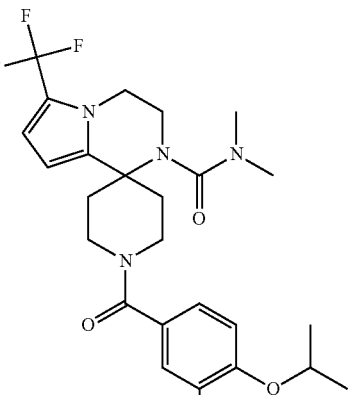 |
| 48 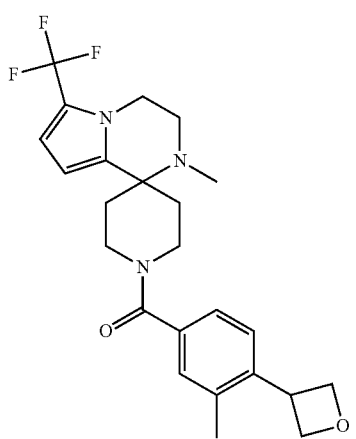 [SMILES: Cc1cc(C(=O)N2CCC3(CC2)c2ccc(C(F)(F)F)n2CCN3C)ccc1C1COC1] | 53 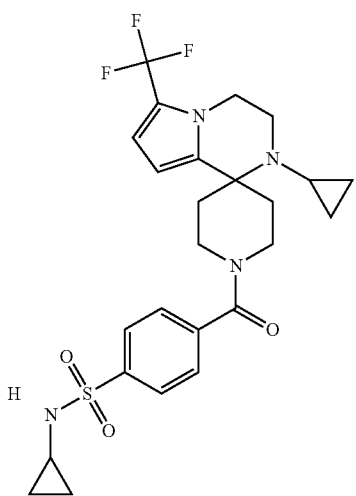 |
| 49 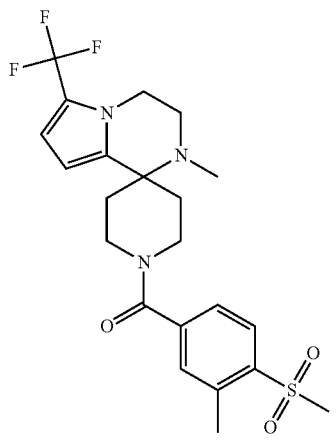 [SMILES: Cc1cc(C(=O)N2CCC3(CC2)c2ccc(C(F)(F)F)n2CCN3C)ccc1S(C)(=O)=O] | 54 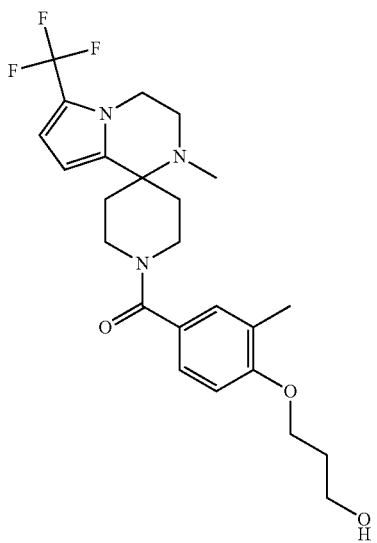 [SMILES: Cc1cc(C(=O)N2CCC3(CC2)c2ccc(C(F)(F)F)n2CCN3C)ccc1OCCCO] |

| 781 -continued | 782 -continued |
|---|---|
| 55 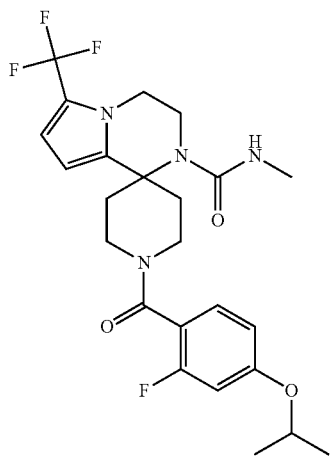 [SMILES: CNC(=O)N1CCn2c(C(F)(F)F)ccc2C12CCN(C(=O)c1ccc(OC(C)C)cc1F)CC2] | 59 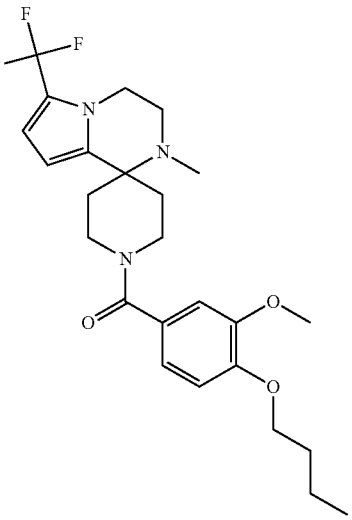 |
| 56 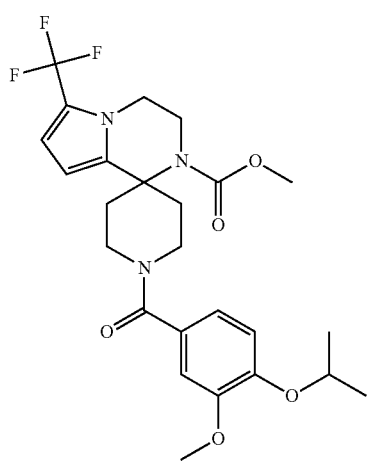 | 61 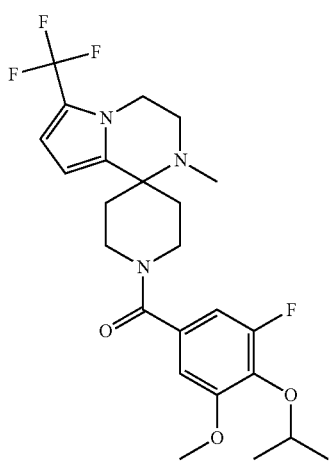 |
| 57 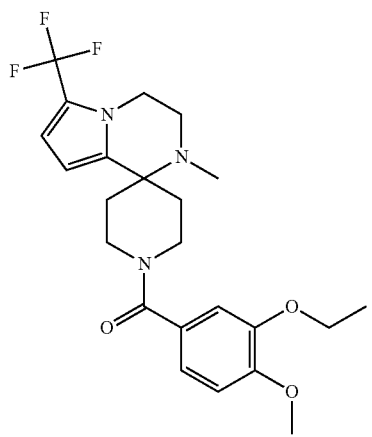 [SMILES: CCOc1cc(C(=O)N2CCC3(CC2)c2ccc(C(F)(F)F)n2CCN3C)ccc1OC] | 62 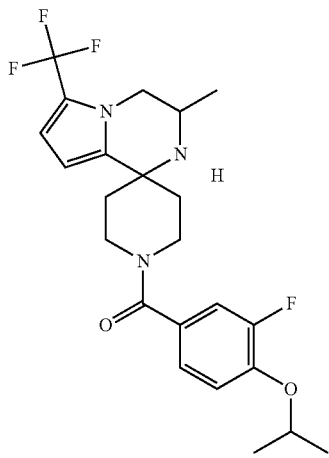 |

| 63 | 68 |
|---|---|
| 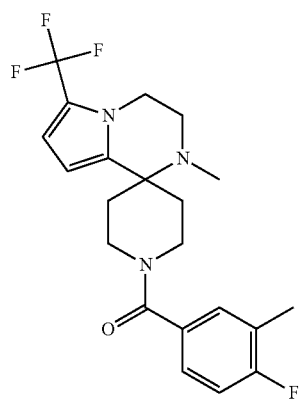 [SMILES: Cc1cc(C(=O)N2CCC3(CC2)c2ccc(C(F)(F)F)n2CCN3C)ccc1F] | 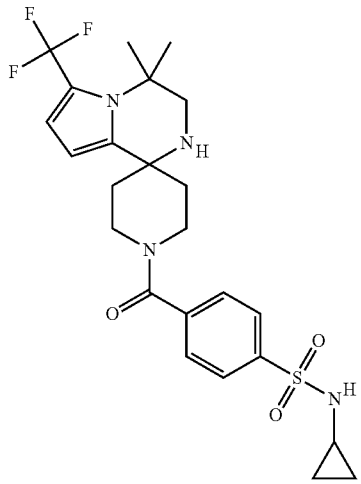 |
| 64 | 69 |
| 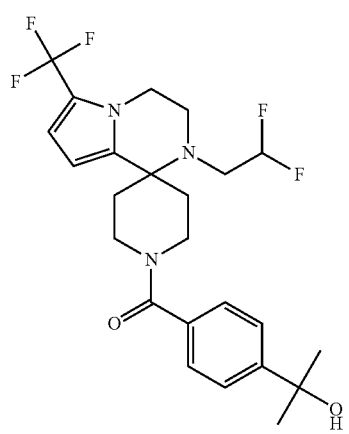 [SMILES: CC(C)(O)c1ccc(C(=O)N2CCC3(CC2)c2ccc(C(F)(F)F)n2CCN3CC(F)F)cc1] | 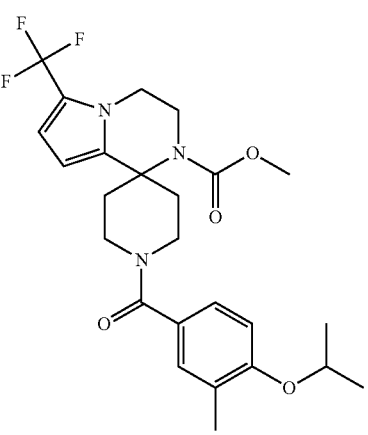 |
| 66 | 70 |
| 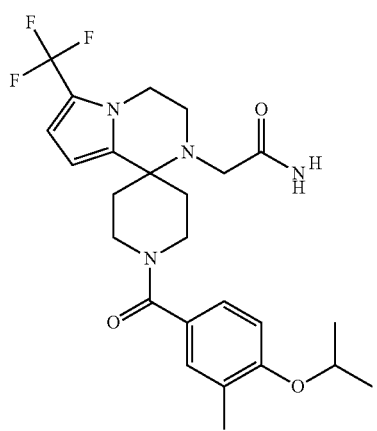 | 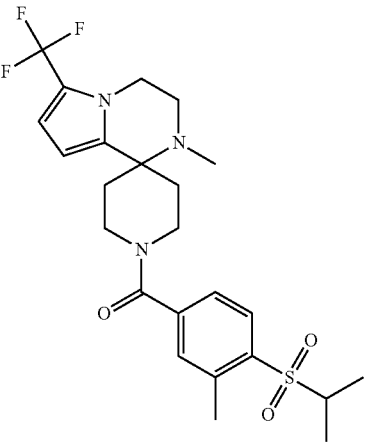 |

| 785 -continued | 786 -continued |
|---|---|
| 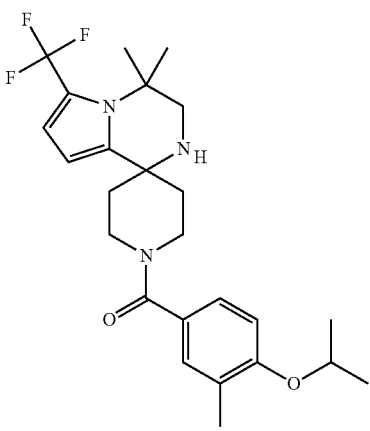 71 | 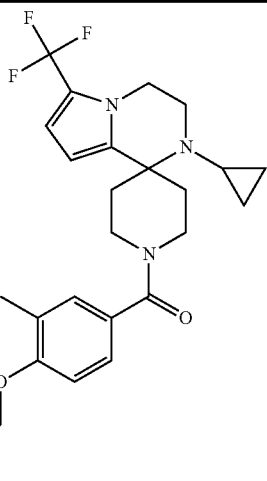 74 |
| 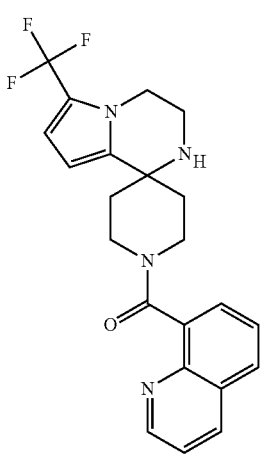 72 | 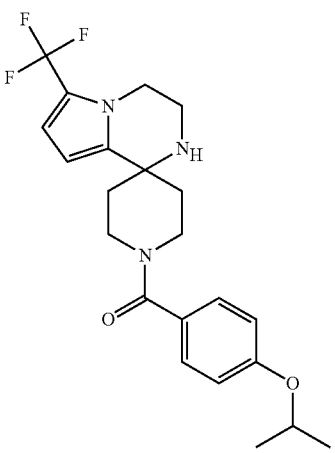 76 |
| 73 | 77 |

| 787 -continued | 788 -continued |
|---|---|
| 78 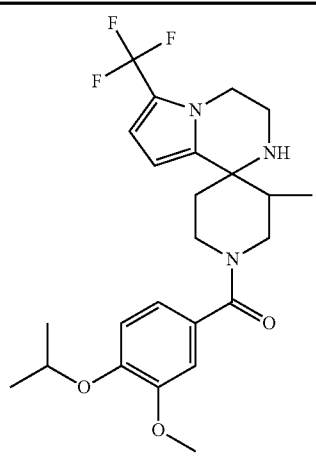 | 81 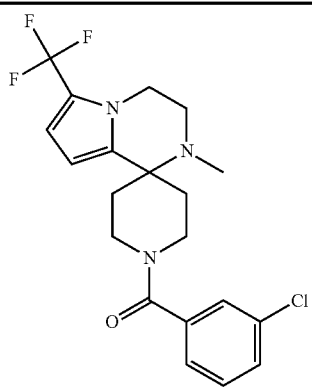 |
| 79 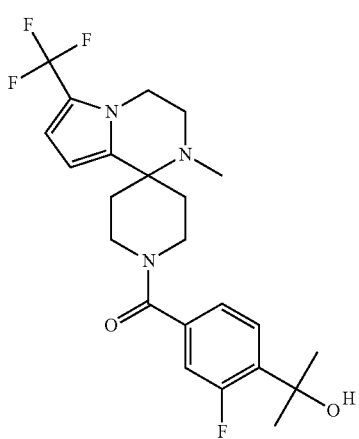 | 82 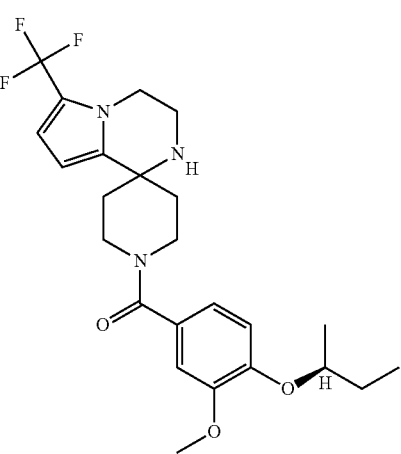 |
| | 83 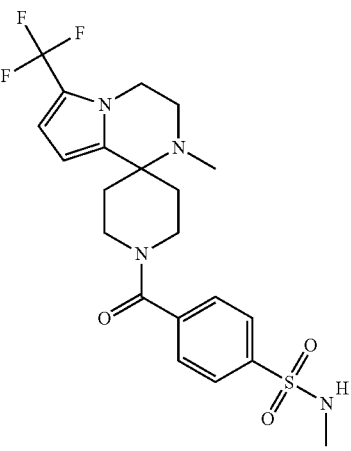 |
| 80 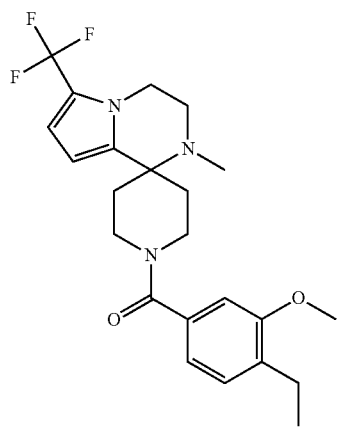 | 84 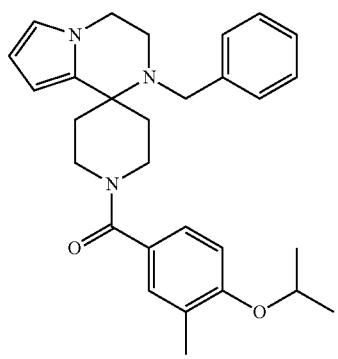 [SMILES: Cc1cc(C(=O)N2CCC3(CC2)c2cccn2CCN3Cc2ccccc2)ccc1OC(C)C] |

| 789 -continued | 790 -continued |
|---|---|
| 85 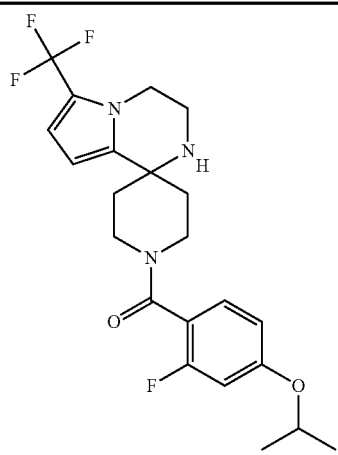 | 90 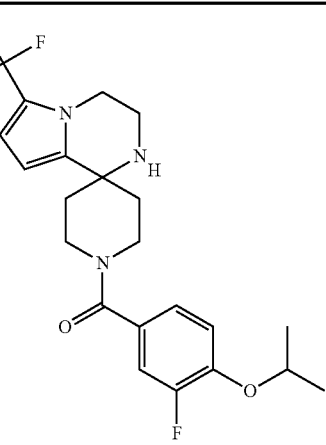 |
| 87 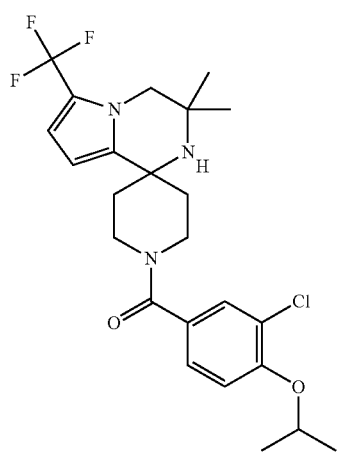 | 91 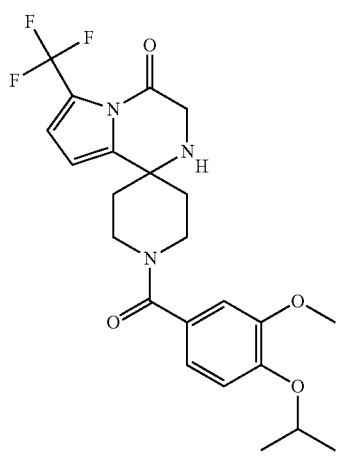 |
| 89 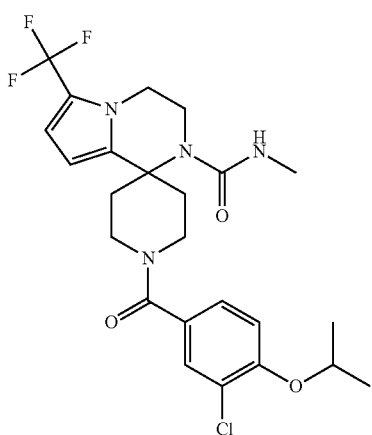 [SMILES: CNC(=O)N1CCn2c(C(F)(F)F)ccc2C12CCN(C(=O)c1ccc(OC(C)C)c(Cl)c1)CC2] | 92 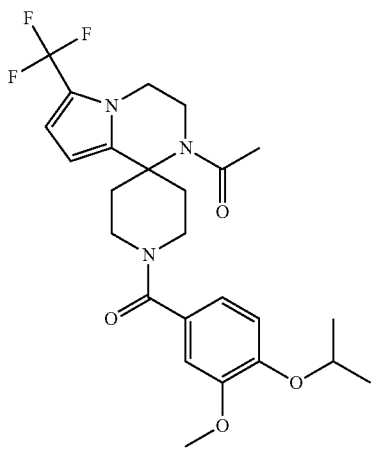 [SMILES: COc1cc(C(=O)N2CCC3(CC2)c2ccc(C(F)(F)F)n2CCN3C(C)=O)ccc1OC(C)C] |

| 791 -continued | 792 -continued |
|---|---|
| 93 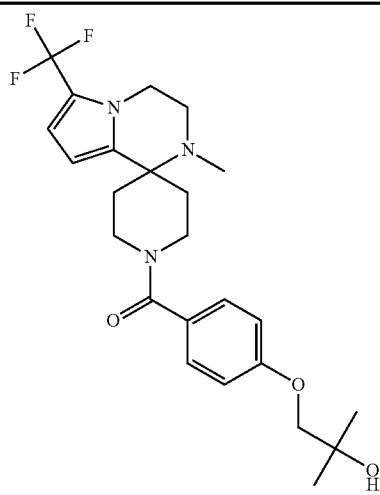 | 97 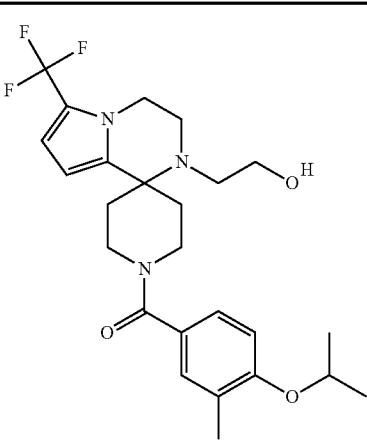 |
| 95 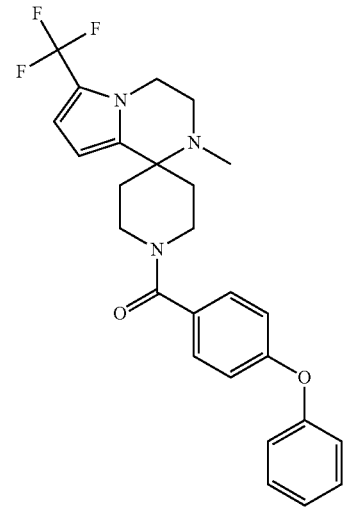 [SMILES: CN1CCn2c(C(F)(F)F)ccc2C12CCN(C(=O)c1ccc(Oc3ccccc3)cc1)CC2] | 98 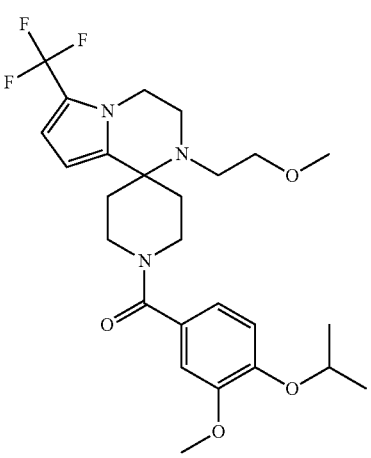 [SMILES: COCCN1CCn2c(C(F)(F)F)ccc2C12CCN(C(=O)c1ccc(OC(C)C)c(OC)c1)CC2] |
| 96 | 99 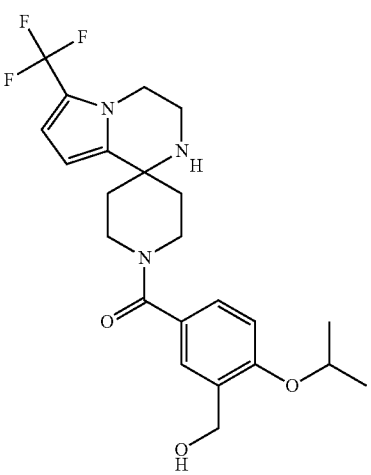 |

| 793 -continued | 794 -continued |
|---|---|
| 100 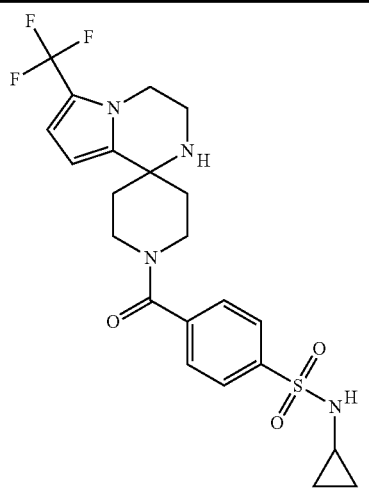 | 104 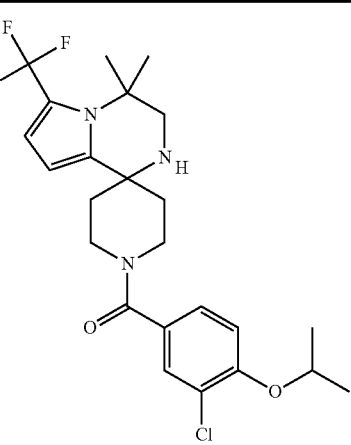 |
| 102 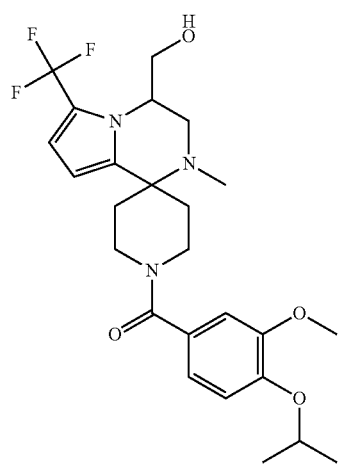 [SMILES: COc1cc(C(=O)N2CCC3(CC2)c2ccc(C(F)(F)F)n2C(CO)CN3C)ccc1OC(C)C] | 105 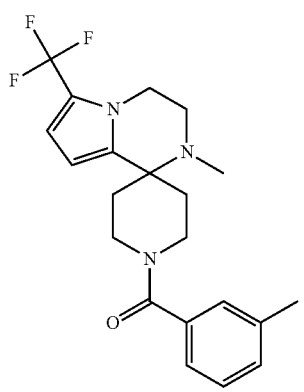 |
| 103 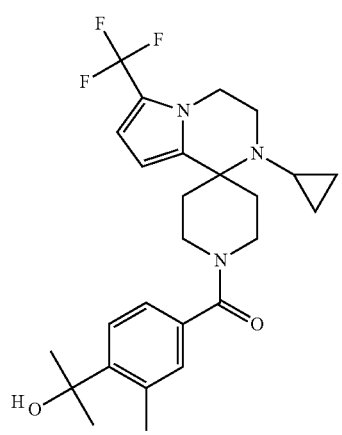 | 106 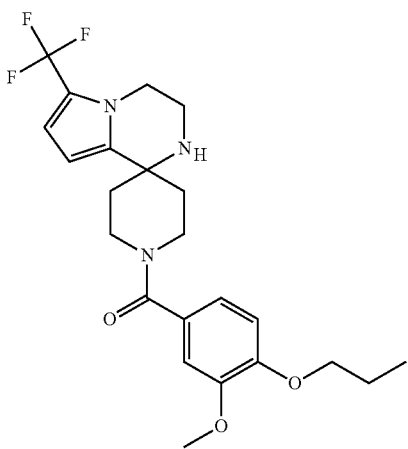 |

| 795 -continued | 796 -continued |
|---|---|
| 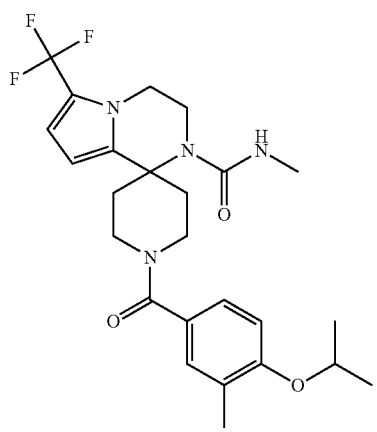 [SMILES: CNC(=O)N1CCn2c(C(F)(F)F)ccc2C12CCN(C(=O)c1ccc(OC(C)C)c(C)c1)CC2] 107 | 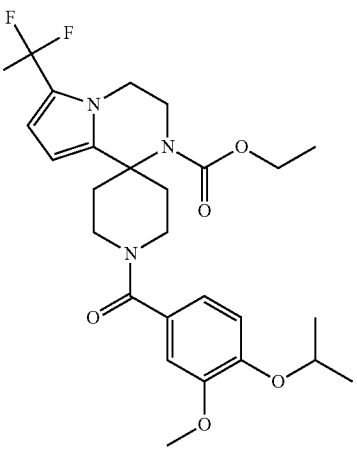 113 |
| 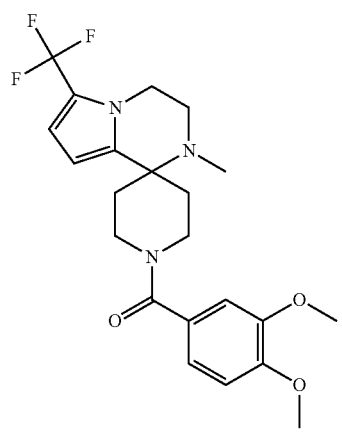 [SMILES: COc1ccc(C(=O)N2CCC3(CC2)c2ccc(C(F)(F)F)n2CCN3C)cc1OC] 108 | 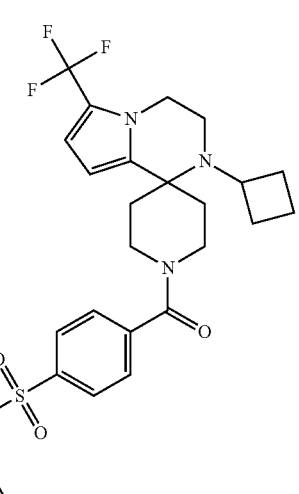 114 |
| 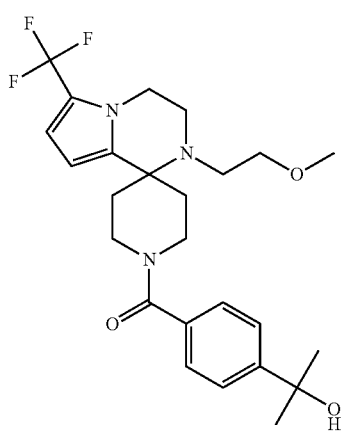 [SMILES: COCCN1CCn2c(C(F)(F)F)ccc2C12CCN(C(=O)c1ccc(C(C)(C)O)cc1)CC2] 109 | 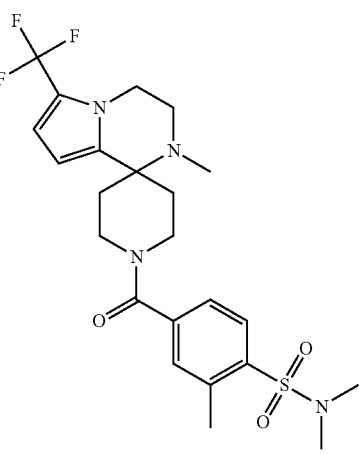 116 |

| 117 | 120 |
|---|---|
| 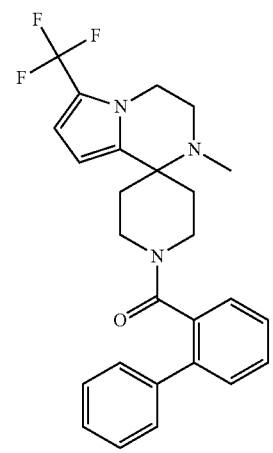 [SMILES: CN1CCn2c(C(F)(F)F)ccc2C12CCN(C(=O)c1ccccc1-c1ccccc1)CC2] | 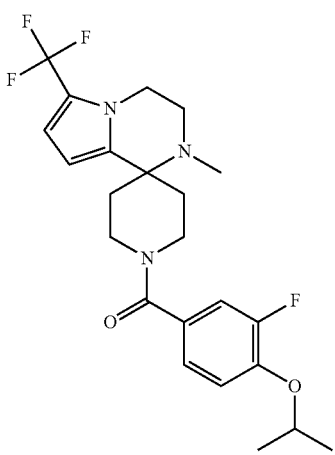 |
| 118 | 121 |
| 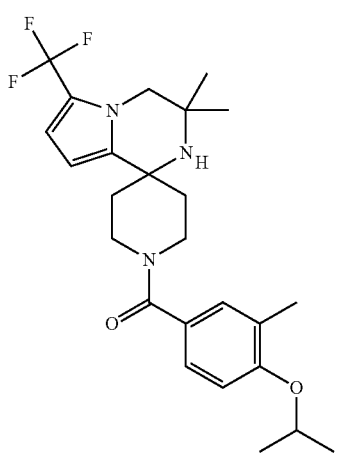 | 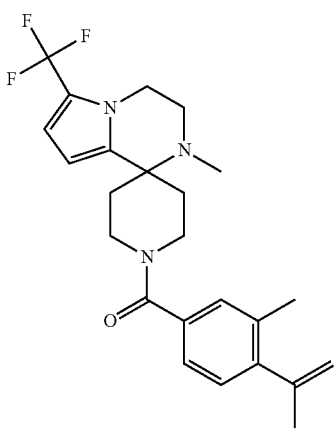 |
| 119 | 122 |
| 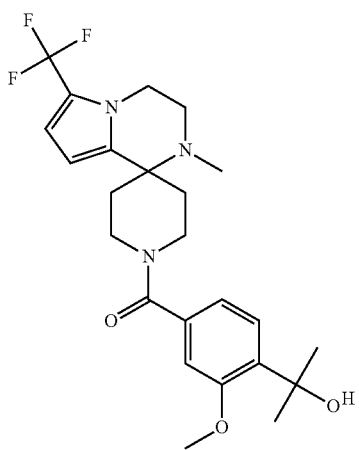 | 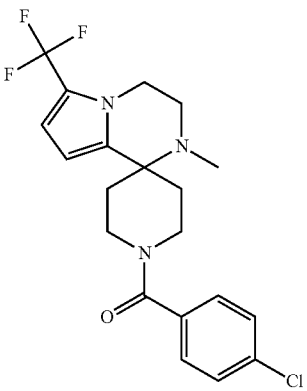 [SMILES: CN1CCn2c(C(F)(F)F)ccc2C12CCN(C(=O)c1ccc(Cl)cc1)CC2] |

| 123 | 126 |
|---|---|
| 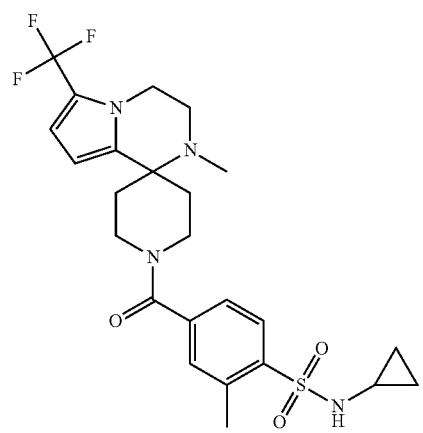 [SMILES: Cc1cc(C(=O)N2CCC3(CC2)c2ccc(C(F)(F)F)n2CCN3C)ccc1S(=O)(=O)NC1CC1] | 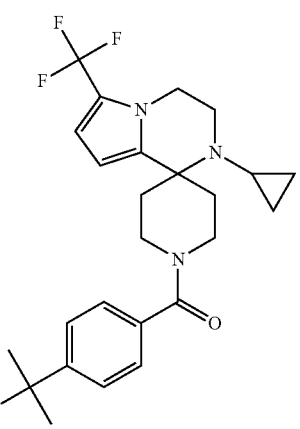 |
| 124 | 127 |
| 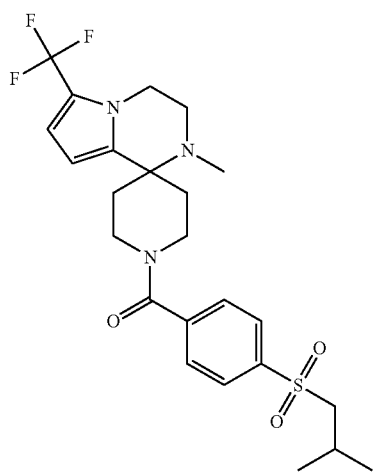 [SMILES: CC(C)CS(=O)(=O)c1ccc(C(=O)N2CCC3(CC2)c2ccc(C(F)(F)F)n2CCN3C)cc1] | 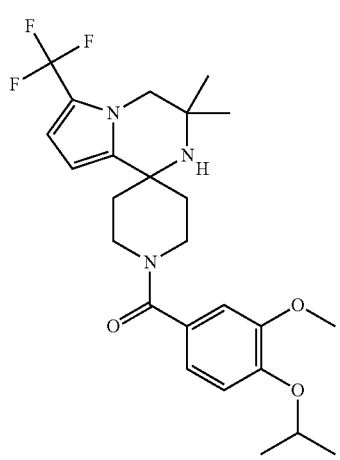 |
| 125 | 128 |
| 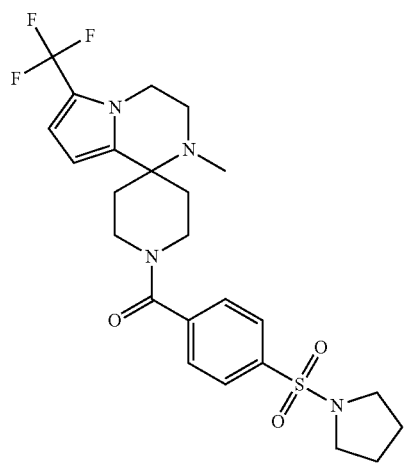 [SMILES: CN1CCn2c(C(F)(F)F)ccc2C12CCN(C(=O)c1ccc(S(=O)(=O)N3CCCC3)cc1)CC2] | 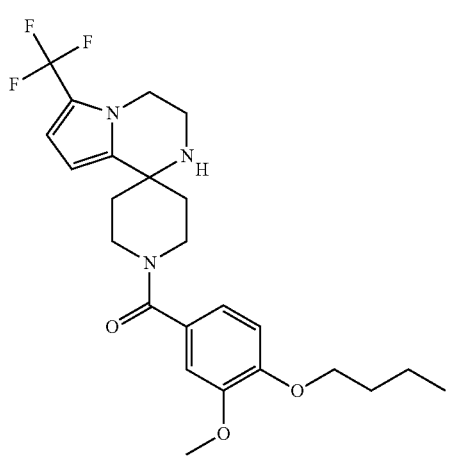 |

| 801 -continued | 802 -continued |
|---|---|
| 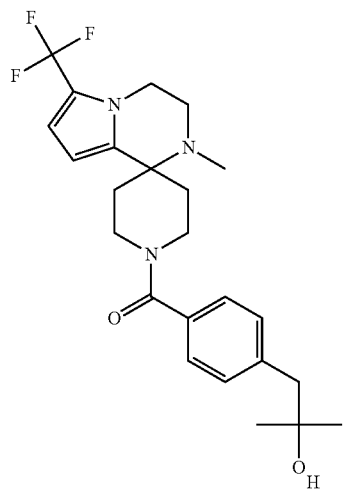 129 | 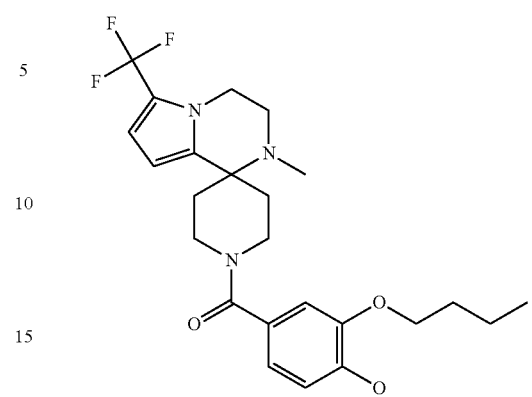 133 |
| 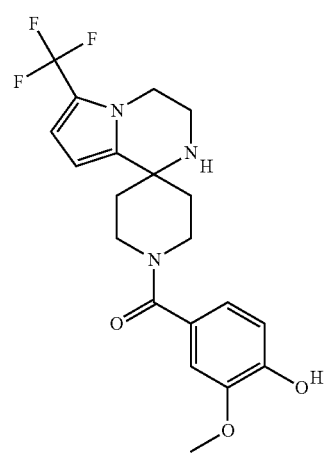 130 | 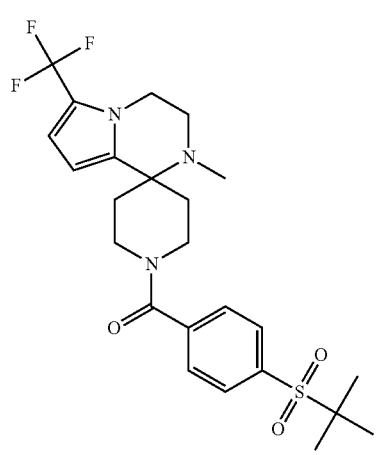 135 |
| 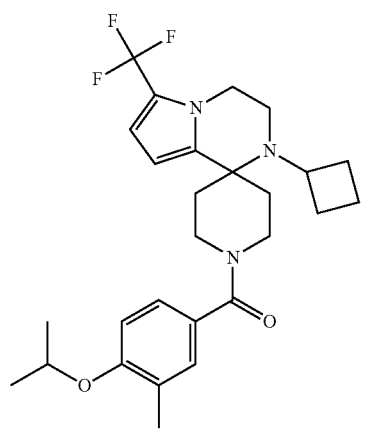 [SMILES: Cc1cc(C(=O)N2CCC3(CC2)c2ccc(C(F)(F)F)n2CCN3C2CCC2)ccc1OC(C)C] 132 | 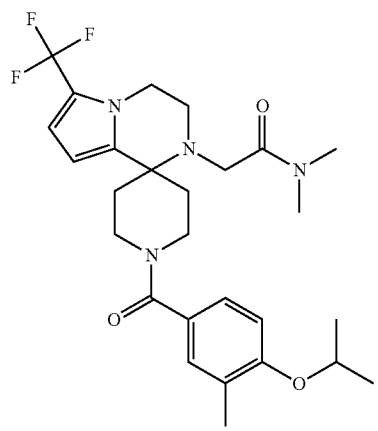 [SMILES: Cc1cc(C(=O)N2CCC3(CC2)c2ccc(C(F)(F)F)n2CCN3CC(=O)N(C)C)ccc1OC(C)C] 136 |

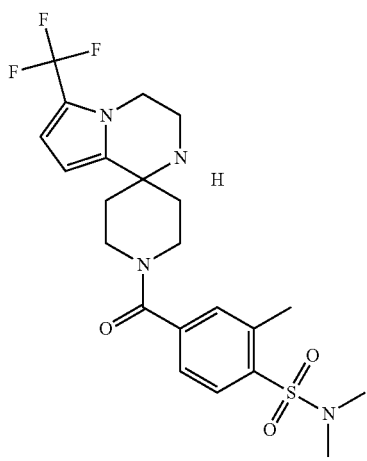
137
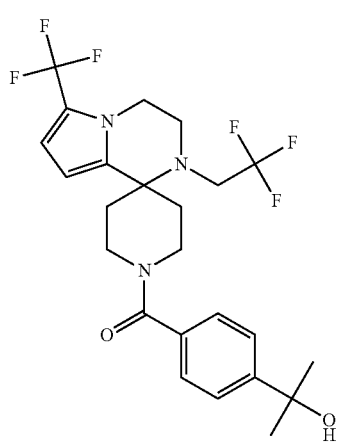
140
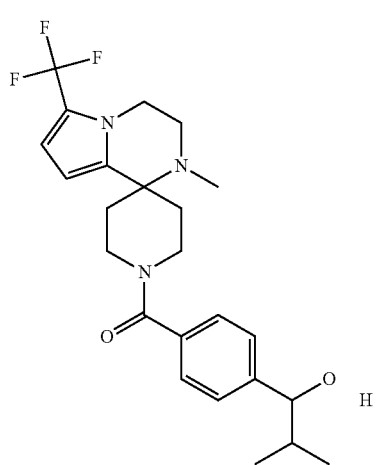
138
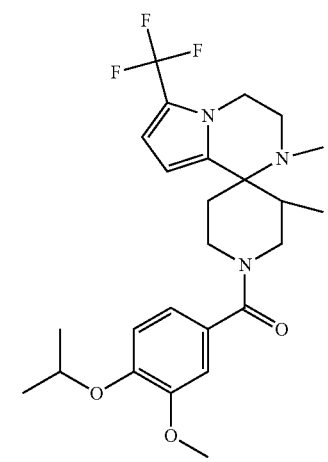 [SMILES: COc1cc(C(=O)N2CCC3(c4ccc(C(F)(F)F)n4CCN3C)C(C)C2)ccc1OC(C)C]
141
139
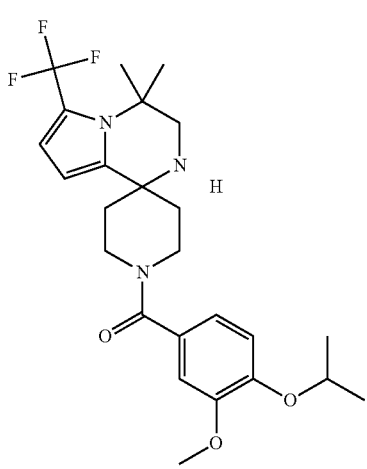
142

| 143 | 148 |
|---|---|
| 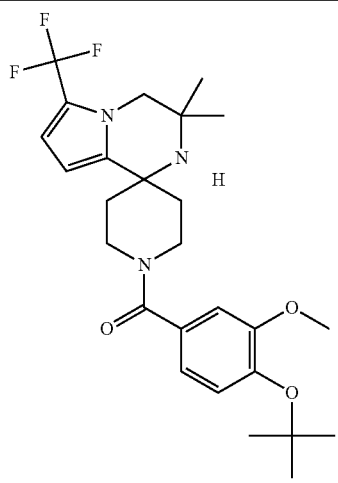 | 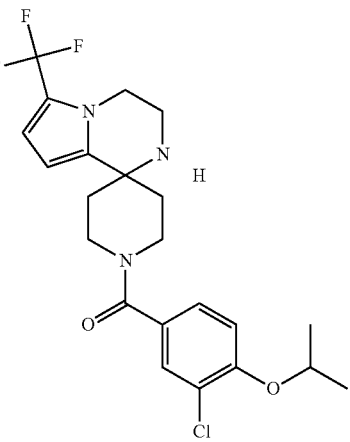 |
| 144 | 149 |
| 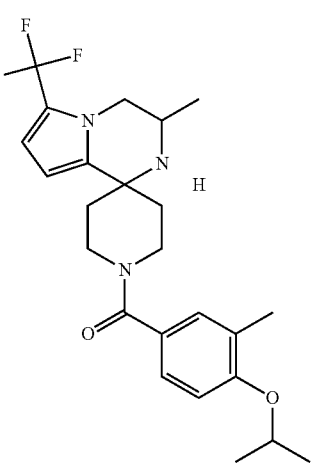 | 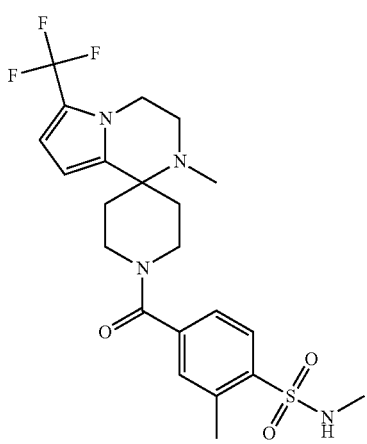 |
| 145 | 150 |
| 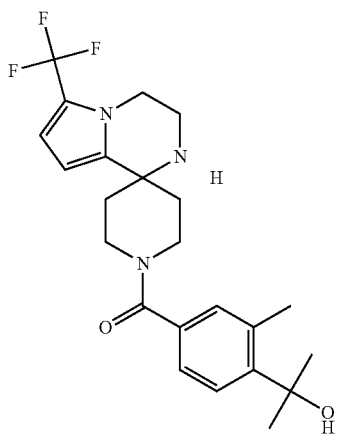 | 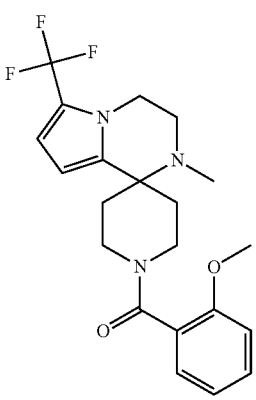 [SMILES: COc1ccccc1C(=O)N1CCC2(CC1)c1ccc(C(F)(F)F)n1CCN2C] |

| 807 -continued | 808 -continued |
|---|---|
| 151 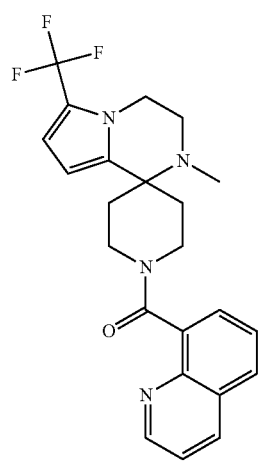 [SMILES: CN1CCn2c(C(F)(F)F)ccc2C12CCN(C(=O)c1cccc3cccnc13)CC2] | 155 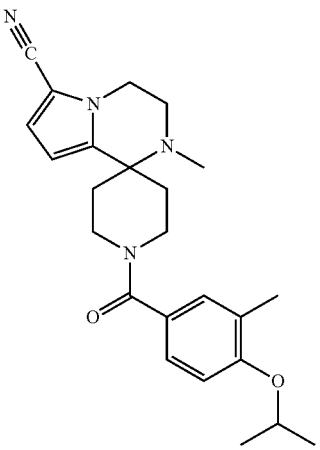 |
| 152 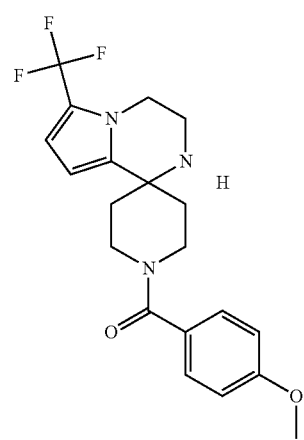 | 156 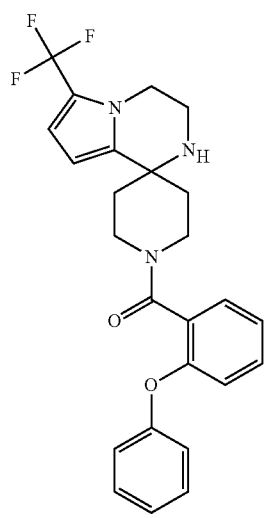 |
| 153 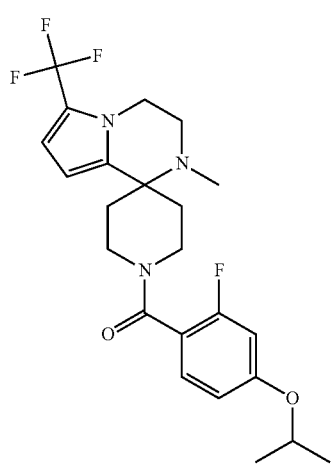 [SMILES: CC(C)Oc1ccc(C(=O)N2CCC3(CC2)c2ccc(C(F)(F)F)n2CCN3C)c(F)c1] | 157 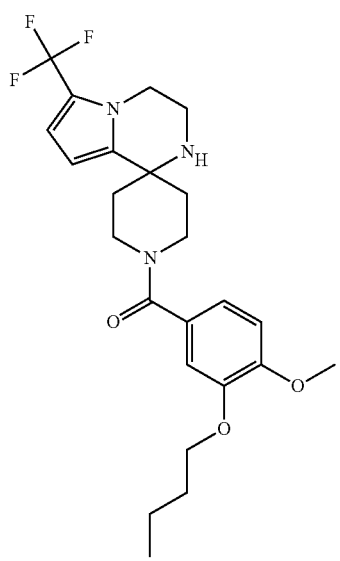 |

| 809 -continued | 810 -continued |
|---|---|
| 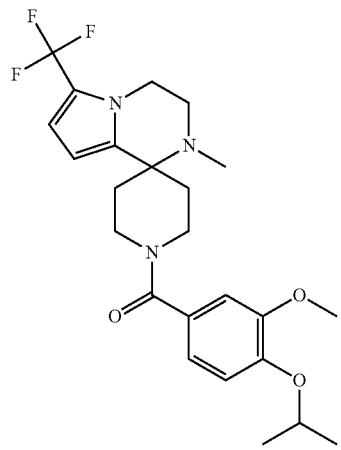 [SMILES: COc1cc(C(=O)N2CCC3(CC2)c2ccc(C(F)(F)F)n2CCN3C)ccc1OC(C)C] 158 | 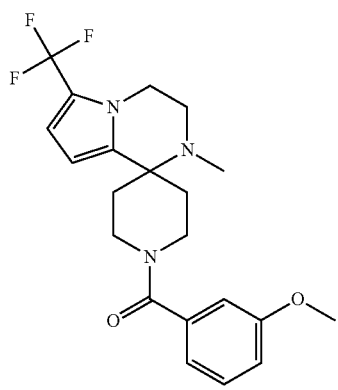 162 |
| 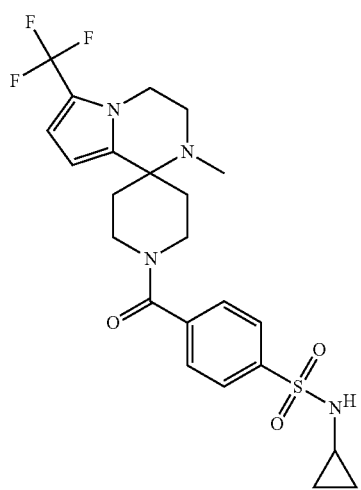 159 | 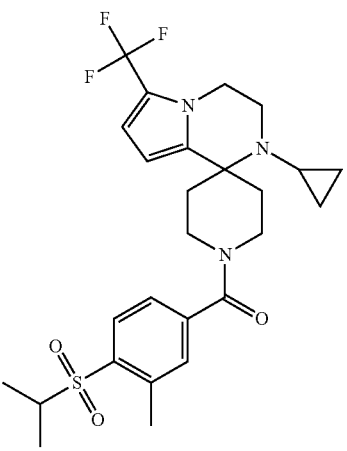 164 |
| 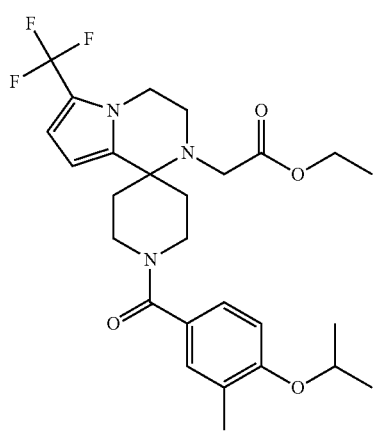 [SMILES: CCOC(=O)CN1CCn2c(C(F)(F)F)ccc2C12CCN(C(=O)c1ccc(OC(C)C)c(C)c1)CC2] 161 | 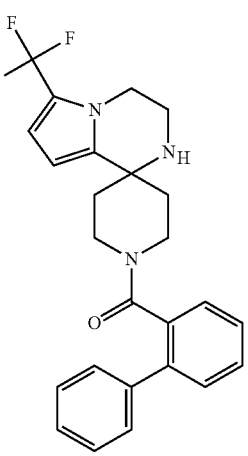 165 |

811
-continued
166
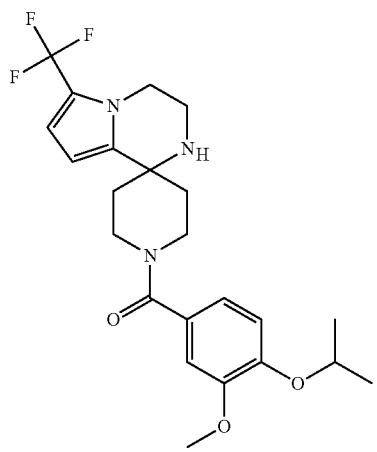
167
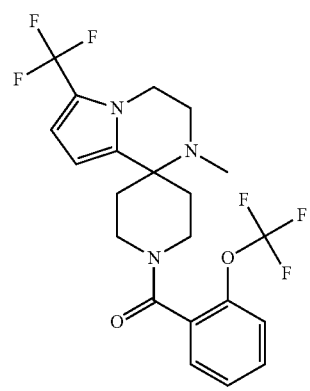 [SMILES: CN1CCn2c(C(F)(F)F)ccc2C12CCN(C(=O)c1ccccc1OC(F)(F)F)CC2]
168
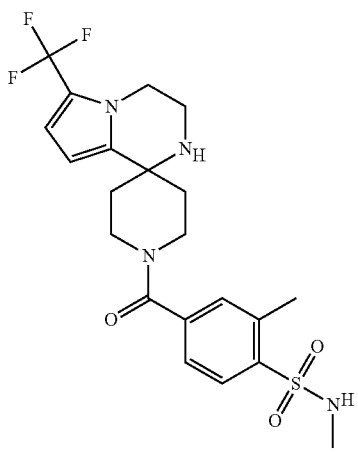
812
-continued
169
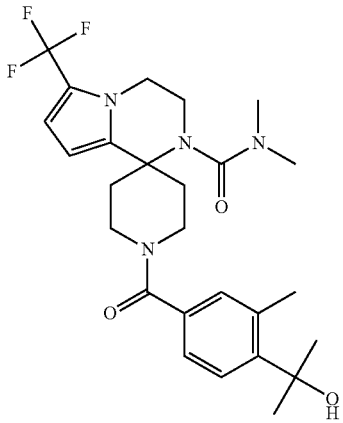 [SMILES: Cc1cc(C(=O)N2CCC3(CC2)c2ccc(C(F)(F)F)n2CCN3C(=O)N(C)C)ccc1C(C)(C)O]
170
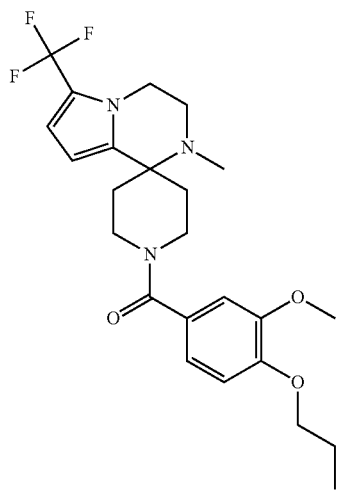 [SMILES: CCCOc1ccc(C(=O)N2CCC3(CC2)c2ccc(C(F)(F)F)n2CCN3C)cc1OC]
171
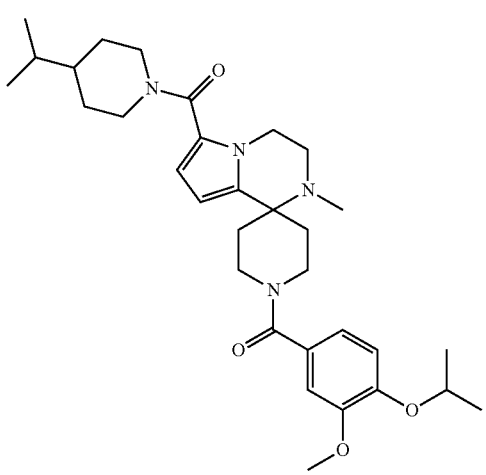 [SMILES: COc1cc(C(=O)N2CCC3(CC2)c2ccc(C(=O)N4CCC(C(C)C)CC4)n2CCN3C)ccc1OC(C)C]

| 813 -continued | 814 -continued |
|---|---|
| 172 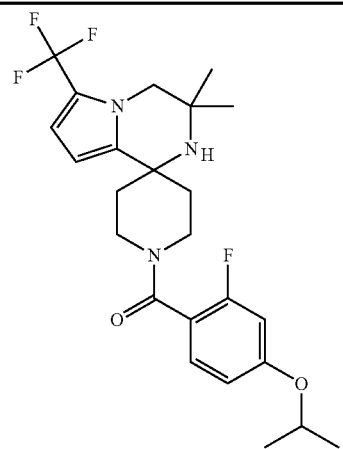 | 179 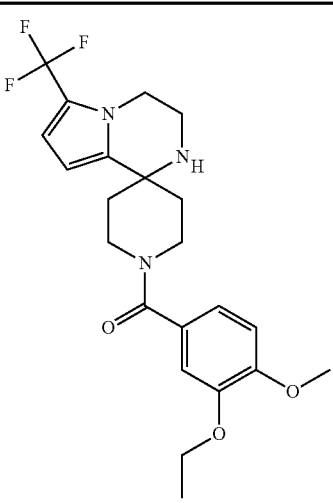 |
| 173 | 180 |
| 177 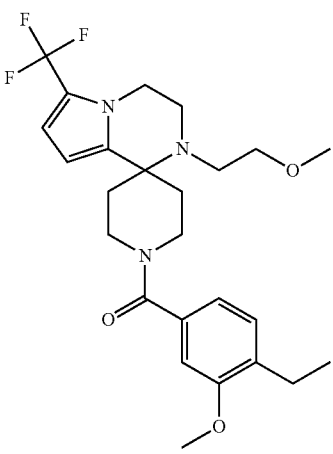 | 181 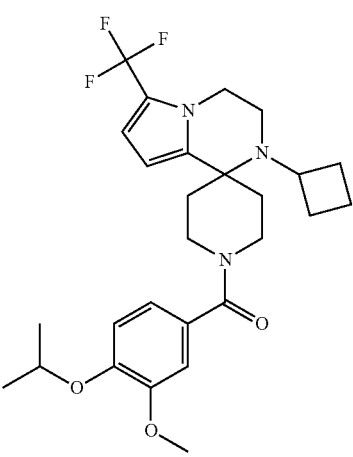 [SMILES: COc1cc(C(=O)N2CCC3(CC2)c2ccc(C(F)(F)F)n2CCN3C2CCC2)ccc1OC(C)C] |

| 182 | 187 |
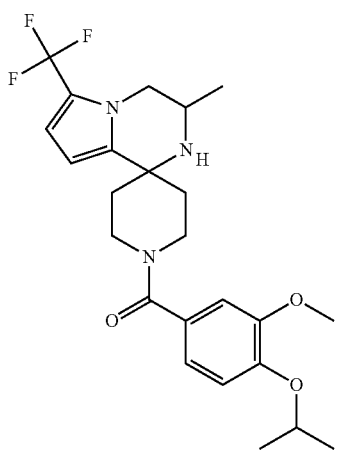
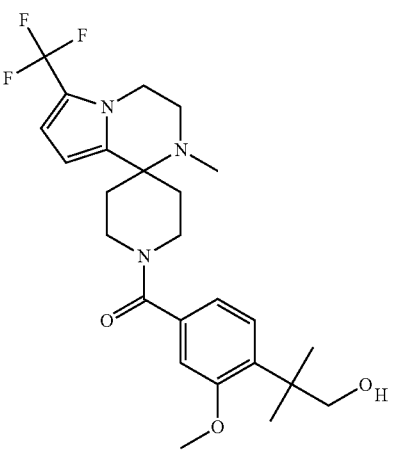
| 184 | |
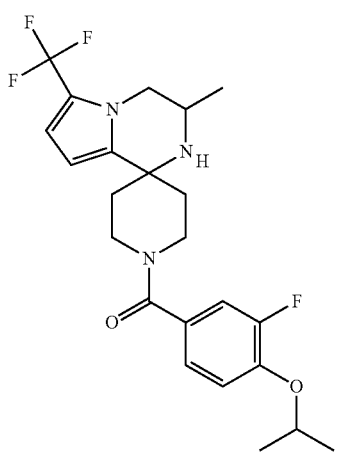
| 186 | 188 |
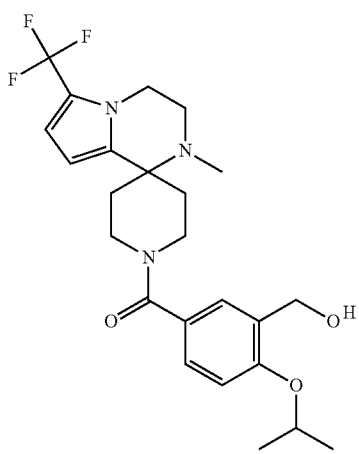

| 817 -continued | 818 -continued |
|---|---|
| 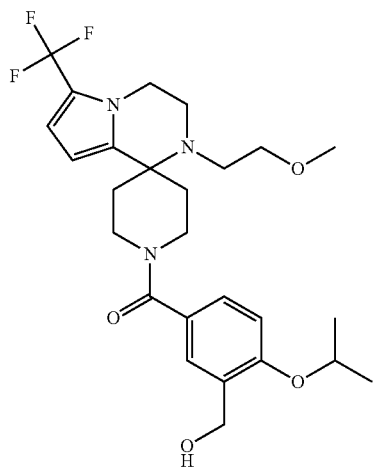 [SMILES: COCCN1CCn2c(C(F)(F)F)ccc2C12CCN(C(=O)c1ccc(OC(C)C)c(CO)c1)CC2] 190 | 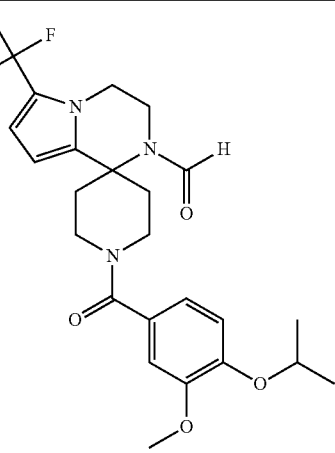 192 |
| 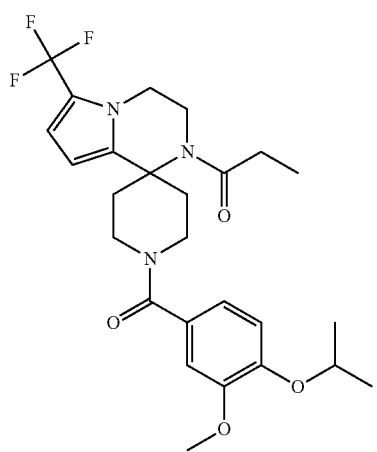 [SMILES: CCC(=O)N1CCn2c(C(F)(F)F)ccc2C12CCN(C(=O)c1ccc(OC(C)C)c(OC)c1)CC2] 191 | 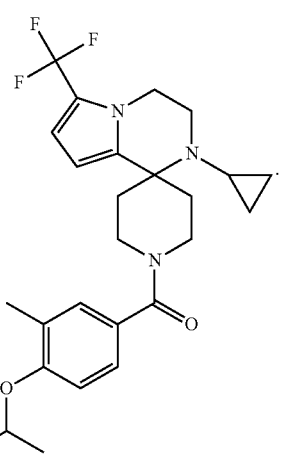 193 |
* * * * *